US007790428B2

(12) United States Patent
Wang et al.

(10) Patent No.: US 7,790,428 B2
(45) Date of Patent: Sep. 7, 2010

(54) ESSENTIAL FUNGAL POLYPEPTIDE, CAYDR341C, AND METHODS OF USE THEREOF

(75) Inventors: Ying-Kai Wang, Rocky Hill, CT (US); Mengping Liu, North Haven, CT (US); Brian A. Dougherty, Killingworth, CT (US); Matthew D. Healy, Hamden, CT (US); Daniel B. Davison, Morrisville, PA (US); Charles E. Mazzucco, Branford, CT (US); Trina Maurice, Bristol, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/726,434

(22) Filed: Mar. 22, 2007

(65) Prior Publication Data

US 2007/0172881 A1 Jul. 26, 2007

Related U.S. Application Data

(62) Division of application No. 10/424,324, filed on Apr. 25, 2003, now Pat. No. 7,465,568.

(60) Provisional application No. 60/376,022, filed on Apr. 26, 2002.

(51) Int. Cl.

| | |
|---|---|
| ***C12N 15/00*** | (2006.01) |
| ***C12N 5/10*** | (2006.01) |
| ***C12N 1/21*** | (2006.01) |
| ***C12P 21/00*** | (2006.01) |
| ***C07H 21/00*** | (2006.01) |
| *C12N 9/00* | (2006.01) |
| *C07K 14/00* | (2006.01) |

(52) U.S. Cl. .................... 435/183; 435/320.1; 435/325; 435/252.3; 435/69.1; 536/23.2; 530/350

(58) Field of Classification Search .............. 435/320.1, 435/69.1, 325, 252.3, 183; 530/350; 536/23.2
See application file for complete search history.

(56) References Cited

U.S. PATENT DOCUMENTS

| | | | |
|---|---|---|---|
| 6,221,597 | B1 | 4/2001 | Roberts |
| 6,280,963 | B1 | 8/2001 | Koltin et al. |
| 6,307,037 | B1 | 10/2001 | Gaffney et al. |
| 6,747,137 | B1 | 6/2004 | Weinstock et al. |
| 2003/0180953 | A1 | 9/2003 | Roemer et al. |

FOREIGN PATENT DOCUMENTS

| | | |
|---|---|---|
| WO | WO00/39342 | 7/2000 |
| WO | WO00/58520 | 10/2000 |
| WO | WO 01/60975 | 8/2001 |
| WO | WO 02/053728 | 7/2002 |
| WO | WO02/086097 A2 | 10/2002 |

OTHER PUBLICATIONS

Altschul, et al., "Basic Local Alignment Search Tool", J. Mol. Biol., vol. 215, pp. 403-410 (1990).

Badger, et al., "CRITICA: Coding Region Identification Tool Invoking Comparative Analysis", Mol. Biol. Evol., vol. 16(4), pp. 512-524 (1999).

Bateman, et al., "The Pfam Protein Families Database", Nuc. Acids Res., vol. 28(1), pp. 263-266 (2000).

Berman, et al., "The Protein Data Bank", Nuc. Acids Res., vol. 28(1), pp. 235-242 (2000).

Bernstein, et al., "The Protein Data Bank: A Computer-based Archival File for Macromolecular Structures", J. Mol. Biol., vol. 112, pp. 535-542 (1977).

Bohm, Hans-Joachim, "The computer program LUDI: A New Method for the De Novo Design of Enzyme Inhibitors", J. Computer-Aided Molec. Design, vol. 6, pp. 61-78 (1992).

Brick, et al., "Structure of Tyrosyl-tRNA Synthetase Refined at 2.3 Å Resolution", J. Mol. Biol., vol. 208, pp. 83-98 (1988).

Bruccoleri, et al., "Concordance Analysis of Microbial Genomes", Nuc. Acids Res., Vo. 26(19), pp. 4482-4486 (1998).

Cardozo, et al., "Homology Modeling by the ICM Method", Proteins: Structure, Function and Genetics, vol. 23, pp. 403-414 (1995).

Care, et al., "The MET3 Promoter: A New Tool for *Candida albicans* Molecular Genetics", Molec. Microbiol., vol. 34(4), pp. 792-798 (1999).

Chibana, et al., "Sequence Finishing and Gene Mapping for *Candida albicans* Chromosome 7 and Syntenic Analysis Against the *Saccharomyces cerevisiae* Genome", Genetics, vol. 170, pp. 1525-1537 (2005).

Delagoutte, et al., "tRNA Aminoacylation by Arginyl-tRNA Synthetase: Induced Conformations During Substrates Binding", EMBO J., vol. 19(21), pp. 5599-5610 (2000).

Fonzi, et al., "Isogenic Strain Construction and Gene Mapping in *Candida albicans*", Genetics, vol. 134, pp. 717-728 (1993).

Gachotte, et al., "Characterization of The *Saccharomyces cerevisiae* ERG27 Gene Encoding the 3-Keto Reductase Involved in C-4 Sterol Dememthylation", PNAS, vol. 96(22), pp. 12655-12660 (1999).

Ghosh, et al., "Porcine Carbonyl Reductase", J. Biol. Chem., vol. 276(21), pp. 18457-18463 (2001).

Goffeau, et al., "Life With 6000 Genes", Science, vol. 274, pp. 546-567 (1996).

Goodford, P.J., "A Computational Procedure for Determining Energetically Favorable Binding Sites on Biologically Important Macromolecules", J. Med. Chem., vol. 28, pp. 849-857 (1985).

Goodsell, et al., "Automated Docking of Substrates to Proteins by Simulated Annealing", Proteins: Structure, Function, Genetics, vol. 8, pp. 195-202 (1990).

Greer, et al., "Comparative Modeling of Homologous Proteins", Methods Enzymol., vol. 202, pp. 239-252 (1991).

Hendlich, et al., "Identification of Native Protein Folds Amongst a Large Number of Incorrect Models", J. Mol. Biol., vol. 216, pp. 167-180 (1990).

(Continued)

*Primary Examiner*—Delia M Ramirez
(74) *Attorney, Agent, or Firm*—Stephen C. D'Amico

(57) ABSTRACT

The present invention provides essential fungal polynucleotides and their encoded polypeptides, homologues thereof and their uses. Additionally, the invention provides methods for the identification of essential polynucleotides and fungal strains which may be used for drug screening.

9 Claims, 79 Drawing Sheets

OTHER PUBLICATIONS

Kohler, et al., "*Candida albicans* Strains Heterozygous and Homozygous for Mutations in Mitogen-Activated Protein Kinase Signaling Components Have Defects in Hyphal Development", PNAS, vol. 93, pp. 13223-13228 (1996).
Koppensteiner, et al., "Characterization of Novel Proteins Based on Known Protein Structures", J. Mol. Biol., vol. 296, pp. 1139-1152 (2000).
Kuntz, et al. "A Geometric Approach to Macromolecule-Ligand Interactions", J. Mol. Biol., vol. 161, pp. 269-288 (1982).
Lesk, et al., "Homology Modelling: Inferences From Tables of Aligned Sequences", Curr. Opin. Struct. Biol., vol. 2, pp. 242-247 (1992).
Levitt, Michael, "Accurate Modeling of Protein Conformation by Automatic Segment Matching", J. Mol. Biol., vol. 226, pp. 507-533 (1992).
Liu, et al., "Suppression of Hyphal Formatation in *Candida albicans* By Mutation of A STE12 Homolog", Science, vol. 266, pp. 1723-1725 (1994).
Martin, Yvonne C., 3D Database Searching in Drug Design, J. Med. Chem., vol. 35(12), pp. 2145-2154 (1992).
Mo, et al., "Erg28p is a Key Protein in the Yeast Sterol Biosynthetic Enzyme Complex", J. Lipid Res., vol. 46, pp. 1991-1998 (2005).
Mo, et al., "In Yeast Sterol Biosynthesis the 3-keto Reductase Protein (Erg27p) is Required gor Oxidosqualene Cyclase (Erg7p) Activity", Biochimica Biophys. Acta, vol. 1633, pp. 68-74 (2003).
Mo, et al., "Protein-Protein Interactions Among C-4 Demethylation Enzymes Involved in Yeast Sterol Biosynthesis", PNAS, vol. 99(15), pp. 9739-9744 (2002).
Nakayama, et al., "Tetracycline-Regulatable System to Tightly Control Gene Expression in the Pathogenic Fungus *Candida albicans*", Infection Immunity, vol. 68(12), pp. 6712-6719 (2000).
Natter, et al., "The Spatial Organization of Lipid Synthesis in the Yeast *Saccharomyces cerevisiae* Derived from Large Scale Green Fluorescent Protein Tagging and High Resolution Microscopy", Mole. Cell. Proteomics, vol. 4, pp. 662-672 (2005).
Novotny, et al., "Criteria that Discriminate between Native Proteins and Incorrectly Folded Models", Proteins: Structure, Function, Genetics, vol. 4, pp. 19-30 (1988).
Palm, et al., "Crystal Structure of RNA3'-Terminal Phosphate Cyclase, a Ubiquitous Enzyme with Unusual Topology", Structure, vol. 8(1), pp. 13-23 (2000).
Pearson, William R., "Flexible Sequence Similarity Searching with the FASTA3 Program Package", Methods Molec. Biol., vol. 132, pp. 185-219 (2000).
Pearson, William. R., "Rapid and Sensitive Sequence Comparison with FASTP and FASTA", Meth. Enzymol., vol. 183, pp. 63-98 (1990).
Perepnikhatka, et al., "Specific Chromosome Alterations in Fluconazole-Resistant Mutants of *Candida albicans*", J. Bacteriology, vol. 181(13), pp. 4041-4049 (1999).
Sali, et al., "Evaluation of Comparative Protein Modeling by Modeller", Proteins: Structure, Function, Genetics, vol. 23, pp. 318-326 (1995).
Schimmel, Paul, "Classes of Aminoacyl-tRNA Synthetases and the Establishment of the Genetic Code", TIBS, vol. 16, pp. 1-3 (1991).
Sherman, Fred, "Getting Started with Yeast", Meth. Enzymol., vol. 194, pp. 3-21 (1991).
Sippl, Manfred J., "Boltzmann's Principle, Knowledge-Based Mean Fields and Protein Folding. An Approach to the Computational Determination of Protein Structures", J. Computer-Aided Molec. Design, vol. 7, pp. 473-501 (1993).
Sippl, et al., "Detection of Native-Like Models for Amino Acid Sequences of Unknown Three-Dimensional Structure in a Data Base of Known Protein Conformations", Proteins: Structure, Function, Genetics, vol. 13, pp. 258-271 (1992).
Wilson, et al., "Rapid Hypothesis Testing with *Candida albicans* Through Gene Disruption with Short Homology Regions", J. Bacteriology, vol. 181(6), pp. 1868-1874 (1999).
Johnston, et al., "The Nucleotide Sequence of *Saccharomyces cerevisiae* Chromosome XII", Nature, vol. 387 (Supp), pp. 87-90 (1997).
NCBI Entrez Accession No. AAB67544 (gi:1256850), Johnston, et al., Aug. 22, 1997.
NCBI Entrez Accession No. AAV02842 (gi:53952845), Weinstock, et al., Oct. 8, 2004.
NCBI Entrez Accession No. AAV03876 (gi:53953879), Weinstock, et al., Oct. 8, 2004.
NCBI Entrez Accession No. AAV04089 (gi:53954092), Weinstock, et al., Oct. 8, 2004.
NCBI Entrez Accession No. AAV0777 (gi:53957780), Weinstock, et al., Oct. 8, 2004.
NCBI Entrez Accession No. AAV07844 (gi:53957847), Weinstock, et al., Oct. 8, 2004.
NCBI Entrez Accession No. BAE44857 (gi:76573773), Chibana, et al., Sep. 30, 2005.
NCBI Entrez Accession No. CAA97664 (gi:1360483), Messenguy, et al., Jun. 17, 1997.
NCBI Entrez Accession No. CAG90997 (gi:49658157), Dujon, et al., Apr. 17, 2005.
NCBI Entrez Accession No. EAK92919 (gi:46433481), Jones, et al., Aug. 6, 2004.
NCBI Entrez Accession No. EAK92945 (gi:46433508), Jones, et al., Aug. 6, 2004.
NCBI Entrez Accession No. EAK93470 (gi:46434048), Jones, et al., Aug. 6, 2004.
NCBI Entrez Accession No. EAK94026 (gi:46434622), Jones, et al., Aug. 6, 2004.
NCBI Entrez Accession No. EAK94072 (gi:46434669), Jones, et al., Aug. 6, 2004.
NCBI Entrez Accession No. EAK94296 (gi:46434900), Jones, et al., Aug. 6, 2004.
NCBI Entrez Accession No. EAK94333 (gi:46434940), Jones, et al., Aug. 6, 2004.
NCBI Entrez Accession No. EAK99232 (gi:46439920), Jones, et al., Aug. 6, 2004.
NCBI Entrez Accession No. EAK99505 (gi:46440196), Jones, et al., Aug. 6, 2004.
NCBI Entrez Accession No. NP_013201 (gi:6323129), Johnston, et al., Feb. 21, 2006.
NCBI Entrez Accession No. Q12452 (gi:60392263), Johnston, et al., Feb. 7, 2006.
NCBI Entrez Accession No. XP_712114 (gi:68488012), Jones, et al., Sep. 29, 2005.
NCBI Entrez Accession No. XP_712139 (gi:68487961), Jones, et al., Feb. 10, 2006.
NCBI Entrez Accession No. XP_713413 (gi:68485304), Jones, et al., Sep. 29, 2005.
NCBI Entrez Accession No. XP_718164 (gi:68475632), Jones, et al., Sep. 29, 2005.
NCBI Entrez Accession No. XP_888960 (gi:77023032), Chibana, et al., Jan. 13, 2006.
Delarue, et al., "The Aminoacyl-tRNA Synthetase Family: Modules at Work", BioEssays, vol. 15(9), pp. 675-687 (1993).
Lee, et al. "Amino Acid Synthetic Media for Fungal Pathogens Based on Aminopeptidase Specificities: Histoplasma Capsulatum, Blastomyces, Dermititidis, *Paracoccidioides brasiliensis* and *Cryptococcus neoformans*", Sabouraudia, vol. 13, pp. 142-147.
Likos, et al., "A tale of two clades: monkeypox viruses", J. General Virology, vol. 86, pp. 2661-2672 (2005).
NCBI Entrez Accession No. AAY97011 (gi:68448889), Likos, et al., Sep. 28, 2005.
Gachotte, et al., "Characterization of the *Saccharomyces cerevisiae ERG27* gene encoding he 3-keto reductase involved in C-4 sterol demethylation", PNAS, vol. 96 (22), pp. 12655-12660 (1999).
Garcia, et al., "Heterogeneity in the haemagglutinin gene and emergence of the highly pathogenic phenotype among recent H5N2 avian influenza viruses from Mexico", J. General Virology, vol. 77, pp. 1493-1504 (1996).
Jones, et al., "The diploid genome sequence of *Candida albicans*", PNAS, vol. 101 (19), pp. 7329-7334 (2004).
Kennedy, et al., "Cloning and Sequencing of the *Candida albicans* C-4 Sterol Methyl Oxidase Gene (ERG25) and Expression of an ERG25 Conditional Lethal Mutation in *Saccharomyces cerevisiae*", Lipids, vol. 35 (3), pp. 257-262 (2000).

Mahairas, et al., "Sequence-tagged connectors: A sequence approach to mapping and scanning the human genome", PNAS, vol. 96, pp. 9739-9744 (1999).
Pierson, et al., "Isolation, characterization, and regulation of he *Candida albicans* ERG27 gene encoding the sterol 3-keto reductase", Medical Mycology, vol. 47, pp. 461-473 (2004).
NCBI Entrez Accession No. AAB19089 (gi:1125737), Garcia, et al., Nov. 19, 1996.
NCBI Entrez Accession No. AQ466871 (gi:4643966), Mahairas, et al., Apr. 23, 1999.
NCBI Entrez Accession No. EAK98915 (gi:46439599), Jones, et al., Aug. 6, 2004.
NCBI Entrez Accession No. EAK98982 (gi:46439667), Jones, et al., Aug. 6, 2004.
NCBI Entrez Accession No. XM_712838 (gi:68475980), Jones, et al., May 4, 2001.
NCBI Entrez Accession No. XP_717865 (gi:68476112), Jones, et al., Jul. 1, 2005.
NCBI Entrez Accession No. XP_717931 (gi::68475981), Jones, et al., Jul. 1, 2005.
Database GenBank, US National Library of Medicine (Bethesda, MD) No. ABZ32111, Roemer, et al., Jan. 2003.
NCBI Entrez Accession No. gi|14719542, Delagoutte, B. et al., Jun. 28, 2000.
NCBI Entrez Accession No. gi|19075209, Wood, V. et al., Jan. 9, 2004.
NCBI Entrez Accession No. gi|19115009, Wood, V. et al., Jan. 9, 2004.
NCBI Entrez Accession No. gi|19115751, Wood, V. et al., Jan. 9, 2004.
NCBI Entrez Accession No. gi|26025670, Johnston, M. et al., Dec. 4, 2002.
NCBI Entrez Accession No. gi|27280506, Koltin, Y. et al., Dec. 20, 2002.
NCBI Entrez Accession No. gi|29465858, Jia, N. et al., Apr. 1, 2003.

FIG. 1A

Alignment of *C. Albicans* Essential Polypeptides with *S. Cervisiae* Sequences and Other Sequences CaYLR100w

```
A: MSLLKDSTVAVITGTSSNLGFNIAVRLLEGLEDNKEITLVVTSRTLPKVKEVISDIKKYIVAKIPTKVNKVEFDYLLVDFTDMVSILSAYYELNKRYKHIDYLFINAAQGVYGGIDWTGAVLEVLQSPIKAVTNPTYKLQKVGVESCDKL   150
B: ----MNRKVAIVTGTNSNLGLNIVFRLIETEDTNVRLTIVVTSRTLPRVQEVINQIKDFYNKSGRVEDLEIDFDYLLVDFTNMVSVLNAYYDINKKYRAINYLFVNAAQGIFDGIDWIGAVKEVFTNPLKAVTNPTYKIQLVGVKSKDDM   146
C: ----MNRKVAIVTGTNSNLGLNIVFRLIETEDTNVRLTIVVTSRTLPRVQEVINQIKDFYNKSGRVEDLEIDFDYLLVDFTNMVSVLNAYYDINKKYRAINYLFVNAAQGIFDGIDWIGAVKEVFTNPLKAVTNPTYKIQLVGVKSKDDM   146
   1.......10........20........30........40........50........60........70........80........90........100.......110.......120.......130.......140.......150
```

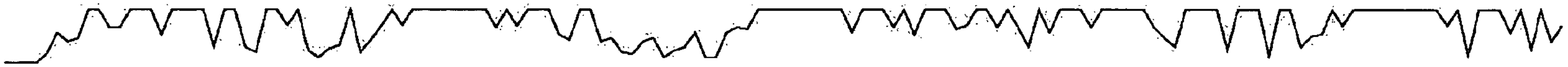

```
A: GLVFQANVFGPYYFIHRIKHILENG-GKIVWVSSLMSSPKYLSFNDLQLLRSEASYEGSKRLVDLMHFGTYNKLEREHGIKQYLVHPGIFTSFSFFQYLNVFTYYGMLFLFYLARFLGSPYHNISGYIAANAPVE----AALGQTKQNCK   295
B: GLIFQANVFGPYYFISKILPCLTRGKAYIVWISSIMSDPKYLSLNDIELLKTNASYEGSKRLVDLLHLATYKDLKKL-GINQYVVQPGIFTSHSFSEYLNFFTYFGMLCLFYLARLLGSPWHNIDGYKAANAPVYVTRLANPNFEKQDVK   295
C: GLIFQANVFGPYYFISKILPCLTRGKAYIVWISSIMSDPKYLSLNDIELLKTNASYEGSKRLVDLLHLATYKDLKKL-GINQYVVQPGIFTSHSFSEYLNFFTYFGMLCLFYLARLLGSPWHNIDGYKAANAPVYVTRLANPNFEKQDVK   295
   .......160.......170.......180.......190.......200.......210.......220.......230.......240.......250.......260.......270.......280.......290.......300
```

```
A: TASACTRSGKEYLLEEEIDSTGLDDVVLYLDTLTKEWDEKLKDQIVNTRQP-   346
B: YGSATSRDGMPYIKTQEIDPTGMSDVFAYIQKKKLEWDEKLKDQIVETRTPI   347
C: YGSATSRDGMPYIKTQEIDPTGMSDVFAYIQKKKLEWDEKLKDQIVETRTPI   347
   .......310.......320.......330.......340.......350...
```

FIG. 1B-1

CaYDR341c

```
A: -MSVETISDSLKQLGLSQPAAIEGTHPQYNVVDVFRNYIAEELHRISSVDKS-IIIQALDTPKVLDQGDIIVPIPKLRLKGINPNEKSKEWAENFNKGKFISEIKPQGVFLQFYFAKTLLYNLVIEDVLKRKSDYGYLPLGVG----KKA   144
B: MASTANMISQLKKLSIAEPAVAKDSHPDVNIVDLMRNYISQELSKISGVDSS-LIFPALEWTNTMERGDLLIPIPRLRIKGANPKDLAVQWAEKFPCGDFLEKVEANGPFIQFFFNPQFLAKLVIPDILTRKEDYGSCKLVEN----KKV   145
C: ------MACCFRRAIACQLSRVLNLPPENLITSISAVPISQKE-EVADFQLS--VDPLLEKDNDHSRPDIQVQAKRL--------------AEKLRCDTVVSEISTGQRTVNFKINRELLTKTVLQQVIEDGSKYGLKSELFSGLPQKKI   127
   1.......10........20........30........40........50........60........70........80........90.......100.......110.......120.......130.......140.......150
```

```
A: IVEFSSPNIAKPFHAGHLRSTIIGGFISNLYEKVGWDVTRINYLGDWGKQFGLLAVGFERYGDESKLASDPINHLFEVYVKINQDVTKETSEATGETPAETIDASEQDEKKIQSSTNEEARRFFRRMEDGDESALKIWARFRDLSIEKYV   294
B: IIEFSSPNIAKPFHAGHLRSTIIGGFLANLYEKLGWEVIRMNYLGDWGKQFGLLAVGFERYGNEEALVKDPIHHLFDVYVRINKDIEEE-------G----------DSIPLEQSTNGKAREYFKRMEDGDEEALKIWKRFREFSIEKYI   278
C: VVEFSSPNVAKKFHVGHLRSTVIGNFIANLKEALGHQVIRINYLGDWGMQFGLLGTGFQLFGYEEKLQSNPLQHLFEVYVQNKEAADD------------------------KSVAKAAQEFFQRLELGDVQALSLWQKFRDLSIEEYI   253
   .......160.......170.......180.......190.......200.......210.......220.......230.......240.......250.......260.......270.......280.......290.......300
```

```
A: DTYGRLNIKYDVYSGESQVPQEKMKEATKLFEDKGLIDID-RGAKLIDLTKFNKKLGKALVEKSDGTSLYLTRDVGEAIKRYETYKFDKMIYVIAAQQDLHCAQFFEILKQMGFEWAHNLEHVNFGMVQGMSTRKGTVVFLDNILQETKE   443
B: DTYARLNIKYDVYSGESQVSKESMLKAIDLFKEKGLTHED-KGAVLIDLTKFNKKLGKAIVQKSDGTTLYLTRDVGAAMDRYEKYHFDKMIYVIASQQDLHAAQFFEILKQMGFEWAKDLQHVNFGMVQGMSTRKGTVVFLDNILEETKE   427
C: RVYKRLGVYFDEYSGES-FYREKSQEVLKLLESKGLLLKTIKGTAVVDLSGNGDPSSICTVMRSDGTSLYATRDLAAAVDRMDKYNFDTMIYVTDKGQKKHFQQVFQMLKIMGYDWAERCQHVPFGVVQGMKTRRGDVTFLEDVLNEIQL   402
   .......310.......320.......330.......340.......350.......360.......370.......380.......390.......400.......410.......420.......430.......440.......450
```

FIG. 1B-2

CaYDR341c (continued)

```
   :* : * . : .  :::.*:: *: :*::*::***::.  : :*:*.*:*: . .**** :***:*:** *::..   :     . :   * ** :  : : * :: :*: :: :  :*  :*:**:.::* .: .:. * : .. ::
A: KMHEVMQKNEEKYAQIEDPDKIADLIGISAVMIQDMQSKRIHNYEFKWDRMTSFEGDTGPYLQYAHSRLCSMQRK-SGISIEELEHANFDLLVEPCASALARTLAQYPDVIKKAVKGLEPSTIVTYLFSVTHIVSQCYDILWVSGQEKDV   592
B: KMHEVMKKNENKYAQIEHPEEVADLVGISAVMIQDMQGKRINNYEFKWERMLSFEGDTGPYLQYAHSRLRSVERNASGITQEKWINADFSLLKEPAAKLLIRLLGQYPDVLRNAIKTHEPTTVVTYLFKLTHQVSSCYDVLWVAGQTEEL   577
C: RMLQNMASIKTTK-ELKNPQETAERVGLAALIIQDFKGLLLSDYKFSWDRVFQSRGDTGVFLQYTHARLHSLEET---FGCGYLNDFNTACLQEPQSVSILQHLLRFDEVLYKSSQDFQPRHIVSYLLTLSHLAAVAHKTLQIKDSPPEV   548
   .......460.......470.......480.......490.......500.......510.......520.......530.......540.......550.......560.......570.......580.......590.......600
```

```
   * *** *: *.*.*: *** ***:*** **
A: AIARLALYEAARQVINNGMTLLGLTPVNRM   622
B: ATARLALYGAARQVLYNGMRLLGLTPVERM   607
C: AGARLHLFKAVRSVLANGMKLLGITPVCRM   578
   .......610.......620.......630
```

FIG. 1C

CaYLR022c

```
A: MAVINQPNSQIRLTNVSLVRMKKGKKRFEIACYQNKVQDWRLKVEKDIDEVLQIEQVFINVSKGQVANNDDLQKCFGTTNQDEIIAEILNKGEIQLNEKERNANLQQKQNEFLNIISTKCINPRSKKRYPPSMIEKVLNEVKFHLNPTKP   150
B: -MPINQPSGQIKLTNVSLVRLKKARKRFEVACYQNKVQDYRKGIEKDLDEVLQIHQVFMNVSKGLVANKEDLQKCFGTTNVDDVIEEIMHKGEIQLSEKERQLMLNKVNNEMLTIVSAKCINPVSKKRYPPTMIHKALQELKFSPVINKP   149
C: -MSIFTPTNQIRLTNVAVVRMKRACKRFEIACYKNKVVGWRSGVEKDLDEVLQTHSVFVNVSKGQVAKKEDLISAFGTDDQTEICKQILTKGEVQVSDKERHTQLEQMFRDIATIVADKCVNPETKRPYTVILIERAMKDIHYSVKTNKS   149
   1.......10........20........30........40........50........60........70........80........90........100.......110.......120.......130.......140.......150
```

```
A: TKIQALDAIKLLVEKQIIPIARAQMKVRITLSKKAYLKTFQDEIKPVIDQIVEEDNNGKQ--YEIVGIIDPINYRVLVTLIENTDGSNKVAKGEGSIEVLDMSAIKE------   255
B: AKLQALEAIKLLVSKQIIPIVRAKMKVKVAISEPSRQPELIEKISKLIASSPGESTKPELDPWTCTGLIDPVNYRDLMTLCDK----------KGTVQVLDMAVIDNTTHN--   250
C: TKQQALEVIKQLKEKMKIERAHMRLRFILPVNE-G--KKLKEKLKPLIKVIESEDYGQQL--EIVC-LIDPGGFREIDELIKK-E-----TKGKGSLEVLNLKDVEECDEKFE   250
   .......160.......170.......180.......190.......200.......210.......220.......230.......240.......250.......260...
```

FIG. 1D

CaYOL077c

```
   **:***** .**.:.:***.:      :*:** *:*****:.********** .****:*****:*:**:*:****:*********::***.*********:*********:**:******:**************:****: *  .. **:
A: MSAIYKALCSKSSKETSEKTKH-----INRQRFLVISSRGITYRHRHLIQDLIALLPHARKEPKFDSKKNLHQLNEVAELYNCNNIFFFECRKHQDLYLWISKPPNGPTLKFHIQNLHTLDELNFTGNCLKGSRPILSFDKSFIENIHYK   145
B: MSSIYKALAGKSKDNKSEKKQGNVKQFMNKQRTLLISSRGVNYRHRHLIQDLSGLLPHSRKEPKLDTKKDLQQLNEIAELYNCNNVLFFEARKHQDLYLWLSKPPNGPTIKFYIQNLHTMDELNFTGNCLKGSRPVLSFDQRFESSPHYQ   150
C: MSSIYKALAGKSKDNKSEKKQGNVKQFMNKQRTLLISSRGVNYRHRHLIQDLSGLLPHSRKEPKLDTKKDLQQLNEIAELYNCNNVLFFEARKHQDLYLWLSKPPNGPTIKFYIQNLHTMDELNFTGNCLKGSRPVLSFDQRFESSPHYQ   150
   1........10........20........30........40........50........60........70........80........90........100.......110.......120.......130.......140.......150
```

```
   *:**::::.* *****************:*****.***:*.*:*..: . **  : **.*:    ::.*******:*:*:* :*****.***************.****:*****::****::**:*****:*::** ***********
A: LLKEMFLQTFCVPPNARKSKPFIDHVMTFSIVDGKIWIRNYQINETLDVKENDKIEDDEDYDVDQLNLVEIGPRLVLTLITVLEGSFSGPKIYENKQYVSPNFVRAQLKQQAADQAKSRSQAALERKIKKRNQVLKADPLSNDALFK   292
B: LIKELLVHNFCVPPNARKSKPFIDHVMSFSIVDDKIWVRTYEISHSTKNKE--EYEDGEE----DISLVEIGPRFVMTVILILEGSFGGPKIYENKQYVSPNVVRAQIKQQAAEEAKSRAEAAVERKIKRRENVLAADPLSNDALFK   291
C: LIKELLVHNFCVPPNARKSKPFIDHVMSFSIVDDKIWVRTYEISHSTKNKE--EYEDGEE----DISLVEIGPRFVMTVILILEGSFGGPKIYENKQYVSPNVVRAQIKQQAAEEAKSRAEAAVERKIKRRENVLAADPLSNDALFK   291
   ......160.......170.......180.......190.......200.......210.......220.......230.......240.......250.......260.......270.......280.......290.......
```

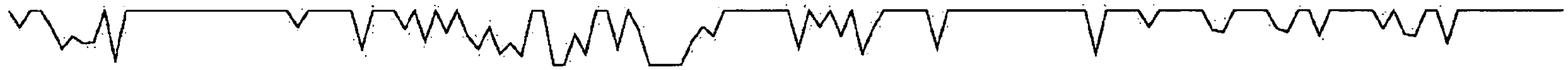

CaYNL132w

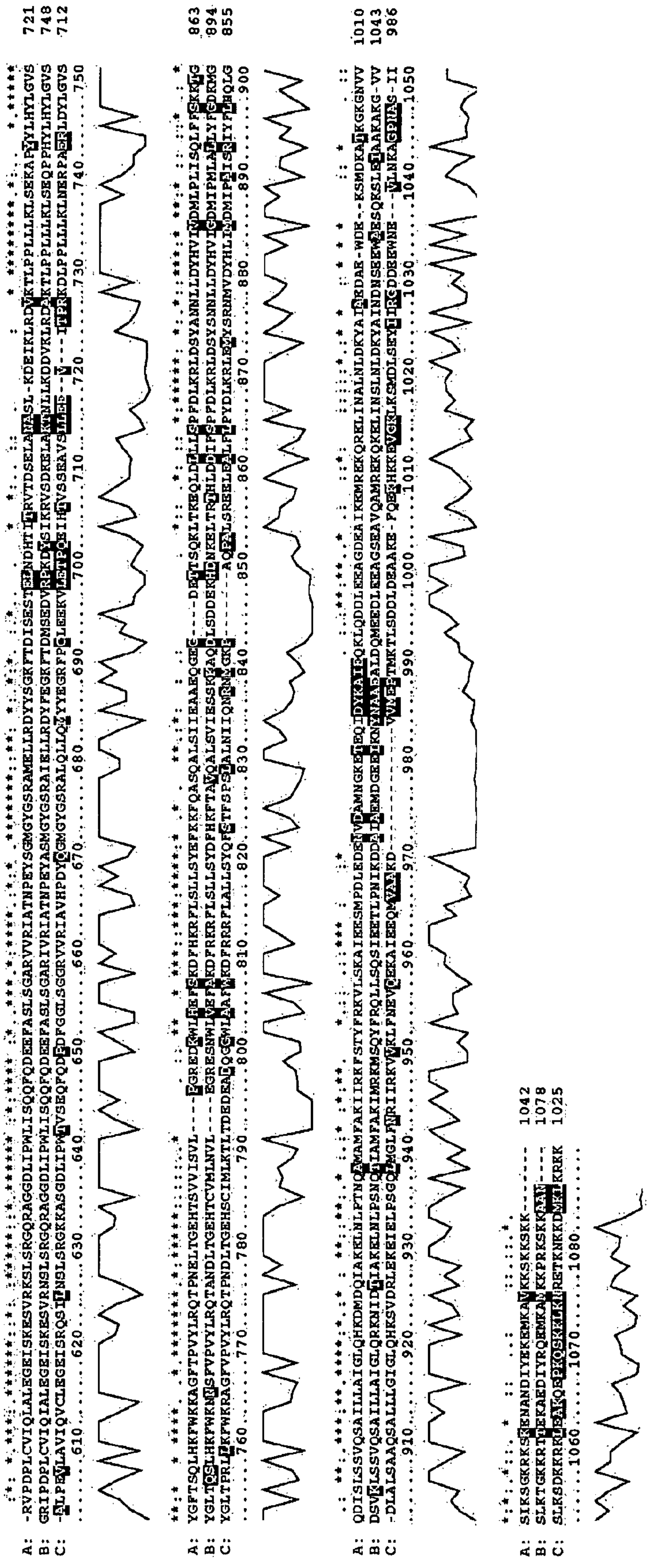

FIG. 1E-2

CaYNL132w (continued)

```
A: -RVPDPLCVIQLALEGEISKKESVRKSLSRGQRAGGDLIPWLISQQFQDEFASLSGARVVRIATNPEYSGMGYGSRAMELLRDYYSGKFTDIGESTENDHTIHRVTDSELANHSL-KDEIKLRDVKTLPPLLLKLSEKAPYLHYLGVS    721
B: GRIPDPLCVIQIALEGEISKKESVRNSLSRGQRAGGDLIPWLISQQFQDEFASLSGARIVRIATNPEYASMGYGSRAIELLRDYFEGKFTDMSEDVRPKDLSIKRVSDKRELAKWNLLKDDVRLRDAKTLPPLLLKLSEQPHYLHYLGVS    748
C: -NLPEVLAVIQVCLBEGEISRQSITNSLSRGKKASGDLIPWLVSERQFQDFDFGGLSGGRVVRIAVHPDYCGMGYGSRALQLLQYYEGRFFPGLEEKVLETPCBIHVSSRAVSMIES---ITFPRKDLPPLLLLMERPAEFLDYLGVS    712
              .610       .620       .630       .640       .650       .660       .670       .680       .690       .700       .710       .720       .730       .740       .750

A: YGFTSQLHKFWKKAGTFPVYLRQTPNELTGEHTSVVISVL----EGREDQWIREFEKDFHKRPLSLLSYEFKKFQASQALSIEAAREQCH------DEMTSQKITKEQLDELISPPDLKRLDSYANNLLDYHVIDMLPLISQLFFSKVTG    863
B: YGLTSSLHKFWKFWKMSPVPVYLRQTANDLTGEHTCVMLANVL----EGRESNWIVEFANDFREKRPLALSYDPHKFTAVQALSVIESSKYAQLSDDEKHENKELTRUHLDDIFPPDLKRLDSYSNNLLDYHVICDMIPMLAUXYFCDRMG    894
C: YGLTPRLMKFWKRAGFVPVYLRQTPNDLTGEHSCIMLKTLTDEDEAQGWIAAFMKDFRRRPLALLSYQFSTFSPSNALNIIQNRNNCKL-----AQFMLSREELALFPYDLKRLEQYSRNMVDYHLIMDMIPPMISRIYFROLG    855
              .760       .770       .780       .790       .800       .810       .820       .830       .840       .850       .860       .870       .880       .890       .900

A: QDISLSLSSVVQSAILLAIGLQHKDMDQLAKKELNLFPNQMAMFAKIIRKFSTYFRKVLSKAIEKSMPDLEDENVDAMNGKEREQIDKRATEQKIQDDLEEAGDEAIKKMREKQRELINALNLDKYAITKDAR-WDK--KSMDKAKGKGNVV    1010
B: DSVLLSSVVQSAILLAIGLQHKNIDITAKKELMLFSNGITAMFAKIIMRKMSQYFRQLLSQSIEETLPNIKDDAIAEMDQMEEDLEEAGSEAVQAMREKQKELINSLNLDKYAINDNSEFWESQKSLEAAKAKG-VV    1043
C: -DLALSAAQSALLLGIGLQHKSVDRLEKEILPSGLUMGLFURIIRKVWKLFPNEVQEEKALEEQWAVANKD-----WVEPTMKTLSDDLDEAAKE-PQEFHKKVGRIKSMDLSKYVIKCDREWNE--HLNKACENAS-II       986
              .910       .920       .930       .940       .950       .960       .970       .980       .990       .1000      .1010      .1020      .1030      .1040      .1050

A: SIKSGKRKSRENANDIYEKERMCAVKKSKKSKK-----        1042
B: SLKTGKKRIDEKAEDITRQEMKAIKKPRKSKKNAN---        1078
C: SLKSDKRRRENQEFKOSKEKRETKNHKKDMEIKREK         1025
              .1060      .1070      .1080
```

FIG. 1F-1

CaYGR145w

```
A: MVLKSTTAGNVSVYQVSGTNVSRSLPDWIDKKRKRAL-KHDLEYQNRIELIQDFEFSEASNKIKVTNDGQYCMATGTYKPQIHVYEFANLSLKFDRHTNVENIDFLILSNDWTKSVHLQGDRSIEFQTAGGVHYRTRIPKFGRCLTYNPI 149
B: MVLKSTSANDVSVYQVSGTNVSRSLPDWIAKKRKRQL-KNDLEYQNRVELIQDFEFSEASNKIKVSRDGQYCMATGTYKPQIHVYDFANLSLKFDRHTDAENVDFTILSDDWTKSVHLQNDRSIQFQNKGGLHYTTRIPKFGRSLVYNKV 149
C: --MQVSSINEVKIYSLS---CGKSLPEWLSDRKKRALQKKDVDVRRRIELIQDFEMPTVCTTIKVSKDGQYHLATGTYKPRVRCYDTYQLSLKFERCLDSEVVTFEILSDDYSKIVFLHNDRYIEFHSQSGFYYKTRIPKFGRDFSYHYP 145
   1......10........20........30........40........50........60........70........80........90........100.......110.......120.......130.......140.......150
```

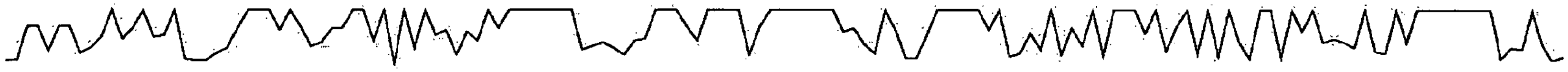

```
A: NCDLIVGSSSDELYRLNLDQGRFLSPLKLDYTDGGNIDSGCNAVDINSMHGLISAGLDDGTVEFWDPRSKQRAGKLFVSDQLINSTNNTEQSSCGITSLAFRFQDALNFACGTSNGQTLLYDLRASEPYQIKDQGYGYDIKKIIWCQDSL 299
B: NCDLYVGASGNELYRLNLEKGRFLNPFKLDT-------EGVNHVSINEVNGLLAAGTETNVVEFWDPRSRSRVSKLYLE-------NNIDNRPFQVTTTSFR-NDGLTFACGTSNGYSYIYDLRTSEPSIIKDQGYGFDIKKIIWLDNVG 284
C: SCDLYFVGASSEVYRLNLEQGRYLNPLQTDA-------AENNVCDINSVHGLFATGTIEGRVECWDPRTRNRVGLLDCA---LNSVTADSEINSLPTISALKFNGALTMAVGTTTGQ-----------------G----------- 253
   .......160.......170.......180.......190.......200.......210.......220.......230.......240.......250.......260.......270.......280.......290.......300
```

```
A: KPEMILTSDKRIVKIWDHTNGKSFASMEPTVDINDICHIPQSGMFFMANEGMPMHTYYIPNLGSAPNWCSFLDNVTEELEEKPSNSIYPTFKFITRDEMVKLNLTHLIGIKVLRSYMHGFFINTELYDKVNLISNPNSIYDQRKREIANK 449
B: TENKIVTCDKRIAKIWDRLDGKAYASMEPSVDINDIEHVPCTGMFFTANESIPMHTYYIPSLGPSPRWCSFLDSITEELEEKPSDTVYSNYRFITRDDVKKLNLTHLVGSRVLRAYMHGFFINTELYDKVSLIANPDAYKDERERERIRRR 434
C: --------------------KIFTSLEPEHDLNDVQLYPNSGMLLTANETPKMGIYYIPVLGPAPRWCSFLDNLTEELEENPESTVYEDYKFVTKKDLENLGLTHLIGSEFLRAYMHGFFMDIRLYHKVKLMVNPFAYEEYRRDKIRQK 382
   .......310.......320.......330.......340.......350.......360.......370.......380.......390.......400.......410.......420.......430.......440.......450
```

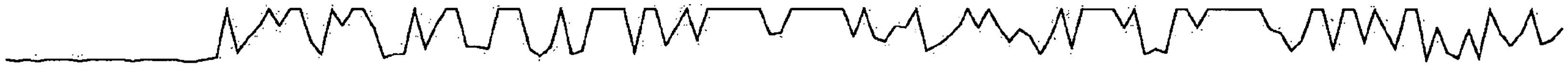

FIG. 1F-2

CaYGR145w (continued)

```
A: INEERKSRILTSSNGNDLFTKIKVNKDLVNKLQTKFAENGTPDGNANGATDYVESIVNDDRFREMFENPDFEIDEESHEYKQLNPVKSTKDITTTNTGTTNSRGRCLTAAEESDEERLNMKDSHHTGLDSDESDEESDSESKEQSEDEAK   599
B: IEKERESRI--RSSGAVQKFKIKVNKTLVDKLSQKRGDK----VAG--------KVLTDDRFKEMFEDEEFQVDEDDYDFKQLNPVKSIKETEEGAA----KRIRALTAAEESDEERIAMKDGRGHYDYEDEESDEEESDDETNQKSNKE   566
C: IEETRAQRV-------QLKKLPKVNKELALKLIEEEEEKQK--STWKKKVKSLFNILTDDRFKVMFENPDLQVDEESEEFRLLNPLVSKISEKRKKK------LRLLEQQELREKEEEEEPEGKPSDAESSESSDDEKAWVEEVRKQRRL   517
   .......460.......470.......480.......490.......500.......510.......520.......530.......540.......550.......560.......570.......580.......590.......600
```

```
A: SAETRERVCKELNKIRQSKQKQQQQDSKKFCNEMKILSQQSSSSSSSTANTEKASVSFGSQVNKLNKISKQNKNNNSISNAKDARLRRHARGEAELTFVPQKSKSK--STKLKFNNNHSDDEKLD-SGKTKDSGRTKQRFEGRRIASKNK   746
B: ELSEKDLRKVEKQKALIERRKKEKEQSERFMNEMK-----A-GTSTSTQRDESAHVTFGEQVGELLEVENGKKSNESI-------LRRNQRGEAELTFIPQRKSKKDGNYKSRRHDNSSDEEGIEENGNKKDNGRSKPRFENRRRASKNA   703
C: LQREEKVKRQERLKEDQQTVLKPQFVEIKAGEEFR-------SFKDSATKQKLMNKTLEDRLKIEAKNGTLSVSDTTV-------------GSKQLTFTLKRSEQQ---------KKQQEAEKLH-RQERKRLRRSAGHLKSRHKRGRSF   637
   .......610.......620.......630.......640.......650.......660.......670.......680.......690.......700.......710.......720.......730.......740.......750
```

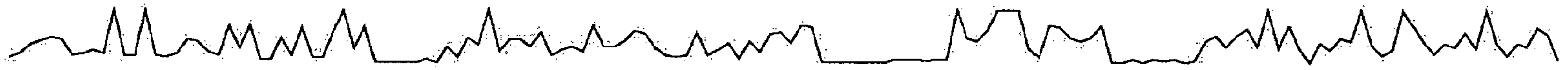

```
A: FRGM   750
B: FRGM   707
C: H---   638
```

CaYDR412w

FIG. 1H

CaYOL010w

```
A: MSSVASKKLLTFEGHRNFRLRLVLATLSGKPIKITKIRSQDLNPGLKDHEVSFLRLLEAVTNGSHIEISYTGTTIIYRPGIIIGGDLTHNCPDTKSIGYFIEPMLMFPLFSKKKFSIIFKGLTNIAGNDTGVDAIKWGLLPVMEKFGVRE   150
B: -MSSSAPKYTTFQGSQNFRLRIVLATLSGKPIKIEKIRSGDLNPGLKDYEVSFLRLIESVTNGSVIEISYTGTTVIYRPGIIVGGASTHICPSSKPVGYFVEPMLYLAPFSKKKFSILFKGITA-SHNDAGIEAIKWGLMPVMEKFGVRE   148
C: -MSSSAPKYTTFQGSQNFRLRIVLATLSGKPIKIEKIRSGDLNPGLKDYEVSFLRLIESVTNGSVIEISYTGTTVIYRPGIIVGGASTHICPSSKPVGYFVEPMLYLAPFSKKKFSILFKGITA-SHNDAGIEAIKWGLMPVMEKFGVRE   148
   1........10........20........30........40........50........60........70........80........90.......100.......110.......120.......130.......140.......150
```

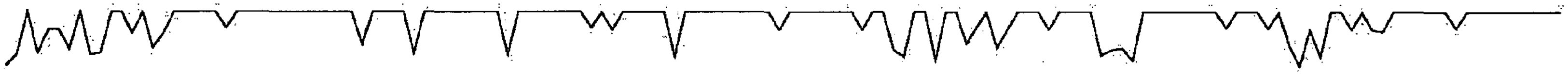

```
A: VSLHQLKRGSAPLGGGEVHLLCSSLIPQPLTIHALDIPKFSAIRGVAYCTRVSPSIVNRMIDSARAVLKPTGCEVNITADVWRGENSGKSPGFGITLVAEFK-RGWRIVTENVGSAGSLPEDSGELTAYQLLEEISNSGVVGRYQLPLAL   299
B: CALHTLKRGSPPLGGGEVHLVVDSLIAQPITMHEIDRPIISSITGVAYSTRVSPSLVNRMIDGAKKVLKNLQCEVNITADVWRGENSGKSPGWGITLVAQSKQKGWSYFAEDIGDAGSIPEELGEKVACQLLEEISKSAAVGRNQLPLAI   298
C: CALHTLKRGSPPLGGGEVHLVVDSLIAQPITMHEIDRPIISSITGVAYSTRVSPSLVNRMIDGAKKVLKNLQCEVNITADVWRGENSGKSPGWGITLVAQSKQKGWSYFAEDIGDAGSIPEELGEKVACQLLEEISKSAAVGRNQLPLAI   298
   .......160.......170.......180.......190.......200.......210.......220.......230.......240.......250.......260.......270.......280.......290.......300
```

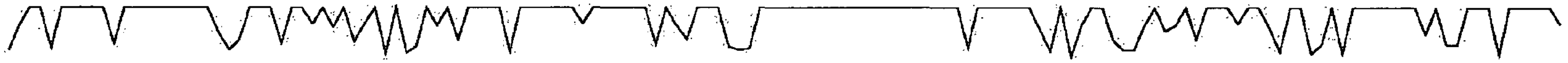

```
A: VYMTIGKEDIGRLKLQKSEIDENLVSVLRDIQEVFGTEAFFKIDAEELDSDDKFMTVSIKGVGFTNVSKKIA   371
B: VYMVIGKEDIGRLRINKEQIDERFIILLRDIKKIFNTEVFLKP-VDE--ADNEDMIATIKGIGFTNTSKKIA   367
C: VYMVIGKEDIGRLRINKEQIDERFIILLRDIKKIFNTEVFLKP-VDE--ADNEDMIATIKGIGFTNTSKKIA   367
   .......310.......320.......330.......340.......350.......360.......370..
```

CaYOR004w

CaYOR056c

FIG. 1K

CaYLR009w

```
                         *** :*:***.* ** **: *****.* ****:***** **::*****::**************.**..:: *  *** *::*:*:*  .*...* *:***:*:*:  *  **:: ***  :   * * * .
A: ---------------------MRIYQCHFCSSPVYPLHGIEFVRNDAKEFRFCRSKCHKAFKQRRNPRKLRWTKAFRKAAGKELVVDSTLTFAARRNVPVRYNRDLVATTLKGMSRIEEIRQRRERAFYKNRMKGNKERQLAADRKLVAD   129
B: ---------------------MRIYQCHFCSSPCYPGHGIMFVRNDAKEFRFCRSKCHKAFKQRRNPRKLKWTKAFRKAAGKELAVDSTLTFAQRRNVPVRYNRELVATTLKAMARIEEIRQKRERAFYKNRMRGNKEKDFLRDKKLVES   129
C: WIPRACREFGTRFGGVTRGFNMRIEKCYFCSGPIYPGHGMMFVRNDCKVFRFCKSKCHKNFKKKRNPRKVRWTKAFRKAAGKELTVDNSFEFEKRRNEPIKYQRELWNKTIDAMKRVEEIKQKRQAKFIMNRLKKNKELQKVQDIKEVKQ   150
   1........10........20........30........40........50........60........70........80........90........100.......110.......120.......130.......140.......150
```

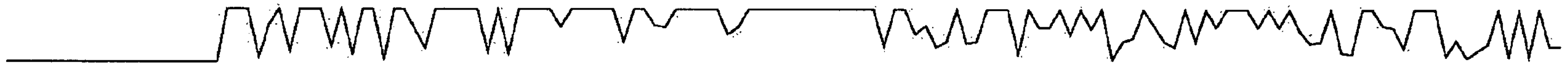

```
   * .*:*  ..   ::  :   :    . : *
A: NPELLRLREVELRRRAEKLAAKENAMEEDEETEVEEEG---EGDEEMISGEEEWESEDESERESDTRTC-   195
B: NPELLRIREVEIARKLAKEQERAESVSEQEESEEEEEDMEIDSDEEEEEQLEKQKILLKNRRRNTKKIAF   199
C: NIHLIRAPLAGKGKQLEEKMVQQLQEDVDMEDAP------------------------------------   184
   .......160.......170.......180.......190.......200.......210.......220
```

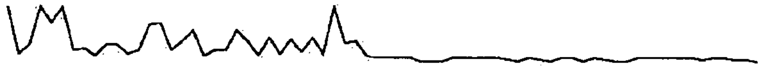

FIG. 1L

CaYJR072c

```
A: ------------------------------------MPTPPPTIICIGMAGSGKTTFVQRLNSHLHSKKTPPYLINLDPAVLKIPFGANIDIRDSVKYKKVMEEYNLGPNGAIVTSLNLFSTKIDQVIKLIDKKQDKINNVVIDTPGQIE  114
B: --------------------------------------MSLSTIICIGMAGSGKTTFMQRLNSHLRAEKTPPYVINLDPAVLRVPYGANIDIRDSIKYKKVMENYQLGPNGAIVTSLNLFSTKIDQVIRLVEQKKDKFQNCIIDTPGQIE  112
C: MDPMESSSEQDIVEESQKLVDSLDKLRVSAASSSSNFKKKPIIIIVVGMAGSGKTSFLHRLVCHTFDSKSHGYVVNLDPAVMSLPFGANIDIRDTVKYKEVMKQYNLGPNGGILTSLNLFATKFDEVVSVIEKRADQLDYVLVDTPGQIE  150
   1.......10........20........30........40........50........60........70........80........90.......100.......110.......120.......130.......140.......150
```

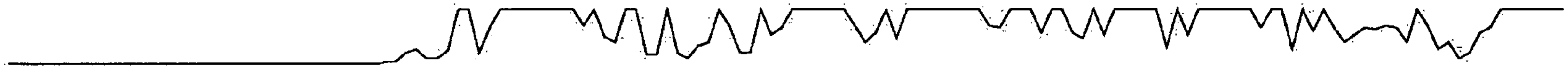

```
A: CFIWSASGSIITESFASEFPTVIAYIVDTPRNTSPTTFMSNMLYACSILYKTKLPMIVVFNKTDVTKDDFAKEWMTDFESFQYAIQKDKDLNNEQG--SGYMSSLINSMSLMLEEFYSNLDVVGVSSYTGQGFDKFMEAVDNKVDEYNEF  262
B: CFVWSASGAIITESFASSFPTVIAYIVDTPRNSSPTTFMSNMLYACSILYKTKLPMIVVFNKTDVCKADFAKEWMTDFESFQAAIKEDQDLNGDNGLGSGYMSSLVNSMSLMLEEFYSQLDVVGVSSFTGDGFDEFMQCVDKKVDEYDQY  262
C: IFTWSASGAIITEAFASTFPTVVTYVVDTPRSSSPITFMSNMLYACSILYKTRLPLVLAFNKTDVADHKFALEWMEDFEVFQAAIQSD----------NSYTATLANSLSLSLYEFYRNIRSVGVSAISGAGMDGFFKAIEASAEEYMET  290
   .........160.......170.......180.......190.......200.......210.......220.......230.......240.......250.......260.......270.......280.......290.......300
```

```
A: YKAEKERILKQKEEDEKKRQTKSLNKLMKDMKMKDTKGDHTKKDSEV--LSDYEEDDNEIDDEIQGEVLRDEDEP-EREYTFP--EDRQSEVNSRTDADLQSRYQQAFESTAKPASSKTAENIANYINRTQ  388
B: YKQERERKALNLKKKKEEMRKQKSLNGLMKDLGLNEKSSAAASDNDSIDAISDLEEDAND------GLVDRDEDEGVEREYTFPGEERTKGEVNENSAPDLQRRYQEAMQQVGKTASSETAENIAKYIRN--  385
C: YKADLDMRKADKERLEEERKKHEMEKLRKD--MESSQGGTVVLNTGL----K-DRDATE-------KMMLEEDDE---DFQVEDEEDSDDAIDEDDEDDETKHYYL------------------------  379
   .........310.......320.......330.......340.......350.......360.......370.......380.......390.......400.......410.......420.......430.
```

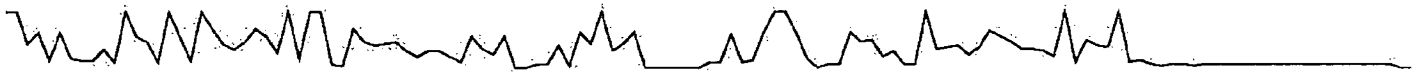

FIG. 2A-1

**Alignment of *C. Albicans* Essential Polypeptides With *A. Fumigatus* Sequences**

CaYLR100w

```
                                                                              **:::::**: :   .*** : ::* :.:**. * : **:*. *
B: -----------------------------------------------------------------------------VDLSNLVSVRALSRRLNKTFPKLDAIVLNAGLGGWTGINWPKA   43
C: -----------------------------------------------------------------------------VDLSNLVSVRALSRRLNKTFPKLDAIVLNAGLGGWTGINWPKA   43
A: MSLLKDSTVAVITGTSSNLGFNIAVRLLEGLPDNKEITLVVTSRTLPKVKEVISDIKKYIVAKIPTKVNKVEFDYLLVDFTDMVSILSAYYELNKRYKHIDYLFINAAQGVYGGIDWTGA  120
   1.......10........20........30........40........50........60........70........80........90.......100.......110.......120
```

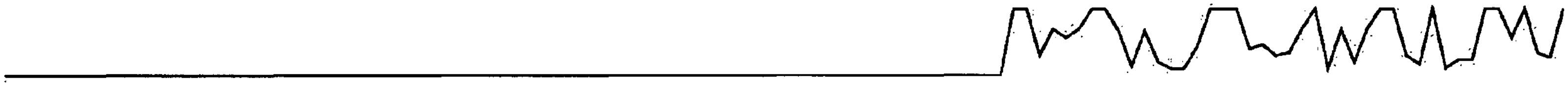

```
   :  *:  . :. *: *::*:  .*: .*         *   ** ** ***** * : *      *  ..:*.. *:*:***** :: *:*.::*:* **: *.**.** *.*::
B: IWGVMTDLVHEVSWPSFKIAPAGMGDGCPDRTGRDKEPRLGAVFCANVFGHYMLAHQCHAAARHSDMLHGPGRIIWVSSLEATVKHLDIDDIQCLRTLAPYESSKALTDIL---------  154
C: IWGVMTDLVHEVSWPSFKIAPAGMGDGCPDRTGRDKEPRLGAVFCANVFGHYMLAHQCHAAARHSDMLHGPGRIIWVSSLEATVKHLDIDDIQCLRTLAPYESSKALTDIL---------  154
A: VLEVLQSPIEAVTNPTYKLQKVGVESGD-------K---LGLVFQANVFGPYYFIH------RIKHLLENGGKIVWVSSLMSSPKYLSFNDLQILRSPASYEGSKRLVDLMHFGTYNKLE  224
   ........130.......140.......150.......160.......170.......180.......190.......200.......210.......220.......230.......240
```

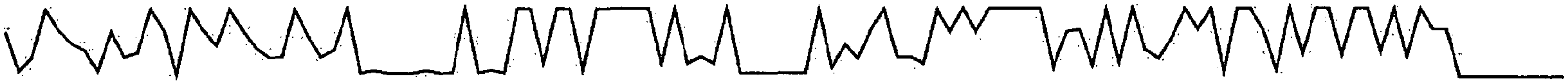

FIG. 2A-2

CaYLR100w (continued)

```
B: ------------------------------------------------------------------------------------------------------------------------ 154
C: ------------------------------------------------------------------------------------------------------------------------ 154
A: REHGIKQYLVHPGIFTSFSFFQYLNVFTYYGMLFLFYLARFLGSPYHNISGYIAANAPVAAALGQTKQNCKTASACTRSGKEYLLEEEIDSTGLDDVVLYLDTLTKEWDEKLKDQIVNTR 344
   .........250.......260.......270.......280.......290.......300.......310.......320.......330.......340.......350.......360
```

```
B: --   154
C: --   154
A: QP   346
   ..
```

CaYDR341c

```
A: MSVETISDSLKQLGLSQPAAIEGTHPQYNVVDVFRNYIAEELHRISSVDKSIIIQALDTPKVLDQGDIIVPIPKLRLKGINPNEKSKEWAENFNKGKFIS  100
B: ----------------------------------------------------------------------------------------------------
C: ----------------------------------------------------------------------------------------------------
D: ----------------------------------------------------------------------------------------------------
   1.......10........20........30........40........50........60........70........80........90.......100

A: EIKPQGVFLQFYFAKTLLYNLVIEDVLKRKSDYGYLPLGVGKKAIVEFSSPNIAKPFHAGHLRSTIIGGFISNLYEKVGWDVTRINYLGDWGKQFGLLAV  200
B: -----------------------------------------KRFIVKFWSPNMARPFN-GSLRSPIIG-FLANLYTVMGWDVIKMNYLGDWGKQYGLLAN   57
C: ----------------------------------------------------------------------------------------------------
D: ----------------------------------------------------------------------------------------------------
   .......110.......120.......130.......140.......150.......160.......170.......180.......190.......200

A: GFERYGDESKLASDPINHLFEVYVKINQDVT---------KETSEATGETPAETIDASEQDEKKIQSSTNEEARRFFRRMEDGDESALKIWARFRDLSIE  291
B: GFKRFGNEEELLKNPINHLFDVYVKINQIVAPAGGPYQGVKEQIKAKKEKNEDVSVLEAELAKLVDVSEDEKARRYFKSMEDGDEEALALWRRFRDLSIE  157
C: ----------------------------------------------------------------------------------------------------
D: ----------------------------------------------------------------------------------------------------
   .......210.......220.......230.......240.......250.......260.......270.......280.......290.......300
```

FIG. 2B-2

CaYDR341c (continued)

```
                                                                                        :   : *:   :           :   *     .*:
A: KYVDTYGRLNIKYDVYSGESQVPQEKMKEATKLFEDKGLIDIDRGAKLIDLTKFN-KKLGKALVEKSDGTSLYLTRDVGEAIKRYETYKFDKMIYVIAAQ   390
B: KYKQTYARLNIDFDVYSGESQIKNESMTAAYETMEKTGVSEKSEGAVIVDFTKHGRKKLGKAIIVRKDGTPLYLTRDIGAIMERDEAYHFDKMIYVVAAQ   257
C: ----------------------------LLTEPHAVDLVRLLATWPDVLLNTTKTLEPTTILTYLFRMTHILSSSYDVLKVVGSEPELKKARMALYEAAR    72
D: -------------------------------------------------------------------MTNIFSSS-DVFKLLGSEPEFKKPVMALYEGAR    32
   .......310.......320.......330.......340.......350.......360.......370.......380.......390.......400
```

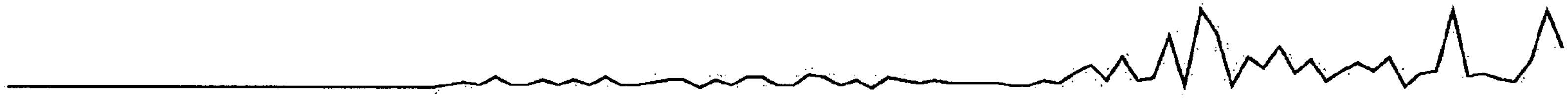

```
   * **  .  .  . :
A: QDLHCAQFFEILKQMGF-EWAHNLEHVNFGMVQGMSTRKGTVVFLDNILQETKEKMHEVMQKNEEKYAQIEDPDKIADLIGISAVMIQDMQSKRIHNYEF   489
B: QDLHLAQLFKITELMGPKDLASRCQHIKFGMVRGMSTRKGTVKFLDDILRDVADKMHEVMKGNAEKYAQVENPEETADILGLTSVMVQDMTGKR------   351
C: QVLHNGMRVLGLSPVER-----------------------------------------------------------------------------------    89
D: QVLHNGMRFMVLSPVER-----------------------------------------------------------------------------------    49
   .......410.......420.......430.......440.......450.......460.......470.......480.......490.......500
```

FIG. 2B-3

CaYDR341c (continued)

```
A: KWDRMTSFEGDTGPYLQYAHSRLCSMQRKSGISIEELEHANFDLLVEPCASALARTLAQYPDVIKKAVKGLEPSTIVTYLFSVTHIVSQCYDILWVSGQE  589
B: ----------------------------------------------------------------------------------------------------  351
C: ----------------------------------------------------------------------------------------------------   89
D: ----------------------------------------------------------------------------------------------------   49
   ........510.......520.......530.......540.......550.......560.......570.......580.......590.......600

A: KDVAIARLALYEAARQVINNGMTLLGLTPVNRM  622
B: ---------------------------------  351
C: ---------------------------------   89
D: ---------------------------------   49
   ........610.......620.......630...
```

FIG. 2C

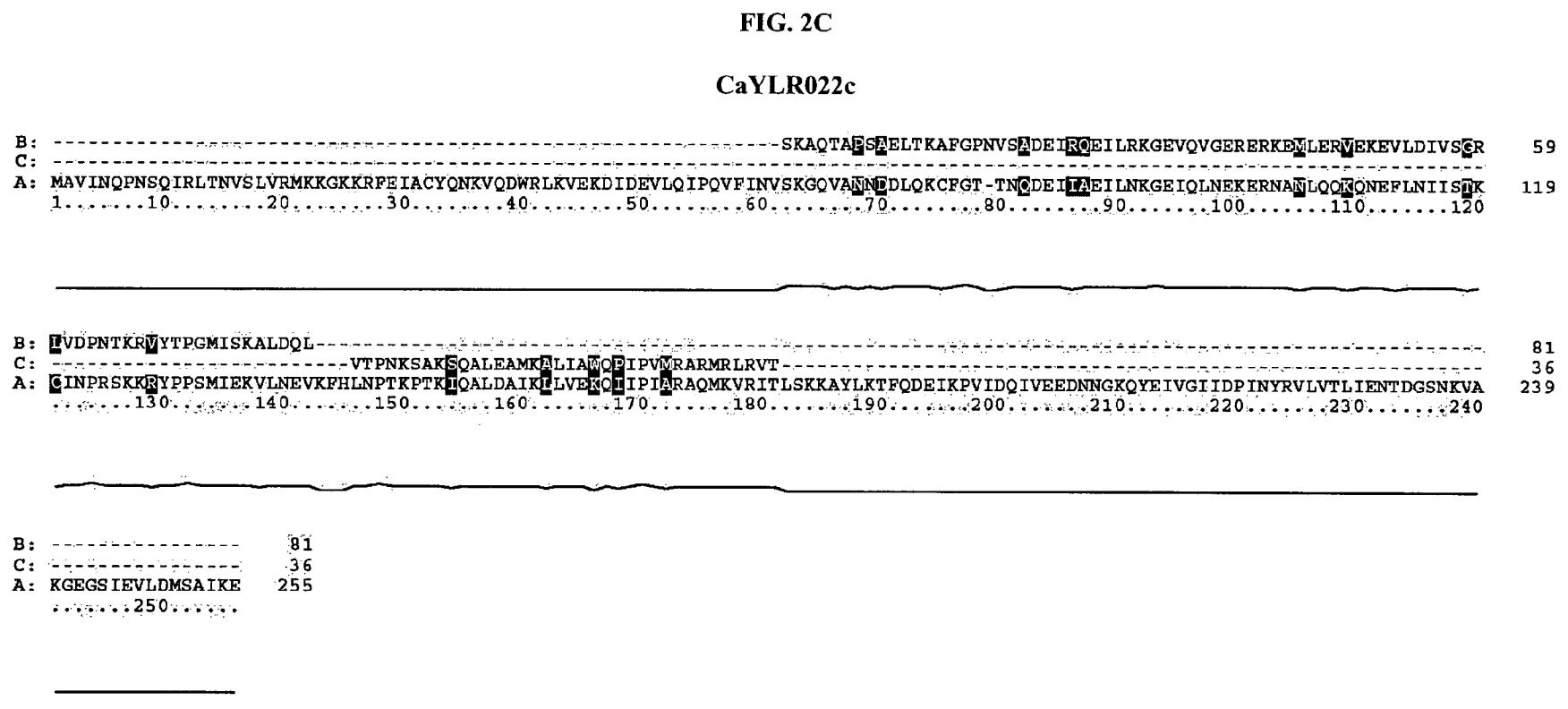

CaYLR022c

```
B: -------------------------------------------------------------SKAQTAPSAELTKAFGPNVSADEIRQEILRKGEVQVGERERKEMLERVEKEVLDIVSCR  59
C: ------------------------------------------------------------------------------------------------------------------------
A: MAVINQPNSQIRLTNVSLVRMKKGKKRFEIACYQNKVQDWRLKVEKDIDEVLQIPQVFINVSKGQVANNDDLQKCFGT-TNQDEIIAEILNKGEIQLNEKERNANLQQKQNEFLNIISTK 119
   1........10........20........30........40........50........60........70........80........90.......100.......110.......120

B: IVDPNTKRVYTPGMISKALDQL--------------------------------------------------------------------------------------------------  81
C: -------------------------VTPNKSAKSQALEAMKALIAWQPIPVMRARMRLRVT-----------------------------------------------------------  36
A: CINPRSKKRYPPSMIEKVLNEVKFHLNPTKPTKIQALDAIKLLVEKQIIPIARAQMKVRITLSKKAYLKTFQDEIKPVIDQIVEEDNNGKQYEIVGIIDPINYRVLVTLIENTDGSNKVA 239
   .........130.......140.......150.......160.......170.......180.......190.......200.......210.......220.......230.......240

B: ----------------  81
C: ----------------  36
A: KGEGSIEVLDMSAIKE 255
   ........250.....
```

FIG. 2D

CaYOL077c

```
                                                                                                   **.:*:*:.** ***:*.**: ******:::******:***: ****:
B: ---------------------------------------HRHLLSDLCALLPHTHKESKLDTKKKTARLQSLLNSLADLHSCNVIFFLEARKRRQDLYLWLARPPNGPTIKFHVTNLHTM    81
C: ------------------------------------------------------------------------LNSLADLHSCNVIFFLEARKRRQDLYLWLARPPNGPTIKFHVTNLHTM    48
A: MSAIYKALQSKSSKETSEKTKHINRQRLLVISSRGITYRHRHLIQDLLALLPHARKEPKFDSKKNLHQ----LNEVAELYNCNNIFFFECRKH-QDLYLWISKPPNGPTLKFHIQNLHTL   115
   1.......10........20........30........40........50........60........70........80........90.......100.......110.......120
```

```
   .***  *:*******.* *: **:** *          *::  *::**:  .* ** .. *. *****:*:  . ******** *:*.*    : . :**.*    . .   ::.*******
B: GELNHWFSGNCLKGGRGIVVFDRSFDEAGSGDEQPRNEYRGLIREMLRGVFCVPKRGVKGHKPFIDRVIGVFGVDGKIWIRVYEIRESRRWSKKDEENSKPAPKGKNAEPEISLVEIGPR   201
C: GELNHWFSGNCLKGGRGIVVFDRSFDEAGSGDEQPRNEYRGLIREMLRGVFCVPKRGVKGHKPFIDRVIGVFGVDGKIWIRVYEIRESRRWSKKDEENSKPAPKGKNAEPEISLVEIGPR   168
A: DELN--FTGNCLKGSRPILSFDKSFLE---------NDHYKLLKEMFLQTFGVPPNARKS-KPFIDHVMTFSIVDGKIWIRNYQINE----TLDVKENDKIEDDEDYDVDQLNLVEIGPR   219
   .......130.......140.......150.......160.......170.......180.......190.......200.......210.......220.......230.......240
```

```
   :*** *.:*****.** *****:***** **:::: . * :  .*
B: FVLTPIVILEGSFGGPVIYENKEYVSPNQVRSEIRLSKAARYAKR---------------------------   246
C: FVLTPIVILEGSFGGPVIYENKEYVSPNQVRSEIRLSKAARYAKR---------------------------   213
A: LVLTLITVLEGSFSGPKIYENKQYVSPNFVRAQLKQQAADQAKSRSQAALERKIKKRNQVLKADPLSNDALFK   292
   ........250.......260.......270.......280.......290.......300.......310...
```

FIG. 2E-1

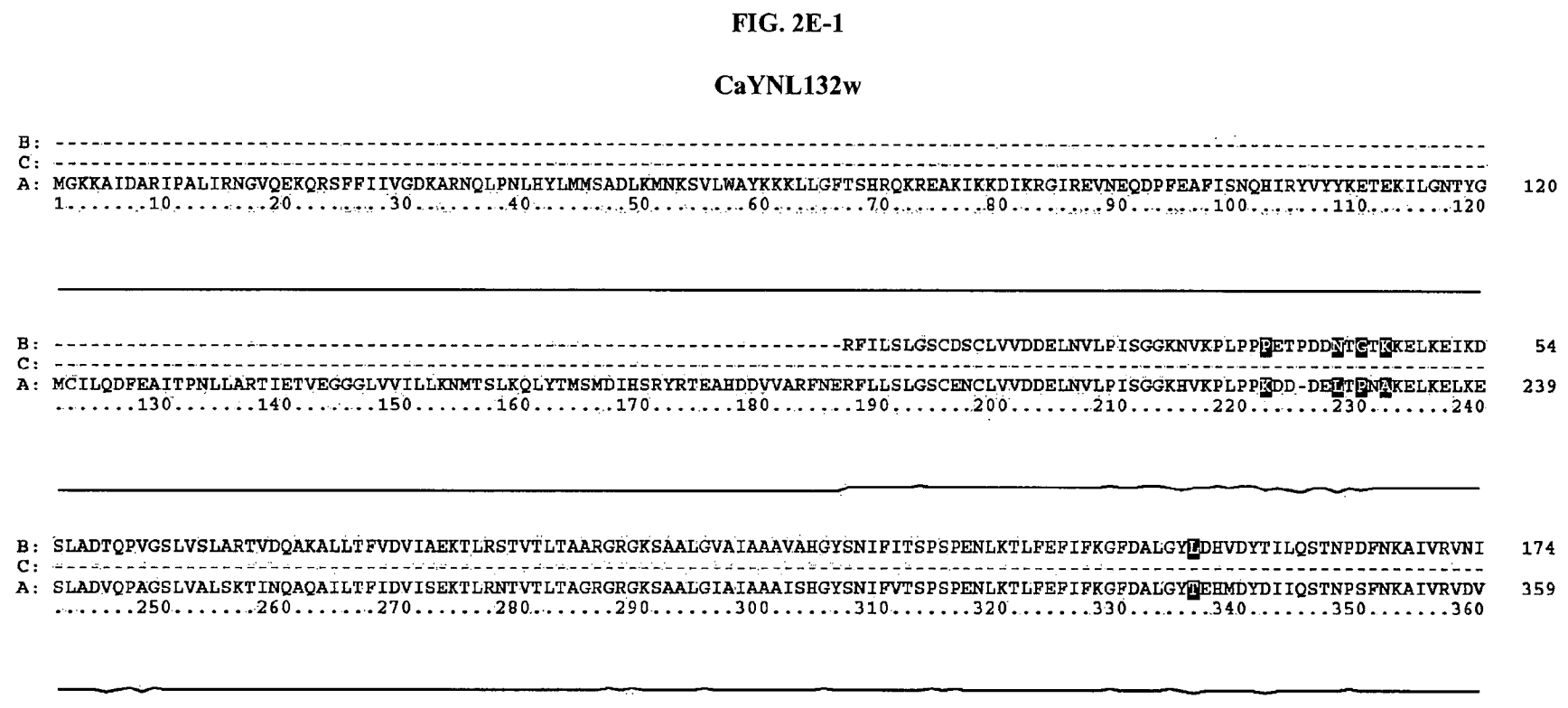

CaYNL132w

```
B: ------------------------------------------------------------------------------------------------------------------------
C: ------------------------------------------------------------------------------------------------------------------------
A: MGKKAIDARIPALIRNGVQEKQRSFFIIVGDKARNQLPNLHYLMMSADLKMNKSVLWAYKKKLLGFTSHRQKREAKIKKDIKRGIREVNEQDPFEAFISNQHIRYVYYKETEKILGNTYG   120
   1.......10........20........30........40........50........60........70........80........90........100.......110.......120

B: ------------------------------------------------------------------RFILSLGSCDSCLVVDDELNVLPISGGKNVKPLPPPETPDDNTGTKKELKEIKD    54
C: ------------------------------------------------------------------------------------------------------------------------
A: MCILQDFEAITPNLLARTIETVEGGGLVVILLKNMTSLKQLYTMSMDIHSRYRTEAHDDVVARFNERFLLSLGSCENCLVVDDELNVLPISGGKHVKPLPPKDD-DELTPNAKELKELKE   239
   .......130.......140.......150.......160.......170.......180.......190.......200.......210.......220.......230.......240

B: SLADTQPVGSLVSLARTVDQAKALLTFVDVIAEKTLRSTVTLTAARGRGKSAALGVAIAAAVAHGYSNIFITSPSPENLKTLFEFIFKGFDALGYLDHVDYTILQSTNPDFNKAIVRVNI   174
C: ------------------------------------------------------------------------------------------------------------------------
A: SLADVQPAGSLVALSKTINQAQAILTFIDVISEKTLRNTVTLTAGRGRGKSAALGIAIAAAISHGYSNIFVTSPSPENLKTLFEFIFKGFDALGYTEHMDYDIIQSTNPSFNKAIVRVDV   359
   .......250.......260.......270.......280.......290.......300.......310.......320.......330.......340.......350.......360
```

FIG. 2E-2

CaYNL132w (continued)

```
                                                                                                     ******************** **...  ::  *  :*  : . .:. *  ***    :*:.*.*****
B: HRQHRQTIQYIQPQDAHVLGQAELLVIDEAAAIPLPLVRKLMGPYLVFMASTINGYEGTGRSLSLKLIQQLREQSRGGLKAQRRTIQISLIEPQARLPRAQRRTLGGRLREITLSEPIRY   294
C: -----------------------------------------------------INGYEGTGRSLSLKLIQQLREQSRGGLKAQRRTIQISLIEPQARLPRAQRRTLGGRLREITLSEPIRY    68
A: KREHRQTIQYISPNDSHVLGQAELLIIDEAAAIPLPIVKKLMGPYLIFMASTINGYEGTGRSLSLKLIQQLRTQSNNATPSE--TTVVSRDKKSNEITGALTRTL----KEVVLDEPIRY   473
   .......370.......380.......390.......400.......410.......420.......430.......440.......450.......460.......470.......480
```

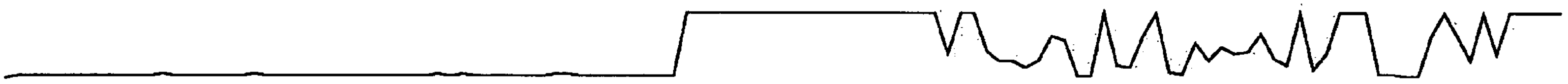

```
   *.**.:******:****.:*.*. *: *:* ********: ********:***** ***:*************:*****************:***:   .::*:******:****.**::
B: APGDSVEKWLNKVLCLDATLPKS-KINTQGCPHPSQCQLLQVNRDTLFSFHPVSEKFLQQMMALYVASHYKNTPNDLQLMSDAPAHQLFVLVPPIDEEATKLPEPLCVIQVALEGRISRQ   413
C: AXGDSVEKWLNKVLCLDATLPKS-KINTQGCPHPSQCQLLQVNRDTLFSFHPVSEKFLQQMMALYVASHYKNTPNDLQLMSDAPAHQLFVLVPPIDEEATKLPEPLCVIQVALEGRISRQ   187
A: APGDPIEKWLNKLLCLDVSLSKNAKFATKGTPHPSQCQLFYVNRDTLFSYHPVSEAFLQKMMALYVASHYKNSPNDLQLMSDAPAHQLFVLLPPIEAGDNRVPDPLCVIQLALEGEISKE   593
   .......490.......500.......510.......520.......530.......540.......550.......560.......570.......580.......590.......600
```

```
   ** :****************:***:***:*********:********* .*******:*** *:*.*****:**.   :. :.****.****:** .*:*::**::::***: ****: *
B: SVLNSLSRGQRAGGDLIPWLVSQQYQDEDFASLSGARIVRIATNPEYMNMGYGSRALELLIDFYEGKFTDLSEKIPDVQEEMVRVTDEELANSSLLDDQIHVRDIRSMPPLFGKLSERRP   533
C: SVLNSLSRGQRAGGDLIPWLVSQQYQDEDFASLSGARIVRIATNPEYMNMGYGSRALELLIDFYEGKFTDLSEKIPDVQEEMVRVTDEELANSSLLDDQIHVRDIRSMPPLFCKLSERRP   307
A: SVRKSLSRGQRAGGDLIPWLISQQFQDEEFASLSGARVVRIATNPEYSGMGYGSRAMELLRDYYSGKFTDISESTELNDHTITRVTDSELANASL-KDEIKLRDVKTLPPLLKKLSEKAP   712
   .......610.......620.......630.......640.......650.......660.......670.......680.......690.......700.......710.......720
```

FIG. 2E-3

CaYNL132w (continued)

```
   *.*:******:*. ******:*.*.****************:.*:: .   *.. : .** **::******::****:*::* :   :*** *:.  *    :*  *.. ***.:**  :***
B: DALDYVGVSYGLTPPLHKFWKRASFVPVYLRQTPNELTGEHSCVMLRTLRLAASDASWLGEFARDFHKRFIALLSYQFREFPSVLSLSICESVTAGAKLDTLVTPSLLTKSDLDAAFSPF   653
C: DALDYVGVSYGLTPPLHKFWKRASFVPVYLRQTPNELTGEHSCVMLRTLRLAASDASWLGEFARDFHKRFIALLSYQFREFPSVLSLSICESATAGAKLDTLVTPSLLTKSDLDAAFSPF   427
A: YYLHYLGVSYGFTSQLHKFWKKAGFTPVYLRQTPNELTGEHTSVVISV--LPGREDKWLHEFSKDFHKRFLSLLSYEFKKFQASQALSIIEAAEQGEGDET--TSQKLTKEQLDLLLSPF   828
   .......730.......740.......750.......760.......770.......780.......790.......800.......810.......820.......830.......840
```

```
   *********************:**:*  *:: :** : .  .:.**.**.:*********:*.:*
B: DLKRLDSYANNLLDYHVILDMVPTIAEYYFSGRLSGKVNLSGVQQSILLAIGLQRKHLD-------------------------------------------------------------   712
C: DLKRLDSYANNLLDYHVILDMVPTIAEYYFSGRLSGKVNLSGVQQSILLAIGLQRKNLDDIEKELNLPSSQLLAMFLKIVRKMSTYFRGLVEGAVAETLPAEKVPIAQSSADAHDEVVDR   547
A: DLKRLDSYANNLLDYHVIVDMLPLISQLFFSKKTGQDISLSSVQSAILLAIGLQHKDMDQIAKELNLPTNQAMAMFAKIIRKFSTYFRKVLSKAIEESMPDLEDENVDAMNGKETEQID-   947
   .......850.......860.......870.......880.......890.......900.......910.......920.......930.......940.......950.......960
```

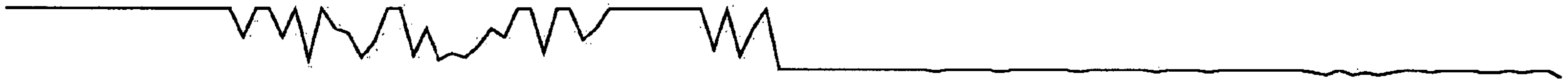

```
B: ----------------------------------------------------------------------------------------------------   712
C: AFKPLDTGLEDELREGGQQVDEELREKQRALIDSLPLDK-------------------------------------------------------------   586
A: -YKAIEQKLQDDLEEAGDEAIKEMREKQRELINALNLDKYAIAEDAEWDEKSMDKATKGKGNVVSIKSGKRKSKENANDIYEKEMKAVKKSKKSKK   1042
   .......970.......980.......990.......1000......1010......1020......1030......1040......1050......
```

FIG. 2F

CaYDR412w

```
                               : *: **  .*:*:*****:*** ** ::***:  :: *  *  ***::
B: ---------------------------IEEINFDPADRQEFLTGFRKRKQQRIRHAQELAAKRAREEKRIERKKL-----------------------------------------------   48
C: ---------------------------IAEINFDPADRQEFLTGFRKRKQQRIRHAQELAAKRAREEKRIERKKV-----------------------------------------------   48
A: MAGFKKNREILTGGKKYIQQKQKKHLVDEVVFDKESRHEYLTGFHKRKLQRQKKAQEFHKEQERLAKIEERKQLKQERERDLQNQLQQFKKTAQEIAAINNDIGFDQSDDNNDNDNENEE  120
   1.......10........20........30........40........50........60........70........80........90........100.......110.......120
```

```
B: ------------------------------------------------------------------------------------------------------------------------   48
C: ------------------------------------------------------------------------------------------------------------------------   48
A: WSGFQEDEEGEGEEVTDEDDEDKEKPLKGILHHTEIYKQDPSLSNITNNGAIIDDETTVVVESLDNPNAVDTEEKLQQLAKLNNVNLDKSDQILEKSIERAKNYAVICGVAKPNPIKQKK  240
   .........130.......140.......150.......160.......170.......180.......190.......200.......210.......220.......230.......240
```

```
B: ----------------------------   48
C: ----------------------------   48
A: KKFRYLTKAERRENVRKEKSKSKSKGKK  268
   .........250.......260.......
```

FIG. 2G

CaYOR004w

```
B: ------------------------------------------------------------------------------------------------------------------------
C: ------------------------------------------------------------------------------------------------------------------------
A: MRQKRAKAYKKQMSVYVHAFKFREPYQIIVDNELITTCQSASFDINKGFTRTIQAENKPMITQCCIQALYDTKNQPAIDIAKSFERRKCNHREAIDPSQCIESIVNIKGQNKHRYIVASQ   120
   1.......10........20........30........40........50........60........70........80........90........100.......110.......120

     :**    *.*****::*::****::**:*   *::  .  .  *.:*:  ****   .  *  *::.  ***    *  :  **:   *  **  ******** *..  *  :**   :::*:
B: --KLRIGARSIPGVPIVYVKRSVMILEPMSTPSEEVRDGVENRKFRVGLND--EAVLGKRKRTEDG---EEKKKKRGPKKPKGPNPLSVKKPKKKPAETASGPKQEKRKEQKRRGAGQDK   113
C: --KLRIGARSIPGVPIVYVKRSVMILEPMSTPSEEVRDGVENRKFRVGLND--EAVLGKRKRTEDG---EEKKKKRGPKKPKGPNPLSVKKPKKKPAETASGPKQEKR-----------   101
A: DLQLRKKLRKIPGVPLIYMNRSVMVMEPISDVSNQYNMNYESKKLTCGLNDIEAGKLEKQNECEDGDGDELEVKKKKRKGPKEPNPLSVKKKKTDNATAASTNQEQKKKPNRRKRHAQVK   240
   .......130.......140.......150.......160.......170.......180.......190.......200.......210.......220.......230.......240
```

```
B: RRRIRRTQAEEKT----   126
C: -----------------   101
A: SRREGRPRTCASERSNN   257
   .......250.......
```

FIG. 2H-1

CaYOR056c

```
B: ------------------------------------------------------------------------------------------------------------------------
C: ------------------------------------------------------------------------------------------------------------------------
D: ------------------------------------------------------------------------------------------------------------------------
A: MSETKNIESLISDAGPLITQPATTLQQYATAYYTTPGVHSELKDEYARQQLAIWGDSLKIKQPKQEYIDRVVKFAKLTGDYSVLSVNDLHIVALAYELECLNNGEDNLRSFPGEVLKNQQ    120
   1.......10........20........30........40........50........60........70........80........90.......100.......110.......120

B: ------------------------------------------------------------------------------------------------------------------------
C: ------------------------------------------------------------------------------------------------------------------------
D: ------------------------------------------------------------------------------------------------------------------------
A: AENENGSNKMSNIIGDDDGFVVATKRRGGRRQREKAELRKKGLLPTFSPKPKGGLETEEPNELSNDKTIDETPQTDLIKGVDVQEQESQEEPVSESNTVGLDEITEEYNEDDDDGEWITP    240
   ........130.......140.......150.......160.......170.......180.......190.......200.......210.......220.......230.......240
```

FIG. 2H-2

CaYOR056c (continued)

```
                                                    :    :*.:  .   :.   :  . : :*.  :  .        :.  .:'      **    .    :     :.:  :  .
B: -----------------------------------CQNVLLQMNLNLLSTTT-LQRIRHLKSFIKRCHGCFFTT----KDMTKQFCPRCGKDTLLTRVSCTTDAN-GQFKMHLKKNMQWNN   79
C: -----------------------------------CPNVLLQMNLNLLSTTT-LQRIRHLKSFIKRCHGCFFTT----KDMTKQFCPRCGKDTLLTRVSCTTDAN-GQFKMHLKKNMQWNN   79
D: ---------------------------------------TKPVHTIILDAGPILEETPPLSTLLTQCEELLITP--SVVREIRDPDARLRVRTLYLPFLKQRTPSPKSVSVISEFAR--K   77
A: ENLQEEIIKDKNEQVQESNTNGPLIKVALATGDFACQNVAMQIGIKLLNAMS-GKQITRVRNYMYRCHACFRLTPMSKDGRPKHFCPKCGGNTLLRCAVSVDNKTGKITPHLKQNFQWIR  359
   .......250.......260.......270.......280.......290.......300.......310.......320.......330.......340.......350.......360
```

```
   *:*   :...
B: RGNRYSIPKP----------------------------------------------------------------------------------------------------   89
C: RGNRYSIPKP----------------------------------------------------------------------------------------------------   89
D: TGDRAVLSKTDL--------------------------------------------------------------------------------------------------   89
A: RGERYSLPSPLSKNQKKLQGNGGYQHNKENRHKSLQTPLILNEDQKEYQRALKNDEWERKQQDKMLQEWIGGGSADNFVSPFGNTIRNSGVKVGRGRYANSSKKKRK  466
   .......370.......380.......390.......400.......410.......420.......430.......440.......450.......460.......
```

FIG. 2I

CaYLR009w

```
                                      *****  **  :*:*****:***:..*  *  ***::***:*    :**  :**:**:*:*:***:*:*.*.*:****  ******  *.*:   *..
B: --------------------------------RSKCHANFKMKRQPRKLKWTKTHRAARGKEMIVDSSLVAVSFAKKRNIPVKYDRNLVAATIKAMERVEEIRARRERAFTKRRLGGKAG    88
C: --------------------------------RSKCHANFKMKRQPRKLKWTKTHRAARGKEMIVDSSLVAVSFAKKRNIPVKYDRNLVAATIKAMERVEEIRARRERAFTKRRLGGKAG    88
A: MRIYQCHFCSSPVYPLHGITFVRNDAKEFRFCRSKCHKAFKQRRNPRKLRWTKAFRKAAGKELVVDSTL---TFAARRNVPVRYNRDLVATTLKGMSRIEEIRQRRERAFYKNRM--KGN   115
   1.......10........20........30........40........50........60........70........80........90........100.......110.......120
```

```
   :**:    **  :**:.
B: RERKREEDRMVVAEGPSTSSARELREREEGPAFGCQQDIKQSGRRGEAQTEEE---------------------------   141
C: RERKREEDRRVVAEGEHLIR------------------------------------------------------------   108
A: KERQLAADRKLVADNPELLRLREVELRRKAEKLAAKENAMEEDEETEVEEEGEGDEEMISGEEEWESEDESERESDTKTC   195
   .......130.......140.......150.......160.......170.......180.......190.......200
```

FIG. 2J-1

CaYOL010w

```
B: ATTSQPPLRFTGHKNFVNRLVFSTLTGRAVHISQIRSSSPTNPGLAPHEISFLRLLEAVTNGSQIEISYTGTIVVYKPGLIHWRHCRQRGHTGGVIRHELPARMTRGVSYFLIPLCLLAP 120
C: ------------------------------------------------------------------------------------------------------------------------
D: ------------------------------------------------------------------------------------------------------------------------
A: ------------------------------------------------------------------------------------------------------------------------
   1.......10........20........30........40........50........60........70........80........90.......100.......110.......120
```

```
                         : . . . :.     *       . : . :  :* .            :
B: FSKAPIKVLFTGPGVITSRHTHGDMSVDSVRTAILPLYNQFGILNNIELRVLRRSP------RTNG--------------RG-------------------------------------- 182
C: -----------------ATTSQPPLRFTGHKNFVNRLVFSTLTGRAVHISQIRSSSPTNPGLAPHEISFLRLLEAVTNGSQIEISYTGTIVVYKPGLVTGG------------------- 84
D: -----------------------DMSVDSVRTAILPLYNQFGILNNIELRVLRRSP------RTNG--------------RG-------------------------------------- 39
A: ---------------MSSVASKKIITFEGHRNFRLRLVLATLSGKPIKITKIRSQD-LNPGLKDHEVSFLRLLEAVTNGSHIEISYTGTTIIYRPGIIIGGDLTHNCPDTKSIGYFIEPM 104
   .......130.......140.......150.......160.......170.......180.......190.......200.......210.......220.......230.......240
```

```
B: -----------------------------------------------------------GGGEVQLVFGHQVRLPKTLHLMNPGRVKKVRGVAYSVGVSASNNARMIDVARGILNPLVPD 243
C: ------------------------------------------------------------------------------------------------------------------------ 84
D: -----------------------------------------------------------GGGEVQLVFGHQVRLPKTLHLMNPGRVKKVRGVAYSVGVSASNNARMIDVARGILNPLVPD 100
A: LMFPLFSKKKFSIIFKGLTNIAGNDTGVDAIKWGLLPVMEKFGVREVSLHILKRGSAPLGGGEVHLLCSSLIPQPLTIHALDIPKFSAIRGVAYCTRVSPSIVNRMIDSARAVLKPTGCE 224
   .......250.......260.......270.......280.......290.......300.......310.......320.......330.......340.......350.......360
```

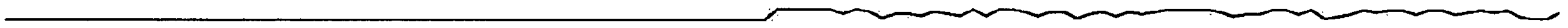

FIG. 2J-2

CaYOL010w (continued)

```
B: TYIFSDVVVCAWVPRNNPSAKKKDRSGFGLSLVAESSTGLLYSADVASPPAGGQAPEDIGKQCAYQLLETISKGGCVAPAAASTMLGLMTMGSEDVGRLQFGREVICDESIIQLARDLAK 363
C: ------------------------------------------------------------------------------------------------------------------------ 84
D: TYIFSDVVVCAWVPRNNPSAKKKDRSGFGLSLVAESSTGLLYSADVASPPAGGQAPEDIGKQCAYQLLETISKGGCVAPAAASTMLGLMTMGSEDVGRLQFGREVICDESIIQLARDLAK 220
A: VNIIADVW---------RGENSGKSPGFGITLVAELKRG--WRIVTENVGSAGSLPEDSGELTAYQLLEEISNSGVVGRYQLPLALVYMTIGKEDIGRLKLQKSEIDENLVSVLRDIQEV 333
   .......370.......380.......390.......400.......410.......420.......430.......440.......450.......460.......470.......480
```

```
B: FGAPGWGLRDATG-ENEQGDVIVSVVGRGIGNVGRKVA 400
C: -------------------------------------- 84
D: FGAPGWGLRDATG-ENEQGDVIVSVVGRGIGNVGRKVA 257
A: FGTEAFFKDDAEELDSDDKFMIVSIKGVGFTNVSKKIA 371
   .......490.......500.......510........
```

FIG. 2K-1

CaYOL010w

```
     :. *     :  :.:*     :     :    :: *. .     :  *:: : : *. :. *   ::      : *  *:  ..
B:  --ATTSQPPLRFTCHKNFVNRLVFSTLTGRAVHISQIRSSSPTNPGLAPHEISFLRLLEAVTNGSQIEISYTGTIVVYKPGLVTGG----------------------------------   84
A:  MSSVASKKIITFEGHRNFRLRLVLATLSGKPIKITKIRSQD-LNPGLKDHEVSFLRLLEAVTNGSHIEISYTGTTIIYRPGIIIGGDLTHNCPDTKSIGYFIEPMLMFPLFSKKKFSIIF  119
C:  DMSVDSVRTAILPLYNQFGILNNIELRVLRRSPRTNGRGGGGEVQLVFGHQVRLPKTLHLMNFGRVKKVRG----VAYSVGVSASN----------------------------------   82
    1.......10........20........30........40........50........60........70........80........90.......100.......110.......120
```

```
B:  ------------------------------------------------------------------------------------------------------------------------   84
A:  KGLTNIAGNDTGVDAIKWGLLPVMEKFGVREVSLHILKRGSAPLGGGEVHLLCSSLIPQPLTIHALDIPKFSAIRGVAYCTRVSPSIVNRMIDSARAVLKPTGCEVNITADVWRGENSGK  239
C:  --------NARMIDVARGILNPLVP-----------------------------------------DTYIFSDVVVCAWVPRNNPSAK-------------------------KKDRSG-  127
    .......130.......140.......150.......160.......170.......180.......190.......200.......210.......220.......230.......240
```

FIG. 2K-2

CaYOL010w (continued)

```
B: ----------------------------------------------------------------------------------------------------------------------   84
A: SPGFGITLVAELKRGWRIVTENVG--SAGSLPEDSGELTAYQLLEEISNSGVVGRYQLPLALVYMTIGKEDIGRLKLQKSEIDENLVSVLRDIQEVFGTEAFFKDDAEELDSDDKFMIVS  357
C: ---FGLSLVAESSTGLLYSADVASPPAGGQAPEDIGKQCAYQLLETISKGGCVAPAAASTMLGLMTMGSEDVGRLQFGREVICDESIIQLARDLAKFGAPGWGLRDATG-ENEQGDVIVS  243
   .......250.......260.......270.......280.......290.......300.......310.......320.......330.......340.......350.......360

B: --------------   84
A: IKGVGFTNVSKKIA  371
C: VVGRGIGNVGRKVA  257
   .......370....
```

FIG. 2L-1

CaYJR072c

```
               *:**:*:  . :  .* :         :*****  .  :    :*:*: :.  :.:*.: :*****.:: .:
B: ---------CHFTLGSGKTTFMQRINAYLHSKKKIPYVINLDPAVYSVPFESNIDIRDSINYKEVMKQYNLGPNGGILTSLNLFATKVDQIISLLEKRHRTQSRKPIAKPIEHILVDTPG  111
C: ---------CHFTLGSGKTTFMQRINAYLHSKKKMPYVINLDPAVYSVPFESNIDIRDSINYKEVMKQYNLGPNGGILTSLNLFATKVDQIISLLEKR-----------------------   89
D: -------VLVMGPAGAGKSTFCSALIQHLQTTRRSCFYVNLDPAAESFNYEPDLDIRELITLEDVMEEMELGPNGGLIYCFEFLLQNLDFLSQALDPL----------SEEYLIIFDMPG  103
E: -------VLVMGPAGAGKSTFCSALIQHLQTTRRSCFYVNLDPAAESFNYEPDLDIRELITLEDVMEEMELGPNGGLIYCFEFLLQNLDFLSQALDPL----------SEEYLIIFDMPG  103
F: --------LVIGPPGAGKSTYCNGMHQFLGAIGRKCSIVNLDPANDKTSYPCALDVRDLVTLEEIMSEDQLGPNGGVLYAL---------------------------------------   73
G: --------LVIGPPGAGKSTYCNGMHQFLGAIGRKCSIVNLDPANDKTSYPCALDVRDLVTLEEIMSEDQLGPNGGVLYAL---------------------------------------   73
A: MPTPPPTIICIGMAGSGKTTFVQRLNSHLHSKKTPPYLINLDPAVLKIPFCANIDIRDSVKYKKVMEEYNLGPNGAIVTSLNLFSTKIDQVIKLIDKK-Q--------DKINNVVIDTPG  111
   1.......10........20........30........40........50........60........70........80........90........100.......110.......120
```

```
B: QIEVFV---WSASGSILLETLASSFPTVIAYVIDTPRTTSTSTFMSNMLYACSILYKTKLPMILVFNKTDVQDAEFAKEWMTDFDAFQQALRDEEEVWCFWRGGQHAGFGAGSGYMGSLL  228
C: ------------------------------------------------------------------------------------------------------------------------   89
D: QIELYTHYPAAVAGAVSFTTGAAEHQPVAAYLLESTFVIDKAKFFAGTLSAMSAMLMLEMPHVNILSKMDQVRDMVSRKELKRFVNVDVNLLQDE-------------------------  198
E: QIELY-------------------------------------------------------------------------------------------------------------------  108
F: ------------------------------------------------------------------------------------------------------------------------   73
G: ------------------------------------------------------------------------------------------------------------------------   73
A: QIECFI---WSASGSIITESFASEFPTVIAYIVDTPRNTSPTTFMSNMLYACSILYKTKLPMIVVFNKTDVTKDDFAKEWMTDFESFQMAIQKDKDL---------NNEQGSGYMSSLI  218
   ........130.......140.......150.......160.......170.......180.......190.......200.......210.......220.......230.......240
```

FIG. 2L-2

CaYJR072c (continued)

```
B: NSMSLMLEEFYRHLSVVGVSSMTGDGIDEFFQAVEEKRQEFERDYKPELERKKKEREETKAAQRELELGKLMKDMSVSDLRGSRVPREAETVSEAEEEEEE-------------------  329
C: ------------------------------------------------------------------------------------------------------------------------   89
D: ------------------------------------------------------------------------------------------------------------------------  198
E: ------------------------------------------------------------------------------------------------------------------------  108
F: ------------------------------------------------------------------------------------------------------------------------   73
G: ------------------------------------------------------------------------------------------------------------------------   73
A: NSMSLMLEEFYSNLDVVGVSSYTGQGFDKFMEAVDNKVDEYNEFYKAEKERILKQKEEDEKKRQTKSLNKLMKDMKMKDTKGDHTKKDSEVLSDYEEDDNEIDDEIQGEVLRDEDEPERE  338
   .......250.......260.......270.......280.......290.......300.......310.......320.......330.......340.......350.......360
```

```
B: --------------------------------------------------  329
C: --------------------------------------------------   89
D: --------------------------------------------------  198
E: --------------------------------------------------  108
F: --------------------------------------------------   73
G: --------------------------------------------------   73
A: YTFPEDRQSEVNSRTDADLQSRYQQAFESTAKPASSKTAENIANYINRTQ  338
   .......370.......380.......390.......400.......410
```

PCR-based gene disruption in *C. albicans* (*YFG1/YFG1*)

**PCR confirmation of *AAH1* disruption strains that were obtained via PCR-based gene disruption tool in *C. albicans***

FIG. 5
Plasmid maps of pUMP and pAMP used for promoter swapping
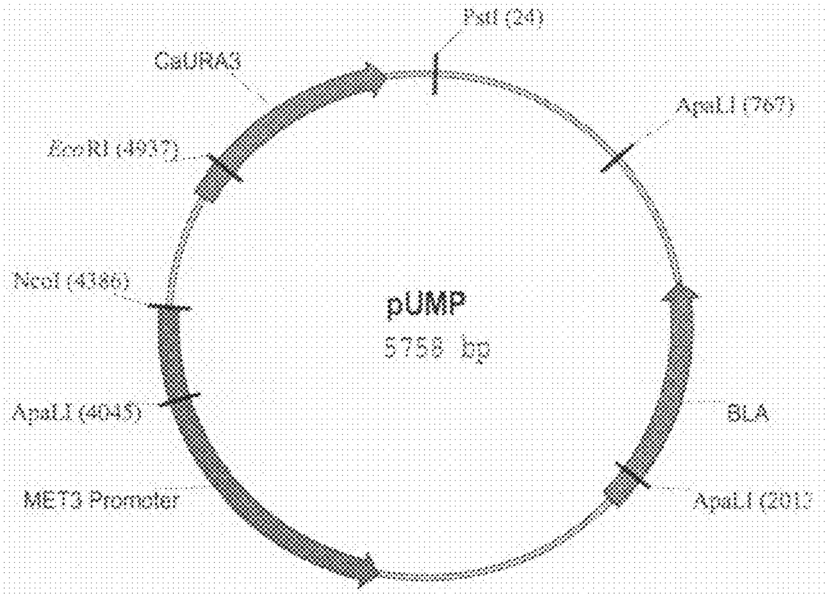
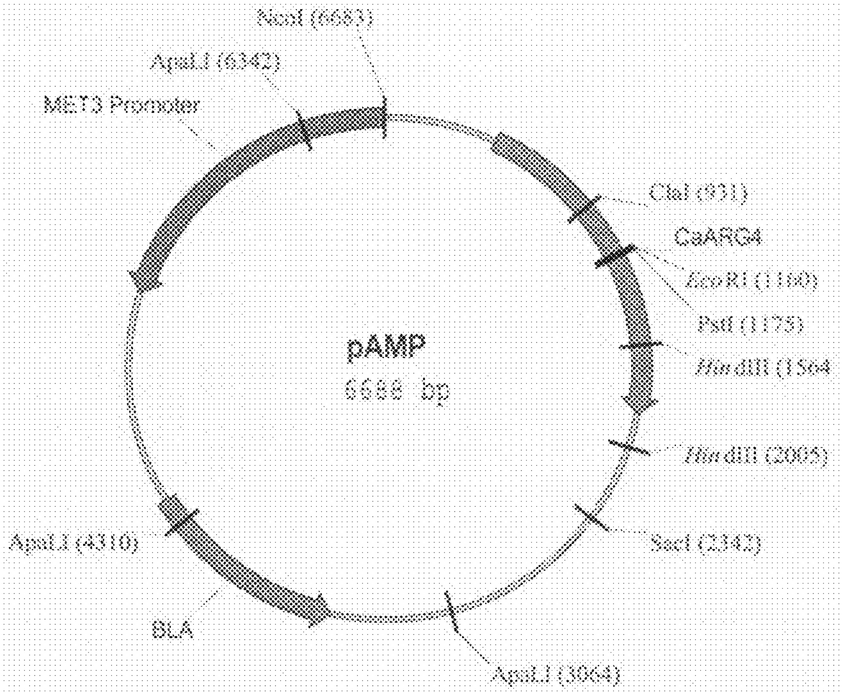

Scheme of promoter swapping

**Confirmation PCR for *C. albicans MET3P-ERG1/erg1::ARG4* strains.**

Down regulation phenotypes by methionine and cysteine

Methionine titration of *MET3P-ERG1* construct

Sensitivity of *MET3P-ERG1* cells to terbinafine in the absence and presence of methionine

FIG. 11A

```
  1  ATGTCACTTTTAAAGGATTCTACAGTTGCAGTCATTACCGGGACATCTTCAAATTTAGGA   60
  1  M  S  L  L  K  D  S  T  V  A  V  I  T  G  T  S  S  N  L  G    20

 61  TTCAATATAGCTGTTCGTTTGTTGGAGGGGCTTCCTGACAACAAAGAAATTACTCTTGTT  120
 21  F  N  I  A  V  R  L  L  E  G  L  P  D  N  K  E  I  T  L  V    40

121  GTTACTTCCAGAACATTACCAAAAGTAAAGGAAGTGATTTCTGATATTAAAAAATATATT  180
 41  V  T  S  R  T  L  P  K  V  K  E  V  I  S  D  I  K  K  Y  I    60

181  GTGGCAAAAATCCCAACTAAAGTAAACAAGGTGGAATTTGACTATTTATTGGTGGATTTC  240
 61  V  A  K  I  P  T  K  V  N  K  V  E  F  D  Y  L  L  V  D  F    80

241  ACTGATATGGTATCAATTTTATCAGCATATTATGAATTGAATAAACGATACAAACATATT  300
 81  T  D  M  V  S  I  L  S  A  Y  Y  E  L  N  K  R  Y  K  H  I   100

301  GATTACTTGTTTATTAATGCGGCCCAAGGAGTATACGGAGGCATAGATTGGACTGGCGCA  360
101  D  Y  L  F  I  N  A  A  Q  G  V  Y  G  G  I  D  W  T  G  A   120

361  GTTCTCGAAGTTTTGCAAAGCCCAATTGAGGCAGTCACTAATCCAACTTATAAATTACAA  420
121  V  L  E  V  L  Q  S  P  I  E  A  V  T  N  P  T  Y  K  L  Q   140

421  AAAGTTGGAGTAGAAAGTGGCGATAAATTGGGATTAGTCTTTCAAGCAAATGTGTTTGGA  480
141  K  V  G  V  E  S  G  D  K  L  G  L  V  F  Q  A  N  V  F  G   160

481  CCATATTATTTTATCCACAGAATCAAACACTTGTTGGAAAATGGTGGGAAAATAGTGTGG  540
161  P  Y  Y  F  I  H  R  I  K  H  L  L  E  N  G  G  K  I  V  W   180

541  GTCAGCTCATTAATGTCAAGTCCAAAATATTTGTCTTTCAATGATTTACAATTATTGAGA  600
181  V  S  S  L  M  S  S  P  K  Y  L  S  F  N  D  L  Q  L  L  R   200

601  TCACCAGCAAGCTATGAAGGCTCAAAAAGATTGGTTGACTTGATGCATTTTGGAACTTAC  660
201  S  P  A  S  Y  E  G  S  K  R  L  V  D  L  M  H  F  G  T  Y   220

661  AACAAGCTAGAAAGAGAACATGGAATCAAACAGTATTTAGTTCATCCTGGGATATTCACA  720
221  N  K  L  E  R  E  H  G  I  K  Q  Y  L  V  H  P  G  I  F  T   240

721  AGTTTCTCGTTTTTCCAATATTTGAACGTTTTCACATACTATGGTATGTTATTTTTATTC  780
241  S  F  S  F  F  Q  Y  L  N  V  F  T  Y  Y  G  M  L  F  L  F   260
```

FIG. 11B

```
781  TACCTTGCAAGATTTTTAGGGTCACCATATCACAATATTTCTGGGTATATTGCTGCGAAC  840
261  Y  L  A  R  F  L  G  S  P  Y  H  N  I  S  G  Y  I  A  A  N   280

841  GCTCCTGTTGCTGCTGCTTTAGGTCAAACTAAACAAAACTGCAAAACTGCCTCGGCTTGT  900
281  A  P  V  A  A  A  L  G  Q  T  K  Q  N  C  K  T  A  S  A  C   300

901  ACTAGATCTGGTAAAGAGTATTTATTAGAAGAAGAGATTGACAGCACTGGTCTGGACGAC  960
301  T  R  S  G  K  E  Y  L  L  E  E  E  I  D  S  T  G  L  D  D   320

961  GTTGTCCTGTATTTGGACACACTTACTAAAGAGTGGGACGAAAAGTTGAAGGATCAAATA  1020
321  V  V  L  Y  L  D  T  L  T  K  E  W  D  E  K  L  K  D  Q  I   340

1021 GTAAATACACGTCAACCTTGA  1041
341  V  N  T  R  Q  P      346
```

FIG. 12A

```
  1  ATGTCAGTCGAAACAATTAGTGATAGTTTGAAACAATTGGGATTAAGTCAACCAGCAGCC   60
  1  M  S  V  E  T  I  S  D  S  L  K  Q  L  G  L  S  Q  P  A  A    20

 61  ATTGAAGGTACCCACCCTCAATATAATGTGGTTGATGTCTTTAGAAACTATATCGCTGAA  120
 21  I  E  G  T  H  P  Q  Y  N  V  V  D  V  F  R  N  Y  I  A  E    40

121  GAATTACATCGTATTTCATCAGTTGACAAATCTATTATCATTCAAGCTTTGGATACACCA  180
 41  E  L  H  R  I  S  S  V  D  K  S  I  I  I  Q  A  L  D  T  P    60

181  AAAGTATTAGATCAAGGTGATATTATTGTTCCTATTCCAAAATTAAGATTAAAAGGAATC  240
 61  K  V  L  D  Q  G  D  I  I  V  P  I  P  K  L  R  L  K  G  I    80

241  AATCCTAATGAAAAATCCAAGGAATGGGCTGAAAATTTCAATAAAGGGAAATTCATTTCT  300
 81  N  P  N  E  K  S  K  E  W  A  E  N  F  N  K  G  K  F  I  S   100

301  GAAATCAAACCTCAAGGAGTGTTTTTACAATTCTATTTTGCTAAAACATTATTGTATAAT  360
101  E  I  K  P  Q  G  V  F  L  Q  F  Y  F  A  K  T  L  L  Y  N   120

361  TTGGTCATTGAAGATGTTTTAAAGAGAAAATCAGATTATGGTTACTTACCTTTGGGTGTT  420
121  L  V  I  E  D  V  L  K  R  K  S  D  Y  G  Y  L  P  L  G  V   140

421  GGTAAAAAAGCCATTGTTGAATTCTCGTCTCCAAATATTGCCAAACCTTTCCATGCTGGA  480
141  G  K  K  A  I  V  E  F  S  S  P  N  I  A  K  P  F  H  A  G   160

481  CATTTAAGATCTACTATTATAGGTGGGTTCATTTCTAACTTGTACGAAAAAGTTGGCTGG  540
161  H  L  R  S  T  I  I  G  G  F  I  S  N  L  Y  E  K  V  G  W   180

541  GATGTCACCAGAATCAATTATTTGGGAGATTGGGGGAAACAATTTGGTTTGTTAGCTGTT  600
181  D  V  T  R  I  N  Y  L  G  D  W  G  K  Q  F  G  L  L  A  V   200

601  GGTTTTGAAAGATACGGTGACGAATCTAAGTTAGCTTCAGATCCAATCAACCACTTGTTT  660
201  G  F  E  R  Y  G  D  E  S  K  L  A  S  D  P  I  N  H  L  F   220

661  GAAGTTTATGTCAAGATTAATCAAGATGTCACCAAGGAGACAAGTGAAGCCACTGGTGAA  720
221  E  V  Y  V  K  I  N  Q  D  V  T  K  E  T  S  E  A  T  G  E   240

721  ACTCCAGCAGAAACCATTGATGCTTCTGAACAGGATGAAAAGAAAATCCAATCCTCTACC  780
241  T  P  A  E  T  I  D  A  S  E  Q  D  E  K  K  I  Q  S  S  T   260
```

FIG. 12B

```
781  AATGAAGAAGCTAGAAGATTTTTCAGAAGAATGGAAGATGGTGATGAATCAGCATTGAAA  840
261  N  E  E  A  R  R  F  F  R  R  M  E  D  G  D  E  S  A  L  K  280

841  ATTTGGGCAAGATTCAGAGATTTGTCTATTGAAAAATATGTTGACACTTATGGTCGACTT  900
281  I  W  A  R  F  R  D  L  S  I  E  K  Y  V  D  T  Y  G  R  L  300

901  AATATTAAATATGATGTTTATTCTGGTGAATCTCAAGTTCCACAAGAGAAAATGAAAGAA  960
301  N  I  K  Y  D  V  Y  S  G  E  S  Q  V  P  Q  E  K  M  K  E  320

961  GCTACCAAATTGTTCGAAGATAAAGGTTTGATTGATATTGACCGTGGTGCCAAATTAATT  1020
321  A  T  K  L  F  E  D  K  G  L  I  D  I  D  R  G  A  K  L  I  340

1021 GACTTGACTAAATTTAACAAAAAATTGGGTAAAGCATTAGTTGAAAAATCAGATGGTACT  1080
341  D  L  T  K  F  N  K  K  L  G  K  A  L  V  E  K  S  D  G  T  360

1081 TCCCTTTATTTGACTCGTGATGTTGGTGAAGCTATTAAGCGTTATGAAACCTACAAGTTT  1140
361  S  L  Y  L  T  R  D  V  G  E  A  I  K  R  Y  E  T  Y  K  F  380

1141 GATAAGATGATTTACGTTATTGCTGCCCAACAAGATTTGCATTGTGCTCAATTCTTTGAA  1200
381  D  K  M  I  Y  V  I  A  A  Q  Q  D  L  H  C  A  Q  F  F  E  400

1201 ATTTTGAAACAAATGGGATTCGAATGGGCCCACAATTTGGAACATGTTAACTTTGGTATG  1260
401  I  L  K  Q  M  G  F  E  W  A  H  N  L  E  H  V  N  F  G  M  420

1261 GTCCAAGGTATGAGTACCAGAAAAGGTACTGTTGTGTTTTTAGATAACATTTTACAAGAA  1320
421  V  Q  G  M  S  T  R  K  G  T  V  V  F  L  D  N  I  L  Q  E  440

1321 ACCAAAGAAAAGATGCACGAAGTTATGCAGAAAAACGAAGAGAAATATGCTCAAATCGAA  1380
441  T  K  E  K  M  H  E  V  M  Q  K  N  E  E  K  Y  A  Q  I  E  460

1381 GACCCAGATAAGATTGCTGATTTGATTGGTATTTCTGCTGTTATGATTCAAGATATGCAA  1440
461  D  P  D  K  I  A  D  L  I  G  I  S  A  V  M  I  Q  D  M  Q  480

1441 TCTAAACGTATTCACAATTACGAATTCAAATGGGACAGAATGACTTCATTTGAAGGTGAC  1500
481  S  K  R  I  H  N  Y  E  F  K  W  D  R  M  T  S  F  E  G  D  500

1501 ACTGGTCCATACTTGCAATATGCTCACTCTCGTTTGTGTTCCATGCAAAGAAAATCAGGT  1560
501  T  G  P  Y  L  Q  Y  A  H  S  R  L  C  S  M  Q  R  K  S  G  520
```

FIG. 12C

```
                .         .         .         .         .         .
1561  ATTTCTATAGAGGAATTAGAACATGCCAACTTTGATTTGTTGGTTGAACCATGTGCCAGT  1620
 521  I  S  I  E  E  L  E  H  A  N  F  D  L  L  V  E  P  C  A  S    540

                .         .         .         .         .         .
1621  GCATTAGCAAGAACTTTAGCGCAATACCCGGACGTTATTAAAAAGGCTGTCAAAGGGTTG  1680
 541  A  L  A  R  T  L  A  Q  Y  P  D  V  I  K  K  A  V  K  G  L    560

                .         .         .         .         .         .
1681  GAACCATCCACAATCGTTACTTATTTGTTCAGTGTGACACATATTGTCTCCCAATGTTAC  1740
 561  E  P  S  T  I  V  T  Y  L  F  S  V  T  H  I  V  S  Q  C  Y    580

                .         .         .         .         .         .
1741  GATATTTTATGGGTTTCTGGTCAAGAAAAGGATGTTGCCATTGCAAGATTGGCTTTATAT  1800
 581  D  I  L  W  V  S  G  Q  E  K  D  V  A  I  A  R  L  A  L  Y    600

                .         .         .         .         .         .
1801  GAAGCTGCTAGACAAGTTATAAATAACGGTATGACCTTGTTAGGTTTGACTCCAGTTAAT  1860
 601  E  A  A  R  Q  V  I  N  N  G  M  T  L  L  G  L  T  P  V  N    620

1861  CGTATGTAA  1869
 621  R  M       622
```

FIG. 13

```
1    ATGGCGGTGATTAATCAACCAAATAGTCAGATCAGACTTACAAATGTTTCCTTAGTCCGA  60
1    M  A  V  I  N  Q  P  N  S  Q  I  R  L  T  N  V  S  L  V  R    20

61   ATGAAAAAGGGAAAGAAAAGATTTGAGATTGCATGTTATCAAAATAAAGTTCAAGATTGG  120
21   M  K  K  G  K  K  R  F  E  I  A  C  Y  Q  N  K  V  Q  D  W    40

121  AGACTGAAAGTGGAAAAGGATATTGACGAAGTGTTACAAATCCCACAAGTTTTCATAAAT  180
41   R  L  K  V  E  K  D  I  D  E  V  L  Q  I  P  Q  V  F  I  N    60

181  GTTTCCAAAGGTCAAGTTGCTAATAATGACGATTTACAAAAATGTTTTGGCACCACTAAT  240
61   V  S  K  G  Q  V  A  N  N  D  D  L  Q  K  C  F  G  T  T  N    80

241  CAAGATGAAATTATAGCTGAAATCTTAAACAAAGGAGAAATTCAGTTGAATGAAAAGGAA  300
81   Q  D  E  I  I  A  E  I  L  N  K  G  E  I  Q  L  N  E  K  E    100

301  AGAAATGCAAATTTACAACAAAAGCAAAATGAATTCTTAAATATAATTTCCACTAAATGT  360
101  R  N  A  N  L  Q  Q  K  Q  N  E  F  L  N  I  I  S  T  K  C    120

361  ATAAATCCAAGATCTAAAAAGAGATATCCTCCAAGCATGATTGAAAAGGTATTGAATGAA  420
121  I  N  P  R  S  K  K  R  Y  P  P  S  M  I  E  K  V  L  N  E    140

421  GTCAAATTTCATTTGAATCCTACTAAACCAACCAAAATTCAAGCATTGGATGCCATCAAA  480
141  V  K  F  H  L  N  P  T  K  P  T  K  I  Q  A  L  D  A  I  K    160

481  TTATTAGTTGAAAAACAAATCATACCTATTGCCAGAGCTCAAATGAAAGTGAGAATTACG  540
161  L  L  V  E  K  Q  I  I  P  I  A  R  A  Q  M  K  V  R  I  T    180

541  TTATCTAAAAAAGCATACTTAAAGACTTTTCAAGATGAAATAAAACCTGTTATTGATCAA  600
181  L  S  K  K  A  Y  L  K  T  F  Q  D  E  I  K  P  V  I  D  Q    200

601  ATTGTGGAGGAAGATAACAATGGGAAACAATATGAGATTGTTGGTATTATAGATCCTATA  660
201  I  V  E  E  D  N  N  G  K  Q  Y  E  I  V  G  I  I  D  P  I    220

661  AATTATAGAGTCTTGGTCACATTAATTGAAAATACAGATGGAAGCAACAAAGTCGCTAAA  720
221  N  Y  R  V  L  V  T  L  I  E  N  T  D  G  S  N  K  V  A  K    240

721  GGAGAAGGGTCTATAGAAGTATTAGATATGTCTGCCATAAAGGAATAA  768
241  G  E  G  S  I  E  V  L  D  M  S  A  I  K  E       255
```

FIG. 14

```
  1  ATGTCAGCTATCTATAAGGCATTACAATCCAAATCATCTAAGGAAACATCGGAAAAAACC    60
  1   M  S  A  I  Y  K  A  L  Q  S  K  S  S  K  E  T  S  E  K  T    20

 61  AAACATATTAATAGACAAAGATTATTGGTGATATCATCTCGTGGTATTACTTATAGGCAT   120
 21   K  H  I  N  R  Q  R  L  L  V  I  S  S  R  G  I  T  Y  R  H    40

121  CGTCATTTAATTCAAGATTTATTAGCATTATTACCACACGCTAGAAAAGAACCAAAATTT   180
 41   R  H  L  I  Q  D  L  L  A  L  L  P  H  A  R  K  E  P  K  F    60

181  GATTCTAAAAAAAATTTACATCAATTAAATGAAGTTGCTGAATTATACAATTGTAATAAT   240
 61   D  S  K  K  N  L  H  Q  L  N  E  V  A  E  L  Y  N  C  N  N    80

241  ATTTTCTTTTTTGAATGTAGAAAACATCAAGATTTATATTTATGGATTTCAAAACCACCA   300
 81   I  F  F  F  E  C  R  K  H  Q  D  L  Y  L  W  I  S  K  P  P   100

301  AATGGACCAACTTTAAAATTTCATATTCAAAATTTACATACTTTAGATGAATTGAATTTC   360
101   N  G  P  T  L  K  F  H  I  Q  N  L  H  T  L  D  E  L  N  F   120

361  ACTGGGAATTGTTTAAAAGGTTCAAGACCAATTTTAAGTTTTGATAAAAGTTTTTTAGAA   420
121   T  G  N  C  L  K  G  S  R  P  I  L  S  F  D  K  S  F  L  E   140

421  AATGATCATTATAAATTATTAAAAGAAATGTTTCTTCAAACTTTTGGAGTTCCACCAAAT   480
141   N  D  H  Y  K  L  L  K  E  M  F  L  Q  T  F  G  V  P  P  N   160

481  GCTAGAAAATCAAAACCATTTATTGATCATGTCATGACTTTTTCTATAGTTGATGGGAAA   540
161   A  R  K  S  K  P  F  I  D  H  V  M  T  F  S  I  V  D  G  K   180

541  ATTTGGATTCGAAACTATCAAATCAATGAAACTTTGGATGTTAAAGAAAATGATAAAATT   600
181   I  W  I  R  N  Y  Q  I  N  E  T  L  D  V  K  E  N  D  K  I   200

601  GAAGATGATGAAGATTATGATGTTGATCAATTGAATTTAGTGGAAATTGGTCCAAGATTA   660
201   E  D  D  E  D  Y  D  V  D  Q  L  N  L  V  E  I  G  P  R  L   220

661  GTATTGACTTTAATCACCGTTTTAGAAGGATCATTTTCTGGTCCAAAAATATATGAAAAT   720
221   V  L  T  L  I  T  V  L  E  G  S  F  S  G  P  K  I  Y  E  N   240

721  AAACAATACGTTTCACCAAACTTTGTTAGAGCTCAATTGAAACAACAAGCTGCTGATCAA   780
241   K  Q  Y  V  S  P  N  F  V  R  A  Q  L  K  Q  Q  A  A  D  Q   260

781  GCAAAATCTAGATCTCAAGCTGCTTTAGAAAGAAAGATTAAAAAGAGAAACCAAGTTTTG   840
261   A  K  S  R  S  Q  A  A  L  E  R  K  I  K  K  R  N  Q  V  L   280

841  AAAGCTGATCCATTATCCAATGATGCTTTATTTAAATAG   879
281   K  A  D  P  L  S  N  D  A  L  F  K         292
```

FIG. 15A

```
  1 ATGGGTAAAAAAGCAATTGATGCACGTATTCCTGCCTTGATACGTAATGGCGTTCAAGAA  60
  1 M  G  K  K  A  I  D  A  R  I  P  A  L  I  R  N  G  V  Q  E   20

 61 AAGCAAAGATCTTTTTTCATCATTGTGGGTGATAAAGCTCGTAATCAATTACCAAACTTG 120
 21 K  Q  R  S  F  F  I  I  V  G  D  K  A  R  N  Q  L  P  N  L   40

121 CATTATTTGATGATGAGTGCTGATTTGAAGATGAATAAGTCAGTATTATGGGCATACAAG 180
 41 H  Y  L  M  M  S  A  D  L  K  M  N  K  S  V  L  W  A  Y  K   60

181 AAAAAATTATTAGGCTTCACCTCCCACAGACAGAAGCGTGAAGCAAAAATTAAGAAAGAC 240
 61 K  K  L  L  G  F  T  S  H  R  Q  K  R  E  A  K  I  K  K  D   80

241 ATAAAGCGTGGAATTAGAGAAGTCAACGAACAAGATCCTTTTGAAGCATTTATATCTAAT 300
 81 I  K  R  G  I  R  E  V  N  E  Q  D  P  F  E  A  F  I  S  N  100

301 CAACATATCAGATATGTTTACTACAAAGAAACTGAAAAAATCTTGGGTAACACTTACGGA 360
101 Q  H  I  R  Y  V  Y  Y  K  E  T  E  K  I  L  G  N  T  Y  G  120

361 ATGTGTATTCTACAAGATTTTGAAGCCATCACCCCTAATTTGTTGGCTAGAACAATTGAA 420
121 M  C  I  L  Q  D  F  E  A  I  T  P  N  L  L  A  R  T  I  E  140

421 ACAGTCGAAGGTGGTGGATTAGTTGTTATCTTGCTCAAGAATATGACATCATTGAAGCAG 480
141 T  V  E  G  G  G  L  V  V  I  L  L  K  N  M  T  S  L  K  Q  160

481 TTATATACTATGTCCATGGATATACATTCAAGATACAGAACTGAAGCACATGATGATGTT 540
161 L  Y  T  M  S  M  D  I  H  S  R  Y  R  T  E  A  H  D  D  V  180

541 GTTGCCAGATTCAATGAAAGATTCTTACTTTCTTTAGGGTCTTGCGAAAATTGTTTAGTT 600
181 V  A  R  F  N  E  R  F  L  L  S  L  G  S  C  E  N  C  L  V  200

601 GTTGATGATGAATTGAATGTCTTACCTATTTCAGGGGGCAAACATGTTAAACCATTGCCA 660
201 V  D  D  E  L  N  V  L  P  I  S  G  G  K  H  V  K  P  L  P  220

661 CCTAAAGACGACGACGAATTGACTCCTAATGCCAAGGAATTAAAGGAGTTGAAAGAGAGT 720
221 P  K  D  D  D  E  L  T  P  N  A  K  E  L  K  E  L  K  E  S  240

721 CTTGCTGACGTACAACCTGCTGGGTCATTAGTGGCCTTGTCCAAAACTATAAATCAAGCA 780
241 L  A  D  V  Q  P  A  G  S  L  V  A  L  S  K  T  I  N  Q  A  260

781 CAAGCAATTTTGACTTTTATTGATGTCATCTCAGAAAAGACATTGAGAAATACAGTCACA 840
261 Q  A  I  L  T  F  I  D  V  I  S  E  K  T  L  R  N  T  V  T  280
```

FIG. 15B

```
841   TTAACTGCAGGAAGAGGTCGTGGTAAATCTGCTGCTTTAGGTATTGCTATTGCTGCAGCT   900
281   L  T  A  G  R  G  R  G  K  S  A  A  L  G  I  A  I  A  A  A     300

901   ATTTCCCATGGATATTCCAATATTTTTGTTACTTCACCATCACCTGAAAACTTGAAGACA   960
301   I  S  H  G  Y  S  N  I  F  V  T  S  P  S  P  E  N  L  K  T     320

961   TTGTTTGAATTTATTTTCAAAGGTTTTGATGCATTAGGATATACCGAACATATGGATTAT   1020
321   L  F  E  F  I  F  K  G  F  D  A  L  G  Y  T  E  H  M  D  Y     340

1021  GACATTATTCAGTCTACTAATCCATCTTTCAACAAAGCTATTGTCAGAGTTGATGTTAAA   1080
341   D  I  I  Q  S  T  N  P  S  F  N  K  A  I  V  R  V  D  V  K     360

1081  AGAGAACACAGACAAACGATTCAGTACATTTCTCCAAATGATAGTCATGTTTTAGGACAA   1140
361   R  E  H  R  Q  T  I  Q  Y  I  S  P  N  D  S  H  V  L  G  Q     380

1141  GCAGAATTATTGATTATCGATGAAGCAGCAGCCATACCACTTCCAATCGTGAAAAAATTG   1200
381   A  E  L  L  I  I  D  E  A  A  A  I  P  L  P  I  V  K  K  L     400

1201  ATGGGGCCCTATTTGATTTTTATGGCTTCTACCATTAATGGGTATGAAGGTACTGGAAGA   1260
401   M  G  P  Y  L  I  F  M  A  S  T  I  N  G  Y  E  G  T  G  R     420

1261  TCATTATCATTGAAATTGATTCAACAATTGAGAACTCAGTCCAATAATGCAACACCTTCA   1320
421   S  L  S  L  K  L  I  Q  Q  L  R  T  Q  S  N  N  A  T  P  S     440

1321  GAAACTACCGTGGTATCCAGAGATAAGAAATCCAATGAAATTACTGGAGCTTTGACTAGA   1380
441   E  T  T  V  V  S  R  D  K  K  S  N  E  I  T  G  A  L  T  R     460

1381  ACATTGAAAGAAGTTGTATTGGATGAGCCTATTAGATATGCACCAGGCGACCCTATTGAA   1440
461   T  L  K  E  V  V  L  D  E  P  I  R  Y  A  P  G  D  P  I  E     480

1441  AAATGGTTAAATAAATTGCTTTGTCTTGATGTTTCATTATCTAAAAATGCCAAGTTTGCA   1500
481   K  W  L  N  K  L  L  C  L  D  V  S  L  S  K  N  A  K  F  A     500

1501  ACAAAGGGCACTCCACATCCATCTCAGTGTCAACTTTTCTATGTAAATAGAGATACTTTG   1560
501   T  K  G  T  P  H  P  S  Q  C  Q  L  F  Y  V  N  R  D  T  L     520

1561  TTCTCCTATCACCCTGTCTCTGAAGCATTCTTACAAAAGATGATGGCATTGTATGTTGCT   1620
521   F  S  Y  H  P  V  S  E  A  F  L  Q  K  M  M  A  L  Y  V  A     540

1621  TCTCATTACAAAAATTCACCTAATGATTTACAATTGATGAGTGATGCTCCAGCACATCAG   1680
541   S  H  Y  K  N  S  P  N  D  L  Q  L  M  S  D  A  P  A  H  Q     560
```

FIG. 15C

```
1681 TTATTCGTGTTGTTACCTCCAATAGAGGCAGGTGATAATAGAGTACCTGACCCATTGTGT 1740
 561 L  F  V  L  L  P  P  I  E  A  G  D  N  R  V  P  D  P  L  C   580

1741 GTTATTCAATTAGCATTGGAGGGTGAAATATCCAAAGAAAGTGTAAGAAAATCTTTATCT 1800
 581 V  I  Q  L  A  L  E  G  E  I  S  K  E  S  V  R  K  S  L  S   600

1801 CGTGGACAAAGAGCCGGAGGGGATTTGATACCTTGGTTAATCTCACAACAATTCCAAGAC 1860
 601 R  G  Q  R  A  G  G  D  L  I  P  W  L  I  S  Q  Q  F  Q  D   620

1861 GAAGAATTTGCCTCATTGTCAGGTGCAAGAGTTGTTAGAATCGCTACAAACCCCGAATAC 1920
 621 E  E  F  A  S  L  S  G  A  R  V  V  R  I  A  T  N  P  E  Y   640

1921 TCTGGTATGGGTTATGGGTCTAGAGCAATGGAATTATTGAGGGACTATTACTCCGGTAAG 1980
 641 S  G  M  G  Y  G  S  R  A  M  E  L  L  R  D  Y  Y  S  G  K   660

1981 TTTACCGATATCAGTGAATCCACCGAATTGAATGATCACACAATTACAAGAGTCACTGAT 2040
 661 F  T  D  I  S  E  S  T  E  L  N  D  H  T  I  T  R  V  T  D   680

2041 AGCGAATTGGCCAACGCATCACTAAAAGATGAAATTAAGTTGAGAGACGTTAAGACATTA 2100
 681 S  E  L  A  N  A  S  L  K  D  E  I  K  L  R  D  V  K  T  L   700

2101 CCTCCGTTGTTATTGAAATTATCAGAAAAAGCCCCTTACTACTTGCACTACTTGGGTGTC 2160
 701 P  P  L  L  L  K  L  S  E  K  A  P  Y  Y  L  H  Y  L  G  V   720

2161 TCTTATGGTTTCACGTCTCAATTACACAAATTCTGGAAGAAAGCAGGGTTCACTCCAGTT 2220
 721 S  Y  G  F  T  S  Q  L  H  K  F  W  K  K  A  G  F  T  P  V   740

2221 TATTTGAGACAAACACCTAATGAATTAACTGGGGAACATACTTCGGTTGTTATAAGTGTT 2280
 741 Y  L  R  Q  T  P  N  E  L  T  G  E  H  T  S  V  V  I  S  V   760

2281 TTACCAGGAAGAGAAGATAAATGGTTACATGAATTCTCGAAAGATTTCCACAAAAGATTT 2340
 761 L  P  G  R  E  D  K  W  L  H  E  F  S  K  D  F  H  K  R  F   780

2341 TTGAGTTTGTTATCATATGAATTCAAAAAATTCCAGGCTTCCCAAGCTTTAAGCATTATT 2400
 781 L  S  L  L  S  Y  E  F  K  K  F  Q  A  S  Q  A  L  S  I  I   800

2401 GAAGCTGCAGAGCAAGGCGAAGGTGATGAAACTACTAGTCAAAAATTAACCAAAGAACAA 2460
 801 E  A  A  E  Q  G  E  G  D  E  T  T  S  Q  K  L  T  K  E  Q   820

2461 TTAGATCTGTTGTTGTCTCCATTTGATTTAAAGAGATTGGACTCGTATGCCAATAATTTA 2520
 821 L  D  L  L  L  S  P  F  D  L  K  R  L  D  S  Y  A  N  N  L   840
```

FIG. 15D

```
2521  TTGGATTATCATGTAATTGTTGATATGTTACCACTAATCTCCCAATTGTTTTTTTCAAAA  2580
 841   L  D  Y  H  V  I  V  D  M  L  P  L  I  S  Q  L  F  F  S  K    860

2581  AAAACTGGGCAAGATATCAGTTTATCATCAGTTCAATCTGCCATTTTATTGGCTATTGGG  2640
 861   K  T  G  Q  D  I  S  L  S  S  V  Q  S  A  I  L  L  A  I  G    880

2641  TTGCAGCATAAAGACATGGACCAGATAGCAAAAGAGTTGAACTTACCAACGAACCAAGCC  2700
 881   L  Q  H  K  D  M  D  Q  I  A  K  E  L  N  L  P  T  N  Q  A    900

2701  ATGGCAATGTTTGCTAAAATTATTCGTAAATTCTCAACCTATTTCAGAAAAGTTCTCAGT  2760
 901   M  A  M  F  A  K  I  I  R  K  F  S  T  Y  F  R  K  V  L  S    920

2761  AAAGCAATTGAAGAAAGTATGCCAGATTTAGAAGATGAGAATGTCGACGCCATGAATGGT  2820
 921   K  A  I  E  E  S  M  P  D  L  E  D  E  N  V  D  A  M  N  G    940

2821  AAGGAAACGGAACAAATCGATTATAAAGCCATTGAGCAGAAATTGCAAGATGACTTGGAA  2880
 941   K  E  T  E  Q  I  D  Y  K  A  I  E  Q  K  L  Q  D  D  L  E    960

2881  GAGGCTGGTGATGAGGCAATAAAAGAAATGAGAGAAAAACAACGTGAATTGATTAATGCT  2940
 961   E  A  G  D  E  A  I  K  E  M  R  E  K  Q  R  E  L  I  N  A    980

2941  CTTAATTTAGATAAATATGCTATTGCAGAAGATGCTGAATGGGATGAAAAATCAATGGAT  3000
 981   L  N  L  D  K  Y  A  I  A  E  D  A  E  W  D  E  K  S  M  D   1000

3001  AAAGCTACTAAGGGAAAAGGTAATGTTGTTAGTATTAAGAGTGGGAAAAGGAAATCTAAA  3060
1001   K  A  T  K  G  K  G  N  V  V  S  I  K  S  G  K  R  K  S  K   1020

3061  GAAAATGCTAATGATATTTATGAGAAAGAAATGAAAGCAGTTAAGAAATCAAAGAAATCA  3120
1021   E  N  A  N  D  I  Y  E  K  E  M  K  A  V  K  K  S  K  K  S   1040

3121  AAAAAATAA  3129
1041   K  K       1042
```

FIG. 16A

```
  1 ATGGTTTTAAAATCAACAACTGCAGGGAATGTATCAGTATATCAAGTTTCTGGTACCAAT  60
  1 M  V  L  K  S  T  T  A  G  N  V  S  V  Y  Q  V  S  G  T  N   20

 61 GTTTCTCGATCATTACCTGATTGGATAGACAAGAAACGTAAACGAGCTCTTAAACATGAT 120
 21 V  S  R  S  L  P  D  W  I  D  K  K  R  K  R  A  L  K  H  D   40

121 TTAGAATATCAAAATAGAATAGAATTAATTCAAGATTTTGAATTCAGTGAAGCATCAAAT 180
 41 L  E  Y  Q  N  R  I  E  L  I  Q  D  F  E  F  S  E  A  S  N   60

181 AAAATTAAAGTGACTAATGATGGACAATATTGTATGGCCACCGGGACTTATAAACCACAA 240
 61 K  I  K  V  T  N  D  G  Q  Y  C  M  A  T  G  T  Y  K  P  Q   80

241 ATTCATGTTTATGAATTTGCCAATTTATCATTAAAATTTGATCGTCATACTAATGTGGAA 300
 81 I  H  V  Y  E  F  A  N  L  S  L  K  F  D  R  H  T  N  V  E  100

301 AACATTGATTTTTTAATTTTAAGTAATGATTGGACTAAAAGTGTTCATTTACAATGTGAT 360
101 N  I  D  F  L  I  L  S  N  D  W  T  K  S  V  H  L  Q  C  D  120

361 AGAAGTATTGAATTTCAAACTGCTGGTGGAGTACATTATCGTACTAGAATACCTAAATTT 420
121 R  S  I  E  F  Q  T  A  G  G  V  H  Y  R  T  R  I  P  K  F  140

421 GGTCGATGTTTGACATATAATCCAATTAATTGTGATTTGATCGTTGGTAGTTCAAGTGAT 480
141 G  R  C  L  T  Y  N  P  I  N  C  D  L  I  V  G  S  S  S  D  160

481 GAATTATATCGATTGAATTTAGATCAAGGAAGGTTTTTATCCCCATTGAAATTGGATATG 540
161 E  L  Y  R  L  N  L  D  Q  G  R  F  L  S  P  L  K  L  D  M  180

541 ACTGATGGTGGCAATATTGACAGTGGATGTAACGCCGTTGATATTAATTCTATGCATGGT 600
181 T  D  G  G  N  I  D  S  G  C  N  A  V  D  I  N  S  M  H  G  200

601 TTAATAAGTGCTGGGTTAGATGATGGTACCGTTGAATTTTGGGATCCAAGATCAAAACAA 660
201 L  I  S  A  G  L  D  D  G  T  V  E  F  W  D  P  R  S  K  Q  220

661 AGAGCCGGGAAACTATTTGTTAGTGATCAATTAATTAATAGTACTAATAACACTGAACAA 720
221 R  A  G  K  L  F  V  S  D  Q  L  I  N  S  T  N  N  T  E  Q  240

721 AGTTCTTGTGGTATTACATCACTTGCATTCCGACCTCAAGATGCATTAAATTTTGCTTGT 780
241 S  S  C  G  I  T  S  L  A  F  R  P  Q  D  A  L  N  F  A  C  260
```

FIG. 16B

```
781  GGGACAAGTAATGGACAAACATTATTATATGATTTACGTGCATCTGAACCCTATCAAATT  840
261  G  T  S  N  G  Q  T  L  L  Y  D  L  R  A  S  E  P  Y  Q  I   280

841  AAAGATCAAGGATATGGGTATGATATTAAAAAAATCATTTGGTGTCAAGATTCATTAAAA  900
281  K  D  Q  G  Y  G  Y  D  I  K  K  I  I  W  C  Q  D  S  L  K   300

901  CCAGAAATGATTTTAACTAGTGATAAAAGAATTGTGAAAATTTGGGATCATACTAATGGT  960
301  P  E  M  I  L  T  S  D  K  R  I  V  K  I  W  D  H  T  N  G   320

961  AAATCATTTGCCTCCATGGAACCGACCGTTGATATCAATGATATTTGTCATATTCCTCAA  1020
321  K  S  F  A  S  M  E  P  T  V  D  I  N  D  I  C  H  I  P  Q   340

1021 TCAGGAATGTTTTTCATGGCTAACGAAGGGATGCCCATGCATACTTATTATATCCCTAAT  1080
341  S  G  M  F  F  M  A  N  E  G  M  P  M  H  T  Y  Y  I  P  N   360

1081 TTGGGTTCAGCACCTAATTGGTGTTCATTCTTGGATAATGTTACTGAAGAATTGGAGGAA  1140
361  L  G  S  A  P  N  W  C  S  F  L  D  N  V  T  E  E  L  E  E   380

1141 AAACCTTCAAATTCAATTTATCCTACCTTTAAATTTATTACTCGTGATGAAATGGTGAAA  1200
381  K  P  S  N  S  I  Y  P  T  F  K  F  I  T  R  D  E  M  V  K   400

1201 TTGAATTTGACTCATTTGATTGGGATCAAAGTTTTACGTTCTTATATGCATGGGTTTTTC  1260
401  L  N  L  T  H  L  I  G  I  K  V  L  R  S  Y  M  H  G  F  F   420

1261 ATTAATACTGAATTATATGATAAAGTCAATTTAATCAGTAATCCCAATTCAATTTATGAT  1320
421  I  N  T  E  L  Y  D  K  V  N  L  I  S  N  P  N  S  I  Y  D   440

1321 CAACGTAAACGTGAAATTGCTAACAAAATCAATGAAGAAAGAAAATCAAGAATTCTTACT  1380
441  Q  R  K  R  E  I  A  N  K  I  N  E  E  R  K  S  R  I  L  T   460

1381 AGTTCCAATGGTAATGACTTACCAACGAAAATTAAAGTCAATAAAGATTTGGTCAATAAA  1440
461  S  S  N  G  N  D  L  P  T  K  I  K  V  N  K  D  L  V  N  K   480

1441 TTACAAACTAAATTTGCTGAAAATGGTACTCCTGATGGTAATGCCAATGGTGCCACCGAT  1500
481  L  Q  T  K  F  A  E  N  G  T  P  D  G  N  A  N  G  A  T  D   500

1501 TATGTTGAATCAATTGTTAATGATGATCGTTTTAGAGAAATGTTTGAAAACCCTGATTTT  1560
501  Y  V  E  S  I  V  N  D  D  R  F  R  E  M  F  E  N  P  D  F   520
```

FIG. 16C

```
1561  GAAATTGATGAAGAATCTCATGAATATAAACAATTGAATCCGGTTAAATCAACCAAAGAT  1620
 521  E  I  D  E  E  S  H  E  Y  K  Q  L  N  P  V  K  S  T  K  D   540

1621  ATAACCACCACCAATACTGGTACTACTAATTCAAGAGGAAGAGGATTGACTGCAGCTGAA  1680
 541  I  T  T  T  N  T  G  T  T  N  S  R  G  R  G  L  T  A  A  E   560

1681  GAGTCAGATGAAGAAAGATTGAACATGAAAGATTCACACCACACTGGATTAGATTCAGAT  1740
 561  E  S  D  E  E  R  L  N  M  K  D  S  H  H  T  G  L  D  S  D   580

1741  GAATCAGATGAAGAATCAGATTCTGAATCTGAAGAACAATCTGAAGATGAAGCTAAATCA  1800
 581  E  S  D  E  E  S  D  S  E  S  E  E  Q  S  E  D  E  A  K  S   600

1801  GCCGAAACTAGAGAAAGAGTCGGTAAGGAATTGAATAAAATACGTCAATCAAAACAAAAA  1860
 601  A  E  T  R  E  R  V  G  K  E  L  N  K  I  R  Q  S  K  Q  K   620

1861  CAACAACAGCAAGATTCAAAGAAATTCCAAAATGAAATGAAAATCTTATCTCAACAATCA  1920
 621  Q  Q  Q  Q  D  S  K  K  F  Q  N  E  M  K  I  L  S  Q  Q  S   640

1921  TCTTCATCTTCATCATCCTTGGCAAATACCGAGAAGGCATCAGTATCATTTGGCTCTCAA  1980
 641  S  S  S  S  S  S  L  A  N  T  E  K  A  S  V  S  F  G  S  Q   660

1981  GTAAACAAATTAAACAAAATTTCTAAACAGAACAAAAATAATAATAGTATTAGTAATGCT  2040
 661  V  N  K  L  N  K  I  S  K  Q  N  K  N  N  N  S  I  S  N  A   680

2041  AAAGATGCTAGATTACGTCGACATGCTCGTGGTGAAGCTGAATTGACATTTGTGCCCCAA  2100
 681  K  D  A  R  L  R  R  H  A  R  G  E  A  E  L  T  F  V  P  Q   700

2101  AAATCAAAATCAAAATCAACTAAACTGAAATTTAATAACAACCACAGTGATGATGAAAAG  2160
 701  K  S  K  S  K  S  T  K  L  K  F  N  N  N  H  S  D  D  E  K   720

2161  CTGGATAGTGGTAAGACTAAAGATAGTGGTAGAACTAAACAGAGATTTGAAGGTCGTAGA  2220
 721  L  D  S  G  K  T  K  D  S  G  R  T  K  Q  R  F  E  G  R  R   740

2221  ATAGCATCCAAGAATAAGTTTAGAGGTATGTAA  2253
 741  I  A  S  K  N  K  F  R  G  M       750
```

FIG. 17

```
  1  ATGGCAGGATTTAAAAAGAATAGAGAAATTTTAACTGGAGGTAAGAAATATATCCAACAA   60
  1  M  A  G  F  K  K  N  R  E  I  L  T  G  G  K  K  Y  I  Q  Q    20

 61  AAACAAAAGAAACATTTAGTTGATGAAGTTGTATTTGATAAAGAATCCCGTCATGAATAT  120
 21  K  Q  K  K  H  L  V  D  E  V  V  F  D  K  E  S  R  H  E  Y    40

121  TTAACTGGTTTCCATAAACGTAAATTACAACGACAGAAAAAAGCTCAAGAATTTCATAAA  180
 41  L  T  G  F  H  K  R  K  L  Q  R  Q  K  K  A  Q  E  F  H  K    60

181  GAACAAGAACGGTTAGCTAAAATTGAAGAACGTAAACAATTAAAACAAGAACGTGAACGA  240
 61  E  Q  E  R  L  A  K  I  E  E  R  K  Q  L  K  Q  E  R  E  R    80

241  GATTTACAAAATCAATTACAACAATTTAAGAAAACTGCTCAAGAAATTGCTGCCATAAAT  300
 81  D  L  Q  N  Q  L  Q  Q  F  K  K  T  A  Q  E  I  A  A  I  N   100

301  AATGATATTGGATTTGATCAATCAGATGACAATAATGACAATGATAATGAAAATGAAGAA  360
101  N  D  I  G  F  D  Q  S  D  D  N  N  D  N  D  N  E  N  E  E   120

361  TGGAGTGGATTCCAAGAAGATGAAGAAGGAGAAGGAGAAGAAGTAACTGATGAAGATGAC  420
121  W  S  G  F  Q  E  D  E  E  G  E  G  E  E  V  T  D  E  D  D   140

421  GAAGATAAGGAAAAACCTTTGAAGGGGATTTTACATCATACTGAAATATATAAACAAGAT  480
141  E  D  K  E  K  P  L  K  G  I  L  H  H  T  E  I  Y  K  Q  D   160

481  CCCTCATTATCAAATATTACTAATAATGGTGCCATAATAGATGATGAAACAACAGTAGTG  540
161  P  S  L  S  N  I  T  N  N  G  A  I  I  D  D  E  T  T  V  V   180

541  GTAGAATCATTAGATAATCCAAATGCTGTTGATACTGAAGAAAAACTTCAACAATTGGCT  600
181  V  E  S  L  D  N  P  N  A  V  D  T  E  E  K  L  Q  Q  L  A   200

601  AAATTAAATAATGTTAATCTTGATAAATCTGATCAAATTTTAGAAAAATCTATTGAACGA  660
201  K  L  N  N  V  N  L  D  K  S  D  Q  I  L  E  K  S  I  E  R   220

661  GCTAAAAATTATGCTGTGATATGTGGAGTTGCTAAACCTAATCCAATCAAACAAAAGAAG  720
221  A  K  N  Y  A  V  I  C  G  V  A  K  P  N  P  I  K  Q  K  K   240

721  AAGAAATTCAGATATTTAACAAAAGCAGAACGTAGAGAAAATGTTCGTAAAGAGAAATCA  780
241  K  K  F  R  Y  L  T  K  A  E  R  R  E  N  V  R  K  E  K  S   260

781  AAATCAAAATCAAAGGGCAAGAAGTAA  807
261  K  S  K  S  K  G  K  K        268
```

FIG. 18A

```
  1  ATGTCCAGTGTTGCTTCCAAAAAGATAATAACATTTGAAGGGCACAGGAATTTCAGATTA   60
  1  M  S  S  V  A  S  K  K  I  I  T  F  E  G  H  R  N  F  R  L    20

 61  AGATTGGTGCTAGCCACATTATCTGGAAAACCTATCAAAATTACTAAAATTCGTTCTCAA  120
 21  R  L  V  L  A  T  L  S  G  K  P  I  K  I  T  K  I  R  S  Q    40

121  GACTTGAACCCAGGTTTGAAAGATCATGAAGTTTCTTTTCTTAGATTACTAGAAGCCGTA  180
 41  D  L  N  P  G  L  K  D  H  E  V  S  F  L  R  L  L  E  A  V    60

181  ACCAATGGATCCCATATTGAAATTTCATATACCGGTACAACAATCATTTATAGACCTGGG  240
 61  T  N  G  S  H  I  E  I  S  Y  T  G  T  T  I  I  Y  R  P  G    80

241  ATTATAATAGGTGGAGATCTTACCCACAATTGTCCTGATACAAAATCTATTGGATATTTC  300
 81  I  I  I  G  G  D  L  T  H  N  C  P  D  T  K  S  I  G  Y  F   100

301  ATTGAACCAATGTTAATGTTCCCGCTTTTTTCGAAAAAAAAATTCAGCATTATTTTCAAA  360
101  I  E  P  M  L  M  F  P  L  F  S  K  K  K  F  S  I  I  F  K   120

361  GGATTGACTAATATAGCAGGTAATGACACTGGAGTTGATGCCATTAAATGGGGGTTATTA  420
121  G  L  T  N  I  A  G  N  D  T  G  V  D  A  I  K  W  G  L  L   140

421  CCAGTAATGGAAAAGTTTGGTGTGAGAGAAGTCTCGTTACATATTTTGAAGAGAGGATCA  480
141  P  V  M  E  K  F  G  V  R  E  V  S  L  H  I  L  K  R  G  S   160

481  GCCCCCTTGGGTGGAGGAGAAGTGCATTTGTTATGTAGCTCTTTGATTCCACAACCATTG  540
161  A  P  L  G  G  G  E  V  H  L  L  C  S  S  L  I  P  Q  P  L   180

541  ACTATTCACGCGTTGGACATTCCCAAGTTCTCTGCCATTAGAGGAGTTGCTTATTGTACA  600
181  T  I  H  A  L  D  I  P  K  F  S  A  I  R  G  V  A  Y  C  T   200

601  AGAGTTTCCCCATCGATTGTTAATAGAATGATTGATTCAGCAAGAGCAGTATTGAAGCCA  660
201  R  V  S  P  S  I  V  N  R  M  I  D  S  A  R  A  V  L  K  P   220

661  ACAGGATGCGAGGTTAATATCACCGCTGATGTCTGGAGAGGAGAAAATTCAGGAAAATCA  720
221  T  G  C  E  V  N  I  T  A  D  V  W  R  G  E  N  S  G  K  S   240

721  CCAGGGTTTGGCATCACCTTAGTCGCTGAGCTGAAGCGTGGATGGAGAATTGTTACCGAG  780
241  P  G  F  G  I  T  L  V  A  E  L  K  R  G  W  R  I  V  T  E   260
```

FIG. 18B

```
781   AATGTTGGTTCGGCTGGGAGTTTACCTGAAGATTCTGGTGAGTTAACAGCTTACCAATTA   840
261   N  V  G  S  A  G  S  L  P  E  D  S  G  E  L  T  A  Y  Q  L     280

841   CTCGAAGAAATATCAAATAGTGGAGTTGTTGGAAGATACCAGTTGCCATTAGCACTTGTG   900
281   L  E  E  I  S  N  S  G  V  V  G  R  Y  Q  L  P  L  A  L  V     300

901   TATATGACTATTGGAAAAGAAGACATTGGTCGTTTGAAACTCCAAAAAAGTGAGATCGAC   960
301   Y  M  T  I  G  K  E  D  I  G  R  L  K  L  Q  K  S  E  I  D     320

961   GAGAATTTGGTGTCCGTGCTCAGAGATATTCAAGAAGTTTTTGGCACAGAAGCTTTCTTC   1020
321   E  N  L  V  S  V  L  R  D  I  Q  E  V  F  G  T  E  A  F  F     340

1021  AAAGATGATGCAGAAGAGCTTGATAGTGATGATAAATTCATGACAGTTTCTATCAAGGGA   1080
341   K  D  D  A  E  E  L  D  S  D  D  K  F  M  T  V  S  I  K  G     360

1081  GTAGGGTTCACCAATGTTTCTAAAAAAATAGCTTGA   1116
361   V  G  F  T  N  V  S  K  K  I  A       371
```

FIG. 19

```
  1 ATGAGACAAAAGCGTGCCAAGGCCTATAAGAAACAAATGAGTGTGTATGTCCACGCATTC  60
  1 M  R  Q  K  R  A  K  A  Y  K  K  Q  M  S  V  Y  V  H  A  F   20

 61 AAATTCAGAGAACCATACCAAATAATAGTAGACAATGAACTCATCACCACTTGTCAATCA 120
 21 K  F  R  E  P  Y  Q  I  I  V  D  N  E  L  I  T  T  C  Q  S   40

121 GCATCATTTGACATTAATAAAGGGTTTACTCGAACTATCCAAGCAGAAAACAAACCCATG 180
 41 A  S  F  D  I  N  K  G  F  T  R  T  I  Q  A  E  N  K  P  M   60

181 ATTACTCAATGTTGTATCCAAGCATTATATGATACTAAGAATCAACCAGCAATAGATATT 240
 61 I  T  Q  C  C  I  Q  A  L  Y  D  T  K  N  Q  P  A  I  D  I   80

241 GCTAAATCATTTGAACGAAGAAAATGTAATCATCGTGAAGCCATCGATCCTAGTCAATGT 300
 81 A  K  S  F  E  R  R  K  C  N  H  R  E  A  I  D  P  S  Q  C   100

301 ATTGAATCAATCGTTAATATTAAAGGACAAAATAAACATCGATATATCGTTGCCAGTCAA 360
101 I  E  S  I  V  N  I  K  G  Q  N  K  H  R  Y  I  V  A  S  Q   120

361 GATTTACAATTACGTAAAAAATTGCGGAAAATCCCTGGAGTACCATTGATTTATATGAAT 420
121 D  L  Q  L  R  K  K  L  R  K  I  P  G  V  P  L  I  Y  M  N   140

421 CGATCAGTGATGGTTATGGAACCGATCAGTGATGTTAGTAATCAATATAATATGAATTAT 480
141 R  S  V  M  V  M  E  P  I  S  D  V  S  N  Q  Y  N  M  N  Y   160

481 GAATCGAAAAAATTGACCGGAGGATTGAATGATATTGAAGCTGGGAAATTGGAAAAGCAA 540
161 E  S  K  K  L  T  G  G  L  N  D  I  E  A  G  K  L  E  K  Q   180

541 AATGAAGGTGAAGATGGGGATGGGGATGAACTGGAAGTTAAAAAGAAGAAAAGAAAAGGA 600
181 N  E  G  E  D  G  D  G  D  E  L  E  V  K  K  K  K  R  K  G   200

601 CCTAAAGAACCAAACCCATTAAGTGTCAAAAAGAAGAAAACAGATAATGCAACTGCTGCC 660
201 P  K  E  P  N  P  L  S  V  K  K  K  K  T  D  N  A  T  A  A   220

661 AGTACTAATCAAGAGCAGAAAAAGAAACCAAATAGAAGAAAAAGACATGCGCAAGTCAAA 720
221 S  T  N  Q  E  Q  K  K  K  P  N  R  R  K  R  H  A  Q  V  K   240

721 AGCAGAAGAGAAGGAAGACCAAGAACAGGAGCAAGTGAACGAAGCAACAACTAA 774
241 S  R  R  E  G  R  P  R  T  G  A  S  E  R  S  N  N     257
```

FIG. 20A

```
1   ATGTCTGAAACAAAAAATATTGAGTCTTTGATTTCGGATGCTGGTCCATTGATTACACAG  60
1   M S E T K N I E S L I S D A G P L I T Q  20

61  CCAGCTACTACTTTGCAGCAATACGCCACTGCATATTATACCACACCAGGGGTGCATAGT  120
21  P A T T L Q Q Y A T A Y Y T T P G V H S  40

121 GAGTTAAAAGATGAATATGCTAGACAACAATTAGCAATTTGGGGTGATAGTTTAAAAATT  180
41  E L K D E Y A R Q Q L A I W G D S L K I  60

181 AAACAGCCAAAACAGGAATATATTGATAGAGTTGTCAAGTTTGCGAAATTAACAGGTGAT  240
61  K Q P K Q E Y I D R V V K F A K L T G D  80

241 TATTCTGTGTTGTCAGTGAACGATTTGCACATTGTTGCGTTAGCATATGAGTTGGAGTGT  300
81  Y S V L S V N D L H I V A L A Y E L E C  100

301 TTGAACAATGGAGAAGACAACTTAAGAAGTTTTCCAGGTGAAGTCTTGAAGAATCAACAA  360
101 L N N G E D N L R S F P G E V L K N Q Q  120

361 GCTGAAAATGAAAATGGCTCAAACAAAATGTCAAACATAATAGGGGATGACGATGGGTTC  420
121 A E N E N G S N K M S N I I G D D D G F  140

421 GTAGTTGCCACAAAAAGAAGAGGAGGTAGAAGACAAAGAGAGAAGGCAGAGTTAAGGAAG  480
141 V V A T K R R G G R R Q R E K A E L R K  160

481 AAAGGGTTGTTGCCAACGTTTTCCCCAAAACCAAAGGGTGGCCTGGAAACAGAAGAACCT  540
161 K G L L P T F S P K P K G G L E T E E P  180

541 AATGAACTGTCAAATGATAAAACTATAGATGAAACACCTCAAACAGACTTGATCAAAGGT  600
181 N E L S N D K T I D E T P Q T D L I K G  200

601 GTTGATGTGCAAGAACAGGAATCCCAAGAAGAACCAGTATCTGAATCTAATACTGTTGGT  660
201 V D V Q E Q E S Q E E P V S E S N T V G  220

661 CTAGATGAAATAACTGAAGAATACAATGAAGACGATGATGACGGGGAATGGATTACTCCA  720
221 L D E I T E E Y N E D D D D G E W I T P  240

721 GAAAATTTACAAGAGGAGATAATAAAAGACAAAAATGAACAAGTCCAAGAGTCTAATACC  780
241 E N L Q E E I I K D K N E Q V Q E S N T  260
```

FIG. 20B

```
781   AATGGTCCGCTTATTAAAGTGGCTCTTGCAACTGGTGATTTTGCCTGTCAAAATGTGGCC   840
261   N  G  P  L  I  K  V  A  L  A  T  G  D  F  A  C  Q  N  V  A     280

841   ATGCAAATTGGTATAAAGTTATTGAACGCGATGTCAGGGAAACAGATTACTCGGGTTCGT   900
281   M  Q  I  G  I  K  L  L  N  A  M  S  G  K  Q  I  T  R  V  R     300

901   AATTACATGTATAGATGCCATGCTTGTTTCAGATTGACGCCAATGAGTAAAGATGGTAGA   960
301   N  Y  M  Y  R  C  H  A  C  F  R  L  T  P  M  S  K  D  G  R     320

961   CCGAAACATTTTTGTCCAAAATGTGGTGGCAATACATTATTGAGATGTGCTGTATCTGTC   1020
321   P  K  H  F  C  P  K  C  G  G  N  T  L  L  R  C  A  V  S  V     340

1021  GACAACAAGACGGGAAAAATAACTCCTCATTTAAAACAGAACTTTCAGTGGATCAGACGT   1080
341   D  N  K  T  G  K  I  T  P  H  L  K  Q  N  F  Q  W  I  R  R     360

1081  GGTGAACGATACTCGTTACCATCACCATTGAGTAAGAACCAAAAGAAATTACAAGGTAAC   1140
361   G  E  R  Y  S  L  P  S  P  L  S  K  N  Q  K  K  L  Q  G  N     380

1141  GGAGGCTATCAGCATAATAAAGAAAACCGTCACAAGTCATTGCAGACACCATTGATATTG   1200
381   G  G  Y  Q  H  N  K  E  N  R  H  K  S  L  Q  T  P  L  I  L     400

1201  AATGAAGACCAGAAGGAGTATCAACGGGCGTTAAAAAATGACGAGTGGGAAAGAAAACAA   1260
401   N  E  D  Q  K  E  Y  Q  R  A  L  K  N  D  E  W  E  R  K  Q     420

1261  CAAGATAAAATGTTACAAGAATGGATTGGAGGAGGCAGTGCTGACAATTTTGTTTCTCCT   1320
421   Q  D  K  M  L  Q  E  W  I  G  G  G  S  A  D  N  F  V  S  P     440

1321  TTTGGGAACACGATTAGAAACTCTGGTGTCAAAGTGGGACGCGGAAGATATGCAAACTCT   1380
441   F  G  N  T  I  R  N  S  G  V  K  V  G  R  G  R  Y  A  N  S     460

1381  TCCAAAAAGAAAAGAAAGTAG   1401
461   S  K  K  K  R  K        466
```

FIG. 21

```
  1 ATGAGGATTTATCAATGTCATTTTTGTTCATCACCGGTATATCCATTACATGGGATCACA  60
  1 M  R  I  Y  Q  C  H  F  C  S  S  P  V  Y  P  L  H  G  I  T   20

 61 TTTGTAAGAAATGATGCCAAAGAATTCCGTTTCTGTCGTTCTAAATGTCATAAAGCATTC 120
 21 F  V  R  N  D  A  K  E  F  R  F  C  R  S  K  C  H  K  A  F   40

121 AAACAACGTAGAAACCCAAGAAAATTACGTTGGACTAAAGCATTTAGAAAAGCTGCTGGT 180
 41 K  Q  R  R  N  P  R  K  L  R  W  T  K  A  F  R  K  A  A  G   60

181 AAAGAATTGGTGGTTGATTCTACATTAACATTTGCTGCTAGAAGAAATGTTCCAGTTAGA 240
 61 K  E  L  V  V  D  S  T  L  T  F  A  A  R  R  N  V  P  V  R   80

241 TATAATAGAGATTTGGTTGCCACTACTTTGAAAGGTATGAGTAGAATTGAAGAAATTAGA 300
 81 Y  N  R  D  L  V  A  T  T  L  K  G  M  S  R  I  E  E  I  R  100

301 CAAAGAAGAGAAAGAGCATTCTATAAGAATAGAATGAAGGGTAATAAAGAAAGACAGTTG 360
101 Q  R  R  E  R  A  F  Y  K  N  R  M  K  G  N  K  E  R  Q  L  120

361 GCTGCTGATAGAAAATTGGTTGCTGATAATCCAGAATTATTAAGATTAAGAGAAGTTGAA 420
121 A  A  D  R  K  L  V  A  D  N  P  E  L  L  R  L  R  E  V  E  140

421 TTAAGAAGAAAAGCCGAGAAATTAGCTGCTAAAGAAAATGCCATGGAAGAAGATGAAGAA 480
141 L  R  R  K  A  E  K  L  A  A  K  E  N  A  M  E  E  D  E  E  160

481 ACAGAGGTTGAAGAGGAAGGAGAAGGTGATGAAGAAATGATAAGTGGAGAGGAAGAATGG 540
161 T  E  V  E  E  E  G  E  G  D  E  E  M  I  S  G  E  E  E  W  180

541 GAAAGTGAAGATGAAAGTGAAAGGGAAAGTGACACAAAAACGTGTTAA 588
181 E  S  E  D  E  S  E  R  E  S  D  T  K  T  C     195
```

FIG. 23
A.
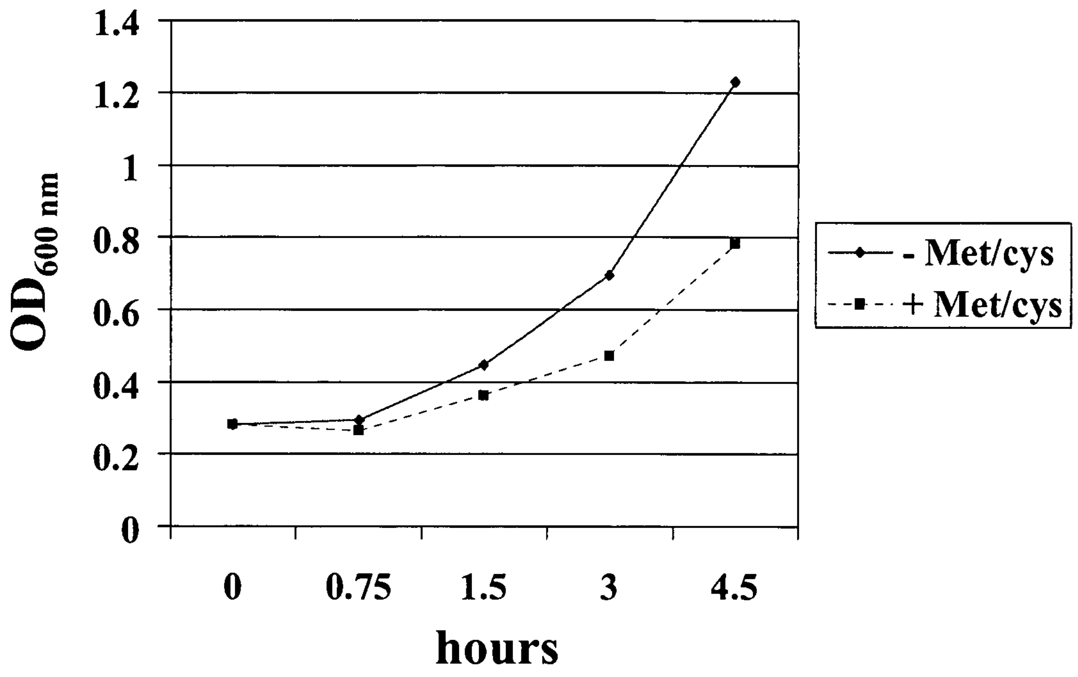
B.
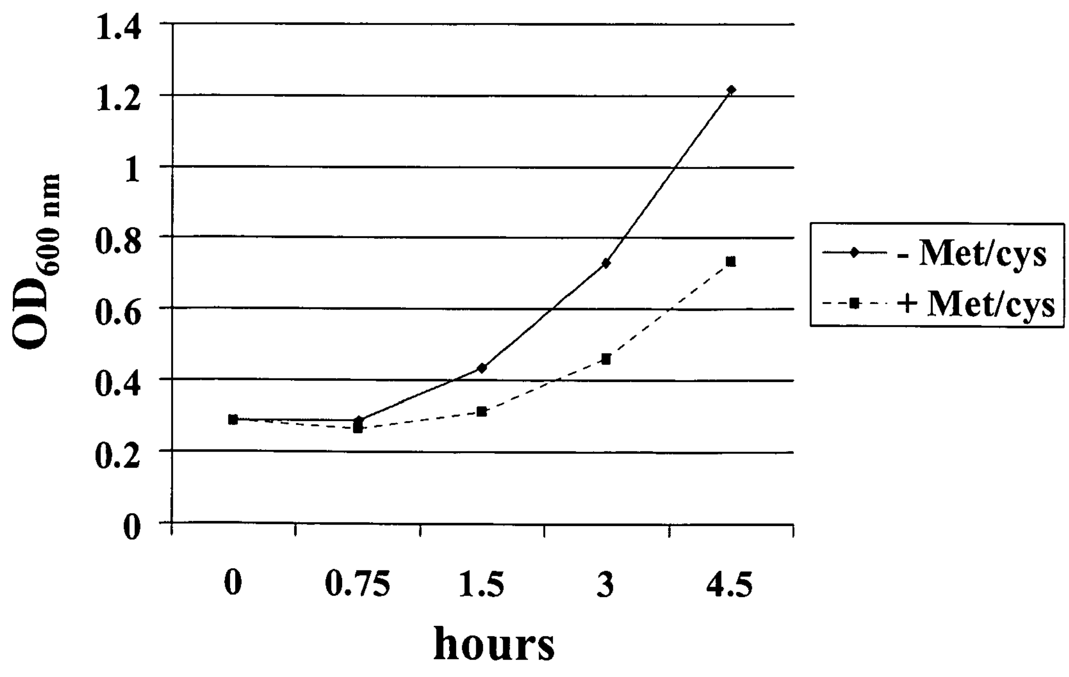

FIG. 24
A.
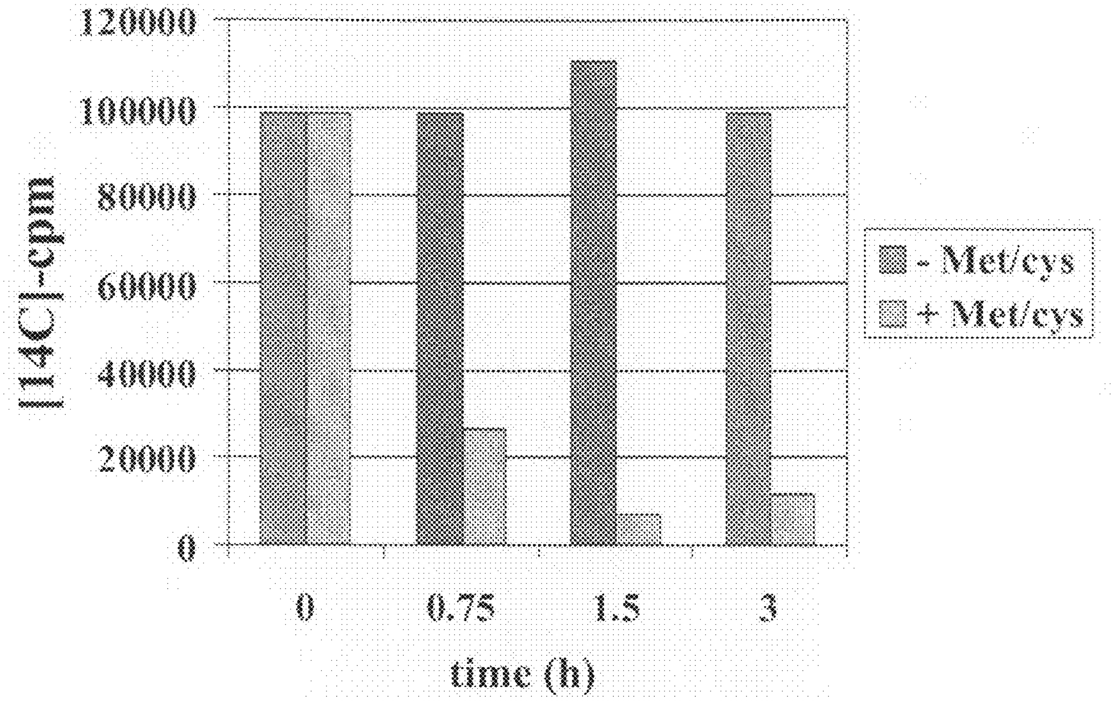
B.
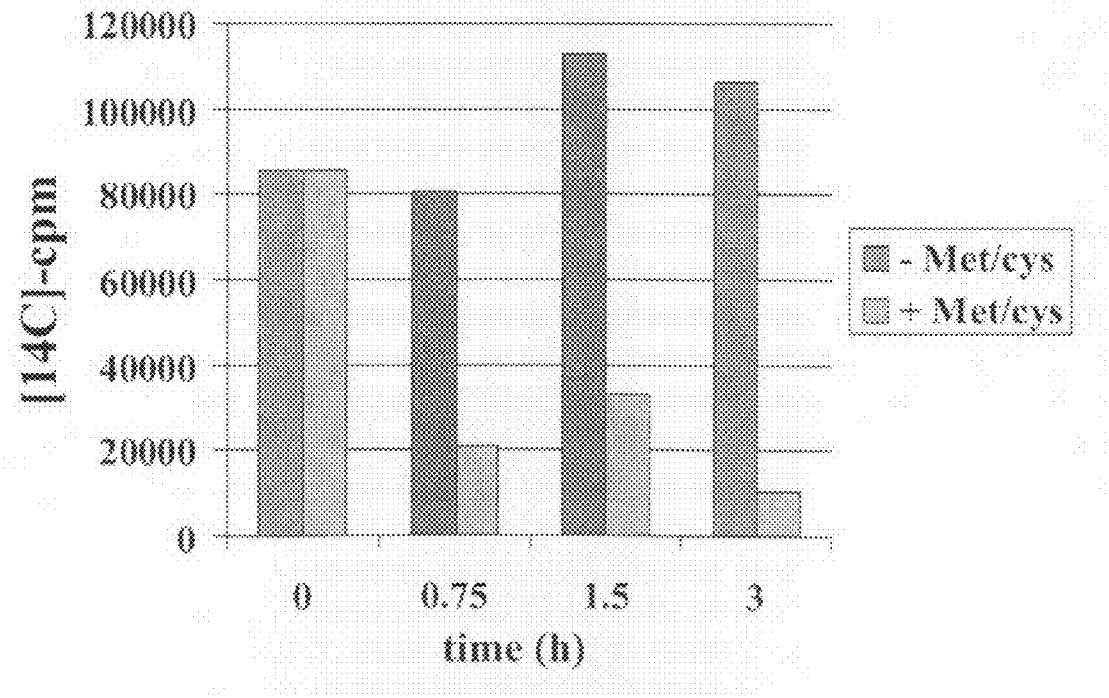

FIG. 25
A.
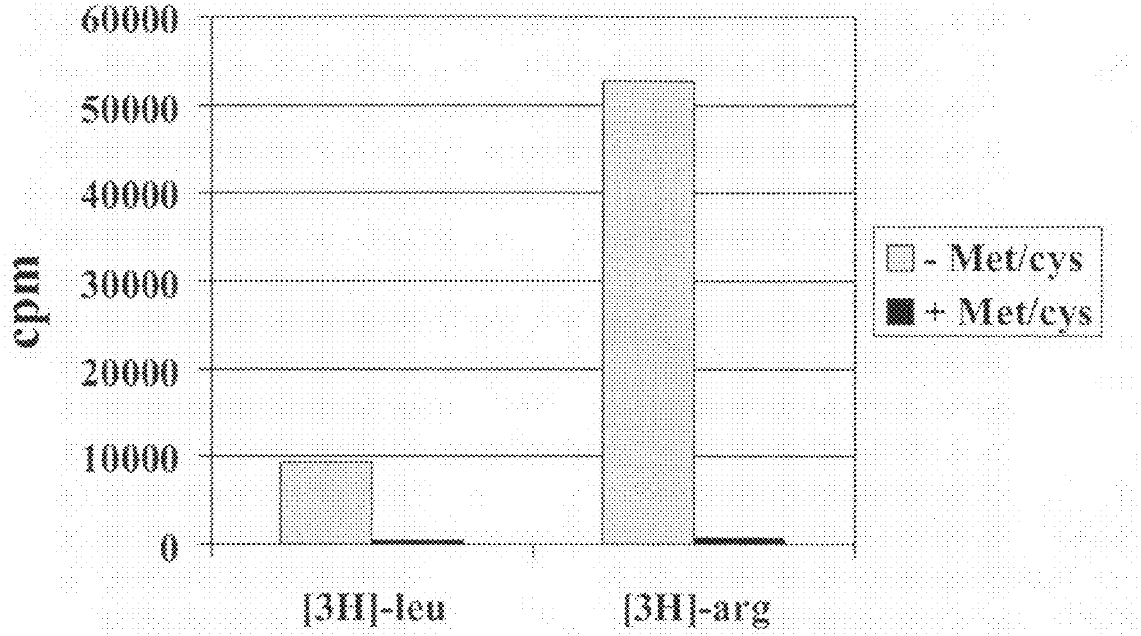
B.
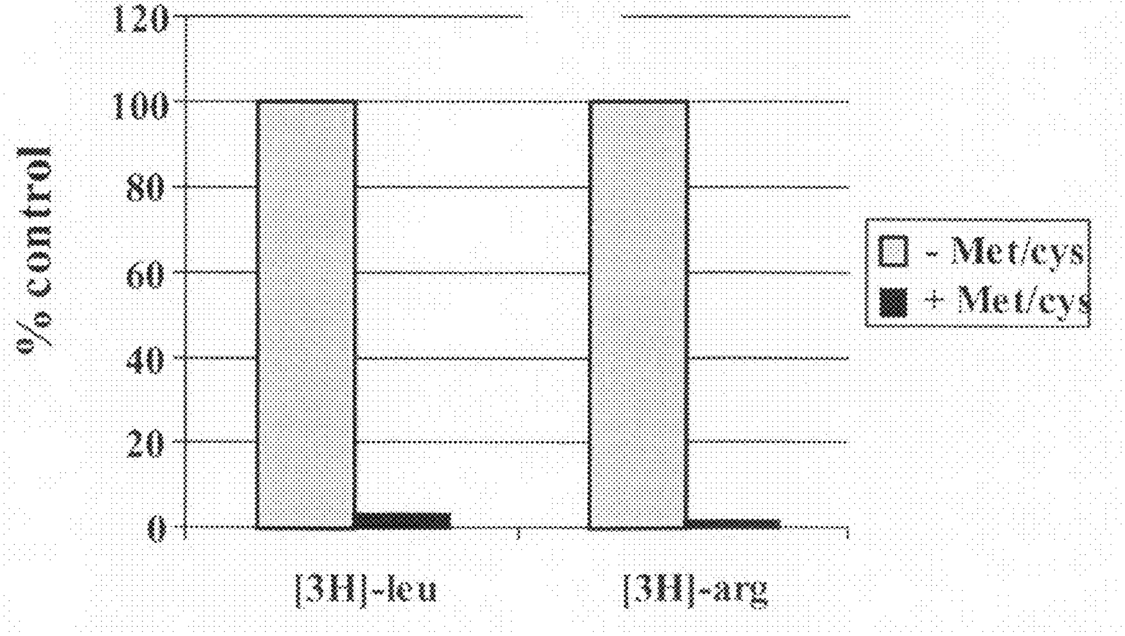

FIG. 26

```
1hu4A       ...SSNTRVA LVTGANKGIG FAIVRDLCRQ FA....GDVV LTARDVARGQ
caYLR100w   MSLLKDSTVA VITGTSSNLG FNIAVRLLEG LPDNKEITLV VTSRTLPKVK

1hu4A       AAVKQLQAE. .........G LSPRFHQLDI IDLQSIRALC DFLRKEYGGL
caYLR100w   EVISDIKKYI VAKIPTKVNK VEFDYLLVDF TDMVSILSAY YELNKRYKHI

1hu4A       DVLVNNAAIA FQLDN..... .......... .......... ..PTPFHIQA
caYLR100w   DYLFINAAQG VYGGIDWTGA VLEVLQSPIE AVTNPTYKLQ KVGVESGDKL

                                                *
1hu4A       ELTMKTNFMG TRNVCTELLP LIKPQGRVVN VSSTEGVRAL NEC.......
caYLR100w   GLVFQANVFG PYYFIHRIKH LLENGGKIVW VSSLMSSPKY LSFNDLQLLR
                                                *

1hu4A       .......SPE LQQKFKSETI TEEELVGLMN KFVEDTKNGV HRKEGWSDST
caYLR100w   SPASYEGSKR LVDLMHFGTY NKLEREHGIK QYLVH..PGI FTSFSFFQ..

            *   *
1hu4A       YGVTKIGVSV LSRIY.ARKL REQRAGDKIL LNACCPGWVR TDMGGPKAPK
caYLR100w   YLNVFTYYGM LFLFYLARFL GS..PYHNIS GYIAANAPVA AALGQTKQNC
            *

1hu4A       SPEVGAETPV YLALLPSDAE GP...HGQFV TDKKVVEWGV PPESYPWVNA
caYLR100w   KTASACTRSG KEYLLEEEID STGLDDVVLY LDTLTKEWDE KLKDQIVNTR

1hu4A       ....
caYLR100w   QP..
```

FIG. 29

```
1F7uA       .ASTANMISQ LKKLSIAEPA VAKDSHPDVN IVDLMRNYIS QELSKISGVD
CaYDR341c   M.SVETISDS LKQLGLSQPA AIEGTHPQYN VVDVFRNYIA EELHRISSVD

1F7uA       SSLIFPALEW TNTMERGDLL IPIPRLRIKG ANPKDLAVQW AEKFPCGDFL
CaYDR341c   KSIIIQALDT PKVLDQGDII VPIPKLRLKG INPNEKSKEW AENFNKGKFI

1F7uA       EKVEANGPFI QFFFNPQFLA KLVIPDILTR KEDYGSCKLV ENKKVIIEFS
CaYDR341c   SEIKPQGVFL QFYFAKTLLY NLVIEDVLKR KSDYGYLPLG VGKKAIVEFS

              *  ** *** **
1F7uA       SPNIAKPFHA GHLRSTIIGG FLANLYEKLG WEVIRMNYLG DWGKQFGLLA
CaYDR341c   SPNIAKPFHA GHLRSTIIGG FISNLYEKVG WDVTRINYLG DWGKQFGLLA

1F7uA       VGFERYGNEE ALVKDPIHHL FDVYVRINKD IEEE...... ...GDSI...
CaYDR341c   VGFERYGDES KLASDPINHL FEVYVKINQD VTKETSEATG ETPAETIDAS

1F7uA       .....PLEQS TNGKAREYFK RMEDGDEEAL KIWKRFREFS IEKYIDTYAR
CaYDR341c   EQDEKKIQSS TNEEARRFFR RMEDGDESAL KIWARFRDLS IEKYVDTYGR

1F7uA       LNIKYDVYSG ESQVSKESML KAIDLFKEKG LTHEDKGAVL IDLTKFNKKL
CaYDR341c   LNIKYDVYSG ESQVPQEKMK EATKLFEDKG LIDIDRGAKL IDLTKFNKKL

1F7uA       GKAIVQKSDG TTLYLTRDVG AAMDRYEKYH FDKMIYVIAS QQDLHAAQFF
CaYDR341c   GKALVEKSDG TSLYLTRDVG EAIKRYETYK FDKMIYVIAA QQDLHCAQFF

1F7uA       EILKQMGFEW AKDLQHVNFG MVQGMSTRKG TVVFLDNILE ETKEKMHEVM
CaYDR341c   EILKQMGFEW AHNLEHVNFG MVQGMSTRKG TVVFLDNILQ ETKEKMHEVM

                                                           ++++
1F7uA       KKNENKYAQI EHPEEVADLV GISAVMIQDM QGKRINNYEF KWERMLSFEG
CaYDR341c   QKNEEKYAQI EDPDKIADLI GISAVMIQDM QSKRIHNYEF KWDRMTSFEG

            ++
1F7uA       DTGPYLQYAH SRLRSVERNA SGITQEKWIN ADFSLLKEPA AKLLIRLLGQ
CaYDR341c   DTGPYLQYAH SRLCSMQRK. SGISIEELEH ANFDLLVEPC ASALARTLAQ

1F7uA       YPDVLRNAIK THEPTTVVTY LFKLTHQVSS CYDVLWVAGQ TEELATARLA
CaYDR341c   YPDVIKKAVK GLEPSTIVTY LFSVTHIVSQ CYDILWVSGQ EKDVAIARLA

1F7uA       LYGAARQVLY NGMRLLGLTP VERM...... .......... ..........
CaYDR341c   LYEAARQVIN NGMTLLGLTP VNRM...... .......... ..........
```

FIG. 32

```
1qmhA         ..MIALDGAQ GEGGGQILRS ALSLSMITGQ PFTITSIRAG RAKPGLLRQH
CaYOL010w     MSSVASKKII TFEGHRNFRL RLVLATLSGK PIKITKIRSQ DLNPGLKDHE

1qmhA         LTAVKAATEI CGATVEGAEL GSQRLLFRPG TVRGGDYRFA IGSAGSCTLV
CaYOL010w     VSFLRLLEAV TNGSHIEISY TGTTIIYRPG IIIGGDLTHN CPDTKSIGYF

1qmhA         LQTVLPALWF ADGPSRVEVS GGTDN.PSAP PADFIRRVLE PLLAK.IGIH
CaYOL010w     IEPMLMFPLF SKKKFSIIFK GLTNIAGNDT GVDAIKWGLL PVMEKFGVRE

                     **   * *****
1qmhA         QQTTLLRHGF YPAGGGVVAT EVSPV.ASFN TLQLGERGNI VQMRGEVLLA
CaYOL010w     VSLHILKRGS APLGGGEVHL LCSSLIPQPL TIHALDIPKF SAIRGVAYCT
                     **   ***** *

1qmhA         GVPRHVAERE IATLAGSFSL HEQNIHNL.. .....PRDQG PGNTVSLEVE
CaYOL010w     RVSPSIVNRM IDSARAVLKP TGCEVNITAD VWRGENSGKS PGFGITLVAE

1qmhA         SE.NITERFF VVGEKRVSAE VVAAQLVKEV KRYLASTAAV GEYLADQLVL
CaYOL010w     LKRGWRIVTE NVGSAGSLPE DSGELTAYQL LEEISNSGVV GRYQLPLALV

1qmhA         PMALAGAGEF TVAHP....S CHLLTNIAVV ERFLPVRFSL IETDGVTRVS
CaYOL010w     YMTIGKEDIG RLKLQKSEID ENLVSVLRDI QEVFGTEAFF KDDAEELDSD

1qmhA         I......... .......... .....
CaYOL010w     DKFMTVSIKG VGFTNVSKKI A....
```

ESSENTIAL FUNGAL POLYPEPTIDE, CAYDR341C, AND METHODS OF USE THEREOF

This application is a divisional application of non-provisional application U.S. Ser. No. 10/424,324, filed Apr. 25, 2003, U.S. Pat. No. 7,465,568, issued Dec. 16, 2008, which claims benefit to provisional application U.S. Ser. No. 60/376,022 filed Apr. 26, 2002, under 35 U.S.C. 119(e). The entire teachings of the referenced application are incorporated herein by reference.

FIELD OF THE INVENTION

The present invention provides essential fungal polynucleotides and their encoded polypeptides, homologues thereof and uses thereof. Additionally, the invention provides methods for the identification of essential polynucleotides and fungal strains which may be used for drug screening.

BACKGROUND OF THE INVENTION

As the number of severe fungal infections continues to rise, the need for a broad spectrum antifungal agent becomes more urgent. The rise in fungal infections is primarily due to the increasing number of immuno-compromised patients as a result of medical advances (transplantation and chemotherapy) and as a result of the increasing population of AIDS patients.

Although fluconazole has been an effective drug against fungal pathogens for a number of years, resistance is increasing. Alternatives such as amphotericin B have serious drawbacks, including such side effects as nephrotoxicity and severe discomfort. Few new antifungals are on the horizon, and more knowledge about the pathogenicity of fungi as well as about their general biology is crucial if new drug targets are to be identified.

More than 80% of fungal infections in immuno-compromised patients are caused by *Candida* species. Cryptococcosis is the second most prevalent fungal infection in AIDS patients following candidiasis. Aspergillosis is responsible for at least 30% of the infections in cancer and organ transplant patients and has a high mortality rate.

In order to discover new drugs to combat fungal infections, compounds are often tested for their effects on particular, suitable polynucleotides and polynucleotide products. Suitable polynucleotides are generally those which are found to be essential to the viability of the pathogen. This determination of essentiality presents substantial obstacles to the identification of appropriate targets for drug screening. These obstacles are especially pronounced in diploid organisms, such as *Candida albicans*.

A central technique used to investigate the role of a *Candida albicans* polynucleotide is to study the phenotype of a cell in which both copies of the polynucleotide have been deleted. Two popular polynucleotide deletion protocols have been reported. The first and most often used method, the 'urablaster' method, requires construction of a disruption cassette consisting of a selectable marker (URA and hisG flanking sequences) and sequences of the polynucleotide to be disrupted that are positioned at the 5' and 3' ends of the hisG-URA3-hisG cassette. A ura3− strain is then transformed and grown on minimal medium lacking uridine. ura3+ clones are isolated and transferred to a medium containing 5-fluoroortic acid, which selects for strains that have a ura3− genotype. These arise spontaneously as a subpopulation of the original transformed cells which will have undergone a recombinational event that retains one of the hisG sequences in the disrupted allele. The heterozygote ura3− strains can then be used in a second transformation event using the same cassette to disrupt the second allele resulting in a homozygous deletion strain.

A second type of popular method utilizes a PCR-based polynucleotide disruption strategy and multiple markers to construct homozygous mutants (Wilson et al *J. Bacteriol.* 181: 1868-74 (1999)). Although more rapid than the urablaster method, both methods have limitations. Since a homozygous deletion strain which lacks both essential polynucleotide copies would not be viable, such results are not an unequivocal explanation establishing the essential nature of the target polynucleotide because alternative explanations, including poor growth of a viable mutant strain, may be as likely a reason as essentiality for the negative results obtained.

Essential polynucleotides may also be identified using inducible promoter-regulated constructs to modify expression of the second polynucleotide copy, rather than completely inactivating it. With these methods, one polynucleotide copy is disrupted and the second copy is only expressed under certain conditions. The essentiality of the polynucleotide can be investigated since the fungal strain will only be viable under conditions in which the promoter is switched on (See, for example Nakayama et al. (*Infection and Immunity* 68: 6712-6719, (2000), and WO 01/60975).

One reportedly effective technique involves the use of the *C. albicans* MET3 promoter (Care et al., *Molecular Microbiology* 34 792-798 (1999)). The activity of the promoter is inhibited by methionine and/or cysteine and completely inactivated with both amino acids. Although the MET3 promoter is not the only regulated promoter to be characterized in *C. albicans*, one advantage of this promoter is that it is controlled by the addition of amino acids to the growth medium rather than a switch in carbon source. Switching carbon sources is likely to cause a bigger disturbance to cell physiology than adding amino acids (Care et at). However, the method developed for use of the MET3 promoter by Care et al. is cumbersome since it requires subcloning a portion of the polynucleotide under evaluation.

Additional methodologies enabling the identification of essential polynucleotides for drug screening which are both easy to use and give rapid results are needed, particularly for *C. albicans*. The *C. albicans* genome-sequencing project has recently begun and novel polynucleotides are being identified. There should be increasing demand to assess essential polynucleotide function and methodologies particularly amenable to high throughput screening will be useful.

Furthermore, although the identification of novel polynucleotides as essential in *C. albicans* is of value, the determination of essentiality for known polynucleotide sequences in *C. albicans* or other fungal genomes is also highly desirable since such polynucleotides will add to the set of drug targets. Furthermore, the use of *C. albicans* essential polynucleotides for drug screening for which orthologs in other pathogenic fungi are identified may result in the discovery of drugs effective in fighting infections from a variety of pathogens.

SUMMARY OF THE INVENTION

The invention provides a nucleic acid molecule including nucleotide sequences that hybridize under stringent conditions to a second nucleic acid molecule having a nucleotide sequence that encodes an essential polypeptide having an amino acid sequence selected from the group consisting of one of SEQ ID NO: 12 to 22.

The invention also provides a substantially pure oligonucleotide, said oligonucleotide comprising a region of nucleotide sequence capable of hybridizing under highly stringent conditions to at least about 12 consecutive nucleotides of one of SEQ ID NO: 1 to SEQ ID NO: 11.

The invention also provides a polynucleotide comprising the nucleotide sequence of a member of the group consisting of SEQ ID NO: 1 to SEQ ID NO: 11, or the nucleotide sequence included in the deposited clone.

The invention also provides a recombinant DNA molecule comprising the isolated nucleic acid molecule comprising a nucleotide sequence of a member of the group consisting of SEQ ID NO: 1 to SEQ ID NO: 11, or the nucleotide sequence included in the deposited clone.

The invention also provides a recombinant DNA molecule comprising a nucleotide sequence of a member of the group consisting of SEQ ID NO: 1 to SEQ ID NO: 11, or the nucleotide sequence included in the deposited clone, wherein said polynucleotide is operably linked to one or more regulatory sequences.

The invention also provides an expression vector comprising an isolated polynucleotide comprising a nucleotide sequence of a member of the group consisting of SEQ ID NO: 1 to SEQ ID NO: 11.

The invention also provides a host cell transformed to contain an expression vector comprising an isolated polynucleotide comprising a nucleotide sequence of a member of the group consisting of SEQ ID NO: 1 to SEQ ID NO: 11, wherein said host cell is either a prokaryote or a eukaryote.

The invention also provides a substantially pure oligonucleotide, said oligonucleotide comprising a region of nucleotide sequence capable of hybridizing under highly stringent conditions to at least about 12 consecutive nucleotides of one of SEQ ID NO: 1 to SEQ ID NO: 11.

The invention also provides a substantially pure oligonucleotide, said oligonucleotide comprising a region of nucleotide sequence capable of hybridizing under highly stringent conditions to at least about 12 consecutive nucleotides of one of SEQ ID NO: 1 to SEQ ID NO: 11, wherein said oligonucleotide further comprises a detectable label attached thereto.

The invention also provides an isolated nucleic acid molecule obtained from an organism other than *Candida albicans* or *Saccromyces cervisiae* comprising a nucleotide sequence having at least 30% identity to a sequence selected from the group consisting of SEQ ID NO: 1 to 11.

The invention also provides a method for producing a polypeptide comprising the step of culturing a host cell transformed with the nucleic acid molecule comprising a nucleotide sequence of a member of the group consisting of SEQ ID NO: 1 to SEQ ID NO: 11 under conditions in which the protein encoded by said nucleic acid molecule is expressed.

The invention also provides a polynucleotide that encodes a full length protein of a member of the group consisting of SEQ ID NO: 12 to 22, or the encoded sequence included in the deposited clone.

The invention also provides an isolated nucleic acid molecule obtained from an organism other than *Candida albicans* or *Saccromyces cervisiae* including a nucleotide sequence having at least 30% identity to a sequence selected from the group consisting of SEQ ID NO: 1 to 11, wherein said identity is determined using the CLUSTALW algorithm with default parameters.

The invention also provides an isolated nucleic acid molecule obtained from an organism other than *Candida albicans* or *Saccromyces cervisiae* including a nucleotide sequence having at least 30% identity to a sequence selected from the group consisting of SEQ ID NO: 1 to 11, wherein said identity is determined using the CLUSTALW algorithm with default parameters, wherein said organism is selected from the group consisting of *Absidia corymbigera, Aspergillus flavis, Aspergillus fumigatus, Aspergillus niger, Botrytis cinerea, Candida dublinensis, Candida glabrata, Candida krusei, Candia parapsilopsis, Candia tropicalis, Coccidioides immitis, Cryptococcus neoformans, Erysiphe graminis, Exophalia dermatiditis, Fusarium osysproum, Histoplasma capsulatum, Magnaporthe grisea, Mucor rouxii, Pneumocystis carinii, Puccinia graminis, Puccinia recodita, Rhizomucor pusillus, Puccinia striiformis, Rhizopus arrhizus, Septoria avenae, Septoria nodorum, Septoria triticii, Tilletia controversa, Tilletia tritici, Trichospoon beigelii* and *Ustilago maydis.*

The invention also provides an isolated nucleic acid molecule obtained from an organism other than *Candida albicans* or *Saccromyces cervisiae* including a nucleotide sequence having at least 30% identity to a sequence selected from the group consisting of SEQ ID NO: 1 to 11, wherein said identity is determined using the CLUSTALW algorithm with default parameters, wherein said organism is *Aspergillus fumigatus.*

Additionally provided is an isolated nucleic acid molecule having a fragment of at least 10 consecutive nucleotides of one of SEQ ID NO 1 to 11.

The invention provides a substantially purified polypeptide including an amino acid sequence selected from the group consisting of one of SEQ ID NO: 12 to SEQ ID NO: 22 or one of SEQ ID NO:48 to one of SEQ ID NO: 73.

Furthermore, the invention provides a strain of *Candida albicans* wherein a first copy of a polynucleotide having a nucleotide sequence selected from the group consisting of one of SEQ ID NO 1 to 11 is inactive and a second copy of the polynucleotide is under the control of a regulatable promoter.

Furthermore, the invention provides a strain of *Candida albicans* wherein a first copy of a polynucleotide having a nucleotide sequence selected from the group consisting of one of SEQ ID NO 1 to 11 is inactive and a second copy of the polynucleotide is under the control of a regulatable promoter, wherein said regulatable promoter is MET3.

The invention also provides a strain of *Candida albicans* comprising a nucleic acid molecule having a nucleotide sequence selected from one of SEQ ID NO: 1 to 11 under the control of a regulatable promoter.

Additionally provided herein is an isolated nucleic acid molecule having a nucleotide sequence encoding a polypeptide required for growth of *Candida albicans*, wherein said polypeptide includes an amino acid sequence of one of SEQ ID NO: 12 to 22.

The invention also provides a method for identifying essential polynucleotides in diploid fungal cells, said method having the steps of:

(a) inactivating a first copy of a polynucleotide in diploid fungal cells by recombination using a PCR-based polynucleotide disruption cassette, thereby providing heterozygous diploid fungal cells;

(b) modifying a second copy of the polynucleotide in the heterozygous diploid fungal cells by recombination using a PCR-based promoter swapping cassette including a nucleotide sequence encoding a regulatable promoter, such that expression of the second copy of the polynucleotide is regulated by said promoter;

(c) culturing said cells with a promoter suppressor; and (d) assessing growth of said cultured cells in comparison to control cells.

The invention also provides a method for identifying essential polynucleotides in diploid fungal cells, said method having the steps of:

(a) inactivating a first copy of a polynucleotide in diploid fungal cells by recombination using a PCR-based polynucleotide disruption cassette, thereby providing heterozygous diploid fungal cells;

(b) modifying a second copy of the polynucleotide in the heterozygous diploid fungal cells by recombination using a PCR-based promoter swapping cassette including a nucleotide sequence encoding a regulatable promoter, such that expression of the second copy of the polynucleotide is regulated by said promoter;

(c) culturing said cells with a promoter suppressor; and (d) assessing growth of said cultured cells in comparison to control cells, wherein said diploid fungal cells are *Candida albicans* cells, wherein said polynucleotide is a conserved gene, wherein said promoter is a MET3 promoter, wherein said promoter suppressor is methionine, wherein said promoter suppressor is cysteine, and/or wherein said promoter suppressor is both cysteine and methionine.

Additionally provided herein is a method for inducing drug hypersensitivity in diploid fungal cells, said method including the steps of:

(a) inactivating a first copy of an essential polynucleotide in diploid fungal cells by recombination using a PCR-based polynucleotide disruption cassette, thereby providing heterozygous diploid fungal cells;

(b) modifying the second copy of the polynucleotide in the heterozygous diploid fungal cells by recombination using a PCR-based promoter swapping cassette including a nucleotide sequence encoding a regulatable promoter, such that expression of the second copy of the polynucleotide is regulated by said promoter;

(c) culturing said cells with a promoter suppressor and with a drug; and (d) comparing the effects of said drug on the growth of said cells in comparison to control cells.

Additionally provided herein is a method for inducing drug hypersensitivity in diploid fungal cells, said method including the steps of:

(a) inactivating a first copy of an essential polynucleotide in diploid fungal cells by recombination using a PCR-based polynucleotide disruption cassette, thereby providing heterozygous diploid fungal cells;

(b) modifying the second copy of the polynucleotide in the heterozygous diploid fungal cells by recombination using a PCR-based promoter swapping cassette including a nucleotide sequence encoding a regulatable promoter, such that expression of the second copy of the polynucleotide is regulated by said promoter;

(c) culturing said cells with a promoter suppressor and with a drug; and (d) comparing the effects of said drug on the growth of said cells in comparison to control cells, wherein said diploid fungal cells are *Candida albicans* cells, wherein said polynucleotide is a conserved gene, wherein said promoter is a MET3 promoter, wherein said promoter suppressor is methionine, wherein said promoter suppressor is cysteine, and/or wherein said promoter suppressor is both cysteine and methionine.

Furthermore, the invention provides a method for titrating the expression of a fungal cell essential polynucleotide product, said method including the steps of:

(a) inactivating a first copy of a polynucleotide in diploid fungal cells by recombination using a PCR-based polynucleotide disruption cassette, thereby providing heterozygous diploid fungal cells;

(b) modifying the second copy of the polynucleotide in the heterozygous diploid fungal cells by recombination using a PCR-based promoter swapping cassette including a nucleotide sequence encoding a MET3 promoter, such that expression of the second copy of the polynucleotide is regulated by said promoter;

(c) adding varying concentrations of a promoter suppressor which modulates said MET3 promoter; and (d) correlating cell growth with each of said concentrations, thereby ascertaining the amount of promoter suppressor required to result in a particular reduction in cell growth.

Furthermore, the invention provides a method for titrating the expression of a fungal cell essential polynucleotide product, said method including the steps of:

(a) inactivating a first copy of a polynucleotide in diploid fungal cells by recombination using a PCR-based polynucleotide disruption cassette, thereby providing heterozygous diploid fungal cells;

(b) modifying the second copy of the polynucleotide in the heterozygous diploid fungal cells by recombination using a PCR-based promoter swapping cassette including a nucleotide sequence encoding a MET3 promoter, such that expression of the second copy of the polynucleotide is regulated by said promoter;

(c) adding varying concentrations of a promoter suppressor which modulates said MET3 promoter; and (d) correlating cell growth with each of said concentrations, thereby ascertaining the amount of promoter suppressor required to result in a particular reduction in cell growth, wherein the promoter suppressor is methionine, wherein the promoter suppressor is cysteine, and/or wherein the promoter suppressor is both cysteine and methionine.

Also provided herein is a nucleic acid molecule microarray having a plurality of nucleic acid molecules, said plurality including at least one nucleic acid molecule having a nucleotide sequence that is hybridizable under stringent conditions to a target nucleotide sequence selected from the group consisting of SEQ ID NO: 1 to SEQ ID NO: 11.

The invention also provides a fusion protein having a fragment of a first polypeptide fused to a second polypeptide, said fragment consisting of at least 5 consecutive residues of an amino acid sequence selected from one of SEQ ID NO: 12 to SEQ ID NO:22.

Additionally provided herein is a method of producing a polypeptide, said method comprising introducing into a cell, a vector comprising a promoter operably linked to a nucleotide sequence encoding a polypeptide consisting of an amino acid sequence selected from the group consisting of one of SEQ ID NO:12 to 22; and culturing the cell such that the nucleotide sequence is expressed.

Additionally, the invention provides a method for identifying a compound which modulates the activity of a polynucleotide product encoded by a nucleic acid molecule including a nucleotide sequence selected from the group consisting of one of SEQ ID NO: 1 to 11; said method including:

(a) contacting said polynucleotide product with a compound; and (b) determining whether said compound modulates the activity of said polynucleotide product.

Also included herein is a method for identifying a compound which modulates the activity of an essential polynucleotide product said method including the steps of:

(a) inactivating a first copy of a polynucleotide in diploid fungal cells by recombination using a PCR-based polynucleotide disruption cassette, thereby providing heterozygous diploid fungal cells;

(b) modifying the second copy of the polynucleotide in the heterozygous diploid fungal cells by recombination using a PCR-based promoter swapping cassette including a nucleotide sequence encoding a MET3 promoter, such that expression of the second copy of the polynucleotide is regulated by said promoter;

(c) contacting said cells with a compound; and (d) determining whether said compound modulates the activity of said polynucleotide product.

Additionally provided is a method of eliciting an immune response in an animal including introducing into the animal a composition including an isolated polypeptide, the amino acid sequence of which includes at least 6 consecutive residues of one of SEQ ID NO: 12 to 22 or one of SEQ ID NO: 48 to SEQ ID NO: 73.

Also included is a method of identifying a compound or binding partner that binds to a polypeptide having an amino acid sequence selected from the group consisting of one of SEQ ID NO: 12 to 22 or one of SEQ ID NO 48 to SEQ ID NO 73 or a fragment thereof, said method including:

(a) contacting the polypeptide or fragment thereof with a plurality of compounds or a preparation comprising one or more binding partners; and (b) identifying a compound or binding partner that binds to the polypeptide or fragment thereof.

Furthermore, provided herein is a method for identifying a compound having the ability to inhibit growth of *Candida albicans*, said method including the steps of:

(a) reducing the level or activity of a polynucleotide product encoded by a nucleic acid selected from group consisting of SEQ ID NO: 1 to 11 in *Candida albicans* cells relative to a wild type cells, wherein said reduced level is not lethal to said cells;

(b) contacting said cell with a compound; and (c) determining whether said compound inhibits the growth of said cells.

Furthermore, provided herein is a method for inhibiting growth of *Candida albicans* cells comprising contacting the cells with a compound that (i) reduces the level of or inhibits the activity of a nucleotide sequence selected from the group consisting of SEQ ID NO 1 to 11 or (ii) reduces the level of or inhibits the activity of a polynucleotide product encoded by a nucleotide sequence selected from the group consisting of SEQ ID NO: 1 to 11, alternatively wherein said compound is an antisense molecule.

Additionally included herein is a method for treating an infection of a subject by *Candida albicans* comprising administering a pharmaceutical composition including a therapeutically effective amount of a compound that reduces the activity or level of a polynucleotide product encoded by a nucleic acid including a sequence selected from the group consisting of SEQ ID NO: 1 toll and a pharmaceutically acceptable carrier to said subject.

Also provided is a pharmaceutical composition including a therapeutically effective amount of an agent which reduces the activity or level of a polynucleotide product encoded by a nucleic acid selected from the group consisting of SEQ ID NO 1 to 11 in a pharmaceutically acceptable carrier.

The present invention also provides structure coordinates of the homology model of the CaYLR100w polypeptide (SEQ ID NO:12) provided in FIG. 27. The complete coordinates are listed in Table 8. The model of the present invention further provide a basis for designing stimulators and inhibitors or antagonists of one or more of the biological functions of CaYLR100w, or of mutants with altered specificity.

The present invention also provides structure coordinates of the homology model of the CaYDR341c polypeptide (SEQ ID NO:13) provided in FIG. 30. The complete coordinates are listed in Table 9. The models present in this invention further provide a basis for designing stimulators and inhibitors or antagonists of one or more of the biological functions of CaYDR341c, or of mutants with altered specificity.

The present invention also provides structure coordinates of the homology model of the CaYOL010w polypeptide (SEQ ID NO:19) provided in FIG. 33. The complete coordinates are listed in Table 10. The models present in this invention further provide a basis for designing stimulators and inhibitors or antagonists of one or more of the biological functions of CaYOL010w, or of mutants with altered specificity.

BRIEF DESCRIPTION OF THE DRAWINGS

FIG. 1A provides an alignment between the encoded CaYLR100w polypeptide ("A"; SEQ ID NO:12) with P1__170752 ("B"; SEQ ID NO:23) and AAB19089 ("C"; SEQ ID NO:24); FIG. 1B provides an alignment between the encoded CaYDR341c polypeptide ("A"; SEQ ID NO:13) with P1__168653 ("B"; SEQ ID NO:25) and AAB94675 ("C"; SEQ ID NO:26); FIG. 1C provides an alignment between the encoded CaYLR022c polypeptide ("A"; SEQ ID NO:14) with P1__178714 ("B"; SEQ ID NO:27) and AAB42957 ("C"; SEQ ID NO:28); FIG. 1D provides an alignment between the encoded CaYOL077c polypeptide ("A"; SEQ ID NO:15) with P1__182338 ("B"; SEQ ID NO:29) and AAB62453 ("C"; SEQ ID NO:30); FIG. 1F provides an alignment between the encoded CaYGR145w polypeptide ("A"; SEQ ID NO:17) with P1__150732 ("B"; SEQ ID NO:33) and AAB95680 ("C"; SEQ ID NO:26); FIG. 1H provides an alignment between the encoded CaYOL010w polypeptide ("A"; SEQ ID NO:19) with P1__182291 ("B"; SEQ ID NO:37) and AAW60075 ("C"; SEQ ID NO:38); FIG. 1K provides an alignment between the encoded CaYRL009W polypeptide ("A"; SEQ ID NO:22) with P1__178703 ("B"; SEQ ID NO:43) and AAB43803 ("C"; SEQ ID NO:44); and FIG. 1L provides an alignment between the encoded CaYJR072c polypeptide ("A"; SEQ ID NO:45) with P1__149006 ("B"; SEQ ID NO:46) and AAG46965 ("C"; SEQ ID NO:47).

FIG. 2: alignment of *C. albicans* essential polypeptides with *A. fumigatus* sequences. FIG. 2A provides an alignment between the encoded CaYLR100w polypeptide ("A"; SEQ ID NO:12) with two versions of the analogous sequence in *A. fumigatus* ("B" and "C"; SEQ ID NO:48 and 49); FIG. 2B provides an alignment between the encoded CaYDR341c polypeptide ("A"; SEQ ID NO:13) with three versions of the analogous sequence in *A. fumigatus* ("B", "C", and "D"; SEQ ID NO:50, 51 and 52); FIG. 2C provides an alignment between the encoded CaYLR022c polypeptide ("A"; SEQ ID NO:14) with two versions of the analogous sequence in *A. fumigatus* ("B" and "C"; SEQ ID NO:53 and 54); FIG. 2D provides an alignment between the encoded CaYOL077c polypeptide ("A"; SEQ ID NO:15) with two versions of the analogous sequence in *A. fumigatus* ("B" and "C"; SEQ ID NO:55 and 56); FIG. 2E provides an alignment between the encoded CaYNL132w polypeptide ("A"; SEQ ID NO:16) with two versions of the analogous sequence in *A. fumigatus* ("B" and "C"; SEQ ID NO:57 and 58); FIG. 2F provides an alignment between the encoded CaYDR412w polypeptide ("A"; SEQ ID NO:18) with two versions of the analogous sequence in *A. fumigatus* ("B" and "C"; SEQ ID NO:62 and 63); FIG. 2G provides an alignment between the encoded CaYOR004w polypeptide ("A"; SEQ ID NO:20) with two versions of the analogous sequence in *A. fumigatus* ("B" and "C"; SEQ ID NO:64 and 65); FIG. 2H provides an alignment between the encoded CaYOR056c polypeptide ("A"; SEQ ID NO:21) with three versions of the analogous sequence in *A. fumigatus* ("B", "C", and "D"; SEQ ID NO:66, 67, and 68); FIG. 2I provides an alignment between the encoded CaYLR009w polypeptide ("A"; SEQ ID NO:22) with two versions of the analogous sequence in *A. fumigatus* ("B" and "C"; SEQ ID NO:69 and 70); FIG. 2J provides an alignment between the encoded CaYOL010w polypeptide ("A"; SEQ ID NO:19) with three versions of the analogous sequence in *A. fumigatus* ("B", "C", and "D"; SEQ ID NO:71, 72, and 73); FIG. 2K provides an alignment between the encoded CaYOL010w polypeptide ("A"; SEQ ID NO:19) two versions of the analogous sequence in *A. fumigatus* ("B" and "C"; SEQ ID NO:71 and 73); and FIG. 2L provides an alignment between the encoded CaYJR072c polypeptide ("A"; SEQ ID NO:45) with six versions of the analogous sequence in *A. fumigatus* ("B", "C", "D", "E", "F", and "G"; SEQ ID NO:74, 75, 76, 77, 78, and 79).

FIG. 5: Plasmid maps of pUMP and pAMP used for promoter swapping.

FIG. 11: The polynucleotide sequence (SEQ ID NO:1) and deduced amino acid sequence (SEQ ID NO:12) of the novel fungal essential gene, CaYLR100w (also referred to as FCG5), of the present invention. The CaYLR100w polypeptide (SEQ ID NO:12) is encoded by nucleotides 1 to 1038 of SEQ ID NO:1 and has a predicted molecular weight of 39.0 kDa. The conserved 3-keto sterol reductase catalytic residues, Y247 and S183, are denoted by light shading.

FIG. 12: The polynucleotide sequence (SEQ ID NO:2) and deduced amino acid sequence (SEQ ID NO:13) of the novel fungal essential gene, CaYDR341c (also referred to as FCG6), of the present invention. The CaYDR341c polypeptide (SEQ ID NO:13) is encoded by nucleotides 1 to 1866 of SEQ ID NO:2 and has a predicted molecular weight of 70.8 kDa. The conserved amino acids comprising the adenylate binding site of arginyl-tRNA synthetases, P151-H161, is denoted by light shading. The conserved amino acids comprising the Ω loop of arginyl-tRNA synthetases, S496-G502, is denoted by double underlining.

FIG. 13: The polynucleotide sequence (SEQ ID NO:3) and deduced amino acid sequence (SEQ ID NO:14) of the novel fungal essential gene, CaYLR022c (also referred to as FCG7), of the present invention. The CaYLR022c polypeptide (SEQ ID NO:14) is encoded by nucleotides 1 to 765 of SEQ ID NO:3 and has a predicted molecular weight of 29.2 kDa.

FIG. 14: The polynucleotide sequence (SEQ ID NO:4) and deduced amino acid sequence (SEQ ID NO:15) of the novel fungal essential gene, CaYOL077c (also referred to as FCG8), of the present invention. The CaYOL077c polypeptide (SEQ ID NO:15) is encoded by nucleotides 1 to 876 of SEQ ID NO:4 and has a predicted molecular weight of 34.0 kDa.

FIG. 15: The polynucleotide sequence (SEQ ID NO:5) and deduced amino acid sequence (SEQ ID NO:16) of the novel fungal essential gene, CaYNL132w (also referred to as FCG10), of the present invention. The CaYNL132w polypeptide (SEQ ID NO:16) is encoded by nucleotides 1 to 3126 of SEQ ID NO:5 and has a predicted molecular weight of 117.3 kDa.

FIG. 16: The polynucleotide sequence (SEQ ID NO:6) and deduced amino acid sequence (SEQ ID NO:17) of the novel fungal essential gene, CaYGR145w (also referred to as FCG12), of the present invention. The CaYGR145w polypeptide (SEQ ID NO:17) is encoded by nucleotides 1 to 2250 of SEQ ID NO:6 and has a predicted molecular weight of 85.0 kDa.

FIG. 17: The polynucleotide sequence (SEQ ID NO:7) and deduced amino acid sequence (SEQ ID NO:18) of the novel fungal essential gene, CaYDR412w (also referred to as FCG13), of the present invention. The CaYDR412w polypeptide (SEQ ID NO:18) is encoded by nucleotides 1 to 804 of SEQ ID NO:7 and has a predicted molecular weight of 31.3 kDa.

FIG. 18: The polynucleotide sequence (SEQ ID NO:8) and deduced amino acid sequence (SEQ ID NO:19) of the novel fungal essential gene, CaYOL010w (also referred to as FCG14), of the present invention. The CaYOL010w polypeptide (SEQ ID NO:19) is encoded by nucleotides 1 to 1113 of SEQ ID NO:8 and has a predicted molecular weight of 40.6 kDa. The conserved RNA 3'-terminal phosphate cyclase comprising the nucleotide binding site residues, R158-V168, are denoted by light shading.

FIG. 19: The polynucleotide sequence (SEQ ID NO:9) and deduced amino acid sequence (SEQ ID NO:20) of the novel fungal essential gene, CaYOR004w (also referred to as FCG15), of the present invention. The CaYOR004w polypeptide (SEQ ID NO:20) is encoded by nucleotides 1 to 771 of SEQ ID NO:9 and has a predicted molecular weight of 29.5 kDa.

FIG. 20: The polynucleotide sequence (SEQ ID NO:10) and deduced amino acid sequence (SEQ ID NO:21) of the novel fungal essential gene, CaYOR056c (also referred to as FCG16), of the present invention. The CaYOR056c polypeptide (SEQ ID NO:21) is encoded by nucleotides 1 to 1398 of SEQ ID NO:10 and has a predicted molecular weight of 52.6 kDa.

FIG. 21: The polynucleotide sequence (SEQ ID NO:11) and deduced amino acid sequence (SEQ ID NO:22) of the novel fungal essential gene, CaYLR009w (also referred to as FCG17), of the present invention. The CaYLR009w polypeptide (SEQ ID NO:22) is encoded by nucleotides 1 to 585 of SEQ ID NO:11 and has a predicted molecular weight of 23.1 kDa.

FIG. 23. Growth curve of strains caerg1Δ/$P_{MET3}$-CaERG1 (A) and fcg5Δ/$P_{MET3}$-FCG5 (B) in the absence and presence of methionine and cysteine. The results further demonstrate that CaYLR100w is a 3-keto sterol reductase. Additional experimental details may be found in Example 11, and described elsewhere herein.

FIG. 24. Incorporation of [$^{14}$C]-acetate into ergosterol and lanosterol in strains caerg1Δ/$P_{MET3}$-CaERG1 (A) and fcg5Δ/$P_{MET3}$-FCG5 (B) in the absence and presence of methionine and cysteine. The results further demonstrate that CaYLR100w is a 3-keto sterol reductase involved in C-4 sterol demethylation. Additional experimental details may be found in Example 11, and described elsewhere herein.

FIG. 25. Incorporation of radio-labeled arginine and leucine into proteins in cells of fcg6Δ/$P_{MET3}$-FCG6 in the absence and presence of methionine and cysteine. (A.) raw counts (cpm) of [3H]-leu and [3H]-arg in the absence and presence of methionine and cysteine. (B.) percent protein synthesis by using the counts of untreated cells as 100%. The results demonstrate that CaYDR341c is involved in whole cell protein synthesis. Additional experimental details may be found in Example 12, and described elsewhere herein.

FIG. 26. Sequence alignment of the conceptual translated sequence of CaYLR100w (FCG5) polypeptide of the present invention (SEQ ID NO:12) with porcine carbonyl reductase (Protein Data Bank entry 1HU4; Genbank Accession No. gi|15826210; SEQ ID NO:251). The alignment was used as the basis for building the CaYLR100w homology model described herein. The coordinates of the CaYLR100w model are provided in Table 8. Amino acids conserved from the short chain dehydrogenase/reductase (SDR) catalytic triad are highlighted with an asterisk (*). Homologous residues in the functional active site domain that are conserved by identity are illustrated in bold.

FIG. 29: Sequence alignment of the conceptual translated sequence of CaYDR341c (FCG6) polypeptide of the present invention (SEQ ID NO:13) with *Saccharomyces cerevisiae* arginyl-tRNA synthetase, (chain A) (Protein Data Bank entry 1F7U; Genbank Accession No. gi|14719542; SEQ ID NO:252). The alignment was used as the basis for building the CaYDR341c homology model described herein. The coordinates of the CaYDR341c model are provided in Table 9. Amino acids defining the ADP binding site region and Q loop in both the model and the 1F7U structure are highlighted with either asterisk ("*"), or plus ("+") sign, respectively. Homologous residues in the functional active site domain that are conserved by identity are illustrated in bold.

FIG. 32: Sequence alignment of the conceptual translated sequence of CaYOL010w (FCG14) of the present invention (SEQ ID NO:19) with *Escherichia coli* RNA 3'-terminal phosphate cyclase (Protein Data Bank entry 1QMH; Genbank Accession No. gi|12644279; SEQ ID NO:253). The alignment was used as the basis for building the CaYOL010w homology model described herein. The coordinates of the CaYOL010w model are provided in Table 10. Amino acids defining the nucleotide binding site region in both the model and the 1 QMH structure are highlighted with an asterisk ("*"). Homologous residues in the functional active site domain that are conserved by identity are illustrated in bold.

Figures 1, 1E:
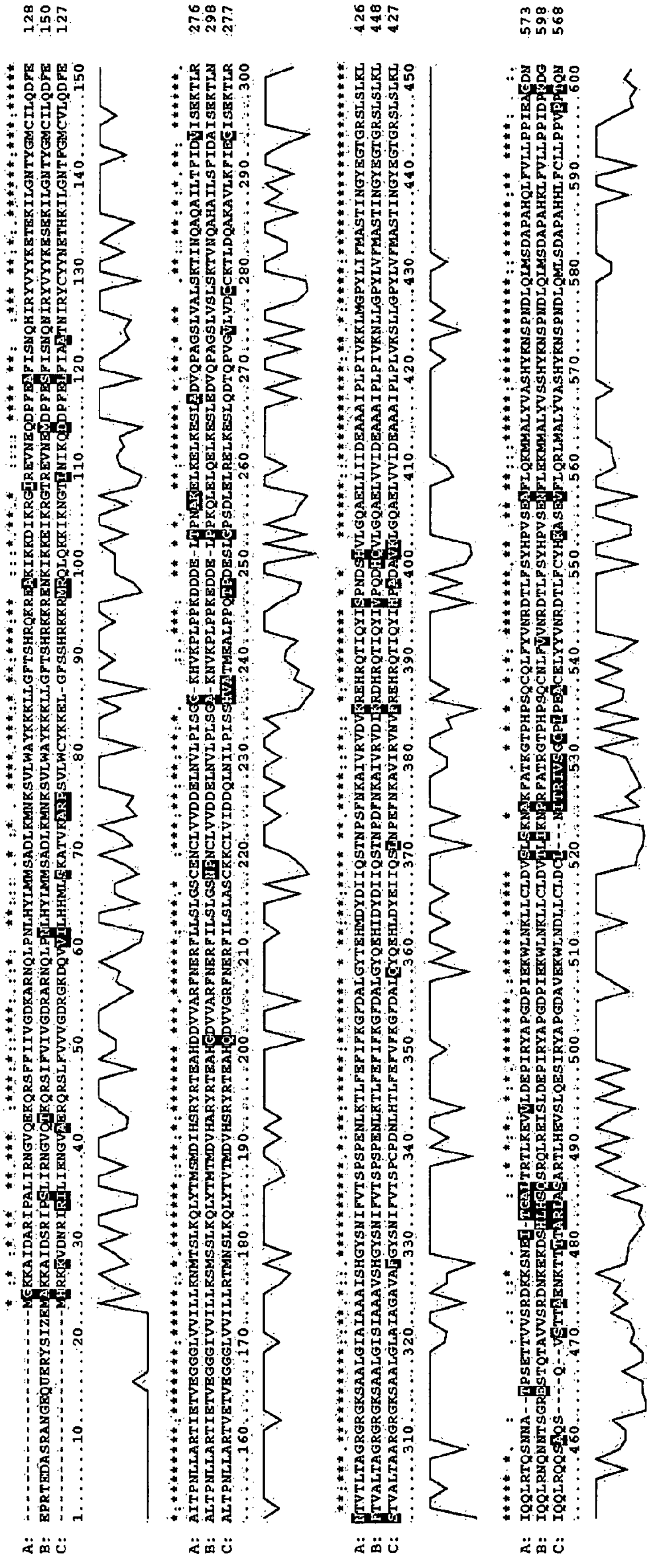
FIG. 1: alignment of *C. albicans* essential polypeptides with *S. cervisiae* and other sequences.
FIG. 1E provides an alignment between the encoded CaYNL132w polypeptide ("A"; SEQ ID NO:16) with P1__137216 ("B"; SEQ ID NO:31) and AAB93917 ("C"; SEQ ID NO:32)
Figure 1G:
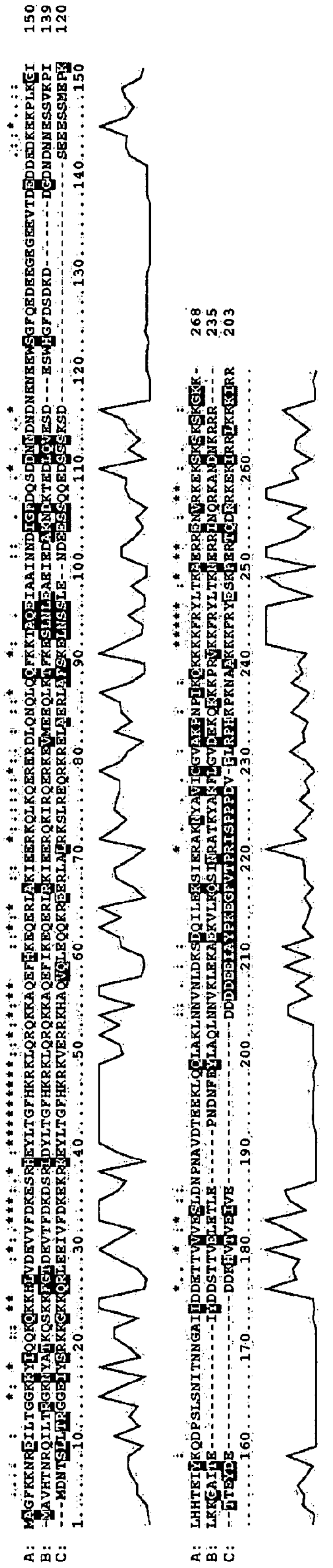
FIG. 1G provides an alignment between the encoded CaYDR412w polypeptide ("A"; SEQ ID NO:18) with P1__142340 ("B"; SEQ ID NO:35) and AAW33110 ("C"; SEQ ID NO:36)
Figure 1I:
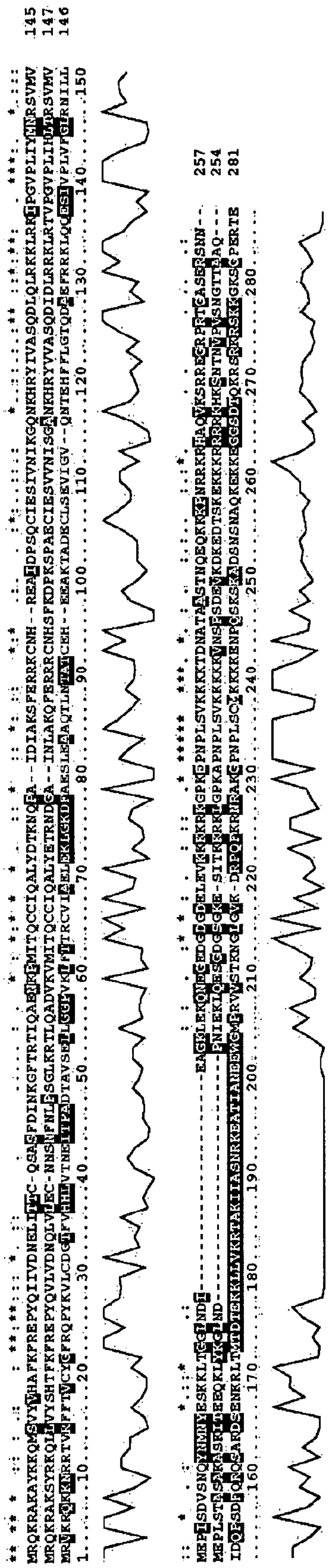
FIG. 1I provides an alignment between the encoded CaYOR004w polypeptide ("A"; SEQ ID NO:20) with P1__161797 ("B"; SEQ ID NO:39) and AAG48012 ("C"; SEQ ID NO:40)
Figure 1J:
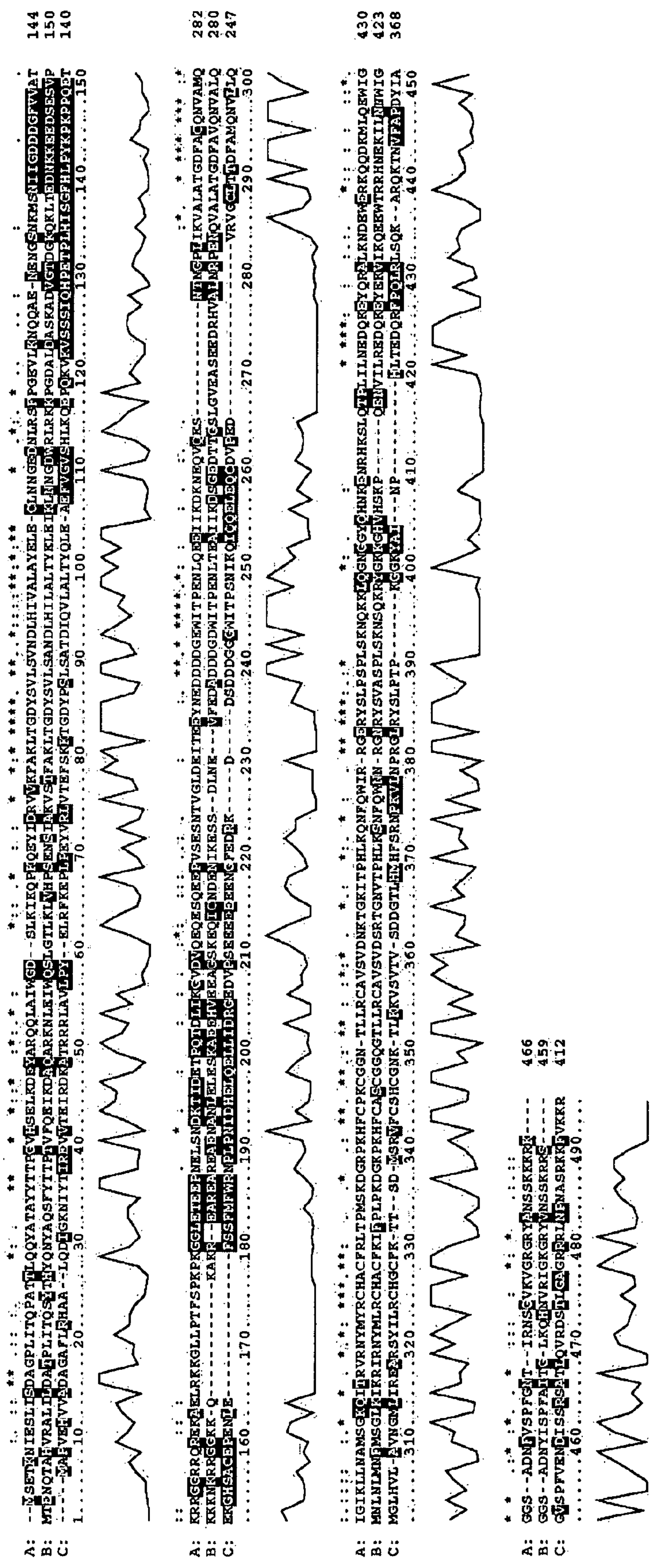
FIG. 1J provides an alignment between the encoded CaYOR056c polypeptide "A"; SEQ ID NO:21) with P1__182387 ("B"; SEQ ID NO:41) and AAB09929 ("C"; SEQ ID NO:42)

Table 1 provides a summary of the percent similarity between the *Candida albicans* CURFs of the present invention to the homologous sequences in *S. cerevisiae.*

Table 2 provides a summary of the percent identity to sequences homologous to the fungal CURFs of the present invention in addition to the functional annotation of the same.

Table 3 identifies the Genbank Accession No. and/or patent or patent application number of homologous sequences that aligning with the CURFs of the present invention.

Table 4 lists the SEQ ID Nos. for the PCR primers used for knockout experiments.

Table 5 lists the predicted function of the novel conserved essential fungal polypeptides of the present invention.

Table 6 lists the SEQ ID NOs of the MET3 promoter swapping primers which may be used to remove the promoters associated with the essential polynucleotides encoded by SEQ ID NO: 1 through to SEQ ID NO: 11.

Table 7 shows the results of experiments designed to assess the sensitivity of the MET3P-ERG1 construct to antifungal drugs.

Table 8 provides the structural coordinates of the three dimensional structure of the CaYLR100w (FCG5) polypeptide of the present invention (SEQ ID NO:12).

Table 9 provides the structural coordinates of the three dimensional structure of the CaYDR341c (FCG6) polypeptide of the present invention (SEQ ID NO:13).

Table 10 provides the structural coordinates of the three dimensional structure of the CaYOL010w (FCG14) polypeptide of the present invention (SEQ ID NO:19).

Table 11: Illustrates the preferred hybridization conditions for the polynucleotides of the present invention. Other hybridization conditions may be known in the art or are described elsewhere herein.

Table 12: Provides a summary of various conservative substitutions encompassed by the present invention.

DETAILED DESCRIPTION OF THE INVENTION

Nucleic Acids Encoding Essential Polynucleotides

The present invention is directed to polynucleotides that encode polypeptides that have been shown to be essential for *Candida albicans* growth and survival. Such polypeptides are referred to herein as Fungal Conserved Genes ("FCG"), or Conserved Unknown Reading Frames ("CURFs").

The present invention is also directed to the homologous polynucleotide and polypeptide sequences of the fungal conserved genes of the present invention in *A. fumigatus.*

In one embodiment, the invention provides nucleotide sequences encoding polypeptides that are essential to *Candida albicans*. A polynucleotide is generally considered essential when the viability of the organism is substantially coupled to or dependent on the expression of the polynucleotide. Such nucleotide sequences include, but are not limited to, SEQ ID NO: 1 through SEQ ID NO:11, fragments and homologues thereof.

The term "essential polynucleotides" refers to a nucleotide sequence that encodes a polynucleotide product (mRNA or protein) having a function which is required for cell viability. The term "essential protein" refers to a polypeptide that is encoded by an essential polynucleotide and has a function that is required for cell viability. Accordingly, a mutation that disrupts the function of the essential polynucleotide or essential proteins results in a loss of viability of cells harboring the mutation.

In another embodiment, the invention provides an isolated nucleic acid molecule having a nucleotide sequence encoding a polypeptide essential to *Candida albicans*, wherein said polypeptide comprises an amino acid sequence of one of SEQ ID NO: 12 to 22.

The invention also includes the complements of SEQ ID 1 to SEQ ID 11 and fragments thereof.

A nucleic acid molecule is said to be the "complement" of another nucleic acid molecule if two single-stranded polynucleotides anneal by bases-pairing. For example, 5'-ACG-3' pairs with its complement 3'-TGC-5'. 100% complementarity occurs when every nucleotide of one of the molecules is complementary to a corresponding nucleotide of the other.

The essential polynucleotides represent potential drug targets for *Candida albicans* and can be used individually or as a collection in various methods of drug screening herein described. The essential polynucleotides provided were found to be homologous with polynucleotides in *S. cervisiae* and/or other fungi and lacked significant similarity with human polynucleotides. Such an essential polynucleotide set can be conveniently investigated as a group in a drug screening program.

As used herein, the terms "gene" and "recombinant gene" refer to nucleic acid molecules comprising a nucleotide sequence encoding a polypeptide or a biologically active ribonucleic acid (RNA). The term can further include nucleic acid molecules comprising upstream, downstream and/or intron nucleotide sequences. The term "open reading frame (ORF)" means a series of nucleotide triplets coding for amino acids without any termination codons and the triplet sequence is translatable into protein using the codon usage information appropriate for a particular organism.

As used herein, the terms "polynucleotide", "nucleotide sequence", "nucleic acid molecule", "nucleic acid" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand. In the sequences herein, A is adenine, C is cytosine, G is guanine, T is thymine and N is G, A, C, or T(U). It is contemplated that where the polynucleotide is RNA, the T (thymine) in the sequences provide herein may be substituted with U (uracil).

By "isolated" polynucleotide(s) is intended a polynucleotide, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated polynucleotide molecules according to the present invention further include such molecules produced synthetically.

"Substantially purified" refers to nucleic or amino acid sequences that are removed from their natural environment, isolated or separated, and are at least 60% free, preferably 75% free, and most preferably 90% free from other components with which they are naturally associated.

The invention also provides a composition including SEQ ID NO: 1 to SEQ ID NO: 11 or fragments or variants thereof. A "composition including a given polynucleotide sequence or polypeptide sequence" refers broadly to any composition containing the given polynucleotide or polypeptide sequence. The composition may comprise a dry formulation or an aqueous solution. Compositions including polynucleotide sequences, and polynucleotide sequences encoding essential polynucleotides may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

Fragment nucleic acid molecules may encode significant portion(s) of, or most of, the polypeptides of the present invention. A fragment may comprise up to the entire length of the defined sequence, minus one nucleotide. For example, a fragment may comprise from 5 to 3128 contiguous nucleotides. Fragments of the target polynucleotides of the invention can also refer to portions of the coding regions of such nucleic acid molecules that encode functional domains such as signal sequences, extracellular domains, transmembrane domains and cytoplasmic domains.

Fragment nucleic molecules of the present invention also include primers and probes. "Probe" refers to polynucleotides encoding essential polynucleotides of the invention, their complements or fragments thereof, which are used to detect allelic or related polynucleotides. Probes are isolated oligonucleotides or polynucleotides attached to a detectable label or reporter molecule. Typical labels include radioactive isotopes, chemiluminescent agents and enzymes (see, e.g., Sambrook et al., Molecular Cloning: A Laboratory Manual, Cold Spring Harbor Laboratories (1989), which is incorporated herein by reference in its entirety).

Probes and primers as used in the present invention typically comprise at least 10 contiguous nucleotides of a known sequence. In order to enhance specificity, longer probes and primers may also be employed, such as probes and primers that comprise at least 10, 20, 25, 30, 40, 50, 60, 70, 80, 90, 100, or at least 150 consecutive nucleotides of the disclosed polynucleotides. Probes and primers may be considerably longer than these examples, and it is understood that any length supported by the specification including the tables, FIGs and Sequence Listing may be used.

The primers of the invention may be used in conjunction with the polymerase chain reaction (PCR). PCR exploits certain features of DNA replication. DNA polymerase uses single-stranded DNA as a template for the synthesis of a complementary new strand. These single-stranded DNA templates can be produced by heating double-stranded DNA to temperatures near boiling. DNA polymerase also requires a small section of double-stranded DNA to initiate ("prime") synthesis. Therefore, the starting point for DNA synthesis can be specified by supplying a PCR primer that anneals to the template at that point. Methods for designing PCR primers are well-known in the art. (See, for example, Innis et al., PCR Protocols: A Guide to Methods and Applications, Academic, N.Y. (1990), herein incorporated by reference). Computer programs may also be used to design PCR primers. For example, Primer3.

In addition to the nucleotide sequences of *Candida albicans* described above, homologues of these target polynucleotide sequences in other species can be identified and isolated by molecular biological techniques well-known in the art and without undue experimentation.

To isolate homologous target polynucleotides, the *C. albicans* target polynucleotide sequences described above can be labeled and used to screen a cDNA library constructed from mRNA obtained from the organism of interest. Hybridization conditions should be of a lower stringency when the cDNA library is derived from an organism different from the type of organism from which the labeled sequence was derived. cDNA screening can also identify clones derived from alternatively spliced transcripts in the same or different species. Alternatively, the labeled fragment can be used to screen a genomic library derived from the organism of interest, again, using appropriately stringent conditions. Reduced stringency conditions will be well-known to those of skill in the art and will vary predictably depending on the specific organisms from which the library and the labeled sequences are derived. (See, for example, Sambrook et al., supra)

Further, a homologous target polynucleotide sequence can be isolated by performing a polymerase chain reaction (PCR) using two degenerate oligonucleotide primer pools designed on the basis of amino acid sequences within the target polynucleotide of interest. The template for the reaction can be cDNA obtained by reverse transcription of mRNA prepared from the organism of interest. The PCR product can be subcloned and sequenced to ensure that the amplified sequences represent the sequences of a homologous target polynucleotide sequence.

Alternatively, homologous target polynucleotides or polypeptides may be identified by searching a dataset to identify sequences having a desired level of homology to an essential polynucleotide of the invention. A variety of such databases are available to those skilled in the art including GenBank. In various embodiments, the databases are screened to identify nucleic acids with at least 97%, at least 95%, at least 90%, at least 85%, at least 80%, at least 70%, at least 60%, at least 50%, at least 40%, or at least 30% identity to an essential polynucleotide of the invention.

"Homologous sequences" or "homologues" as used herein are those sequences in which a first amino acid or nucleotide sequence contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity when optimally aligned. For example, amino acid or nucleotide sequences which share common structural domains have at least about 30-40% homology, preferably 40-50% homology, more preferably 50-60%, and even more preferably 60-70%, 70-80%, or 80-90% or 95% homology across the amino acid sequences of the domains and contain at least one and preferably two structural domains or motifs. Furthermore, amino acid or nucleotide sequences which share at least 30-40%, preferably 40-50%, more preferably 50-60%, 60-70%, 70-80%, or 80-90% or 95% homology and share a common functional activity are homologous.

In one embodiment, the invention provides for homologues of the essential polynucleotides of the invention encoded by SEQ ID NO: 1 through to SEQ ID NO: 11 in species including, but not limited to, *Aspergillus fumigatus, Aspergillus falvus, Aspergillus niger, Coccidiodes immitis, Cryptoccoccus neoformans, Histoplasma capsulatum, Phytophthora infestans, Puccinia seconditii, Pneumocystis carinii* or any species falling within the genera of any of the above species. Other yeasts in the genera of *Candida, Saccharomyces, Schizosaccharomyces Sporobolomyces, Torulopsis, Trichosporon, Tricophyton, Dermatophytes, Microsproum, Wickerhamia, Ashbya, Blastomyces, Citeromyces, Crebrothecium, Cryptococcus, Debaryomyces, Endomycopsis, Geotrichum, Hansenula, Kloecker, Kluveromyces, Libomyces, Pichia, Rhodosporidium, Rhodotorula*, and *Yarrowia* are also contemplated.

Preferably, homologues of the essential polynucleotides of the invention encoded by SEQ ID NO: 1 through to SEQ ID NO: 11 are from *Absidia corymbigera, Aspergillus flavis, Aspergillus fumigatus, Aspergillus niger, Botrytis cinerea, Candida dublinensis, Candida glabrata, Candida krusei, Candia parapsilopsis, Candia tropicalis, Coccidioides immitis, Cryptococcus neoformans, Erysiphe graminis, Exophalia dermatiditis, Fusarium osysproum, Histoplasma capsulatum, Magnaporthe grisea, Mucor rouxii, Pneumocystis carinii, Puccinia graminis, Puccinia recodita, Rhizomucor pusillus, Puccinia striiformis, Rhizopus arrhizus, Septoria avenae, Septoria nodorum, Septoria triticii, Tilletia controversa,*

*Tilletia tritici, Trichospoon beigelii* and *Ustilago maydis*. Particularly preferred are homologues from *Aspergillus fumigatus*.

The invention also provides nucleotide sequences that are hybridizable under stringent conditions to the polynucleotides of SEQ ID NO: 1 through SEQ ID NO: 11 and that are of a species other than *Saccharomyces cerevisiae* and *Candida albicans*.

The term "stringent conditions" or "hybridizable under stringent conditions" includes reference to conditions under which a probe will selectively hybridize to its target sequence, to a detectably greater degree than to other sequences (e.g., at least two-fold over background). Stringent conditions are sequence-dependent and will be different in different circumstances. By controlling the stringency of the hybridization and/or washing conditions, target sequences can be identified which are 100% complementary to the probe. Alternatively, stringency conditions can be adjusted to allow some mismatching in sequences so that lower degrees of similarity are detected. Generally, a probe is less than about 1000 nucleotides in length, optionally less than 500 nucleotides in length.

Typically, stringent conditions will be those in which the salt concentration is less than about 1.5 M Na+ ion, typically about 0.01 to 1.0 M Na+ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267-284 (1984): $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2, "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995), herein incorporated by reference. The duration of hybridization is generally less than about 24 hours, usually about 4 to about 12 hours.

Additional examples of stringency conditions are shown in Table 11 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 11

| Stringency Condition | Polynucleotide Hybrid± | Hybrid Length (bp)‡ | Hyridization Temperature and Buffer† | Wash Temperature and Buffer† |
|---|---|---|---|---|
| A | DNA:DNA | >or equal to 50 | 65° C.; 1xSSC -or- 42° C.; 1xSSC, 50% formamide | 65° C.; 0.3xSSC |
| B | DNA:DNA | <50 | Tb*; 1xSSC | Tb*; 1xSSC |
| C | DNA:RNA | >or equal to 50 | 67° C.; 1xSSC -or- 45° C.; 1xSSC, 50% formamide | 67° C.; 0.3xSSC |
| D | DNA:RNA | <50 | Td*; 1xSSC | Td*; 1xSSC |
| E | RNA:RNA | >or equal to 50 | 70° C.; 1xSSC -or- 50° C.; 1xSSC, 50% formamide | 70° C.; 0.3xSSC |
| F | RNA:RNA | <50 | Tf*; 1xSSC | Tf*; 1xSSC |
| G | DNA:DNA | >or equal to 50 | 65° C.; 4xSSC -or- 45° C.; | 65° C.; 1xSSC |

TABLE 11-continued

| Stringency Condition | Polynucleotide Hybrid± | Hybrid Length (bp)‡ | Hyridization Temperature and Buffer† | Wash Temperature and Buffer† |
|---|---|---|---|---|
| | | | 4xSSC, 50% formamide | |
| H | DNA:DNA | <50 | Th*; 4xSSC | Th*; 4xSSC |
| I | DNA:RNA | >or equal to 50 | 67° C.; 4xSSC -or- 45° C.; 4xSSC, 50% formamide | 67° C.; 1xSSC |
| J | DNA:RNA | <50 | Tj*; 4xSSC | Tj*; 4xSSC |
| K | RNA:RNA | >or equal to 50 | 70° C.; 4xSSC -or- 40° C.; 6xSSC, 50% formamide | 67° C.; 1xSSC |
| L | RNA:RNA | <50 | Tl*; 2xSSC | Tl*; 2xSSC |
| M | DNA:DNA | >or equal to 50 | 50° C.; 4xSSC -or- 40° C. 6xSSC, 50% formamide | 50° C.; 2xSSC |
| N | DNA:DNA | <50 | Tn*; 6xSSC | Tn*; 6xSSC |
| O | DNA:RNA | >or equal to 50 | 55° C.; 4xSSC -or- 42° C.; 6xSSC, 50% formamide | 55° C.; 2xSSC |
| P | DNA:RNA | <50 | Tp*; 6xSSC | Tp*; 6xSSC |
| Q | RNA:RNA | >or equal to 50 | 60° C.; 4xSSC -or- 45° C.; 6xSSC, 50% formamide | 60° C.; 2Xssc |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucletotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity.Methods of aligning two or more polynucleotide sequences and/or determining the percent identity between two polynucleotide sequences are well known in the art (e.g., MegAlign program of the DNA*Star suite of programs, etc).

†SSPE (1xSSPE is 0.15M NaCl, 10 mM NaH2PO4, and 1.25 mM EDTA, pH 7.4) can be substituted for SSC (1xSSC is 0.15M NaCl anmd 15 mM sodium citrate) in the hybridization and wash buffers; washes are performed for 15 minutes after hybridization is complete. The hydridizations and washes may additionally include 5X Denhardt's reagent, .5-1.0% SDS, 100 ug/ml denatured, fragmented salmon sperm DNA, 0.5% sodium pyrophosphate, and up to 50% formamide.

*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 +16.6($log_{10}$[Na+]) + 0.41 (% G + C) − (600/N), where N is the number of bases in the hybrid, and [Na+] is the concentration of sodium ions in the hybridization buffer ([NA+] for 1xSSC = .165 M).

±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

In another embodiment, the present invention encompasses isolated nucleic acids comprising a nucleotide sequence that has at least 40%, 45%, 55%, 60%, 65%, 70%, 75%, 80%, 85%, 90%, 95%, 98% or more nucleotide sequence identity to the nucleotide sequences set forth in SEQ ID NO 1 to SEQ ID NO 11. The nucleotide sequences of the invention also include nucleotide sequences that encode polypeptides having at least 25%, 30%, 40%, 50%, 55%, 60%, 65%, 70%, 75%, 80%, 85%, 90%, 95%, 98% or higher amino acid sequence identity or similarity to the amino acid sequences set forth in SEQ ID NO 12 to SEQ ID NO 22.

The following terms are used to describe the sequence relationships between a polynucleotide or polypeptide of the present invention with a reference polynucleotide or a polypeptide to determine sequence identity: (a) "reference sequence", (b) "comparison window", (c) "sequence identity", and (d) "percentage of sequence identity".

As used herein, "reference sequence" is a defined sequence used as a basis for sequence comparison with a polynucleotide or a polypeptide of the present invention. A reference sequence may be a subset or the entirety of a specified sequence; for example, as a segment of a full-length cDNA or polynucleotide sequence, or the complete cDNA or polynucleotide sequence.

As used herein. "sequence identity" or "identity" in the context of two nucleic acid or polypeptide sequences includes reference to the nucleotides or residues in the two sequences which are the same when aligned for maximum correspondence over a specified comparison window. As used herein, "comparison window" includes reference to a contiguous and specified segment of a polynucleotide or polypeptide sequence, wherein the polynucleotide or polypeptide sequence may be compared to a reference sequence and wherein the portion of the polynucleotide or polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide or polypeptide sequence, a gap penalty is typically introduced and is subtracted from the number of matches.

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have “sequence similarity” or “similarity”. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4: 11-17 (1988), e.g., as implemented in the program PC/GENE (Intelligenetics, Mountain View, Calif., USA).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table 12 below.

TABLE 12

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple polynucleotides with related function and assessing the relative penalty of each substitution to proper polynucleotide function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes, may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J Mol. Biol.* 48: 443 (1970); by the search for similarity method of Pearson and Lipman, *Proc. Nad. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5. 151.153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994). These references are herein incorporated.

Unless otherwise stated, sequence identity/similarity values provided herein refer to the value obtained using the Smith-Waterman algorithm (supra) on a DeCypher system using default parameters (Matrix=Blosum62, Gap Opening penalty: 12, Gap Extension Penalty: 2).

Additionally, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in herein (SEQ ID NO:12-22) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off, % Identity for Alignment Delay-40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

Although the nucleotide sequences and amino acid sequences from *S. cervisiae* which are homologues of the essential polynucleotide encoded by SEQ ID NO: 1 to SEQ ID NO: 11 is mostly published, uses of such homologues in *S. cerevisae* in drug screening are not known and are thus specifically provided by the invention. To use such nucleotide and/or amino acid sequences of *S. cervisiae*, public databases, such as Stanford Genomic Resources or Proteome may be used to identify and retrieve the sequences.

The nucleic acid molecules of the invention also include peptide nucleic acids (PNAs), or derivative molecules such as phosphorothioate, phosphotriester, phosphoramidate, and methylphosphonate, that specifically bind to single-stranded DNA or RNA in a base pair-dependent manner (Zamecnik, P. C. et al., *Proc. Natl. Acad. Sci.* 75:280 284 (1978); Goodchild, P. C., et al., *Proc. Natl. Acad. Sci.* 83:4143-4146).

PNA molecules comprise a nucleic acid oligomer to which an amino acid residue, such as lysine, and an amino group have been added. These small molecules, also designated anti-polynucleotide agents, stop transcript elongation by binding to their complementary (template) strand of nucleic acid (Nielsen, P. E. et al., *Anticancer Drug Des* 8:53-63 (1993)). For example, reviews of methods for synthesis of DNA, RNA and their analogues can be found in: Oligonucleotides and Analogues, eds. F. Eckstein, IRL Press, New York (1991); Oligonucleotide Synthesis, ed. M. J. Gait, IRL Press, Oxford, England (1984). Additionally, methods for antisense RNA technology are described in U.S. Pat. Nos. 5,194,428 and 5,110, 802. A skilled artisan can readily obtain these classes of nucleic acid molecules using the herein described polynucleotide sequences; see, for example, *Innovative and Perspectives in Solid Phase Synthesis*, Egholm, et al. pp 325-328 (1992) or U.S. Pat. No. 5,539,082.

As will be appreciated by the skilled practitioner, should the amino acid fragment comprise an antigenic epitope, for example, biological function per se need not be maintained. The terms fungal essential polypeptide and fungal essential protein are used interchangeably herein to refer to the encoded product of the fungal essential nucleic acid sequence according to the present invention.

It is another aspect of the present invention to provide modulators of the fungal essential polypeptides and fungal essential peptide targets which can affect the function or activity of fungal essential polynucleotides in a cell in which fungal essential polynucleotide function or activity is to be modulated or affected. In addition, modulators of fungal essential polypeptides can affect downstream systems and molecules that are regulated by, or which interact with, fungal essential polypeptides in the cell. Modulators of fungal essential polypeptides include compounds, materials, agents, drugs, and the like, that antagonize, inhibit, reduce, block, suppress, diminish, decrease, or eliminate fungal essential polypeptides function and/or activity. Such compounds, materials, agents, drugs and the like can be collectively termed “antagonists”. Alternatively, modulators of fungal essential polypeptides include compounds, materials, agents, drugs, and the like, that agonize, enhance, increase, augment, or amplify fungal essential polypeptides function in a cell. Such compounds, materials, agents, drugs and the like can be collectively termed “agonists”.

As used herein the terms “modulate” or “modulates” refer to an increase or decrease in the amount, quality or effect of a particular activity, DNA, RNA, or protein. The definition of “modulate” or “modulates” as used herein is meant to encompass agonists and/or antagonists of a particular activity, DNA, RNA, or protein.

The present invention is also directed to polynucleotides encoding the fungal essential polynucleotides of the present invention lacking a start methionine. In addition, polypeptides of the invention may also include an initial modified methionine residue, in some cases as a result of host-mediated processes. It is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In specific embodiments, the present invention is directed to the following polynucleotides which encode fungal essential polypeptides of the present invention lacking a start methionine: nucleotides 4 to 1038 of SEQ ID NO:1 (CaYLR100w); nucleotides 4 to 1866 of SEQ ID NO:2 (CaYDR341c); nucleotides 4 to 765 of SEQ ID NO:3 (CaYLR022c); nucleotides 4 to 876 of SEQ ID NO:4 (CaYOL077c); nucleotides 4 to 3126 of SEQ ID NO:5 (CaYNL132w); nucleotides 4 to 2250 of SEQ ID NO:6 (CaYGR145w); nucleotides 4 to 804 of SEQ ID NO:7 (CaYDR412w); nucleotides 4 to 1113 of SEQ ID NO:8 (CaYOL010w); nucleotides 4 to 771 of SEQ ID NO:9 (CaYOR004w); nucleotides 4 to 1398 of SEQ ID NO:10 (CaYOR056c); and/or nucleotides 4 to 585 of SEQ ID NO:11 (CaYLR009w).

In another embodiment, the present invention is directed to representative clones containing all or most of the sequence for SEQ ID NO:1 to SEQ ID NO:11 (encoding the polypeptides provided as SEQ ID NO:12 to SEQ ID NO:22) that were deposited with the American Type Culture Collection (“ATCC”). The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid (Life Technologies) using the NotI and SalI restriction endonuclease cleavage sites.

Polypeptides

The polypeptides of the invention used and encompassed in the methods and compositions of the present invention include those polypeptides that are encoded by the essential polynucleotide sequences as described above, such as the essential polynucleotide sequences set forth in SEQ ID NO: 1 through to SEQ ID NO: 11. The amino acid sequences of SEQ ID NO: 12 to SEQ ID NO: 22 are deduced using the codon usage of *C. albicans* from the respective nucleotide sequences of SEQ ID NO: 12 to SEQ ID NO: 22. However, when expressed in an organism other than *C. albicans*, protein products for the target polynucleotides having the amino acid sequences of SEQ ID NO: 12 to 22 may be encoded by nucleotide sequences that are translated using the universal genetic code. One of skill in the art would know the modifications that are necessary to accommodate for such a difference in codon usage.

As used herein, the term “polypeptide” refers to any peptide or protein including two or more amino acids joined to each other by peptide bonds or modified peptide bonds, i.e., peptide isosteres. “Polypeptide” refers to both short chains, commonly referred to as peptides, oligopeptides or oligomers, and to longer chains, generally referred to as proteins. "Polypeptides" may contain amino acids other than the 20 gene-encoded amino acids. "Polypeptides" include amino acid sequences modified either by natural processes, such as posttranslational processing, or by chemical modification techniques which are well-known in the art. Such modifications are well described in basic texts and in more detailed monographs, as well as in research literature.

Modifications can occur anywhere in a polypeptide, including the peptide backbone, the amino acid side-chains and the amino or carboxyl termini. A given polypeptide may contain many types of modifications. Polypeptides may be branched, or cyclic, with or without branching. Cyclic, branched and branched-cyclic polypeptides may result from posttranslational natural processes or may be made by synthetic methods. Modifications include but are not limited to acetylation, acylations, amidation, covalent attachment of flavin, disulfide bond formation, formation of covalent cross-links, and glycosylation. See, for instance, *Proteins—structure and molecular properties,* $2^{nd}$ Ed., T. E. Creighton, W.H. Freeman and Company, New York (1993); F. Wold, *Post-translational protein modifications: perspectives and prospects*, pgs 1-12 in Posttranslational covalent modification of proteins, B. C. Johnson, Ed., Academic Press, New York (1983); S. Seifter and S. Englard, *Analysis for protein modifications and nonprotein cofactors,* 182 *Methods of Enzymology* 626 (1990); and S. I. Rattan et al., *Protein synthesis, posttranslational modifications, and aging,* 663 Ann NY Acad Sci 48 (1992).

In addition, however, the methods and compositions of the invention also use and encompass proteins and polypeptides that represent functionally equivalent polynucleotide products. Such functionally equivalent polynucleotide products include, but are not limited to, natural variants of the polypeptides having an amino acid sequence set forth in SEQ ID NO; 12 to SEQ ID NO: 22.

The term "variant" (or analog) as used herein is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence. A typical variant of a polypeptide differs in amino acid sequence from another, reference polypeptide. Generally, differences are limited so that the sequence of the reference polypeptide and the variant are closely similar overall and, in many regions, identical. A variant and reference polypeptide may differ in amino acid sequence by one or more substitutions, additions and/or deletions in any combination.

Variants of the defined sequence and fragments thereof also form part of the present invention. Preferred variants are those that vary from the reference sequence by conservative amino acid substitutions, i.e., those that substitute a residue with another of like characteristics. Typical conservative substitutions are among Ala, Val, Leu and Ile; among Ser and Thr; among the acid residues Asp and Glu; among Asn and Gln; among the basic residues Lys and Arg; and among the aromatic residues Phe and Tyr.

The term "functionally equivalent", as utilized herein, refers to a polypeptide capable of exhibiting a substantially similar in vivo activity as the *Candida albicans* essential polypeptide encoded by one or more of the essential polynucleotide sequences described herein. Alternatively, when utilized as part of assays described herein below, the term "functionally equivalent" can refer to peptides or polypeptides that are capable of interacting with other cellular or extracellular molecules in a manner substantially similar to the way in which the corresponding portion of the target polynucleotide product would interact with such other molecules. Preferably, the functionally equivalent essential polynucleotide polypeptide of the invention are also the same size or about the same size as a essential polynucleotide polypeptide encoded by one or more of the essential polynucleotide sequences described herein.

Fragments of the essential polynucleotide polypeptides are also included in the invention. A fragment is a polypeptide having an amino acid sequence that is entirely the same as part, but not all, of the amino acid sequence of the aforementioned essential polynucleotide polypeptides. As with essential polynucleotide polypeptides, fragments may be "free-standing" or comprised within a larger polypeptide of which they form a part or region, most preferably as a single continuous region.

Preferred fragments of the invention are biologically active fragments. The term "active" refers to those forms of the polypeptide that retain the biologic and/or immunologic activities of any naturally occurring polypeptide. According to the invention, the terms "biologically active" or "biological activity" refer to a protein or peptides having structural, regulatory or biochemical functions of a naturally occurring molecule. Likewise "biologically active" or "biological activity" refers to the capability of the natural, recombinant or synthetic essential polynucleotide peptide, or any peptide thereof, to include a specific biological response in appropriate animals or cells and to bind with specific antibodies.

Additionally, preferred polypeptides are those containing fragments including at least about a contiguous 5 amino acid region, more preferably including at least a contiguous 10, 40, 50, 75 or 125 amino acid region of a protein or fragment thereof of the present invention. In another preferred embodiment, the proteins of the present invention include between about 10 and about 25 contiguous amino acid region, more preferably between about 20 and about 50 contiguous amino acid region and even more preferably between about 40 and about 80 contiguous amino acid region.

Such fragments are conventionally employed by themselves or with unrelated proteins as part of fusion proteins. As used herein, a fusion protein comprises all or part (preferably a biologically active part) of a polypeptide of the invention operably linked to a heterologous or unrelated polypeptide. The unrelated polypeptide may be a detectable label for enabling detection of the polypeptide of the invention or a matrix-binding domain for immobilizing the fusion protein. The fusion proteins can be produced by standard recombinant DNA techniques.

Possible fusion protein expression vectors include but are not limited to vectors incorporating sequences that encode beta-galactosidease and trpE fusions, maltose-binding protein fusions (pMal series; New England Biolabs), glutathionie-S-transferase fusions (pGEX series; Pharmacia) polyhistidine fusions (PET series; Novagen Inc., Madison, Wis.), and thioredoxin fusion s(pTrxFus; Invitrogen, Carlsbad, Calif.).

Expression vectors may be constructed that will express a fusion protein including any protein or polypeptide of the present invention including fragments or variants thereof. Such fusion proteins can be used, e.g., to raise antisera against the protein, to study the biochemical properties of the protein, to engineer a protein exhibiting different immunological or functional properties, to aid in the identification or purification of the protein, to improve the stability of a recombinantly-expressed protein or as therapeutic agents. Methods are well-known in the art for constructing expression vectors encoding these and other fusion proteins.

The essential polynucleotide polypeptides of the invention can be prepared in any suitable manner. The polypeptides include isolated naturally occurring polypeptides, recombinantly produced polypeptides, synthetically produced polypeptides and polypeptides produced by a combination of these methods. These methods are well understood in the art.

The present invention also provides for homologous proteins. A homologue protein may be derived from, but not limited to, *Aspergillus fumigatus, Aspergillus* falvus, *Aspergillus niger, Coccidiodes immitis, Cryptoccoccus neoformans, Histoplasma capsulatum, Phytophthora infestans, Puccinia seconditii, Pneumocystis carinii* or any species falling within the genera of any of the above species. Other yeasts in the genera of *Candida, Saccharomyces, Schizosaccharomyces Sporobolomyces, Torulopsis, Trichosporon, Tricophyton, Dermatophytes, Microsproum, Wickerhamia, Ashbya, Blastomyces, Citeromyces, Crebrothecium, Cryptococcus, Debaryomyces, Endomycopsis, Geotrichum, Hansenula, Kloecker, Kluveromyces, Libomyces, Pichia* are also contemplated.

Preferably, homologues of the polypeptides of the invention encoded by SEQ ID NO: 1 through to SEQ ID NO: 11 are from *Absidia corymbigera, Aspergillus flavis, Aspergillus fumigatus, Aspergillus niger, Botrytis cinerea, Candida dublinensis, Candida glabrata, Candida krusei, Candia parapsilopsis, Candia tropicalis, Coccidioides immitis, Cryptococcus neoformans, Erysiphe graminis, Exophalia dermatiditis, Fusarium osysproum, Histoplasma capsulatum, Magnaporthe grisea, Mucor rouxii, Pneumocystis carinii, Puccinia graminis, Puccinia recodita, Rhizomucor pusillus, Puccinia striiformis, Rhizopus arrhizus, Septoria avenae, Septoria nodorum, Septoria triticii, Tilletia controversa, Tilletia tritici, Trichospoon beigelii* and *Ustilago maydis fumigatus*.

Particularly preferred homologues of the present invention are from *Aspergillus fumigatus*. Particularly preferred homologous have an amino acid sequence comprising SEQ ID NO: 48 to SEQ ID NO: 73.

Desirably, a homologue can be derived by using one or more of the disclosed sequences to define a pair of primers to isolate the homologue-encoding nucleic acid molecules from any desired species. Such molecules can be expressed to yield protein homologues by recombinant means.

A homologue of an essential polynucleotide polypeptide is a polypeptide having an amino acid sequence that is homologous to a natural essential polynucleotide polypeptide amino acid sequence that a nucleic acid sequence encoding the homologue is capable of hybridizing under reduced and/or high stringent conditions to a nucleic acid sequence encoding the natural essential polynucleotide polypeptide amino acid sequence disclosed herein. Preferably the homologue retains one or more biological activities of essential polynucleotide.

Essential polynucleotide protein homologues of the invention include allelic variations of the natural polynucleotide encoding the essential polynucleotide protein. A "natural" polynucleotide is one that is found in nature. Essential polynucleotide protein homologues can be produced using techniques known in the art, including but not limited to direct modifications to a polynucleotide encoding a protein using, for example, classic or recombinant DNA techniques to effect random or targeted mutapolynucleotidesis.

The present invention encompasses the essential polynucleotide proteins that have undergone posttranslational modification. Such modification can include, for example, glycosylation (e.g., including the addition of N-linked and/or O-lined oligosaccharides) or post translation conformation changes or post translation deletions.

The present invention is also directed to polypeptides lacking a start methionine. It is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In specific embodiments, the present invention is directed to the following polypeptides which correspond to fungal essential polypeptides of the present invention lacking a start methionine: amino acids 2 to 346 of SEQ ID NO:12 (CaYLR100w); amino acids 2 to 622 of SEQ ID NO:13 (CaYDR341c); amino acids 2 to 255 of SEQ ID NO:14 (CaYLR022c); amino acids 2 to 292 of SEQ ID NO:15 (CaYOL077c); amino acids 2 to 1042 of SEQ ID NO:16 (CaYNL132w); amino acids 2 to 750 of SEQ ID NO:17 (CaYGR145w); amino acids 2 to 268 of SEQ ID NO:18 (CaYDR412w); amino acids 2 to 371 of SEQ ID NO:19 (CaYOL010w); amino acids 2 to 257 of SEQ ID NO:20 (CaYOR004w); amino acids 2 to 466 of SEQ ID NO:21 (CaYOR056c); and/or amino acids 2 to 195 of SEQ ID NO:22 (CaYLR009w).

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity].". In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Features of the Polypeptide Encoded by Polynucleotide No:1

The polynucleotide sequence (SEQ ID NO: 1) and deduced amino acid sequence (SEQ ID NO:12) of the novel fungal essential gene, CaYLR100w (also referred to as FCG5), of the present invention. The CaYLR100w polypeptide (SEQ ID NO:12) is encoded by nucleotides 1 to 1038 of SEQ ID NO:1 and has a predicted molecular weight of 39.0 kDa.

In preferred embodiments, the present invention encompasses a polynucleotide lacking the initiating start codon, in addition to, the resulting encoded polypeptide of CaYLR100w. Specifically, the present invention encompasses the polynucleotide corresponding to nucleotides 4 thru 1038 of SEQ ID NO:1, and the polypeptide corresponding to amino acids 2 thru 346 of SEQ ID NO:13. Also encompassed are recombinant vectors comprising said encoding sequence, and host cells comprising said vector.

As illustrated in FIGS. 1 and 2 and described elsewhere herein, the *C. albicans* CaYLR100w (FCG5) polynucleotide of the present invention, has been found to share 60% identity at the protein level with the *S. cerevisiae* ERG27 ("ScERG27") polynucleotide which encodes 3-keto sterol reductase involved in ergosterol biosynthesis. The CaYLR100w has been demonstrated biochemically to represent a 3-keto sterol reductase involved in C-4 sterol demethylation.

Briefly, CaYLR100w was determined to represent a homolog of ScERG27 by using a genetically modified strain where the target CaYLR100w polynucleotide was placed under the control of the CaMET3 promoter. Using this system, reduced synthetic activity of the ergosterol pathway was observed upon reduced CaYLR100w expression via downregulation of the CaMET3 promoter by methionine and cysteine (see FIG. 22B). A similar effect was also observed with a known polynucleotide CaERG1 (encoding squalene epoxidase) used as a control (see FIG. 22A).

Figure 22A:
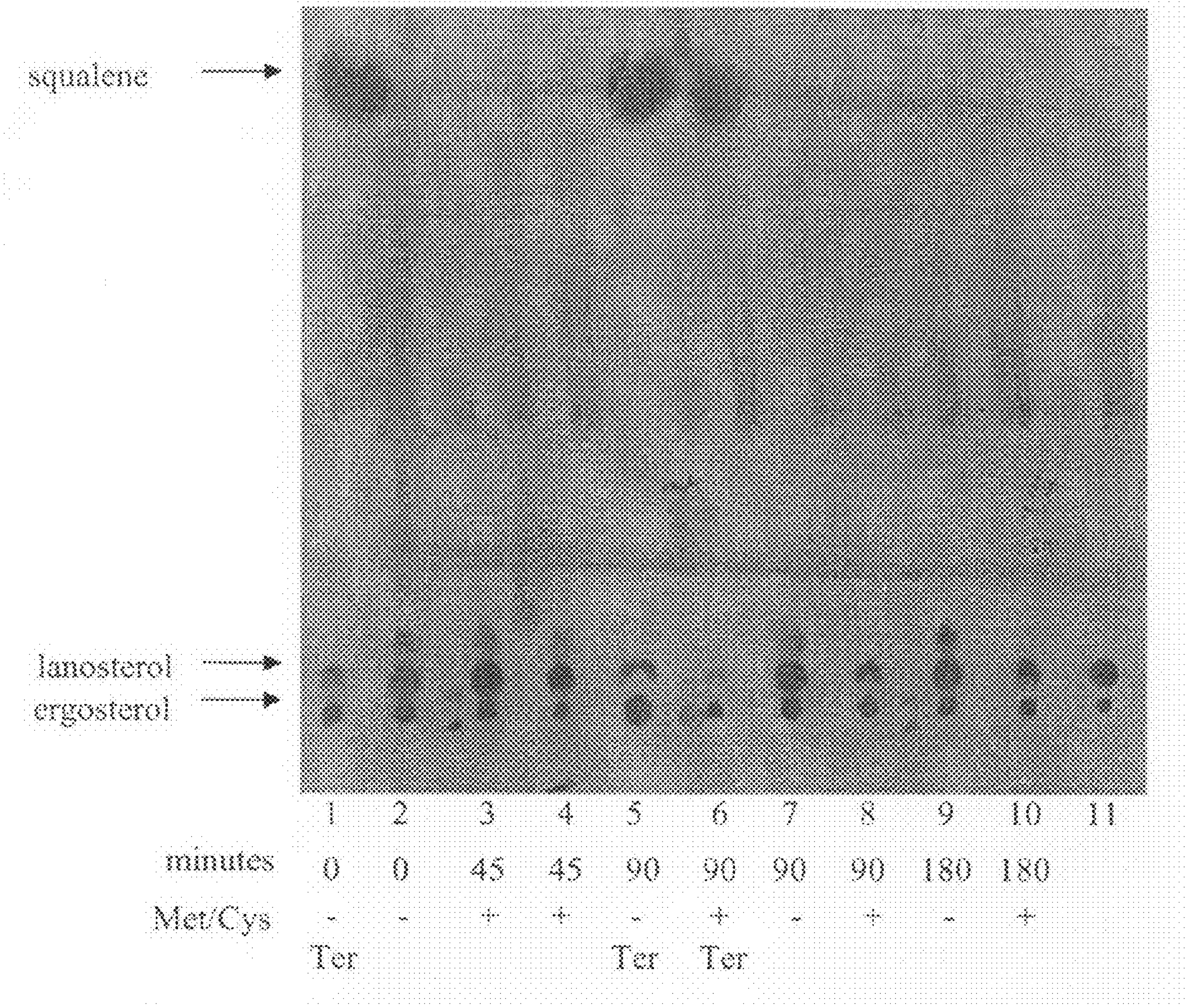
FIG. 22. TLC autoradiogram of labeled sterols from strains caerg1Δ/$P_{MET3}$-CaERG1 (A) and fcg5Δ/$P_{MET3}$-FCG5 (B). The position of ergosterol, lanosterol and squalene are indicated by arrows, as labelled. The squalene epoxidase (Erg1) inhibitor, terbinafine ("Ter"), was added to both a set of control tubes and a set of Met/Cys-containing tubes for a 90 minute induction period. Note that [$^{14}$C]-cholesterol was used as a migration standard for ergosterol in Lane 11. The results demonstrate that CaYLR100w is a 3-keto sterol reductase. Additional experimental details may be found in Example 11, and described elsewhere herein.

As shown in FIG. 22A, where a control strain caerg1Δ/PMET3-CaERG1 was used (see FIG. 22A), downregulation of the CaERG1 promoter in the presence of methionine and cysteine decreased incorporation of [$^{14}$C]-acetate into the ergosterol biosynthetic pathway. The observed decrease, ranging from 62 to 88% compared with untreated cells (FIG. 24A), in incorporation of [$^{14}$C]-acetate into ergosterol was observed beginning within 1 hour of methionine and cysteine addition and continued to decrease over the 4.5 hour experimental period (FIG. 22A). Downregulation of CaYLR100w also had a significant effect on cell growth as demonstrated by decreased absorbance at $OD_{600}$ (FIG. 23A). However, the decrease in ergosterol synthesis by methionine and cysteine was not the result of having fewer cells present compared with untreated cells over the 4.5 hour time frame since all samples were adjusted to the same density prior to addition of radolabeled actetate.

Terbinofine is a specific inhibitor of CaErg1 (squalene epoxidase) and therefore is capable of blocking ergosterol synthesis at squalene in the biosynthetic pathway. The caerg1Δ/$P_{MET3}$-CaERG1 strain treated with terbinofine demonstrated a block in ergosterol biosynthesis at squalene as can be visualized in lanes 1 and 2 in FIG. 22A. Downregulation of the ergosterol biosynthetic pathway in the caerg1Δ/$P_{MET3}$-CaERG1 strain with methionine and cysteine resulted in the decreased accumulation of [$^{14}$C]-acetate into squalene as compared with the untreated cells (FIG. 22A, lanes 5 and 6).

Figure 22B:
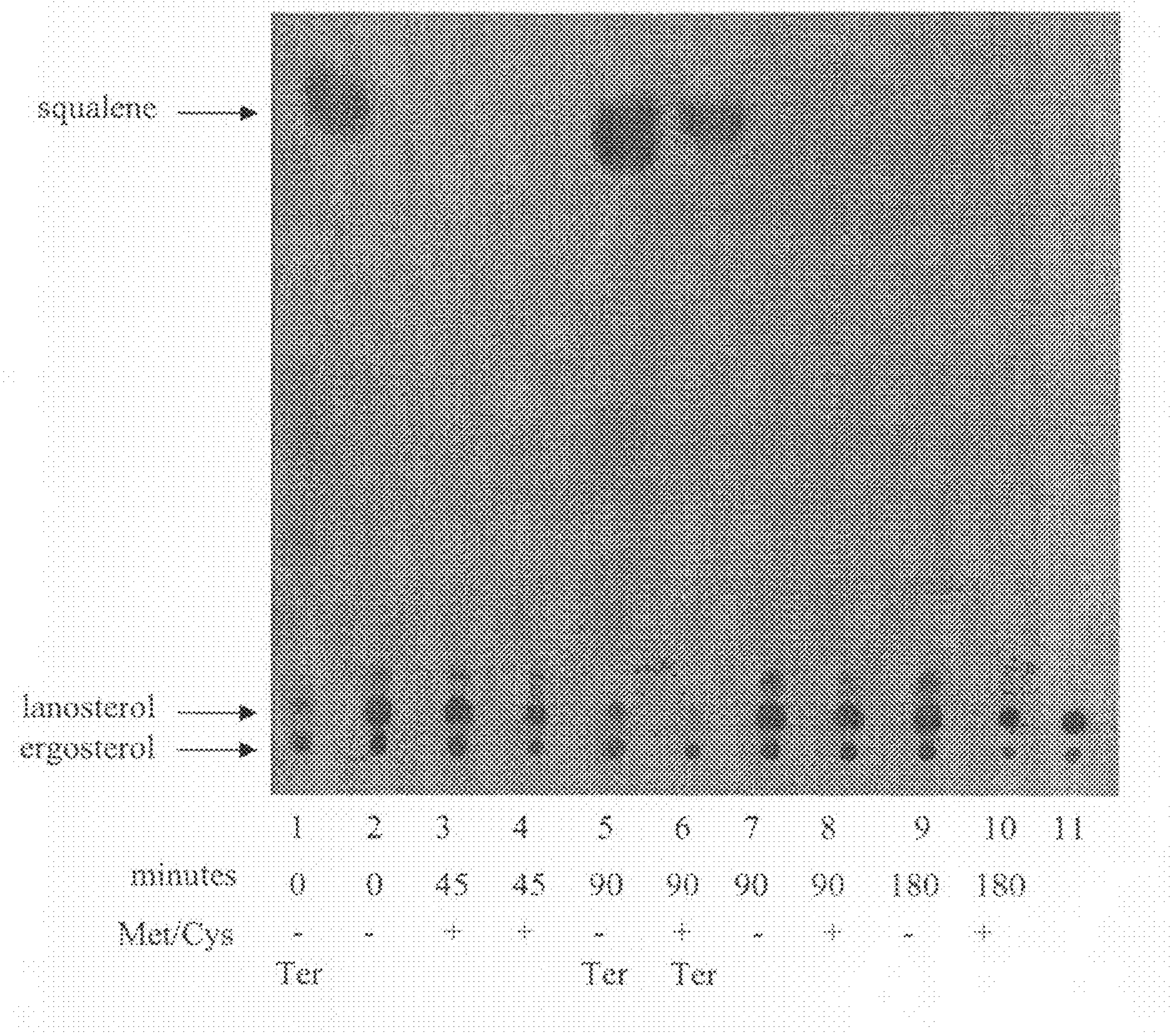

Results obtained with the test strain fcg5Δ/$P_{MET3}$-FCG5 were similar to those obtained with the caerg1Δ/$P_{MET3}$-CaERG1 control strain as seen in FIG. 22B and FIG. 23B. [$^{14}$C]-acetate counts incorporated into the ergosterol and lanosterol intermediates decreased between 62 to 88% compared with untreated cells following the 45 minute to 4.5 hour downregulation period (FIGS. 22B and 24B). Cell growth of this strain was also retarded in the presence of methionine and cysteine, as expected (FIG. 23B). As seen with the caerg1Δ/$P_{MET3}$-CaERG1 control strain, terbinofine treatment blocked the incorporation of radiolabelled acetate into ergosterol, with a majority of the counts trapped in squalene. Methionine and cysteine treated fcg5Δ/$P_{MET3}$-FCG5 cells that were subsequently treated with terbinofine prior to the incorporation of [$^{14}$C]-acetate demonstrated decreased counts associated with squalene as compared with non-downregulated, terbinofine treated cells (FIG. 22B, lanes 5 and 6). These results demonstrate that downregulation of either the CaERG1 or the CaFCG5 genes will result in decreased activity of the ergosterol biosynthetic pathway in general.

Given its high homology with the *S. cerevisiae* counterpart, CaYLR100w or FCG5, in conjunction with the biochemical data provided herein, is therefore an otholog of ScERG27 that encodes 3-keto sterol reductase in *C. albicans*.

The CaYLR100w (FCG5) has been formally renamed "CaERG27". As CaERG27 is an essential polynucleotide in *C. albicans*, downregulation with methionine and cysteine would presumably render cells more susceptible to inhibition by antifungal agents and thus would be extremely useful in drug discovery for fungal therapeutics.

CaYLR100w polynucleotides and polypeptides, including fragments and modualtors thereof, are useful for the treatment, amelioration, and/or detection of fungal diseases and/or disorders, and are also useful in drug discovery for identifying additional fungal therapeutics.

The invention also encompasses N- and/or C-terminal deletions of the CaYLR100w polypeptide of the present invention.

In preferred embodiments, the following N-terminal CaYLR100w deletion polypeptides are encompassed by the present invention: M1-P346, S2-P346, L3-P346, L4-P346, K5-P346, D6-P346, S7-P346, T8-P346, V9-P346, A10-P346, V11-P346, I12-P346, T13-P346, G14-P346, T15-P346, S16-P346, S17-P346, N18-P346, L19-P346, G20-P346, F21-P346, N22-P346, I23-P346, A24-P346, V25-P346, R26-P346, L27-P346, L28-P346, E29-P346, G30-P346, L31-P346, P32-P346, D33-P346, N34-P346, K35-P346, E36-P346, I37-P346, T38-P346, L39-P346, V40-P346, V41-P346, T42-P346, S43-P346, R44-P346, T45-P346, L46-P346, P47-P346, K48-P346, V49-P346, K50-P346, E51-P346, V52-P346, I53-P346, S54-P346, D55-P346, I56-P346, K57-P346, K58-P346, Y59-P346, I60-P346, V61-P346, A62-P346, K63-P346, I64-P346, P65-P346, T66-P346, K67-P346, V68-P346, N69-P346, K70-P346, V71-

P346, E72-P346, F73-P346, D74-P346, Y75-P346, L76-P346, L77-P346, V78-P346, D79-P346, F80-P346, T81-P346, D82-P346, M83-P346, V84-P346, S85-P346, I86-P346, L87-P346, S88-P346, A89-P346, Y90-P346, Y91-P346, E92-P346, L93-P346, N94-P346, K95-P346, R96-P346, Y97-P346, K98-P346, H99-P346, I100-P346, D101-P346, Y102-P346, L103-P346, F104-P346, I105-P346, N106-P346, A107-P346, A108-P346, Q109-P346, G110-P346, V111-P346, Y112-P346, G113-P346, G114-P346, I115-P346, D116-P346, W117-P346, T118-P346, G119-P346, A120-P346, V121-P346, L122-P346, E123-P346, V124-P346, L125-P346, Q126-P346, S127-P346, P128-P346, I129-P346, E130-P346, A131-P346, V132-P346, T133-P346, N134-P346, P135-P346, T136-P346, Y137-P346, K138-P346, L139-P346, Q140-P346, K141-P346, V142-P346, G143-P346, V144-P346, E145-P346, S146-P346, G147-P346, D148-P346, K149-P346, L150-P346, G151-P346, L152-P346, V153-P346, F154-P346, Q155-P346, A156-P346, N157-P346, V158-P346, F159-P346, G160-P346, P161-P346, Y162-P346, Y163-P346, F164-P346, I165-P346, H166-P346, R167-P346, I168-P346, K169-P346, H170-P346, L171-P346, L172-P346, E173-P346, N174-P346, G175-P346, G176-P346, K177-P346, I178-P346, V179-P346, W180-P346, V181-P346, S182-P346, S183-P346, L184-P346, M185-P346, S186-P346, S187-P346, P188-P346, K189-P346, Y190-P346, L191-P346, S192-P346, F193-P346, N194-P346, D195-P346, L196-P346, Q197-P346, L198-P346, L199-P346, R200-P346, S201-P346, P202-P346, A203-P346, S204-P346, Y205-P346, E206-P346, G207-P346, S208-P346, K209-P346, R210-P346, L211-P346, V212-P346, D213-P346, L214-P346, M215-P346, H216-P346, F217-P346, G218-P346, T219-P346, Y220-P346, N221-P346, K222-P346, L223-P346, E224-P346, R225-P346, E226-P346, H227-P346, G228-P346, I229-P346, K230-P346, Q231-P346, Y232-P346, L233-P346, V234-P346, H235-P346, P236-P346, G237-P346, I238-P346, F239-P346, T240-P346, S241-P346, F242-P346, S243-P346, F244-P346, F245-P346, Q246-P346, Y247-P346, L248-P346, N249-P346, V250-P346, F251-P346, T252-P346, Y253-P346, Y254-P346, G255-P346, M256-P346, L257-P346, F258-P346, L259-P346, F260-P346, Y261-P346, L262-P346, A263-P346, R264-P346, F265-P346, L266-P346, G267-P346, S268-P346, P269-P346, Y270-P346, H271-P346, N272-P346, I273-P346, S274-P346, G275-P346, Y276-P346, I277-P346, A278-P346, A279-P346, N280-P346, A281-P346, P282-P346, V283-P346, A284-P346, A285-P346, A286-P346, L287-P346, G288-P346, Q289-P346, T290-P346, K291-P346, Q292-P346, N293-P346, C294-P346, K295-P346, T296-P346, A297-P346, S298-P346, A299-P346, C300-P346, T301-P346, R302-P346, S303-P346, G304-P346, K305-P346, E306-P346, Y307-P346, L308-P346, L309-P346, E310-P346, E311-P346, E312-P346, I313-P346, D314-P346, S315-P346, T316-P346, G317-P346, L318-P346, D319-P346, D320-P346, V321-P346, V322-P346, L323-P346, Y324-P346, L325-P346, D326-P346, T327-P346, L328-P346, T329-P346, K330-P346, E331-P346, W332-P346, D333-P346, E334-P346, K335-P346, L336-P346, K337-P346, D338-P346, Q339-P346, and/or I340-P346 of SEQ ID NO:12. Polynucleotide sequences encoding these polypeptides are also provided. The present invention also encompasses the use of these N-terminal CaYLR100w deletion polypeptides as immunogenic and/or antigenic epitopes as described elsewhere herein.

In preferred embodiments, the following C-terminal CaYLR100w deletion polypeptides are encompassed by the present invention: M1-P346, M1-Q345, M1-R344, M1-T343, M1-N342, M1-V341, M1-I340, M1-Q339, M1-D338, M1-K337, M1-L336, M1-K335, M1-E334, M1-D333, M1-W332, M1-E331, M1-K330, M1-T329, M1-L328, M1-T327, M1-D326, M1-L325, M1-Y324, M1-L323, M1-V322, M1-V321, M1-D320, M1-D319, M1-L318, M1-G317, M1-T316, M1-S315, M1-D314, M1-I313, M1-E312, M1-E311, M1-E310, M1-L309, M1-L308, M1-Y307, M1-E306, M1-K305, M1-G304, M1-S303, M1-R302, M1-T301, M1-C300, M1-A299, M1-S298, M1-A297, M1-T296, M1-K295, M1-C294, M1-N293, M1-Q292, M1-K291, M1-T290, M1-Q289, M1-G288, M1-L287, M1-A286, M1-A285, M1-A284, M1-V283, M1-P282, M1-A281, M1-N280, M1-A279, M1-A278, M1-I277, M1-Y276, M1-G275, M1-S274, M1-I273, M1-N272, M1-H271, M1-Y270, M1-P269, M1-S268, M1-G267, M1-L266, M1-F265, M1-R264, M1-A263, M1-L262, M1-Y261, M1-F260, M1-L259, M1-F258, M1-L257, M1-M256, M1-G255, M1-Y254, M1-Y253, M1-T252, M1-F251, M1-V250, M1-N249, M1-L248, M1-Y247, M1-Q246, M1-F245, M1-F244, M1-S243, M1-F242, M1-S241, M1-T240, M1-F239, M1-I238, M1-G237, M1-P236, M1-H235, M1-V234, M1-L233, M1-Y232, M1-Q231, M1-K230, M1-I229, M1-G228, M1-H227, M1-E226, M1-R225, M1-E224, M1-L223, M1-K222, M1-N221, M1-Y220, M1-T219, M1-G218, M1-F217, M1-H216, M1-M215, M1-L214, M1-D213, M1-V212, M1-L211, M1-R210, M1-K209, M1-S208, M1-G207, M1-E206, M1-Y205, M1-S204, M1-A203, M1-P202, M1-S201, M1-R200, M1-L199, M1-L198, M1-Q197, M1-L196, M1-D195, M1-N194, M1-F193, M1-S192, M1-L191, M1-Y190, M1-K189, M1-P188, M1-S187, M1-S186, M1-M185, M1-L184, M1-S183, M1-S182, M1-V181, M1-W180, M1-V179, M1-I178, M1-K177, M1-G176, M1-G175, M1-N174, M1-E173, M1-L172, M1-L171, M1-H170, M1-K169, M1-I168, M1-R167, M1-H166, M1-I165, M1-F164, M1-Y163, M1-Y162, M1-P161, M1-G160, M1-F159, M1-V158, M1-N157, M1-A156, M1-Q155, M1-F154, M1-V153, M1-L152, M1-G151, M1-L150, M1-K149, M1-D148, M1-G147, M1-S146, M1-E145, M1-V144, M1-G143, M1-V142, M1-K141, M1-Q140, M1-L139, M1-K138, M1-Y137, M1-T136, M1-P135, M1-N134, M1-T133, M1-V132, M1-A131, M1-E130, M1-I129, M1-P128, M1-S127, M1-Q126, M1-L125, M1-V124, M1-E123, M1-L122, M1-V121, M1-A120, M1-G119, M1-T118, M1-W117, M1-D116, M1-I115, M1-G114, M1-G113, M1-Y112, M1-V111, M1-G110, M1-Q109, M1-A108, M1-A107, M1-N106, M1-I105, M1-F104, M1-L103, M1-Y102, M1-D101, M1-I100, M1-H99, M1-K98, M1-Y97, M1-R96, M1-K95, M1-N94, M1-L93, M1-E92, M1-Y91, M1-Y90, M1-A89, M1-S88, M1-L87, M1-I86, M1-S85, M1-V84, M1-M83, M1-D82, M1-T81, M1-F80, M1-D79, M1-V78, M1-L77, M1-L76, M1-Y75, M1-D74, M1-F73, M1-E72, M1-V71, M1-K70, M1-N69, M1-V68, M1-K67, M1-T66, M1-P65, M1-I64, M1-K63, M1-A62, M1-V61, M1-I60, M1-Y59, M1-K58, M1-K57, M1-I56, M1-D55, M1-S54, M1-I53, M1-V52, M1-E51, M1-K50, M1-V49, M1-K48, M1-P47, M1-L46, M1-T45, M1-R44, M1-S43, M1-T42, M1-V41, M1-V40, M1-L39, M1-T38, M1-I37, M1-E36, M1-K35, M1-N34, M1-D33, M1-P32, M1-L31, M1-G30, M1-E29, M1-L28, M1-L27, M1-R26, M1-V25, M1-A24, M1-I23, M1-N22, M1-F21, M1-G20, M1-L19, M1-N18, M1-S17, M1-S16, M1-T15, M1-G14, M1-T13, M1-I12, M1-V11, M1-A10, M1-V9, M1-T8, and/or M1-S7 of SEQ ID NO:12. Polynucleotide sequences encoding these polypeptides are also provided.

The present invention also encompasses the use of these C-terminal CaYLR100w deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:1, and in particular to the coding region of the polynucleotide sequence provided in SEQ ID NO:1. Preferably such polynucleotides encode polypeptides that have biological activity, particularly 3-keto sterol reductase activity.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:12.

Most preferred are polypeptides that share at least about 99.5% identity with the polypeptide sequence provided in SEQ ID NO:12.

The present invention is also directed to a homology model detailing the three-dimensional structure of the CaYLR100w polypeptide (SEQ ID NO:12) of the present invention.

Protein threading and molecular modeling of CaYLR100w suggest that CaYLR100w has a three dimensional fold similar to that of the porcine carbonyl reductase EC number 1.1.1.- (Ghosh et al., 2001), Protein Data Bank (PDB, Bernstein et. al., 1977 & Berman et. al., 2000) entry 1HU4. Based on sequence, structure, motifs and known short chain dehydrogenase/reductase family signature sequences, CaYLR100w contains a novel known short chain dehydrogenase/reductase domain found also in 3-keto sterol reductases.

The polypeptide CaYLR100w contains a distinct structural domain know as the short chain dehydrogenase/reductase (SDR) superfamily catalytic domain which contains the active site. The three dimensional crystallographic structure for several short chain dehydrogenase/reductases have been reported and are deposited into the Protein Data Bank (Ghosh et al., 2001, 2000, Bernstein et. al., 1977, Berman et. al., 2000). The structure (Protein Data Bank, PDB entry 1HU4) of the carbonyl reductase from pig (porcine) is similar to the other short chain dehydrogenase/reductases (EC 1.1.1.-) and is the closest structural homolog of CaYLR100w.

The short chain dehydrogenase/reductase (SDR) family is a very large family of enzymes that are known to be NAD- or NADP-dependent oxidoreductases. Most members of this family are 250 to 300 amino acids in length. This family of proteins uses a Tyr-Lys-Ser triad as catalytic residues. The SDRs catalyze the activation and inactivation of steroids, vitamins, protstaglandins and other bioactive molecules by oxidation and reduction of hydroxyl and carbonyl groups, respectively. CaYLR100w is thought to have the 3-keto sterol reductase activity and the 3-keto sterol reductases are members of the SDR superfamily.

The basic SDR fold includes a seven stranded parallel beta sheet flanked by three parallel helices on each side. The core of this domain contains the classic "Rossman fold" that has been associated with coenzyme NADPH binding. Mutagenesis and modeling experiments have suggested that a Tyr and Lys (part of a catalytic triad) comprising the YXXXK (SEQ ID NO:254) motif, demonstrate that the Tyr proton as a donor in electrophilic attack on the substrate carbonyl in a reduction reaction. These SDRs are also referred to as short chain dehydrogenase/reductases and seem to share the same core domain tertiary structure based on a Rossmann fold.

This structure-based information and sequence information from novel genes can be used to identify other protein family members that share this same fold.

The present invention provides a three dimensional model of the CaYLR100w polypeptide. The three dimensional model provides for a specific description of the catalytic core and functional sites in the 3-keto sterol CaYLR100w polypeptide.

The catalytic core and functional sites are defined by atomic coordinates (Table 8). Based on these data, the inventors have ascribed the CaYLR100w polypeptide as having dehydrogenase/reductase activity(s), specifically the 3-keto sterol reductase activity and cellular and systemic regulatory function(s). Specifically the reductase activity relates to the activation and/or inactivation of steroids, vitamins, protstaglandins and other bioactive molecules by reduction of hydroxyl groups. For CaYLR100w it is the reductase activity at the 3-keto position of steroids during the biosynthesis of ergosterol.

Homology models are useful when there is no experimental information available on the protein of interest. A three dimensional model can be constructed on the basis of the known structure of a homologous protein (Greer et. al., 1991, Lesk, et. al., 1992, Levitt, 1992, Cardozo, et. al., 1995, Sali, et. al., 1995).

Those of skill in the art will understand that a homology model is constructed on the basis of first identifying a template, or, protein of known structure which is similar to the protein without known structure. This can be accomplished by pairwise alignment of sequences using such programs as FASTA (Pearson, et. al. 1990) and BLAST (Altschul, et. al., 1990). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et. al., 1990, Koppensteiner et. al. 2000, Sippl & Weitckus 1992, Sippl 1993), where the compatibility of a particular sequence with the three dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation, etc.). Next, structurally conserved regions can be identified and are used to construct the core secondary structure (Levitt, 1992, Sali, et. al., 1995) elements in the three dimensional model. Variable regions, called "unconserved regions" and loops can be added using knowledge-based techniques. The complete model with variable regions and loops can be refined performing forcefield calculations (Sali, et. al., 1995, Cardozo, et. al., 1995).

For CaYLR100w, a multiple sequence alignment generated manually by combining results from protein threading pairwise alignments and these pairwise alignments were used to align the sequence of CaYLR100w with the sequence of porcine carbonyl reductase, alcohol dehydrogenases, 17β hydroxysteroid dehydrogenases and other SDRs for which three dimensional structures exist. The alignment produced a sequence identity of 20% between the porcine carbonyl reductase (Gosh et. al. 2001, Protein Data Bank entry 1HU4; Genbank Accession No. gi|15826210; SEQ ID NO:251). The alignment of CaYLR100w with PDB entry 1 HU4 chain A is set forth in FIG. 26.

Figure 27:
FIG. 27 shows the three-dimensional homology model of the CaYLR100w (FCG5) polypeptide of the present invention (SEQ ID NO:12). The model is based upon an alignment to a structural homologue porcine carbonyl reductase (Protein Data Bank entry 1HU4; Genbank Accession No. gi|15826210; SEQ ID NO:251) that was used as the basis for building the CaYLR100w homology model. The coordinates of the CaYLR100w model are provided in Table 8.

For the present invention, the homology model of CaYLR100w was derived from the sequence alignment set forth in FIG. 26. An overall atomic model including plausible sidechain orientations was generated using the program LOOK (Levitt, 1992). The three dimensional model for CaYLR100w is defined by the set of structure coordinates as set forth in Table 8 and is shown in FIG. 27 rendered by backbone secondary structures.

Figure 28:
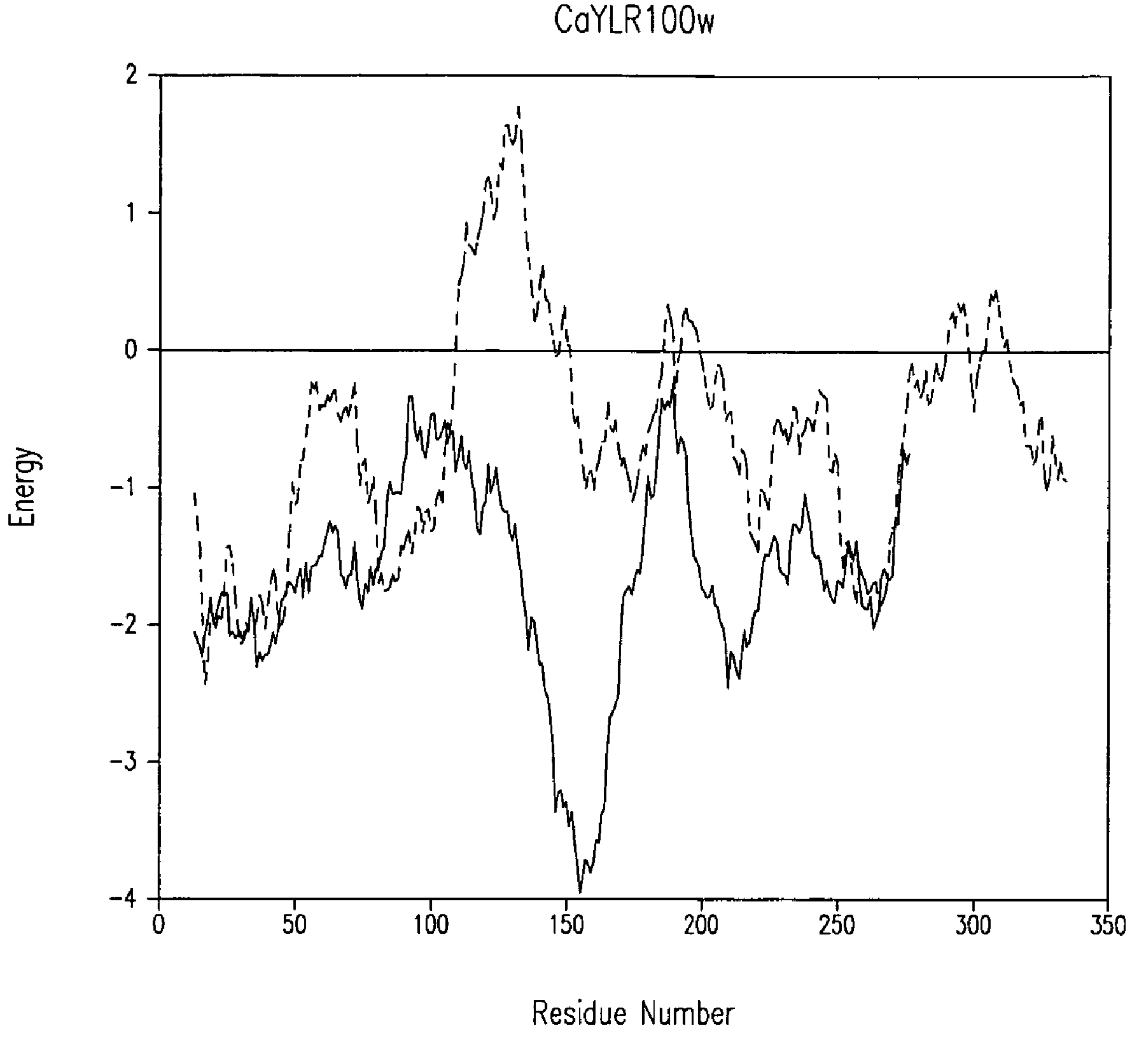
FIG. 28 shows a comparison of the energy of CaYLR100w 3-keto sterol reductase homology model to the crystal structure of the porcine carbonyl reductase (Protein Data Bank entry 1HU4; Genbank Accession No. gi|5826210; SEQ ID NO:251) on which the CaYLR100w model was based. The CaYLR100w homology model is represented by the dotted (dashed) line and the porcince carbonyl reductase crystal structure is represented by the solid line.
Figure 30:
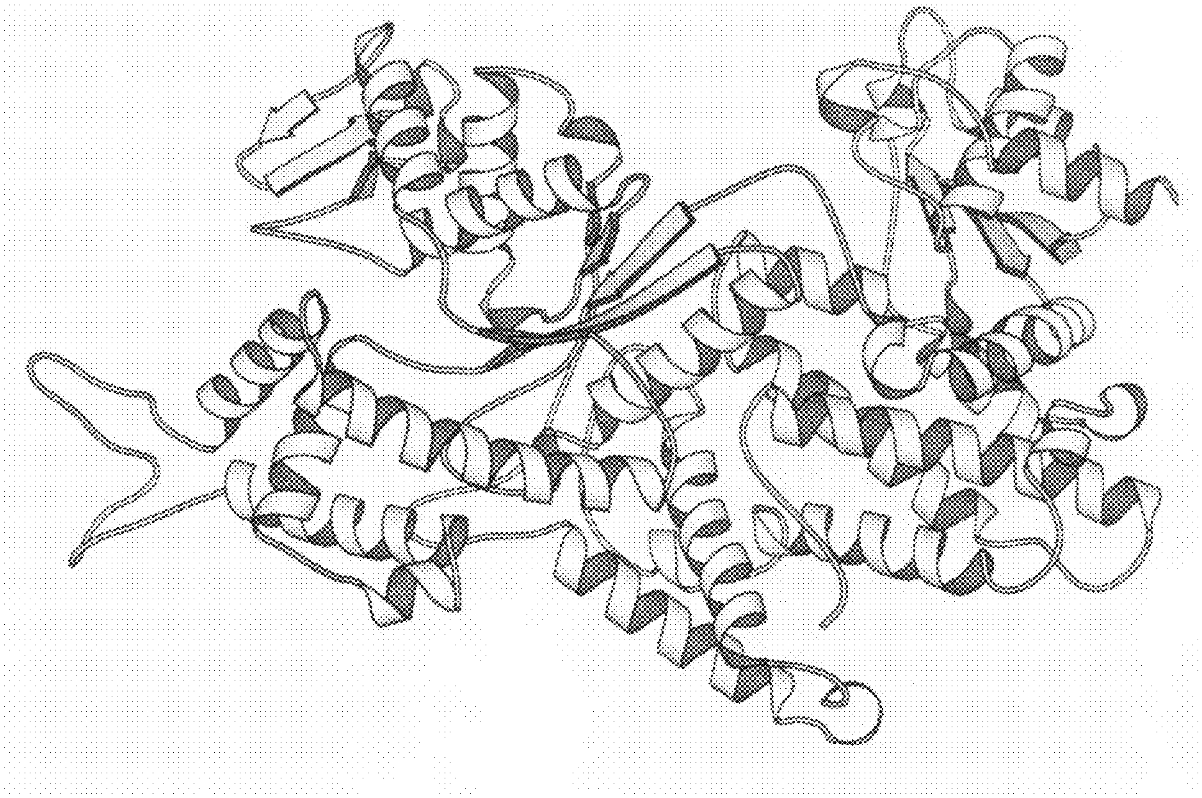
FIG. 30 shows the three-dimensional homology model of the CaYDR341c (FCG6) polypeptide of the present invention (SEQ ID NO:13). The model is based upon an alignment to a structural homologue *Saccharomyces cerevisiae* arginyl-tRNA synthetase, (chain A) (Protein Data Bank entry 1F7U; Genbank Accession No. gi|4719542; SEQ ID NO:252) that was used as the basis for building the CaYDR341c homology model. The coordinates of the CaYDR341c model are provided in Table 9.

In order to recognize errors in three-dimensional structures, knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model, the energy distribution is plotted and compared to the energy distribution of the template from which the model was generated. FIG. 28 shows the energy graph for the CaYLR100w model (dotted line) and the template (porcine carbonyl reductase) from which the model was generated. The model has virtually an identical energy plot when compared to the short chain dehydrogenase/reductase template demonstrating that CaYLR100w has similar structural characteristics except for one region corresponding to residues 100-150 of CaYLR 100w. However the energy plot suggests the overall model three-dimensional fold for CaYLR 100w is "native-like". This graph supports the motif and sequence alignments described herein in confirming that the three dimensional structure coordinates of CaYLR100w are an accurate and useful representation for the polypeptide.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1HU4), and/or using different methods in generating the homology model, will have minor effects on the overall shape. Variations in coordinates may also be generated because of mathematical manipulations of the structure coordinates. For example, the structure coordinates set forth in Table 8 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of CaYLR100w described above as to be considered the same. Such analyses may be carried out in current software applications, such as INSIGHTII (Accelrys Inc., San Diego, Calif.) version 2000 as described in the User's Guide, online or software applications available in the SYBYL software suite (Tripos Inc., St. Louis, Mo.).

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention equivalent atoms are defined as protein backbone atoms. (N, Cα, C and O) for all conserved residues between the two structures being compared. Also, only rigid fitting operations were considered. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII.

For the purpose of this invention, any homology model of a CaYLR100w that has a root mean square deviation of conserved residue backbone atoms (N, Cα, C, O) of less than about 2.0 A when superimposed on the relevant backbone atoms described by structure coordinates listed in Table 8 are considered identical. More preferably, the root mean square deviation is less than about 1.0, 0.9, 0.8, 0.7, 0.6, 0.5, 0.4, 0.3, 0.2, or 0.1 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of CaYLR100w as defined by the structure coordinates described herein.

This invention as embodied by the three-dimensional model enables the structure-based design of modulators of the biological function of CaYLR100w, as well as mutants with altered biological function and/or specificity.

The sequence alignment (FIG. 26) used as a template for creating the three-dimensional model of CaYLR100w short chain dehydrogenase/reductase domain shows 20% sequence identity between catalytic domain of CaYLR100w and porcine carbonyl reductase, PDB code 1HU4.

In the active site of short chain dehydrogenase/reductases ("SDRS"), there is a catalytic triad (YKS) that catalyzes the activation and inactivation of steroids, vitamins, protstaglandins and other bioactive molecules by oxidation and reduction of hydroxyl and carbonyl groups, respectively. The tyrosine side chain is thought to act as the proton donor in electrophilic attack on the substrate carbonyl in a reduction reaction. In porcine carbonyl reductase, the catalytic triad consists of Y193, K197 and S139. In the model and alignment, FIG. 26 and FIG. 27 of CaYLR100w shows that two of the three catalytic residues are conserved and are displayed in the active site. The tyrosine and serine are conserved in CaYLR100w (Y247 and S183) but the lysine position is a phenylalanine (F251) in CaYLR100w. The fact that two of the three catalytic residues are conserved supports the assignment of function for CaYLR100w as a 3-keto sterol reductase member of the SDR superfamily.

The conservation of the catalytic amino acids as part of the active site and the overall 20% sequence identity emphasizes the significance of the three-dimensional model of the CaYLR100w polypeptide. The conserved residues are located in the functional sites that are essential for coenzyme and substrate binding. These active site residues play critical roles in the mechanism of catalysis, substrate specificity, and coenzyme binding.

The structure coordinates of the CaYLR100w homology model, portion thereofs, are preferably stored in a machine-readable storage medium. Such data may be used for a variety of purposes, such as drug discovery and target prioritization and validation.

Accordingly, in one embodiment of this invention is provided a machine-readable data storage medium comprising a data storage material encoded with the structure coordinates set forth in Table 8.

For the first time, the present invention permits the use, through homology modeling based upon the sequence of CaYLR100w (FIGS. 26 and 27) of structure-based or rational drug design techniques to design, select, and synthesizes chemical entities that are capable of modulating the biological function of CaYLR100w. Comparison of the CaYLR100w homology model with the structures of other SDRs enable the use of rational or structure based drug design methods to design, select or synthesize specific chemical modulators of CaYLR100w.

Accordingly, the present invention is also directed to the entire sequence in FIG. 11, or any portion thereof for the purpose of generating a homology model for the purpose of three dimensional structure-based drug designs.

The present invention also encompasses mutants or homologues of the sequence in FIG. 11, or any portion thereof. In a preferred embodiment, the mutants or homologues have at least 25% identity, more preferably 50% identity, more preferably 75% identity, and most preferably 90% identity to the amino acid residues in FIG. 11 (SEQ ID NO:12).

The three-dimensional model structure of the CaYLR100w will also provide methods for identifying modulators of biological function. Various methods or combination thereof can be used to identify these compounds.

Structure coordinates of the active site region defined above can also be used to identify structural and chemical features. Identified structural or chemical features can then be employed to design or select compounds as potential CaYLR100w modulators. By structural and chemical features it is meant to include, but is not limited to, van der Waals interactions, hydrogen bonding interactions, charge interaction, hydrophobic interactions, and dipole interaction. Alternatively, or in conjunction, the three-dimensional structural model can be employed to design or select compounds as potential CaYLR100w modulators. Compounds identified as potential CaYLR100w modulators can then be synthesized and screened in an assay characterized by binding of a test compound to the CaYLR100w, or in characterizing CaYLR100w deactivation in the presence of a small molecule. Examples of assays useful in screening of potential CaYLR100w modulators include, but are not limited to, screening in silico, in vitro assays and high throughput assays. Finally, these methods may also involve modifying or replacing one or more amino acids from CaYLR100w according to Table 8.

However, as will be understood by those of skill in the art upon this disclosure, other structure based design methods can be used. Various computational structure based design methods have been disclosed in the art.

For example, a number of computer modeling systems are available in which the sequence of the CaYLR100w and the CaYLR100w structure (i.e., atomic coordinates of CaYLR100w and/or the atomic coordinates of the active site region as provided in Table 8) can be input. The computer system then generates the structural details of one or more these regions in which a potential CaYLR100w modulator binds so that complementary structural details of the potential modulators can be determined. Design in these modeling systems is generally based upon the compound being capable of physically and structurally associating with CaYLR100w. In addition, the compound must be able to assume a conformation that allows it to associate with CaYLR100w. Some modeling systems estimate the potential inhibitory or binding effect of a potential CaYLR100w modulator prior to actual synthesis and testing.

Methods for screening chemical entities or fragments for their ability to associate with a given protein target are well known. Often these methods begin by visual inspection of the binding site on the computer screen. Selected fragments or chemical entities are then positioned in one or more positions and orientations within the active site region in CaYLR100w. Molecular docking is accomplished using software such as INSIGHTII, ICM (Molsoft LLC, La Jolla, Calif.), and SYBYL, following by energy minimization and molecular dynamics with standard molecular mechanic forcefields such as CHARMM and MMFF. Examples of computer programs which assist in the selection of chemical fragment or chemical entities useful in the present invention include, but are not limited to, GRID (Goodford, 1985), AUTODOCK (Goodsell, 1990), and DOCK (Kuntz et. al. 1982).

Alternatively, compounds may be designed de novo using either an empty active site or optionally including some portion of a known inhibitor. Methods of this type of design include, but are not limited to LUDI (Bohm 1992), LeapFrog (Tripos Associates, St. Louis Mo.) and DOCK (Kuntz et. al., 1982). Programs such as DOCK (Kuntz et. al. 1982) can be used with the atomic coordinates from the homology model to identify potential ligands from databases or virtual databases which potentially bind the in the active site region, and which may therefore be suitable candidates for synthesis and testing. The computer programs may utilize a combination of the following steps:

1) Selection of fragments or chemical entities from a database and then positioning the chemical entity in one or more orientations within the CaYLR100w catalytic domain defined by Table 8

2) Characterization of the structural and chemical features of the chemical entity and active site including van der Waals interactions, hydrogen bonding interactions, charge interaction, hydrophobic bonding interaction, and dipole interactions 3) Search databases for molecular fragments which can be joined to or replace the docked chemical entity and spatially fit into regions defined by the said CaYLR100w catalytic domain or catalytic domain active/functional sites 4) Evaluate the docked chemical entity and fragments using a combination of scoring schemes which account for van der Waals interactions, hydrogen bonding interactions, charge interaction, hydrophobic interactions Databases that may be used include ACD (Molecular Designs Limited), Aldrich (Aldrich Chemical Company), NCI (National Cancer Institute), Maybridge (Maybridge Chemical Company Ltd), CCDC (Cambridge Crystallographic Data Center), CAST (Chemical Abstract Service), Derwent (Derwent Information Limited).

Upon selection of preferred chemical entities or fragments, their relationship to each other and CaYLR100w, can be visualized and then assembled into a single potential modulator. Programs useful in assembling the individual chemical entities include, but are not limited to SYBYL and LeapFrog (Tripos Associates, St. Louis Mo.), LUDI (Bohm 1992) as well as 3D Database systems (Martin 1992).

Additionally, the three-dimensional homology model of CaYLR100w will aid in the design of mutants with altered biological activity. Site directed mutagenesis can be used to generate proteins with similar or varying degrees of biological activity compared to native CaYLR100w. This invention also relates to the generation of mutants or homologs of CaYLR100w. It is clear that molecular modeling using the three dimensional structure coordinates set forth in Table 8 and visualization of the CaYLR100w model, FIG. 27 and alignment in FIG. 26 can be utilized to design homologs or mutant polypeptides of CaYLR100w that have similar or altered biological activities, function or reactivities.

The invention also relates to in silico screening methods including in silico docking and methods of structure based drug design which utilize the three dimensional coordinates of CaYLR100w (Table 8). Also provided are methods of identifying modulators of CaYLR100w that include modulator building or searching utilizing computer programs and algorithms. In an embodiment of the invention a method is provided for designing potential modulators of CaYLR100w comprising any combination of steps which utilize said three dimensional structure to design or select potential modulators.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 1024 of SEQ ID NO:1, b is an integer between 15 to 1038, where both a and b correspond to the positions of nucleotide residues shown in SEQ ID NO:1, and where b is greater than or equal to a+14

Features of the Polypeptide Encoded by Polynucleotide No:2

The polynucleotide sequence (SEQ ID NO:2) and deduced amino acid sequence (SEQ ID NO:13) of the novel fungal essential gene, CaYDR341c (also referred to as FCG6), of the present invention. The CaYDR341c polypeptide (SEQ ID NO:13) is encoded by nucleotides 1 to 1866 of SEQ ID NO:2 and has a predicted molecular weight of 70.8 kDa.

In preferred embodiments, the present invention encompasses a polynucleotide lacking the initiating start codon, in addition to, the resulting encoded polypeptide of CaYDR341c. Specifically, the present invention encompasses the polynucleotide corresponding to nucleotides 4 thru 1866 of SEQ ID NO:2, and the polypeptide corresponding to amino acids 2 thru 622 of SEQ ID NO:14. Also encompassed are recombinant vectors comprising said encoding sequence, and host cells comprising said vector.

As illustrated in FIGS. 1 and 2 and described elsewhere herein, the CaYDR341c polypeptide of the present invention shares 65% identity with *S. cerevisiae* CaYDR341c. Based upon homology to known proteins, CaYDR341c has been predicted to encode an arginine tRNA synthetase involved in protein synthesis. Experiments described herein demonstrate that downregulation of a genetically manipulated strain having CaYDR341c (FCG6) placed under the control of the CaMET3 promoter with methionine and cysteine affects protein synthesis. As shown in FIG. 25, incorporation of radiolabelled leucine and arginine into charged tRNAs and protein was greatly reduced in the presence of methionine and cysteine after a 3.5 hour induction period as compared with strains in the absence of methionine and cysteine.

Based upon homology to known arginine tRNA synthetases, in conjunction with the biochemical data shown herein, it is clear that CaYDR341c is involved in protein synthesis.

Briefly, the results illustrated in FIG. 25 clearly show a dramatic effect of the 3.5 hour methionine/cysteine downregulation on general protein synthesis. This is demonstrated by the fact that arginine incorporation into polypeptide is almost completely inhibited (98.6% inhibition as seen in FIGS. 25A and 25B) in the presence of methionine and cysteine as compared with that in the absence of methionine and cysteine. Leucine incorporation is also greatly impaired by as much as 96.6% with methionine and cysteine treated cells compared to untreated cells (FIGS. 25A and 25B). This result is expected since a block obtained by insufficient argininyl-tRNA would be expected to halt the further elongation of polypeptide synthesis, including the further incorporation of [$^3$H]-leucine. Therefore, the results provide direct biochemical evidence that CaYDR341c is indeed involved in protein synthesis, and encodes an argininyl-tRNA synthetase.

CaYDR341c polynucleotides and polypeptides, including fragments and modualtors thereof, are useful for the treatment, amelioration, and/or detection of fungal diseases and/or disorders, and are also useful in drug discovery for identifying additional fungal therapeutics.

The invention also encompasses N- and/or C-terminal deletions of the CaYDR341c polypeptide of the present invention.

In preferred embodiments, the following N-terminal CaYDR341c deletion polypeptides are encompassed by the present invention: M1-M622, S2-M622, V3-M622, E4-M622, T5-M622, I6-M622, S7-M622, D8-M622, S9-M622, L10-M622, K11'-M622, Q12-M622, L13-M622, G14-M622, L15-M622, S16-M622, Q17-M622, P18-M622, A19-M622, A20-M622, I21-M622, E22-M622, G23-M622, T24-M622, H25-M622, P26-M622, Q27-M622, Y28-M622, N29-M622, V30-M622, V31-M622, D32-M622, V33-M622, F34-M622, R35-M622, N36-M622, Y37-M622, I38-M622, A39-M622, E40-M622, E41-M622, L42-M622, H43-M622, R44-M622, I45-M622, S46-M622, S47-M622, V48-M622, D49-M622, K50-M622, S51-M622, I52-M622, I53-M622, I54-M622, Q55-M622, A56-M622, L57-M622, D58-M622, T59-M622, P60-M622, K61-M622, V62-M622, L63-M622, D64-M622, Q65-M622, G66-M622, D67-M622, I68-M622, I69-M622, V70-M622, P71-M622, I72-M622, P73-M622, K74-M622, L75-M622, R76-M622, L77-M622, K78-M622, G79-M622, I80-M622, N81-M622, P82-M622, N83-M622, E84-M622, K85-M622, S86-M622, K87-M622, E88-M622, W89-M622, A90-M622, E91-M622, N92-M622, F93-M622, N94-M622, K95-M622, G96-M622, K97-M622, F98-M622, I99-M622, S100-M622, E101-M622, I102-M622, K103-M622, P104-M622, Q105-M622, G106-M622, V107-M622, F108-M622, L109-M622, Q 110-M622, F111-M622, Y112-M622, F113-M622, A114-M622, K115-M622, T116-M622, L117-M622, L118-M622, Y119-M622, N120-M622, L121-M622, V122-M622, I123-M622, E124-M622, D125-M622, V126-M622, L127-M622, K128-M622, R129-M622, K130-M622, S131-M622, D132-M622, Y133-M622, G134-M622, Y135-M622, L136-M622, P137-M622, L138-M622, G139-M622, V140-M622, G141-M622, K142-M622, K143-M622, A144-M622, I145-M622, V146-M622, E147-M622, F148-M622, S149-M622, S150-M622, P151-M622, N152-M622, I153-M622, A154-M622, K155-M622, P156-M622, F157-M622, H158-M622, A159-M622, G160-M622, H161-M622, L162-M622, R163-M622, S164-M622, T165-M622, I166-M622, I167-M622, G168-M622, G169-M622, F170-M622, I171-M622, S172-M622, N173-M622, L174-M622, Y175-

M622, E176-M622, K177-M622, V178-M622, G179-M622, W180-M622, D181-M622, V182-M622, T183-M622, R184-M622, I185-M622, N186-M622, Y187-M622, L188-M622, G189-M622, D190-M622, W191-M622, G192-M622, K193-M622, Q194-M622, F195-M622, G196-M622, L197-M622, L198-M622, A199-M622, V200-M622, G201-M622, F202-M622, E203-M622, R204-M622, Y205-M622, G206-M622, D207-M622, E208-M622, S209-M622, K210-M622, L211-M622, A212-M622, S213-M622, D214-M622, P215-M622, I216-M622, N217-M622, H218-M622, L219-M622, F220-M622, E221-M622, V222-M622, Y223-M622, V224-M622, K225-M622, I226-M622, N227-M622, Q228-M622, D229-M622, V230-M622, T231-M622, K232-M622, E233-M622, T234-M622, S235-M622, E236-M622, A237-M622, T238-M622, G239-M622, E240-M622, T241-M622, P242-M622, A243-M622, E244-M622, T245-M622, I246-M622, D247-M622, A248-M622, S249-M622, E250-M622, Q251-M622, D252-M622, E253-M622, K254-M622, K255-M622, I256-M622, Q257-M622, S258-M622, S259-M622, T260-M622, N261-M622, E262-M622, E263-M622, A264-M622, R265-M622, R266-M622, F267-M622, F268-M622, R269-M622, R270-M622, M271-M622, E272-M622, D273-M622, G274-M622, D275-M622, E276-M622, S277-M622, A278-M622, L279-M622, K280-M622, I281-M622, W282-M622, A283-M622, R284-M622, F285-M622, R286-M622, D287-M622, L288-M622, S289-M622, I290-M622, E291-M622, K292-M622, Y293-M622, V294-M622, D295-M622, T296-M622, Y297-M622, G298-M622, R299-M622, L300-M622, N301-M622, I302-M622, K303-M622, Y304-M622, D305-M622, V306-M622, Y307-M622, S308-M622, G309-M622, E310-M622, S311-M622, Q312-M622, V313-M622, P314-M622, Q315-M622, E316-M622, K317-M622, M318-M622, K319-M622, E320-M622, A321-M622, T322-M622, K323-M622, L324-M622, F325-M622, E326-M622, D327-M622, K328-M622, G329-M622, L330-M622, I331-M622, D332-M622, I333-M622, D334-M622, R335-M622, G336-M622, A337-M622, K338-M622, L339-M622, I340-M622, D341-M622, L342-M622, T343-M622, K344-M622, F345-M622, N346-M622, K347-M622, K348-M622, L349-M622, G350-M622, K351-M622, A352-M622, L353-M622, V354-M622, E355-M622, K356-M622, S357-M622, D358-M622, G359-M622, T360-M622, S361-M622, L362-M622, Y363-M622, L364-M622, T365-M622, R366-M622, D367-M622, V368-M622, G369-M622, E370-M622, A371-M622, I372-M622, K373-M622, R374-M622, Y375-M622, E376-M622, T377-M622, Y378-M622, K379-M622, F380-M622, D381-M622, K382-M622, M383-M622, I384-M622, Y385-M622, V386-M622, I387-M622, A388-M622, A389-M622, Q390-M622, Q391-M622, D392-M622, L393-M622, H394-M622, C395-M622, A396-M622, Q397-M622, F398-M622, F399-M622, E400-M622, I401-M622, L402-M622, K403-M622, Q404-M622, M405-M622, G406-M622, F407-M622, E408-M622, W409-M622, A410-M622, H411-M622, N412-M622, L413-M622, E414-M622, H415-M622, V416-M622, N417-M622, F418-M622, G419-M622, M420-M622, V421-M622, Q422-M622, G423-M622, M424-M622, S425-M622, T426-M622, R427-M622, K428-M622, G429-M622, T430-M622, V431-M622, V432-M622, F433-M622, L434-M622, D435-M622, N436-M622, I437-M622, L438-M622, Q439-M622, E440-M622, T441-M622, K442-M622, E443-M622, K444-M622, M445-M622, H446-M622, E447-M622, V448-M622, M449-M622, Q450-M622, K451-M622, N452-M622, E453-M622, E454-M622, K455-M622, Y456-M622, A457-M622, Q458-M622, I459-M622, E460-M622, D461-M622, P462-M622, D463-M622, K464-M622, I465-M622, A466-M622, D467-M622, L468-M622, I469-M622, G470-M622, I471-M622, S472-M622, A473-M622, V474-M622, M475-M622, I476-M622, Q477-M622, D478-M622, M479-M622, Q480-M622, S481-M622, K482-M622, R483-M622, I484-M622, H485-M622, N486-M622, Y487-M622, E488-M622, F489-M622, K490-M622, W491-M622, D492-M622, R493-M622, M494-M622, T495-M622, S496-M622, F497-M622, E498-M622, G499-M622, D500-M622, T501-M622, G502-M622, P503-M622, Y504-M622, L505-M622, Q506-M622, Y507-M622, A508-M622, H509-M622, S510-M622, R511-M622, L512-M622, C513-M622, S514-M622, M515-M622, Q516-M622, R517-M622, K518-M622, S519-M622, G520-M622, I521-M622, S522-M622, I523-M622, E524-M622, E525-M622, L526-M622, E527-M622, H528-M622, A529-M622, N530-M622, F531-M622, D532-M622, L533-M622, L534-M622, V535-M622, E536-M622, P537-M622, C538-M622, A539-M622, S540-M622, A541-M622, L542-M622, A543-M622, R544-M622, T545-M622, L546-M622, A547-M622, Q548-M622, Y549-M622, P550-M622, D551-M622, V552-M622, I553-M622, K554-M622, K555-M622, A556-M622, V557-M622, K558-M622, G559-M622, L560-M622, E561-M622, P562-M622, S563-M622, T564-M622, I565-M622, V566-M622, T567-M622, Y568-M622, L569-M622, F570-M622, S571-M622, V572-M622, T573-M622, H574-M622, I575-M622, V576-M622, S577-M622, Q578-M622, C579-M622, Y580-M622, D581-M622, I582-M622, L583-M622, W584-M622, V585-M622, S586-M622, G587-M622, Q588-M622, E589-M622, K590-M622, D591-M622, V592-M622, A593-M622, I594-M622, A595-M622, R596-M622, L597-M622, A598-M622, L599-M622, Y600-M622, E601-M622, A602-M622, A603-M622, R604-M622, Q605-M622, V606-M622, I607-M622, N608-M622, N609-M622, G610-M622, M611-M622, T612-M622, L613-M622, L614-M622, G615-M622, and/or L616-M622 of SEQ ID NO:13. Polynucleotide sequences encoding these polypeptides are also provided. The present invention also encompasses the use of these N-terminal CaYDR341c deletion polypeptides as immunogenic and/or antigenic epitopes as described elsewhere herein.

In preferred embodiments, the following C-terminal CaYDR341c deletion polypeptides are encompassed by the present invention: M1-M622, M1-R621, M1-N620, M1-V619, M1-P618, M1-T617, M1-L616, M1-G615, M1-L614, M1-L613, M1-T612, M1-M611, M1-G610, M1-N609, M1-N608, M1-I607, M1-V606, M1-Q605, M1-R604, M1-A603, M1-A602, M1-E601, M1-Y600, M1-L599, M1-A598, M1-L597, M1-R596, M1-A595, M1-I594, M1-A593, M1-V592, M1-D591, M1-K590, M1-E589, M1-Q588, M1-G587, M1-S586, M1-V585, M1-W584, M1-L583, M1-I582, M1-D581, M1-Y580, M1-C579, M1-Q578, M1-S577, M1-V576, M1-I575, M1-H574, M1-T573, M1-V572, M1-S571, M1-F570, M1-L569, M1-Y568, M1-T567, M1-V566, M1-I565, M1-T564, M1-S563, M1-P562, M1-E561, M1-L560, M1-G559, M1-K558, M1-V557, M1-A556, M1-K555, M1-K554, M1-I553, M1-V552, M1-D551, M1-P550, M1-Y549, M1-Q548, M1-A547, M1-L546, M1-T545, M1-R544, M1-A543, M1-L542, M1-A541, M1-S540, M1-A539, M1-C538, M1-P537, M1-E536, M1-V535, M1-L534, M1-L533, M1-D532, M1-F531, M1-N530, M1-A529, M1-H528, M1-E527, M1-L526, M1-E525, M1-E524, M1-I523, M1-S522, M1-I521, M1-G520, M1-S519, M1-K518, M1-R517, M1-Q516, M1-M515, M1-S514, M1-C513, M1-L512, M1-R511, M1-S510, M1-H509, M1-A508, M1-Y507, M1-Q506, M1-L505, M1-Y504, M1-P503, M1-G502, M1-T501, M1-D500, M1-G499, M1-E498, M1-F497, M1-S496, M1-T495, M1-M494, M1-R493, M1-D492, M1-W491, M1-K490, M1-F489, M1-E488, M1-Y487, M1-N486, M1-H485, M1-I484, M1-R483, M1-K482, M1-S481, M1-Q480, M1-M479, M1-D478, M1-Q477, M1-I476, M1-M475, M1-V474, M1-A473, M1-S472, M1-I471, M1-G470, M1-I469, M1-L468, M1-D467, M1-A466, M1-I465, M1-K464, M1-D463, M1-P462, M1-D461, M1-E460, M1-I459, M1-Q458, M1-A457, M1-Y456, M1-K455, M1-E454, M1-E453, M1-N452, M1-K451, M1-Q450, M1-M449, M1-V448, M1-E447, M1-H446, M1-M445, M1-K444, M1-E443, M1-K442, M1-T441, M1-E440, M1-Q439, M1-L438, M1-I437, M1-N436, M1-D435, M1-L434, M1-F433, M1-V432, M1-V431, M1-T430, M1-G429, M1-K428, M1-R427, M1-T426, M1-S425, M1-M424, M1-G423, M1-Q422, M1-V421, M1-M420, M1-G419, M1-F418, M1-N417, M1-V416, M1-H415, M1-E414, M1-L413, M1-N412, M1-H411, M1-A410, M1-W409, M1-E408, M1-F407, M1-G406, M1-M405, M1-Q404, M1-K403, M1-L402, M1-I401, M1-E400, M1-F399, M1-F398, M1-Q397, M1-A396, M1-C395, M1-H394, M1-L393, M1-D392, M1-Q391, M1-Q390, M1-A389, M1-A388, M1-I387, M1-V386, M1-Y385, M1-I384, M1-M383, M1-K382, M1-D381, M1-F380, M1-K379, M1-Y378, M1-T377, M1-E376, M1-Y375, M1-R374, M1-K373, M1-I372, M1-A371, M1-E370, M1-G369, M1-V368, M1-D367, M1-R366, M1-T365, M1-L364, M1-Y363, M1-L362, M1-S361, M1-T360, M1-G359, M1-D358, M1-S357, M1-K356, M1-E355, M1-V354, M1-L353, M1-A352, M1-K351, M1-G350, M1-L349, M1-K348, M1-K347, M1-N346, M1-F345, M1-K344, M1-T343, M1-L342, M1-D341, M1-I340, M1-L339, M1-K338, M1-A337, M1-G336, M1-R335, M1-D334, M1-I333, M1-D332, M1-I331, M1-L330, M1-G329, M1-K328, M1-D327, M1-E326, M1-F325, M1-L324, M1-K323, M1-T322, M1-A321, M1-E320, M1-K319, M1-M318, M1-K317, M1-E316, M1-Q315, M1-P314, M1-V313, M1-Q312, M1-S311, M1-E310, M1-G309, M1-S308, M1-Y307, M1-V306, M1-D305, M1-Y304, M1-K303, M1-I302, M1-N301, M1-L300, M1-R299, M1-G298, M1-Y297, M1-T296, M1-D295, M1-V294, M1-Y293, M1-K292, M1-E291, M1-I290, M1-S289, M1-L288, M1-D287, M1-R286, M1-F285, M1-R284, M1-A283, M1-W282, M1-I281, M1-K280, M1-L279, M1-A278, M1-S277, M1-E276, M1-D275, M1-G274, M1-D273, M1-E272, M1-M271, M1-R270, M1-R269, M1-F268, M1-F267, M1-R266, M1-R265, M1-A264, M1-E263, M1-E262, M1-N261, M1-T260, M1-S259, M1-S258, M1-Q257, M1-I256, M1-K255, M1-K254, M1-E253, M1-D252, M1-Q251, M1-E250, M1-S249, M1-A248, M1-D247, M1-I246, M1-T245, M1-E244, M1-A243, M1-P242, M1-T241, M1-E240, M1-G239, M1-T238, M1-A237, M1-E236, M1-S235, M1-T234, M1-E233, M1-K232, M1-T231, M1-V230, M1-D229, M1-Q228, M1-N227, M1-I226, M1-K225, M1-V224, M1-Y223, M1-V222, M1-E221, M1-F220, M1-L219, M1-H218, M1-N217, M1-I216, M1-P215, M1-D214, M1-S213, M1-A212, M1-L211, M1-K210, M1-S209, M1-E208, M1-D207, M1-G206, M1-Y205, M1-R204, M1-E203, M1-F202, M1-G201, M1-V200, M1-A199, M1-L198, M1-L197, M1-G196, M1-F195, M1-Q194, M1-K193, M1-G192, M1-W191, M1-D190, M1-G189, M1-L188, M1-Y187, M1-N186, M1-I185, M1-R184, M1-T183, M1-V182, M1-D181, M1-W180, M1-G179, M1-V178, M1-K177, M1-E176, M1-Y175, M1-L174, M1-N173, M1-S172, M1-I171, M1-F170, M1-G169, M1-G168, M1-I167, M1-I166, M1-T165, M1-S164, M1-R163, M1-L162, M1-H161, M1-G160, M1-A159, M1-H158, M1-F157, M1-P156, M1-K155, M1-A154, M1-I153, M1-N152, M1-P151, M1-S150, M1-S149, M1-F148, M1-E147, M1-V146, M1-I145, M1-A144, M1-K143, M1-K142, M1-G141, M1-V140, M1-G139, M1-L138, M1-P137, M1-L136, M1-Y135, M1-G134, M1-Y133, M1-D132, M1-S131, M1-K130, M1-R129, M1-K128, M1-L127, M1-V126, M1-D125, M1-E124, M1-I123, M1-V122, M1-L121, M1-N120, M1-Y119, M1-L118, M1-L117, M1-T116, M1-K115, M1-A114, M1-F113, M1-Y112, M1-F111, M1-Q110, M1-L109, M1-F108, M1-V107, M1-G106, M1-Q105, M1-P104, M1-K103, M1-I102, M1-E101, M1-S100, M1-I99, M1-F98, M1-K97, M1-G96, M1-K95, M1-N94, M1-F93, M1-N92, M1-E91, M1-A90, M1-W89, M1-E88, M1-K87, M1-S86, M1-K85, M1-E84, M1-N83, M1-P82, M1-N81, M1-I80, M1-G79, M1-K78, M1-L77, M1-R76, M1-L75, M1-K74, M1-P73, M1-I72, M1-P71, M1-V70, M1-I69, M1-I68, M1-D67, M1-G66, M1-Q65, M1-D64, M1-L63, M1-V62, M1-K61, M1-P60, M1-T59, M1-D58, M1-L57, M1-A56, M1-Q55, M1-I54, M1-I53, M1-I52, M1-S51, M1-K50, M1-D49, M1-V48, M1-S47, M1-S46, M1-I45, M1-R44, M1-H43, M1-L42, M1-E41, M1-E40, M1-A39, M1-I38, M1-Y37, M1-N36, M1-R35, M1-F34, M1-V33, M1-D32, M1-V31, M1-V30, M1-N29, M1-Y28, M1-Q27, M1-P26, M1-H25, M1-T24, M1-G23, M1-E22, M1-I21, M1-A20, M1-A19, M1-P18, M1-Q17, M1-S16, M1-L15, M1-G14, M1-L13, M1-Q12, M1-K11, M1-L10, M1-S9, M1-D8, and/or M1-S7 of SEQ ID NO:13. Polynucleotide sequences encoding these polypeptides are also provided. The present invention also encompasses the use of these C-terminal CaYDR341c deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:2, and in particular to the coding region of the polynucleotide sequence provided in SEQ ID NO:2. Preferably such polynucleotides encode polypeptides that have biological activity, particularly arginyl-tRNA synthetase activity.

Most preferred are polynucleotides that share at least about 96.8% identity with the polynucleotide sequence provided in SEQ ID NO:2.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:12.

Most preferred are polypeptides that share at least about 96.8% identity with the polypeptide sequence provided in SEQ ID NO:12.

The present invention is also directed to a homology model detailing the three-dimensional structure of the CaYDR341c polypeptide (SEQ ID NO:13) of the present invention.

Protein threading and molecular modeling of CaYDR341c suggest that CaYDR341c has a three dimensional fold similar to that of the arginyl-tRNA synthetase (EC number 6.1.1.-) from yeast (Delagoutte et. al., 2000), Protein Data Bank (PDB, Bernstein et. al., 1977 & Berman et. al., 2000) (Protein Data Bank entry 1F7U; Genbank Accession No. gi|14719542; SEQ ID NO:252). Based on sequence, structure, motifs and known RNA binding signature sequences, CaYDR341c contains a novel RNA synthetase class 1 domain.

The polypeptide CaYDR341c contains several distinct structural domains including the arginyl-tRNA synthetase catalytic domain which contains the active site.

The three dimensional crystallographic structure for several arginyl-tRNA synthetases have been reported and are deposited into the Protein Data Bank (Delagoutte et. al., 2000, Bernstein et. al., 1977, Berman et. al., 2000). The structure (Protein Data Bank, PDB entry 1F7u) of the arginyl-tRNA synthetase from yeast (*Saccharomyces cerevisiae*) is similar to the other aminoacyl-tRNA synthetases (EC 6.1.1.-). They constitute a family of RNA-binding proteins that are responsible for the correct translation of the genetic code by linking the 3' end of the correct tRNA. In most organisms there are 20 aminoacyl-tRNA synthetases, each one responsible for its cognate tRNA(s). The structure of the yeast (*Saccharomyces cerevisiae*) arginyl-tRNA synthetase has the catalytic domain at the core to which four structurally defined domains are appended. Domains attached to the N-terminus and C-terminus are defined as Add1 and Add2, respectively. The other two domains (Ins1 and Ins2) are inserted into regions of the catalytic core.

The arginyl-tRNA synthetase enzyme is a ternery complex with $tRNA^{arg}$ and forms an extensive interface with a large burried surface area described in detail by Delagoutte et. al., 2000. The interactions between the enzyme and RNA include (I) exposed aromatic and alaphatic interactions that are involved in van der Waals and hydrophobic intereactions; (II) positively charged residues that interact with the sugar phosphate backbone; (III) polar side chains for hydrogen bonds directly with nucleic acids or water-mediated hydrogen bonds. The recognition surface is marked by a series of amino acids that are conserved in all known arginyl-tRNA synthetases (e.g. Y491, A495, R501, Y565, and M607). In addition a structural motif known as the Ω loop, which contains residues 480-485, forms a critical protruding loop that has a dual functional role by forming part of a binding pocket and stabilizing the tRNA conformation by correct positioning of the RNA anticodon. A second structural feature that several aminoacyl-tRNA synthetases share is located in the N-terminal region and is a tetrapeptide sequence 'HIGH' (SEQ ID NO:255). The 'HIGH' (SEQ ID NO:255) region has been shown (Brick et al. 1988) to be part of the adenylate binding site. The 'HIGH' (SEQ ID NO:255) signature has been found in the aminoacyl-tRNA synthetases specific for arginine, cysteine, glutamic acid, glutamine, isoleucine, leucine, methionine, tyrosine, tryptophan, and valine. These aminoacyl-tRNA synthetases are referred to as class-I synthetases (Delarue and Moras, 1993; Schimmel, 1991) and seem to share the same core domain tertiary structure based on a Rossmann fold.

This structure-based information and sequence information from novel genes can be used to identify other protein family members that share this same fold.

The three dimensional model of the CaYDR341c polypeptide provides for a specific description of the catalytic core and functional sites in the arginyl-tRNA synthetase, CaYDR341c polypeptide.

The catalytic core and functional sites are defined by atomic coordinates (Table 9). Based on this data, the inventors have ascribed the CaYDR341c polypeptide as having arginyl-tRNA synthetase activity(s) and cellular and systemic regulatory function(s).

The invention also relates to in silico screening methods including in silico docking and methods of structure based drug design which utilize the three dimensional coordinates of CaYDR341c (Table 9). Also provided are methods of identifying modulators of CaYDR341c that include modulator building or searching utilizing computer programs and algorithms. In an embodiment of the invention a method is provided for designing potential modulators of CaYDR341c comprising any combination of steps which utilize said three dimensional structure to design or select potential modulators.

Homology models are useful when there is no experimental information available on the protein of interest. A three dimensional model can be constructed on the basis of the known structure of a homologous protein (Greer et. al., 1991, Lesk, et. al., 1992, Levitt, 1992, Cardozo, et. al., 1995, Sali, et. al., 1995).

Those of skill in the art will understand that a homology model is constructed on the basis of first identifying a template, or, protein of known structure which is similar to the protein without known structure. This can be accomplished by pairwise alignment of sequences using such programs as FASTA (Pearson, et. al. 1990) and BLAST (Altschul, et. al., 1990). In cases where sequence similarity is high (greater than 30%), these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et. al., 1990, Koppensteiner et. al. 2000, Sippl & Weitckus 1992, Sippl 1993), where the compatibility of a particular sequence with the three dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and are used to construct the core secondary structure (Levitt, 1992, Sali, et. al., 1995) elements in the three dimensional model. Variable regions, called "unconserved regions" and loops can be added using knowledge-based techniques. The complete model with variable regions and loops can be refined performing forcefield calculations (Sali, et. al., 1995, Cardozo, et. al., 1995).

Figure 31:
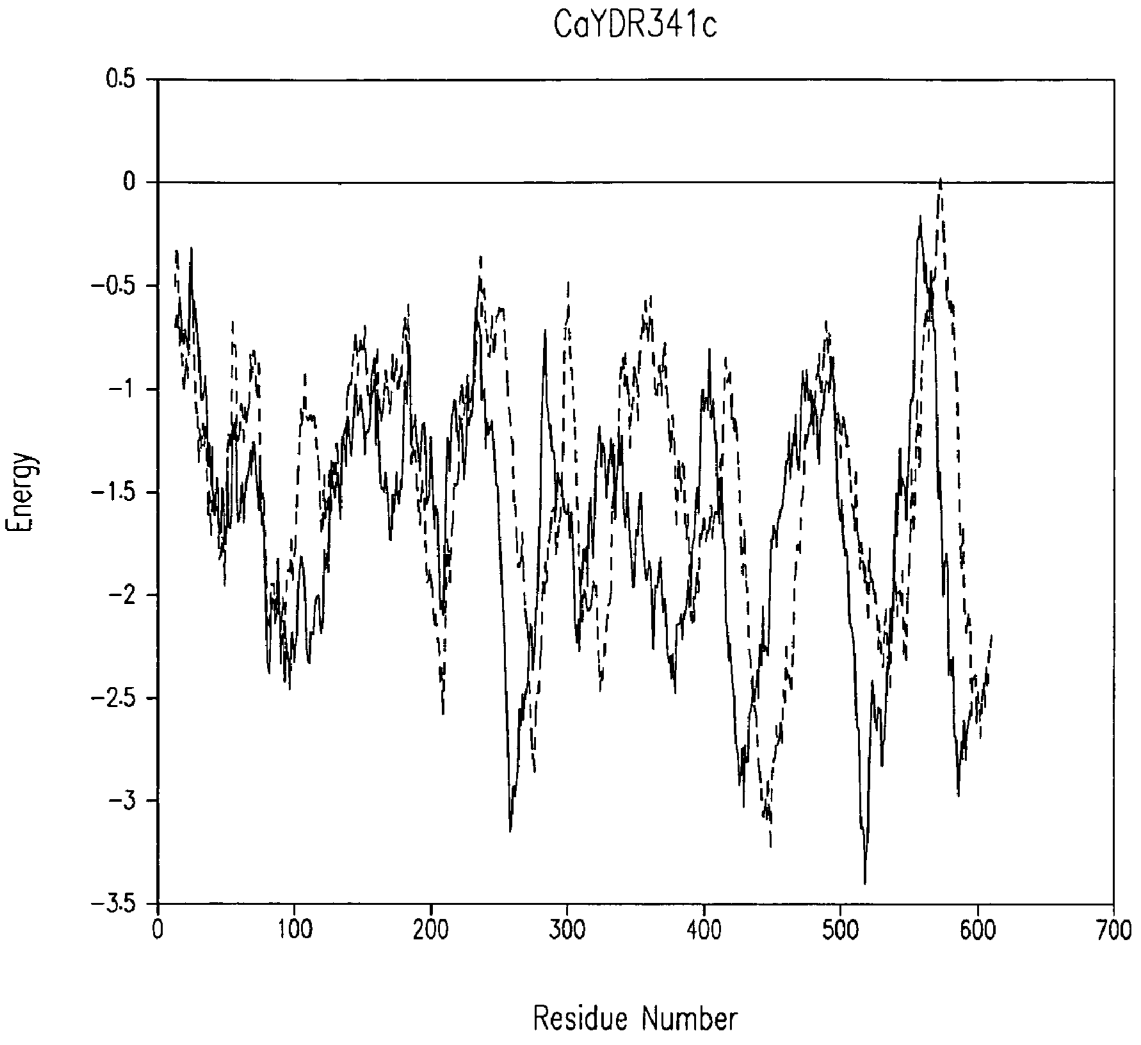
FIG. 31 shows a comparison of the energy of the CaYDR341c arginyl-tRNA synthetase homology model to the crystal structure of the *Saccharomyces cerevisiae* arginyl-tRNA synthetase, (chain A) (Protein Data Bank entry 1F7U; Genbank Accession No. gi|14719542; SEQ ID NO:252) on which the CaYDR341c model was based. The CaYDR341c homology model is represented by the dotted (dashed) line and the *Saccharomyces cerevisiae* arginyl-tRNA synthetase crystal structure is represented by the solid line.

For CaYDR341c a pairwise alignment generated by FASTA was used to align the sequence of CaYDR341c with the sequence the arginyl-tRNA synthetase, EC number 6.1.1.- from yeast, *Saccharomyces cerevisiae* (Delagoutte et. al., 2000), (Protein Data Bank code 1F7U). The alignment of CaYDR341c with PDB entry 1F7U chain A is set forth in FIG. 29. In this invention, the homology model of CaYDR341c was derived from the sequence alignment set forth in FIG. 29. An overall atomic model including plausible sidechain orientations was generated using the program LOOK (Levitt, 1992). The three dimensional model for CaYDR341c is defined by the set of structure coordinates as set forth in Table 9 and is shown in FIG. 31 rendered by backbone secondary structures.

In order to recognize errors in three-dimensional structures, knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model, the energy distribution is plotted and compared to the energy distribution of the template from which the model was generated. FIG. 31 shows the energy graph for the CaYDR341c model (dotted line) and the template (arginyl-tRNA synthetase) from which the model was generated. The model has virtually an identical energy plot when compared to arginyl-tRNA synthetase template demonstrating that CaYDR341c has similar structural characteristics and suggest the overall three-dimensional fold is "native-like". This graph supports the motif and sequence alignments in confirming that the three dimensional structure coordinates of CaYDR341c are an accurate and useful representation for the polypeptide.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1F7u), and/or using different methods in generating the homology model, will have minor effects on the overall shape. Variations in coordinates may also be generated because of mathematical manipulations of the structure coordinates. For example, the structure coordinates set forth in Table 9 could be manipulated by fractionalization of the structure coordinates; integer additions or subtractions to sets of the structure coordinates, inversion of the structure coordinates or any combination of the above.

Various computational analyses are therefore necessary to determine whether a molecule, or a portion thereof, is sufficiently similar to all or parts of CaYDR341c described above as to be considered the same. Such analyses may be carried out in current software applications, such as INSIGHTII (Accelrys Inc., San Diego, Calif.) version 2000 as described in the User's Guide, online or software applications available in the SYBYL software suite (Tripos Inc., St. Louis, Mo.).

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention, equivalent atoms are defined as protein backbone atoms (N, Cα, C and O) for all conserved residues between the two structures being compared. Also, only rigid fitting operations are considered. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII.

For the purpose of this invention, any homology model of a CaYDR341c that has a root mean square deviation of conserved residue backbone atoms (N, Cα, C, O) of less than about 2.0 A when superimposed on the relevant backbone atoms described by structure coordinates listed in Table 9 are considered identical. More preferably, the root mean square deviation is less than about 1.0, 0.9, 0.8, 0.7, 0.6, 0.5, 0.4, 0.3, 0.2, or 0.1 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of CaYDR341c as defined by the structure coordinates described herein.

This invention as embodied by the three-dimensional model enables the structure-based design of modulators of the biological function of CaYDR341c, as well as mutants with altered biological function and/or specificity.

The sequence alignment (FIG. 29) used as a template for creating the three-dimensional model of CaYDR341c arginyl-tRNA synthetase domain shows 67% sequence identity between catalytic domain of CaYDR341c and yeast arginyl-tRNA synthetase, PDB code 1F7U. For the arginyl-tRNA synthetases there are at least two functional regions that are critical. In the N-terminal region of the enzyme the adenylate binding site has been shown to be highly conserved. The motifs and structure of this region are similar for class 1 synthetases aminoacyl-tRNA synthetases specific for arginine, cysteine, glutamic acid, glutamine, isoleucine, leucine, methionine, tyrosine, tryptophan, and valine (Brick et al. 1988). FIG. 29 shows this region highlighted by (*) and corresponds to H158-H161 in the three dimensional model for CaYDR341c (Table 9). The adenylate binding site, including the canonical "HIGH" (SEQ ID NO:255) motif, and surrounding sequence is completely conserved at the sequence and structure level. The Ω loop in aminoacyl-tRNA synthetases forms a critical protruding structure that functions by forming part of a binding pocket for the tRNA molecule and stabilizing the tRNA conformation by correct positioning of the tRNA anticodon. FIG. 29 shows that the Ω loop in CaYDR341c is completely conserved (denoted by "+") both in sequence and structurally.

The conservation of the amino acids in both of these functional sites, and the overall 67% sequence identity, emphasizes the significance of the CaYDR341c three-dimensional model. The conserved residues are located in the functional sites at the tRNA interface presenting a well structured catalytic domain. These functional site residues play critical roles in the mechanism of catalysis, substrate specificity and tRNA binding.

The structure coordinates of a CaYDR341c homology model, and portions thereof, are stored in a machine-readable storage medium. Such data may be used for a variety of purposes, such as drug discovery and target prioritization and validation.

Accordingly, in one embodiment of this invention is provided a machine-readable data storage medium comprising a data storage material encoded with the structure coordinates set forth in Table 9.

For the first time, the present invention permits the use, through homology modeling based upon the sequence of CaYDR341c (FIG. 12) of structure-based or rational drug design techniques to design, select, and synthesizes chemical entities that are capable of modulating the biological function of CaYDR341c. Comparison of the CaYDR341c homology model with the structures of other the arginyl-tRNA synthetases enable the use of rational or structure based drug design methods to design, select or synthesize specific chemical modulators of CaYDR341c.

Accordingly, the present invention is also directed to the entire sequence in FIG. 12, or any portion thereof, for the purpose of generating a homology model for the purpose of three dimensional structure-based drug designs.

The present invention also encompasses mutants or homologues of the sequence in FIG. 12, or any portion thereof. In a preferred embodiment, the mutants or homologues have at least 25% identity, more preferably 50% identity, more preferably 75% identity, and most preferably 90% identity to the amino acid residues in FIG. 12.

The three-dimensional model structure of the CaYDR341c will also provide methods for identifying modulators of biological function. Various methods or combination thereof can be used to identify these compounds.

Structure coordinates of the active site region defined above can also be used to identify structural and chemical features. Identified structural or chemical features can then be employed to design or select compounds as potential CaYDR341c modulators. By structural and chemical features it is meant to include, but is not limited to, van der Waals interactions, hydrogen bonding interactions, charge interaction, hydrophobic interactions, and dipole interaction. Alternatively, or in conjunction, the three-dimensional structural model can be employed to design or select compounds as potential CaYDR341c modulators. Compounds identified as potential CaYDR341c modulators can then be synthesized and screened in an assay characterized by binding of a test compound to the CaYDR341c, or in characterizing CaYDR341c deactivation in the presence of a small molecule. Examples of assays useful in screening of potential CaYDR341c modulators include, but are not limited to, screening in silico, in vitro assays and high throughput assays. Finally, these methods may also involve modifying or replacing one or more amino acids from CaYDR341c according to Table 9.

However, as will be understood by those of skill in the art upon this disclosure, other structure based design methods can be used. Various computational structure based design methods have been disclosed in the art.

For example, a number of computer modeling systems are available in which the sequence of the CaYDR341c and the CaYDR341c structure (i.e., atomic coordinates of CaYDR341c and/or the atomic coordinates of the active site region as provided in Table 9) can be input. The computer system then generates the structural details of one or more these regions in which a potential CaYDR341c modulator binds so that complementary structural details of the potential modulators can be determined. Design in these modeling systems is generally based upon the compound being capable of physically and structurally associating with CaYDR341c. In addition, the compound must be able to assume a conformation that allows it to associate with CaYDR341c. Some modeling systems estimate the potential inhibitory or binding effect of a potential CaYDR341c modulator prior to actual synthesis and testing.

Methods for screening chemical entities or fragments for their ability to associate with a given protein target are well known. Often these methods begin by visual inspection of the binding site on the computer screen. Selected fragments or chemical entities are then positioned in one or more positions and orientations within the active site region in CaYDR341c. Molecular docking is accomplished using software such as INSIGHTII, ICM (Molsoft LLC, La Jolla, Calif.), and SYBYL, following by energy minimization and molecular dynamics with standard molecular mechanic forcefields such as CHARMM and MMFF. Examples of computer programs which assist in the selection of chemical fragment or chemical entities useful in the present invention include, but are not limited to, GRID (Goodford, 1985), AUTODOCK (Goodsell, 1990), and DOCK (Kuntz et. al. 1982).

Alternatively, compounds may be designed de novo using either an empty active site or optionally including some portion of a known inhibitor. Methods of this type of design include, but are not limited to LUDI (Bohm 1992), LeapFrog (Tripos Associates, St. Louis Mo.) and DOCK (Kuntz et. al., 1982). Programs such as DOCK (Kuntz et. al. 1982) can be used with the atomic coordinates from the homology model to identify potential ligands from databases or virtual databases which potentially bind the in the active site region, and which may therefore be suitable candidates for synthesis and testing. The computer programs may utilize a combination of the following steps:

1) Selection of fragments or chemical entities from a database and then positioning the chemical entity in one or more orientations within the CaYDR341c catalytic domain defined by Table 9

2) Characterization of the structural and chemical features of the chemical entity and active site including van der Waals interactions, hydrogen bonding interactions, charge interaction, hydrophobic bonding interaction, and dipole interactions 3) Search databases for molecular fragments which can be joined to or replace the docked chemical entity and spatially fit into regions defined by the said CaYDR341c catalytic domain or catalytic domain functional sites 4) Evaluate the docked chemical entity and fragments using a combination of scoring schemes which account for van der Waals interactions, hydrogen bonding interactions, charge interaction, hydrophobic interactions Databases that may be used include ACD (Molecular Designs Limited), Aldrich (Aldrich Chemical Company), NCI (National Cancer Institute), Maybridge (Maybridge Chemical Company Ltd), CCDC (Cambridge Crystallographic Data Center), CAST (Chemical Abstract Service), Derwent (Derwent Information Limited).

Upon selection of preferred chemical entities or fragments, their relationship to each other and CaYDR341c can be visualized and then assembled into a single potential modulator. Programs useful in assembling the individual chemical entities include, but are not limited to SYBYL and LeapFrog (Tripos Associates, St. Louis Mo.), LUDI (Bohm 1992) as well as 3D Database systems (Martin 1992).

Additionally, the three-dimensional homology model of CaYDR341c will aid in the design of mutants with altered biological activity. Site directed mutagenesis can be used to generate proteins with similar or varying degrees of biological activity compared to native CaYDR341c. This invention also relates to the generation of mutants or homologs of CaYDR341c. It is clear that molecular modeling using the three dimensional structure coordinates set forth in Table 9 and visualization of the CaYDR341c model, FIG. 31 can be utilized to design homologs or mutant polypeptides of CaYDR341c that have similar or altered biological activities, function or reactivities.

Many polynucleotide sequences, such as EST sequences, are publicly available and accessible through sequence databases. Some of these sequences are related to SEQ ID NO:2 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 1852 of SEQ ID NO:2, b is an integer between 15 to 1866, where both a and b correspond to the positions of nucleotide residues shown in SEQ ID NO:2, and where b is greater than or equal to a+14.

Features of the Polypeptide Encoded by Polynucleotide No:3

The polynucleotide sequence (SEQ ID NO:3) and deduced amino acid sequence (SEQ ID NO:14) of the novel fungal essential gene, CaYLR022c (also referred to as FCG7), of the present invention. The CaYLR022c polypeptide (SEQ ID NO:14) is encoded by nucleotides 1 to 765 of SEQ ID NO:3 and has a predicted molecular weight of 29.2 kDa.

In preferred embodiments, the present invention encompasses a polynucleotide lacking the initiating start codon, in addition to, the resulting encoded polypeptide of CaYLR022c. Specifically, the present invention encompasses the polynucleotide corresponding to nucleotides 4 thru 765 of SEQ ID NO:3, and the polypeptide corresponding to amino acids 2 thru 255 of SEQ ID NO:15. Also encompassed are recombinant vectors comprising said encoding sequence, and host cells comprising said vector.

The invention also encompasses N- and/or C-terminal deletions of the CaYLR022c polypeptide of the present invention.

In preferred embodiments, the following N-terminal CaYLR022c deletion polypeptides are encompassed by the present invention: M1-E255, A2-E255, V3-E255, I4-E255, N5-E255, Q6-E255, P7-E255, N8-E255, S9-E255, Q10-E255, I11-E255, R12-E255, L13-E255, T14-E255, N15-E255, V16-E255, S17-E255, L18-E255, V19-E255, R20-E255, M21-E255, K22-E255, K23-E255, G24-E255, K25-E255, K26-E255, R27-E255, F28-E255, E29-E255, I30-E255, A31-E255, C32-E255, Y33-E255, Q34-E255, N35-E255, K36-E255, V37-E255, Q38-E255, D39-E255, W40-E255, R41-E255, L42-E255, K43-E255, V44-E255, E45-E255, K46-E255, D47-E255, I48-E255, D49-E255, E50-E255, V51-E255, L52-E255, Q53-E255, I54-E255, P55-E255, Q56-E255, V57-E255, F58-E255, I59-E255, N60-E255, V61-E255, S62-E255, K63-E255, G64-E255, Q65-E255, V66-E255, A67-E255, N68-E255, N69-E255, D70-E255, D71-E255, L72-E255, Q73-E255, K74-E255, C75-E255, F76-E255, G77-E255, T78-E255, T79-E255, N80-E255, Q81-E255, D82-E255, E83-E255, I84-E255, I85-E255, A86-E255, E87-E255, I88-E255, L89-E255, N90-E255, K91-E255, G92-E255, E93-E255, I94-E255, Q95-E255, L96-E255, N97-E255, E98-E255, K99-E255, E100-E255, R101-E255, N102-E255, A103-E255, N104-E255, L105-E255, Q106-E255, Q107-E255, K108-E255, Q109-E255, N110-E255, E111-E255, F112-E255, L113-E255, N114-E255, I115-E255, I116-E255, S117-E255, T118-E255, K119-E255, C120-E255, I121-E255, N122-E255, P123-E255, R124-E255, S125-E255, K126-E255, K127-E255, R128-E255, Y129-E255, P130-E255, P131-E255, S132-E255, M133-E255, I134-E255, E135-E255, K136-E255, V137-E255, L138-E255, N139-E255, E140-E255, V141-E255, K142-E255, F143-E255, H144-E255, L145-E255, N146-E255, P147-E255, T148-E255, K149-E255, P150-E255, T151-E255, K152-E255, I153-E255, Q154-E255, A155-E255, L156-E255, D157-E255, A158-E255, I159-E255, K160-E255, L161-E255, L162-E255, V163-E255, E164-E255, K165-E255, Q166-E255, I167-E255, I168-E255, P169-E255, I170-E255, A171-E255, R172-E255, A173-E255, Q174-E255, M175-E255, K176-E255, V177-E255, R178-E255, I179-E255, T180-E255, L181-E255, S182-E255, K183-E255, K184-E255, A185-E255, Y186-E255, L187-E255, K188-E255, T189-E255, F190-E255, Q191-E255, D192-E255, E193-E255, I194-E255, K195-E255, P196-E255, V197-E255, I198-E255, D199-E255, Q200-E255, I201-E255, V202-E255, E203-E255, E204-E255, D205-E255, N206-E255, N207-E255, G208-E255, K209-E255, Q210-E255, Y211-E255, E212-E255, I213-E255, V214-E255, G215-E255, I216-E255, I217-E255, D218-E255, P219-E255, I220-E255, N221-E255, Y222-E255, R223-E255, V224-E255, L225-E255, V226-E255, T227-E255, L228-E255, I229-E255, E230-E255, N231-E255, T232-E255, D233-E255, G234-E255, S235-E255, N236-E255, K237-E255, V238-E255, A239-E255, K240-E255, G241-E255, E242-E255, G243-E255, S244-E255, I245-E255, E246-E255, V247-E255, L248-E255, and/or D249-E255 of SEQ ID NO:14. Polynucleotide sequences encoding these polypeptides are also provided. The present invention also encompasses the use of these N-terminal CaYLR022c deletion polypeptides as immunogenic and/or antigenic epitopes as described elsewhere herein.

In preferred embodiments, the following C-terminal CaYLR022c deletion polypeptides are encompassed by the present invention: M1-E255, M1-K254, M1-I253, M1-A252, M1-S251, M1-M250, M1-D249, M1-L248, M1-V247, M1-E246, M1-I245, M1-S244, M1-G243, M1-E242, M1-G241, M1-K240, M1-A239, M1-V238, M1-K237, M1-N236, M1-S235, M1-G234, M1-D233, M1-T232, M1-N231, M1-E230, M1-I229, M1-L228, M1-T227, M1-V226, M1-L225, M1-V224, M1-R223, M1-Y222, M1-N221, M1-I220, M1-P219, M1-D218, M1-I217, M1-I216, M1-G215, M1-V214, M1-I213, M1-E212, M1-Y211, M1-Q210, M1-K209, M1-G208, M1-N207, M1-N206, M1-D205, M1-E204, M1-E203, M1-V202, M1-I201, M1-Q200, M1-D199, M1-I198, M1-V197, M1-P196, M1-K195, M1-I194, M1-E193, M1-D192, M1-Q191, M1-F190, M1-T189, M1-K188, M1-L187, M1-Y186, M1-A185, M1-K184, M1-K183, M1-S182, M1-L181, M1-T180, M1-I179, M1-R178, M1-V177, M1-K176, M1-M175, M1-Q174, M1-A173, M1-R172, M1-A171, M1-I170, M1-P169, M1-I168, M1-I167, M1-Q166, M1-K165, M1-E164, M1-V163, M1-L162, M1-L161, M1-K160, M1-I159, M1-A158, M1-D157, M1-L156, M1-A155, M1-Q154, M1-I153, M1-K152, M1-T151, M1-P150, M1-K149, M1-T148, M1-P147, M1-N146, M1-L145, M1-H144, M1-F143, M1-K142, M1-V141, M1-E140, M1-N139, M1-L138, M1-V137, M1-K136, M1-E135, M1-I134, M1-M133, M1-S132, M1-P131, M1-P130, M1-Y129, M1-R128, M1-K127, M1-K126, M1-S125, M1-R124, M1-P123, M1-N122, M1-I121, M1-C120, M1-K119, M1-T118, M1-S117, M1-I116, M1-I115, M1-N114, M1-L113, M1-F112, M1-E111, M1-N110, M1-Q109, M1-K108, M1-Q107, M1-Q106, M1-L105, M1-N104, M1-A103, M1-N102, M1-R101, M1-E100, M1-K99, M1-E98, M1-N97, M1-L96, M1-Q95, M1-I94, M1-E93, M1-G92, M1-K91, M1-N90, M1-L89, M1-I88, M1-E87, M1-A86, M1-I85, M1-I84, M1-E83, M1-D82, M1-Q81, M1-N80, M1-T79, M1-T78, M1-G77, M1-F76, M1-C75, M1-K74, M1-Q73, M1-L72, M1-D71, M1-D70, M1-N69, M1-N68, M1-A67, M1-V66, M1-Q65, M1-G64, M1-K63, M1-S62, M1-V61, M1-N60, M1-I59, M1-F58, M1-V57, M1-Q56, M1-P55, M1-I54, M1-Q53, M1-L52, M1-V51, M1-E50, M1-D49, M1-I48, M1-D47, M1-K46, M1-E45, M1-V44, M1-K43, M1-L42, M1-R41, M1-W40, M1-D39, M1-Q38, M1-V37, M1-K36, M1-N35, M1-Q34, M1-Y33, M1-C32, M1-A31, M1-I30, M1-E29, M1-F28, M1-R27, M1-K26, M1-K25, M1-G24, M1-K23, M1-K22, M1-M21, M1-R20, M1-V19, M1-L18, M1-S17, M1-V16, M1-N15, M1-T14, M1-L13, M1-R12, M1-I11, M1-Q10, M1-S9, M1-N8, and/or M1-P7 of SEQ ID NO:14. Polynucleotide sequences encoding these polypeptides are also provided. The present invention also encompasses the use of these C-terminal CaYLR022c deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:3, and in particular to the coding region of the polynucleotide sequence provided in SEQ ID NO:3. Preferably such polynucleotides encode polypeptides that have biological activity.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:13.

Most preferred are polypeptides that share at least about 99.7% identity with the polypeptide sequence provided in SEQ ID NO:13.

Many polynucleotide sequences, such as EST sequences, are publicly available and accessible through sequence databases. Some of these sequences are related to SEQ ID NO:3 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 751 of SEQ ID NO:3, b is an integer between 15 to 765, where both a and b correspond to the positions of nucleotide residues shown in SEQ ID NO:3, and where b is greater than or equal to a+14.

Features of the Polypeptide Encoded by Polynucleotide No:4

The polynucleotide sequence (SEQ ID NO:4) and deduced amino acid sequence (SEQ ID NO:15) of the novel fungal essential gene, CaYOL077c (also referred to as FCG8), of the present invention. The CaYOL077c polypeptide (SEQ ID NO:15) is encoded by nucleotides 1 to 876 of SEQ ID NO:4 and has a predicted molecular weight of 34.0 kDa.

In preferred embodiments, the present invention encompasses a polynucleotide lacking the initiating start codon, in addition to, the resulting encoded polypeptide of CaYOL077c. Specifically, the present invention encompasses the polynucleotide corresponding to nucleotides 4 thru 876 of SEQ ID NO:4, and the polypeptide corresponding to amino acids 2 thru 292 of SEQ ID NO:16. Also encompassed are recombinant vectors comprising said encoding sequence, and host cells comprising said vector.

The invention also encompasses N- and/or C-terminal deletions of the CaYOL077c polypeptide of the present invention.

In preferred embodiments, the following N-terminal CaYOL077c deletion polypeptides are encompassed by the present invention: M1-K292, S2-K292, A3-K292, I4-K292, Y5-K292, K6-K292, A7-K292, L8-K292, Q9-K292, S10-K292, K 11-K292, S12-K292, S13-K292, K14-K292, E15-K292, T16-K292, S17-K292, E18-K292, K19-K292, T20-K292, K21-K292, H22-K292, I23-K292, N24-K292, R25-K292, Q26-K292, R27-K292, L28-K292, L29-K292, V30-K292, I31-K292, S32-K292, S33-K292, R34-K292, G35-K292, I36-K292, T37-K292, Y38-K292, R39-K292, H40-K292, R41-K292, H42-K292, L43-K292, I44-K292, Q45-K292, D46-K292, L47-K292, L48-K292, A49-K292, L50-K292, L51-K292, P52-K292, H53-K292, A54-K292, R55-K292, K56-K292, E57-K292, P58-K292, K59-K292, F60-K292, D61-K292, S62-K292, K63-K292, K64-K292, N65-K292, L66-K292, H67-K292, Q68-K292, L69-K292, N70-K292, E71-K292, V72-K292, A73-K292, E74-K292, L75-K292, Y76-K292, N77-K292, C78-K292, N79-K292, N80-K292, I81-K292, F82-K292, F83-K292, F84-K292, E85-K292, C86-K292, R87-K292, K88-K292, H89-K292, Q90-K292, D91-K292, L92-K292, Y93-K292, L94-K292, W95-K292, I96-K292, S97-K292, K98-K292, P99-K292, P100-K292, N101-K292, G102-K292, P103-K292, T104-K292, L105-K292, K106-K292, F107-K292, H108-K292, I109-K292, Q110-K292, N111-K292, L112-K292, H113-K292, T114-K292, L115-K292, D116-K292, E117-K292, L118-K292, N119-K292, F120-K292, T121-K292, G122-K292, N123-K292, C124-K292, L125-K292, K126-K292, G127-K292, S128-K292, R129-K292, P130-K292, I131-K292, L132-K292, S133-K292, F134-K292, D135-K292, K136-K292, S137-K292, F138-K292, L139-K292, E140-K292, N141-K292, D142-K292, H143-K292, Y144-K292, K145-K292, L146-K292, L147-K292, K148-K292, E149-K292, M150-K292, F151-K292, L152-K292, Q153-K292, T154-K292, F155-K292, G156-K292, V157-K292, P158-K292, P159-K292, N160-K292, A161-K292, R162-K292, K163-K292, S164-K292, K165-K292, P166-K292, F167-K292, I168-K292, D169-K292, H170-K292, V171-K292, M172-K292, T173-K292, F174-K292, S175-K292, I176-K292, V177-K292, D178-K292, G179-K292, K180-K292, I181-K292, W182-K292, I183-K292, R184-K292, N185-K292, Y186-K292, Q187-K292, I188-K292, N189-K292, E190-K292, T191-K292, L192-K292, D193-K292, V194-K292, K195-K292, E196-K292, N197-K292, D198-K292, K199-K292, I200-K292, E201-K292, D202-K292, D203-K292, E204-K292, D205-K292, Y206-K292, D207-K292, V208-K292, D209-K292, Q210-K292, L211-K292, N212-K292, L213-K292, V214-K292, E215-K292, I216-K292, G217-K292, P218-K292, R219-K292, L220-K292, V221-K292, L222-K292, T223-K292, L224-K292, I225-K292, T226-K292, V227-K292, L228-K292, E229-K292, G230-K292, S231-K292, F232-K292, S233-K292, G234-K292, P235-K292, K236-K292, I237-K292, Y238-K292, E239-K292, N240-K292, K241-K292, Q242-K292, Y243-K292, V244-K292, S245-K292, P246-K292, N247-K292, F248-K292, V249-K292, R250-K292, A251-K292, Q252-K292, L253-K292, K254-K292, Q255-K292, Q256-K292, A257-K292, A258-K292, D259-K292, Q260-K292, A261-K292, K262-K292, S263-K292, R264-K292, S265-K292, Q266-K292, A267-K292, A268-K292, L269-K292, E270-K292, R271-K292, K272-K292, I273-K292, K274-K292, K275-K292, R276-K292, N277-K292, Q278-K292, V279-K292, L280-K292, K281-K292, A282-K292, D283-K292, P284-K292, L285-K292, and/or S286-K292 of SEQ ID NO:15. Polynucleotide sequences encoding these polypeptides are also provided. The present invention also encompasses the use of these N-terminal CaYOL077c deletion polypeptides as immunogenic and/or antigenic epitopes as described elsewhere herein.

In preferred embodiments, the following C-terminal CaYOL077c deletion polypeptides are encompassed by the present invention: M1-K292, M1-F291, M1-L290, M1-A289, M1-D288, M1-N287, M1-S286, M1-L285, M1-P284, M1-D283, M1-A282, M1-K281, M1-L280, M1-V279, M1-Q278, M1-N277, M1-R276, M1-K275, M1-K274, M1-I273, M1-K272, M1-R271, M1-E270, M1-L269, M1-A268, M1-A267, M1-Q266, M1-S265, M1-R264, M1-S263, M1-K262, M1-A261, M1-Q260, M1-D259, M1-A258, M1-A257, M1-Q256, M1-Q255, M1-K254, M1-L253, M1-Q252, M1-A251, M1-R250, M1-V249, M1-F248, M1-N247, M1-P246, M1-S245, M1-V244, M1-Y243, M1-Q242, M1-K241, M1-N240, M1-E239, M1-Y238, M1-I237, M1-K236, M1-P235, M1-G234, M1-S233, M1-F232, M1-S231, M1-G230, M1-E229, M1-L228, M1-V227, M1-T226, M1-I225, M1-L224, M1-T223, M1-L222, M1-V221, M1-L220, M1-R219, M1-P218, M1-G217, M1-I216, M1-E215, M1-V214, M1-L213, M1-N212, M1-L211, M1-Q210, M1-D209, M1-V208, M1-D207, M1-Y206, M1-D205, M1-E204, M1-D203, M1-D202, M1-E201, M1-I200, M1-K199, M1-D198, M1-N197, M1-E196, M1-K195, M1-V194, M1-D193, M1-L192, M1-T191, M1-E190, M1-N189, M1-I188, M1-Q187, M1-Y186, M1-N185, M1-R184, M1-I183, M1-W182, M1-I181, M1-K180, M1-G179, M1-D178, M1-V177, M1-I176, M1-S175, M1-F174, M1-T173, M1-M172, M1-V171, M1-H170, M1-D169, M1-I168, M1-F167, M1-P166, M1-K165, M1-S164, M1-K163, M1-R162, M1-A161, M1-N160, M1-P159, M1-P158, M1-V157, M1-G156, M1-F155, M1-T154, M1-Q153, M1-L152, M1-F151, M1-M150, M1-E149, M1-K148, M1-L147, M1-L146, M1-K145, M1-Y144, M1-H143, M1-D142, M1-N141, M1-E140, M1-L139, M1-F138, M1-S137, M1-K136, M1-D135, M1-F134, M1-S133, M1-L132, M1-I131, M1-P130, M1-R129, M1-S128, M1-G127, M1-K126, M1-L125, M1-C124, M1-N123, M1-G122, M1-T121, M1-F120, M1-N119, M1-L118, M1-E117, M1-D116, M1-L115, M1-T114, M1-H113, M1-L112, M1-N111, M1-Q110, M1-I109, M1-H108, M1-F107, M1-K106, M1-L105, M1-T104, M1-P103, M1-G102, M1-N101, M1-P100, M1-P99, M1-K98, M1-S97, M1-I96, M1-W95, M1-L94, M1-Y93, M1-L92, M1-D91, M1-Q90, M1-H89, M1-K88, M1-R87, M1-C86, M1-E85, M1-F84, M1-F83, M1-F82, M1-I81, M1-N80, M1-N79, M1-C78, M1-N77, M1-Y76, M1-L75, M1-E74, M1-A73, M1-V72, M1-E71, M1-N70, M1-L69, M1-Q68, M1-H67, M1-L66, M1-N65, M1-K64, M1-K63, M1-S62, M1-D61, M1-F60, M1-K59, M1-P58, M1-E57, M1-K56, M1-R55, M1-A54, M1-H53, M1-P52, M1-L51, M1-L50, M1-A49, M1-L48, M1-L47, M1-D46, M1-Q45, M1-I44, M1-L43, M1-H42, M1-R41, M1-H40, M1-R39, M1-Y38, M1-T37, M1-I36, M1-G35, M1-R34, M1-S33, M1-S32, M1-I31, M1-V30, M1-L29, M1-L28, M1-R27, M1-Q26, M1-R25, M1-N24, M1-I23, M1-H22, M1-K21, M1-T20, M1-K19, M1-E18, M1-S17, M1-T16, M1-E15, M1-K14, M1-S13, M1-S12, M1-K11, M1-S10, M1-Q9, M1-L8, and/or M1-A7 of SEQ ID NO: 15. Polynucleotide sequences encoding these polypeptides are also provided. The present invention also encompasses the use of these C-terminal CaYOL077c deletion polypeptides as immunogenic and/or antigenic epitopes as described elsewhere herein.

Many polynucleotide sequences, such as EST sequences, are publicly available and accessible through sequence databases. Some of these sequences are related to SEQ ID NO:4 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 862 of SEQ ID NO:4, b is an integer between 15 to 876, where both a and b correspond to the positions of nucleotide residues shown in SEQ ID NO:4, and where b is greater than or equal to a+14.

Features of the Polypeptide Encoded by Polynucleotide No:5

The polynucleotide sequence (SEQ ID NO:5) and deduced amino acid sequence (SEQ ID NO:16) of the novel fungal essential gene, CaYNL132w (also referred to as FCG10), of the present invention. The CaYNL132w polypeptide (SEQ ID NO:16) is encoded by nucleotides 1 to 3126 of SEQ ID NO:5 and has a predicted molecular weight of 117.3 kDa.

In preferred embodiments, the present invention encompasses a polynucleotide lacking the initiating start codon, in addition to, the resulting encoded polypeptide of CaYNL132w. Specifically, the present invention encompasses the polynucleotide corresponding to nucleotides 4 thru 3126 of SEQ ID NO:5, and the polypeptide corresponding to amino acids 2 thru 1042 of SEQ ID NO:17. Also encompassed are recombinant vectors comprising said encoding sequence, and host cells comprising said vector.

The invention also encompasses N- and/or C-terminal deletions of the CaYNL132w polypeptide of the present invention.

In preferred embodiments, the following N-terminal CaYNL132w deletion polypeptides are encompassed by the present invention: M1-K1042, G2-K1042, K3-K1042, K4-K1042, A5-K1042, I6-K1042, D7-K1042, A8-K1042, R9-K1042, I10-K1042, P11-K1042, A12-K1042, L13-K1042, I14-K1042, R15-K1042, N16-K1042, G17-K1042, V18-K1042, Q19-K1042, E20-K1042, K21-K1042, Q22-K1042, R23-K1042, S24-K1042, F25-K1042, F26-K1042, I27-K1042, I28-K1042, V29-K1042, G30-K1042, D31-K1042, K32-K1042, A33-K1042, R34-K1042, N35-K1042, Q36-K1042, L37-K1042, P38-K1042, N39-K1042, L40-K1042, H41-K1042, Y42-K1042, L43-K1042, M44-K1042, M45-K1042, S46-K1042, A47-K1042, D48-K1042, L49-K1042, K50-K1042, M51-K1042, N52-K1042, K53-K1042, S54-K1042, V55-K1042, L56-K1042, W57-K1042, A58-K1042, Y59-K1042, K60-K1042, K61-K1042, K62-K1042, L63-K1042, L64-K1042, G65-K1042, F66-K1042, T67-K1042, S68-K1042, H69-K1042, R70-K1042, Q71-K1042, K72-K1042, R73-K1042, E74-K1042, A75-K1042, K76-K1042, I77-K1042, K78-K1042, K79-K1042, D80-K1042, I81-K1042, K82-K1042, R83-K1042, G84-K1042, I85-K1042, R86-K1042, E87-K1042, V88-K1042, N89-K1042, E90-K1042, Q91-K1042, D92-K1042, P93-K1042, F94-K1042, E95-K1042, A96-K1042, F97-K1042, I98-K1042, S99-K1042, N100-K1042, Q101-K1042, H102-K1042, I103-K1042, R104-K1042, Y105-K1042, V106-K1042, Y107-K1042, Y108-K1042, K109-K1042, E110-K1042, T111-K1042, E112-K1042, K113-K1042, I114-K1042, L115-K1042, G116-K1042, N117-K1042, T118-K1042, Y119-K1042, G120-K1042, M121-K1042, C122-K1042, I123-K1042, L124-K1042, Q125-K1042, D126-K1042, F127-K1042, E128-K1042, A129-K1042, I130-K1042, T131-K1042, P132-K1042, N133-K1042, L134-K1042, L135-K1042, A136-K1042, R137-K1042, T138-K1042, I139-K1042, E140-K1042, T141-K1042, V142-K1042, E143-K1042, G144-K1042, G145-K1042, G146-K1042, L147-K1042, V148-K1042, V149-K1042, I150-K1042, L151-K1042, L152-K1042, K153-K1042, N154-K1042, M155-K1042, T156-K1042, S157-K1042, L158-K1042, K159-K1042, Q160-K1042, L161-K1042, Y162-K1042, T163-K1042, M164-K1042, S165-K1042, M166-K1042, D167-K1042, I168-K1042, H169-K1042, S170-K1042, R171-K1042, Y172-K1042, R173-K1042, T174-K1042, E175-K1042, A176-K1042, H177-K1042, D178-K1042, D179-K1042, V180-K1042, V181-K1042, A182-K1042, R183-K1042, F184-K1042, N185-K1042, E186-K1042, R187-K1042, F188-K1042, L189-K1042, L190-K1042, S191-K1042, L192-K1042, G193-K1042, S194-K1042, C195-K1042, E196-K1042, N197-K1042, C198-K1042, L199-K1042, V200-K1042, V201-K1042, D202-K1042, D203-K1042, E204-K1042, L205-K1042, N206-K1042, V207-K1042, L208-K1042, P209-K1042, I210-K1042, S211-K1042, G212-K1042, G213-K1042, K214-K1042, H215-K1042, V216-K1042, K217-K1042, P218-K1042, L219-K1042, P220-K1042, P221-K1042, K222-K1042, D223-K1042, D224-K1042, D225-K1042, E226-K1042, L227-K1042, T228-K1042, P229-K1042, N230-K1042, A231-K1042, K232-K1042, E233-K1042, L234-K1042, K235-K1042, E236-K1042, L237-K1042, K238-K1042, E239-K1042, S240-K1042, L241-K1042, A242-K1042, D243-K1042, V244-K1042, Q245-K1042, P246-K1042, A247-K1042, G248-K1042, S249-K1042, L250-K1042, V251-K1042, A252-K1042, L253-K1042, S254-K1042, K255-K1042, T256-K1042, I257-K1042, N258-K1042, Q259-K1042, A260-K1042, Q261-K1042, A262-K1042, I263-K1042, L264-K1042, T265-K1042, F266-K1042, I267-K1042, D268-K1042, V269-K1042, I270-K1042, S271-K1042, E272-K1042, K273-K1042, T274-K1042, L275-K1042, R276-K1042, N277-K1042, T278-K1042, V279-K1042, T280-K1042, L281-K1042, T282-K1042, A283-K1042, G284-K1042, R285-K1042, G286-K1042, R287-K1042, G288-K1042, K289-K1042, S290-K1042, A291-K1042, A292-K1042, L293-K1042, G294-K1042, I295-K1042, A296-K1042, I297-K1042, A298-K1042, A299-K1042, A300-K1042, I301-K1042, S302-K1042, H303-K1042, G304-K1042, Y305-K1042, S306-K1042, N307-K1042, I308-K1042, F309-K1042, V310-K1042, T311-K1042, S312-K1042, P313-K1042, S314-K1042, P315-K1042, E316-K1042, N317-K1042, L318-K1042, K319-K1042, T320-K1042, L321-K1042, F322-K1042, E323-K1042, F324-K1042, I325-K1042, F326-K1042, K327-K1042, G328-K1042, F329-K1042, D330-K1042, A331-K1042, L332-K1042, G333-K1042, Y334-K1042, T335-K1042, E336-K1042, H337-K1042, M338-K1042, D339-K1042, Y340-K1042, D341-K1042, I342-K1042, I343-K1042, Q344-K1042, S345-K1042, T346-K1042, N347-K1042, P348-K1042, S349-K1042, F350-K1042, N351-K1042, K352-K1042, A353-K1042, I354-K1042, V355-K1042, R356-K1042, V357-K1042, D358-K1042, V359-K1042, K360-K1042, R361-K1042, E362-K1042, H363-K1042, R364-K1042, Q365-K1042, T366-K1042, I367-K1042, Q368-K1042, Y369-K1042, I370-K1042, S371-K1042, P372-K1042, N373-K1042, D374-K1042, S375-K1042, H376-K1042, V377-K1042, L378-K1042, G379-K1042, Q380-K1042, A381-K1042, E382-K1042, L383-K1042, L384-K1042, I385-K1042, I386-K1042, D387-K1042, E388-K1042, A389-K1042, A390-K1042, A391-K1042, I392-K1042, P393-K1042, L394-K1042, P395-K1042, I396-K1042, V397-K1042, K398-K1042, K399-K1042, L400-K1042, M401-K1042, G402-K1042, P403-K1042, Y404-K1042, L405-K1042, I406-K1042, F407-K1042, M408-K1042, A409-K1042, S410-K1042, T411-K1042, I412-K1042, N413-K1042, G414-K1042, Y415-K1042, E416-K1042, G417-K1042, T418-K1042, G419-K1042, R420-K1042, S421-K1042, L422-K1042, S423-K1042, L424-K1042, K425-K1042, L426-K1042, I427-K1042, Q428-K1042, Q429-K1042, L430-K1042, R431-K1042, T432-K1042, Q433-K1042, S434-K1042, N435-K1042, N436-K1042, A437-K1042, T438-K1042, P439-K1042, S440-K1042, E441-K1042, T442-K1042, T443-K1042, V444-K1042, V445-K1042, S446-K1042, R447-K1042, D448-K1042, K449-K1042, K450-K1042, S451-K1042, N452-K1042, E453-K1042, I454-K1042, T455-K1042, G456-K1042, A457-K1042, L458-K1042, T459-K1042, R460-K1042, T461-K1042, L462-K1042, K463-K1042, E464-K1042, V465-K1042, V466-K1042, L467-K1042, D468-K1042, E469-K1042, P470-K1042, I471-K1042, R472-K1042, Y473-K1042, A474-K1042, P475-K1042, G476-K1042, D477-K1042, P478-K1042, I479-K1042, E480-K1042, K481-K1042, W482-K1042, L483-K1042, N484-K1042, K485-K1042, L486-K1042, L487-K1042, C488-K1042, L489-K1042, D490-K1042, V491-K1042, S492-K1042, L493-K1042, S494-K1042, K495-K1042, N496-K1042, A497-K1042, K498-K1042, F499-K1042, A500-K1042, T501-K1042, K502-K1042, G503-K1042, T504-K1042, P505-K1042, H506-K1042, P507-K1042, S508-K1042, Q509-K1042, C510-K1042, Q511-K1042, L512-K1042, F513-K1042, Y514-K1042, V515-K1042, N516-K1042, R517-K1042, D518-K1042, T519-K1042, L520-K1042, F521-K1042, S522-K1042, Y523-K1042, H524-K1042, P525-K1042, V526-K1042, S527-K1042, E528-K1042, A529-K1042, F530-K1042, L531-K1042, Q532-K1042, K533-K1042, M534-K1042, M535-K1042, A536-K1042, L537-K1042, Y538-K1042, V539-K1042, A540-K1042, S541-K1042, H542-K1042, Y543-K1042, K544-K1042, N545-K1042, S546-K1042, P547-K1042, N548-K1042, D549-K1042, L550-K1042, Q551-K1042, L552-K1042, M553-K1042, S554-K1042, D555-K1042, A556-K1042, P557-K1042, A558-K1042, H559-K1042, Q560-K1042, L561-K1042, F562-K1042, V563-K1042, L564-K1042, L565-K1042, P566-K1042, P567-K1042, 1568-K1042, E569-K1042, A570-K1042, G571-K1042, D572-K1042, N573-K1042, R574-K1042, V575-K1042, P576-K1042, D577-K1042, P578-K1042, L579-K1042, C580-K1042, V581-K1042, I582-K1042, Q583-K1042, L584-K1042, A585-K1042, L586-K1042, E587-K1042, G588-K1042, E589-K1042, I590-K1042, S591-K1042, K592-K1042, E593-K1042, S594-K1042, V595-K1042, R596-K1042, K597-K1042, S598-K1042, L599-K1042, S600-K1042, R601-K1042, G602-K1042, Q603-K1042, R604-K1042, A605-K1042, G606-K1042, G607-K1042, D608-K1042, L609-K1042, I610-K1042, P611-K1042, W612-K1042, L613-K1042, I614-K1042, S615-K1042, Q616-K1042, Q617-K1042, F618-K1042, Q619-K1042, D620-K1042, E621-K1042, E622-K1042, F623-K1042, A624-K1042, S625-K1042, L626-K1042, S627-K1042, G628-K1042, A629-K1042, R630-K1042, V631-K1042, V632-K1042, R633-K1042, I634-K1042, A635-K1042, T636-K1042, N637-K1042, P638-K1042, E639-K1042, Y640-K1042, S641-K1042, G642-K1042, M643-K1042, G644-K1042, Y645-K1042, G646-K1042, S647-K1042, R648-K1042, A649-K1042, M650-K1042, E651-K1042, L652-K1042, L653-K1042, R654-K1042, D655-K1042, Y656-K1042, Y657-K1042, S658-K1042, G659-K1042, K660-K1042, F661-K1042, T662-K1042, D663-K1042, I664-K1042, S665-K1042, E666-K1042, S667-K1042, T668-K1042, E669-K1042, L670-K1042, N671-K1042, D672-K1042, H673-K1042, T674-K1042, I675-K1042, T676-K1042, R677-K1042, V678-K1042, T679-K1042, D680-K1042, S681-K1042, E682-K1042, L683-K1042, A684-K1042, N685-K1042, A686-K1042, S687-K1042, L688-K1042, K689-K1042, D690-K1042, E691-K1042, I692-K1042, K693-K1042, L694-K1042, R695-K1042, D696-K1042, V697-K1042, K698-K1042, T699-K1042, L700-K1042, P701-K1042, P702-K1042, L703-K1042, L704-K1042, L705-K1042, K706-K1042, L707-K1042, S708-K1042, E709-K1042, K710-K1042, A711-K1042, P712-K1042, Y713-K1042, Y714-K1042, L715-K1042, H716-K1042, Y717-K1042, L718-K1042, G719-K1042, V720-K1042, S721-K1042, Y722-K1042, G723-K1042, F724-K1042, T725-K1042, S726-K1042, Q727-K1042, L728-K1042, H729-K1042, K730-K1042, F731-K1042, W732-K1042, K733-K1042, K734-K1042, A735-K1042, G736-K1042, F737-K1042, T738-K1042, P739-K1042, V740-K1042, Y741-K1042, L742-K1042, R743-K1042, Q744-K1042, T745-K1042, P746-K1042, N747-K1042, E748-K1042, L749-K1042, T750-K1042, G751-K1042, E752-K1042, H753-K1042, T754-K1042, S755-K1042, V756-K1042, V757-K1042, I758-K1042, S759-K1042, V760-K1042, L761-K1042, P762-K1042, G763-K1042, R764-K1042, E765-K1042, D766-K1042, K767-K1042, W768-K1042, L769-K1042, H770-K1042, E771-K1042, F772-K1042, S773-K1042, K774-K1042, D775-K1042, F776-K1042, H777-K1042, K778-K1042, R779-K1042, F780-K1042, L781-K1042, S782-K1042, L783-K1042, L784-K1042, S785-K1042, Y786-K1042, E787-K1042, F788-K1042, K789-K1042, K790-K1042, F791-K1042, Q792-K1042, A793-K1042, S794-K1042, Q795-K1042, A796-K1042, L797-K1042, S798-K1042, I799-K1042, I800-K1042, E801-K1042, A802-K1042, A803-K1042, E804-K1042, Q805-K1042, G806-K1042, E807-K1042, G808-K1042, D809-K1042, E810-K1042, T811-K1042, T812-K1042, S813-K1042, Q814-K1042, K815-K1042, L816-K1042, T817-K1042, K818-K1042, E819-K1042, Q820-K1042, L821-K1042, D822-K1042, L823-K1042, L824-K1042, L825-K1042, S826-K1042, P827-K1042, F828-K1042, D829-K1042, L830-K1042, K831-K1042, R832-K1042, L833-K1042, D834-K1042, S835-K1042, Y836-K1042, A837-K1042, N838-K1042, N839-K1042, L840-K1042, L841-K1042, D842-K1042, Y843-K1042, H844-K1042, V845-K1042, I846-K1042, V847-K1042, D848-K1042, M849-K1042, L850-K1042, P851-K1042, L852-K1042, I853-K1042, S854-K1042, Q855-K1042, L856-K1042, F857-K1042, F858-K1042, S859-K1042, K860-K1042, K861-K1042, T862-K1042, G863-K1042, Q864-K1042, D865-K1042, I866-K1042, S867-K1042, L868-K1042, S869-K1042, S870-K1042, V871-K1042, Q872-K1042, S873-K1042, A874-K1042, I875-K1042, L876-K1042, L877-K1042, A878-K1042, I879-K1042, G880-K1042, L881-K1042, Q882-K1042, H883-K1042, K884-K1042, D885-K1042, M886-K1042, D887-K1042, Q888-K1042, I889-K1042, A890-K1042, K891-K1042, E892-K1042, L893-K1042, N894-K1042, L895-K1042, P896-K1042, T897-K1042, N898-K1042, Q899-K1042, A900-K1042, M901-K1042, A902-K1042, M903-K1042, F904-K1042, A905-K1042, K906-K1042, I907-K1042, I908-K1042, R909-K1042, K910-K1042, F911-K1042, S912-K1042, T913-K1042, Y914-K1042, F915-K1042, R916-K1042, K917-K1042, V918-K1042, L919-K1042, S920-K1042, K921-K1042, A922-K1042, I923-K1042, E924-K1042, E925-K1042, S926-K1042, M927-K1042, P928-K1042, D929-K1042, L930-K1042, E931-K1042, D932-K1042, E933-K1042, N934-K1042, V935-K1042, D936-K1042, A937-K1042, M938-K1042, N939-K1042, G940-K1042, K941-K1042, E942-K1042, T943-K1042, E944-K1042, Q945-K1042, I946-K1042, D947-K1042, Y948-K1042, K949-K1042, A950-K1042, I951-K1042, E952-K1042, Q953-K1042, K954-K1042, L955-K1042, Q956-K1042, D957-K1042, D958-K1042, L959-K1042, E960-K1042, E961-K1042, A962-K1042, G963-K1042, D964-K1042, E965-K1042, A966-K1042, I967-K1042, K968-K1042, E969-K1042, M970-K1042, R971-K1042, E972-K1042, K973-K1042, Q974-K1042, R975-K1042, E976-K1042, L977-K1042, I978-K1042, N979-K1042, A980-K1042, L981-K1042, N982-K1042, L983-K1042, D984-K1042, K985-K1042, Y986-K1042, A987-K1042, I988-K1042, A989-K1042, E990-K1042, D991-K1042, A992-K1042, E993-K1042, W994-K1042, D995-K1042, E996-K1042, K997-K1042, S998-K1042, M999-K1042, D1000-K1042, K1001-K1042, A1002-K1042, T1003-K1042, K1004-K1042, G1005-K1042, K1006-K1042, G1007-K1042, N1008-K1042, V1009-K1042, V1010-K1042, S1011-K1042, I1012-K1042, K1013-K1042, S1014-K1042, G1015-K1042, K1016-K1042, R1017-K1042, K1018-K1042, S1019-K1042, K1020-K1042, E1021-K1042, N1022-K1042, A1023-K1042, N1024-K1042, D1025-K1042, I1026-K1042, Y1027-K1042, E1028-K1042, K1029-K1042, E1030-K1042, M1031-K1042, K1032-K1042, A1033-K1042, V1034-K1042, K1035-K1042, and/or K1036-K1042 of SEQ ID NO:16. Polynucleotide sequences encoding these polypeptides are also provided. The present invention also encompasses the use of these N-terminal CaYNL132w deletion polypeptides as immunogenic and/or antigenic epitopes as described elsewhere herein.

In preferred embodiments, the following C-terminal CaYNL132w deletion polypeptides are encompassed by the present invention: M1-K1042, M1-K1041, M1-S1040, M1-K1039, M1-K1038, M1-S1037, M1-K1036, M1-K1035, M1-V1034, M1-A1033, M1-K1032, M1-M1031, M1-E1030, M1-K1029, M1-E1028, M1-Y1027, M1-I1026, M1-D1025, M1-N1024, M1-A1023, M1-N1022, M1-E1021, M1-K1020, M1-S1019, M1-K1018, M1-R1017, M1-K1016, M1-G1015, M1-S1014, M1-K1013, M1-I1012, M1-S1011, M1-V1010, M1-V1009, M1-N1008, M1-G1007, M1-K1006, M1-G1005, M1-K1004, M1-T1003, M1-A1002, M1-K1001, M1-D1000, M1-M999, M1-S998, M1-K997, M1-E996, M1-D995, M1-W994, M1-E993, M1-A992, M1-D991, M1-E990, M1-A989, M1-I988, M1-A987, M1-Y986, M1-K985, M1-D984, M1-L983, M1-N982, M1-L981, M1-A980, M1-N979, M1-I978, M1-L977, M1-E976, M1-R975, M1-Q974, M1-K973, M1-E972, M1-R971, M1-M970, M1-E969, M1-K968, M1-I967, M1-A966, M1-E965, M1-D964, M1-G963, M1-A962, M1-E961, M1-E960, M1-L959, M1-D958, M1-D957, M1-Q956, M1-L955, M1-K954, M1-Q953, M1-E952, M1-I951, M1-A950, M1-K949, M1-Y948, M1-D947, M1-I946, M1-Q945, M1-E944, M1-T943, M1-E942, M1-K941, M1-G940, M1-N939, M1-M938, M1-A937, M1-D936, M1-V935, M1-N934, M1-E933, M1-D932, M1-E931, M1-L930, M1-D929, M1-P928, M1-M927, M1-S926, M1-E925, M1-E924, M1-I923, M1-A922, M1-K921, M1-S920, M1-L919, M1-V918, M1-K917, M1-R916, M1-F915, M1-Y914, M1-T913, M1-S912, M1-F911, M1-K910, M1-R909, M1-I908, M1-I907, M1-K906, M1-A905, M1-F904, M1-M903, M1-A902, M1-M901, M1-A900, M1-Q899, M1-N898, M1-T897, M1-P896, M1-L895, M1-N894, M1-L893, M1-E892, M1-K891, M1-A890, M1-I889, M1-Q888, M1-D887, M1-M886, M1-D885, M1-K884, M1-H883, M1-Q882, M1-L881, M1-G880, M1-I879, M1-A878, M1-L877, M1-L876, M1-I875, M1-A874, M1-S873, M1-Q872, M1-V871, M1-S870, M1-S869, M1-L868, M1-S867, M1-I866, M1-D865, M1-Q864, M1-G863, M1-T862, M1-K861, M1-K860, M1-S859, M1-F858, M1-F857, M1-L856, M1-Q855, M1-S854, M1-I853, M1-L852, M1-P851, M1-L850, M1-M849, M1-D848, M1-V847, M1-I846, M1-V845, M1-H844, M1-Y843, M1-D842, M1-L841, M1-L840, M1-N839, M1-N838, M1-A837, M1-Y836, M1-S835, M1-D834, M1-L833, M1-R832, M1-K831, M1-L830, M1-D829, M1-F828, M1-P827, M1-S826, M1-L825, M1-L824, M1-L823, M1-D822, M1-L821, M1-Q820, M1-E819, M1-K818, M1-T817, M1-L816, M1-K815, M1-Q814, M1-S813, M1-T812, M1-T811, M1-E810, M1-D809, M1-G808, M1-E807, M1-G806, M1-Q805, M1-E804, M1-A803, M1-A802, M1-E801, M1-I800, M1-I799, M1-S798, M1-L797, M1-A796, M1-Q795, M1-S794, M1-A793, M1-Q792, M1-F791, M1-K790, M1-K789, M1-F788, M1-E787, M1-Y786, M1-S785, M1-L784, M1-L783, M1-S782, M1-L781, M1-F780, M1-R779, M1-K778, M1-H777, M1-F776, M1-D775, M1-K774, M1-S773, M1-F772, M1-E771, M1-H770, M1-L769, M1-W768, M1-K767, M1-D766, M1-E765, M1-R764, M1-G763, M1-P762, M1-L761, M1-V760, M1-S759, M1-I758, M1-V757, M1-V756, M1-S755, M1-T754, M1-H753, M1-E752, M1-G751, M1-T750, M1-L749, M1-E748, M1-N747, M1-P746, M1-T745, M1-Q744, M1-R743, M1-L742, M1-Y741, M1-V740, M1-P739, M1-T738, M1-F737, M1-G736, M1-A735, M1-K734, M1-K733, M1-W732, M1-F731, M1-K730, M1-H729, M1-L728, M1-Q727, M1-S726, M1-T725, M1-F724, M1-G723, M1-Y722, M1-S721, M1-V720, M1-G719, M1-L718, M1-Y717, M1-H716, M1-L715, M1-Y714, M1-Y713, M1-P712, M1-A711, M1-K710, M1-E709, M1-S708, M1-L707, M1-K706, M1-L705, M1-L704, M1-L703, M1-P702, M1-P701, M1-L700, M1-T699, M1-K698, M1-V697, M1-D696, M1-R695, M1-L694, M1-K693, M1-I692, M1-E691, M1-D690, M1-K689, M1-L688, M1-S687, M1-A686, M1-N685, M1-A684, M1-L683, M1-E682, M1-S681, M1-D680, M1-T679, M1-V678, M1-R677, M1-T676, M1-I675, M1-T674, M1-H673, M1-D672, M1-N671, M1-L670, M1-E669, M1-T668, M1-S667, M1-E666, M1-S665, M1-I664, M1-D663, M1-T662, M1-F661, M1-K660, M1-G659, M1-S658, M1-Y657, M1-Y656, M1-D655, M1-R654, M1-L653, M1-L652, M1-E651, M1-M650, M1-A649, M1-R648, M1-S647, M1-G646, M1-Y645, M1-G644, M1-M643, M1-G642, M1-S641, M1-Y640, M1-E639, M1-P638, M1-N637, M1-T636, M1-A635, M1-I634, M1-R633, M1-V632, M1-V631, M1-R630, M1-A629, M1-G628, M1-S627, M1-L626, M1-S625, M1-A624, M1-F623, M1-E622, M1-E621, M1-D620, M1-Q619, M1-F618, M1-Q617, M1-Q616, M1-S615, M1-I614, M1-L613, M1-W612, M1-P611, M1-I610, M1-L609, M1-D608, M1-G607, M1-G606, M1-A605, M1-R604, M1-Q603, M1-G602, M1-R601, M1-S600, M1-L599, M1-S598, M1-K597, M1-R596, M1-V595, M1-S594, M1-E593, M1-K592, M1-S591, M1-I590, M1-E589, M1-G588, M1-E587, M1-L586, M1-A585, M1-L584, M1-Q583, M1-I582, M1-V581, M1-C580, M1-L579, M1-P578, M1-D577, M1-P576, M1-V575, M1-R574, M1-N573, M1-D572, M1-G571, M1-A570, M1-E569, M1-I568, M1-P567, M1-P566, M1-L565, M1-L564, M1-V563, M1-F562, M1-L561, M1-Q560, M1-H559, M1-A558, M1-P557, M1-A556, M1-D555, M1-S554, M1-M553, M1-L552, M1-Q551, M1-L550, M1-D549, M1-N548, M1-P547, M1-S546, M1-N545, M1-K544, M1-Y543, M1-H542, M1-S541, M1-A540, M1-V539, M1-Y538, M1-L537, M1-A536, M1-M535, M1-M534, M1-K533, M1-Q532, M1-L531, M1-F530, M1-A529, M1-E528, M1-S527, M1-V526, M1-P525, M1-H524, M1-Y523, M1-S522, M1-F521, M1-L520, M1-T519, M1-D518, M1-R517, M1-N516, M1-V515, M1-Y514, M1-F513, M1-L512, M1-Q511, M1-C510, M1-Q509, M1-S508, M1-P507, M1-H506, M1-P505, M1-T504, M1-G503, M1-K502, M1-T501, M1-A500, M1-F499, M1-K498, M1-A497, M1-N496, M1-K495, M1-S494, M1-L493, M1-S492, M1-V491, M1-D490, M1-L489, M1-C488, M1-L487, M1-L486, M1-K485, M1-N484, M1-L483, M1-W482, M1-K481, M1-E480, M1-I479, M1-P478, M1-D477, M1-G476, M1-P475, M1-A474, M1-Y473, M1-R472, M1-I471, M1-P470, M1-E469, M1-D468, M1-L467, M1-V466, M1-V465, M1-E464, M1-K463, M1-L462, M1-T461, M1-R460, M1-T459, M1-L458, M1-A457, M1-G456, M1-T455, M1-I454, M1-E453, M1-N452, M1-S451, M1-K450, M1-K449, M1-D448, M1-R447, M1-S446, M1-V445, M1-V444, M1-T443, M1-T442, M1-E441, M1-S440, M1-P439, M1-T438, M1-A437, M1-N436, M1-N435, M1-S434, M1-Q433, M1-T432, M1-R431, M1-L430, M1-Q429, M1-Q428, M1-I427, M1-L426, M1-K425, M1-L424, M1-S423, M1-L422, M1-S421, M1-R420, M1-G419, M1-T418, M1-G417, M1-E416, M1-Y415, M1-G414, M1-N413, M1-I412, M1-T411, M1-S410, M1-A409, M1-M408, M1-F407, M1-I406, M1-L405, M1-Y404, M1-P403, M1-G402, M1-M401, M1-L400, M1-K399, M1-K398, M1-V397, M1-I396, M1-P395, M1-L394, M1-P393, M1-I392, M1-A391, M1-A390, M1-A389, M1-E388, M1-D387, M1-I386, M1-I385, M1-L384, M1-L383, M1-E382, M1-A381, M1-Q380, M1-G379, M1-L378, M1-V377, M1-H376, M1-S375, M1-D374, M1-N373, M1-P372, M1-S371, M1-I370, M1-Y369, M1-Q368, M1-I367, M1-T366, M1-Q365, M1-R364, M1-H363, M1-E362, M1-R361, M1-K360, M1-V359, M1-D358, M1-V357, M1-R356, M1-V355, M1-I354, M1-A353, M1-K352, M1-N351, M1-F350, M1-S349, M1-P348, M1-N347, M1-T346, M1-S345, M1-Q344, M1-I343, M1-I342, M1-D341, M1-Y340, M1-D339, M1-M338, M1-H337, M1-E336, M1-T335, M1-Y334, M1-G333, M1-L332, M1-A331, M1-D330, M1-F329, M1-G328, M1-K327, M1-F326, M1-I325, M1-F324, M1-E323, M1-F322, M1-L321, M1-T320, M1-K319, M1-L318, M1-N317, M1-E316, M1-P315, M1-S314, M1-P313, M1-S312, M1-T311, M1-V310, M1-F309, M1-I308, M1-N307, M1-S306, M1-Y305, M1-G304, M1-H303, M1-S302, M1-I301, M1-A300, M1-A299, M1-A298, M1-I297, M1-A296, M1-I295, M1-G294, M1-L293, M1-A292, M1-A291, M1-S290, M1-K289, M1-G288, M1-R287, M1-G286, M1-R285, M1-G284, M1-A283, M1-T282, M1-L281, M1-T280, M1-V279, M1-T278, M1-N277, M1-R276, M1-L275, M1-T274, M1-K273, M1-E272, M1-S271, M1-I270, M1-V269, M1-D268, M1-I267, M1-F266, M1-T265, M1-L264, M1-I263, M1-A262, M1-Q261, M1-A260, M1-Q259, M1-N258, M1-I257, M1-T256, M1-K255, M1-S254, M1-L253, M1-A252, M1-V251, M1-L250, M1-S249, M1-G248, M1-A247, M1-P246, M1-Q245, M1-V244, M1-D243, M1-A242, M1-L241, M1-S240, M1-E239, M1-K238, M1-L237, M1-E236, M1-K235, M1-L234, M1-E233, M1-K232, M1-A231, M1-N230, M1-P229, M1-T228, M1-L227, M1-E226, M1-D225, M1-D224, M1-D223, M1-K222, M1-P221, M1-P220, M1-L219, M1-P218, M1-K217, M1-V216, M1-H215, M1-K214, M1-G213, M1-G212, M1-S211, M1-I210, M1-P209, M1-L208, M1-V207, M1-N206, M1-L205, M1-E204, M1-D203, M1-D202, M1-V201, M1-V200, M1-L199, M1-C198, M1-N197, M1-E196, M1-C195, M1-S194, M1-G193, M1-L192, M1-S191, M1-L190, M1-L189, M1-F188, M1-R187, M1-E186, M1-N185, M1-F184, M1-R183, M1-A182, M1-V181, M1-V180, M1-D179, M1-D178, M1-H177, M1-A176, M1-E175, M1-T174, M1-R173, M1-Y172, M1-R171, M1-S170, M1-H169, M1-I168, M1-D167, M1-M166, M1-S165, M1-M164, M1-T163, M1-Y162, M1-L161, M1-Q160, M1-K159, M1-L158, M1-S157, M1-T156, M1-M155, M1-N154, M1-K153, M1-L152, M1-L151, M1-I150, M1-V149, M1-V148, M1-L147, M1-G146, M1-G145, M1-G144, M1-E143, M1-V142, M1-T141, M1-E140, M1-I139, M1-T138, M1-R137, M1-A136, M1-L135, M1-L134, M1-N133, M1-P132, M1-T131, M1-I130, M1-A129, M1-E128, M1-F127, M1-D126, M1-Q125, M1-L124, M1-I123, M1-C122, M1-M121, M1-G120, M1-Y119, M1-T118, M1-N117, M1-G116, M1-L115, M1-I114, M1-K113, M1-E112, M1-T111, M1-E110, M1-K109, M1-Y108, M1-Y107, M1-V106, M1-Y105, M1-R104, M1-I103, M1-H102, M1-Q101, M1-N100, M1-S99, M1-I98, M1-F97, M1-A96, M1-E95, M1-F94, M1-P93, M1-D92, M1-Q91, M1-E90, M1-N89, M1-V88, M1-E87, M1-R86, M1-I85, M1-G84, M1-R83, M1-K82, M1-I81, M1-D80, M1-K79, M1-K78, M1-I77, M1-K76, M1-A75, M1-E74, M1-R73, M1-K72, M1-Q71, M1-R70, M1-H69, M1-S68, M1-T67, M1-F66, M1-G65, M1-L64, M1-L63, M1-K62, M1-K61, M1-K60, M1-Y59, M1-A58, M1-W57, M1-L56, M1-V55, M1-S54, M1-K53, M1-N52, M1-M51, M1-K50, M1-L49, M1-D48, M1-A47, M1-S46, M1-M45, M1-M44, M1-L43, M1-Y42, M1-H41, M1-L40, M1-N39, M1-P38, M1-L37, M1-Q36, M1-N35, M1-R34, M1-A33, M1-K32, M1-D31, M1-G30, M1-V29, M1-I28, M1-I27, M1-F26, M1-F25, M1-S24, M1-R23, M1-Q22, M1-K21, M1-E20, M1-Q19, M1-V18, M1-G17, M1-N16, M1-R15, M1-I14, M1-L13, M1-A12, M1-P11, M1-I10, M1-R9, M1-A8, and/or M1-D7 of SEQ ID NO:16. Polynucleotide sequences encoding these polypeptides are also provided. The present invention also encompasses the use of these C-terminal CaYNL132w deletion polypeptides as immunogenic and/or antigenic epitopes as described elsewhere herein.

Many polynucleotide sequences, such as EST sequences, are publicly available and accessible through sequence databases. Some of these sequences are related to SEQ ID NO:5 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 3112 of SEQ ID NO:5, b is an integer between 15 to 3126, where both a and b correspond to the positions of nucleotide residues shown in SEQ ID NO:5, and where b is greater than or equal to a+14.

Features of the Polypeptide Encoded by Polynucleotide No:6

The polynucleotide sequence (SEQ ID NO:6) and deduced amino acid sequence (SEQ ID NO:17) of the novel fungal essential gene, CaYGR145w (also referred to as FCG12), of the present invention. The CaYGR145w polypeptide (SEQ ID NO:17) is encoded by nucleotides 1 to 2250 of SEQ ID NO:6 and has a predicted molecular weight of 85.0 kDa.

In preferred embodiments, the present invention encompasses a polynucleotide lacking the initiating start codon, in addition to, the resulting encoded polypeptide of CaYGR145w. Specifically, the present invention encompasses the polynucleotide corresponding to nucleotides 4 thru 2250 of SEQ ID NO:6, and the polypeptide corresponding to amino acids 2 thru 1042 of SEQ ID NO:18. Also encompassed are recombinant vectors comprising said encoding sequence, and host cells comprising said vector.

The invention also encompasses N- and/or C-terminal deletions of the CaYGR145w polypeptide of the present invention.

In preferred embodiments, the following N-terminal CaYGR145w deletion polypeptides are encompassed by the present invention: M1-M750, V2-M750, L3-M750, K4-M750, S5-M750, T6-M750, T7-M750, A8-M750, G9-M750, N10-M750, V11-M750, S12-M750, V13-M750, Y14-M750, Q15-M750, V16-M750, S17-M750, G18-M750, T19-M750, N20-M750, V21-M750, S22-M750, R23-M750, S24-M750, L25-M750, P26-M750, D27-M750, W28-M750, I29-M750, D30-M750, K31-M750, K32-M750, R33-M750, K34-M750, R35-M750, A36-M750, L37-M750, K38-M750, H39-M750, D40-M750, L41-M750, E42-M750, Y43-M750, Q44-M750, N45-M750, R46-M750, I47-M750, E48-M750, L49-M750, I50-M750, Q51-M750, D52-M750, F53-M750, E54-M750, F55-M750, S56-M750, E57-M750, A58-M750, S59-M750, N60-M750, K61-M750, I62-M750, K63-M750, V64-M750, T65-M750, N66-M750, D67-M750, G68-M750, Q69-M750, Y70-M750, C71-M750, M72-M750, A73-M750, T74-M750, G75-M750, T76-M750, Y77-M750, K78-M750, P79-M750, Q80-M750, I81-M750, H82-M750, V83-M750, Y84-M750, E85-M750, F86-M750, A87-M750, N88-M750, L89-M750, S90-M750, L91-M750, K92-M750, F93-M750, D94-M750, R95-M750, H96-M750, T97-M750, N98-M750, V99-M750, E100-M750, N101-M750, I102-M750, D103-M750, F104-M750, L105-M750, I106-M750, L107-M750, S108-M750, N109-M750, D110-M750, W111-M750, T112-M750, K113-M750, S114-M750, V115-M750, H116-M750, L117-M750, Q118-M750, C119-M750, D120-M750, R121-M750, S122-M750, I123-M750, E124-M750, F125-M750, Q126-M750, T127-M750, A128-M750, G129-M750, G130-M750, V131-M750, H132-M750, Y133-M750, R134-M750, T135-M750, R136-M750, I137-M750, P138-M750, K139-M750, F140-M750, G141-M750, R142-M750, C143-M750, L144-M750, T145-M750, Y146-M750, N147-M750, P148-M750, I149-M750, N150-M750, C151-M750, D152-M750, L153-M750, I154-M750, V155-M750, G156-M750, S157-M750, S158-M750, S159-M750, D160-M750, E161-M750, L162-M750, Y163-M750, R164-M750, L165-M750, N166-M750, L167-M750, D168-M750, Q169-M750, G170-M750, R171-M750, F172-M750, L173-M750, S174-M750, P175-M750, L176-M750, K177-M750, L178-M750, D179-M750, M180-M750, T181-M750, D182-M750, G183-M750, G184-M750, N185-M750, I186-M750, D187-M750, S188-M750, G189-M750, C190-M750, N191-M750, A192-M750, V193-M750, D194-M750, I195-M750, N196-M750, S197-M750, M198-M750, H199-M750, G200-M750, L201-M750, I202-M750, S203-M750, A204-M750, G205-M750, L206-M750, D207-M750, D208-M750, G209-M750, T210-M750, V211-M750, E212-M750, F213-M750, W214-M750, D215-M750, P216-M750, R217-M750, S218-M750, K219-M750, Q220-M750, R221-M750, A222-M750, G223-M750, K224-M750, L225-M750, F226-M750, V227-M750, S228-M750, D229-M750, Q230-M750, L231-M750, I232-M750, N233-M750, S234-M750, T235-M750, N236-M750, N237-M750, T238-M750, E239-M750, Q240-M750, S241-M750, S242-M750, C243-M750, G244-M750, I245-M750, T246-M750, S247-M750, L248-M750, A249-M750, F250-M750, R251-M750, P252-M750, Q253-M750, D254-M750, A255-M750, L256-M750, N257-M750, F258-M750, A259-M750, C260-M750, G261-M750, T262-M750, S263-M750, N264-M750, G265-M750, Q266-M750, T267-M750, L268-M750, L269-M750, Y270-M750, D271-M750, L272-M750, R273-M750, A274-M750, S275-M750, E276-M750, P277-M750, Y278-M750, Q279-M750, I280-M750, K281-M750, D282-M750, Q283-M750, G284-M750, Y285-M750, G286-M750, Y287-M750, D288-M750, I289-M750, K290-M750, K291-M750, I292-M750, I293-M750, W294-M750, C295-M750, Q296-M750, D297-M750, S298-M750, L299-M750, K300-M750, P301-M750, E302-M750, M303-M750, I304-M750, L305-M750, T306-M750, S307-M750, D308-M750, K309-

M750, R310-M750, I311-M750, V312-M750, K313-M750, I314-M750, W315-M750, D316-M750, H317-M750, T318-M750, N319-M750, G320-M750, K321-M750, S322-M750, F323-M750, A324-M750, S325-M750, M326-M750, E327-M750, P328-M750, T329-M750, V330-M750, D331-M750, I332-M750, N333-M750, D334-M750, I335-M750, C336-M750, H337-M750, I338-M750, P339-M750, Q340-M750, S341-M750, G342-M750, M343-M750, F344-M750, F345-M750, M346-M750, A347-M750, N348-M750, E349-M750, G350-M750, M351-M750, P352-M750, M353-M750, H354-M750, T355-M750, Y356-M750, Y357-M750, 1358-M750, P359-M750, N360-M750, L361-M750, G362-M750, S363-M750, A364-M750, P365-M750, N366-M750, W367-M750, C368-M750, S369-M750, F370-M750, L371-M750, D372-M750, N373-M750, V374-M750, T375-M750, E376-M750, E377-M750, L378-M750, E379-M750, E380-M750, K381-M750, P382-M750, S383-M750, N384-M750, S385-M750, I386-M750, Y387-M750, P388-M750, T389-M750, F390-M750, K391-M750, F392-M750, I393-M750, T394-M750, R395-M750, D396-M750, E397-M750, M398-M750, V399-M750, K400-M750, L401-M750, N402-M750, L403-M750, T404-M750, H405-M750, L406-M750, I407-M750, G408-M750, I409-M750, K410-M750, V411-M750, L412-M750, R413-M750, S414-M750, Y415-M750, M416-M750, H417-M750, G418-M750, F419-M750, F420-M750, I421-M750, N422-M750, T423-M750, E424-M750, L425-M750, Y426-M750, D427-M750, K428-M750, V429-M750, N430-M750, L431-M750, I432-M750, S433-M750, N434-M750, P435-M750, N436-M750, S437-M750, I438-M750, Y439-M750, D440-M750, Q441-M750, R442-M750, K443-M750, R444-M750, E445-M750, I446-M750, A447-M750, N448-M750, K449-M750, I450-M750, N451-M750, E452-M750, E453-M750, R454-M750, K455-M750, S456-M750, R457-M750, I458-M750, L459-M750, T460-M750, S461-M750, S462-M750, N463-M750, G464-M750, N465-M750, D466-M750, L467-M750, P468-M750, T469-M750, K470-M750, I471-M750, K472-M750, V473-M750, N474-M750, K475-M750, D476-M750, L477-M750, V478-M750, N479-M750, K480-M750, L481-M750, Q482-M750, T483-M750, K484-M750, F485-M750, A486-M750, E487-M750, N488-M750, G489-M750, T490-M750, P491-M750, D492-M750, G493-M750, N494-M750, A495-M750, N496-M750, G497-M750, A498-M750, T499-M750, D500-M750, Y501-M750, V502-M750, E503-M750, S504-M750, I505-M750, V506-M750, N507-M750, D508-M750, D509-M750, R510-M750, F511-M750, R512-M750, E513-M750, M514-M750, F515-M750, E516-M750, N517-M750, P518-M750, D519-M750, F520-M750, E521-M750, I522-M750, D523-M750, E524-M750, E525-M750, S526-M750, H527-M750, E528-M750, Y529-M750, K530-M750, Q531-M750, L532-M750, N533-M750, P534-M750, V535-M750, K536-M750, S537-M750, T538-M750, K539-M750, D540-M750, I541-M750, T542-M750, T543-M750, T544-M750, N545-M750, T546-M750, G547-M750, T548-M750, T549-M750, N550-M750, S551-M750, R552-M750, G553-M750, R554-M750, G555-M750, L556-M750, T557-M750, A558-M750, A559-M750, E560-M750, E561-M750, S562-M750, D563-M750, E564-M750, E565-M750, R566-M750, L567-M750, N568-M750, M569-M750, K570-M750, D571-M750, S572-M750, H573-M750, H574-M750, T575-M750, G576-M750, L577-M750, D578-M750, S579-M750, D580-M750, E581-M750, S582-M750, D583-M750, E584-M750, E585-M750, S586-M750, D587-M750, S588-M750, E589-M750, S590-M750, E591-M750, E592-M750, Q593-M750, S594-M750, E595-M750, D596-M750, E597-M750, A598-M750, K599-M750, S600-M750, A601-M750, E602-M750, T603-M750, R604-M750, E605-M750, R606-M750, V607-M750, G608-M750, K609-M750, E610-M750, L611-M750, N612-M750, K613-M750, I614-M750, R615-M750, Q616-M750, S617-M750, K618-M750, Q619-M750, K620-M750, Q621-M750, Q622-M750, Q623-M750, Q624-M750, D625-M750, S626-M750, K627-M750, K628-M750, F629-M750, Q630-M750, N631-M750, E632-M750, M633-M750, K634-M750, I635-M750, L636-M750, S637-M750, Q638-M750, Q639-M750, S640-M750, S641-M750, S642-M750, S643-M750, S644-M750, S645-M750, S646-M750, L647-M750, A648-M750, N649-M750, T650-M750, E651-M750, K652-M750, A653-M750, S654-M750, V655-M750, S656-M750, F657-M750, G658-M750, S659-M750, Q660-M750, V661-M750, N662-M750, K663-M750, L664-M750, N665-M750, K666-M750, I667-M750, S668-M750, K669-M750, Q670-M750, N671-M750, K672-M750, N673-M750, N674-M750, N675-M750, S676-M750, I677-M750, S678-M750, N679-M750, A680-M750, K681-M750, D682-M750, A683-M750, R684-M750, L685-M750, R686-M750, R687-M750, H688-M750, A689-M750, R690-M750, G691-M750, E692-M750, A693-M750, E694-M750, L695-M750, T696-M750, F697-M750, V698-M750, P699-M750, Q700-M750, K701-M750, S702-M750, K703-M750, S704-M750, K705-M750, S706-M750, T707-M750, K708-M750, L709-M750, K710-M750, F711-M750, N712-M750, N713-M750, N714-M750, H715-M750, S716-M750, D717-M750, D718-M750, E719-M750, K720-M750, L721-M750, D722-M750, S723-M750, G724-M750, K725-M750, T726-M750, K727-M750, D728-M750, S729-M750, G730-M750, R731-M750, T732-M750, K733-M750, Q734-M750, R735-M750, F736-M750, E737-M750, G738-M750, R739-M750, R740-M750, I741-M750, A742-M750, S743-M750, and/or K744-M750 of SEQ ID NO:17. Polynucleotide sequences encoding these polypeptides are also provided. The present invention also encompasses the use of these N-terminal CaYGR145w deletion polypeptides as immunogenic and/or antigenic epitopes as described elsewhere herein.

In preferred embodiments, the following C-terminal CaYGR145w deletion polypeptides are encompassed by the present invention: M1-M750, M1-G749, M1-R748, M1-F747, M1-K746, M1-N745, M1-K744, M1-S743, M1-A742, M1-I741, M1-R740, M1-R739, M1-G738, M1-E737, M1-F736, M1-R735, M1-Q734, M1-K733, M1-T732, M1-R731, M1-G730, M1-S729, M1-D728, M1-K727, M1-T726, M1-K725, M1-G724, M1-S723, M1-D722, M1-L721, M1-K720, M1-E719, M1-D718, M1-D717, M1-S716, M1-H715, M1-N714, M1-N713, M1-N712, M1-F711, M1-K710, M1-L709, M1-K708, M1-T707, M1-S706, M1-K705, M1-S704, M1-K703, M1-S702, M1-K701, M1-Q700, M1-P699, M1-V698, M1-F697, M1-T696, M1-L695, M1-E694, M1-A693, M1-E692, M1-G691, M1-R690, M1-A689, M1-H688, M1-R687, M1-R686, M1-L685, M1-R684, M1-A683, M1-D682, M1-K681, M1-A680, M1-N679, M1-S678, M1-I677, M1-S676, M1-N675, M1-N674, M1-N673, M1-K672, M1-N671, M1-Q670, M1-K669, M1-S668, M1-I667, M1-K666, M1-N665, M1-L664, M1-K663, M1-N662, M1-V661, M1-Q660, M1-S659, M1-G658, M1-F657, M1-S656, M1-V655, M1-S654, M1-A653, M1-K652, M1-E651, M1-T650, M1-N649, M1-A648, M1-L647, M1-S646, M1-S645, M1-S644, M1-S643, M1-S642, M1-S641, M1-S640, M1-Q639, M1-Q638, M1-S637, M1-L636, M1-I635, M1-K634, M1-M633, M1-E632, M1-N631, M1-Q630, M1-F629, M1-K628, M1-K627, M1-S626, M1-D625, M1-Q624, M1-Q623, M1-Q622, M1-Q621, M1-K620, M1-Q619, M1-K618, M1-S617, M1-Q616, M1-R615, M1-I614, M1-K613, M1-N612, M1-L611, M1-E610, M1-K609, M1-G608, M1-V607, M1-R606, M1-E605, M1-R604, M1-T603, M1-E602, M1-A601, M1-S600, M1-K599, M1-A598, M1-E597, M1-D596, M1-E595, M1-S594, M1-Q593, M1-E592, M1-E591, M1-S590, M1-E589, M1-S588, M1-D587, M1-S586, M1-E585, M1-E584, M1-D583, M1-S582, M1-E581, M1-D580, M1-S579, M1-D578, M1-L577, M1-G576, M1-T575, M1-H574, M1-H573, M1-S572, M1-D571, M1-K570, M1-M569, M1-N568, M1-L567, M1-R566, M1-E565, M1-E564, M1-D563, M1-S562, M1-E561, M1-E560, M1-A559, M1-A558, M1-T557, M1-L556, M1-G555, M1-R554, M1-G553, M1-R552, M1-S551, M1-N550, M1-T549, M1-T548, M1-G547, M1-T546, M1-N545, M1-T544, M1-T543, M1-T542, M1-I541, M1-D540, M1-K539, M1-T538, M1-S537, M1-K536, M1-V535, M1-P534, M1-N533, M1-L532, M1-Q531, M1-K530, M1-Y529, M1-E528, M1-H527, M1-S526, M1-E525, M1-E524, M1-D523, M1-I522, M1-E521, M1-F520, M1-D519, M1-P518, M1-N517, M1-E516, M1-F515, M1-M514, M1-E513, M1-R512, M1-F511, M1-R510, M1-D509, M1-D508, M1-N507, M1-V506, M1-I505, M1-S504, M1-E503, M1-V502, M1-Y501, M1-D500, M1-T499, M1-A498, M1-G497, M1-N496, M1-A495, M1-N494, M1-G493, M1-D492, M1-P491, M1-T490, M1-G489, M1-N488, M1-E487, M1-A486, M1-F485, M1-K484, M1-T483, M1-Q482, M1-L481, M1-K480, M1-N479, M1-V478, M1-L477, M1-D476, M1-K475, M1-N474, M1-V473, M1-K472, M1-I471, M1-K470, M1-T469, M1-P468, M1-L467, M1-D466, M1-N465, M1-G464, M1-N463, M1-S462, M1-S461, M1-T460, M1-L459, M1-I458, M1-R457, M1-S456, M1-K455, M1-R454, M1-E453, M1-E452, M1-N451, M1-I450, M1-K449, M1-N448, M1-A447, M1-1446, M1-E445, M1-R444, M1-K443, M1-R442, M1-Q441, M1-D440, M1-Y439, M1-I438, M1-S437, M1-N436, M1-P435, M1-N434, M1-S433, M1-I432, M1-L431, M1-N430, M1-V429, M1-K428, M1-D427, M1-Y426, M1-L425, M1-E424, M1-T423, M1-N422, M1-I421, M1-F420, M1-F419, M1-G418, M1-H417, M1-M416, M1-Y415, M1-S414, M1-R413, M1-L412, M1-V411, M1-K410, M1-I409, M1-G408, M1-I407, M1-L406, M1-H405, M1-T404, M1-L403, M1-N402, M1-L401, M1-K400, M1-V399, M1-M398, M1-E397, M1-D396, M1-R395, M1-T394, M1-I393, M1-F392, M1-K391, M1-F390, M1-T389, M1-P388, M1-Y387, M1-I386, M1-S385, M1-N384, M1-S383, M1-P382, M1-K381, M1-E380, M1-E379, M1-L378, M1-E377, M1-E376, M1-T375, M1-V374, M1-N373, M1-D372, M1-L371, M1-F370, M1-S369, M1-C368, M1-W367, M1-N366, M1-P365, M1-A364, M1-S363, M1-G362, M1-L361, M1-N360, M1-P359, M1-I358, M1-Y357, M1-Y356, M1-T355, M1-H354, M1-M353, M1-P352, M1-M351, M1-G350, M1-E349, M1-N348, M1-A347, M1-M346, M1-F345, M1-F344, M1-M343, M1-G342, M1-S341, M1-Q340, M1-P339, M1-I338, M1-H337, M1-C336, M1-I335, M1-D334, M1-N333, M1-I332, M1-D331, M1-V330, M1-T329, M1-P328, M1-E327, M1-M326, M1-S325, M1-A324, M1-F323, M1-S322, M1-K321, M1-G320, M1-N319, M1-T318, M1-H317, M1-D316, M1-W315, M1-I314, M1-K313, M1-V312, M1-I311, M1-R310, M1-K309, M1-D308, M1-S307, M1-T306, M1-L305, M1-I304, M1-M303, M1-E302, M1-P301, M1-K300, M1-L299, M1-S298, M1-D297, M1-Q296, M1-C295, M1-W294, M1-I293, M1-I292, M1-K291, M1-K290, M1-I289, M1-D288, M1-Y287, M1-G286, M1-Y285, M1-G284, M1-Q283, M1-D282, M1-K281, M1-I280, M1-Q279, M1-Y278, M1-P277, M1-E276, M1-S275, M1-A274, M1-R273, M1-L272, M1-D271, M1-Y270, M1-L269, M1-L268, M1-T267, M1-Q266, M1-G265, M1-N264, M1-S263, M1-T262, M1-G261, M1-C260, M1-A259, M1-F258, M1-N257, M1-L256, M1-A255, M1-D254, M1-Q253, M1-P252, M1-R251, M1-F250, M1-A249, M1-L248, M1-S247, M1-T246, M1-I245, M1-G244, M1-C243, M1-S242, M1-S241, M1-Q240, M1-E239, M1-T238, M1-N237, M1-N236, M1-T235, M1-S234, M1-N233, M1-I232, M1-L231, M1-Q230, M1-D229, M1-S228, M1-V227, M1-F226, M1-L225, M1-K224, M1-G223, M1-A222, M1-R221, M1-Q220, M1-K219, M1-S218, M1-R217, M1-P216, M1-D215, M1-W214, M1-F213, M1-E212, M1-V211, M1-T210, M1-G209, M1-D208, M1-D207, M1-L206, M1-G205, M1-A204, M1-S203, M1-I202, M1-L201, M1-G200, M1-H199, M1-M198, M1-S197, M1-N196, M1-I195, M1-D194, M1-V193, M1-A192, M1-N191, M1-C190, M1-G189, M1-S188, M1-D187, M1-I186, M1-N185, M1-G184, M1-G183, M1-D182, M1-T181, M1-M180, M1-D179, M1-L178, M1-K177, M1-L176, M1-P175, M1-S174, M1-L173, M1-F172, M1-R171, M1-G170, M1-Q169, M1-D168, M1-L167, M1-N166, M1-L165, M1-R164, M1-Y163, M1-L162, M1-E161, M1-D160, M1-S159, M1-S158, M1-S157, M1-G156, M1-V155, M1-I154, M1-L153, M1-D152, M1-C151, M1-N150, M1-I149, M1-P148, M1-N147, M1-Y146, M1-T145, M1-L144, M1-C143, M1-R142, M1-G141, M1-F140, M1-K139, M1-P138, M1-I137, M1-R136, M1-T135, M1-R134, M1-Y133, M1-H132, M1-V131, M1-G130, M1-G129, M1-A128, M1-T127, M1-Q126, M1-F125, M1-E124, M1-I123, M1-S122, M1-R121, M1-D120, M1-C119, M1-Q118, M1-L117, M1-H116, M1-V115, M1-S114, M1-K113, M1-T112, M1-W111, M1-D110, M1-N109, M1-S108, M1-L107, M1-I106, M1-L105, M1-F104, M1-D103, M1-I102, M1-N101, M1-E100, M1-V99, M1-N98, M1-T97, M1-H96, M1-R95, M1-D94, M1-F93, M1-K92, M1-L91, M1-S90, M1-L89, M1-N88, M1-A87, M1-F86, M1-E85, M1-Y84, M1-V83, M1-H82, M1-I81, M1-Q80, M1-P79, M1-K78, M1-Y77, M1-T76, M1-G75, M1-T74, M1-A73, M1-M72, M1-C71, M1-Y70, M1-Q69, M1-G68, M1-D67, M1-N66, M1-T65, M1-V64, M1-K63, M1-I62, M1-K61, M1-N60, M1-S59, M1-A58, M1-E57, M1-S56, M1-F55, M1-E54, M1-F53, M1-D52, M1-Q51, M1-I50, M1-L49, M1-E48, M1-I47, M1-R46, M1-N45, M1-Q44, M1-Y43, M1-E42, M1-L41, M1-D40, M1-H39, M1-K38, M1-L37, M1-A36, M1-R35, M1-K34, M1-R33, M1-K32, M1-K31, M1-D30, M1-I29, M1-W28, M1-D27, M1-P26, M1-L25, M1-S24, M1-R23, M1-S22, M1-V21, M1-N20, M1-T19, M1-G18, M1-S17, M1-V16, M1-Q15, M1-Y14, M1-V13, M1-S12, M1-V11, M1-N10, M1-G9, M1-A8, and/or M1-T7 of SEQ ID NO:17. Polynucleotide sequences encoding these polypeptides are also provided. The present invention also encompasses the use of these C-terminal CaYGR145w deletion polypeptides as immunogenic and/or antigenic epitopes as described elsewhere herein.

The present invention also encompasses polynucleotides sharing at least about 50%, 60%, 70%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:6, and in particular to the coding region of the polynucleotide sequence provided in SEQ ID NO:6. Preferably such polynucleotides encode polypeptides that have biological activity.

The present invention also encompasses polypeptides sharing at least about 50%, 60%, 70%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:17.

Many polynucleotide sequences, such as EST sequences, are publicly available and accessible through sequence databases. Some of these sequences are related to SEQ ID NO:6 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 2236 of SEQ ID NO:6, b is an integer between 15 to 2250, where both a and b correspond to the positions of nucleotide residues shown in SEQ ID NO:6, and where b is greater than or equal to a+14.

Features of the Polypeptide Encoded by Polynucleotide No:7

The polynucleotide sequence (SEQ ID NO:7) and deduced amino acid sequence (SEQ ID NO:18) of the novel fungal essential gene, CaYDR412w (also referred to as FCG13), of the present invention. The CaYDR412w polypeptide (SEQ ID NO:18) is encoded by nucleotides 1 to 804 of SEQ ID NO:7 and has a predicted molecular weight of 31.3 kDa.

In preferred embodiments, the present invention encompasses a polynucleotide lacking the initiating start codon, in addition to, the resulting encoded polypeptide of CaYDR412w. Specifically, the present invention encompasses the polynucleotide corresponding to nucleotides 4 thru 2250 of SEQ ID NO:7, and the polypeptide corresponding to amino acids 2 thru 268 of SEQ ID NO:18. Also encompassed are recombinant vectors comprising said encoding sequence, and host cells comprising said vector.

The invention also encompasses N- and/or C-terminal deletions of the CaYDR412w polypeptide of the present invention.

In preferred embodiments, the following N-terminal CaYDR412w deletion polypeptides are encompassed by the present invention: M1-K268, A2-K268, G3-K268, F4-K268, K5-K268, K6-K268, N7-K268, R8-K268, E9-K268, I10-K268, L11-K268, T12-K268, G13-K268, G14-K268, K15-K268, K16-K268, Y17-K268, I18-K268, Q19-K268, Q20-K268, K21-K268, Q22-K268, K23-K268, K24-K268, H25-K268, L26-K268, V27-K268, D28-K268, E29-K268, V30-K268, V31-K268, F32-K268, D33-K268, K34-K268, E35-K268, S36-K268, R37-K268, H38-K268, E39-K268, Y40-K268, L41-K268, T42-K268, G43-K268, F44-K268, H45-K268, K46-K268, R47-K268, K48-K268, L49-K268, Q50-K268, R51-K268, Q52-K268, K53-K268, K54-K268, A55-K268, Q56-K268, E57-K268, F58-K268, H59-K268, K60-K268, E61-K268, Q62-K268, E63-K268, R64-K268, L65-K268, A66-K268, K67-K268, I68-K268, E69-K268, E70-K268, R71-K268, K72-K268, Q73-K268, L74-K268, K75-K268, Q76-K268, E77-K268, R78-K268, E79-K268, R80-K268, D81-K268, L82-K268, Q83-K268, N84-K268, Q85-K268, L86-K268, Q87-K268, Q88-K268, F89-K268, K90-K268, K91-K268, T92-K268, A93-K268, Q94-K268, E95-K268, I96-K268, A97-K268, A98-K268, I99-K268, N100-K268, N101-K268, D102-K268, I103-K268, G104-K268, F105-K268, D106-K268, Q107-K268, S108-K268, D109-K268, D 110-K268, N111-K268, N112-K268, D113-K268, N114-K268, D115-K268, N116-K268, E117-K268, N118-K268, E119-K268, E120-K268, W121-K268, S122-K268, G123-K268, F124-K268, Q125-K268, E126-K268, D127-K268, E128-K268, E129-K268, G130-K268, E131-K268, G132-K268, E133-K268, E134-K268, V135-K268, T136-K268, D137-K268, E138-K268, D139-K268, D140-K268, E141-K268, D142-K268, K143-K268, E144-K268, K145-K268, P146-K268, L147-K268, K148-K268, G149-K268, I150-K268, L151-K268, H152-K268, H153-K268, T154-K268, E155-K268, I156-K268, Y157-K268, K158-K268, Q159-K268, D160-K268, P161-K268, S162-K268, L163-K268, S164-K268, N165-K268, I166-K268, T167-K268, N168-K268, N169-K268, G170-K268, A171-K268, I172-K268, I173-K268, D174-K268, D175-K268, E176-K268, T177-K268, T178-K268, V179-K268, V180-K268, V181-K268, E182-K268, S183-K268, L184-K268, D185-K268, N186-K268, P187-K268, N188-K268, A189-K268, V190-K268, D191-K268, T192-K268, E193-K268, E194-K268, K195-K268, L196-K268, Q197-K268, Q198-K268, L199-K268, A200-K268, K201-K268, L202-K268, N203-K268, N204-K268, V205-K268, N206-K268, L207-K268, D208-K268, K209-K268, S210-K268, D211-K268, Q212-K268, I213-K268, L214-K268, E215-K268, K216-K268, S217-K268, I218-K268, E219-K268, R220-K268, A221-K268, K222-K268, N223-K268, Y224-K268, A225-K268, V226-K268, I227-K268, C228-K268, G229-K268, V230-K268, A231-K268, K232-K268, P233-K268, N234-K268, P235-K268, I236-K268, K237-K268, Q238-K268, K239-K268, K240-K268, K241-K268, K242-K268, F243-K268, R244-K268, Y245-K268, L246-K268, T247-K268, K248-K268, A249-K268, E250-K268, R251-K268, R252-K268, E253-K268, N254-K268, V255-K268, R256-K268, K257-K268, E258-K268, K259-K268, S260-K268, K261-K268, and/or S262-K268 of SEQ ID NO:18. Polynucleotide sequences encoding these polypeptides are also provided. The present invention also encompasses the use of these N-terminal CaYDR412w deletion polypeptides as immunogenic and/or antigenic epitopes as described elsewhere herein.

In preferred embodiments, the following C-terminal CaYDR412w deletion polypeptides are encompassed by the present invention: M1-K268, M1-K267, M1-G266, M1-K265, M1-S264, M1-K263, M1-S262, M1-K261, M1-S260, M1-K259, M1-E258, M1-K257, M1-R256, M1-V255, M1-N254, M1-E253, M1-R252, M1-R251, M1-E250, M1-A249, M1-K248, M1-T247, M1-L246, M1-Y245, M1-R244, M1-F243, M1-K242, M1-K241, M1-K240, M1-K239, M1-Q238, M1-K237, M1-I236, M1-P235, M1-N234, M1-P233, M1-K232, M1-A231, M1-V230, M1-G229, M1-C228, M1-I227, M1-V226, M1-A225, M1-Y224, M1-N223, M1-K222, M1-A221, M1-R220, M1-E219, M1-I218, M1-S217, M1-K216, M1-E215, M1-L214, M1-I213, M1-Q212, M1-D211, M1-S210, M1-K209, M1-D208, M1-L207, M1-N206, M1-V205, M1-N204, M1-N203, M1-L202, M1-K201, M1-A200, M1-L199, M1-Q198, M1-Q197, M1-L196, M1-K195, M1-E194, M1-E193, M1-T192, M1-D191, M1-V190, M1-A189, M1-N188, M1-P187, M1-N186, M1-D185, M1-L184, M1-S183, M1-E182, M1-V181, M1-V180, M1-V179, M1-T178, M1-T177, M1-E176, M1-D175, M1-D174, M1-I173, M1-I172, M1-A171, M1-G170, M1-N169, M1-N168, M1-T167, M1-I166, M1-N165, M1-S164, M1-L163, M1-S162, M1-P161, M1-D160, M1-Q159, M1-K158, M1-Y157, M1-I156, M1-E155, M1-T154, M1-H153, M1-H152, M1-L151, M1-I150, M1-G149, M1-K148, M1-L147, M1-P146, M1-K145, M1-E144, M1-K143, M1-D142, M1-E141, M1-D140, M1-D139, M1-E138, M1-D137, M1-T136, M1-V135, M1-E134, M1-E133, M1-G132, M1-E131, M1-G130, M1-E129, M1-E128, M1-D127, M1-E126, M1-Q125, M1-F124, M1-G123, M1-S122, M1-W121, M1-E120, M1-E119, M1-N118, M1-E117, M1-N116, M1-D115, M1-N114, M1-D113, M1-N112, M1-N111, M1-D110, M1-D109, M1-S108, M1-Q107, M1-D106, M1-F105, M1-G104, M1-I103, M1-D102, M1-N101, M1-N100, M1-I99, M1-A98, M1-A97, M1-I96, M1-E95, M1-Q94, M1-A93, M1-T92, M1-K91, M1-K90, M1-F89, M1-Q88, M1-Q87, M1-L86, M1-Q85, M1-N84, M1-Q83, M1-L82, M1-D81, M1-R80, M1-E79, M1-R78, M1-E77, M1-Q76, M1-K75, M1-L74, M1-Q73, M1-K72, M1-R71, M1-E70, M1-E69, M1-I68, M1-K67, M1-A66, M1-L65, M1-R64, M1-E63, M1-Q62, M1-E61, M1-K60, M1-H59, M1-F58, M1-E57, M1-Q56, M1-A55, M1-K54, M1-K53, M1-Q52, M1-R51, M1-Q50, M1-L49, M1-K48, M1-R47, M1-K46, M1-H45, M1-F44, M1-G43, M1-T42, M1-L41, M1-Y40, M1-E39, M1-H38, M1-R37, M1-S36, M1-E35, M1-K34, M1-D33, M1-F32, M1-V31, M1-V30, M1-E29, M1-D28, M1-V27, M1-L26, M1-H25, M1-K24, M1-K23, M1-Q22, M1-K21, M1-Q20, M1-Q19, M1-I18, M1-Y17, M1-K16, M1-K15, M1-G14, M1-G13, M1-T12, M1-L11, M1-I10, M1-E9, M1-R8, and/or M1-N7 of SEQ ID NO:18. Polynucleotide sequences encoding these polypeptides are also provided. The present invention also encompasses the use of these C-terminal CaYDR412w deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:7, and in particular to the coding region of the polynucleotide sequence provided in SEQ ID NO:7. Preferably such polynucleotides encode polypeptides that have biological activity.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:18.

Most preferred are polypeptides that share at least about 99.4% identity with the polypeptide sequence provided in SEQ ID NO: 18.

Many polynucleotide sequences, such as EST sequences, are publicly available and accessible through sequence databases. Some of these sequences are related to SEQ ID NO:7 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 790 of SEQ ID NO:7, b is an integer between 15 to 804, where both a and b correspond to the positions of nucleotide residues shown in SEQ ID NO:7, and where b is greater than or equal to a+14.

Features of the Polypeptide Encoded by Polynucleotide No:8

The polynucleotide sequence (SEQ ID NO:8) and deduced amino acid sequence (SEQ ID NO:19) of the novel fungal essential gene, CaYOL010w (also referred to as FCG14), of the present invention. The CaYOL010w polypeptide (SEQ ID NO:19) is encoded by nucleotides 1 to 1113 of SEQ ID NO:8 and has a predicted molecular weight of 40.6 kDa.

In preferred embodiments, the present invention encompasses a polynucleotide lacking the initiating start codon, in addition to, the resulting encoded polypeptide of CaYOL010w. Specifically, the present invention encompasses the polynucleotide corresponding to nucleotides 4 thru 1113 of SEQ ID NO:8, and the polypeptide corresponding to amino acids 2 thru 371 of SEQ ID NO:19. Also encompassed are recombinant vectors comprising said encoding sequence, and host cells comprising said vector.

The invention also encompasses N- and/or C-terminal deletions of the CaYOL010w polypeptide of the present invention.

In preferred embodiments, the following N-terminal CaYOL010w deletion polypeptides are encompassed by the present invention: M1-A371, S2-A371, S3-A371, V4-A371, A5-A371, S6-A371, K7-A371, K8-A371, I9-A371, I10-A371, T11-A371, F12-A371, E13-A371, G14-A371, H15-A371, R16-A371, N17-A371, F18-A371, R19-A371, L20-A371, R21-A371, L22-A371, V23-A371, L24-A371, A25-A371, T26-A371, L27-A371, S28-A371, G29-A371, K30-A371, P31-A371, I32-A371, K33-A371, I34-A371, T35-A371, K36-A371, I37-A371, R38-A371, S39-A371, Q40-A371, D41-A371, L42-A371, N43-A371, P44-A371, G45-A371, L46-A371, K47-A371, D48-A371, H49-A371, E50-A371, V51-A371, S52-A371, F53-A371, L54-A371, R55-A371, L56-A371, L57-A371, E58-A371, A59-A371, V60-A371, T61-A371, N62-A371, G63-A371, S64-A371, H65-A371, I66-A371, E67-A371, I68-A371, S69-A371, Y70-A371, T71-A371, G72-A371, T73-A371, T74-A371, I75-A371, I76-A371, Y77-A371, R78-A371, P79-A371, G80-A371, I81-A371, I82-A371, I83-A371, G84-A371, G85-A371, D86-A371, L87-A371, T88-A371, H89-A371, N90-A371, C91-A371, P92-A371, D93-A371, T94-A371, K95-A371, S96-A371, I97-A371, G98-A371, Y99-A371, F100-A371, I101-A371, E102-A371, P103-A371, M104-A371, L105-A371, M106-A371, F107-A371, P108-A371, L109-A371, F110-A371, S111-A371, K112-A371, K113-A371, K114-A371, F115-A371, S116-A371, I117-A371, I118-A371, F119-A371, K120-A371, G121-A371, L122-A371, T123-A371, N124-A371, I125-A371, A126-A371, G127-A371, N128-A371, D129-A371, T130-A371, G131-A371, V132-A371, D133-A371, A134-A371, I135-A371, K136-A371, W137-A371, G138-A371, L139-A371, L140-A371, P141-A371, V142-A371, M143-A371, E144-A371, K145-A371, F146-A371, G147-A371, V148-A371, R149-A371, E150-A371, V151-A371, S152-A371, L153-A371, H154-A371, I155-A371, L156-A371, K157-A371, R158-A371, G159-A371, S160-A371, A161-A371, P162-A371, L163-A371, G164-A371, G165-A371, G166-A371, E167-A371, V168-A371, H169-A371, L170-A371, L171-A371, C172-A371, S173-A371, S174-A371, L175-A371, I176-A371, P177-A371, Q178-A371, P179-A371, L180-A371, T181-A371, I182-A371, H183-A371, A184-A371, L185-A371, D186-A371, I187-A371, P188-A371, K189-A371, F190-A371, S191-A371, A192-A371, I193-A371, R194-A371, G195-A371, V196-A371, A197-A371, Y198-A371, C199-A371, T200-A371, R201-A371, V202-A371, S203-A371, P204-A371, S205-A371, I206-A371, V207-A371, N208-A371, R209-A371, M210-A371, I211-A371, D212-A371, S213-A371, A214-A371, R215-A371, A216-A371, V217-A371, L218-A371, K219-A371, P220-A371, T221-A371, G222-A371, C223-A371, E224-A371, V225-A371, N226-A371, I227-A371, T228-A371, A229-A371, D230-A371, V231-A371, W232-A371, R233-A371, G234-A371, E235-A371, N236-A371, S237-A371, G238-A371, K239-A371, S240-A371, P241-A371, G242-A371, F243-A371, G244-A371, I245-A371, T246-A371, L247-A371, V248-A371, A249-A371, E250-A371, L251-A371, K252-A371, R253-A371, G254-A371, W255-A371, R256-A371, I257-A371, V258-A371, T259-A371, E260-A371, N261-A371, V262-A371, G263-A371, S264-A371, A265-A371, G266-A371, S267-A371, L268-A371, P269-A371, E270-A371, D271-A371, S272-A371, G273-A371, E274-A371, L275-A371, T276-A371, A277-A371, Y278-A371, Q279-A371, L280-A371, L281-A371, E282-A371, E283-A371, I284-A371, S285-A371, N286-A371, S287-A371, G288-A371, V289-A371, V290-A371, G291-A371, R292-A371, Y293-A371, Q294-A371, L295-A371, P296-A371, L297-A371, A298-A371, L299-A371, V300-A371, Y301-A371, M302-A371, T303-A371, I304-A371, G305-A371, K306-A371, E307-A371, D308-A371, I309-A371, G310-A371, R311-A371, L312-A371, K313-A371, L314-A371, Q315-A371, K316-A371, S317-A371, E318-A371, I319-A371, D320-A371, E321-A371, N322-A371, L323-A371, V324-A371, S325-A371, V326-A371, L327-A371, R328-A371, D329-A371, I330-A371, Q331-A371, E332-A371, V333-A371, F334-A371, G335-A371, T336-A371, E337-A371, A338-A371, F339-A371, F340-A371, K341-A371, D342-A371, D343-A371, A344-A371, E345-A371, E346-A371, L347-A371, D348-A371, S349-A371, D350-A371, D351-A371, K352-A371, F353-A371, M354-A371, T355-A371, V356-A371, S357-A371, I358-A371, K359-A371, G360-A371, V361-A371, G362-A371, F363-A371, T364-A371, and/or N365-A371 of SEQ ID NO:19. Polynucleotide sequences encoding these polypeptides are also provided. The present invention also encompasses the use of these N-terminal CaYOL010w deletion polypeptides as immunogenic and/or antigenic epitopes as described elsewhere herein.

In preferred embodiments, the following C-terminal CaYOL010w deletion polypeptides are encompassed by the present invention: M1-A371, M1-I370, M1-K369, M1-K368, M1-S367, M1-V366, M1-N365, M1-T364, M1-F363, M1-G362, M1-V361, M1-G360, M1-K359, M1-I358, M1-S357, M1-V356, M1-T355, M1-M354, M1-F353, M1-K352, M1-D351, M1-D350, M1-S349, M1-D348, M1-L347, M1-E346, M1-E345, M1-A344, M1-D343, M1-D342, M1-K341, M1-F340, M1-F339, M1-A338, M1-E337, M1-T336, M1-G335, M1-F334, M1-V333, M1-E332, M1-Q331, M1-I330, M1-D329, M1-R328, M1-L327, M1-V326, M1-S325, M1-V324, M1-L323, M1-N322, M1-E321, M1-D320, M1-I319, M1-E318, M1-S317, M1-K316, M1-Q315, M1-L314, M1-K313, M1-L312, M1-R311, M1-G310, M1-I309, M1-D308, M1-E307, M1-K306, M1-G305, M1-I304, M1-T303, M1-M302, M1-Y301, M1-V300, M1-L299, M1-A298, M1-L297, M1-P296, M1-L295, M1-Q294, M1-Y293, M1-R292, M1-G291, M1-V290, M1-V289, M1-G288, M1-S287, M1-N286, M1-S285, M1-I284, M1-E283, M1-E282, M1-L281, M1-L280, M1-Q279, M1-Y278, M1-A277, M1-T276, M1-L275, M1-E274, M1-G273, M1-S272, M1-D271, M1-E270, M1-P269, M1-L268, M1-S267, M1-G266, M1-A265, M1-S264, M1-G263, M1-V262, M1-N261, M1-E260, M1-T259, M1-V258, M1-I257, M1-R256, M1-W255, M1-G254, M1-R253, M1-K252, M1-L251, M1-E250, M1-A249, M1-V248, M1-L247, M1-T246, M1-I245, M1-G244, M1-F243, M1-G242, M1-P241, M1-S240, M1-K239, M1-G238, M1-S237, M1-N236, M1-E235, M1-G234, M1-R233, M1-W232, M1-V231, M1-D230, M1-A229, M1-T228, M1-I227, M1-N226, M1-V225, M1-E224, M1-C223, M1-G222, M1-T221, M1-P220, M1-K219, M1-L218, M1-V217, M1-A216, M1-R215, M1-A214, M1-S213, M1-D212, M1-I211, M1-M210, M1-R209, M1-N208, M1-V207, M1-I206, M1-S205, M1-P204, M1-S203, M1-V202, M1-R201, M1-T200, M1-C199, M1-Y198, M1-A197, M1-V196, M1-G195, M1-R194, M1-I193, M1-A192, M1-S191, M1-F190, M1-K189, M1-P188, M1-I187, M1-D186, M1-L185, M1-A184, M1-H183, M1-I182, M1-T181, M1-L180, M1-P179, M1-Q178, M1-P177, M1-I176, M1-L175, M1-S174, M1-S173, M1-C172, M1-L171, M1-L170, M1-H169, M1-V168, M1-E167, M1-G166, M1-G165, M1-G164, M1-L163, M1-P162, M1-A161, M1-S160, M1-G159, M1-R158, M1-K157, M1-L156, M1-I155, M1-H154, M1-L153, M1-S152, M1-V151, M1-E150, M1-R149, M1-V148, M1-G147, M1-F146, M1-K145, M1-E144, M1-M143, M1-V142, M1-P141, M1-L140, M1-L139, M1-G138, M1-W137, M1-K136, M1-I135, M1-A134, M1-D133, M1-V132, M1-G131, M1-T130, M1-D129, M1-N128, M1-G127, M1-A126, M1-I125, M1-N124, M1-T123, M1-L122, M1-G121, M1-K120, M1-F119, M1-I118, M1-I117, M1-S116, M1-F115, M1-K114, M1-K113, M1-K112, M1-S111, M1-F110, M1-L109, M1-P108, M1-F107, M1-M106, M1-L105, M1-M104, M1-P103, M1-E102, M1-I101, M1-F100, M1-Y99, M1-G98, M1-I97, M1-S96, M1-K95, M1-T94, M1-D93, M1-P92, M1-C91, M1-N90, M1-H89, M1-T88, M1-L87, M1-D86, M1-G85, M1-G84, M1-I83, M1-I82, M1-I81, M1-G80, M1-P79, M1-R78, M1-Y77, M1-I76, M1-I75, M1-T74, M1-T73, M1-G72, M1-T71, M1-Y70, M1-S69, M1-168, M1-E67, M1-I66, M1-H65, M1-S64, M1-G63, M1-N62, M1-T61, M1-V60, M1-A59, M1-E58, M1-L57, M1-L56, M1-R55, M1-L54, M1-F53, M1-S52, M1-V51, M1-E50, M1-H49, M1-D48, M1-K47, M1-L46, M1-G45, M1-P44, M1-N43, M1-L42, M1-D41, M1-Q40, M1-S39, M1-R38, M1-I37, M1-K36, M1-T35, M1-I34, M1-K33, M1-I32, M1-P31, M1-K30, M1-G29, M1-S28, M1-L27, M1-T26, M1-A25, M1-L24, M1-V23, M1-L22, M1-R21, M1-L20, M1-R19, M1-F18, M1-N17, M1-R16, M1-H15, M1-G14, M1-E13, M1-F12, M1-T11, M1-I10, M1-I9, M1-K8, and/or M1-K7 of SEQ ID NO:19. Polynucleotide sequences encoding these polypeptides are also provided. The present invention also encompasses the use of these C-terminal CaYOL010w deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:8, and in particular to the coding region of the polynucleotide sequence provided in SEQ ID NO:8. Preferably such polynucleotides encode polypeptides that have biological activity, particularly RNA 3'-terminal phosphate cyclase activity.

Most preferred are polynucleotides that share at least about 99.5% identity with the polynucleotide sequence provided in SEQ ID NO:8.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:19.

Most preferred are polypeptides that share at least about 99.0% identity with the polypeptide sequence provided in SEQ ID NO:19.

The present invention is also directed to a homology model detailing the three-dimensional structure of the CaYOL010w polypeptide (SEQ ID NO:19) of the present invention.

Protein threading and molecular modeling of CaYOL010w suggest that CaYOL010w has a three dimensional fold similar to that of the RNA 3'-terminal phosphate cyclase from *E. coli* (Palm et. al., 1999), Protein Data Bank (PDB, Bernstein et. al., 1977 & Berman et. al., 2000) (Protein Data Bank entry 1QMH; Genbank Accession No. gi|12644279; SEQ ID NO:253). Based on sequence, structure, motifs and known cyclase signature sequences, CaYOL010w contains a novel RNA cyclase domain.

The polypeptide CaYOL010w contains a distinct structural domain similar to the RNA cyclase domains that are a family of RNA modifying enzymes conserved in eucarya, bacteria and archaea.

The Three Dimensional Crystallographic Structure for *Escherichia coli*

RNA 3'-terminal phosphate cyclase has been reported and was deposited into the Protein Data Bank (Palm et. al., 1999, Bernstein et. al., 1977, Berman et. al., 2000).

The structure (Protein Data Bank, PDB entry 1QMH) of RNA 3'-terminal phosphate cyclase *Escherichia coli* is a novel fold that consists on known structural elements connected in a unique manner. The structure of cyclase consists of two structurally distinct domains. The larger domain is composed of the N-terminal 184 amino acids (1-184) and the C-terminal 59 amino acids (280-339). The domain contains three repeats of a folding unit comprising two α-helices and a four-stranded β-sheet. The smaller domain of the cyclase, residues 185-279, comprises the same 4 stranded sheet covered by two α-helices but the connection topology is different. The active site of the of RNA 3'-terminal phosphate cyclase contains a histidine (H309) at the active site that was identified by labeling and lysines in the active site have been reported as part of the catalytic mechanism of nucleotidyl transferases including cyclases. The H309 lies at the bottom of a deep cleft surrounded by 5 loops containing conserved residues (from across the orthologs of cyclases). A RNA 3'-terminal phosphate cyclase signature sequence is found in the N-terminal region of the larger domain. This motif H/R-G-X-P-G-G-G-X-V (SEQ ID NO:256) is similar to the glycine rich loops known to contact ATP, GTP and other nucleotides at binding sites in other enzymes. The histidine or arginine residue is thought to bind to the nucleotide. For the *E. coli* RNA 3'-terminal phosphate cyclase H158 through V168 comprises the cyclase functional signature.

This structure-based information and sequence information from novel genes can be used to identify other protein family members that share this same fold.

The CaYOL010w three dimensional model provides for a specific description of the distinct domain and functional/active sites in the RNA 3'-terminal phosphate cyclase, CaYOL010w polypeptide.

The structural domain and functional/active sites are defined by atomic coordinates (Table 10). Based on this data, the inventors have ascribed the CaYOL010w polypeptide as having RNA cyclase activity(s) and cellular and systemic regulatory function(s).

The invention also relates to in silico screening methods including in silico docking and methods of structure based drug design which utilize the three dimensional coordinates of CaYOL010w (Table 10). Also provided are methods of identifying modulators of CaYOL010w that include modulator building or searching utilizing computer programs and algorithms. In an embodiment of the invention a method is provided for designing potential modulators of CaYOL010w comprising any combination of steps which utilize said three dimensional structure to design or select potential modulators.

Homology models are useful when there is no experimental information available on the protein of interest. A three dimensional model can be constructed on the basis of the known structure of a homologous protein (Greer et. al., 1991, Lesk, et. al., 1992, Levitt, 1992, Cardozo, et. al., 1995, Sali, et. al., 1995).

Those of skill in the art will understand that a homology model is constructed on the basis of first identifying a template, or, protein of known structure which is similar to the protein without known structure. This can be accomplished by through pairwise alignment of sequences using such programs as FASTA (Pearson, et. al. 1990) and BLAST (Altschul, et. al., 1990). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et. al., 1990, Koppensteiner et. al. 2000, Sippl & Weitckus 1992, Sippl 1993), where the compatibility of a particular sequence with the three dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and are used to construct the core secondary structure (Levitt, 1992, Sali, et. al., 1995) elements in the three dimensional model. Variable regions, called "unconserved regions" and loops can be added using knowledge-based techniques. The complete model with variable regions and loops can be refined performing forcefield calculations (Sali, et. al., 1995, Cardozo, et. al., 1995).

Figure 33:
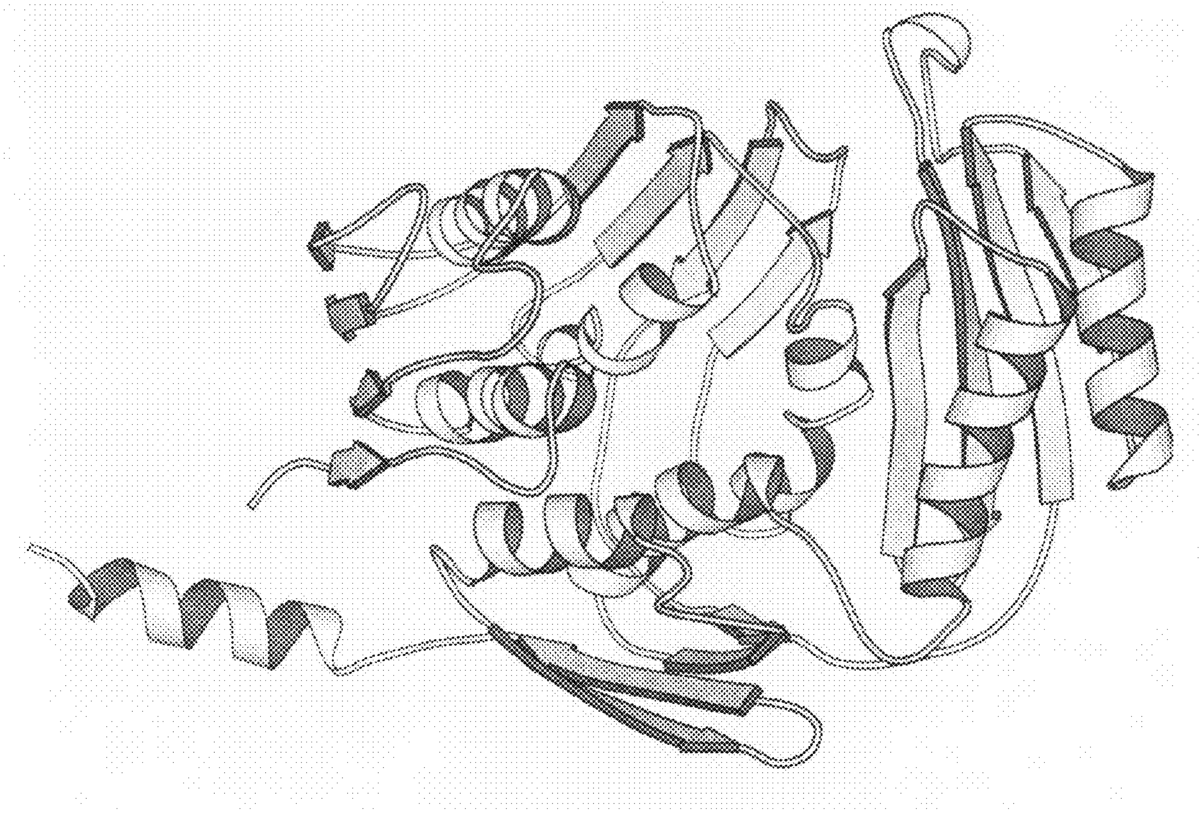
FIG. 33 shows the three-dimensional homology model of the CaYOL010w (FCG6) polypeptide of the present invention (SEQ ID NO:19). The model is based upon an alignment to a structural homologue *Escherichia coli* RNA 3'-terminal phosphate cyclase (Protein Data Bank entry 1QMH; Genbank Accession No. gi|12644279; SEQ ID NO:253) that was used as the basis for building the CaYOL010w homology model. The coordinates of the CaYOL010w model are provided in Table 10.

For CaYOL010w a pairwise alignment generated by protein threading (Hendlich, et. al., 1990, Koppensteiner et. al. 2000, Sippl & Weitckus 1992, Sippl 1993) was used to align the sequence of CaYOL010w with the sequence the RNA 3'-terminal phosphate cyclase, *Escherichia coli* (Palm et. al., 1999), (Protein Data Bank code 1QMH). The alignment of CaYOL010w with PDB entry 1QMH chain A is set forth in FIG. 32. In this invention, the homology model of CaYOL010w was derived from the sequence alignment set forth in FIG. 32. An overall atomic model including plausible sidechain orientations was generated using the program LOOK (Levitt, 1992). The three dimensional model for CaYOL010w is defined by the set of structure coordinates as set forth in Table 10 and is shown in FIG. 33 rendered by backbone secondary structures.

Figure 34:
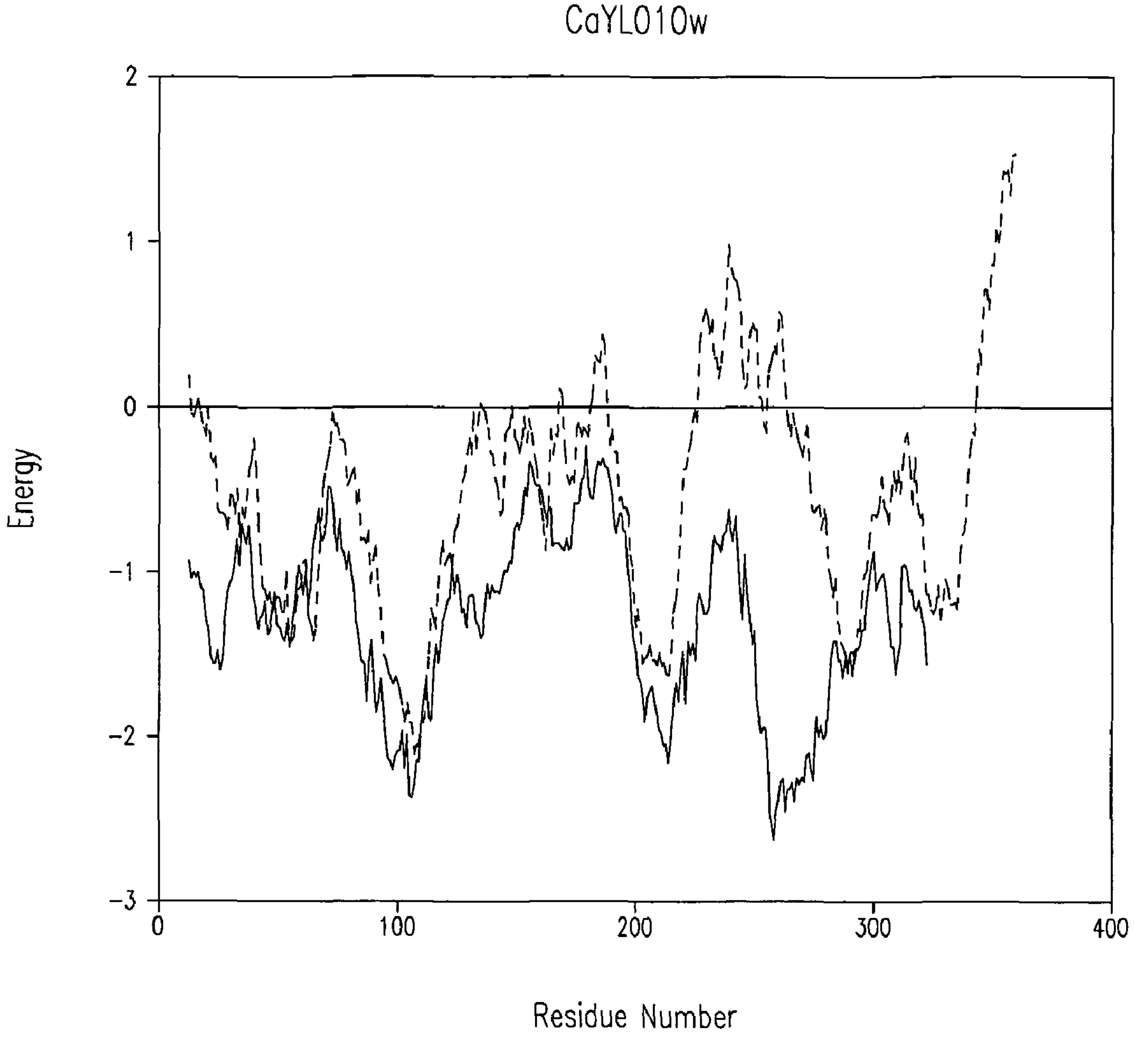
FIG. 34 shows a comparison of the energy of the CaYOL010w arginyl-tRNA synthetase homology model to the crystal structure of the *Escherichia coli* RNA 3'-terminal phosphate cyclase (Protein Data Bank entry 1QMH; Genbank Accession No. gi|12644279; SEQ ID NO:253) on which the CaYOL010w model was based. The CaYOL010w homology model is represented by the dotted (dashed) line and the *Saccharomyces cerevisiae* arginyl-tRNA synthetase crystal structure is represented by the solid line.

In order to recognize errors in three-dimensional structures knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model the energy distribution is plotted and compared to the energy distribution of the template from which the model was generated. FIG. 34 shows the energy graph for the CaYOL010w model (dotted line) and the template (RNA 3'-terminal phosphate cyclase) from which the model was generated. The model has virtually an identical energy plot when compared to RNA 3'-terminal phosphate cyclase template demonstrating that CaYOL010w has similar structural characteristics and suggest the overall three-dimensional fold is "native-like". This graph supports the motif and sequence alignments in confirming that the three dimensional structure coordinates of CaYOL010w are an accurate and useful representation for the polypeptide.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1QMH), and/or using different methods in generating the homology model, will have minor effects on the overall shape. Variations in coordinates may also be generated because of mathematical manipulations of the structure coordinates. For example, the structure coordinates set forth in Table 10 could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of CaYOL010w described above as to be considered the same. Such analyses may be carried out in current software applications, such as INSIGHTII (Accelrys Inc., San Diego, Calif.) version 2000 as described in the User's Guide, online or software applications available in the SYBYL software suite (Tripos Inc., St. Louis, Mo.).

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by INSIGHTII.

For the purpose of this invention, any homology model of a CaYOL010w that has a root mean square deviation of conserved residue backbone atoms (N, Cα, C, O) of less than 2.0 A when superimposed on the relevant backbone atoms described by structure coordinates listed in Table 10 are considered identical. More preferably, the root mean square deviation is less than 1.0, 0.9, 0.8, 0.7, 0.6, 0.5, 0.4, 0.3, 0.2, or 0.1 Angstroms.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of CaYOL010w as defined by the structure coordinates described herein.

This invention as embodied by the three-dimensional model enables the structure-based design of modulators of the biological function of CaYOL010w, as well as mutants with altered biological function and/or specificity.

The sequence alignment (FIG. 32) used as a template for creating the three-dimensional model of CaYOL010w RNA 3'-terminal phosphate cyclase domain shows 24% sequence identity between catalytic domain of CaYOL010w and yeast RNA 3'-terminal phosphate cyclase, PDB code 1QMH. For the RNA 3'-terminal phosphate cyclases there are at least two functional regions that are critical. In the N-terminal region of the enzyme the cyclase signature motif is thought to contain the nucleotide binding site has been shown to be highly conserved among cyclases. FIG. 32 shows this region highlighted by (*) and corresponds to R158-V168 in the three dimensional model for YOL010w (Table 10). The nucleotide binding site and surrounding sequence is completely conserved at the sequence and structure level. The second functional site is the region corresponding to RNA 3'-terminal phosphate cyclase H309. FIG. 32 shows that this region is not conserved in the model but there are several lysines and arginines nearby in the sequence alignment that suggest that this protein utilizes a basic residue like the DNA or RNA ligases. The nucleotidyl group is transferred and a covalent lysyl-NMP intermediate is formed. The conservation of the amino acids in the functional sites and the overall 24% sequence identity emphasize the significance of the three-dimensional model. The conserved residues are located in the functional sites at the cyclase signature sequence which is the presumed nucleotide binding site and region of the cyclase active site presenting a well structured catalytic domain. These functional site residues play critical roles in the mechanism of catalysis, substrate specificity and RNA processing and modification.

The structure coordinates of a CaYOL010w homology model, and portions thereof, are stored in a machine-readable storage medium. Such data may be used for a variety of purposes, such as drug discovery and target prioritization and validation.

Accordingly, in one embodiment of this invention is provided a machine-readable data storage medium comprising a data storage material encoded with the structure coordinates set forth in Table 10.

For the first time, the present invention permits the use, through homology modeling based upon the sequence of CaYOL010w (FIGS. 18 and 33) of structure-based or rational drug design techniques to design, select, and synthesizes chemical entities that are capable of modulating the biological function of CaYOL010w. Comparison of the CaYOL010w homology model with the structures of other the RNA cyclases enable the use of rational or structure based drug design methods to design, select or synthesize specific chemical modulators of CaYOL010w.

Accordingly, the present invention is also directed to the entire sequence in FIG. 18 or any portion thereof for the purpose of generating a homology model for the purpose of three dimensional structure-based drug designs.

For purposes of this invention, we include mutants or homologues of the sequence in FIG. 18 or any portion thereof. In a preferred embodiment, the mutants or homologues have at least 25% identity, more preferably 50% identity, more preferably 75% identity, and most preferably 90% identity to the amino acid residues in FIG. 18.

The three-dimensional model structure of the CaYOL010w will also provide methods for identifying modulators of biological function. Various methods or combination thereof can be used to identify these compounds.

Structure coordinates of the active site region defined above can also be used to identify structural and chemical features. Identified structural or chemical features can then be employed to design or select compounds as potential CaYOL010w modulators. By structural and chemical features it is meant to include, but is not limited to, van der Waals interactions, hydrogen bonding interactions, charge interaction, hydrophobic interactions, and dipole interaction. Alternatively, or in conjunction, the three-dimensional structural model can be employed to design or select compounds as potential CaYOL010w modulators. Compounds identified as potential CaYOL010w modulators can then be synthesized and screened in an assay characterized by binding of a test compound to the CaYOL010w, or in characterizing CaYOL010w deactivation in the presence of a small molecule. Examples of assays useful in screening of potential CaYOL010w modulators include, but are not limited to, screening in silico, in vitro assays and high throughput assays. Finally, these methods may also involve modifying or replacing one or more amino acids from CaYOL010w according to Table 10.

However, as will be understood by those of skill in the art upon this disclosure, other structure based design methods can be used. Various computational structure based design methods have been disclosed in the art.

For example, a number of computer modeling systems are available in which the sequence of the CaYOL010w and the CaYOL010w structure (i.e., atomic coordinates of CaYOL010w and/or the atomic coordinates of the active site region as provided in Table 10) can be input. The computer system then generates the structural details of one or more these regions in which a potential CaYOL010w modulator binds so that complementary structural details of the potential modulators can be determined. Design in these modeling systems is generally based upon the compound being capable of physically and structurally associating with CaYOL010w. In addition, the compound must be able to assume a conformation that allows it to associate with CaYOL010w. Some modeling systems estimate the potential inhibitory or binding effect of a potential CaYOL010w modulator prior to actual synthesis and testing.

Methods for screening chemical entities or fragments for their ability to associate with a given protein target are well known. Often these methods begin by visual inspection of the binding site on the computer screen. Selected fragments or chemical entities are then positioned in one or more positions and orientations within the active site region in CaYOL010w. Molecular docking is accomplished using software such as INSIGHTII, ICM (Molsoft LLC, La Jolla, Calif.), and SYBYL, following by energy minimization and molecular dynamics with standard molecular mechanic forcefields such as CHARMM and MMFF. Examples of computer programs which assist in the selection of chemical fragment or chemical entities useful in the present invention include, but are not limited to, GRID (Goodford, 1985), AUTODOCK (Goodsell, 1990), and DOCK (Kuntz et. al. 1982).

Alternatively, compounds may be designed de novo using either an empty active site or optionally including some portion of a known inhibitor. Methods of this type of design include, but are not limited to LUDI (Bohm 1992), LeapFrog (Tripos Associates, St. Louis Mo.) and DOCK (Kuntz et. al., 1982). Programs such as DOCK (Kuntz et. al. 1982) can be used with the atomic coordinates from the homology model to identify potential ligands from databases or virtual databases which potentially bind the in the active site region, and which may therefore be suitable candidates for synthesis and testing. The computer programs may utilize a combination of the following steps:

1) Selection of fragments or chemical entities from a database and then positioning the chemical entity in one or more orientations within the CaYOL010w catalytic domain defined by Table 10.

2) Characterization of the structural and chemical features of the chemical entity and active site including van der Waals interactions, hydrogen bonding interactions, charge interaction, hydrophobic bonding interaction, and dipole interactions 3) Search databases for molecular fragments which can be joined to or replace the docked chemical entity and spatially fit into regions defined by the said CaYOL010w catalytic domain or catalytic domain functional sites 4) Evaluate the docked chemical entity and fragments using a combination of scoring schemes which account for van der Waals interactions, hydrogen bonding interactions, charge interaction, hydrophobic interactions Databases that may be used include ACD (Molecular Designs Limited), Aldrich (Aldrich Chemical Company), NCI (National Cancer Institute), Maybridge (Maybridge Chemical Company Ltd), CCDC (Cambridge Crystallographic Data Center), CAST (Chemical Abstract Service), Derwent (Derwent Information Limited).

Upon selection of preferred chemical entities or fragments, their relationship to each other and CaYOL010w can be visualized and then assembled into a single potential modulator. Programs useful in assembling the individual chemical entities include, but are not limited to SYBYL and LeapFrog (Tripos Associates, St. Louis Mo.), LUDI (Bohm 1992) as well as 3D Database systems (Martin 1992).

Additionally, the three-dimensional homology model of CaYOL010w will aid in the design of mutants with altered biological activity. Site directed mutagenesis can be used to generate proteins with similar or varying degrees of biological activity compared to native CaYOL010w. This invention also relates to the generation of mutants or homologs of CaYOL010w. It is clear that molecular modeling using the three dimensional structure coordinates set forth in Table 10 and visualization of the CaYOL010w model, FIG. 34 can be utilized to design homologs or mutant polypeptides of CaYOL010w that have similar or altered biological activities, function or reactivities.

Many polynucleotide sequences, such as EST sequences, are publicly available and accessible through sequence databases. Some of these sequences are related to SEQ ID NO:8 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 1099 of SEQ ID NO:8, b is an integer between 15 to 1113, where both a and b correspond to the positions of nucleotide residues shown in SEQ ID NO:8, and where b is greater than or equal to a+14.

Features of the Polypeptide Encoded by Polynucleotide No:9

The polynucleotide sequence (SEQ ID NO:9) and deduced amino acid sequence (SEQ ID NO:20) of the novel fungal essential gene, CaYOR004w (also referred to as FCG 15), of the present invention. The CaYOR004w polypeptide (SEQ ID NO:20) is encoded by nucleotides 1 to 771 of SEQ ID NO:9 and has a predicted molecular weight of 29.5 kDa.

In preferred embodiments, the present invention encompasses a polynucleotide lacking the initiating start codon, in addition to, the resulting encoded polypeptide of CaYOR004w. Specifically, the present invention encompasses the polynucleotide corresponding to nucleotides 4 thru 771 of SEQ ID NO:9, and the polypeptide corresponding to amino acids 2 thru 257 of SEQ ID NO:20. Also encompassed are recombinant vectors comprising said encoding sequence, and host cells comprising said vector.

The invention also encompasses N- and/or C-terminal deletions of the CaYOR004w polypeptide of the present invention.

In preferred embodiments, the following N-terminal CaYOR004w deletion polypeptides are encompassed by the present invention: M1-N257, R2-N257, Q3-N257, K4-N257, R5-N257, A6-N257, K7-N257, A8-N257, Y9-N257, K10-N257, K11-N257, Q12-N257, M13-N257, S14-N257, V15-N257, Y16-N257, V17-N257, H18-N257, A19-N257, F20-N257, K21-N257, F22-N257, R23-N257, E24-N257, P25-N257, Y26-N257, Q27-N257, I28-N257, I29-N257, V30-N257, D31-N257, N32-N257, E33-N257, L34-N257, I35-N257, T36-N257, T37-N257, C38-N257, Q39-N257, S40-N257, A41-N257, S42-N257, F43-N257, D44-N257, I45-N257, N46-N257, K47-N257, G48-N257, F49-N257, T50-N257, R51-N257, T52-N257, I53-N257, Q54-N257, A55-N257, E56-N257, N57-N257, K58-N257, P59-N257, M60-N257, I61-N257, T62-N257, Q63-N257, C64-N257, C65-N257, I66-N257, Q67-N257, A68-N257, L69-N257, Y70-N257, D71-N257, T72-N257, K73-N257, N74-N257, Q75-N257, P76-N257, A77-N257, I78-N257, D79-N257, I80-N257, A81-N257, K82-N257, S83-N257, F84-N257, E85-N257, R86-N257, R87-N257, K88-N257, C89-N257, N90-N257, H91-N257, R92-N257, E93-N257, A94-N257, I95-N257, D96-N257, P97-N257, S98-N257, Q99-N257, C100-N257, I101-N257, E102-N257, S103-N257, I104-N257, V105-N257, N106-N257, I107-N257, K108-N257, G109-N257, Q110-N257, N111-N257, K112-N257, H113-N257, R114-N257, Y115-N257, I116-N257, V117-N257, A118-N257, S119-N257, Q120-N257, D121-N257, L122-N257, Q123-N257, L124-N257, R125-N257, K126-N257, K127-N257, L128-N257, R129-N257, K130-N257, I131-N257, P132-N257, G133-N257, V134-N257, P135-N257, L136-N257, I137-N257, Y138-N257, M139-N257, N140-N257, R141-N257, S142-N257, V143-N257, M144-N257 V145-N257, M146-N257, E147-N257, P148-N257, I149-N257, S150-N257, D151-N257, V152-N257, S153-N257, N154-N257, Q155-N257, Y156-N257, N157-N257, M158-N257, N159-N257, Y160-N257, E161-N257, S162-N257, K163-N257, K164-N257, L165-N257, T166-N257, G167-N257, G168-N257, L169-N257, N170-N257, D171-N257, I172-N257, E173-N257, A174-N257, G175-N257, K176-N257, L177-N257, E178-N257, K179-N257, Q180-N257, N181-N257, E182-N257, G183-N257, E184-N257, D185-N257, G186-N257, D187-N257, G188-N257, D189-N257, E190-N257, L191-N257, E192-N257, V193-N257, K194-N257, K195-N257, K196-N257, K197-N257, R198-N257, K199-N257, G200-N257, P201-N257, K202-N257, E203-N257, P204-N257, N205-N257, P206-N257, L207-N257, S208-N257, V209-N257, K210-N257, K211-N257, K212-N257, K213-N257, T214-N257, D215-N257, N216-N257, A217-N257, T218-N257, A219-N257, A220-N257, S221-N257, T222-N257, N223-N257, Q224-N257, E225-N257, Q226-N257, K227-N257, K228-N257, K229-N257, P230-N257, N231-N257, R232-N257, R233-N257, K234-N257, R235-N257, H236-N257, A237-N257, Q238-N257, V239-N257, K240-N257, S241-N257, R242-N257, R243-N257, E244-N257, G245-N257, R246-N257, P247-N257, R248-N257, T249-N257, G250-N257, and/or A251-N257 of SEQ ID NO:20. Polynucleotide sequences encoding these polypeptides are also provided. The present invention also encompasses the use of these N-terminal CaYOR004w deletion polypeptides as immunogenic and/or antigenic epitopes as described elsewhere herein.

In preferred embodiments, the following C-terminal CaYOR004w deletion polypeptides are encompassed by the present invention: M1-N257, M1-N256, M1-S255, M1-R254, M1-E253, M1-S252, M1-A251, M1-G250, M1-T249, M1-R248, M1-P247, M1-R246, M1-G245, M1-E244, M1-R243, M1-R242, M1-S241, M1-K240, M1-V239, M1-Q238, M1-A237, M1-H236, M1-R235, M1-K234, M1-R233, M1-R232, M1-N231, M1-P230, M1-K229, M1-K228, M1-K227, M1-Q226, M1-E225, M1-Q224, M1-N223, M1-T222, M1-S221, M1-A220, M1-A219, M1-T218, M1-A217, M1-N216, M1-D215, M1-T214, M1-K213, M1-K212, M1-K211, M1-K210, M1-V209, M1-S208, M1-L207, M1-P206, M1-N205, M1-P204, M1-E203, M1-K202, M1-P201, M1-G200, M1-K199, M1-R198, M1-K197, M1-K196, M1-K195, M1-K194, M1-V193, M1-E192, M1-L191, M1-E190, M1-D189, M1-G188, M1-D187, M1-G186, M1-D185, M1-E184, M1-G183, M1-E182, M1-N181, M1-Q180, M1-K179, M1-E178, M1-L177, M1-K176, M1-G175, M1-A174, M1-E173, M1-I172, M1-D171, M1-N170, M1-L169, M1-G168, M1-G167, M1-T166, M1-L165, M1-K164, M1-K163, M1-S162, M1-E161, M1-Y160, M1-N159, M1-M158, M1-N157, M1-Y156, M1-Q155, M1-N154, M1-S153, M1-V152, M1-D151, M1-S150, M1-I149, M1-P148, M1-E147, M1-M146, M1-V145, M1-M144, M1-V143, M1-S142, M1-R141, M1-N140, M1-M139, M1-Y138, M1-I137, M1-L136, M1-P135, M1-V134, M1-G133, M1-P132, M1-I131, M1-K130, M1-R129, M1-L128, M1-K127, M1-K126, M1-R125, M1-L124, M1-Q123, M1-L122, M1-D121, M1-Q120, M1-S119, M1-A118, M1-V117, M1-I116, M1-Y115, M1-R114, M1-H113, M1-K112, M1-N111, M1-Q110, M1-G109, M1-K108, M1-I107, M1-N106, M1-V105, M1-I104, M1-S103, M1-E102, M1-I101, M1-C100, M1-Q99, M1-S98, M1-P97, M1-D96, M1-I95, M1-A94, M1-E93, M1-R92, M1-H91, M1-N90, M1-C89, M1-K88, M1-R87, M1-R86, M1-E85, M1-F84, M1-S83, M1-K82, M1-A81, M1-I80, M1-D79, M1-I78, M1-A77, M1-P76, M1-Q75, M1-N74, M1-K73, M1-T72, M1-D71, M1-Y70, M1-L69, M1-A68, M1-Q67, M1-I66, M1-C65, M1-C64, M1-Q63, M1-T62, M1-I61, M1-M60, M1-P59, M1-K58, M1-N57, M1-E56, M1-A55, M1-Q54, M1-I53, M1-T52, M1-R51, M1-T50, M1-F49, M1-G48, M1-K47, M1-N46, M1-I45, M1-D44, M1-F43, M1-S42, M1-A41, M1-S40, M1-Q39, M1-C38, M1-T37, M1-T36, M1-I35, M1-L34, M1-E33, M1-N32, M1-D31, M1-V30, M1-I29, M1-I28, M1-Q27, M1-Y26, M1-P25, M1-E24, M1-R23, M1-F22, M1-K21, M1-F20, M1-A19, M1-H18, M1-V17, M1-Y16, M1-V15, M1-S14, M1-M13, M1-Q12, M1-K11, M1-K10, M1-Y9, M1-A8, and/or M1-K7 of SEQ ID NO:20. Polynucleotide sequences encoding these polypeptides are also provided. The present invention also encompasses the use of these C-terminal CaYOR004w deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:9, and in particular to the coding region of the polynucleotide sequence provided in SEQ ID NO:9. Preferably such polynucleotides encode polypeptides that have biological activity.

Most preferred are polynucleotides that share at least about 88.9% identity with the polynucleotide sequence provided in SEQ ID NO:9.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:20.

Most preferred are polypeptides that share at least about 95.4% identity with the polypeptide sequence provided in SEQ ID NO:20.

Many polynucleotide sequences, such as EST sequences, are publicly available and accessible through sequence databases. Some of these sequences are related to SEQ ID NO:9 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 757 of SEQ ID NO:9, b is an integer between 15 to 771, where both a and b correspond to the positions of nucleotide residues shown in SEQ ID NO:9, and where b is greater than or equal to a+14.

Features of the Polypeptide Encoded by Polynucleotide No:10

The polynucleotide sequence (SEQ ID NO:10) and deduced amino acid sequence (SEQ ID NO:21) of the novel fungal essential gene, CaYOR056c (also referred to as FCG16), of the present invention. The CaYOR056c polypeptide (SEQ ID NO:21) is encoded by nucleotides 1 to 1398 of SEQ ID NO:10 and has a predicted molecular weight of 52.6 kDa.

In preferred embodiments, the present invention encompasses a polynucleotide lacking the initiating start codon, in addition to, the resulting encoded polypeptide of CaYOR056c. Specifically, the present invention encompasses the polynucleotide corresponding to nucleotides 4 thru 1398 of SEQ ID NO:10, and the polypeptide corresponding to amino acids 2 thru 466 of SEQ ID NO:21. Also encompassed are recombinant vectors comprising said encoding sequence, and host cells comprising said vector.

The invention also encompasses N- and/or C-terminal deletions of the CaYOR056c polypeptide of the present invention.

In preferred embodiments, the following N-terminal CaYOR056c deletion polypeptides are encompassed by the present invention: M1-K466, S2-K466, E3-K466, T4-K466, K5-K466, N6-K466, I7-K466, E8-K466, S9-K466, L10-K466, I11-K466, S12-K466, D13-K466, A14-K466, G15-K466, P16-K466, L17-K466, I18-K466, T19-K466, Q20-K466, P21-K466, A22-K466, T23-K466, T24-K466, L25-K466, Q26-K466, Q27-K466, Y28-K466, A29-K466, T30-K466, A31-K466, Y32-K466, Y33-K466, T34-K466, T35-K466, P36-K466, G37-K466, V38-K466, H39-K466, S40-K466, E41-K466, L42-K466, K43-K466, D44-K466, E45-K466, Y46-K466, A47-K466, R48-K466, Q49-K466, Q50-K466, L51-K466, A52-K466, I53-K466, W54-K466, G55-K466, D56-K466, S57-K466, L58-K466, K59-K466, I60-K466, K61-K466, Q62-K466, P63-K466, K64-K466, Q65-K466, E66-K466, Y67-K466, I68-K466, D69-K466, R70-K466, V71-K466, V72-K466, K73-K466, F74-K466, A75-K466, K76-K466, L77-K466, T78-K466, G79-K466, D80-K466, Y81-K466, S82-K466, V83-K466, L84-K466, S85-K466, V86-K466, N87-K466, D88-K466, L89-K466, H90-K466, I91-K466, V92-K466, A93-K466, L94-K466, A95-K466, Y96-K466, E97-K466, L98-K466, E99-K466, C100-K466, L101-K466, N102-K466, N103-K466, G104-K466, E105-K466, D106-K466, N107-K466, L108-K466, R109-K466, S110-K466, F111-K466, P112-K466, G113-K466, E114-K466, V115-K466, L116-K466, K117-K466, N118-K466, Q119-K466, Q120-K466, A121-K466, E122-K466, N123-K466, E124-K466, N125-K466, G126-K466, S127-K466, N128-K466, K129-K466, M130-K466, S13'-K466, N132-K466, I133-K466, I134-K466, G135-K466, D136-K466, D137-K466, D138-K466, G139-K466, F140-K466, V141-K466, V142-K466, A143-K466, T144-K466, K145-K466, R146-K466, R147-K466, G148-K466, G149-K466, R150-K466, R151-K466, Q152-K466, R153-K466, E154-K466, K155-K466, A156-K466, E157-K466, L158-K466, R159-K466, K160-K466, K161-K466, G162-K466, L163-K466, L164-K466, P165-K466, T166-K466, F167-K466, S168-K466, P169-K466, K170-K466, P171-K466, K172-K466, G173-K466, G174-K466, L175-K466, E176-K466, T177-K466, E178-K466, E179-K466, P180-K466, N181-K466, E182-K466, L183-K466, S184-K466, N185-K466, D186-K466, K187-K466, T188-K466, I189-K466, D190-K466, E191-K466, T192-K466, P193-K466, Q194-K466, T195-K466, D196-K466, L197-K466, I198-K466, K199-K466, G200-K466, V201-K466, D202-K466, V203-K466, Q204-K466, E205-K466, Q206-K466, E207-K466, S208-K466, Q209-K466, E210-K466, E211-K466, P212-K466, V213-K466, S214-K466, E215-K466, S216-K466, N217-K466, T218-K466, V219-K466, G220-K466, L221-K466, D222-K466, E223-K466, I224-K466, T225-K466, E226-K466, E227-K466, Y228-K466, N229-K466, E230-K466, D231-K466, D232-K466, D233-K466, D234-K466, G235-K466, E236-K466, W237-K466, I238-K466, T239-K466, P240-K466, E241-K466, N242-K466, L243-K466, Q244-K466, E245-K466, E246-K466, I247-K466, I248-K466, K249-K466, D250-K466, K251-K466, N252-K466, E253-K466, Q254-K466, V255-K466, Q256-K466, E257-K466, S258-K466, N259-K466, T260-K466, N261-K466, G262-K466, P263-K466, L264-K466, I265-K466, K266-K466, V267-K466, A268-K466, L269-K466, A270-K466, T271-K466, G272-K466, D273-K466, F274-K466, A275-K466, C276-K466, Q277-K466, N278-K466, V279-K466, A280-K466, M281-K466, Q282-K466, I283-K466, G284-K466, I285-K466, K286-K466, L287-K466, L288-K466, N289-K466, A290-K466, M291-K466, S292-K466, G293-K466, K294-K466, Q295-K466, I296-K466, T297-K466, R298-K466, V299-K466, R300-K466, N301-K466, Y302-K466, M303-K466, Y304-K466, R305-K466, C306-K466, H307-K466, A308-K466, C309-K466, F310-K466, R311-K466, L312-K466, T313-K466, P314-K466, M315-K466, S316-K466, K317-K466, D318-K466, G319-K466, R320-K466, P321-K466, K322-K466, H323-K466, F324-K466, C325-K466, P326-K466, K327-K466, C328-K466, G329-K466, G330-K466, N331-K466, T332-K466, L333-K466, L334-K466, R335-K466, C336-K466, A337-K466, V338-K466, S339-K466, V340-K466, D341-K466, N342-K466, K343-K466, T344-K466, G345-K466, K346-K466, I347-K466, T348-K466, P349-K466, H350-K466, L351-K466, K352-K466, Q353-K466, N354-K466, F355-K466, Q356-K466, W357-K466, I358-K466, R359-K466, R360-K466, G361-K466, E362-K466, R363-K466, Y364-K466, S365-K466, L366-K466, P367-K466, S368-K466, P369-K466, L370-

K466, S371-K466, K372-K466, N373-K466, Q374-K466, K375-K466, K376-K466, L377-K466, Q378-K466, G379-K466, N380-K466, G381-K466, G382-K466, Y383-K466, Q384-K466, H385-K466, N386-K466, K387-K466, E388-K466, N389-K466, R390-K466, H391-K466, K392-K466, S393-K466, L394-K466, Q395-K466, T396-K466, P397-K466, L398-K466, I399-K466, L400-K466, N401-K466, E402-K466, D403-K466, Q404-K466, K405-K466, E406-K466, Y407-K466, Q408-K466, R409-K466, A410-K466, L411-K466, K412-K466, N413-K466, D414-K466, E415-K466, W416-K466, E417-K466, R418-K466, K419-K466, Q420-K466, Q421-K466, D422-K466, K423-K466, M424-K466, L425-K466, Q426-K466, E427-K466, W428-K466, I429-K466, G430-K466, G431-K466, G432-K466, S433-K466, A434-K466, D435-K466, N436-K466, F437-K466, V438-K466, S439-K466, P440-K466, F441-K466, G442-K466, N443-K466, T444-K466, I445-K466, R446-K466, N447-K466, S448-K466, G449-K466, V450-K466, K451-K466, V452-K466, G453-K466, R454-K466, G455-K466, R456-K466, Y457-K466, A458-K466, N459-K466, and/or S460-K466 of SEQ ID NO:21. Polynucleotide sequences encoding these polypeptides are also provided. The present invention also encompasses the use of these N-terminal CaYOR056c deletion polypeptides as immunogenic and/or antigenic epitopes as described elsewhere herein.

In preferred embodiments, the following C-terminal CaYOR056c deletion polypeptides are encompassed by the present invention: M1-K466, M1-R465, M1-K464, M1-K463, M1-K462, M1-S461, M1-S460, M1-N459, M1-A458, M1-Y457, M1-R456, M1-G455, M1-R454, M1-G453, M1-V452, M1-K451, M1-V450, M1-G449, M1-S448, M1-N447, M1-R446, M1-I445, M1-T444, M1-N443, M1-G442, M1-F441, M1-P440, M1-S439, M1-V438, M1-F437, M1-N436, M1-D435, M1-A434, M1-S433, M1-G432, M1-G431, M1-G430, M1-I429, M1-W428, M1-E427, M1-Q426, M1-L425, M1-M424, M1-K423, M1-D422, M1-Q421, M1-Q420, M1-K419, M1-R418, M1-E417, M1-W416, M1-E415, M1-D414, M1-N413, M1-K412, M1-L411, M1-A410, M1-R409, M1-Q408, M1-Y407, M1-E406, M1-K405, M1-Q404, M1-D403, M1-E402, M1-N401, M1-L400, M1-I399, M1-L398, M1-P397, M1-T396, M1-Q395, M1-L394, M1-S393, M1-K392, M1-H391, M1-R390, M1-N389, M1-E388, M1-K387, M1-N386, M1-H385, M1-Q384, M1-Y383, M1-G382, M1-G381, M1-N380, M1-G379, M1-Q378, M1-L377, M1-K376, M1-K375, M1-Q374, M1-N373, M1-K372, M1-S371, M1-L370, M1-P369, M1-S368, M1-P367, M1-L366, M1-S365, M1-Y364, M1-R363, M1-E362, M1-G361, M1-R360, M1-R359, M1-I358, M1-W357, M1-Q356, M1-F355, M1-N354, M1-Q353, M1-K352, M1-L351, M1-H350, M1-P349, M1-T348, M1-I347, M1-K346, M1-G345, M1-T344, M1-K343, M1-N342, M1-D341, M1-V340, M1-S339, M1-V338, M1-A337, M1-C336, M1-R335, M1-L334, M1-L333, M1-T332, M1-N331, M1-G330, M1-G329, M1-C328, M1-K327, M1-P326, M1-C325, M1-F324, M1-H323, M1-K322, M1-P321, M1-R320, M1-G319, M1-D318, M1-K317, M1-S316, M1-M315, M1-P314, M1-T313, M1-L312, M1-R311, M1-F310, M1-C309, M1-A308, M1-H307, M1-C306, M1-R305, M1-Y304, M1-M303, M1-Y302, M1-N301, M1-R300, M1-V299, M1-R298, M1-T297, M1-I296, M1-Q295, M1-K294, M1-G293, M1-S292, M1-M291, M1-A290, M1-N289, M1-L288, M1-L287, M1-K286, M1-I285, M1-G284, M1-I283, M1-Q282, M1-M281, M1-A280, M1-V279, M1-N278, M1-Q277, M1-C276, M1-A275, M1-F274, M1-D273, M1-G272, M1-T271, M1-A270, M1-L269, M1-A268, M1-V267, M1-K266, M1-I265, M1-L264, M1-P263, M1-G262, M1-N261, M1-T260, M1-N259, M1-S258, M1-E257, M1-Q256, M1-V255, M1-Q254, M1-E253, M1-N252, M1-K251, M1-D250, M1-K249, M1-I248, M1-I247, M1-E246, M1-E245, M1-Q244, M1-L243, M1-N242, M1-E241, M1-P240, M1-T239, M1-I238, M1-W237, M1-E236, M1-G235, M1-D234, M1-D233, M1-D232, M1-D231, M1-E230, M1-N229, M1-Y228, M1-E227, M1-E226, M1-T225, M1-I224, M1-E223, M1-D222, M1-L221, M1-G220, M1-V219, M1-T218, M1-N217, M1-S216, M1-E215, M1-S214, M1-V213, M1-P212, M1-E211, M1-E210, M1-Q209, M1-S208, M1-E207, M1-Q206, M1-E205, M1-Q204, M1-V203, M1-D202, M1-V201, M1-G200, M1-K199, M1-I198, M1-L197, M1-D196, M1-T195, M1-Q194, M1-P193, M1-T192, M1-E191, M1-D190, M1-I189, M1-T188, M1-K187, M1-D186, M1-N185, M1-S184, M1-L183, M1-E182, M1-N181, M1-P180, M1-E179, M1-E178, M1-T177, M1-E176, M1-L175, M1-G174, M1-G173, M1-K172, M1-P171, M1-K170, M1-P169, M1-S168, M1-F167, M1-T166, M1-P165, M1-L164, M1-L163, M1-G162, M1-K161, M1-K160, M1-R159, M1-L158, M1-E157, M1-A156, M1-K155, M1-E154, M1-R153, M1-Q152, M1-R151, M1-R150, M1-G149, M1-G148, M1-R147, M1-R146, M1-K145, M1-T144, M1-A143, M1-V142, M1-V141, M1-F140, M1-G139, M1-D138, M1-D137, M1-D136, M1-G135, M1-I134, M1-I133, M1-N132, M1-S131, M1-M130, M1-K129, M1-N128, M1-S127, M1-G126, M1-N125, M1-E124, M1-N123, M1-E122, M1-A121, M1-Q120, M1-Q19, M1-N118, M1-K117, M1-L116, M1-V115, M1-E114, M1-G113, M1-P112, M1-F111, M1-S110, M1-R109, M1-L108, M1-N107, M1-D106, M1-E105, M1-G104, M1-N103, M1-N102, M1-L101M1-C100, M1-E99, M1-L98, M1-E97, M1-Y96, M1-A95, M1-L94, M1-A93, M1-V92, M1-I91, M1-H90, M1-L89, M1-D88, M1-N87, M1-V86, M1-S85, M1-L84, M1-V83, M1-S82, M1-Y81, M1-D80, M1-G79, M1-T78, M1-L77, M1-K76, M1-A75, M1-F74, M1-K73, M1-V72, M1-V71, M1-R70, M1-D69, M1-I68, M1-Y67, M1-E66, M1-Q65, M1-K64, M1-P63, M1-Q62, M1-K61, M1-I60, M1-K59, M1-L58, M1-S57, M1-D56, M1-G55, M1-W54, M1-I53, M1-A52, M1-L51, M1-Q50, M1-Q49, M1-R48, M1-A47, M1-Y46, M1-E45, M1-D44, M1-K43, M1-L42, M1-E41, M1-S40, M1-H39, M1-V38, M1-G37, M1-P36, M1-T35, M1-T34, M1-Y33, M1-Y32, M1-A31, M1-T30, M1-A29, M1-Y28, M1-Q27, M1-Q26, M1-L25, M1-T24, M1-T23, M1-A22, M1-P21, M1-Q20, M1-T19, M1-I18, M1-L17, M1-P16, M1-G15, M1-A14, M1-D13, M1-S12, M1-I11, M1-L10, M1-S9, M1-E8, and/or M1-17 of SEQ ID NO:21. Polynucleotide sequences encoding these polypeptides are also provided. The present invention also encompasses the use of these C-terminal CaYOR056c deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:10, and in particular to the coding region of the polynucleotide sequence provided in SEQ ID NO:10. Preferably such polynucleotides encode polypeptides that have biological activity.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:21.

Most preferred are polypeptides that share at least about 99.5% identity with the polypeptide sequence provided in SEQ ID NO:21.

Many polynucleotide sequences, such as EST sequences, are publicly available and accessible through sequence databases. Some of these sequences are related to SEQ ID NO:10 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 1384 of SEQ ID NO:10, b is an integer between 15 to 1398, where both a and b correspond to the positions of nucleotide residues shown in SEQ ID NO:10, and where b is greater than or equal to a+14.

Features of the Polypeptide Encoded by Polynucleotide No:11

The polynucleotide sequence (SEQ ID NO:11) and deduced amino acid sequence (SEQ ID NO:22) of the novel fungal essential gene, CaYLR009w (also referred to as FCG17), of the present invention. The CaYLR009w polypeptide (SEQ ID NO:22) is encoded by nucleotides 1 to 585 of SEQ ID NO:11 and has a predicted molecular weight of 23.1 kDa.

In preferred embodiments, the present invention encompasses a polynucleotide lacking the initiating start codon, in addition to, the resulting encoded polypeptide of CaYLR009w. Specifically, the present invention encompasses the polynucleotide corresponding to nucleotides 4 thru 585 of SEQ ID NO:11, and the polypeptide corresponding to amino acids 2 thru 195 of SEQ ID NO:22. Also encompassed are recombinant vectors comprising said encoding sequence, and host cells comprising said vector.

The invention also encompasses N- and/or C-terminal deletions of the CaYLR009w polypeptide of the present invention.

In preferred embodiments, the following N-terminal CaYLR009w deletion polypeptides are encompassed by the present invention: M1-C195, R2-C195, I3-C195, Y4-C195, Q5-C195, C6-C195, H7-C195, F8-C195, C9-C195, S10-C195, S11-C195, P12-C195, V13-C195, Y14-C195, P15-C195, L16-C195, H17-C195, G18-C195, I19-C195, T20-C195, F21-C195, V22-C195, R23-C195, N24-C195, D25-C195, A26-C195, K27-C195, E28-C195, F29-C195, R30-C195, F31-C195, C32-C195, R33-C195, S34-C195, K35-C195, C36-C195, H37-C195, K38-C195, A39-C195, F40-C195, K41-C195, Q42-C195, R43-C195, R44-C195, N45-C195, P46-C195, R47-C195, K48-C195, L49, C195, R50-C195, W51-C195, T52-C195, K53-C195, A54-C195, F55-C195, R56-C195, K57-C195, A58-C195, A59-C195, G60-C195, K61-C195, E62-C195, L63-C195, V64-C195, V65-C195, D66-C195, S67-C195, T68-C195, L69-C195, T70-C195, F71-C195, A72-C195, A73-C195, R74-C195, R75-C195, N76-C195, V77-C195, P78-C195, V79-C195, R80-C195, Y81-C195, N82-C195, R83-C195, D84-C195, L85-C195, V86-C195, A87-C195, T88-C195, T89-C195, L90-C195, K91-C195, G92-C195, M93-C195, S94-C195, R95-C195, I96-C195, E97-C195, E98-C195, I99-C195, R100-C195, Q101-C195, R102-C195, R103-C195, E104-C195, R105-C195, A106-C195, F107-C195, Y108-C195, K109-C195, N110-C195, R111'-C195, M112-C195, K113-C195, G114-C195, N115-C195, K116-C195, E117-C195, R118-C195, Q119-C195, L120-C195, A121-C195, A122-C195, D123-C195, R124-C195, K125-C195, L126-C195, V127-C195, A128-C195, D129-C195, N130-C195, P131-C195, E132-C195, L133-C195, L134-C195, R135-C195, L136-C195, R137-C195, E138-C195, V139-C195, E140-C195, L141-C195, R142-C195, R143-C195, K144-C195, A145-C195, E146-C195, K147-C195, L148-C195, A149-C195, A150-C195, K151-C195, E152-C195, N153-C195, A154-C195, M155-C195, E156-C195, E157-C195, D158-C195, E159-C195, E160-C195, T161-C195, E162-C195, V163-C195, E164-C195, E165-C195, E166-C195, G167-C195, E168-C195, G169-C195, D170-C195, E171-C195, E172-C195, M173-C195, I174-C195, S175-C195, G176-C195, E177-C195, E178-C195, E179-C195, W180-C195, E181-C195, S182-C195, E183-C195, D184-C195, E185-C195, S186-C195, E187-C195, R188-C195, and/or E189-C195 of SEQ ID NO:22. Polynucleotide sequences encoding these polypeptides are also provided. The present invention also encompasses the use of these N-terminal CaYLR009w deletion polypeptides as immunogenic and/or antigenic epitopes as described elsewhere herein.

In preferred embodiments, the following C-terminal CaYLR009w deletion polypeptides are encompassed by the present invention: M1-C195, M1-T194, M1-K193, M1-T192, M1-D191, M1-S190, M1-E189, M1-R188, M1-E187, M1-S186, M1-E185, M1-D184, M1-E183, M1-S182, M1-E181, M1-W180, M1-E179, M1-E178, M1-E177, M1-G176, M1-S175, M1-I174, M1-M173, M1-E172, M1-E171, M1-D170, M1-G169, M1-E168, M1-G167, M1-E166, M1-E165, M1-E164, M1-V163, M1-E162, M1-T161, M1-E160, M1-E159, M1-D158, M1-E157, M1-E156, M1-M155, M1-A154, M1-N153, M1-E152, M1-K151, M1-A150, M1-A149, M1-L148, M1-K147, M1-E146, M1-A145, M1-K144, M1-R143, M1-R142, M1-L141, M1-E140, M1-V139, M1-E138, M1-R137, M1-L136, M1-R135, M1-L134, M1-L133, M1-E132, M1-P131, M1-N130, M1-D129, M1-A128, M1-V127, M1-L126, M1-K125, M1-R124, M1-D123, M1-A122, M1-A121, M1-L120, M1-Q119, M1-R118, M1-E117, M1-K116, M1-N115, M1-G114, M1-K113, M1-M112, M1-R111, M1-N110, M1-K109, M1-Y108, M1-F107, M1-A106, M1-R105, M1-E104, M1-R103, M1-R102, M1-Q101, M1-R100, M1-I99, M1-E98, M1-E97, M1-I96, M1-R95, M1-S94, M1-M93, M1-G92, M1-K91, M1-L90, M1-T89, M1-T88, M1-A87, M1-V86, M1-L85, M1-D84, M1-R83, M1-N82, M1-Y81, M1-R80, M1-V79, M1-P78, M1-V77, M1-N76, M1-R75, M1-R74, M1-A73, M1-A72, M1-F71, M1-T70, M1-L69, M1-T68, M1-S67, M1-D66, M1-V65, M1-V64, M1-L63, M1-E62, M1-K61, M1-G60, M1-A59, M1-A58, M1-K57, M1-R56, M1-F55, M1-A54, M1-K53, M1-T52, M1-W51, M1-R50, M1-L49, M1-K48, M1-R47, M1-P46, M1-N45, M1-R44, M1-R43, M1-Q42, M1-K41, M1-F40, M1-A39, M1-K38, M1-H37, M1-C36, M1-K35, M1-S34, M1-R33, M1-C32, M1-F31, M1-R30, M1-F29, M1-E28, M1-K27, M1-A26, M1-D25, M1-N24, M1-R23, M1-V22, M1-F21, M1-T20, M1-I19, M1-G18, M1-H17, M1-L16, M1-P15, M1-Y14, M1-V13, M1-P12, M1-S11, M1-S10, M1-C9, M1-F8, and/or M1-H7 of SEQ ID NO:22. Polynucleotide sequences encoding these polypeptides are also provided. The present invention also encompasses the use of these C-terminal CaYLR009w deletion polypeptides as immunogenic and/or antigenic epitopes as described elsewhere herein.

The present invention also encompasses polynucleotides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polynucleotide sequence provided in SEQ ID NO:11, and in particular to the coding region of the polynucleotide sequence provided in SEQ ID NO:11. Preferably such polynucleotides encode polypeptides that have biological activity.

Most preferred are polynucleotides that share at least about 91.8% identity with the polynucleotide sequence provided in SEQ ID NO:22.

The present invention also encompasses polypeptides sharing at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a the polypeptide sequence provided in SEQ ID NO:22.

Most preferred are polypeptides that share at least about 88.6% identity with the polypeptide sequence provided in SEQ ID NO:22.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 571 of SEQ ID NO:11, b is an integer between 15 to 585, where both a and b correspond to the positions of nucleotide residues shown in SEQ ID NO:11, and where b is greater than or equal to a+14.

Homology Models

One embodiment of the homology models of the present invention utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bi-directional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Recombinants and Expression

The present invention provides recombinant DNA molecules containing polynucleotide sequences encoding essential polynucleotide polypeptides. "Recombinant DNA molecules" include both cloning and expression vectors.

In bacterial systems, a number of cloning and expression vectors may be selected depending upon the use intended for polynucleotide sequences encoding essential polynucleotide. For example, in one embodiment, routine cloning, subcloning, and propagation of polynucleotide sequences encoding essential polynucleotides can be achieved using a multifunctional *E. coli* vector such as PBLUESCRIPT (Stratagene, La Jolla Calif.) or PSPORT plasmid (Life Technologies). Ligation of sequences encoding essential polynucleotide into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster *J. Biol* 264: 5503-5509 (1989)).

In a preferred embodiment, the present invention provides expression vectors containing a polynucleotide that encodes essential polynucleotide polypeptides. Preferably, the expression vectors of the present invention comprise polynucleotides that encode polypeptides including the amino acid residue sequences of SEQ ID NO: 12 through SEQ ID NO: 24.

An "expression vector" refers to an assembly which is capable of directing the expression of desired proteins. The vector must include regulatory sequences which are operably linked to a gene(s) of interest. The vector may be composed of either DNA or RNA or a combination of the two. Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription and selectable markers, may also be incorporated in the vectors described herein.

The invention provides expression vectors including a polynucleotide disclosed herein operatively linked to a regulatory sequence. "Regulatory sequences" include enhancers and promoters. Preferably, the expression vectors of the invention comprise polynucleotide operatively linked to a prokaryotic promoter. More preferably, the expression vectors of the present invention comprise a polynucleotide operatively linked to a eukaryotic promoter, and the expression vectors further comprise a polyadenylation signal that is positioned 3' of the carboxy-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different polynucleotides. As used herein, the term "promoter" includes what is referred to in the art as an upstream promoter region, a promoter region or a promoter of a generalized eukaryotic RNA Polymerase II transcription unit.

Another type of regulatory sequence is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

In one aspect of the invention, the enhancer and/or promoter is operatively linked to a coding sequence that encodes at least one polynucleotide product. As used herein, the phrase "operatively linked" means that a regulatory sequence is connected to a coding sequence in such a way that the transcription of that coding sequence is controlled and regulated by that enhancer and/or promoter. Means for operatively linking an enhancer and/or promoter to a coding sequence are well-known in the art. As is also well-known in the art, the precise orientation and location relative to a coding sequence whose transcription is controlled, is dependent upon the specific nature of the regulatory sequence. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

Microbial promoters most commonly used in recombinant DNA construction include the beta-lactamase (penicillinase) and lactose promoter systems and a tryptophan (TRP) promoter system (EPO Appl. Publ. No. 0036776). While these are the most commonly used, other microbial promoters have been discovered and utilized, and details concerning their nucleotide sequences have been published, enabling a skilled worker to introduce functional promoters into plasmid vectors.

Suitable promoter sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these polynucleotides are also introduced into the expression vector downstream from the sequences to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In one embodiment, a regulatable promoter is used. By "regulatable promoter" is meant a promoter other than the native promoter for the essential polynucleotide which can be regulated by the addition and/or removal of specific materials or for example by other environmental changes.

Some examples of regulatable promoters for use in organisms include GAL I for use in *S. cerevisiae* (repressed by glucose induced by galactose); NMT1 for use in *S. pombe* (repressed by thiamine); for use in *C. albicans*: MALI (repressed by glucose, induced by maltose, sucrose); for use in *E. coli*: araB (repressed by glucose, induced by arabinose); for use in Gram-positive bacteria such as Staphylococci, Enterococci, Streptococci and Bacilli: xylA/xylR (from *S. xylosus*) (repressed by glucose, induced by xylose); for use in *E. coli* and *B. subtilis* pSPAC (an artificial promoter derived from *E. coli* lac, regulated by IPTG, see Vagner et al. *Microbiology,* 144, 3097-3104 (1998)); and for all of the above organisms plus further unspecified fungi, bacteria and mammalian cell lines: tetA/tetR (from various bacterial tetracycline resistance cassettes) this system exists in various versions, see Gossen et al. *Current Opin. Biotechnol.* 5, pp 516-520 (1994), that are repressible or inducible by various tetracycline analogues.

Other conditional regulatable promoters include, but are not limited to, those such as MET25, MAL2, PHO5,5 GAL I; STE2, or STE3.

A preferred regulatable promoter for use in some embodiments includes the MET3 promoter (repressible by methionine, cysteine or both).

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired polynucleotide sequence, provided such control sequences are compatible with the host cell systems.

An origin of replication can be provided constructing the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well-known in the art.

The invention provides an expression vector having a polynucleotide that encodes an essential polynucleotide polypeptide. Such a polypeptide is meant to include a sequence of nucleotide bases encoding an essential polynucleotide polypeptide sufficient in length to distinguish said fragment from a polynucleotide fragment encoding a non-essential polynucleotide polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutapolynucleotidesis.

The present invention also provides recombinant vectors that may be used to integrate exogenously provided sequences into the genome of a host cell. The recombinant integration vectors of the present invention include a polynucleotide that encodes a selectable marker and polynucleotide sequences of the invention or fragment thereof. The integration vectors are used to integrate the essential polynucleotide sequences into a target polynucleotide sequence that resides within the fungal host genome (e.g., endogenous sequence), thereby disrupting the function of the target polynucleotide sequence within the fungal cells. These integration vectors may be used in a polynucleotide disruption assay to screen candidate sequences in order to identify the candidate sequences that encode a polynucleotide product that is required for fungal cell viability.

Accordingly, these recombinant integration vectors include candidate sequences such as homologues of SEQ ID NO: 1 through to SEQ ID NO: 11, SEQ ID NO: 1 through to SEQ ID NO. 11, SEQ ID NO: 12 or a fragment thereof to determine if the candidate sequences encode a polynucleotide product that is required for cell viability. The candidate sequences that is included as part of the recombinant integration vector is the "exogenous" candidate sequence that is employed as the "disrupting" sequence in a polynucleotide disruption assay. The candidate sequence that resides within the host genome is the "endogenous" or target candidate sequence.

The integration event rarely occurs, for example, by non-homologous recombination in which a recombinant vector, that includes the exogenous candidate sequence, inserts the exogenous candidate sequence into a random location within the host genome.

In a more preferred embodiment, the integration event inserts the exogenous candidate sequence into a specific target site within the host genome. The targeted integration event can involve homologous recombination in which the integration vector, that includes the exogenous candidate sequence, inserts the exogenous candidate sequence into its homologous target candidate sequence that resides within the host's genome (e.g., the endogenous candidate sequence). The exogenous candidate sequences can result in disruption of the function of the endogenous candidate sequence. For example, disrupting the function of the endogenous sequence may result in the loss of fungal cell viability.

Host Cells and Host Organisms

In yet another embodiment, the present invention provides recombinant host cells transformed or transfected with a polynucleotide that encodes essential polynucleotide polypeptides, as well as transgenic cells derived from those transformed or transfected cells. Preferably, the recombinant host cells of the present invention are transfected with the polynucleotide of SEQ ID NO: 1 to SEQ ID NO: 11, or a variant or fragment thereof.

A variety of cells are amenable to the method of the invention involving polypeptide expression, for instance, yeast cells, human cell lines, and other eukaryotic cell lines well-known to those of skill in the art.

Means of transforming or transfecting cells with an exogenous polynucleotide such as DNA molecules are well-known in the art and include techniques such as calcium-phosphate- or DEAE-dextran-mediated transfection, protoplast fusion, electroporation, liposome mediated transfection, direct microinjection and adenovirus infection (Sambrook, et al., supra).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of foreign DNA in large numbers of cells. Calcium phosphate-mediated transfection is also used to establish cell lines that integrate copies of foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion frequently yields multiple copies of the plasmid DNA tandemly integrated into the host chromosome.

The application of brief, high-voltage electric pulses to a variety of mammalian cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned polynucleotides and for establishment of cell lines that carry integrated copies of the polynucleotide of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well-known in the art. Adenovirus vector-mediated cell transfection has been reported for various cells (Stratford-Perricaudet, et al., *J Clin Invest.* 90(2):626-630).

A transfected cell can be prokaryotic or eukaryotic. In one embodiment, the host cells of the invention are eukaryotic host cells.

When the recombinant host cells of the present invention are prokaryotic host cells *Escherichia coli* bacterial cells are preferred. In general, prokaryotes are preferred for the initial cloning of DNA sequences and constructing the vectors useful in the invention. For example, *E. coli* K12 strains can be particularly useful. Another microbial strain which can be used includes *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratus marcesens*, and various *Pseudomonas* species can be used.

In addition to prokaryotes, eukaryotic microbes such as yeast can also be used. *Saccharomyces cerevisiae* or common baker's yeast is the most commonly used among eukaryotic microorganisms, although a number of other strains are commonly available. For expression in *Saccharomyces*, the plasmid YRp7, for example, is used. This plasmid already contains the trpl polynucleotide which provides a selection marker for a mutant strain of yeast lacking the ability to grow in tryptophan, for example, ATCC No. 44076. The presence of the trpl lesion as a characteristic of the yeast host cell genome then provides an effective environment for detecting transformation by growth in the absence of tryptophan.

In addition to microorganisms, cultures of cells derived from multicellular organisms can also be used as hosts. In principle, any such cell culture is workable, whether from vertebrate or invertebrate culture. Examples of such useful host cell lines are AtT-20, VERO and HeLa cells, Chinese hamster ovary (CHO) cell lines, and W138, BHK, COSM6, COS-7, 293 and MDCK cell lines.

Following transfection, the cell is maintained under culture conditions for a period of time sufficient for expression of an essential polynucleotide polypeptide. Culture conditions are well-known in the art and include ionic composition and concentration, temperature, pH and the like. Typically, transfected cells are maintained under culture conditions in a culture medium. Suitable medium for various cell types are well-known in the art. In a preferred embodiment, temperature is from about 20° C. to about 50° C., more preferably from about 30° C. to about 40° C. and, even more preferably, about 37° C. pH is preferably from about a value of 6.0 to a value of about 8.0, more preferably from about a value of about 6.8 to a value of about 7.8 and, most preferably, about 7.4. Osmolality is preferably from about 200 milliosmols per liter (mosm/L) to about 400 mosm/L and, more preferably, from about 290 mosm/L to about 310 mosm/L. Other biological conditions needed for transfection and expression of an encoded protein are well-known in the art.

Transfected cells are maintained for a period of time sufficient for expression of an essential polynucleotide polypeptide. A suitable time depends upon the cell type used and is readily determinable by a skilled artisan. Typically, maintenance time is from about 2 to about 14 days. Recombinant essential polynucleotide polypeptide is recovered or collected either from the transfected cells or the medium in which those cells are cultured. Recovery comprises isolating and purifying the essential polynucleotide polypeptide. Isolation and purification techniques for polypeptides are well-known in the art and include such procedures as precipitation, filtration, chromatography, electrophoresis and the like.

Fungal Strains of the Invention

The invention also provides *Candida albicans* strains which may be used for drug screening. According to the invention, one copy of an essential polynucleotide of the invention is eliminated (such as those encoding an essential polypeptide having the amino acid sequence of SEQ ID NO:12 through to SEQ ID NO 22), while the second allele is placed under the control of a regulatable promoter.

In a preferred embodiment, precise replacement of one copy of a target polynucleotide is facilitated by using a PCR-based polynucleotide disruption tool (see, e.g., Wilson et al., *J. Bacteriol.* 181:1868-1874 (1999), herein incorporated by reference). Genes are disrupted by using PCR to generate a selectable marker (for example, URA3) surrounded by the 5' and 3' sequences of the polynucleotide to be disrupted. The marker sequences are part of a plasmid (see, e.g., Example 4). Disruption cassettes are synthesized by PCR using primers containing both short flanking homology (SFH) regions and regions which anneal to the marker in the plasmid. The SHF regions are about 25 to about 60 bp long. The disruption cassettes are generated in one-step PCR synthesis and homologous recombination transplaces the recombinant null construct into the genome, generating an allele such as yfg1::URA3 (yfg1 is "your favorite gene").

Where the polynucleotide is essential, elimination of both alleles will be lethal or severely crippling for growth. Therefore, in the present invention, a regulatable promoter is used to provide a range of levels of expression of the second allele. Depending on the conditions, the second allele can be non-expressing, underexpressing, or expressing at a normal level relative to that when the allele is linked to its native promoter.

Regulatable promoters include, but are not limited to, those such as MET25, MAL2, PHO5,5 GAL I; STE2, or STE3. A preferred regulatable promoter is the MET3 promoter.

Preferably, replacement of the promoter of the second copy with the MET3 promoter is accomplished by the use of a promoter swapping cassette. The "PCR-based promoter swapping cassette" as used herein refers to a cassette comprised of a regulatable promoter, a selectable marker, and short flanking regions to on the 5' and 3' ends of the cassette which are homologous to the native promoter and the start of the polynucleotide coding region, respectively.

This promoter swapping cassette works analogously to the PCR based polynucleotide disruption cassette described above. A promoter of 'YFG' is disrupted by using PCR to generate a selectable marker (for example, URA3 or ARG4) containing a sequence of the promoter region to be disrupted. Disruption cassettes are synthesized by PCR, using short flanking homology (SFH) regions to the promoter of interest. SHF regions are about 25 to about 60 bp long. When the disruption cassette is transformed into yeast cells, the promoter of YFG is displaced by homologous recombination.

In order to replace the endogenous promoter of YFG, the PCR-based promoter swapping cassette contains a selective marker amplified from a plasmid using a pair of primers designed so that the forward primer contains about 50 to about 60 bp of flanking sequences that are derived from sequences 500-100 bp upstream of the ATG codon of YFG to ensure it will anneal upstream or on the boundary of the endogenous promoter and this portion of the forward primer is attached to the 5'-end of the forward common promoter primer. The forward common promoter primer region is common to the plasmid.

The reverse primer has 20 to 60 or preferably about 50 to about 60 bp of flanking sequences, which are derived from the start codon region of the polynucleotide or ORF including ATG attached to the 3' end of the reverse common primer. The resulting PCR product contains the promoter cassette that is flanked by about 50 to about 60 bp of sequences, on either end, homologous to the upstream promoter region and to the coding region of the polynucleotide of interest, respectively. Once introduced into the cells heterozygous for the polynucleotide of interest obtained via the regular PCR-based polynucleotide disruption approach, the PCR-based promoter swapping cassette would replace the endogenous promoter of the remaining allele via homologous recombination.

The MET3 promoter for use in the construction of the *C. albicans* strains as described above is a homologue of *S. cervisiae* MET3. The cloning of this promoter is described in Care et al., supra). The MET3 polynucleotide of *S. cervisiae* encodes ATP sulphurylase (ATP: sulphate adenyltransferase, E.C. 2.7.7.4) which catalyses the production of adenosine 5'-phosphosulphate (APS) from inorganic sulphate and ATP, the first step in the assimilation of inorganic sulphate. Expression of MET3 is repressed by exogenous methionine and S-adenysl methionine (SAM). Methionine is converted into SAM, which is thought to be the true repressor. Sulphur assimilation is also required for the biosynthesis of cysteine. According to an alternative view, cysteine is the true repressor of the enzymes of sulphur metabolism, the action of methionine and SAM being dependent on the interconversion of sulphur-containing amino acids through transulphurylation pathways (Care et al. supra, herein incorporated by reference).

In the methods of the invention, the MET3 promoter may be completely or partially repressed using cysteine, methionine or both amino acids.

In particular, the present invention encompasses strains of *Candida albicans* cells in which both alleles of a polynucleotide are modified. A first copy of a polynucleotide comprising a nucleotide sequence selected from the group consisting of one of SEQ ID NO 1 to 11 is inactive and a second copy of the polynucleotide is under the control of a regulatable promoter.

Additionally, the invention also provides a strain of *Candida albicans* having a nucleic acid molecule comprising a nucleotide sequence selected from one of SEQ ID NO: 1 to 11 under the control of a regulatable promoter.

Target Evaluation in Animal Model Systems

In one embodiment, the essential strains provided by the invention are used in animal studies to examine the effect of polynucleotide inactivation by conditional expression. Animal studies, using mice, for example, may be inoculated with one or more of the strains of the invention. In a more desirable embodiment of the invention, the effect on mice injected with a lethal inoculum of one of the essential strains could be determined depending on whether the mice were provided with an appropriate concentration of promoter repressor to inactivate expression of a drug target polynucleotide. The lack of expression of a polynucleotide demonstrated to be essential under laboratory conditions can thus be correlated with prevention of a terminal *C. albicans* infection. In this type of experiment, only mice "treated" with promoter repressor supplements are predicted to survive infection because inactivation of the target polynucleotide has killed the essential strain pathogen within the host.

Identification of Essential Genes

Also provided herein are methods to identify essential polynucleotides. In order to determine essentially, a strain is constructed as described above and then the strain is cultured under conditions wherein the second modified allele of the polynucleotide which is under conditional expression is substantially underexpressed or not expressed. A "promoter repressor", i.e., a substance that inhibits the ability of a regulatable promoter to cause expression in the second allele is added to the culture medium. The preferred promoter repressor used herein may be methionine and cysteine or a combination thereof when the MET3 promoter is used in the compositions and methods of the invention. The preferred regulatable promoter is MET3. The viability and/or growth of the strain is compared with that of control cells cultured without the addition of promoter supressor. A loss or reduction of viability or growth in the cells cultured with promoter suppressor indicates that the polynucleotide is essential to the survival of the fungus.

The fungal strains and cells used to identify essential polynucleotides with the method of the invention, include but are not limited to *Absidia corymbigera, Aspergillus flavis, Aspergillus fumigatus, Aspergillus niger, Botrytis cinerea, Candida dublinensis, Candida glabrata, Candida krusei, Candia parapsilopsis, Candia tropicalis, Coccidioides immitis, Cryptococcus neoformans, Erysiphe graminis, Exophalia dermatiditis, Fusarium osysproum, Histoplasma capsulatum, Magnaporthe grisea, Mucor rouxii, Pneumocystis carinii, Puccinia graminis, Puccinia recodita, Rhizomucor pusillus, Puccinia striiformis, Rhizopus arrhizus, Septoria avenae, Septoria nodorum, Septoria triticii, Tilletia controversa, Tilletia tritici, Trichospoon beigelii* and *Ustilago maydis*. Preferably, *Candida albicans* strains are used.

Haploid or diploid strains may used to identify essential polynucleotides by the method of the invention. In the case of haploid strains, the promoter of the polynucleotide of interest is replaced with a regulatable promoter and tested for essentiality as described herein. Since there is no diploidy, the first step using a PCR based disruption cassette is not required.

The nucleotide sequences encoding candidate polynucleotides which are assayed using the method of the invention to determine essentiality are preferably conserved polynucleotides. A polynucleotide can be identified as belonging to a repertoire of conserved polynucleotides using several methods. For example, an isolated polynucleotide may be used as a hybridization probe under low stringency conditions to detect other members of the repertoire of conserved polynucleotides present in genomic DNA using the methods described by Southern, *J. Mol. Biol.,* 98:503 (1975). Additionally, conserved polynucleotides can be identified using a concordance analysis such as that described herein.

Strains Hypersensitive to Drugs and Titration of Gene Products

Also, provided herein are methods to create strains which are hypersensitive to potential antifungal drugs. Current cell based assays used to identify or to characterize compounds for drug discovery and development frequently depend on detecting the ability of a test compound to modulate the activity of a target molecule located within a cell or located on the surface of a cell. Most often such target molecules are proteins such as enzymes, receptors and the like. However, target molecules also include other molecules such as DNAs, lipids, carbohydrates and RNAs including messenger RNAs, ribosomal RNAs, tRNAs and the like. A number of highly sensitive cell-based assay methods are available to those of skill in the art to detect binding and interaction of test compounds with specific target molecules. However, these methods are generally not highly effective when the test compounds binds to or otherwise interacts with its target molecule with moderate or low affinity. Thus, current cell-based assay methods are limited in that they are not effective in identifying or characterizing compounds that interact with their targets with moderate to low affinity or compounds that interact with targets that are not readily accessible.

The methods of the invention to create cells which are hypersensitive to potential antifungal compounds may be used to overcome these limitations. The sensitizing assays of the present invention are capable of detecting compounds exhibiting low or moderate potency against the target molecule of interest because such compounds are substantially more potent on sensitized cells than on non-sensitized cells. The effect may be such that a test compound may be two to several times more potent, at least 10 times more potent, at least 20 times more potent, at least 50 times more potent, at least 100 times more potent, at least 1000 times more potent, or even more than 1000 times more potent when tested on the sensitized cells as compared to the non-sensitized cells.

Such assays are useful to identify compounds that previously would not have been readily identified. A target which expresses a significant amount of product may not result in a particular effect by a particular compound. However, when the amount of product is reduced, the compound may be revealed to in fact have an effect on the polynucleotide product. An initial hit compound which exhibits moderate or even low potency may be able to be developed into a drug. For example, once a hit compound is identified with low or moderate potency, a combinatorial chemical library consisting of compounds with structures related to the hit compound but containing systematic variations including additions, subtractions and substitutions of various structural features may be included. When tested for activity against the target molecule, structural features may be identified that either alone or in combination with other features enhance or reduce activity. This information may be used to design subsequent directed libraries containing compounds with enhanced activity against the target molecule. After one or several iterations of this process, compounds with substantially increased activity against target molecules are identified and may be further developed as drugs. This process is facilitated by the use of the sensitized strains of the present invention since compounds acting at the selected targets exhibit increased potency in such cell-based assays, thus, more compounds can now be characterized providing more useful information than would be obtained otherwise.

The method of sensitizing a cell entails selecting an essential polynucleotide such as those identified in the present invention. The next step is to obtain a cell in which the level or activity of the target can be reduced to a level where it is rate limiting for viability. For example, the cell may be a strain of the present invention in which the selected polynucleotide is under the control of a MET3 promoter. The amount of RNA transcribed from the selected polynucleotide is limited by varying the concentration of methionine, cysteine or both, which acts on the MET3 promoter, thereby varying the activity of the promoter driving transcription of the RNA. Thus, cells are sensitized by exposing them to a repressor concentration that results in an RNA level such that the function of the selected polynucleotide product becomes rate limiting for fungal growth, survival or proliferation.

In one embodiment of the present invention, a *Candida* strain is created by inactivating one copy of a polynucleotide by the insertion of a nucleotide sequence encoding a selectable marker and the second polynucleotide copy has been modified by recombination with a promoter swapping cassette, to place the second copy under the controlled expression of a MET3 promoter. The strain is then grown under a first set of conditions where the MET3 promoter is expressed at a relatively low level and the extent of growth is determined. This measurement may be carried out using any appropriate standard known to those skilled in the art, including optical density, wet weight of pelleted cells, total cell count, viable count, DNA content and the like. This experiment is repeated in the presence of a test compound and a second measurement of growth is obtained. The estimate of growth in the presence and in the absence of the test compound, which can conveniently be expressed in terms of indicator values, are then compared. A dissimilarity in the extent of growth or indicator values provides an indication that the test compound may interact with the target essential polynucleotide product.

To gain additional information, additional experiments may be performed in various embodiments. For example, using a second set of non-repressing growth conditions where the second polynucleotide copy, under the control of the MET3 promoter, is expressed at various levels higher that in the rest set of conditions described above. The extent of growth or indicator values is determined in the presence and absence of the test compound under this second set of conditions. The extent of growth or indicator values in the presence and in the absence of the test compound are then compared. A dissimilarity in the extent of growth or indicator values provides an indication that the test compounds may interact with the target essential polynucleotide product.

Furthermore, the extent of growth in the first and in the second set of growth conditions can also be compared. If the extent of growth is essentially the same, the data suggest that the test compound does not inhibit the polynucleotide product encoded by the modified allelic polynucleotide pair carried by the strain tested. However, if the extent of growth is substantially different, the data indicate that the level of expression of the subject polynucleotide product may determine the degree of inhibition by the test compound and therefore it is likely that the subject polynucleotide product is the target of that test compound.

In one embodiment, the strains of the invention in which the sequence required for fungal growth, survival or proliferation of *Candida* described herein is under the control of MET3, and grown in the presence of a concentration of promoter repressor which causes the function of the polynucleotide products encoded by these sequences to be rate limiting for fungal growth. To achieve that goal, a growth inhibition dose curve is calculated by plotting various doses of repressor against corresponding growth inhibition caused by the limited levels of the polynucleotide product required for fungal proliferation. From this dose-response curve, conditions providing various growth rates for 1 to 100%, as compared to repressor-free growth, can be determined. For example, the diploid fungal strains of the invention are grown in medium comprising a range of methionine concentrations to obtain the growth inhibitory response curve for each strain. First, seed cultures of the diploid fungal strains of the invention are grown in the appropriate medium. Subsequently, aliquots of the seed cultures are diluted into medium containing varying concentrations of methionine. For example, the strains may be grown in duplicate cultures containing two-fold serial dilutions of methionine Additionally, control cells are grown in duplicate without methionine. The control cultures are started from equal amounts of cells derived from the same initial seed culture of the strain of interest. The cells are grown for an appropriate period of time and the extent of growth is determined using any appropriate technique For example, the extent of growth may be determined by measuring the optical density of the cultures. When the control culture reaches mid-log phase the percent growth (relative to the control culture) for each of the methionine containing cultures is plotted against the log concentrations of methionine to produce a growth inhibitory dose response curve for methionine. The concentration of methionine that inhibits cell growth at 50% (IC50) as compared to the 0 mM methionine control (0% growth inhibition) is then calculated from the curve. Alternative methods of measuring growth are also contemplated. Examples of these methods include measurements of protein, the expression of which is engineered of the cells being tested and can readily be measured.

Thus, in one embodiment, the method described above may be used to titrate the amount of essential polynucleotide product expressed in a diploid fungal cell.

In another embodiment, a homologue of the essential polynucleotide sequences of the present invention that are identified in a haploid organism may similarly be used as the basis for detection of an antifungal or therapeutic agent. In this embodiment, the test organism (e.g., *Aspergillus fumigatus* or *Cryptococcus neoformans*) or any other haploid organism in a strain constructed by modifying the single allele of the target polynucleotide in one step recombination with a promoter swapping cassette such that the expression of the polynucleotide is conditionally regulated by the promoter. Like individual diploid strains of the invention, sensitized haploid cells may be similarly used in whole cell-based assay methods to identify compounds displaying a preferential activity against the affected target.

In various embodiments, the modified strain is grown under a first set of conditions where the regulatable promoter is expressed at a relatively low level and the extent of growth determined. This experiment is repeated in the presence of a test compound and a second measurement of growth obtained. The extent of growth in the presence and in the absence of the test compounds are then compared to provide a first indicator value. Two further experiments are performed using non-repressing growth conditions where the target polynucleotide is expressed at substantially higher levels than in the first set of conditions. Extent of growth is determined in the presence and absence of the test compound under the second set of conditions to obtain a second indicator value. The first and second indicator values are then compared. If the indicator values are essentially the same, the data suggest that the test compound does not inhibit the test target. However, if the two indicator values are substantially different, the data indicate that the level of expression of the target polynucleotide product may determine the degree of inhibition by the test compounds and therefore it is likely that the polynucleotide product is the target of that test compound. Whole-cell assays comprising collections or subsets of multiple sensitized strains may be screened, for example, in a series of 96 well, 384 well or even 1586 well microtiter plates.

Cells to be assayed are exposed to the above-determined concentrations of methionine or other promoter repressor. The presence of the repressor at this sub-lethal concentration reduces the amount of the proliferation-required polynucleotide product to the lowest amount in the cell that will support growth. Cells grown in the presence of this concentration of repressor are more sensitive to inhibitors of the proliferation-required protein or RNA of interest as well as to inhibitors of proteins or RNAs in the same biological pathway as the proliferation-required protein or RNA of interest but not specifically more sensitive to inhibitors of unrelated proteins or RNAs.

Cells pretreated with sub-inhibitory concentrations of repressors which therefore contain a reduced amount of proliferation-required target polynucleotide product are used to screen for compounds that reduce cell growth. The sub-lethal concentration of repressor may be any concentration consistent with the intended use of the assay to identify candidate compounds to which the cells are more sensitive than are control cells in which this polynucleotide product is not rate-limiting. For example, the sub-lethal concentration of the repressor may be such that growth inhibition is at least about 5%, at least about 10%, at least about 20%, at least about 30%, at least about 40%, at least about 50%, at least about 60%, at least about 75%, at least 80%, at least 90%, at least 95% or more than 96%. Cells which are pre-sensitized using the preceding method are more sensitive to inhibitors of the target protein because these cells contain less target protein to inhibit than wild-type cells. Cells are then contacted with a candidate compound and growth of the cells in the methionine containing medium is compared to growth of the control cells in medium which lacks methionine to determine whether the candidate compound inhibits growth of the sensitized cells (i.e., cells grown in the presence of methionine) to a greater extent than the candidate compound inhibits the growth of cells grown in the absence of methionine. For example, if a significant difference in growth is observed between the sensitized cells and the non-sensitized cells, the candidate compound may be used to inhibit the proliferation of the organism or may be further optimized to identify compounds which have an even greater ability to inhibit the growth survival or proliferation of the organism.

When screening for antimicrobial agents against a polynucleotide product required for fungal growth, survival or proliferation or growth inhibition of cells containing a limiting amount of that polynucleotide product can be assayed. Growth inhibition can be measured by directly comparing the amount of growth measured by the optical density of the culture relative to uninoculated growth medium between and experimental sample and a control sample. Alternative methods for assaying cell proliferation include measuring green fluorescent protein report construct emissions, various enzymatic activity assays and other methods well-known in the art.

It will be appreciated that the above cell-based assays may be used to identify compounds which inhibit the activity of polynucleotide products from organisms other than *Candida albicans* which are homologous to the *Candida albicans* nucleotide sequences encoding essential polypeptides described herein. For example, the nucleotide sequences encoding polypeptides may be from animal fungal pathogens such as *Aspergillus fumigatus, Aspergillus niger, Aspergillus flavis, Candida tropicalis, Candida parapsilopsis, Candida krusei, Cryptococcus neofomras, Coccidioides immitis, Exophalia dermatiditis, Fusarium oxygporum, Histoplasma capsulaturm, Pneumocystis carinii, Trichosporan beigelii, Rhizopus arrhizus, Mucor rouxii, Rhizomucor pusillus* or *Absidia corymbigera* or the plant fungal pathogens such as *Botrytis cinerea, Erysiphe graminis, Magnaporthe grisea, Puccinia recodita, Spetoria triticii, Tilletia controversa, Ustilago maydis* or any species falling with the genera of any of the above species. In some embodiments, the essential polynucleotides are from an organism other than *Saccharomyces cerevisiae.*

Protein Based Assays

The present invention also provides methods for identifying an antimycotic compound comprising screening a plurality of compounds to identify a compound that modulates the activity or level of a polynucleotide product (mRNA or protein), said polynucleotide product being encoded by a nucleotide sequence selected from the group consisting of SEQ ID NO: 1 to SEQ ID NO: 11, or a nucleotide sequence that is the homologue of a polynucleotide having a nucleotide sequence selected from the group consisting of SEQ ID NO: 1 to SEQ ID NO: 11.

Binding assays may be used to identify antimycotic compounds. These assays involve preparing a reaction mixture comprising the target polynucleotide product and the test compound under conditions and for a time sufficient to allow the two components to interact and bind, thus forming a complex which is removed and/or detected within the reaction mixture. These assays may be conducted in a variety of ways. For example, one method involves anchoring a target polynucleotide product or the test substance onto a solid phase and detecting target polynucleotide product/test compound complexes anchored, via the intermolecular binding reaction to the solid phase at the end of the reaction. In one embodiment, the target polynucleotide product is anchored onto a solid surface and the test compound which is not anchored is labeled either directly or indirectly.

Microtiter plates may be utilized as the solid phase. The anchored component is immobilized by non-covalent or covalent attachments. Non-covalent attachment can be accomplished by simply coating the solid surface with a solution of the protein and drying the coated surface. Alternatively, an immobilized antibody, preferably a monoclonal antibody, specific for the protein to be immobilized is used to anchor the protein to the solid surface.

Alternatively, a reaction is conducted in a liquid phase, the reaction products are separated from unreacted components, and complexes are detected; e.g., using an immobilized antibody specific for the target polynucleotide product or for the test compound, to anchor complexes formed in solution, and a second labeled antibody, specific for the other component of the complex to allow detection of anchored complexes.

In another aspect of the invention, methods are employed to for detecting protein-protein interactions for identifying novel target protein-cellular or extracellular protein interactions. Any suitable method may be used.

The target polynucleotide products of the invention may interact, in vivo, with one or more cellular or extracellular macromolecules, such as proteins. Such macromolecules include, but are not limited to, nucleic acid molecules and proteins identified via methods such as those described above. For purposes of this discussion, such cellular and extracellular macromolecules are referred to herein as "binding partners." Compounds that disrupt such interactions can be useful in regulating the activity of the target polynucleotide protein, especially mutant target polynucleotide proteins. Such compounds include, but are not limited to molecules such as antibodies, peptides, and the like.

The basic principle of the assay systems used to identify compounds that interfere with the interaction between the target polynucleotide product and its cellular or extracellular binding partner or partners involves preparing a reaction mixture containing the target polynucleotide product and the binding partner under conditions and for a time sufficient to allow the two to interact and bind, thus forming a complex. In order to test a compound for inhibitory activity, the reaction mixture is prepared in the presence and absence of the test compound. The test compound is initially included in the reaction mixture, or added at a time subsequent to the addition of target polynucleotide product and its cellular or extracellular binding partner. Control reaction mixtures are incubated without the test compound. The formation of complexes between the target polynucleotide protein and the cellular or extracellular binding partner is then detected. The formation of a complex in the control reaction, but not in the reaction mixture containing the test compound, indicates that the compound interferes with the interaction of the target polynucleotide protein and the interactive binding partner. Additionally, complex formation within reaction mixtures containing the test compound and normal target polynucleotide protein can also be compared to complex formation within reaction mixtures containing the test compound and a mutant target polynucleotide protein. This comparison can be important in those cases wherein it is desirable to identify compounds that disrupt intermolecular interactions involving mutant but not normal target polynucleotide proteins.

The assay for compounds that interfere with the interaction of the target polynucleotide products and binding partners is conducted in either a heterogeneous or a homogeneous format.

Heterogeneous assays involve anchoring either the target polynucleotide product or the binding partner onto a solid phase and detecting complexes anchored on the solid phase at the end of the reaction. In homogeneous assays, the entire reaction is carried out in a liquid phase. In either approach, the order of addition of reactants is varied to obtain different information about the compounds being tested. For example, test compounds that interfere with the interaction between the target polynucleotide products and the binding partners, e.g., by competition, are identified by conducting the reaction in the presence of the test substance; i.e., by adding the test substance to the reaction mixture prior to or simultaneously with the target polynucleotide protein and an interacting cellular or extracellular binding partner. Alternatively, test compounds that disrupt preformed complexes, e.g., compounds with higher binding constants that displace one of the components from the complex, are tested by adding the test compound to the reaction mixture after complexes have been formed. The various formats are described briefly below.

In a heterogeneous assay system, either the target polynucleotide protein or the interactive cellular or extracellular binding partner, is anchored onto a solid surface, while the non-anchored species is labeled, either directly or indirectly. In practice, microtiter plates are conveniently utilized. The anchored species is immobilized either by non-covalent or covalent attachment.

Non-covalent attachment is accomplished simply by coating the solid surface with a solution of the target polynucleotide product or binding partner and drying the coated surface. Alternatively, an immobilized antibody specific for the species to be anchored is used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface is accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, is directly labeled or indirectly labeled with a labeled anti-Ig antibody). Depending upon the order of addition of reaction components, test compounds which inhibit complex formation or which disrupt preformed complexes are detected.

Alternatively, the reaction is conducted in a liquid phase in the presence or absence of the test compound, the reaction products separated from unreacted components, and complexes detected; e.g., using an immobilized antibody specific for one of the binding components to anchor any complexes formed in solution, and a second, labeled antibody specific for the other partner to detect anchored complexes. Again, depending upon the order of addition of reactants to the liquid phase, test compounds which inhibit complex or which disrupt preformed complexes are identified.

In an alternate embodiment of the invention, a homogeneous assay can be used. In this approach, a preformed complex of the target polynucleotide protein and the interacting cellular or extracellular binding partner is prepared in which either the target polynucleotide product or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex results in the generation of a signal above background. In this way, test substances which disrupt target polynucleotide protein/cellular or extracellular binding partner interaction are identified.

In a particular embodiment the target polynucleotide product is prepared for immobilization using recombinant DNA techniques described above. For example, the target polynucleotide coding region is fused to a glutathione-5-transferase (GST) polynucleotide using a fusion vector, such as pGEX-5X-1, in such a manner that its binding activity is maintained in the resulting fusion protein. The interactive cellular or extracellular binding partner is purified and used to raise a monoclonal antibody, using methods routinely practiced in the art and as described below. This antibody is labeled with the radioactive isotope " ", for example, by methods routinely practiced in the art. In a heterogeneous assay, e.g., the GST-target polynucleotide fusion protein is anchored to glutathione-agarose beads. The interactive cellular or extracellular binding partner is then added in the presence or absence of the test compound in a manner that allows interaction and binding to occur. At the end of the reaction period, unbound material can be washed away, and the labeled monoclonal antibody is added to the system and allowed to bind to the complexed components. The interaction between the target polynucleotide protein and the interactive cellular or extracellular binding partner is detected by measuring the amount of radioactivity that remains associated with the glutathione-agarose beads. A successful inhibition of the interaction by the test compound results in a decrease in measured radioactivity.

Alternatively, the GST-target polynucleotide fusion protein and the interactive cellular or extracellular binding partner are mixed together in liquid in the absence of the solid glutathione-agarose beads. The test compound is added either during or after the species are allowed to interact. This mixture is added to the glutathione-agarose beads and unbound material is washed away. Again the extent of inhibition of the target polynucleotide product/binding partner interaction is detected by adding the labeled antibody and measuring the radioactivity associated with the beads.

In another embodiment of the invention, these same techniques are employed using peptide fragments that correspond to the binding domains of the target polynucleotide product and/or the interactive cellular or extracellular binding partner (in cases where the binding partner is a protein), in place of one or both of the full length proteins. Any number of methods routinely practiced in the art are used to identify and isolate the binding sites. These methods include, but are not limited to, mutapolynucleotidesis of the polynucleotide encoding one of the proteins and screening for disruption of binding in a co-immunoprecipitation assay. Compensating mutations in the polynucleotide encoding the second species in the complex are then selected. Sequence analysis of the polynucleotides encoding the respective proteins reveals the mutations that correspond to the region of the protein involved in interactive binding. Alternatively, one protein is anchored to a solid surface using methods described above, and allowed to interact with and bind to its labeled binding partner, which has been treated with a proteolytic enzyme, such as trypsin. After washing, a short, labeled peptide comprising the binding domain remains associated with the solid material, and can be isolated and identified by amino acid sequencing. Also, once the polynucleotide coding for the cellular or extracellular binding partner is obtained, short polynucleotide segments are engineered to express peptide fragments of the protein, which are tested for binding activity and purified or synthesized.

For example, and not by way of limitation, a target polynucleotide product is anchored to a solid material as described, above, by making a GST-target polynucleotide fusion protein and allowing it to bind to glutathione agarose beads. The interactive cellular or extracellular binding partner is labeled with a radioactive isotope, and cleaved with a proteolytic enzyme such as trypsin. Cleavage products are added to the anchored GST-target polynucleotide fusion protein and allowed to bind. After washing away unbound peptides, labeled bound material, representing the cellular or extracellular binding partner binding domain, is eluted, purified, and analyzed for amino acid sequence by well-known methods. Peptides so identified are produced synthetically or fused to appropriate facilitative proteins using well-known recombinant DNA technology.

In one embodiment of the present invention, the proteins encoded by the fungal polynucleotides identified using the methods of the present invention are isolated and expressed. These recombinant proteins are then used as targets in assays to screen libraries of compounds for potential drug candidates. The generation of chemical libraries is well-known in the art. For example, combinatorial chemistry is used to generate a library of compounds to be screened in the assays described herein. A combinatorial chemical library is a collection of diverse chemical compounds generated by either chemical synthesis or biological synthesis by combining a number of chemical "building block" reagents. For example, a linear combinatorial chemical library such as a polypeptide library is formed by combining amino acids in every possible combination to yield peptides of a given length. Millions of chemical compounds theoretically can be synthesized through such combinatorial mixings of chemical building blocks. For example, one commentator observed that the systematic, combinatorial mixing of interchangeable chemical building blocks results in the theoretical synthesis of million tetrameric compounds or billion pentameric compounds. (Gallop et al., "Applications of Combinatorial Technologies to Drug Discovery, Background and Peptide Combinatorial Libraries," Journal of Medicinal Chemistry, Vol. 37, No. 9, 1233-1250 (1994). Other chemical libraries known to those in the art may also be used, including natural product libraries.

Once generated, combinatorial libraries are screened for compounds that possess desirable biological properties. For example, compounds which may be useful as drugs or to develop drugs would likely have the ability to bind to the target protein identified, expressed and purified as discussed above. Further, if the identified target protein is an enzyme, candidate compounds would likely interfere with the enzymatic properties of the target protein. For example, the enzymatic function of a target protein may be to serve as a protease, nuclease, phosphatase, dehydrogenase, transporter protein, transcriptional enzyme, replication component, and any other type of enzyme known or unknown. Thus, the present invention contemplates using the protein products described above to screen combinatorial chemical libraries.

In some embodiments of the present invention, the biochemical activity of the protein, as well as the chemical structure of a substrate on which the protein acts is known. In other embodiments of the present invention, the biochemical activity of the target protein is unknown and the target protein has no known substrates.

In some embodiments of the present invention, libraries of compounds are to identify compounds that function as inhibitors of the target polynucleotide product. First, a library of small molecules is generated using methods of combinatorial library formation well-known in the art. U.S. Pat. Nos. 5,463, 564 and 5,574, 656, to Agraflotis, et al., entitled "System and Method of Automatically Generating Chemical Compounds with Desired Properties", the disclosures of which are incorporated herein by reference in their entireties, are two such teachings. Then the library compounds are screened to identify those compounds that possess desired structural and functional properties. U.S. Pat. No. 5,684,711, the disclosure of which is incorporated herein by reference in its entirety, also discusses a method for screening libraries.

To illustrate the screening process, the target polynucleotide product, an enzyme, and chemical compounds of the library are combined and permitted to interact with one another. A labeled substrate is added to the incubation. The label on the substrate is such that a detectable signal is emitted from metabolized substrate molecules. The emission of this signal permits one to measure the effect of the combinatorial library compounds on the enzymatic activity of target enzymes by comparing it to the signal emitted in the absence of combinatorial library compounds. The characteristics of each library compound are encoded so that compounds demonstrating activity against the enzyme can be analyzed and features common to the various compounds identified can be isolated and combined into future iterations of libraries.

Once a library of compounds is screened, subsequent libraries are generated using those chemical building blocks that possess the features shown in the first round of screen to have activity against the target enzyme. Using this method, subsequent iterations of candidate compounds will possess more and more of those structural and functional features required to inhibit the function of the target enzyme, until a group of enzyme inhibitors with high specificity or the enzyme can be found. These compounds can then be further tested for their safety and efficacy as antibiotics for use in mammals.

It will be readily appreciated that this particular screening methodology is exemplary only. Other methods are well-known to those skilled in the art. For example, a wide variety of screening techniques are known for a large number of naturally-occurring targets when the biochemical function of the target protein is known. For example, some techniques involve the generation and use of small peptides to probe and analyze target proteins both biochemically and genetically in order to identify and develop drug leads. Such techniques include the methods described in PCT Publications Nos. WO9935494 and WO9819162.

Drug Screening

The fungal essential polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a fungal essential polypeptide, or a bindable peptide fragment, of this invention, comprising providing a plurality of compounds, combining the fungal essential polypeptide, or a bindable peptide fragment, with each of a plurality of compounds for a time sufficient to allow binding under suitable conditions and detecting binding of the fungal essential polypeptide or peptide to each of the plurality of test compounds, thereby identifying the compounds that specifically bind to the fungal essential polypeptide or peptide.

Methods of identifying compounds that modulate the activity of the novel fungal essential polypeptides and/or peptides are provided by the present invention and comprise combining a potential or candidate compound or drug modulator of biological activity with an fungal essential polypeptide or peptide, for example, the fungal essential amino acid sequence as set forth in SEQ ID NO:2, and measuring an effect of the candidate compound or drug modulator on the biological activity of the fungal essential polypeptide or peptide. Such measurable effects include, for example, physical binding interaction; the ability to cleave a suitable substrate; effects on native and cloned fungal essential-expressing cell line; and effects of modulators or other-mediated physiological measures.

Another method of identifying compounds that modulate the biological activity of the novel fungal essential polypeptides of the present invention comprises combining a potential or candidate compound or drug modulator of a biological activity with a host cell that expresses the fungal essential polypeptide and measuring an effect of the candidate compound or drug modulator on the biological activity of the fungal essential polypeptide. The host cell can also be capable of being induced to express the fungal essential polypeptide, e.g., via inducible expression. Physiological effects of a given modulator candidate on the fungal essential polypeptide can also be measured. Thus, cellular assays for particular modulators may be either direct measurement or quantification of the physical biological activity of the fungal essential polypeptide, or they may be measurement or quantification of a physiological effect. Such methods preferably employ a fungal essential polypeptide as described herein, or an overexpressed recombinant fungal essential polypeptide in suitable host cells containing an expression vector as described herein, wherein the fungal essential polypeptide is expressed, overexpressed, or undergoes upregulated expression.

Another aspect of the present invention embraces a method of screening for a compound that is capable of modulating the biological activity of a fungal essential polypeptide, comprising providing a host cell containing an expression vector harboring a nucleic acid sequence encoding a fungal essential polypeptide, or a functional peptide or portion thereof (e.g., SEQ ID NOS:2); determining the biological activity of the expressed fungal essential polypeptide in the absence of a modulator compound; contacting the cell with the modulator compound and determining the biological activity of the expressed fungal essential polypeptide in the presence of the modulator compound. In such a method, a difference between the activity of the fungal essential polypeptide in the presence of the modulator compound and in the absence of the modulator compound indicates a modulating effect of the compound.

Essentially any chemical compound can be employed as a potential modulator or ligand in the assays according to the present invention. Compounds tested as modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel fungal essential polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.,* 37:487-493; and Houghton et al., 1991, *Nature,* 354:84-88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA,* 90:6909-6913), vinylogous polypeptides (Hagihara et al., 1992, *J. Amer. Chem. Soc.,* 114:6568), nonpeptidal peptidomimetics with glucose scaffolding (Hirschmann et al., 1992, *J. Amer. Chem. Soc.,* 114:9217-9218), analogous organic synthesis of small compound libraries (Chen et al., 1994, *J. Amer. Chem. Soc.,* 116:2661), oligocarbamates (Cho et al., 1993, *Science,* 261:1303), and/or peptidyl phosphonates (Campbell et al., 1994, *J. Org. Chem.,* 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology,* 14(3):309-314) and PCT/US96/10287), carbohydrate libraries (e.g., Liang et al., 1996, *Science,* 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a fungal essential polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News,* 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a fungal essential polypeptide or peptide to measure a biological binding or ligand binding activity, the source may be a whole cell lysate that can be prepared by successive freeze-thaw cycles (e.g., one to three) in the presence of standard protease inhibitors. The fungal essential polypeptide may be partially or completely purified by standard protein purification methods, e.g., affinity chromatography using specific antibody described infra, or by ligands specific for an epitope tag engineered into the recombinant fungal essential polypeptide molecule, also as described herein. Binding activity can then be measured as described.

Compounds which are identified according to the methods provided herein, and which modulate or regulate the biological activity or physiology of the fungal essential polypeptides according to the present invention are a preferred embodiment of this invention. It is contemplated that such modulatory compounds may be employed in treatment and therapeutic methods for treating a condition that is mediated by the novel fungal essential polypeptides by administering to an individual in need of such treatment a therapeutically effective amount of the compound identified by the methods described herein.

In addition, the present invention provides methods for treating an individual in need of such treatment for a disease, disorder, or condition that is mediated by the fungal essential polypeptides of the invention, comprising administering to the individual a therapeutically effective amount of the fungal essential-modulating compound identified by a method provided herein.

Antibodies

Described herein are methods for the production of antibodies capable of specifically recognizing epitopes of one or more of the essential polynucleotide polypeptides described above.

On one embodiment, the antibodies of the present invention are human antibodies capable of neutralizing a fungal pathogen in a human host, such that the human host can effectively combat the invading pathogen, and thus treat or ameliorate the symptoms caused by the invading pathogen.

In the present invention, "epitopes" refer to polypeptide fragments having antigenic or immunogenic activity in an animal. A preferred embodiment of the present invention relates to a polypeptide fragment including an epitope, as well as the polynucleotide encoding this fragment. A region of a protein molecule to which an antibody can bind is defined as an "antigenic epitope". In contrast, an "immunogenic epitope" is defined as a part of a protein that elicits an antibody response. (See, for instance, Geysen et al., Proc. Natl. Acad. Sci. USA 81:3998-4002 (1983).) In the present invention, antigenic epitopes preferably contain a sequence of at least six, more preferably at least nine, and most preferably between about 15 to about 30 amino acids. Antigenic epitopes are useful to raise antibodies, including monoclonal antibodies, that specifically bind the epitope. (See, for instance, Wilson et al., *Cell* 37:767-778 (1984); Sutcliffe, J. G. et al., *Science* 219:660-666 (1983)). Similarly, immunogenic epitopes can be used to induce antibodies according to methods well-known in the art. (See, for instance, Chow, M. et al., *Proc. Natl. Acad. Sci. USA* 82:910-914; and Bittle, F. J. et al., *J. Gen. Virol.* 66:2347-2354 (1985), both of which are herein incorporated by reference.) The immunogenic epitopes may be presented together with a carrier protein, such as an albumin, to an animal system (such as rabbit or mouse) or, if it is long enough (at least about 25 amino acids), without a carrier.

Accordingly, the invention provides a method of eliciting an immune response in an animal, comprising introducing into the animal an immunogenic composition comprising an isolated polypeptide, the amino acid sequence of which comprises at least 6 consecutive residues of one of SEQ ID NO: 12 to SEQ ID NO: 22 or one of SEQ ID NO: 48 to SEQ ID NO: 73.

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody (Wahl et al., J. Nucl. Med. 24:316-325 (1983).). Thus, these fragments are preferred, as well as the products of a FAB or other immunoglobulin expression library.

As described above, the antibodies are preferably monoclonal, but may also be polyclonal. Monoclonal antibodies may be produced by methods known in the art. These methods include the immunological method described by Kohler and Millstein in *Nature vol.* 256, pp 495-497 (1975) and by Campbell in "Monoclonal Antibody Technology, The Production And Characterization Of Rodent And Human Hybridomas," in Burdon, et al. (Eds.), *Laboratory Techniques in Biochemistry and Molecular Biology*, vol. 13, Elsebier Science Publishers, Amsterdam, Nebr. (1985); and Coligan, J. E., et al. (Eds.), *Current Protocols in Immunology*, Wiley Intersciences, Inc., New York, (1999); as well as the recombinant DNA method described by Huse, et al., *Science,* 246: 1275-1281 (1989). The recombinant DNA method preferably comprises screening phage libraries for human antibody fragments.

In order to produce monoclonal antibodies, a host mammal is inoculated with an essential polynucleotide peptide or peptide fragment as described above, and then boosted. Spleens are collected from inoculated mammals a few days after the final boost. Cell suspensions from the spleens are fused with a target cell in accordance with the general method described by Kohler and Millstein, *Nature,* 256:495-497 (1975). In order to be useful, the peptide fragment must contain sufficient amino acid residues to define the epitope of the molecule being detected.

Antibodies directed against an essential polynucleotide polypeptide or fragment thereof can be used therapeutically to treat an infectious disease by preventing infection and/or inhibiting growth of the pathogen. Antibodies can also be used to modify a biological activity of an essential polynucleotide polypeptide. Antibodies to essential polynucleotide polypeptides can also be used to alleviate one or more symptoms associated with infection by the organism. To facilitate or enhance its therapeutic effect, an antibody (or fragment thereof) may be conjugated to a therapeutic moiety such as a toxin or fungicidal agent. Techniques for conjugating a therapeutic moiety to antibodies are well-known, see, e.g., Thorpe et al., *Immunol. Rev.,* 62: 119-58 (1982).

Further polypeptides of the invention relate to antibodies and T-cell antigen receptors (TCR) which immunospecifically bind a polypeptide, polypeptide fragment, or variant of SEQ ID NO:12 to 22, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than 5x10-2 M, 10-2 M, 5x10-3 M, 10-3 M, 5x10-4 M, 10-4 M, 5x10-5 M, 10-5 M, 5x10-6 M, 10-6M, 5x10-7 M, 107 M, 5x10-8 M, 10-8 M, 5x10-9 M, 10-9 M, 5x10-10 M, 10-10 M, 5x10-11 M, 10-11 M, 5x10-12 M, 10-12 M, 5x10-13 M, 10-13 M, 5x10-14 M, 10-14 M, 5x10-15 M, or 10-15 M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the fungal essential polynucleotide protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an fungal essential polynucleotide polypeptide or, more preferably, with a fungal essential polynucleotide polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually, transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP20) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or, enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to polynucleotides encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage polynucleotide III or polynucleotide VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807, 715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592, 106; EP 519,596; Padlan, Molecular Immunology 28(4/5): 489-498 (1991); Studnicka et al., Protein Engineering 7(6): 805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239: 1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988)l and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin polynucleotides. For example, the human heavy and light chain immunoglobulin polynucleotide complexes may be introduced randomly or by homologous recombination into mouse embryonic stem cells. Alternatively, the human variable region, constant region, and diversity region may be introduced into mouse embryonic stem cells in addition to the human heavy and light chain polynucleotides. The mouse heavy and light chain immunoglobulin polynucleotides may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transpolynucleotides harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin polynucleotides have been partially or completely inactivated. Upon challenge, human antibody production is observed, which closely resembles that seen in humans in all respects, including polynucleotide rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the fungal essential polynucleotide polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:12 to 22.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular polynucleotide sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutapolynucleotidesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing polynucleotides from a mouse antibody molecule of appropriate antigen specificity together with polynucleotides from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

More preferably, a clone encoding an antibody of the present invention may be obtained according to the method described in the Example section herein.

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early polynucleotide promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target polynucleotide product can be released from the GST moiety.

In an insect system, *Autographa californica* nuclear polyhedrosis virus (AcNPV) is used as a vector to express foreign polynucleotides. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric polynucleotide may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the polynucleotide product in the specific fashion desired. Such modifications (e.g., glycosylation) and processing (e.g., cleavage) of protein products may be important for the function of the protein. Different host cells have characteristic and specific mechanisms for the post-translational processing and modification of proteins and polynucleotide products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the polynucleotide product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) polynucleotides can be employed in tk−, hgprt− or aprt− cells, respectively. Also, antimetabolite resistance can be used as the basis of selection for the following polynucleotides: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on polynucleotide amplification for the expression of cloned polynucleotides in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker polynucleotide. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:12 to 22 may be fused or conjugated to the above antibody portions to increase the in vivo half life of the polypeptides or for use in immunoassays using methods known in the art. Further, the polypeptides corresponding to SEQ ID NO:12 to 22 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem . . . 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6): 798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072-3, (2001); and Quaglia, M., Chenon, K., Hall, A, J., De, Lorenzi, E., Sellergren, B, J. Am. Chem, Soc., 123(10): 2146-54, (2001); which are hereby incorporated by reference in their entirety herein.

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219 (1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

The antibodies of the invention may be utilized for immunophenotyping of cell lines and biological samples. The translation product of the polynucleotide of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than 5×10-2 M, 10-2 M, 5×10-3 M, 10-3 M, 5×10-4 M, 10-4 M, 5×10-5 M, 10-5 M, 5×10-6 M, 10-6 M, 5×10-7 M, 10-7 M, 5×10-8 M, 10-8 M, 5×10-9 M, 10-9 M, 5×10-10 M, 10-10 M, 5×10-11 M, 10-11 M, 5×10-12 M, 10-12 M, 5×10-13 M, 10-13 M, 5×10-14 M, 10-14 M, 5×10-15 M, and 10-15 M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the polynucleotide encoding an antibody directed against a polypeptide of the present invention, said polypeptide having the potential to elicit an allergic and/or immune response in an organism, and transforming the organism with said antibody polynucleotide such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or polynucleotide therapy applications of the present invention are provided elsewhere herein.

Alternatively, antibodies of the present invention could be produced in a plant (e.g., cloning the polynucleotide of the antibody directed against a polypeptide of the present invention, and transforming a plant with a suitable vector comprising said polynucleotide for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting polynucleotide expression of a particular gene, or polynucleotides, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of polynucleotide therapy. Gene therapy refers to therapy performed by the administration to a subject of an expressed or expressible nucleic acid. In this embodiment of the invention, the nucleic acids produce their encoded protein that mediates a therapeutic effect.

Any of the methods for polynucleotide therapy available in the art can be used according to the present invention. Exemplary methods are described below.

For general reviews of the methods of polynucleotide therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises polynucleotides encoding an antibody, said polynucleotides being part of expression vectors that express the antibody or fragments or chimeric proteins or heavy or light chains thereof in a suitable host. In particular, such polynucleotides have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the polynucleotides include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo polynucleotide therapy.

In a specific embodiment, the polynucleotides are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a polynucleotide gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem . . . 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains polynucleotides encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The polynucleotides encoding the antibody to be used in polynucleotide therapy are cloned into one or more vectors, which facilitates delivery of the polynucleotide into a patient. More detail about retroviral vectors can be found in Boesen et al., Biotherapy 6:291-302 (1994), which describes the use of a retroviral vector to deliver the mdr1 polynucleotide to hematopoietic stem cells in order to make the stem cells more resistant to chemotherapy. Other references illustrating the use of retroviral vectors in polynucleotide therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in polynucleotide therapy. Adenoviruses are especially attractive vehicles for delivering polynucleotides to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based polynucleotide therapy. Bout et al., Human Gene Therapy 5:3-10 (1994) demonstrated the use of adenovirus vectors to transfer polynucleotides to the respiratory epithelia of rhesus monkeys. Other instances of the use of adenoviruses in polynucleotide therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in polynucleotide therapy (Walsh et al., Proc. Soc. Exp. Biol. Med. 204:289-300 (1993); U.S. Pat. No. 5,436,146).

Another approach to polynucleotide therapy involves transferring a polynucleotide to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred polynucleotide. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the polynucleotides, cell fusion, chromosome-mediated polynucleotide transfer, microcell-mediated polynucleotide transfer, spheroplast fusion, etc. Numerous techniques are known in the art for the introduction of foreign polynucleotides into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of polynucleotide therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for polynucleotide therapy is autologous to the patient.

In an embodiment in which recombinant cells are used in polynucleotide therapy, polynucleotides encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of polynucleotide therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a polynucleotide gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of polynucleotide expression with a standard polynucleotide expression level, whereby an increase or decrease in the assayed polypeptide polynucleotide expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of polynucleotide expression with a standard polynucleotide expression level, whereby an increase or decrease in the assayed polypeptide polynucleotide expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein polynucleotide expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Antisense Molecules

The invention also provides for the identification of compounds that modulate (e.g., activate or inhibit) the function of a polypeptide of the invention. Such compounds can provide lead-compounds for developing drugs for diagnosing and/or treating conditions associated with fungal infections. The modulator is a compound that may alter the function of a polypeptide of the invention including SEQ ID NO: 12 through to SEQ ID NO 22, such as activating or inhibiting the function of a polypeptide of the invention. For example, the compound can act as an agonist, antagonist, partial agonist, partial antagonist, cytotoxic agent, inhibitor of cell proliferation, and cell proliferation-promoting agents. The activity of the compound may be known, unknown or partially known.

In one embodiment, an antisense molecule is used as an antagonist of a polynucleotide product of the nucleic acid molecules of the invention. The present invention also provides the therapeutic or prophylactic use of nucleic acids of at least six nucleotides that are antisense to a target essential polynucleotide or a portion thereof. An "antisense" target nucleic acid as used herein refers to a nucleic acid capable of hybridizing to a portion of a target polynucleotide RNA or mRNA by virtue of some sequence complementarity. The invention further provides pharmaceutical compositions comprising an effective amount of the antisense nucleic acids of the invention in a pharmaceutical acceptable carrier as described below.

In another embodiment, the invention is directed to methods for inhibiting the expression of a target polynucleotide in an organism of interest, such as *C. albicans* either in vitro or in vivo comprising providing the cell with an effective amount of a composition comprising an antisense nucleic acid of the invention.

It is preferred that in vitro studies are first performed to quantitate the ability of the antisense molecule to inhibit polynucleotide expression. It is preferred that these studies utilize controls that distinguish between antisense polynucleotide inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Antisense molecules of the invention may be synthesized by standard methods known in the art, e.g., by use of an automated DNA synthesizer (such as are commercially available from Applied Biosystems, Palo Alto, Calif.). As examples, phosphorothioate oligonucleotides may be synthesized by the method of Steinet et al. (1988, Nucl. Acids Res. 16:3209), methylphosphonate oligonucleotides can be prepared by use of controlled pore glass polymer supports (Sarin et al., 1988, *Proc. Natl. Acad. Sci. U.S.A.* 85:7448-7451), etc.

Antisense nucleotides complementary to the coding region of a target polynucleotide may be used, as well as those complementary to the transcribed untranslated region.

Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference.

Pharmaceutical compositions of the invention comprising an effective amount of an antisense nucleic acid in a pharmaceutically acceptable carrier can be administered to a subject infected with the pathogen of interest.

The amount of antisense nucleic acid which will be effective in the treatment of a particular disease caused by the fungal pathogen will depend on the site of the infection or condition. Where possible, it is desirable to determine the antisense cytotoxicity of the fungus to be treated in vitro, and then in useful animal model systems prior to testing and use in humans.

A number of methods have been developed for delivering antisense DNA or RNA to cells; e.g., antisense molecules can be injected directly into the tissue site in which the pathogens are residing, or modified antisense molecules, designed to target the desired cells (e.g., antisense molecule linked to peptides or antibodies that specifically bind receptors or antigens expressed on the pathogen's cell surface) can be administered systemically. Antisense molecules can be delivered to the desired cell population via a delivery complex. In a specific embodiment, pharmaceutical compositions comprising antisense nucleic acids of the target polynucleotides are administered via biopolymers (e.g., poly-β-1-4-N-acetylglucosamine polysaccharide), liposomes, microparticles, or microcapsules.

In various embodiments of the invention, it may be useful to use such compositions to achieve sustained release of the antisense nucleic acids. In a specific embodiment, it may be desirable to utilize liposomes targeted via antibodies to specific identifiable pathogen antigens (Leonetti et al., 1990, *Proc. Nat. Acad. Sci. U.S.A.* 87:2448-2451; Renneisen et al., 1990, *J. Biol. Chem.* 265:16337-16342).

Transcriptional Profiling

Gene expression profiling techniques are important tools for the identification of antifungal compounds. To carry out profiling, polynucleotide expression arrays and microarrays can be employed. Gene expression arrays are high density arrays of DNA samples deposited at specific locations on, for example, a glass surface or nylon membrane. Such arrays are used by researchers to quantify relative polynucleotide expression under different conditions. An example of this technology is found in U.S. Pat. No. 5,807,522, which is hereby incorporated by reference.

It is possible to study the expression of substantially all of the polynucleotides in the genome of a particular microbial organism using a single array. For example, the arrays may consist of 12×24 cm nylon filters containing a PCR product corresponding to ORFs from *Candida albicans*. 10 ng of each PCR product may be spotted for example every 1.5 mm on the filter. Single stranded labeled cDNAs are prepared for hybridization to the array and placed in contact with the filter. Thus, the labeled cDNAs are of "antisense" orientation. Quantitative analysis may be done using a phosphorimager.

Hybridization of cDNA made from a sample of total cellular mRNA to such an array followed by detection of binding by one or more of various techniques known to those in the art provides a signal at each location on the array to which cDNA is hybridized. The intensity of the hybridization signal obtained at each location in the array thus reflects the amount of mRNA for that specific polynucleotide that was present in the sample. Comparing the results obtained for mRNA isolated from cells grown under different conditions thus allows for a comparison of the relative amount of expression of each individual polynucleotides during growth under different conditions.

Gene expression arrays are use to analyze the total mRNA expression pattern at various time points after reduction in the level or activity of a polynucleotide product required for fungal proliferation. Reduction of the level or activity of the polynucleotide product is accomplished by growing a diploid strain of the invention under conditions in which the product of the nucleic acid linked to the MET3 promoter is rate limiting for fungal growth or survival or proliferation or by contacting the cells with an agent which reduces the level or activity of the target polynucleotide product. Analysis of the expression pattern indicated by hybridization to the array provides information on other polynucleotides whose expression is influenced by reduction in the level or activity of the polynucleotide product. For example, levels of other mRNAs may be observed to increase, decrease or stay the same following reduction in the level or activity of the polynucleotide product required for growth survival or proliferation. Thus, the mRNA expression pattern observed following reduction in the level or activity of a polynucleotide product required for growth, survival or proliferation identifies other nucleic acids required for expression patterns observed when the fungi are exposed to candidate drug compounds or known antibiotics are compared to those observed when the level or activity of a polynucleotide product required for fungal growth survival or proliferation is reduced. If the mRNA expression pattern observed with the candidate drug compound is similar to that observed with the level of the polynucleotide product is reduced, the drug compound is a promising therapeutic candidate. The assay is useful in assisting in the selection of promising candidate drug compounds for use in drug development.

In another embodiment, the present invention provides a method of quantitative analysis of the expressed protein complement of a diploid fungal cell: a first protein expression profile is developed for a control diploid fungus, which has two unmodified copies of the target polynucleotide. Mutants of the control strain, in which one copy of the target polynucleotide is inactivated, for example, one of the strains of the present invention, by insertion of disruption cassette is generated. The allele is modified such that expression of the allele is under the control of a MET3 promoter. A second protein expression profile is developed for this mutant fungus under conditions where the second allele is substantially overexpressed as compared to the expression of the two alleles of the polynucleotide in the control strain. Similarly, if desired, a third protein expression profile is developed under conditions where the second allele is substantially underexpressed as compared to the expression of the two alleles of the polynucleotide in the control strain. The first protein expression profile is then compared with the second expression profile and if applicable to a third, forth, fifth or sixth or more expression profile to identify an expressed protein detected a higher level in the second profile and if applicable at a lower level in the third profile, etc., as compared to the level in the first profile.

Accordingly, the invention provides a method for evaluating a compound against a target polynucleotide product encoded by a nucleotide sequence comprising one of SEQ ID NO 1 to 11 said method comprising the steps of (a) contacting wild type diploid fungal cells or control cells with the compound and generating a first protein expression profile; (b) determining the protein expression profile of mutant diploid fungal cells such as a strain of the invention which have been cultured under conditions wherein the second allele of the target polynucleotide is substantially underexpressed not expressed or overexpressed and generating a second protein expression profile for the cultured cells and comparing the first protein expression profile with the second protein expression profile to identify similarity in profiles. For comparisons, similarities of profiles can be expressed as an indicator value; and the higher the indicator value, the more desirable is the compound.

The pattern of expression of a set of proteins in a strain of the invention may be determined by methods well-known in the art for establishing a protein expression pattern such as two-dimensional gel electrophoresis. A plurality of protein expression patterns will be generated for a strain of the invention when the strain is cultured under different conditions and different levels of expression of one of the modified alleles.

Pharmaceutical Compositions and Uses Thereof

Compounds including nucleic acid molecules that are identified by the methods of the invention as described herein can be administered to a subject at therapeutically effective doses to treat or prevent infections by a fungal organism such as *Candia albicans*. A therapeutically effective dose refers to that amount of a compound (including nucleic acid molecules) sufficient to result in a healthful benefit in the treated subject. Typically, but not so limited, the compounds act by reducing the activity or level of polynucleotide product encoded by a nucleic acid comprising a sequence selected from the group consisting of SEQ ID NO 1 to SEQ ID NO: 11, or homologues thereof.

To treat a patient afflicted with a fungal infection it may be beneficial to deliver an essential polynucleotide polypeptide, polynucleotide or modulating agent to the intracellular space. Such targeting may be achieved using well-known techniques, such as through the use of polyethylene glycol or liposomes, as described in Turrens, *Xenobiotica* 21:103 3-1040 (1991), herein incorporated by reference.

For certain embodiments, it may be beneficial to also link a drug to a polypeptide or modulating agent. As used herein, the term "drug" refers to any bioactive agent intended for administration to a mammal to prevent or treat an undesirable condition.

To prepare a pharmaceutical composition, an effective amount of one or more polypeptides, polynucleotides and/or modulating agents is mixed with a suitable pharmaceutical carrier. Solutions or suspensions used for parenteral, intradermal, subcutaneous or topical application can include, for example, a sterile diluent (such as water), saline solution, fixed oil, polyethylene glycol, glycerin, propylene glycol or other synthetic solvent; antimicrobial agents (such as benzyl alcohol and methylparabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof. In addition, other pharmaceutically active ingredients and/or suitable excipients such as salts, buffers and stabilizers may, but need not, be present within the composition.

A pharmaceutical composition is generally formulated and administered to exert a therapeutically useful effect while minimizing undesirable side effects. The number and degree of acceptable side effects depend upon the condition for which the composition is administered. For example, certain toxic and undesirable side effects that are tolerated when treating life-threatening illnesses, such as tumors, would not be tolerated when treating disorders of lesser consequence. The concentration of active component in the composition will depend on absorption, inactivation and excretion rates thereof, the dosage schedule and the amount administered, as well as other factors that may be readily determined by those of skill in the art.

A polypeptide, polynucleotide or modulating agent may be prepared with carriers that protect it against rapid elimination from the body, such as time release formulations or coatings. Such carriers include controlled release formulations such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art. Such formulations may generally be prepared using well-known technology and administered by, for example, oral, rectal or subcutaneous implantation, or by implantation at the desired target site. Sustained-release formulations may contain a polynucleotide, polypeptide or modulating agent dispersed in a carrier matrix and/or contained within a reservoir surrounded by a rate controlling membrane. Preferably the formulation provides a relatively constant level of modulating agent release. The amount of active component contained within a sustained release formulation depends upon the site of implantation, the rate and expected duration of release and the nature of the condition to be treated or prevented.

Administration may be effected by incubation of cells ex vivo or in vivo, such as by topical treatment, delivery by specific carrier or by vascular supply. Appropriate dosages and a suitable duration and frequency of administration will be determined by such factors as the condition of the patient, the type and severity of the patient's disease and the method of administration. In general, an appropriate dosage and treatment regimen provides the polypeptide, polynucleotide and/or modulating agent(s) in an amount sufficient to provide therapeutic and/or prophylactic benefit (i.e., an amount that ameliorates the symptoms or treats or delays or prevents progression of the condition).

The precise dosage and duration of treatment is a function of the condition being treated and may be determined empirically using known testing protocols or by testing the compositions in model systems known in the art and extrapolating therefrom. Dosages may also vary with the severity of the condition to be alleviated. The composition may be administered one time, or may be divided into a number of smaller doses to be administered at intervals of time. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art, and for any particular subject, specific dosage regimens may be adjusted over time according to the individual need.

For pharmaceutical compositions comprising polynucleotides, the polynucleotide may be present within any of a variety of delivery systems known to those of ordinary skill in the art, including nucleic acid, bacterial and viral expression systems, and colloidal dispersion systems such as liposomes. Appropriate nucleic acid expression systems contain the necessary DNA sequences for expression in the patient (such as a suitable promoter and terminating signal, as described above). The DNA may also be "naked", as described, for example, in Ulmer et al., Science 259:1745-1749 (1993).

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well-known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV).

A retroviral vector may additionally transfer or incorporate a polynucleotide for a selectable marker (to aid in the identification or selection of transduced cells) and/or a polynucleotide that encodes the ligand for a receptor on a specific target cell (to render the vector target specific).

Viral vectors are typically non-pathogenic (defective), replication competent viruses, which require assistance in order to produce infectious vector particles. This assistance can be provided, for example, by using helper cell lines that contain plasmids that encode all of the structural polynucleotides of the retrovirus under the control of regulatory sequences, but that are missing a nucleotide sequence which enables the packaging mechanism to recognize an RNA transcript for encapsulation. Such helper cell lines include (but are not limited to) PA317 and PA12. A retroviral vector introduced into such cells can be packaged and vector virion produced. The vector virions produced by this method can then be used to infect a tissue cell line, such as NIH3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). RNA. DNA and intact virions can be encapsulated within the aqueous interior and delivered to cells in a biologically active form. The preparation and use of liposomes is well-known to those of ordinary skill in the art.

Modulation of an essential gene-like function, either in vitro or in vivo, may generally be achieved by administering a modulating agent that inhibits essential polynucleotide transcription, translation or activity.

Routes and frequency of administration, as well as dosage, will vary from individual to individual, and may be readily established using standard techniques.

In general, the pharmaceutical compositions may be administered by injection (e.g., intracutaneous, intramuscular, intravenous or subcutaneous), intranasally (e.g., by aspiration) or orally. A suitable dose is an amount of a compound that, when administered as described above, is capable of causing modulation of an essential gene-like activity that leads to an improved clinical outcome (e.g., more frequent remissions, complete or partial or longer disease-free survival) in vaccinated patients as compared to non-vaccinated patients. In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. In general, suitable dose sizes will vary with the size of the patient, but will typically range from about 0.1 mL to about 5 mL.

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria*, Mycoplasmatales, *Mycobacterium leprae, Vibrio cholerae*, Neisseriaceae (e.g., *Acinetobacter*, Gonorrhea, Menigococcal), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

REFERENCES

Altschul, S. F., Gish, W., Miller, W., Myers, E W., Lipman, D. J. Basic local alignment search tool. J. Mol. Biol. 215:403-410, 1990.

Berman, H. M., Westbrook, J., Feng, Z., Gilliland, G., Bhat, T. N., Weissig, H., Shindyalov, I. N., Bourne, P. E. The Protein Data Bank Nucleic Acids Research, 28:235-242, 2000

Bernstein, F C, Koetzle, T F, Williams, G J B, Meyer, E F Jr., Brice, M D, Rodgers, J R, Kennard, O, Simanouchi, T, Tasumi, M. 1977. The Protein Data Bank: A computer-based archival file for macromolecular structures. J. Mol. Biol. 112:535-542.

Bohm, H-J., LUDI: rule-based automatic design of new substituents for enzyme inhibitor leads. J. Comp. Aid. Molec. Design 6:61-78, 1992.

Brick, P., Bhat, T. N., and Blow, D. M., Structure of tyrosyl-tRNA synthetase refined at 2.3 A resolution. Interaction of the enzyme with the tyrosyl adenylate intermediate. J. Mol. Biol. 1989 208:83-98.

Cardozo, T., Totrov, M., Abagyan, R. Homology modeling by the ICM method. Proteins 23:403-14, 1995.

Delagoutte, B., Moras, D., and Cavarelli, J. tRNA aminoacylation by arginyl-tRNA-synthetase: induced conformations during substrate binding. The EMBO J. 19:5599-5610.

Delarue M, Moras D. The aminoacyl-tRNA synthetase family: modules at work. Bioessays. 1993 15:675-87.

Goodford, P. J. A computational procedure for determining energetically favorable binding sites on biologically important macromolecules. J. Med. Chem. 28:849-857, 1985.

Goodsell, D. S. and Olsen, A. J. Automated docking of substrates to proteins by simulated annealing. Proteins 8:195-202, 1990.

Gosh, D., Sawicki, M., Pletnev, V., Erman, M., Ohno, S., Nakajin, S., and Duax, W. L. Porcine carbonyl reductase. J. Biol. Chem. 276: 18457-18463, 2001.

Greer, J. Comparative modeling of homologous proteins. Meth. Enzymol. 202:239-52, 1991.

Hendlich, M., Lackner, P., Weitckus, S., Floeckner, H., Froschauer, R., Gottsbacher, K., Casari, G., Sippl, M. J. Identification of native protein folds amongst a large number of incorrect models. The calculation of low energy conformations from potentials of mean force. J. Mol. Biol. 216:167-80, 1990.

Koppensteiner, W. A., Lackner, P., Wiederstein, M., and Sippl, M. Characterization of novel proteins based upon know protein structures. J. Mol. Biol. 296:1139-1152, 2000.

Kuntz, I. D., Blaney, J. M., Oatley, S. J., Langridge, R., and Ferrin, T. E. A geometric approach to macromolecule-ligand interactions. J. Mol. Biol. 161:269-288, 1982.

Lesk, A. M., Boswell, D. R. Homology Modeling: Inferences from Tables of Aligned Sequences. Curr. Op. Struc. Biol. 2: 242-247, 1992.

Levitt, M. Accurate modeling of protein conformation by automatic segment matching J. Mol. Biol. 226: 507-533, 1992.

Martin, Y. C. 3D database searching in drug design. J. Med. Chem. 35:2145-2154, 1992.

Novotny, J., Rashin, A. A., and Bruccoleri, R. E. Criteria that discriminate between native proteins and incorrectly folded models. Proteins 4:19-30, 1988.

Palm, G. J., Billy, E., Filipowicz, W., and Wlodawer, A. Crystal structure of RNA 3'-terminal phosphate cyclase, a ubiquitous enzyme with unusual topology. Structure 8:1-13, 1999.

Pearson, W. R. Rapid and sensitive sequence comparison with FASTP and FASTA. Meth. Enzymol. 183:63-98, 1990.

Sali, A., Potterton, L., Yuan, F., van Vlijmen H. and Karplus, M. Evaluation of comparative protein modeling by MODELLER. Proteins 23:318-326, 1995.

Schimmel. P. Classes of aminoacyl-tRNA synthetases and the establishment of the genetic code. Trends Biochem Sci. 1991 16:1-3.

Sippl. M and Weitckus S. Detection of native-like models for amino acid sequences of unknown three-dimensional structure in a data base of protein conformations. Proteins 13: 258-271, 1992.

Sippl, M. Boltzmann's principle, knowledge-based mean fields and protein folding. An approach to computational determination of protein structures. J. Computer-Aided Molecular Design 7:473-501, 1993.

EXAMPLES

Example 1

Target Identification

A concordance or whole genome parallel comparison was performed as described by Bruccoleri, et al. Nucleic Acids Res 26:4482-4486 (1998) to find polynucleotides that are conserved in both *S. cervisiae* and *C. albicans*. To generate the dataset, all *C. albicans* open reading frames with an overall sequence similarity to *S. cervisiae* protein sequences greater than or equal to 40% were selected. The data were further required not to match bacterial (*E. coli* and *B. subtilis*) or human sequences at greater than 30% overall protein sequence similarity.

The sequences used herein were obtained from a variety of sources. These sources include the PathoGenome™ system from Genome Therapeutics Corporation (Waltham, Mass.), GenBank, The Institute for Genomic Research (TIGR), the Yeast Proteome Database, Proteome, Inc. Beverly, Mass., *Saccharomyces* Genome database, Stanford University, Stanford, Calif., the *Candida albicans* Sequencing Project, Stanford Genome Technology Center, Stanford, Calif., and the Sanger Center of the Medical Research Council of the United Kingdom. Additionally, non-microbial sequence data such as those from humans was obtained from the LifeSeq Database from Incyte Pharmaceuticals, Palo Alto, Calif., as well as from public sources such as Genbank.

Where required, Incyte nucleotide sequences were translated into protein sequences in all six possible reading frames. GTC supplied predicted protein sequences with their data. In the case of other nucleotide sequences, the program CRITICA (Badger, J. and Olsen, G., *Molecular Biology and Evolution* 16: 512-524 (1999) was used. The sequences were stored in flat files on a UNIX computer system. Each predicted amino acid sequences used was greater than 90 amino acids.

Each predicted protein sequence was compared to every other sequence (an "all-against-all" comparison). The program FASTA (Pearson, W. R. *Methods in Molecular Biology* 132: 185-219 (2000)) was used for this comparison, using ktup=2 as a parameter, and all scores above the default cutoff were stored. The output was processed and stored in a PostGres 95 database. Graphical user interfaces, using web browser technology were constructed to query the database.

A Concordance Analysis was performed on the data. A total of 560 fungal conserved polynucleotides were identified (FCGs) of which 125 polynucleotides had a known function and 435 polynucleotides had an unknown or partially known function (denoted Conserved Unknown Reading Frames or CURFs). 49 CURFs were selected and tested for essentiality in *S. cervisiae*, and 11 of these were found essential in *C. albicans* (see below).

In many cases, the function of the essential polynucleotides determined herein was suggested by the results of similarity searches. Table 2 lists the putative functions of these polynucleotides encoded by SEQ ID NO: 1 through to SEQ ID NO: 11.

The putative function of the essential polypeptides was determined using computer-aided bioinformatic approaches including motif searching. The motif searching approach involved using hidden Markov models (e.g., Profile HMM, Bateman et al, Nucleic Acids Research 28: 263-266 (2000)).

Global sequence similarity searches were performed using the amino acid sequences of all the conserved essential polynucleotide sequence against a non-redundant protein database using the Smith-Waterman algorithm with default parameters on a TimeLogic DeCypher system (Crystal Bay, Nev.).

The percentage sequence similarity between these subsets of CURFs and *S. cervisiae* is listed in Table 1. Percent similarity ranged from 61% to 87%. Additionally, these sequences were aligned with *A. fumigatus, S. pombe* and *Homo sapiens*. The percentage identity between the 11 essential polynucleotides of the invention and homologues of these species including those from *S. cervisiae* is listed in Table 2. Based on this analysis, the CURFs of the invention should be homologues to polynucleotides from additional fungal species.

TABLE 1

Similarity Between *Candida albicans*, CURFs and *S. cervisiae*

| Seq ID No. | Clone ID No. | Sequence Name | Species of Closest Homolog | Genbank Accessions for Closest Homolog | % Similarity |
|---|---|---|---|---|---|
| 12 | FCG5 | CaYLR100wORF | Saccharomyces cerevisiae | Z73272, S64936 | 75% |
| 13 | FCG6 | CaYDR341cORF | Saccharomyces cerevisiae | S70106 | 79% |
| 14 | FCG7 | CaYLR022cORF | Saccharomyces cerevisiae | Z73149, S64849 | 73% |
| 15 | FCG8 | CaYOL077cORF | Saccharomyces cerevisiae | Z74819, S66770 | 84% |
| 16 | FCG10 | CaYNL132wORF | Saccharomyces cerevisiae | Z46843 | 87% |
| 17 | FCG12 | CaYGR145wORF | Saccharomyces cerevisiae | X85807 | 73% |
| 18 | FCG13 | CaYDR412wORF | Saccharomyces cerevisiae | U33007, S69697 | 61% |
| 19 | FCG14 | CaYOL010wORF | Saccharomyces cerevisiae | Z74752, Q08096 | 81% |
| 20 | FCG15 | CaYOR004wORF | Saccharomyces cerevisiae | Z74912, S61987 | 73% |
| 21 | FCG16 | CaYOR056cORF | Saccharomyces cerevisiae | Z70678, S66939 | 62% |
| 22 | FCG17 | CaYLR009wORF | Saccharomyces cerevisiae | Z73181, S64831 | 82% |

Table 2 also includes the putative function and putative cellular role based on the annotation of the CURF homologues.

TABLE 2

Fungal CURFs Annotation, Similarity and Identity

| SEQ ID # | FCG # | Name in YPD | % Identity with S. cerevisiae | % Identity with A. fumigatus* | % Identity with S. pombe | % Identity with human (d2) | Function* | Cellular Role** |
|---|---|---|---|---|---|---|---|---|
| 12 | 5 | ERG27/ YLR100w | 60 | 34, 15 | 31 | 22 | 3-keto sterol reductase | Ergosterol biosynthesis |
| 13 | 6 | YDR341c/ RRS1 | 65 | 54, 51 | 25 | 23 | Arginine tRNA synthetase | Protein synthesis |
| 14 | 7 | YLR022c | 56 | 46, 22 | 46 | 10 | Unknown | Unknown |
| 15 | 8 | YOL077c/ BRX1 | 70 | 51, 43 | 7 | 36 | Unknown/required for biopolynucleotidesis of the 60S ribosomal subunit | Protein synthesis |
| 16 | 10 | YNL132w/ KRE33 | 74 | 68, 65 | 62 | 12 | Unknown (P-loop) | Unknown/killer toxin resistant |
| 17 | 12 | YGR145w | 57 | 38, 31 | 42 | 8 | Component of NuA3 histone acetyltransferase | Unknown/WD domain, G-beta repeat |
| 18 | 13 | YDR412w | 43 | 48, 9 | 20 | 16 | Unknown | Unknown |
| 19 | 14 | YOL010w/ RCL1 | 68 | 38, 41 | 41 | 22 | RNA cyclase-like | RNA processing/modification |
| 20 | 15 | YOR004w | 55 | 41, 21 | 46 | 13 | Unknown | Unknown |

TABLE 2-continued

Fungal CURFs Annotation, Similarity and Identity

| SEQ ID # | FCG # | Name in YPD | % Identity with S. cerevisiae | % Identity with A. fumigatus* | % Identity with S. pombe | % Identity with human (d2) | Function* | Cellular Role** |
|---|---|---|---|---|---|---|---|---|
| 21 | 16 | YOR056c/ NOB1 | 46 | 43, 9 | 45 | 15 | Unknown/nin one-p binding protein | Unknown/associated with the 26S proteasome |
| 22 | 17 | YLR009w | 73 | 46, 31 | 34 | 7 | RNA-binding protein/ribosome-associated | Protein synthesis |

*The two numbers represent percent identities derived from alignment and query sequences, respective FIG. 1 depicts the alignments of the top hits from a nonredundant database (Bristol-Meyers Squibb, Princeton, N.J.) containing sequences included from Genbank (infra). The aligned sequences of FIG. 1 containing "NR" in their sequence name depict the top hit from this database. All of the top hits are *S. cervisiae* species. Additionally, FIG. 1 depicts the alignment between the top hit in the DERWENT patent database (Alexandria, Va.). Table 3 shows the Genbank Accession No. and/or patent or patent application number in which the aligned CURF homolog sequence can be found. As is evident from the alignment, the percent identity for each of the 11 essential polynucleotides of the invention is less than that from the non-redundant database hits.

TABLE 3

Sequences Aligning With CURFs of the Invention

| Sequence Name | ID | Patent No. | Species |
|---|---|---|---|
| PAT_PROT\BMSPATENT_AAB94675 | AAB94675 | WO 200107628-A2 | *Saccharomyces cerevisiae* |
| PAT_PROT\BMSPATENT_AAW33110 | AAW33110 | JP 09263600-A | Yeast |
| PAT_PROT\BMSPATENT_AAB95680 | AAB95680 | EP1074617-A2 | *Homo sapiens* |
| PAT_PROT\BMSPATENT_AAG46965 | AAG46965 | EP 1033405-A2 | *Arabidopsis thaliana* |
| PAT_PROT\BMSPATENT_AAB43803 | AAB43803 | WO 200055351-A1 | *Homo sapiens* |
| PAT_PROT\BMSPATENT_AAB42957 | AAB42957 | WO 200058473-A2 | *Homo sapiens* |
| PAT_PROT\BMSPATENT_AAB19089 | AAB19089 | WO 200058520-A1 | *Saccharomyces cerevisiae* |
| PAT_PROT\BMSPATENT_AAB93917 | AAB93917 | EP 1074617-A2 | *Homo sapiens* |
| PAT_PROT\BMSPATENT_AAW60075 | AAW60075 | WO 9745535-A1 | *Saccharomyces cerevisiae* |
| PAT_PROT\BMSPATENT_AAB62453 | AAB62453 | US 6221597-B1 | *Saccharomyces cerevisiae* |
| PAT_PROT\BMSPATENT_AAG48012 | AAG48012 | EP 1033406-A2 | *Arabidopsis thaliana* |
| PAT_PROT\BMSPATENT_AAB09929 | AAB09929 | JP 2000116383-A | *Homo sapiens* |

FIG. 2 depicts the alignments between the CURFs of the invention and sequences from *A. fumigatus*. As seen in Table 2, the percent identity between these homologues ranges from 34% to 68%.

Example 2

Strains and Growth Media Used for Identifying Essential Genes

49 CURFs were selected and tested for essentiality in *S. cervisiae* and then in *C. albicans*. Three polynucleotides whose functions were known, ERG1, RAM2 and NMT1, were also used for verification of essentiality in *C. albicans*.

The strains used for this analysis included the *C. albicans* strains SC5314 (wild type, BMS collection) and its derivative BWP17 (ura3Δ::λimm434/ura3Δ::λimm434 his1::hisG/his1::hisG arg4::hisG/arg4::hisG) obtained from A. P. Mitchell of Columbia University. The yeast strain of *S. cerevisiae* used is ATCC 201390 (MATa/MATα his3Δ1/his3Δ1 leu2Δ0/leu2Δ1 lys2Δ0/LYS2 met15Δ0/MET15 ura3Δ0/ura30); *Escherichia coli* strain DH5α was used for plasmids propagation.

Yeast extract/peptone/dextrose (YPD), synthetic complete medium (SC), and synthetic dextrose (SD) were prepared according to the standard procedure described by Sherman, F. et al. *Methods Enzymol.* 184:3-21 (1991). 5-Fluoroorotic acid (FOA) plates were used to select for the $Ura^-$ revertant strains (Sherman, et al. (1991)). Spider (Liu, et al., *Science* 266: 1723-1725 (1994)) and LBC media (Lee, et al., *Sabouraudia* 13:148-153 (1975)) were used to induce hyphal growth. Twenty percent bovine serum (Köhler, et al., *Proc. Natl. Acad. Sci.* 93:13223-13228 (1996)) and medium 199 (Gibco BRL, Gaithersburg, Md.) were used to induce germ tube formation. Uridine (25 μg/ml) was added according to Fonzi & Irwin (Fonzi, et al., *Genetics* 134:717-728 (1993)) when needed to grow uridine-auxotrophic *C. albicans* strains.

Other supplements such as histidine and arginine were added to a concentration described by Sherman, F. et al. *Methods Enzymol.* 184:3-21 (1991). Strains were grown at 30° C., unless otherwise noted. The storage and maintenance of *C. albicans*, which prevented chromosomal instability, was as previously described (Perepnikhatka, et al., *J. Bacteriol.* 181: 4041-4049).

Example 3

Evaluation of Gene Essentiality in *S. cervisiae*

To evaluate polynucleotide essentiality for the homologues of the sequences encoding essential polynucleotides including SEQ ID NO: 1 through to SEQ ID NO: 11 in *S. cervisiae*, one copy of the essential polynucleotides of the invention were disrupted in a diploid strain background. The resulting heterozygous strains were then sporulated and the tetrads dissected to determine essentiality.

Disruption of the first allele of the polynucleotides of the invention was achieved via a PCR-based polynucleotide disruption approach where a PCR product containing the URA3 marker flanked by 40-50 bp of polynucleotide specific sequence was introduced into diploid yeast cells to replace the wild type copy of the polynucleotide via homologous recombination. Confirmation PCR was used to verify polynucleotide replacement using primers designed within 100 bp upstream or downstream of the site of crossover. A 2:2 ratio of segregation of meiotic progenies after tetrad dissection indicated that the polynucleotide of interest was essential for cell survival or synthetic medium. Gene disruption techniques are well documented in the literature for *S. cervisiae* and can be found at the web site (sequences-stanford.edu/group deletion project).

Example 4

PCR Based Gene Disruption in *C. albicans*

Gene essentiality in *C. albicans* was identified by two methods: PCR-based polynucleotide disruption and promoter swapping. Gene disruption was accomplished using a PCR-based polynucleotide disruption tool (Wilson et al., *J. Bacteriol.* 181:1868-1874 (1999)).

The PCR-based polynucleotide disruption system used herein was purchased from Dr. A. P. Mitchell of Columbia University. This system requires the use of two markers to create homozygous disruptions in *C. albicans*. A triply-marked auxotroph ($Ura^-$ $Arg^-$ $His^-$) strain BWP17 and three sets of plasmids -pGEM-URA3, pRS-ARG4ΔSpeI and pGEM-HIS1, each carrying a unique marker -URA3, ARG4 or HIS1 was used herein. A sequential disruption (from start to stop codons) of the two copies of any single polynucleotide can be achieved with any combination of the two selective markers.

Figure 3:
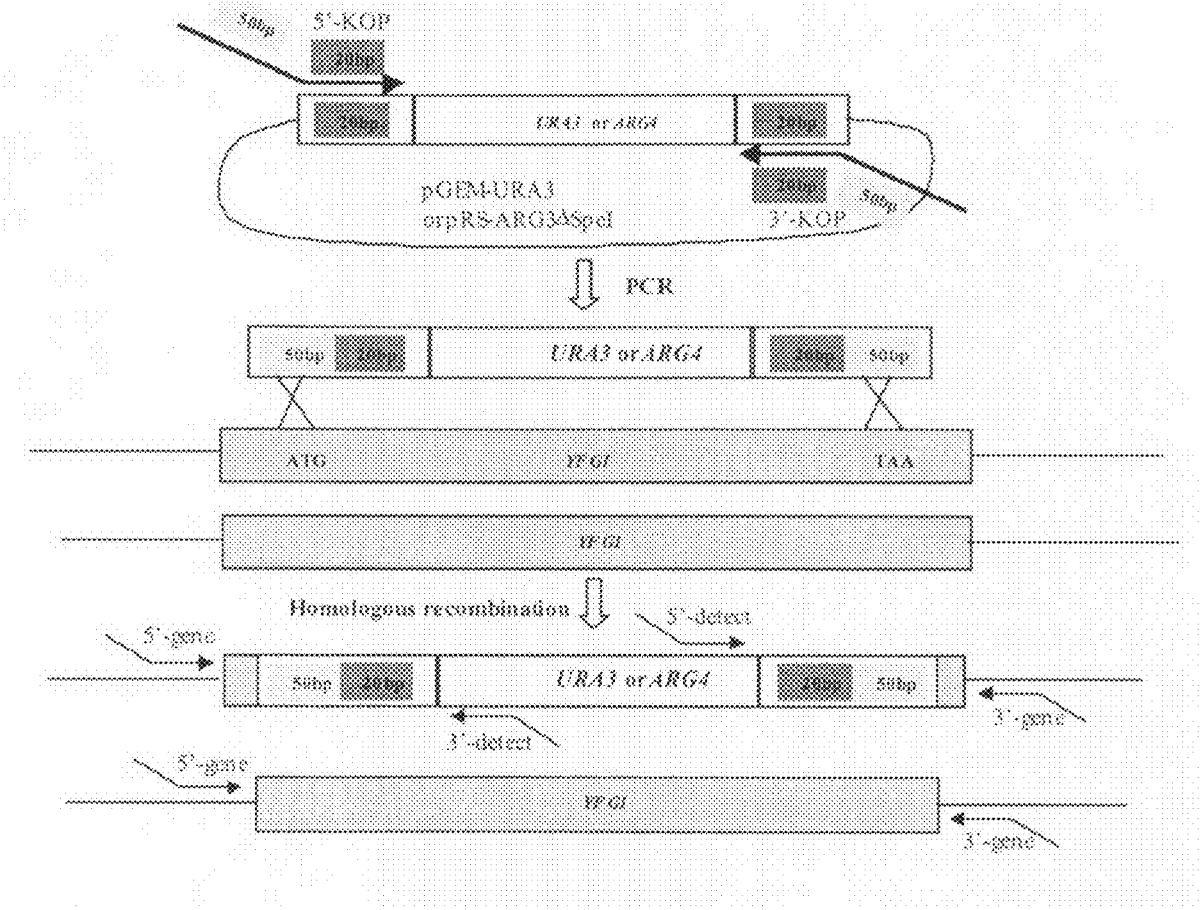
FIG. 3: PCR-based polynucleotide disruption in *C. albicans*.

The general scheme of the approach is illustrated in FIG. 3. Basically, the scheme involves (1) design a pair of PCR primers which incorporate sequences that are able to anneal to plasmids containing markers. Examples of such marker containing plasmids include pGEM-URA3, pRS-ARSΔSpeI and pGEM-HIS1 (see FIG. 3). An example of sequences which may be incorporated into the primers includes 5DR, (SEQ ID NO: 221) and 3DR (SEQ ID NO: 222). The forward primer additionally contains about 50 to about 60 bp of flanking sequences derived from the start codon region of a polynucleotide of interest or an open reading frame (ORF) of interest and this flanking sequence is attached to the 5' end of the forward (e.g., 5DR) primer. The reverse primer additionally contains 50-60 bp of flanking sequences that were derived from the stop codon region of the polynucleotide of interest or ORF of interest attached to the 3' end of the reverse primer (e.g., 3DR, SEQ ID NO: 222). (2) A selective marker (e.g. URA3) is then amplified from one of the plasmid templates resulting in a PCR product which includes short regions of homology to the polynucleotide or ORF of interest on both ends that allows for homologous recombination at the chromosomal locus when introduced into cells. (3) The PCR product is then used to transform the strain (in this case BWP17) and transformants are selected that grow on an appropriate selective medium (e.g., SC-Uridine). (4) Total DNA is isolated from the transformants and the presence of the PCR constructs are verified using detection primers which are common primers used for all three plasmids. The correct construct should have its chromosomal allele replaced with the PCR fragment introduced via homologous recombination. (5) Finally, once the first allele of the polynucleotide or ORF is disrupted, a second round of transformation with the PCR product amplified from a different marker (e.g., ARG4 in pRS-ARG4ΔSpeI) can be conducted to disrupt the remaining allele.

FIG. 3 depicts PCR-based polynucleotide disruption in *C. albicans* using YFG1 (or your favorite polynucleotide or the polynucleotide of interest). As seen in FIG. 3, a first copy of YFG1 is disrupted. Disrupting the second polynucleotide copy in a heterozygous strain (YFG1/yfg1) would give rise to a null mutant that has the remaining copy of the polynucleotide disrupted (yfg1/yfg1). In the FIG., 5'-KOP and 3'-KOP are a pair of polynucleotide disruption primers that are designed based on the common primers 5DR and 3DR (see below). Confirmation PCR primers are also indicated in the FIG and they include, in pairs, 5' gene/3'-polynucleotide detecting primers, 5' gene/3' plasmid detecting primers and 5' plasmid detecting primer and 3' polynucleotide detecting primer.

Table 4 lists the SEQ ID Nos. for the primers which contain 5DR and 3DR along with appropriate flanking sequences (under the column "PCR based knockout primers, Mitchell's") as well as the confirmation primers which may be used for this methodology. These knockout and confirmation primers were used for both the essential polynucleotides of the invention encoded by SEQ ID NO: 1 through to SEQ ID NO: 11 as well as the polynucleotide encoded by SEQ ID NO: 45. Three polynucleotides whose homologues are known to be essential in *S. cervisiae*, CaERG, CaRAM2 and CaNMT1 were also tested. CaAaH1 and CaNMT1 are homologues of *S. cervisiae* known to not be essential and these were also examined.

TABLE 4

| PCR-Knockout and Gene Confirmation Primers | | | | | | |
|---|---|---|---|---|---|---|
| Gene Name | Seq. ID No. | SEQ ID NO of translation | Gene specific confirmation primers-5') | Gene specific confirmation primers-3') | PCR based knockout primers (Mitchell's) forward | PCR-based knockout primers (Mitchell's) reverse) |
| CaYLR100wORF | 1 | 12 | 159 | 160 | 195 | 196 |
| CaYDR341cORF | 2 | 13 | 161 | 162 | 197 | 198 |
| CaYLR022cORF | 3 | 14 | 163 | 164 | 199 | 200 |
| CaYOL077cORF | 4 | 15 | 165 | 166 | 201 | 202 |
| CaYNL132wORF | 5 | 16 | 167 | 168 | 203 | 204 |
| CaYGR145wORF | 6 | 17 | 171 | 172 | 207 | 208 |
| CaYDR412wORF | 7 | 18 | 173 | 174 | 209 | 210 |
| CaYOL010wORF | 8 | 19 | 175 | 176 | 211 | 212 |
| CaYOR004wORF | 9 | 20 | 177 | 178 | 213 | 214 |
| YOR056cORF | 10 | 21 | 179 | 180 | 215 | 216 |
| YOR009wORF | 11 | 22 | 181 | 182 | 217 | 218 |
| CaYJR072c | — | 45 | 169 | 170 | 205 | 206 |
| CaERG | — | — | 151 | 152 | 185 | 186 |
| CaRAM2 | — | — | 153 | 154 | 187 | 188 |
| CaPFY1 | — | — | 155 | 156 | 189 | 190 |
| CaNMT1 | — | — | 157 | 158 | 191/193 | 192/194 |
| CaAAH1 | — | — | 183 | 184 | 219 | 220 |

Figure 4:
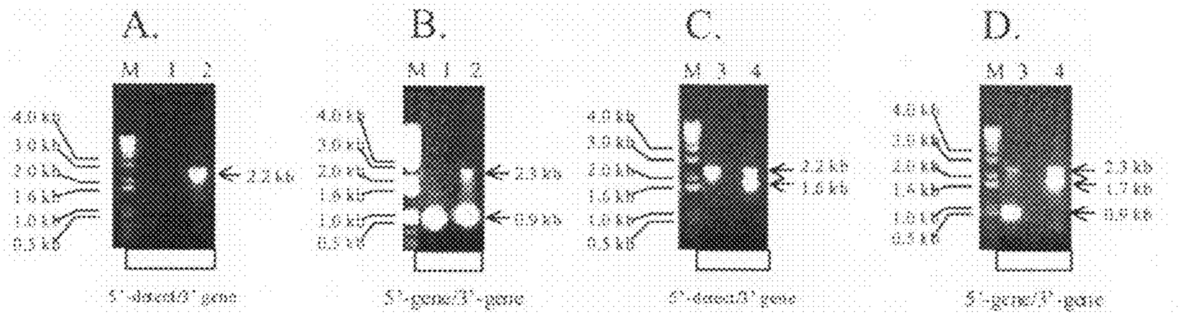
FIG. 4: PCT confirmation of AAH/disruption strains that were obtained via PRC-based polynucleotide disruption in *C. albicans*.

FIG. 4 depicts the results this polynucleotide disruption scheme using CaAAH1. The knockout primers used for this assay are listed in SEQ ID NO: 219 and SEQ ID NO: 220.

Panels A and B depict the identification of a heterozygous AAH1/aah1 construct. Lane M in both panels shows a 1 kb marker with sizes of some of the fragments indicated. Lane 1 in Panel A depicts a wild type strain that did not result in any PCR products when using a 5' primer (e.g. SEQ ID NO: 221) which anneals to any of the plasmids used herein (pGEM-URA3, pRS-ARSΔSpeI and pGEM-HIS1) and a 3' primer which anneals to the 3' region of the AAHI polynucleotide (e.g., SEQ ID NOs: 184). The wild type strain, however seen in panel B, Lane 1, did produce the wild type polynucleotide fragment of 0.9 kb when using 5' and 3' primers which anneal to the 5' and 3' regions of AAH1 (e.g., SEQ ID NOs 183-184). Lane 2 (Panel A) shows the construct of the heterozygous strain that gives a 2.2 kb band via a common 5' plasmid primer and a 3' polynucleotide detecting primer (e.g., SEQ ID NOs: 221 and 184, respectively, for example). Panel B, lane 2 shows the expected size fragments of 0.9 kb and 2.3 kb when using the 5' and 3' polynucleotide primers.

Panel C and D show the identification of the homozygous aah1/aah1 null mutant. Lane M is the 1 kb marker on both panels. Lane 3 contains the heterozygous strain used for obtaining the double disruptant of AAH1. Lane 4 shows the aah1/aah1 construct which correctly results in two PCR bands of 1.6 and 2.2 kb, respectively (panel C), via a 5' common primer and a 3' polynucleotide specific primer (primers 5' detect/3' gene) and two bands of 1.7 kb and 2.3 kb bands, respectively, via the 5' and 3' polynucleotide specific primers (panel D).

Table 5 lists the results of this methodology for the essential polynucleotides of the invention encoded by SEQ ID NO:1 through to SEQ ID NO:11, SEQ ID NO:45. Genes with known essential function were also examined. These include the *C. albicans* homologues of ERG1, RAM2 and NMT1. The non-essential gene, PFY1 was also tested.

TABLE 5

| | | Essential Genes Identified By PCR-Based Knockout and Promoter Swapping Cassette | | | | |
|---|---|---|---|---|---|---|
| SEQ ID# | | FCG # | Name in YPD | Essentiality via PCR-based KO | Essentiality via MET3 promoter | Functions |
| — | Known Genes | 1 | ERG1 | Essential | Essential | Squaline epoxidase |
| — | | 2 | RAM2/YKL019w | Essential | Essential | Alpha subunit of farnesyl transferase |
| — | | 3 | PFY1/YOR122c | Not essential | Not essential | Cell polarity |
| — | | 4 | NMT1/YLR195c | ND* | Essential | N-myristoyl transferase |
| 12 | Unknown polynucleotides | 5 | ERG27/YLR100w | Essential | Essential | 3-keto sterol reductase |
| 13 | or CURFs | 6 | YDR341c/RRS1 | Essential | Essential | Arginine tRNA synthetase |
| 14 | | 7 | YLR022c | Essential | Essential | Unknown |
| 15 | | 8 | YOL077c/BRX1 | Essential | Essential | Unknown |

TABLE 5-continued

Essential Genes Identified By PCR-Based Knockout and Promoter Swapping Cassette

| SEQ ID# | FCG # | Name in YPD | Essentiality via PCR-based KO | Essentiality via MET3 promoter | Functions |
|---|---|---|---|---|---|
| 16 | 10 | YNL132w/KRE33 | ?** | Essential | Unknown (P-loop) |
| 45 | 11 | YJR072c | Essential | Not essential | Unknown |
| 17 | 12 | YGR145w | ?** | Essential | Component of NuA3 histone acetyltransferase |
| 18 | 13 | YDR412w | ?** | Essential | Unknown |
| 19 | 14 | YOL010w/RCL1 | Essential | Essential | RNA processing |
| 20 | 15 | YOR004w | Essential | Essential | Unknown |
| 21 | 16 | YOR056c | ?** | Essential | Protein degradation |
| 22 | 17 | YLR009w | ?** | Essential | Protein synthesis |

*Not determined.

**? Essentiality couldn't be established by this methodology.

The results as shown in Table 5 show that essentiality could not be ascertained using this methodology for CaYNL132w, CaYGR145w, CaYDR412w, CaYOR056c and CaYLR009w. The remainder of the polynucleotides encoded by SEQ ID NO: 1 through SEQ ID NO: 11 were determined to be essential. As expected, CaERG1 and CaRAM2 were found to be essential and PFY1 was found not to be essential. Essentiality for NMT1 was not determined.

Example 5

Construction of MET3 Promoter Plasmids

Two plasmids, pUMP and pAMP, were constructed which contain a MET3 promoter cassette with one plasmid harboring the URA3 polynucleotide and the other harboring ARG4 as the selective marker, respectively (see FIG. 5 for plasmid maps). The *C. albicans* MET3 promoter region was amplified by PCR from the total DNA of strain SC5324 using the primers MET3SPHI (SEQ ID NO:222) and MET3NCOI (SEQ ID NO:224). The primers contain the SpeI and NcoI restriction sites, respectively. To construct pUMP, the MET3 promoter PCR product was cut with restriction enzymes SphI and NcoI, gel-purified and ligated to pGEM-URA3 that was linearized by SphI and NcoI. This placed the MET3 promoter sequence adjacent to URA3 yet in opposite orientation to avoid transcription read-through (FIG. 5). Construction of pAMP involved two steps. First, the *C. albicans* ARG4 polynucleotide was released from pRS-ARG4ΔSpeI after digestion with SacI and KpnI (blunt-ended), and then ligated to the SacII (blunt-ended) and SacI sites of pGEM-URA3 thus replacing URA3. The resulting plasmid was named pGEM-ARG4. Second, pGEM-ARG4 was linearized with SphI and NcoI, gel-purified and ligated with the MET3 promoter PCR product treated with SphI and NcoI, yielding plasmid pAMP.

Example 6

Promoter Swapping

Similar to the PCR-based polynucleotide disruption approach, two common primer sequences that allow annealing to the plasmid template were designed based on pUMP and pAMP. The forward common primer MET3PF (Seq ID NO:225) is derived from the same sequence as primer 3DR described above while the reverse common primer MET3PR (SEQ ID NO:224) is derived from MET3 promoter sequence so that the primer will anneal to the sequence right in front of the ATG start codon. In order to replace the endogenous promoter of the polynucleotide of interest, the MET3 promoter swapping cassette with either URA3 or ARG4 as the selective marker is amplified from the plasmid pUMP or pAMP, respectively, using a pair of primers designed similarly to the ones used in the PCR-based polynucleotide disruption technique described above. The forward primer contains 50-60 bp of flanking sequences that are derived of sequences 500-1000 bp upstream of the ATG codon of the polynucleotide of interest to ensure it would anneal upstream or on the boundary of the endogenous promoter and this portion of the forward primer is attached to the 5' end of the forward common promoter primer MET3 PF. The reverse primer has the 50-60 bp of flanking sequences which are derived from the start codon region of the polynucleotide or ORF including ATG attached to the 3' end of reverse common primer MET3PR. The resulting PCR product contains the MET3 promoter cassette that is flanked by 50-60 bp of sequences, on either end, homologous to the upstream promoter region and to the coding region of the polynucleotide of interest, respectively.

Once introduced into the cells heterozygous for the polynucleotide of interest obtained via the regular PCR-based polynucleotide disruption approach (supra), the MET3 promoter cassette would replace the endogenous promoter of the remaining allele via homologous recombination.

Figure 6:
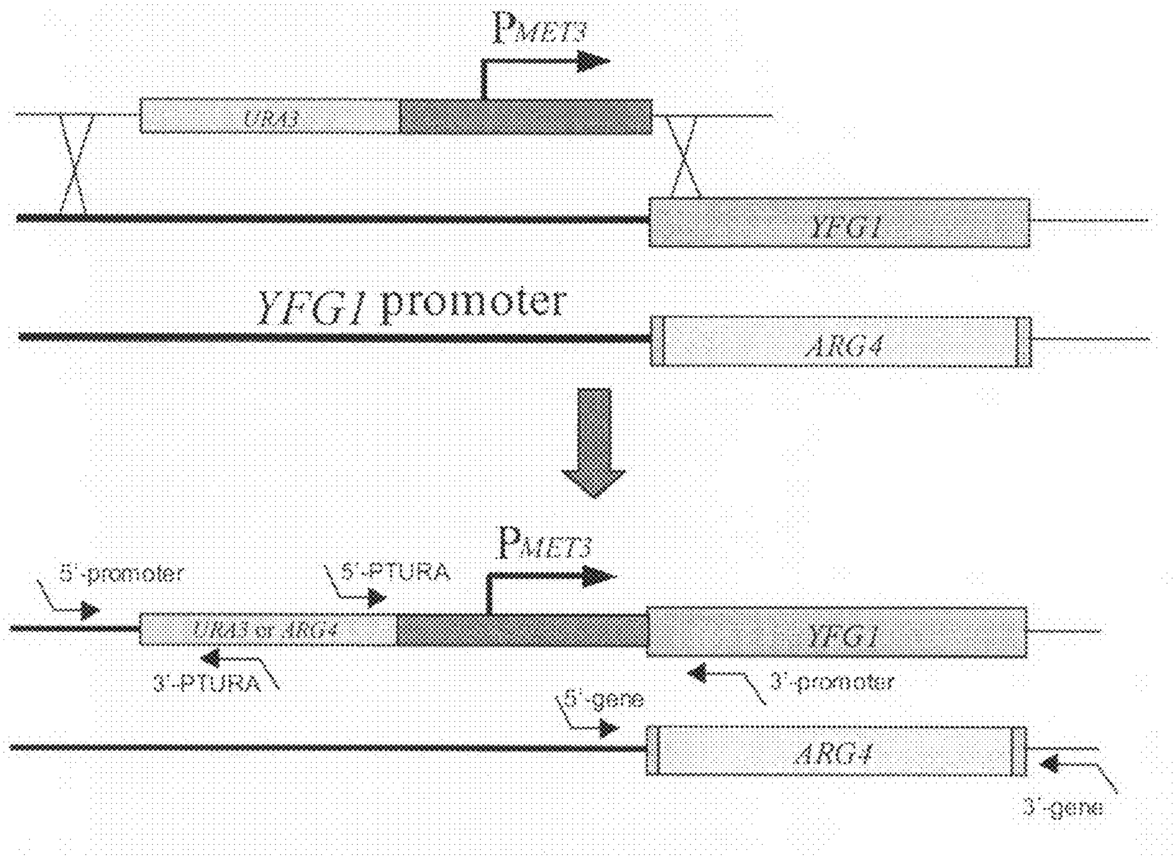
FIG. 6: Scheme of promoter swapping.

FIG. 6 depicts this promoter swapping scheme. The first copy of YFG1, as seen in the FIG, is disrupted via the PCR-based polynucleotide disruption approach. ARG4 is the selective marker used in this example. The native promoter of the remaining copy of YFG1 is subsequently replaced by the MET3 promoter via homologous recombination. Primers used for confirmation PCR in pairs include 5' promoter (i.e., a promoter-specific confirmation primer, upstream of the introduced MET3 promoter)/3'-PTURA (e.g. SEQ ID NO: 114 and SEQ ID NO: 146), 5'-PTURA/3'-promoter (i.e., a promoter-specific confirmation reverse primer, downstream of the ATG start codon (see, e.g., SEQ ID NO: 147 and SEQ ID NO: 115), 5'-gene/3' polynucleotide (e.g., if using CaERG as YFG1, SEQ ID NO: 151 and SEQ ID NO: 152). If, alternatively, URA3 is used as the selective marker and acts to disrupt the first copy of YFG1, the primer pair 5'-PTARG and 3'-PTARG will replace 5'-PTURA and 3'-PTURA, respectively, for confirmation PCR (i.e., SEQ ID NO: 149 and SEQ ID NO: 150).

Figure 7:
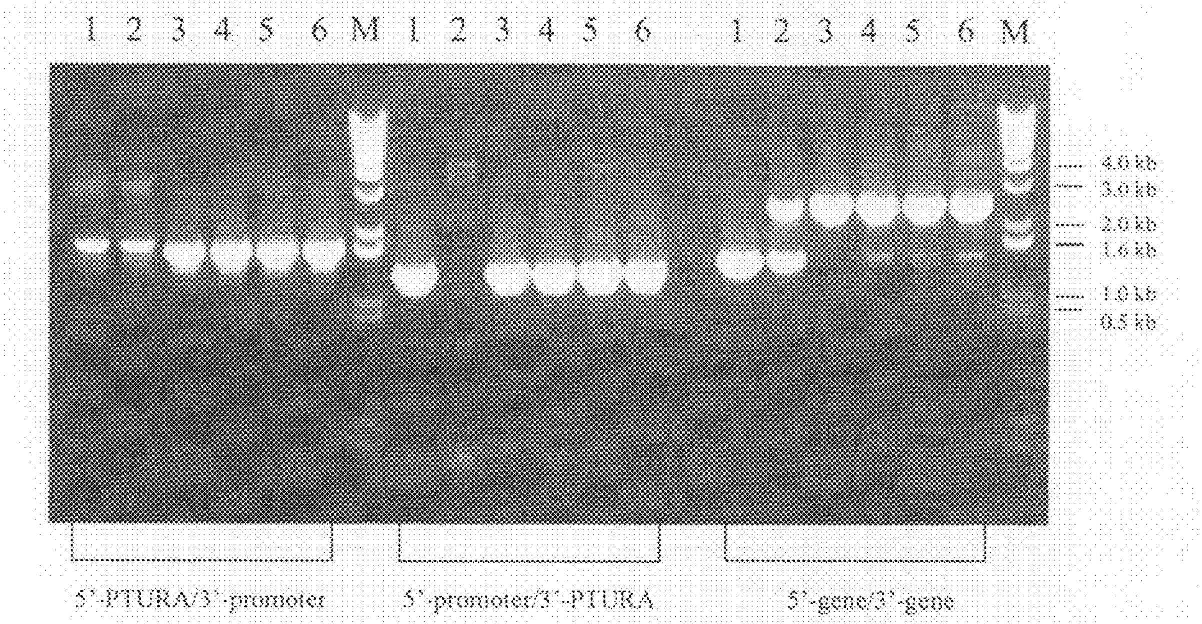
FIG. 7: Confirmation PCR for *C. albicans* MET3P-E RG1/erg1::ARG4 strains.

For example, FIG. 7 shows the results of confirmation PCR for *C. albicans* MET3P-ERG/erg1::ARG4 strains. Lanes labeled "M" contain 1 kb DNA markers with some fragment sizes indicated. Lanes 1 and 2 are transformants putatively not containing the correct constructs. Lanes 3 to 6 putatively contain the correct constructs (see below regarding methionine and cysteine construct regulation). The primer pair, SEQ ID NOs 147 and 115, respectively, are used. These primers correspond to 5'PTURA and sequences downstream of the ATG start codon of CaERG. The resulting PCR was 1.6 kb (Lanes 3-6) indicating the correct construct. Similarly, the primer pair SEQ ID NOs 114, and 146 is expected to yield a 1.2 kb single band since this primer pair corresponds to a sequence upstream of the ERG promoter and 3'-PTURA. Additionally, the FIG shows the expected single 2.4 kb band for a correct construct resulting from use of the polynucleotide specific primers SEQ ID NO: 151 and SEQ ID NO: 152.

Table 6 lists the SEQ ID NOs of the MET3 promoter swapping primers which may be used to remove the promoters associated with the essential polynucleotides encoded by SEQ ID NO: 1 through to SEQ ID NO: 11, SEQ ID NO: 45 and known essential and non-essential *C. albicans* homologues of *S. cervisiae* described herein. Additionally, this table lists the SEQ ID Nos. for PCR confirmation primers for promoter constructs. The 5' primers listed in this table are upstream of the introduced MET3 promoter and the introduced selective marker. The 3' primers are located downstream of the ATG start codon of the polynucleotide. SEQ ID NOs for polynucleotide specific primers which may be used for confirmation to detect MET3 promoter strain constructs in *Candida albicans* are listed in Table 4.

Example 7

Further Means to Identify MET3 Promoter Constructs

MET3 promoter constructs were identified by phenotypic analysis via down-regulation of the MET3 promoter as well as by a PCR confirmation method described below. Phenotypic analysis was conducted first for two reasons. First, if the polynucleotide of interest is essential for cell growth, switching the MET3 promoter by adding methionine and cysteine in the growing culture will block the cell growth yielding no growth or inhibited growth phenotype. In this way, the correct constructs are identified without screening a large number of transformants via a PCR confirmation test. Second, the inability to inhibit cell growth via down-regulation of the MET3 promoter would be an early indication that the polynucleotide being tested might not be essential. Therefore, the final conclusion on whether a polynucleotide is essential depends on both the phenotypic analysis and PCR confirmation tests.

Figure 8:
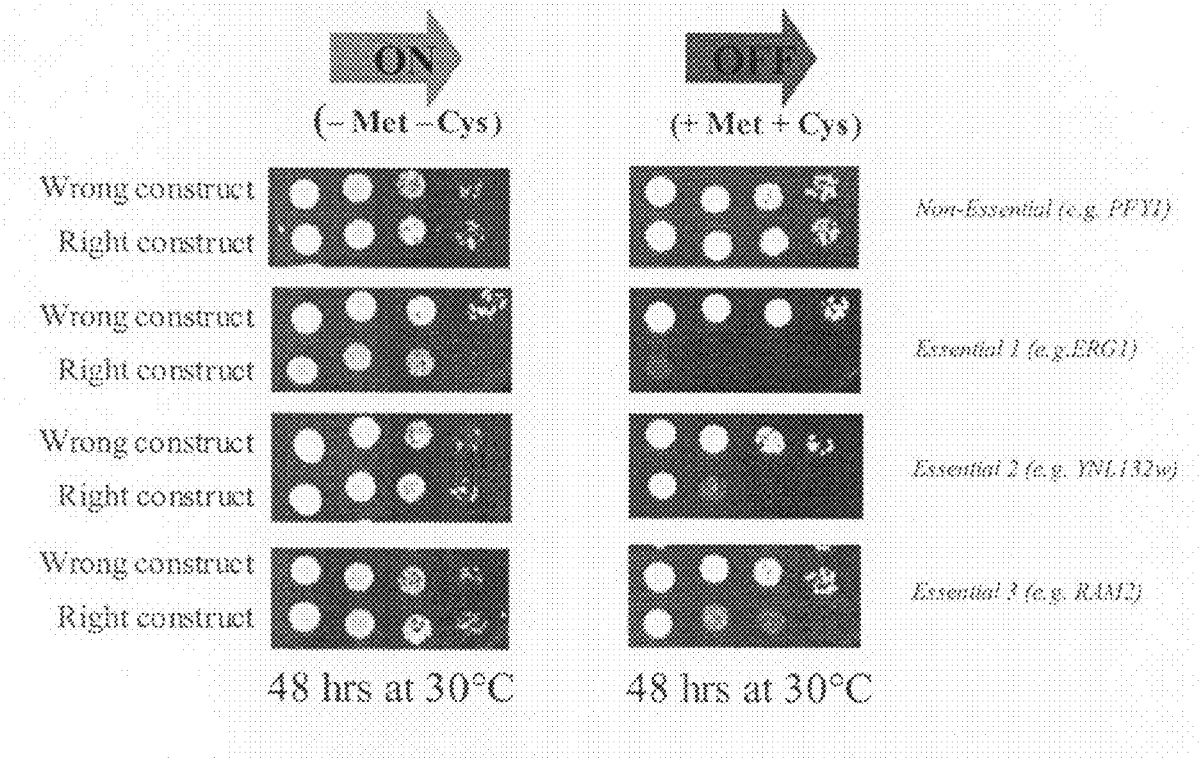
FIG. 8: Down regulation phenotypes by methionine and cysteine.

FIG. 8 shows examples of phenotypes containing constructs resulting in down regulation of polynucleotide expression by methionine and cysteine. This figure depicts the phenotypes resulting from the incorporation of correct and incorrect promoter swapping cassettes. 1/10 serial dilutions of cells were made and 5 μl of diluted cells were spotted from left to right on SD medium (left panel) and SD supplemented with 2.5 mM of methionine and 0.5 mM of cysteine (right panel). The known essential polynucleotides are "turned off" by the addition of the amino acids when the correct construct was introduced into the strain after 48 hours at 30° C. as evident by the lack of growth seen on the right panel. There is no difference in growth when the polynucleotide is non-essential without regard to the incorporation of the appropriate construct.

TABLE 6

MET3 Promoter Swapping Primers and Promoter Construct Confirmation Primers

| Gene Name | Seq ID No. | SEQ ID NO of translation | MET3 Promoter Swapping Primers (forward) | MET3 Promoter Swapping Primers (reverse) | PCR confirmation primers for promoter constructs (5') | PCR confirmation primers for promoter constructs (3') |
|---|---|---|---|---|---|---|
| CaYLR100wORF | 1 | 12 | 88 | 89 | 121 | 122 |
| CaYDR341cORF | 2 | 13 | 90 | 91 | 123 | 124 |
| CaYLR022cORF | 3 | 14 | 92 | 93) | 125 | 126 |
| CaYOL077cORF | 4 | 15 | 94 | 95 | 127 | 128 |
| CaYNL132wORF | 5 | 16 | 96 | 97 | 129 | 130 |
| CaYGR145wORF | 6 | 17 | 100 | 101 | 133 | 134 |
| CaYDR412wORF | 7 | 18 | 102 | 103 | 135 | 136 |
| CaYOL010wORF | 8 | 19 | 104 | 105 | 137 | 138 |
| CaYOR004wORF | 9 | 20 | 106 | 107 | 139 | 140 |
| YOR056cORF | 10 | 21 | 108 | 109 | 141 | 142 |
| YOR009wORF | 11 | 22 | 110 | 111 | 143 | 144 |
| CaYJR072c | — | 45 | 98 | 99 | 131 | 132 |
| CaERG | — | — | 80 | 81 | 114 | 115 |
| RAM2 | — | — | 82 | 83 | 116 | 117 |
| PFY1 | — | — | 84 | 85 | 118 | 119 |
| CaNMT1 | — | — | 86 | 87 | — | 120 |
| CaAAH1 | — | — | 112 | 113 | 145 | 146 |

Example 8

Drug Hypersensitivity

In order to determine if essential polynucleotide products could be reduced in fungal cells resulting in drug hypersensitivity, a high throughput whole cell assay was designed. The known *C. albicans* essential polynucleotide corresponding ERG1 polynucleotide in *S. cervisiae* was tested. CaERG 1 codes for squaline epoxidase and is known to be inhibited by terbinafine. The first polynucleotide copy was disrupted as described above and the second polynucleotide copy was modified by promoter swapping with MET3 promoter, also as described above.

The optimal cell density needed to control cell growth in a 384-well plate within the log phase after 18 hours incubation at 35° C. was first determined. For this determination, 50 ml of SD+His broth (minimal media with histidine) was inoculated with colonies grown on an SD plate with histidine and shaken at 35° C. overnight. Plates which contain colonies were streaked out once a week and stored on the bench at room temperature to eliminate any shock to the cells upon culturing. Cells were then diluted to varying concentrations in SD+His medium. 35 μl of the diluted cells were dispensed into wells of a 384-well plate containing 8 μl of 10.26% DMSO. To these wells, 10 μl of SD+His broth was added for a final volume in ach well of 53 μl. The plate was sealed and incubated at 35° C. At different time intervals, the plate was withdrawn from the incubator and the cell growth was determined by reading absorbance at 590 nm on a Perkin Elmer 7000 machine. 7.5×105 cfu/ml was found to be the optimal stock concentration of cell density for inoculation of the 384 well plate within the log phase after 18 hours incubation at 35° C.

Figure 9:
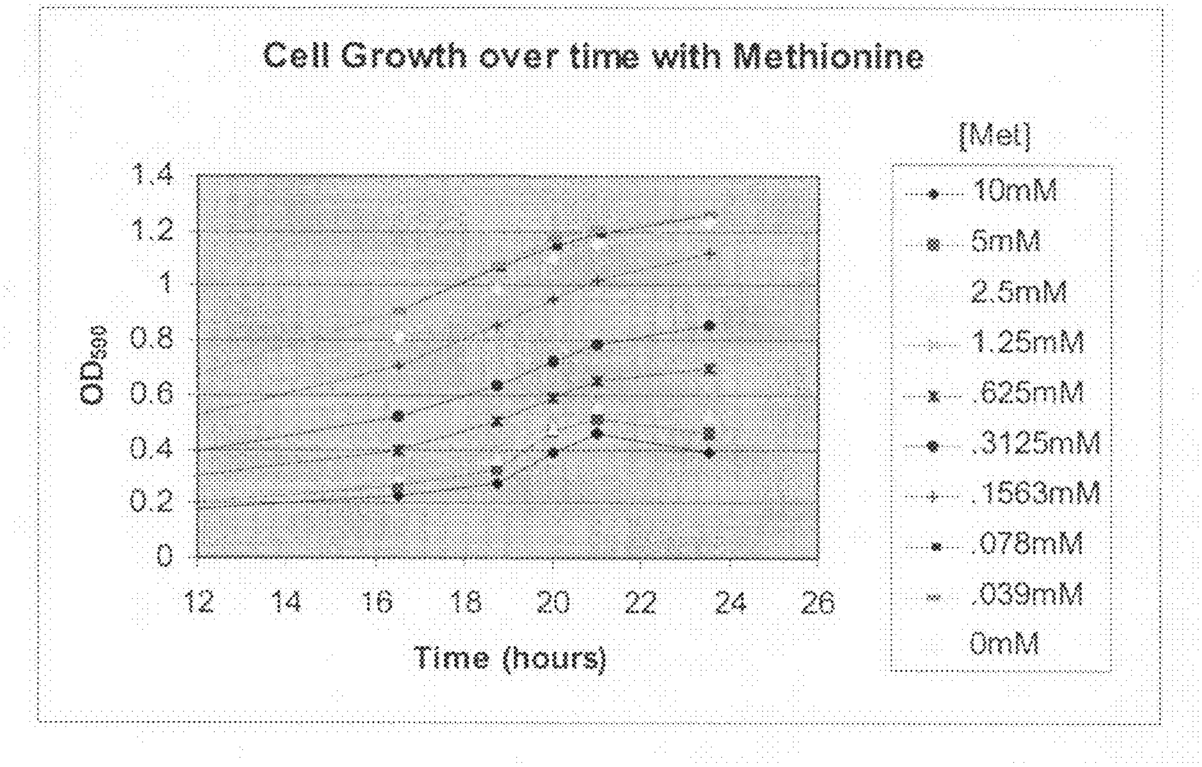
FIG. 9: Methionine titration of MET3P-ERG1 construct.

In order to determine the titratability of the MET3 promoter and the optimal methionine concentration to be used for drug sensitivity tests 50 mol of SD+His broth medium was inoculated with colonies grown on an SD+His plate and shaken at 35° C. overnight. Cells were diluted from these cultures to 757,002 cfu/ml in SD+His medium. 35 μl of the diluted cells were dispensed into wells of a 384-well plate containing 8 μl of 10.26% DMSO. 10 μl of methionine stock solution made in SD+His broth was added to the plates. 10 mM, 5 mM, 2.5 mM, 1.25 mM, 0.625 mM, 0.3125 mM, 0.1563 mM, 0.078 mM, 0.039 mM and no methionine concentrations were added to the plate. Cell growth was monitored between 16 and 24 hours by reading the optical density at 595 nm. FIG. 9, depicts the cell growth over time with the different methionine concentrations. As is evident from FIG. 9 cell growth increases with decreasing concentration of methionine. A 0.5 mM concentration of methionine reduces cell growth by approximately 50%.

TABLE 7

Sensitivity of the MET3P-ERG1 Construct to Antifungal Drugs
MICs μg/ml at 20 hrs

| Terbinafine | | Sordarin | | Fluconazole | |
|---|---|---|---|---|---|
| −Met | +Met | −Met | +Met | −Met | +Met |
| 4 or 8 | 0.5 | 0.5 | 0.5 | 1 | 1 |

Figure 10:
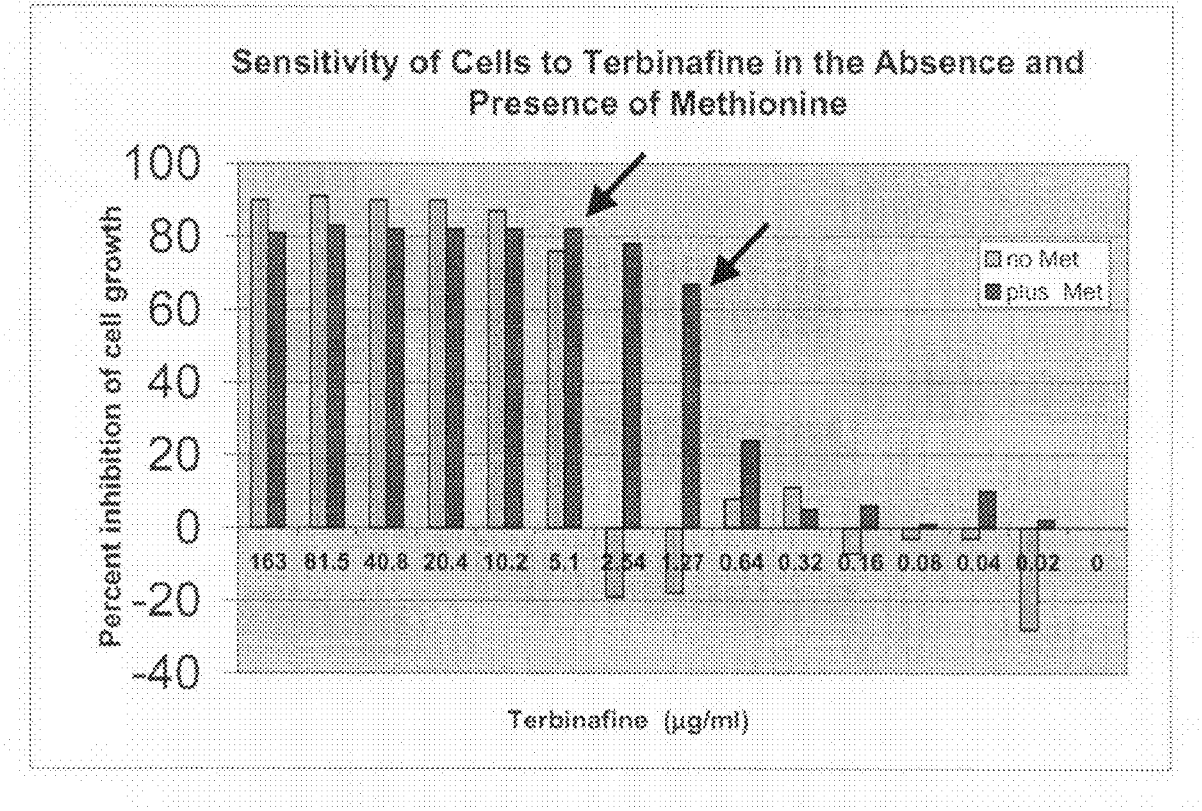
FIG. 10: Sensitivity of MET3P-ERG1 cells to terbinafine in the absence and presence of methionine.

In order to assess whether cells containing the ERG1-MET promoter construct would display hypersensitivity to terbinafine upon the addition of methionine in comparison to cells for which no methionine was added, cells were grown in the 384 well-plate as described above. A final concentration of 0.05 mM methinone was added to wells within one plate of cells and a control plate, in which SD+His broth was added in lieu of methionine was added to a second plate. 8 μl of various concentrations of terbinafine in 10.26% DMSO was added to both the control and test plates. The concentrations of terbinafine added to different wells ranged from 163 μg/ml to 0.02 μg/ml. FIG. 10 shows the results of the sensitivity of MET3 promoter-CaERG1 cells to terbinafine in the absence and presence of methionine and lists the particular concentrations of terbinafine inhibitor used. After the addition of this inhibitor, both the control and experimental plates were incubated at 35° C. After 18 hours of incubation, the OD readings were taken of the plates to measure cell growth (595 nm). FIG. 10 shows that a 4-8 fold increase in sensitivity to the specific inhibitor terbinafine which is known to target the CaERG1 polynucleotide product squalene epoxidase were obtained in the presence of methionine comparing to the no methionine control. Increased sensitivity of cells containing the ERG1-MET3 was confirmed in a separate experiment using a 96-well format plate. Table 7 shows that when the promoter activity was down regulated by the presence of methionine in these experiments, sensitivity to terbinafine increased by 16-32 fold.

Furthermore, results of additional experiments conducted with the drugs sordarin and fluconazole which are not known to be inhibitors of the CaERG1 polynucleotide product confirm that sensitivity to these drugs is not altered by the presence of methionine.

These results establish that the MET3 promoter is titratable and target polynucleotide expression directed by the promoter, when down-regulated, result in cells more sensitive to specific drugs.

Example 9

High Throughput Screen

In order to test compounds on polynucleotide products efficiently and quickly, a high throughput screen was used. Using the known target ERG1 under the control of the MET3 promoter and a specific inhibitor as a control, a high throughput screen was carried out as follows. Overnight cultures were seeded from multiple colonies grown on an SD+His plate into 50 mls of SD+His broth. The culture was shaken overnight at 35° C. Plates which contain colonies were freshly streaked once per week and stored on the bench at room temperature to eliminate any shock to the cells upon culturing. Stock solution was prepared from the overnight culture. 0.350 mls of overnight culture were added to 14 mls of SD+His media at room temperature. The stock solution is adjusted to contain $1.0\times10^7$ cells. The stock solution is diluted in preparation for use to contain 757,002 cells/ml. 26,500 cells/well are plated. 35 μl of the 757,002 cells/ml solution is added to each well. A 500 ml culture is used for 37 plates. For a 500 ml culture 37.85 ml of stock solution was added to 500 mls of SD+His at room temperature. In order to prepare the plates, 35 μl of Millipore water is added to each well in columns 1-24 of the plates. 100% DMSO is added to wells in columns 21-24 using a stacking multidrop.

Preparation of QC Plates

Two plates are used as control plates. One of the control plates contains 4 ul of compounds and antibiotics in each well with known MICs in 100% DMSO. Wells also contain 162.6 μg/ml to 0 μg/ml of terbinafine titration ranging from 162.6

μg/ml to 0 μg/ml. The blank plate contains 4 μl of 100% DMSO in all wells. These are diluted as above and 8 μl stamped into daughter plates as well. SD+His media is added only to columns 23 and 24 using the stacking multipdrop. 35 μl of *Candia albicans* culture is added to columns 1-22 using a Multidrop on the microbial robot. 10 μl of 2.65 mM methionine which has been diluted from 250 mM in SD+His broth is added to all wells with a multidrop. Plates are placed in an incubator at 35° C. for 18 hours. Readings to assess the amount of cell culture growth are taken at OD590 using a Perkin Elmer 7000 spectrophotometer using the following additional settings: Gain 50, Integration Time 40, 3 flashes, flash delay 10, Dark #10, Top Read, X-direction.

The screen is run using 384 well plates containing 4 μl of 100% DMSO of a 1 mM stock in the last four columns. 25 μl of water is added to columns 1-24 and 8 μl of each compound is transferred to a "daughter" plate on a Cybio Cybiwell. The daughter plates used were clear tissue culture treated plates from Becton Dickinson (Bedford, Mass., catalog number 358058).

Example 10

Method of Cloning the Fungal CURFs of the Present Invention

The fungal CURFs of the present invention may be cloned into expression vectors for protein purification. Such vectors would be useful in the further elucidation of polynucleotide function, and enable the application of biochemical assays and the development of screening assays either biophysically or biochemically. All 11 CURFs may be amplified by PCR from the genome of *C. albicans* and cloned to the Gateway™ Expression System (Invitrogen, CA) for overexpression in *E. coli*. The Gateway™ Expression System allows for construction of either 6×His-tagged or GST-tagged fusion proteins to facilitate easy and high yield protein overexpression and purification.

In brief, the cloning procedure involves three steps: 1) PCR amplifying the polynucleotide of interest from *C. albicans* genomic DNA by a primer pair of the corresponding gene; 2) cloning of PCR products via the BP reaction to the Donor vector pDONR201 to create an entry clone; 3) sequencing the cloned polynucleotide in the entry clone via PCR primer pair SeqL-A (5'-TCGCGTTAACGCTAGCATGGATCTC-3' (SEQ ID NO:227) and SeqL-B (5'-GTAACATCAGAGATTTTGAGACAC-3' (SEQ ID NO:228)). Once the entry clone is made, an overexpression construct containing either 6× Histidine tag or GST-tag can be created by transferring polynucleotides from entry clones into destination vectors such as pDEST 17 via the LR reaction.

The PCR reactions are carried out using Pfu Trubo™ DNA polymerase (Stragegene, La Jolla, Calif. 92037) as described in the preceding session (session 3. DNA manipulations). As for the polynucleotide cloning procedure, the manufacture protocol as described in GATEWAY™ Cloning Technology Instruction Manual may be followed essentially as described (Invitrogen, Carlsbad, Calif. 92008).

Representative primer pairs for cloning the fungal CURFs of the present invention are provided below.

| Primer Name | Primer Sequence | SEQ ID NO: |
|---|---|---|
| FCG5-fp | GGGGACAAGTTTGTACAAAAAAGCAGGCTTGGTTCCGCG TGGTAGCATGTCACTTTTAAAGGATTC | 229 |
| FCG5-rp | GGGGACCACTTTGTACAAGAAAGCTGGGTCCTAAGGTTG ACGTGTATTTACTATTTG | 230 |
| FCG6-fp | GGGGACAAGTTTGTACAAAAAAGCAGGCTTGGTTCCGCG TGGTAGCATGTCAGTCGAAACAATTAG | 231 |
| FCG6-rp | GGGGACCACTTTGTACAAGAAAGCTGGGTCCTACATACG ATTAACTGGAGTCAAAC | 232 |
| FCG7-fp | GGGGACAAGTTTGTACAAAAAAGCAGGCTTGGTTCCGCG TGGTAGCATGGCGGTGATTAATCAACC | 233 |
| FCG7-rp | GGGGACCACTTTGTACAAGAAAGCTGGGTCCTATTCCTT TATGGCAGACATATC | 234 |
| FCG8-fp | GGGGACAAGTTTGTACAAAAAAGCAGGCTTGGTTCCGCG TGGTAGCATGTCAGCTATCTATAAGGC | 235 |
| FCG8-rp | GGGGACCACTTTGTACAAGAAAGCTGGGTCCTATTTAAA TAAAGCATCATTGG | 236 |
| FCG10-fp | GGGGACAAGTTTGTACAAAAAAGCAGGCTTGGTTCCGCG TGGTAGCATGGGTAAAAAAGCAATTGATG | 237 |
| FCG10-rp | GGGGACCACTTTGTACAAGAAAGCTGGGTCCTATTTTTT TGATTTCTTTGATTTC | 238 |
| FCG12-fp | GGGGACAAGTTTGTACAAAAAAGCAGGCTTGGTTCCGCG TGGTAGCATGGTTTTAAAATCAACAAC | 239 |
| FCG12-rp | GGGGACCACTTTGTACAAGAAAGCTGGGTCCTACATACC TCTAAACTTATTCTTG | 240 |
| FCG13-fp | GGGGACAAGTTTGTACAAAAAAGCAGGCTTGGTTCCGCG TGGTAGCATGGCAGGATTTAAAAAGAATAG | 241 |
| FCG13-rp | GGGGACCACTTTGTACAAGAAAGCTGGGTCCTACTTCTT GCCCTTTGATTTTG | 242 |
| FCG14-fp | GGGGACAAGTTTGTACAAAAAAGCAGGCTTGGTTCCGCG TGGTAGCATGTCCAGTGTTGCTTCCAAAAAG | 243 |
| FCG14-rp | GGGGACCACTTTGTACAAGAAAGCTGGGTCCTAAGCTAT TTTTTTAGAAACATTG | 244 |
| FCG15-fp | GGGGACAAGTTTGTACAAAAAAGCAGGCTTGGTTCCGCG TGGTAGCATGAGACAAAAGCGTGCCAAG | 245 |
| FCG15-rp | GGGGACCACTTTGTACAAGAAAGCTGGGTCCTAGTTGTT GCTTCGTTCACTTGC | 246 |
| FCG16-fp | GGGGACAAGTTTGTACAAAAAAGCAGGCTTGGTTCCGCG TGGTAGCATGTCTGAAACAAAAAATATTG | 247 |
| FCG16-rp | GGGGACCACTTTGTACAAGAAAGCTGGGTCCTACTTTCT TTTCTTTTTGGAAG | 248 |
| FCG17-fp | GGGGACAAGTTTGTACAAAAAAGCAGGCTTGGTTCCGCG TGGTAGCATGAGGATTTATCAATGTCA | 249 |
| FCG17-rp | GGGGACCACTTTGTACAAGAAAGCTGGGTCCTAACACGT TTTTGTGTCACTTTC | 250 |

Example 11

Biochemical Demonstration that CaYLR100w is a 3-Keto Sterol Reductase Involved in C-4 Sterol Demethylation Overnight cultures were diluted into fresh SD+histidine (His) broth and grown at 30° C. until logarithmic growth was established. Cultures were harvested by centrifugation. Cells were then separated into tubes at a final density of 0.25 $OD_{600}$ containing either fresh SD+His broth or SD+His broth containing 5 mM methionine (Met) and 2.5 mM cysteine (Cys). At the end of either a 0.75, 1.5, 3 or 4.5 hour incubation period, the $OD_{600}$ values of each tube were measured and cultures were adjusted to a density of 0.25 $OD_{600}$ units per ml (2 mls per tube). Cultures were then pulsed with 2 μCi/tube of [$^3$H]-acetic acid for 60 minutes.

At the end of the labeling period, cells were pelleted and rinsed 1× with medium. The washed pellet was resuspended with 1 ml of 0.1 N HCl, transferred to glass screw-capped tubes, and incubated for 5 minutes at 85° C. Two mls of 90% ethanol: 15% KOH: 0.25% pyrogallol (w/v) was added and the sample allowed to saponify for 30 minutes at 85° C.

Tubes were extracted with three mls of petroleum ether with vigorous vortexing. The ether layer was removed and the residual aqueous layer was extracted a second time with 3 mls of petroleum ether. The ether layers were pooled and evaporated to dryness under an $N_2$ stream.

Dried samples were dissolved in petroleum ether and spotted onto a 20 cm×20 cm silica gel 60 TLC plate. The plate was developed in a solvent system of benzene: ethyl acetate (99.5: 0.5% v/v) until solvent front was 2 cm from the top of the TLC plate. The plate was dried completely then exposed for 1 to 3 days against X-ray film. The location of radiolabeled spots on the TLC plate was determined by matching the exposed spots on the autoradiogram. Results are shown in FIGS. 22A and B.

The affect of downregulating CaYLR100w expression on cell growth was also assessed by tracking the absorbance at $OD_{600}$ for both the caerg1Δ/$P_{MET3}$-CaERG1 (FIG. 23A) and fcg5Δ/$P_{MET3}$-FCG5 (FIG. 23B) in the presence or absence of methionine and cysteine.

In order to quantitate the radioactivity associated with the ergosterol pathway products, the silica gel corresponding to the exposed spots was excised from the plate and mixed with 0.5 ml of water, then mixed with 5 mls of scintillation cocktail prior to scintillation counting. [$^{14}$C]-cholesterol was used as a standard for the migration of ergosterol on the TLC plate. Results are shown in FIG. 24.

Example 12

Biochemical Demonstration that CaYDR341c is Involved in Whole Cell Protein Synthesis A plate containing SD+His agar was inoculated with *C. albicans* mutant fcg6Δ/$P_{MET3}$-FCG6 and incubated for 2 days at 30° C. An overnight culture was prepared from several colonies in SD+His broth and incubated at 30° C. on a rotary wheel for 18 hours. The overnight culture was diluted to 0.125 $OD_{600}$ and incubated at 30° C. until 0.28 $OD_{600}$ was achieved. A 100 μl aliquot of this culture was pipetted into the wells of a 96-well filter plate. Half of the wells then received 50 μl of SD+His broth, while the other half received 50 μl of SD+His broth containing 15 mM Met and 7.5 mM Cys solution to give a final concentration of methionine and cysteine of 5 mM and 2.5 mM, respectively. The plate was incubated at 30° C. without shaking for 3.5 hours prior to labelling.

A 4× radiolabelled amino acid labelling stock was prepared by adding 20 μl of 1 mCi/ml [$^3$H]-leucine (42.5 Ci/mmole) or [$^3$H]-arginine (57 Ci/mmole) to 1 ml of SD+His broth. Wells were labelled for 1 hour at 30° C. with the addition of 50 μl of the above [$^3$H]-leucine or [$^3$H]-arginine solution into the well (Final radioactive concentration of 5 μCi/ml or 1 μCi per well). After one hour, labelling was terminated with the addition of 100 μl of 20% trichloroacetic acid (TCA) per well (final [TCA]=6.7%). Plates were incubated at 4° C. overnight to precipitate proteins and amino acid-charged tRNA. Precipitates were collected by filtering on a vacuum manifold, washing filter wells 2× with 10% TCA, then 2× with water and finally 1× with ethanol. The plate was counted by adding 100 μl of Microscint-A scintillation fluid to the dried filter plate, then counting in a Packard Top-count scintillation counter. Results are shown in FIGS. 25A and 25B.

Example 13

Bacterial Expression of a Polypeptide

A polynucleotide encoding a polypeptide of the present invention is amplified using PCR oligonucleotide primers corresponding to the 5' and 3' ends of the DNA sequence, as outlined in herein, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased polynucleotide expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Other methods of purifying a polypeptide of the present invention are known in the art or disclosed elsewhere herein.

Example 14

Purification of a Polypeptide from an Inclusion Body

The following alternative method can be used to purify a polypeptide expressed in *E. coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Other methods of purifying a polypeptide of the present invention are known in the art or disclosed elsewhere herein.

Example 15

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase polynucleotide from *E. coli* under control of a weak *Drosophila* promoter in the same orientation, followed by the polyadenylation signal of the polyhedrin polynucleotide. The inserted polynucleotides are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

A polynucleotide encoding a polypeptide of the present invention is amplified using PCR oligonucleotide primers corresponding to the 5' and 3' ends of the DNA sequence, as outlined in Example 12, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described herein. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratapolynucleotide Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413-7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Other methods of purifying a polypeptide of the present invention are known in the art or disclosed elsewhere herein.

Example 16

Expression of the Fungal Conserved Essential Polypeptides in Mammalian Cells The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed polynucleotide can also be amplified to express large amounts of the encoded protein. The DHFR (dihydrofolate reductase) marker is useful in developing cell lines that carry several hundred or even several thousand copies of the polynucleotide of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR polynucleotide is used for transformation. Five μg of an expression plasmid is cotransformed with 0.5 ug of the plasmid pSVneo using lipofectin (Felgner et al., supra). The plasmid pSV2-neo contains a dominant selectable marker, the neo polynucleotide from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired polynucleotide product is analyzed, for instance, by SDS-PAGE and Western blot or by reversed phase HPLC analysis.

Other methods of purifying a polypeptide of the present invention are known in the art or disclosed elsewhere herein.

Example 17

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, pharmaceutical, and/or industrial applications. Among these traits, a short physiological half-life is the most prominent problem, and is present either at the level of the protein, or the level of the proteins mRNA. The ability to extend the half-life, for example, would be particularly important for a proteins use in polynucleotide therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered CURF may be constitutively active upon binding of its cognate ligand. Alternatively, an engineered CURF may be constitutively active in the absence of ligand binding. In yet another example, an engineered CURF may be capable of being activated with less than all of the regulatory factors and/or conditions typically required for CURF activation (e.g., ligand binding, phosphorylation, conformational changes, etc.). Such CURFs would be useful in screens to identify CURF modulators, among other uses described herein.

Directed evolution is comprised of several steps. The first step is to establish a library of variants for the polynucleotide or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments-further diversifying the potential hybridation sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM MgCl2 for 10-20 min. at room temperature. The resulting fragments of 10-50 bp could then be purified by running them through a 2% low-melting point agarose gel by electrophoresis onto DE81 ion-exchange paper (Whatman) or could be purified using Microcon concentrators (Amicon) of the appropriate molecular weight cuttoff, or could use oligonucleotide purification columns (Qiagen), in addition to other methods known in the art. If using DE81 ion-exchange paper, the 10-50 bp fragments could be eluted from said paper using 1 M NaCL, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 30-45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host, particularly if the polynucleotides and polypeptides provide a therapeutic use. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the polynucleotide sequence for a xenobiotic ortholog of the native protein in with the polynucleotide sequence of the novel variant polynucleotide in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the polynucleotide template DNA, oligonucleotides coding for known allelic sequences, optimized codon sequences, known variant sequences, known polynucleotide polymorphism sequences, known ortholog sequences, known homolog sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in polynucleotide therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. The forgoing are hereby incorporated in their entirety herein for all purposes.

Example 18

Method of Creating N- and C-Terminal Deletion Mutants Corresponding to the Fungal Essential Conserved Polypeptides of the Present Invention As described elsewhere herein, the present invention encompasses the creation of N- and C-terminal deletion mutants, in addition to any combination of N- and C-terminal deletions thereof, corresponding to the fungal essential conserved polypeptides of the present invention. A number of methods are available to one skilled in the art for creating such mutants. Such methods may include a combination of PCR amplification and polynucleotide cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length fungal essential conserved polypeptides sequence (as described in herein, for example), appropriate primers of about 15-25 nucleotides derived from the desired 5' and 3' positions of SEQ ID NO:1, 2, 3, 4, 5, 6, 7, 8, 9, 10, or 11 may be designed to PCR amplify, and subsequently clone, the intended N- and/or C-terminal deletion mutant. Such primers could comprise, for example, an initiation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

Representative PCR amplification conditions are provided below, although the skilled artisan would appreciate that other conditions may be required for efficient amplification. A 100 ul PCR reaction mixture may be prepared using long of the template DNA (cDNA clone of fungal essential conserved polypeptides), 200 uM 4dNTPs, 1 uM primers, 0.25 U Taq DNA polymerase (PE), and standard Taq DNA polymerase buffer. Typical PCR cycling condition are as follows:

20-25 cycles:
45 sec, 93 degrees
2 min, 50 degrees
2 min, 72 degrees
1 cycle: 10 min, 72 degrees After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E. coli* cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the fungal essential conserved polypeptides polynucleotide (SEQ ID NO:1, 2, 3, 4, 5, 6, 7, 8, 9, 10, or 11), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, 2, 3, 4, 5, 6, 7, 8, 9, 10, or 11. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))−25), wherein 'S' is equal to the nucleotide position of the initiating start codon of the fungal essential conserved polypeptides polynucleotide (SEQ ID NO:1, 2, 3, 4, 5, 6, 7, 8, 9, 10, or 11), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, 2, 3, 4, 5, 6, 7, 8, 9, 10, or 11. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

One skilled in the art could easily modify the exemplified studies to test the activity of polynucleotides of the invention (e.g., polynucleotide therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

TABLE 8

| Atom No. | Atom Type | Residue | Residue Position | X Coord. | Y Coord. | Z Coord. |
|---|---|---|---|---|---|---|
| 1 | N | MET | 1 | 89.886 | 75.280 | 32.999 |
| 2 | CA | MET | 1 | 89.364 | 75.553 | 31.649 |
| 3 | C | MET | 1 | 89.998 | 74.642 | 30.605 |
| 4 | O | MET | 1 | 89.639 | 74.684 | 29.424 |
| 5 | CB | MET | 1 | 89.592 | 77.010 | 31.266 |
| 6 | CG | MET | 1 | 88.726 | 77.938 | 32.110 |
| 7 | SD | MET | 1 | 86.945 | 77.666 | 31.958 |
| 8 | CE | MET | 1 | 86.766 | 77.911 | 30.174 |
| 9 | N | SER | 2 | 90.875 | 73.766 | 31.066 |
| 10 | CA | SER | 2 | 91.477 | 72.765 | 30.173 |
| 11 | C | SER | 2 | 90.562 | 71.553 | 30.024 |
| 12 | O | SER | 2 | 90.684 | 70.769 | 29.079 |
| 13 | CB | SER | 2 | 92.812 | 72.318 | 30.759 |
| 14 | OG | SER | 2 | 93.346 | 71.313 | 29.906 |
| 15 | N | LEU | 3 | 89.584 | 71.463 | 30.903 |
| 16 | CA | LEU | 3 | 88.626 | 70.369 | 30.827 |
| 17 | C | LEU | 3 | 87.524 | 70.715 | 29.839 |
| 18 | O | LEU | 3 | 87.647 | 70.463 | 28.637 |
| 19 | CB | LEU | 3 | 88.021 | 70.153 | 32.209 |
| 20 | CG | LEU | 3 | 89.080 | 69.793 | 33.245 |
| 21 | CD1 | LEU | 3 | 88.496 | 69.821 | 34.652 |
| 22 | CD2 | LEU | 3 | 89.706 | 68.436 | 32.949 |

TABLE 8-continued

| Atom No. | Atom Type | Residue | Residue Position | X Coord. | Y Coord. | Z Coord. |
|---|---|---|---|---|---|---|
| 23 | N | LEU | 4 | 86.535 | 71.430 | 30.342 |
| 24 | CA | LEU | 4 | 85.284 | 71.656 | 29.608 |
| 25 | C | LEU | 4 | 85.357 | 72.691 | 28.489 |
| 26 | O | LEU | 4 | 86.225 | 73.574 | 28.494 |
| 27 | CB | LEU | 4 | 84.214 | 72.144 | 30.590 |
| 28 | CG | LEU | 4 | 83.396 | 71.037 | 31.260 |
| 29 | CD1 | LEU | 4 | 82.789 | 70.108 | 30.217 |
| 30 | CD2 | LEU | 4 | 84.168 | 70.240 | 32.307 |
| 31 | N | LYS | 5 | 84.612 | 72.370 | 27.437 |
| 32 | CA | LYS | 5 | 84.031 | 73.345 | 26.489 |
| 33 | C | LYS | 5 | 84.957 | 74.020 | 25.465 |
| 34 | O | LYS | 5 | 84.446 | 74.621 | 24.513 |
| 35 | CB | LYS | 5 | 83.421 | 74.435 | 27.376 |
| 36 | CG | LYS | 5 | 82.435 | 75.357 | 26.664 |
| 37 | CD | LYS | 5 | 81.128 | 74.640 | 26.345 |
| 38 | CE | LYS | 5 | 80.431 | 74.158 | 27.615 |
| 39 | NZ | LYS | 5 | 80.114 | 75.280 | 28.516 |
| 40 | N | ASP | 6 | 86.257 | 73.802 | 25.530 |
| 41 | CA | ASP | 6 | 87.159 | 74.650 | 24.742 |
| 42 | C | ASP | 6 | 87.397 | 74.157 | 23.312 |
| 43 | O | ASP | 6 | 86.456 | 73.984 | 22.526 |
| 44 | CB | ASP | 6 | 88.471 | 74.821 | 25.508 |
| 45 | CG | ASP | 6 | 88.321 | 75.848 | 26.641 |
| 46 | OD1 | ASP | 6 | 87.198 | 76.283 | 26.862 |
| 47 | OD2 | ASP | 6 | 89.349 | 76.418 | 26.983 |
| 48 | N | SER | 7 | 88.672 | 74.011 | 22.988 |
| 49 | CA | SER | 7 | 89.145 | 73.697 | 21.632 |
| 50 | C | SER | 7 | 88.514 | 72.438 | 21.025 |
| 51 | O | SER | 7 | 88.172 | 71.482 | 21.734 |
| 52 | CB | SER | 7 | 90.657 | 73.551 | 21.737 |
| 53 | OG | SER | 7 | 91.198 | 73.565 | 20.429 |
| 54 | N | THR | 8 | 88.406 | 72.441 | 19.705 |
| 55 | CA | THR | 8 | 87.672 | 71.390 | 18.976 |
| 56 | C | THR | 8 | 88.549 | 70.157 | 18.740 |
| 57 | O | THR | 8 | 89.432 | 70.163 | 17.872 |
| 58 | CB | THR | 8 | 87.225 | 71.958 | 17.632 |
| 59 | OG1 | THR | 8 | 86.924 | 73.337 | 17.790 |
| 60 | CG2 | THR | 8 | 85.986 | 71.244 | 17.101 |
| 61 | N | VAL | 9 | 88.240 | 69.095 | 19.468 |
| 62 | CA | VAL | 9 | 89.052 | 67.864 | 19.461 |
| 63 | C | VAL | 9 | 88.716 | 66.858 | 18.348 |
| 64 | O | VAL | 9 | 87.574 | 66.381 | 18.210 |
| 65 | CB | VAL | 9 | 88.864 | 67.236 | 20.837 |
| 66 | CG1 | VAL | 9 | 87.417 | 67.358 | 21.295 |
| 67 | CG2 | VAL | 9 | 89.374 | 65.801 | 20.933 |
| 68 | N | ALA | 10 | 89.752 | 66.537 | 17.581 |
| 69 | CA | ALA | 10 | 89.677 | 65.513 | 16.523 |
| 70 | C | ALA | 10 | 90.813 | 64.488 | 16.650 |
| 71 | O | ALA | 10 | 91.980 | 64.803 | 16.388 |
| 72 | CB | ALA | 10 | 89.764 | 66.209 | 15.170 |
| 73 | N | VAL | 11 | 90.453 | 63.258 | 16.982 |
| 74 | CA | VAL | 11 | 91.437 | 62.195 | 17.268 |
| 75 | C | VAL | 11 | 91.539 | 61.146 | 16.149 |
| 76 | O | VAL | 11 | 90.544 | 60.489 | 15.823 |
| 77 | CB | VAL | 11 | 90.980 | 61.523 | 18.561 |
| 78 | CG1 | VAL | 11 | 91.917 | 60.401 | 18.992 |
| 79 | CG2 | VAL | 11 | 90.831 | 62.546 | 19.680 |
| 80 | N | ILE | 12 | 92.742 | 60.942 | 15.628 |
| 81 | CA | ILE | 12 | 92.972 | 59.966 | 14.539 |
| 82 | C | ILE | 12 | 93.796 | 58.764 | 15.013 |
| 83 | O | ILE | 12 | 94.903 | 58.951 | 15.530 |
| 84 | CB | ILE | 12 | 93.779 | 60.645 | 13.435 |
| 85 | CG1 | ILE | 12 | 93.256 | 62.027 | 13.090 |
| 86 | CG2 | ILE | 12 | 93.809 | 59.789 | 12.171 |
| 87 | CD1 | ILE | 12 | 94.165 | 62.659 | 12.045 |
| 88 | N | THR | 13 | 93.306 | 57.554 | 14.785 |
| 89 | CA | THR | 13 | 94.070 | 56.350 | 15.154 |
| 90 | C | THR | 13 | 95.005 | 55.881 | 14.043 |
| 91 | O | THR | 13 | 94.634 | 55.818 | 12.864 |
| 92 | CB | THR | 13 | 93.122 | 55.200 | 15.478 |
| 93 | OG1 | THR | 13 | 92.574 | 54.687 | 14.267 |
| 94 | CG2 | THR | 13 | 91.997 | 55.636 | 16.409 |
| 95 | N | GLY | 14 | 96.213 | 55.525 | 14.441 |
| 96 | CA | GLY | 14 | 97.161 | 54.894 | 13.521 |
| 97 | C | GLY | 14 | 97.808 | 55.923 | 12.610 |
| 98 | O | GLY | 14 | 97.975 | 55.688 | 11.407 |

TABLE 8-continued

| Atom No. | Atom Type | Residue | Residue Position | X Coord. | Y Coord. | Z Coord. |
|---|---|---|---|---|---|---|
| 99 | N | THR | 15 | 98.289 | 56.996 | 13.211 |
| 100 | CA | THR | 15 | 98.884 | 58.094 | 12.435 |
| 101 | C | THR | 15 | 100.352 | 57.874 | 12.097 |
| 102 | O | THR | 15 | 100.981 | 58.711 | 11.445 |
| 103 | CB | THR | 15 | 98.704 | 59.392 | 13.191 |
| 104 | OG1 | THR | 15 | 99.332 | 59.272 | 14.464 |
| 105 | CG2 | THR | 15 | 97.218 | 59.630 | 13.395 |
| 106 | N | SER | 16 | 100.870 | 56.728 | 12.505 |
| 107 | CA | SER | 16 | 102.194 | 56.294 | 12.065 |
| 108 | C | SER | 16 | 102.096 | 55.512 | 10.749 |
| 109 | O | SER | 16 | 103.120 | 55.069 | 10.217 |
| 110 | CB | SER | 16 | 102.836 | 55.441 | 13.154 |
| 111 | OG | SER | 16 | 102.054 | 54.269 | 13.345 |
| 112 | N | SER | 17 | 100.878 | 55.273 | 10.281 |
| 113 | CA | SER | 17 | 100.681 | 54.748 | 8.926 |
| 114 | C | SER | 17 | 100.698 | 55.929 | 7.969 |
| 115 | O | SER | 17 | 100.332 | 57.041 | 8.370 |
| 116 | CB | SER | 17 | 99.327 | 54.046 | 8.806 |
| 117 | OG | SER | 17 | 98.292 | 55.024 | 8.690 |
| 118 | N | ASN | 18 | 100.919 | 55.659 | 6.692 |
| 119 | CA | ASN | 18 | 100.924 | 56.744 | 5.699 |
| 120 | C | ASN | 18 | 99.521 | 57.307 | 5.479 |
| 121 | O | ASN | 18 | 99.384 | 58.526 | 5.310 |
| 122 | CB | ASN | 18 | 101.475 | 56.235 | 4.370 |
| 123 | CG | ASN | 18 | 102.928 | 55.774 | 4.494 |
| 124 | OD1 | ASN | 18 | 103.611 | 56.038 | 5.490 |
| 125 | ND2 | ASN | 18 | 103.401 | 55.137 | 3.437 |
| 126 | N | LEU | 19 | 98.507 | 56.495 | 5.739 |
| 127 | CA | LEU | 19 | 97.126 | 56.986 | 5.720 |
| 128 | C | LEU | 19 | 96.908 | 58.004 | 6.833 |
| 129 | O | LEU | 19 | 96.700 | 59.178 | 6.507 |
| 130 | CB | LEU | 19 | 96.138 | 55.833 | 5.890 |
| 131 | CG | LEU | 19 | 95.523 | 55.353 | 4.572 |
| 132 | CD1 | LEU | 19 | 96.546 | 54.670 | 3.669 |
| 133 | CD2 | LEU | 19 | 94.360 | 54.401 | 4.840 |
| 134 | N | GLY | 20 | 97.258 | 57.651 | 8.064 |
| 135 | CA | GLY | 20 | 97.099 | 58.566 | 9.204 |
| 136 | C | GLY | 20 | 97.902 | 59.854 | 9.058 |
| 137 | O | GLY | 20 | 97.345 | 60.942 | 9.244 |
| 138 | N | PHE | 21 | 99.119 | 59.729 | 8.556 |
| 139 | CA | PHE | 21 | 99.992 | 60.879 | 8.302 |
| 140 | C | PHE | 21 | 99.402 | 61.858 | 7.280 |
| 141 | O | PHE | 21 | 99.301 | 63.056 | 7.577 |
| 142 | CB | PHE | 21 | 101.295 | 60.294 | 7.761 |
| 143 | CG | PHE | 21 | 102.427 | 61.277 | 7.488 |
| 144 | CD1 | PHE | 21 | 103.369 | 61.522 | 8.476 |
| 145 | CD2 | PHE | 21 | 102.539 | 61.898 | 6.250 |
| 146 | CE1 | PHE | 21 | 104.413 | 62.403 | 8.236 |
| 147 | CE2 | PHE | 21 | 103.582 | 62.782 | 6.010 |
| 148 | CZ | PHE | 21 | 104.518 | 63.035 | 7.003 |
| 149 | N | ASN | 22 | 98.811 | 61.337 | 6.214 |
| 150 | CA | ASN | 22 | 98.297 | 62.201 | 5.138 |
| 151 | C | ASN | 22 | 96.938 | 62.783 | 5.513 |
| 152 | O | ASN | 22 | 96.661 | 63.955 | 5.224 |
| 153 | CB | ASN | 22 | 98.173 | 61.403 | 3.833 |
| 154 | CG | ASN | 22 | 99.487 | 61.347 | 3.041 |
| 155 | OD1 | ASN | 22 | 99.576 | 61.892 | 1.933 |
| 156 | ND2 | ASN | 22 | 100.427 | 60.547 | 3.514 |
| 157 | N | ILE | 23 | 96.239 | 62.076 | 6.385 |
| 158 | CA | ILE | 23 | 94.959 | 62.561 | 6.894 |
| 159 | C | ILE | 23 | 95.167 | 63.633 | 7.958 |
| 160 | O | ILE | 23 | 94.469 | 64.652 | 7.920 |
| 161 | CB | ILE | 23 | 94.207 | 61.366 | 7.468 |
| 162 | CG1 | ILE | 23 | 93.907 | 60.367 | 6.356 |
| 163 | CG2 | ILE | 23 | 92.920 | 61.817 | 8.143 |
| 164 | CD1 | ILE | 23 | 93.420 | 59.026 | 6.884 |
| 165 | N | ALA | 24 | 96.291 | 63.564 | 8.653 |
| 166 | CA | ALA | 24 | 96.643 | 64.595 | 9.630 |
| 167 | C | ALA | 24 | 97.036 | 65.895 | 8.940 |
| 168 | O | ALA | 24 | 96.499 | 66.952 | 9.298 |
| 169 | CB | ALA | 24 | 97.812 | 64.090 | 10.466 |
| 170 | N | VAL | 25 | 97.686 | 65.764 | 7.793 |
| 171 | CA | VAL | 25 | 98.053 | 66.930 | 6.986 |
| 172 | C | VAL | 25 | 96.819 | 67.624 | 6.417 |
| 173 | O | VAL | 25 | 96.673 | 68.845 | 6.579 |
| 174 | CB | VAL | 25 | 98.928 | 66.448 | 5.832 |

TABLE 8-continued

| Atom No. | Atom Type | Residue | Residue Position | X Coord. | Y Coord. | Z Coord. |
|---|---|---|---|---|---|---|
| 175 | CG1 | VAL | 25 | 99.155 | 67.543 | 4.799 |
| 176 | CG2 | VAL | 25 | 100.256 | 65.886 | 6.323 |
| 177 | N | ARG | 26 | 95.838 | 66.830 | 6.019 |
| 178 | CA | ARG | 26 | 94.610 | 67.387 | 5.449 |
| 179 | C | ARG | 26 | 93.708 | 68.021 | 6.504 |
| 180 | O | ARG | 26 | 93.249 | 69.153 | 6.301 |
| 181 | CB | ARG | 26 | 93.860 | 66.260 | 4.752 |
| 182 | CG | ARG | 26 | 92.512 | 66.730 | 4.218 |
| 183 | CD | ARG | 26 | 91.817 | 65.623 | 3.438 |
| 184 | NE | ARG | 26 | 90.494 | 66.049 | 2.952 |
| 185 | CZ | ARG | 26 | 90.231 | 66.321 | 1.673 |
| 186 | NH1 | ARG | 26 | 91.215 | 66.311 | 0.771 |
| 187 | NH2 | ARG | 26 | 88.995 | 66.668 | 1.307 |
| 188 | N | LEU | 27 | 93.686 | 67.456 | 7.700 |
| 189 | CA | LEU | 27 | 92.817 | 68.009 | 8.743 |
| 190 | C | LEU | 27 | 93.395 | 69.284 | 9.342 |
| 191 | O | LEU | 27 | 92.669 | 70.285 | 9.407 |
| 192 | CB | LEU | 27 | 92.625 | 66.965 | 9.832 |
| 193 | CG | LEU | 27 | 91.974 | 65.706 | 9.273 |
| 194 | CD1 | LEU | 27 | 91.890 | 64.621 | 10.332 |
| 195 | CD2 | LEU | 27 | 90.598 | 65.989 | 8.687 |
| 196 | N | LEU | 28 | 94.717 | 69.362 | 9.385 |
| 197 | CA | LEU | 28 | 95.391 | 70.567 | 9.892 |
| 198 | C | LEU | 28 | 95.351 | 71.734 | 8.913 |
| 199 | O | LEU | 28 | 95.574 | 72.884 | 9.304 |
| 200 | CB | LEU | 28 | 96.855 | 70.239 | 10.134 |
| 201 | CG | LEU | 28 | 97.049 | 69.355 | 11.351 |
| 202 | CD1 | LEU | 28 | 98.502 | 68.912 | 11.454 |
| 203 | CD2 | LEU | 28 | 96.602 | 70.083 | 12.612 |
| 204 | N | GLU | 29 | 95.030 | 71.442 | 7.665 |
| 205 | CA | GLU | 29 | 94.918 | 72.481 | 6.651 |
| 206 | C | GLU | 29 | 93.458 | 72.767 | 6.294 |
| 207 | O | GLU | 29 | 93.198 | 73.589 | 5.406 |
| 208 | CB | GLU | 29 | 95.709 | 72.017 | 5.434 |
| 209 | CG | GLU | 29 | 97.180 | 71.850 | 5.810 |
| 210 | CD | GLU | 29 | 97.957 | 71.148 | 4.702 |
| 211 | OE1 | GLU | 29 | 99.131 | 70.870 | 4.920 |
| 212 | OE2 | GLU | 29 | 97.397 | 70.963 | 3.631 |
| 213 | N | GLY | 30 | 92.522 | 72.138 | 6.989 |
| 214 | CA | GLY | 30 | 91.111 | 72.326 | 6.644 |
| 215 | C | GLY | 30 | 90.197 | 72.693 | 7.814 |
| 216 | O | GLY | 30 | 89.600 | 73.777 | 7.818 |
| 217 | N | LEU | 31 | 90.095 | 71.796 | 8.781 |
| 218 | CA | LEU | 31 | 89.063 | 71.884 | 9.829 |
| 219 | C | LEU | 31 | 89.438 | 70.833 | 10.885 |
| 220 | O | LEU | 31 | 90.117 | 69.876 | 10.500 |
| 221 | CB | LEU | 31 | 87.738 | 71.540 | 9.136 |
| 222 | CG | LEU | 31 | 86.548 | 72.401 | 9.557 |
| 223 | CD1 | LEU | 31 | 86.776 | 73.871 | 9.224 |
| 224 | CD2 | LEU | 31 | 85.267 | 71.906 | 8.899 |
| 225 | N | PRO | 32 | 88.985 | 70.884 | 12.135 |
| 226 | CA | PRO | 32 | 87.797 | 71.615 | 12.626 |
| 227 | C | PRO | 32 | 87.936 | 73.130 | 12.788 |
| 228 | O | PRO | 32 | 89.020 | 73.715 | 12.721 |
| 229 | CB | PRO | 32 | 87.482 | 71.015 | 13.959 |
| 230 | CG | PRO | 32 | 88.559 | 70.020 | 14.344 |
| 231 | CD | PRO | 32 | 89.473 | 69.934 | 13.141 |
| 232 | N | ASP | 33 | 86.784 | 73.740 | 13.018 |
| 233 | CA | ASP | 33 | 86.674 | 75.186 | 13.246 |
| 234 | C | ASP | 33 | 86.515 | 75.501 | 14.740 |
| 235 | O | ASP | 33 | 87.335 | 75.023 | 15.533 |
| 236 | CB | ASP | 33 | 85.535 | 75.753 | 12.389 |
| 237 | CG | ASP | 33 | 84.282 | 74.882 | 12.397 |
| 238 | OD1 | ASP | 33 | 84.154 | 74.046 | 11.508 |
| 239 | OD2 | ASP | 33 | 83.440 | 75.104 | 13.259 |
| 240 | N | ASN | 34 | 85.527 | 76.319 | 15.098 |
| 241 | CA | ASN | 34 | 85.293 | 76.753 | 16.494 |
| 242 | C | ASN | 34 | 86.579 | 77.395 | 17.038 |
| 243 | O | ASN | 34 | 87.417 | 77.829 | 16.236 |
| 244 | CB | ASN | 34 | 84.818 | 75.535 | 17.310 |
| 245 | CG | ASN | 34 | 84.139 | 75.916 | 18.630 |
| 246 | OD1 | ASN | 34 | 83.591 | 77.018 | 18.748 |
| 247 | ND2 | ASN | 34 | 84.380 | 75.111 | 19.650 |
| 248 | N | LYS | 35 | 86.650 | 77.650 | 18.333 |
| 249 | CA | LYS | 35 | 87.902 | 78.104 | 18.939 |
| 250 | C | LYS | 35 | 88.971 | 77.002 | 18.899 |

TABLE 8-continued

| Atom No. | Atom Type | Residue | Residue Position | X Coord. | Y Coord. | Z Coord. |
|---|---|---|---|---|---|---|
| 251 | O | LYS | 35 | 89.005 | 76.078 | 19.722 |
| 252 | CB | LYS | 35 | 87.615 | 78.596 | 20.357 |
| 253 | CG | LYS | 35 | 86.655 | 77.669 | 21.095 |
| 254 | CD | LYS | 35 | 86.204 | 78.254 | 22.430 |
| 255 | CE | LYS | 35 | 85.093 | 77.404 | 23.040 |
| 256 | NZ | LYS | 35 | 84.607 | 77.970 | 24.310 |
| 257 | N | GLU | 36 | 89.744 | 77.069 | 17.825 |
| 258 | CA | GLU | 36 | 90.947 | 76.261 | 17.591 |
| 259 | C | GLU | 36 | 90.680 | 74.804 | 17.227 |
| 260 | O | GLU | 36 | 90.026 | 74.049 | 17.956 |
| 261 | CB | GLU | 36 | 91.883 | 76.335 | 18.792 |
| 262 | CG | GLU | 36 | 92.414 | 77.746 | 18.992 |
| 263 | CD | GLU | 36 | 93.409 | 77.769 | 20.148 |
| 264 | OE1 | GLU | 36 | 93.519 | 78.811 | 20.780 |
| 265 | OE2 | GLU | 36 | 94.114 | 76.784 | 20.303 |
| 266 | N | ILE | 37 | 91.153 | 74.465 | 16.041 |
| 267 | CA | ILE | 37 | 91.287 | 73.075 | 15.597 |
| 268 | C | ILE | 37 | 92.404 | 72.375 | 16.368 |
| 269 | O | ILE | 37 | 93.575 | 72.767 | 16.287 |
| 270 | CB | ILE | 37 | 91.651 | 73.146 | 14.112 |
| 271 | CG1 | ILE | 37 | 92.372 | 71.907 | 13.588 |
| 272 | CG2 | ILE | 37 | 92.459 | 74.409 | 13.822 |
| 273 | CD1 | ILE | 37 | 92.838 | 72.121 | 12.152 |
| 274 | N | THR | 38 | 92.052 | 71.349 | 17.119 |
| 275 | CA | THR | 38 | 93.099 | 70.588 | 17.810 |
| 276 | C | THR | 38 | 93.104 | 69.125 | 17.408 |
| 277 | O | THR | 38 | 92.309 | 68.303 | 17.889 |
| 278 | CB | THR | 38 | 92.979 | 70.724 | 19.317 |
| 279 | OG1 | THR | 38 | 91.601 | 70.838 | 19.637 |
| 280 | CG2 | THR | 38 | 93.698 | 71.970 | 19.822 |
| 281 | N | LEU | 39 | 94.049 | 68.825 | 16.532 |
| 282 | CA | LEU | 39 | 94.226 | 67.461 | 16.040 |
| 283 | C | LEU | 39 | 95.084 | 66.641 | 17.001 |
| 284 | O | LEU | 39 | 96.140 | 67.095 | 17.461 |
| 285 | CB | LEU | 39 | 94.908 | 67.536 | 14.682 |
| 286 | CG | LEU | 39 | 94.739 | 66.235 | 13.913 |
| 287 | CD1 | LEU | 39 | 93.260 | 65.961 | 13.678 |
| 288 | CD2 | LEU | 39 | 95.482 | 66.288 | 12.588 |
| 289 | N | VAL | 40 | 94.569 | 65.476 | 17.352 |
| 290 | CA | VAL | 40 | 95.277 | 64.533 | 18.222 |
| 291 | C | VAL | 40 | 95.571 | 63.236 | 17.465 |
| 292 | O | VAL | 40 | 94.689 | 62.391 | 17.258 |
| 293 | CB | VAL | 40 | 94.407 | 64.237 | 19.439 |
| 294 | CG1 | VAL | 40 | 95.137 | 63.320 | 20.412 |
| 295 | CG2 | VAL | 40 | 93.987 | 65.522 | 20.144 |
| 296 | N | VAL | 41 | 96.816 | 63.096 | 17.049 |
| 297 | CA | VAL | 41 | 97.230 | 61.918 | 16.287 |
| 298 | C | VAL | 41 | 97.787 | 60.829 | 17.197 |
| 299 | O | VAL | 41 | 98.730 | 61.030 | 17.973 |
| 300 | CB | VAL | 41 | 98.240 | 62.352 | 15.236 |
| 301 | CG1 | VAL | 41 | 97.554 | 63.244 | 14.209 |
| 302 | CG2 | VAL | 41 | 99.460 | 63.037 | 15.839 |
| 303 | N | THR | 42 | 97.145 | 59.679 | 17.132 |
| 304 | CA | THR | 42 | 97.494 | 58.587 | 18.033 |
| 305 | C | THR | 42 | 98.205 | 57.431 | 17.337 |
| 306 | O | THR | 42 | 97.961 | 57.119 | 16.163 |
| 307 | CB | THR | 42 | 96.219 | 58.083 | 18.686 |
| 308 | OG1 | THR | 42 | 95.491 | 57.317 | 17.741 |
| 309 | CG2 | THR | 42 | 95.341 | 59.221 | 19.191 |
| 310 | N | SER | 43 | 99.107 | 56.824 | 18.088 |
| 311 | CA | SER | 43 | 99.837 | 55.626 | 17.642 |
| 312 | C | SER | 43 | 100.556 | 54.981 | 18.827 |
| 313 | O | SER | 43 | 100.892 | 55.653 | 19.807 |
| 314 | CB | SER | 43 | 100.827 | 56.013 | 16.543 |
| 315 | OG | SER | 43 | 101.686 | 54.913 | 16.259 |
| 316 | N | ARG | 44 | 100.757 | 53.676 | 18.746 |
| 317 | CA | ARG | 44 | 101.459 | 52.940 | 19.803 |
| 318 | C | ARG | 44 | 102.985 | 53.014 | 19.690 |
| 319 | O | ARG | 44 | 103.688 | 52.663 | 20.646 |
| 320 | CB | ARG | 44 | 101.022 | 51.482 | 19.705 |
| 321 | CG | ARG | 44 | 101.223 | 50.950 | 18.291 |
| 322 | CD | ARG | 44 | 100.784 | 49.499 | 18.153 |
| 323 | NE | ARG | 44 | 101.051 | 49.019 | 16.788 |
| 324 | CZ | ARG | 44 | 100.740 | 47.791 | 16.367 |
| 325 | NH1 | ARG | 44 | 101.032 | 47.421 | 15.117 |
| 326 | NH2 | ARG | 44 | 100.150 | 46.930 | 17.198 |

TABLE 8-continued

| Atom No. | Atom Type | Residue | Residue Position | X Coord. | Y Coord. | Z Coord. |
|---|---|---|---|---|---|---|
| 327 | N | THR | 45 | 103.492 | 53.564 | 18.599 |
| 328 | CA | THR | 45 | 104.947 | 53.577 | 18.397 |
| 329 | C | THR | 45 | 105.560 | 54.935 | 18.719 |
| 330 | O | THR | 45 | 105.853 | 55.701 | 17.795 |
| 331 | CB | THR | 45 | 105.249 | 53.189 | 16.949 |
| 332 | OG1 | THR | 45 | 104.499 | 54.026 | 16.071 |
| 333 | CG2 | THR | 45 | 104.845 | 51.748 | 16.664 |
| 334 | N | LEU | 46 | 105.921 | 55.135 | 19.979 |
| 335 | CA | LEU | 46 | 106.467 | 56.426 | 20.471 |
| 336 | C | LEU | 46 | 107.481 | 57.136 | 19.547 |
| 337 | O | LEU | 46 | 107.112 | 58.216 | 19.065 |
| 338 | CB | LEU | 46 | 107.042 | 56.227 | 21.877 |
| 339 | CG | LEU | 46 | 107.720 | 57.482 | 22.432 |
| 340 | CD1 | LEU | 46 | 106.786 | 58.689 | 22.457 |
| 341 | CD2 | LEU | 46 | 108.290 | 57.221 | 23.821 |
| 342 | N | PRO | 47 | 108.613 | 56.550 | 19.151 |
| 343 | CA | PRO | 47 | 109.556 | 57.327 | 18.334 |
| 344 | C | PRO | 47 | 109.059 | 57.624 | 16.914 |
| 345 | O | PRO | 47 | 109.341 | 58.715 | 16.405 |
| 346 | CB | PRO | 47 | 110.810 | 56.509 | 18.284 |
| 347 | CG | PRO | 47 | 110.562 | 55.162 | 18.942 |
| 348 | CD | PRO | 47 | 109.138 | 55.209 | 19.465 |
| 349 | N | LYS | 48 | 108.124 | 56.835 | 16.411 |
| 350 | CA | LYS | 48 | 107.609 | 57.068 | 15.066 |
| 351 | C | LYS | 48 | 106.443 | 58.052 | 15.095 |
| 352 | O | LYS | 48 | 106.344 | 58.883 | 14.185 |
| 353 | CB | LYS | 48 | 107.209 | 55.729 | 14.459 |
| 354 | CG | LYS | 48 | 106.732 | 55.880 | 13.020 |
| 355 | CD | LYS | 48 | 106.666 | 54.528 | 12.318 |
| 356 | CE | LYS | 48 | 105.844 | 53.522 | 13.113 |
| 357 | NZ | LYS | 48 | 105.751 | 52.235 | 12.406 |
| 358 | N | VAL | 49 | 105.808 | 58.186 | 16.252 |
| 359 | CA | VAL | 49 | 104.770 | 59.211 | 16.419 |
| 360 | C | VAL | 49 | 105.430 | 60.576 | 16.537 |
| 361 | O | VAL | 49 | 105.027 | 61.520 | 15.848 |
| 362 | CB | VAL | 49 | 103.989 | 58.973 | 17.707 |
| 363 | CG1 | VAL | 49 | 102.821 | 59.943 | 17.809 |
| 364 | CG2 | VAL | 49 | 103.477 | 57.552 | 17.812 |
| 365 | N | LYS | 50 | 106.592 | 60.583 | 17.168 |
| 366 | CA | LYS | 50 | 107.379 | 61.807 | 17.312 |
| 367 | C | LYS | 50 | 108.039 | 62.222 | 15.995 |
| 368 | O | LYS | 50 | 108.070 | 63.418 | 15.676 |
| 369 | CB | LYS | 50 | 108.438 | 61.516 | 18.366 |
| 370 | CG | LYS | 50 | 109.450 | 62.644 | 18.511 |
| 371 | CD | LYS | 50 | 110.526 | 62.273 | 19.524 |
| 372 | CE | LYS | 50 | 111.233 | 60.976 | 19.136 |
| 373 | NZ | LYS | 50 | 111.911 | 61.099 | 17.833 |
| 374 | N | GLU | 51 | 108.307 | 61.251 | 15.137 |
| 375 | CA | GLU | 51 | 108.840 | 61.561 | 13.810 |
| 376 | C | GLU | 51 | 107.747 | 62.074 | 12.880 |
| 377 | O | GLU | 51 | 107.973 | 63.092 | 12.215 |
| 378 | CB | GLU | 51 | 109.478 | 60.303 | 13.240 |
| 379 | CG | GLU | 51 | 110.743 | 59.956 | 14.015 |
| 380 | CD | GLU | 51 | 111.190 | 58.535 | 13.691 |
| 381 | OE1 | GLU | 51 | 110.319 | 57.697 | 13.496 |
| 382 | OE2 | GLU | 51 | 112.387 | 58.287 | 13.741 |
| 383 | N | VAL | 52 | 106.522 | 61.613 | 13.083 |
| 384 | CA | VAL | 52 | 105.382 | 62.134 | 12.320 |
| 385 | C | VAL | 52 | 105.040 | 63.559 | 12.752 |
| 386 | O | VAL | 52 | 104.875 | 64.427 | 11.881 |
| 387 | CB | VAL | 52 | 104.181 | 61.215 | 12.544 |
| 388 | CG1 | VAL | 52 | 102.881 | 61.839 | 12.047 |
| 389 | CG2 | VAL | 52 | 104.400 | 59.849 | 11.905 |
| 390 | N | ILE | 53 | 105.251 | 63.850 | 14.028 |
| 391 | CA | ILE | 53 | 105.049 | 65.211 | 14.538 |
| 392 | C | ILE | 53 | 106.077 | 66.171 | 13.950 |
| 393 | O | ILE | 53 | 105.679 | 67.146 | 13.296 |
| 394 | CB | ILE | 53 | 105.175 | 65.209 | 16.060 |
| 395 | CG1 | ILE | 53 | 104.095 | 64.358 | 16.713 |
| 396 | CG2 | ILE | 53 | 105.110 | 66.633 | 16.604 |
| 397 | CD1 | ILE | 53 | 102.713 | 64.968 | 16.523 |
| 398 | N | SER | 54 | 107.321 | 65.718 | 13.885 |
| 399 | CA | SER | 54 | 108.407 | 66.559 | 13.372 |
| 400 | C | SER | 54 | 108.303 | 66.773 | 11.866 |
| 401 | O | SER | 54 | 108.422 | 67.915 | 11.402 |
| 402 | CB | SER | 54 | 109.731 | 65.875 | 13.688 |

TABLE 8-continued

| Atom No. | Atom Type | Residue | Residue Position | X Coord. | Y Coord. | Z Coord. |
|---|---|---|---|---|---|---|
| 403 | OG | SER | 54 | 109.812 | 65.706 | 15.097 |
| 404 | N | ASP | 55 | 107.812 | 65.763 | 11.168 |
| 405 | CA | ASP | 55 | 107.647 | 65.864 | 9.719 |
| 406 | C | ASP | 55 | 106.548 | 66.848 | 9.348 |
| 407 | O | ASP | 55 | 106.817 | 67.793 | 8.596 |
| 408 | CB | ASP | 55 | 107.261 | 64.498 | 9.161 |
| 409 | CG | ASP | 55 | 108.347 | 63.448 | 9.381 |
| 410 | OD1 | ASP | 55 | 109.514 | 63.816 | 9.349 |
| 411 | OD2 | ASP | 55 | 107.992 | 62.275 | 9.448 |
| 412 | N | ILE | 56 | 105.428 | 66.790 | 10.050 |
| 413 | CA | ILE | 56 | 104.287 | 67.619 | 9.654 |
| 414 | C | ILE | 56 | 104.346 | 69.052 | 10.192 |
| 415 | O | ILE | 56 | 103.907 | 69.962 | 9.475 |
| 416 | CB | ILE | 56 | 103.010 | 66.896 | 10.064 |
| 417 | CG1 | ILE | 56 | 102.924 | 65.564 | 9.327 |
| 418 | CG2 | ILE | 56 | 101.766 | 67.729 | 9.782 |
| 419 | CD1 | ILE | 56 | 101.613 | 64.840 | 9.612 |
| 420 | N | LYS | 57 | 105.152 | 69.298 | 11.212 |
| 421 | CA | LYS | 57 | 105.321 | 70.692 | 11.648 |
| 422 | C | LYS | 57 | 106.362 | 71.433 | 10.799 |
| 423 | O | LYS | 57 | 106.394 | 72.669 | 10.789 |
| 424 | CB | LYS | 57 | 105.650 | 70.742 | 13.144 |
| 425 | CG | LYS | 57 | 106.926 | 70.021 | 13.578 |
| 426 | CD | LYS | 57 | 108.186 | 70.869 | 13.420 |
| 427 | CE | LYS | 57 | 109.433 | 70.095 | 13.828 |
| 428 | NZ | LYS | 57 | 110.644 | 70.890 | 13.580 |
| 429 | N | LYS | 58 | 107.116 | 70.684 | 10.008 |
| 430 | CA | LYS | 58 | 108.105 | 71.262 | 9.097 |
| 431 | C | LYS | 58 | 107.647 | 71.117 | 7.638 |
| 432 | O | LYS | 58 | 108.324 | 71.597 | 6.714 |
| 433 | CB | LYS | 58 | 109.402 | 70.493 | 9.334 |
| 434 | CG | LYS | 58 | 110.588 | 71.042 | 8.553 |
| 435 | CD | LYS | 58 | 111.831 | 70.188 | 8.762 |
| 436 | CE | LYS | 58 | 112.970 | 70.660 | 7.867 |
| 437 | NZ | LYS | 58 | 112.577 | 70.587 | 6.453 |
| 438 | N | TYR | 59 | 106.433 | 70.613 | 7.463 |
| 439 | CA | TYR | 59 | 105.938 | 70.141 | 6.161 |
| 440 | C | TYR | 59 | 105.530 | 71.273 | 5.230 |
| 441 | O | TYR | 59 | 104.337 | 71.522 | 5.042 |
| 442 | CB | TYR | 59 | 104.747 | 69.218 | 6.408 |
| 443 | CG | TYR | 59 | 104.173 | 68.540 | 5.167 |
| 444 | CD1 | TYR | 59 | 104.931 | 67.599 | 4.483 |
| 445 | CD2 | TYR | 59 | 102.896 | 68.862 | 4.724 |
| 446 | CE1 | TYR | 59 | 104.415 | 66.983 | 3.351 |
| 447 | CE2 | TYR | 59 | 102.381 | 68.248 | 3.591 |
| 448 | CZ | TYR | 59 | 103.141 | 67.310 | 2.905 |
| 449 | OH | TYR | 59 | 102.626 | 66.693 | 1.785 |
| 450 | N | ILE | 60 | 106.521 | 71.697 | 4.461 |
| 451 | CA | ILE | 60 | 106.478 | 72.782 | 3.464 |
| 452 | C | ILE | 60 | 106.645 | 74.138 | 4.157 |
| 453 | O | ILE | 60 | 105.835 | 75.068 | 4.015 |
| 454 | CB | ILE | 60 | 105.240 | 72.723 | 2.552 |
| 455 | CG1 | ILE | 60 | 105.067 | 71.342 | 1.917 |
| 456 | CG2 | ILE | 60 | 105.312 | 73.775 | 1.444 |
| 457 | CD1 | ILE | 60 | 106.270 | 70.953 | 1.068 |
| 458 | N | VAL | 61 | 107.682 | 74.201 | 4.979 |
| 459 | CA | VAL | 61 | 108.174 | 75.496 | 5.462 |
| 460 | C | VAL | 61 | 109.508 | 75.795 | 4.789 |
| 461 | O | VAL | 61 | 109.797 | 76.939 | 4.417 |
| 462 | CB | VAL | 61 | 108.402 | 75.431 | 6.968 |
| 463 | CG1 | VAL | 61 | 108.808 | 76.799 | 7.516 |
| 464 | CG2 | VAL | 61 | 107.177 | 74.920 | 7.705 |
| 465 | N | ALA | 62 | 110.197 | 74.722 | 4.435 |
| 466 | CA | ALA | 62 | 111.578 | 74.827 | 3.944 |
| 467 | C | ALA | 62 | 111.745 | 75.150 | 2.458 |
| 468 | O | ALA | 62 | 112.852 | 75.522 | 2.050 |
| 469 | CB | ALA | 62 | 112.290 | 73.517 | 4.250 |
| 470 | N | LYS | 63 | 110.686 | 75.064 | 1.669 |
| 471 | CA | LYS | 63 | 110.806 | 75.472 | 0.262 |
| 472 | C | LYS | 63 | 110.642 | 76.978 | 0.219 |
| 473 | O | LYS | 63 | 109.511 | 77.472 | 0.200 |
| 474 | CB | LYS | 63 | 109.729 | 74.809 | −0.582 |
| 475 | CG | LYS | 63 | 109.796 | 73.290 | −0.499 |
| 476 | CD | LYS | 63 | 108.864 | 72.661 | −1.527 |
| 477 | CE | LYS | 63 | 107.470 | 73.268 | −1.443 |
| 478 | NZ | LYS | 63 | 106.553 | 72.627 | −2.397 |

TABLE 8-continued

| Atom No. | Atom Type | Residue | Residue Position | X Coord. | Y Coord. | Z Coord. |
|---|---|---|---|---|---|---|
| 479 | N | ILE | 64 | 111.766 | 77.667 | 0.091 |
| 480 | CA | ILE | 64 | 111.847 | 79.094 | 0.431 |
| 481 | C | ILE | 64 | 111.394 | 79.211 | 1.885 |
| 482 | O | ILE | 64 | 110.192 | 79.325 | 2.156 |
| 483 | CB | ILE | 64 | 110.992 | 79.943 | −0.511 |
| 484 | CG1 | ILE | 64 | 111.431 | 79.747 | −1.958 |
| 485 | CG2 | ILE | 64 | 111.070 | 81.420 | −0.135 |
| 486 | CD1 | ILE | 64 | 110.575 | 80.568 | −2.917 |
| 487 | N | PRO | 65 | 112.375 | 79.336 | 2.773 |
| 488 | CA | PRO | 65 | 112.347 | 78.723 | 4.128 |
| 489 | C | PRO | 65 | 111.428 | 79.349 | 5.192 |
| 490 | O | PRO | 65 | 111.592 | 79.071 | 6.386 |
| 491 | CB | PRO | 65 | 113.764 | 78.757 | 4.612 |
| 492 | CG | PRO | 65 | 114.649 | 79.398 | 3.561 |
| 493 | CD | PRO | 65 | 113.746 | 79.677 | 2.376 |
| 494 | N | THR | 66 | 110.506 | 80.195 | 4.774 |
| 495 | CA | THR | 66 | 109.546 | 80.827 | 5.674 |
| 496 | C | THR | 66 | 108.125 | 80.458 | 5.226 |
| 497 | O | THR | 66 | 107.143 | 81.105 | 5.612 |
| 498 | CB | THR | 66 | 109.787 | 82.336 | 5.626 |
| 499 | OG1 | THR | 66 | 108.960 | 82.976 | 6.590 |
| 500 | CG2 | THR | 66 | 109.499 | 82.932 | 4.250 |
| 501 | N | LYS | 67 | 108.039 | 79.413 | 4.414 |
| 502 | CA | LYS | 67 | 106.775 | 78.990 | 3.791 |
| 503 | C | LYS | 67 | 105.694 | 78.621 | 4.808 |
| 504 | O | LYS | 67 | 105.974 | 78.192 | 5.934 |
| 505 | CB | LYS | 67 | 107.058 | 77.831 | 2.843 |
| 506 | CG | LYS | 67 | 106.530 | 78.124 | 1.444 |
| 507 | CD | LYS | 67 | 107.093 | 79.440 | 0.917 |
| 508 | CE | LYS | 67 | 106.606 | 79.744 | −0.492 |
| 509 | NZ | LYS | 67 | 107.174 | 81.013 | −0.976 |
| 510 | N | VAL | 68 | 104.465 | 78.660 | 4.317 |
| 511 | CA | VAL | 68 | 103.250 | 78.705 | 5.148 |
| 512 | C | VAL | 68 | 102.816 | 77.397 | 5.830 |
| 513 | O | VAL | 68 | 102.077 | 77.465 | 6.823 |
| 514 | CB | VAL | 68 | 102.153 | 79.205 | 4.195 |
| 515 | CG1 | VAL | 68 | 102.157 | 78.433 | 2.875 |
| 516 | CG2 | VAL | 68 | 100.753 | 79.218 | 4.812 |
| 517 | N | ASN | 69 | 103.414 | 76.269 | 5.495 |
| 518 | CA | ASN | 69 | 102.895 | 75.015 | 6.042 |
| 519 | C | ASN | 69 | 103.658 | 74.516 | 7.271 |
| 520 | O | ASN | 69 | 104.317 | 73.468 | 7.260 |
| 521 | CB | ASN | 69 | 102.884 | 73.967 | 4.950 |
| 522 | CG | ASN | 69 | 101.739 | 74.138 | 3.959 |
| 523 | OD1 | ASN | 69 | 101.368 | 75.248 | 3.556 |
| 524 | ND2 | ASN | 69 | 101.184 | 73.000 | 3.582 |
| 525 | N | LYS | 70 | 103.403 | 75.197 | 8.375 |
| 526 | CA | LYS | 70 | 103.989 | 74.856 | 9.681 |
| 527 | C | LYS | 70 | 102.951 | 74.225 | 10.617 |
| 528 | O | LYS | 70 | 102.887 | 74.550 | 11.810 |
| 529 | CB | LYS | 70 | 104.525 | 76.150 | 10.281 |
| 530 | CG | LYS | 70 | 103.444 | 77.226 | 10.317 |
| 531 | CD | LYS | 70 | 103.984 | 78.548 | 10.848 |
| 532 | CE | LYS | 70 | 105.005 | 79.158 | 9.893 |
| 533 | NZ | LYS | 70 | 104.381 | 79.501 | 8.603 |
| 534 | N | VAL | 71 | 102.182 | 73.290 | 10.083 |
| 535 | CA | VAL | 71 | 101.002 | 72.775 | 10.796 |
| 536 | C | VAL | 71 | 101.333 | 71.931 | 12.031 |
| 537 | O | VAL | 71 | 101.953 | 70.863 | 11.979 |
| 538 | CB | VAL | 71 | 100.129 | 72.018 | 9.798 |
| 539 | CG1 | VAL | 71 | 99.320 | 72.990 | 8.946 |
| 540 | CG2 | VAL | 71 | 100.952 | 71.090 | 8.913 |
| 541 | N | GLU | 72 | 100.898 | 72.466 | 13.161 |
| 542 | CA | GLU | 72 | 101.145 | 71.849 | 14.469 |
| 543 | C | GLU | 72 | 99.968 | 70.998 | 14.937 |
| 544 | O | GLU | 72 | 98.804 | 71.296 | 14.646 |
| 545 | CB | GLU | 72 | 101.428 | 72.958 | 15.478 |
| 546 | CG | GLU | 72 | 102.670 | 73.770 | 15.105 |
| 547 | CD | GLU | 72 | 103.947 | 72.947 | 15.276 |
| 548 | OE1 | GLU | 72 | 103.841 | 71.838 | 15.787 |
| 549 | OE2 | GLU | 72 | 105.014 | 73.511 | 15.078 |
| 550 | N | PHE | 73 | 100.296 | 69.975 | 15.708 |
| 551 | CA | PHE | 73 | 99.303 | 68.980 | 16.145 |
| 552 | C | PHE | 73 | 99.807 | 68.146 | 17.325 |
| 553 | O | PHE | 73 | 101.008 | 67.889 | 17.471 |
| 554 | CB | PHE | 73 | 98.899 | 68.076 | 14.973 |

TABLE 8-continued

| Atom No. | Atom Type | Residue | Residue Position | X Coord. | Y Coord. | Z Coord. |
|---|---|---|---|---|---|---|
| 555 | CG | PHE | 73 | 99.943 | 67.173 | 14.292 |
| 556 | CD1 | PHE | 73 | 101.267 | 67.563 | 14.117 |
| 557 | CD2 | PHE | 73 | 99.524 | 65.950 | 13.792 |
| 558 | CE1 | PHE | 73 | 102.170 | 66.715 | 13.489 |
| 559 | CE2 | PHE | 73 | 100.422 | 65.102 | 13.165 |
| 560 | CZ | PHE | 73 | 101.746 | 65.478 | 13.019 |
| 561 | N | ASP | 74 | 98.866 | 67.729 | 18.154 |
| 562 | CA | ASP | 74 | 99.170 | 66.985 | 19.384 |
| 563 | C | ASP | 74 | 99.292 | 65.492 | 19.105 |
| 564 | O | ASP | 74 | 98.605 | 64.964 | 18.223 |
| 565 | CB | ASP | 74 | 98.024 | 67.205 | 20.369 |
| 566 | CG | ASP | 74 | 97.831 | 68.692 | 20.654 |
| 567 | OD1 | ASP | 74 | 96.690 | 69.133 | 20.648 |
| 568 | OD2 | ASP | 74 | 98.835 | 69.375 | 20.809 |
| 569 | N | TYR | 75 | 100.182 | 64.829 | 19.822 |
| 570 | CA | TYR | 75 | 100.303 | 63.371 | 19.688 |
| 571 | C | TYR | 75 | 99.831 | 62.653 | 20.950 |
| 572 | O | TYR | 75 | 99.883 | 63.204 | 22.056 |
| 573 | CB | TYR | 75 | 101.742 | 62.977 | 19.356 |
| 574 | CG | TYR | 75 | 102.800 | 63.152 | 20.448 |
| 575 | CD1 | TYR | 75 | 103.479 | 64.357 | 20.584 |
| 576 | CD2 | TYR | 75 | 103.107 | 62.084 | 21.284 |
| 577 | CE1 | TYR | 75 | 104.445 | 64.503 | 21.572 |
| 578 | CE2 | TYR | 75 | 104.072 | 62.228 | 22.272 |
| 579 | CZ | TYR | 75 | 104.736 | 63.439 | 22.414 |
| 580 | OH | TYR | 75 | 105.688 | 63.585 | 23.399 |
| 581 | N | LEU | 76 | 99.317 | 61.451 | 20.755 |
| 582 | CA | LEU | 76 | 98.848 | 60.625 | 21.873 |
| 583 | C | LEU | 76 | 99.269 | 59.166 | 21.674 |
| 584 | O | LEU | 76 | 98.985 | 58.550 | 20.639 |
| 585 | CB | LEU | 76 | 97.326 | 60.783 | 21.943 |
| 586 | CG | LEU | 76 | 96.674 | 60.217 | 23.206 |
| 587 | CD1 | LEU | 76 | 95.406 | 60.986 | 23.554 |
| 588 | CD2 | LEU | 76 | 96.379 | 58.726 | 23.103 |
| 589 | N | LEU | 77 | 99.940 | 58.619 | 22.671 |
| 590 | CA | LEU | 77 | 100.364 | 57.217 | 22.597 |
| 591 | C | LEU | 77 | 99.232 | 56.275 | 22.987 |
| 592 | O | LEU | 77 | 98.761 | 56.283 | 24.129 |
| 593 | CB | LEU | 77 | 101.531 | 56.997 | 23.546 |
| 594 | CG | LEU | 77 | 102.737 | 57.836 | 23.151 |
| 595 | CD1 | LEU | 77 | 103.848 | 57.673 | 24.181 |
| 596 | CD2 | LEU | 77 | 103.223 | 57.464 | 21.754 |
| 597 | N | VAL | 78 | 98.832 | 55.439 | 22.046 |
| 598 | CA | VAL | 78 | 97.774 | 54.467 | 22.336 |
| 599 | C | VAL | 78 | 98.002 | 53.153 | 21.593 |
| 600 | O | VAL | 78 | 98.177 | 53.088 | 20.369 |
| 601 | CB | VAL | 78 | 96.398 | 55.058 | 22.021 |
| 602 | CG1 | VAL | 78 | 96.198 | 55.289 | 20.532 |
| 603 | CG2 | VAL | 78 | 95.276 | 54.175 | 22.557 |
| 604 | N | ASP | 79 | 98.063 | 52.100 | 22.383 |
| 605 | CA | ASP | 79 | 98.191 | 50.758 | 21.816 |
| 606 | C | ASP | 79 | 96.799 | 50.248 | 21.465 |
| 607 | O | ASP | 79 | 95.998 | 49.953 | 22.360 |
| 608 | CB | ASP | 79 | 98.900 | 49.834 | 22.801 |
| 609 | CG | ASP | 79 | 99.139 | 48.476 | 22.146 |
| 610 | OD1 | ASP | 79 | 98.187 | 47.701 | 22.131 |
| 611 | OD2 | ASP | 79 | 100.131 | 48.355 | 21.449 |
| 612 | N | PHE | 80 | 96.643 | 49.881 | 20.202 |
| 613 | CA | PHE | 80 | 95.324 | 49.584 | 19.620 |
| 614 | C | PHE | 80 | 94.715 | 48.234 | 20.035 |
| 615 | O | PHE | 80 | 93.532 | 47.992 | 19.778 |
| 616 | CB | PHE | 80 | 95.526 | 49.607 | 18.108 |
| 617 | CG | PHE | 80 | 94.263 | 49.770 | 17.271 |
| 618 | CD1 | PHE | 80 | 93.423 | 50.853 | 17.492 |
| 619 | CD2 | PHE | 80 | 93.966 | 48.852 | 16.273 |
| 620 | CE1 | PHE | 80 | 92.279 | 51.014 | 16.722 |
| 621 | CE2 | PHE | 80 | 92.822 | 49.013 | 15.504 |
| 622 | CZ | PHE | 80 | 91.980 | 50.094 | 15.727 |
| 623 | N | THR | 81 | 95.486 | 47.385 | 20.695 |
| 624 | CA | THR | 81 | 94.955 | 46.110 | 21.190 |
| 625 | C | THR | 81 | 94.863 | 46.114 | 22.715 |
| 626 | O | THR | 81 | 94.475 | 45.110 | 23.325 |
| 627 | CB | THR | 81 | 95.899 | 44.988 | 20.777 |
| 628 | OG1 | THR | 81 | 97.084 | 45.101 | 21.554 |
| 629 | CG2 | THR | 81 | 96.274 | 45.072 | 19.304 |
| 630 | N | ASP | 82 | 95.280 | 47.208 | 23.326 |
| 631 | CA | ASP | 82 | 95.387 | 47.252 | 24.782 |
| 632 | C | ASP | 82 | 94.319 | 48.167 | 25.371 |
| 633 | O | ASP | 82 | 94.459 | 49.396 | 25.339 |
| 634 | CB | ASP | 82 | 96.791 | 47.759 | 25.107 |
| 635 | CG | ASP | 82 | 97.175 | 47.561 | 26.572 |
| 636 | OD1 | ASP | 82 | 96.366 | 47.903 | 27.426 |
| 637 | OD2 | ASP | 82 | 98.337 | 47.272 | 26.805 |
| 638 | N | MET | 83 | 93.448 | 47.566 | 26.167 |
| 639 | CA | MET | 83 | 92.316 | 48.296 | 26.752 |
| 640 | C | MET | 83 | 92.726 | 49.307 | 27.825 |
| 641 | O | MET | 83 | 92.173 | 50.411 | 27.831 |
| 642 | CB | MET | 83 | 91.374 | 47.277 | 27.378 |
| 643 | CG | MET | 83 | 90.910 | 46.246 | 26.357 |
| 644 | SD | MET | 83 | 89.797 | 44.977 | 27.001 |
| 645 | CE | MET | 83 | 88.450 | 46.045 | 27.560 |
| 646 | N | VAL | 84 | 93.859 | 49.084 | 28.473 |
| 647 | CA | VAL | 84 | 94.337 | 50.025 | 29.492 |
| 648 | C | VAL | 84 | 95.044 | 51.217 | 28.848 |
| 649 | O | VAL | 84 | 94.928 | 52.345 | 29.341 |
| 650 | CB | VAL | 84 | 95.302 | 49.282 | 30.411 |
| 651 | CG1 | VAL | 84 | 95.840 | 50.193 | 31.510 |
| 652 | CG2 | VAL | 84 | 94.632 | 48.055 | 31.018 |
| 653 | N | SER | 85 | 95.475 | 51.026 | 27.612 |
| 654 | CA | SER | 85 | 96.097 | 52.112 | 26.861 |
| 655 | C | SER | 85 | 95.021 | 52.939 | 26.162 |
| 656 | O | SER | 85 | 95.185 | 54.152 | 25.986 |
| 657 | CB | SER | 85 | 97.047 | 51.500 | 25.844 |
| 658 | OG | SER | 85 | 97.690 | 52.560 | 25.158 |
| 659 | N | ILE | 86 | 93.855 | 52.335 | 25.996 |
| 660 | CA | ILE | 86 | 92.686 | 53.061 | 25.496 |
| 661 | C | ILE | 86 | 92.027 | 53.848 | 26.630 |
| 662 | O | ILE | 86 | 91.561 | 54.970 | 26.401 |
| 663 | CB | ILE | 86 | 91.714 | 52.045 | 24.900 |
| 664 | CG1 | ILE | 86 | 92.355 | 51.328 | 23.715 |
| 665 | CG2 | ILE | 86 | 90.407 | 52.710 | 24.478 |
| 666 | CD1 | ILE | 86 | 91.426 | 50.274 | 23.123 |
| 667 | N | LEU | 87 | 92.252 | 53.406 | 27.860 |
| 668 | CA | LEU | 87 | 91.808 | 54.169 | 29.034 |
| 669 | C | LEU | 87 | 92.754 | 55.335 | 29.311 |
| 670 | O | LEU | 87 | 92.306 | 56.406 | 29.742 |
| 671 | CB | LEU | 87 | 91.803 | 53.253 | 30.253 |
| 672 | CG | LEU | 87 | 90.837 | 52.084 | 30.101 |
| 673 | CD1 | LEU | 87 | 91.009 | 51.080 | 31.235 |
| 674 | CD2 | LEU | 87 | 89.393 | 52.562 | 30.018 |
| 675 | N | SER | 88 | 93.989 | 55.200 | 28.856 |
| 676 | CA | SER | 88 | 94.959 | 56.292 | 28.964 |
| 677 | C | SER | 88 | 94.628 | 57.378 | 27.952 |
| 678 | O | SER | 88 | 94.492 | 58.548 | 28.337 |
| 679 | CB | SER | 88 | 96.353 | 55.745 | 28.682 |
| 680 | OG | SER | 88 | 96.615 | 54.705 | 29.614 |
| 681 | N | ALA | 89 | 94.223 | 56.954 | 26.764 |
| 682 | CA | ALA | 89 | 93.771 | 57.894 | 25.733 |
| 683 | C | ALA | 89 | 92.504 | 58.622 | 26.171 |
| 684 | O | ALA | 89 | 92.483 | 59.861 | 26.166 |
| 685 | CB | ALA | 89 | 93.475 | 57.106 | 24.462 |
| 686 | N | TYR | 90 | 91.609 | 57.875 | 26.799 |
| 687 | CA | TYR | 90 | 90.368 | 58.421 | 27.354 |
| 688 | C | TYR | 90 | 90.638 | 59.532 | 28.366 |
| 689 | O | TYR | 90 | 90.331 | 60.694 | 28.065 |
| 690 | CB | TYR | 90 | 89.631 | 57.270 | 28.034 |
| 691 | CG | TYR | 90 | 88.319 | 57.646 | 28.712 |
| 692 | CD1 | TYR | 90 | 88.261 | 57.799 | 30.092 |
| 693 | CD2 | TYR | 90 | 87.176 | 57.812 | 27.945 |
| 694 | CE1 | TYR | 90 | 87.061 | 58.145 | 30.703 |
| 695 | CE2 | TYR | 90 | 85.977 | 58.155 | 28.554 |
| 696 | CZ | TYR | 90 | 85.924 | 58.325 | 29.928 |
| 697 | OH | TYR | 90 | 84.744 | 58.722 | 30.519 |
| 698 | N | TYR | 91 | 91.493 | 59.248 | 29.338 |
| 699 | CA | TYR | 91 | 91.772 | 60.218 | 30.402 |
| 700 | C | TYR | 91 | 92.566 | 61.434 | 29.924 |
| 701 | O | TYR | 91 | 92.260 | 62.555 | 30.351 |
| 702 | CB | TYR | 91 | 92.552 | 59.510 | 31.506 |
| 703 | CG | TYR | 91 | 93.028 | 60.440 | 32.620 |
| 704 | CD1 | TYR | 91 | 92.110 | 61.002 | 33.499 |
| 705 | CD2 | TYR | 91 | 94.382 | 60.732 | 32.748 |
| 706 | CE1 | TYR | 91 | 92.543 | 61.854 | 34.505 |

TABLE 8-continued

| Atom No. | Atom Type | Residue | Residue Position | X Coord. | Y Coord. | Z Coord. |
|---|---|---|---|---|---|---|
| 707 | CE2 | TYR | 91 | 94.817 | 61.585 | 33.754 |
| 708 | CZ | TYR | 91 | 93.895 | 62.144 | 34.629 |
| 709 | OH | TYR | 91 | 94.323 | 63.007 | 35.613 |
| 710 | N | GLU | 92 | 93.378 | 61.267 | 28.893 |
| 711 | CA | GLU | 92 | 94.135 | 62.405 | 28.364 |
| 712 | C | GLU | 92 | 93.228 | 63.356 | 27.592 |
| 713 | O | GLU | 92 | 93.244 | 64.563 | 27.866 |
| 714 | CB | GLU | 92 | 95.223 | 61.870 | 27.443 |
| 715 | CG | GLU | 92 | 96.227 | 61.025 | 28.218 |
| 716 | CD | GLU | 92 | 97.142 | 60.272 | 27.257 |
| 717 | OE1 | GLU | 92 | 97.630 | 60.896 | 26.324 |
| 718 | OE2 | GLU | 92 | 97.363 | 59.089 | 27.486 |
| 719 | N | LEU | 93 | 92.242 | 62.799 | 26.911 |
| 720 | CA | LEU | 93 | 91.314 | 63.633 | 26.151 |
| 721 | C | LEU | 93 | 90.253 | 64.247 | 27.057 |
| 722 | O | LEU | 93 | 89.965 | 65.443 | 26.910 |
| 723 | CB | LEU | 93 | 90.688 | 62.769 | 25.068 |
| 724 | CG | LEU | 93 | 91.769 | 62.330 | 24.086 |
| 725 | CD1 | LEU | 93 | 91.321 | 61.171 | 23.206 |
| 726 | CD2 | LEU | 93 | 92.263 | 63.505 | 23.249 |
| 727 | N | ASN | 94 | 89.971 | 63.583 | 28.167 |
| 728 | CA | ASN | 94 | 89.051 | 64.142 | 29.164 |
| 729 | C | ASN | 94 | 89.678 | 65.279 | 29.965 |
| 730 | O | ASN | 94 | 88.978 | 66.243 | 30.297 |
| 731 | CB | ASN | 94 | 88.639 | 63.044 | 30.139 |
| 732 | CG | ASN | 94 | 87.589 | 62.134 | 29.516 |
| 733 | OD1 | ASN | 94 | 87.788 | 60.922 | 29.374 |
| 734 | ND2 | ASN | 94 | 86.453 | 62.731 | 29.205 |
| 735 | N | LYS | 95 | 90.996 | 65.284 | 30.062 |
| 736 | CA | LYS | 95 | 91.680 | 66.325 | 30.824 |
| 737 | C | LYS | 95 | 92.072 | 67.528 | 29.960 |
| 738 | O | LYS | 95 | 92.358 | 68.604 | 30.502 |
| 739 | CB | LYS | 95 | 92.924 | 65.676 | 31.426 |
| 740 | CG | LYS | 95 | 93.585 | 66.538 | 32.494 |
| 741 | CD | LYS | 95 | 94.823 | 65.847 | 33.051 |
| 742 | CE | LYS | 95 | 95.487 | 66.680 | 34.141 |
| 743 | NZ | LYS | 95 | 96.711 | 66.025 | 34.628 |
| 744 | N | ARG | 96 | 92.049 | 67.361 | 28.646 |
| 745 | CA | ARG | 96 | 92.482 | 68.449 | 27.759 |
| 746 | C | ARG | 96 | 91.367 | 69.046 | 26.895 |
| 747 | O | ARG | 96 | 91.602 | 70.072 | 26.244 |
| 748 | CB | ARG | 96 | 93.578 | 67.914 | 26.843 |
| 749 | CG | ARG | 96 | 94.782 | 67.410 | 27.632 |
| 750 | CD | ARG | 96 | 95.437 | 68.522 | 28.443 |
| 751 | NE | ARG | 96 | 96.531 | 67.983 | 29.264 |
| 752 | CZ | ARG | 96 | 96.708 | 68.308 | 30.546 |
| 753 | NH1 | ARG | 96 | 95.879 | 69.171 | 31.135 |
| 754 | NH2 | ARG | 96 | 97.720 | 67.776 | 31.235 |
| 755 | N | TYR | 97 | 90.240 | 68.357 | 26.781 |
| 756 | CA | TYR | 97 | 89.116 | 68.857 | 25.965 |
| 757 | C | TYR | 97 | 87.775 | 68.472 | 26.576 |
| 758 | O | TYR | 97 | 86.725 | 69.004 | 26.180 |
| 759 | CB | TYR | 97 | 89.170 | 68.216 | 24.580 |
| 760 | CG | TYR | 97 | 90.472 | 68.420 | 23.816 |
| 761 | CD1 | TYR | 97 | 90.771 | 69.666 | 23.285 |
| 762 | CD2 | TYR | 97 | 91.357 | 67.360 | 23.660 |
| 763 | CE1 | TYR | 97 | 91.965 | 69.857 | 22.603 |
| 764 | CE2 | TYR | 97 | 92.550 | 67.550 | 22.975 |
| 765 | CZ | TYR | 97 | 92.850 | 68.799 | 22.451 |
| 766 | OH | TYR | 97 | 94.041 | 68.994 | 21.789 |
| 767 | N | LYS | 98 | 87.827 | 67.341 | 27.266 |
| 768 | CA | LYS | 98 | 86.706 | 66.693 | 27.980 |
| 769 | C | LYS | 98 | 85.762 | 65.900 | 27.063 |
| 770 | O | LYS | 98 | 85.142 | 64.922 | 27.505 |
| 771 | CB | LYS | 98 | 85.925 | 67.738 | 28.769 |
| 772 | CG | LYS | 98 | 84.921 | 67.091 | 29.711 |
| 773 | CD | LYS | 98 | 85.623 | 66.210 | 30.735 |
| 774 | CE | LYS | 98 | 84.611 | 65.475 | 31.603 |
| 775 | NZ | LYS | 98 | 83.716 | 66.428 | 32.276 |
| 776 | N | HIS | 99 | 85.690 | 66.279 | 25.800 |
| 777 | CA | HIS | 99 | 84.854 | 65.566 | 24.836 |
| 778 | C | HIS | 99 | 85.698 | 65.139 | 23.648 |
| 779 | O | HIS | 99 | 86.914 | 65.363 | 23.617 |
| 780 | CB | HIS | 99 | 83.758 | 66.507 | 24.341 |
| 781 | CG | HIS | 99 | 83.036 | 67.263 | 25.439 |
| 782 | ND1 | HIS | 99 | 82.392 | 66.738 | 26.500 |
| 783 | CD2 | HIS | 99 | 82.926 | 68.631 | 25.541 |
| 784 | CE1 | HIS | 99 | 81.886 | 67.736 | 27.251 |
| 785 | NE2 | HIS | 99 | 82.217 | 68.907 | 26.658 |
| 786 | N | ILE | 100 | 85.065 | 64.400 | 22.755 |
| 787 | CA | ILE | 100 | 85.660 | 64.060 | 21.459 |
| 788 | C | ILE | 100 | 84.602 | 64.278 | 20.388 |
| 789 | O | ILE | 100 | 83.589 | 63.571 | 20.338 |
| 790 | CB | ILE | 100 | 86.162 | 62.617 | 21.448 |
| 791 | CG1 | ILE | 100 | 87.331 | 62.445 | 22.411 |
| 792 | CG2 | ILE | 100 | 86.579 | 62.189 | 20.044 |
| 793 | CD1 | ILE | 100 | 87.928 | 61.050 | 22.320 |
| 794 | N | ASP | 101 | 84.819 | 65.279 | 19.551 |
| 795 | CA | ASP | 101 | 83.794 | 65.618 | 18.565 |
| 796 | C | ASP | 101 | 84.046 | 64.852 | 17.280 |
| 797 | O | ASP | 101 | 83.106 | 64.441 | 16.591 |
| 798 | CB | ASP | 101 | 83.844 | 67.115 | 18.282 |
| 799 | CG | ASP | 101 | 83.682 | 67.902 | 19.579 |
| 800 | OD1 | ASP | 101 | 84.566 | 68.706 | 19.850 |
| 801 | OD2 | ASP | 101 | 82.841 | 67.512 | 20.380 |
| 802 | N | TYR | 102 | 85.311 | 64.575 | 17.024 |
| 803 | CA | TYR | 102 | 85.665 | 63.801 | 15.837 |
| 804 | C | TYR | 102 | 86.571 | 62.624 | 16.191 |
| 805 | O | TYR | 102 | 87.640 | 62.809 | 16.789 |
| 806 | CB | TYR | 102 | 86.364 | 64.739 | 14.859 |
| 807 | CG | TYR | 102 | 85.493 | 65.865 | 14.309 |
| 808 | CD1 | TYR | 102 | 85.950 | 67.176 | 14.338 |
| 809 | CD2 | TYR | 102 | 84.240 | 65.578 | 13.783 |
| 810 | CE1 | TYR | 102 | 85.155 | 68.200 | 13.835 |
| 811 | CE2 | TYR | 102 | 83.444 | 66.599 | 13.284 |
| 812 | CZ | TYR | 102 | 83.905 | 67.907 | 13.308 |
| 813 | OH | TYR | 102 | 83.139 | 68.909 | 12.753 |
| 814 | N | LEU | 103 | 86.135 | 61.427 | 15.834 |
| 815 | CA | LEU | 103 | 86.965 | 60.227 | 16.040 |
| 816 | C | LEU | 103 | 87.226 | 59.521 | 14.704 |
| 817 | O | LEU | 103 | 86.334 | 59.402 | 13.858 |
| 818 | CB | LEU | 103 | 86.270 | 59.285 | 17.019 |
| 819 | CG | LEU | 103 | 87.140 | 58.077 | 17.356 |
| 820 | CD1 | LEU | 103 | 88.428 | 58.505 | 18.049 |
| 821 | CD2 | LEU | 103 | 86.384 | 57.067 | 18.205 |
| 822 | N | PHE | 104 | 88.476 | 59.159 | 14.479 |
| 823 | CA | PHE | 104 | 88.873 | 58.537 | 13.220 |
| 824 | C | PHE | 104 | 89.514 | 57.163 | 13.423 |
| 825 | O | PHE | 104 | 90.667 | 57.066 | 13.860 |
| 826 | CB | PHE | 104 | 89.899 | 59.481 | 12.617 |
| 827 | CG | PHE | 104 | 90.113 | 59.326 | 11.126 |
| 828 | CD1 | PHE | 104 | 89.744 | 60.364 | 10.284 |
| 829 | CD2 | PHE | 104 | 90.680 | 58.171 | 10.608 |
| 830 | CE1 | PHE | 104 | 89.930 | 60.240 | 8.917 |
| 831 | CE2 | PHE | 104 | 90.864 | 58.045 | 9.242 |
| 832 | CZ | PHE | 104 | 90.487 | 59.079 | 8.400 |
| 833 | N | ILE | 105 | 88.822 | 56.121 | 13.001 |
| 834 | CA | ILE | 105 | 89.388 | 54.771 | 13.084 |
| 835 | C | ILE | 105 | 89.999 | 54.370 | 11.741 |
| 836 | O | ILE | 105 | 89.305 | 54.100 | 10.751 |
| 837 | CB | ILE | 105 | 88.308 | 53.787 | 13.506 |
| 838 | CG1 | ILE | 105 | 87.659 | 54.228 | 14.813 |
| 839 | CG2 | ILE | 105 | 88.912 | 52.398 | 13.684 |
| 840 | CD1 | ILE | 105 | 88.619 | 54.104 | 15.992 |
| 841 | N | ASN | 106 | 91.320 | 54.363 | 11.750 |
| 842 | CA | ASN | 106 | 92.129 | 54.080 | 10.559 |
| 843 | C | ASN | 106 | 93.088 | 52.913 | 10.780 |
| 844 | O | ASN | 106 | 93.343 | 52.137 | 9.850 |
| 845 | CB | ASN | 106 | 92.907 | 55.354 | 10.231 |
| 846 | CG | ASN | 106 | 94.166 | 55.089 | 9.406 |
| 847 | OD1 | ASN | 106 | 94.114 | 54.689 | 8.237 |
| 848 | ND2 | ASN | 106 | 95.295 | 55.346 | 10.042 |
| 849 | N | ALA | 107 | 93.516 | 52.730 | 12.020 |
| 850 | CA | ALA | 107 | 94.500 | 51.675 | 12.320 |
| 851 | C | ALA | 107 | 93.962 | 50.266 | 12.052 |
| 852 | O | ALA | 107 | 92.876 | 49.912 | 12.526 |
| 853 | CB | ALA | 107 | 94.916 | 51.798 | 13.780 |
| 854 | N | ALA | 108 | 94.724 | 49.491 | 11.291 |
| 855 | CA | ALA | 108 | 94.349 | 48.102 | 10.964 |
| 856 | C | ALA | 108 | 95.503 | 47.316 | 10.326 |
| 857 | O | ALA | 108 | 96.252 | 47.850 | 9.500 |
| 858 | CB | ALA | 108 | 93.172 | 48.128 | 9.995 |

TABLE 8-continued

| Atom No. | Atom Type | Residue | Residue Position | X Coord. | Y Coord. | Z Coord. |
|---|---|---|---|---|---|---|
| 859 | N | GLN | 109 | 95.624 | 46.053 | 10.706 |
| 860 | CA | GLN | 109 | 96.628 | 45.145 | 10.116 |
| 861 | C | GLN | 109 | 96.222 | 44.652 | 8.728 |
| 862 | O | GLN | 109 | 95.029 | 44.589 | 8.399 |
| 863 | CB | GLN | 109 | 96.761 | 43.908 | 10.991 |
| 864 | CG | GLN | 109 | 97.253 | 44.203 | 12.399 |
| 865 | CD | GLN | 109 | 97.059 | 42.934 | 13.219 |
| 866 | OE1 | GLN | 109 | 98.009 | 42.346 | 13.748 |
| 867 | NE2 | GLN | 109 | 95.817 | 42.491 | 13.245 |
| 868 | N | GLY | 110 | 97.217 | 44.202 | 7.979 |
| 869 | CA | GLY | 110 | 96.990 | 43.640 | 6.641 |
| 870 | C | GLY | 110 | 97.864 | 42.411 | 6.376 |
| 871 | O | GLY | 110 | 99.064 | 42.534 | 6.105 |
| 872 | N | VAL | 111 | 97.253 | 41.238 | 6.448 |
| 873 | CA | VAL | 111 | 97.985 | 39.985 | 6.200 |
| 874 | C | VAL | 111 | 98.128 | 39.713 | 4.705 |
| 875 | O | VAL | 111 | 97.141 | 39.513 | 3.988 |
| 876 | CB | VAL | 111 | 97.252 | 38.830 | 6.876 |
| 877 | CG1 | VAL | 111 | 97.869 | 37.482 | 6.516 |
| 878 | CG2 | VAL | 111 | 97.243 | 39.018 | 8.387 |
| 879 | N | TYR | 112 | 99.369 | 39.750 | 4.251 |
| 880 | CA | TYR | 112 | 99.674 | 39.524 | 2.837 |
| 881 | C | TYR | 112 | 99.713 | 38.037 | 2.523 |
| 882 | O | TYR | 112 | 100.270 | 37.240 | 3.292 |
| 883 | CB | TYR | 112 | 101.014 | 40.179 | 2.532 |
| 884 | CG | TYR | 112 | 101.031 | 41.635 | 2.976 |
| 885 | CD1 | TYR | 112 | 101.982 | 42.075 | 3.889 |
| 886 | CD2 | TYR | 112 | 100.086 | 42.517 | 2.468 |
| 887 | CE1 | TYR | 112 | 101.968 | 43.397 | 4.315 |
| 888 | CE2 | TYR | 112 | 100.071 | 43.836 | 2.894 |
| 889 | CZ | TYR | 112 | 101.005 | 44.268 | 3.824 |
| 890 | OH | TYR | 112 | 100.888 | 45.523 | 4.366 |
| 891 | N | GLY | 113 | 99.153 | 37.709 | 1.369 |
| 892 | CA | GLY | 113 | 99.019 | 36.328 | 0.890 |
| 893 | C | GLY | 113 | 100.308 | 35.531 | 1.000 |
| 894 | O | GLY | 113 | 101.399 | 36.036 | 0.696 |
| 895 | N | GLY | 114 | 100.163 | 34.354 | 1.587 |
| 896 | CA | GLY | 114 | 101.280 | 33.429 | 1.804 |
| 897 | C | GLY | 114 | 102.421 | 34.110 | 2.544 |
| 898 | O | GLY | 114 | 103.470 | 34.360 | 1.939 |
| 899 | N | ILE | 115 | 102.143 | 34.501 | 3.781 |
| 900 | CA | ILE | 115 | 103.098 | 35.183 | 4.681 |
| 901 | C | ILE | 115 | 104.011 | 36.173 | 3.954 |
| 902 | O | ILE | 115 | 105.104 | 35.822 | 3.501 |
| 903 | CB | ILE | 115 | 103.909 | 34.118 | 5.425 |
| 904 | CG1 | ILE | 115 | 102.987 | 33.262 | 6.283 |
| 905 | CG2 | ILE | 115 | 104.972 | 34.748 | 6.320 |
| 906 | CD1 | ILE | 115 | 102.364 | 34.104 | 7.391 |
| 907 | N | ASP | 116 | 103.524 | 37.397 | 3.813 |
| 908 | CA | ASP | 116 | 104.239 | 38.492 | 3.121 |
| 909 | C | ASP | 116 | 104.863 | 38.079 | 1.784 |
| 910 | O | ASP | 116 | 106.075 | 38.222 | 1.580 |
| 911 | CB | ASP | 116 | 105.277 | 39.173 | 4.034 |
| 912 | CG | ASP | 116 | 106.383 | 38.264 | 4.582 |
| 913 | OD1 | ASP | 116 | 106.189 | 37.770 | 5.683 |
| 914 | OD2 | ASP | 116 | 107.475 | 38.303 | 4.026 |
| 915 | N | TRP | 117 | 104.001 | 37.634 | 0.877 |
| 916 | CA | TRP | 117 | 104.351 | 37.325 | −0.523 |
| 917 | C | TRP | 117 | 105.541 | 36.372 | −0.640 |
| 918 | O | TRP | 117 | 106.483 | 36.673 | −1.383 |
| 919 | CB | TRP | 117 | 104.734 | 38.604 | −1.280 |
| 920 | CG | TRP | 117 | 104.127 | 39.915 | −0.806 |
| 921 | CD1 | TRP | 117 | 102.835 | 40.362 | −0.976 |
| 922 | CD2 | TRP | 117 | 104.831 | 40.955 | −0.092 |
| 923 | NE1 | TRP | 117 | 102.722 | 41.579 | −0.384 |
| 924 | CE2 | TRP | 117 | 103.887 | 41.963 | 0.171 |
| 925 | CE3 | TRP | 117 | 106.137 | 41.088 | 0.353 |
| 926 | CZ2 | TRP | 117 | 104.261 | 43.079 | 0.903 |
| 927 | CZ3 | TRP | 117 | 106.506 | 42.214 | 1.077 |
| 928 | CH2 | TRP | 117 | 105.569 | 43.205 | 1.354 |
| 929 | N | THR | 118 | 105.515 | 35.252 | 0.062 |
| 930 | CA | THR | 118 | 106.665 | 34.343 | 0.000 |
| 931 | C | THR | 118 | 106.358 | 33.046 | −0.736 |
| 932 | O | THR | 118 | 105.476 | 32.967 | −1.599 |
| 933 | CB | THR | 118 | 107.203 | 34.048 | 1.398 |
| 934 | OG1 | THR | 118 | 106.163 | 33.515 | 2.207 |

TABLE 8-continued

| Atom No. | Atom Type | Residue | Residue Position | X Coord. | Y Coord. | Z Coord. |
|---|---|---|---|---|---|---|
| 935 | CG2 | THR | 118 | 107.738 | 35.310 | 2.067 |
| 936 | N | GLY | 119 | 107.196 | 32.063 | −0.460 |
| 937 | CA | GLY | 119 | 107.144 | 30.780 | −1.166 |
| 938 | C | GLY | 119 | 108.479 | 30.562 | −1.872 |
| 939 | O | GLY | 119 | 109.538 | 30.707 | −1.248 |
| 940 | N | ALA | 120 | 108.425 | 30.485 | −3.194 |
| 941 | CA | ALA | 120 | 109.630 | 30.293 | −4.031 |
| 942 | C | ALA | 120 | 110.400 | 31.591 | −4.332 |
| 943 | O | ALA | 120 | 111.066 | 31.703 | −5.367 |
| 944 | CB | ALA | 120 | 109.210 | 29.634 | −5.341 |
| 945 | N | VAL | 121 | 110.307 | 32.549 | −3.423 |
| 946 | CA | VAL | 121 | 110.858 | 33.889 | −3.627 |
| 947 | C | VAL | 121 | 112.146 | 34.116 | −2.828 |
| 948 | O | VAL | 121 | 112.917 | 35.036 | −3.127 |
| 949 | CB | VAL | 121 | 109.781 | 34.863 | −3.142 |
| 950 | CG1 | VAL | 121 | 110.149 | 36.320 | −3.401 |
| 951 | CG2 | VAL | 121 | 108.431 | 34.548 | −3.777 |
| 952 | N | LEU | 122 | 112.410 | 33.249 | −1.864 |
| 953 | CA | LEU | 122 | 113.513 | 33.515 | −0.928 |
| 954 | C | LEU | 122 | 114.776 | 32.694 | −1.181 |
| 955 | O | LEU | 122 | 114.738 | 31.615 | −1.781 |
| 956 | CB | LEU | 122 | 113.018 | 33.260 | 0.491 |
| 957 | CG | LEU | 122 | 111.914 | 34.237 | 0.885 |
| 958 | CD1 | LEU | 122 | 111.360 | 33.897 | 2.264 |
| 959 | CD2 | LEU | 122 | 112.416 | 35.678 | 0.848 |
| 960 | N | GLU | 123 | 115.867 | 33.224 | −0.642 |
| 961 | CA | GLU | 123 | 117.206 | 32.597 | −0.641 |
| 962 | C | GLU | 123 | 117.803 | 32.442 | −2.035 |
| 963 | O | GLU | 123 | 117.599 | 31.417 | −2.694 |
| 964 | CB | GLU | 123 | 117.160 | 31.225 | 0.030 |
| 965 | CG | GLU | 123 | 116.674 | 31.300 | 1.473 |
| 966 | CD | GLU | 123 | 116.833 | 29.935 | 2.136 |
| 967 | OE1 | GLU | 123 | 117.828 | 29.285 | 1.843 |
| 968 | OE2 | GLU | 123 | 116.064 | 29.654 | 3.044 |
| 969 | N | VAL | 124 | 118.603 | 33.418 | −2.434 |
| 970 | CA | VAL | 124 | 119.271 | 33.347 | −3.740 |
| 971 | C | VAL | 124 | 120.788 | 33.231 | −3.575 |
| 972 | O | VAL | 124 | 121.396 | 32.234 | −3.980 |
| 973 | CB | VAL | 124 | 118.931 | 34.603 | −4.543 |
| 974 | CG1 | VAL | 124 | 119.558 | 34.552 | −5.934 |
| 975 | CG2 | VAL | 124 | 117.422 | 34.795 | −4.657 |
| 976 | N | LEU | 125 | 121.373 | 34.221 | −2.923 |
| 977 | CA | LEU | 125 | 122.829 | 34.262 | −2.756 |
| 978 | C | LEU | 125 | 123.240 | 33.876 | −1.340 |
| 979 | O | LEU | 125 | 122.760 | 34.458 | −0.360 |
| 980 | CB | LEU | 125 | 123.289 | 35.681 | −3.104 |
| 981 | CG | LEU | 125 | 124.793 | 35.906 | −2.950 |
| 982 | CD1 | LEU | 125 | 125.353 | 36.685 | −4.134 |
| 983 | CD2 | LEU | 125 | 125.130 | 36.608 | −1.636 |
| 984 | N | GLN | 126 | 124.064 | 32.845 | −1.244 |
| 985 | CA | GLN | 126 | 124.646 | 32.474 | 0.050 |
| 986 | C | GLN | 126 | 126.170 | 32.619 | 0.022 |
| 987 | O | GLN | 126 | 126.857 | 32.103 | −0.866 |
| 988 | CB | GLN | 126 | 124.218 | 31.057 | 0.424 |
| 989 | CG | GLN | 126 | 122.700 | 30.982 | 0.583 |
| 990 | CD | GLN | 126 | 122.275 | 29.634 | 1.157 |
| 991 | OE1 | GLN | 126 | 123.068 | 28.947 | 1.809 |
| 992 | NE2 | GLN | 126 | 121.021 | 29.285 | 0.925 |
| 993 | N | SER | 127 | 126.657 | 33.421 | 0.952 |
| 994 | CA | SER | 127 | 128.090 | 33.727 | 1.086 |
| 995 | C | SER | 127 | 128.510 | 33.368 | 2.536 |
| 996 | O | SER | 127 | 127.922 | 32.387 | 3.004 |
| 997 | CB | SER | 127 | 128.241 | 35.174 | 0.622 |
| 998 | OG | SER | 127 | 127.964 | 35.197 | −0.772 |
| 999 | N | PRO | 128 | 129.433 | 34.005 | 3.265 |
| 1000 | CA | PRO | 128 | 130.268 | 35.173 | 2.925 |
| 1001 | C | PRO | 128 | 131.546 | 34.818 | 2.168 |
| 1002 | O | PRO | 128 | 131.794 | 33.666 | 1.802 |
| 1003 | CB | PRO | 128 | 130.626 | 35.786 | 4.239 |
| 1004 | CG | PRO | 128 | 130.407 | 34.745 | 5.321 |
| 1005 | CD | PRO | 128 | 129.727 | 33.575 | 4.636 |
| 1006 | N | ILE | 129 | 132.325 | 35.858 | 1.913 |
| 1007 | CA | ILE | 129 | 133.635 | 35.708 | 1.272 |
| 1008 | C | ILE | 129 | 134.722 | 35.503 | 2.335 |
| 1009 | O | ILE | 129 | 135.735 | 34.838 | 2.088 |
| 1010 | CB | ILE | 129 | 133.914 | 36.987 | 0.481 |

TABLE 8-continued

| Atom No. | Atom Type | Residue | Residue Position | X Coord. | Y Coord. | Z Coord. |
|---|---|---|---|---|---|---|
| 1011 | CG1 | ILE | 129 | 132.841 | 37.230 | −0.577 |
| 1012 | CG2 | ILE | 129 | 135.292 | 36.959 | −0.171 |
| 1013 | CD1 | ILE | 129 | 132.829 | 36.127 | −1.631 |
| 1014 | N | GLU | 130 | 134.456 | 35.998 | 3.533 |
| 1015 | CA | GLU | 130 | 135.382 | 35.806 | 4.655 |
| 1016 | C | GLU | 130 | 134.627 | 35.523 | 5.948 |
| 1017 | O | GLU | 130 | 133.510 | 34.997 | 5.911 |
| 1018 | CB | GLU | 130 | 136.287 | 37.023 | 4.819 |
| 1019 | CG | GLU | 130 | 137.741 | 36.639 | 4.554 |
| 1020 | CD | GLU | 130 | 138.668 | 37.778 | 4.963 |
| 1021 | OE1 | GLU | 130 | 138.249 | 38.547 | 5.819 |
| 1022 | OE2 | GLU | 130 | 139.796 | 37.805 | 4.495 |
| 1023 | N | ALA | 131 | 135.181 | 35.981 | 7.062 |
| 1024 | CA | ALA | 131 | 134.684 | 35.605 | 8.400 |
| 1025 | C | ALA | 131 | 133.506 | 36.430 | 8.931 |
| 1026 | O | ALA | 131 | 133.565 | 36.960 | 10.046 |
| 1027 | CB | ALA | 131 | 135.845 | 35.703 | 9.381 |
| 1028 | N | VAL | 132 | 132.416 | 36.455 | 8.184 |
| 1029 | CA | VAL | 132 | 131.208 | 37.148 | 8.636 |
| 1030 | C | VAL | 132 | 130.323 | 36.142 | 9.366 |
| 1031 | O | VAL | 132 | 129.433 | 35.515 | 8.779 |
| 1032 | CB | VAL | 132 | 130.485 | 37.746 | 7.436 |
| 1033 | CG1 | VAL | 132 | 129.263 | 38.549 | 7.877 |
| 1034 | CG2 | VAL | 132 | 131.428 | 38.626 | 6.622 |
| 1035 | N | THR | 133 | 130.579 | 36.020 | 10.657 |
| 1036 | CA | THR | 133 | 129.957 | 34.971 | 11.470 |
| 1037 | C | THR | 133 | 128.501 | 35.267 | 11.817 |
| 1038 | O | THR | 133 | 128.191 | 36.158 | 12.614 |
| 1039 | CB | THR | 133 | 130.781 | 34.820 | 12.741 |
| 1040 | OG1 | THR | 133 | 132.120 | 34.532 | 12.357 |
| 1041 | CG2 | THR | 133 | 130.274 | 33.673 | 13.607 |
| 1042 | N | ASN | 134 | 127.624 | 34.556 | 11.127 |
| 1043 | CA | ASN | 134 | 126.181 | 34.597 | 11.384 |
| 1044 | C | ASN | 134 | 125.602 | 33.185 | 11.322 |
| 1045 | O | ASN | 134 | 126.244 | 32.276 | 10.783 |
| 1046 | CB | ASN | 134 | 125.511 | 35.495 | 10.343 |
| 1047 | CG | ASN | 134 | 125.508 | 36.948 | 10.815 |
| 1048 | OD1 | ASN | 134 | 124.775 | 37.305 | 11.745 |
| 1049 | ND2 | ASN | 134 | 126.308 | 37.771 | 10.160 |
| 1050 | N | PRO | 135 | 124.473 | 32.978 | 11.984 |
| 1051 | CA | PRO | 135 | 123.744 | 31.713 | 11.845 |
| 1052 | C | PRO | 135 | 123.371 | 31.454 | 10.388 |
| 1053 | O | PRO | 135 | 123.020 | 32.375 | 9.643 |
| 1054 | CB | PRO | 135 | 122.531 | 31.852 | 12.712 |
| 1055 | CG | PRO | 135 | 122.526 | 33.232 | 13.351 |
| 1056 | CD | PRO | 135 | 123.775 | 33.936 | 12.848 |
| 1057 | N | THR | 136 | 123.497 | 30.201 | 9.985 |
| 1058 | CA | THR | 136 | 123.233 | 29.825 | 8.591 |
| 1059 | C | THR | 136 | 121.806 | 29.313 | 8.364 |
| 1060 | O | THR | 136 | 121.360 | 29.183 | 7.218 |
| 1061 | CB | THR | 136 | 124.263 | 28.766 | 8.194 |
| 1062 | OG1 | THR | 136 | 124.006 | 28.350 | 6.859 |
| 1063 | CG2 | THR | 136 | 124.215 | 27.535 | 9.095 |
| 1064 | N | TYR | 137 | 121.068 | 29.097 | 9.440 |
| 1065 | CA | TYR | 137 | 119.705 | 28.581 | 9.294 |
| 1066 | C | TYR | 137 | 118.672 | 29.698 | 9.354 |
| 1067 | O | TYR | 137 | 118.418 | 30.291 | 10.407 |
| 1068 | CB | TYR | 137 | 119.451 | 27.531 | 10.367 |
| 1069 | CG | TYR | 137 | 120.279 | 26.266 | 10.155 |
| 1070 | CD1 | TYR | 137 | 120.361 | 25.703 | 8.887 |
| 1071 | CD2 | TYR | 137 | 120.943 | 25.676 | 11.223 |
| 1072 | CE1 | TYR | 137 | 121.117 | 24.557 | 8.683 |
| 1073 | CE2 | TYR | 137 | 121.700 | 24.529 | 11.020 |
| 1074 | CZ | TYR | 137 | 121.786 | 23.974 | 9.750 |
| 1075 | OH | TYR | 137 | 122.548 | 22.845 | 9.544 |
| 1076 | N | LYS | 138 | 117.987 | 29.861 | 8.234 |
| 1077 | CA | LYS | 138 | 116.993 | 30.930 | 8.052 |
| 1078 | C | LYS | 138 | 115.561 | 30.528 | 8.437 |
| 1079 | O | LYS | 138 | 114.607 | 31.232 | 8.086 |
| 1080 | CB | LYS | 138 | 117.032 | 31.325 | 6.579 |
| 1081 | CG | LYS | 138 | 118.452 | 31.681 | 6.144 |
| 1082 | CD | LYS | 138 | 118.517 | 32.029 | 4.661 |
| 1083 | CE | LYS | 138 | 119.944 | 32.331 | 4.215 |
| 1084 | NZ | LYS | 138 | 119.991 | 32.660 | 2.780 |
| 1085 | N | LEU | 139 | 115.411 | 29.427 | 9.158 |
| 1086 | CA | LEU | 139 | 114.075 | 28.886 | 9.436 |
| 1087 | C | LEU | 139 | 113.741 | 28.914 | 10.928 |
| 1088 | O | LEU | 139 | 114.477 | 28.348 | 11.746 |
| 1089 | CB | LEU | 139 | 114.059 | 27.445 | 8.930 |
| 1090 | CG | LEU | 139 | 112.689 | 26.788 | 9.065 |
| 1091 | CD1 | LEU | 139 | 111.639 | 27.539 | 8.253 |
| 1092 | CD2 | LEU | 139 | 112.749 | 25.326 | 8.637 |
| 1093 | N | GLN | 140 | 112.657 | 29.597 | 11.270 |
| 1094 | CA | GLN | 140 | 112.178 | 29.585 | 12.661 |
| 1095 | C | GLN | 140 | 110.672 | 29.884 | 12.753 |
| 1096 | O | GLN | 140 | 109.853 | 29.039 | 12.380 |
| 1097 | CB | GLN | 140 | 113.046 | 30.541 | 13.490 |
| 1098 | CG | GLN | 140 | 112.970 | 30.307 | 15.005 |
| 1099 | CD | GLN | 140 | 113.205 | 28.846 | 15.406 |
| 1100 | OE1 | GLN | 140 | 112.398 | 28.276 | 16.150 |
| 1101 | NE2 | GLN | 140 | 114.278 | 28.252 | 14.908 |
| 1102 | N | LYS | 141 | 110.319 | 31.087 | 13.182 |
| 1103 | CA | LYS | 141 | 108.913 | 31.433 | 13.464 |
| 1104 | C | LYS | 141 | 108.192 | 32.136 | 12.313 |
| 1105 | O | LYS | 141 | 107.020 | 32.512 | 12.445 |
| 1106 | CB | LYS | 141 | 108.903 | 32.346 | 14.683 |
| 1107 | CG | LYS | 141 | 109.574 | 31.672 | 15.872 |
| 1108 | CD | LYS | 141 | 109.681 | 32.615 | 17.064 |
| 1109 | CE | LYS | 141 | 110.370 | 31.933 | 18.240 |
| 1110 | NZ | LYS | 141 | 110.485 | 32.846 | 19.388 |
| 1111 | N | VAL | 142 | 108.890 | 32.344 | 11.212 |
| 1112 | CA | VAL | 142 | 108.296 | 33.059 | 10.080 |
| 1113 | C | VAL | 142 | 107.459 | 32.120 | 9.215 |
| 1114 | O | VAL | 142 | 107.995 | 31.358 | 8.403 |
| 1115 | CB | VAL | 142 | 109.426 | 33.667 | 9.256 |
| 1116 | CG1 | VAL | 142 | 108.877 | 34.502 | 8.103 |
| 1117 | CG2 | VAL | 142 | 110.339 | 34.514 | 10.136 |
| 1118 | N | GLY | 143 | 106.153 | 32.175 | 9.412 |
| 1119 | CA | GLY | 143 | 105.236 | 31.373 | 8.598 |
| 1120 | C | GLY | 143 | 104.068 | 30.824 | 9.411 |
| 1121 | O | GLY | 143 | 103.837 | 29.609 | 9.436 |
| 1122 | N | VAL | 144 | 103.327 | 31.720 | 10.043 |
| 1123 | CA | VAL | 144 | 102.159 | 31.306 | 10.829 |
| 1124 | C | VAL | 144 | 101.029 | 30.820 | 9.924 |
| 1125 | O | VAL | 144 | 100.886 | 31.246 | 8.773 |
| 1126 | CB | VAL | 144 | 101.681 | 32.466 | 11.699 |
| 1127 | CG1 | VAL | 144 | 102.745 | 32.854 | 12.719 |
| 1128 | CG2 | VAL | 144 | 101.267 | 33.676 | 10.868 |
| 1129 | N | GLU | 145 | 100.264 | 29.883 | 10.451 |
| 1130 | CA | GLU | 145 | 99.141 | 29.297 | 9.710 |
| 1131 | C | GLU | 145 | 97.992 | 30.291 | 9.595 |
| 1132 | O | GLU | 145 | 97.917 | 31.265 | 10.356 |
| 1133 | CB | GLU | 145 | 98.650 | 28.021 | 10.402 |
| 1134 | CG | GLU | 145 | 99.470 | 26.767 | 10.073 |
| 1135 | CD | GLU | 145 | 100.812 | 26.696 | 10.808 |
| 1136 | OE1 | GLU | 145 | 101.667 | 25.956 | 10.348 |
| 1137 | OE2 | GLU | 145 | 100.919 | 27.317 | 11.857 |
| 1138 | N | SER | 146 | 97.012 | 29.933 | 8.778 |
| 1139 | CA | SER | 146 | 95.858 | 30.813 | 8.527 |
| 1140 | C | SER | 146 | 94.937 | 30.950 | 9.738 |
| 1141 | O | SER | 146 | 94.386 | 32.036 | 9.956 |
| 1142 | CB | SER | 146 | 95.065 | 30.260 | 7.349 |
| 1143 | OG | SER | 146 | 95.906 | 30.299 | 6.204 |
| 1144 | N | GLY | 147 | 95.003 | 29.983 | 10.640 |
| 1145 | CA | GLY | 147 | 94.302 | 30.077 | 11.925 |
| 1146 | C | GLY | 147 | 94.853 | 31.227 | 12.767 |
| 1147 | O | GLY | 147 | 94.080 | 32.078 | 13.222 |
| 1148 | N | ASP | 148 | 96.169 | 31.391 | 12.748 |
| 1149 | CA | ASP | 148 | 96.821 | 32.438 | 13.540 |
| 1150 | C | ASP | 148 | 96.673 | 33.799 | 12.871 |
| 1151 | O | ASP | 148 | 96.492 | 34.805 | 13.569 |
| 1152 | CB | ASP | 148 | 98.309 | 32.126 | 13.642 |
| 1153 | CG | ASP | 148 | 98.532 | 30.686 | 14.092 |
| 1154 | OD1 | ASP | 148 | 98.090 | 30.351 | 15.181 |
| 1155 | OD2 | ASP | 148 | 99.049 | 29.919 | 13.290 |
| 1156 | N | LYS | 149 | 96.527 | 33.790 | 11.553 |
| 1157 | CA | LYS | 149 | 96.292 | 35.032 | 10.816 |
| 1158 | C | LYS | 149 | 94.915 | 35.583 | 11.159 |
| 1159 | O | LYS | 149 | 94.823 | 36.705 | 11.674 |
| 1160 | CB | LYS | 149 | 96.343 | 34.746 | 9.319 |
| 1161 | CG | LYS | 149 | 97.673 | 34.146 | 8.877 |
| 1162 | CD | LYS | 149 | 97.655 | 33.862 | 7.377 |

TABLE 8-continued

| Atom No. | Atom Type | Residue | Residue Position | X Coord. | Y Coord. | Z Coord. |
|---|---|---|---|---|---|---|
| 1163 | CE | LYS | 149 | 98.940 | 33.192 | 6.910 |
| 1164 | NZ | LYS | 149 | 98.936 | 32.992 | 5.452 |
| 1165 | N | LEU | 150 | 93.924 | 34.704 | 11.165 |
| 1166 | CA | LEU | 150 | 92.555 | 35.111 | 11.500 |
| 1167 | C | LEU | 150 | 92.422 | 35.461 | 12.978 |
| 1168 | O | LEU | 150 | 91.803 | 36.481 | 13.301 |
| 1169 | CB | LEU | 150 | 91.613 | 33.960 | 11.164 |
| 1170 | CG | LEU | 150 | 91.589 | 33.676 | 9.667 |
| 1171 | CD1 | LEU | 150 | 90.907 | 32.345 | 9.368 |
| 1172 | CD2 | LEU | 150 | 90.932 | 34.817 | 8.897 |
| 1173 | N | GLY | 151 | 93.175 | 34.771 | 13.819 |
| 1174 | CA | GLY | 151 | 93.242 | 35.081 | 15.251 |
| 1175 | C | GLY | 151 | 93.686 | 36.516 | 15.509 |
| 1176 | O | GLY | 151 | 92.863 | 37.335 | 15.944 |
| 1177 | N | LEU | 152 | 94.860 | 36.864 | 15.005 |
| 1178 | CA | LEU | 152 | 95.446 | 38.187 | 15.258 |
| 1179 | C | LEU | 152 | 94.704 | 39.318 | 14.553 |
| 1180 | O | LEU | 152 | 94.611 | 40.432 | 15.091 |
| 1181 | CB | LEU | 152 | 96.882 | 38.163 | 14.744 |
| 1182 | CG | LEU | 152 | 97.726 | 37.117 | 15.463 |
| 1183 | CD1 | LEU | 152 | 99.067 | 36.920 | 14.766 |
| 1184 | CD2 | LEU | 152 | 97.923 | 37.478 | 16.931 |
| 1185 | N | VAL | 153 | 94.032 | 39.007 | 13.459 |
| 1186 | CA | VAL | 153 | 93.282 | 40.044 | 12.758 |
| 1187 | C | VAL | 153 | 91.876 | 40.235 | 13.329 |
| 1188 | O | VAL | 153 | 91.407 | 41.376 | 13.379 |
| 1189 | CB | VAL | 153 | 93.262 | 39.698 | 11.278 |
| 1190 | CG1 | VAL | 153 | 92.472 | 40.723 | 10.487 |
| 1191 | CG2 | VAL | 153 | 94.687 | 39.644 | 10.746 |
| 1192 | N | PHE | 154 | 91.340 | 39.234 | 14.005 |
| 1193 | CA | PHE | 154 | 90.082 | 39.456 | 14.724 |
| 1194 | C | PHE | 154 | 90.368 | 40.250 | 15.991 |
| 1195 | O | PHE | 154 | 89.675 | 41.233 | 16.283 |
| 1196 | CB | PHE | 154 | 89.444 | 38.124 | 15.116 |
| 1197 | CG | PHE | 154 | 88.814 | 37.313 | 13.985 |
| 1198 | CD1 | PHE | 154 | 88.230 | 37.950 | 12.898 |
| 1199 | CD2 | PHE | 154 | 88.800 | 35.927 | 14.063 |
| 1200 | CE1 | PHE | 154 | 87.650 | 37.200 | 11.883 |
| 1201 | CE2 | PHE | 154 | 88.222 | 35.177 | 13.047 |
| 1202 | CZ | PHE | 154 | 87.648 | 35.814 | 11.955 |
| 1203 | N | GLN | 155 | 91.532 | 39.999 | 16.562 |
| 1204 | CA | GLN | 155 | 91.941 | 40.711 | 17.767 |
| 1205 | C | GLN | 155 | 92.182 | 42.192 | 17.499 |
| 1206 | O | GLN | 155 | 91.328 | 43.007 | 17.871 |
| 1207 | CB | GLN | 155 | 93.186 | 40.026 | 18.307 |
| 1208 | CG | GLN | 155 | 92.813 | 38.616 | 18.750 |
| 1209 | CD | GLN | 155 | 94.050 | 37.767 | 19.013 |
| 1210 | OE1 | GLN | 155 | 95.155 | 38.083 | 18.557 |
| 1211 | NE2 | GLN | 155 | 93.824 | 36.642 | 19.668 |
| 1212 | N | ALA | 156 | 93.154 | 42.520 | 16.667 |
| 1213 | CA | ALA | 156 | 93.480 | 43.940 | 16.499 |
| 1214 | C | ALA | 156 | 92.656 | 44.692 | 15.453 |
| 1215 | O | ALA | 156 | 92.578 | 45.921 | 15.535 |
| 1216 | CB | ALA | 156 | 94.960 | 44.073 | 16.173 |
| 1217 | N | ASN | 157 | 91.970 | 43.999 | 14.560 |
| 1218 | CA | ASN | 157 | 91.169 | 44.717 | 13.561 |
| 1219 | C | ASN | 157 | 89.689 | 44.750 | 13.933 |
| 1220 | O | ASN | 157 | 88.934 | 45.540 | 13.355 |
| 1221 | CB | ASN | 157 | 91.289 | 44.061 | 12.186 |
| 1222 | CG | ASN | 157 | 92.667 | 44.166 | 11.534 |
| 1223 | OD1 | ASN | 157 | 93.724 | 43.984 | 12.155 |
| 1224 | ND2 | ASN | 157 | 92.628 | 44.425 | 10.240 |
| 1225 | N | VAL | 158 | 89.271 | 43.909 | 14.866 |
| 1226 | CA | VAL | 158 | 87.862 | 43.921 | 15.278 |
| 1227 | C | VAL | 158 | 87.698 | 44.319 | 16.741 |
| 1228 | O | VAL | 158 | 87.053 | 45.337 | 17.024 |
| 1229 | CB | VAL | 158 | 87.251 | 42.546 | 15.026 |
| 1230 | CG1 | VAL | 158 | 85.886 | 42.392 | 15.687 |
| 1231 | CG2 | VAL | 158 | 87.167 | 42.244 | 13.536 |
| 1232 | N | PHE | 159 | 88.408 | 43.650 | 17.635 |
| 1233 | CA | PHE | 159 | 88.228 | 43.926 | 19.066 |
| 1234 | C | PHE | 159 | 88.930 | 45.213 | 19.463 |
| 1235 | O | PHE | 159 | 88.358 | 46.017 | 20.211 |
| 1236 | CB | PHE | 159 | 88.753 | 42.754 | 19.886 |
| 1237 | CG | PHE | 159 | 87.922 | 41.484 | 19.732 |
| 1238 | CD1 | PHE | 159 | 88.465 | 40.359 | 19.126 |
| 1239 | CD2 | PHE | 159 | 86.617 | 41.456 | 20.206 |
| 1240 | CE1 | PHE | 159 | 87.700 | 39.208 | 18.985 |
| 1241 | CE2 | PHE | 159 | 85.852 | 40.305 | 20.067 |
| 1242 | CZ | PHE | 159 | 86.393 | 39.182 | 19.455 |
| 1243 | N | GLY | 160 | 90.048 | 45.477 | 18.807 |
| 1244 | CA | GLY | 160 | 90.735 | 46.778 | 18.887 |
| 1245 | C | GLY | 160 | 89.776 | 47.963 | 18.728 |
| 1246 | O | GLY | 160 | 89.409 | 48.594 | 19.732 |
| 1247 | N | PRO | 161 | 89.275 | 48.189 | 17.518 |
| 1248 | CA | PRO | 161 | 88.346 | 49.304 | 17.295 |
| 1249 | C | PRO | 161 | 86.987 | 49.165 | 17.992 |
| 1250 | O | PRO | 161 | 86.403 | 50.201 | 18.324 |
| 1251 | CB | PRO | 161 | 88.154 | 49.368 | 15.813 |
| 1252 | CG | PRO | 161 | 88.873 | 48.205 | 15.157 |
| 1253 | CD | PRO | 161 | 89.584 | 47.470 | 16.277 |
| 1254 | N | TYR | 162 | 86.580 | 47.967 | 18.388 |
| 1255 | CA | TYR | 162 | 85.333 | 47.821 | 19.144 |
| 1256 | C | TYR | 162 | 85.465 | 48.410 | 20.545 |
| 1257 | O | TYR | 162 | 84.643 | 49.258 | 20.916 |
| 1258 | CB | TYR | 162 | 84.988 | 46.339 | 19.239 |
| 1259 | CG | TYR | 162 | 83.761 | 46.019 | 20.087 |
| 1260 | CD1 | TYR | 162 | 83.916 | 45.400 | 21.322 |
| 1261 | CD2 | TYR | 162 | 82.490 | 46.335 | 19.623 |
| 1262 | CE1 | TYR | 162 | 82.802 | 45.107 | 22.097 |
| 1263 | CE2 | TYR | 162 | 81.375 | 46.041 | 20.397 |
| 1264 | CZ | TYR | 162 | 81.534 | 45.427 | 21.631 |
| 1265 | OH | TYR | 162 | 80.425 | 45.063 | 22.364 |
| 1266 | N | TYR | 163 | 86.605 | 48.199 | 21.184 |
| 1267 | CA | TYR | 163 | 86.805 | 48.755 | 22.527 |
| 1268 | C | TYR | 163 | 87.115 | 50.247 | 22.463 |
| 1269 | O | TYR | 163 | 86.582 | 51.017 | 23.273 |
| 1270 | CB | TYR | 163 | 87.967 | 48.032 | 23.203 |
| 1271 | CG | TYR | 163 | 87.750 | 46.538 | 23.432 |
| 1272 | CD1 | TYR | 163 | 86.523 | 46.068 | 23.884 |
| 1273 | CD2 | TYR | 163 | 88.795 | 45.650 | 23.209 |
| 1274 | CE1 | TYR | 163 | 86.331 | 44.707 | 24.086 |
| 1275 | CE2 | TYR | 163 | 88.604 | 44.289 | 23.408 |
| 1276 | CZ | TYR | 163 | 87.372 | 43.822 | 23.843 |
| 1277 | OH | TYR | 163 | 87.175 | 42.470 | 24.015 |
| 1278 | N | PHE | 164 | 87.707 | 50.665 | 21.356 |
| 1279 | CA | PHE | 164 | 88.039 | 52.079 | 21.174 |
| 1280 | C | PHE | 164 | 86.781 | 52.909 | 20.916 |
| 1281 | O | PHE | 164 | 86.543 | 53.888 | 21.637 |
| 1282 | CB | PHE | 164 | 88.984 | 52.185 | 19.984 |
| 1283 | CG | PHE | 164 | 90.138 | 53.162 | 20.182 |
| 1284 | CD1 | PHE | 164 | 90.010 | 54.231 | 21.058 |
| 1285 | CD2 | PHE | 164 | 91.329 | 52.966 | 19.497 |
| 1286 | CE1 | PHE | 164 | 91.068 | 55.112 | 21.238 |
| 1287 | CE2 | PHE | 164 | 92.388 | 53.847 | 19.676 |
| 1288 | CZ | PHE | 164 | 92.256 | 54.921 | 20.546 |
| 1289 | N | ILE | 165 | 85.866 | 52.365 | 20.129 |
| 1290 | CA | ILE | 165 | 84.614 | 53.071 | 19.845 |
| 1291 | C | ILE | 165 | 83.641 | 52.982 | 21.012 |
| 1292 | O | ILE | 165 | 82.985 | 53.984 | 21.303 |
| 1293 | CB | ILE | 165 | 83.963 | 52.471 | 18.600 |
| 1294 | CG1 | ILE | 165 | 84.799 | 52.733 | 17.357 |
| 1295 | CG2 | ILE | 165 | 82.562 | 53.041 | 18.394 |
| 1296 | CD1 | ILE | 165 | 84.753 | 54.207 | 16.985 |
| 1297 | N | HIS | 166 | 83.765 | 51.955 | 21.835 |
| 1298 | CA | HIS | 166 | 82.857 | 51.815 | 22.974 |
| 1299 | C | HIS | 166 | 83.221 | 52.795 | 24.088 |
| 1300 | O | HIS | 166 | 82.328 | 53.453 | 24.640 |
| 1301 | CB | HIS | 166 | 82.980 | 50.387 | 23.493 |
| 1302 | CG | HIS | 166 | 81.771 | 49.891 | 24.257 |
| 1303 | ND1 | HIS | 166 | 80.787 | 49.115 | 23.764 |
| 1304 | CD2 | HIS | 166 | 81.465 | 50.136 | 25.575 |
| 1305 | CE1 | HIS | 166 | 79.880 | 48.873 | 24.732 |
| 1306 | NE2 | HIS | 166 | 80.299 | 49.506 | 25.851 |
| 1307 | N | ARG | 167 | 84.507 | 53.084 | 24.210 |
| 1308 | CA | ARG | 167 | 84.971 | 53.992 | 25.261 |
| 1309 | C | ARG | 167 | 84.878 | 55.460 | 24.839 |
| 1310 | O | ARG | 167 | 84.712 | 56.348 | 25.681 |
| 1311 | CB | ARG | 167 | 86.424 | 53.640 | 25.563 |
| 1312 | CG | ARG | 167 | 86.886 | 54.282 | 26.863 |
| 1313 | CD | ARG | 167 | 86.013 | 53.799 | 28.014 |
| 1314 | NE | ARG | 167 | 86.405 | 54.413 | 29.289 |

TABLE 8-continued

| Atom No. | Atom Type | Residue | Residue Position | X Coord. | Y Coord. | Z Coord. |
|---|---|---|---|---|---|---|
| 1315 | CZ | ARG | 167 | 85.711 | 54.232 | 30.414 |
| 1316 | NH1 | ARG | 167 | 84.590 | 53.508 | 30.395 |
| 1317 | NH2 | ARG | 167 | 86.123 | 54.796 | 31.551 |
| 1318 | N | ILE | 168 | 84.860 | 55.705 | 23.541 |
| 1319 | CA | ILE | 168 | 84.735 | 57.082 | 23.055 |
| 1320 | C | ILE | 168 | 83.307 | 57.424 | 22.618 |
| 1321 | O | ILE | 168 | 82.966 | 58.605 | 22.449 |
| 1322 | CB | ILE | 168 | 85.755 | 57.263 | 21.938 |
| 1323 | CG1 | ILE | 168 | 87.153 | 57.059 | 22.513 |
| 1324 | CG2 | ILE | 168 | 85.650 | 58.634 | 21.282 |
| 1325 | CD1 | ILE | 168 | 88.235 | 57.328 | 21.477 |
| 1326 | N | LYS | 169 | 82.426 | 56.444 | 22.719 |
| 1327 | CA | LYS | 169 | 81.034 | 56.624 | 22.294 |
| 1328 | C | LYS | 169 | 80.272 | 57.556 | 23.227 |
| 1329 | O | LYS | 169 | 79.560 | 58.444 | 22.747 |
| 1330 | CB | LYS | 169 | 80.390 | 55.245 | 22.292 |
| 1331 | CG | LYS | 169 | 78.945 | 55.253 | 21.819 |
| 1332 | CD | LYS | 169 | 78.429 | 53.823 | 21.728 |
| 1333 | CE | LYS | 169 | 78.649 | 53.087 | 23.045 |
| 1334 | NZ | LYS | 169 | 78.195 | 51.691 | 22.954 |
| 1335 | N | HIS | 170 | 80.675 | 57.563 | 24.487 |
| 1336 | CA | HIS | 170 | 80.076 | 58.469 | 25.470 |
| 1337 | C | HIS | 170 | 80.838 | 59.794 | 25.616 |
| 1338 | O | HIS | 170 | 80.559 | 60.568 | 26.538 |
| 1339 | CB | HIS | 170 | 79.918 | 57.741 | 26.805 |
| 1340 | CG | HIS | 170 | 81.108 | 56.937 | 27.306 |
| 1341 | ND1 | HIS | 170 | 81.297 | 55.610 | 27.163 |
| 1342 | CD2 | HIS | 170 | 82.174 | 57.419 | 28.027 |
| 1343 | CE1 | HIS | 170 | 82.459 | 55.259 | 27.755 |
| 1344 | NE2 | HIS | 170 | 82.998 | 56.377 | 28.289 |
| 1345 | N | LEU | 171 | 81.806 | 60.033 | 24.741 |
| 1346 | CA | LEU | 171 | 82.522 | 61.314 | 24.718 |
| 1347 | C | LEU | 171 | 82.047 | 62.176 | 23.553 |
| 1348 | O | LEU | 171 | 82.382 | 63.368 | 23.475 |
| 1349 | CB | LEU | 171 | 84.014 | 61.063 | 24.538 |
| 1350 | CG | LEU | 171 | 84.605 | 60.252 | 25.680 |
| 1351 | CD1 | LEU | 171 | 86.092 | 60.025 | 25.442 |
| 1352 | CD2 | LEU | 171 | 84.376 | 60.953 | 27.013 |
| 1353 | N | LEU | 172 | 81.326 | 61.547 | 22.639 |
| 1354 | CA | LEU | 172 | 80.775 | 62.247 | 21.476 |
| 1355 | C | LEU | 172 | 79.636 | 63.171 | 21.882 |
| 1356 | O | LEU | 172 | 78.772 | 62.802 | 22.684 |
| 1357 | CB | LEU | 172 | 80.228 | 61.205 | 20.507 |
| 1358 | CG | LEU | 172 | 81.304 | 60.241 | 20.023 |
| 1359 | CD1 | LEU | 172 | 80.675 | 59.037 | 19.334 |
| 1360 | CD2 | LEU | 172 | 82.306 | 60.935 | 19.106 |
| 1361 | N | GLU | 173 | 79.675 | 64.388 | 21.374 |
| 1362 | CA | GLU | 173 | 78.561 | 65.312 | 21.605 |
| 1363 | C | GLU | 173 | 77.976 | 65.809 | 20.292 |
| 1364 | O | GLU | 173 | 77.831 | 65.051 | 19.325 |
| 1365 | CB | GLU | 173 | 79.007 | 66.507 | 22.437 |
| 1366 | CG | GLU | 173 | 79.342 | 66.125 | 23.873 |
| 1367 | CD | GLU | 173 | 79.341 | 67.394 | 24.715 |
| 1368 | OE1 | GLU | 173 | 78.989 | 67.301 | 25.882 |
| 1369 | OE2 | GLU | 173 | 79.476 | 68.452 | 24.114 |
| 1370 | N | ASN | 174 | 77.576 | 67.070 | 20.320 |
| 1371 | CA | ASN | 174 | 77.025 | 67.752 | 19.148 |
| 1372 | C | ASN | 174 | 78.048 | 67.777 | 18.020 |
| 1373 | O | ASN | 174 | 79.189 | 68.223 | 18.201 |
| 1374 | CB | ASN | 174 | 76.684 | 69.185 | 19.550 |
| 1375 | CG | ASN | 174 | 75.774 | 69.201 | 20.777 |
| 1376 | OD1 | ASN | 174 | 74.666 | 68.653 | 20.753 |
| 1377 | ND2 | ASN | 174 | 76.239 | 69.856 | 21.830 |
| 1378 | N | GLY | 175 | 77.650 | 67.229 | 16.887 |
| 1379 | CA | GLY | 175 | 78.541 | 67.155 | 15.729 |
| 1380 | C | GLY | 175 | 79.602 | 66.083 | 15.944 |
| 1381 | O | GLY | 175 | 80.798 | 66.334 | 15.740 |
| 1382 | N | GLY | 176 | 79.153 | 64.912 | 16.363 |
| 1383 | CA | GLY | 176 | 80.054 | 63.781 | 16.614 |
| 1384 | C | GLY | 176 | 80.238 | 62.940 | 15.356 |
| 1385 | O | GLY | 176 | 79.480 | 61.994 | 15.105 |
| 1386 | N | LYS | 177 | 81.228 | 63.298 | 14.559 |
| 1387 | CA | LYS | 177 | 81.463 | 62.583 | 13.300 |
| 1388 | C | LYS | 177 | 82.648 | 61.628 | 13.410 |
| 1389 | O | LYS | 177 | 83.696 | 61.947 | 13.989 |
| 1390 | CB | LYS | 177 | 81.652 | 63.602 | 12.186 |

TABLE 8-continued

| Atom No. | Atom Type | Residue | Residue Position | X Coord. | Y Coord. | Z Coord. |
|---|---|---|---|---|---|---|
| 1391 | CG | LYS | 177 | 80.408 | 64.480 | 12.108 |
| 1392 | CD | LYS | 177 | 80.515 | 65.570 | 11.053 |
| 1393 | CE | LYS | 177 | 79.265 | 66.444 | 11.072 |
| 1394 | NZ | LYS | 177 | 78.055 | 65.649 | 10.809 |
| 1395 | N | ILE | 178 | 82.415 | 60.411 | 12.947 |
| 1396 | CA | ILE | 178 | 83.423 | 59.353 | 13.062 |
| 1397 | C | ILE | 178 | 83.671 | 58.625 | 11.743 |
| 1398 | O | ILE | 178 | 82.798 | 57.942 | 11.187 |
| 1399 | CB | ILE | 178 | 83.012 | 58.358 | 14.149 |
| 1400 | CG1 | ILE | 178 | 82.964 | 59.032 | 15.515 |
| 1401 | CG2 | ILE | 178 | 83.959 | 57.162 | 14.201 |
| 1402 | CD1 | ILE | 178 | 82.843 | 58.006 | 16.634 |
| 1403 | N | VAL | 179 | 84.899 | 58.764 | 11.274 |
| 1404 | CA | VAL | 179 | 85.345 | 58.040 | 10.083 |
| 1405 | C | VAL | 179 | 85.796 | 56.644 | 10.496 |
| 1406 | O | VAL | 179 | 86.435 | 56.455 | 11.537 |
| 1407 | CB | VAL | 179 | 86.470 | 58.822 | 9.421 |
| 1408 | CG1 | VAL | 179 | 87.012 | 58.121 | 8.182 |
| 1409 | CG2 | VAL | 179 | 85.964 | 60.201 | 9.042 |
| 1410 | N | TRP | 180 | 85.398 | 55.675 | 9.698 |
| 1411 | CA | TRP | 180 | 85.625 | 54.267 | 10.005 |
| 1412 | C | TRP | 180 | 86.069 | 53.546 | 8.736 |
| 1413 | O | TRP | 180 | 85.235 | 53.151 | 7.913 |
| 1414 | CB | TRP | 180 | 84.260 | 53.822 | 10.498 |
| 1415 | CG | TRP | 180 | 84.014 | 52.374 | 10.836 |
| 1416 | CD1 | TRP | 180 | 83.262 | 51.498 | 10.098 |
| 1417 | CD2 | TRP | 180 | 84.469 | 51.654 | 12.000 |
| 1418 | NE1 | TRP | 180 | 83.218 | 50.319 | 10.756 |
| 1419 | CE2 | TRP | 180 | 83.913 | 50.371 | 11.903 |
| 1420 | CE3 | TRP | 180 | 85.239 | 52.002 | 13.105 |
| 1421 | CZ2 | TRP | 180 | 84.128 | 49.446 | 12.919 |
| 1422 | CZ3 | TRP | 180 | 85.450 | 51.072 | 14.107 |
| 1423 | CH2 | TRP | 180 | 84.899 | 49.797 | 14.019 |
| 1424 | N | VAL | 181 | 87.377 | 53.478 | 8.542 |
| 1425 | CA | VAL | 181 | 87.943 | 53.048 | 7.254 |
| 1426 | C | VAL | 181 | 87.961 | 51.531 | 7.053 |
| 1427 | O | VAL | 181 | 88.773 | 50.807 | 7.642 |
| 1428 | CB | VAL | 181 | 89.361 | 53.602 | 7.162 |
| 1429 | CG1 | VAL | 181 | 90.030 | 53.201 | 5.851 |
| 1430 | CG2 | VAL | 181 | 89.358 | 55.119 | 7.315 |
| 1431 | N | SER | 182 | 87.101 | 51.088 | 6.152 |
| 1432 | CA | SER | 182 | 87.000 | 49.675 | 5.788 |
| 1433 | C | SER | 182 | 87.687 | 49.448 | 4.443 |
| 1434 | O | SER | 182 | 87.797 | 50.364 | 3.620 |
| 1435 | CB | SER | 182 | 85.518 | 49.298 | 5.701 |
| 1436 | OG | SER | 182 | 85.405 | 47.908 | 5.408 |
| 1437 | N | SER | 183 | 88.237 | 48.260 | 4.273 |
| 1438 | CA | SER | 183 | 88.824 | 47.888 | 2.984 |
| 1439 | C | SER | 183 | 87.748 | 47.806 | 1.914 |
| 1440 | O | SER | 183 | 86.657 | 47.283 | 2.168 |
| 1441 | CB | SER | 183 | 89.483 | 46.519 | 3.119 |
| 1442 | OG | SER | 183 | 89.820 | 46.048 | 1.817 |
| 1443 | N | LEU | 184 | 88.128 | 48.128 | 0.687 |
| 1444 | CA | LEU | 184 | 87.212 | 47.997 | −0.451 |
| 1445 | C | LEU | 184 | 86.898 | 46.550 | −0.829 |
| 1446 | O | LEU | 184 | 85.847 | 46.305 | −1.431 |
| 1447 | CB | LEU | 184 | 87.825 | 48.678 | −1.666 |
| 1448 | CG | LEU | 184 | 87.178 | 50.032 | −1.881 |
| 1449 | CD1 | LEU | 184 | 87.533 | 50.584 | −3.255 |
| 1450 | CD2 | LEU | 184 | 85.672 | 49.871 | −1.768 |
| 1451 | N | MET | 185 | 87.638 | 45.597 | −0.282 |
| 1452 | CA | MET | 185 | 87.379 | 44.196 | −0.585 |
| 1453 | C | MET | 185 | 86.312 | 43.603 | 0.331 |
| 1454 | O | MET | 185 | 85.817 | 42.510 | 0.033 |
| 1455 | CB | MET | 185 | 88.687 | 43.436 | −0.433 |
| 1456 | CG | MET | 185 | 89.754 | 44.020 | −1.351 |
| 1457 | SD | MET | 185 | 89.356 | 43.993 | −3.115 |
| 1458 | CE | MET | 185 | 90.766 | 44.936 | −3.740 |
| 1459 | N | SER | 186 | 85.812 | 44.385 | 1.279 |
| 1460 | CA | SER | 186 | 84.787 | 43.877 | 2.193 |
| 1461 | C | SER | 186 | 83.421 | 43.774 | 1.512 |
| 1462 | O | SER | 186 | 82.702 | 42.793 | 1.744 |
| 1463 | CB | SER | 186 | 84.696 | 44.797 | 3.407 |
| 1464 | OG | SER | 186 | 84.237 | 46.082 | 3.018 |
| 1465 | N | SER | 187 | 83.202 | 44.603 | 0.503 |
| 1466 | CA | SER | 187 | 81.959 | 44.515 | −0.275 |

TABLE 8-continued

| Atom No. | Atom Type | Residue | Residue Position | X Coord. | Y Coord. | Z Coord. |
|---|---|---|---|---|---|---|
| 1467 | C | SER | 187 | 81.890 | 43.250 | −1.152 |
| 1468 | O | SER | 187 | 80.938 | 42.489 | −0.948 |
| 1469 | CB | SER | 187 | 81.762 | 45.777 | −1.106 |
| 1470 | OG | SER | 187 | 80.575 | 45.600 | −1.868 |
| 1471 | N | PRO | 188 | 82.848 | 42.949 | −2.032 |
| 1472 | CA | PRO | 188 | 82.808 | 41.644 | −2.710 |
| 1473 | C | PRO | 188 | 83.049 | 40.436 | −1.798 |
| 1474 | O | PRO | 188 | 82.498 | 39.364 | −2.083 |
| 1475 | CB | PRO | 188 | 83.859 | 41.719 | −3.775 |
| 1476 | CG | PRO | 188 | 84.658 | 43.003 | −3.618 |
| 1477 | CD | PRO | 188 | 84.009 | 43.749 | −2.469 |
| 1478 | N | LYS | 189 | 83.629 | 40.634 | −0.624 |
| 1479 | CA | LYS | 189 | 83.831 | 39.518 | 0.307 |
| 1480 | C | LYS | 189 | 82.533 | 39.083 | 0.970 |
| 1481 | O | LYS | 189 | 82.337 | 37.874 | 1.162 |
| 1482 | CB | LYS | 189 | 84.825 | 39.935 | 1.382 |
| 1483 | CG | LYS | 189 | 85.227 | 38.739 | 2.230 |
| 1484 | CD | LYS | 189 | 85.987 | 37.707 | 1.410 |
| 1485 | CE | LYS | 189 | 86.566 | 36.627 | 2.311 |
| 1486 | NZ | LYS | 189 | 85.514 | 36.045 | 3.153 |
| 1487 | N | TYR | 190 | 81.564 | 39.982 | 0.959 |
| 1488 | CA | TYR | 190 | 80.232 | 39.710 | 1.497 |
| 1489 | C | TYR | 190 | 79.424 | 38.756 | 0.603 |
| 1490 | O | TYR | 190 | 78.496 | 38.086 | 1.076 |
| 1491 | CB | TYR | 190 | 79.524 | 41.060 | 1.569 |
| 1492 | CG | TYR | 190 | 78.159 | 41.047 | 2.244 |
| 1493 | CD1 | TYR | 190 | 78.002 | 40.453 | 3.491 |
| 1494 | CD2 | TYR | 190 | 77.076 | 41.650 | 1.616 |
| 1495 | CE1 | TYR | 190 | 76.762 | 40.454 | 4.110 |
| 1496 | CE2 | TYR | 190 | 75.833 | 41.651 | 2.237 |
| 1497 | CZ | TYR | 190 | 75.681 | 41.053 | 3.482 |
| 1498 | OH | TYR | 190 | 74.458 | 41.092 | 4.115 |
| 1499 | N | LEU | 191 | 79.826 | 38.595 | −0.646 |
| 1500 | CA | LEU | 191 | 79.155 | 37.597 | −1.492 |
| 1501 | C | LEU | 191 | 80.069 | 36.393 | −1.740 |
| 1502 | O | LEU | 191 | 79.599 | 35.253 | −1.831 |
| 1503 | CB | LEU | 191 | 78.745 | 38.198 | −2.834 |
| 1504 | CG | LEU | 191 | 77.399 | 38.916 | −2.836 |
| 1505 | CD1 | LEU | 191 | 77.435 | 40.286 | −2.171 |
| 1506 | CD2 | LEU | 191 | 76.886 | 39.071 | −4.257 |
| 1507 | N | SER | 192 | 81.366 | 36.617 | −1.599 |
| 1508 | CA | SER | 192 | 82.350 | 35.564 | −1.887 |
| 1509 | C | SER | 192 | 82.570 | 34.590 | −0.734 |
| 1510 | O | SER | 192 | 83.208 | 33.553 | −0.947 |
| 1511 | CB | SER | 192 | 83.670 | 36.212 | −2.270 |
| 1512 | OG | SER | 192 | 84.138 | 36.847 | −1.097 |
| 1513 | N | PHE | 193 | 82.035 | 34.864 | 0.447 |
| 1514 | CA | PHE | 193 | 82.091 | 33.834 | 1.505 |
| 1515 | C | PHE | 193 | 80.862 | 32.908 | 1.451 |
| 1516 | O | PHE | 193 | 80.047 | 32.878 | 2.381 |
| 1517 | CB | PHE | 193 | 82.327 | 34.430 | 2.908 |
| 1518 | CG | PHE | 193 | 81.521 | 35.649 | 3.394 |
| 1519 | CD1 | PHE | 193 | 82.173 | 36.621 | 4.138 |
| 1520 | CD2 | PHE | 193 | 80.166 | 35.769 | 3.137 |
| 1521 | CE1 | PHE | 193 | 81.472 | 37.731 | 4.594 |
| 1522 | CE2 | PHE | 193 | 79.466 | 36.868 | 3.593 |
| 1523 | CZ | PHE | 193 | 80.115 | 37.857 | 4.318 |
| 1524 | N | ASN | 194 | 80.842 | 32.082 | 0.412 |
| 1525 | CA | ASN | 194 | 79.754 | 31.139 | 0.105 |
| 1526 | C | ASN | 194 | 78.400 | 31.831 | −0.013 |
| 1527 | O | ASN | 194 | 77.590 | 31.762 | 0.918 |
| 1528 | CB | ASN | 194 | 79.711 | 30.053 | 1.179 |
| 1529 | CG | ASN | 194 | 80.908 | 29.120 | 1.052 |
| 1530 | OD1 | ASN | 194 | 81.461 | 28.930 | −0.039 |
| 1531 | ND2 | ASN | 194 | 81.333 | 28.626 | 2.199 |
| 1532 | N | ASP | 195 | 78.152 | 32.521 | −1.119 |
| 1533 | CA | ASP | 195 | 76.844 | 33.165 | −1.253 |
| 1534 | C | ASP | 195 | 76.365 | 33.268 | −2.698 |
| 1535 | O | ASP | 195 | 76.749 | 34.189 | −3.426 |
| 1536 | CB | ASP | 195 | 76.870 | 34.558 | −0.606 |
| 1537 | CG | ASP | 195 | 75.532 | 35.256 | −0.832 |
| 1538 | OD1 | ASP | 195 | 74.525 | 34.711 | −0.378 |
| 1539 | OD2 | ASP | 195 | 75.502 | 36.186 | −1.629 |
| 1540 | N | LEU | 196 | 75.614 | 32.248 | −3.096 |
| 1541 | CA | LEU | 196 | 74.792 | 32.207 | −4.327 |
| 1542 | C | LEU | 196 | 75.504 | 31.851 | −5.641 |

TABLE 8-continued

| Atom No. | Atom Type | Residue | Residue Position | X Coord. | Y Coord. | Z Coord. |
|---|---|---|---|---|---|---|
| 1543 | O | LEU | 196 | 74.825 | 31.324 | −6.527 |
| 1544 | CB | LEU | 196 | 74.110 | 33.568 | −4.479 |
| 1545 | CG | LEU | 196 | 73.035 | 33.588 | −5.557 |
| 1546 | CD1 | LEU | 196 | 71.872 | 32.691 | −5.168 |
| 1547 | CD2 | LEU | 196 | 72.569 | 35.013 | −5.823 |
| 1548 | N | GLN | 197 | 76.826 | 31.876 | −5.716 |
| 1549 | CA | GLN | 197 | 77.495 | 31.625 | −7.019 |
| 1550 | C | GLN | 197 | 77.768 | 30.150 | −7.354 |
| 1551 | O | GLN | 197 | 78.691 | 29.864 | −8.126 |
| 1552 | CB | GLN | 197 | 78.811 | 32.406 | −7.133 |
| 1553 | CG | GLN | 197 | 78.643 | 33.909 | −7.355 |
| 1554 | CD | GLN | 197 | 78.522 | 34.634 | −6.024 |
| 1555 | OE1 | GLN | 197 | 79.272 | 34.344 | −5.086 |
| 1556 | NE2 | GLN | 197 | 77.552 | 35.529 | −5.946 |
| 1557 | N | LEU | 198 | 76.952 | 29.234 | −6.859 |
| 1558 | CA | LEU | 198 | 77.192 | 27.816 | −7.158 |
| 1559 | C | LEU | 198 | 76.173 | 27.295 | −8.173 |
| 1560 | O | LEU | 198 | 74.988 | 27.077 | −7.871 |
| 1561 | CB | LEU | 198 | 77.169 | 26.991 | −5.874 |
| 1562 | CG | LEU | 198 | 77.491 | 25.522 | −6.139 |
| 1563 | CD1 | LEU | 198 | 78.871 | 25.367 | −6.772 |
| 1564 | CD2 | LEU | 198 | 77.401 | 24.714 | −4.851 |
| 1565 | N | LEU | 199 | 76.687 | 27.132 | −9.386 |
| 1566 | CA | LEU | 199 | 75.923 | 26.680 | −10.557 |
| 1567 | C | LEU | 199 | 74.788 | 27.663 | −10.858 |
| 1568 | O | LEU | 199 | 73.640 | 27.255 | −11.077 |
| 1569 | CB | LEU | 199 | 75.391 | 25.268 | −10.287 |
| 1570 | CG | LEU | 199 | 74.863 | 24.571 | −11.540 |
| 1571 | CD1 | LEU | 199 | 75.959 | 24.424 | −12.590 |
| 1572 | CD2 | LEU | 199 | 74.263 | 23.214 | −11.192 |
| 1573 | N | ARG | 200 | 75.144 | 28.944 | −10.864 |
| 1574 | CA | ARG | 200 | 74.251 | 30.111 | −11.085 |
| 1575 | C | ARG | 200 | 73.103 | 30.345 | −10.076 |
| 1576 | O | ARG | 200 | 72.886 | 31.490 | −9.664 |
| 1577 | CB | ARG | 200 | 73.672 | 30.009 | −12.496 |
| 1578 | CG | ARG | 200 | 72.707 | 31.152 | −12.791 |
| 1579 | CD | ARG | 200 | 72.182 | 31.099 | −14.218 |
| 1580 | NE | ARG | 200 | 73.280 | 31.273 | −15.181 |
| 1581 | CZ | ARG | 200 | 73.484 | 32.404 | −15.862 |
| 1582 | NH1 | ARG | 200 | 72.648 | 33.435 | −15.715 |
| 1583 | NH2 | ARG | 200 | 74.511 | 32.495 | −16.710 |
| 1584 | N | SER | 201 | 72.374 | 29.308 | −9.701 |
| 1585 | CA | SER | 201 | 71.212 | 29.455 | −8.816 |
| 1586 | C | SER | 201 | 71.098 | 28.438 | −7.661 |
| 1587 | O | SER | 201 | 70.934 | 28.914 | −6.531 |
| 1588 | CB | SER | 201 | 69.947 | 29.426 | −9.672 |
| 1589 | OG | SER | 201 | 69.999 | 30.533 | −10.563 |
| 1590 | N | PRO | 202 | 71.146 | 27.116 | −7.869 |
| 1591 | CA | PRO | 202 | 70.623 | 26.213 | −6.826 |
| 1592 | C | PRO | 202 | 71.471 | 26.122 | −5.556 |
| 1593 | O | PRO | 202 | 70.867 | 25.990 | −4.482 |
| 1594 | CB | PRO | 202 | 70.526 | 24.859 | −7.459 |
| 1595 | CG | PRO | 202 | 71.087 | 24.914 | −8.866 |
| 1596 | CD | PRO | 202 | 71.423 | 26.371 | −9.112 |
| 1597 | N | ALA | 203 | 72.757 | 26.445 | −5.669 |
| 1598 | CA | ALA | 203 | 73.756 | 26.416 | −4.577 |
| 1599 | C | ALA | 203 | 73.258 | 25.892 | −3.234 |
| 1600 | O | ALA | 203 | 73.040 | 24.691 | −3.042 |
| 1601 | CB | ALA | 203 | 74.220 | 27.853 | −4.373 |
| 1602 | N | SER | 204 | 73.156 | 26.813 | −2.294 |
| 1603 | CA | SER | 204 | 72.504 | 26.540 | −1.015 |
| 1604 | C | SER | 204 | 71.573 | 27.704 | −0.717 |
| 1605 | O | SER | 204 | 71.849 | 28.526 | 0.175 |
| 1606 | CB | SER | 204 | 73.554 | 26.388 | 0.077 |
| 1607 | OG | SER | 204 | 74.382 | 25.288 | −0.274 |
| 1608 | N | TYR | 205 | 70.525 | 27.785 | −1.525 |
| 1609 | CA | TYR | 205 | 69.559 | 28.894 | −1.489 |
| 1610 | C | TYR | 205 | 68.953 | 29.061 | −0.102 |
| 1611 | O | TYR | 205 | 68.339 | 28.136 | 0.441 |
| 1612 | CB | TYR | 205 | 68.458 | 28.598 | −2.504 |
| 1613 | CG | TYR | 205 | 67.440 | 29.720 | −2.692 |
| 1614 | CD1 | TYR | 205 | 67.682 | 30.712 | −3.633 |
| 1615 | CD2 | TYR | 205 | 66.266 | 29.737 | −1.947 |
| 1616 | CE1 | TYR | 205 | 66.764 | 31.739 | −3.811 |
| 1617 | CE2 | TYR | 205 | 65.348 | 30.765 | −2.122 |
| 1618 | CZ | TYR | 205 | 65.603 | 31.764 | −3.050 |

TABLE 8-continued

| Atom No. | Atom Type | Residue | Residue Position | X Coord. | Y Coord. | Z Coord. |
|---|---|---|---|---|---|---|
| 1619 | OH | TYR | 205 | 64.730 | 32.823 | −3.167 |
| 1620 | N | GLU | 206 | 69.213 | 30.231 | 0.468 |
| 1621 | CA | GLU | 206 | 68.824 | 30.597 | 1.839 |
| 1622 | C | GLU | 206 | 69.219 | 29.526 | 2.870 |
| 1623 | O | GLU | 206 | 68.413 | 29.086 | 3.697 |
| 1624 | CB | GLU | 206 | 67.323 | 30.866 | 1.848 |
| 1625 | CG | GLU | 206 | 66.884 | 31.671 | 3.064 |
| 1626 | CD | GLU | 206 | 65.396 | 31.985 | 2.939 |
| 1627 | OE1 | GLU | 206 | 64.753 | 31.357 | 2.109 |
| 1628 | OE2 | GLU | 206 | 64.961 | 32.944 | 3.561 |
| 1629 | N | GLY | 207 | 70.443 | 29.048 | 2.724 |
| 1630 | CA | GLY | 207 | 71.072 | 28.133 | 3.678 |
| 1631 | C | GLY | 207 | 72.475 | 28.647 | 3.961 |
| 1632 | O | GLY | 207 | 72.764 | 29.107 | 5.068 |
| 1633 | N | SER | 208 | 73.259 | 28.802 | 2.907 |
| 1634 | CA | SER | 208 | 74.578 | 29.414 | 3.091 |
| 1635 | C | SER | 208 | 74.427 | 30.934 | 3.052 |
| 1636 | O | SER | 208 | 75.151 | 31.666 | 3.737 |
| 1637 | CB | SER | 208 | 75.533 | 28.943 | 2.001 |
| 1638 | OG | SER | 208 | 76.814 | 29.464 | 2.318 |
| 1639 | N | LYS | 209 | 73.286 | 31.340 | 2.515 |
| 1640 | CA | LYS | 209 | 72.870 | 32.742 | 2.472 |
| 1641 | C | LYS | 209 | 72.260 | 33.237 | 3.795 |
| 1642 | O | LYS | 209 | 72.067 | 34.451 | 3.931 |
| 1643 | CB | LYS | 209 | 71.838 | 32.872 | 1.353 |
| 1644 | CG | LYS | 209 | 71.494 | 34.319 | 1.018 |
| 1645 | CD | LYS | 209 | 70.330 | 34.378 | 0.036 |
| 1646 | CE | LYS | 209 | 70.631 | 33.584 | −1.229 |
| 1647 | NZ | LYS | 209 | 69.469 | 33.582 | −2.130 |
| 1648 | N | ARG | 210 | 72.153 | 32.395 | 4.818 |
| 1649 | CA | ARG | 210 | 71.602 | 32.868 | 6.101 |
| 1650 | C | ARG | 210 | 72.531 | 33.875 | 6.775 |
| 1651 | O | ARG | 210 | 72.033 | 34.886 | 7.288 |
| 1652 | CB | ARG | 210 | 71.398 | 31.696 | 7.053 |
| 1653 | CG | ARG | 210 | 70.382 | 30.688 | 6.534 |
| 1654 | CD | ARG | 210 | 70.200 | 29.553 | 7.538 |
| 1655 | NE | ARG | 210 | 71.507 | 29.000 | 7.932 |
| 1656 | CZ | ARG | 210 | 71.842 | 27.716 | 7.779 |
| 1657 | NH1 | ARG | 210 | 73.076 | 27.306 | 8.082 |
| 1658 | NH2 | ARG | 210 | 70.960 | 26.856 | 7.265 |
| 1659 | N | LEU | 211 | 73.817 | 33.777 | 6.473 |
| 1660 | CA | LEU | 211 | 74.800 | 34.753 | 6.955 |
| 1661 | C | LEU | 211 | 74.493 | 36.137 | 6.394 |
| 1662 | O | LEU | 211 | 74.174 | 37.054 | 7.162 |
| 1663 | CB | LEU | 211 | 76.169 | 34.330 | 6.435 |
| 1664 | CG | LEU | 211 | 76.523 | 32.901 | 6.830 |
| 1665 | CD1 | LEU | 211 | 77.734 | 32.408 | 6.046 |
| 1666 | CD2 | LEU | 211 | 76.753 | 32.779 | 8.333 |
| 1667 | N | VAL | 212 | 74.245 | 36.164 | 5.094 |
| 1668 | CA | VAL | 212 | 73.998 | 37.412 | 4.373 |
| 1669 | C | VAL | 212 | 72.598 | 37.966 | 4.641 |
| 1670 | O | VAL | 212 | 72.450 | 39.182 | 4.787 |
| 1671 | CB | VAL | 212 | 74.172 | 37.091 | 2.892 |
| 1672 | CG1 | VAL | 212 | 73.837 | 38.277 | 1.999 |
| 1673 | CG2 | VAL | 212 | 75.586 | 36.592 | 2.615 |
| 1674 | N | ASP | 213 | 71.671 | 37.091 | 4.998 |
| 1675 | CA | ASP | 213 | 70.319 | 37.523 | 5.365 |
| 1676 | C | ASP | 213 | 70.313 | 38.219 | 6.724 |
| 1677 | O | ASP | 213 | 69.821 | 39.352 | 6.823 |
| 1678 | CB | ASP | 213 | 69.410 | 36.298 | 5.439 |
| 1679 | CG | ASP | 213 | 69.299 | 35.585 | 4.092 |
| 1680 | OD1 | ASP | 213 | 69.300 | 36.271 | 3.078 |
| 1681 | OD2 | ASP | 213 | 69.132 | 34.369 | 4.097 |
| 1682 | N | LEU | 214 | 71.097 | 37.695 | 7.655 |
| 1683 | CA | LEU | 214 | 71.171 | 38.292 | 8.995 |
| 1684 | C | LEU | 214 | 71.982 | 39.578 | 8.966 |
| 1685 | O | LEU | 214 | 71.561 | 40.584 | 9.548 |
| 1686 | CB | LEU | 214 | 71.849 | 37.300 | 9.930 |
| 1687 | CG | LEU | 214 | 71.030 | 36.025 | 10.089 |
| 1688 | CD1 | LEU | 214 | 71.819 | 34.956 | 10.837 |
| 1689 | CD2 | LEU | 214 | 69.698 | 36.306 | 10.777 |
| 1690 | N | MET | 215 | 72.932 | 39.616 | 8.046 |
| 1691 | CA | MET | 215 | 73.763 | 40.800 | 7.823 |
| 1692 | C | MET | 215 | 73.139 | 41.839 | 6.877 |
| 1693 | O | MET | 215 | 73.820 | 42.791 | 6.473 |
| 1694 | CB | MET | 215 | 75.116 | 40.319 | 7.315 |

TABLE 8-continued

| Atom No. | Atom Type | Residue | Residue Position | X Coord. | Y Coord. | Z Coord. |
|---|---|---|---|---|---|---|
| 1695 | CG | MET | 215 | 75.831 | 39.534 | 8.412 |
| 1696 | SD | MET | 215 | 77.574 | 39.143 | 8.127 |
| 1697 | CE | MET | 215 | 77.415 | 38.056 | 6.694 |
| 1698 | N | HIS | 216 | 71.904 | 41.608 | 6.460 |
| 1699 | CA | HIS | 216 | 71.130 | 42.615 | 5.735 |
| 1700 | C | HIS | 216 | 70.019 | 43.195 | 6.603 |
| 1701 | O | HIS | 216 | 69.474 | 44.260 | 6.286 |
| 1702 | CB | HIS | 216 | 70.480 | 41.971 | 4.517 |
| 1703 | CG | HIS | 216 | 71.307 | 42.019 | 3.252 |
| 1704 | ND1 | HIS | 216 | 72.173 | 42.987 | 2.896 |
| 1705 | CD2 | HIS | 216 | 71.305 | 41.091 | 2.238 |
| 1706 | CE1 | HIS | 216 | 72.704 | 42.689 | 1.695 |
| 1707 | NE2 | HIS | 216 | 72.169 | 41.515 | 1.289 |
| 1708 | N | PHE | 217 | 69.689 | 42.508 | 7.684 |
| 1709 | CA | PHE | 217 | 68.572 | 42.958 | 8.523 |
| 1710 | C | PHE | 217 | 69.006 | 43.966 | 9.578 |
| 1711 | O | PHE | 217 | 69.870 | 43.681 | 10.419 |
| 1712 | CB | PHE | 217 | 67.921 | 41.752 | 9.193 |
| 1713 | CG | PHE | 217 | 67.195 | 40.813 | 8.232 |
| 1714 | CD1 | PHE | 217 | 66.551 | 41.322 | 7.110 |
| 1715 | CD2 | PHE | 217 | 67.163 | 39.449 | 8.489 |
| 1716 | CE1 | PHE | 217 | 65.895 | 40.465 | 6.236 |
| 1717 | CE2 | PHE | 217 | 66.506 | 38.592 | 7.615 |
| 1718 | CZ | PHE | 217 | 65.875 | 39.099 | 6.487 |
| 1719 | N | GLY | 218 | 68.232 | 45.038 | 9.669 |
| 1720 | CA | GLY | 218 | 68.487 | 46.119 | 10.639 |
| 1721 | C | GLY | 218 | 67.887 | 45.856 | 12.025 |
| 1722 | O | GLY | 218 | 67.155 | 46.681 | 12.582 |
| 1723 | N | THR | 219 | 68.213 | 44.689 | 12.554 |
| 1724 | CA | THR | 219 | 67.816 | 44.247 | 13.889 |
| 1725 | C | THR | 219 | 69.005 | 43.523 | 14.506 |
| 1726 | O | THR | 219 | 68.964 | 43.095 | 15.667 |
| 1727 | CB | THR | 219 | 66.651 | 43.266 | 13.785 |
| 1728 | OG1 | THR | 219 | 67.061 | 42.201 | 12.937 |
| 1729 | CG2 | THR | 219 | 65.392 | 43.888 | 13.188 |
| 1730 | N | TYR | 220 | 70.034 | 43.361 | 13.687 |
| 1731 | CA | TYR | 220 | 71.239 | 42.624 | 14.075 |
| 1732 | C | TYR | 220 | 72.107 | 43.449 | 15.026 |
| 1733 | O | TYR | 220 | 72.784 | 44.398 | 14.617 |
| 1734 | CB | TYR | 220 | 71.995 | 42.317 | 12.785 |
| 1735 | CG | TYR | 220 | 73.052 | 41.223 | 12.885 |
| 1736 | CD1 | TYR | 220 | 72.864 | 40.157 | 13.754 |
| 1737 | CD2 | TYR | 220 | 74.182 | 41.272 | 12.079 |
| 1738 | CE1 | TYR | 220 | 73.825 | 39.160 | 13.847 |
| 1739 | CE2 | TYR | 220 | 75.145 | 40.275 | 12.171 |
| 1740 | CZ | TYR | 220 | 74.968 | 39.226 | 13.063 |
| 1741 | OH | TYR | 220 | 75.985 | 38.316 | 13.267 |
| 1742 | N | ASN | 221 | 72.053 | 43.086 | 16.297 |
| 1743 | CA | ASN | 221 | 72.810 | 43.804 | 17.327 |
| 1744 | C | ASN | 221 | 74.225 | 43.258 | 17.459 |
| 1745 | O | ASN | 221 | 74.492 | 42.088 | 17.148 |
| 1746 | CB | ASN | 221 | 72.074 | 43.742 | 18.665 |
| 1747 | CG | ASN | 221 | 71.884 | 42.313 | 19.168 |
| 1748 | OD1 | ASN | 221 | 72.857 | 41.595 | 19.445 |
| 1749 | ND2 | ASN | 221 | 70.627 | 41.935 | 19.321 |
| 1750 | N | LYS | 222 | 75.060 | 44.032 | 18.133 |
| 1751 | CA | LYS | 222 | 76.487 | 43.709 | 18.209 |
| 1752 | C | LYS | 222 | 76.839 | 42.535 | 19.125 |
| 1753 | O | LYS | 222 | 77.866 | 41.906 | 18.858 |
| 1754 | CB | LYS | 222 | 77.274 | 44.951 | 18.617 |
| 1755 | CG | LYS | 222 | 76.834 | 45.537 | 19.955 |
| 1756 | CD | LYS | 222 | 77.721 | 46.720 | 20.334 |
| 1757 | CE | LYS | 222 | 77.311 | 47.351 | 21.661 |
| 1758 | NZ | LYS | 222 | 75.959 | 47.926 | 21.579 |
| 1759 | N | LEU | 223 | 75.908 | 42.040 | 19.927 |
| 1760 | CA | LEU | 223 | 76.218 | 40.876 | 20.759 |
| 1761 | C | LEU | 223 | 76.147 | 39.604 | 19.918 |
| 1762 | O | LEU | 223 | 77.085 | 38.796 | 19.957 |
| 1763 | CB | LEU | 223 | 75.210 | 40.799 | 21.898 |
| 1764 | CG | LEU | 223 | 75.532 | 39.650 | 22.846 |
| 1765 | CD1 | LEU | 223 | 76.920 | 39.821 | 23.457 |
| 1766 | CD2 | LEU | 223 | 74.475 | 39.528 | 23.938 |
| 1767 | N | GLU | 224 | 75.269 | 39.631 | 18.926 |
| 1768 | CA | GLU | 224 | 75.137 | 38.505 | 17.996 |
| 1769 | C | GLU | 224 | 76.247 | 38.536 | 16.952 |
| 1770 | O | GLU | 224 | 76.724 | 37.483 | 16.513 |

TABLE 8-continued

| Atom No. | Atom Type | Residue | Residue Position | X Coord. | Y Coord. | Z Coord. |
|---|---|---|---|---|---|---|
| 1771 | CB | GLU | 224 | 73.802 | 38.645 | 17.282 |
| 1772 | CG | GLU | 224 | 72.634 | 38.631 | 18.254 |
| 1773 | CD | GLU | 224 | 71.377 | 39.122 | 17.545 |
| 1774 | OE1 | GLU | 224 | 71.512 | 40.007 | 16.708 |
| 1775 | OE2 | GLU | 224 | 70.302 | 38.795 | 18.028 |
| 1776 | N | ARG | 225 | 76.796 | 39.721 | 16.750 |
| 1777 | CA | ARG | 225 | 77.914 | 39.898 | 15.830 |
| 1778 | C | ARG | 225 | 79.232 | 39.489 | 16.483 |
| 1779 | O | ARG | 225 | 80.085 | 38.874 | 15.827 |
| 1780 | CB | ARG | 225 | 77.962 | 41.375 | 15.478 |
| 1781 | CG | ARG | 225 | 76.647 | 41.858 | 14.889 |
| 1782 | CD | ARG | 225 | 76.756 | 43.329 | 14.518 |
| 1783 | NE | ARG | 225 | 77.985 | 43.518 | 13.741 |
| 1784 | CZ | ARG | 225 | 78.004 | 43.568 | 12.411 |
| 1785 | NH1 | ARG | 225 | 79.153 | 43.344 | 11.772 |
| 1786 | NH2 | ARG | 225 | 76.854 | 43.548 | 11.734 |
| 1787 | N | GLU | 226 | 79.295 | 39.623 | 17.798 |
| 1788 | CA | GLU | 226 | 80.478 | 39.189 | 18.544 |
| 1789 | C | GLU | 226 | 80.490 | 37.673 | 18.686 |
| 1790 | O | GLU | 226 | 81.549 | 37.057 | 18.510 |
| 1791 | CB | GLU | 226 | 80.461 | 39.851 | 19.918 |
| 1792 | CG | GLU | 226 | 80.652 | 41.359 | 19.797 |
| 1793 | CD | GLU | 226 | 80.397 | 42.048 | 21.134 |
| 1794 | OE1 | GLU | 226 | 79.274 | 42.489 | 21.350 |
| 1795 | OE2 | GLU | 226 | 81.350 | 42.197 | 21.886 |
| 1796 | N | HIS | 227 | 79.303 | 37.084 | 18.707 |
| 1797 | CA | HIS | 227 | 79.205 | 35.625 | 18.678 |
| 1798 | C | HIS | 227 | 79.597 | 35.110 | 17.302 |
| 1799 | O | HIS | 227 | 80.460 | 34.230 | 17.227 |
| 1800 | CB | HIS | 227 | 77.779 | 35.192 | 18.986 |
| 1801 | CG | HIS | 227 | 77.300 | 35.542 | 20.381 |
| 1802 | ND1 | HIS | 227 | 76.027 | 35.769 | 20.744 |
| 1803 | CD2 | HIS | 227 | 78.072 | 35.676 | 21.511 |
| 1804 | CE1 | HIS | 227 | 75.982 | 36.052 | 22.063 |
| 1805 | NE2 | HIS | 227 | 77.247 | 35.995 | 22.536 |
| 1806 | N | GLY | 228 | 79.186 | 35.830 | 16.268 |
| 1807 | CA | GLY | 228 | 79.563 | 35.530 | 14.879 |
| 1808 | C | GLY | 228 | 81.068 | 35.360 | 14.686 |
| 1809 | O | GLY | 228 | 81.523 | 34.246 | 14.389 |
| 1810 | N | ILE | 229 | 81.845 | 36.378 | 15.027 |
| 1811 | CA | ILE | 229 | 83.301 | 36.276 | 14.832 |
| 1812 | C | ILE | 229 | 84.003 | 35.359 | 15.837 |
| 1813 | O | ILE | 229 | 84.956 | 34.671 | 15.443 |
| 1814 | CB | ILE | 229 | 83.921 | 37.670 | 14.836 |
| 1815 | CG1 | ILE | 229 | 83.876 | 38.259 | 13.435 |
| 1816 | CG2 | ILE | 229 | 85.350 | 37.680 | 15.369 |
| 1817 | CD1 | ILE | 229 | 84.859 | 39.414 | 13.321 |
| 1818 | N | LYS | 230 | 83.374 | 35.105 | 16.972 |
| 1819 | CA | LYS | 230 | 83.920 | 34.135 | 17.923 |
| 1820 | C | LYS | 230 | 83.745 | 32.705 | 17.409 |
| 1821 | O | LYS | 230 | 84.711 | 31.932 | 17.419 |
| 1822 | CB | LYS | 230 | 83.172 | 34.313 | 19.239 |
| 1823 | CG | LYS | 230 | 83.496 | 33.218 | 20.248 |
| 1824 | CD | LYS | 230 | 82.671 | 33.391 | 21.518 |
| 1825 | CE | LYS | 230 | 81.174 | 33.390 | 21.221 |
| 1826 | NZ | LYS | 230 | 80.739 | 32.115 | 20.627 |
| 1827 | N | GLN | 231 | 82.658 | 32.476 | 16.690 |
| 1828 | CA | GLN | 231 | 82.391 | 31.166 | 16.098 |
| 1829 | C | GLN | 231 | 83.211 | 30.952 | 14.832 |
| 1830 | O | GLN | 231 | 83.768 | 29.862 | 14.657 |
| 1831 | CB | GLN | 231 | 80.902 | 31.102 | 15.796 |
| 1832 | CG | GLN | 231 | 80.123 | 31.182 | 17.102 |
| 1833 | CD | GLN | 231 | 78.675 | 31.604 | 16.871 |
| 1834 | OE1 | GLN | 231 | 78.356 | 32.340 | 15.928 |
| 1835 | NE2 | GLN | 231 | 77.827 | 31.218 | 17.808 |
| 1836 | N | TYR | 232 | 83.567 | 32.047 | 14.181 |
| 1837 | CA | TYR | 232 | 84.442 | 31.969 | 13.007 |
| 1838 | C | TYR | 232 | 85.881 | 31.654 | 13.407 |
| 1839 | O | TYR | 232 | 86.558 | 30.876 | 12.724 |
| 1840 | CB | TYR | 232 | 84.422 | 33.311 | 12.281 |
| 1841 | CG | TYR | 232 | 83.105 | 33.692 | 11.610 |
| 1842 | CD1 | TYR | 232 | 82.199 | 32.712 | 11.223 |
| 1843 | CD2 | TYR | 232 | 82.820 | 35.032 | 11.376 |
| 1844 | CE1 | TYR | 232 | 81.006 | 33.072 | 10.612 |
| 1845 | CE2 | TYR | 232 | 81.629 | 35.393 | 10.762 |
| 1846 | CZ | TYR | 232 | 80.725 | 34.411 | 10.380 |

TABLE 8-continued

| Atom No. | Atom Type | Residue | Residue Position | X Coord. | Y Coord. | Z Coord. |
|---|---|---|---|---|---|---|
| 1847 | OH | TYR | 232 | 79.562 | 34.762 | 9.734 |
| 1848 | N | LEU | 233 | 86.260 | 32.074 | 14.604 |
| 1849 | CA | LEU | 233 | 87.607 | 31.800 | 15.103 |
| 1850 | C | LEU | 233 | 87.710 | 30.424 | 15.770 |
| 1851 | O | LEU | 233 | 88.798 | 29.835 | 15.793 |
| 1852 | CB | LEU | 233 | 87.948 | 32.901 | 16.104 |
| 1853 | CG | LEU | 233 | 89.389 | 32.820 | 16.595 |
| 1854 | CD1 | LEU | 233 | 90.366 | 32.793 | 15.425 |
| 1855 | CD2 | LEU | 233 | 89.706 | 33.975 | 17.539 |
| 1856 | N | VAL | 234 | 86.585 | 29.850 | 16.164 |
| 1857 | CA | VAL | 234 | 86.624 | 28.526 | 16.794 |
| 1858 | C | VAL | 234 | 86.290 | 27.387 | 15.827 |
| 1859 | O | VAL | 234 | 86.002 | 26.272 | 16.282 |
| 1860 | CB | VAL | 234 | 85.706 | 28.475 | 18.014 |
| 1861 | CG1 | VAL | 234 | 86.123 | 29.504 | 19.059 |
| 1862 | CG2 | VAL | 234 | 84.237 | 28.638 | 17.653 |
| 1863 | N | HIS | 235 | 86.271 | 27.649 | 14.529 |
| 1864 | CA | HIS | 235 | 86.045 | 26.541 | 13.582 |
| 1865 | C | HIS | 235 | 87.222 | 26.300 | 12.631 |
| 1866 | O | HIS | 235 | 87.044 | 26.490 | 11.422 |
| 1867 | CB | HIS | 235 | 84.819 | 26.844 | 12.726 |
| 1868 | CG | HIS | 235 | 83.495 | 26.919 | 13.452 |
| 1869 | ND1 | HIS | 235 | 83.164 | 26.322 | 14.617 |
| 1870 | CD2 | HIS | 235 | 82.384 | 27.617 | 13.037 |
| 1871 | CE1 | HIS | 235 | 81.896 | 26.634 | 14.935 |
| 1872 | NE2 | HIS | 235 | 81.412 | 27.437 | 13.957 |
| 1873 | N | PRO | 236 | 88.305 | 25.693 | 13.104 |
| 1874 | CA | PRO | 236 | 89.449 | 25.411 | 12.223 |
| 1875 | C | PRO | 236 | 89.098 | 24.320 | 11.214 |
| 1876 | O | PRO | 236 | 88.663 | 23.229 | 11.594 |
| 1877 | CB | PRO | 236 | 90.548 | 24.964 | 13.137 |
| 1878 | CG | PRO | 236 | 89.984 | 24.763 | 14.535 |
| 1879 | CD | PRO | 236 | 88.524 | 25.175 | 14.459 |
| 1880 | N | GLY | 237 | 89.137 | 24.679 | 9.940 |
| 1881 | CA | GLY | 237 | 88.736 | 23.764 | 8.857 |
| 1882 | C | GLY | 237 | 87.241 | 23.870 | 8.527 |
| 1883 | O | GLY | 237 | 86.854 | 24.196 | 7.396 |
| 1884 | N | ILE | 238 | 86.438 | 23.790 | 9.579 |
| 1885 | CA | ILE | 238 | 84.973 | 23.751 | 9.507 |
| 1886 | C | ILE | 238 | 84.338 | 25.084 | 9.096 |
| 1887 | O | ILE | 238 | 83.236 | 25.091 | 8.529 |
| 1888 | CB | ILE | 238 | 84.516 | 23.395 | 10.918 |
| 1889 | CG1 | ILE | 238 | 85.313 | 22.211 | 11.449 |
| 1890 | CG2 | ILE | 238 | 83.030 | 23.074 | 10.955 |
| 1891 | CD1 | ILE | 238 | 84.911 | 21.872 | 12.880 |
| 1892 | N | PHE | 239 | 85.124 | 26.148 | 9.126 |
| 1893 | CA | PHE | 239 | 84.631 | 27.460 | 8.706 |
| 1894 | C | PHE | 239 | 84.376 | 27.535 | 7.200 |
| 1895 | O | PHE | 239 | 83.351 | 28.119 | 6.830 |
| 1896 | CB | PHE | 239 | 85.634 | 28.539 | 9.129 |
| 1897 | CG | PHE | 239 | 87.004 | 28.550 | 8.436 |
| 1898 | CD1 | PHE | 239 | 88.089 | 27.897 | 9.005 |
| 1899 | CD2 | PHE | 239 | 87.174 | 29.255 | 7.251 |
| 1900 | CE1 | PHE | 239 | 89.326 | 27.913 | 8.374 |
| 1901 | CE2 | PHE | 239 | 88.409 | 29.271 | 6.618 |
| 1902 | CZ | PHE | 239 | 89.485 | 28.597 | 7.177 |
| 1903 | N | THR | 240 | 85.009 | 26.664 | 6.425 |
| 1904 | CA | THR | 240 | 84.827 | 26.696 | 4.972 |
| 1905 | C | THR | 240 | 83.582 | 25.917 | 4.548 |
| 1906 | O | THR | 240 | 82.966 | 26.232 | 3.521 |
| 1907 | CB | THR | 240 | 86.065 | 26.071 | 4.337 |
| 1908 | OG1 | THR | 240 | 87.206 | 26.763 | 4.829 |
| 1909 | CG2 | THR | 240 | 86.059 | 26.184 | 2.817 |
| 1910 | N | SER | 241 | 83.105 | 25.058 | 5.436 |
| 1911 | CA | SER | 241 | 81.923 | 24.257 | 5.122 |
| 1912 | C | SER | 241 | 80.641 | 24.890 | 5.657 |
| 1913 | O | SER | 241 | 79.547 | 24.414 | 5.332 |
| 1914 | CB | SER | 241 | 82.081 | 22.866 | 5.727 |
| 1915 | OG | SER | 241 | 82.003 | 22.976 | 7.143 |
| 1916 | N | PHE | 242 | 80.765 | 25.933 | 6.463 |
| 1917 | CA | PHE | 242 | 79.563 | 26.567 | 7.018 |
| 1918 | C | PHE | 242 | 79.475 | 28.065 | 6.750 |
| 1919 | O | PHE | 242 | 78.371 | 28.599 | 6.586 |
| 1920 | CB | PHE | 242 | 79.535 | 26.342 | 8.528 |
| 1921 | CG | PHE | 242 | 79.175 | 24.921 | 8.953 |
| 1922 | CD1 | PHE | 242 | 79.857 | 24.314 | 9.999 |

TABLE 8-continued

| Atom No. | Atom Type | Residue | Residue Position | X Coord. | Y Coord. | Z Coord. |
|---|---|---|---|---|---|---|
| 1923 | CD2 | PHE | 242 | 78.161 | 24.233 | 8.298 |
| 1924 | CE1 | PHE | 242 | 79.526 | 23.023 | 10.389 |
| 1925 | CE2 | PHE | 242 | 77.830 | 22.941 | 8.687 |
| 1926 | CZ | PHE | 242 | 78.513 | 22.335 | 9.733 |
| 1927 | N | SER | 243 | 80.607 | 28.744 | 6.726 |
| 1928 | CA | SER | 243 | 80.572 | 30.205 | 6.671 |
| 1929 | C | SER | 243 | 81.651 | 30.835 | 5.799 |
| 1930 | O | SER | 243 | 81.703 | 30.637 | 4.580 |
| 1931 | CB | SER | 243 | 80.724 | 30.730 | 8.092 |
| 1932 | OG | SER | 243 | 79.587 | 30.326 | 8.843 |
| 1933 | N | PHE | 244 | 82.452 | 31.658 | 6.455 |
| 1934 | CA | PHE | 244 | 83.414 | 32.540 | 5.784 |
| 1935 | C | PHE | 244 | 84.594 | 31.804 | 5.165 |
| 1936 | O | PHE | 244 | 84.956 | 30.681 | 5.539 |
| 1937 | CB | PHE | 244 | 83.919 | 33.587 | 6.774 |
| 1938 | CG | PHE | 244 | 85.093 | 33.185 | 7.668 |
| 1939 | CD1 | PHE | 244 | 84.927 | 32.283 | 8.710 |
| 1940 | CD2 | PHE | 244 | 86.342 | 33.745 | 7.431 |
| 1941 | CE1 | PHE | 244 | 86.009 | 31.945 | 9.512 |
| 1942 | CE2 | PHE | 244 | 87.423 | 33.407 | 8.232 |
| 1943 | CZ | PHE | 244 | 87.255 | 32.507 | 9.275 |
| 1944 | N | PHE | 245 | 85.207 | 32.503 | 4.227 |
| 1945 | CA | PHE | 245 | 86.346 | 31.972 | 3.490 |
| 1946 | C | PHE | 245 | 87.680 | 32.415 | 4.094 |
| 1947 | O | PHE | 245 | 88.452 | 31.573 | 4.562 |
| 1948 | CB | PHE | 245 | 86.215 | 32.478 | 2.057 |
| 1949 | CG | PHE | 245 | 87.230 | 31.918 | 1.067 |
| 1950 | CD1 | PHE | 245 | 87.685 | 32.720 | 0.028 |
| 1951 | CD2 | PHE | 245 | 87.692 | 30.616 | 1.197 |
| 1952 | CE1 | PHE | 245 | 88.610 | 32.217 | −0.879 |
| 1953 | CE2 | PHE | 245 | 88.616 | 30.114 | 0.292 |
| 1954 | CZ | PHE | 245 | 89.075 | 30.913 | −0.746 |
| 1955 | N | GLN | 246 | 87.973 | 33.707 | 4.036 |
| 1956 | CA | GLN | 246 | 89.284 | 34.193 | 4.498 |
| 1957 | C | GLN | 246 | 89.263 | 35.523 | 5.245 |
| 1958 | O | GLN | 246 | 88.238 | 36.004 | 5.745 |
| 1959 | CB | GLN | 246 | 90.229 | 34.355 | 3.312 |
| 1960 | CG | GLN | 246 | 90.688 | 33.019 | 2.744 |
| 1961 | CD | GLN | 246 | 91.703 | 33.255 | 1.635 |
| 1962 | OE1 | GLN | 246 | 91.994 | 34.401 | 1.279 |
| 1963 | NE2 | GLN | 246 | 92.239 | 32.168 | 1.111 |
| 1964 | N | TYR | 247 | 90.392 | 36.193 | 5.090 |
| 1965 | CA | TYR | 247 | 90.773 | 37.387 | 5.857 |
| 1966 | C | TYR | 247 | 90.000 | 38.672 | 5.541 |
| 1967 | O | TYR | 247 | 89.823 | 39.498 | 6.444 |
| 1968 | CB | TYR | 247 | 92.258 | 37.592 | 5.556 |
| 1969 | CG | TYR | 247 | 92.770 | 39.015 | 5.743 |
| 1970 | CD1 | TYR | 247 | 92.999 | 39.512 | 7.019 |
| 1971 | CD2 | TYR | 247 | 93.012 | 39.812 | 4.630 |
| 1972 | CE1 | TYR | 247 | 93.439 | 40.818 | 7.183 |
| 1973 | CE2 | TYR | 247 | 93.452 | 41.118 | 4.793 |
| 1974 | CZ | TYR | 247 | 93.654 | 41.619 | 6.071 |
| 1975 | OH | TYR | 247 | 93.976 | 42.943 | 6.243 |
| 1976 | N | LEU | 248 | 89.324 | 38.733 | 4.405 |
| 1977 | CA | LEU | 248 | 88.587 | 39.958 | 4.064 |
| 1978 | C | LEU | 248 | 87.218 | 40.017 | 4.750 |
| 1979 | O | LEU | 248 | 86.642 | 41.107 | 4.879 |
| 1980 | CB | LEU | 248 | 88.456 | 40.054 | 2.550 |
| 1981 | CG | LEU | 248 | 89.824 | 40.153 | 1.883 |
| 1982 | CD1 | LEU | 248 | 89.720 | 39.989 | 0.371 |
| 1983 | CD2 | LEU | 248 | 90.519 | 41.461 | 2.247 |
| 1984 | N | ASN | 249 | 86.881 | 38.936 | 5.445 |
| 1985 | CA | ASN | 249 | 85.672 | 38.877 | 6.267 |
| 1986 | C | ASN | 249 | 85.835 | 39.703 | 7.541 |
| 1987 | O | ASN | 249 | 84.858 | 40.306 | 8.006 |
| 1988 | CB | ASN | 249 | 85.451 | 37.415 | 6.640 |
| 1989 | CG | ASN | 249 | 84.334 | 37.282 | 7.662 |
| 1990 | OD1 | ASN | 249 | 83.184 | 37.640 | 7.389 |
| 1991 | ND2 | ASN | 249 | 84.686 | 36.770 | 8.829 |
| 1992 | N | VAL | 250 | 87.079 | 39.986 | 7.901 |
| 1993 | CA | VAL | 250 | 87.338 | 40.826 | 9.066 |
| 1994 | C | VAL | 250 | 87.015 | 42.285 | 8.763 |
| 1995 | O | VAL | 250 | 86.360 | 42.935 | 9.583 |
| 1996 | CB | VAL | 250 | 88.812 | 40.709 | 9.419 |
| 1997 | CG1 | VAL | 250 | 89.128 | 41.534 | 10.658 |
| 1998 | CG2 | VAL | 250 | 89.210 | 39.253 | 9.622 |

TABLE 8-continued

| Atom No. | Atom Type | Residue | Residue Position | X Coord. | Y Coord. | Z Coord. |
|---|---|---|---|---|---|---|
| 1999 | N | PHE | 251 | 87.200 | 42.687 | 7.515 |
| 2000 | CA | PHE | 251 | 86.853 | 44.053 | 7.119 |
| 2001 | C | PHE | 251 | 85.391 | 44.167 | 6.718 |
| 2002 | O | PHE | 251 | 84.824 | 45.266 | 6.773 |
| 2003 | CB | PHE | 251 | 87.742 | 44.503 | 5.970 |
| 2004 | CG | PHE | 251 | 89.097 | 45.032 | 6.420 |
| 2005 | CD1 | PHE | 251 | 89.159 | 46.205 | 7.162 |
| 2006 | CD2 | PHE | 251 | 90.263 | 44.353 | 6.094 |
| 2007 | CE1 | PHE | 251 | 90.388 | 46.705 | 7.570 |
| 2008 | CE2 | PHE | 251 | 91.492 | 44.854 | 6.503 |
| 2009 | CZ | PHE | 251 | 91.555 | 46.031 | 7.238 |
| 2010 | N | THR | 252 | 84.758 | 43.028 | 6.496 |
| 2011 | CA | THR | 252 | 83.324 | 43.011 | 6.233 |
| 2012 | C | THR | 252 | 82.586 | 43.215 | 7.548 |
| 2013 | O | THR | 252 | 81.798 | 44.164 | 7.657 |
| 2014 | CB | THR | 252 | 82.959 | 41.670 | 5.604 |
| 2015 | OG1 | THR | 252 | 83.699 | 41.535 | 4.396 |
| 2016 | CG2 | THR | 252 | 81.477 | 41.583 | 5.261 |
| 2017 | N | TYR | 253 | 83.087 | 42.570 | 8.591 |
| 2018 | CA | TYR | 253 | 82.520 | 42.754 | 9.929 |
| 2019 | C | TYR | 253 | 82.862 | 44.129 | 10.480 |
| 2020 | O | TYR | 253 | 81.992 | 44.790 | 11.059 |
| 2021 | CB | TYR | 253 | 83.111 | 41.706 | 10.860 |
| 2022 | CG | TYR | 253 | 82.587 | 41.784 | 12.293 |
| 2023 | CD1 | TYR | 253 | 81.518 | 40.983 | 12.667 |
| 2024 | CD2 | TYR | 253 | 83.176 | 42.634 | 13.223 |
| 2025 | CE1 | TYR | 253 | 81.032 | 41.041 | 13.964 |
| 2026 | CE2 | TYR | 253 | 82.686 | 42.696 | 14.520 |
| 2027 | CZ | TYR | 253 | 81.615 | 41.897 | 14.888 |
| 2028 | OH | TYR | 253 | 81.148 | 41.933 | 16.183 |
| 2029 | N | TYR | 254 | 84.073 | 44.584 | 10.194 |
| 2030 | CA | TYR | 254 | 84.502 | 45.929 | 10.575 |
| 2031 | C | TYR | 254 | 83.511 | 46.941 | 10.025 |
| 2032 | O | TYR | 254 | 82.754 | 47.513 | 10.821 |
| 2033 | CB | TYR | 254 | 85.900 | 46.161 | 10.003 |
| 2034 | CG | TYR | 254 | 86.542 | 47.526 | 10.263 |
| 2035 | CD1 | TYR | 254 | 87.469 | 47.683 | 11.286 |
| 2036 | CD2 | TYR | 254 | 86.218 | 48.603 | 9.450 |
| 2037 | CE1 | TYR | 254 | 88.064 | 48.921 | 11.500 |
| 2038 | CE2 | TYR | 254 | 86.805 | 49.840 | 9.669 |
| 2039 | CZ | TYR | 254 | 87.733 | 49.997 | 10.686 |
| 2040 | OH | TYR | 254 | 88.422 | 51.187 | 10.788 |
| 2041 | N | GLY | 255 | 83.315 | 46.918 | 8.714 |
| 2042 | CA | GLY | 255 | 82.385 | 47.830 | 8.038 |
| 2043 | C | GLY | 255 | 80.999 | 47.849 | 8.674 |
| 2044 | O | GLY | 255 | 80.624 | 48.860 | 9.285 |
| 2045 | N | MET | 256 | 80.400 | 46.675 | 8.787 |
| 2046 | CA | MET | 256 | 79.018 | 46.562 | 9.264 |
| 2047 | C | MET | 256 | 78.809 | 46.758 | 10.766 |
| 2048 | O | MET | 256 | 77.655 | 46.897 | 11.183 |
| 2049 | CB | MET | 256 | 78.544 | 45.157 | 8.978 |
| 2050 | CG | MET | 256 | 78.791 | 44.696 | 7.561 |
| 2051 | SD | MET | 256 | 78.303 | 42.976 | 7.363 |
| 2052 | CE | MET | 256 | 76.689 | 43.184 | 8.143 |
| 2053 | N | LEU | 257 | 79.857 | 46.920 | 11.555 |
| 2054 | CA | LEU | 257 | 79.669 | 47.050 | 13.004 |
| 2055 | C | LEU | 257 | 79.019 | 48.386 | 13.371 |
| 2056 | O | LEU | 257 | 78.154 | 48.417 | 14.259 |
| 2057 | CB | LEU | 257 | 81.045 | 46.936 | 13.651 |
| 2058 | CG | LEU | 257 | 80.989 | 46.917 | 15.175 |
| 2059 | CD1 | LEU | 257 | 80.121 | 45.771 | 15.684 |
| 2060 | CD2 | LEU | 257 | 82.394 | 46.821 | 15.761 |
| 2061 | N | PHE | 258 | 79.148 | 49.359 | 12.482 |
| 2062 | CA | PHE | 258 | 78.553 | 50.676 | 12.724 |
| 2063 | C | PHE | 258 | 77.065 | 50.789 | 12.394 |
| 2064 | O | PHE | 258 | 76.463 | 51.766 | 12.867 |
| 2065 | CB | PHE | 258 | 79.320 | 51.729 | 11.937 |
| 2066 | CG | PHE | 258 | 80.392 | 52.446 | 12.749 |
| 2067 | CD1 | PHE | 258 | 80.933 | 51.850 | 13.881 |
| 2068 | CD2 | PHE | 258 | 80.813 | 53.710 | 12.364 |
| 2069 | CE1 | PHE | 258 | 81.903 | 52.511 | 14.618 |
| 2070 | CE2 | PHE | 258 | 81.786 | 54.372 | 13.099 |
| 2071 | CZ | PHE | 258 | 82.332 | 53.772 | 14.226 |
| 2072 | N | LEU | 259 | 76.443 | 49.752 | 11.842 |
| 2073 | CA | LEU | 259 | 75.019 | 49.870 | 11.493 |
| 2074 | C | LEU | 259 | 74.121 | 49.804 | 12.723 |

TABLE 8-continued

| Atom No. | Atom Type | Residue | Residue Position | X Coord. | Y Coord. | Z Coord. |
|---|---|---|---|---|---|---|
| 2075 | O | LEU | 259 | 73.080 | 50.467 | 12.753 |
| 2076 | CB | LEU | 259 | 74.610 | 48.860 | 10.408 |
| 2077 | CG | LEU | 259 | 74.818 | 47.367 | 10.685 |
| 2078 | CD1 | LEU | 259 | 73.706 | 46.752 | 11.526 |
| 2079 | CD2 | LEU | 259 | 74.892 | 46.606 | 9.366 |
| 2080 | N | PHE | 260 | 74.601 | 49.199 | 13.794 |
| 2081 | CA | PHE | 260 | 73.874 | 49.317 | 15.052 |
| 2082 | C | PHE | 260 | 74.591 | 50.315 | 15.940 |
| 2083 | O | PHE | 260 | 73.976 | 51.317 | 16.335 |
| 2084 | CB | PHE | 260 | 73.803 | 47.972 | 15.752 |
| 2085 | CG | PHE | 260 | 73.151 | 48.047 | 17.128 |
| 2086 | CD1 | PHE | 260 | 73.680 | 47.319 | 18.186 |
| 2087 | CD2 | PHE | 260 | 72.043 | 48.861 | 17.341 |
| 2088 | CE1 | PHE | 260 | 73.094 | 47.390 | 19.445 |
| 2089 | CE2 | PHE | 260 | 71.458 | 48.932 | 18.599 |
| 2090 | CZ | PHE | 260 | 71.985 | 48.195 | 19.647 |
| 2091 | N | TYR | 261 | 75.914 | 50.195 | 15.934 |
| 2092 | CA | TYR | 261 | 76.794 | 50.921 | 16.862 |
| 2093 | C | TYR | 261 | 76.510 | 52.413 | 16.915 |
| 2094 | O | TYR | 261 | 75.931 | 52.895 | 17.893 |
| 2095 | CB | TYR | 261 | 78.229 | 50.713 | 16.406 |
| 2096 | CG | TYR | 261 | 79.209 | 50.424 | 17.531 |
| 2097 | CD1 | TYR | 261 | 78.863 | 50.692 | 18.849 |
| 2098 | CD2 | TYR | 261 | 80.449 | 49.873 | 17.233 |
| 2099 | CE1 | TYR | 261 | 79.759 | 50.415 | 19.872 |
| 2100 | CE2 | TYR | 261 | 81.346 | 49.595 | 18.254 |
| 2101 | CZ | TYR | 261 | 80.998 | 49.866 | 19.571 |
| 2102 | OH | TYR | 261 | 81.877 | 49.557 | 20.580 |
| 2103 | N | LEU | 262 | 76.831 | 53.133 | 15.856 |
| 2104 | CA | LEU | 262 | 76.569 | 54.569 | 15.922 |
| 2105 | C | LEU | 262 | 75.295 | 54.927 | 15.180 |
| 2106 | O | LEU | 262 | 74.576 | 55.833 | 15.615 |
| 2107 | CB | LEU | 262 | 77.733 | 55.362 | 15.346 |
| 2108 | CG | LEU | 262 | 79.046 | 55.114 | 16.082 |
| 2109 | CD1 | LEU | 262 | 80.087 | 56.101 | 15.582 |
| 2110 | CD2 | LEU | 262 | 78.905 | 55.257 | 17.594 |
| 2111 | N | ALA | 263 | 74.907 | 54.092 | 14.231 |
| 2112 | CA | ALA | 263 | 73.730 | 54.410 | 13.424 |
| 2113 | C | ALA | 263 | 72.444 | 54.386 | 14.236 |
| 2114 | O | ALA | 263 | 71.895 | 55.453 | 14.537 |
| 2115 | CB | ALA | 263 | 73.634 | 53.436 | 12.263 |
| 2116 | N | ARG | 264 | 72.064 | 53.223 | 14.732 |
| 2117 | CA | ARG | 264 | 70.785 | 53.160 | 15.435 |
| 2118 | C | ARG | 264 | 70.912 | 53.543 | 16.903 |
| 2119 | O | ARG | 264 | 70.030 | 54.241 | 17.421 |
| 2120 | CB | ARG | 264 | 70.211 | 51.754 | 15.327 |
| 2121 | CG | ARG | 264 | 70.160 | 51.295 | 13.876 |
| 2122 | CD | ARG | 264 | 69.243 | 50.091 | 13.688 |
| 2123 | NE | ARG | 264 | 69.527 | 49.004 | 14.641 |
| 2124 | CZ | ARG | 264 | 70.107 | 47.852 | 14.297 |
| 2125 | NH1 | ARG | 264 | 70.673 | 47.726 | 13.097 |
| 2126 | NH2 | ARG | 264 | 70.249 | 46.881 | 15.202 |
| 2127 | N | PHE | 265 | 72.077 | 53.315 | 17.487 |
| 2128 | CA | PHE | 265 | 72.233 | 53.583 | 18.918 |
| 2129 | C | PHE | 265 | 72.576 | 55.043 | 19.226 |
| 2130 | O | PHE | 265 | 72.332 | 55.490 | 20.352 |
| 2131 | CB | PHE | 265 | 73.307 | 52.644 | 19.461 |
| 2132 | CG | PHE | 265 | 73.513 | 52.710 | 20.970 |
| 2133 | CD1 | PHE | 265 | 72.609 | 52.082 | 21.817 |
| 2134 | CD2 | PHE | 265 | 74.598 | 53.398 | 21.499 |
| 2135 | CE1 | PHE | 265 | 72.788 | 52.144 | 23.193 |
| 2136 | CE2 | PHE | 265 | 74.776 | 53.461 | 22.875 |
| 2137 | CZ | PHE | 265 | 73.871 | 52.834 | 23.722 |
| 2138 | N | LEU | 266 | 73.047 | 55.795 | 18.242 |
| 2139 | CA | LEU | 266 | 73.282 | 57.228 | 18.463 |
| 2140 | C | LEU | 266 | 72.407 | 58.117 | 17.582 |
| 2141 | O | LEU | 266 | 72.689 | 59.314 | 17.445 |
| 2142 | CB | LEU | 266 | 74.752 | 57.582 | 18.287 |
| 2143 | CG | LEU | 266 | 75.563 | 57.153 | 19.505 |
| 2144 | CD1 | LEU | 266 | 77.004 | 57.632 | 19.387 |
| 2145 | CD2 | LEU | 266 | 74.942 | 57.704 | 20.784 |
| 2146 | N | GLY | 267 | 71.406 | 57.524 | 16.946 |
| 2147 | CA | GLY | 267 | 70.385 | 58.309 | 16.238 |
| 2148 | C | GLY | 267 | 69.679 | 59.199 | 17.255 |
| 2149 | O | GLY | 267 | 69.496 | 60.404 | 17.046 |
| 2150 | N | SER | 268 | 69.184 | 58.560 | 18.300 |

TABLE 8-continued

| Atom No. | Atom Type | Residue | Residue Position | X Coord. | Y Coord. | Z Coord. |
|---|---|---|---|---|---|---|
| 2151 | CA | SER | 268 | 68.784 | 59.293 | 19.502 |
| 2152 | C | SER | 268 | 69.974 | 59.270 | 20.462 |
| 2153 | O | SER | 268 | 70.671 | 58.253 | 20.513 |
| 2154 | CB | SER | 268 | 67.572 | 58.617 | 20.138 |
| 2155 | OG | SER | 268 | 67.949 | 57.306 | 20.543 |
| 2156 | N | PRO | 269 | 70.258 | 60.363 | 21.156 |
| 2157 | CA | PRO | 269 | 69.610 | 61.665 | 20.953 |
| 2158 | C | PRO | 269 | 70.041 | 62.338 | 19.650 |
| 2159 | O | PRO | 269 | 71.106 | 62.034 | 19.100 |
| 2160 | CB | PRO | 269 | 70.020 | 62.490 | 22.131 |
| 2161 | CG | PRO | 269 | 71.136 | 61.770 | 22.871 |
| 2162 | CD | PRO | 269 | 71.322 | 60.442 | 22.158 |
| 2163 | N | TYR | 270 | 69.341 | 63.421 | 19.352 |
| 2164 | CA | TYR | 270 | 69.386 | 64.107 | 18.045 |
| 2165 | C | TYR | 270 | 70.530 | 65.128 | 17.903 |
| 2166 | O | TYR | 270 | 70.346 | 66.183 | 17.284 |
| 2167 | CB | TYR | 270 | 68.058 | 64.852 | 17.883 |
| 2168 | CG | TYR | 270 | 66.840 | 64.192 | 18.537 |
| 2169 | CD1 | TYR | 270 | 66.302 | 64.749 | 19.695 |
| 2170 | CD2 | TYR | 270 | 66.249 | 63.065 | 17.973 |
| 2171 | CE1 | TYR | 270 | 65.204 | 64.164 | 20.305 |
| 2172 | CE2 | TYR | 270 | 65.149 | 62.479 | 18.584 |
| 2173 | CZ | TYR | 270 | 64.630 | 63.025 | 19.753 |
| 2174 | OH | TYR | 270 | 63.559 | 62.425 | 20.379 |
| 2175 | N | HIS | 271 | 71.720 | 64.774 | 18.364 |
| 2176 | CA | HIS | 271 | 72.851 | 65.714 | 18.429 |
| 2177 | C | HIS | 271 | 73.739 | 65.760 | 17.183 |
| 2178 | O | HIS | 271 | 74.823 | 66.357 | 17.243 |
| 2179 | CB | HIS | 271 | 73.692 | 65.374 | 19.653 |
| 2180 | CG | HIS | 271 | 72.991 | 65.721 | 20.953 |
| 2181 | ND1 | HIS | 271 | 72.236 | 66.813 | 21.170 |
| 2182 | CD2 | HIS | 271 | 73.024 | 65.008 | 22.126 |
| 2183 | CE1 | HIS | 271 | 71.773 | 66.783 | 22.438 |
| 2184 | NE2 | HIS | 271 | 72.263 | 65.671 | 23.028 |
| 2185 | N | ASN | 272 | 73.257 | 65.227 | 16.070 |
| 2186 | CA | ASN | 272 | 74.031 | 65.168 | 14.819 |
| 2187 | C | ASN | 272 | 75.300 | 64.365 | 15.024 |
| 2188 | O | ASN | 272 | 76.355 | 64.900 | 15.388 |
| 2189 | CB | ASN | 272 | 74.345 | 66.564 | 14.278 |
| 2190 | CG | ASN | 272 | 73.238 | 67.056 | 13.345 |
| 2191 | OD1 | ASN | 272 | 73.417 | 67.063 | 12.117 |
| 2192 | ND2 | ASN | 272 | 72.157 | 67.549 | 13.922 |
| 2193 | N | ILE | 273 | 75.130 | 63.060 | 14.938 |
| 2194 | CA | ILE | 273 | 76.234 | 62.121 | 15.143 |
| 2195 | C | ILE | 273 | 76.285 | 61.171 | 13.952 |
| 2196 | O | ILE | 273 | 75.308 | 60.472 | 13.665 |
| 2197 | CB | ILE | 273 | 75.995 | 61.350 | 16.443 |
| 2198 | CG1 | ILE | 273 | 75.929 | 62.296 | 17.642 |
| 2199 | CG2 | ILE | 273 | 77.080 | 60.301 | 16.667 |
| 2200 | CD1 | ILE | 273 | 75.682 | 61.542 | 18.944 |
| 2201 | N | SER | 274 | 77.414 | 61.147 | 13.266 |
| 2202 | CA | SER | 274 | 77.503 | 60.335 | 12.050 |
| 2203 | C | SER | 274 | 78.778 | 59.505 | 11.946 |
| 2204 | O | SER | 274 | 79.866 | 60.003 | 11.627 |
| 2205 | CB | SER | 274 | 77.344 | 61.233 | 10.830 |
| 2206 | OG | SER | 274 | 75.986 | 61.665 | 10.803 |
| 2207 | N | GLY | 275 | 78.592 | 58.218 | 12.185 |
| 2208 | CA | GLY | 275 | 79.626 | 57.204 | 11.968 |
| 2209 | C | GLY | 275 | 79.423 | 56.520 | 10.615 |
| 2210 | O | GLY | 275 | 78.342 | 55.999 | 10.298 |
| 2211 | N | TYR | 276 | 80.473 | 56.577 | 9.816 |
| 2212 | CA | TYR | 276 | 80.446 | 56.057 | 8.442 |
| 2213 | C | TYR | 276 | 81.116 | 54.703 | 8.267 |
| 2214 | O | TYR | 276 | 81.462 | 54.017 | 9.234 |
| 2215 | CB | TYR | 276 | 81.215 | 57.018 | 7.550 |
| 2216 | CG | TYR | 276 | 80.423 | 58.219 | 7.074 |
| 2217 | CD1 | TYR | 276 | 80.647 | 59.475 | 7.620 |
| 2218 | CD2 | TYR | 276 | 79.467 | 58.044 | 6.085 |
| 2219 | CE1 | TYR | 276 | 79.937 | 60.569 | 7.145 |
| 2220 | CE2 | TYR | 276 | 78.758 | 59.135 | 5.612 |
| 2221 | CZ | TYR | 276 | 79.006 | 60.397 | 6.130 |
| 2222 | OH | TYR | 276 | 78.551 | 61.494 | 5.439 |
| 2223 | N | ILE | 277 | 81.099 | 54.268 | 7.016 |
| 2224 | CA | ILE | 277 | 81.955 | 53.168 | 6.549 |
| 2225 | C | ILE | 277 | 82.756 | 53.676 | 5.347 |
| 2226 | O | ILE | 277 | 82.301 | 53.580 | 4.202 |

TABLE 8-continued

| Atom No. | Atom Type | Residue | Residue Position | X Coord. | Y Coord. | Z Coord. |
|---|---|---|---|---|---|---|
| 2227 | CB | ILE | 277 | 81.102 | 51.981 | 6.119 |
| 2228 | CG1 | ILE | 277 | 80.113 | 51.563 | 7.197 |
| 2229 | CG2 | ILE | 277 | 81.988 | 50.794 | 5.759 |
| 2230 | CD1 | ILE | 277 | 79.317 | 50.345 | 6.726 |
| 2231 | N | ALA | 278 | 83.945 | 54.191 | 5.611 |
| 2232 | CA | ALA | 278 | 84.744 | 54.875 | 4.579 |
| 2233 | C | ALA | 278 | 85.571 | 53.914 | 3.737 |
| 2234 | O | ALA | 278 | 86.340 | 53.117 | 4.283 |
| 2235 | CB | ALA | 278 | 85.696 | 55.835 | 5.276 |
| 2236 | N | ALA | 279 | 85.449 | 54.022 | 2.425 |
| 2237 | CA | ALA | 279 | 86.256 | 53.184 | 1.532 |
| 2238 | C | ALA | 279 | 87.174 | 54.020 | 0.639 |
| 2239 | O | ALA | 279 | 86.821 | 54.374 | −0.493 |
| 2240 | CB | ALA | 279 | 85.313 | 52.337 | 0.697 |
| 2241 | N | ASN | 280 | 88.427 | 54.094 | 1.062 |
| 2242 | CA | ASN | 280 | 89.453 | 54.944 | 0.419 |
| 2243 | C | ASN | 280 | 90.168 | 54.352 | −0.802 |
| 2244 | O | ASN | 280 | 91.287 | 54.798 | −1.082 |
| 2245 | CB | ASN | 280 | 90.535 | 55.272 | 1.448 |
| 2246 | CG | ASN | 280 | 90.068 | 56.260 | 2.513 |
| 2247 | OD1 | ASN | 280 | 89.280 | 57.179 | 2.248 |
| 2248 | ND2 | ASN | 280 | 90.599 | 56.064 | 3.706 |
| 2249 | N | ALA | 281 | 89.607 | 53.337 | −1.448 |
| 2250 | CA | ALA | 281 | 90.249 | 52.691 | −2.613 |
| 2251 | C | ALA | 281 | 91.579 | 51.998 | −2.274 |
| 2252 | O | ALA | 281 | 92.052 | 52.110 | −1.137 |
| 2253 | CB | ALA | 281 | 90.422 | 53.736 | −3.719 |
| 2254 | N | PRO | 282 | 92.029 | 51.096 | −3.138 |
| 2255 | CA | PRO | 282 | 93.356 | 50.483 | −2.967 |
| 2256 | C | PRO | 282 | 94.496 | 51.504 | −3.076 |
| 2257 | O | PRO | 282 | 94.923 | 51.901 | −4.168 |
| 2258 | CB | PRO | 282 | 93.451 | 49.436 | −4.034 |
| 2259 | CG | PRO | 282 | 92.210 | 49.496 | −4.910 |
| 2260 | CD | PRO | 282 | 91.342 | 50.604 | −4.341 |
| 2261 | N | VAL | 283 | 94.998 | 51.871 | −1.908 |
| 2262 | CA | VAL | 283 | 96.073 | 52.859 | −1.763 |
| 2263 | C | VAL | 283 | 97.452 | 52.226 | −1.954 |
| 2264 | O | VAL | 283 | 97.716 | 51.131 | −1.450 |
| 2265 | CB | VAL | 283 | 95.947 | 53.410 | −0.343 |
| 2266 | CG1 | VAL | 283 | 96.767 | 54.681 | −0.123 |
| 2267 | CG2 | VAL | 283 | 94.489 | 53.697 | −0.010 |
| 2268 | N | ALA | 284 | 98.370 | 53.019 | −2.486 |
| 2269 | CA | ALA | 284 | 99.788 | 52.647 | −2.683 |
| 2270 | C | ALA | 284 | 100.648 | 52.639 | −1.410 |
| 2271 | O | ALA | 284 | 101.868 | 52.442 | −1.490 |
| 2272 | CB | ALA | 284 | 100.390 | 53.649 | −3.668 |
| 2273 | N | ALA | 285 | 100.014 | 52.773 | −0.254 |
| 2274 | CA | ALA | 285 | 100.715 | 52.813 | 1.031 |
| 2275 | C | ALA | 285 | 101.303 | 51.448 | 1.370 |
| 2276 | O | ALA | 285 | 101.231 | 50.507 | 0.570 |
| 2277 | CB | ALA | 285 | 99.728 | 53.214 | 2.122 |
| 2278 | N | ALA | 286 | 101.706 | 51.286 | 2.620 |
| 2279 | CA | ALA | 286 | 102.365 | 50.039 | 3.035 |
| 2280 | C | ALA | 286 | 101.423 | 48.836 | 3.105 |
| 2281 | O | ALA | 286 | 101.880 | 47.697 | 2.987 |
| 2282 | CB | ALA | 286 | 103.000 | 50.264 | 4.400 |
| 2283 | N | LEU | 287 | 100.123 | 49.090 | 3.146 |
| 2284 | CA | LEU | 287 | 99.130 | 48.011 | 3.138 |
| 2285 | C | LEU | 287 | 98.574 | 47.705 | 1.743 |
| 2286 | O | LEU | 287 | 97.891 | 46.687 | 1.587 |
| 2287 | CB | LEU | 287 | 97.970 | 48.417 | 4.047 |
| 2288 | CG | LEU | 287 | 98.389 | 48.579 | 5.503 |
| 2289 | CD1 | LEU | 287 | 97.272 | 49.206 | 6.327 |
| 2290 | CD2 | LEU | 287 | 98.820 | 47.248 | 6.112 |
| 2291 | N | GLY | 288 | 98.933 | 48.488 | 0.736 |
| 2292 | CA | GLY | 288 | 98.311 | 48.321 | −0.585 |
| 2293 | C | GLY | 288 | 99.341 | 48.157 | −1.696 |
| 2294 | O | GLY | 288 | 99.003 | 47.793 | −2.831 |
| 2295 | N | GLN | 289 | 100.578 | 48.483 | −1.356 |
| 2296 | CA | GLN | 289 | 101.764 | 48.238 | −2.193 |
| 2297 | C | GLN | 289 | 101.870 | 49.229 | −3.343 |
| 2298 | O | GLN | 289 | 100.866 | 49.755 | −3.843 |
| 2299 | CB | GLN | 289 | 101.804 | 46.808 | −2.743 |
| 2300 | CG | GLN | 289 | 101.684 | 45.732 | −1.666 |
| 2301 | CD | GLN | 289 | 102.648 | 45.990 | −0.515 |
| 2302 | OE1 | GLN | 289 | 103.814 | 46.348 | −0.716 |

TABLE 8-continued

| Atom No. | Atom Type | Residue | Residue Position | X Coord. | Y Coord. | Z Coord. |
|---|---|---|---|---|---|---|
| 2303 | NE2 | GLN | 289 | 102.121 | 45.833 | 0.687 |
| 2304 | N | THR | 290 | 103.067 | 49.249 | −3.911 |
| 2305 | CA | THR | 290 | 103.429 | 50.169 | −5.005 |
| 2306 | C | THR | 290 | 102.858 | 49.798 | −6.383 |
| 2307 | O | THR | 290 | 103.271 | 50.380 | −7.392 |
| 2308 | CB | THR | 290 | 104.948 | 50.200 | −5.117 |
| 2309 | OG1 | THR | 290 | 105.383 | 48.930 | −5.586 |
| 2310 | CG2 | THR | 290 | 105.607 | 50.480 | −3.770 |
| 2311 | N | LYS | 291 | 102.009 | 48.783 | −6.438 |
| 2312 | CA | LYS | 291 | 101.281 | 48.451 | −7.664 |
| 2313 | C | LYS | 291 | 99.888 | 49.073 | −7.666 |
| 2314 | O | LYS | 291 | 99.104 | 48.827 | −8.593 |
| 2315 | CB | LYS | 291 | 101.181 | 46.938 | −7.805 |
| 2316 | CG | LYS | 291 | 102.474 | 46.365 | −8.371 |
| 2317 | CD | LYS | 291 | 102.733 | 46.948 | −9.756 |
| 2318 | CE | LYS | 291 | 104.023 | 46.420 | −10.369 |
| 2319 | NZ | LYS | 291 | 104.240 | 47.015 | −11.696 |
| 2320 | N | GLN | 292 | 99.537 | 49.746 | −6.581 |
| 2321 | CA | GLN | 292 | 98.276 | 50.481 | −6.554 |
| 2322 | C | GLN | 292 | 98.465 | 51.943 | −6.905 |
| 2323 | O | GLN | 292 | 99.397 | 52.611 | −6.448 |
| 2324 | CB | GLN | 292 | 97.590 | 50.319 | −5.209 |
| 2325 | CG | GLN | 292 | 96.979 | 48.928 | −5.126 |
| 2326 | CD | GLN | 292 | 96.143 | 48.677 | −6.381 |
| 2327 | OE1 | GLN | 292 | 95.377 | 49.543 | −6.829 |
| 2328 | NE2 | GLN | 292 | 96.334 | 47.502 | −6.957 |
| 2329 | N | ASN | 293 | 97.504 | 52.446 | −7.658 |
| 2330 | CA | ASN | 293 | 97.624 | 53.791 | −8.226 |
| 2331 | C | ASN | 293 | 97.025 | 54.891 | −7.351 |
| 2332 | O | ASN | 293 | 97.257 | 56.077 | −7.618 |
| 2333 | CB | ASN | 293 | 96.946 | 53.787 | −9.593 |
| 2334 | CG | ASN | 293 | 97.620 | 52.765 | −10.508 |
| 2335 | OD1 | ASN | 293 | 98.847 | 52.605 | −10.488 |
| 2336 | ND2 | ASN | 293 | 96.808 | 52.098 | −11.309 |
| 2337 | N | CYS | 294 | 96.321 | 54.528 | −6.291 |
| 2338 | CA | CYS | 294 | 95.753 | 55.566 | −5.426 |
| 2339 | C | CYS | 294 | 96.752 | 56.002 | −4.362 |
| 2340 | O | CYS | 294 | 96.959 | 55.311 | −3.361 |
| 2341 | CB | CYS | 294 | 94.487 | 55.032 | −4.772 |
| 2342 | SG | CYS | 294 | 93.209 | 54.504 | −5.934 |
| 2343 | N | LYS | 295 | 97.341 | 57.166 | −4.569 |
| 2344 | CA | LYS | 295 | 98.307 | 57.715 | −3.609 |
| 2345 | C | LYS | 295 | 97.686 | 57.944 | −2.236 |
| 2346 | O | LYS | 295 | 96.462 | 58.023 | −2.080 |
| 2347 | CB | LYS | 295 | 98.849 | 59.033 | −4.145 |
| 2348 | CG | LYS | 295 | 99.619 | 58.825 | −5.443 |
| 2349 | CD | LYS | 295 | 100.230 | 60.132 | −5.936 |
| 2350 | CE | LYS | 295 | 101.046 | 59.919 | −7.206 |
| 2351 | NZ | LYS | 295 | 101.657 | 61.179 | −7.656 |
| 2352 | N | THR | 296 | 98.542 | 58.169 | −1.256 |
| 2353 | CA | THR | 296 | 98.064 | 58.370 | 0.120 |
| 2354 | C | THR | 296 | 97.400 | 59.738 | 0.317 |
| 2355 | O | THR | 296 | 96.470 | 59.848 | 1.125 |
| 2356 | CB | THR | 296 | 99.243 | 58.212 | 1.068 |
| 2357 | OG1 | THR | 296 | 100.209 | 59.203 | 0.746 |
| 2358 | CG2 | THR | 296 | 99.896 | 56.844 | 0.913 |
| 2359 | N | ALA | 297 | 97.651 | 60.646 | −0.614 |
| 2360 | CA | ALA | 297 | 96.948 | 61.929 | −0.638 |
| 2361 | C | ALA | 297 | 95.546 | 61.825 | −1.253 |
| 2362 | O | ALA | 297 | 94.722 | 62.716 | −1.032 |
| 2363 | CB | ALA | 297 | 97.785 | 62.926 | −1.430 |
| 2364 | N | SER | 298 | 95.225 | 60.709 | −1.892 |
| 2365 | CA | SER | 298 | 93.850 | 60.521 | −2.360 |
| 2366 | C | SER | 298 | 93.104 | 59.661 | −1.345 |
| 2367 | O | SER | 298 | 91.895 | 59.839 | −1.146 |
| 2368 | CB | SER | 298 | 93.824 | 59.876 | −3.746 |
| 2369 | OG | SER | 298 | 94.249 | 58.524 | −3.645 |
| 2370 | N | ALA | 299 | 93.878 | 58.960 | −0.528 |
| 2371 | CA | ALA | 299 | 93.321 | 58.153 | 0.564 |
| 2372 | C | ALA | 299 | 93.006 | 58.981 | 1.806 |
| 2373 | O | ALA | 299 | 92.325 | 58.500 | 2.720 |
| 2374 | CB | ALA | 299 | 94.335 | 57.085 | 0.939 |
| 2375 | N | CYS | 300 | 93.465 | 60.220 | 1.831 |
| 2376 | CA | CYS | 300 | 93.036 | 61.121 | 2.893 |
| 2377 | C | CYS | 300 | 91.824 | 61.937 | 2.462 |
| 2378 | O | CYS | 300 | 91.097 | 62.429 | 3.332 |

TABLE 8-continued

| Atom No. | Atom Type | Residue | Residue Position | X Coord. | Y Coord. | Z Coord. |
|---|---|---|---|---|---|---|
| 2379 | CB | CYS | 300 | 94.179 | 62.059 | 3.269 |
| 2380 | SG | CYS | 300 | 94.677 | 63.295 | 2.051 |
| 2381 | N | THR | 301 | 91.457 | 61.846 | 1.194 |
| 2382 | CA | THR | 301 | 90.441 | 62.746 | 0.652 |
| 2383 | C | THR | 301 | 89.032 | 62.366 | 1.087 |
| 2384 | O | THR | 301 | 88.361 | 63.191 | 1.721 |
| 2385 | CB | THR | 301 | 90.541 | 62.707 | −0.867 |
| 2386 | OG1 | THR | 301 | 91.882 | 63.003 | −1.232 |
| 2387 | CG2 | THR | 301 | 89.629 | 63.733 | −1.524 |
| 2388 | N | ARG | 302 | 88.717 | 61.082 | 1.026 |
| 2389 | CA | ARG | 302 | 87.358 | 60.640 | 1.349 |
| 2390 | C | ARG | 302 | 87.072 | 60.743 | 2.834 |
| 2391 | O | ARG | 302 | 86.095 | 61.384 | 3.251 |
| 2392 | CB | ARG | 302 | 87.218 | 59.186 | 0.927 |
| 2393 | CG | ARG | 302 | 87.382 | 59.061 | −0.578 |
| 2394 | CD | ARG | 302 | 86.345 | 58.101 | −1.155 |
| 2395 | NE | ARG | 302 | 84.997 | 58.246 | −0.553 |
| 2396 | CZ | ARG | 302 | 84.173 | 59.304 | −0.588 |
| 2397 | NH1 | ARG | 302 | 82.917 | 59.161 | −0.164 |
| 2398 | NH2 | ARG | 302 | 84.538 | 60.449 | −1.172 |
| 2399 | N | SER | 303 | 88.089 | 60.399 | 3.598 |
| 2400 | CA | SER | 303 | 87.967 | 60.421 | 5.044 |
| 2401 | C | SER | 303 | 88.052 | 61.827 | 5.628 |
| 2402 | O | SER | 303 | 87.298 | 62.125 | 6.561 |
| 2403 | CB | SER | 303 | 89.065 | 59.529 | 5.576 |
| 2404 | OG | SER | 303 | 88.747 | 58.210 | 5.161 |
| 2405 | N | GLY | 304 | 88.718 | 62.728 | 4.926 |
| 2406 | CA | GLY | 304 | 88.735 | 64.137 | 5.317 |
| 2407 | C | GLY | 304 | 87.357 | 64.753 | 5.115 |
| 2408 | O | GLY | 304 | 86.777 | 65.268 | 6.081 |
| 2409 | N | LYS | 305 | 86.769 | 64.504 | 3.952 |
| 2410 | CA | LYS | 305 | 85.422 | 65.009 | 3.631 |
| 2411 | C | LYS | 305 | 84.399 | 64.629 | 4.692 |
| 2412 | O | LYS | 305 | 83.895 | 65.510 | 5.401 |
| 2413 | CB | LYS | 305 | 84.951 | 64.381 | 2.325 |
| 2414 | CG | LYS | 305 | 85.780 | 64.803 | 1.122 |
| 2415 | CD | LYS | 305 | 85.329 | 64.041 | −0.117 |
| 2416 | CE | LYS | 305 | 86.115 | 64.458 | −1.352 |
| 2417 | NZ | LYS | 305 | 85.696 | 63.676 | −2.527 |
| 2418 | N | GLU | 306 | 84.336 | 63.341 | 4.992 |
| 2419 | CA | GLU | 306 | 83.333 | 62.829 | 5.939 |
| 2420 | C | GLU | 306 | 83.675 | 63.042 | 7.424 |
| 2421 | O | GLU | 306 | 82.846 | 62.736 | 8.288 |
| 2422 | CB | GLU | 306 | 83.138 | 61.347 | 5.655 |
| 2423 | CG | GLU | 306 | 84.431 | 60.575 | 5.850 |
| 2424 | CD | GLU | 306 | 84.250 | 59.113 | 5.469 |
| 2425 | OE1 | GLU | 306 | 83.958 | 58.325 | 6.359 |
| 2426 | OE2 | GLU | 306 | 84.566 | 58.784 | 4.333 |
| 2427 | N | TYR | 307 | 84.829 | 63.622 | 7.710 |
| 2428 | CA | TYR | 307 | 85.221 | 63.924 | 9.085 |
| 2429 | C | TYR | 307 | 84.960 | 65.394 | 9.379 |
| 2430 | O | TYR | 307 | 84.723 | 65.785 | 10.527 |
| 2431 | CB | TYR | 307 | 86.724 | 63.695 | 9.163 |
| 2432 | CG | TYR | 307 | 87.305 | 63.397 | 10.538 |
| 2433 | CD1 | TYR | 307 | 88.483 | 64.014 | 10.936 |
| 2434 | CD2 | TYR | 307 | 86.670 | 62.500 | 11.384 |
| 2435 | CE1 | TYR | 307 | 89.041 | 63.716 | 12.172 |
| 2436 | CE2 | TYR | 307 | 87.228 | 62.198 | 12.615 |
| 2437 | CZ | TYR | 307 | 88.417 | 62.800 | 13.005 |
| 2438 | OH | TYR | 307 | 89.014 | 62.437 | 14.192 |
| 2439 | N | LEU | 308 | 84.943 | 66.184 | 8.318 |
| 2440 | CA | LEU | 308 | 84.841 | 67.641 | 8.449 |
| 2441 | C | LEU | 308 | 83.489 | 68.196 | 8.009 |
| 2442 | O | LEU | 308 | 83.380 | 69.400 | 7.748 |
| 2443 | CB | LEU | 308 | 85.942 | 68.282 | 7.611 |
| 2444 | CG | LEU | 308 | 87.331 | 67.791 | 8.010 |
| 2445 | CD1 | LEU | 308 | 88.400 | 68.442 | 7.137 |
| 2446 | CD2 | LEU | 308 | 87.614 | 68.037 | 9.490 |
| 2447 | N | LEU | 309 | 82.498 | 67.331 | 7.876 |
| 2448 | CA | LEU | 309 | 81.161 | 67.767 | 7.447 |
| 2449 | C | LEU | 309 | 80.556 | 68.794 | 8.402 |
| 2450 | O | LEU | 309 | 80.835 | 68.798 | 9.606 |
| 2451 | CB | LEU | 309 | 80.244 | 66.554 | 7.385 |
| 2452 | CG | LEU | 309 | 80.705 | 65.550 | 6.339 |
| 2453 | CD1 | LEU | 309 | 79.917 | 64.254 | 6.456 |
| 2454 | CD2 | LEU | 309 | 80.595 | 66.128 | 4.932 |
| 2455 | N | GLU | 310 | 79.783 | 69.700 | 7.831 |
| 2456 | CA | GLU | 310 | 79.096 | 70.712 | 8.637 |
| 2457 | C | GLU | 310 | 77.948 | 70.089 | 9.426 |
| 2458 | O | GLU | 310 | 77.307 | 69.127 | 8.987 |
| 2459 | CB | GLU | 310 | 78.587 | 71.830 | 7.731 |
| 2460 | CG | GLU | 310 | 77.682 | 71.301 | 6.624 |
| 2461 | CD | GLU | 310 | 77.201 | 72.444 | 5.734 |
| 2462 | OE1 | GLU | 310 | 76.290 | 72.207 | 4.956 |
| 2463 | OE2 | GLU | 310 | 77.875 | 73.463 | 5.728 |
| 2464 | N | GLU | 311 | 77.747 | 70.614 | 10.621 |
| 2465 | CA | GLU | 311 | 76.687 | 70.124 | 11.510 |
| 2466 | C | GLU | 311 | 75.309 | 70.610 | 11.067 |
| 2467 | O | GLU | 311 | 75.187 | 71.406 | 10.128 |
| 2468 | CB | GLU | 311 | 76.962 | 70.618 | 12.924 |
| 2469 | CG | GLU | 311 | 78.330 | 70.180 | 13.436 |
| 2470 | CD | GLU | 311 | 78.507 | 70.679 | 14.867 |
| 2471 | OE1 | GLU | 311 | 79.358 | 71.534 | 15.059 |
| 2472 | OE2 | GLU | 311 | 77.627 | 70.378 | 15.665 |
| 2473 | N | GLU | 312 | 74.296 | 70.033 | 11.698 |
| 2474 | CA | GLU | 312 | 72.881 | 70.388 | 11.488 |
| 2475 | C | GLU | 312 | 72.375 | 69.942 | 10.127 |
| 2476 | O | GLU | 312 | 71.749 | 70.721 | 9.399 |
| 2477 | CB | GLU | 312 | 72.653 | 71.887 | 11.670 |
| 2478 | CG | GLU | 312 | 72.698 | 72.296 | 13.138 |
| 2479 | CD | GLU | 312 | 71.502 | 71.704 | 13.885 |
| 2480 | OE1 | GLU | 312 | 71.648 | 70.612 | 14.421 |
| 2481 | OE2 | GLU | 312 | 70.475 | 72.362 | 13.928 |
| 2482 | N | ILE | 313 | 72.630 | 68.684 | 9.811 |
| 2483 | CA | ILE | 313 | 72.109 | 68.101 | 8.576 |
| 2484 | C | ILE | 313 | 71.467 | 66.745 | 8.849 |
| 2485 | O | ILE | 313 | 70.313 | 66.512 | 8.471 |
| 2486 | CB | ILE | 313 | 73.239 | 67.898 | 7.570 |
| 2487 | CG1 | ILE | 313 | 74.007 | 69.181 | 7.292 |
| 2488 | CG2 | ILE | 313 | 72.686 | 67.349 | 6.260 |
| 2489 | CD1 | ILE | 313 | 75.069 | 68.941 | 6.228 |
| 2490 | N | ASP | 314 | 72.179 | 65.924 | 9.612 |
| 2491 | CA | ASP | 314 | 71.862 | 64.494 | 9.799 |
| 2492 | C | ASP | 314 | 71.257 | 63.816 | 8.570 |
| 2493 | O | ASP | 314 | 70.206 | 63.171 | 8.642 |
| 2494 | CB | ASP | 314 | 70.955 | 64.294 | 11.007 |
| 2495 | CG | ASP | 314 | 71.811 | 64.056 | 12.240 |
| 2496 | OD1 | ASP | 314 | 72.988 | 63.745 | 12.079 |
| 2497 | OD2 | ASP | 314 | 71.320 | 64.280 | 13.346 |
| 2498 | N | SER | 315 | 72.010 | 63.847 | 7.484 |
| 2499 | CA | SER | 315 | 71.586 | 63.202 | 6.239 |
| 2500 | C | SER | 315 | 72.815 | 62.628 | 5.556 |
| 2501 | O | SER | 315 | 72.718 | 61.871 | 4.581 |
| 2502 | CB | SER | 315 | 70.904 | 64.216 | 5.324 |
| 2503 | OG | SER | 315 | 70.453 | 63.519 | 4.169 |
| 2504 | N | THR | 316 | 73.938 | 62.828 | 6.228 |
| 2505 | CA | THR | 316 | 75.264 | 62.499 | 5.690 |
| 2506 | C | THR | 316 | 75.475 | 61.001 | 5.437 |
| 2507 | O | THR | 316 | 75.612 | 60.194 | 6.365 |
| 2508 | CB | THR | 316 | 76.290 | 63.035 | 6.686 |
| 2509 | OG1 | THR | 316 | 76.130 | 62.373 | 7.936 |
| 2510 | CG2 | THR | 316 | 76.114 | 64.531 | 6.923 |
| 2511 | N | GLY | 317 | 75.522 | 60.661 | 4.157 |
| 2512 | CA | GLY | 317 | 75.695 | 59.269 | 3.715 |
| 2513 | C | GLY | 317 | 74.533 | 58.385 | 4.161 |
| 2514 | O | GLY | 317 | 74.754 | 57.317 | 4.742 |
| 2515 | N | LEU | 318 | 73.324 | 58.844 | 3.855 |
| 2516 | CA | LEU | 318 | 72.066 | 58.265 | 4.368 |
| 2517 | C | LEU | 318 | 72.152 | 58.139 | 5.879 |
| 2518 | O | LEU | 318 | 71.622 | 57.187 | 6.463 |
| 2519 | CB | LEU | 318 | 71.769 | 56.915 | 3.733 |
| 2520 | CG | LEU | 318 | 71.482 | 57.046 | 2.245 |
| 2521 | CD1 | LEU | 318 | 71.227 | 55.676 | 1.627 |
| 2522 | CD2 | LEU | 318 | 70.292 | 57.969 | 2.002 |
| 2523 | N | ASP | 319 | 72.456 | 59.296 | 6.444 |
| 2524 | CA | ASP | 319 | 72.950 | 59.472 | 7.818 |
| 2525 | C | ASP | 319 | 73.419 | 58.182 | 8.467 |
| 2526 | O | ASP | 319 | 72.598 | 57.424 | 9.001 |
| 2527 | CB | ASP | 319 | 71.892 | 60.115 | 8.694 |
| 2528 | CG | ASP | 319 | 72.618 | 60.903 | 9.775 |
| 2529 | OD1 | ASP | 319 | 73.511 | 61.641 | 9.362 |
| 2530 | OD2 | ASP | 319 | 72.010 | 61.093 | 10.821 |

TABLE 8-continued

| Atom No. | Atom Type | Residue | Residue Position | X Coord. | Y Coord. | Z Coord. |
|---|---|---|---|---|---|---|
| 2531 | N | ASP | 320 | 74.732 | 57.984 | 8.462 |
| 2532 | CA | ASP | 320 | 75.368 | 56.828 | 9.130 |
| 2533 | C | ASP | 320 | 75.137 | 55.561 | 8.322 |
| 2534 | O | ASP | 320 | 74.477 | 55.607 | 7.278 |
| 2535 | CB | ASP | 320 | 74.821 | 56.583 | 10.547 |
| 2536 | CG | ASP | 320 | 75.088 | 57.720 | 11.531 |
| 2537 | OD1 | ASP | 320 | 74.733 | 58.848 | 11.219 |
| 2538 | OD2 | ASP | 320 | 75.845 | 57.463 | 12.460 |
| 2539 | N | VAL | 321 | 75.667 | 54.457 | 8.843 |
| 2540 | CA | VAL | 321 | 75.512 | 53.045 | 8.379 |
| 2541 | C | VAL | 321 | 75.907 | 52.669 | 6.935 |
| 2542 | O | VAL | 321 | 76.529 | 51.616 | 6.758 |
| 2543 | CB | VAL | 321 | 74.106 | 52.479 | 8.709 |
| 2544 | CG1 | VAL | 321 | 72.905 | 53.404 | 8.529 |
| 2545 | CG2 | VAL | 321 | 73.822 | 51.168 | 7.985 |
| 2546 | N | VAL | 322 | 75.650 | 53.492 | 5.935 |
| 2547 | CA | VAL | 322 | 75.916 | 53.073 | 4.559 |
| 2548 | C | VAL | 322 | 77.374 | 53.343 | 4.157 |
| 2549 | O | VAL | 322 | 78.097 | 54.114 | 4.806 |
| 2550 | CB | VAL | 322 | 74.899 | 53.790 | 3.675 |
| 2551 | CG1 | VAL | 322 | 74.628 | 53.025 | 2.382 |
| 2552 | CG2 | VAL | 322 | 73.583 | 53.918 | 4.432 |
| 2553 | N | LEU | 323 | 77.829 | 52.552 | 3.199 |
| 2554 | CA | LEU | 323 | 79.193 | 52.624 | 2.665 |
| 2555 | C | LEU | 323 | 79.429 | 53.943 | 1.927 |
| 2556 | O | LEU | 323 | 78.571 | 54.425 | 1.180 |
| 2557 | CB | LEU | 323 | 79.320 | 51.438 | 1.707 |
| 2558 | CG | LEU | 323 | 80.681 | 51.292 | 1.031 |
| 2559 | CD1 | LEU | 323 | 81.796 | 51.097 | 2.052 |
| 2560 | CD2 | LEU | 323 | 80.654 | 50.122 | 0.055 |
| 2561 | N | TYR | 324 | 80.565 | 54.558 | 2.199 |
| 2562 | CA | TYR | 324 | 80.940 | 55.792 | 1.508 |
| 2563 | C | TYR | 324 | 82.011 | 55.501 | 0.460 |
| 2564 | O | TYR | 324 | 83.164 | 55.199 | 0.796 |
| 2565 | CB | TYR | 324 | 81.451 | 56.789 | 2.539 |
| 2566 | CG | TYR | 324 | 80.749 | 58.140 | 2.462 |
| 2567 | CD1 | TYR | 324 | 81.368 | 59.278 | 2.962 |
| 2568 | CD2 | TYR | 324 | 79.489 | 58.228 | 1.883 |
| 2569 | CE1 | TYR | 324 | 80.722 | 60.505 | 2.893 |
| 2570 | CE2 | TYR | 324 | 78.842 | 59.454 | 1.814 |
| 2571 | CZ | TYR | 324 | 79.457 | 60.588 | 2.326 |
| 2572 | OH | TYR | 324 | 78.753 | 61.770 | 2.397 |
| 2573 | N | LEU | 325 | 81.636 | 55.672 | −0.797 |
| 2574 | CA | LEU | 325 | 82.524 | 55.308 | −1.909 |
| 2575 | C | LEU | 325 | 82.448 | 56.280 | −3.082 |
| 2576 | O | LEU | 325 | 81.390 | 56.440 | −3.700 |
| 2577 | CB | LEU | 325 | 82.121 | 53.927 | −2.408 |
| 2578 | CG | LEU | 325 | 83.239 | 52.910 | −2.224 |
| 2579 | CD1 | LEU | 325 | 82.767 | 51.523 | −2.630 |
| 2580 | CD2 | LEU | 325 | 84.488 | 53.299 | −3.006 |
| 2581 | N | ASP | 326 | 83.612 | 56.796 | −3.456 |
| 2582 | CA | ASP | 326 | 83.790 | 57.716 | −4.603 |
| 2583 | C | ASP | 326 | 82.664 | 58.737 | −4.727 |
| 2584 | O | ASP | 326 | 81.823 | 58.651 | −5.628 |
| 2585 | CB | ASP | 326 | 83.886 | 56.898 | −5.888 |
| 2586 | CG | ASP | 326 | 85.135 | 56.018 | −5.870 |
| 2587 | OD1 | ASP | 326 | 85.052 | 54.900 | −6.358 |
| 2588 | OD2 | ASP | 326 | 86.127 | 56.451 | −5.300 |
| 2589 | N | THR | 327 | 82.640 | 59.637 | −3.752 |
| 2590 | CA | THR | 327 | 81.634 | 60.702 | −3.506 |
| 2591 | C | THR | 327 | 80.155 | 60.268 | −3.563 |
| 2592 | O | THR | 327 | 79.261 | 61.109 | −3.716 |
| 2593 | CB | THR | 327 | 81.909 | 61.893 | −4.434 |
| 2594 | OG1 | THR | 327 | 81.250 | 63.041 | −3.916 |
| 2595 | CG2 | THR | 327 | 81.468 | 61.691 | −5.881 |
| 2596 | N | LEU | 328 | 79.895 | 58.993 | −3.330 |
| 2597 | CA | LEU | 328 | 78.527 | 58.485 | −3.303 |
| 2598 | C | LEU | 328 | 78.291 | 57.640 | −2.062 |
| 2599 | O | LEU | 328 | 79.223 | 57.243 | −1.348 |
| 2600 | CB | LEU | 328 | 78.297 | 57.615 | −4.535 |
| 2601 | CG | LEU | 328 | 78.363 | 58.407 | −5.836 |
| 2602 | CD1 | LEU | 328 | 78.377 | 57.477 | −7.044 |
| 2603 | CD2 | LEU | 328 | 77.215 | 59.408 | −5.932 |
| 2604 | N | THR | 329 | 77.018 | 57.428 | −1.791 |
| 2605 | CA | THR | 329 | 76.607 | 56.530 | −0.715 |
| 2606 | C | THR | 329 | 76.186 | 55.198 | −1.332 |
| 2607 | O | THR | 329 | 75.117 | 55.082 | −1.942 |
| 2608 | CB | THR | 329 | 75.454 | 57.185 | 0.029 |
| 2609 | OG1 | THR | 329 | 75.916 | 58.434 | 0.522 |
| 2610 | CG2 | THR | 329 | 75.012 | 56.347 | 1.215 |
| 2611 | N | LYS | 330 | 77.048 | 54.209 | −1.184 |
| 2612 | CA | LYS | 330 | 76.880 | 52.937 | −1.888 |
| 2613 | C | LYS | 330 | 76.178 | 51.895 | −1.016 |
| 2614 | O | LYS | 330 | 76.496 | 51.719 | 0.168 |
| 2615 | CB | LYS | 330 | 78.269 | 52.470 | −2.311 |
| 2616 | CG | LYS | 330 | 78.224 | 51.479 | −3.467 |
| 2617 | CD | LYS | 330 | 79.612 | 51.282 | −4.060 |
| 2618 | CE | LYS | 330 | 79.597 | 50.409 | −5.308 |
| 2619 | NZ | LYS | 330 | 80.942 | 50.318 | −5.896 |
| 2620 | N | GLU | 331 | 75.240 | 51.193 | −1.633 |
| 2621 | CA | GLU | 331 | 74.444 | 50.176 | −0.937 |
| 2622 | C | GLU | 331 | 75.322 | 49.045 | −0.418 |
| 2623 | O | GLU | 331 | 76.289 | 48.633 | −1.076 |
| 2624 | CB | GLU | 331 | 73.427 | 49.605 | −1.917 |
| 2625 | CG | GLU | 331 | 72.551 | 50.701 | −2.510 |
| 2626 | CD | GLU | 331 | 71.575 | 50.097 | −3.515 |
| 2627 | OE1 | GLU | 331 | 71.094 | 49.005 | −3.253 |
| 2628 | OE2 | GLU | 331 | 71.287 | 50.767 | −4.497 |
| 2629 | N | TRP | 332 | 74.950 | 48.506 | 0.731 |
| 2630 | CA | TRP | 332 | 75.735 | 47.422 | 1.334 |
| 2631 | C | TRP | 332 | 75.344 | 46.055 | 0.767 |
| 2632 | O | TRP | 332 | 74.542 | 45.305 | 1.337 |
| 2633 | CB | TRP | 332 | 75.583 | 47.442 | 2.850 |
| 2634 | CG | TRP | 332 | 76.287 | 46.265 | 3.489 |
| 2635 | CD1 | TRP | 332 | 75.704 | 45.289 | 4.264 |
| 2636 | CD2 | TRP | 332 | 77.690 | 45.933 | 3.391 |
| 2637 | NE1 | TRP | 332 | 76.652 | 44.378 | 4.588 |
| 2638 | CE2 | TRP | 332 | 77.850 | 44.712 | 4.068 |
| 2639 | CE3 | TRP | 332 | 78.770 | 46.527 | 2.755 |
| 2640 | CZ2 | TRP | 332 | 79.088 | 44.087 | 4.072 |
| 2641 | CZ3 | TRP | 332 | 80.011 | 45.903 | 2.780 |
| 2642 | CH2 | TRP | 332 | 80.168 | 44.685 | 3.434 |
| 2643 | N | ASP | 333 | 75.885 | 45.812 | −0.417 |
| 2644 | CA | ASP | 333 | 75.711 | 44.584 | −1.203 |
| 2645 | C | ASP | 333 | 76.243 | 44.870 | −2.600 |
| 2646 | O | ASP | 333 | 76.329 | 43.985 | −3.461 |
| 2647 | CB | ASP | 333 | 74.233 | 44.182 | −1.313 |
| 2648 | CG | ASP | 333 | 73.403 | 45.224 | −2.066 |
| 2649 | OD1 | ASP | 333 | 73.106 | 46.258 | −1.479 |
| 2650 | OD2 | ASP | 333 | 73.194 | 45.024 | −3.255 |
| 2651 | N | GLU | 334 | 76.597 | 46.127 | −2.807 |
| 2652 | CA | GLU | 334 | 76.971 | 46.590 | −4.139 |
| 2653 | C | GLU | 334 | 78.480 | 46.511 | −4.324 |
| 2654 | O | GLU | 334 | 79.238 | 47.327 | −3.790 |
| 2655 | CB | GLU | 334 | 76.471 | 48.023 | −4.262 |
| 2656 | CG | GLU | 334 | 76.494 | 48.545 | −5.691 |
| 2657 | CD | GLU | 334 | 75.898 | 49.949 | −5.704 |
| 2658 | OE1 | GLU | 334 | 76.107 | 50.655 | −6.680 |
| 2659 | OE2 | GLU | 334 | 75.232 | 50.291 | −4.732 |
| 2660 | N | LYS | 335 | 78.891 | 45.496 | −5.063 |
| 2661 | CA | LYS | 335 | 80.309 | 45.265 | −5.349 |
| 2662 | C | LYS | 335 | 80.896 | 46.355 | −6.241 |
| 2663 | O | LYS | 335 | 80.176 | 47.208 | −6.774 |
| 2664 | CB | LYS | 335 | 80.445 | 43.893 | −5.994 |
| 2665 | CG | LYS | 335 | 79.953 | 42.817 | −5.030 |
| 2666 | CD | LYS | 335 | 80.009 | 41.428 | −5.652 |
| 2667 | CE | LYS | 335 | 79.101 | 41.331 | −6.872 |
| 2668 | NZ | LYS | 335 | 79.138 | 39.977 | −7.448 |
| 2669 | N | LEU | 336 | 82.217 | 46.370 | −6.304 |
| 2670 | CA | LEU | 336 | 82.950 | 47.417 | −7.028 |
| 2671 | C | LEU | 336 | 82.690 | 47.415 | −8.527 |
| 2672 | O | LEU | 336 | 83.072 | 46.492 | −9.256 |
| 2673 | CB | LEU | 336 | 84.437 | 47.226 | −6.775 |
| 2674 | CG | LEU | 336 | 84.791 | 47.591 | −5.343 |
| 2675 | CD1 | LEU | 336 | 86.243 | 47.247 | −5.035 |
| 2676 | CD2 | LEU | 336 | 84.515 | 49.070 | −5.101 |
| 2677 | N | LYS | 337 | 82.131 | 48.521 | −8.987 |
| 2678 | CA | LYS | 337 | 81.864 | 48.689 | −10.417 |
| 2679 | C | LYS | 337 | 83.084 | 49.305 | −11.096 |
| 2680 | O | LYS | 337 | 83.377 | 49.036 | −12.266 |
| 2681 | CB | LYS | 337 | 80.676 | 49.634 | −10.578 |
| 2682 | CG | LYS | 337 | 79.490 | 49.245 | −9.698 |

TABLE 8-continued

| Atom No. | Atom Type | Residue | Residue Position | X Coord. | Y Coord. | Z Coord. |
|---|---|---|---|---|---|---|
| 2683 | CD | LYS | 337 | 78.896 | 47.887 | −10.064 |
| 2684 | CE | LYS | 337 | 77.756 | 47.526 | −9.120 |
| 2685 | NZ | LYS | 337 | 77.223 | 46.186 | −9.414 |
| 2686 | N | ASP | 338 | 83.850 | 50.038 | −10.306 |
| 2687 | CA | ASP | 338 | 85.076 | 50.673 | −10.800 |
| 2688 | C | ASP | 338 | 86.268 | 49.748 | −10.594 |
| 2689 | O | ASP | 338 | 86.562 | 49.346 | −9.462 |
| 2690 | CB | ASP | 338 | 85.298 | 51.976 | −10.034 |
| 2691 | CG | ASP | 338 | 84.126 | 52.934 | −10.241 |
| 2692 | OD1 | ASP | 338 | 84.141 | 53.642 | −11.238 |
| 2693 | OD2 | ASP | 338 | 83.199 | 52.884 | −9.441 |
| 2694 | N | GLN | 339 | 86.891 | 49.360 | −11.693 |
| 2695 | CA | GLN | 339 | 88.068 | 48.483 | −11.629 |
| 2696 | C | GLN | 339 | 89.346 | 49.220 | −12.028 |
| 2697 | O | GLN | 339 | 89.376 | 49.962 | −13.018 |
| 2698 | CB | GLN | 339 | 87.829 | 47.284 | −12.541 |
| 2699 | CG | GLN | 339 | 86.642 | 46.452 | −12.060 |
| 2700 | CD | GLN | 339 | 86.925 | 45.899 | −10.665 |
| 2701 | OE1 | GLN | 339 | 88.066 | 45.537 | −10.350 |
| 2702 | NE2 | GLN | 339 | 85.894 | 45.850 | −9.841 |
| 2703 | N | ILE | 340 | 90.389 | 49.014 | −11.243 |
| 2704 | CA | ILE | 340 | 91.662 | 49.714 | −11.472 |
| 2705 | C | ILE | 340 | 92.647 | 48.899 | −12.311 |
| 2706 | O | ILE | 340 | 93.139 | 47.844 | −11.886 |
| 2707 | CB | ILE | 340 | 92.273 | 50.054 | −10.114 |
| 2708 | CG1 | ILE | 340 | 91.373 | 51.023 | −9.360 |
| 2709 | CG2 | ILE | 340 | 93.674 | 50.639 | −10.253 |
| 2710 | CD1 | ILE | 340 | 92.027 | 51.489 | −8.065 |
| 2711 | N | VAL | 341 | 92.930 | 49.424 | −13.494 |
| 2712 | CA | VAL | 341 | 93.926 | 48.833 | −14.399 |
| 2713 | C | VAL | 341 | 95.316 | 48.888 | −13.764 |
| 2714 | O | VAL | 341 | 95.774 | 49.945 | −13.313 |
| 2715 | CB | VAL | 341 | 93.907 | 49.629 | −15.703 |
| 2716 | CG1 | VAL | 341 | 94.909 | 49.086 | −16.718 |
| 2717 | CG2 | VAL | 341 | 92.504 | 49.647 | −16.302 |
| 2718 | N | ASN | 342 | 95.914 | 47.718 | −13.626 |
| 2719 | CA | ASN | 342 | 97.220 | 47.595 | −12.975 |
| 2720 | C | ASN | 342 | 98.121 | 46.636 | −13.748 |
| 2721 | O | ASN | 342 | 97.679 | 45.963 | −14.687 |
| 2722 | CB | ASN | 342 | 97.017 | 47.114 | −11.535 |
| 2723 | CG | ASN | 342 | 96.425 | 45.703 | −11.460 |
| 2724 | OD1 | ASN | 342 | 97.149 | 44.710 | −11.602 |
| 2725 | ND2 | ASN | 342 | 95.124 | 45.623 | −11.231 |
| 2726 | N | THR | 343 | 99.390 | 46.614 | −13.383 |
| 2727 | CA | THR | 343 | 100.343 | 45.745 | −14.082 |
| 2728 | C | THR | 343 | 100.775 | 44.570 | −13.211 |
| 2729 | O | THR | 343 | 101.618 | 44.707 | −12.315 |
| 2730 | CB | THR | 343 | 101.554 | 46.575 | −14.488 |
| 2731 | OG1 | THR | 343 | 101.091 | 47.621 | −15.331 |
| 2732 | CG2 | THR | 343 | 102.574 | 45.751 | −15.270 |
| 2733 | N | ARG | 344 | 100.234 | 43.406 | −13.529 |
| 2734 | CA | ARG | 344 | 100.586 | 42.179 | −12.806 |
| 2735 | C | ARG | 344 | 101.875 | 41.555 | −13.334 |
| 2736 | O | ARG | 344 | 101.855 | 40.748 | −14.270 |
| 2737 | CB | ARG | 344 | 99.448 | 41.183 | −12.973 |
| 2738 | CG | ARG | 344 | 98.147 | 41.744 | −12.420 |
| 2739 | CD | ARG | 344 | 96.984 | 40.791 | −12.665 |
| 2740 | NE | ARG | 344 | 95.727 | 41.343 | −12.132 |
| 2741 | CZ | ARG | 344 | 94.825 | 41.983 | −12.881 |
| 2742 | NH1 | ARG | 344 | 93.687 | 42.409 | −12.331 |
| 2743 | NH2 | ARG | 344 | 95.041 | 42.159 | −14.187 |
| 2744 | N | GLN | 345 | 102.984 | 41.930 | −12.722 |
| 2745 | CA | GLN | 345 | 104.277 | 41.337 | −13.076 |
| 2746 | C | GLN | 345 | 104.350 | 39.882 | −12.624 |
| 2747 | O | GLN | 345 | 103.873 | 39.536 | −11.539 |
| 2748 | CB | GLN | 345 | 105.390 | 42.129 | −12.403 |
| 2749 | CG | GLN | 345 | 105.437 | 43.564 | −12.905 |
| 2750 | CD | GLN | 345 | 106.624 | 44.279 | −12.271 |
| 2751 | OE1 | GLN | 345 | 107.116 | 45.283 | −12.797 |
| 2752 | NE2 | GLN | 345 | 107.088 | 43.735 | −11.159 |
| 2753 | N | PRO | 346 | 104.930 | 39.049 | −13.473 |
| 2754 | CA | PRO | 346 | 105.153 | 37.641 | −13.137 |
| 2755 | C | PRO | 346 | 106.089 | 37.489 | −11.933 |
| 2756 | O | PRO | 346 | 105.587 | 37.191 | −10.862 |
| 2757 | CB | PRO | 346 | 105.779 | 37.033 | −14.353 |
| 2758 | CG | PRO | 346 | 105.987 | 38.115 | −15.404 |
| 2759 | CD | PRO | 346 | 105.451 | 39.401 | −14.797 |
| 2760 | OXT | PRO | 346 | 107.280 | 37.680 | −12.116 |

TABLE 9

| Atom No. | Atom Type | Residue | Residue Position | X Coord. | Y Coord. | Z Coord. |
|---|---|---|---|---|---|---|
| 1 | N | MET | 1 | 57.469 | −9.726 | 32.676 |
| 2 | CA | MET | 1 | 56.765 | −10.527 | 31.662 |
| 3 | C | MET | 1 | 55.259 | −10.345 | 31.785 |
| 4 | O | MET | 1 | 54.577 | −9.998 | 30.809 |
| 5 | CB | MET | 1 | 57.113 | −12.004 | 31.816 |
| 6 | CG | MET | 1 | 56.425 | −12.851 | 30.751 |
| 7 | SD | MET | 1 | 56.830 | −12.425 | 29.042 |
| 8 | CE | MET | 1 | 58.617 | −12.699 | 29.097 |
| 9 | N | SER | 2 | 54.797 | −10.346 | 33.026 |
| 10 | CA | SER | 2 | 53.358 | −10.282 | 33.302 |
| 11 | C | SER | 2 | 52.774 | −8.887 | 33.101 |
| 12 | O | SER | 2 | 51.590 | −8.778 | 32.766 |
| 13 | CB | SER | 2 | 53.113 | −10.724 | 34.738 |
| 14 | OG | SER | 2 | 51.713 | −10.650 | 34.975 |
| 15 | N | VAL | 3 | 53.636 | −7.887 | 33.002 |
| 16 | CA | VAL | 3 | 53.173 | −6.527 | 32.728 |
| 17 | C | VAL | 3 | 52.744 | −6.415 | 31.272 |
| 18 | O | VAL | 3 | 51.620 | −5.985 | 30.988 |
| 19 | CB | VAL | 3 | 54.337 | −5.572 | 32.965 |
| 20 | CG1 | VAL | 3 | 53.896 | −4.123 | 32.794 |
| 21 | CG2 | VAL | 3 | 54.960 | −5.789 | 34.339 |
| 22 | N | GLU | 4 | 53.471 | −7.133 | 30.433 |
| 23 | CA | GLU | 4 | 53.218 | −7.113 | 28.996 |
| 24 | C | GLU | 4 | 52.064 | −8.048 | 28.674 |
| 25 | O | GLU | 4 | 51.153 | −7.656 | 27.934 |
| 26 | CB | GLU | 4 | 54.470 | −7.573 | 28.247 |
| 27 | CG | GLU | 4 | 55.692 | −6.693 | 28.516 |
| 28 | CD | GLU | 4 | 56.667 | −7.360 | 29.489 |
| 29 | OE1 | GLU | 4 | 57.680 | −7.866 | 29.029 |
| 30 | OE2 | GLU | 4 | 56.398 | −7.322 | 30.686 |
| 31 | N | THR | 5 | 51.937 | −9.084 | 29.486 |
| 32 | CA | THR | 5 | 50.857 | −10.055 | 29.304 |
| 33 | C | THR | 5 | 49.505 | −9.450 | 29.672 |
| 34 | O | THR | 5 | 48.580 | −9.485 | 28.849 |
| 35 | CB | THR | 5 | 51.138 | −11.253 | 30.203 |
| 36 | OG1 | THR | 5 | 52.409 | −11.786 | 29.849 |
| 37 | CG2 | THR | 5 | 50.093 | −12.349 | 30.026 |
| 38 | N | ILE | 6 | 49.483 | −8.665 | 30.737 |
| 39 | CA | ILE | 6 | 48.233 | −8.036 | 31.157 |
| 40 | C | ILE | 6 | 47.901 | −6.809 | 30.308 |
| 41 | O | ILE | 6 | 46.732 | −6.651 | 29.937 |
| 42 | CB | ILE | 6 | 48.343 | −7.688 | 32.639 |
| 43 | CG1 | ILE | 6 | 48.481 | −8.965 | 33.462 |
| 44 | CG2 | ILE | 6 | 47.133 | −6.895 | 33.118 |
| 45 | CD1 | ILE | 6 | 48.488 | −8.667 | 34.957 |
| 46 | N | SER | 7 | 48.911 | −6.175 | 29.734 |
| 47 | CA | SER | 7 | 48.644 | −5.069 | 28.805 |
| 48 | C | SER | 7 | 48.044 | −5.591 | 27.504 |
| 49 | O | SER | 7 | 46.955 | −5.145 | 27.120 |
| 50 | CB | SER | 7 | 49.946 | −4.339 | 28.495 |
| 51 | OG | SER | 7 | 50.434 | −3.769 | 29.701 |
| 52 | N | ASP | 8 | 48.557 | −6.723 | 27.047 |
| 53 | CA | ASP | 8 | 48.072 | −7.341 | 25.810 |
| 54 | C | ASP | 8 | 46.652 | −7.868 | 25.972 |
| 55 | O | ASP | 8 | 45.780 | −7.522 | 25.163 |
| 56 | CB | ASP | 8 | 48.980 | −8.516 | 25.451 |
| 57 | CG | ASP | 8 | 50.414 | −8.067 | 25.173 |
| 58 | OD1 | ASP | 8 | 50.575 | −6.968 | 24.658 |
| 59 | OD2 | ASP | 8 | 51.300 | −8.902 | 25.309 |
| 60 | N | SER | 9 | 46.371 | −8.453 | 27.125 |
| 61 | CA | SER | 9 | 45.040 | −9.018 | 27.367 |
| 62 | C | SER | 9 | 43.982 | −7.956 | 27.667 |
| 63 | O | SER | 9 | 42.836 | −8.125 | 27.238 |
| 64 | CB | SER | 9 | 45.127 | −10.003 | 28.531 |
| 65 | OG | SER | 9 | 45.568 | −9.304 | 29.688 |

TABLE 9-continued

| Atom No. | Atom Type | Residue | Residue Position | X Coord. | Y Coord. | Z Coord. |
|---|---|---|---|---|---|---|
| 66 | N | LEU | 10 | 44.385 | −6.792 | 28.151 |
| 67 | CA | LEU | 10 | 43.403 | −5.731 | 28.397 |
| 68 | C | LEU | 10 | 43.168 | −4.878 | 27.152 |
| 69 | O | LEU | 10 | 42.097 | −4.271 | 27.022 |
| 70 | CB | LEU | 10 | 43.815 | −4.858 | 29.582 |
| 71 | CG | LEU | 10 | 43.280 | −5.389 | 30.917 |
| 72 | CD1 | LEU | 10 | 41.826 | −5.811 | 30.774 |
| 73 | CD2 | LEU | 10 | 44.074 | −6.561 | 31.476 |
| 74 | N | LYS | 11 | 44.048 | −5.001 | 26.171 |
| 75 | CA | LYS | 11 | 43.811 | −4.382 | 24.861 |
| 76 | C | LYS | 11 | 43.020 | −5.310 | 23.938 |
| 77 | O | LYS | 11 | 42.591 | −4.899 | 22.852 |
| 78 | CB | LYS | 11 | 45.149 | −4.052 | 24.215 |
| 79 | CG | LYS | 11 | 45.910 | −3.023 | 25.038 |
| 80 | CD | LYS | 11 | 47.275 | −2.720 | 24.435 |
| 81 | CE | LYS | 11 | 48.039 | −1.714 | 25.288 |
| 82 | NZ | LYS | 11 | 49.360 | −1.425 | 24.709 |
| 83 | N | GLN | 12 | 42.863 | −6.556 | 24.359 |
| 84 | CA | GLN | 12 | 42.021 | −7.514 | 23.640 |
| 85 | C | GLN | 12 | 40.698 | −7.758 | 24.363 |
| 86 | O | GLN | 12 | 39.838 | −8.491 | 23.856 |
| 87 | CB | GLN | 12 | 42.781 | −8.827 | 23.516 |
| 88 | CG | GLN | 12 | 44.033 | −8.645 | 22.670 |
| 89 | CD | GLN | 12 | 44.866 | −9.921 | 22.663 |
| 90 | OE1 | GLN | 12 | 44.338 | −11.038 | 22.701 |
| 91 | NE2 | GLN | 12 | 46.174 | −9.734 | 22.641 |
| 92 | N | LEU | 13 | 40.541 | −7.157 | 25.532 |
| 93 | CA | LEU | 13 | 39.319 | −7.355 | 26.317 |
| 94 | C | LEU | 13 | 38.145 | −6.575 | 25.735 |
| 95 | O | LEU | 13 | 38.043 | −5.351 | 25.890 |
| 96 | CB | LEU | 13 | 39.554 | −6.893 | 27.751 |
| 97 | CG | LEU | 13 | 38.410 | −7.348 | 28.651 |
| 98 | CD1 | LEU | 13 | 38.446 | −8.863 | 28.809 |
| 99 | CD2 | LEU | 13 | 38.463 | −6.678 | 30.019 |
| 100 | N | GLY | 14 | 37.224 | −7.307 | 25.136 |
| 101 | CA | GLY | 14 | 36.005 | −6.697 | 24.608 |
| 102 | C | GLY | 14 | 34.777 | −7.223 | 25.341 |
| 103 | O | GLY | 14 | 33.937 | −7.913 | 24.755 |
| 104 | N | LEU | 15 | 34.693 | −6.913 | 26.625 |
| 105 | CA | LEU | 15 | 33.578 | −7.426 | 27.427 |
| 106 | C | LEU | 15 | 32.576 | −6.360 | 27.863 |
| 107 | O | LEU | 15 | 31.650 | −6.683 | 28.616 |
| 108 | CB | LEU | 15 | 34.102 | −8.202 | 28.627 |
| 109 | CG | LEU | 15 | 34.651 | −9.559 | 28.192 |
| 110 | CD1 | LEU | 15 | 35.148 | −10.367 | 29.385 |
| 111 | CD2 | LEU | 15 | 33.598 | −10.357 | 27.431 |
| 112 | N | SER | 16 | 32.775 | −5.114 | 27.462 |
| 113 | CA | SER | 16 | 31.725 | −4.117 | 27.693 |
| 114 | C | SER | 16 | 30.623 | −4.364 | 26.676 |
| 115 | O | SER | 16 | 30.874 | −4.970 | 25.628 |
| 116 | CB | SER | 16 | 32.248 | −2.697 | 27.519 |
| 117 | OG | SER | 16 | 32.327 | −2.425 | 26.128 |
| 118 | N | GLN | 17 | 29.426 | −3.892 | 26.979 |
| 119 | CA | GLN | 17 | 28.291 | −4.081 | 26.067 |
| 120 | C | GLN | 17 | 28.616 | −3.507 | 24.688 |
| 121 | O | GLN | 17 | 29.367 | −2.529 | 24.582 |
| 122 | CB | GLN | 17 | 27.064 | −3.433 | 26.697 |
| 123 | CG | GLN | 17 | 26.717 | −4.172 | 27.985 |
| 124 | CD | GLN | 17 | 25.440 | −3.624 | 28.606 |
| 125 | OB1 | GLN | 17 | 25.487 | −2.778 | 29.506 |
| 126 | NE2 | GLN | 17 | 24.317 | −4.150 | 28.152 |
| 127 | N | PRO | 18 | 28.080 | −4.125 | 23.643 |
| 128 | CA | PRO | 18 | 28.749 | −4.095 | 22.329 |
| 129 | C | PRO | 18 | 28.801 | −2.727 | 21.642 |
| 130 | O | PRO | 18 | 29.812 | −2.434 | 20.996 |
| 131 | CB | PRO | 18 | 28.001 | −5.078 | 21.481 |
| 132 | CG | PRO | 18 | 26.922 | −5.750 | 22.315 |
| 133 | CD | PRO | 18 | 27.057 | −5.174 | 23.713 |
| 134 | N | ALA | 19 | 27.904 | −1.818 | 21.988 |
| 135 | CA | ALA | 19 | 27.961 | −0.473 | 21.402 |
| 136 | C | ALA | 19 | 29.068 | 0.373 | 22.036 |
| 137 | O | ALA | 19 | 29.795 | 1.066 | 21.314 |
| 138 | CB | ALA | 19 | 26.612 | 0.207 | 21.605 |
| 139 | N | ALA | 20 | 29.401 | 0.053 | 23.277 |
| 140 | CA | ALA | 20 | 30.474 | 0.759 | 23.971 |
| 141 | C | ALA | 20 | 31.825 | 0.157 | 23.605 |
| 142 | O | ALA | 20 | 32.795 | 0.906 | 23.448 |
| 143 | CB | ALA | 20 | 30.251 | 0.646 | 25.476 |
| 144 | N | ILE | 21 | 31.812 | −1.099 | 23.184 |
| 145 | CA | ILE | 21 | 33.039 | −1.757 | 22.721 |
| 146 | C | ILE | 21 | 33.295 | −1.479 | 21.233 |
| 147 | O | ILE | 21 | 34.412 | −1.666 | 20.739 |
| 148 | CB | ILE | 21 | 32.930 | −3.253 | 23.025 |
| 149 | CG1 | ILE | 21 | 34.104 | −3.709 | 23.887 |
| 150 | CG2 | ILE | 21 | 32.821 | −4.113 | 21.769 |
| 151 | CD1 | ILE | 21 | 35.454 | −3.370 | 23.262 |
| 152 | N | GLU | 22 | 32.319 | −0.871 | 20.577 |
| 153 | CA | GLU | 22 | 32.496 | −0.402 | 19.203 |
| 154 | C | GLU | 22 | 33.003 | 1.044 | 19.195 |
| 155 | O | GLU | 22 | 33.363 | 1.585 | 18.142 |
| 156 | CB | GLU | 22 | 31.142 | −0.510 | 18.506 |
| 157 | CG | GLU | 22 | 31.223 | −0.242 | 17.008 |
| 158 | CD | GLU | 22 | 29.836 | −0.369 | 16.389 |
| 159 | OB1 | GLU | 22 | 28.871 | −0.230 | 17.129 |
| 160 | OE2 | GLU | 22 | 29.764 | −0.683 | 15.209 |
| 161 | N | GLY | 23 | 33.065 | 1.646 | 20.372 |
| 162 | CA | GLY | 23 | 33.584 | 3.006 | 20.505 |
| 163 | C | GLY | 23 | 34.946 | 2.986 | 21.187 |
| 164 | O | GLY | 23 | 35.858 | 3.727 | 20.798 |
| 165 | N | THR | 24 | 35.055 | 2.181 | 22.230 |
| 166 | CA | THR | 24 | 36.326 | 2.044 | 22.950 |
| 167 | C | THR | 24 | 37.289 | 1.120 | 22.214 |
| 168 | O | THR | 24 | 37.043 | −0.076 | 22.031 |
| 169 | CB | THR | 24 | 36.081 | 1.521 | 24.365 |
| 170 | OG1 | THR | 24 | 35.447 | 0.248 | 24.296 |
| 171 | CG2 | THR | 24 | 35.187 | 2.460 | 25.166 |
| 172 | N | HIS | 25 | 38.430 | 1.688 | 21.878 |
| 173 | CA | HIS | 25 | 39.479 | 0.946 | 21.180 |
| 174 | C | HIS | 25 | 40.765 | 0.996 | 21.991 |
| 175 | O | HIS | 25 | 41.564 | 1.924 | 21.817 |
| 176 | CB | HIS | 25 | 39.711 | 1.597 | 19.820 |
| 177 | CG | HIS | 25 | 38.524 | 1.531 | 18.878 |
| 178 | ND1 | HIS | 25 | 37.648 | 2.519 | 18.603 |
| 179 | CD2 | HIS | 25 | 38.140 | 0.439 | 18.136 |
| 180 | CE1 | HIS | 25 | 36.738 | 2.072 | 17.714 |
| 181 | NE2 | HIS | 25 | 37.041 | 0.786 | 17.428 |
| 182 | N | PRO | 26 | 41.021 | −0.039 | 22.780 |
| 183 | CA | PRO | 26 | 42.041 | 0.047 | 23.840 |
| 184 | C | PRO | 26 | 43.485 | 0.102 | 23.328 |
| 185 | O | PRO | 26 | 44.320 | 0.789 | 23.925 |
| 186 | CB | PRO | 26 | 41.829 | −1.177 | 24.679 |
| 187 | CG | PRO | 26 | 40.740 | −2.039 | 24.059 |
| 188 | CD | PRO | 26 | 40.232 | −1.274 | 22.851 |
| 189 | N | GLN | 27 | 43.694 | −0.352 | 22.107 |
| 190 | CA | GLN | 27 | 45.029 | −0.344 | 21.503 |
| 191 | C | GLN | 27 | 45.335 | 0.987 | 20.806 |
| 192 | O | GLN | 27 | 46.466 | 1.196 | 20.353 |
| 193 | CB | GLN | 27 | 45.178 | −1.505 | 20.509 |
| 194 | CG | GLN | 27 | 44.325 | −1.405 | 19.235 |
| 195 | CD | GLN | 27 | 42.869 | −1.804 | 19.466 |
| 196 | OE1 | GLN | 27 | 42.031 | −0.960 | 19.809 |
| 197 | NE2 | GLN | 27 | 42.627 | −3.101 | 19.441 |
| 198 | N | TYR | 28 | 44.349 | 1.867 | 20.716 |
| 199 | CA | TYR | 28 | 44.585 | 3.203 | 20.164 |
| 200 | C | TYR | 28 | 44.409 | 4.242 | 21.265 |
| 201 | O | TYR | 28 | 45.075 | 5.284 | 21.280 |
| 202 | CB | TYR | 28 | 43.586 | 3.465 | 19.041 |
| 203 | CG | TYR | 28 | 43.643 | 2.439 | 17.914 |
| 204 | CD1 | TYR | 28 | 44.825 | 2.242 | 17.212 |
| 205 | CD2 | TYR | 28 | 42.509 | 1.705 | 17.590 |
| 206 | CE1 | TYR | 28 | 44.879 | 1.300 | 16.194 |
| 207 | CE2 | TYR | 28 | 42.560 | 0.762 | 16.572 |
| 208 | CZ | TYR | 28 | 43.747 | 0.560 | 15.880 |
| 209 | OH | TYR | 28 | 43.803 | −0.390 | 14.884 |
| 210 | N | ASN | 29 | 43.484 | 3.957 | 22.160 |
| 211 | CA | ASN | 29 | 43.264 | 4.805 | 23.325 |
| 212 | C | ASN | 29 | 43.702 | 4.047 | 24.568 |
| 213 | O | ASN | 29 | 42.955 | 3.205 | 25.090 |
| 214 | CB | ASN | 29 | 41.784 | 5.170 | 23.393 |
| 215 | CG | ASN | 29 | 41.477 | 6.149 | 24.528 |
| 216 | OD1 | ASN | 29 | 42.364 | 6.556 | 25.290 |
| 217 | ND2 | ASN | 29 | 40.206 | 6.476 | 24.658 |

TABLE 9-continued

| Atom No. | Atom Type | Residue | Residue Position | X Coord. | Y Coord. | Z Coord. |
|---|---|---|---|---|---|---|
| 218 | N | VAL | 30 | 44.738 | 4.587 | 25.190 |
| 219 | CA | VAL | 30 | 45.383 | 3.945 | 26.341 |
| 220 | C | VAL | 30 | 44.553 | 4.074 | 27.621 |
| 221 | O | VAL | 30 | 44.571 | 3.152 | 28.448 |
| 222 | CB | VAL | 30 | 46.746 | 4.608 | 26.529 |
| 223 | CG1 | VAL | 30 | 47.533 | 3.969 | 27.668 |
| 224 | CG2 | VAL | 30 | 47.554 | 4.551 | 25.237 |
| 225 | N | VAL | 31 | 43.603 | 4.997 | 27.623 |
| 226 | CA | VAL | 31 | 42.705 | 5.121 | 28.771 |
| 227 | C | VAL | 31 | 41.603 | 4.057 | 28.731 |
| 228 | O | VAL | 31 | 41.159 | 3.618 | 29.798 |
| 229 | CB | VAL | 31 | 42.124 | 6.528 | 28.774 |
| 230 | CG1 | VAL | 31 | 41.219 | 6.756 | 29.980 |
| 231 | CG2 | VAL | 31 | 43.256 | 7.548 | 28.772 |
| 232 | N | ASP | 32 | 41.428 | 3.414 | 27.584 |
| 233 | CA | ASP | 32 | 40.503 | 2.279 | 27.502 |
| 234 | C | ASP | 32 | 41.160 | 1.006 | 28.030 |
| 235 | O | ASP | 32 | 40.460 | 0.159 | 28.596 |
| 236 | CB | ASP | 32 | 40.092 | 2.022 | 26.058 |
| 237 | CG | ASP | 32 | 39.317 | 3.186 | 25.461 |
| 238 | OD1 | ASP | 32 | 38.599 | 3.842 | 26.200 |
| 239 | OD2 | ASP | 32 | 39.335 | 3.309 | 24.242 |
| 240 | N | VAL | 33 | 42.485 | 0.976 | 28.072 |
| 241 | CA | VAL | 33 | 43.181 | −0.173 | 28.664 |
| 242 | C | VAL | 33 | 43.085 | −0.089 | 30.178 |
| 243 | O | VAL | 33 | 42.802 | −1.092 | 30.846 |
| 244 | CB | VAL | 33 | 44.658 | −0.127 | 28.293 |
| 245 | CG1 | VAL | 33 | 45.401 | −1.346 | 28.833 |
| 246 | CG2 | VAL | 33 | 44.850 | −0.014 | 26.793 |
| 247 | N | PHE | 34 | 43.072 | 1.139 | 30.673 |
| 248 | CA | PHE | 34 | 42.913 | 1.357 | 32.106 |
| 249 | C | PHE | 34 | 41.467 | 1.169 | 32.536 |
| 250 | O | PHE | 34 | 41.242 | 0.510 | 33.555 |
| 251 | CB | PHE | 34 | 43.371 | 2.764 | 32.447 |
| 252 | CG | PHE | 34 | 44.868 | 2.994 | 32.285 |
| 253 | CD1 | PHE | 34 | 45.335 | 3.929 | 31.371 |
| 254 | CD2 | PHE | 34 | 45.767 | 2.277 | 33.064 |
| 255 | CE1 | PHE | 34 | 46.699 | 4.140 | 31.229 |
| 256 | CE2 | PHE | 34 | 47.132 | 2.489 | 32.922 |
| 257 | CZ | PHE | 34 | 47.598 | 3.420 | 32.004 |
| 258 | N | ARG | 35 | 40.522 | 1.472 | 31.660 |
| 259 | CA | ARG | 35 | 39.112 | 1.211 | 31.968 |
| 260 | C | ARG | 35 | 38.805 | −0.283 | 31.976 |
| 261 | O | ARG | 35 | 38.191 | −0.762 | 32.938 |
| 262 | CB | ARG | 35 | 38.231 | 1.902 | 30.935 |
| 263 | CG | ARG | 35 | 38.229 | 3.413 | 31.123 |
| 264 | CD | ARG | 35 | 37.347 | 4.095 | 30.083 |
| 265 | NE | ARG | 35 | 37.235 | 5.537 | 30.357 |
| 266 | CZ | ARG | 35 | 37.500 | 6.485 | 29.456 |
| 267 | NH1 | ARG | 35 | 37.923 | 6.148 | 28.236 |
| 268 | NH2 | ARG | 35 | 37.364 | 7.772 | 29.782 |
| 269 | N | ASN | 36 | 39.469 | −1.028 | 31.108 |
| 270 | CA | ASN | 36 | 39.302 | −2.480 | 31.094 |
| 271 | C | ASN | 36 | 39.990 | −3.153 | 32.281 |
| 272 | O | ASN | 36 | 39.383 | −4.031 | 32.907 |
| 273 | CB | ASN | 36 | 39.883 | −3.021 | 29.794 |
| 274 | CG | ASN | 36 | 38.954 | −2.745 | 28.615 |
| 275 | OD1 | ASN | 36 | 37.837 | −2.238 | 28.776 |
| 276 | ND2 | ASN | 36 | 39.430 | −3.106 | 27.437 |
| 277 | N | TYR | 37 | 41.102 | −2.595 | 32.733 |
| 278 | CA | TYR | 37 | 41.786 | −3.145 | 33.910 |
| 279 | C | TYR | 37 | 41.026 | −2.836 | 35.196 |
| 280 | O | TYR | 37 | 40.783 | −3.748 | 35.998 |
| 281 | CB | TYR | 37 | 43.188 | −2.546 | 33.994 |
| 282 | CG | TYR | 37 | 43.939 | −2.901 | 35.276 |
| 283 | CD1 | TYR | 37 | 44.473 | −4.173 | 35.442 |
| 284 | CD2 | TYR | 37 | 44.084 | −1.949 | 36.279 |
| 285 | CE1 | TYR | 37 | 45.143 | −4.497 | 36.615 |
| 286 | CE2 | TYR | 37 | 44.751 | −2.272 | 37.452 |
| 287 | CZ | TYR | 37 | 45.273 | −3.546 | 37.619 |
| 288 | OH | TYR | 37 | 45.820 | −3.898 | 38.831 |
| 289 | N | ILE | 38 | 40.451 | −1.648 | 35.270 |
| 290 | CA | ILE | 38 | 39.696 | −1.249 | 36.458 |
| 291 | C | ILE | 38 | 38.373 | −1.995 | 36.551 |
| 292 | O | ILE | 38 | 38.081 | −2.565 | 37.611 |
| 293 | CB | ILE | 38 | 39.445 | 0.252 | 36.376 |

TABLE 9-continued

| Atom No. | Atom Type | Residue | Residue Position | X Coord. | Y Coord. | Z Coord. |
|---|---|---|---|---|---|---|
| 294 | CG1 | ILE | 38 | 40.749 | 1.024 | 36.535 |
| 295 | CG2 | ILE | 38 | 38.431 | 0.694 | 37.423 |
| 296 | CD1 | ILE | 38 | 40.544 | 2.511 | 36.276 |
| 297 | N | ALA | 39 | 37.764 | −2.260 | 35.407 |
| 298 | CA | ALA | 39 | 36.515 | −3.014 | 35.398 |
| 299 | C | ALA | 39 | 36.746 | −4.502 | 35.624 |
| 300 | O | ALA | 39 | 35.941 | −5.132 | 36.315 |
| 301 | CB | ALA | 39 | 35.834 | −2.806 | 34.056 |
| 302 | N | GLU | 40 | 37.924 | −4.993 | 35.277 |
| 303 | CA | GLU | 40 | 38.262 | −6.392 | 35.538 |
| 304 | C | GLU | 40 | 38.540 | −6.630 | 37.018 |
| 305 | O | GLU | 40 | 37.953 | −7.550 | 37.604 |
| 306 | CB | GLU | 40 | 39.509 | −6.731 | 34.731 |
| 307 | CG | GLU | 40 | 39.987 | −8.157 | 34.975 |
| 308 | CD | GLU | 40 | 41.272 | −8.391 | 34.188 |
| 309 | OE1 | GLU | 40 | 41.943 | −7.408 | 33.903 |
| 310 | OE2 | GLU | 40 | 41.495 | −9.523 | 33.783 |
| 311 | N | GLU | 41 | 39.207 | −5.680 | 37.657 |
| 312 | CA | GLU | 41 | 39.512 | −5.852 | 39.079 |
| 313 | C | GLU | 41 | 38.243 | −5.654 | 39.901 |
| 314 | O | GLU | 41 | 37.890 | −6.540 | 40.687 |
| 315 | CB | GLU | 41 | 40.546 | −4.831 | 39.555 |
| 316 | CG | GLU | 41 | 41.789 | −4.689 | 38.678 |
| 317 | CD | GLU | 41 | 42.596 | −5.978 | 38.549 |
| 318 | OE1 | GLU | 41 | 43.550 | −6.135 | 39.303 |
| 319 | OE2 | GLU | 41 | 42.365 | −6.681 | 37.575 |
| 320 | N | LEU | 42 | 37.433 | −4.681 | 39.512 |
| 321 | CA | LEU | 42 | 36.215 | −4.382 | 40.270 |
| 322 | C | LEU | 42 | 35.098 | −5.387 | 39.995 |
| 323 | O | LEU | 42 | 34.330 | −5.680 | 40.918 |
| 324 | CB | LEU | 42 | 35.745 | −2.975 | 39.917 |
| 325 | CG | LEU | 42 | 34.636 | −2.503 | 40.853 |
| 326 | CD1 | LEU | 42 | 35.087 | −2.568 | 42.309 |
| 327 | CD2 | LEU | 42 | 34.182 | −1.092 | 40.496 |
| 328 | N | HIS | 43 | 35.190 | −6.112 | 38.893 |
| 329 | CA | HIS | 43 | 34.238 | −7.184 | 38.616 |
| 330 | C | HIS | 43 | 34.365 | −8.278 | 39.664 |
| 331 | O | HIS | 43 | 33.393 | −8.541 | 40.380 |
| 332 | CB | HIS | 43 | 34.570 | −7.768 | 37.250 |
| 333 | CG | HIS | 43 | 33.608 | −8.834 | 36.775 |
| 334 | ND1 | HIS | 43 | 32.278 | −8.845 | 36.971 |
| 335 | CD2 | HIS | 43 | 33.918 | −9.965 | 36.061 |
| 336 | CE1 | HIS | 43 | 31.750 | −9.946 | 36.401 |
| 337 | NE2 | HIS | 43 | 32.766 | −10.639 | 35.838 |
| 338 | N | ARG | 44 | 35.600 | −8.628 | 39.980 |
| 339 | CA | ARG | 44 | 35.849 | −9.679 | 40.967 |
| 340 | C | ARG | 44 | 35.909 | −9.179 | 42.416 |
| 341 | O | ARG | 44 | 35.969 | −10.002 | 43.336 |
| 342 | CB | ARG | 44 | 37.154 | −10.355 | 40.576 |
| 343 | CG | ARG | 44 | 37.015 | −10.980 | 39.191 |
| 344 | CD | ARG | 44 | 38.342 | −11.515 | 38.670 |
| 345 | NE | ARG | 44 | 39.311 | −10.422 | 38.506 |
| 346 | CZ | ARG | 44 | 40.521 | −10.433 | 39.065 |
| 347 | NH1 | ARG | 44 | 40.899 | −11.467 | 39.818 |
| 348 | NH2 | ARG | 44 | 41.350 | −9.405 | 38.880 |
| 349 | N | ILE | 45 | 35.832 | −7.874 | 42.632 |
| 350 | CA | ILE | 45 | 35.831 | −7.348 | 44.005 |
| 351 | C | ILE | 45 | 34.434 | −6.910 | 44.466 |
| 352 | O | ILE | 45 | 34.110 | −6.995 | 45.658 |
| 353 | CB | ILE | 45 | 36.804 | −6.168 | 44.058 |
| 354 | CG1 | ILE | 45 | 38.222 | −6.625 | 43.740 |
| 355 | CG2 | ILE | 45 | 36.786 | −5.479 | 45.417 |
| 356 | CD1 | ILE | 45 | 39.187 | −5.447 | 43.706 |
| 357 | N | SER | 46 | 33.593 | −6.518 | 43.523 |
| 358 | CA | SER | 46 | 32.255 | −6.031 | 43.877 |
| 359 | C | SER | 46 | 31.144 | −6.949 | 43.389 |
| 360 | O | SER | 46 | 29.975 | −6.722 | 43.721 |
| 361 | CB | SER | 46 | 32.048 | −4.684 | 43.200 |
| 362 | OG | SER | 46 | 31.856 | −4.931 | 41.815 |
| 363 | N | SER | 47 | 31.501 | −7.832 | 42.467 |
| 364 | CA | SER | 47 | 30.579 | −8.761 | 41.796 |
| 365 | C | SER | 47 | 29.612 | −8.047 | 40.831 |
| 366 | O | SER | 47 | 28.627 | −8.645 | 40.383 |
| 367 | CB | SER | 47 | 29.830 | −9.571 | 42.856 |
| 368 | OG | SER | 47 | 29.130 | −10.633 | 42.222 |
| 369 | N | VAL | 48 | 29.908 | −6.808 | 40.459 |

TABLE 9-continued

| Atom No. | Atom Type | Residue | Residue Position | X Coord. | Y Coord. | Z Coord. |
|---|---|---|---|---|---|---|
| 370 | CA | VAL | 48 | 29.100 | −6.132 | 39.446 |
| 371 | C | VAL | 48 | 29.708 | −6.410 | 38.078 |
| 372 | O | VAL | 48 | 30.934 | −6.494 | 37.950 |
| 373 | CB | VAL | 48 | 29.101 | −4.635 | 39.760 |
| 374 | CG1 | VAL | 48 | 28.203 | −3.845 | 38.814 |
| 375 | CG2 | VAL | 48 | 28.665 | −4.392 | 41.199 |
| 376 | N | ASP | 49 | 28.848 | −6.684 | 37.109 |
| 377 | CA | ASP | 49 | 29.269 | −6.946 | 35.727 |
| 378 | C | ASP | 49 | 30.137 | −5.793 | 35.221 |
| 379 | O | ASP | 49 | 29.687 | −4.643 | 35.134 |
| 380 | CB | ASP | 49 | 27.993 | −7.073 | 34.889 |
| 381 | CG | ASP | 49 | 28.221 | −7.645 | 33.486 |
| 382 | OD1 | ASP | 49 | 29.348 | −7.594 | 33.013 |
| 383 | OD2 | ASP | 49 | 27.231 | −7.986 | 32.858 |
| 384 | N | LYS | 50 | 31.309 | −6.138 | 34.712 |
| 385 | CA | LYS | 50 | 32.262 | −5.119 | 34.267 |
| 386 | C | LYS | 50 | 31.901 | −4.475 | 32.930 |
| 387 | O | LYS | 50 | 32.336 | −3.345 | 32.679 |
| 388 | CB | LYS | 50 | 33.657 | −5.715 | 34.221 |
| 389 | CG | LYS | 50 | 33.780 | −6.952 | 33.348 |
| 390 | CD | LYS | 50 | 35.216 | −7.458 | 33.407 |
| 391 | CE | LYS | 50 | 35.399 | −8.764 | 32.647 |
| 392 | NZ | LYS | 50 | 36.789 | −9.238 | 32.770 |
| 393 | N | SER | 51 | 30.893 | −5.018 | 32.263 |
| 394 | CA | SER | 51 | 30.344 | −4.371 | 31.072 |
| 395 | C | SER | 51 | 29.557 | −3.105 | 31.415 |
| 396 | O | SER | 51 | 29.479 | −2.208 | 30.568 |
| 397 | CB | SER | 51 | 29.410 | −5.352 | 30.370 |
| 398 | OG | SER | 51 | 28.284 | −5.589 | 31.205 |
| 399 | N | ILE | 52 | 29.085 | −2.973 | 32.649 |
| 400 | CA | ILE | 52 | 28.427 | −1.733 | 33.060 |
| 401 | C | ILE | 52 | 29.351 | −0.910 | 33.957 |
| 402 | O | ILE | 52 | 29.221 | 0.319 | 34.004 |
| 403 | CB | ILE | 52 | 27.095 | −2.030 | 33.753 |
| 404 | CG1 | ILE | 52 | 27.269 | −2.789 | 35.063 |
| 405 | CG2 | ILE | 52 | 26.171 | −2.801 | 32.816 |
| 406 | CD1 | ILE | 52 | 25.925 | −3.057 | 35.729 |
| 407 | N | ILE | 53 | 30.425 | −1.534 | 34.424 |
| 408 | CA | ILE | 53 | 31.415 | −0.810 | 35.227 |
| 409 | C | ILE | 53 | 32.280 | 0.071 | 34.337 |
| 410 | O | ILE | 53 | 32.505 | 1.231 | 34.699 |
| 411 | CB | ILE | 53 | 32.290 | −1.800 | 35.988 |
| 412 | CG1 | ILE | 53 | 31.468 | −2.593 | 36.995 |
| 413 | CG2 | ILE | 53 | 33.436 | −1.084 | 36.694 |
| 414 | CD1 | ILE | 53 | 32.346 | −3.556 | 37.784 |
| 415 | N | ILE | 54 | 32.434 | −0.329 | 33.082 |
| 416 | CA | ILE | 54 | 33.139 | 0.518 | 32.112 |
| 417 | C | ILE | 54 | 32.318 | 1.750 | 31.717 |
| 418 | O | ILE | 54 | 32.896 | 2.837 | 31.599 |
| 419 | CB | ILE | 54 | 33.455 | −0.322 | 30.876 |
| 420 | CG1 | ILE | 54 | 34.442 | −1.424 | 31.229 |
| 421 | CG2 | ILE | 54 | 34.009 | 0.536 | 29.743 |
| 422 | CD1 | ILE | 54 | 34.778 | −2.300 | 30.029 |
| 423 | N | GLN | 55 | 31.003 | 1.663 | 31.860 |
| 424 | CA | GLN | 55 | 30.132 | 2.803 | 31.553 |
| 425 | C | GLN | 55 | 29.976 | 3.738 | 32.758 |
| 426 | O | GLN | 55 | 29.479 | 4.862 | 32.617 |
| 427 | CB | GLN | 55 | 28.764 | 2.269 | 31.144 |
| 428 | CG | GLN | 55 | 28.859 | 1.383 | 29.906 |
| 429 | CD | GLN | 55 | 27.482 | 0.828 | 29.549 |
| 430 | OE1 | GLN | 55 | 26.575 | 1.569 | 29.153 |
| 431 | NE2 | GLN | 55 | 27.357 | −0.481 | 29.672 |
| 432 | N | ALA | 56 | 30.449 | 3.295 | 33.912 |
| 433 | CA | ALA | 56 | 30.423 | 4.116 | 35.123 |
| 434 | C | ALA | 56 | 31.786 | 4.739 | 35.429 |
| 435 | O | ALA | 56 | 31.918 | 5.466 | 36.421 |
| 436 | CB | ALA | 56 | 29.974 | 3.247 | 36.291 |
| 437 | N | LEU | 57 | 32.781 | 4.470 | 34.595 |
| 438 | CA | LEU | 57 | 34.126 | 5.034 | 34.807 |
| 439 | C | LEU | 57 | 34.269 | 6.410 | 34.155 |
| 440 | O | LEU | 57 | 34.884 | 6.550 | 33.092 |
| 441 | CB | LEU | 57 | 35.160 | 4.085 | 34.209 |
| 442 | CG | LEU | 57 | 35.144 | 2.721 | 34.890 |
| 443 | CD1 | LEU | 57 | 36.098 | 1.749 | 34.207 |
| 444 | CD2 | LEU | 57 | 35.459 | 2.823 | 36.378 |
| 445 | N | ASP | 58 | 33.821 | 7.430 | 34.866 |

TABLE 9-continued

| Atom No. | Atom Type | Residue | Residue Position | X Coord. | Y Coord. | Z Coord. |
|---|---|---|---|---|---|---|
| 446 | CA | ASP | 58 | 33.799 | 8.789 | 34.322 |
| 447 | C | ASP | 58 | 35.045 | 9.585 | 34.710 |
| 448 | O | ASP | 58 | 35.354 | 9.753 | 35.894 |
| 449 | CB | ASP | 58 | 32.559 | 9.482 | 34.877 |
| 450 | CG | ASP | 58 | 32.347 | 10.831 | 34.198 |
| 451 | OD1 | ASP | 58 | 31.831 | 11.723 | 34.856 |
| 452 | OD2 | ASP | 58 | 32.581 | 10.896 | 32.998 |
| 453 | N | THR | 59 | 35.740 | 10.094 | 33.709 |
| 454 | CA | THR | 59 | 36.901 | 10.959 | 33.957 |
| 455 | C | THR | 59 | 36.456 | 12.280 | 34.590 |
| 456 | O | THR | 59 | 35.476 | 12.885 | 34.146 |
| 457 | CB | THR | 59 | 37.602 | 11.196 | 32.618 |
| 458 | OG1 | THR | 59 | 38.157 | 9.954 | 32.209 |
| 459 | CG2 | THR | 59 | 38.750 | 12.197 | 32.708 |
| 460 | N | PRO | 60 | 37.053 | 12.604 | 35.728 |
| 461 | CA | PRO | 60 | 36.763 | 13.858 | 36.425 |
| 462 | C | PRO | 60 | 37.243 | 15.075 | 35.643 |
| 463 | O | PRO | 60 | 37.980 | 14.970 | 34.656 |
| 464 | CB | PRO | 60 | 37.480 | 13.765 | 37.734 |
| 465 | CG | PRO | 60 | 38.337 | 12.513 | 37.739 |
| 466 | CD | PRO | 60 | 38.052 | 11.801 | 36.430 |
| 467 | N | LYS | 61 | 36.810 | 16.235 | 36.107 |
| 468 | CA | LYS | 61 | 37.212 | 17.499 | 35.483 |
| 469 | C | LYS | 61 | 38.518 | 18.017 | 36.087 |
| 470 | O | LYS | 61 | 39.216 | 18.843 | 35.490 |
| 471 | CB | LYS | 61 | 36.105 | 18.510 | 35.755 |
| 472 | CG | LYS | 61 | 34.742 | 17.952 | 35.360 |
| 473 | CD | LYS | 61 | 33.615 | 18.893 | 35.769 |
| 474 | CE | LYS | 61 | 32.250 | 18.301 | 35.437 |
| 475 | NZ | LYS | 61 | 31.167 | 19.201 | 35.864 |
| 476 | N | VAL | 62 | 38.837 | 17.513 | 37.268 |
| 477 | CA | VAL | 62 | 40.065 | 17.903 | 37.964 |
| 478 | C | VAL | 62 | 40.952 | 16.675 | 38.150 |
| 479 | O | VAL | 62 | 40.498 | 15.688 | 38.741 |
| 480 | CB | VAL | 62 | 39.662 | 18.465 | 39.331 |
| 481 | CG1 | VAL | 62 | 40.842 | 19.090 | 40.067 |
| 482 | CG2 | VAL | 62 | 38.545 | 19.495 | 39.202 |
| 483 | N | LEU | 63 | 42.241 | 16.814 | 37.868 |
| 484 | CA | LEU | 63 | 43.188 | 15.692 | 38.033 |
| 485 | C | LEU | 63 | 43.533 | 15.394 | 39.496 |
| 486 | O | LEU | 63 | 43.960 | 14.281 | 39.818 |
| 487 | CB | LEU | 63 | 44.474 | 15.999 | 37.276 |
| 488 | CG | LEU | 63 | 44.256 | 16.002 | 35.769 |
| 489 | CD1 | LEU | 63 | 45.543 | 16.372 | 35.042 |
| 490 | CD2 | LEU | 63 | 43.741 | 14.647 | 35.292 |
| 491 | N | ASP | 64 | 43.122 | 16.275 | 40.396 |
| 492 | CA | ASP | 64 | 43.245 | 16.024 | 41.838 |
| 493 | C | ASP | 64 | 42.113 | 15.127 | 42.350 |
| 494 | O | ASP | 64 | 42.071 | 14.802 | 43.539 |
| 495 | CB | ASP | 64 | 43.198 | 17.354 | 42.583 |
| 496 | CG | ASP | 64 | 44.337 | 18.261 | 42.129 |
| 497 | OD1 | ASP | 64 | 45.447 | 18.055 | 42.597 |
| 498 | OD2 | ASP | 64 | 44.098 | 19.071 | 41.243 |
| 499 | N | GLN | 65 | 41.183 | 14.802 | 41.464 |
| 500 | CA | GLN | 65 | 40.118 | 13.843 | 41.730 |
| 501 | C | GLN | 65 | 40.378 | 12.524 | 40.989 |
| 502 | O | GLN | 65 | 39.503 | 11.651 | 40.959 |
| 503 | CB | GLN | 65 | 38.804 | 14.460 | 41.255 |
| 504 | CG | GLN | 65 | 38.432 | 15.724 | 42.029 |
| 505 | CD | GLN | 65 | 37.924 | 15.373 | 43.426 |
| 506 | OE1 | GLN | 65 | 38.702 | 15.093 | 44.346 |
| 507 | NE2 | GLN | 65 | 36.611 | 15.353 | 43.564 |
| 508 | N | GLY | 66 | 41.515 | 12.422 | 40.318 |
| 509 | CA | GLY | 66 | 41.869 | 11.184 | 39.613 |
| 510 | C | GLY | 66 | 41.734 | 11.309 | 38.099 |
| 511 | O | GLY | 66 | 41.492 | 12.392 | 37.556 |
| 512 | N | ASP | 67 | 41.963 | 10.195 | 37.423 |
| 513 | CA | ASP | 67 | 41.751 | 10.130 | 35.974 |
| 514 | C | ASP | 67 | 40.432 | 9.438 | 35.685 |
| 515 | O | ASP | 67 | 39.778 | 9.706 | 34.670 |
| 516 | CB | ASP | 67 | 42.837 | 9.288 | 35.323 |
| 517 | CG | ASP | 67 | 44.217 | 9.901 | 35.483 |
| 518 | OD1 | ASP | 67 | 44.547 | 10.757 | 34.674 |
| 519 | OD2 | ASP | 67 | 44.975 | 9.369 | 36.287 |
| 520 | N | ILE | 68 | 40.067 | 8.533 | 36.577 |
| 521 | CA | ILE | 68 | 38.802 | 7.801 | 36.450 |

TABLE 9-continued

| Atom No. | Atom Type | Residue | Residue Position | X Coord. | Y Coord. | Z Coord. |
|---|---|---|---|---|---|---|
| 522 | C | ILE | 68 | 38.066 | 7.754 | 37.786 |
| 523 | O | ILE | 68 | 38.619 | 7.289 | 38.789 |
| 524 | CB | ILE | 68 | 39.107 | 6.380 | 35.966 |
| 525 | CG1 | ILE | 68 | 39.541 | 6.357 | 34.505 |
| 526 | CG2 | ILE | 68 | 37.909 | 5.462 | 36.157 |
| 527 | CD1 | ILE | 68 | 38.421 | 6.841 | 33.590 |
| 528 | N | ILE | 69 | 36.873 | 8.320 | 37.814 |
| 529 | CA | ILE | 69 | 36.003 | 8.230 | 38.987 |
| 530 | C | ILE | 69 | 34.761 | 7.392 | 38.697 |
| 531 | O | ILE | 69 | 34.004 | 7.676 | 37.761 |
| 532 | CB | ILE | 69 | 35.580 | 9.637 | 39.405 |
| 533 | CG1 | ILE | 69 | 36.701 | 10.359 | 40.130 |
| 534 | CG2 | ILE | 69 | 34.325 | 9.631 | 40.270 |
| 535 | CD1 | ILE | 69 | 36.206 | 11.695 | 40.675 |
| 536 | N | VAL | 70 | 34.586 | 6.328 | 39.460 |
| 537 | CA | VAL | 70 | 33.313 | 5.602 | 39.390 |
| 538 | C | VAL | 70 | 32.435 | 5.971 | 40.587 |
| 539 | O | VAL | 70 | 32.812 | 5.754 | 41.747 |
| 540 | CB | VAL | 70 | 33.542 | 4.093 | 39.293 |
| 541 | CG1 | VAL | 70 | 34.481 | 3.566 | 40.367 |
| 542 | CG2 | VAL | 70 | 32.226 | 3.321 | 39.309 |
| 543 | N | PRO | 71 | 31.382 | 6.721 | 40.299 |
| 544 | CA | PRO | 71 | 30.313 | 6.920 | 41.272 |
| 545 | C | PRO | 71 | 29.582 | 5.607 | 41.510 |
| 546 | O | PRO | 71 | 28.801 | 5.134 | 40.672 |
| 547 | CB | PRO | 71 | 29.414 | 7.951 | 40.666 |
| 548 | CG | PRO | 71 | 29.868 | 8.217 | 39.239 |
| 549 | CD | PRO | 71 | 31.061 | 7.309 | 38.999 |
| 550 | N | ILE | 72 | 29.728 | 5.112 | 42.724 |
| 551 | CA | ILE | 72 | 29.193 | 3.792 | 43.084 |
| 552 | C | ILE | 72 | 27.663 | 3.573 | 42.964 |
| 553 | O | ILE | 72 | 27.316 | 2.498 | 42.455 |
| 554 | CB | ILE | 72 | 29.677 | 3.481 | 44.492 |
| 555 | CG1 | ILE | 72 | 31.200 | 3.489 | 44.538 |
| 556 | CG2 | ILE | 72 | 29.157 | 2.127 | 44.936 |
| 557 | CD1 | ILE | 72 | 31.799 | 2.425 | 43.625 |
| 558 | N | PRO | 73 | 26.759 | 4.520 | 43.238 |
| 559 | CA | PRO | 73 | 25.334 | 4.238 | 42.984 |
| 560 | C | PRO | 73 | 24.924 | 4.087 | 41.508 |
| 561 | O | PRO | 73 | 23.825 | 3.574 | 41.274 |
| 562 | CB | PRO | 73 | 24.571 | 5.364 | 43.611 |
| 563 | CG | PRO | 73 | 25.544 | 6.421 | 44.094 |
| 564 | CD | PRO | 73 | 26.926 | 5.865 | 43.812 |
| 565 | N | LYS | 74 | 25.820 | 4.299 | 40.549 |
| 566 | CA | LYS | 74 | 25.496 | 4.027 | 39.141 |
| 567 | C | LYS | 74 | 25.577 | 2.536 | 38.803 |
| 568 | O | LYS | 74 | 25.163 | 2.125 | 37.714 |
| 569 | CB | LYS | 74 | 26.450 | 4.786 | 38.230 |
| 570 | CG | LYS | 74 | 26.208 | 6.288 | 38.281 |
| 571 | CD | LYS | 74 | 27.060 | 7.000 | 37.238 |
| 572 | CE | LYS | 74 | 26.780 | 8.498 | 37.214 |
| 573 | NZ | LYS | 74 | 27.630 | 9.172 | 36.220 |
| 574 | N | LEU | 75 | 26.037 | 1.733 | 39.752 |
| 575 | CA | LEU | 75 | 25.997 | 0.274 | 39.614 |
| 576 | C | LEU | 75 | 24.667 | −0.290 | 40.127 |
| 577 | O | LEU | 75 | 24.408 | −1.492 | 39.987 |
| 578 | CB | LEU | 75 | 27.150 | −0.313 | 40.423 |
| 579 | CG | LEU | 75 | 28.498 | 0.251 | 39.982 |
| 580 | CD1 | LEU | 75 | 29.612 | −0.197 | 40.922 |
| 581 | CD2 | LEU | 75 | 28.824 | −0.127 | 38.539 |
| 582 | N | ARG | 76 | 23.841 | 0.590 | 40.685 |
| 583 | CA | ARG | 76 | 22.501 | 0.267 | 41.196 |
| 584 | C | ARG | 76 | 22.492 | −0.912 | 42.158 |
| 585 | O | ARG | 76 | 21.882 | −1.955 | 41.897 |
| 586 | CB | ARG | 76 | 21.569 | 0.012 | 40.013 |
| 587 | CG | ARG | 76 | 21.382 | 1.240 | 39.113 |
| 588 | CD | ARG | 76 | 20.314 | 2.228 | 39.598 |
| 589 | NE | ARG | 76 | 20.706 | 2.983 | 40.802 |
| 590 | CZ | ARG | 76 | 19.836 | 3.607 | 41.598 |
| 591 | NH1 | ARG | 76 | 18.534 | 3.600 | 41.301 |
| 592 | NH2 | ARG | 76 | 20.271 | 4.253 | 42.682 |
| 593 | N | LEU | 77 | 23.137 | −0.713 | 43.294 |
| 594 | CA | LEU | 77 | 23.181 | −1.757 | 44.321 |
| 595 | C | LEU | 77 | 22.359 | −1.325 | 45.528 |
| 596 | O | LEU | 77 | 22.839 | −0.587 | 46.394 |
| 597 | CB | LEU | 77 | 24.629 | −1.991 | 44.733 |

TABLE 9-continued

| Atom No. | Atom Type | Residue | Residue Position | X Coord. | Y Coord. | Z Coord. |
|---|---|---|---|---|---|---|
| 598 | CG | LEU | 77 | 25.494 | −2.425 | 43.554 |
| 599 | CD1 | LEU | 77 | 26.967 | −2.439 | 43.941 |
| 600 | CD2 | LEU | 77 | 25.060 | −3.785 | 43.015 |
| 601 | N | LYS | 78 | 21.132 | −1.807 | 45.583 |
| 602 | CA | LYS | 78 | 20.202 | −1.392 | 46.643 |
| 603 | C | LYS | 78 | 20.625 | −1.885 | 48.026 |
| 604 | O | LYS | 78 | 21.265 | −2.934 | 48.170 |
| 605 | CB | LYS | 78 | 18.816 | −1.936 | 46.315 |
| 606 | CG | LYS | 78 | 18.322 | −1.418 | 44.970 |
| 607 | CD | LYS | 78 | 18.187 | 0.101 | 44.967 |
| 608 | CE | LYS | 78 | 17.811 | 0.603 | 43.580 |
| 609 | NZ | LYS | 78 | 18.813 | 0.169 | 42.594 |
| 610 | N | GLY | 79 | 20.371 | −1.048 | 49.019 |
| 611 | CA | GLY | 79 | 20.567 | −1.447 | 50.418 |
| 612 | C | GLY | 79 | 21.856 | −0.912 | 51.037 |
| 613 | O | GLY | 79 | 21.821 | −0.143 | 52.006 |
| 614 | N | ILE | 80 | 22.976 | −1.385 | 50.520 |
| 615 | CA | ILE | 80 | 24.290 | −1.029 | 51.074 |
| 616 | C | ILE | 80 | 24.609 | 0.442 | 50.779 |
| 617 | O | ILE | 80 | 24.143 | 1.003 | 49.781 |
| 618 | CB | ILE | 80 | 25.319 | −1.984 | 50.454 |
| 619 | CG1 | ILE | 80 | 24.879 | −3.435 | 50.635 |
| 620 | CG2 | ILE | 80 | 26.709 | −1.813 | 51.064 |
| 621 | CD1 | ILE | 80 | 24.910 | −3.854 | 52.104 |
| 622 | N | ASN | 81 | 25.256 | 1.098 | 51.728 |
| 623 | CA | ASN | 81 | 25.636 | 2.504 | 51.562 |
| 624 | C | ASN | 81 | 26.889 | 2.646 | 50.691 |
| 625 | O | ASN | 81 | 27.934 | 2.050 | 50.986 |
| 626 | CB | ASN | 81 | 25.863 | 3.067 | 52.965 |
| 627 | CG | ASN | 81 | 26.500 | 4.449 | 52.927 |
| 628 | OD1 | ASN | 81 | 27.733 | 4.570 | 52.888 |
| 629 | ND2 | ASN | 81 | 25.661 | 5.469 | 52.895 |
| 630 | N | PRO | 82 | 26.820 | 3.541 | 49.711 |
| 631 | CA | PRO | 82 | 27.879 | 3.670 | 48.693 |
| 632 | C | PRO | 82 | 29.237 | 4.179 | 49.197 |
| 633 | O | PRO | 82 | 30.252 | 3.757 | 48.632 |
| 634 | CB | PRO | 82 | 27.324 | 4.612 | 47.669 |
| 635 | CG | PRO | 82 | 25.957 | 5.102 | 48.115 |
| 636 | CD | PRO | 82 | 25.661 | 4.390 | 49.423 |
| 637 | N | ASN | 83 | 29.287 | 4.791 | 50.373 |
| 638 | CA | ASN | 83 | 30.567 | 5.256 | 50.917 |
| 639 | C | ASN | 83 | 31.310 | 4.089 | 51.557 |
| 640 | O | ASN | 83 | 32.536 | 3.971 | 51.425 |
| 641 | CB | ASN | 83 | 30.318 | 6.296 | 52.003 |
| 642 | CG | ASN | 83 | 29.369 | 7.405 | 51.558 |
| 643 | OD1 | ASN | 83 | 29.424 | 7.911 | 50.431 |
| 644 | ND2 | ASN | 83 | 28.534 | 7.817 | 52.496 |
| 645 | N | GLU | 84 | 30.537 | 3.116 | 52.013 |
| 646 | CA | GLU | 84 | 31.110 | 1.903 | 52.592 |
| 647 | C | GLU | 84 | 31.636 | 1.015 | 51.480 |
| 648 | O | GLU | 84 | 32.778 | 0.547 | 51.567 |
| 649 | CB | GLU | 84 | 30.018 | 1.152 | 53.341 |
| 650 | CG | GLU | 84 | 29.419 | 1.988 | 54.462 |
| 651 | CD | GLU | 84 | 28.213 | 1.261 | 55.048 |
| 652 | OE1 | GLU | 84 | 27.460 | 0.695 | 54.263 |
| 653 | OE2 | GLU | 84 | 27.974 | 1.421 | 56.236 |
| 654 | N | LYS | 85 | 30.944 | 1.042 | 50.351 |
| 655 | CA | LYS | 85 | 31.376 | 0.277 | 49.182 |
| 656 | C | LYS | 85 | 32.652 | 0.864 | 48.594 |
| 657 | O | LYS | 85 | 33.624 | 0.124 | 48.405 |
| 658 | CB | LYS | 85 | 30.309 | 0.376 | 48.108 |
| 659 | CG | LYS | 85 | 28.922 | −0.041 | 48.566 |
| 660 | CD | LYS | 85 | 27.961 | 0.239 | 47.422 |
| 661 | CE | LYS | 85 | 26.498 | 0.137 | 47.804 |
| 662 | NZ | LYS | 85 | 25.670 | 0.767 | 46.766 |
| 663 | N | SER | 86 | 32.730 | 2.186 | 48.546 |
| 664 | CA | SER | 86 | 33.920 | 2.849 | 48.005 |
| 665 | C | SER | 86 | 35.140 | 2.607 | 48.882 |
| 666 | O | SER | 86 | 36.171 | 2.146 | 48.373 |
| 667 | CB | SER | 86 | 33.678 | 4.351 | 47.934 |
| 668 | OG | SER | 86 | 32.581 | 4.607 | 47.069 |
| 669 | N | LYS | 87 | 34.942 | 2.653 | 50.188 |
| 670 | CA | LYS | 87 | 36.041 | 2.416 | 51.125 |
| 671 | C | LYS | 87 | 36.555 | 0.978 | 51.063 |
| 672 | O | LYS | 87 | 37.755 | 0.774 | 50.834 |
| 673 | CB | LYS | 87 | 35.515 | 2.716 | 52.522 |

TABLE 9-continued

| Atom No. | Atom Type | Residue | Residue Position | X Coord. | Y Coord. | Z Coord. |
|---|---|---|---|---|---|---|
| 674 | CG | LYS | 87 | 36.553 | 2.437 | 53.603 |
| 675 | CD | LYS | 87 | 35.965 | 2.680 | 54.987 |
| 676 | CE | LYS | 87 | 34.760 | 1.783 | 55.247 |
| 677 | NZ | LYS | 87 | 35.140 | 0.361 | 55.232 |
| 678 | N | GLU | 88 | 35.639 | 0.029 | 50.957 |
| 679 | CA | GLU | 88 | 36.024 | −1.385 | 50.931 |
| 680 | C | GLU | 88 | 36.639 | −1.796 | 49.600 |
| 681 | O | GLU | 88 | 37.678 | −2.471 | 49.594 |
| 682 | CB | GLU | 88 | 34.767 | −2.213 | 51.161 |
| 683 | CG | GLU | 88 | 34.185 | −1.949 | 52.542 |
| 684 | CD | GLU | 88 | 32.733 | −2.412 | 52.598 |
| 685 | OE1 | GLU | 88 | 32.102 | −2.440 | 51.550 |
| 686 | OE2 | GLU | 88 | 32.246 | −2.618 | 53.701 |
| 687 | N | TRP | 89 | 36.154 | −1.224 | 48.513 |
| 688 | CA | TRP | 89 | 36.650 | −1.640 | 47.204 |
| 689 | C | TRP | 89 | 37.934 | −0.923 | 46.818 |
| 690 | O | TRP | 89 | 38.793 | −1.566 | 46.210 |
| 691 | CB | TRP | 89 | 35.575 | −1.416 | 46.148 |
| 692 | CG | TRP | 89 | 34.339 | −2.279 | 46.349 |
| 693 | CD1 | TRP | 89 | 34.272 | −3.485 | 47.003 |
| 694 | CD2 | TRP | 89 | 33.008 | −1.997 | 45.875 |
| 695 | NE1 | TRP | 89 | 32.994 | −3.923 | 46.975 |
| 696 | CE2 | TRP | 89 | 32.198 | −3.059 | 46.319 |
| 697 | CE3 | TRP | 89 | 32.454 | −0.953 | 45.145 |
| 698 | CZ2 | TRP | 89 | 30.837 | −3.050 | 46.045 |
| 699 | CZ3 | TRP | 89 | 31.095 | −0.964 | 44.863 |
| 700 | CH2 | TRP | 89 | 30.290 | −2.002 | 45.312 |
| 701 | N | ALA | 90 | 38.189 | 0.248 | 47.380 |
| 702 | CA | ALA | 90 | 39.470 | 0.912 | 47.113 |
| 703 | C | ALA | 90 | 40.571 | 0.349 | 48.000 |
| 704 | O | ALA | 90 | 41.684 | 0.114 | 47.516 |
| 705 | CB | ALA | 90 | 39.336 | 2.403 | 47.379 |
| 706 | N | GLU | 91 | 40.165 | −0.159 | 49.153 |
| 707 | CA | GLU | 91 | 41.100 | −0.780 | 50.098 |
| 708 | C | GLU | 91 | 41.574 | −2.157 | 49.633 |
| 709 | O | GLU | 91 | 42.681 | −2.585 | 49.977 |
| 710 | CB | GLU | 91 | 40.333 | −0.940 | 51.407 |
| 711 | CG | GLU | 91 | 41.105 | −1.703 | 52.475 |
| 712 | CD | GLU | 91 | 40.160 | −2.016 | 53.628 |
| 713 | OE1 | GLU | 91 | 40.144 | −1.245 | 54.577 |
| 714 | OE2 | GLU | 91 | 39.363 | −2.933 | 53.467 |
| 715 | N | ASN | 92 | 40.778 | −2.800 | 48.796 |
| 716 | CA | ASN | 92 | 41.121 | −4.132 | 48.299 |
| 717 | C | ASN | 92 | 41.426 | −4.120 | 46.801 |
| 718 | O | ASN | 92 | 41.624 | −5.184 | 46.199 |
| 719 | CB | ASN | 92 | 39.964 | −5.086 | 48.607 |
| 720 | CG | ASN | 92 | 39.899 | −5.408 | 50.105 |
| 721 | OD1 | ASN | 92 | 40.686 | −6.217 | 50.608 |
| 722 | ND2 | ASN | 92 | 38.969 | −4.775 | 50.803 |
| 723 | N | PHE | 93 | 41.478 | −2.937 | 46.211 |
| 724 | CA | PHE | 93 | 41.672 | −2.843 | 44.763 |
| 725 | C | PHE | 93 | 43.145 | −2.979 | 44.404 |
| 726 | O | PHE | 93 | 44.001 | −2.234 | 44.892 |
| 727 | CB | PHE | 93 | 41.151 | −1.496 | 44.281 |
| 728 | CG | PHE | 93 | 40.575 | −1.501 | 42.866 |
| 729 | CD1 | PHE | 93 | 41.414 | −1.494 | 41.759 |
| 730 | CD2 | PHE | 93 | 39.198 | −1.518 | 42.690 |
| 731 | CE1 | PHE | 93 | 40.879 | −1.486 | 40.479 |
| 732 | CE2 | PHE | 93 | 38.662 | −1.514 | 41.410 |
| 733 | CZ | PHE | 93 | 39.501 | −1.495 | 40.305 |
| 734 | N | ASN | 94 | 43.422 | −3.958 | 43.562 |
| 735 | CA | ASN | 94 | 44.782 | −4.165 | 43.066 |
| 736 | C | ASN | 94 | 45.188 | −3.024 | 42.137 |
| 737 | O | ASN | 94 | 44.486 | −2.693 | 41.173 |
| 738 | CB | ASN | 94 | 44.818 | −5.499 | 42.330 |
| 739 | CG | ASN | 94 | 46.223 | −5.806 | 41.822 |
| 740 | OD1 | ASN | 94 | 47.225 | −5.447 | 42.455 |
| 741 | ND2 | ASN | 94 | 46.273 | −6.341 | 40.616 |
| 742 | N | LYS | 95 | 46.333 | −2.438 | 42.446 |
| 743 | CA | LYS | 95 | 46.858 | −1.315 | 41.666 |
| 744 | C | LYS | 95 | 47.678 | −1.868 | 40.506 |
| 745 | O | LYS | 95 | 47.622 | −1.373 | 39.365 |
| 746 | CB | LYS | 95 | 47.820 | −0.522 | 42.552 |
| 747 | CG | LYS | 95 | 47.409 | −0.442 | 44.020 |
| 748 | CD | LYS | 95 | 46.233 | 0.486 | 44.304 |
| 749 | CE | LYS | 95 | 45.920 | 0.456 | 45.798 |
| 750 | NZ | LYS | 95 | 44.783 | 1.320 | 46.143 |
| 751 | N | GLY | 96 | 48.280 | −3.015 | 40.783 |
| 752 | CA | GLY | 96 | 49.169 | −3.685 | 39.835 |
| 753 | C | GLY | 96 | 50.327 | −2.774 | 39.458 |
| 754 | O | GLY | 96 | 51.161 | −2.395 | 40.286 |
| 755 | N | LYS | 97 | 50.345 | −2.432 | 38.185 |
| 756 | CA | LYS | 97 | 51.343 | −1.519 | 37.636 |
| 757 | C | LYS | 97 | 50.662 | −0.500 | 36.734 |
| 758 | O | LYS | 97 | 51.319 | 0.205 | 35.960 |
| 759 | CB | LYS | 97 | 52.393 | −2.317 | 36.863 |
| 760 | CG | LYS | 97 | 51.767 | −3.397 | 35.982 |
| 761 | CD | LYS | 97 | 52.059 | −4.795 | 36.526 |
| 762 | CE | LYS | 97 | 51.300 | −5.870 | 35.763 |
| 763 | NZ | LYS | 97 | 51.637 | −7.205 | 36.277 |
| 764 | N | PHE | 98 | 49.341 | −0.457 | 36.814 |
| 765 | CA | PHE | 98 | 48.579 | 0.419 | 35.925 |
| 766 | C | PHE | 98 | 47.944 | 1.560 | 36.700 |
| 767 | O | PHE | 98 | 47.703 | 2.641 | 36.147 |
| 768 | CB | PHE | 98 | 47.504 | −0.407 | 35.227 |
| 769 | CG | PHE | 98 | 48.067 | −1.503 | 34.329 |
| 770 | CD1 | PHE | 98 | 48.028 | −2.831 | 34.735 |
| 771 | CD2 | PHE | 98 | 48.615 | −1.170 | 33.097 |
| 772 | CE1 | PHE | 98 | 48.548 | −3.822 | 33.915 |
| 773 | CE2 | PHE | 98 | 49.133 | −2.162 | 32.276 |
| 774 | CZ | PHE | 98 | 49.101 | −3.489 | 32.686 |
| 775 | N | ILE | 99 | 47.692 | 1.322 | 37.974 |
| 776 | CA | ILE | 99 | 47.181 | 2.383 | 38.843 |
| 777 | C | ILE | 99 | 48.199 | 2.614 | 39.958 |
| 778 | O | ILE | 99 | 48.731 | 1.652 | 40.521 |
| 779 | CB | ILE | 99 | 45.830 | 1.953 | 39.416 |
| 780 | CG1 | ILE | 99 | 44.863 | 1.506 | 38.323 |
| 781 | CG2 | ILE | 99 | 45.193 | 3.100 | 40.186 |
| 782 | CD1 | ILE | 99 | 44.415 | 2.676 | 37.449 |
| 783 | N | SER | 100 | 48.504 | 3.871 | 40.232 |
| 784 | CA | SER | 100 | 49.491 | 4.189 | 41.266 |
| 785 | C | SER | 100 | 48.824 | 4.439 | 42.617 |
| 786 | O | SER | 100 | 49.440 | 4.200 | 43.662 |
| 787 | CB | SER | 100 | 50.283 | 5.424 | 40.841 |
| 788 | OG | SER | 100 | 49.393 | 6.528 | 40.736 |
| 789 | N | GLU | 101 | 47.565 | 4.850 | 42.597 |
| 790 | CA | GLU | 101 | 46.825 | 5.064 | 43.853 |
| 791 | C | GLU | 101 | 45.322 | 5.198 | 43.619 |
| 792 | O | GLU | 101 | 44.872 | 5.760 | 42.612 |
| 793 | CB | GLU | 101 | 47.355 | 6.302 | 44.574 |
| 794 | CG | GLU | 101 | 47.332 | 7.535 | 43.683 |
| 795 | CD | GLU | 101 | 47.769 | 8.772 | 44.457 |
| 796 | OE1 | GLU | 101 | 46.909 | 9.382 | 45.077 |
| 797 | OE2 | GLU | 101 | 48.942 | 9.108 | 44.381 |
| 798 | N | ILE | 102 | 44.564 | 4.632 | 44.543 |
| 799 | CA | ILE | 102 | 43.095 | 4.669 | 44.479 |
| 800 | C | ILE | 102 | 42.504 | 5.124 | 45.808 |
| 801 | O | ILE | 102 | 42.574 | 4.403 | 46.810 |
| 802 | CB | ILE | 102 | 42.588 | 3.265 | 44.177 |
| 803 | CG1 | ILE | 102 | 43.206 | 2.754 | 42.889 |
| 804 | CG2 | ILE | 102 | 41.066 | 3.244 | 44.080 |
| 805 | CD1 | ILE | 102 | 42.947 | 1.275 | 42.679 |
| 806 | N | LYS | 103 | 41.904 | 6.300 | 45.813 |
| 807 | CA | LYS | 103 | 41.301 | 6.785 | 47.058 |
| 808 | C | LYS | 103 | 39.775 | 6.819 | 46.993 |
| 809 | O | LYS | 103 | 39.168 | 7.137 | 45.960 |
| 810 | CB | LYS | 103 | 41.872 | 8.155 | 47.406 |
| 811 | CG | LYS | 103 | 41.651 | 9.174 | 46.300 |
| 812 | CD | LYS | 103 | 42.254 | 10.519 | 46.687 |
| 813 | CE | LYS | 103 | 43.750 | 10.388 | 46.950 |
| 814 | NZ | LYS | 103 | 44.342 | 11.688 | 47.303 |
| 815 | N | PRO | 104 | 39.172 | 6.307 | 48.052 |
| 816 | CA | PRO | 104 | 37.730 | 6.441 | 48.245 |
| 817 | C | PRO | 104 | 37.350 | 7.845 | 48.707 |
| 818 | O | PRO | 104 | 37.620 | 8.230 | 49.851 |
| 819 | CB | PRO | 104 | 37.409 | 5.448 | 49.317 |
| 820 | CG | PRO | 104 | 38.704 | 4.996 | 49.978 |
| 821 | CD | PRO | 104 | 39.824 | 5.649 | 49.186 |
| 822 | N | GLN | 105 | 36.634 | 8.564 | 47.864 |
| 823 | CA | GLN | 105 | 36.124 | 9.878 | 48.263 |
| 824 | C | GLN | 105 | 34.606 | 9.801 | 48.391 |
| 825 | O | GLN | 105 | 33.851 | 10.282 | 47.533 |

TABLE 9-continued

| Atom No. | Atom Type | Residue | Residue Position | X Coord. | Y Coord. | Z Coord. |
|---|---|---|---|---|---|---|
| 826 | CB | GLN | 105 | 36.538 | 10.950 | 47.258 |
| 827 | CG | GLN | 105 | 36.223 | 12.350 | 47.790 |
| 828 | CD | GLN | 105 | 36.660 | 13.426 | 46.798 |
| 829 | OE1 | GLN | 105 | 35.887 | 13.832 | 45.919 |
| 830 | NE2 | GLN | 105 | 37.902 | 13.862 | 46.934 |
| 831 | N | GLY | 106 | 34.180 | 9.123 | 49.445 |
| 832 | CA | GLY | 106 | 32.752 | 8.958 | 49.749 |
| 833 | C | GLY | 106 | 32.046 | 8.033 | 48.763 |
| 834 | O | GLY | 106 | 32.164 | 6.809 | 48.831 |
| 835 | N | VAL | 107 | 31.355 | 8.651 | 47.821 |
| 836 | CA | VAL | 107 | 30.597 | 7.937 | 46.791 |
| 837 | C | VAL | 107 | 31.461 | 7.634 | 45.561 |
| 838 | O | VAL | 107 | 31.132 | 6.754 | 44.752 |
| 839 | CB | VAL | 107 | 29.446 | 8.874 | 46.416 |
| 840 | CG1 | VAL | 107 | 28.726 | 8.485 | 45.132 |
| 841 | CG2 | VAL | 107 | 28.455 | 9.032 | 47.563 |
| 842 | N | PHE | 108 | 32.600 | 8.301 | 45.475 |
| 843 | CA | PHE | 108 | 33.447 | 8.186 | 44.284 |
| 844 | C | PHE | 108 | 34.723 | 7.389 | 44.524 |
| 845 | O | PHE | 108 | 35.465 | 7.652 | 45.476 |
| 846 | CB | PHE | 108 | 33.849 | 9.597 | 43.870 |
| 847 | CG | PHE | 108 | 32.684 | 10.555 | 43.649 |
| 848 | CD1 | PHE | 108 | 32.605 | 11.725 | 44.392 |
| 849 | CD2 | PHE | 108 | 31.706 | 10.262 | 42.707 |
| 850 | CE1 | PHE | 108 | 31.545 | 12.601 | 44.196 |
| 851 | CE2 | PHE | 108 | 30.647 | 11.138 | 42.512 |
| 852 | CZ | PHE | 108 | 30.566 | 12.307 | 43.256 |
| 853 | N | LEU | 109 | 34.987 | 6.436 | 43.649 |
| 854 | CA | LEU | 109 | 36.306 | 5.789 | 43.648 |
| 855 | C | LEU | 109 | 37.226 | 6.472 | 42.647 |
| 856 | O | LEU | 109 | 36.928 | 6.511 | 41.446 |
| 857 | CB | LEU | 109 | 36.176 | 4.314 | 43.304 |
| 858 | CG | LEU | 109 | 35.660 | 3.532 | 44.498 |
| 859 | CD1 | LEU | 109 | 35.553 | 2.046 | 44.173 |
| 860 | CD2 | LEU | 109 | 36.599 | 3.755 | 45.673 |
| 861 | N | GLN | 110 | 38.315 | 7.025 | 43.156 |
| 862 | CA | GLN | 110 | 39.251 | 7.782 | 42.317 |
| 863 | C | GLN | 110 | 40.512 | 6.999 | 41.979 |
| 864 | O | GLN | 110 | 41.355 | 6.714 | 42.840 |
| 865 | CB | GLN | 110 | 39.641 | 9.041 | 43.065 |
| 866 | CG | GLN | 110 | 38.397 | 9.763 | 43.548 |
| 867 | CD | GLN | 110 | 38.784 | 11.130 | 44.080 |
| 868 | OE1 | GLN | 110 | 39.901 | 11.344 | 44.564 |
| 869 | NE2 | GLN | 110 | 37.845 | 12.047 | 43.965 |
| 870 | N | PHE | 111 | 40.650 | 6.733 | 40.694 |
| 871 | CA | PHE | 111 | 41.792 | 5.987 | 40.159 |
| 872 | C | PHE | 111 | 42.805 | 6.910 | 39.487 |
| 873 | O | PHE | 111 | 42.501 | 7.598 | 38.499 |
| 874 | CB | PHE | 111 | 41.268 | 4.985 | 39.134 |
| 875 | CG | PHE | 111 | 40.209 | 4.028 | 39.678 |
| 876 | CD1 | PHE | 111 | 40.594 | 2.939 | 40.447 |
| 877 | CD2 | PHE | 111 | 38.864 | 4.237 | 39.402 |
| 878 | CE1 | PHE | 111 | 39.635 | 2.071 | 40.953 |
| 879 | CE2 | PHE | 111 | 37.906 | 3.371 | 39.908 |
| 880 | CZ | PHE | 111 | 38.291 | 2.288 | 40.687 |
| 881 | N | TYR | 112 | 43.990 | 6.950 | 40.071 |
| 882 | CA | TYR | 112 | 45.111 | 7.723 | 39.521 |
| 883 | C | TYR | 112 | 46.079 | 6.768 | 38.836 |
| 884 | O | TYR | 112 | 46.685 | 5.915 | 39.501 |
| 885 | CB | TYR | 112 | 45.852 | 8.434 | 40.653 |
| 886 | CG | TYR | 112 | 45.050 | 9.431 | 41.493 |
| 887 | CD1 | TYR | 112 | 45.204 | 10.794 | 41.279 |
| 888 | CD2 | TYR | 112 | 44.212 | 8.980 | 42.507 |
| 889 | CE1 | TYR | 112 | 44.486 | 11.704 | 42.043 |
| 890 | CE2 | TYR | 112 | 43.487 | 9.887 | 43.265 |
| 891 | CZ | TYR | 112 | 43.620 | 11.245 | 43.027 |
| 892 | OH | TYR | 112 | 42.810 | 12.128 | 43.704 |
| 893 | N | PHE | 113 | 46.299 | 6.990 | 37.552 |
| 894 | CA | PHE | 113 | 47.091 | 6.060 | 36.734 |
| 895 | C | PHE | 113 | 48.562 | 6.061 | 37.133 |
| 896 | O | PHE | 113 | 49.010 | 6.899 | 37.926 |
| 897 | CB | PHE | 113 | 46.989 | 6.434 | 35.257 |
| 898 | CG | PHE | 113 | 45.602 | 6.363 | 34.614 |
| 899 | CD1 | PHE | 113 | 44.598 | 5.569 | 35.155 |
| 900 | CD2 | PHE | 113 | 45.356 | 7.097 | 33.460 |
| 901 | CE1 | PHE | 113 | 43.346 | 5.526 | 34.555 |
| 902 | CE2 | PHE | 113 | 44.107 | 7.049 | 32.856 |
| 903 | CZ | PHE | 113 | 43.100 | 6.265 | 33.405 |
| 904 | N | ALA | 114 | 49.249 | 5.006 | 36.737 |
| 905 | CA | ALA | 114 | 50.687 | 4.923 | 36.984 |
| 906 | C | ALA | 114 | 51.422 | 5.824 | 36.005 |
| 907 | O | ALA | 114 | 51.470 | 5.556 | 34.798 |
| 908 | CB | ALA | 114 | 51.150 | 3.481 | 36.827 |
| 909 | N | LYS | 115 | 52.150 | 6.773 | 36.565 |
| 910 | CA | LYS | 115 | 52.830 | 7.790 | 35.757 |
| 911 | C | LYS | 115 | 53.955 | 7.221 | 34.896 |
| 912 | O | LYS | 115 | 54.017 | 7.567 | 33.713 |
| 913 | CB | LYS | 115 | 53.406 | 8.842 | 36.698 |
| 914 | CG | LYS | 115 | 52.321 | 9.510 | 37.537 |
| 915 | CD | LYS | 115 | 52.583 | 9.303 | 39.026 |
| 916 | CE | LYS | 115 | 53.984 | 9.771 | 39.409 |
| 917 | NZ | LYS | 115 | 54.251 | 9.512 | 40.832 |
| 918 | N | THR | 116 | 54.613 | 6.166 | 35.352 |
| 919 | CA | THR | 116 | 55.696 | 5.577 | 34.549 |
| 920 | C | THR | 116 | 55.166 | 4.681 | 33.428 |
| 921 | O | THR | 116 | 55.728 | 4.709 | 32.325 |
| 922 | CB | THR | 116 | 56.629 | 4.799 | 35.470 |
| 923 | OG1 | THR | 116 | 57.219 | 5.733 | 36.365 |
| 924 | CG2 | THR | 116 | 57.758 | 4.124 | 34.697 |
| 925 | N | LEU | 117 | 53.929 | 4.233 | 33.580 |
| 926 | CA | LEU | 117 | 53.295 | 3.412 | 32.550 |
| 927 | C | LEU | 117 | 52.773 | 4.341 | 31.455 |
| 928 | O | LEU | 117 | 52.902 | 4.028 | 30.263 |
| 929 | CB | LEU | 117 | 52.157 | 2.637 | 33.221 |
| 930 | CG | LEU | 117 | 51.679 | 1.411 | 32.442 |
| 931 | CD1 | LEU | 117 | 50.737 | 1.748 | 31.290 |
| 932 | CD2 | LEU | 117 | 52.849 | 0.547 | 31.983 |
| 933 | N | LEU | 118 | 52.466 | 5.567 | 31.853 |
| 934 | CA | LEU | 118 | 52.061 | 6.599 | 30.900 |
| 935 | C | LEU | 118 | 53.264 | 7.172 | 30.163 |
| 936 | O | LEU | 118 | 53.178 | 7.383 | 28.949 |
| 937 | CB | LEU | 118 | 51.376 | 7.730 | 31.659 |
| 938 | CG | LEU | 118 | 50.064 | 7.286 | 32.290 |
| 939 | CD1 | LEU | 118 | 49.518 | 8.369 | 33.210 |
| 940 | CD2 | LEU | 118 | 49.044 | 6.921 | 31.218 |
| 941 | N | TYR | 119 | 54.414 | 7.220 | 30.811 |
| 942 | CA | TYR | 119 | 55.608 | 7.728 | 30.128 |
| 943 | C | TYR | 119 | 56.072 | 6.716 | 29.091 |
| 944 | O | TYR | 119 | 56.220 | 7.063 | 27.912 |
| 945 | CB | TYR | 119 | 56.740 | 7.944 | 31.124 |
| 946 | CG | TYR | 119 | 56.465 | 8.870 | 32.302 |
| 947 | CD1 | TYR | 119 | 55.725 | 10.036 | 32.145 |
| 948 | CD2 | TYR | 119 | 57.002 | 8.552 | 33.541 |
| 949 | CE1 | TYR | 119 | 55.478 | 10.851 | 33.240 |
| 950 | CE2 | TYR | 119 | 56.756 | 9.365 | 34.639 |
| 951 | CZ | TYR | 119 | 55.983 | 10.506 | 34.485 |
| 952 | OH | TYR | 119 | 55.665 | 11.259 | 35.591 |
| 953 | N | ASN | 120 | 56.075 | 5.453 | 29.483 |
| 954 | CA | ASN | 120 | 56.421 | 4.376 | 28.557 |
| 955 | C | ASN | 120 | 55.479 | 4.313 | 27.366 |
| 956 | O | ASN | 120 | 55.837 | 4.766 | 26.268 |
| 957 | CB | ASN | 120 | 56.346 | 3.052 | 29.304 |
| 958 | CG | ASN | 120 | 57.717 | 2.675 | 29.851 |
| 959 | OD1 | ASN | 120 | 57.985 | 2.760 | 31.057 |
| 960 | ND2 | ASN | 120 | 58.589 | 2.298 | 28.933 |
| 961 | N | LEU | 121 | 54.230 | 3.982 | 27.639 |
| 962 | CA | LEU | 121 | 53.280 | 3.703 | 26.559 |
| 963 | C | LEU | 121 | 52.951 | 4.940 | 25.736 |
| 964 | O | LEU | 121 | 53.222 | 4.948 | 24.528 |
| 965 | CB | LEU | 121 | 51.984 | 3.143 | 27.145 |
| 966 | CG | LEU | 121 | 51.874 | 1.618 | 27.057 |
| 967 | CD1 | LEU | 121 | 52.932 | 0.893 | 27.883 |
| 968 | CD2 | LEU | 121 | 50.483 | 1.161 | 27.484 |
| 969 | N | VAL | 122 | 52.661 | 6.041 | 26.403 |
| 970 | CA | VAL | 122 | 52.158 | 7.202 | 25.676 |
| 971 | C | VAL | 122 | 53.262 | 8.004 | 25.002 |
| 972 | O | VAL | 122 | 53.082 | 8.316 | 23.821 |
| 973 | CB | VAL | 122 | 51.364 | 8.083 | 26.632 |
| 974 | CG1 | VAL | 122 | 50.845 | 9.338 | 25.941 |
| 975 | CG2 | VAL | 122 | 50.216 | 7.292 | 27.246 |
| 976 | N | ILE | 123 | 54.461 | 8.065 | 25.561 |
| 977 | CA | ILE | 123 | 55.484 | 8.878 | 24.890 |

TABLE 9-continued

| Atom No. | Atom Type | Residue | Residue Position | X Coord. | Y Coord. | Z Coord. |
|---|---|---|---|---|---|---|
| 978 | C | ILE | 123 | 56.129 | 8.120 | 23.732 |
| 979 | O | ILE | 123 | 56.302 | 8.714 | 22.659 |
| 980 | CB | ILE | 123 | 56.537 | 9.342 | 25.889 |
| 981 | CG1 | ILE | 123 | 55.902 | 10.216 | 26.966 |
| 982 | CG2 | ILE | 123 | 57.654 | 10.103 | 25.185 |
| 983 | CD1 | ILE | 123 | 56.945 | 10.715 | 27.959 |
| 984 | N | GLU | 124 | 56.146 | 6.799 | 23.820 |
| 985 | CA | GLU | 124 | 56.640 | 6.012 | 22.687 |
| 986 | C | GLU | 124 | 55.595 | 5.965 | 21.574 |
| 987 | O | GLU | 124 | 55.938 | 6.181 | 20.406 |
| 988 | CB | GLU | 124 | 56.935 | 4.594 | 23.160 |
| 989 | CG | GLU | 124 | 58.051 | 4.559 | 24.197 |
| 990 | CD | GLU | 124 | 58.126 | 3.165 | 24.813 |
| 991 | OE1 | GLU | 124 | 57.785 | 2.219 | 24.117 |
| 992 | OE2 | GLU | 124 | 58.401 | 3.071 | 26.006 |
| 993 | N | ASP | 125 | 54.331 | 6.005 | 21.965 |
| 994 | CA | ASP | 125 | 53.239 | 5.947 | 20.995 |
| 995 | C | ASP | 125 | 53.047 | 7.280 | 20.273 |
| 996 | O | ASP | 125 | 52.986 | 7.287 | 19.036 |
| 997 | CB | ASP | 125 | 51.971 | 5.590 | 21.759 |
| 998 | CG | ASP | 125 | 50.910 | 5.061 | 20.808 |
| 999 | OD1 | ASP | 125 | 51.281 | 4.306 | 19.921 |
| 1000 | OD2 | ASP | 125 | 49.741 | 5.313 | 21.061 |
| 1001 | N | VAL | 126 | 53.240 | 8.383 | 20.981 |
| 1002 | CA | VAL | 126 | 53.104 | 9.705 | 20.357 |
| 1003 | C | VAL | 126 | 54.297 | 10.021 | 19.467 |
| 1004 | O | VAL | 126 | 54.108 | 10.525 | 18.356 |
| 1005 | CB | VAL | 126 | 53.015 | 10.780 | 21.441 |
| 1006 | CG1 | VAL | 126 | 53.015 | 12.178 | 20.837 |
| 1007 | CG2 | VAL | 126 | 51.790 | 10.605 | 22.325 |
| 1008 | N | LEU | 127 | 55.457 | 9.494 | 19.817 |
| 1009 | CA | LEU | 127 | 56.657 | 9.769 | 19.022 |
| 1010 | C | LEU | 127 | 56.813 | 8.816 | 17.837 |
| 1011 | O | LEU | 127 | 57.680 | 9.043 | 16.986 |
| 1012 | CB | LEU | 127 | 57.893 | 9.679 | 19.916 |
| 1013 | CG | LEU | 127 | 58.371 | 11.028 | 20.462 |
| 1014 | CD1 | LEU | 127 | 57.360 | 11.706 | 21.379 |
| 1015 | CD2 | LEU | 127 | 59.688 | 10.859 | 21.205 |
| 1016 | N | LYS | 128 | 55.986 | 7.784 | 17.769 |
| 1017 | CA | LYS | 128 | 56.039 | 6.872 | 16.628 |
| 1018 | C | LYS | 128 | 54.856 | 7.082 | 15.680 |
| 1019 | O | LYS | 128 | 55.013 | 6.972 | 14.458 |
| 1020 | CB | LYS | 128 | 56.034 | 5.449 | 17.173 |
| 1021 | CG | LYS | 128 | 56.285 | 4.415 | 16.083 |
| 1022 | CD | LYS | 128 | 56.288 | 3.004 | 16.659 |
| 1023 | CE | LYS | 128 | 56.594 | 1.964 | 15.587 |
| 1024 | NZ | LYS | 128 | 56.587 | 0.606 | 16.153 |
| 1025 | N | ARG | 129 | 53.707 | 7.452 | 16.228 |
| 1026 | CA | ARG | 129 | 52.525 | 7.678 | 15.388 |
| 1027 | C | ARG | 129 | 52.346 | 9.143 | 15.005 |
| 1028 | O | ARG | 129 | 51.630 | 9.428 | 14.036 |
| 1029 | CB | ARG | 129 | 51.274 | 7.222 | 16.130 |
| 1030 | CG | ARG | 129 | 51.338 | 5.752 | 16.518 |
| 1031 | CD | ARG | 129 | 50.028 | 5.298 | 17.153 |
| 1032 | NE | ARG | 129 | 48.930 | 5.275 | 16.173 |
| 1033 | CZ | ARG | 129 | 47.645 | 5.162 | 16.520 |
| 1034 | NH1 | ARG | 129 | 47.297 | 5.197 | 17.808 |
| 1035 | NH2 | ARG | 129 | 46.703 | 5.095 | 15.576 |
| 1036 | N | LYS | 130 | 53.081 | 10.025 | 15.666 |
| 1037 | CA | LYS | 130 | 53.012 | 11.482 | 15.458 |
| 1038 | C | LYS | 130 | 51.592 | 12.023 | 15.300 |
| 1039 | O | LYS | 130 | 50.783 | 11.969 | 16.238 |
| 1040 | CB | LYS | 130 | 53.860 | 11.825 | 14.242 |
| 1041 | CG | LYS | 130 | 55.304 | 11.407 | 14.490 |
| 1042 | CD | LYS | 130 | 56.207 | 11.753 | 13.315 |
| 1043 | CE | LYS | 130 | 57.646 | 11.332 | 13.594 |
| 1044 | NZ | LYS | 130 | 58.526 | 11.680 | 12.468 |
| 1045 | N | SER | 131 | 51.257 | 12.453 | 14.093 |
| 1046 | CA | SER | 131 | 49.934 | 13.052 | 13.842 |
| 1047 | C | SER | 131 | 48.799 | 12.026 | 13.877 |
| 1048 | O | SER | 131 | 47.714 | 12.330 | 14.387 |
| 1049 | CB | SER | 131 | 49.950 | 13.721 | 12.470 |
| 1050 | OG | SER | 131 | 50.103 | 12.708 | 11.481 |
| 1051 | N | ASP | 132 | 49.168 | 10.769 | 13.697 |
| 1052 | CA | ASP | 132 | 48.221 | 9.658 | 13.658 |
| 1053 | C | ASP | 132 | 47.957 | 9.077 | 15.046 |

TABLE 9-continued

| Atom No. | Atom Type | Residue | Residue Position | X Coord. | Y Coord. | Z Coord. |
|---|---|---|---|---|---|---|
| 1054 | O | ASP | 132 | 47.169 | 8.133 | 15.155 |
| 1055 | CB | ASP | 132 | 48.797 | 8.560 | 12.768 |
| 1056 | CG | ASP | 132 | 49.209 | 9.115 | 11.404 |
| 1057 | OD1 | ASP | 132 | 48.512 | 9.983 | 10.896 |
| 1058 | OD2 | ASP | 132 | 50.218 | 8.654 | 10.889 |
| 1059 | N | TYR | 133 | 48.460 | 9.715 | 16.096 |
| 1060 | CA | TYR | 133 | 48.271 | 9.208 | 17.467 |
| 1061 | C | TYR | 133 | 46.823 | 9.316 | 17.968 |
| 1062 | O | TYR | 133 | 46.441 | 8.583 | 18.886 |
| 1063 | CB | TYR | 133 | 49.206 | 9.983 | 18.400 |
| 1064 | CG | TYR | 133 | 48.922 | 9.798 | 19.892 |
| 1065 | CD1 | TYR | 133 | 49.184 | 8.583 | 20.517 |
| 1066 | CD2 | TYR | 133 | 48.381 | 10.850 | 20.621 |
| 1067 | CE1 | TYR | 133 | 48.899 | 8.422 | 21.868 |
| 1068 | CE2 | TYR | 133 | 48.097 | 10.690 | 21.971 |
| 1069 | CZ | TYR | 133 | 48.354 | 9.475 | 22.591 |
| 1070 | OH | TYR | 133 | 48.039 | 9.311 | 23.923 |
| 1071 | N | GLY | 134 | 45.985 | 10.079 | 17.289 |
| 1072 | CA | GLY | 134 | 44.571 | 10.104 | 17.659 |
| 1073 | C | GLY | 134 | 43.682 | 9.543 | 16.549 |
| 1074 | O | GLY | 134 | 42.482 | 9.843 | 16.511 |
| 1075 | N | TYR | 135 | 44.254 | 8.723 | 15.682 |
| 1076 | CA | TYR | 135 | 43.508 | 8.216 | 14.526 |
| 1077 | C | TYR | 135 | 42.803 | 6.889 | 14.797 |
| 1078 | O | TYR | 135 | 43.413 | 5.895 | 15.206 |
| 1079 | CB | TYR | 135 | 44.466 | 8.055 | 13.347 |
| 1080 | CG | TYR | 135 | 43.798 | 7.509 | 12.089 |
| 1081 | CD1 | TYR | 135 | 42.923 | 8.312 | 11.369 |
| 1082 | CD2 | TYR | 135 | 44.057 | 6.209 | 11.670 |
| 1083 | CE1 | TYR | 135 | 42.289 | 7.810 | 10.240 |
| 1084 | CE2 | TYR | 135 | 43.424 | 5.707 | 10.540 |
| 1085 | CZ | TYR | 135 | 42.535 | 6.506 | 9.835 |
| 1086 | OH | TYR | 135 | 41.785 | 5.959 | 8.817 |
| 1087 | N | LEU | 136 | 41.512 | 6.890 | 14.519 |
| 1088 | CA | LEU | 136 | 40.721 | 5.660 | 14.527 |
| 1089 | C | LEU | 136 | 40.533 | 5.171 | 13.093 |
| 1090 | O | LEU | 136 | 40.203 | 5.959 | 12.199 |
| 1091 | CB | LEU | 136 | 39.359 | 5.938 | 15.154 |
| 1092 | CG | LEU | 136 | 39.481 | 6.377 | 16.606 |
| 1093 | CD1 | LEU | 136 | 38.126 | 6.806 | 17.153 |
| 1094 | CD2 | LEU | 136 | 40.091 | 5.276 | 17.466 |
| 1095 | N | PRO | 137 | 40.997 | 3.963 | 12.840 |
| 1096 | CA | PRO | 137 | 40.671 | 3.283 | 11.591 |
| 1097 | C | PRO | 137 | 39.273 | 2.669 | 11.636 |
| 1098 | O | PRO | 137 | 38.995 | 1.798 | 12.469 |
| 1099 | CB | PRO | 137 | 41.706 | 2.207 | 11.487 |
| 1100 | CG | PRO | 137 | 42.366 | 2.036 | 12.849 |
| 1101 | CD | PRO | 137 | 41.782 | 3.122 | 13.740 |
| 1102 | N | LEU | 138 | 38.399 | 3.129 | 10.757 |
| 1103 | CA | LEU | 138 | 37.101 | 2.461 | 10.607 |
| 1104 | C | LEU | 138 | 37.258 | 1.153 | 9.845 |
| 1105 | O | LEU | 138 | 38.204 | 0.973 | 9.068 |
| 1106 | CB | LEU | 138 | 36.110 | 3.344 | 9.857 |
| 1107 | CG | LEU | 138 | 35.524 | 4.441 | 10.735 |
| 1108 | CD1 | LEU | 138 | 34.437 | 5.187 | 9.973 |
| 1109 | CD2 | LEU | 138 | 34.949 | 3.858 | 12.021 |
| 1110 | N | GLY | 139 | 36.383 | 0.214 | 10.156 |
| 1111 | CA | GLY | 139 | 36.336 | −1.041 | 9.406 |
| 1112 | C | GLY | 139 | 35.714 | −0.744 | 8.049 |
| 1113 | O | GLY | 139 | 36.390 | −0.741 | 7.014 |
| 1114 | N | VAL | 140 | 34.421 | −0.480 | 8.078 |
| 1115 | CA | VAL | 140 | 33.722 | −0.013 | 6.881 |
| 1116 | C | VAL | 140 | 33.971 | 1.481 | 6.675 |
| 1117 | O | VAL | 140 | 33.987 | 2.263 | 7.635 |
| 1118 | CB | VAL | 140 | 32.235 | −0.304 | 7.045 |
| 1119 | CG1 | VAL | 140 | 31.945 | −1.789 | 6.855 |
| 1120 | CG2 | VAL | 140 | 31.727 | 0.173 | 8.401 |
| 1121 | N | GLY | 141 | 34.212 | 1.851 | 5.429 |
| 1122 | CA | GLY | 141 | 34.465 | 3.256 | 5.081 |
| 1123 | C | GLY | 141 | 33.170 | 4.059 | 4.983 |
| 1124 | O | GLY | 141 | 32.463 | 4.023 | 3.969 |
| 1125 | N | LYS | 142 | 32.841 | 4.729 | 6.074 |
| 1126 | CA | LYS | 142 | 31.615 | 5.530 | 6.132 |
| 1127 | C | LYS | 142 | 31.810 | 6.909 | 5.510 |
| 1128 | O | LYS | 142 | 32.734 | 7.644 | 5.877 |
| 1129 | CB | LYS | 142 | 31.216 | 5.682 | 7.593 |

TABLE 9-continued

| Atom No. | Atom Type | Residue | Residue Position | X Coord. | Y Coord. | Z Coord. |
|---|---|---|---|---|---|---|
| 1130 | CG | LYS | 142 | 30.804 | 4.359 | 8.226 |
| 1131 | CD | LYS | 142 | 29.557 | 3.797 | 7.553 |
| 1132 | CE | LYS | 142 | 29.048 | 2.552 | 8.266 |
| 1133 | NZ | LYS | 142 | 27.861 | 2.005 | 7.589 |
| 1134 | N | LYS | 143 | 30.919 | 7.270 | 4.602 |
| 1135 | CA | LYS | 143 | 30.988 | 8.592 | 3.965 |
| 1136 | C | LYS | 143 | 30.178 | 9.643 | 4.729 |
| 1137 | O | LYS | 143 | 29.003 | 9.436 | 5.071 |
| 1138 | CB | LYS | 143 | 30.504 | 8.472 | 2.520 |
| 1139 | CG | LYS | 143 | 30.574 | 9.810 | 1.788 |
| 1140 | CD | LYS | 143 | 30.372 | 9.659 | 0.289 |
| 1141 | CE | LYS | 143 | 31.487 | 8.824 | −0.330 |
| 1142 | NZ | LYS | 143 | 31.339 | 8.745 | −1.792 |
| 1143 | N | ALA | 144 | 30.830 | 10.765 | 4.987 |
| 1144 | CA | ALA | 144 | 30.205 | 11.897 | 5.678 |
| 1145 | C | ALA | 144 | 30.326 | 13.181 | 4.860 |
| 1146 | O | ALA | 144 | 31.402 | 13.786 | 4.776 |
| 1147 | CB | ALA | 144 | 30.893 | 12.104 | 7.022 |
| 1148 | N | ILE | 145 | 29.215 | 13.599 | 4.285 |
| 1149 | CA | ILE | 145 | 29.171 | 14.865 | 3.550 |
| 1150 | C | ILE | 145 | 29.181 | 16.010 | 4.557 |
| 1151 | O | ILE | 145 | 28.563 | 15.896 | 5.619 |
| 1152 | CB | ILE | 145 | 27.897 | 14.875 | 2.708 |
| 1153 | CG1 | ILE | 145 | 27.952 | 13.775 | 1.656 |
| 1154 | CG2 | ILE | 145 | 27.649 | 16.226 | 2.046 |
| 1155 | CD1 | ILE | 145 | 26.727 | 13.821 | 0.752 |
| 1156 | N | VAL | 146 | 30.004 | 17.015 | 4.311 |
| 1157 | CA | VAL | 146 | 30.096 | 18.153 | 5.232 |
| 1158 | C | VAL | 146 | 29.868 | 19.472 | 4.493 |
| 1159 | O | VAL | 146 | 30.761 | 19.974 | 3.798 |
| 1160 | CB | VAL | 146 | 31.476 | 18.165 | 5.893 |
| 1161 | CG1 | VAL | 146 | 31.571 | 19.278 | 6.931 |
| 1162 | CG2 | VAL | 146 | 31.799 | 16.827 | 6.550 |
| 1163 | N | GLU | 147 | 28.663 | 20.001 | 4.622 |
| 1164 | CA | GLU | 147 | 28.348 | 21.311 | 4.047 |
| 1165 | C | GLU | 147 | 28.625 | 22.413 | 5.065 |
| 1166 | O | GLU | 147 | 28.046 | 22.416 | 6.157 |
| 1167 | CB | GLU | 147 | 26.874 | 21.354 | 3.656 |
| 1168 | CG | GLU | 147 | 26.525 | 22.694 | 3.015 |
| 1169 | CD | GLU | 147 | 25.023 | 22.830 | 2.813 |
| 1170 | OE1 | GLU | 147 | 24.400 | 21.843 | 2.454 |
| 1171 | OE2 | GLU | 147 | 24.530 | 23.934 | 2.997 |
| 1172 | N | PHE | 148 | 29.480 | 23.351 | 4.692 |
| 1173 | CA | PHE | 148 | 29.819 | 24.460 | 5.595 |
| 1174 | C | PHE | 148 | 30.202 | 25.713 | 4.817 |
| 1175 | O | PHE | 148 | 30.471 | 25.626 | 3.616 |
| 1176 | CB | PHE | 148 | 30.953 | 24.033 | 6.525 |
| 1177 | CG | PHE | 148 | 32.296 | 23.670 | 5.885 |
| 1178 | CD1 | PHE | 148 | 32.538 | 22.374 | 5.444 |
| 1179 | CD2 | PHE | 148 | 33.296 | 24.629 | 5.791 |
| 1180 | CE1 | PHE | 148 | 33.765 | 22.045 | 4.886 |
| 1181 | CE2 | PHE | 148 | 34.524 | 24.299 | 5.235 |
| 1182 | CZ | PHE | 148 | 34.758 | 23.008 | 4.781 |
| 1183 | N | SER | 149 | 30.211 | 26.848 | 5.512 |
| 1184 | CA | SER | 149 | 30.536 | 28.197 | 4.992 |
| 1185 | C | SER | 149 | 29.488 | 28.745 | 4.024 |
| 1186 | O | SER | 149 | 28.754 | 29.676 | 4.374 |
| 1187 | CB | SER | 149 | 31.906 | 28.200 | 4.330 |
| 1188 | OG | SER | 149 | 32.167 | 29.525 | 3.887 |
| 1189 | N | SER | 150 | 29.470 | 28.182 | 2.826 |
| 1190 | CA | SER | 150 | 28.491 | 28.454 | 1.760 |
| 1191 | C | SER | 150 | 28.030 | 29.906 | 1.640 |
| 1192 | O | SER | 150 | 26.960 | 30.286 | 2.128 |
| 1193 | CB | SER | 150 | 27.328 | 27.518 | 2.034 |
| 1194 | OG | SER | 150 | 27.894 | 26.210 | 2.056 |
| 1195 | N | PRO | 151 | 28.858 | 30.707 | 0.991 |
| 1196 | CA | PRO | 151 | 28.587 | 32.133 | 0.839 |
| 1197 | C | PRO | 151 | 27.688 | 32.427 | −0.354 |
| 1198 | O | PRO | 151 | 27.615 | 31.650 | −1.315 |
| 1199 | CB | PRO | 151 | 29.934 | 32.736 | 0.598 |
| 1200 | CG | PRO | 151 | 30.887 | 31.627 | 0.175 |
| 1201 | CD | PRO | 151 | 30.126 | 30.329 | 0.366 |
| 1202 | N | ASN | 152 | 26.952 | 33.517 | −0.244 |
| 1203 | CA | ASN | 152 | 26.294 | 34.093 | −1.416 |
| 1204 | C | ASN | 152 | 27.374 | 34.711 | −2.291 |
| 1205 | O | ASN | 152 | 28.255 | 35.401 | −1.768 |

TABLE 9-continued

| Atom No. | Atom Type | Residue | Residue Position | X Coord. | Y Coord. | Z Coord. |
|---|---|---|---|---|---|---|
| 1206 | CB | ASN | 152 | 25.332 | 35.177 | −0.961 |
| 1207 | CG | ASN | 152 | 24.175 | 34.585 | −0.170 |
| 1208 | OD1 | ASN | 152 | 23.460 | 33.706 | −0.666 |
| 1209 | ND2 | ASN | 152 | 23.932 | 35.157 | 0.996 |
| 1210 | N | ILE | 153 | 27.253 | 34.575 | −3.600 |
| 1211 | CA | ILE | 153 | 28.347 | 34.996 | −4.485 |
| 1212 | C | ILE | 153 | 28.360 | 36.498 | −4.780 |
| 1213 | O | ILE | 153 | 29.329 | 37.001 | −5.361 |
| 1214 | CB | ILE | 153 | 28.308 | 34.190 | −5.779 |
| 1215 | CG1 | ILE | 153 | 27.068 | 34.481 | −6.610 |
| 1216 | CG2 | ILE | 153 | 28.394 | 32.698 | −5.471 |
| 1217 | CD1 | ILE | 153 | 27.135 | 33.730 | −7.933 |
| 1218 | N | ALA | 154 | 27.340 | 37.212 | −4.326 |
| 1219 | CA | ALA | 154 | 27.374 | 38.675 | −4.374 |
| 1220 | C | ALA | 154 | 27.937 | 39.274 | −3.083 |
| 1221 | O | ALA | 154 | 28.183 | 40.483 | −3.016 |
| 1222 | CB | ALA | 154 | 25.956 | 39.187 | −4.590 |
| 1223 | N | LYS | 155 | 28.182 | 38.432 | −2.091 |
| 1224 | CA | LYS | 155 | 28.649 | 38.924 | −0.790 |
| 1225 | C | LYS | 155 | 30.109 | 38.556 | −0.541 |
| 1226 | O | LYS | 155 | 30.483 | 37.378 | −0.504 |
| 1227 | CB | LYS | 155 | 27.795 | 38.360 | 0.352 |
| 1228 | CG | LYS | 155 | 26.438 | 39.048 | 0.547 |
| 1229 | CD | LYS | 155 | 25.358 | 38.558 | −0.414 |
| 1230 | CE | LYS | 155 | 23.987 | 39.141 | −0.100 |
| 1231 | NZ | LYS | 155 | 22.965 | 38.540 | −0.973 |
| 1232 | N | PRO | 156 | 30.911 | 39.584 | −0.320 |
| 1233 | CA | PRO | 156 | 32.249 | 39.405 | 0.244 |
| 1234 | C | PRO | 156 | 32.164 | 38.862 | 1.669 |
| 1235 | O | PRO | 156 | 31.147 | 39.028 | 2.355 |
| 1236 | CB | PRO | 156 | 32.872 | 40.766 | 0.215 |
| 1237 | CG | PRO | 156 | 31.812 | 41.786 | −0.173 |
| 1238 | CD | PRO | 156 | 30.538 | 40.995 | −0.420 |
| 1239 | N | PHE | 157 | 33.226 | 38.201 | 2.092 |
| 1240 | CA | PHE | 157 | 33.253 | 37.590 | 3.425 |
| 1241 | C | PHE | 157 | 33.359 | 38.609 | 4.548 |
| 1242 | O | PHE | 157 | 34.434 | 39.168 | 4.781 |
| 1243 | CB | PHE | 157 | 34.456 | 36.658 | 3.545 |
| 1244 | CG | PHE | 157 | 34.229 | 35.197 | 3.162 |
| 1245 | CD1 | PHE | 157 | 33.557 | 34.859 | 1.995 |
| 1246 | CD2 | PHE | 157 | 34.715 | 34.198 | 3.996 |
| 1247 | CE1 | PHE | 157 | 33.367 | 33.523 | 1.668 |
| 1248 | CE2 | PHE | 157 | 34.523 | 32.862 | 3.669 |
| 1249 | CZ | PHE | 157 | 33.847 | 32.525 | 2.505 |
| 1250 | N | HIS | 158 | 32.239 | 38.896 | 5.188 |
| 1251 | CA | HIS | 158 | 32.271 | 39.583 | 6.482 |
| 1252 | C | HIS | 158 | 32.466 | 38.522 | 7.562 |
| 1253 | O | HIS | 158 | 32.359 | 37.323 | 7.262 |
| 1254 | CB | HIS | 158 | 31.012 | 40.424 | 6.705 |
| 1255 | CG | HIS | 158 | 29.697 | 39.674 | 6.801 |
| 1256 | ND1 | HIS | 158 | 29.022 | 39.395 | 7.932 |
| 1257 | CD2 | HIS | 158 | 28.945 | 39.195 | 5.755 |
| 1258 | CE1 | HIS | 158 | 27.900 | 38.714 | 7.620 |
| 1259 | NE2 | HIS | 158 | 27.852 | 38.593 | 6.275 |
| 1260 | N | ALA | 159 | 32.678 | 38.948 | 8.799 |
| 1261 | CA | ALA | 159 | 33.050 | 38.030 | 9.900 |
| 1262 | C | ALA | 159 | 32.033 | 36.950 | 10.306 |
| 1263 | O | ALA | 159 | 32.441 | 35.940 | 10.893 |
| 1264 | CB | ALA | 159 | 33.371 | 38.874 | 11.126 |
| 1265 | N | GLY | 160 | 30.808 | 37.033 | 9.812 |
| 1266 | CA | GLY | 160 | 29.794 | 36.002 | 10.069 |
| 1267 | C | GLY | 160 | 30.134 | 34.664 | 9.405 |
| 1268 | O | GLY | 160 | 29.966 | 33.611 | 10.034 |
| 1269 | N | HIS | 161 | 30.816 | 34.723 | 8.266 |
| 1270 | CA | HIS | 161 | 31.161 | 33.509 | 7.509 |
| 1271 | C | HIS | 161 | 32.298 | 32.710 | 8.146 |
| 1272 | O | HIS | 161 | 32.338 | 31.483 | 7.975 |
| 1273 | CB | HIS | 161 | 31.627 | 33.899 | 6.109 |
| 1274 | CG | HIS | 161 | 30.605 | 34.569 | 5.214 |
| 1275 | ND1 | HIS | 161 | 30.443 | 35.893 | 5.039 |
| 1276 | CD2 | HIS | 161 | 29.686 | 33.943 | 4.405 |
| 1277 | CE1 | HIS | 161 | 29.448 | 36.110 | 4.156 |
| 1278 | NE2 | HIS | 161 | 28.980 | 34.903 | 3.764 |
| 1279 | N | LEU | 162 | 33.018 | 33.332 | 9.071 |
| 1280 | CA | LEU | 162 | 34.171 | 32.692 | 9.707 |
| 1281 | C | LEU | 162 | 33.757 | 31.510 | 10.567 |

TABLE 9-continued

| Atom No. | Atom Type | Residue | Residue Position | X Coord. | Y Coord. | Z Coord. |
|---|---|---|---|---|---|---|
| 1282 | O | LEU | 162 | 34.361 | 30.436 | 10.433 |
| 1283 | CB | LEU | 162 | 34.835 | 33.714 | 10.623 |
| 1284 | CG | LEU | 162 | 35.986 | 33.103 | 11.417 |
| 1285 | CD1 | LEU | 162 | 37.178 | 32.800 | 10.515 |
| 1286 | CD2 | LEU | 162 | 36.403 | 34.025 | 12.555 |
| 1287 | N | ARG | 163 | 32.580 | 31.611 | 11.165 |
| 1288 | CA | ARG | 163 | 32.117 | 30.577 | 12.084 |
| 1289 | C | ARG | 163 | 31.910 | 29.246 | 11.378 |
| 1290 | O | ARG | 163 | 32.659 | 28.304 | 11.660 |
| 1291 | CB | ARG | 163 | 30.800 | 31.022 | 12.690 |
| 1292 | CG | ARG | 163 | 30.889 | 32.426 | 13.269 |
| 1293 | CD | ARG | 163 | 29.691 | 32.680 | 14.168 |
| 1294 | NE | ARG | 163 | 29.701 | 31.683 | 15.246 |
| 1295 | CZ | ARG | 163 | 29.527 | 31.990 | 16.531 |
| 1296 | NH1 | ARG | 163 | 29.141 | 33.221 | 16.873 |
| 1297 | NH2 | ARG | 163 | 29.621 | 31.035 | 17.457 |
| 1298 | N | SER | 164 | 31.166 | 29.251 | 10.284 |
| 1299 | CA | SER | 164 | 30.882 | 27.976 | 9.621 |
| 1300 | C | SER | 164 | 32.038 | 27.496 | 8.762 |
| 1301 | O | SER | 164 | 32.192 | 26.282 | 8.580 |
| 1302 | CB | SER | 164 | 29.670 | 28.112 | 8.724 |
| 1303 | OG | SER | 164 | 29.398 | 26.814 | 8.210 |
| 1304 | N | THR | 165 | 32.931 | 28.399 | 8.398 |
| 1305 | CA | THR | 165 | 34.097 | 27.990 | 7.628 |
| 1306 | C | THR | 165 | 35.051 | 27.203 | 8.518 |
| 1307 | O | THR | 165 | 35.325 | 26.034 | 8.218 |
| 1308 | CB | THR | 165 | 34.787 | 29.235 | 7.080 |
| 1309 | OG1 | THR | 165 | 33.868 | 29.912 | 6.234 |
| 1310 | CG2 | THR | 165 | 36.004 | 28.878 | 6.240 |
| 1311 | N | ILE | 166 | 35.287 | 27.698 | 9.723 |
| 1312 | CA | ILE | 166 | 36.247 | 27.020 | 10.595 |
| 1313 | C | ILE | 166 | 35.625 | 25.897 | 11.428 |
| 1314 | O | ILE | 166 | 36.330 | 24.928 | 11.735 |
| 1315 | CB | ILE | 166 | 36.935 | 28.055 | 11.482 |
| 1316 | CG1 | ILE | 166 | 35.976 | 28.724 | 12.460 |
| 1317 | CG2 | ILE | 166 | 37.616 | 29.104 | 10.613 |
| 1318 | CD1 | ILE | 166 | 36.699 | 29.755 | 13.314 |
| 1319 | N | ILE | 167 | 34.311 | 25.892 | 11.592 |
| 1320 | CA | ILE | 167 | 33.680 | 24.772 | 12.295 |
| 1321 | C | ILE | 167 | 33.496 | 23.598 | 11.341 |
| 1322 | O | ILE | 167 | 33.789 | 22.458 | 11.720 |
| 1323 | CB | ILE | 167 | 32.344 | 25.219 | 12.883 |
| 1324 | CG1 | ILE | 167 | 32.563 | 26.260 | 13.976 |
| 1325 | CG2 | ILE | 167 | 31.565 | 24.032 | 13.442 |
| 1326 | CD1 | ILE | 167 | 31.239 | 26.763 | 14.541 |
| 1327 | N | GLY | 168 | 33.321 | 23.911 | 10.067 |
| 1328 | CA | GLY | 168 | 33.276 | 22.874 | 9.040 |
| 1329 | C | GLY | 168 | 34.666 | 22.289 | 8.841 |
| 1330 | O | GLY | 168 | 34.821 | 21.063 | 8.826 |
| 1331 | N | GLY | 169 | 35.661 | 23.162 | 8.786 |
| 1332 | CA | GLY | 169 | 37.072 | 22.752 | 8.766 |
| 1333 | C | GLY | 169 | 37.399 | 21.762 | 9.884 |
| 1334 | O | GLY | 169 | 37.709 | 20.598 | 9.595 |
| 1335 | N | PHE | 170 | 37.148 | 22.153 | 11.124 |
| 1336 | CA | PHE | 170 | 37.409 | 21.264 | 12.261 |
| 1337 | C | PHE | 170 | 36.644 | 19.943 | 12.188 |
| 1338 | O | PHE | 170 | 37.284 | 18.889 | 12.275 |
| 1339 | CB | PHE | 170 | 37.025 | 21.974 | 13.555 |
| 1340 | CG | PHE | 170 | 36.993 | 21.037 | 14.761 |
| 1341 | CD1 | PHE | 170 | 38.174 | 20.503 | 15.259 |
| 1342 | CD2 | PHE | 170 | 35.778 | 20.691 | 15.340 |
| 1343 | CE1 | PHE | 170 | 38.143 | 19.640 | 16.346 |
| 1344 | CE2 | PHE | 170 | 35.747 | 19.824 | 16.423 |
| 1345 | CZ | PHE | 170 | 36.929 | 19.301 | 16.928 |
| 1346 | N | ILE | 171 | 35.377 | 19.974 | 11.804 |
| 1347 | CA | ILE | 171 | 34.572 | 18.747 | 11.780 |
| 1348 | C | ILE | 171 | 34.929 | 17.812 | 10.622 |
| 1349 | O | ILE | 171 | 34.985 | 16.593 | 10.832 |
| 1350 | CB | ILE | 171 | 33.105 | 19.165 | 11.708 |
| 1351 | CG1 | ILE | 171 | 32.667 | 19.797 | 13.024 |
| 1352 | CG2 | ILE | 171 | 32.196 | 17.997 | 11.354 |
| 1353 | CD1 | ILE | 171 | 31.200 | 20.206 | 12.977 |
| 1354 | N | SER | 172 | 35.449 | 18.364 | 9.540 |
| 1355 | CA | SER | 172 | 35.852 | 17.528 | 8.409 |
| 1356 | C | SER | 172 | 37.225 | 16.894 | 8.637 |
| 1357 | O | SER | 172 | 37.397 | 15.705 | 8.327 |

TABLE 9-continued

| Atom No. | Atom Type | Residue | Residue Position | X Coord. | Y Coord. | Z Coord. |
|---|---|---|---|---|---|---|
| 1358 | CB | SER | 172 | 35.842 | 18.374 | 7.140 |
| 1359 | OG | SER | 172 | 36.771 | 19.439 | 7.272 |
| 1360 | N | ASN | 173 | 38.057 | 17.552 | 9.433 |
| 1361 | CA | ASN | 173 | 39.339 | 16.957 | 9.820 |
| 1362 | C | ASN | 173 | 39.110 | 15.910 | 10.902 |
| 1363 | O | ASN | 173 | 39.614 | 14.783 | 10.805 |
| 1364 | CB | ASN | 173 | 40.239 | 18.034 | 10.419 |
| 1365 | CG | ASN | 173 | 40.545 | 19.171 | 9.450 |
| 1366 | OD1 | ASN | 173 | 40.575 | 18.996 | 8.225 |
| 1367 | ND2 | ASN | 173 | 40.815 | 20.326 | 10.031 |
| 1368 | N | LEU | 174 | 38.137 | 16.199 | 11.748 |
| 1369 | CA | LEU | 174 | 37.790 | 15.349 | 12.886 |
| 1370 | C | LEU | 174 | 37.181 | 14.021 | 12.454 |
| 1371 | O | LEU | 174 | 37.668 | 12.968 | 12.882 |
| 1372 | CB | LEU | 174 | 36.773 | 16.136 | 13.699 |
| 1373 | CG | LEU | 174 | 36.350 | 15.432 | 14.975 |
| 1374 | CD1 | LEU | 174 | 37.530 | 15.279 | 15.930 |
| 1375 | CD2 | LEU | 174 | 35.224 | 16.214 | 15.635 |
| 1376 | N | TYR | 175 | 36.321 | 14.050 | 11.449 |
| 1377 | CA | TYR | 175 | 35.738 | 12.797 | 10.972 |
| 1378 | C | TYR | 175 | 36.712 | 11.995 | 10.118 |
| 1379 | O | TYR | 175 | 36.753 | 10.771 | 10.291 |
| 1380 | CB | TYR | 175 | 34.449 | 13.068 | 10.208 |
| 1381 | CG | TYR | 175 | 33.213 | 13.204 | 11.094 |
| 1382 | CD1 | TYR | 175 | 32.789 | 14.452 | 11.528 |
| 1383 | CD2 | TYR | 175 | 32.508 | 12.065 | 11.466 |
| 1384 | CE1 | TYR | 175 | 31.661 | 14.563 | 12.329 |
| 1385 | CE2 | TYR | 175 | 31.378 | 12.174 | 12.267 |
| 1386 | CZ | TYR | 175 | 30.956 | 13.425 | 12.694 |
| 1387 | OH | TYR | 175 | 29.801 | 13.546 | 13.440 |
| 1388 | N | GLU | 176 | 37.689 | 12.646 | 9.505 |
| 1389 | CA | GLU | 176 | 38.715 | 11.885 | 8.781 |
| 1390 | C | GLU | 176 | 39.745 | 11.280 | 9.730 |
| 1391 | O | GLU | 176 | 40.206 | 10.162 | 9.475 |
| 1392 | CB | GLU | 176 | 39.408 | 12.785 | 7.774 |
| 1393 | CG | GLU | 176 | 38.436 | 13.167 | 6.673 |
| 1394 | CD | GLU | 176 | 39.120 | 14.050 | 5.642 |
| 1395 | OE1 | GLU | 176 | 40.104 | 14.685 | 5.995 |
| 1396 | OE2 | GLU | 176 | 38.636 | 14.081 | 4.519 |
| 1397 | N | LYS | 177 | 39.834 | 11.839 | 10.926 |
| 1398 | CA | LYS | 177 | 40.677 | 11.286 | 11.988 |
| 1399 | C | LYS | 177 | 39.972 | 10.131 | 12.718 |
| 1400 | O | LYS | 177 | 40.614 | 9.370 | 13.448 |
| 1401 | CB | LYS | 177 | 40.987 | 12.436 | 12.948 |
| 1402 | CG | LYS | 177 | 42.014 | 12.075 | 14.016 |
| 1403 | CD | LYS | 177 | 43.359 | 11.693 | 13.403 |
| 1404 | CE | LYS | 177 | 43.991 | 12.844 | 12.629 |
| 1405 | NZ | LYS | 177 | 45.268 | 12.422 | 12.030 |
| 1406 | N | VAL | 178 | 38.684 | 9.959 | 12.460 |
| 1407 | CA | VAL | 178 | 37.943 | 8.800 | 12.971 |
| 1408 | C | VAL | 178 | 37.799 | 7.720 | 11.887 |
| 1409 | O | VAL | 178 | 37.404 | 6.582 | 12.177 |
| 1410 | CB | VAL | 178 | 36.579 | 9.295 | 13.453 |
| 1411 | CG1 | VAL | 178 | 35.731 | 8.176 | 14.052 |
| 1412 | CG2 | VAL | 178 | 36.752 | 10.404 | 14.483 |
| 1413 | N | GLY | 179 | 38.175 | 8.057 | 10.662 |
| 1414 | CA | GLY | 179 | 38.177 | 7.081 | 9.566 |
| 1415 | C | GLY | 179 | 37.030 | 7.298 | 8.581 |
| 1416 | O | GLY | 179 | 36.675 | 6.390 | 7.819 |
| 1417 | N | TRP | 180 | 36.417 | 8.466 | 8.655 |
| 1418 | CA | TRP | 180 | 35.296 | 8.804 | 7.773 |
| 1419 | C | TRP | 180 | 35.763 | 9.485 | 6.497 |
| 1420 | O | TRP | 180 | 36.624 | 10.376 | 6.498 |
| 1421 | CB | TRP | 180 | 34.326 | 9.739 | 8.489 |
| 1422 | CG | TRP | 180 | 33.496 | 9.116 | 9.595 |
| 1423 | CD1 | TRP | 180 | 33.926 | 8.715 | 10.839 |
| 1424 | CD2 | TRP | 180 | 32.078 | 8.848 | 9.546 |
| 1425 | NE1 | TRP | 180 | 32.866 | 8.211 | 11.519 |
| 1426 | CE2 | TRP | 180 | 31.741 | 8.274 | 10.783 |
| 1427 | CE3 | TRP | 180 | 31.105 | 9.047 | 8.578 |
| 1428 | CZ2 | TRP | 180 | 30.429 | 7.897 | 11.032 |
| 1429 | CZ3 | TRP | 180 | 29.793 | 8.671 | 8.837 |
| 1430 | CH2 | TRP | 180 | 29.457 | 8.097 | 10.058 |
| 1431 | N | ASP | 181 | 35.072 | 9.136 | 5.427 |
| 1432 | CA | ASP | 181 | 35.314 | 9.709 | 4.103 |
| 1433 | C | ASP | 181 | 34.524 | 11.006 | 3.955 |

TABLE 9-continued

| Atom No. | Atom Type | Residue | Residue Position | X Coord. | Y Coord. | Z Coord. |
|---|---|---|---|---|---|---|
| 1434 | O | ASP | 181 | 33.349 | 10.998 | 3.565 |
| 1435 | CB | ASP | 181 | 34.850 | 8.703 | 3.054 |
| 1436 | CG | ASP | 181 | 35.561 | 7.366 | 3.255 |
| 1437 | OD1 | ASP | 181 | 34.893 | 6.412 | 3.627 |
| 1438 | OD2 | ASP | 181 | 36.759 | 7.324 | 3.016 |
| 1439 | N | VAL | 182 | 35.162 | 12.099 | 4.333 |
| 1440 | CA | VAL | 182 | 34.512 | 13.411 | 4.318 |
| 1441 | C | VAL | 182 | 34.408 | 14.004 | 2.917 |
| 1442 | O | VAL | 182 | 35.347 | 13.969 | 2.116 |
| 1443 | CB | VAL | 182 | 35.284 | 14.324 | 5.264 |
| 1444 | CG1 | VAL | 182 | 35.086 | 15.804 | 4.971 |
| 1445 | CG2 | VAL | 182 | 34.940 | 14.001 | 6.713 |
| 1446 | N | THR | 183 | 33.203 | 14.443 | 2.605 |
| 1447 | CA | THR | 183 | 32.946 | 15.115 | 1.336 |
| 1448 | C | THR | 183 | 32.562 | 16.569 | 1.596 |
| 1449 | O | THR | 183 | 31.383 | 16.875 | 1.811 |
| 1450 | CB | THR | 183 | 31.809 | 14.379 | 0.640 |
| 1451 | OG1 | THR | 183 | 32.105 | 12.989 | 0.678 |
| 1452 | CG2 | THR | 183 | 31.657 | 14.810 | −0.814 |
| 1453 | N | ARG | 184 | 33.561 | 17.438 | 1.621 |
| 1454 | CA | ARG | 184 | 33.334 | 18.875 | 1.840 |
| 1455 | C | ARG | 184 | 32.596 | 19.490 | 0.661 |
| 1456 | O | ARG | 184 | 33.137 | 19.545 | −0.454 |
| 1457 | CB | ARG | 184 | 34.681 | 19.574 | 1.958 |
| 1458 | CG | ARG | 184 | 35.518 | 19.050 | 3.112 |
| 1459 | CD | ARG | 184 | 36.898 | 19.699 | 3.090 |
| 1460 | NE | ARG | 184 | 37.737 | 19.229 | 4.201 |
| 1461 | CZ | ARG | 184 | 38.605 | 18.218 | 4.109 |
| 1462 | NH1 | ARG | 184 | 38.765 | 17.571 | 2.952 |
| 1463 | NH2 | ARG | 184 | 39.323 | 17.862 | 5.177 |
| 1464 | N | ILE | 185 | 31.395 | 19.978 | 0.925 |
| 1465 | CA | ILE | 185 | 30.548 | 20.534 | −0.136 |
| 1466 | C | ILE | 185 | 30.007 | 21.919 | 0.222 |
| 1467 | O | ILE | 185 | 29.262 | 22.095 | 1.194 |
| 1468 | CB | ILE | 185 | 29.374 | 19.590 | −0.406 |
| 1469 | CG1 | ILE | 185 | 29.843 | 18.189 | −0.768 |
| 1470 | CG2 | ILE | 185 | 28.497 | 20.124 | −1.530 |
| 1471 | CD1 | ILE | 185 | 28.670 | 17.318 | −1.200 |
| 1472 | N | ASN | 186 | 30.380 | 22.889 | −0.593 |
| 1473 | CA | ASN | 186 | 29.846 | 24.246 | −0.466 |
| 1474 | C | ASN | 186 | 28.458 | 24.295 | −1.092 |
| 1475 | O | ASN | 186 | 28.147 | 23.450 | −1.937 |
| 1476 | CB | ASN | 186 | 30.771 | 25.204 | −1.208 |
| 1477 | CG | ASN | 186 | 31.117 | 26.351 | −0.273 |
| 1478 | OD1 | ASN | 186 | 30.679 | 26.361 | 0.879 |
| 1479 | ND2 | ASN | 186 | 31.916 | 27.288 | −0.744 |
| 1480 | N | TYR | 187 | 27.587 | 25.136 | −0.565 |
| 1481 | CA | TYR | 187 | 26.281 | 25.353 | −1.190 |
| 1482 | C | TYR | 187 | 26.087 | 26.847 | −1.447 |
| 1483 | O | TYR | 187 | 25.443 | 27.559 | −0.670 |
| 1484 | CB | TYR | 187 | 25.225 | 24.823 | −0.231 |
| 1485 | CG | TYR | 187 | 23.799 | 24.808 | −0.762 |
| 1486 | CD1 | TYR | 187 | 23.468 | 24.007 | −1.847 |
| 1487 | CD2 | TYR | 187 | 22.830 | 25.595 | −0.155 |
| 1488 | CE1 | TYR | 187 | 22.161 | 23.983 | −2.317 |
| 1489 | CE2 | TYR | 187 | 21.526 | 25.573 | −0.626 |
| 1490 | CZ | TYR | 187 | 21.193 | 24.762 | −1.701 |
| 1491 | OH | TYR | 187 | 19.880 | 24.670 | −2.106 |
| 1492 | N | LEU | 188 | 26.651 | 27.290 | −2.555 |
| 1493 | CA | LEU | 188 | 26.685 | 28.707 | −2.928 |
| 1494 | C | LEU | 188 | 25.308 | 29.335 | −3.116 |
| 1495 | O | LEU | 188 | 24.372 | 28.742 | −3.673 |
| 1496 | CB | LEU | 188 | 27.447 | 28.824 | −4.243 |
| 1497 | CG | LEU | 188 | 28.884 | 28.334 | −4.109 |
| 1498 | CD1 | LEU | 188 | 29.542 | 28.187 | −5.475 |
| 1499 | CD2 | LEU | 188 | 29.697 | 29.254 | −3.206 |
| 1500 | N | GLY | 189 | 25.224 | 30.568 | −2.651 |
| 1501 | CA | GLY | 189 | 24.045 | 31.402 | −2.878 |
| 1502 | C | GLY | 189 | 24.206 | 32.081 | −4.230 |
| 1503 | O | GLY | 189 | 24.917 | 33.081 | −4.370 |
| 1504 | N | ASP | 190 | 23.588 | 31.488 | −5.233 |
| 1505 | CA | ASP | 190 | 23.798 | 31.934 | −6.609 |
| 1506 | C | ASP | 190 | 22.491 | 31.945 | −7.389 |
| 1507 | O | ASP | 190 | 22.488 | 32.134 | −8.609 |
| 1508 | CB | ASP | 190 | 24.784 | 30.979 | −7.280 |
| 1509 | CG | ASP | 190 | 24.124 | 29.645 | −7.627 |
| 1510 | OD1 | ASP | 190 | 23.949 | 28.819 | −6.740 |
| 1511 | OD2 | ASP | 190 | 23.799 | 29.468 | −8.791 |
| 1512 | N | TRP | 191 | 21.399 | 31.658 | −6.703 |
| 1513 | CA | TRP | 191 | 20.113 | 31.566 | −7.390 |
| 1514 | C | TRP | 191 | 19.122 | 32.591 | −6.841 |
| 1515 | O | TRP | 191 | 19.514 | 33.663 | −6.351 |
| 1516 | CB | TRP | 191 | 19.603 | 30.139 | −7.208 |
| 1517 | CG | TRP | 191 | 18.962 | 29.485 | −8.424 |
| 1518 | CD1 | TRP | 191 | 17.898 | 28.615 | −8.397 |
| 1519 | CD2 | TRP | 191 | 19.332 | 29.635 | −9.816 |
| 1520 | NE1 | TRP | 191 | 17.617 | 28.231 | −9.665 |
| 1521 | CE2 | TRP | 191 | 18.452 | 28.814 | −10.546 |
| 1522 | CE3 | TRP | 191 | 20.312 | 30.363 | −10.475 |
| 1523 | CZ2 | TRP | 191 | 18.570 | 28.730 | −11.925 |
| 1524 | CZ3 | TRP | 191 | 20.420 | 30.274 | −11.858 |
| 1525 | CH2 | TRP | 191 | 19.554 | 29.461 | −12.579 |
| 1526 | N | GLY | 192 | 17.850 | 32.311 | −7.067 |
| 1527 | CA | GLY | 192 | 16.754 | 33.163 | −6.593 |
| 1528 | C | GLY | 192 | 16.824 | 34.566 | −7.183 |
| 1529 | O | GLY | 192 | 17.489 | 34.810 | −8.200 |
| 1530 | N | LYS | 193 | 16.343 | 35.513 | −6.397 |
| 1531 | CA | LYS | 193 | 16.410 | 36.917 | −6.803 |
| 1532 | C | LYS | 193 | 17.778 | 37.547 | −6.545 |
| 1533 | O | LYS | 193 | 18.003 | 38.670 | −7.005 |
| 1534 | CB | LYS | 193 | 15.330 | 37.727 | −6.100 |
| 1535 | CG | LYS | 193 | 13.939 | 37.360 | −6.604 |
| 1536 | CD | LYS | 193 | 12.904 | 38.367 | −6.114 |
| 1537 | CE | LYS | 193 | 11.514 | 38.054 | −6.654 |
| 1538 | NZ | LYS | 193 | 10.567 | 39.130 | −6.319 |
| 1539 | N | GLN | 194 | 18.724 | 36.796 | −5.995 |
| 1540 | CA | GLN | 194 | 20.077 | 37.330 | −5.847 |
| 1541 | C | GLN | 194 | 20.715 | 37.405 | −7.224 |
| 1542 | O | GLN | 194 | 21.069 | 38.506 | −7.659 |
| 1543 | CB | GLN | 194 | 20.916 | 36.429 | −4.943 |
| 1544 | CG | GLN | 194 | 22.356 | 36.937 | −4.830 |
| 1545 | CD | GLN | 194 | 23.180 | 36.019 | −3.930 |
| 1546 | OE1 | GLN | 194 | 24.412 | 36.141 | −3.836 |
| 1547 | NE2 | GLN | 194 | 22.478 | 35.119 | −3.263 |
| 1548 | N | PHE | 195 | 20.556 | 36.349 | −8.008 |
| 1549 | CA | PHE | 195 | 21.148 | 36.386 | −9.343 |
| 1550 | C | PHE | 195 | 20.211 | 37.037 | −10.358 |
| 1551 | O | PHE | 195 | 20.687 | 37.638 | −11.328 |
| 1552 | CB | PHE | 195 | 21.533 | 34.988 | −9.791 |
| 1553 | CG | PHE | 195 | 22.827 | 35.022 | −10.592 |
| 1554 | CD1 | PHE | 195 | 24.019 | 34.650 | −9.985 |
| 1555 | CD2 | PHE | 195 | 22.823 | 35.452 | −11.912 |
| 1556 | CE1 | PHE | 195 | 25.206 | 34.702 | −10.701 |
| 1557 | CE2 | PHE | 195 | 24.011 | 35.508 | −12.626 |
| 1558 | CZ | PHE | 195 | 25.201 | 35.133 | −12.019 |
| 1559 | N | GLY | 196 | 18.934 | 37.117 | −10.023 |
| 1560 | CA | GLY | 196 | 17.997 | 37.898 | −10.837 |
| 1561 | C | GLY | 196 | 18.352 | 39.386 | −10.788 |
| 1562 | O | GLY | 196 | 18.547 | 40.031 | −11.830 |
| 1563 | N | LEU | 197 | 18.619 | 39.868 | −9.584 |
| 1564 | CA | LEU | 197 | 18.978 | 41.272 | −9.385 |
| 1565 | C | LEU | 197 | 20.437 | 41.545 | −9.765 |
| 1566 | O | LEU | 197 | 20.742 | 42.655 | −10.215 |
| 1567 | CB | LEU | 197 | 18.735 | 41.602 | −7.915 |
| 1568 | CG | LEU | 197 | 18.733 | 43.099 | −7.635 |
| 1569 | CD1 | LEU | 197 | 17.688 | 43.813 | −8.482 |
| 1570 | CD2 | LEU | 197 | 18.477 | 43.370 | −6.158 |
| 1571 | N | LEU | 198 | 21.260 | 40.508 | −9.810 |
| 1572 | CA | LEU | 198 | 22.632 | 40.652 | −10.322 |
| 1573 | C | LEU | 198 | 22.662 | 40.738 | −11.846 |
| 1574 | O | LEU | 198 | 23.477 | 41.490 | −12.398 |
| 1575 | CB | LEU | 198 | 23.464 | 39.437 | −9.917 |
| 1576 | CG | LEU | 198 | 24.526 | 39.758 | −8.868 |
| 1577 | CD1 | LEU | 198 | 25.377 | 40.948 | −9.297 |
| 1578 | CD2 | LEU | 198 | 23.909 | 40.017 | −7.503 |
| 1579 | N | ALA | 199 | 21.678 | 40.138 | −12.496 |
| 1580 | CA | ALA | 199 | 21.603 | 40.190 | −13.955 |
| 1581 | C | ALA | 199 | 21.224 | 41.586 | −14.422 |
| 1582 | O | ALA | 199 | 22.008 | 42.198 | −15.162 |
| 1583 | CB | ALA | 199 | 20.570 | 39.180 | −14.439 |
| 1584 | N | VAL | 200 | 20.234 | 42.185 | −13.775 |
| 1585 | CA | VAL | 200 | 19.863 | 43.558 | −14.145 |

TABLE 9-continued

| Atom No. | Atom Type | Residue | Residue Position | X Coord. | Y Coord. | Z Coord. |
|---|---|---|---|---|---|---|
| 1586 | C | VAL | 200 | 20.852 | 44.576 | −13.569 |
| 1587 | O | VAL | 200 | 21.142 | 45.582 | −14.229 |
| 1588 | CB | VAL | 200 | 18.428 | 43.848 | −13.700 |
| 1589 | CG1 | VAL | 200 | 18.211 | 43.610 | −12.214 |
| 1590 | CG2 | VAL | 200 | 17.987 | 45.255 | −14.088 |
| 1591 | N | GLY | 201 | 21.570 | 44.170 | −12.534 |
| 1592 | CA | GLY | 201 | 22.654 | 44.970 | −11.971 |
| 1593 | C | GLY | 201 | 23.776 | 45.166 | −12.977 |
| 1594 | O | GLY | 201 | 24.055 | 46.308 | −13.357 |
| 1595 | N | PHE | 202 | 24.266 | 44.081 | −13.555 |
| 1596 | CA | PHE | 202 | 25.374 | 44.189 | −14.511 |
| 1597 | C | PHE | 202 | 24.909 | 44.633 | −15.903 |
| 1598 | O | PHE | 202 | 25.728 | 45.070 | −16.716 |
| 1599 | CB | PHE | 202 | 26.083 | 42.842 | −14.591 |
| 1600 | CG | PHE | 202 | 27.459 | 42.897 | −15.252 |
| 1601 | CD1 | PHE | 202 | 28.542 | 43.397 | −14.541 |
| 1602 | CD2 | PHE | 202 | 27.633 | 42.449 | −16.556 |
| 1603 | CE1 | PHE | 202 | 29.798 | 43.450 | −15.132 |
| 1604 | CE2 | PHE | 202 | 28.889 | 42.502 | −17.147 |
| 1605 | CZ | PHE | 202 | 29.971 | 43.003 | −16.435 |
| 1606 | N | GLU | 203 | 23.606 | 44.665 | −16.128 |
| 1607 | CA | GLU | 203 | 23.082 | 45.257 | −17.361 |
| 1608 | C | GLU | 203 | 22.865 | 46.766 | −17.217 |
| 1609 | O | GLU | 203 | 22.698 | 47.465 | −18.223 |
| 1610 | CB | GLU | 203 | 21.770 | 44.565 | −17.702 |
| 1611 | CG | GLU | 203 | 22.017 | 43.109 | −18.077 |
| 1612 | CD | GLU | 203 | 20.702 | 42.338 | −18.087 |
| 1613 | OE1 | GLU | 203 | 19.845 | 42.667 | −17.277 |
| 1614 | OE2 | GLU | 203 | 20.612 | 41.371 | −18.830 |
| 1615 | N | ARG | 204 | 22.935 | 47.262 | −15.992 |
| 1616 | CA | ARG | 204 | 22.814 | 48.697 | −15.739 |
| 1617 | C | ARG | 204 | 24.189 | 49.305 | −15.461 |
| 1618 | O | ARG | 204 | 24.481 | 50.439 | −15.857 |
| 1619 | CB | ARG | 204 | 21.949 | 48.852 | −14.492 |
| 1620 | CG | ARG | 204 | 21.441 | 50.275 | −14.299 |
| 1621 | CD | ARG | 204 | 20.316 | 50.580 | −15.280 |
| 1622 | NE | ARG | 204 | 19.214 | 49.616 | −15.102 |
| 1623 | CZ | ARG | 204 | 18.088 | 49.887 | −14.436 |
| 1624 | NH1 | ARG | 204 | 17.884 | 51.105 | −13.928 |
| 1625 | NH2 | ARG | 204 | 17.148 | 48.948 | −14.308 |
| 1626 | N | TYR | 205 | 25.037 | 48.515 | −14.823 |
| 1627 | CA | TYR | 205 | 26.380 | 48.958 | −14.431 |
| 1628 | C | TYR | 205 | 27.438 | 47.941 | −14.851 |
| 1629 | O | TYR | 205 | 28.225 | 47.477 | −14.014 |
| 1630 | CB | TYR | 205 | 26.428 | 49.081 | −12.908 |
| 1631 | CG | TYR | 205 | 25.343 | 49.944 | −12.267 |
| 1632 | CD1 | TYR | 205 | 24.314 | 49.340 | −11.553 |
| 1633 | CD2 | TYR | 205 | 25.391 | 51.328 | −12.381 |
| 1634 | CE1 | TYR | 205 | 23.328 | 50.119 | −10.963 |
| 1635 | CE2 | TYR | 205 | 24.407 | 52.108 | −11.788 |
| 1636 | CZ | TYR | 205 | 23.379 | 51.502 | −11.079 |
| 1637 | OH | TYR | 205 | 22.454 | 52.277 | −10.412 |
| 1638 | N | GLY | 206 | 27.492 | 47.640 | −16.137 |
| 1639 | CA | GLY | 206 | 28.411 | 46.606 | −16.634 |
| 1640 | C | GLY | 206 | 29.811 | 47.120 | −16.957 |
| 1641 | O | GLY | 206 | 30.176 | 47.293 | −18.126 |
| 1642 | N | ASP | 207 | 30.604 | 47.327 | −15.922 |
| 1643 | CA | ASP | 207 | 31.978 | 47.777 | −16.136 |
| 1644 | C | ASP | 207 | 32.921 | 46.576 | −16.189 |
| 1645 | O | ASP | 207 | 33.416 | 46.097 | −15.158 |
| 1646 | CB | ASP | 207 | 32.378 | 48.741 | −15.026 |
| 1647 | CG | ASP | 207 | 33.669 | 49.449 | −15.421 |
| 1648 | OD1 | ASP | 207 | 34.696 | 48.784 | −15.391 |
| 1649 | OD2 | ASP | 207 | 33.570 | 50.534 | −15.971 |
| 1650 | N | GLU | 208 | 33.373 | 46.305 | −17.404 |
| 1651 | CA | GLU | 208 | 34.203 | 45.128 | −17.689 |
| 1652 | C | GLU | 208 | 35.558 | 45.150 | −16.982 |
| 1653 | O | GLU | 208 | 35.922 | 44.146 | −16.358 |
| 1654 | CB | GLU | 208 | 34.454 | 45.110 | −19.195 |
| 1655 | CG | GLU | 208 | 35.088 | 43.806 | −19.672 |
| 1656 | CD | GLU | 208 | 34.010 | 42.752 | −19.914 |
| 1657 | OE1 | GLU | 208 | 32.858 | 43.062 | −19.642 |
| 1658 | OE2 | GLU | 208 | 34.322 | 41.781 | −20.589 |
| 1659 | N | SER | 209 | 36.147 | 46.327 | −16.839 |
| 1660 | CA | SER | 209 | 37.486 | 46.408 | −16.245 |
| 1661 | C | SER | 209 | 37.458 | 46.327 | −14.719 |

TABLE 9-continued

| Atom No. | Atom Type | Residue | Residue Position | X Coord. | Y Coord. | Z Coord. |
|---|---|---|---|---|---|---|
| 1662 | O | SER | 209 | 38.397 | 45.778 | −14.137 |
| 1663 | CB | SER | 209 | 38.158 | 47.708 | −16.679 |
| 1664 | OG | SER | 209 | 37.427 | 48.802 | −16.142 |
| 1665 | N | LYS | 210 | 36.315 | 46.601 | −14.113 |
| 1666 | CA | LYS | 210 | 36.203 | 46.482 | −12.658 |
| 1667 | C | LYS | 210 | 35.884 | 45.051 | −12.254 |
| 1668 | O | LYS | 210 | 36.476 | 44.543 | −11.291 |
| 1669 | CB | LYS | 210 | 35.110 | 47.417 | −12.166 |
| 1670 | CG | LYS | 210 | 35.590 | 48.858 | −12.100 |
| 1671 | CD | LYS | 210 | 36.686 | 49.001 | −11.051 |
| 1672 | CE | LYS | 210 | 37.137 | 50.449 | −10.904 |
| 1673 | NZ | LYS | 210 | 38.162 | 50.572 | −9.855 |
| 1674 | N | LEU | 211 | 35.247 | 44.333 | −13.164 |
| 1675 | CA | LEU | 211 | 34.956 | 42.923 | −12.914 |
| 1676 | C | LEU | 211 | 36.205 | 42.084 | −13.167 |
| 1677 | O | LEU | 211 | 36.451 | 41.101 | −12.457 |
| 1678 | CB | LEU | 211 | 33.845 | 42.487 | −13.858 |
| 1679 | CG | LEU | 211 | 33.291 | 41.126 | −13.461 |
| 1680 | CD1 | LEU | 211 | 32.623 | 41.201 | −12.094 |
| 1681 | CD2 | LEU | 211 | 32.294 | 40.633 | −14.496 |
| 1682 | N | ALA | 212 | 37.077 | 42.599 | −14.020 |
| 1683 | CA | ALA | 212 | 38.372 | 41.961 | −14.269 |
| 1684 | C | ALA | 212 | 39.448 | 42.367 | −13.257 |
| 1685 | O | ALA | 212 | 40.499 | 41.719 | −13.191 |
| 1686 | CB | ALA | 212 | 38.830 | 42.334 | −15.675 |
| 1687 | N | SER | 213 | 39.182 | 43.389 | −12.457 |
| 1688 | CA | SER | 213 | 40.112 | 43.751 | −11.385 |
| 1689 | C | SER | 213 | 39.782 | 42.954 | −10.133 |
| 1690 | O | SER | 213 | 40.681 | 42.542 | −9.390 |
| 1691 | CB | SER | 213 | 39.996 | 45.241 | −11.086 |
| 1692 | OG | SER | 213 | 40.433 | 45.952 | −12.234 |
| 1693 | N | ASP | 214 | 38.495 | 42.735 | −9.922 |
| 1694 | CA | ASP | 214 | 38.040 | 41.816 | −8.875 |
| 1695 | C | ASP | 214 | 36.553 | 41.551 | −9.053 |
| 1696 | O | ASP | 214 | 35.708 | 42.383 | −8.688 |
| 1697 | CB | ASP | 214 | 38.312 | 42.372 | −7.475 |
| 1698 | CG | ASP | 214 | 38.140 | 41.260 | −6.432 |
| 1699 | OD1 | ASP | 214 | 39.149 | 40.828 | −5.896 |
| 1700 | OD2 | ASP | 214 | 37.033 | 40.735 | −6.355 |
| 1701 | N | PRO | 215 | 36.264 | 40.301 | −9.370 |
| 1702 | CA | PRO | 215 | 34.898 | 39.868 | −9.657 |
| 1703 | C | PRO | 215 | 33.919 | 40.125 | −8.515 |
| 1704 | O | PRO | 215 | 33.011 | 40.945 | −8.695 |
| 1705 | CB | PRO | 215 | 35.006 | 38.407 | −9.948 |
| 1706 | CG | PRO | 215 | 36.465 | 37.981 | −9.893 |
| 1707 | CD | PRO | 215 | 37.248 | 39.231 | −9.544 |
| 1708 | N | ILE | 216 | 34.247 | 39.688 | −7.308 |
| 1709 | CA | ILE | 216 | 33.285 | 39.802 | −6.202 |
| 1710 | C | ILE | 216 | 33.198 | 41.220 | −5.635 |
| 1711 | O | ILE | 216 | 32.092 | 41.659 | −5.294 |
| 1712 | CB | ILE | 216 | 33.677 | 38.819 | −5.105 |
| 1713 | CG1 | ILE | 216 | 33.682 | 37.396 | −5.646 |
| 1714 | CG2 | ILE | 216 | 32.732 | 38.920 | −3.911 |
| 1715 | CD1 | ILE | 216 | 33.971 | 36.393 | −4.538 |
| 1716 | N | ASN | 217 | 34.242 | 42.010 | −5.835 |
| 1717 | CA | ASN | 217 | 34.192 | 43.415 | −5.417 |
| 1718 | C | ASN | 217 | 33.287 | 44.212 | −6.342 |
| 1719 | O | ASN | 217 | 32.394 | 44.924 | −5.859 |
| 1720 | CB | ASN | 217 | 35.583 | 44.039 | −5.463 |
| 1721 | CG | ASN | 217 | 36.445 | 43.618 | −4.277 |
| 1722 | OD1 | ASN | 217 | 36.743 | 42.435 | −4.083 |
| 1723 | ND2 | ASN | 217 | 36.923 | 44.615 | −3.554 |
| 1724 | N | HIS | 218 | 33.325 | 43.892 | −7.624 |
| 1725 | CA | HIS | 218 | 32.470 | 44.609 | −8.560 |
| 1726 | C | HIS | 218 | 31.037 | 44.098 | −8.505 |
| 1727 | O | HIS | 218 | 30.115 | 44.923 | −8.524 |
| 1728 | CB | HIS | 218 | 33.013 | 44.452 | −9.967 |
| 1729 | CG | HIS | 218 | 32.255 | 45.304 | −10.959 |
| 1730 | ND1 | HIS | 218 | 31.944 | 46.605 | −10.813 |
| 1731 | CD2 | HIS | 218 | 31.746 | 44.903 | −12.170 |
| 1732 | CE1 | HIS | 218 | 31.266 | 47.026 | −11.899 |
| 1733 | NE2 | HIS | 218 | 31.144 | 45.971 | −12.737 |
| 1734 | N | LEU | 219 | 30.862 | 42.841 | −8.129 |
| 1735 | CA | LEU | 219 | 29.510 | 42.292 | −7.983 |
| 1736 | C | LEU | 219 | 28.816 | 42.804 | −6.725 |
| 1737 | O | LEU | 219 | 27.621 | 43.109 | −6.794 |

TABLE 9-continued

| Atom No. | Atom Type | Residue | Residue Position | X Coord. | Y Coord. | Z Coord. |
|---|---|---|---|---|---|---|
| 1738 | CB | LEU | 219 | 29.581 | 40.770 | −7.935 |
| 1739 | CG | LEU | 219 | 30.037 | 40.191 | −9.270 |
| 1740 | CD1 | LEU | 219 | 30.215 | 38.679 | −9.180 |
| 1741 | CD2 | LEU | 219 | 29.067 | 40.561 | −10.387 |
| 1742 | N | PHE | 220 | 29.583 | 43.150 | −5.704 |
| 1743 | CA | PHE | 220 | 28.984 | 43.755 | −4.513 |
| 1744 | C | PHE | 220 | 28.693 | 45.239 | −4.727 |
| 1745 | O | PHE | 220 | 27.616 | 45.706 | −4.337 |
| 1746 | CB | PHE | 220 | 29.943 | 43.591 | −3.343 |
| 1747 | CG | PHE | 220 | 29.391 | 44.125 | −2.026 |
| 1748 | CD1 | PHE | 220 | 28.164 | 43.673 | −1.556 |
| 1749 | CD2 | PHE | 220 | 30.113 | 45.058 | −1.295 |
| 1750 | CE1 | PHE | 220 | 27.659 | 44.156 | −0.356 |
| 1751 | CE2 | PHE | 220 | 29.608 | 45.542 | −0.095 |
| 1752 | CZ | PHE | 220 | 28.381 | 45.091 | 0.374 |
| 1753 | N | GLU | 221 | 29.498 | 45.893 | −5.551 |
| 1754 | CA | GLU | 221 | 29.253 | 47.305 | −5.882 |
| 1755 | C | GLU | 221 | 28.001 | 47.439 | −6.737 |
| 1756 | O | GLU | 221 | 27.070 | 48.170 | −6.370 |
| 1757 | CB | GLU | 221 | 30.439 | 47.825 | −6.682 |
| 1758 | CG | GLU | 221 | 31.710 | 47.865 | −5.848 |
| 1759 | CD | GLU | 221 | 32.919 | 47.907 | −6.776 |
| 1760 | OE1 | GLU | 221 | 34.027 | 47.774 | −6.271 |
| 1761 | OE2 | GLU | 221 | 32.704 | 47.875 | −7.982 |
| 1762 | N | VAL | 222 | 27.881 | 46.525 | −7.684 |
| 1763 | CA | VAL | 222 | 26.726 | 46.474 | −8.576 |
| 1764 | C | VAL | 222 | 25.458 | 46.030 | −7.857 |
| 1765 | O | VAL | 222 | 24.403 | 46.634 | −8.082 |
| 1766 | CB | VAL | 222 | 27.076 | 45.488 | −9.684 |
| 1767 | CG1 | VAL | 222 | 25.850 | 44.871 | −10.334 |
| 1768 | CG2 | VAL | 222 | 27.992 | 46.123 | −10.721 |
| 1769 | N | TYR | 223 | 25.609 | 45.225 | −6.818 |
| 1770 | CA | TYR | 223 | 24.449 | 44.762 | −6.065 |
| 1771 | C | TYR | 223 | 23.940 | 45.841 | −5.118 |
| 1772 | O | TYR | 223 | 22.720 | 45.998 | −4.983 |
| 1773 | CB | TYR | 223 | 24.853 | 43.533 | −5.264 |
| 1774 | CG | TYR | 223 | 23.673 | 42.718 | −4.753 |
| 1775 | CD1 | TYR | 223 | 22.582 | 42.497 | −5.585 |
| 1776 | CD2 | TYR | 223 | 23.691 | 42.186 | −3.470 |
| 1777 | CE1 | TYR | 223 | 21.509 | 41.742 | −5.136 |
| 1778 | CE2 | TYR | 223 | 22.615 | 41.434 | −3.019 |
| 1779 | CZ | TYR | 223 | 21.528 | 41.212 | −3.854 |
| 1780 | OH | TYR | 223 | 20.459 | 40.466 | −3.409 |
| 1781 | N | VAL | 224 | 24.823 | 46.711 | −4.658 |
| 1782 | CA | VAL | 224 | 24.379 | 47.820 | −3.816 |
| 1783 | C | VAL | 224 | 23.676 | 48.880 | −4.655 |
| 1784 | O | VAL | 224 | 22.513 | 49.184 | −4.360 |
| 1785 | CB | VAL | 224 | 25.582 | 48.429 | −3.102 |
| 1786 | CG1 | VAL | 224 | 25.202 | 49.711 | −2.368 |
| 1787 | CG2 | VAL | 224 | 26.205 | 47.430 | −2.135 |
| 1788 | N | LYS | 225 | 24.197 | 49.124 | −5.847 |
| 1789 | CA | LYS | 225 | 23.607 | 50.146 | −6.717 |
| 1790 | C | LYS | 225 | 22.306 | 49.691 | −7.376 |
| 1791 | O | LYS | 225 | 21.354 | 50.481 | −7.445 |
| 1792 | CB | LYS | 225 | 24.631 | 50.511 | −7.782 |
| 1793 | CG | LYS | 225 | 25.876 | 51.135 | −7.166 |
| 1794 | CD | LYS | 225 | 26.923 | 51.441 | −8.230 |
| 1795 | CE | LYS | 225 | 27.324 | 50.178 | −8.983 |
| 1796 | NZ | LYS | 225 | 28.400 | 50.446 | −9.950 |
| 1797 | N | ILE | 226 | 22.157 | 48.394 | −7.595 |
| 1798 | CA | ILE | 226 | 20.894 | 47.912 | −8.154 |
| 1799 | C | ILE | 226 | 19.833 | 47.724 | −7.061 |
| 1800 | O | ILE | 226 | 18.654 | 47.969 | −7.343 |
| 1801 | CB | ILE | 226 | 21.133 | 46.641 | −8.969 |
| 1802 | CG1 | ILE | 226 | 19.936 | 46.336 | −9.860 |
| 1803 | CG2 | ILE | 226 | 21.454 | 45.436 | −8.094 |
| 1804 | CD1 | ILE | 226 | 19.777 | 47.392 | −10.949 |
| 1805 | N | ASN | 227 | 20.258 | 47.648 | −5.805 |
| 1806 | CA | ASN | 227 | 19.308 | 47.678 | −4.686 |
| 1807 | C | ASN | 227 | 18.854 | 49.103 | −4.414 |
| 1808 | O | ASN | 227 | 17.676 | 49.319 | −4.111 |
| 1809 | CB | ASN | 227 | 19.955 | 47.129 | −3.418 |
| 1810 | CG | ASN | 227 | 19.618 | 45.655 | −3.212 |
| 1811 | OD1 | ASN | 227 | 18.512 | 45.307 | −2.782 |
| 1812 | ND2 | ASN | 227 | 20.574 | 44.804 | −3.526 |
| 1813 | N | GLN | 228 | 19.673 | 50.066 | −4.801 |

TABLE 9-continued

| Atom No. | Atom Type | Residue | Residue Position | X Coord. | Y Coord. | Z Coord. |
|---|---|---|---|---|---|---|
| 1814 | CA | GLN | 228 | 19.262 | 51.466 | −4.709 |
| 1815 | C | GLN | 228 | 18.313 | 51.830 | −5.848 |
| 1816 | O | GLN | 228 | 17.310 | 52.508 | −5.593 |
| 1817 | CB | GLN | 228 | 20.516 | 52.325 | −4.735 |
| 1818 | CG | GLN | 228 | 21.387 | 51.966 | −3.538 |
| 1819 | CD | GLN | 228 | 22.730 | 52.681 | −3.599 |
| 1820 | OE1 | GLN | 228 | 23.646 | 52.269 | −4.321 |
| 1821 | NE2 | GLN | 228 | 22.849 | 53.719 | −2.790 |
| 1822 | N | ASP | 229 | 18.413 | 51.091 | −6.944 |
| 1823 | CA | ASP | 229 | 17.461 | 51.230 | −8.053 |
| 1824 | C | ASP | 229 | 16.135 | 50.519 | −7.765 |
| 1825 | O | ASP | 229 | 15.126 | 50.828 | −8.412 |
| 1826 | CB | ASP | 229 | 18.066 | 50.615 | −9.313 |
| 1827 | CG | ASP | 229 | 19.405 | 51.245 | −9.684 |
| 1828 | OD1 | ASP | 229 | 19.522 | 52.458 | −9.580 |
| 1829 | OD2 | ASP | 229 | 20.230 | 50.517 | −10.219 |
| 1830 | N | VAL | 230 | 16.102 | 49.663 | −6.755 |
| 1831 | CA | VAL | 230 | 14.844 | 49.035 | −6.339 |
| 1832 | C | VAL | 230 | 14.203 | 49.790 | −5.175 |
| 1833 | O | VAL | 230 | 12.979 | 49.947 | −5.143 |
| 1834 | CB | VAL | 230 | 15.123 | 47.598 | −5.899 |
| 1835 | CG1 | VAL | 230 | 13.864 | 46.923 | −5.367 |
| 1836 | CG2 | VAL | 230 | 15.720 | 46.770 | −7.027 |
| 1837 | N | THR | 231 | 15.019 | 50.393 | −4.328 |
| 1838 | CA | THR | 231 | 14.479 | 51.091 | −3.147 |
| 1839 | C | THR | 231 | 14.123 | 52.555 | −3.403 |
| 1840 | O | THR | 231 | 13.278 | 53.115 | −2.698 |
| 1841 | CB | THR | 231 | 15.495 | 51.019 | −2.009 |
| 1842 | OG1 | THR | 231 | 16.725 | 51.574 | −2.454 |
| 1843 | CG2 | THR | 231 | 15.745 | 49.578 | −1.574 |
| 1844 | N | LYS | 232 | 14.768 | 53.166 | −4.383 |
| 1845 | CA | LYS | 232 | 14.414 | 54.530 | −4.783 |
| 1846 | C | LYS | 232 | 13.662 | 54.494 | −6.115 |
| 1847 | O | LYS | 232 | 12.981 | 55.458 | −6.493 |
| 1848 | CB | LYS | 232 | 15.693 | 55.352 | −4.909 |
| 1849 | CG | LYS | 232 | 16.529 | 55.254 | −3.636 |
| 1850 | CD | LYS | 232 | 17.786 | 56.116 | −3.699 |
| 1851 | CE | LYS | 232 | 17.426 | 57.593 | −3.869 |
| 1852 | NZ | LYS | 232 | 18.619 | 58.452 | −3.842 |
| 1853 | N | GLU | 233 | 13.689 | 53.309 | −6.707 |
| 1854 | CA | GLU | 233 | 13.052 | 52.961 | −7.991 |
| 1855 | C | GLU | 233 | 13.059 | 54.004 | −9.099 |
| 1856 | O | GLU | 233 | 12.297 | 54.979 | −9.039 |
| 1857 | CB | GLU | 233 | 11.624 | 52.476 | −7.780 |
| 1858 | CG | GLU | 233 | 11.561 | 50.971 | −7.545 |
| 1859 | CD | GLU | 233 | 12.145 | 50.185 | −8.727 |
| 1860 | OE1 | GLU | 233 | 12.307 | 50.768 | −9.796 |
| 1861 | OE2 | GLU | 233 | 12.304 | 48.978 | −8.595 |
| 1862 | N | THR | 234 | 13.618 | 53.554 | −10.215 |
| 1863 | CA | THR | 234 | 13.707 | 54.302 | −11.486 |
| 1864 | C | THR | 234 | 13.736 | 55.822 | −11.355 |
| 1865 | O | THR | 234 | 14.451 | 56.367 | −10.507 |
| 1866 | CB | THR | 234 | 12.544 | 53.862 | −12.365 |
| 1867 | OG1 | THR | 234 | 11.349 | 53.933 | −11.593 |
| 1868 | CG2 | THR | 234 | 12.721 | 52.416 | −12.810 |
| 1869 | N | SER | 235 | 13.153 | 56.481 | −12.342 |
| 1870 | CA | SER | 235 | 13.152 | 57.946 | −12.364 |
| 1871 | C | SER | 235 | 11.791 | 58.534 | −12.736 |
| 1872 | O | SER | 235 | 11.288 | 59.423 | −12.039 |
| 1873 | CB | SER | 235 | 14.201 | 58.412 | −13.362 |
| 1874 | OG | SER | 235 | 15.450 | 57.883 | −12.940 |
| 1875 | N | GLU | 236 | 11.247 | 58.061 | −13.854 |
| 1876 | CA | GLU | 236 | 9.971 | 58.532 | −14.456 |
| 1877 | C | GLU | 236 | 9.956 | 60.052 | −14.724 |
| 1878 | O | GLU | 236 | 10.209 | 60.867 | −13.824 |
| 1879 | CB | GLU | 236 | 8.807 | 58.099 | −13.566 |
| 1880 | CG | GLU | 236 | 7.444 | 58.429 | −14.166 |
| 1881 | CD | GLU | 236 | 6.302 | 57.935 | −13.273 |
| 1882 | OE1 | GLU | 236 | 5.548 | 58.775 | −12.805 |
| 1883 | OE2 | GLU | 236 | 6.020 | 56.749 | −13.371 |
| 1884 | N | ALA | 237 | 9.583 | 60.403 | −15.950 |
| 1885 | CA | ALA | 237 | 9.606 | 61.792 | −16.452 |
| 1886 | C | ALA | 237 | 9.229 | 62.860 | −15.423 |
| 1887 | O | ALA | 237 | 8.303 | 62.695 | −14.618 |
| 1888 | CB | ALA | 237 | 8.681 | 61.896 | −17.663 |
| 1889 | N | THR | 238 | 10.041 | 63.907 | −15.436 |

TABLE 9-continued

| Atom No. | Atom Type | Residue | Residue Position | X Coord. | Y Coord. | Z Coord. |
|---|---|---|---|---|---|---|
| 1890 | CA | THR | 238 | 10.026 | 65.015 | −14.464 |
| 1891 | C | THR | 238 | 9.830 | 64.605 | −13.002 |
| 1892 | O | THR | 238 | 8.912 | 65.110 | −12.344 |
| 1893 | CB | THR | 238 | 8.987 | 66.055 | −14.880 |
| 1894 | OG1 | THR | 238 | 7.734 | 65.420 | −15.104 |
| 1895 | CG2 | THR | 238 | 9.401 | 66.745 | −16.177 |
| 1896 | N | GLY | 239 | 10.655 | 63.672 | −12.539 |
| 1897 | CA | GLY | 239 | 10.727 | 63.289 | −11.123 |
| 1898 | C | GLY | 239 | 9.407 | 62.762 | −10.569 |
| 1899 | O | GLY | 239 | 9.005 | 63.140 | −9.461 |
| 1900 | N | GLU | 240 | 8.722 | 61.922 | −11.327 |
| 1901 | CA | GLU | 240 | 7.379 | 61.533 | −10.897 |
| 1902 | C | GLU | 240 | 7.312 | 60.073 | −10.436 |
| 1903 | O | GLU | 240 | 7.886 | 59.157 | −11.033 |
| 1904 | CB | GLU | 240 | 6.406 | 61.910 | −12.016 |
| 1905 | CG | GLU | 240 | 6.388 | 63.436 | −12.217 |
| 1906 | CD | GLU | 240 | 5.518 | 63.865 | −13.405 |
| 1907 | OE1 | GLU | 240 | 5.140 | 62.996 | −14.180 |
| 1908 | OE2 | GLU | 240 | 5.204 | 65.049 | −13.502 |
| 1909 | N | THR | 241 | 6.572 | 59.898 | −9.356 |
| 1910 | CA | THR | 241 | 6.466 | 58.634 | −8.592 |
| 1911 | C | THR | 241 | 7.820 | 57.983 | −8.206 |
| 1912 | O | THR | 241 | 8.039 | 56.809 | −8.535 |
| 1913 | CB | THR | 241 | 5.639 | 57.640 | −9.416 |
| 1914 | OG1 | THR | 241 | 4.582 | 58.337 | −10.066 |
| 1915 | CG2 | THR | 241 | 5.022 | 56.549 | −8.545 |
| 1916 | N | PRO | 242 | 8.683 | 58.659 | −7.449 |
| 1917 | CA | PRO | 242 | 9.881 | 57.977 | −6.935 |
| 1918 | C | PRO | 242 | 9.514 | 57.016 | −5.800 |
| 1919 | O | PRO | 242 | 8.508 | 57.227 | −5.109 |
| 1920 | CB | PRO | 242 | 10.779 | 59.081 | −6.462 |
| 1921 | CG | PRO | 242 | 9.981 | 60.377 | −6.412 |
| 1922 | CD | PRO | 242 | 8.586 | 60.029 | −6.913 |
| 1923 | N | ALA | 243 | 10.233 | 55.900 | −5.740 |
| 1924 | CA | ALA | 243 | 10.086 | 54.820 | −4.727 |
| 1925 | C | ALA | 243 | 8.848 | 53.913 | −4.867 |
| 1926 | O | ALA | 243 | 8.932 | 52.718 | −4.556 |
| 1927 | CB | ALA | 243 | 10.169 | 55.408 | −3.324 |
| 1928 | N | GLU | 244 | 7.767 | 54.435 | −5.424 |
| 1929 | CA | GLU | 244 | 6.573 | 53.640 | −5.728 |
| 1930 | C | GLU | 244 | 6.600 | 53.132 | −7.168 |
| 1931 | O | GLU | 244 | 5.562 | 52.705 | −7.681 |
| 1932 | CB | GLU | 244 | 5.315 | 54.464 | −5.483 |
| 1933 | CG | GLU | 244 | 4.532 | 53.978 | −4.256 |
| 1934 | CD | GLU | 244 | 5.333 | 54.158 | −2.966 |
| 1935 | OE1 | GLU | 244 | 6.056 | 55.139 | −2.866 |
| 1936 | OE2 | GLU | 244 | 5.156 | 53.341 | −2.078 |
| 1937 | N | THR | 245 | 7.757 | 53.282 | −7.802 |
| 1938 | CA | THR | 245 | 8.108 | 52.733 | −9.126 |
| 1939 | C | THR | 245 | 7.484 | 53.527 | −10.249 |
| 1940 | O | THR | 245 | 6.488 | 54.237 | −10.084 |
| 1941 | CB | THR | 245 | 7.753 | 51.261 | −9.322 |
| 1942 | OG1 | THR | 245 | 6.408 | 51.154 | −9.773 |
| 1943 | CG2 | THR | 245 | 7.993 | 50.395 | −8.090 |
| 1944 | N | ILE | 246 | 8.102 | 53.390 | −11.404 |
| 1945 | CA | ILE | 246 | 7.553 | 54.061 | −12.580 |
| 1946 | C | ILE | 246 | 6.316 | 53.270 | −12.997 |
| 1947 | O | ILE | 246 | 6.293 | 52.041 | −12.856 |
| 1948 | CB | ILE | 246 | 8.628 | 54.096 | −13.676 |
| 1949 | CG1 | ILE | 246 | 8.171 | 54.732 | −14.981 |
| 1950 | CG2 | ILE | 246 | 9.174 | 52.718 | −13.972 |
| 1951 | CD1 | ILE | 246 | 9.132 | 54.376 | −16.113 |
| 1952 | N | ASP | 247 | 5.279 | 53.986 | −13.402 |
| 1953 | CA | ASP | 247 | 4.039 | 53.383 | −13.896 |
| 1954 | C | ASP | 247 | 4.308 | 52.377 | −15.009 |
| 1955 | O | ASP | 247 | 5.267 | 52.527 | −15.779 |
| 1956 | CB | ASP | 247 | 3.147 | 54.502 | −14.427 |
| 1957 | CG | ASP | 247 | 2.749 | 55.467 | −13.310 |
| 1958 | OD1 | ASP | 247 | 2.128 | 54.991 | −12.366 |
| 1959 | OD2 | ASP | 247 | 2.840 | 56.662 | −13.541 |
| 1960 | N | ALA | 248 | 3.438 | 51.380 | −15.101 |
| 1961 | CA | ALA | 248 | 3.611 | 50.306 | −16.090 |
| 1962 | C | ALA | 248 | 3.529 | 50.806 | −17.527 |
| 1963 | O | ALA | 248 | 3.340 | 51.993 | −17.809 |
| 1964 | CB | ALA | 248 | 2.593 | 49.199 | −15.859 |
| 1965 | N | SER | 249 | 3.581 | 49.850 | −18.435 |
| 1966 | CA | SER | 249 | 3.740 | 50.162 | −19.856 |
| 1967 | C | SER | 249 | 2.446 | 50.596 | −20.559 |
| 1968 | O | SER | 249 | 2.511 | 51.133 | −21.670 |
| 1969 | CB | SER | 249 | 4.307 | 48.915 | −20.523 |
| 1970 | OG | SER | 249 | 5.542 | 48.597 | −19.885 |
| 1971 | N | GLU | 250 | 1.304 | 50.432 | −19.905 |
| 1972 | CA | GLU | 250 | 0.019 | 50.909 | −20.456 |
| 1973 | C | GLU | 250 | −1.002 | 51.186 | −19.355 |
| 1974 | O | GLU | 250 | −0.658 | 51.683 | −18.276 |
| 1975 | CB | GLU | 250 | −0.571 | 49.929 | −21.469 |
| 1976 | CG | GLU | 250 | −0.164 | 50.279 | −22.900 |
| 1977 | CD | GLU | 250 | −1.000 | 49.491 | −23.905 |
| 1978 | OE1 | GLU | 250 | −1.835 | 50.112 | −24.554 |
| 1979 | OE2 | GLU | 250 | −0.786 | 48.293 | −24.016 |
| 1980 | N | GLN | 251 | −2.217 | 50.708 | −19.584 |
| 1981 | CA | GLN | 251 | −3.372 | 51.025 | −18.733 |
| 1982 | C | GLN | 251 | −3.477 | 50.106 | −17.508 |
| 1983 | O | GLN | 251 | −4.315 | 50.335 | −16.628 |
| 1984 | CB | GLN | 251 | −4.651 | 50.863 | −19.567 |
| 1985 | CG | GLN | 251 | −4.639 | 51.611 | −20.903 |
| 1986 | CD | GLN | 251 | −4.285 | 50.695 | −22.082 |
| 1987 | OE1 | GLN | 251 | −3.608 | 49.672 | −21.912 |
| 1988 | NE2 | GLN | 251 | −4.668 | 51.120 | −23.273 |
| 1989 | N | ASP | 252 | −2.626 | 49.097 | −17.431 |
| 1990 | CA | ASP | 252 | −2.715 | 48.141 | −16.325 |
| 1991 | C | ASP | 252 | −1.649 | 48.402 | −15.256 |
| 1992 | O | ASP | 252 | −0.489 | 48.018 | −15.433 |
| 1993 | CB | ASP | 252 | −2.558 | 46.720 | −16.879 |
| 1994 | CG | ASP | 252 | −3.682 | 46.372 | −17.859 |
| 1995 | OD1 | ASP | 252 | −3.495 | 46.622 | −19.040 |
| 1996 | OD2 | ASP | 252 | −4.708 | 45.874 | −17.412 |
| 1997 | N | GLU | 253 | −2.091 | 48.954 | −14.129 |
| 1998 | CA | GLU | 253 | −1.274 | 49.118 | −12.895 |
| 1999 | C | GLU | 253 | −0.097 | 50.107 | −12.980 |
| 2000 | O | GLU | 253 | 0.550 | 50.288 | −14.014 |
| 2001 | CB | GLU | 253 | −0.754 | 47.759 | −12.432 |
| 2002 | CG | GLU | 253 | −1.889 | 46.817 | −12.056 |
| 2003 | CD | GLU | 253 | −1.304 | 45.521 | −11.509 |
| 2004 | OE1 | GLU | 253 | −0.324 | 45.616 | −10.787 |
| 2005 | OE2 | GLU | 253 | −1.896 | 44.481 | −11.744 |
| 2006 | N | LYS | 254 | 0.199 | 50.707 | −11.839 |
| 2007 | CA | LYS | 254 | 1.275 | 51.702 | −11.716 |
| 2008 | C | LYS | 254 | 2.643 | 51.130 | −11.319 |
| 2009 | O | LYS | 254 | 3.604 | 51.894 | −11.210 |
| 2010 | CB | LYS | 254 | 0.844 | 52.636 | −10.595 |
| 2011 | CG | LYS | 254 | −0.591 | 53.120 | −10.787 |
| 2012 | CD | LYS | 254 | −1.165 | 53.696 | −9.496 |
| 2013 | CE | LYS | 254 | −0.292 | 54.825 | −8.948 |
| 2014 | NZ | LYS | 254 | −0.827 | 55.336 | −7.675 |
| 2015 | N | LYS | 255 | 2.766 | 49.820 | −11.201 |
| 2016 | CA | LYS | 255 | 3.899 | 49.273 | −10.454 |
| 2017 | C | LYS | 255 | 5.085 | 48.697 | −11.240 |
| 2018 | O | LYS | 255 | 5.214 | 48.843 | −12.465 |
| 2019 | CB | LYS | 255 | 3.376 | 48.278 | −9.431 |
| 2020 | CG | LYS | 255 | 2.341 | 47.301 | −9.973 |
| 2021 | CD | LYS | 255 | 1.806 | 46.481 | −8.807 |
| 2022 | CE | LYS | 255 | 1.220 | 47.394 | −7.737 |
| 2023 | NZ | LYS | 255 | 0.750 | 46.609 | −6.588 |
| 2024 | N | ILE | 256 | 5.811 | 47.859 | −10.507 |
| 2025 | CA | ILE | 256 | 7.219 | 47.514 | −10.753 |
| 2026 | C | ILE | 256 | 7.590 | 46.641 | −11.952 |
| 2027 | O | ILE | 256 | 8.773 | 46.295 | −12.056 |
| 2028 | CB | ILE | 256 | 7.715 | 46.796 | −9.505 |
| 2029 | CG1 | ILE | 256 | 6.822 | 47.100 | −8.314 |
| 2030 | CG2 | ILE | 256 | 9.146 | 47.196 | −9.189 |
| 2031 | CD1 | ILE | 256 | 7.297 | 46.366 | −7.070 |
| 2032 | N | GLN | 257 | 6.691 | 46.347 | −12.874 |
| 2033 | CA | GLN | 257 | 7.097 | 45.508 | −14.008 |
| 2034 | C | GLN | 257 | 7.784 | 46.349 | −15.082 |
| 2035 | O | GLN | 257 | 8.588 | 45.842 | −15.875 |
| 2036 | CB | GLN | 257 | 5.884 | 44.794 | −14.585 |
| 2037 | CG | GLN | 257 | 6.274 | 43.770 | −15.651 |
| 2038 | CD | GLN | 257 | 7.173 | 42.674 | −15.067 |
| 2039 | OE1 | GLN | 257 | 6.721 | 41.848 | −14.265 |
| 2040 | NE2 | GLN | 257 | 8.439 | 42.697 | −15.453 |
| 2041 | N | SER | 258 | 7.581 | 47.653 | −14.989 |

TABLE 9-continued

| Atom No. | Atom Type | Residue | Residue Position | X Coord. | Y Coord. | Z Coord. |
|---|---|---|---|---|---|---|
| 2042 | CA | SER | 258 | 8.335 | 48.606 | −15.809 |
| 2043 | C | SER | 258 | 9.542 | 49.136 | −15.030 |
| 2044 | O | SER | 258 | 10.278 | 50.004 | −15.512 |
| 2045 | CB | SER | 258 | 7.426 | 49.763 | −16.201 |
| 2046 | OG | SER | 258 | 7.018 | 50.418 | −15.009 |
| 2047 | N | SER | 259 | 9.709 | 48.630 | −13.818 |
| 2048 | CA | SER | 259 | 10.803 | 49.032 | −12.936 |
| 2049 | C | SER | 259 | 11.765 | 47.883 | −12.650 |
| 2050 | O | SER | 259 | 11.523 | 46.720 | −13.004 |
| 2051 | CB | SER | 259 | 10.240 | 49.559 | −11.625 |
| 2052 | OG | SER | 259 | 10.048 | 50.964 | −11.730 |
| 2053 | N | THR | 260 | 12.703 | 48.198 | −11.775 |
| 2054 | CA | THR | 260 | 13.889 | 47.360 | −11.569 |
| 2055 | C | THR | 260 | 13.601 | 46.007 | −10.923 |
| 2056 | O | THR | 260 | 14.057 | 44.977 | −11.437 |
| 2057 | CB | THR | 260 | 14.847 | 48.123 | −10.660 |
| 2058 | OG1 | THR | 260 | 15.052 | 49.437 | −11.164 |
| 2059 | CG2 | THR | 260 | 16.196 | 47.426 | −10.563 |
| 2060 | N | ASN | 261 | 12.685 | 45.976 | −9.969 |
| 2061 | CA | ASN | 261 | 12.448 | 44.735 | −9.225 |
| 2062 | C | ASN | 261 | 11.767 | 43.636 | −10.042 |
| 2063 | O | ASN | 261 | 12.285 | 42.511 | −10.073 |
| 2064 | CB | ASN | 261 | 11.611 | 45.067 | −7.998 |
| 2065 | CG | ASN | 261 | 11.127 | 43.785 | −7.332 |
| 2066 | OD1 | ASN | 261 | 9.934 | 43.468 | −7.377 |
| 2067 | ND2 | ASN | 261 | 12.065 | 43.038 | −6.776 |
| 2068 | N | GLU | 262 | 10.790 | 43.972 | −10.868 |
| 2069 | CA | GLU | 262 | 10.139 | 42.896 | −11.615 |
| 2070 | C | GLU | 262 | 10.860 | 42.596 | −12.929 |
| 2071 | O | GLU | 262 | 10.653 | 41.528 | −13.520 |
| 2072 | CB | GLU | 262 | 8.660 | 43.202 | −11.792 |
| 2073 | CG | GLU | 262 | 7.957 | 43.200 | −10.436 |
| 2074 | CD | GLU | 262 | 6.477 | 43.543 | −10.577 |
| 2075 | OE1 | GLU | 262 | 5.963 | 44.177 | −9.664 |
| 2076 | OE2 | GLU | 262 | 5.965 | 43.415 | −11.677 |
| 2077 | N | GLU | 263 | 11.849 | 43.412 | −13.259 |
| 2078 | CA | GLU | 263 | 12.761 | 43.053 | −14.345 |
| 2079 | C | GLU | 263 | 13.798 | 42.052 | −13.832 |
| 2080 | O | GLU | 263 | 14.015 | 41.023 | −14.484 |
| 2081 | CB | GLU | 263 | 13.444 | 44.319 | −14.853 |
| 2082 | CG | GLU | 263 | 12.446 | 45.224 | −15.568 |
| 2083 | CD | GLU | 263 | 13.054 | 46.604 | −15.803 |
| 2084 | OE1 | GLU | 263 | 13.765 | 47.070 | −14.922 |
| 2085 | OE2 | GLU | 263 | 12.742 | 47.199 | −16.824 |
| 2086 | N | ALA | 264 | 14.135 | 42.177 | −12.557 |
| 2087 | CA | ALA | 264 | 15.094 | 41.271 | −11.917 |
| 2088 | C | ALA | 264 | 14.513 | 39.890 | −11.637 |
| 2089 | O | ALA | 264 | 15.186 | 38.877 | −11.868 |
| 2090 | CB | ALA | 264 | 15.501 | 41.891 | −10.590 |
| 2091 | N | ARG | 265 | 13.223 | 39.827 | −11.348 |
| 2092 | CA | ARG | 265 | 12.617 | 38.513 | −11.125 |
| 2093 | C | ARG | 265 | 12.258 | 37.835 | −12.450 |
| 2094 | O | ARG | 265 | 12.271 | 36.599 | −12.519 |
| 2095 | CB | ARG | 265 | 11.390 | 38.636 | −10.227 |
| 2096 | CG | ARG | 265 | 10.212 | 39.303 | −10.919 |
| 2097 | CD | ARG | 265 | 8.993 | 39.365 | −10.012 |
| 2098 | NE | ARG | 265 | 7.803 | 39.721 | −10.798 |
| 2099 | CZ | ARG | 265 | 6.556 | 39.541 | −10.359 |
| 2100 | NH1 | ARG | 265 | 6.345 | 39.072 | −9.127 |
| 2101 | NH2 | ARG | 265 | 5.523 | 39.858 | −11.141 |
| 2102 | N | ARG | 266 | 12.237 | 38.605 | −13.529 |
| 2103 | CA | ARG | 266 | 12.017 | 38.014 | −14.842 |
| 2104 | C | ARG | 266 | 13.335 | 37.489 | −15.406 |
| 2105 | O | ARG | 266 | 13.331 | 36.472 | −16.107 |
| 2106 | CB | ARG | 266 | 11.416 | 39.059 | −15.773 |
| 2107 | CG | ARG | 266 | 10.940 | 38.391 | −17.054 |
| 2108 | CD | ARG | 266 | 9.936 | 37.296 | −16.718 |
| 2109 | NE | ARG | 266 | 9.581 | 36.504 | −17.903 |
| 2110 | CZ | ARG | 266 | 8.475 | 35.761 | −17.969 |
| 2111 | NH1 | ARG | 266 | 7.613 | 35.759 | −16.950 |
| 2112 | NH2 | ARG | 266 | 8.214 | 35.049 | −19.067 |
| 2113 | N | PHE | 267 | 14.445 | 37.990 | −14.885 |
| 2114 | CA | PHE | 267 | 15.753 | 37.431 | −15.245 |
| 2115 | C | PHE | 267 | 16.045 | 36.157 | −14.457 |
| 2116 | O | PHE | 267 | 16.666 | 35.233 | −14.999 |
| 2117 | CB | PHE | 267 | 16.838 | 38.469 | −14.991 |

TABLE 9-continued

| Atom No. | Atom Type | Residue | Residue Position | X Coord. | Y Coord. | Z Coord. |
|---|---|---|---|---|---|---|
| 2118 | CG | PHE | 267 | 16.772 | 39.655 | −15.947 |
| 2119 | CD1 | PHE | 267 | 16.557 | 39.440 | −17.302 |
| 2120 | CD2 | PHE | 267 | 16.941 | 40.947 | −15.468 |
| 2121 | CE1 | PHE | 267 | 16.490 | 40.517 | −18.175 |
| 2122 | CE2 | PHE | 267 | 16.871 | 42.024 | −16.341 |
| 2123 | CZ | PHE | 267 | 16.644 | 41.810 | −17.694 |
| 2124 | N | PHE | 268 | 15.372 | 35.999 | −13.328 |
| 2125 | CA | PHE | 268 | 15.446 | 34.732 | −12.597 |
| 2126 | C | PHE | 268 | 14.660 | 33.652 | −13.342 |
| 2127 | O | PHE | 268 | 15.215 | 32.574 | −13.603 |
| 2128 | CB | PHE | 268 | 14.879 | 34.930 | −11.194 |
| 2129 | CG | PHE | 268 | 14.781 | 33.655 | −10.360 |
| 2130 | CD1 | PHE | 268 | 15.785 | 32.695 | −10.418 |
| 2131 | CD2 | PHE | 268 | 13.684 | 33.459 | −9.532 |
| 2132 | CE1 | PHE | 268 | 15.680 | 31.534 | −9.664 |
| 2133 | CE2 | PHE | 268 | 13.581 | 32.299 | −8.774 |
| 2134 | CZ | PHE | 268 | 14.578 | 31.335 | −8.843 |
| 2135 | N | ARG | 269 | 13.541 | 34.041 | −13.935 |
| 2136 | CA | ARG | 269 | 12.760 | 33.094 | −14.739 |
| 2137 | C | ARG | 269 | 13.407 | 32.810 | −16.090 |
| 2138 | O | ARG | 269 | 13.390 | 31.658 | −16.534 |
| 2139 | CB | ARG | 269 | 11.380 | 33.680 | −14.980 |
| 2140 | CG | ARG | 269 | 10.653 | 33.926 | −13.670 |
| 2141 | CD | ARG | 269 | 9.269 | 34.495 | −13.935 |
| 2142 | NE | ARG | 269 | 8.568 | 34.781 | −12.679 |
| 2143 | CZ | ARG | 269 | 8.099 | 35.992 | −12.378 |
| 2144 | NH1 | ARG | 269 | 8.280 | 37.008 | −13.226 |
| 2145 | NH2 | ARG | 269 | 7.463 | 36.188 | −11.223 |
| 2146 | N | ARG | 270 | 14.210 | 33.745 | −16.563 |
| 2147 | CA | ARG | 270 | 14.944 | 33.584 | −17.818 |
| 2148 | C | ARG | 270 | 16.065 | 32.553 | −17.676 |
| 2149 | O | ARG | 270 | 16.190 | 31.659 | −18.530 |
| 2150 | CB | ARG | 270 | 15.523 | 34.958 | −18.125 |
| 2151 | CG | ARG | 270 | 16.113 | 35.086 | −19.518 |
| 2152 | CD | ARG | 270 | 16.642 | 36.501 | −19.713 |
| 2153 | NE | ARG | 270 | 17.103 | 36.726 | −21.089 |
| 2154 | CZ | ARG | 270 | 18.249 | 37.345 | −21.379 |
| 2155 | NH1 | ARG | 270 | 19.066 | 37.731 | −20.396 |
| 2156 | NH2 | ARG | 270 | 18.593 | 37.544 | −22.652 |
| 2157 | N | MET | 271 | 16.655 | 32.497 | −16.491 |
| 2158 | CA | MET | 271 | 17.662 | 31.472 | −16.216 |
| 2159 | C | MET | 271 | 17.019 | 30.116 | −15.931 |
| 2160 | O | MET | 271 | 17.491 | 29.106 | −16.465 |
| 2161 | CB | MET | 271 | 18.490 | 31.903 | −15.014 |
| 2162 | CG | MET | 271 | 19.241 | 33.199 | −15.288 |
| 2163 | SD | MET | 271 | 20.310 | 33.770 | −13.949 |
| 2164 | CE | MET | 271 | 19.076 | 33.895 | −12.633 |
| 2165 | N | GLU | 272 | 15.811 | 30.135 | −15.385 |
| 2166 | CA | GLU | 272 | 15.072 | 28.887 | −15.122 |
| 2167 | C | GLU | 272 | 14.433 | 28.293 | −16.381 |
| 2168 | O | GLU | 272 | 14.119 | 27.099 | −16.411 |
| 2169 | CB | GLU | 272 | 13.954 | 29.183 | −14.131 |
| 2170 | CG | GLU | 272 | 14.482 | 29.644 | −12.782 |
| 2171 | CD | GLU | 272 | 13.310 | 30.058 | −11.898 |
| 2172 | OE1 | GLU | 272 | 12.888 | 29.243 | −11.087 |
| 2173 | OE2 | GLU | 272 | 12.882 | 31.198 | −12.016 |
| 2174 | N | ASP | 273 | 14.308 | 29.102 | −17.422 |
| 2175 | CA | ASP | 273 | 13.788 | 28.631 | −18.708 |
| 2176 | C | ASP | 273 | 14.899 | 28.093 | −19.605 |
| 2177 | O | ASP | 273 | 14.615 | 27.512 | −20.660 |
| 2178 | CB | ASP | 273 | 13.097 | 29.792 | −19.422 |
| 2179 | CG | ASP | 273 | 11.879 | 30.295 | −18.645 |
| 2180 | OD1 | ASP | 273 | 11.228 | 29.479 | −18.007 |
| 2181 | OD2 | ASP | 273 | 11.562 | 31.469 | −18.792 |
| 2182 | N | GLY | 274 | 16.143 | 28.279 | −19.194 |
| 2183 | CA | GLY | 274 | 17.272 | 27.761 | −19.966 |
| 2184 | C | GLY | 274 | 17.712 | 28.731 | −21.056 |
| 2185 | O | GLY | 274 | 18.101 | 28.306 | −22.151 |
| 2186 | N | ASP | 275 | 17.584 | 30.020 | −20.791 |
| 2187 | CA | ASP | 275 | 18.077 | 31.003 | −21.757 |
| 2188 | C | ASP | 275 | 19.597 | 31.031 | −21.673 |
| 2189 | O | ASP | 275 | 20.156 | 31.540 | −20.693 |
| 2190 | CB | ASP | 275 | 17.486 | 32.370 | −21.435 |
| 2191 | CG | ASP | 275 | 18.035 | 33.416 | −22.397 |
| 2192 | OD1 | ASP | 275 | 19.128 | 33.899 | −22.121 |
| 2193 | OD2 | ASP | 275 | 17.484 | 33.541 | −23.478 |

TABLE 9-continued

| Atom No. | Atom Type | Residue | Residue Position | X Coord. | Y Coord. | Z Coord. |
|---|---|---|---|---|---|---|
| 2194 | N | GLU | 276 | 20.251 | 30.704 | −22.776 |
| 2195 | CA | GLU | 276 | 21.697 | 30.457 | −22.724 |
| 2196 | C | GLU | 276 | 22.549 | 31.719 | −22.555 |
| 2197 | O | GLU | 276 | 23.612 | 31.595 | −21.944 |
| 2198 | CB | GLU | 276 | 22.099 | 29.686 | −23.984 |
| 2199 | CG | GLU | 276 | 23.405 | 28.895 | −23.832 |
| 2200 | CD | GLU | 276 | 24.653 | 29.758 | −24.029 |
| 2201 | OE1 | GLU | 276 | 25.711 | 29.338 | −23.584 |
| 2202 | OE2 | GLU | 276 | 24.543 | 30.724 | −24.774 |
| 2203 | N | SER | 277 | 22.033 | 32.908 | −22.820 |
| 2204 | CA | SER | 277 | 22.856 | 34.099 | −22.569 |
| 2205 | C | SER | 277 | 22.756 | 34.534 | −21.105 |
| 2206 | O | SER | 277 | 23.772 | 34.924 | −20.516 |
| 2207 | CB | SER | 277 | 22.442 | 35.234 | −23.501 |
| 2208 | OG | SER | 277 | 21.097 | 35.590 | −23.222 |
| 2209 | N | ALA | 278 | 21.660 | 34.155 | −20.463 |
| 2210 | CA | ALA | 278 | 21.494 | 34.419 | −19.035 |
| 2211 | C | ALA | 278 | 22.229 | 33.363 | −18.215 |
| 2212 | O | ALA | 278 | 22.830 | 33.689 | −17.184 |
| 2213 | CB | ALA | 278 | 20.007 | 34.394 | −18.702 |
| 2214 | N | LEU | 279 | 22.396 | 32.189 | −18.800 |
| 2215 | CA | LEU | 279 | 23.200 | 31.143 | −18.158 |
| 2216 | C | LEU | 279 | 24.691 | 31.325 | −18.445 |
| 2217 | O | LEU | 279 | 25.521 | 30.915 | −17.626 |
| 2218 | CB | LEU | 279 | 22.765 | 29.752 | −18.626 |
| 2219 | CG | LEU | 279 | 21.614 | 29.145 | −17.815 |
| 2220 | CD1 | LEU | 279 | 21.850 | 29.311 | −16.319 |
| 2221 | CD2 | LEU | 279 | 20.246 | 29.700 | −18.186 |
| 2222 | N | LYS | 280 | 25.016 | 32.105 | −19.462 |
| 2223 | CA | LYS | 280 | 26.416 | 32.396 | −19.770 |
| 2224 | C | LYS | 280 | 26.968 | 33.452 | −18.824 |
| 2225 | O | LYS | 280 | 28.032 | 33.238 | −18.227 |
| 2226 | CB | LYS | 280 | 26.505 | 32.908 | −21.202 |
| 2227 | CG | LYS | 280 | 27.930 | 33.315 | −21.553 |
| 2228 | CD | LYS | 280 | 28.010 | 33.930 | −22.944 |
| 2229 | CE | LYS | 280 | 29.423 | 34.419 | −23.239 |
| 2230 | NZ | LYS | 280 | 29.848 | 35.413 | −22.239 |
| 2231 | N | ILE | 281 | 26.141 | 34.428 | −18.481 |
| 2232 | CA | ILE | 281 | 26.580 | 35.434 | −17.510 |
| 2233 | C | ILE | 281 | 26.447 | 34.896 | −16.080 |
| 2234 | O | ILE | 281 | 27.280 | 35.225 | −15.222 |
| 2235 | CB | ILE | 281 | 25.794 | 36.730 | −17.732 |
| 2236 | CG1 | ILE | 281 | 26.248 | 37.830 | −16.782 |
| 2237 | CG2 | ILE | 281 | 24.288 | 36.527 | −17.615 |
| 2238 | CD1 | ILE | 281 | 25.448 | 39.110 | −16.999 |
| 2239 | N | TRP | 282 | 25.631 | 33.863 | −15.929 |
| 2240 | CA | TRP | 282 | 25.545 | 33.140 | −14.665 |
| 2241 | C | TRP | 282 | 26.801 | 32.319 | −14.408 |
| 2242 | O | TRP | 282 | 27.433 | 32.502 | −13.360 |
| 2243 | CB | TRP | 282 | 24.324 | 32.229 | −14.711 |
| 2244 | CG | TRP | 282 | 24.295 | 31.185 | −13.615 |
| 2245 | CD1 | TRP | 282 | 23.938 | 31.370 | −12.299 |
| 2246 | CD2 | TRP | 282 | 24.649 | 29.793 | −13.755 |
| 2247 | NE1 | TRP | 282 | 24.075 | 30.188 | −11.650 |
| 2248 | CE2 | TRP | 282 | 24.509 | 29.221 | −12.481 |
| 2249 | CE3 | TRP | 282 | 25.084 | 29.024 | −14.825 |
| 2250 | CZ2 | TRP | 282 | 24.822 | 27.884 | −12.292 |
| 2251 | CZ3 | TRP | 282 | 25.388 | 27.684 | −14.628 |
| 2252 | CH2 | TRP | 282 | 25.259 | 27.117 | −13.366 |
| 2253 | N | ALA | 283 | 27.296 | 31.658 | −15.442 |
| 2254 | CA | ALA | 283 | 28.496 | 30.835 | −15.295 |
| 2255 | C | ALA | 283 | 29.746 | 31.692 | −15.195 |
| 2256 | O | ALA | 283 | 30.621 | 31.390 | −14.373 |
| 2257 | CB | ALA | 283 | 28.606 | 29.908 | −16.500 |
| 2258 | N | ARG | 284 | 29.701 | 32.871 | −15.793 |
| 2259 | CA | ARG | 284 | 30.822 | 33.798 | −15.679 |
| 2260 | C | ARG | 284 | 30.975 | 34.293 | −14.245 |
| 2261 | O | ARG | 284 | 32.001 | 33.986 | −13.620 |
| 2262 | CB | ARG | 284 | 30.588 | 34.983 | −16.605 |
| 2263 | CG | ARG | 284 | 31.786 | 35.922 | −16.563 |
| 2264 | CD | ARG | 284 | 31.599 | 37.138 | −17.458 |
| 2265 | NE | ARG | 284 | 32.802 | 37.980 | −17.401 |
| 2266 | CZ | ARG | 284 | 32.828 | 39.261 | −17.770 |
| 2267 | NH1 | ARG | 284 | 31.712 | 39.855 | −18.199 |
| 2268 | NH2 | ARG | 284 | 33.964 | 39.956 | −17.678 |
| 2269 | N | PHE | 285 | 29.883 | 34.745 | −13.646 |

TABLE 9-continued

| Atom No. | Atom Type | Residue | Residue Position | X Coord. | Y Coord. | Z Coord. |
|---|---|---|---|---|---|---|
| 2270 | CA | PHE | 285 | 29.971 | 35.288 | −12.283 |
| 2271 | C | PHE | 285 | 30.172 | 34.191 | −11.247 |
| 2272 | O | PHE | 285 | 31.019 | 34.346 | −10.358 |
| 2273 | CB | PHE | 285 | 28.692 | 36.039 | −11.930 |
| 2274 | CG | PHE | 285 | 28.431 | 37.335 | −12.692 |
| 2275 | CD1 | PHE | 285 | 29.466 | 38.010 | −13.326 |
| 2276 | CD2 | PHE | 285 | 27.141 | 37.848 | −12.731 |
| 2277 | CE1 | PHE | 285 | 29.206 | 39.188 | −14.011 |
| 2278 | CE2 | PHE | 285 | 26.882 | 39.029 | −13.412 |
| 2279 | CZ | PHE | 285 | 27.916 | 39.697 | −14.054 |
| 2280 | N | ARG | 286 | 29.615 | 33.022 | −11.513 |
| 2281 | CA | ARG | 286 | 29.772 | 31.896 | −10.596 |
| 2282 | C | ARG | 286 | 31.199 | 31.357 | −10.597 |
| 2283 | O | ARG | 286 | 31.797 | 31.281 | −9.519 |
| 2284 | CB | ARG | 286 | 28.809 | 30.795 | −11.018 |
| 2285 | CG | ARG | 286 | 29.015 | 29.538 | −10.186 |
| 2286 | CD | ARG | 286 | 28.073 | 28.421 | −10.616 |
| 2287 | NE | ARG | 286 | 28.404 | 27.177 | −9.907 |
| 2288 | CZ | ARG | 286 | 27.740 | 26.727 | −8.840 |
| 2289 | NH1 | ARG | 286 | 26.653 | 27.366 | −8.406 |
| 2290 | NH2 | ARG | 286 | 28.132 | 25.602 | −8.244 |
| 2291 | N | ASP | 287 | 31.830 | 31.309 | −11.760 |
| 2292 | CA | ASP | 287 | 33.194 | 30.773 | −11.840 |
| 2293 | C | ASP | 287 | 34.221 | 31.777 | −11.328 |
| 2294 | O | ASP | 287 | 35.159 | 31.382 | −10.623 |
| 2295 | CB | ASP | 287 | 33.519 | 30.424 | −13.290 |
| 2296 | CG | ASP | 287 | 32.609 | 29.315 | −13.818 |
| 2297 | OD1 | ASP | 287 | 32.145 | 28.519 | −13.010 |
| 2298 | OD2 | ASP | 287 | 32.496 | 29.204 | −15.032 |
| 2299 | N | LEU | 288 | 33.906 | 33.056 | −11.446 |
| 2300 | CA | LEU | 288 | 34.803 | 34.089 | −10.925 |
| 2301 | C | LEU | 288 | 34.719 | 34.179 | −9.403 |
| 2302 | O | LEU | 288 | 35.761 | 34.229 | −8.732 |
| 2303 | CB | LEU | 288 | 34.400 | 35.421 | −11.542 |
| 2304 | CG | LEU | 288 | 34.703 | 35.485 | −13.034 |
| 2305 | CD1 | LEU | 288 | 34.171 | 36.781 | −13.637 |
| 2306 | CD2 | LEU | 288 | 36.198 | 35.342 | −13.298 |
| 2307 | N | SER | 289 | 33.535 | 33.918 | −8.872 |
| 2308 | CA | SER | 289 | 33.354 | 33.907 | −7.423 |
| 2309 | C | SER | 289 | 33.943 | 32.643 | −6.810 |
| 2310 | O | SER | 289 | 34.650 | 32.747 | −5.802 |
| 2311 | CB | SER | 289 | 31.865 | 33.979 | −7.104 |
| 2312 | OG | SER | 289 | 31.363 | 35.215 | −7.596 |
| 2313 | N | ILE | 290 | 33.913 | 31.548 | −7.554 |
| 2314 | CA | ILE | 290 | 34.508 | 30.297 | −7.076 |
| 2315 | C | ILE | 290 | 36.033 | 30.342 | −7.075 |
| 2316 | O | ILE | 290 | 36.624 | 29.885 | −6.091 |
| 2317 | CB | ILE | 290 | 34.026 | 29.143 | −7.954 |
| 2318 | CG1 | ILE | 290 | 32.544 | 28.873 | −7.731 |
| 2319 | CG2 | ILE | 290 | 34.834 | 27.874 | −7.700 |
| 2320 | CD1 | ILE | 290 | 32.059 | 27.716 | −8.597 |
| 2321 | N | GLU | 291 | 36.634 | 31.141 | −7.944 |
| 2322 | CA | GLU | 291 | 38.099 | 31.248 | −7.926 |
| 2323 | C | GLU | 291 | 38.570 | 32.087 | −6.741 |
| 2324 | O | GLU | 291 | 39.475 | 31.655 | −6.013 |
| 2325 | CB | GLU | 291 | 38.589 | 31.884 | −9.223 |
| 2326 | CG | GLU | 291 | 38.205 | 31.065 | −10.451 |
| 2327 | CD | GLU | 291 | 38.737 | 29.637 | −10.361 |
| 2328 | OE1 | GLU | 291 | 39.881 | 29.435 | −10.744 |
| 2329 | OE2 | GLU | 291 | 37.947 | 28.759 | −10.040 |
| 2330 | N | LYS | 292 | 37.767 | 33.071 | −6.373 |
| 2331 | CA | LYS | 292 | 38.105 | 33.897 | −5.212 |
| 2332 | C | LYS | 292 | 37.791 | 33.171 | −3.907 |
| 2333 | O | LYS | 292 | 38.585 | 33.256 | −2.960 |
| 2334 | CB | LYS | 292 | 37.318 | 35.198 | −5.289 |
| 2335 | CG | LYS | 292 | 37.718 | 36.011 | −6.513 |
| 2336 | CD | LYS | 292 | 39.191 | 36.402 | −6.452 |
| 2337 | CE | LYS | 292 | 39.620 | 37.156 | −7.705 |
| 2338 | NZ | LYS | 292 | 41.040 | 37.530 | −7.635 |
| 2339 | N | TYR | 293 | 36.840 | 32.252 | −3.960 |
| 2340 | CA | TYR | 293 | 36.530 | 31.433 | −2.788 |
| 2341 | C | TYR | 293 | 37.573 | 30.338 | −2.591 |
| 2342 | O | TYR | 293 | 38.011 | 30.151 | −1.451 |
| 2343 | CB | TYR | 293 | 35.140 | 30.820 | −2.935 |
| 2344 | CG | TYR | 293 | 33.994 | 31.826 | −2.845 |
| 2345 | CD1 | TYR | 293 | 34.131 | 32.964 | −2.059 |

TABLE 9-continued

| Atom No. | Atom Type | Residue | Residue Position | X Coord. | Y Coord. | Z Coord. |
|---|---|---|---|---|---|---|
| 2346 | CD2 | TYR | 293 | 32.810 | 31.599 | −3.537 |
| 2347 | CE1 | TYR | 293 | 33.095 | 33.885 | −1.980 |
| 2348 | CE2 | TYR | 293 | 31.772 | 32.520 | −3.460 |
| 2349 | CZ | TYR | 293 | 31.919 | 33.662 | −2.683 |
| 2350 | OH | TYR | 293 | 30.893 | 34.579 | −2.600 |
| 2351 | N | VAL | 294 | 38.191 | 29.885 | −3.671 |
| 2352 | CA | VAL | 294 | 39.294 | 28.923 | −3.557 |
| 2353 | C | VAL | 294 | 40.534 | 29.583 | −2.960 |
| 2354 | O | VAL | 294 | 41.151 | 28.999 | −2.062 |
| 2355 | CB | VAL | 294 | 39.633 | 28.373 | −4.942 |
| 2356 | CG1 | VAL | 294 | 40.928 | 27.569 | −4.926 |
| 2357 | CG2 | VAL | 294 | 38.497 | 27.530 | −5.508 |
| 2358 | N | ASP | 295 | 40.691 | 30.875 | −3.207 |
| 2359 | CA | ASP | 295 | 41.806 | 31.621 | −2.615 |
| 2360 | C | ASP | 295 | 41.577 | 31.871 | −1.122 |
| 2361 | O | ASP | 295 | 42.481 | 31.628 | −0.309 |
| 2362 | CB | ASP | 295 | 41.911 | 32.972 | −3.319 |
| 2363 | CG | ASP | 295 | 42.087 | 32.811 | −4.827 |
| 2364 | OD1 | ASP | 295 | 42.836 | 31.928 | −5.225 |
| 2365 | OD2 | ASP | 295 | 41.594 | 33.673 | −5.544 |
| 2366 | N | THR | 296 | 40.322 | 32.081 | −0.758 |
| 2367 | CA | THR | 296 | 39.976 | 32.381 | 0.635 |
| 2368 | C | THR | 296 | 40.022 | 31.133 | 1.510 |
| 2369 | O | THR | 296 | 40.682 | 31.147 | 2.558 |
| 2370 | CB | THR | 296 | 38.566 | 32.961 | 0.656 |
| 2371 | OG1 | THR | 296 | 38.550 | 34.119 | −0.168 |
| 2372 | CG2 | THR | 296 | 38.142 | 33.370 | 2.062 |
| 2373 | N | TYR | 297 | 39.567 | 30.017 | 0.966 |
| 2374 | CA | TYR | 297 | 39.586 | 28.762 | 1.720 |
| 2375 | C | TYR | 297 | 40.987 | 28.157 | 1.730 |
| 2376 | O | TYR | 297 | 41.407 | 27.625 | 2.766 |
| 2377 | CB | TYR | 297 | 38.602 | 27.786 | 1.090 |
| 2378 | CG | TYR | 297 | 37.138 | 28.218 | 1.126 |
| 2379 | CD1 | TYR | 297 | 36.536 | 28.614 | 2.315 |
| 2380 | CD2 | TYR | 297 | 36.401 | 28.200 | −0.050 |
| 2381 | CE1 | TYR | 297 | 35.197 | 28.987 | 2.324 |
| 2382 | CE2 | TYR | 297 | 35.067 | 28.578 | −0.044 |
| 2383 | CZ | TYR | 297 | 34.464 | 28.962 | 1.144 |
| 2384 | OH | TYR | 297 | 33.096 | 29.129 | 1.171 |
| 2385 | N | GLY | 298 | 41.778 | 28.497 | 0.726 |
| 2386 | CA | GLY | 298 | 43.201 | 28.143 | 0.699 |
| 2387 | C | GLY | 298 | 43.943 | 28.776 | 1.873 |
| 2388 | O | GLY | 298 | 44.531 | 28.047 | 2.683 |
| 2389 | N | ARG | 299 | 43.678 | 30.054 | 2.109 |
| 2390 | CA | ARG | 299 | 44.300 | 30.791 | 3.223 |
| 2391 | C | ARG | 299 | 43.761 | 30.377 | 4.606 |
| 2392 | O | ARG | 299 | 44.431 | 30.589 | 5.623 |
| 2393 | CB | ARG | 299 | 44.011 | 32.273 | 2.982 |
| 2394 | CG | ARG | 299 | 44.687 | 33.182 | 4.003 |
| 2395 | CD | ARG | 299 | 44.338 | 34.649 | 3.771 |
| 2396 | NE | ARG | 299 | 45.017 | 35.507 | 4.756 |
| 2397 | CZ | ARG | 299 | 44.679 | 36.777 | 4.991 |
| 2398 | NH1 | ARG | 299 | 43.663 | 37.335 | 4.329 |
| 2399 | NH2 | ARG | 299 | 45.349 | 37.485 | 5.903 |
| 2400 | N | LEU | 300 | 42.632 | 29.686 | 4.629 |
| 2401 | CA | LEU | 300 | 42.065 | 29.166 | 5.879 |
| 2402 | C | LEU | 300 | 42.364 | 27.677 | 6.104 |
| 2403 | O | LEU | 300 | 41.808 | 27.086 | 7.040 |
| 2404 | CB | LEU | 300 | 40.558 | 29.394 | 5.842 |
| 2405 | CG | LEU | 300 | 40.236 | 30.884 | 5.812 |
| 2406 | CD1 | LEU | 300 | 38.763 | 31.132 | 5.508 |
| 2407 | CD2 | LEU | 300 | 40.648 | 31.567 | 7.113 |
| 2408 | N | ASN | 301 | 43.192 | 27.090 | 5.246 |
| 2409 | CA | ASN | 301 | 43.563 | 25.659 | 5.299 |
| 2410 | C | ASN | 301 | 42.369 | 24.742 | 5.043 |
| 2411 | O | ASN | 301 | 42.202 | 23.713 | 5.711 |
| 2412 | CB | ASN | 301 | 44.170 | 25.298 | 6.653 |
| 2413 | CG | ASN | 301 | 45.526 | 25.961 | 6.875 |
| 2414 | OD1 | ASN | 301 | 46.369 | 26.023 | 5.973 |
| 2415 | ND2 | ASN | 301 | 45.720 | 26.434 | 8.092 |
| 2416 | N | ILE | 302 | 41.565 | 25.101 | 4.056 |
| 2417 | CA | ILE | 302 | 40.360 | 24.332 | 3.725 |
| 2418 | C | ILE | 302 | 40.234 | 24.096 | 2.220 |
| 2419 | O | ILE | 302 | 40.069 | 25.031 | 1.426 |
| 2420 | CB | ILE | 302 | 39.143 | 25.097 | 4.245 |
| 2421 | CG1 | ILE | 302 | 39.136 | 25.130 | 5.769 |

TABLE 9-continued

| Atom No. | Atom Type | Residue | Residue Position | X Coord. | Y Coord. | Z Coord. |
|---|---|---|---|---|---|---|
| 2422 | CG2 | ILE | 302 | 37.843 | 24.496 | 3.724 |
| 2423 | CD1 | ILE | 302 | 37.935 | 25.890 | 6.308 |
| 2424 | N | LYS | 303 | 40.307 | 22.833 | 1.837 |
| 2425 | CA | LYS | 303 | 40.127 | 22.474 | 0.427 |
| 2426 | C | LYS | 303 | 38.859 | 21.645 | 0.230 |
| 2427 | O | LYS | 303 | 38.804 | 20.470 | 0.607 |
| 2428 | CB | LYS | 303 | 41.344 | 21.686 | −0.044 |
| 2429 | CG | LYS | 303 | 41.248 | 21.356 | −1.530 |
| 2430 | CD | LYS | 303 | 42.470 | 20.584 | −2.012 |
| 2431 | CE | LYS | 303 | 42.370 | 20.269 | −3.500 |
| 2432 | NZ | LYS | 303 | 43.557 | 19.533 | −3.964 |
| 2433 | N | TYR | 304 | 37.854 | 22.268 | −0.363 |
| 2434 | CA | TYR | 304 | 36.589 | 21.579 | −0.654 |
| 2435 | C | TYR | 304 | 36.756 | 20.510 | −1.719 |
| 2436 | O | TYR | 304 | 37.715 | 20.513 | −2.498 |
| 2437 | CB | TYR | 304 | 35.547 | 22.568 | −1.156 |
| 2438 | CG | TYR | 304 | 34.916 | 23.439 | −0.084 |
| 2439 | CD1 | TYR | 304 | 33.768 | 23.006 | 0.566 |
| 2440 | CD2 | TYR | 304 | 35.487 | 24.659 | 0.248 |
| 2441 | CE1 | TYR | 304 | 33.175 | 23.805 | 1.535 |
| 2442 | CE2 | TYR | 304 | 34.898 | 25.454 | 1.217 |
| 2443 | CZ | TYR | 304 | 33.740 | 25.032 | 1.849 |
| 2444 | OH | TYR | 304 | 33.065 | 25.911 | 2.661 |
| 2445 | N | ASP | 305 | 35.822 | 19.578 | −1.722 |
| 2446 | CA | ASP | 305 | 35.821 | 18.547 | −2.754 |
| 2447 | C | ASP | 305 | 34.779 | 18.912 | −3.799 |
| 2448 | O | ASP | 305 | 34.976 | 18.702 | −5.002 |
| 2449 | CB | ASP | 305 | 35.466 | 17.200 | −2.130 |
| 2450 | CG | ASP | 305 | 36.446 | 16.833 | −1.018 |
| 2451 | OD1 | ASP | 305 | 37.530 | 16.372 | −1.341 |
| 2452 | OD2 | ASP | 305 | 36.067 | 16.981 | 0.138 |
| 2453 | N | VAL | 306 | 33.692 | 19.503 | −3.328 |
| 2454 | CA | VAL | 306 | 32.603 | 19.912 | −4.221 |
| 2455 | C | VAL | 306 | 32.160 | 21.348 | −3.940 |
| 2456 | O | VAL | 306 | 31.820 | 21.704 | −2.805 |
| 2457 | CB | VAL | 306 | 31.417 | 18.967 | −4.005 |
| 2458 | CG1 | VAL | 306 | 30.240 | 19.311 | −4.912 |
| 2459 | CG2 | VAL | 306 | 31.805 | 17.504 | −4.197 |
| 2460 | N | TYR | 307 | 32.211 | 22.181 | −4.965 |
| 2461 | CA | TYR | 307 | 31.607 | 23.516 | −4.874 |
| 2462 | C | TYR | 307 | 30.219 | 23.490 | −5.507 |
| 2463 | O | TYR | 307 | 30.073 | 23.751 | −6.704 |
| 2464 | CB | TYR | 307 | 32.475 | 24.544 | −5.595 |
| 2465 | CG | TYR | 307 | 33.672 | 25.065 | −4.803 |
| 2466 | CD1 | TYR | 307 | 34.899 | 24.415 | −4.863 |
| 2467 | CD2 | TYR | 307 | 33.530 | 26.210 | −4.029 |
| 2468 | CE1 | TYR | 307 | 35.981 | 24.906 | −4.142 |
| 2469 | CE2 | TYR | 307 | 34.610 | 26.703 | −3.309 |
| 2470 | CZ | TYR | 307 | 35.833 | 26.048 | −3.367 |
| 2471 | OH | TYR | 307 | 36.911 | 26.548 | −2.668 |
| 2472 | N | SER | 308 | 29.227 | 23.135 | −4.709 |
| 2473 | CA | SER | 308 | 27.843 | 23.047 | −5.182 |
| 2474 | C | SER | 308 | 27.129 | 24.369 | −4.892 |
| 2475 | O | SER | 308 | 27.703 | 25.265 | −4.260 |
| 2476 | CB | SER | 308 | 27.182 | 21.876 | −4.451 |
| 2477 | OG | SER | 308 | 25.904 | 21.602 | −5.008 |
| 2478 | N | GLY | 309 | 25.961 | 24.545 | −5.482 |
| 2479 | CA | GLY | 309 | 25.168 | 25.752 | −5.255 |
| 2480 | C | GLY | 309 | 23.675 | 25.458 | −5.286 |
| 2481 | O | GLY | 309 | 23.248 | 24.332 | −5.568 |
| 2482 | N | GLU | 310 | 22.895 | 26.520 | −5.168 |
| 2483 | CA | GLU | 310 | 21.428 | 26.414 | −5.186 |
| 2484 | C | GLU | 310 | 20.883 | 26.175 | −6.590 |
| 2485 | O | GLU | 310 | 19.761 | 25.686 | −6.747 |
| 2486 | CB | GLU | 310 | 20.855 | 27.731 | −4.694 |
| 2487 | CG | GLU | 310 | 21.227 | 28.032 | −3.253 |
| 2488 | CD | GLU | 310 | 20.962 | 29.508 | −3.010 |
| 2489 | OE1 | GLU | 310 | 20.669 | 29.874 | −1.884 |
| 2490 | OE2 | GLU | 310 | 21.166 | 30.261 | −3.959 |
| 2491 | N | SER | 311 | 21.711 | 26.430 | −7.589 |
| 2492 | CA | SER | 311 | 21.347 | 26.150 | −8.982 |
| 2493 | C | SER | 311 | 21.751 | 24.753 | −9.440 |
| 2494 | O | SER | 311 | 21.719 | 24.491 | −10.646 |
| 2495 | CB | SER | 311 | 22.110 | 27.114 | −9.873 |
| 2496 | OG | SER | 311 | 23.481 | 26.731 | −9.803 |
| 2497 | N | GLN | 312 | 22.293 | 23.938 | −8.549 |

TABLE 9-continued

| Atom No. | Atom Type | Residue | Residue Position | X Coord. | Y Coord. | Z Coord. |
|---|---|---|---|---|---|---|
| 2498 | CA | GLN | 312 | 22.845 | 22.657 | −8.993 |
| 2499 | C | GLN | 312 | 21.900 | 21.491 | −8.731 |
| 2500 | O | GLN | 312 | 22.186 | 20.357 | −9.134 |
| 2501 | CB | GLN | 312 | 24.190 | 22.458 | −8.314 |
| 2502 | CG | GLN | 312 | 25.134 | 23.606 | −8.660 |
| 2503 | CD | GLN | 312 | 25.557 | 23.575 | −10.127 |
| 2504 | OE1 | GLN | 312 | 26.316 | 22.690 | −10.534 |
| 2505 | NE2 | GLN | 312 | 25.135 | 24.576 | −10.883 |
| 2506 | N | VAL | 313 | 20.785 | 21.776 | −8.079 |
| 2507 | CA | VAL | 313 | 19.724 | 20.778 | −7.923 |
| 2508 | C | VAL | 313 | 19.108 | 20.436 | −9.281 |
| 2509 | O | VAL | 313 | 18.610 | 21.311 | −9.998 |
| 2510 | CB | VAL | 313 | 18.675 | 21.357 | −6.974 |
| 2511 | CG1 | VAL | 313 | 18.386 | 22.825 | −7.267 |
| 2512 | CG2 | VAL | 313 | 17.392 | 20.539 | −6.974 |
| 2513 | N | PRO | 314 | 19.197 | 19.167 | −9.644 |
| 2514 | CA | PRO | 314 | 18.667 | 18.711 | −10.926 |
| 2515 | C | PRO | 314 | 17.151 | 18.832 | −10.967 |
| 2516 | O | PRO | 314 | 16.461 | 18.601 | −9.965 |
| 2517 | CB | PRO | 314 | 19.108 | 17.286 | −11.057 |
| 2518 | CG | PRO | 314 | 19.831 | 16.872 | −9.786 |
| 2519 | CD | PRO | 314 | 19.817 | 18.088 | −8.874 |
| 2520 | N | GLN | 315 | 16.639 | 18.971 | −12.178 |
| 2521 | CA | GLN | 315 | 15.198 | 19.143 | −12.382 |
| 2522 | C | GLN | 315 | 14.444 | 17.828 | −12.194 |
| 2523 | O | GLN | 315 | 13.300 | 17.839 | −11.726 |
| 2524 | CB | GLN | 315 | 14.990 | 19.674 | −13.795 |
| 2525 | CG | GLN | 315 | 13.533 | 20.020 | −14.081 |
| 2526 | CD | GLN | 315 | 13.423 | 20.598 | −15.487 |
| 2527 | OE1 | GLN | 315 | 13.627 | 19.891 | −16.480 |
| 2528 | NE2 | GLN | 315 | 13.168 | 21.894 | −15.552 |
| 2529 | N | GLU | 316 | 15.185 | 16.732 | −12.229 |
| 2530 | CA | GLU | 316 | 14.612 | 15.410 | −11.968 |
| 2531 | C | GLU | 316 | 14.357 | 15.221 | −10.476 |
| 2532 | O | GLU | 316 | 13.291 | 14.707 | −10.119 |
| 2533 | CB | GLU | 316 | 15.557 | 14.302 | −12.449 |
| 2534 | CG | GLU | 316 | 15.646 | 14.137 | −13.971 |
| 2535 | CD | GLU | 316 | 16.639 | 15.108 | −14.614 |
| 2536 | OE1 | GLU | 316 | 17.383 | 15.731 | −13.864 |
| 2537 | OE2 | GLU | 316 | 16.501 | 15.354 | −15.802 |
| 2538 | N | LYS | 317 | 15.134 | 15.907 | −9.649 |
| 2539 | CA | LYS | 317 | 14.937 | 15.824 | −8.200 |
| 2540 | C | LYS | 317 | 13.823 | 16.766 | −7.778 |
| 2541 | O | LYS | 317 | 13.030 | 16.424 | −6.894 |
| 2542 | CB | LYS | 317 | 16.222 | 16.224 | −7.486 |
| 2543 | CG | LYS | 317 | 17.370 | 15.286 | −7.827 |
| 2544 | CD | LYS | 317 | 17.070 | 13.856 | −7.407 |
| 2545 | CE | LYS | 317 | 18.216 | 12.923 | −7.769 |
| 2546 | NZ | LYS | 317 | 17.894 | 11.540 | −7.391 |
| 2547 | N | MET | 318 | 13.600 | 17.790 | −8.585 |
| 2548 | CA | MET | 318 | 12.492 | 18.709 | −8.330 |
| 2549 | C | MET | 318 | 11.157 | 18.097 | −8.743 |
| 2550 | O | MET | 318 | 10.191 | 18.185 | −7.973 |
| 2551 | CB | MET | 318 | 12.734 | 19.994 | −9.112 |
| 2552 | CG | MET | 318 | 13.965 | 20.726 | −8.595 |
| 2553 | SD | MET | 318 | 13.876 | 21.238 | −6.864 |
| 2554 | CE | MET | 318 | 12.398 | 22.270 | −6.956 |
| 2555 | N | LYS | 319 | 11.166 | 17.280 | −9.785 |
| 2556 | CA | LYS | 319 | 9.929 | 16.604 | −10.185 |
| 2557 | C | LYS | 319 | 9.619 | 15.413 | −9.285 |
| 2558 | O | LYS | 319 | 8.448 | 15.200 | −8.950 |
| 2559 | CB | LYS | 319 | 10.038 | 16.132 | −11.631 |
| 2560 | CG | LYS | 319 | 10.195 | 17.299 | −12.600 |
| 2561 | CD | LYS | 319 | 9.966 | 16.856 | −14.040 |
| 2562 | CE | LYS | 319 | 10.970 | 15.810 | −14.502 |
| 2563 | NZ | LYS | 319 | 12.314 | 16.383 | −14.646 |
| 2564 | N | GLU | 320 | 10.647 | 14.819 | −8.700 |
| 2565 | CA | GLU | 320 | 10.427 | 13.722 | −7.754 |
| 2566 | C | GLU | 320 | 10.013 | 14.243 | −6.382 |
| 2567 | O | GLU | 320 | 9.134 | 13.646 | −5.746 |
| 2568 | CB | GLU | 320 | 11.717 | 12.923 | −7.639 |
| 2569 | CG | GLU | 320 | 12.021 | 12.204 | −8.947 |
| 2570 | CD | GLU | 320 | 13.468 | 11.725 | −8.957 |
| 2571 | OE1 | GLU | 320 | 13.752 | 10.783 | −9.684 |
| 2572 | OE2 | GLU | 320 | 14.285 | 12.377 | −8.320 |
| 2573 | N | ALA | 321 | 10.432 | 15.456 | −6.065 |

TABLE 9-continued

| Atom No. | Atom Type | Residue | Residue Position | X Coord. | Y Coord. | Z Coord. |
|---|---|---|---|---|---|---|
| 2574 | CA | ALA | 321 | 10.007 | 16.090 | −4.820 |
| 2575 | C | ALA | 321 | 8.560 | 16.545 | −4.918 |
| 2576 | O | ALA | 321 | 7.766 | 16.195 | −4.037 |
| 2577 | CB | ALA | 321 | 10.904 | 17.291 | −4.543 |
| 2578 | N | THR | 322 | 8.167 | 17.009 | −6.093 |
| 2579 | CA | THR | 322 | 6.783 | 17.445 | −6.305 |
| 2580 | C | THR | 322 | 5.831 | 16.256 | −6.388 |
| 2581 | O | THR | 322 | 4.762 | 16.286 | −5.761 |
| 2582 | CB | THR | 322 | 6.733 | 18.238 | −7.607 |
| 2583 | OG1 | THR | 322 | 7.573 | 19.376 | −7.461 |
| 2584 | CG2 | THR | 322 | 5.324 | 18.726 | −7.922 |
| 2585 | N | LYS | 323 | 6.337 | 15.144 | −6.896 |
| 2586 | CA | LYS | 323 | 5.539 | 13.925 | −6.968 |
| 2587 | C | LYS | 323 | 5.339 | 13.319 | −5.585 |
| 2588 | O | LYS | 323 | 4.191 | 13.046 | −5.215 |
| 2589 | CB | LYS | 323 | 6.259 | 12.931 | −7.873 |
| 2590 | CG | LYS | 323 | 5.420 | 11.684 | −8.120 |
| 2591 | CD | LYS | 323 | 4.118 | 12.030 | −8.834 |
| 2592 | CE | LYS | 323 | 4.379 | 12.662 | −10.198 |
| 2593 | NZ | LYS | 323 | 3.111 | 13.012 | −10.856 |
| 2594 | N | LEU | 324 | 6.348 | 13.404 | −4.733 |
| 2595 | CA | LEU | 324 | 6.186 | 12.889 | −3.372 |
| 2596 | C | LEU | 324 | 5.424 | 13.847 | −2.459 |
| 2597 | O | LEU | 324 | 4.683 | 13.360 | −1.598 |
| 2598 | CB | LEU | 324 | 7.551 | 12.564 | −2.785 |
| 2599 | CG | LEU | 324 | 8.149 | 11.339 | −3.465 |
| 2600 | CD1 | LEU | 324 | 9.565 | 11.068 | −2.973 |
| 2601 | CD2 | LEU | 324 | 7.263 | 10.116 | −3.250 |
| 2602 | N | PHE | 325 | 5.344 | 15.119 | −2.818 |
| 2603 | CA | PHE | 325 | 4.493 | 16.039 | −2.052 |
| 2604 | C | PHE | 325 | 3.029 | 15.759 | −2.368 |
| 2605 | O | PHE | 325 | 2.176 | 15.768 | −1.471 |
| 2606 | CB | PHE | 325 | 4.777 | 17.493 | −2.427 |
| 2607 | CG | PHE | 325 | 6.188 | 18.031 | −2.194 |
| 2608 | CD1 | PHE | 325 | 7.023 | 17.476 | −1.233 |
| 2609 | CD2 | PHE | 325 | 6.632 | 19.103 | −2.958 |
| 2610 | CE1 | PHE | 325 | 8.302 | 17.984 | −1.048 |
| 2611 | CE2 | PHE | 325 | 7.910 | 19.613 | −2.771 |
| 2612 | CZ | PHE | 325 | 8.747 | 19.051 | −1.817 |
| 2613 | N | GLU | 326 | 2.779 | 15.299 | −3.580 |
| 2614 | CA | GLU | 326 | 1.421 | 14.926 | −3.962 |
| 2615 | C | GLU | 326 | 1.046 | 13.556 | −3.401 |
| 2616 | O | GLU | 326 | 0.045 | 13.460 | −2.681 |
| 2617 | CB | GLU | 326 | 1.372 | 14.915 | −5.483 |
| 2618 | CG | GLU | 326 | 1.683 | 16.306 | −6.022 |
| 2619 | CD | GLU | 326 | 2.065 | 16.242 | −7.496 |
| 2620 | OE1 | GLU | 326 | 1.879 | 17.241 | −8.176 |
| 2621 | OE2 | GLU | 326 | 2.643 | 15.238 | −7.889 |
| 2622 | N | ASP | 327 | 1.994 | 12.631 | −3.441 |
| 2623 | CA | ASP | 327 | 1.739 | 11.242 | −3.025 |
| 2624 | C | ASP | 327 | 1.672 | 11.042 | −1.512 |
| 2625 | O | ASP | 327 | 1.041 | 10.085 | −1.051 |
| 2626 | CB | ASP | 327 | 2.874 | 10.360 | −3.543 |
| 2627 | CG | ASP | 327 | 2.964 | 10.365 | −5.067 |
| 2628 | OD1 | ASP | 327 | 1.929 | 10.489 | −5.707 |
| 2629 | OD2 | ASP | 327 | 4.060 | 10.130 | −5.561 |
| 2630 | N | LYS | 328 | 2.281 | 11.934 | −0.749 |
| 2631 | CA | LYS | 328 | 2.233 | 11.811 | 0.710 |
| 2632 | C | LYS | 328 | 1.168 | 12.712 | 1.334 |
| 2633 | O | LYS | 328 | 0.959 | 12.661 | 2.552 |
| 2634 | CB | LYS | 328 | 3.603 | 12.166 | 1.274 |
| 2635 | CG | LYS | 328 | 4.698 | 11.258 | 0.724 |
| 2636 | CD | LYS | 328 | 4.523 | 9.810 | 1.166 |
| 2637 | CE | LYS | 328 | 5.625 | 8.930 | 0.588 |
| 2638 | NZ | LYS | 328 | 5.490 | 7.540 | 1.051 |
| 2639 | N | GLY | 329 | 0.501 | 13.513 | 0.517 |
| 2640 | CA | GLY | 329 | −0.526 | 14.426 | 1.032 |
| 2641 | C | GLY | 329 | 0.111 | 15.614 | 1.745 |
| 2642 | O | GLY | 329 | −0.266 | 15.969 | 2.868 |
| 2643 | N | LEU | 330 | 1.129 | 16.168 | 1.110 |
| 2644 | CA | LEU | 330 | 1.850 | 17.318 | 1.657 |
| 2645 | C | LEU | 330 | 1.503 | 18.577 | 0.872 |
| 2646 | O | LEU | 330 | 1.757 | 19.699 | 1.327 |
| 2647 | CB | LEU | 330 | 3.348 | 17.058 | 1.521 |
| 2648 | CG | LEU | 330 | 3.804 | 15.791 | 2.236 |
| 2649 | CD1 | LEU | 330 | 5.270 | 15.495 | 1.933 |

TABLE 9-continued

| Atom No. | Atom Type | Residue | Residue Position | X Coord. | Y Coord. | Z Coord. |
|---|---|---|---|---|---|---|
| 2650 | CD2 | LEU | 330 | 3.577 | 15.885 | 3.741 |
| 2651 | N | ILE | 331 | 0.912 | 18.372 | −0.294 |
| 2652 | CA | ILE | 331 | 0.557 | 19.475 | −1.199 |
| 2653 | C | ILE | 331 | −0.649 | 20.289 | −0.715 |
| 2654 | O | ILE | 331 | −1.815 | 19.919 | −0.894 |
| 2655 | CB | ILE | 331 | 0.300 | 18.875 | −2.583 |
| 2656 | CG1 | ILE | 331 | −0.259 | 19.910 | −3.555 |
| 2657 | CG2 | ILE | 331 | −0.607 | 17.650 | −2.499 |
| 2658 | CD1 | ILE | 331 | −0.515 | 19.305 | −4.929 |
| 2659 | N | ASP | 332 | −0.346 | 21.415 | −0.091 |
| 2660 | CA | ASP | 332 | −1.394 | 22.330 | 0.367 |
| 2661 | C | ASP | 332 | −1.303 | 23.655 | −0.389 |
| 2662 | O | ASP | 332 | −0.455 | 24.509 | −0.098 |
| 2663 | CB | ASP | 332 | −1.205 | 22.585 | 1.858 |
| 2664 | CG | ASP | 332 | −1.082 | 21.277 | 2.639 |
| 2665 | OD1 | ASP | 332 | −1.913 | 20.407 | 2.428 |
| 2666 | OD2 | ASP | 332 | −0.271 | 21.250 | 3.556 |
| 2667 | N | ILE | 333 | −2.175 | 23.817 | −1.368 |
| 2668 | CA | ILE | 333 | −2.166 | 25.045 | −2.174 |
| 2669 | C | ILE | 333 | −2.952 | 26.159 | −1.486 |
| 2670 | O | ILE | 333 | −4.188 | 26.202 | −1.507 |
| 2671 | CB | ILE | 333 | −2.752 | 24.740 | −3.547 |
| 2672 | CG1 | ILE | 333 | −1.971 | 23.612 | −4.211 |
| 2673 | CG2 | ILE | 333 | −2.735 | 25.982 | −4.432 |
| 2674 | CD1 | ILE | 333 | −2.536 | 23.284 | −5.589 |
| 2675 | N | ASP | 334 | −2.205 | 27.087 | −0.920 |
| 2676 | CA | ASP | 334 | −2.784 | 28.203 | −0.182 |
| 2677 | C | ASP | 334 | −2.744 | 29.466 | −1.031 |
| 2678 | O | ASP | 334 | −1.737 | 30.187 | −1.066 |
| 2679 | CB | ASP | 334 | −1.976 | 28.407 | 1.090 |
| 2680 | CG | ASP | 334 | −2.602 | 29.513 | 1.930 |
| 2681 | OD1 | ASP | 334 | −3.823 | 29.608 | 1.924 |
| 2682 | OD2 | ASP | 334 | −1.855 | 30.218 | 2.591 |
| 2683 | N | ARG | 335 | −3.881 | 29.739 | −1.655 |
| 2684 | CA | ARG | 335 | −4.048 | 30.890 | −2.557 |
| 2685 | C | ARG | 335 | −2.899 | 30.974 | −3.557 |
| 2686 | O | ARG | 335 | −2.054 | 31.876 | −3.481 |
| 2687 | CB | ARG | 335 | −4.101 | 32.164 | −1.719 |
| 2688 | CG | ARG | 335 | −5.252 | 32.128 | −0.719 |
| 2689 | CD | ARG | 335 | −5.227 | 33.344 | 0.200 |
| 2690 | NE | ARG | 335 | −5.306 | 34.591 | −0.574 |
| 2691 | CZ | ARG | 335 | −4.525 | 35.647 | −0.335 |
| 2692 | NH1 | ARG | 335 | −3.609 | 35.590 | 0.633 |
| 2693 | NH2 | ARG | 335 | −4.648 | 36.750 | −1.075 |
| 2694 | N | GLY | 336 | −2.805 | 29.965 | −4.408 |
| 2695 | CA | GLY | 336 | −1.707 | 29.899 | −5.379 |
| 2696 | C | GLY | 336 | −0.463 | 29.196 | −4.825 |
| 2697 | O | GLY | 336 | −0.100 | 28.108 | −5.286 |
| 2698 | N | ALA | 337 | 0.145 | 29.805 | −3.818 |
| 2699 | CA | ALA | 337 | 1.413 | 29.322 | −3.256 |
| 2700 | C | ALA | 337 | 1.284 | 27.938 | −2.637 |
| 2701 | O | ALA | 337 | 0.373 | 27.659 | −1.850 |
| 2702 | CB | ALA | 337 | 1.886 | 30.312 | −2.200 |
| 2703 | N | LYS | 338 | 2.200 | 27.068 | −3.012 |
| 2704 | CA | LYS | 338 | 2.147 | 25.694 | −2.515 |
| 2705 | C | LYS | 338 | 3.027 | 25.532 | −1.282 |
| 2706 | O | LYS | 338 | 4.239 | 25.790 | −1.322 |
| 2707 | CB | LYS | 338 | 2.596 | 24.751 | −3.625 |
| 2708 | CG | LYS | 338 | 2.580 | 23.293 | −3.178 |
| 2709 | CD | LYS | 338 | 3.081 | 22.371 | −4.283 |
| 2710 | CE | LYS | 338 | 3.222 | 20.939 | −3.782 |
| 2711 | NZ | LYS | 338 | 3.623 | 20.034 | −4.869 |
| 2712 | N | LEU | 339 | 2.394 | 25.175 | −0.179 |
| 2713 | CA | LEU | 339 | 3.126 | 24.888 | 1.055 |
| 2714 | C | LEU | 339 | 2.826 | 23.491 | 1.590 |
| 2715 | O | LEU | 339 | 1.866 | 22.829 | 1.179 |
| 2716 | CB | LEU | 339 | 2.825 | 25.967 | 2.099 |
| 2717 | CG | LEU | 339 | 1.342 | 26.285 | 2.296 |
| 2718 | CD1 | LEU | 339 | 0.653 | 25.276 | 3.208 |
| 2719 | CD2 | LEU | 339 | 1.193 | 27.673 | 2.908 |
| 2720 | N | ILE | 340 | 3.744 | 23.009 | 2.403 |
| 2721 | CA | ILE | 340 | 3.548 | 21.755 | 3.130 |
| 2722 | C | ILE | 340 | 3.309 | 22.043 | 4.606 |
| 2723 | O | ILE | 340 | 4.138 | 22.689 | 5.259 |
| 2724 | CB | ILE | 340 | 4.807 | 20.912 | 2.974 |
| 2725 | CG1 | ILE | 340 | 5.064 | 20.594 | 1.510 |

TABLE 9-continued

| Atom No. | Atom Type | Residue | Residue Position | X Coord. | Y Coord. | Z Coord. |
|---|---|---|---|---|---|---|
| 2726 | CG2 | ILE | 340 | 4.717 | 19.624 | 3.784 |
| 2727 | CD1 | ILE | 340 | 6.291 | 19.707 | 1.372 |
| 2728 | N | ASP | 341 | 2.160 | 21.636 | 5.116 |
| 2729 | CA | ASP | 341 | 1.895 | 21.817 | 6.544 |
| 2730 | C | ASP | 341 | 2.617 | 20.746 | 7.355 |
| 2731 | O | ASP | 341 | 2.135 | 19.619 | 7.526 |
| 2732 | CB | ASP | 341 | 0.394 | 21.759 | 6.810 |
| 2733 | CG | ASP | 341 | 0.121 | 22.057 | 8.283 |
| 2734 | OD1 | ASP | 341 | 0.179 | 21.125 | 9.073 |
| 2735 | OD2 | ASP | 341 | 0.005 | 23.228 | 8.613 |
| 2736 | N | LEU | 342 | 3.685 | 21.181 | 7.997 |
| 2737 | CA | LEU | 342 | 4.512 | 20.298 | 8.812 |
| 2738 | C | LEU | 342 | 4.035 | 20.279 | 10.254 |
| 2739 | O | LEU | 342 | 4.388 | 19.352 | 10.991 |
| 2740 | CB | LEU | 342 | 5.951 | 20.776 | 8.740 |
| 2741 | CG | LEU | 342 | 6.511 | 20.610 | 7.335 |
| 2742 | CD1 | LEU | 342 | 7.861 | 21.297 | 7.212 |
| 2743 | CD2 | LEU | 342 | 6.615 | 19.135 | 6.960 |
| 2744 | N | THR | 343 | 3.045 | 21.111 | 10.550 |
| 2745 | CA | THR | 343 | 2.394 | 21.155 | 11.870 |
| 2746 | C | THR | 343 | 1.688 | 19.853 | 12.261 |
| 2747 | O | THR | 343 | 1.737 | 19.485 | 13.442 |
| 2748 | CB | THR | 343 | 1.369 | 22.287 | 11.843 |
| 2749 | OG1 | THR | 343 | 2.081 | 23.510 | 11.793 |
| 2750 | CG2 | THR | 343 | 0.490 | 22.322 | 13.088 |
| 2751 | N | LYS | 344 | 1.325 | 19.041 | 11.278 |
| 2752 | CA | LYS | 344 | 0.710 | 17.734 | 11.551 |
| 2753 | C | LYS | 344 | 1.712 | 16.672 | 12.022 |
| 2754 | O | LYS | 344 | 1.298 | 15.629 | 12.541 |
| 2755 | CB | LYS | 344 | 0.087 | 17.244 | 10.251 |
| 2756 | CG | LYS | 344 | −0.916 | 18.247 | 9.700 |
| 2757 | CD | LYS | 344 | −1.380 | 17.851 | 8.304 |
| 2758 | CE | LYS | 344 | −2.330 | 18.891 | 7.721 |
| 2759 | NZ | LYS | 344 | −2.728 | 18.529 | 6.352 |
| 2760 | N | PHE | 345 | 3.000 | 16.934 | 11.866 |
| 2761 | CA | PHE | 345 | 4.031 | 15.988 | 12.304 |
| 2762 | C | PHE | 345 | 4.845 | 16.634 | 13.419 |
| 2763 | O | PHE | 345 | 5.521 | 15.974 | 14.218 |
| 2764 | CB | PHE | 345 | 4.944 | 15.702 | 11.114 |
| 2765 | CG | PHE | 345 | 4.203 | 15.453 | 9.801 |
| 2766 | CD1 | PHE | 345 | 3.420 | 14.317 | 9.642 |
| 2767 | CD2 | PHE | 345 | 4.309 | 16.374 | 8.765 |
| 2768 | CE1 | PHE | 345 | 2.740 | 14.104 | 8.450 |
| 2769 | CE2 | PHE | 345 | 3.629 | 16.160 | 7.574 |
| 2770 | CZ | PHE | 345 | 2.843 | 15.026 | 7.416 |
| 2771 | N | ASN | 346 | 4.792 | 17.953 | 13.402 |
| 2772 | CA | ASN | 346 | 5.455 | 18.811 | 14.377 |
| 2773 | C | ASN | 346 | 4.862 | 20.207 | 14.246 |
| 2774 | O | ASN | 346 | 5.198 | 20.946 | 13.307 |
| 2775 | CB | ASN | 346 | 6.944 | 18.855 | 14.061 |
| 2776 | CG | ASN | 346 | 7.676 | 19.682 | 15.110 |
| 2777 | OD1 | ASN | 346 | 7.564 | 20.915 | 15.148 |
| 2778 | ND2 | ASN | 346 | 8.368 | 18.984 | 15.990 |
| 2779 | N | LYS | 347 | 4.214 | 20.653 | 15.308 |
| 2780 | CA | LYS | 347 | 3.437 | 21.902 | 15.267 |
| 2781 | C | LYS | 347 | 4.289 | 23.169 | 15.169 |
| 2782 | O | LYS | 347 | 3.856 | 24.138 | 14.530 |
| 2783 | CB | LYS | 347 | 2.573 | 21.999 | 16.526 |
| 2784 | CG | LYS | 347 | 1.593 | 20.835 | 16.676 |
| 2785 | CD | LYS | 347 | 2.066 | 19.801 | 17.697 |
| 2786 | CE | LYS | 347 | 1.115 | 18.614 | 17.774 |
| 2787 | NZ | LYS | 347 | 1.596 | 17.622 | 18.748 |
| 2788 | N | LYS | 348 | 5.563 | 23.050 | 15.504 |
| 2789 | CA | LYS | 348 | 6.468 | 24.198 | 15.526 |
| 2790 | C | LYS | 348 | 7.117 | 24.402 | 14.160 |
| 2791 | O | LYS | 348 | 7.695 | 25.463 | 13.902 |
| 2792 | CB | LYS | 348 | 7.560 | 23.992 | 16.583 |
| 2793 | CG | LYS | 348 | 7.027 | 23.899 | 18.016 |
| 2794 | CD | LYS | 348 | 6.750 | 22.464 | 18.468 |
| 2795 | CE | LYS | 348 | 6.072 | 22.423 | 19.831 |
| 2796 | NZ | LYS | 348 | 5.731 | 21.040 | 20.200 |
| 2797 | N | LEU | 349 | 6.926 | 23.443 | 13.265 |
| 2798 | CA | LEU | 349 | 7.428 | 23.575 | 11.896 |
| 2799 | C | LEU | 349 | 6.404 | 24.224 | 10.964 |
| 2800 | O | LEU | 349 | 6.667 | 24.337 | 9.757 |
| 2801 | CB | LEU | 349 | 7.832 | 22.205 | 11.370 |

TABLE 9-continued

| Atom No. | Atom Type | Residue | Residue Position | X Coord. | Y Coord. | Z Coord. |
|---|---|---|---|---|---|---|
| 2802 | CG | LEU | 349 | 9.005 | 21.635 | 12.157 |
| 2803 | CD1 | LEU | 349 | 9.395 | 20.262 | 11.628 |
| 2804 | CD2 | LEU | 349 | 10.202 | 22.577 | 12.118 |
| 2805 | N | GLY | 350 | 5.243 | 24.568 | 11.508 |
| 2806 | CA | GLY | 350 | 4.234 | 25.388 | 10.813 |
| 2807 | C | GLY | 350 | 3.925 | 24.936 | 9.392 |
| 2808 | O | GLY | 350 | 3.595 | 23.770 | 9.140 |
| 2809 | N | LYS | 351 | 3.988 | 25.892 | 8.482 |
| 2810 | CA | LYS | 351 | 3.848 | 25.605 | 7.052 |
| 2811 | C | LYS | 351 | 5.113 | 26.013 | 6.302 |
| 2812 | O | LYS | 351 | 5.635 | 27.121 | 6.477 |
| 2813 | CB | LYS | 351 | 2.648 | 26.364 | 6.499 |
| 2814 | CG | LYS | 351 | 1.346 | 25.877 | 7.123 |
| 2815 | CD | LYS | 351 | 0.146 | 26.632 | 6.566 |
| 2816 | CE | LYS | 351 | −1.164 | 26.083 | 7.116 |
| 2817 | NZ | LYS | 351 | −2.314 | 26.791 | 6.531 |
| 2818 | N | ALA | 352 | 5.608 | 25.099 | 5.491 |
| 2819 | CA | ALA | 352 | 6.815 | 25.353 | 4.704 |
| 2820 | C | ALA | 352 | 6.495 | 25.555 | 3.225 |
| 2821 | O | ALA | 352 | 6.081 | 24.616 | 2.535 |
| 2822 | CB | ALA | 352 | 7.741 | 24.157 | 4.876 |
| 2823 | N | LEU | 353 | 6.661 | 26.782 | 2.761 |
| 2824 | CA | LEU | 353 | 6.421 | 27.101 | 1.346 |
| 2825 | C | LEU | 353 | 7.470 | 26.469 | 0.441 |
| 2826 | O | LEU | 353 | 8.671 | 26.739 | 0.556 |
| 2827 | CB | LEU | 353 | 6.447 | 28.614 | 1.168 |
| 2828 | CG | LEU | 353 | 5.121 | 29.258 | 1.551 |
| 2829 | CD1 | LEU | 353 | 5.264 | 30.770 | 1.674 |
| 2830 | CD2 | LEU | 353 | 4.045 | 28.902 | 0.532 |
| 2831 | N | VAL | 354 | 6.991 | 25.661 | −0.487 |
| 2832 | CA | VAL | 354 | 7.896 | 24.979 | −1.401 |
| 2833 | C | VAL | 354 | 7.985 | 25.713 | −2.739 |
| 2834 | O | VAL | 354 | 9.043 | 25.695 | −3.387 |
| 2835 | CB | VAL | 354 | 7.455 | 23.519 | −1.549 |
| 2836 | CG1 | VAL | 354 | 7.671 | 22.757 | −0.248 |
| 2837 | CG2 | VAL | 354 | 6.019 | 23.352 | −2.022 |
| 2838 | N | GLU | 355 | 6.958 | 26.483 | −3.062 |
| 2839 | CA | GLU | 355 | 7.023 | 27.331 | −4.261 |
| 2840 | C | GLU | 355 | 6.050 | 28.505 | −4.190 |
| 2841 | O | GLU | 355 | 4.911 | 28.387 | −3.714 |
| 2842 | CB | GLU | 355 | 6.784 | 26.512 | −5.529 |
| 2843 | CG | GLU | 355 | 5.403 | 25.880 | −5.582 |
| 2844 | CD | GLU | 355 | 5.231 | 25.111 | −6.890 |
| 2845 | OE1 | GLU | 355 | 4.449 | 25.573 | −7.709 |
| 2846 | OE2 | GLU | 355 | 5.672 | 23.970 | −6.923 |
| 2847 | N | LYS | 356 | 6.501 | 29.605 | −4.767 |
| 2848 | CA | LYS | 356 | 5.758 | 30.871 | −4.774 |
| 2849 | C | LYS | 356 | 4.519 | 30.751 | −5.672 |
| 2850 | O | LYS | 356 | 4.425 | 29.818 | −6.478 |
| 2851 | CB | LYS | 356 | 6.725 | 31.937 | −5.292 |
| 2852 | CG | LYS | 356 | 6.426 | 33.332 | −4.749 |
| 2853 | CD | LYS | 356 | 7.414 | 34.361 | −5.286 |
| 2854 | CE | LYS | 356 | 7.050 | 35.766 | −4.821 |
| 2855 | NZ | LYS | 356 | 7.962 | 36.764 | −5.402 |
| 2856 | N | SER | 357 | 3.649 | 31.753 | −5.633 |
| 2857 | CA | SER | 357 | 2.371 | 31.720 | −6.375 |
| 2858 | C | SER | 357 | 2.515 | 31.889 | −7.891 |
| 2859 | O | SER | 357 | 1.539 | 31.728 | −8.629 |
| 2860 | CB | SER | 357 | 1.488 | 32.854 | −5.865 |
| 2861 | OG | SER | 357 | 1.246 | 32.657 | −4.480 |
| 2862 | N | ASP | 358 | 3.713 | 32.214 | −8.348 |
| 2863 | CA | ASP | 358 | 3.986 | 32.292 | −9.783 |
| 2864 | C | ASP | 358 | 4.672 | 31.024 | −10.302 |
| 2865 | O | ASP | 358 | 5.130 | 31.007 | −11.450 |
| 2866 | CB | ASP | 358 | 4.852 | 33.518 | −10.064 |
| 2867 | CG | ASP | 358 | 6.145 | 33.461 | −9.257 |
| 2868 | OD1 | ASP | 358 | 7.033 | 32.723 | −9.660 |
| 2869 | OD2 | ASP | 358 | 6.171 | 34.051 | −8.187 |
| 2870 | N | GLY | 359 | 4.868 | 30.037 | −9.441 |
| 2871 | CA | GLY | 359 | 5.476 | 28.781 | −9.888 |
| 2872 | C | GLY | 359 | 6.869 | 28.533 | −9.313 |
| 2873 | O | GLY | 359 | 7.139 | 27.431 | −8.817 |
| 2874 | N | THR | 360 | 7.729 | 29.542 | −9.391 |
| 2875 | CA | THR | 360 | 9.144 | 29.406 | −8.995 |
| 2876 | C | THR | 360 | 9.338 | 28.760 | −7.629 |
| 2877 | O | THR | 360 | 8.721 | 29.144 | −6.624 |
| 2878 | CB | THR | 360 | 9.811 | 30.777 | −8.984 |
| 2879 | OG1 | THR | 360 | 9.096 | 31.613 | −8.081 |
| 2880 | CG2 | THR | 360 | 9.802 | 31.423 | −10.365 |
| 2881 | N | SER | 361 | 10.176 | 27.738 | −7.640 |
| 2882 | CA | SER | 361 | 10.493 | 26.981 | −6.429 |
| 2883 | C | SER | 361 | 11.337 | 27.826 | −5.493 |
| 2884 | O | SER | 361 | 12.068 | 28.727 | −5.921 |
| 2885 | CB | SER | 361 | 11.273 | 25.731 | −6.805 |
| 2886 | OG | SER | 361 | 12.563 | 26.141 | −7.238 |
| 2887 | N | LEU | 362 | 11.184 | 27.565 | −4.212 |
| 2888 | CA | LEU | 362 | 11.913 | 28.345 | −3.214 |
| 2889 | C | LEU | 362 | 13.196 | 27.656 | −2.771 |
| 2890 | O | LEU | 362 | 13.479 | 26.506 | −3.130 |
| 2891 | CB | LEU | 362 | 10.996 | 28.596 | −2.025 |
| 2892 | CG | LEU | 362 | 9.801 | 29.448 | −2.440 |
| 2893 | CD1 | LEU | 362 | 8.837 | 29.644 | −1.279 |
| 2894 | CD2 | LEU | 362 | 10.248 | 30.800 | −2.990 |
| 2895 | N | TYR | 363 | 13.877 | 28.321 | −1.851 |
| 2896 | CA | TYR | 363 | 15.153 | 27.842 | −1.299 |
| 2897 | C | TYR | 363 | 14.995 | 26.539 | −0.513 |
| 2898 | O | TYR | 363 | 15.790 | 25.613 | −0.716 |
| 2899 | CB | TYR | 363 | 15.662 | 28.947 | −0.379 |
| 2900 | CG | TYR | 363 | 16.960 | 28.650 | 0.362 |
| 2901 | CD1 | TYR | 363 | 18.050 | 28.113 | −0.312 |
| 2902 | CD2 | TYR | 363 | 17.056 | 28.949 | 1.715 |
| 2903 | CE1 | TYR | 363 | 19.224 | 27.844 | 0.377 |
| 2904 | CE2 | TYR | 363 | 18.230 | 28.681 | 2.405 |
| 2905 | CZ | TYR | 363 | 19.309 | 28.120 | 1.735 |
| 2906 | OH | TYR | 363 | 20.427 | 27.737 | 2.442 |
| 2907 | N | LEU | 364 | 13.807 | 26.356 | 0.044 |
| 2908 | CA | LEU | 364 | 13.452 | 25.125 | 0.753 |
| 2909 | C | LEU | 364 | 13.484 | 23.900 | −0.165 |
| 2910 | O | LEU | 364 | 14.182 | 22.929 | 0.157 |
| 2911 | CB | LEU | 364 | 12.031 | 25.321 | 1.266 |
| 2912 | CG | LEU | 364 | 11.517 | 24.119 | 2.043 |
| 2913 | CD1 | LEU | 364 | 12.215 | 24.003 | 3.392 |
| 2914 | CD2 | LEU | 364 | 10.016 | 24.244 | 2.245 |
| 2915 | N | THR | 365 | 13.017 | 24.056 | −1.395 |
| 2916 | CA | THR | 365 | 13.009 | 22.914 | −2.318 |
| 2917 | C | THR | 365 | 14.318 | 22.755 | −3.067 |
| 2918 | O | THR | 365 | 14.639 | 21.634 | −3.475 |
| 2919 | CB | THR | 365 | 11.886 | 23.028 | −3.333 |
| 2920 | OG1 | THR | 365 | 11.960 | 24.286 | −3.988 |
| 2921 | CG2 | THR | 365 | 10.544 | 22.919 | −2.648 |
| 2922 | N | ARG | 366 | 15.147 | 23.784 | −3.071 |
| 2923 | CA | ARG | 366 | 16.472 | 23.622 | −3.658 |
| 2924 | C | ARG | 366 | 17.388 | 22.917 | −2.664 |
| 2925 | O | ARG | 366 | 18.204 | 22.084 | −3.072 |
| 2926 | CB | ARG | 366 | 17.016 | 24.988 | −4.050 |
| 2927 | CG | ARG | 366 | 16.045 | 25.669 | −5.005 |
| 2928 | CD | ARG | 366 | 16.634 | 26.929 | −5.622 |
| 2929 | NE | ARG | 366 | 17.039 | 27.910 | −4.604 |
| 2930 | CZ | ARG | 366 | 16.624 | 29.178 | −4.623 |
| 2931 | NH1 | ARG | 366 | 15.713 | 29.568 | −5.518 |
| 2932 | NH2 | ARG | 366 | 17.060 | 30.037 | −3.700 |
| 2933 | N | ASP | 367 | 17.069 | 23.034 | −1.384 |
| 2934 | CA | ASP | 367 | 17.770 | 22.249 | −0.365 |
| 2935 | C | ASP | 367 | 17.301 | 20.797 | −0.366 |
| 2936 | O | ASP | 367 | 18.141 | 19.887 | −0.375 |
| 2937 | CB | ASP | 367 | 17.505 | 22.866 | 1.002 |
| 2938 | CG | ASP | 367 | 18.243 | 24.192 | 1.121 |
| 2939 | OD1 | ASP | 367 | 19.462 | 24.162 | 1.037 |
| 2940 | OD2 | ASP | 367 | 17.595 | 25.198 | 1.366 |
| 2941 | N | VAL | 368 | 16.010 | 20.594 | −0.586 |
| 2942 | CA | VAL | 368 | 15.457 | 19.234 | −0.664 |
| 2943 | C | VAL | 368 | 15.992 | 18.479 | −1.881 |
| 2944 | O | VAL | 368 | 16.618 | 17.424 | −1.709 |
| 2945 | CB | VAL | 368 | 13.933 | 19.338 | −0.734 |
| 2946 | CG1 | VAL | 368 | 13.275 | 18.014 | −1.109 |
| 2947 | CG2 | VAL | 368 | 13.357 | 19.869 | 0.573 |
| 2948 | N | GLY | 369 | 16.005 | 19.143 | −3.026 |
| 2949 | CA | GLY | 369 | 16.506 | 18.538 | −4.261 |
| 2950 | C | GLY | 369 | 18.009 | 18.285 | −4.214 |
| 2951 | O | GLY | 369 | 18.464 | 17.198 | −4.594 |
| 2952 | N | GLU | 370 | 18.747 | 19.210 | −3.617 |
| 2953 | CA | GLU | 370 | 20.199 | 19.060 | −3.501 |

TABLE 9-continued

| Atom No. | Atom Type | Residue | Residue Position | X Coord. | Y Coord. | Z Coord. |
|---|---|---|---|---|---|---|
| 2954 | C | GLU | 370 | 20.565 | 17.897 | −2.582 |
| 2955 | O | GLU | 370 | 21.423 | 17.090 | −2.956 |
| 2956 | CB | GLU | 370 | 20.764 | 20.333 | −2.885 |
| 2957 | CG | GLU | 370 | 22.171 | 20.635 | −3.380 |
| 2958 | CD | GLU | 370 | 22.091 | 21.367 | −4.716 |
| 2959 | OE1 | GLU | 370 | 23.087 | 21.374 | −5.423 |
| 2960 | OE2 | GLU | 370 | 21.096 | 22.045 | −4.929 |
| 2961 | N | ALA | 371 | 19.768 | 17.668 | −1.549 |
| 2962 | CA | ALA | 371 | 20.028 | 16.562 | −0.624 |
| 2963 | C | ALA | 371 | 19.685 | 15.201 | −1.228 |
| 2964 | O | ALA | 371 | 20.450 | 14.245 | −1.040 |
| 2965 | CB | ALA | 371 | 19.189 | 16.784 | 0.629 |
| 2966 | N | ILE | 372 | 18.721 | 15.175 | −2.136 |
| 2967 | CA | ILE | 372 | 18.382 | 13.916 | −2.809 |
| 2968 | C | ILE | 372 | 19.416 | 13.596 | −3.885 |
| 2969 | O | ILE | 372 | 19.852 | 12.440 | −3.992 |
| 2970 | CB | ILE | 372 | 17.002 | 14.037 | −3.450 |
| 2971 | CG1 | ILE | 372 | 15.964 | 14.526 | −2.450 |
| 2972 | CG2 | ILE | 372 | 16.566 | 12.688 | −4.010 |
| 2973 | CD1 | ILE | 372 | 14.614 | 14.745 | −3.123 |
| 2974 | N | LYS | 373 | 20.001 | 14.639 | −4.455 |
| 2975 | CA | LYS | 373 | 21.068 | 14.456 | −5.439 |
| 2976 | C | LYS | 373 | 22.357 | 13.989 | −4.771 |
| 2977 | O | LYS | 373 | 22.985 | 13.044 | −5.261 |
| 2978 | CB | LYS | 373 | 21.352 | 15.786 | −6.120 |
| 2979 | CG | LYS | 373 | 22.458 | 15.619 | −7.156 |
| 2980 | CD | LYS | 373 | 23.077 | 16.955 | −7.542 |
| 2981 | CE | LYS | 373 | 23.718 | 17.619 | −6.329 |
| 2982 | NZ | LYS | 373 | 24.434 | 18.840 | −6.723 |
| 2983 | N | ARG | 374 | 22.605 | 14.457 | −3.559 |
| 2984 | CA | ARG | 374 | 23.805 | 14.032 | −2.838 |
| 2985 | C | ARG | 374 | 23.691 | 12.600 | −2.331 |
| 2986 | O | ARG | 374 | 24.676 | 11.854 | −2.413 |
| 2987 | CB | ARG | 374 | 24.033 | 14.959 | −1.655 |
| 2988 | CG | ARG | 374 | 24.302 | 16.387 | −2.104 |
| 2989 | CD | ARG | 374 | 24.486 | 17.288 | −0.893 |
| 2990 | NE | ARG | 374 | 24.593 | 18.702 | −1.276 |
| 2991 | CZ | ARG | 374 | 25.017 | 19.635 | −0.423 |
| 2992 | NH1 | ARG | 374 | 25.468 | 19.275 | 0.781 |
| 2993 | NH2 | ARG | 374 | 25.067 | 20.914 | −0.802 |
| 2994 | N | TYR | 375 | 22.482 | 12.139 | −2.055 |
| 2995 | CA | TYR | 375 | 22.358 | 10.735 | −1.677 |
| 2996 | C | TYR | 375 | 22.505 | 9.838 | −2.895 |
| 2997 | O | TYR | 375 | 23.317 | 8.909 | −2.841 |
| 2998 | CB | TYR | 375 | 21.016 | 10.451 | −1.021 |
| 2999 | CG | TYR | 375 | 20.930 | 9.004 | −0.547 |
| 3000 | CD1 | TYR | 375 | 21.704 | 8.591 | 0.531 |
| 3001 | CD2 | TYR | 375 | 20.115 | 8.093 | −1.208 |
| 3002 | CE1 | TYR | 375 | 21.643 | 7.274 | 0.968 |
| 3003 | CE2 | TYR | 375 | 20.052 | 6.775 | −0.771 |
| 3004 | CZ | TYR | 375 | 20.813 | 6.372 | 0.318 |
| 3005 | OH | TYR | 375 | 20.724 | 5.074 | 0.772 |
| 3006 | N | GLU | 376 | 22.022 | 10.296 | −4.037 |
| 3007 | CA | GLU | 376 | 22.095 | 9.484 | −5.253 |
| 3008 | C | GLU | 376 | 23.489 | 9.465 | −5.888 |
| 3009 | O | GLU | 376 | 23.807 | 8.524 | −6.623 |
| 3010 | CB | GLU | 376 | 21.103 | 10.077 | −6.248 |
| 3011 | CG | GLU | 376 | 20.921 | 9.204 | −7.486 |
| 3012 | CD | GLU | 376 | 20.256 | 7.885 | −7.102 |
| 3013 | OE1 | GLU | 376 | 19.454 | 7.915 | −6.178 |
| 3014 | OE2 | GLU | 376 | 20.437 | 6.921 | −7.831 |
| 3015 | N | THR | 377 | 24.328 | 10.435 | −5.564 |
| 3016 | CA | THR | 377 | 25.670 | 10.471 | −6.153 |
| 3017 | C | THR | 377 | 26.785 | 10.084 | −5.185 |
| 3018 | O | THR | 377 | 27.903 | 9.808 | −5.635 |
| 3019 | CB | THR | 377 | 25.947 | 11.879 | −6.675 |
| 3020 | OG1 | THR | 377 | 25.859 | 12.790 | −5.586 |
| 3021 | CG2 | THR | 377 | 24.941 | 12.302 | −7.740 |
| 3022 | N | TYR | 378 | 26.520 | 10.098 | −3.889 |
| 3023 | CA | TYR | 378 | 27.595 | 9.805 | −2.932 |
| 3024 | C | TYR | 378 | 27.262 | 8.653 | −1.991 |
| 3025 | O | TYR | 378 | 28.177 | 8.000 | −1.476 |
| 3026 | CB | TYR | 378 | 27.862 | 11.054 | −2.095 |
| 3027 | CG | TYR | 378 | 28.245 | 12.294 | −2.897 |
| 3028 | CD1 | TYR | 378 | 29.374 | 12.283 | −3.708 |
| 3029 | CD2 | TYR | 378 | 27.466 | 13.440 | −2.806 |

TABLE 9-continued

| Atom No. | Atom Type | Residue | Residue Position | X Coord. | Y Coord. | Z Coord. |
|---|---|---|---|---|---|---|
| 3030 | CE1 | TYR | 378 | 29.710 | 13.412 | −4.443 |
| 3031 | CE2 | TYR | 378 | 27.800 | 14.569 | −3.541 |
| 3032 | CZ | TYR | 378 | 28.919 | 14.550 | −4.361 |
| 3033 | OH | TYR | 378 | 29.218 | 15.652 | −5.130 |
| 3034 | N | LYS | 379 | 25.976 | 8.376 | −1.836 |
| 3035 | CA | LYS | 379 | 25.479 | 7.384 | −0.867 |
| 3036 | C | LYS | 379 | 26.075 | 7.636 | 0.516 |
| 3037 | O | LYS | 379 | 26.859 | 6.834 | 1.035 |
| 3038 | CB | LYS | 379 | 25.814 | 5.975 | −1.352 |
| 3039 | CG | LYS | 379 | 25.188 | 5.691 | −2.714 |
| 3040 | CD | LYS | 379 | 23.665 | 5.758 | −2.661 |
| 3041 | CE | LYS | 379 | 23.057 | 5.619 | −4.052 |
| 3042 | NZ | LYS | 379 | 21.593 | 5.758 | −4.001 |
| 3043 | N | PHE | 380 | 25.714 | 8.774 | 1.084 |
| 3044 | CA | PHE | 380 | 26.260 | 9.171 | 2.382 |
| 3045 | C | PHE | 380 | 25.655 | 8.356 | 3.515 |
| 3046 | O | PHE | 380 | 24.515 | 7.881 | 3.442 |
| 3047 | CB | PHE | 380 | 26.000 | 10.658 | 2.632 |
| 3048 | CG | PHE | 380 | 24.533 | 11.078 | 2.752 |
| 3049 | CD1 | PHE | 380 | 23.860 | 10.934 | 3.960 |
| 3050 | CD2 | PHE | 380 | 23.876 | 11.628 | 1.659 |
| 3051 | CE1 | PHE | 380 | 22.528 | 11.309 | 4.068 |
| 3052 | CE2 | PHE | 380 | 22.545 | 12.007 | 1.768 |
| 3053 | CZ | PHE | 380 | 21.871 | 11.843 | 2.970 |
| 3054 | N | ASP | 381 | 26.438 | 8.203 | 4.567 |
| 3055 | CA | ASP | 381 | 25.923 | 7.605 | 5.794 |
| 3056 | C | ASP | 381 | 25.595 | 8.730 | 6.764 |
| 3057 | O | ASP | 381 | 24.705 | 8.605 | 7.612 |
| 3058 | CB | ASP | 381 | 26.978 | 6.688 | 6.399 |
| 3059 | CG | ASP | 381 | 27.354 | 5.589 | 5.411 |
| 3060 | OD1 | ASP | 381 | 26.634 | 4.603 | 5.357 |
| 3061 | OD2 | ASP | 381 | 28.416 | 5.707 | 4.812 |
| 3062 | N | LYS | 382 | 26.264 | 9.852 | 6.558 |
| 3063 | CA | LYS | 382 | 25.990 | 11.063 | 7.338 |
| 3064 | C | LYS | 382 | 26.088 | 12.297 | 6.439 |
| 3065 | O | LYS | 382 | 26.928 | 12.337 | 5.531 |
| 3066 | CB | LYS | 382 | 27.024 | 11.129 | 8.461 |
| 3067 | CG | LYS | 382 | 26.810 | 12.308 | 9.406 |
| 3068 | CD | LYS | 382 | 27.816 | 12.298 | 10.550 |
| 3069 | CE | LYS | 382 | 27.630 | 11.078 | 11.444 |
| 3070 | NZ | LYS | 382 | 26.290 | 11.070 | 12.054 |
| 3071 | N | MET | 383 | 25.164 | 13.229 | 6.605 |
| 3072 | CA | MET | 383 | 25.257 | 14.503 | 5.878 |
| 3073 | C | MET | 383 | 25.104 | 15.688 | 6.830 |
| 3074 | O | MET | 383 | 24.000 | 16.053 | 7.252 |
| 3075 | CB | MET | 383 | 24.224 | 14.557 | 4.759 |
| 3076 | CG | MET | 383 | 24.379 | 15.840 | 3.949 |
| 3077 | SD | MET | 383 | 23.617 | 15.844 | 2.311 |
| 3078 | CE | MET | 383 | 21.925 | 15.416 | 2.762 |
| 3079 | N | ILE | 384 | 26.241 | 16.293 | 7.120 |
| 3080 | CA | ILE | 384 | 26.361 | 17.408 | 8.061 |
| 3081 | C | ILE | 384 | 26.059 | 18.753 | 7.395 |
| 3082 | O | ILE | 384 | 26.498 | 19.029 | 6.270 |
| 3083 | CB | ILE | 384 | 27.804 | 17.366 | 8.563 |
| 3084 | CG1 | ILE | 384 | 28.111 | 15.981 | 9.119 |
| 3085 | CG2 | ILE | 384 | 28.086 | 18.426 | 9.620 |
| 3086 | CD1 | ILE | 384 | 29.552 | 15.878 | 9.597 |
| 3087 | N | TYR | 385 | 25.269 | 19.551 | 8.091 |
| 3088 | CA | TYR | 385 | 24.905 | 20.901 | 7.649 |
| 3089 | C | TYR | 385 | 25.297 | 21.940 | 8.694 |
| 3090 | O | TYR | 385 | 24.528 | 22.160 | 9.637 |
| 3091 | CB | TYR | 385 | 23.389 | 20.971 | 7.493 |
| 3092 | CG | TYR | 385 | 22.794 | 20.290 | 6.265 |
| 3093 | CD1 | TYR | 385 | 22.372 | 18.967 | 6.320 |
| 3094 | CD2 | TYR | 385 | 22.651 | 21.017 | 5.091 |
| 3095 | CE1 | TYR | 385 | 21.818 | 18.371 | 5.195 |
| 3096 | CE2 | TYR | 385 | 22.096 | 20.422 | 3.967 |
| 3097 | CZ | TYR | 385 | 21.680 | 19.101 | 4.023 |
| 3098 | OH | TYR | 385 | 21.079 | 18.532 | 2.922 |
| 3099 | N | VAL | 386 | 26.413 | 22.622 | 8.495 |
| 3100 | CA | VAL | 386 | 26.839 | 23.662 | 9.446 |
| 3101 | C | VAL | 386 | 26.210 | 25.007 | 9.070 |
| 3102 | O | VAL | 386 | 26.788 | 25.824 | 8.342 |
| 3103 | CB | VAL | 386 | 28.361 | 23.756 | 9.446 |
| 3104 | CG1 | VAL | 386 | 28.844 | 24.650 | 10.584 |
| 3105 | CG2 | VAL | 386 | 28.987 | 22.372 | 9.580 |

TABLE 9-continued

| Atom No. | Atom Type | Residue | Residue Position | X Coord. | Y Coord. | Z Coord. |
|---|---|---|---|---|---|---|
| 3106 | N | ILE | 387 | 24.987 | 25.188 | 9.540 |
| 3107 | CA | ILE | 387 | 24.172 | 26.355 | 9.185 |
| 3108 | C | ILE | 387 | 23.870 | 27.166 | 10.452 |
| 3109 | O | ILE | 387 | 24.027 | 26.666 | 11.569 |
| 3110 | CB | ILE | 387 | 22.907 | 25.827 | 8.490 |
| 3111 | CG1 | ILE | 387 | 23.281 | 24.854 | 7.378 |
| 3112 | CG2 | ILE | 387 | 22.049 | 26.931 | 7.884 |
| 3113 | CD1 | ILE | 387 | 22.054 | 24.408 | 6.592 |
| 3114 | N | ALA | 388 | 23.606 | 28.450 | 10.282 |
| 3115 | CA | ALA | 388 | 23.342 | 29.329 | 11.424 |
| 3116 | C | ALA | 388 | 22.113 | 28.896 | 12.210 |
| 3117 | O | ALA | 388 | 21.133 | 28.398 | 11.641 |
| 3118 | CB | ALA | 388 | 23.142 | 30.752 | 10.915 |
| 3119 | N | ALA | 389 | 22.098 | 29.281 | 13.476 |
| 3120 | CA | ALA | 389 | 20.976 | 28.984 | 14.379 |
| 3121 | C | ALA | 389 | 19.718 | 29.801 | 14.071 |
| 3122 | O | ALA | 389 | 18.600 | 29.362 | 14.376 |
| 3123 | CB | ALA | 389 | 21.422 | 29.268 | 15.806 |
| 3124 | N | GLN | 390 | 19.886 | 30.815 | 13.238 |
| 3125 | CA | GLN | 390 | 18.765 | 31.608 | 12.731 |
| 3126 | C | GLN | 390 | 17.955 | 30.825 | 11.692 |
| 3127 | O | GLN | 390 | 16.733 | 30.989 | 11.606 |
| 3128 | CB | GLN | 390 | 19.384 | 32.830 | 12.065 |
| 3129 | CG | GLN | 390 | 18.353 | 33.736 | 11.406 |
| 3130 | CD | GLN | 390 | 19.090 | 34.777 | 10.572 |
| 3131 | OE1 | GLN | 390 | 19.985 | 34.433 | 9.790 |
| 3132 | NE2 | GLN | 390 | 18.735 | 36.033 | 10.776 |
| 3133 | N | GLN | 391 | 18.589 | 29.831 | 11.089 |
| 3134 | CA | GLN | 391 | 17.929 | 28.988 | 10.097 |
| 3135 | C | GLN | 391 | 17.495 | 27.645 | 10.681 |
| 3136 | O | GLN | 391 | 17.067 | 26.771 | 9.917 |
| 3137 | CB | GLN | 391 | 18.861 | 28.798 | 8.908 |
| 3138 | CG | GLN | 391 | 19.115 | 30.141 | 8.233 |
| 3139 | CD | GLN | 391 | 20.040 | 29.994 | 7.029 |
| 3140 | OE1 | GLN | 391 | 20.085 | 28.947 | 6.375 |
| 3141 | NE2 | GLN | 391 | 20.771 | 31.059 | 6.750 |
| 3142 | N | ASP | 392 | 17.419 | 27.554 | 12.005 |
| 3143 | CA | ASP | 392 | 16.983 | 26.319 | 12.685 |
| 3144 | C | ASP | 392 | 15.605 | 25.846 | 12.232 |
| 3145 | O | ASP | 392 | 15.465 | 24.679 | 11.840 |
| 3146 | CB | ASP | 392 | 16.882 | 26.576 | 14.188 |
| 3147 | CG | ASP | 392 | 18.229 | 26.508 | 14.901 |
| 3148 | OD1 | ASP | 392 | 19.236 | 26.342 | 14.228 |
| 3149 | OD2 | ASP | 392 | 18.208 | 26.377 | 16.117 |
| 3150 | N | LEU | 393 | 14.693 | 26.787 | 12.037 |
| 3151 | CA | LEU | 393 | 13.332 | 26.439 | 11.619 |
| 3152 | C | LEU | 393 | 13.308 | 25.880 | 10.200 |
| 3153 | O | LEU | 393 | 12.847 | 24.747 | 10.031 |
| 3154 | CB | LEU | 393 | 12.467 | 27.693 | 11.680 |
| 3155 | CG | LEU | 393 | 11.024 | 27.394 | 11.285 |
| 3156 | CD1 | LEU | 393 | 10.404 | 26.363 | 12.221 |
| 3157 | CD2 | LEU | 393 | 10.187 | 28.668 | 11.267 |
| 3158 | N | HIS | 394 | 14.112 | 26.463 | 9.326 |
| 3159 | CA | HIS | 394 | 14.148 | 26.041 | 7.925 |
| 3160 | C | HIS | 394 | 14.853 | 24.700 | 7.744 |
| 3161 | O | HIS | 394 | 14.341 | 23.832 | 7.021 |
| 3162 | CB | HIS | 394 | 14.888 | 27.120 | 7.144 |
| 3163 | CG | HIS | 394 | 15.425 | 26.650 | 5.809 |
| 3164 | ND1 | HIS | 394 | 14.707 | 26.333 | 4.716 |
| 3165 | CD2 | HIS | 394 | 16.748 | 26.447 | 5.497 |
| 3166 | CE1 | HIS | 394 | 15.545 | 25.948 | 3.733 |
| 3167 | NE2 | HIS | 394 | 16.806 | 26.016 | 4.218 |
| 3168 | N | CYS | 395 | 15.851 | 24.446 | 8.574 |
| 3169 | CA | CYS | 395 | 16.582 | 23.186 | 8.482 |
| 3170 | C | CYS | 395 | 15.746 | 22.031 | 9.005 |
| 3171 | O | CYS | 395 | 15.575 | 21.044 | 8.278 |
| 3172 | CB | CYS | 395 | 17.874 | 23.307 | 9.276 |
| 3173 | SG | CYS | 395 | 19.012 | 24.564 | 8.657 |
| 3174 | N | ALA | 396 | 14.975 | 22.290 | 10.049 |
| 3175 | CA | ALA | 396 | 14.103 | 21.247 | 10.591 |
| 3176 | C | ALA | 396 | 12.853 | 21.060 | 9.733 |
| 3177 | O | ALA | 396 | 12.382 | 19.925 | 9.583 |
| 3178 | CB | ALA | 396 | 13.715 | 21.628 | 12.014 |
| 3179 | N | GLN | 397 | 12.491 | 22.091 | 8.986 |
| 3180 | CA | GLN | 397 | 11.382 | 21.979 | 8.045 |
| 3181 | C | GLN | 397 | 11.738 | 21.093 | 6.862 |
| 3182 | O | GLN | 397 | 11.020 | 20.112 | 6.640 |
| 3183 | CB | GLN | 397 | 10.978 | 23.361 | 7.545 |
| 3184 | CG | GLN | 397 | 10.226 | 24.142 | 8.615 |
| 3185 | CD | GLN | 397 | 9.873 | 25.532 | 8.099 |
| 3186 | OE1 | GLN | 397 | 10.755 | 26.310 | 7.708 |
| 3187 | NE2 | GLN | 397 | 8.594 | 25.854 | 8.176 |
| 3188 | N | PHE | 398 | 12.918 | 21.248 | 6.279 |
| 3189 | CA | PHE | 398 | 13.216 | 20.386 | 5.129 |
| 3190 | C | PHE | 398 | 13.732 | 19.011 | 5.557 |
| 3191 | O | PHE | 398 | 13.509 | 18.046 | 4.816 |
| 3192 | CB | PHE | 398 | 14.143 | 21.059 | 4.112 |
| 3193 | CG | PHE | 398 | 15.644 | 21.129 | 4.385 |
| 3194 | CD1 | PHE | 398 | 16.470 | 20.095 | 3.959 |
| 3195 | CD2 | PHE | 398 | 16.195 | 22.244 | 5.001 |
| 3196 | CE1 | PHE | 398 | 17.839 | 20.160 | 4.182 |
| 3197 | CE2 | PHE | 398 | 17.565 | 22.310 | 5.224 |
| 3198 | CZ | PHE | 398 | 18.386 | 21.267 | 4.818 |
| 3199 | N | PHE | 399 | 14.138 | 18.866 | 6.811 |
| 3200 | CA | PHE | 399 | 14.465 | 17.526 | 7.321 |
| 3201 | C | PHE | 399 | 13.181 | 16.733 | 7.536 |
| 3202 | O | PHE | 399 | 13.074 | 15.591 | 7.068 |
| 3203 | CB | PHE | 399 | 15.188 | 17.608 | 8.666 |
| 3204 | CG | PHE | 399 | 16.596 | 18.203 | 8.690 |
| 3205 | CD1 | PHE | 399 | 17.332 | 18.365 | 7.523 |
| 3206 | CD2 | PHE | 399 | 17.144 | 18.580 | 9.909 |
| 3207 | CE1 | PHE | 399 | 18.608 | 18.912 | 7.575 |
| 3208 | CE2 | PHE | 399 | 18.420 | 19.123 | 9.961 |
| 3209 | CZ | PHE | 399 | 19.153 | 19.290 | 8.794 |
| 3210 | N | GLU | 400 | 12.144 | 17.429 | 7.978 |
| 3211 | CA | GLU | 400 | 10.845 | 16.791 | 8.194 |
| 3212 | C | GLU | 400 | 10.128 | 16.536 | 6.875 |
| 3213 | O | GLU | 400 | 9.477 | 15.494 | 6.742 |
| 3214 | CB | GLU | 400 | 9.992 | 17.712 | 9.058 |
| 3215 | CG | GLU | 400 | 8.693 | 17.042 | 9.493 |
| 3216 | CD | GLU | 400 | 9.003 | 15.864 | 10.410 |
| 3217 | OE1 | GLU | 400 | 9.874 | 16.018 | 11.254 |
| 3218 | OE2 | GLU | 400 | 8.363 | 14.833 | 10.250 |
| 3219 | N | ILE | 401 | 10.420 | 17.338 | 5.865 |
| 3220 | CA | ILE | 401 | 9.858 | 17.100 | 4.536 |
| 3221 | C | ILE | 401 | 10.481 | 15.870 | 3.885 |
| 3222 | O | ILE | 401 | 9.724 | 14.978 | 3.489 |
| 3223 | CB | ILE | 401 | 10.094 | 18.334 | 3.671 |
| 3224 | CG1 | ILE | 401 | 9.266 | 19.508 | 4.173 |
| 3225 | CG2 | ILE | 401 | 9.769 | 18.053 | 2.211 |
| 3226 | CD1 | ILE | 401 | 9.512 | 20.755 | 3.335 |
| 3227 | N | LEU | 402 | 11.776 | 15.669 | 4.080 |
| 3228 | CA | LEU | 402 | 12.437 | 14.483 | 3.520 |
| 3229 | C | LEU | 402 | 12.036 | 13.217 | 4.274 |
| 3230 | O | LEU | 402 | 11.717 | 12.195 | 3.646 |
| 3231 | CB | LEU | 402 | 13.946 | 14.679 | 3.621 |
| 3232 | CG | LEU | 402 | 14.430 | 15.837 | 2.756 |
| 3233 | CD1 | LEU | 402 | 15.879 | 16.189 | 3.065 |
| 3234 | CD2 | LEU | 402 | 14.254 | 15.532 | 1.275 |
| 3235 | N | LYS | 403 | 11.778 | 13.375 | 5.562 |
| 3236 | CA | LYS | 403 | 11.297 | 12.260 | 6.379 |
| 3237 | C | LYS | 403 | 9.899 | 11.817 | 5.953 |
| 3238 | O | LYS | 403 | 9.732 | 10.644 | 5.592 |
| 3239 | CB | LYS | 403 | 11.263 | 12.727 | 7.829 |
| 3240 | CG | LYS | 403 | 10.710 | 11.653 | 8.756 |
| 3241 | CD | LYS | 403 | 10.587 | 12.176 | 10.182 |
| 3242 | CE | LYS | 403 | 9.969 | 11.132 | 11.104 |
| 3243 | NZ | LYS | 403 | 9.817 | 11.662 | 12.468 |
| 3244 | N | GLN | 404 | 9.035 | 12.783 | 5.676 |
| 3245 | CA | GLN | 404 | 7.649 | 12.488 | 5.286 |
| 3246 | C | GLN | 404 | 7.488 | 12.154 | 3.800 |
| 3247 | O | GLN | 404 | 6.403 | 11.741 | 3.379 |
| 3248 | CB | GLN | 404 | 6.772 | 13.683 | 5.645 |
| 3249 | CG | GLN | 404 | 6.785 | 13.962 | 7.146 |
| 3250 | CD | GLN | 404 | 6.246 | 12.770 | 7.934 |
| 3251 | OE1 | GLN | 404 | 5.318 | 12.083 | 7.493 |
| 3252 | NE2 | GLN | 404 | 6.768 | 12.599 | 9.136 |
| 3253 | N | MET | 405 | 8.558 | 12.280 | 3.029 |
| 3254 | CA | MET | 405 | 8.571 | 11.795 | 1.644 |
| 3255 | C | MET | 405 | 8.980 | 10.323 | 1.575 |
| 3256 | O | MET | 405 | 8.963 | 9.724 | 0.493 |
| 3257 | CB | MET | 405 | 9.557 | 12.625 | 0.833 |

TABLE 9-continued

| Atom No. | Atom Type | Residue | Residue Position | X Coord. | Y Coord. | Z Coord. |
|---|---|---|---|---|---|---|
| 3258 | CG | MET | 405 | 9.080 | 14.061 | 0.664 |
| 3259 | SD | MET | 405 | 10.296 | 15.201 | −0.035 |
| 3260 | CE | MET | 405 | 10.518 | 14.445 | −1.658 |
| 3261 | N | GLY | 406 | 9.367 | 9.763 | 2.711 |
| 3262 | CA | GLY | 406 | 9.684 | 8.337 | 2.792 |
| 3263 | C | GLY | 406 | 11.179 | 8.098 | 2.644 |
| 3264 | O | GLY | 406 | 11.608 | 7.078 | 2.090 |
| 3265 | N | PHE | 407 | 11.971 | 9.043 | 3.118 |
| 3266 | CA | PHE | 407 | 13.416 | 8.902 | 2.948 |
| 3267 | C | PHE | 407 | 14.102 | 8.308 | 4.169 |
| 3268 | O | PHE | 407 | 14.311 | 8.978 | 5.189 |
| 3269 | CB | PHE | 407 | 14.021 | 10.247 | 2.579 |
| 3270 | CG | PHE | 407 | 13.664 | 10.684 | 1.161 |
| 3271 | CD1 | PHE | 407 | 13.543 | 9.734 | 0.154 |
| 3272 | CD2 | PHE | 407 | 13.472 | 12.027 | 0.872 |
| 3273 | CE1 | PHE | 407 | 13.225 | 10.127 | −1.139 |
| 3274 | CE2 | PHE | 407 | 13.156 | 12.420 | −0.421 |
| 3275 | CZ | PHE | 407 | 13.032 | 11.471 | −1.427 |
| 3276 | N | GLU | 408 | 14.712 | 7.161 | 3.915 |
| 3277 | CA | GLU | 408 | 15.459 | 6.407 | 4.937 |
| 3278 | C | GLU | 408 | 16.877 | 6.942 | 5.168 |
| 3279 | O | GLU | 408 | 17.682 | 6.301 | 5.848 |
| 3280 | CB | GLU | 408 | 15.549 | 4.947 | 4.502 |
| 3281 | CG | GLU | 408 | 16.334 | 4.793 | 3.202 |
| 3282 | CD | GLU | 408 | 16.443 | 3.321 | 2.816 |
| 3283 | OE1 | GLU | 408 | 15.461 | 2.620 | 3.012 |
| 3284 | OE2 | GLU | 408 | 17.428 | 2.976 | 2.180 |
| 3285 | N | TRP | 409 | 17.212 | 8.029 | 4.497 |
| 3286 | CA | TRP | 409 | 18.484 | 8.700 | 4.710 |
| 3287 | C | TRP | 409 | 18.279 | 10.071 | 5.341 |
| 3288 | O | TRP | 409 | 19.257 | 10.713 | 5.743 |
| 3289 | CB | TRP | 409 | 19.210 | 8.821 | 3.374 |
| 3290 | CG | TRP | 409 | 18.380 | 9.362 | 2.222 |
| 3291 | CD1 | TRP | 409 | 17.717 | 8.617 | 1.271 |
| 3292 | CD2 | TRP | 409 | 18.137 | 10.748 | 1.894 |
| 3293 | NE1 | TRP | 409 | 17.111 | 9.463 | 0.403 |
| 3294 | CE2 | TRP | 409 | 17.339 | 10.747 | 0.737 |
| 3295 | CE3 | TRP | 409 | 18.531 | 11.948 | 2.467 |
| 3296 | CZ2 | TRP | 409 | 16.951 | 11.949 | 0.166 |
| 3297 | CZ3 | TRP | 409 | 18.133 | 13.148 | 1.893 |
| 3298 | CH2 | TRP | 409 | 17.346 | 13.148 | 0.748 |
| 3299 | N | ALA | 410 | 17.027 | 10.435 | 5.585 |
| 3300 | CA | ALA | 410 | 16.718 | 11.790 | 6.064 |
| 3301 | C | ALA | 410 | 17.057 | 12.003 | 7.535 |
| 3302 | O | ALA | 410 | 17.449 | 13.111 | 7.917 |
| 3303 | CB | ALA | 410 | 15.236 | 12.054 | 5.849 |
| 3304 | N | HIS | 411 | 17.182 | 10.909 | 8.268 |
| 3305 | CA | HIS | 411 | 17.587 | 10.974 | 9.676 |
| 3306 | C | HIS | 411 | 19.110 | 10.956 | 9.849 |
| 3307 | O | HIS | 411 | 19.605 | 11.055 | 10.977 |
| 3308 | CB | HIS | 411 | 16.921 | 9.831 | 10.439 |
| 3309 | CG | HIS | 411 | 16.976 | 8.473 | 9.767 |
| 3310 | ND1 | HIS | 411 | 15.951 | 7.833 | 9.171 |
| 3311 | CD2 | HIS | 411 | 18.073 | 7.647 | 9.672 |
| 3312 | CE1 | HIS | 411 | 16.381 | 6.649 | 8.695 |
| 3313 | NE2 | HIS | 411 | 17.694 | 6.536 | 9.004 |
| 3314 | N | ASN | 412 | 19.835 | 10.919 | 8.739 |
| 3315 | CA | ASN | 412 | 21.298 | 11.018 | 8.763 |
| 3316 | C | ASN | 412 | 21.741 | 12.467 | 8.552 |
| 3317 | O | ASN | 412 | 22.946 | 12.753 | 8.472 |
| 3318 | CB | ASN | 412 | 21.882 | 10.171 | 7.634 |
| 3319 | CG | ASN | 412 | 21.449 | 8.709 | 7.712 |
| 3320 | OD1 | ASN | 412 | 21.035 | 8.203 | 8.763 |
| 3321 | ND2 | ASN | 412 | 21.550 | 8.041 | 6.576 |
| 3322 | N | LEU | 413 | 20.770 | 13.347 | 8.364 |
| 3323 | CA | LEU | 413 | 21.046 | 14.773 | 8.155 |
| 3324 | C | LEU | 413 | 21.282 | 15.457 | 9.500 |
| 3325 | O | LEU | 413 | 20.373 | 15.615 | 10.322 |
| 3326 | CB | LEU | 413 | 19.876 | 15.432 | 7.416 |
| 3327 | CG | LEU | 413 | 19.937 | 15.317 | 5.885 |
| 3328 | CD1 | LEU | 413 | 19.771 | 13.898 | 5.353 |
| 3329 | CD2 | LEU | 413 | 18.880 | 16.201 | 5.240 |
| 3330 | N | GLU | 414 | 22.505 | 15.920 | 9.676 |
| 3331 | CA | GLU | 414 | 22.944 | 16.435 | 10.975 |
| 3332 | C | GLU | 414 | 23.182 | 17.941 | 10.949 |
| 3333 | O | GLU | 414 | 24.247 | 18.405 | 10.521 |
| 3334 | CB | GLU | 414 | 24.235 | 15.707 | 11.337 |
| 3335 | CG | GLU | 414 | 24.726 | 16.051 | 12.739 |
| 3336 | CD | GLU | 414 | 25.991 | 15.254 | 13.047 |
| 3337 | OE1 | GLU | 414 | 26.895 | 15.279 | 12.222 |
| 3338 | OE2 | GLU | 414 | 26.018 | 14.608 | 14.084 |
| 3339 | N | HIS | 415 | 22.204 | 18.687 | 11.435 |
| 3340 | CA | HIS | 415 | 22.342 | 20.145 | 11.529 |
| 3341 | C | HIS | 415 | 23.275 | 20.536 | 12.675 |
| 3342 | O | HIS | 415 | 23.087 | 20.147 | 13.833 |
| 3343 | CB | HIS | 415 | 20.967 | 20.766 | 11.753 |
| 3344 | CG | HIS | 415 | 20.957 | 22.283 | 11.799 |
| 3345 | ND1 | HIS | 415 | 20.212 | 23.050 | 12.616 |
| 3346 | CD2 | HIS | 415 | 21.703 | 23.137 | 11.021 |
| 3347 | CE1 | HIS | 415 | 20.474 | 24.349 | 12.370 |
| 3348 | NE2 | HIS | 415 | 21.399 | 24.403 | 11.387 |
| 3349 | N | VAL | 416 | 24.290 | 21.295 | 12.309 |
| 3350 | CA | VAL | 416 | 25.286 | 21.819 | 13.241 |
| 3351 | C | VAL | 416 | 25.174 | 23.342 | 13.263 |
| 3352 | O | VAL | 416 | 25.734 | 24.028 | 12.398 |
| 3353 | CB | VAL | 416 | 26.653 | 21.386 | 12.716 |
| 3354 | CG1 | VAL | 416 | 27.800 | 21.938 | 13.549 |
| 3355 | CG2 | VAL | 416 | 26.742 | 19.868 | 12.631 |
| 3356 | N | ASN | 417 | 24.381 | 23.852 | 14.190 |
| 3357 | CA | ASN | 417 | 24.127 | 25.295 | 14.212 |
| 3358 | C | ASN | 417 | 25.176 | 26.121 | 14.946 |
| 3359 | O | ASN | 417 | 25.689 | 25.765 | 16.015 |
| 3360 | CB | ASN | 417 | 22.730 | 25.602 | 14.745 |
| 3361 | CG | ASN | 417 | 22.448 | 25.097 | 16.159 |
| 3362 | OD1 | ASN | 417 | 23.336 | 24.701 | 16.925 |
| 3363 | ND2 | ASN | 417 | 21.176 | 25.163 | 16.501 |
| 3364 | N | PHE | 418 | 25.551 | 27.194 | 14.278 |
| 3365 | CA | PHE | 418 | 26.438 | 28.186 | 14.882 |
| 3366 | C | PHE | 418 | 25.672 | 29.476 | 15.160 |
| 3367 | O | PHE | 418 | 24.709 | 29.814 | 14.458 |
| 3368 | CB | PHE | 418 | 27.653 | 28.439 | 13.988 |
| 3369 | CG | PHE | 418 | 27.381 | 29.048 | 12.613 |
| 3370 | CD1 | PHE | 418 | 27.361 | 30.428 | 12.459 |
| 3371 | CD2 | PHE | 418 | 27.184 | 28.229 | 11.510 |
| 3372 | CE1 | PHE | 418 | 27.122 | 30.992 | 11.214 |
| 3373 | CE2 | PHE | 418 | 26.942 | 28.793 | 10.264 |
| 3374 | CZ | PHE | 418 | 26.910 | 30.173 | 10.114 |
| 3375 | N | GLY | 419 | 26.093 | 30.174 | 16.195 |
| 3376 | CA | GLY | 419 | 25.465 | 31.435 | 16.584 |
| 3377 | C | GLY | 419 | 25.795 | 32.561 | 15.612 |
| 3378 | O | GLY | 419 | 26.195 | 32.337 | 14.464 |
| 3379 | N | MET | 420 | 25.520 | 33.774 | 16.048 |
| 3380 | CA | MET | 420 | 25.765 | 34.941 | 15.199 |
| 3381 | C | MET | 420 | 26.866 | 35.844 | 15.742 |
| 3382 | O | MET | 420 | 27.042 | 35.987 | 16.960 |
| 3383 | CB | MET | 420 | 24.466 | 35.731 | 15.085 |
| 3384 | CG | MET | 420 | 23.357 | 34.883 | 14.470 |
| 3385 | SD | MET | 420 | 21.761 | 35.707 | 14.267 |
| 3386 | CE | MET | 420 | 22.269 | 37.036 | 13.152 |
| 3387 | N | VAL | 421 | 27.633 | 36.404 | 14.819 |
| 3388 | CA | VAL | 421 | 28.591 | 37.461 | 15.169 |
| 3389 | C | VAL | 421 | 27.837 | 38.785 | 15.281 |
| 3390 | O | VAL | 421 | 27.517 | 39.456 | 14.289 |
| 3391 | CB | VAL | 421 | 29.683 | 37.556 | 14.106 |
| 3392 | CG1 | VAL | 421 | 30.668 | 38.675 | 14.432 |
| 3393 | CG2 | VAL | 421 | 30.425 | 36.234 | 13.970 |
| 3394 | N | GLN | 422 | 27.558 | 39.143 | 16.520 |
| 3395 | CA | GLN | 422 | 26.716 | 40.299 | 16.814 |
| 3396 | C | GLN | 422 | 27.480 | 41.601 | 16.626 |
| 3397 | O | GLN | 422 | 28.448 | 41.901 | 17.336 |
| 3398 | CB | GLN | 422 | 26.206 | 40.146 | 18.240 |
| 3399 | CG | GLN | 422 | 25.389 | 38.862 | 18.354 |
| 3400 | CD | GLN | 422 | 25.006 | 38.591 | 19.804 |
| 3401 | OE1 | GLN | 422 | 23.926 | 38.055 | 20.092 |
| 3402 | NE2 | GLN | 422 | 25.923 | 38.921 | 20.696 |
| 3403 | N | GLY | 423 | 27.052 | 42.335 | 15.614 |
| 3404 | CA | GLY | 423 | 27.678 | 43.609 | 15.266 |
| 3405 | C | GLY | 423 | 27.665 | 43.814 | 13.754 |
| 3406 | O | GLY | 423 | 27.786 | 44.948 | 13.276 |
| 3407 | N | MET | 424 | 27.445 | 42.730 | 13.024 |
| 3408 | CA | MET | 424 | 27.451 | 42.773 | 11.554 |
| 3409 | C | MET | 424 | 26.143 | 43.314 | 10.969 |

TABLE 9-continued

| Atom No. | Atom Type | Residue | Residue Position | X Coord. | Y Coord. | Z Coord. |
|---|---|---|---|---|---|---|
| 3410 | O | MET | 424 | 25.258 | 42.542 | 10.585 |
| 3411 | CB | MET | 424 | 27.657 | 41.351 | 11.041 |
| 3412 | CG | MET | 424 | 28.964 | 40.714 | 11.511 |
| 3413 | SD | MET | 424 | 30.498 | 41.439 | 10.884 |
| 3414 | CE | MET | 424 | 30.978 | 42.448 | 12.305 |
| 3415 | N | SER | 425 | 26.024 | 44.628 | 10.910 |
| 3416 | CA | SER | 425 | 24.844 | 45.238 | 10.290 |
| 3417 | C | SER | 425 | 25.215 | 45.960 | 9.000 |
| 3418 | O | SER | 425 | 25.928 | 46.978 | 9.006 |
| 3419 | CB | SER | 425 | 24.207 | 46.204 | 11.276 |
| 3420 | OG | SER | 425 | 23.959 | 45.479 | 12.472 |
| 3421 | N | THR | 426 | 24.593 | 45.517 | 7.919 |
| 3422 | CA | THR | 426 | 24.918 | 46.056 | 6.592 |
| 3423 | C | THR | 426 | 24.409 | 47.481 | 6.402 |
| 3424 | O | THR | 426 | 25.212 | 48.348 | 6.042 |
| 3425 | CB | THR | 426 | 24.331 | 45.152 | 5.504 |
| 3426 | OG1 | THR | 426 | 22.918 | 45.087 | 5.646 |
| 3427 | CG2 | THR | 426 | 24.872 | 43.730 | 5.584 |
| 3428 | N | ARG | 427 | 23.263 | 47.777 | 6.997 |
| 3429 | CA | ARG | 427 | 22.643 | 49.099 | 6.846 |
| 3430 | C | ARG | 427 | 23.167 | 50.143 | 7.837 |
| 3431 | O | ARG | 427 | 22.735 | 51.300 | 7.806 |
| 3432 | CB | ARG | 427 | 21.125 | 48.929 | 6.943 |
| 3433 | CG | ARG | 427 | 20.689 | 47.993 | 8.072 |
| 3434 | CD | ARG | 427 | 20.722 | 48.648 | 9.449 |
| 3435 | NE | ARG | 427 | 20.469 | 47.656 | 10.502 |
| 3436 | CZ | ARG | 427 | 20.780 | 47.865 | 11.782 |
| 3437 | NH1 | ARG | 427 | 21.323 | 49.026 | 12.154 |
| 3438 | NH2 | ARG | 427 | 20.533 | 46.921 | 12.691 |
| 3439 | N | LYS | 428 | 24.079 | 49.735 | 8.703 |
| 3440 | CA | LYS | 428 | 24.693 | 50.675 | 9.634 |
| 3441 | C | LYS | 428 | 26.151 | 50.902 | 9.235 |
| 3442 | O | LYS | 428 | 26.803 | 51.844 | 9.702 |
| 3443 | CB | LYS | 428 | 24.602 | 50.080 | 11.034 |
| 3444 | CG | LYS | 428 | 24.933 | 51.103 | 12.113 |
| 3445 | CD | LYS | 428 | 23.964 | 52.278 | 12.056 |
| 3446 | CE | LYS | 428 | 24.286 | 53.320 | 13.121 |
| 3447 | NZ | LYS | 428 | 23.349 | 54.452 | 13.047 |
| 3448 | N | GLY | 429 | 26.631 | 50.057 | 8.335 |
| 3449 | CA | GLY | 429 | 28.020 | 50.134 | 7.872 |
| 3450 | C | GLY | 429 | 28.976 | 49.527 | 8.894 |
| 3451 | O | GLY | 429 | 30.121 | 49.970 | 9.034 |
| 3452 | N | THR | 430 | 28.502 | 48.514 | 9.600 |
| 3453 | CA | THR | 430 | 29.315 | 47.892 | 10.649 |
| 3454 | C | THR | 430 | 29.570 | 46.408 | 10.354 |
| 3455 | O | THR | 430 | 30.051 | 45.648 | 11.205 |
| 3456 | CB | THR | 430 | 28.664 | 48.178 | 12.004 |
| 3457 | OG1 | THR | 430 | 29.353 | 47.495 | 13.044 |
| 3458 | CG2 | THR | 430 | 27.203 | 47.774 | 12.055 |
| 3459 | N | VAL | 431 | 29.284 | 46.007 | 9.125 |
| 3460 | CA | VAL | 431 | 29.680 | 44.667 | 8.657 |
| 3461 | C | VAL | 431 | 31.168 | 44.600 | 8.315 |
| 3462 | O | VAL | 431 | 31.556 | 44.691 | 7.145 |
| 3463 | CB | VAL | 431 | 28.882 | 44.297 | 7.415 |
| 3464 | CG1 | VAL | 431 | 27.665 | 43.451 | 7.751 |
| 3465 | CG2 | VAL | 431 | 28.526 | 45.524 | 6.582 |
| 3466 | N | VAL | 432 | 31.981 | 44.400 | 9.337 |
| 3467 | CA | VAL | 432 | 33.425 | 44.287 | 9.147 |
| 3468 | C | VAL | 432 | 33.771 | 42.974 | 8.452 |
| 3469 | O | VAL | 432 | 33.340 | 41.884 | 8.854 |
| 3470 | CB | VAL | 432 | 34.100 | 44.383 | 10.510 |
| 3471 | CG1 | VAL | 432 | 35.619 | 44.397 | 10.376 |
| 3472 | CG2 | VAL | 432 | 33.632 | 45.637 | 11.240 |
| 3473 | N | PHE | 433 | 34.449 | 43.129 | 7.329 |
| 3474 | CA | PHE | 433 | 34.872 | 41.990 | 6.524 |
| 3475 | C | PHE | 433 | 36.000 | 41.219 | 7.191 |
| 3476 | O | PHE | 433 | 36.981 | 41.791 | 7.685 |
| 3477 | CB | PHE | 433 | 35.285 | 42.485 | 5.144 |
| 3478 | CG | PHE | 433 | 34.126 | 43.116 | 4.376 |
| 3479 | CD1 | PHE | 433 | 34.202 | 44.435 | 3.949 |
| 3480 | CD2 | PHE | 433 | 32.986 | 42.367 | 4.112 |
| 3481 | CE1 | PHE | 433 | 33.139 | 45.004 | 3.260 |
| 3482 | CE2 | PHE | 433 | 31.922 | 42.936 | 3.425 |
| 3483 | CZ | PHE | 433 | 31.998 | 44.255 | 2.999 |
| 3484 | N | LEU | 434 | 35.949 | 39.919 | 6.969 |
| 3485 | CA | LEU | 434 | 36.845 | 38.952 | 7.596 |
| 3486 | C | LEU | 434 | 38.232 | 39.002 | 6.973 |
| 3487 | O | LEU | 434 | 39.232 | 38.890 | 7.692 |
| 3488 | CB | LEU | 434 | 36.235 | 37.576 | 7.355 |
| 3489 | CG | LEU | 434 | 37.060 | 36.462 | 7.978 |
| 3490 | CD1 | LEU | 434 | 37.106 | 36.612 | 9.495 |
| 3491 | CD2 | LEU | 434 | 36.494 | 35.103 | 7.583 |
| 3492 | N | ASP | 435 | 38.291 | 39.499 | 5.748 |
| 3493 | CA | ASP | 435 | 39.580 | 39.678 | 5.075 |
| 3494 | C | ASP | 435 | 40.343 | 40.875 | 5.652 |
| 3495 | O | ASP | 435 | 41.552 | 40.759 | 5.885 |
| 3496 | CB | ASP | 435 | 39.317 | 39.910 | 3.589 |
| 3497 | CG | ASP | 435 | 38.471 | 38.777 | 3.006 |
| 3498 | OD1 | ASP | 435 | 38.996 | 37.680 | 2.880 |
| 3499 | OD2 | ASP | 435 | 37.295 | 39.013 | 2.757 |
| 3500 | N | ASN | 436 | 39.602 | 41.835 | 6.186 |
| 3501 | CA | ASN | 436 | 40.210 | 43.029 | 6.776 |
| 3502 | C | ASN | 436 | 40.639 | 42.739 | 8.210 |
| 3503 | O | ASN | 436 | 41.741 | 43.124 | 8.621 |
| 3504 | CB | ASN | 436 | 39.159 | 44.135 | 6.772 |
| 3505 | CG | ASN | 436 | 39.737 | 45.433 | 7.325 |
| 3506 | OD1 | ASN | 436 | 40.566 | 46.078 | 6.674 |
| 3507 | ND2 | ASN | 436 | 39.281 | 45.815 | 8.506 |
| 3508 | N | ILE | 437 | 39.912 | 41.828 | 8.837 |
| 3509 | CA | ILE | 437 | 40.240 | 41.398 | 10.197 |
| 3510 | C | ILE | 437 | 41.483 | 40.521 | 10.196 |
| 3511 | O | ILE | 437 | 42.405 | 40.768 | 10.982 |
| 3512 | CB | ILE | 437 | 39.069 | 40.582 | 10.725 |
| 3513 | CG1 | ILE | 437 | 37.789 | 41.402 | 10.700 |
| 3514 | CG2 | ILE | 437 | 39.351 | 40.080 | 12.136 |
| 3515 | CD1 | ILE | 437 | 36.585 | 40.536 | 11.042 |
| 3516 | N | LEU | 438 | 41.618 | 39.718 | 9.155 |
| 3517 | CA | LEU | 438 | 42.774 | 38.831 | 9.029 |
| 3518 | C | LEU | 438 | 44.035 | 39.613 | 8.669 |
| 3519 | O | LEU | 438 | 45.072 | 39.417 | 9.316 |
| 3520 | CB | LEU | 438 | 42.464 | 37.809 | 7.939 |
| 3521 | CG | LEU | 438 | 42.171 | 36.408 | 8.478 |
| 3522 | CD1 | LEU | 438 | 41.050 | 36.389 | 9.511 |
| 3523 | CD2 | LEU | 438 | 41.850 | 35.451 | 7.335 |
| 3524 | N | GLN | 439 | 43.872 | 40.652 | 7.864 |
| 3525 | CA | GLN | 439 | 45.001 | 41.519 | 7.512 |
| 3526 | C | GLN | 439 | 45.462 | 42.367 | 8.691 |
| 3527 | O | GLN | 439 | 46.652 | 42.337 | 9.029 |
| 3528 | CB | GLN | 439 | 44.567 | 42.448 | 6.384 |
| 3529 | CG | GLN | 439 | 44.519 | 41.735 | 5.038 |
| 3530 | CD | GLN | 439 | 45.938 | 41.443 | 4.560 |
| 3531 | OE1 | GLN | 439 | 46.838 | 42.278 | 4.702 |
| 3532 | NE2 | GLN | 439 | 46.112 | 40.281 | 3.956 |
| 3533 | N | GLU | 440 | 44.517 | 42.870 | 9.468 |
| 3534 | CA | GLU | 440 | 44.885 | 43.730 | 10.591 |
| 3535 | C | GLU | 440 | 45.403 | 42.937 | 11.788 |
| 3536 | O | GLU | 440 | 46.317 | 43.414 | 12.470 |
| 3537 | CB | GLU | 440 | 43.674 | 44.556 | 11.004 |
| 3538 | CG | GLU | 440 | 44.074 | 45.677 | 11.958 |
| 3539 | CD | GLU | 440 | 44.999 | 46.666 | 11.248 |
| 3540 | OE1 | GLU | 440 | 46.207 | 46.533 | 11.390 |
| 3541 | OE2 | GLU | 440 | 44.469 | 47.565 | 10.611 |
| 3542 | N | THR | 441 | 45.024 | 41.676 | 11.896 |
| 3543 | CA | THR | 441 | 45.563 | 40.852 | 12.977 |
| 3544 | C | THR | 441 | 46.938 | 40.304 | 12.601 |
| 3545 | O | THR | 441 | 47.836 | 40.281 | 13.451 |
| 3546 | CB | THR | 441 | 44.590 | 39.720 | 13.269 |
| 3547 | OG1 | THR | 441 | 43.343 | 40.298 | 13.632 |
| 3548 | CG2 | THR | 441 | 45.071 | 38.890 | 14.446 |
| 3549 | N | LYS | 442 | 47.177 | 40.188 | 11.304 |
| 3550 | CA | LYS | 442 | 48.509 | 39.843 | 10.800 |
| 3551 | C | LYS | 442 | 49.488 | 41.000 | 10.998 |
| 3552 | O | LYS | 442 | 50.616 | 40.781 | 11.457 |
| 3553 | CB | LYS | 442 | 48.366 | 39.547 | 9.311 |
| 3554 | CG | LYS | 442 | 49.710 | 39.447 | 8.603 |
| 3555 | CD | LYS | 442 | 49.515 | 39.228 | 7.108 |
| 3556 | CE | LYS | 442 | 50.851 | 39.145 | 6.381 |
| 3557 | NZ | LYS | 442 | 50.654 | 38.867 | 4.950 |
| 3558 | N | GLU | 443 | 48.981 | 42.221 | 10.901 |
| 3559 | CA | GLU | 443 | 49.811 | 43.408 | 11.137 |
| 3560 | C | GLU | 443 | 50.090 | 43.599 | 12.624 |
| 3561 | O | GLU | 443 | 51.254 | 43.779 | 13.009 |

TABLE 9-continued

| Atom No. | Atom Type | Residue | Residue Position | X Coord. | Y Coord. | Z Coord. |
|---|---|---|---|---|---|---|
| 3562 | CB | GLU | 443 | 49.062 | 44.627 | 10.609 |
| 3563 | CG | GLU | 443 | 48.831 | 44.530 | 9.106 |
| 3564 | CD | GLU | 443 | 47.898 | 45.644 | 8.638 |
| 3565 | OE1 | GLU | 443 | 46.696 | 45.403 | 8.603 |
| 3566 | OE2 | GLU | 443 | 48.405 | 46.689 | 8.255 |
| 3567 | N | LYS | 444 | 49.103 | 43.278 | 13.443 |
| 3568 | CA | LYS | 444 | 49.242 | 43.384 | 14.897 |
| 3569 | C | LYS | 444 | 50.253 | 42.378 | 15.442 |
| 3570 | O | LYS | 444 | 51.223 | 42.788 | 16.095 |
| 3571 | CB | LYS | 444 | 47.868 | 43.114 | 15.502 |
| 3572 | CG | LYS | 444 | 47.867 | 43.212 | 17.022 |
| 3573 | CD | LYS | 444 | 48.267 | 44.604 | 17.496 |
| 3574 | CE | LYS | 444 | 48.156 | 44.713 | 19.012 |
| 3575 | NZ | LYS | 444 | 48.966 | 43.678 | 19.672 |
| 3576 | N | MET | 445 | 50.203 | 41.158 | 14.932 |
| 3577 | CA | MET | 445 | 51.128 | 40.124 | 15.401 |
| 3578 | C | MET | 445 | 52.517 | 40.268 | 14.784 |
| 3579 | O | MET | 445 | 53.506 | 39.961 | 15.461 |
| 3580 | CB | MET | 445 | 50.541 | 38.758 | 15.071 |
| 3581 | CG | MET | 445 | 49.178 | 38.587 | 15.734 |
| 3582 | SD | MET | 445 | 49.151 | 38.771 | 17.533 |
| 3583 | CE | MET | 445 | 47.365 | 38.681 | 17.797 |
| 3584 | N | HIS | 446 | 52.612 | 40.981 | 13.672 |
| 3585 | CA | HIS | 446 | 53.923 | 41.257 | 13.085 |
| 3586 | C | HIS | 446 | 54.626 | 42.364 | 13.856 |
| 3587 | O | HIS | 446 | 55.816 | 42.221 | 14.153 |
| 3588 | CB | HIS | 446 | 53.744 | 41.691 | 11.635 |
| 3589 | CG | HIS | 446 | 55.043 | 41.783 | 10.862 |
| 3590 | ND1 | HIS | 446 | 55.809 | 42.877 | 10.692 |
| 3591 | CD2 | HIS | 446 | 55.668 | 40.749 | 10.207 |
| 3592 | CE1 | HIS | 446 | 56.879 | 42.555 | 9.937 |
| 3593 | NE2 | HIS | 446 | 56.794 | 41.239 | 9.641 |
| 3594 | N | GLU | 447 | 53.849 | 43.263 | 14.436 |
| 3595 | CA | GLU | 447 | 54.422 | 44.339 | 15.247 |
| 3596 | C | GLU | 447 | 54.878 | 43.828 | 16.609 |
| 3597 | O | GLU | 447 | 55.964 | 44.208 | 17.063 |
| 3598 | CB | GLU | 447 | 53.359 | 45.413 | 15.420 |
| 3599 | CG | GLU | 447 | 53.004 | 46.032 | 14.074 |
| 3600 | CD | GLU | 447 | 51.705 | 46.822 | 14.190 |
| 3601 | OE1 | GLU | 447 | 51.439 | 47.322 | 15.274 |
| 3602 | OE2 | GLU | 447 | 50.958 | 46.842 | 13.219 |
| 3603 | N | VAL | 448 | 54.223 | 42.784 | 17.095 |
| 3604 | CA | VAL | 448 | 54.654 | 42.149 | 18.347 |
| 3605 | C | VAL | 448 | 55.885 | 41.270 | 18.120 |
| 3606 | O | VAL | 448 | 56.806 | 41.258 | 18.948 |
| 3607 | CB | VAL | 448 | 53.501 | 41.299 | 18.870 |
| 3608 | CG1 | VAL | 448 | 53.888 | 40.554 | 20.143 |
| 3609 | CG2 | VAL | 448 | 52.266 | 42.155 | 19.111 |
| 3610 | N | MET | 449 | 56.022 | 40.803 | 16.891 |
| 3611 | CA | MET | 449 | 57.175 | 40.003 | 16.481 |
| 3612 | C | MET | 449 | 58.407 | 40.881 | 16.252 |
| 3613 | O | MET | 449 | 59.512 | 40.507 | 16.661 |
| 3614 | CB | MET | 449 | 56.740 | 39.330 | 15.188 |
| 3615 | CG | MET | 449 | 57.743 | 38.349 | 14.615 |
| 3616 | SD | MET | 449 | 57.103 | 37.491 | 13.163 |
| 3617 | CE | MET | 449 | 55.587 | 36.848 | 13.907 |
| 3618 | N | GLN | 450 | 58.153 | 42.141 | 15.926 |
| 3619 | CA | GLN | 450 | 59.215 | 43.144 | 15.785 |
| 3620 | C | GLN | 450 | 59.694 | 43.688 | 17.131 |
| 3621 | O | GLN | 450 | 60.771 | 44.298 | 17.191 |
| 3622 | CB | GLN | 450 | 58.665 | 44.312 | 14.975 |
| 3623 | CG | GLN | 450 | 58.230 | 43.876 | 13.585 |
| 3624 | CD | GLN | 450 | 57.562 | 45.034 | 12.854 |
| 3625 | OE1 | GLN | 450 | 56.335 | 45.063 | 12.675 |
| 3626 | NE2 | GLN | 450 | 58.393 | 45.942 | 12.376 |
| 3627 | N | LYS | 451 | 58.973 | 43.387 | 18.202 |
| 3628 | CA | LYS | 451 | 59.404 | 43.812 | 19.535 |
| 3629 | C | LYS | 451 | 60.512 | 42.906 | 20.060 |
| 3630 | O | LYS | 451 | 61.386 | 43.363 | 20.808 |
| 3631 | CB | LYS | 451 | 58.217 | 43.762 | 20.491 |
| 3632 | CG | LYS | 451 | 57.143 | 44.784 | 20.136 |
| 3633 | CD | LYS | 451 | 55.990 | 44.715 | 21.132 |
| 3634 | CE | LYS | 451 | 54.959 | 45.815 | 20.896 |
| 3635 | NZ | LYS | 451 | 54.336 | 45.698 | 19.570 |
| 3636 | N | ASN | 452 | 60.538 | 41.663 | 19.610 |
| 3637 | CA | ASN | 452 | 61.689 | 40.822 | 19.925 |

TABLE 9-continued

| Atom No. | Atom Type | Residue | Residue Position | X Coord. | Y Coord. | Z Coord. |
|---|---|---|---|---|---|---|
| 3638 | C | ASN | 452 | 62.520 | 40.680 | 18.666 |
| 3639 | O | ASN | 452 | 62.416 | 39.675 | 17.951 |
| 3640 | CB | ASN | 452 | 61.266 | 39.448 | 20.429 |
| 3641 | CG | ASN | 452 | 62.499 | 38.706 | 20.953 |
| 3642 | OD1 | ASN | 452 | 63.419 | 38.365 | 20.195 |
| 3643 | ND2 | ASN | 452 | 62.521 | 38.498 | 22.255 |
| 3644 | N | GLU | 453 | 63.535 | 41.522 | 18.580 |
| 3645 | CA | GLU | 453 | 64.344 | 41.607 | 17.360 |
| 3646 | C | GLU | 453 | 65.315 | 40.439 | 17.174 |
| 3647 | O | GLU | 453 | 65.683 | 40.151 | 16.031 |
| 3648 | CB | GLU | 453 | 65.119 | 42.917 | 17.408 |
| 3649 | CG | GLU | 453 | 64.171 | 44.109 | 17.502 |
| 3650 | CD | GLU | 453 | 64.971 | 45.406 | 17.580 |
| 3651 | OE1 | GLU | 453 | 66.102 | 45.398 | 17.114 |
| 3652 | OE2 | GLU | 453 | 64.484 | 46.340 | 18.200 |
| 3653 | N | GLU | 454 | 65.504 | 39.627 | 18.203 |
| 3654 | CA | GLU | 454 | 66.412 | 38.484 | 18.092 |
| 3655 | C | GLU | 454 | 65.694 | 37.357 | 17.361 |
| 3656 | O | GLU | 454 | 66.076 | 37.028 | 16.231 |
| 3657 | CB | GLU | 454 | 66.849 | 38.000 | 19.479 |
| 3658 | CG | GLU | 454 | 67.895 | 38.886 | 20.168 |
| 3659 | CD | GLU | 454 | 67.305 | 40.168 | 20.761 |
| 3660 | OE1 | GLU | 454 | 67.984 | 41.181 | 20.718 |
| 3661 | OE2 | GLU | 454 | 66.136 | 40.139 | 21.131 |
| 3662 | N | LYS | 455 | 64.481 | 37.092 | 17.822 |
| 3663 | CA | LYS | 455 | 63.653 | 36.040 | 17.232 |
| 3664 | C | LYS | 455 | 63.062 | 36.495 | 15.905 |
| 3665 | O | LYS | 455 | 63.072 | 35.712 | 14.946 |
| 3666 | CB | LYS | 455 | 62.527 | 35.710 | 18.205 |
| 3667 | CG | LYS | 455 | 63.060 | 35.117 | 19.504 |
| 3668 | CD | LYS | 455 | 63.713 | 33.761 | 19.263 |
| 3669 | CE | LYS | 455 | 64.313 | 33.191 | 20.542 |
| 3670 | NZ | LYS | 455 | 64.950 | 31.890 | 20.284 |
| 3671 | N | TYR | 456 | 62.885 | 37.800 | 15.770 |
| 3672 | CA | TYR | 456 | 62.402 | 38.388 | 14.519 |
| 3673 | C | TYR | 456 | 63.443 | 38.292 | 13.404 |
| 3674 | O | TYR | 456 | 63.086 | 37.900 | 12.287 |
| 3675 | CB | TYR | 456 | 62.094 | 39.853 | 14.800 |
| 3676 | CG | TYR | 456 | 61.544 | 40.645 | 13.620 |
| 3677 | CD1 | TYR | 456 | 60.331 | 40.283 | 13.050 |
| 3678 | CD2 | TYR | 456 | 62.252 | 41.732 | 13.123 |
| 3679 | CE1 | TYR | 456 | 59.825 | 41.007 | 11.979 |
| 3680 | CE2 | TYR | 456 | 61.748 | 42.456 | 12.051 |
| 3681 | CZ | TYR | 456 | 60.535 | 42.091 | 11.483 |
| 3682 | OH | TYR | 456 | 60.014 | 42.831 | 10.445 |
| 3683 | N | ALA | 457 | 64.716 | 38.365 | 13.765 |
| 3684 | CA | ALA | 457 | 65.801 | 38.243 | 12.781 |
| 3685 | C | ALA | 457 | 66.187 | 36.792 | 12.486 |
| 3686 | O | ALA | 457 | 67.030 | 36.537 | 11.617 |
| 3687 | CB | ALA | 457 | 67.020 | 38.995 | 13.300 |
| 3688 | N | GLN | 458 | 65.572 | 35.853 | 13.188 |
| 3689 | CA | GLN | 458 | 65.789 | 34.433 | 12.906 |
| 3690 | C | GLN | 458 | 64.732 | 33.898 | 11.947 |
| 3691 | O | GLN | 458 | 64.879 | 32.795 | 11.403 |
| 3692 | CB | GLN | 458 | 65.676 | 33.665 | 14.214 |
| 3693 | CG | GLN | 458 | 66.694 | 34.138 | 15.240 |
| 3694 | CD | GLN | 458 | 66.382 | 33.482 | 16.577 |
| 3695 | OE1 | GLN | 458 | 66.536 | 34.092 | 17.644 |
| 3696 | NE2 | GLN | 458 | 65.871 | 32.266 | 16.494 |
| 3697 | N | ILE | 459 | 63.666 | 34.657 | 11.761 |
| 3698 | CA | ILE | 459 | 62.590 | 34.209 | 10.877 |
| 3699 | C | ILE | 459 | 62.887 | 34.602 | 9.437 |
| 3700 | O | ILE | 459 | 63.034 | 35.786 | 9.122 |
| 3701 | CB | ILE | 459 | 61.299 | 34.868 | 11.337 |
| 3702 | CG1 | ILE | 459 | 61.159 | 34.737 | 12.840 |
| 3703 | CG2 | ILE | 459 | 60.095 | 34.217 | 10.672 |
| 3704 | CD1 | ILE | 459 | 59.967 | 35.534 | 13.336 |
| 3705 | N | GLU | 460 | 62.821 | 33.620 | 8.551 |
| 3706 | CA | GLU | 460 | 63.106 | 33.869 | 7.131 |
| 3707 | C | GLU | 460 | 61.922 | 34.496 | 6.390 |
| 3708 | O | GLU | 460 | 62.092 | 35.022 | 5.286 |
| 3709 | CB | GLU | 460 | 63.487 | 32.549 | 6.471 |
| 3710 | CG | GLU | 460 | 64.742 | 31.943 | 7.095 |
| 3711 | CD | GLU | 460 | 65.940 | 32.877 | 6.924 |
| 3712 | OE1 | GLU | 460 | 66.513 | 32.876 | 5.845 |
| 3713 | OE2 | GLU | 460 | 66.269 | 33.554 | 7.888 |

TABLE 9-continued

| Atom No. | Atom Type | Residue | Residue Position | X Coord. | Y Coord. | Z Coord. |
|---|---|---|---|---|---|---|
| 3714 | N | ASP | 461 | 60.745 | 34.453 | 6.990 |
| 3715 | CA | ASP | 461 | 59.609 | 35.212 | 6.455 |
| 3716 | C | ASP | 461 | 58.645 | 35.560 | 7.585 |
| 3717 | O | ASP | 461 | 57.615 | 34.894 | 7.770 |
| 3718 | CB | ASP | 461 | 58.900 | 34.406 | 5.367 |
| 3719 | CG | ASP | 461 | 57.926 | 35.288 | 4.579 |
| 3720 | OD1 | ASP | 461 | 57.172 | 36.021 | 5.215 |
| 3721 | OD2 | ASP | 461 | 57.849 | 35.109 | 3.374 |
| 3722 | N | PRO | 462 | 58.880 | 36.708 | 8.199 |
| 3723 | CA | PRO | 462 | 58.109 | 37.091 | 9.382 |
| 3724 | C | PRO | 462 | 56.669 | 37.511 | 9.073 |
| 3725 | O | PRO | 462 | 55.792 | 37.273 | 9.910 |
| 3726 | CB | PRO | 462 | 58.878 | 38.227 | 9.981 |
| 3727 | CG | PRO | 462 | 59.990 | 38.648 | 9.031 |
| 3728 | CD | PRO | 462 | 59.941 | 37.668 | 7.873 |
| 3729 | N | ASP | 463 | 56.379 | 37.840 | 7.823 |
| 3730 | CA | ASP | 463 | 55.029 | 38.279 | 7.460 |
| 3731 | C | ASP | 463 | 54.082 | 37.095 | 7.343 |
| 3732 | O | ASP | 463 | 52.972 | 37.151 | 7.883 |
| 3733 | CB | ASP | 463 | 55.081 | 39.017 | 6.126 |
| 3734 | CG | ASP | 463 | 55.878 | 40.311 | 6.260 |
| 3735 | OD1 | ASP | 463 | 57.090 | 40.255 | 6.099 |
| 3736 | OD2 | ASP | 463 | 55.267 | 41.324 | 6.566 |
| 3737 | N | LYS | 464 | 54.604 | 35.958 | 6.914 |
| 3738 | CA | LYS | 464 | 53.759 | 34.768 | 6.827 |
| 3739 | C | LYS | 464 | 53.622 | 34.081 | 8.180 |
| 3740 | O | LYS | 464 | 52.527 | 33.603 | 8.498 |
| 3741 | CB | LYS | 464 | 54.343 | 33.808 | 5.801 |
| 3742 | CG | LYS | 464 | 54.291 | 34.422 | 4.408 |
| 3743 | CD | LYS | 464 | 54.800 | 33.453 | 3.350 |
| 3744 | CE | LYS | 464 | 54.734 | 34.083 | 1.965 |
| 3745 | NZ | LYS | 464 | 53.356 | 34.482 | 1.636 |
| 3746 | N | ILE | 465 | 54.577 | 34.320 | 9.065 |
| 3747 | CA | ILE | 465 | 54.466 | 33.777 | 10.420 |
| 3748 | C | ILE | 465 | 53.476 | 34.597 | 11.241 |
| 3749 | O | ILE | 465 | 52.580 | 34.014 | 11.867 |
| 3750 | CB | ILE | 465 | 55.840 | 33.796 | 11.075 |
| 3751 | CG1 | ILE | 465 | 56.794 | 32.854 | 10.352 |
| 3752 | CG2 | ILE | 465 | 55.733 | 33.414 | 12.545 |
| 3753 | CD1 | ILE | 465 | 56.339 | 31.402 | 10.458 |
| 3754 | N | ALA | 466 | 53.422 | 35.889 | 10.954 |
| 3755 | CA | ALA | 466 | 52.448 | 36.772 | 11.599 |
| 3756 | C | ALA | 466 | 51.059 | 36.617 | 10.997 |
| 3757 | O | ALA | 466 | 50.054 | 36.816 | 11.688 |
| 3758 | CB | ALA | 466 | 52.912 | 38.202 | 11.395 |
| 3759 | N | ASP | 467 | 51.001 | 36.075 | 9.793 |
| 3760 | CA | ASP | 467 | 49.720 | 35.757 | 9.172 |
| 3761 | C | ASP | 467 | 49.130 | 34.489 | 9.772 |
| 3762 | O | ASP | 467 | 47.943 | 34.485 | 10.120 |
| 3763 | CB | ASP | 467 | 49.958 | 35.551 | 7.682 |
| 3764 | CG | ASP | 467 | 48.639 | 35.298 | 6.966 |
| 3765 | OD1 | ASP | 467 | 47.649 | 35.878 | 7.384 |
| 3766 | OD2 | ASP | 467 | 48.661 | 34.593 | 5.966 |
| 3767 | N | LEU | 468 | 49.985 | 33.549 | 10.143 |
| 3768 | CA | LEU | 468 | 49.499 | 32.302 | 10.743 |
| 3769 | C | LEU | 468 | 49.110 | 32.509 | 12.201 |
| 3770 | O | LEU | 468 | 48.073 | 31.993 | 12.637 |
| 3771 | CB | LEU | 468 | 50.601 | 31.254 | 10.663 |
| 3772 | CG | LEU | 468 | 51.014 | 30.983 | 9.221 |
| 3773 | CD1 | LEU | 468 | 52.256 | 30.103 | 9.163 |
| 3774 | CD2 | LEU | 468 | 49.871 | 30.381 | 8.410 |
| 3775 | N | ILE | 469 | 49.781 | 33.439 | 12.859 |
| 3776 | CA | ILE | 469 | 49.424 | 33.786 | 14.236 |
| 3777 | C | ILE | 469 | 48.192 | 34.692 | 14.281 |
| 3778 | O | ILE | 469 | 47.292 | 34.468 | 15.103 |
| 3779 | CB | ILE | 469 | 50.630 | 34.486 | 14.847 |
| 3780 | CG1 | ILE | 469 | 51.822 | 33.541 | 14.893 |
| 3781 | CG2 | ILE | 469 | 50.317 | 35.005 | 16.240 |
| 3782 | CD1 | ILE | 469 | 53.060 | 34.248 | 15.426 |
| 3783 | N | GLY | 470 | 48.044 | 35.506 | 13.250 |
| 3784 | CA | GLY | 470 | 46.871 | 36.363 | 13.091 |
| 3785 | C | GLY | 470 | 45.603 | 35.551 | 12.868 |
| 3786 | O | GLY | 470 | 44.659 | 35.630 | 13.668 |
| 3787 | N | ILE | 471 | 45.660 | 34.649 | 11.902 |
| 3788 | CA | ILE | 471 | 44.501 | 33.815 | 11.583 |
| 3789 | C | ILE | 471 | 44.199 | 32.809 | 12.693 |

TABLE 9-continued

| Atom No. | Atom Type | Residue | Residue Position | X Coord. | Y Coord. | Z Coord. |
|---|---|---|---|---|---|---|
| 3790 | O | ILE | 471 | 43.020 | 32.642 | 13.025 |
| 3791 | CB | ILE | 471 | 44.783 | 33.078 | 10.276 |
| 3792 | CG1 | ILE | 471 | 45.029 | 34.059 | 9.137 |
| 3793 | CG2 | ILE | 471 | 43.632 | 32.148 | 9.914 |
| 3794 | CD1 | ILE | 471 | 45.352 | 33.322 | 7.843 |
| 3795 | N | SER | 472 | 45.208 | 32.383 | 13.440 |
| 3796 | CA | SER | 472 | 44.941 | 31.472 | 14.559 |
| 3797 | C | SER | 472 | 44.379 | 32.189 | 15.786 |
| 3798 | O | SER | 472 | 43.583 | 31.582 | 16.508 |
| 3799 | CB | SER | 472 | 46.201 | 30.698 | 14.941 |
| 3800 | OG | SER | 472 | 47.238 | 31.597 | 15.318 |
| 3801 | N | ALA | 473 | 44.577 | 33.491 | 15.896 |
| 3802 | CA | ALA | 473 | 43.947 | 34.232 | 16.989 |
| 3803 | C | ALA | 473 | 42.462 | 34.416 | 16.704 |
| 3804 | O | ALA | 473 | 41.628 | 34.002 | 17.523 |
| 3805 | CB | ALA | 473 | 44.615 | 35.596 | 17.106 |
| 3806 | N | VAL | 474 | 42.169 | 34.666 | 15.437 |
| 3807 | CA | VAL | 474 | 40.787 | 34.883 | 14.997 |
| 3808 | C | VAL | 474 | 39.986 | 33.579 | 14.925 |
| 3809 | O | VAL | 474 | 38.798 | 33.565 | 15.277 |
| 3810 | CB | VAL | 474 | 40.852 | 35.541 | 13.621 |
| 3811 | CG1 | VAL | 474 | 39.464 | 35.825 | 13.065 |
| 3812 | CG2 | VAL | 474 | 41.666 | 36.829 | 13.673 |
| 3813 | N | MET | 475 | 40.662 | 32.471 | 14.672 |
| 3814 | CA | MET | 475 | 39.977 | 31.180 | 14.690 |
| 3815 | C | MET | 475 | 39.789 | 30.670 | 16.111 |
| 3816 | O | MET | 475 | 38.661 | 30.302 | 16.464 |
| 3817 | CB | MET | 475 | 40.783 | 30.161 | 13.893 |
| 3818 | CG | MET | 475 | 40.789 | 30.480 | 12.403 |
| 3819 | SD | MET | 475 | 41.768 | 29.360 | 11.372 |
| 3820 | CE | MET | 475 | 40.958 | 27.796 | 11.775 |
| 3821 | N | ILE | 476 | 40.757 | 30.918 | 16.979 |
| 3822 | CA | ILE | 476 | 40.652 | 30.401 | 18.345 |
| 3823 | C | ILE | 476 | 39.680 | 31.193 | 19.209 |
| 3824 | O | ILE | 476 | 38.887 | 30.528 | 19.880 |
| 3825 | CB | ILE | 476 | 42.034 | 30.327 | 18.983 |
| 3826 | CG1 | ILE | 476 | 42.811 | 29.168 | 18.378 |
| 3827 | CG2 | ILE | 476 | 41.944 | 30.137 | 20.490 |
| 3828 | CD1 | ILE | 476 | 42.108 | 27.850 | 18.682 |
| 3829 | N | GLN | 477 | 39.436 | 32.458 | 18.892 |
| 3830 | CA | GLN | 477 | 38.405 | 33.193 | 19.646 |
| 3831 | C | GLN | 477 | 36.980 | 32.791 | 19.241 |
| 3832 | O | GLN | 477 | 36.040 | 32.977 | 20.021 |
| 3833 | CB | GLN | 477 | 38.636 | 34.704 | 19.513 |
| 3834 | CG | GLN | 477 | 38.589 | 35.248 | 18.084 |
| 3835 | CD | GLN | 477 | 37.173 | 35.648 | 17.666 |
| 3836 | OE1 | GLN | 477 | 36.522 | 36.463 | 18.328 |
| 3837 | NE2 | GLN | 477 | 36.756 | 35.149 | 16.516 |
| 3838 | N | ASP | 478 | 36.853 | 32.054 | 18.147 |
| 3839 | CA | ASP | 478 | 35.553 | 31.541 | 17.730 |
| 3840 | C | ASP | 478 | 35.399 | 30.106 | 18.242 |
| 3841 | O | ASP | 478 | 34.324 | 29.728 | 18.723 |
| 3842 | CB | ASP | 478 | 35.542 | 31.567 | 16.204 |
| 3843 | CG | ASP | 478 | 34.131 | 31.587 | 15.623 |
| 3844 | OD1 | ASP | 478 | 33.387 | 30.646 | 15.854 |
| 3845 | OD2 | ASP | 478 | 33.838 | 32.546 | 14.920 |
| 3846 | N | MET | 479 | 36.531 | 29.427 | 18.365 |
| 3847 | CA | MET | 479 | 36.585 | 28.021 | 18.795 |
| 3848 | C | MET | 479 | 36.690 | 27.816 | 20.307 |
| 3849 | O | MET | 479 | 36.661 | 26.670 | 20.764 |
| 3850 | CB | MET | 479 | 37.806 | 27.382 | 18.150 |
| 3851 | CG | MET | 479 | 37.642 | 27.208 | 16.648 |
| 3852 | SD | MET | 479 | 39.097 | 26.543 | 15.810 |
| 3853 | CE | MET | 479 | 38.341 | 26.133 | 14.224 |
| 3854 | N | GLN | 480 | 36.822 | 28.893 | 21.065 |
| 3855 | CA | GLN | 480 | 36.812 | 28.796 | 22.529 |
| 3856 | C | GLN | 480 | 35.392 | 28.739 | 23.075 |
| 3857 | O | GLN | 480 | 35.182 | 28.379 | 24.239 |
| 3858 | CB | GLN | 480 | 37.519 | 30.018 | 23.103 |
| 3859 | CG | GLN | 480 | 39.004 | 29.977 | 22.780 |
| 3860 | CD | GLN | 480 | 39.691 | 31.287 | 23.149 |
| 3861 | OE1 | GLN | 480 | 40.100 | 32.065 | 22.276 |
| 3862 | NE2 | GLN | 480 | 39.823 | 31.504 | 24.443 |
| 3863 | N | SER | 481 | 34.430 | 29.060 | 22.230 |
| 3864 | CA | SER | 481 | 33.030 | 28.954 | 22.624 |
| 3865 | C | SER | 481 | 32.401 | 27.721 | 21.994 |

TABLE 9-continued

| Atom No. | Atom Type | Residue | Residue Position | X Coord. | Y Coord. | Z Coord. |
|---|---|---|---|---|---|---|
| 3866 | O | SER | 481 | 32.965 | 27.100 | 21.087 |
| 3867 | CB | SER | 481 | 32.283 | 30.183 | 22.126 |
| 3868 | OG | SER | 481 | 32.195 | 30.091 | 20.710 |
| 3869 | N | LYS | 482 | 31.256 | 27.345 | 22.536 |
| 3870 | CA | LYS | 482 | 30.408 | 26.358 | 21.870 |
| 3871 | C | LYS | 482 | 29.896 | 26.979 | 20.580 |
| 3872 | O | LYS | 482 | 29.800 | 28.209 | 20.486 |
| 3873 | CB | LYS | 482 | 29.240 | 26.006 | 22.778 |
| 3874 | CG | LYS | 482 | 29.731 | 25.410 | 24.091 |
| 3875 | CD | LYS | 482 | 28.573 | 25.151 | 25.045 |
| 3876 | CE | LYS | 482 | 27.853 | 26.448 | 25.404 |
| 3877 | NZ | LYS | 482 | 28.759 | 27.387 | 26.089 |
| 3878 | N | ARG | 483 | 29.437 | 26.146 | 19.660 |
| 3879 | CA | ARG | 483 | 29.051 | 26.646 | 18.333 |
| 3880 | C | ARG | 483 | 27.820 | 27.543 | 18.384 |
| 3881 | O | ARG | 483 | 27.792 | 28.564 | 17.695 |
| 3882 | CB | ARG | 483 | 28.685 | 25.470 | 17.446 |
| 3883 | CG | ARG | 483 | 29.624 | 24.287 | 17.596 |
| 3884 | CD | ARG | 483 | 29.083 | 23.150 | 16.747 |
| 3885 | NE | ARG | 483 | 27.614 | 23.129 | 16.854 |
| 3886 | CZ | ARG | 483 | 26.900 | 22.116 | 17.347 |
| 3887 | NH1 | ARG | 483 | 27.513 | 21.031 | 17.821 |
| 3888 | NH2 | ARG | 483 | 25.569 | 22.201 | 17.390 |
| 3889 | N | ILE | 484 | 26.961 | 27.317 | 19.364 |
| 3890 | CA | ILE | 484 | 25.721 | 28.085 | 19.512 |
| 3891 | C | ILE | 484 | 25.902 | 29.424 | 20.260 |
| 3892 | O | ILE | 484 | 24.937 | 30.185 | 20.403 |
| 3893 | CB | ILE | 484 | 24.746 | 27.159 | 20.246 |
| 3894 | CG1 | ILE | 484 | 23.316 | 27.686 | 20.253 |
| 3895 | CG2 | ILE | 484 | 25.220 | 26.886 | 21.670 |
| 3896 | CD1 | ILE | 484 | 22.780 | 27.835 | 18.836 |
| 3897 | N | HIS | 485 | 27.117 | 29.759 | 20.670 |
| 3898 | CA | HIS | 485 | 27.305 | 30.990 | 21.446 |
| 3899 | C | HIS | 485 | 27.466 | 32.231 | 20.568 |
| 3900 | O | HIS | 485 | 28.499 | 32.418 | 19.919 |
| 3901 | CB | HIS | 485 | 28.538 | 30.832 | 22.328 |
| 3902 | CG | HIS | 485 | 28.921 | 32.102 | 23.064 |
| 3903 | ND1 | HIS | 485 | 28.269 | 32.655 | 24.105 |
| 3904 | CD2 | HIS | 485 | 29.992 | 32.918 | 22.785 |
| 3905 | CE1 | HIS | 485 | 28.906 | 33.782 | 24.482 |
| 3906 | NE2 | HIS | 485 | 29.971 | 33.945 | 23.665 |
| 3907 | N | ASN | 486 | 26.469 | 33.099 | 20.620 |
| 3908 | CA | ASN | 486 | 26.554 | 34.404 | 19.948 |
| 3909 | C | ASN | 486 | 27.587 | 35.293 | 20.632 |
| 3910 | O | ASN | 486 | 27.446 | 35.619 | 21.817 |
| 3911 | CB | ASN | 486 | 25.222 | 35.135 | 20.083 |
| 3912 | CG | ASN | 486 | 24.052 | 34.479 | 19.361 |
| 3913 | OD1 | ASN | 486 | 24.207 | 33.508 | 18.611 |
| 3914 | ND2 | ASN | 486 | 22.914 | 35.141 | 19.470 |
| 3915 | N | TYR | 487 | 28.592 | 35.722 | 19.892 |
| 3916 | CA | TYR | 487 | 29.553 | 36.655 | 20.488 |
| 3917 | C | TYR | 487 | 29.540 | 37.986 | 19.752 |
| 3918 | O | TYR | 487 | 29.232 | 38.051 | 18.557 |
| 3919 | CB | TYR | 487 | 30.959 | 36.055 | 20.545 |
| 3920 | CG | TYR | 487 | 31.736 | 35.871 | 19.241 |
| 3921 | CD1 | TYR | 487 | 32.423 | 36.943 | 18.683 |
| 3922 | CD2 | TYR | 487 | 31.797 | 34.621 | 18.639 |
| 3923 | CE1 | TYR | 487 | 33.146 | 36.774 | 17.510 |
| 3924 | CE2 | TYR | 487 | 32.522 | 34.449 | 17.467 |
| 3925 | CZ | TYR | 487 | 33.195 | 35.526 | 16.906 |
| 3926 | OH | TYR | 487 | 33.993 | 35.335 | 15.798 |
| 3927 | N | GLU | 488 | 29.749 | 39.054 | 20.501 |
| 3928 | CA | GLU | 488 | 29.811 | 40.385 | 19.891 |
| 3929 | C | GLU | 488 | 31.186 | 40.580 | 19.260 |
| 3930 | O | GLU | 488 | 32.194 | 40.131 | 19.818 |
| 3931 | CB | GLU | 488 | 29.542 | 41.437 | 20.967 |
| 3932 | CG | GLU | 488 | 29.414 | 42.846 | 20.389 |
| 3933 | CD | GLU | 488 | 29.018 | 43.826 | 21.486 |
| 3934 | OE1 | GLU | 488 | 28.439 | 43.366 | 22.461 |
| 3935 | OE2 | GLU | 488 | 29.294 | 45.007 | 21.335 |
| 3936 | N | PHE | 489 | 31.205 | 41.154 | 18.069 |
| 3937 | CA | PHE | 489 | 32.468 | 41.399 | 17.373 |
| 3938 | C | PHE | 489 | 33.294 | 42.471 | 18.077 |
| 3939 | O | PHE | 489 | 32.903 | 43.642 | 18.155 |
| 3940 | CB | PHE | 489 | 32.178 | 41.845 | 15.945 |
| 3941 | CG | PHE | 489 | 33.438 | 42.267 | 15.196 |
| 3942 | CD1 | PHE | 489 | 34.359 | 41.309 | 14.797 |
| 3943 | CD2 | PHE | 489 | 33.675 | 43.611 | 14.934 |
| 3944 | CE1 | PHE | 489 | 35.517 | 41.694 | 14.135 |
| 3945 | CE2 | PHE | 489 | 34.833 | 43.994 | 14.272 |
| 3946 | CZ | PHE | 489 | 35.755 | 43.035 | 13.874 |
| 3947 | N | LYS | 490 | 34.407 | 42.039 | 18.641 |
| 3948 | CA | LYS | 490 | 35.353 | 42.969 | 19.257 |
| 3949 | C | LYS | 490 | 36.735 | 42.778 | 18.651 |
| 3950 | O | LYS | 490 | 37.244 | 41.651 | 18.600 |
| 3951 | CB | LYS | 490 | 35.420 | 42.692 | 20.754 |
| 3952 | CG | LYS | 490 | 34.047 | 42.775 | 21.409 |
| 3953 | CD | LYS | 490 | 34.104 | 42.363 | 22.874 |
| 3954 | CE | LYS | 490 | 32.721 | 42.423 | 23.510 |
| 3955 | NZ | LYS | 490 | 32.174 | 43.786 | 23.433 |
| 3956 | N | TRP | 491 | 37.417 | 43.885 | 18.406 |
| 3957 | CA | TRP | 491 | 38.769 | 43.817 | 17.836 |
| 3958 | C | TRP | 491 | 39.816 | 43.315 | 18.827 |
| 3959 | O | TRP | 491 | 40.764 | 42.642 | 18.406 |
| 3960 | CB | TRP | 491 | 39.189 | 45.196 | 17.343 |
| 3961 | CG | TRP | 491 | 38.634 | 45.571 | 15.987 |
| 3962 | CD1 | TRP | 491 | 37.580 | 46.419 | 15.720 |
| 3963 | CD2 | TRP | 491 | 39.124 | 45.110 | 14.710 |
| 3964 | NE1 | TRP | 491 | 37.420 | 46.492 | 14.373 |
| 3965 | CE2 | TRP | 491 | 38.326 | 45.728 | 13.731 |
| 3966 | CE3 | TRP | 491 | 40.152 | 44.256 | 14.338 |
| 3967 | CZ2 | TRP | 491 | 38.571 | 45.486 | 12.389 |
| 3968 | CZ3 | TRP | 491 | 40.390 | 44.016 | 12.990 |
| 3969 | CH2 | TRP | 491 | 39.602 | 44.629 | 12.020 |
| 3970 | N | ASP | 492 | 39.503 | 43.352 | 20.114 |
| 3971 | CA | ASP | 492 | 40.454 | 42.826 | 21.093 |
| 3972 | C | ASP | 492 | 40.446 | 41.297 | 21.131 |
| 3973 | O | ASP | 492 | 41.521 | 40.724 | 21.334 |
| 3974 | CB | ASP | 492 | 40.155 | 43.369 | 22.483 |
| 3975 | CG | ASP | 492 | 41.299 | 42.961 | 23.410 |
| 3976 | OD1 | ASP | 492 | 41.009 | 42.450 | 24.481 |
| 3977 | OD2 | ASP | 492 | 42.428 | 42.998 | 22.941 |
| 3978 | N | ARG | 493 | 39.413 | 40.674 | 20.581 |
| 3979 | CA | ARG | 493 | 39.365 | 39.209 | 20.547 |
| 3980 | C | ARG | 493 | 40.241 | 38.663 | 19.420 |
| 3981 | O | ARG | 493 | 40.711 | 37.523 | 19.485 |
| 3982 | CB | ARG | 493 | 37.925 | 38.782 | 20.298 |
| 3983 | CG | ARG | 493 | 36.974 | 39.410 | 21.307 |
| 3984 | CD | ARG | 493 | 35.532 | 39.005 | 21.027 |
| 3985 | NE | ARG | 493 | 35.351 | 37.558 | 21.210 |
| 3986 | CZ | ARG | 493 | 34.384 | 37.044 | 21.970 |
| 3987 | NH1 | ARG | 493 | 33.500 | 37.852 | 22.560 |
| 3988 | NH2 | ARG | 493 | 34.281 | 35.720 | 22.113 |
| 3989 | N | MET | 494 | 40.600 | 39.540 | 18.495 |
| 3990 | CA | MET | 494 | 41.486 | 39.162 | 17.401 |
| 3991 | C | MET | 494 | 42.929 | 39.552 | 17.719 |
| 3992 | O | MET | 494 | 43.866 | 38.957 | 17.180 |
| 3993 | CB | MET | 494 | 41.043 | 39.943 | 16.167 |
| 3994 | CG | MET | 494 | 39.525 | 39.978 | 16.028 |
| 3995 | SD | MET | 494 | 38.705 | 38.390 | 15.759 |
| 3996 | CE | MET | 494 | 36.990 | 38.937 | 15.918 |
| 3997 | N | THR | 495 | 43.099 | 40.487 | 18.642 |
| 3998 | CA | THR | 495 | 44.429 | 41.057 | 18.907 |
| 3999 | C | THR | 495 | 45.061 | 40.589 | 20.215 |
| 4000 | O | THR | 495 | 46.223 | 40.921 | 20.483 |
| 4001 | CB | THR | 495 | 44.319 | 42.577 | 18.944 |
| 4002 | OG1 | THR | 495 | 43.400 | 42.931 | 19.971 |
| 4003 | CG2 | THR | 495 | 43.818 | 43.146 | 17.620 |
| 4004 | N | SER | 496 | 44.302 | 39.900 | 21.048 |
| 4005 | CA | SER | 496 | 44.868 | 39.395 | 22.300 |
| 4006 | C | SER | 496 | 45.779 | 38.201 | 22.046 |
| 4007 | O | SER | 496 | 45.360 | 37.162 | 21.528 |
| 4008 | CB | SER | 496 | 43.742 | 39.013 | 23.253 |
| 4009 | OG | SER | 496 | 43.060 | 40.206 | 23.619 |
| 4010 | N | PHE | 497 | 47.049 | 38.409 | 22.344 |
| 4011 | CA | PHE | 497 | 48.047 | 37.350 | 22.196 |
| 4012 | C | PHE | 497 | 48.391 | 36.696 | 23.532 |
| 4013 | O | PHE | 497 | 48.893 | 35.568 | 23.567 |
| 4014 | CB | PHE | 497 | 49.295 | 37.920 | 21.511 |
| 4015 | CG | PHE | 497 | 50.003 | 39.105 | 22.172 |
| 4016 | CD1 | PHE | 497 | 49.640 | 40.409 | 21.854 |
| 4017 | CD2 | PHE | 497 | 51.046 | 38.877 | 23.062 |

TABLE 9-continued

| Atom No. | Atom Type | Residue | Residue Position | X Coord. | Y Coord. | Z Coord. |
|---|---|---|---|---|---|---|
| 4018 | CE1 | PHE | 497 | 50.291 | 41.479 | 22.453 |
| 4019 | CE2 | PHE | 497 | 51.699 | 39.947 | 23.659 |
| 4020 | CZ | PHE | 497 | 51.319 | 41.249 | 23.358 |
| 4021 | N | GLU | 498 | 47.975 | 37.343 | 24.607 |
| 4022 | CA | GLU | 498 | 48.266 | 36.852 | 25.958 |
| 4023 | C | GLU | 498 | 47.151 | 35.962 | 26.497 |
| 4024 | O | GLU | 498 | 46.022 | 35.976 | 25.996 |
| 4025 | CB | GLU | 498 | 48.441 | 38.054 | 26.878 |
| 4026 | CG | GLU | 498 | 49.628 | 38.909 | 26.451 |
| 4027 | CD | GLU | 498 | 49.721 | 40.161 | 27.318 |
| 4028 | OE1 | GLU | 498 | 48.672 | 40.679 | 27.669 |
| 4029 | OE2 | GLU | 498 | 50.833 | 40.616 | 27.542 |
| 4030 | N | GLY | 499 | 47.504 | 35.172 | 27.497 |
| 4031 | CA | GLY | 499 | 46.524 | 34.349 | 28.215 |
| 4032 | C | GLY | 499 | 46.065 | 33.159 | 27.388 |
| 4033 | O | GLY | 499 | 46.858 | 32.511 | 26.703 |
| 4034 | N | ASP | 500 | 44.765 | 32.932 | 27.387 |
| 4035 | CA | ASP | 500 | 44.201 | 31.807 | 26.632 |
| 4036 | C | ASP | 500 | 43.779 | 32.242 | 25.235 |
| 4037 | O | ASP | 500 | 42.580 | 32.387 | 24.969 |
| 4038 | CB | ASP | 500 | 42.981 | 31.249 | 27.362 |
| 4039 | CG | ASP | 500 | 43.371 | 30.397 | 28.568 |
| 4040 | OD1 | ASP | 500 | 43.990 | 30.930 | 29.479 |
| 4041 | OD2 | ASP | 500 | 42.909 | 29.266 | 28.615 |
| 4042 | N | THR | 501 | 44.754 | 32.455 | 24.366 |
| 4043 | CA | THR | 501 | 44.458 | 32.873 | 22.989 |
| 4044 | C | THR | 501 | 45.276 | 32.110 | 21.951 |
| 4045 | O | THR | 501 | 46.254 | 31.422 | 22.272 |
| 4046 | CB | THR | 501 | 44.760 | 34.359 | 22.840 |
| 4047 | OG1 | THR | 501 | 46.102 | 34.581 | 23.256 |
| 4048 | CG2 | THR | 501 | 43.843 | 35.230 | 23.693 |
| 4049 | N | GLY | 502 | 44.853 | 32.270 | 20.706 |
| 4050 | CA | GLY | 502 | 45.572 | 31.766 | 19.514 |
| 4051 | C | GLY | 502 | 47.102 | 31.832 | 19.602 |
| 4052 | O | GLY | 502 | 47.750 | 30.779 | 19.661 |
| 4053 | N | PRO | 503 | 47.681 | 33.028 | 19.630 |
| 4054 | CA | PRO | 503 | 49.146 | 33.163 | 19.729 |
| 4055 | C | PRO | 503 | 49.819 | 32.626 | 21.005 |
| 4056 | O | PRO | 503 | 51.023 | 32.356 | 20.941 |
| 4057 | CB | PRO | 503 | 49.419 | 34.624 | 19.576 |
| 4058 | CG | PRO | 503 | 48.111 | 35.364 | 19.364 |
| 4059 | CD | PRO | 503 | 47.017 | 34.327 | 19.483 |
| 4060 | N | TYR | 504 | 49.077 | 32.262 | 22.039 |
| 4061 | CA | TYR | 504 | 49.693 | 31.586 | 23.185 |
| 4062 | C | TYR | 504 | 49.924 | 30.107 | 22.878 |
| 4063 | O | TYR | 504 | 50.989 | 29.574 | 23.215 |
| 4064 | CB | TYR | 504 | 48.768 | 31.718 | 24.386 |
| 4065 | CG | TYR | 504 | 49.077 | 30.760 | 25.535 |
| 4066 | CD1 | TYR | 504 | 48.227 | 29.686 | 25.775 |
| 4067 | CD2 | TYR | 504 | 50.188 | 30.962 | 26.345 |
| 4068 | CE1 | TYR | 504 | 48.492 | 28.810 | 26.818 |
| 4069 | CE2 | TYR | 504 | 50.455 | 30.084 | 27.390 |
| 4070 | CZ | TYR | 504 | 49.605 | 29.011 | 27.624 |
| 4071 | OH | TYR | 504 | 49.831 | 28.169 | 28.694 |
| 4072 | N | LEU | 505 | 49.085 | 29.550 | 22.018 |
| 4073 | CA | LEU | 505 | 49.268 | 28.164 | 21.575 |
| 4074 | C | LEU | 505 | 50.383 | 28.103 | 20.543 |
| 4075 | O | LEU | 505 | 51.249 | 27.219 | 20.606 |
| 4076 | CB | LEU | 505 | 47.976 | 27.691 | 20.922 |
| 4077 | CG | LEU | 505 | 46.808 | 27.746 | 21.894 |
| 4078 | CD1 | LEU | 505 | 45.488 | 27.497 | 21.172 |
| 4079 | CD2 | LEU | 505 | 47.006 | 26.756 | 23.036 |
| 4080 | N | GLN | 506 | 50.499 | 29.194 | 19.802 |
| 4081 | CA | GLN | 506 | 51.588 | 29.357 | 18.842 |
| 4082 | C | GLN | 506 | 52.930 | 29.462 | 19.557 |
| 4083 | O | GLN | 506 | 53.829 | 28.672 | 19.256 |
| 4084 | CB | GLN | 506 | 51.348 | 30.637 | 18.045 |
| 4085 | CG | GLN | 506 | 50.116 | 30.559 | 17.147 |
| 4086 | CD | GLN | 506 | 50.416 | 29.749 | 15.889 |
| 4087 | OE1 | GLN | 506 | 51.382 | 28.986 | 15.837 |
| 4088 | NE2 | GLN | 506 | 49.559 | 29.906 | 14.898 |
| 4089 | N | TYR | 507 | 52.962 | 30.196 | 20.660 |
| 4090 | CA | TYR | 507 | 54.207 | 30.374 | 21.414 |
| 4091 | C | TYR | 507 | 54.613 | 29.127 | 22.195 |
| 4092 | O | TYR | 507 | 55.809 | 28.808 | 22.227 |
| 4093 | CB | TYR | 507 | 54.020 | 31.534 | 22.386 |

TABLE 9-continued

| Atom No. | Atom Type | Residue | Residue Position | X Coord. | Y Coord. | Z Coord. |
|---|---|---|---|---|---|---|
| 4094 | CG | TYR | 507 | 55.267 | 31.869 | 23.200 |
| 4095 | CD1 | TYR | 507 | 56.503 | 31.960 | 22.571 |
| 4096 | CD2 | TYR | 507 | 55.163 | 32.094 | 24.567 |
| 4097 | CE1 | TYR | 507 | 57.639 | 32.259 | 23.311 |
| 4098 | CE2 | TYR | 507 | 56.298 | 32.395 | 25.308 |
| 4099 | CZ | TYR | 507 | 57.533 | 32.473 | 24.678 |
| 4100 | OH | TYR | 507 | 58.664 | 32.738 | 25.419 |
| 4101 | N | ALA | 508 | 53.647 | 28.315 | 22.592 |
| 4102 | CA | ALA | 508 | 53.975 | 27.068 | 23.286 |
| 4103 | C | ALA | 508 | 54.576 | 26.043 | 22.328 |
| 4104 | O | ALA | 508 | 55.646 | 25.494 | 22.628 |
| 4105 | CB | ALA | 508 | 52.705 | 26.511 | 23.918 |
| 4106 | N | HIS | 509 | 54.085 | 26.031 | 21.098 |
| 4107 | CA | HIS | 509 | 54.633 | 25.125 | 20.083 |
| 4108 | C | HIS | 509 | 56.008 | 25.614 | 19.639 |
| 4109 | O | HIS | 509 | 56.976 | 24.838 | 19.638 |
| 4110 | CB | HIS | 509 | 53.688 | 25.133 | 18.887 |
| 4111 | CG | HIS | 509 | 53.968 | 24.061 | 17.855 |
| 4112 | ND1 | HIS | 509 | 54.830 | 24.124 | 16.820 |
| 4113 | CD2 | HIS | 509 | 53.374 | 22.822 | 17.806 |
| 4114 | CE1 | HIS | 509 | 54.783 | 22.965 | 16.132 |
| 4115 | NE2 | HIS | 509 | 53.883 | 22.161 | 16.742 |
| 4116 | N | SER | 510 | 56.121 | 26.929 | 19.555 |
| 4117 | CA | SER | 510 | 57.364 | 27.602 | 19.181 |
| 4118 | C | SER | 510 | 58.520 | 27.287 | 20.114 |
| 4119 | O | SER | 510 | 59.513 | 26.708 | 19.658 |
| 4120 | CB | SER | 510 | 57.113 | 29.104 | 19.210 |
| 4121 | OG | SER | 510 | 56.270 | 29.425 | 18.112 |
| 4122 | N | ARG | 511 | 58.323 | 27.441 | 21.414 |
| 4123 | CA | ARG | 511 | 59.440 | 27.205 | 22.335 |
| 4124 | C | ARG | 511 | 59.682 | 25.729 | 22.654 |
| 4125 | O | ARG | 511 | 60.826 | 25.378 | 22.969 |
| 4126 | CB | ARG | 511 | 59.235 | 28.007 | 23.612 |
| 4127 | CG | ARG | 511 | 57.882 | 27.738 | 24.250 |
| 4128 | CD | ARG | 511 | 57.699 | 28.600 | 25.486 |
| 4129 | NE | ARG | 511 | 56.303 | 28.565 | 25.936 |
| 4130 | CZ | ARG | 511 | 55.914 | 29.056 | 27.113 |
| 4131 | NH1 | ARG | 511 | 56.822 | 29.502 | 27.984 |
| 4132 | NH2 | ARG | 511 | 54.622 | 29.040 | 27.442 |
| 4133 | N | LEU | 512 | 58.738 | 24.854 | 22.343 |
| 4134 | CA | LEU | 512 | 59.024 | 23.424 | 22.487 |
| 4135 | C | LEU | 512 | 59.877 | 22.951 | 21.320 |
| 4136 | O | LEU | 512 | 60.971 | 22.415 | 21.549 |
| 4137 | CB | LEU | 512 | 57.727 | 22.632 | 22.531 |
| 4138 | CG | LEU | 512 | 56.978 | 22.870 | 23.833 |
| 4139 | CD1 | LEU | 512 | 55.644 | 22.135 | 23.824 |
| 4140 | CD2 | LEU | 512 | 57.820 | 22.442 | 25.030 |
| 4141 | N | CYS | 513 | 59.580 | 23.488 | 20.146 |
| 4142 | CA | CYS | 513 | 60.380 | 23.157 | 18.969 |
| 4143 | C | CYS | 513 | 61.713 | 23.902 | 18.966 |
| 4144 | O | CYS | 513 | 62.705 | 23.342 | 18.492 |
| 4145 | CB | CYS | 513 | 59.599 | 23.502 | 17.710 |
| 4146 | SG | CYS | 513 | 60.418 | 23.024 | 16.173 |
| 4147 | N | SER | 514 | 61.799 | 24.998 | 19.703 |
| 4148 | CA | SER | 514 | 63.073 | 25.705 | 19.880 |
| 4149 | C | SER | 514 | 63.990 | 25.016 | 20.885 |
| 4150 | O | SER | 514 | 65.213 | 25.034 | 20.705 |
| 4151 | CB | SER | 514 | 62.783 | 27.114 | 20.381 |
| 4152 | OG | SER | 514 | 64.033 | 27.742 | 20.629 |
| 4153 | N | MET | 515 | 63.409 | 24.233 | 21.778 |
| 4154 | CA | MET | 515 | 64.209 | 23.455 | 22.724 |
| 4155 | C | MET | 515 | 64.711 | 22.185 | 22.038 |
| 4156 | O | MET | 515 | 65.847 | 21.748 | 22.263 |
| 4157 | CB | MET | 515 | 63.314 | 23.088 | 23.901 |
| 4158 | CG | MET | 515 | 64.128 | 22.752 | 25.143 |
| 4159 | SD | MET | 515 | 65.092 | 24.137 | 25.790 |
| 4160 | CE | MET | 515 | 65.717 | 23.382 | 27.306 |
| 4161 | N | GLN | 516 | 63.968 | 21.762 | 21.028 |
| 4162 | CA | GLN | 516 | 64.387 | 20.636 | 20.186 |
| 4163 | C | GLN | 516 | 65.362 | 21.082 | 19.090 |
| 4164 | O | GLN | 516 | 66.224 | 20.297 | 18.672 |
| 4165 | CB | GLN | 516 | 63.125 | 20.056 | 19.566 |
| 4166 | CG | GLN | 516 | 62.170 | 19.587 | 20.658 |
| 4167 | CD | GLN | 516 | 60.794 | 19.316 | 20.062 |
| 4168 | OE1 | GLN | 516 | 59.766 | 19.704 | 20.632 |
| 4169 | NE2 | GLN | 516 | 60.792 | 18.658 | 18.917 |

TABLE 9-continued

| Atom No. | Atom Type | Residue | Residue Position | X Coord. | Y Coord. | Z Coord. |
|---|---|---|---|---|---|---|
| 4170 | N | ARG | 517 | 65.373 | 22.381 | 18.824 |
| 4171 | CA | ARG | 517 | 66.319 | 23.011 | 17.894 |
| 4172 | C | ARG | 517 | 67.676 | 23.316 | 18.525 |
| 4173 | O | ARG | 517 | 68.549 | 23.888 | 17.862 |
| 4174 | CB | ARG | 517 | 65.711 | 24.280 | 17.302 |
| 4175 | CG | ARG | 517 | 64.841 | 23.937 | 16.095 |
| 4176 | CD | ARG | 517 | 64.356 | 25.173 | 15.339 |
| 4177 | NE | ARG | 517 | 63.177 | 25.805 | 15.957 |
| 4178 | CZ | ARG | 517 | 63.154 | 27.060 | 16.411 |
| 4179 | NH1 | ARG | 517 | 64.291 | 27.749 | 16.530 |
| 4180 | NH2 | ARG | 517 | 62.018 | 27.571 | 16.888 |
| 4181 | N | LYS | 518 | 67.877 | 22.859 | 19.754 |
| 4182 | CA | LYS | 518 | 69.214 | 22.838 | 20.350 |
| 4183 | C | LYS | 518 | 70.005 | 21.630 | 19.824 |
| 4184 | O | LYS | 518 | 71.225 | 21.568 | 20.013 |
| 4185 | CB | LYS | 518 | 69.078 | 22.750 | 21.867 |
| 4186 | CG | LYS | 518 | 68.243 | 23.899 | 22.427 |
| 4187 | CD | LYS | 518 | 68.901 | 25.256 | 22.200 |
| 4188 | CE | LYS | 518 | 67.999 | 26.387 | 22.689 |
| 4189 | NZ | LYS | 518 | 67.668 | 26.207 | 24.112 |
| 4190 | N | SER | 519 | 69.303 | 20.734 | 19.133 |
| 4191 | CA | SER | 519 | 69.852 | 19.620 | 18.332 |
| 4192 | C | SER | 519 | 71.030 | 18.864 | 18.937 |
| 4193 | O | SER | 519 | 72.192 | 19.277 | 18.850 |
| 4194 | CB | SER | 519 | 70.225 | 20.153 | 16.950 |
| 4195 | OG | SER | 519 | 71.131 | 21.239 | 17.100 |
| 4196 | N | GLY | 520 | 70.715 | 17.694 | 19.459 |
| 4197 | CA | GLY | 520 | 71.744 | 16.816 | 20.010 |
| 4198 | C | GLY | 520 | 71.233 | 15.384 | 20.004 |
| 4199 | O | GLY | 520 | 71.679 | 14.539 | 19.219 |
| 4200 | N | ILE | 521 | 70.293 | 15.134 | 20.898 |
| 4201 | CA | ILE | 521 | 69.672 | 13.814 | 21.021 |
| 4202 | C | ILE | 521 | 68.608 | 13.630 | 19.942 |
| 4203 | O | ILE | 521 | 67.752 | 14.500 | 19.742 |
| 4204 | CB | ILE | 521 | 69.049 | 13.761 | 22.410 |
| 4205 | CG1 | ILE | 521 | 70.088 | 14.210 | 23.432 |
| 4206 | CG2 | ILE | 521 | 68.558 | 12.355 | 22.734 |
| 4207 | CD1 | ILE | 521 | 69.474 | 14.413 | 24.809 |
| 4208 | N | SER | 522 | 68.718 | 12.532 | 19.213 |
| 4209 | CA | SER | 522 | 67.772 | 12.230 | 18.134 |
| 4210 | C | SER | 522 | 66.447 | 11.718 | 18.685 |
| 4211 | O | SER | 522 | 66.398 | 11.135 | 19.777 |
| 4212 | CB | SER | 522 | 68.374 | 11.165 | 17.226 |
| 4213 | OG | SER | 522 | 68.346 | 9.926 | 17.925 |
| 4214 | N | ILE | 523 | 65.451 | 11.703 | 17.811 |
| 4215 | CA | ILE | 523 | 64.082 | 11.299 | 18.177 |
| 4216 | C | ILE | 523 | 63.947 | 9.795 | 18.420 |
| 4217 | O | ILE | 523 | 63.190 | 9.385 | 19.309 |
| 4218 | CB | ILE | 523 | 63.165 | 11.717 | 17.032 |
| 4219 | CG1 | ILE | 523 | 63.197 | 13.230 | 16.851 |
| 4220 | CG2 | ILE | 523 | 61.735 | 11.233 | 17.253 |
| 4221 | CD1 | ILE | 523 | 62.248 | 13.678 | 15.746 |
| 4222 | N | GLU | 524 | 64.898 | 9.040 | 17.895 |
| 4223 | CA | GLU | 524 | 64.942 | 7.592 | 18.122 |
| 4224 | C | GLU | 524 | 65.318 | 7.309 | 19.573 |
| 4225 | O | GLU | 524 | 64.573 | 6.603 | 20.263 |
| 4226 | CB | GLU | 524 | 65.985 | 6.939 | 17.210 |
| 4227 | CG | GLU | 524 | 65.774 | 7.216 | 15.721 |
| 4228 | CD | GLU | 524 | 66.724 | 8.312 | 15.237 |
| 4229 | OE1 | GLU | 524 | 67.873 | 7.991 | 14.987 |
| 4230 | OE2 | GLU | 524 | 66.359 | 9.471 | 15.413 |
| 4231 | N | GLU | 525 | 66.204 | 8.141 | 20.101 |
| 4232 | CA | GLU | 525 | 66.634 | 8.005 | 21.493 |
| 4233 | C | GLU | 525 | 65.604 | 8.589 | 22.450 |
| 4234 | O | GLU | 525 | 65.487 | 8.099 | 23.576 |
| 4235 | CB | GLU | 525 | 67.941 | 8.761 | 21.676 |
| 4236 | CG | GLU | 525 | 69.049 | 8.204 | 20.796 |
| 4237 | CD | GLU | 525 | 70.259 | 9.125 | 20.876 |
| 4238 | OE1 | GLU | 525 | 71.177 | 8.816 | 21.620 |
| 4239 | OE2 | GLU | 525 | 70.238 | 10.131 | 20.176 |
| 4240 | N | LEU | 526 | 64.722 | 9.433 | 21.938 |
| 4241 | CA | LEU | 526 | 63.649 | 9.991 | 22.763 |
| 4242 | C | LEU | 526 | 62.498 | 8.994 | 22.887 |
| 4243 | O | LEU | 526 | 61.878 | 8.903 | 23.954 |
| 4244 | CB | LEU | 526 | 63.144 | 11.276 | 22.115 |
| 4245 | CG | LEU | 526 | 64.253 | 12.299 | 21.901 |

TABLE 9-continued

| Atom No. | Atom Type | Residue | Residue Position | X Coord. | Y Coord. | Z Coord. |
|---|---|---|---|---|---|---|
| 4246 | CD1 | LEU | 526 | 63.713 | 13.547 | 21.212 |
| 4247 | CD2 | LEU | 526 | 64.934 | 12.668 | 23.211 |
| 4248 | N | GLU | 527 | 62.423 | 8.071 | 21.940 |
| 4249 | CA | GLU | 527 | 61.445 | 6.978 | 22.012 |
| 4250 | C | GLU | 527 | 61.960 | 5.846 | 22.901 |
| 4251 | O | GLU | 527 | 61.194 | 4.963 | 23.308 |
| 4252 | CB | GLU | 527 | 61.233 | 6.433 | 20.603 |
| 4253 | CG | GLU | 527 | 60.717 | 7.507 | 19.655 |
| 4254 | CD | GLU | 527 | 60.700 | 6.989 | 18.221 |
| 4255 | OE1 | GLU | 527 | 59.777 | 6.256 | 17.895 |
| 4256 | OE2 | GLU | 527 | 61.659 | 7.257 | 17.509 |
| 4257 | N | HIS | 528 | 63.246 | 5.900 | 23.212 |
| 4258 | CA | HIS | 528 | 63.885 | 4.925 | 24.101 |
| 4259 | C | HIS | 528 | 64.309 | 5.574 | 25.421 |
| 4260 | O | HIS | 528 | 65.085 | 4.976 | 26.178 |
| 4261 | CB | HIS | 528 | 65.125 | 4.365 | 23.408 |
| 4262 | CG | HIS | 528 | 64.884 | 3.721 | 22.056 |
| 4263 | ND1 | HIS | 528 | 63.822 | 2.977 | 21.683 |
| 4264 | CD2 | HIS | 528 | 65.727 | 3.778 | 20.972 |
| 4265 | CE1 | HIS | 528 | 63.975 | 2.588 | 20.403 |
| 4266 | NE2 | HIS | 528 | 65.154 | 3.085 | 19.963 |
| 4267 | N | ALA | 529 | 63.805 | 6.772 | 25.681 |
| 4268 | CA | ALA | 529 | 64.204 | 7.567 | 26.851 |
| 4269 | C | ALA | 529 | 63.973 | 6.858 | 28.178 |
| 4270 | O | ALA | 529 | 63.190 | 5.905 | 28.272 |
| 4271 | CB | ALA | 529 | 63.402 | 8.861 | 26.841 |
| 4272 | N | ASN | 530 | 64.718 | 7.266 | 29.190 |
| 4273 | CA | ASN | 530 | 64.478 | 6.681 | 30.507 |
| 4274 | C | ASN | 530 | 63.313 | 7.396 | 31.175 |
| 4275 | O | ASN | 530 | 63.478 | 8.417 | 31.858 |
| 4276 | CB | ASN | 530 | 65.711 | 6.744 | 31.394 |
| 4277 | CG | ASN | 530 | 65.383 | 5.977 | 32.672 |
| 4278 | OD1 | ASN | 530 | 64.801 | 6.529 | 33.614 |
| 4279 | ND2 | ASN | 530 | 65.615 | 4.677 | 32.624 |
| 4280 | N | PHE | 531 | 62.200 | 6.687 | 31.196 |
| 4281 | CA | PHE | 531 | 60.939 | 7.231 | 31.703 |
| 4282 | C | PHE | 531 | 60.823 | 7.209 | 33.232 |
| 4283 | O | PHE | 531 | 59.974 | 7.914 | 33.789 |
| 4284 | CB | PHE | 531 | 59.828 | 6.428 | 31.042 |
| 4285 | CG | PHE | 531 | 59.847 | 6.543 | 29.516 |
| 4286 | CD1 | PHE | 531 | 59.669 | 7.782 | 28.912 |
| 4287 | CD2 | PHE | 531 | 60.054 | 5.417 | 28.731 |
| 4288 | CE1 | PHE | 531 | 59.693 | 7.892 | 27.528 |
| 4289 | CE2 | PHE | 531 | 60.077 | 5.527 | 27.346 |
| 4290 | CZ | PHE | 531 | 59.897 | 6.765 | 26.744 |
| 4291 | N | ASP | 532 | 61.831 | 6.663 | 33.898 |
| 4292 | CA | ASP | 532 | 61.859 | 6.635 | 35.365 |
| 4293 | C | ASP | 532 | 62.401 | 7.959 | 35.905 |
| 4294 | O | ASP | 532 | 62.178 | 8.301 | 37.072 |
| 4295 | CB | ASP | 532 | 62.792 | 5.518 | 35.826 |
| 4296 | CG | ASP | 532 | 62.481 | 4.201 | 35.125 |
| 4297 | OD1 | ASP | 532 | 63.396 | 3.649 | 34.521 |
| 4298 | OD2 | ASP | 532 | 61.328 | 3.796 | 35.143 |
| 4299 | N | LEU | 533 | 62.998 | 8.747 | 35.023 |
| 4300 | CA | LEU | 533 | 63.484 | 10.076 | 35.395 |
| 4301 | C | LEU | 533 | 62.417 | 11.157 | 35.224 |
| 4302 | O | LEU | 533 | 62.644 | 12.303 | 35.625 |
| 4303 | CB | LEU | 533 | 64.675 | 10.409 | 34.507 |
| 4304 | CG | LEU | 533 | 65.806 | 9.413 | 34.719 |
| 4305 | CD1 | LEU | 533 | 66.880 | 9.557 | 33.648 |
| 4306 | CD2 | LEU | 533 | 66.402 | 9.544 | 36.117 |
| 4307 | N | LEU | 534 | 61.245 | 10.787 | 34.730 |
| 4308 | CA | LEU | 534 | 60.180 | 11.765 | 34.471 |
| 4309 | C | LEU | 534 | 59.127 | 11.860 | 35.573 |
| 4310 | O | LEU | 534 | 58.122 | 12.550 | 35.375 |
| 4311 | CB | LEU | 534 | 59.494 | 11.381 | 33.169 |
| 4312 | CG | LEU | 534 | 60.398 | 11.625 | 31.975 |
| 4313 | CD1 | LEU | 534 | 59.807 | 11.013 | 30.712 |
| 4314 | CD2 | LEU | 534 | 60.644 | 13.117 | 31.797 |
| 4315 | N | VAL | 535 | 59.411 | 11.323 | 36.751 |
| 4316 | CA | VAL | 535 | 58.390 | 11.167 | 37.805 |
| 4317 | C | VAL | 535 | 58.001 | 12.472 | 38.538 |
| 4318 | O | VAL | 535 | 56.987 | 12.497 | 39.247 |
| 4319 | CB | VAL | 535 | 58.936 | 10.108 | 38.769 |
| 4320 | CG1 | VAL | 535 | 58.018 | 9.824 | 39.957 |
| 4321 | CG2 | VAL | 535 | 59.200 | 8.808 | 38.018 |

TABLE 9-continued

| Atom No. | Atom Type | Residue | Residue Position | X Coord. | Y Coord. | Z Coord. |
|---|---|---|---|---|---|---|
| 4322 | N | GLU | 536 | 58.687 | 13.567 | 38.240 |
| 4323 | CA | GLU | 536 | 58.360 | 14.890 | 38.804 |
| 4324 | C | GLU | 536 | 56.918 | 15.265 | 38.469 |
| 4325 | O | GLU | 536 | 56.464 | 15.014 | 37.348 |
| 4326 | CB | GLU | 536 | 59.294 | 15.957 | 38.213 |
| 4327 | CG | GLU | 536 | 60.734 | 15.892 | 38.731 |
| 4328 | CD | GLU | 536 | 61.673 | 15.192 | 37.747 |
| 4329 | OE1 | GLU | 536 | 61.221 | 14.254 | 37.106 |
| 4330 | OE2 | GLU | 536 | 62.844 | 15.540 | 37.741 |
| 4331 | N | PRO | 537 | 56.244 | 15.957 | 39.378 |
| 4332 | CA | PRO | 537 | 54.775 | 16.055 | 39.314 |
| 4333 | C | PRO | 537 | 54.224 | 16.841 | 38.117 |
| 4334 | O | PRO | 537 | 53.164 | 16.468 | 37.598 |
| 4335 | CB | PRO | 537 | 54.371 | 16.710 | 40.599 |
| 4336 | CG | PRO | 537 | 55.608 | 17.025 | 41.424 |
| 4337 | CD | PRO | 537 | 56.788 | 16.482 | 40.635 |
| 4338 | N | CYS | 538 | 55.026 | 17.717 | 37.526 |
| 4339 | CA | CYS | 538 | 54.555 | 18.454 | 36.349 |
| 4340 | C | CYS | 538 | 54.594 | 17.565 | 35.108 |
| 4341 | O | CYS | 538 | 53.610 | 17.526 | 34.360 |
| 4342 | CB | CYS | 538 | 55.441 | 19.672 | 36.116 |
| 4343 | SG | CYS | 538 | 54.740 | 20.882 | 34.974 |
| 4344 | N | ALA | 539 | 55.546 | 16.645 | 35.085 |
| 4345 | CA | ALA | 539 | 55.683 | 15.718 | 33.961 |
| 4346 | C | ALA | 539 | 54.718 | 14.553 | 34.125 |
| 4347 | O | ALA | 539 | 54.158 | 14.063 | 33.136 |
| 4348 | CB | ALA | 539 | 57.114 | 15.195 | 33.952 |
| 4349 | N | SER | 540 | 54.328 | 14.328 | 35.368 |
| 4350 | CA | SER | 540 | 53.317 | 13.321 | 35.687 |
| 4351 | C | SER | 540 | 51.955 | 13.755 | 35.163 |
| 4352 | O | SER | 540 | 51.387 | 13.058 | 34.313 |
| 4353 | CB | SER | 540 | 53.247 | 13.166 | 37.205 |
| 4354 | OG | SER | 540 | 54.543 | 12.817 | 37.680 |
| 4355 | N | ALA | 541 | 51.604 | 15.007 | 35.420 |
| 4356 | CA | ALA | 541 | 50.309 | 15.529 | 34.969 |
| 4357 | C | ALA | 541 | 50.293 | 15.843 | 33.475 |
| 4358 | O | ALA | 541 | 49.264 | 15.634 | 32.816 |
| 4359 | CB | ALA | 541 | 49.992 | 16.791 | 35.760 |
| 4360 | N | LEU | 542 | 51.463 | 16.094 | 32.912 |
| 4361 | CA | LEU | 542 | 51.553 | 16.315 | 31.472 |
| 4362 | C | LEU | 542 | 51.385 | 15.002 | 30.712 |
| 4363 | O | LEU | 542 | 50.568 | 14.961 | 29.787 |
| 4364 | CB | LEU | 542 | 52.907 | 16.941 | 31.155 |
| 4365 | CG | LEU | 542 | 53.004 | 17.366 | 29.695 |
| 4366 | CD1 | LEU | 542 | 51.849 | 18.289 | 29.315 |
| 4367 | CD2 | LEU | 542 | 54.343 | 18.037 | 29.414 |
| 4368 | N | ALA | 543 | 51.876 | 13.906 | 31.268 |
| 4369 | CA | ALA | 543 | 51.694 | 12.606 | 30.613 |
| 4370 | C | ALA | 543 | 50.282 | 12.061 | 30.806 |
| 4371 | O | ALA | 543 | 49.726 | 11.470 | 29.871 |
| 4372 | CB | ALA | 543 | 52.696 | 11.617 | 31.187 |
| 4373 | N | ARG | 544 | 49.634 | 12.470 | 31.886 |
| 4374 | CA | ARG | 544 | 48.235 | 12.098 | 32.106 |
| 4375 | C | ARG | 544 | 47.337 | 12.772 | 31.077 |
| 4376 | O | ARG | 544 | 46.631 | 12.065 | 30.345 |
| 4377 | CB | ARG | 544 | 47.828 | 12.530 | 33.510 |
| 4378 | CG | ARG | 544 | 48.584 | 11.736 | 34.569 |
| 4379 | CD | ARG | 544 | 48.397 | 12.326 | 35.962 |
| 4380 | NE | ARG | 544 | 46.981 | 12.350 | 36.351 |
| 4381 | CZ | ARG | 544 | 46.577 | 12.227 | 37.617 |
| 4382 | NH1 | ARG | 544 | 47.476 | 12.088 | 38.594 |
| 4383 | NH2 | ARG | 544 | 45.276 | 12.247 | 37.907 |
| 4384 | N | THR | 545 | 47.597 | 14.043 | 30.815 |
| 4385 | CA | THR | 545 | 46.794 | 14.767 | 29.824 |
| 4386 | C | THR | 545 | 47.160 | 14.409 | 28.384 |
| 4387 | O | THR | 545 | 46.245 | 14.297 | 27.563 |
| 4388 | CB | THR | 545 | 46.930 | 16.271 | 30.041 |
| 4389 | OG1 | THR | 545 | 48.302 | 16.635 | 29.963 |
| 4390 | CG2 | THR | 545 | 46.406 | 16.682 | 31.410 |
| 4391 | N | LEU | 546 | 48.377 | 13.941 | 28.147 |
| 4392 | CA | LEU | 546 | 48.742 | 13.492 | 26.794 |
| 4393 | C | LEU | 546 | 48.121 | 12.134 | 26.463 |
| 4394 | O | LEU | 546 | 47.693 | 11.925 | 25.320 |
| 4395 | CB | LEU | 546 | 50.260 | 13.384 | 26.675 |
| 4396 | CG | LEU | 546 | 50.951 | 14.738 | 26.797 |
| 4397 | CD1 | LEU | 546 | 52.467 | 14.578 | 26.783 |

TABLE 9-continued

| Atom No. | Atom Type | Residue | Residue Position | X Coord. | Y Coord. | Z Coord. |
|---|---|---|---|---|---|---|
| 4398 | CD2 | LEU | 546 | 50.497 | 15.700 | 25.707 |
| 4399 | N | ALA | 547 | 47.833 | 11.351 | 27.492 |
| 4400 | CA | ALA | 547 | 47.144 | 10.070 | 27.307 |
| 4401 | C | ALA | 547 | 45.636 | 10.257 | 27.157 |
| 4402 | O | ALA | 547 | 44.957 | 9.403 | 26.572 |
| 4403 | CB | ALA | 547 | 47.416 | 9.195 | 28.524 |
| 4404 | N | GLN | 548 | 45.165 | 11.443 | 27.508 |
| 4405 | CA | GLN | 548 | 43.753 | 11.792 | 27.379 |
| 4406 | C | GLN | 548 | 43.417 | 12.379 | 26.010 |
| 4407 | O | GLN | 548 | 42.226 | 12.543 | 25.710 |
| 4408 | CB | GLN | 548 | 43.412 | 12.786 | 28.481 |
| 4409 | CG | GLN | 548 | 43.569 | 12.126 | 29.845 |
| 4410 | CD | GLN | 548 | 43.540 | 13.164 | 30.962 |
| 4411 | OE1 | GLN | 548 | 43.469 | 14.374 | 30.713 |
| 4412 | NE2 | GLN | 548 | 43.710 | 12.683 | 32.181 |
| 4413 | N | TYR | 549 | 44.407 | 12.535 | 25.142 |
| 4414 | CA | TYR | 549 | 44.143 | 13.015 | 23.772 |
| 4415 | C | TYR | 549 | 43.109 | 12.166 | 23.003 |
| 4416 | O | TYR | 549 | 42.097 | 12.769 | 22.623 |
| 4417 | CB | TYR | 549 | 45.443 | 13.118 | 22.977 |
| 4418 | CG | TYR | 549 | 45.296 | 13.888 | 21.663 |
| 4419 | CD1 | TYR | 549 | 44.433 | 14.975 | 21.599 |
| 4420 | CD2 | TYR | 549 | 46.027 | 13.516 | 20.541 |
| 4421 | CE1 | TYR | 549 | 44.294 | 15.688 | 20.415 |
| 4422 | CE2 | TYR | 549 | 45.888 | 14.226 | 19.355 |
| 4423 | CZ | TYR | 549 | 45.020 | 15.310 | 19.295 |
| 4424 | OH | TYR | 549 | 44.839 | 15.986 | 18.108 |
| 4425 | N | PRO | 550 | 43.214 | 10.840 | 22.887 |
| 4426 | CA | PRO | 550 | 42.136 | 10.109 | 22.199 |
| 4427 | C | PRO | 550 | 40.775 | 10.140 | 22.918 |
| 4428 | O | PRO | 550 | 39.752 | 10.160 | 22.223 |
| 4429 | CB | PRO | 550 | 42.631 | 8.703 | 22.053 |
| 4430 | CG | PRO | 550 | 43.960 | 8.556 | 22.774 |
| 4431 | CD | PRO | 550 | 44.290 | 9.930 | 23.324 |
| 4432 | N | ASP | 551 | 40.750 | 10.408 | 24.219 |
| 4433 | CA | ASP | 551 | 39.474 | 10.585 | 24.928 |
| 4434 | C | ASP | 551 | 38.786 | 11.853 | 24.447 |
| 4435 | O | ASP | 551 | 37.666 | 11.786 | 23.925 |
| 4436 | CB | ASP | 551 | 39.717 | 10.780 | 26.422 |
| 4437 | CG | ASP | 551 | 40.368 | 9.571 | 27.070 |
| 4438 | OD1 | ASP | 551 | 39.948 | 8.465 | 26.754 |
| 4439 | OD2 | ASP | 551 | 41.162 | 9.781 | 27.976 |
| 4440 | N | VAL | 552 | 39.564 | 12.921 | 24.361 |
| 4441 | CA | VAL | 552 | 39.030 | 14.231 | 23.983 |
| 4442 | C | VAL | 552 | 38.716 | 14.331 | 22.492 |
| 4443 | O | VAL | 552 | 37.734 | 14.992 | 22.131 |
| 4444 | CB | VAL | 552 | 40.066 | 15.277 | 24.377 |
| 4445 | CG1 | VAL | 552 | 39.635 | 16.678 | 23.964 |
| 4446 | CG2 | VAL | 552 | 40.331 | 15.224 | 25.877 |
| 4447 | N | ILE | 553 | 39.334 | 13.486 | 21.682 |
| 4448 | CA | ILE | 553 | 38.977 | 13.444 | 20.262 |
| 4449 | C | ILE | 553 | 37.632 | 12.755 | 20.057 |
| 4450 | O | ILE | 553 | 36.771 | 13.321 | 19.371 |
| 4451 | CB | ILE | 553 | 40.058 | 12.697 | 19.492 |
| 4452 | CG1 | ILE | 553 | 41.372 | 13.460 | 19.545 |
| 4453 | CG2 | ILE | 553 | 39.641 | 12.465 | 18.043 |
| 4454 | CD1 | ILE | 553 | 42.443 | 12.749 | 18.731 |
| 4455 | N | LYS | 554 | 37.343 | 11.758 | 20.878 |
| 4456 | CA | LYS | 554 | 36.055 | 11.069 | 20.774 |
| 4457 | C | LYS | 554 | 34.931 | 11.895 | 21.396 |
| 4458 | O | LYS | 554 | 33.834 | 11.948 | 20.826 |
| 4459 | CB | LYS | 554 | 36.165 | 9.721 | 21.476 |
| 4460 | CG | LYS | 554 | 37.248 | 8.864 | 20.830 |
| 4461 | CD | LYS | 554 | 37.401 | 7.515 | 21.523 |
| 4462 | CE | LYS | 554 | 38.536 | 6.710 | 20.897 |
| 4463 | NZ | LYS | 554 | 38.639 | 5.370 | 21.494 |
| 4464 | N | LYS | 555 | 35.278 | 12.741 | 22.353 |
| 4465 | CA | LYS | 555 | 34.289 | 13.649 | 22.944 |
| 4466 | C | LYS | 555 | 34.001 | 14.841 | 22.032 |
| 4467 | O | LYS | 555 | 32.836 | 15.243 | 21.901 |
| 4468 | CB | LYS | 555 | 34.842 | 14.144 | 24.275 |
| 4469 | CG | LYS | 555 | 35.092 | 12.979 | 25.223 |
| 4470 | CD | LYS | 555 | 35.842 | 13.423 | 26.473 |
| 4471 | CE | LYS | 555 | 36.169 | 12.235 | 27.371 |
| 4472 | NZ | LYS | 555 | 36.954 | 12.657 | 28.542 |
| 4473 | N | ALA | 556 | 34.977 | 15.202 | 21.213 |

TABLE 9-continued

| Atom No. | Atom Type | Residue | Residue Position | X Coord. | Y Coord. | Z Coord. |
|---|---|---|---|---|---|---|
| 4474 | CA | ALA | 556 | 34.782 | 16.270 | 20.233 |
| 4475 | C | ALA | 556 | 34.003 | 15.786 | 19.017 |
| 4476 | O | ALA | 556 | 33.315 | 16.596 | 18.387 |
| 4477 | CB | ALA | 556 | 36.144 | 16.787 | 19.788 |
| 4478 | N | VAL | 557 | 33.973 | 14.480 | 18.793 |
| 4479 | CA | VAL | 557 | 33.119 | 13.924 | 17.738 |
| 4480 | C | VAL | 557 | 31.693 | 13.749 | 18.248 |
| 4481 | O | VAL | 557 | 30.744 | 14.171 | 17.575 |
| 4482 | CB | VAL | 557 | 33.648 | 12.551 | 17.330 |
| 4483 | CG1 | VAL | 557 | 32.782 | 11.929 | 16.239 |
| 4484 | CG2 | VAL | 557 | 35.096 | 12.614 | 16.872 |
| 4485 | N | LYS | 558 | 31.584 | 13.410 | 19.523 |
| 4486 | CA | LYS | 558 | 30.286 | 13.116 | 20.142 |
| 4487 | C | LYS | 558 | 29.452 | 14.366 | 20.425 |
| 4488 | O | LYS | 558 | 28.217 | 14.302 | 20.405 |
| 4489 | CB | LYS | 558 | 30.581 | 12.392 | 21.453 |
| 4490 | CG | LYS | 558 | 29.316 | 12.014 | 22.213 |
| 4491 | CD | LYS | 558 | 29.652 | 11.359 | 23.547 |
| 4492 | CE | LYS | 558 | 28.388 | 11.009 | 24.325 |
| 4493 | NZ | LYS | 558 | 28.722 | 10.395 | 25.620 |
| 4494 | N | GLY | 559 | 30.105 | 15.508 | 20.551 |
| 4495 | CA | GLY | 559 | 29.361 | 16.753 | 20.746 |
| 4496 | C | GLY | 559 | 29.657 | 17.783 | 19.661 |
| 4497 | O | GLY | 559 | 29.181 | 18.921 | 19.762 |
| 4498 | N | LEU | 560 | 30.354 | 17.349 | 18.617 |
| 4499 | CA | LEU | 560 | 30.850 | 18.221 | 17.532 |
| 4500 | C | LEU | 560 | 31.318 | 19.575 | 18.044 |
| 4501 | O | LEU | 560 | 30.714 | 20.611 | 17.753 |
| 4502 | CB | LEU | 560 | 29.754 | 18.409 | 16.494 |
| 4503 | CG | LEU | 560 | 29.463 | 17.101 | 15.774 |
| 4504 | CD1 | LEU | 560 | 28.304 | 17.269 | 14.802 |
| 4505 | CD2 | LEU | 560 | 30.708 | 16.601 | 15.048 |
| 4506 | N | GLU | 561 | 32.380 | 19.570 | 18.826 |
| 4507 | CA | GLU | 561 | 32.774 | 20.822 | 19.467 |
| 4508 | C | GLU | 561 | 34.243 | 21.160 | 19.314 |
| 4509 | O | GLU | 561 | 35.114 | 20.541 | 19.942 |
| 4510 | CB | GLU | 561 | 32.398 | 20.779 | 20.945 |
| 4511 | CG | GLU | 561 | 30.973 | 21.271 | 21.188 |
| 4512 | CD | GLU | 561 | 30.884 | 22.759 | 20.859 |
| 4513 | OE1 | GLU | 561 | 31.934 | 23.392 | 20.850 |
| 4514 | OE2 | GLU | 561 | 29.779 | 23.265 | 20.708 |
| 4515 | N | PRO | 562 | 34.470 | 22.285 | 18.650 |
| 4516 | CA | PRO | 562 | 35.818 | 22.847 | 18.535 |
| 4517 | C | PRO | 562 | 36.396 | 23.263 | 19.888 |
| 4518 | O | PRO | 562 | 37.545 | 22.892 | 20.163 |
| 4519 | CB | PRO | 562 | 35.671 | 24.027 | 17.623 |
| 4520 | CG | PRO | 562 | 34.200 | 24.234 | 17.293 |
| 4521 | CD | PRO | 562 | 33.451 | 23.117 | 17.999 |
| 4522 | N | SER | 563 | 35.528 | 23.644 | 20.817 |
| 4523 | CA | SER | 563 | 35.966 | 24.012 | 22.168 |
| 4524 | C | SER | 563 | 36.369 | 22.819 | 23.037 |
| 4525 | O | SER | 563 | 37.081 | 23.024 | 24.023 |
| 4526 | CB | SER | 563 | 34.843 | 24.774 | 22.862 |
| 4527 | OG | SER | 563 | 33.742 | 23.890 | 23.020 |
| 4528 | N | THR | 564 | 36.133 | 21.597 | 22.585 |
| 4529 | CA | THR | 564 | 36.591 | 20.438 | 23.352 |
| 4530 | C | THR | 564 | 38.090 | 20.265 | 23.137 |
| 4531 | O | THR | 564 | 38.862 | 20.289 | 24.106 |
| 4532 | CB | THR | 564 | 35.863 | 19.194 | 22.856 |
| 4533 | OG1 | THR | 564 | 34.465 | 19.434 | 22.927 |
| 4534 | CG2 | THR | 564 | 36.182 | 17.972 | 23.709 |
| 4535 | N | ILE | 565 | 38.496 | 20.450 | 21.890 |
| 4536 | CA | ILE | 565 | 39.912 | 20.330 | 21.540 |
| 4537 | C | ILE | 565 | 40.668 | 21.611 | 21.885 |
| 4538 | O | ILE | 565 | 41.799 | 21.530 | 22.377 |
| 4539 | CB | ILE | 565 | 40.021 | 20.034 | 20.046 |
| 4540 | CG1 | ILE | 565 | 39.387 | 18.689 | 19.712 |
| 4541 | CG2 | ILE | 565 | 41.475 | 20.054 | 19.586 |
| 4542 | CD1 | ILE | 565 | 40.152 | 17.532 | 20.346 |
| 4543 | N | VAL | 566 | 39.960 | 22.729 | 21.914 |
| 4544 | CA | VAL | 566 | 40.597 | 23.995 | 22.291 |
| 4545 | C | VAL | 566 | 40.805 | 24.120 | 23.802 |
| 4546 | O | VAL | 566 | 41.890 | 24.547 | 24.217 |
| 4547 | CB | VAL | 566 | 39.732 | 25.139 | 21.773 |
| 4548 | CG1 | VAL | 566 | 40.221 | 26.489 | 22.274 |
| 4549 | CG2 | VAL | 566 | 39.695 | 25.133 | 20.252 |

TABLE 9-continued

| Atom No. | Atom Type | Residue | Residue Position | X Coord. | Y Coord. | Z Coord. |
|---|---|---|---|---|---|---|
| 4550 | N | THR | 567 | 39.942 | 23.502 | 24.594 |
| 4551 | CA | THR | 567 | 40.128 | 23.542 | 26.049 |
| 4552 | C | THR | 567 | 41.148 | 22.501 | 26.497 |
| 4553 | O | THR | 567 | 41.982 | 22.791 | 27.367 |
| 4554 | CB | THR | 567 | 38.788 | 23.289 | 26.728 |
| 4555 | OG1 | THR | 567 | 37.918 | 24.354 | 26.371 |
| 4556 | CG2 | THR | 567 | 38.914 | 23.278 | 28.248 |
| 4557 | N | TYR | 568 | 41.257 | 21.430 | 25.728 |
| 4558 | CA | TYR | 568 | 42.300 | 20.440 | 25.992 |
| 4559 | C | TYR | 568 | 43.669 | 20.975 | 25.590 |
| 4560 | O | TYR | 568 | 44.633 | 20.830 | 26.353 |
| 4561 | CB | TYR | 568 | 41.990 | 19.182 | 25.189 |
| 4562 | CG | TYR | 568 | 43.131 | 18.171 | 25.158 |
| 4563 | CD1 | TYR | 568 | 43.349 | 17.325 | 26.239 |
| 4564 | CD2 | TYR | 568 | 43.958 | 18.104 | 24.044 |
| 4565 | CE1 | TYR | 568 | 44.397 | 16.415 | 26.206 |
| 4566 | CE2 | TYR | 568 | 45.009 | 17.199 | 24.013 |
| 4567 | CZ | TYR | 568 | 45.226 | 16.358 | 25.094 |
| 4568 | OH | TYR | 568 | 46.287 | 15.479 | 25.066 |
| 4569 | N | LEU | 569 | 43.694 | 21.790 | 24.551 |
| 4570 | CA | LEU | 569 | 44.948 | 22.370 | 24.087 |
| 4571 | C | LEU | 569 | 45.423 | 23.461 | 25.041 |
| 4572 | O | LEU | 569 | 46.590 | 23.428 | 25.450 |
| 4573 | CB | LEU | 569 | 44.699 | 22.941 | 22.698 |
| 4574 | CG | LEU | 569 | 45.997 | 23.256 | 21.973 |
| 4575 | CD1 | LEU | 569 | 46.901 | 22.030 | 21.941 |
| 4576 | CD2 | LEU | 569 | 45.704 | 23.748 | 20.562 |
| 4577 | N | PHE | 570 | 44.486 | 24.204 | 25.609 |
| 4578 | CA | PHE | 570 | 44.847 | 25.209 | 26.612 |
| 4579 | C | PHE | 570 | 45.343 | 24.575 | 27.901 |
| 4580 | O | PHE | 570 | 46.452 | 24.908 | 28.329 |
| 4581 | CB | PHE | 570 | 43.643 | 26.086 | 26.926 |
| 4582 | CG | PHE | 570 | 43.377 | 27.160 | 25.882 |
| 4583 | CD1 | PHE | 570 | 44.444 | 27.815 | 25.282 |
| 4584 | CD2 | PHE | 570 | 42.074 | 27.504 | 25.550 |
| 4585 | CE1 | PHE | 570 | 44.210 | 28.795 | 24.328 |
| 4586 | CE2 | PHE | 570 | 41.841 | 28.485 | 24.596 |
| 4587 | CZ | PHE | 570 | 42.907 | 29.127 | 23.981 |
| 4588 | N | SER | 571 | 44.709 | 23.499 | 28.334 |
| 4589 | CA | SER | 571 | 45.135 | 22.860 | 29.585 |
| 4590 | C | SER | 571 | 46.472 | 22.128 | 29.446 |
| 4591 | O | SER | 571 | 47.331 | 22.294 | 30.323 |
| 4592 | CB | SER | 571 | 44.045 | 21.903 | 30.065 |
| 4593 | OG | SER | 571 | 43.798 | 20.929 | 29.059 |
| 4594 | N | VAL | 572 | 46.760 | 21.604 | 28.264 |
| 4595 | CA | VAL | 572 | 48.052 | 20.948 | 28.054 |
| 4596 | C | VAL | 572 | 49.168 | 21.972 | 27.895 |
| 4597 | O | VAL | 572 | 50.200 | 21.826 | 28.561 |
| 4598 | CB | VAL | 572 | 47.972 | 20.052 | 26.822 |
| 4599 | CG1 | VAL | 572 | 49.349 | 19.550 | 26.398 |
| 4600 | CG2 | VAL | 572 | 47.034 | 18.880 | 27.074 |
| 4601 | N | THR | 573 | 48.860 | 23.117 | 27.306 |
| 4602 | CA | THR | 573 | 49.880 | 24.162 | 27.164 |
| 4603 | C | THR | 573 | 50.076 | 24.966 | 28.446 |
| 4604 | O | THR | 573 | 51.162 | 25.520 | 28.638 |
| 4605 | CB | THR | 573 | 49.523 | 25.112 | 26.026 |
| 4606 | OG1 | THR | 573 | 48.258 | 25.698 | 26.297 |
| 4607 | CG2 | THR | 573 | 49.447 | 24.389 | 24.688 |
| 4608 | N | HIS | 574 | 49.146 | 24.885 | 29.384 |
| 4609 | CA | HIS | 574 | 49.358 | 25.534 | 30.680 |
| 4610 | C | HIS | 574 | 50.315 | 24.698 | 31.508 |
| 4611 | O | HIS | 574 | 51.354 | 25.222 | 31.934 |
| 4612 | CB | HIS | 574 | 48.040 | 25.678 | 31.432 |
| 4613 | CG | HIS | 574 | 47.035 | 26.620 | 30.799 |
| 4614 | ND1 | HIS | 574 | 47.295 | 27.649 | 29.972 |
| 4615 | CD2 | HIS | 574 | 45.672 | 26.572 | 30.968 |
| 4616 | CE1 | HIS | 574 | 46.133 | 28.244 | 29.625 |
| 4617 | NE2 | HIS | 574 | 45.132 | 27.576 | 30.240 |
| 4618 | N | ILE | 575 | 50.161 | 23.387 | 31.390 |
| 4619 | CA | ILE | 575 | 51.070 | 22.468 | 32.075 |
| 4620 | C | ILE | 575 | 52.447 | 22.485 | 31.419 |
| 4621 | O | ILE | 575 | 53.446 | 22.584 | 32.141 |
| 4622 | CB | ILE | 575 | 50.486 | 21.061 | 32.032 |
| 4623 | CG1 | ILE | 575 | 49.098 | 21.036 | 32.657 |
| 4624 | CG2 | ILE | 575 | 51.396 | 20.079 | 32.759 |
| 4625 | CD1 | ILE | 575 | 48.500 | 19.635 | 32.607 |

TABLE 9-continued

| Atom No. | Atom Type | Residue | Residue Position | X Coord. | Y Coord. | Z Coord. |
|---|---|---|---|---|---|---|
| 4626 | N | VAL | 576 | 52.480 | 22.735 | 30.119 |
| 4627 | CA | VAL | 576 | 53.752 | 22.892 | 29.406 |
| 4628 | C | VAL | 576 | 54.483 | 24.187 | 29.767 |
| 4629 | O | VAL | 576 | 55.698 | 24.121 | 29.981 |
| 4630 | CB | VAL | 576 | 53.476 | 22.866 | 27.904 |
| 4631 | CG1 | VAL | 576 | 54.657 | 23.396 | 27.100 |
| 4632 | CG2 | VAL | 576 | 53.089 | 21.469 | 27.435 |
| 4633 | N | SER | 577 | 53.756 | 25.234 | 30.132 |
| 4634 | CA | SER | 577 | 54.398 | 26.492 | 30.542 |
| 4635 | C | SER | 577 | 55.058 | 26.322 | 31.903 |
| 4636 | O | SER | 577 | 56.252 | 26.615 | 32.071 |
| 4637 | CB | SER | 577 | 53.332 | 27.576 | 30.678 |
| 4638 | OG | SER | 577 | 52.640 | 27.705 | 29.446 |
| 4639 | N | GLN | 578 | 54.360 | 25.596 | 32.761 |
| 4640 | CA | GLN | 578 | 54.851 | 25.321 | 34.109 |
| 4641 | C | GLN | 578 | 56.057 | 24.390 | 34.075 |
| 4642 | O | GLN | 578 | 57.112 | 24.728 | 34.628 |
| 4643 | CB | GLN | 578 | 53.727 | 24.620 | 34.856 |
| 4644 | CG | GLN | 578 | 52.435 | 25.432 | 34.821 |
| 4645 | CD | GLN | 578 | 51.264 | 24.503 | 35.125 |
| 4646 | OE1 | GLN | 578 | 50.111 | 24.783 | 34.771 |
| 4647 | NE2 | GLN | 578 | 51.599 | 23.346 | 35.669 |
| 4648 | N | CYS | 579 | 55.994 | 23.387 | 33.214 |
| 4649 | CA | CYS | 579 | 57.061 | 22.386 | 33.171 |
| 4650 | C | CYS | 579 | 58.284 | 22.913 | 32.435 |
| 4651 | O | CYS | 579 | 59.391 | 22.677 | 32.922 |
| 4652 | CB | CYS | 579 | 56.582 | 21.119 | 32.462 |
| 4653 | SG | CYS | 579 | 55.139 | 20.227 | 33.104 |
| 4654 | N | TYR | 580 | 58.094 | 23.860 | 31.530 |
| 4655 | CA | TYR | 580 | 59.213 | 24.445 | 30.780 |
| 4656 | C | TYR | 580 | 59.983 | 25.459 | 31.632 |
| 4657 | O | TYR | 580 | 61.160 | 25.737 | 31.374 |
| 4658 | CB | TYR | 580 | 58.613 | 25.141 | 29.560 |
| 4659 | CG | TYR | 580 | 59.573 | 25.506 | 28.431 |
| 4660 | CD1 | TYR | 580 | 59.942 | 24.535 | 27.507 |
| 4661 | CD2 | TYR | 580 | 60.062 | 26.803 | 28.313 |
| 4662 | CE1 | TYR | 580 | 60.801 | 24.858 | 26.465 |
| 4663 | CE2 | TYR | 580 | 60.922 | 27.127 | 27.271 |
| 4664 | CZ | TYR | 580 | 61.286 | 26.154 | 26.348 |
| 4665 | OH | TYR | 580 | 62.085 | 26.491 | 25.276 |
| 4666 | N | ASP | 581 | 59.365 | 25.881 | 32.724 |
| 4667 | CA | ASP | 581 | 60.016 | 26.766 | 33.686 |
| 4668 | C | ASP | 581 | 60.735 | 25.991 | 34.798 |
| 4669 | O | ASP | 581 | 61.591 | 26.561 | 35.489 |
| 4670 | CB | ASP | 581 | 58.911 | 27.636 | 34.282 |
| 4671 | CG | ASP | 581 | 59.457 | 28.627 | 35.303 |
| 4672 | OD1 | ASP | 581 | 59.282 | 28.381 | 36.489 |
| 4673 | OD2 | ASP | 581 | 59.978 | 29.649 | 34.879 |
| 4674 | N | ILE | 582 | 60.485 | 24.694 | 34.905 |
| 4675 | CA | ILE | 582 | 61.065 | 23.922 | 36.014 |
| 4676 | C | ILE | 582 | 61.993 | 22.800 | 35.543 |
| 4677 | O | ILE | 582 | 63.110 | 22.644 | 36.052 |
| 4678 | CB | ILE | 582 | 59.914 | 23.308 | 36.808 |
| 4679 | CG1 | ILE | 582 | 58.950 | 24.379 | 37.306 |
| 4680 | CG2 | ILE | 582 | 60.440 | 22.494 | 37.986 |
| 4681 | CD1 | ILE | 582 | 57.758 | 23.759 | 38.025 |
| 4682 | N | LEU | 583 | 61.565 | 22.094 | 34.513 |
| 4683 | CA | LEU | 583 | 62.253 | 20.888 | 34.043 |
| 4684 | C | LEU | 583 | 63.132 | 21.192 | 32.835 |
| 4685 | O | LEU | 583 | 62.840 | 20.776 | 31.707 |
| 4686 | CB | LEU | 583 | 61.187 | 19.869 | 33.652 |
| 4687 | CG | LEU | 583 | 60.225 | 19.557 | 34.796 |
| 4688 | CD1 | LEU | 583 | 59.066 | 18.692 | 34.312 |
| 4689 | CD2 | LEU | 583 | 60.937 | 18.891 | 35.969 |
| 4690 | N | TRP | 584 | 64.213 | 21.904 | 33.091 |
| 4691 | CA | TRP | 584 | 65.121 | 22.319 | 32.019 |
| 4692 | C | TRP | 584 | 65.961 | 21.159 | 31.513 |
| 4693 | O | TRP | 584 | 66.691 | 20.528 | 32.277 |
| 4694 | CB | TRP | 584 | 66.045 | 23.408 | 32.552 |
| 4695 | CG | TRP | 584 | 65.326 | 24.684 | 32.935 |
| 4696 | CD1 | TRP | 584 | 64.811 | 25.012 | 34.168 |
| 4697 | CD2 | TRP | 584 | 65.057 | 25.807 | 32.065 |
| 4698 | NE1 | TRP | 584 | 64.237 | 26.239 | 34.083 |
| 4699 | CE2 | TRP | 584 | 64.364 | 26.747 | 32.846 |
| 4700 | CE3 | TRP | 584 | 65.336 | 26.065 | 30.734 |
| 4701 | CZ2 | TRP | 584 | 63.957 | 27.947 | 32.273 |
| 4702 | CZ3 | TRP | 584 | 64.926 | 27.268 | 30.170 |
| 4703 | CH2 | TRP | 584 | 64.240 | 28.203 | 30.937 |
| 4704 | N | VAL | 585 | 65.934 | 20.963 | 30.206 |
| 4705 | CA | VAL | 585 | 66.746 | 19.918 | 29.568 |
| 4706 | C | VAL | 585 | 68.185 | 20.390 | 29.350 |
| 4707 | O | VAL | 585 | 69.134 | 19.592 | 29.330 |
| 4708 | CB | VAL | 585 | 66.110 | 19.630 | 28.212 |
| 4709 | CG1 | VAL | 585 | 66.910 | 18.611 | 27.416 |
| 4710 | CG2 | VAL | 585 | 64.664 | 19.182 | 28.363 |
| 4711 | N | SER | 586 | 68.342 | 21.703 | 29.333 |
| 4712 | CA | SER | 586 | 69.657 | 22.317 | 29.132 |
| 4713 | C | SER | 586 | 70.594 | 22.050 | 30.305 |
| 4714 | O | SER | 586 | 70.229 | 22.216 | 31.477 |
| 4715 | CB | SER | 586 | 69.474 | 23.821 | 28.953 |
| 4716 | OG | SER | 586 | 68.883 | 24.344 | 30.137 |
| 4717 | N | GLY | 587 | 71.749 | 21.504 | 29.959 |
| 4718 | CA | GLY | 587 | 72.834 | 21.267 | 30.918 |
| 4719 | C | GLY | 587 | 72.535 | 20.139 | 31.901 |
| 4720 | O | GLY | 587 | 72.861 | 20.255 | 33.087 |
| 4721 | N | GLN | 588 | 71.849 | 19.109 | 31.436 |
| 4722 | CA | GLN | 588 | 71.526 | 17.987 | 32.320 |
| 4723 | C | GLN | 588 | 72.361 | 16.764 | 32.005 |
| 4724 | O | GLN | 588 | 73.204 | 16.770 | 31.100 |
| 4725 | CB | GLN | 588 | 70.057 | 17.623 | 32.157 |
| 4726 | CG | GLN | 588 | 69.165 | 18.808 | 32.482 |
| 4727 | CD | GLN | 588 | 69.416 | 19.294 | 33.905 |
| 4728 | OE1 | GLN | 588 | 69.512 | 18.491 | 34.843 |
| 4729 | NE2 | GLN | 588 | 69.571 | 20.600 | 34.033 |
| 4730 | N | GLU | 589 | 72.160 | 15.742 | 32.817 |
| 4731 | CA | GLU | 589 | 72.734 | 14.432 | 32.508 |
| 4732 | C | GLU | 589 | 72.113 | 13.945 | 31.210 |
| 4733 | O | GLU | 589 | 70.921 | 14.187 | 30.977 |
| 4734 | CB | GLU | 589 | 72.430 | 13.452 | 33.635 |
| 4735 | CG | GLU | 589 | 73.172 | 13.826 | 34.913 |
| 4736 | CD | GLU | 589 | 74.680 | 13.737 | 34.684 |
| 4737 | OE1 | GLU | 589 | 75.083 | 12.890 | 33.898 |
| 4738 | OE2 | GLU | 589 | 75.392 | 14.529 | 35.282 |
| 4739 | N | LYS | 590 | 72.858 | 13.157 | 30.453 |
| 4740 | CA | LYS | 590 | 72.419 | 12.777 | 29.103 |
| 4741 | C | LYS | 590 | 71.073 | 12.061 | 29.092 |
| 4742 | O | LYS | 590 | 70.135 | 12.589 | 28.487 |
| 4743 | CB | LYS | 590 | 73.467 | 11.873 | 28.468 |
| 4744 | CG | LYS | 590 | 73.057 | 11.498 | 27.048 |
| 4745 | CD | LYS | 590 | 74.073 | 10.576 | 26.388 |
| 4746 | CE | LYS | 590 | 73.638 | 10.207 | 24.974 |
| 4747 | NZ | LYS | 590 | 74.619 | 9.311 | 24.342 |
| 4748 | N | ASP | 591 | 70.879 | 11.132 | 30.015 |
| 4749 | CA | ASP | 591 | 69.628 | 10.359 | 30.046 |
| 4750 | C | ASP | 591 | 68.436 | 11.143 | 30.606 |
| 4751 | O | ASP | 591 | 67.304 | 10.899 | 30.170 |
| 4752 | CB | ASP | 591 | 69.853 | 9.111 | 30.895 |
| 4753 | CG | ASP | 591 | 71.005 | 8.287 | 30.325 |
| 4754 | OD1 | ASP | 591 | 72.112 | 8.431 | 30.827 |
| 4755 | OD2 | ASP | 591 | 70.769 | 7.575 | 29.361 |
| 4756 | N | VAL | 592 | 68.705 | 12.230 | 31.314 |
| 4757 | CA | VAL | 592 | 67.625 | 13.042 | 31.879 |
| 4758 | C | VAL | 592 | 67.185 | 14.077 | 30.850 |
| 4759 | O | VAL | 592 | 65.982 | 14.320 | 30.680 |
| 4760 | CB | VAL | 592 | 68.144 | 13.749 | 33.126 |
| 4761 | CG1 | VAL | 592 | 67.036 | 14.551 | 33.797 |
| 4762 | CG2 | VAL | 592 | 68.742 | 12.753 | 34.111 |
| 4763 | N | ALA | 593 | 68.124 | 14.438 | 29.992 |
| 4764 | CA | ALA | 593 | 67.827 | 15.337 | 28.883 |
| 4765 | C | ALA | 593 | 67.125 | 14.577 | 27.761 |
| 4766 | O | ALA | 593 | 66.174 | 15.106 | 27.173 |
| 4767 | CB | ALA | 593 | 69.142 | 15.921 | 28.379 |
| 4768 | N | ILE | 594 | 67.401 | 13.285 | 27.667 |
| 4769 | CA | ILE | 594 | 66.692 | 12.428 | 26.710 |
| 4770 | C | ILE | 594 | 65.248 | 12.216 | 27.152 |
| 4771 | O | ILE | 594 | 64.326 | 12.469 | 26.364 |
| 4772 | CB | ILE | 594 | 67.382 | 11.066 | 26.640 |
| 4773 | CG1 | ILE | 594 | 68.826 | 11.172 | 26.174 |
| 4774 | CG2 | ILE | 594 | 66.625 | 10.129 | 25.712 |
| 4775 | CD1 | ILE | 594 | 69.486 | 9.799 | 26.110 |
| 4776 | N | ALA | 595 | 65.059 | 12.050 | 28.451 |
| 4777 | CA | ALA | 595 | 63.718 | 11.827 | 28.990 |

TABLE 9-continued

| Atom No. | Atom Type | Residue | Residue Position | X Coord. | Y Coord. | Z Coord. |
|---|---|---|---|---|---|---|
| 4778 | C | ALA | 595 | 62.836 | 13.067 | 28.885 |
| 4779 | O | ALA | 595 | 61.713 | 12.971 | 28.371 |
| 4780 | CB | ALA | 595 | 63.857 | 11.413 | 30.451 |
| 4781 | N | ARG | 596 | 63.407 | 14.237 | 29.118 |
| 4782 | CA | ARG | 596 | 62.590 | 15.445 | 29.033 |
| 4783 | C | ARG | 596 | 62.473 | 16.021 | 27.623 |
| 4784 | O | ARG | 596 | 61.458 | 16.669 | 27.339 |
| 4785 | CB | ARG | 596 | 63.096 | 16.473 | 30.031 |
| 4786 | CG | ARG | 596 | 62.845 | 15.945 | 31.436 |
| 4787 | CD | ARG | 596 | 62.944 | 17.030 | 32.494 |
| 4788 | NE | ARG | 596 | 64.319 | 17.504 | 32.688 |
| 4789 | CZ | ARG | 596 | 64.824 | 17.654 | 33.914 |
| 4790 | NH1 | ARG | 596 | 64.092 | 17.322 | 34.979 |
| 4791 | NH2 | ARG | 596 | 66.069 | 18.097 | 34.078 |
| 4792 | N | LEU | 597 | 63.324 | 15.605 | 26.698 |
| 4793 | CA | LEU | 597 | 63.091 | 15.970 | 25.296 |
| 4794 | C | LEU | 597 | 62.067 | 15.039 | 24.662 |
| 4795 | O | LEU | 597 | 61.283 | 15.486 | 23.817 |
| 4796 | CB | LEU | 597 | 64.382 | 15.914 | 24.492 |
| 4797 | CG | LEU | 597 | 65.230 | 17.162 | 24.679 |
| 4798 | CD1 | LEU | 597 | 66.544 | 17.037 | 23.917 |
| 4799 | CD2 | LEU | 597 | 64.467 | 18.407 | 24.236 |
| 4800 | N | ALA | 598 | 61.925 | 13.848 | 25.220 |
| 4801 | CA | ALA | 598 | 60.863 | 12.945 | 24.785 |
| 4802 | C | ALA | 598 | 59.518 | 13.460 | 25.275 |
| 4803 | O | ALA | 598 | 58.594 | 13.632 | 24.469 |
| 4804 | CB | ALA | 598 | 61.121 | 11.575 | 25.392 |
| 4805 | N | LEU | 599 | 59.512 | 13.958 | 26.501 |
| 4806 | CA | LEU | 599 | 58.296 | 14.531 | 27.083 |
| 4807 | C | LEU | 599 | 57.868 | 15.819 | 26.381 |
| 4808 | O | LEU | 599 | 56.708 | 15.921 | 25.958 |
| 4809 | CB | LEU | 599 | 58.581 | 14.847 | 28.545 |
| 4810 | CG | LEU | 599 | 57.367 | 15.457 | 29.234 |
| 4811 | CD1 | LEU | 599 | 56.252 | 14.428 | 29.396 |
| 4812 | CD2 | LEU | 599 | 57.756 | 16.038 | 30.585 |
| 4813 | N | TYR | 600 | 58.822 | 16.677 | 26.053 |
| 4814 | CA | TYR | 600 | 58.474 | 17.944 | 25.399 |
| 4815 | C | TYR | 600 | 58.135 | 17.775 | 23.925 |
| 4816 | O | TYR | 600 | 57.195 | 18.426 | 23.456 |
| 4817 | CB | TYR | 600 | 59.624 | 18.931 | 25.543 |
| 4818 | CG | TYR | 600 | 59.776 | 19.507 | 26.947 |
| 4819 | CD1 | TYR | 600 | 58.655 | 19.692 | 27.747 |
| 4820 | CD2 | TYR | 600 | 61.034 | 19.862 | 27.418 |
| 4821 | CE1 | TYR | 600 | 58.792 | 20.218 | 29.024 |
| 4822 | CE2 | TYR | 600 | 61.172 | 20.389 | 28.694 |
| 4823 | CZ | TYR | 600 | 60.051 | 20.564 | 29.493 |
| 4824 | OH | TYR | 600 | 60.189 | 21.086 | 30.755 |
| 4825 | N | GLU | 601 | 58.666 | 16.740 | 23.297 |
| 4826 | CA | GLU | 601 | 58.313 | 16.473 | 21.904 |
| 4827 | C | GLU | 601 | 56.983 | 15.733 | 21.803 |
| 4828 | O | GLU | 601 | 56.242 | 15.957 | 20.841 |
| 4829 | CB | GLU | 601 | 59.431 | 15.655 | 21.275 |
| 4830 | CG | GLU | 601 | 59.178 | 15.366 | 19.803 |
| 4831 | CD | GLU | 601 | 60.415 | 14.715 | 19.204 |
| 4832 | OE1 | GLU | 601 | 61.200 | 15.438 | 18.607 |
| 4833 | OE2 | GLU | 601 | 60.562 | 13.505 | 19.350 |
| 4834 | N | ALA | 602 | 56.583 | 15.054 | 22.867 |
| 4835 | CA | ALA | 602 | 55.261 | 14.426 | 22.891 |
| 4836 | C | ALA | 602 | 54.189 | 15.471 | 23.167 |
| 4837 | O | ALA | 602 | 53.168 | 15.506 | 22.467 |
| 4838 | CB | ALA | 602 | 55.234 | 13.367 | 23.988 |
| 4839 | N | ALA | 603 | 54.546 | 16.458 | 23.973 |
| 4840 | CA | ALA | 603 | 53.632 | 17.562 | 24.256 |
| 4841 | C | ALA | 603 | 53.479 | 18.468 | 23.042 |
| 4842 | O | ALA | 603 | 52.344 | 18.706 | 22.613 |
| 4843 | CB | ALA | 603 | 54.183 | 18.363 | 25.430 |
| 4844 | N | ARG | 604 | 54.574 | 18.699 | 22.334 |
| 4845 | CA | ARG | 604 | 54.533 | 19.531 | 21.130 |
| 4846 | C | ARG | 604 | 53.867 | 18.813 | 19.960 |
| 4847 | O | ARG | 604 | 53.106 | 19.444 | 19.218 |
| 4848 | CB | ARG | 604 | 55.959 | 19.874 | 20.727 |
| 4849 | CG | ARG | 604 | 55.962 | 20.783 | 19.506 |
| 4850 | CD | ARG | 604 | 57.173 | 20.508 | 18.626 |
| 4851 | NE | ARG | 604 | 57.269 | 19.066 | 18.338 |
| 4852 | CZ | ARG | 604 | 56.662 | 18.437 | 17.326 |
| 4853 | NH1 | ARG | 604 | 55.910 | 19.118 | 16.458 |
| 4854 | NH2 | ARG | 604 | 56.819 | 17.120 | 17.178 |
| 4855 | N | GLN | 605 | 53.950 | 17.492 | 19.934 |
| 4856 | CA | GLN | 605 | 53.278 | 16.728 | 18.884 |
| 4857 | C | GLN | 605 | 51.770 | 16.707 | 19.095 |
| 4858 | O | GLN | 605 | 51.021 | 16.903 | 18.129 |
| 4859 | CB | GLN | 605 | 53.799 | 15.296 | 18.907 |
| 4860 | CG | GLN | 605 | 53.168 | 14.443 | 17.811 |
| 4861 | CD | GLN | 605 | 53.663 | 14.886 | 16.437 |
| 4862 | OE1 | GLN | 605 | 54.812 | 14.617 | 16.070 |
| 4863 | NE2 | GLN | 605 | 52.767 | 15.467 | 15.660 |
| 4864 | N | VAL | 606 | 51.338 | 16.727 | 20.344 |
| 4865 | CA | VAL | 606 | 49.903 | 16.786 | 20.620 |
| 4866 | C | VAL | 606 | 49.361 | 18.207 | 20.462 |
| 4867 | O | VAL | 606 | 48.243 | 18.366 | 19.955 |
| 4868 | CB | VAL | 606 | 49.658 | 16.254 | 22.028 |
| 4869 | CG1 | VAL | 606 | 48.218 | 16.476 | 22.471 |
| 4870 | CG2 | VAL | 606 | 50.018 | 14.774 | 22.111 |
| 4871 | N | ILE | 607 | 50.228 | 19.200 | 20.605 |
| 4872 | CA | ILE | 607 | 49.835 | 20.586 | 20.323 |
| 4873 | C | ILE | 607 | 49.728 | 20.818 | 18.819 |
| 4874 | O | ILE | 607 | 48.711 | 21.358 | 18.362 |
| 4875 | CB | ILE | 607 | 50.873 | 21.532 | 20.922 |
| 4876 | CG1 | ILE | 607 | 50.900 | 21.417 | 22.440 |
| 4877 | CG2 | ILE | 607 | 50.601 | 22.976 | 20.511 |
| 4878 | CD1 | ILE | 607 | 51.993 | 22.295 | 23.037 |
| 4879 | N | ASN | 608 | 50.587 | 20.141 | 18.073 |
| 4880 | CA | ASN | 608 | 50.541 | 20.160 | 16.610 |
| 4881 | C | ASN | 608 | 49.248 | 19.542 | 16.112 |
| 4882 | O | ASN | 608 | 48.479 | 20.213 | 15.414 |
| 4883 | CB | ASN | 608 | 51.706 | 19.316 | 16.091 |
| 4884 | CG | ASN | 608 | 51.736 | 19.277 | 14.563 |
| 4885 | OD1 | ASN | 608 | 52.213 | 20.223 | 13.926 |
| 4886 | ND2 | ASN | 608 | 51.239 | 18.192 | 13.988 |
| 4887 | N | ASN | 609 | 48.894 | 18.405 | 16.689 |
| 4888 | CA | ASN | 609 | 47.725 | 17.663 | 16.219 |
| 4889 | C | ASN | 609 | 46.425 | 18.336 | 16.652 |
| 4890 | O | ASN | 609 | 45.466 | 18.357 | 15.872 |
| 4891 | CB | ASN | 609 | 47.765 | 16.252 | 16.799 |
| 4892 | CG | ASN | 609 | 49.014 | 15.457 | 16.411 |
| 4893 | OD1 | ASN | 609 | 49.819 | 15.842 | 15.545 |
| 4894 | ND2 | ASN | 609 | 49.174 | 14.348 | 17.114 |
| 4895 | N | GLY | 610 | 46.459 | 19.041 | 17.771 |
| 4896 | CA | GLY | 610 | 45.305 | 19.820 | 18.227 |
| 4897 | C | GLY | 610 | 45.056 | 21.003 | 17.298 |
| 4898 | O | GLY | 610 | 43.987 | 21.086 | 16.676 |
| 4899 | N | MET | 611 | 46.109 | 21.765 | 17.040 |
| 4900 | CA | MET | 611 | 45.995 | 22.947 | 16.183 |
| 4901 | C | MET | 611 | 45.650 | 22.580 | 14.746 |
| 4902 | O | MET | 611 | 44.651 | 23.097 | 14.233 |
| 4903 | CB | MET | 611 | 47.316 | 23.710 | 16.194 |
| 4904 | CG | MET | 611 | 47.645 | 24.238 | 17.585 |
| 4905 | SD | MET | 611 | 49.116 | 25.279 | 17.705 |
| 4906 | CE | MET | 611 | 48.549 | 26.668 | 16.699 |
| 4907 | N | THR | 612 | 46.231 | 21.505 | 14.243 |
| 4908 | CA | THR | 612 | 45.976 | 21.087 | 12.860 |
| 4909 | C | THR | 612 | 44.607 | 20.423 | 12.681 |
| 4910 | O | THR | 612 | 43.975 | 20.633 | 11.638 |
| 4911 | CB | THR | 612 | 47.088 | 20.125 | 12.454 |
| 4912 | OG1 | THR | 612 | 48.327 | 20.811 | 12.585 |
| 4913 | CG2 | THR | 612 | 46.952 | 19.667 | 11.006 |
| 4914 | N | LEU | 613 | 44.036 | 19.917 | 13.765 |
| 4915 | CA | LEU | 613 | 42.684 | 19.351 | 13.713 |
| 4916 | C | LEU | 613 | 41.642 | 20.469 | 13.691 |
| 4917 | O | LEU | 613 | 40.632 | 20.369 | 12.982 |
| 4918 | CB | LEU | 613 | 42.488 | 18.507 | 14.968 |
| 4919 | CG | LEU | 613 | 41.226 | 17.657 | 14.913 |
| 4920 | CD1 | LEU | 613 | 41.325 | 16.636 | 13.787 |
| 4921 | CD2 | LEU | 613 | 41.006 | 16.948 | 16.245 |
| 4922 | N | LEU | 614 | 42.005 | 21.602 | 14.271 |
| 4923 | CA | LEU | 614 | 41.147 | 22.791 | 14.236 |
| 4924 | C | LEU | 614 | 41.317 | 23.578 | 12.933 |
| 4925 | O | LEU | 614 | 40.389 | 24.274 | 12.504 |
| 4926 | CB | LEU | 614 | 41.554 | 23.686 | 15.402 |
| 4927 | CG | LEU | 614 | 41.349 | 23.008 | 16.752 |
| 4928 | CD1 | LEU | 614 | 42.137 | 23.712 | 17.850 |
| 4929 | CD2 | LEU | 614 | 39.871 | 22.917 | 17.114 |

TABLE 9-continued

| Atom No. | Atom Type | Residue | Residue Position | X Coord. | Y Coord. | Z Coord. |
|---|---|---|---|---|---|---|
| 4930 | N | GLY | 615 | 42.454 | 23.410 | 12.278 |
| 4931 | CA | GLY | 615 | 42.714 | 24.092 | 11.005 |
| 4932 | C | GLY | 615 | 43.767 | 25.187 | 11.172 |
| 4933 | O | GLY | 615 | 43.939 | 26.054 | 10.305 |
| 4934 | N | LEU | 616 | 44.464 | 25.139 | 12.292 |
| 4935 | CA | LEU | 616 | 45.489 | 26.138 | 12.613 |
| 4936 | C | LEU | 616 | 46.859 | 25.687 | 12.129 |
| 4937 | O | LEU | 616 | 47.187 | 24.496 | 12.166 |
| 4938 | CB | LEU | 616 | 45.569 | 26.293 | 14.126 |
| 4939 | CG | LEU | 616 | 44.222 | 26.586 | 14.768 |
| 4940 | CD1 | LEU | 616 | 44.320 | 26.438 | 16.280 |
| 4941 | CD2 | LEU | 616 | 43.709 | 27.969 | 14.391 |
| 4942 | N | THR | 617 | 47.667 | 26.654 | 11.728 |
| 4943 | CA | THR | 617 | 49.050 | 26.358 | 11.337 |
| 4944 | C | THR | 617 | 50.020 | 26.837 | 12.419 |
| 4945 | O | THR | 617 | 50.165 | 28.048 | 12.635 |
| 4946 | CB | THR | 617 | 49.358 | 27.067 | 10.023 |
| 4947 | OG1 | THR | 617 | 48.365 | 26.707 | 9.071 |
| 4948 | CG2 | THR | 617 | 50.720 | 26.660 | 9.471 |
| 4949 | N | PRO | 618 | 50.594 | 25.884 | 13.138 |
| 4950 | CA | PRO | 618 | 51.557 | 26.187 | 14.203 |
| 4951 | C | PRO | 618 | 52.881 | 26.726 | 13.660 |
| 4952 | O | PRO | 618 | 53.355 | 26.315 | 12.593 |
| 4953 | CB | PRO | 618 | 51.757 | 24.890 | 14.921 |
| 4954 | CG | PRO | 618 | 51.057 | 23.775 | 14.160 |
| 4955 | CD | PRO | 618 | 50.363 | 24.445 | 12.987 |
| 4956 | N | VAL | 619 | 53.400 | 27.722 | 14.354 |
| 4957 | CA | VAL | 619 | 54.694 | 28.318 | 14.012 |
| 4958 | C | VAL | 619 | 55.764 | 27.909 | 15.019 |
| 4959 | O | VAL | 619 | 55.463 | 27.485 | 16.142 |
| 4960 | CB | VAL | 619 | 54.559 | 29.839 | 13.996 |
| 4961 | CG1 | VAL | 619 | 53.478 | 30.281 | 13.013 |
| 4962 | CG2 | VAL | 619 | 54.265 | 30.394 | 15.385 |
| 4963 | N | ASN | 620 | 57.008 | 27.988 | 14.579 |
| 4964 | CA | ASN | 620 | 58.142 | 27.713 | 15.467 |
| 4965 | C | ASN | 620 | 58.889 | 29.009 | 15.755 |
| 4966 | O | ASN | 620 | 58.896 | 29.507 | 16.885 |
| 4967 | CB | ASN | 620 | 59.062 | 26.695 | 14.807 |
| 4968 | CG | ASN | 620 | 58.293 | 25.401 | 14.564 |
| 4969 | OD1 | ASN | 620 | 57.401 | 25.039 | 15.342 |
| 4970 | ND2 | ASN | 620 | 58.629 | 24.730 | 13.476 |
| 4971 | N | ARG | 621 | 59.459 | 29.594 | 14.720 |
| 4972 | CA | ARG | 621 | 60.071 | 30.913 | 14.890 |
| 4973 | C | ARG | 621 | 59.013 | 32.000 | 14.774 |
| 4974 | O | ARG | 621 | 58.289 | 32.072 | 13.775 |
| 4975 | CB | ARG | 621 | 61.152 | 31.116 | 13.840 |
| 4976 | CG | ARG | 621 | 62.391 | 30.299 | 14.172 |
| 4977 | CD | ARG | 621 | 63.445 | 30.438 | 13.084 |
| 4978 | NE | ARG | 621 | 64.706 | 29.786 | 13.473 |
| 4979 | CZ | ARG | 621 | 65.059 | 28.558 | 13.086 |
| 4980 | NH1 | ARG | 621 | 64.217 | 27.811 | 12.367 |
| 4981 | NH2 | ARG | 621 | 66.233 | 28.053 | 13.472 |
| 4982 | N | MET | 622 | 58.888 | 32.787 | 15.829 |
| 4983 | CA | MET | 622 | 57.944 | 33.909 | 15.834 |
| 4984 | C | MET | 622 | 58.490 | 35.083 | 16.642 |
| 4985 | O | MET | 622 | 59.688 | 35.106 | 16.880 |
| 4986 | CB | MET | 622 | 56.618 | 33.452 | 16.429 |
| 4987 | CG | MET | 622 | 56.793 | 32.908 | 17.840 |
| 4988 | SD | MET | 622 | 55.257 | 32.516 | 18.703 |
| 4989 | CE | MET | 622 | 54.573 | 34.182 | 18.857 |
| 4990 | OXT | MET | 622 | 57.696 | 35.943 | 16.999 |

TABLE 10

| Atom No. | Atom Type | Residue | Residue Position | X Coord. | Y Coord. | Z Coord. |
|---|---|---|---|---|---|---|
| 1 | N | MET | 1 | 46.935 | 97.191 | 59.424 |
| 2 | CA | MET | 1 | 47.094 | 97.465 | 57.985 |
| 3 | C | MET | 1 | 48.019 | 98.650 | 57.738 |
| 4 | O | MET | 1 | 47.573 | 99.746 | 57.382 |
| 5 | CB | MET | 1 | 45.747 | 97.742 | 57.332 |
| 6 | CG | MET | 1 | 44.891 | 96.482 | 57.263 |

TABLE 10-continued

| Atom No. | Atom Type | Residue | Residue Position | X Coord. | Y Coord. | Z Coord. |
|---|---|---|---|---|---|---|
| 7 | SD | MET | 1 | 45.564 | 95.151 | 56.241 |
| 8 | CE | MET | 1 | 45.637 | 96.017 | 54.653 |
| 9 | N | SER | 2 | 49.311 | 98.403 | 57.888 |
| 10 | CA | SER | 2 | 50.313 | 99.422 | 57.558 |
| 11 | C | SER | 2 | 50.751 | 99.268 | 56.106 |
| 12 | O | SER | 2 | 51.413 | 100.148 | 55.547 |
| 13 | CB | SER | 2 | 51.530 | 99.264 | 58.463 |
| 14 | OG | SER | 2 | 52.195 | 98.059 | 58.102 |
| 15 | N | SER | 3 | 50.383 | 98.142 | 55.519 |
| 16 | CA | SER | 3 | 50.665 | 97.882 | 54.111 |
| 17 | C | SER | 3 | 49.373 | 98.017 | 53.323 |
| 18 | O | SER | 3 | 48.570 | 97.078 | 53.261 |
| 19 | CB | SER | 3 | 51.214 | 96.468 | 53.980 |
| 20 | OG | SER | 3 | 52.324 | 96.368 | 54.861 |
| 21 | N | VAL | 4 | 49.187 | 99.179 | 52.725 |
| 22 | CA | VAL | 4 | 47.920 | 99.475 | 52.056 |
| 23 | C | VAL | 4 | 47.839 | 98.759 | 50.709 |
| 24 | O | VAL | 4 | 48.759 | 98.838 | 49.885 |
| 25 | CB | VAL | 4 | 47.814 | 100.985 | 51.880 |
| 26 | CG1 | VAL | 4 | 46.379 | 101.393 | 51.558 |
| 27 | CG2 | VAL | 4 | 48.275 | 101.701 | 53.144 |
| 28 | N | ALA | 5 | 46.792 | 97.965 | 50.562 |
| 29 | CA | ALA | 5 | 46.553 | 97.240 | 49.312 |
| 30 | C | ALA | 5 | 45.693 | 98.053 | 48.349 |
| 31 | O | ALA | 5 | 44.592 | 98.502 | 48.686 |
| 32 | CB | ALA | 5 | 45.870 | 95.917 | 49.633 |
| 33 | N | SER | 6 | 46.219 | 98.228 | 47.152 |
| 34 | CA | SER | 6 | 45.521 | 98.987 | 46.111 |
| 35 | C | SER | 6 | 44.971 | 98.081 | 45.024 |
| 36 | O | SER | 6 | 45.656 | 97.162 | 44.555 |
| 37 | CB | SER | 6 | 46.505 | 99.947 | 45.465 |
| 38 | OG | SER | 6 | 45.840 | 100.611 | 44.397 |
| 39 | N | LYS | 7 | 43.752 | 98.357 | 44.600 |
| 40 | CA | LYS | 7 | 43.218 | 97.627 | 43.458 |
| 41 | C | LYS | 7 | 43.747 | 98.212 | 42.152 |
| 42 | O | LYS | 7 | 44.023 | 99.411 | 42.051 |
| 43 | CB | LYS | 7 | 41.697 | 97.645 | 43.485 |
| 44 | CG | LYS | 7 | 41.174 | 96.880 | 44.696 |
| 45 | CD | LYS | 7 | 39.651 | 96.874 | 44.736 |
| 46 | CE | LYS | 7 | 39.090 | 98.285 | 44.877 |
| 47 | NZ | LYS | 7 | 39.512 | 98.900 | 46.147 |
| 48 | N | LYS | 8 | 44.180 | 97.276 | 41.332 |
| 49 | CA | LYS | 8 | 44.590 | 97.475 | 39.933 |
| 50 | C | LYS | 8 | 43.994 | 98.633 | 39.125 |
| 51 | O | LYS | 8 | 44.251 | 99.820 | 39.379 |
| 52 | CB | LYS | 8 | 44.248 | 96.165 | 39.230 |
| 53 | CG | LYS | 8 | 43.213 | 95.342 | 39.994 |
| 54 | CD | LYS | 8 | 42.904 | 94.040 | 39.267 |
| 55 | CE | LYS | 8 | 41.960 | 93.163 | 40.081 |
| 56 | NZ | LYS | 8 | 41.676 | 91.901 | 39.377 |
| 57 | N | ILE | 9 | 43.141 | 98.238 | 38.190 |
| 58 | CA | ILE | 9 | 42.675 | 99.034 | 37.036 |
| 59 | C | ILE | 9 | 41.731 | 100.227 | 37.310 |
| 60 | O | ILE | 9 | 41.400 | 100.931 | 36.347 |
| 61 | CB | ILE | 9 | 41.994 | 98.001 | 36.127 |
| 62 | CG1 | ILE | 9 | 42.924 | 96.819 | 35.880 |
| 63 | CG2 | ILE | 9 | 41.567 | 98.568 | 34.781 |
| 64 | CD1 | ILE | 9 | 42.286 | 95.800 | 34.942 |
| 65 | N | ILE | 10 | 41.523 | 100.591 | 38.574 |
| 66 | CA | ILE | 10 | 40.505 | 101.588 | 38.989 |
| 67 | C | ILE | 10 | 40.470 | 102.795 | 38.042 |
| 68 | O | ILE | 10 | 41.524 | 103.288 | 37.609 |
| 69 | CB | ILE | 10 | 40.790 | 102.021 | 40.425 |
| 70 | CG1 | ILE | 10 | 41.372 | 100.875 | 41.231 |
| 71 | CG2 | ILE | 10 | 39.511 | 102.459 | 41.127 |
| 72 | CD1 | ILE | 10 | 41.560 | 101.298 | 42.684 |
| 73 | N | THR | 11 | 39.268 | 103.326 | 37.855 |
| 74 | CA | THR | 11 | 38.880 | 104.048 | 36.629 |
| 75 | C | THR | 11 | 39.349 | 103.284 | 35.395 |
| 76 | O | THR | 11 | 38.708 | 102.301 | 35.008 |
| 77 | CB | THR | 11 | 39.296 | 105.523 | 36.567 |
| 78 | OG1 | THR | 11 | 40.413 | 105.778 | 37.405 |
| 79 | CG2 | THR | 11 | 38.162 | 106.427 | 37.039 |
| 80 | N | PHE | 12 | 40.374 | 103.778 | 34.727 |
| 81 | CA | PHE | 12 | 40.794 | 103.130 | 33.482 |
| 82 | C | PHE | 12 | 42.278 | 102.806 | 33.410 |

TABLE 10-continued

| Atom No. | Atom Type | Residue | Residue Position | X Coord. | Y Coord. | Z Coord. |
|---|---|---|---|---|---|---|
| 83 | O | PHE | 12 | 42.761 | 102.473 | 32.319 |
| 84 | CB | PHE | 12 | 40.429 | 104.033 | 32.307 |
| 85 | CG | PHE | 12 | 38.986 | 103.904 | 31.831 |
| 86 | CD1 | PHE | 12 | 37.971 | 104.646 | 32.423 |
| 87 | CD2 | PHE | 12 | 38.688 | 103.031 | 30.792 |
| 88 | CE1 | PHE | 12 | 36.663 | 104.514 | 31.980 |
| 89 | CE2 | PHE | 12 | 37.377 | 102.900 | 30.347 |
| 90 | CZ | PHE | 12 | 36.365 | 103.642 | 30.943 |
| 91 | N | GLU | 13 | 42.997 | 102.860 | 34.517 |
| 92 | CA | GLU | 13 | 44.450 | 102.790 | 34.360 |
| 93 | C | GLU | 13 | 45.219 | 102.067 | 35.458 |
| 94 | O | GLU | 13 | 44.693 | 101.287 | 36.257 |
| 95 | CB | GLU | 13 | 44.971 | 104.214 | 34.237 |
| 96 | CG | GLU | 13 | 44.473 | 105.111 | 35.365 |
| 97 | CD | GLU | 13 | 45.218 | 106.432 | 35.270 |
| 98 | OE1 | GLU | 13 | 46.432 | 106.305 | 35.181 |
| 99 | OE2 | GLU | 13 | 44.587 | 107.354 | 34.763 |
| 100 | N | GLY | 14 | 46.525 | 102.222 | 35.335 |
| 101 | CA | GLY | 14 | 47.466 | 101.712 | 36.324 |
| 102 | C | GLY | 14 | 48.597 | 102.717 | 36.504 |
| 103 | O | GLY | 14 | 49.028 | 102.954 | 37.639 |
| 104 | N | HIS | 15 | 48.925 | 103.410 | 35.420 |
| 105 | CA | HIS | 15 | 50.039 | 104.378 | 35.382 |
| 106 | C | HIS | 15 | 50.006 | 105.406 | 36.507 |
| 107 | O | HIS | 15 | 50.690 | 105.212 | 37.519 |
| 108 | CB | HIS | 15 | 50.003 | 105.109 | 34.047 |
| 109 | CG | HIS | 15 | 50.742 | 104.417 | 32.920 |
| 110 | ND1 | HIS | 15 | 52.003 | 103.946 | 32.962 |
| 111 | CD2 | HIS | 15 | 50.267 | 104.182 | 31.652 |
| 112 | CE1 | HIS | 15 | 52.317 | 103.409 | 31.765 |
| 113 | NE2 | HIS | 15 | 51.244 | 103.556 | 30.956 |
| 114 | N | ARG | 16 | 49.062 | 106.333 | 36.452 |
| 115 | CA | ARG | 16 | 48.985 | 107.390 | 37.470 |
| 116 | C | ARG | 16 | 48.472 | 106.902 | 38.821 |
| 117 | O | ARG | 16 | 48.874 | 107.472 | 39.842 |
| 118 | CB | ARG | 16 | 48.036 | 108.471 | 36.985 |
| 119 | CG | ARG | 16 | 48.657 | 109.397 | 35.951 |
| 120 | CD | ARG | 16 | 49.743 | 110.259 | 36.583 |
| 121 | NE | ARG | 16 | 50.126 | 111.359 | 35.685 |
| 122 | CZ | ARG | 16 | 49.969 | 112.641 | 36.023 |
| 123 | NH1 | ARG | 16 | 50.186 | 113.602 | 35.123 |
| 124 | NH2 | ARG | 16 | 49.480 | 112.953 | 37.225 |
| 125 | N | ASN | 17 | 47.894 | 105.711 | 38.841 |
| 126 | CA | ASN | 17 | 47.380 | 105.141 | 40.086 |
| 127 | C | ASN | 17 | 48.584 | 104.768 | 40.946 |
| 128 | O | ASN | 17 | 48.825 | 105.396 | 41.987 |
| 129 | CB | ASN | 17 | 46.558 | 103.878 | 39.784 |
| 130 | CG | ASN | 17 | 45.293 | 104.121 | 38.944 |
| 131 | OD1 | ASN | 17 | 45.118 | 105.166 | 38.301 |
| 132 | ND2 | ASN | 17 | 44.477 | 103.084 | 38.861 |
| 133 | N | PHE | 18 | 49.508 | 104.086 | 40.290 |
| 134 | CA | PHE | 18 | 50.738 | 103.627 | 40.926 |
| 135 | C | PHE | 18 | 51.764 | 104.743 | 41.111 |
| 136 | O | PHE | 18 | 52.397 | 104.804 | 42.172 |
| 137 | CB | PHE | 18 | 51.315 | 102.553 | 40.013 |
| 138 | CG | PHE | 18 | 52.740 | 102.135 | 40.340 |
| 139 | CD1 | PHE | 18 | 53.037 | 101.557 | 41.567 |
| 140 | CD2 | PHE | 18 | 53.743 | 102.340 | 39.403 |
| 141 | CE1 | PHE | 18 | 54.342 | 101.187 | 41.857 |
| 142 | CE2 | PHE | 18 | 55.048 | 101.968 | 39.692 |
| 143 | CZ | PHE | 18 | 55.345 | 101.393 | 40.920 |
| 144 | N | ARG | 19 | 51.761 | 105.732 | 40.231 |
| 145 | CA | ARG | 19 | 52.729 | 106.823 | 40.369 |
| 146 | C | ARG | 19 | 52.344 | 107.790 | 41.483 |
| 147 | O | ARG | 19 | 53.225 | 108.232 | 42.233 |
| 148 | CB | ARG | 19 | 52.851 | 107.570 | 39.045 |
| 149 | CG | ARG | 19 | 53.467 | 106.672 | 37.979 |
| 150 | CD | ARG | 19 | 53.871 | 107.448 | 36.730 |
| 151 | NE | ARG | 19 | 52.718 | 107.992 | 35.995 |
| 152 | CZ | ARG | 19 | 52.575 | 107.802 | 34.681 |
| 153 | NH1 | ARG | 19 | 53.454 | 107.047 | 34.021 |
| 154 | NH2 | ARG | 19 | 51.536 | 108.331 | 34.033 |
| 155 | N | LEU | 20 | 51.058 | 107.876 | 41.776 |
| 156 | CA | LEU | 20 | 50.633 | 108.728 | 42.881 |
| 157 | C | LEU | 20 | 50.780 | 107.978 | 44.201 |
| 158 | O | LEU | 20 | 51.153 | 108.585 | 45.212 |
| 159 | CB | LEU | 20 | 49.182 | 109.131 | 42.650 |
| 160 | CG | LEU | 20 | 48.948 | 110.607 | 42.958 |
| 161 | CD1 | LEU | 20 | 49.002 | 110.905 | 44.451 |
| 162 | CD2 | LEU | 20 | 49.928 | 111.489 | 42.191 |
| 163 | N | ARG | 21 | 50.778 | 106.657 | 44.134 |
| 164 | CA | ARG | 21 | 50.993 | 105.863 | 45.343 |
| 165 | C | ARG | 21 | 52.468 | 105.681 | 45.677 |
| 166 | O | ARG | 21 | 52.792 | 105.415 | 46.841 |
| 167 | CB | ARG | 21 | 50.311 | 104.522 | 45.174 |
| 168 | CG | ARG | 21 | 48.827 | 104.765 | 44.970 |
| 169 | CD | ARG | 21 | 48.044 | 103.466 | 44.990 |
| 170 | NE | ARG | 21 | 48.269 | 102.776 | 46.267 |
| 171 | CZ | ARG | 21 | 47.522 | 102.959 | 47.359 |
| 172 | NH1 | ARG | 21 | 47.709 | 102.178 | 48.422 |
| 173 | NH2 | ARG | 21 | 46.512 | 103.831 | 47.345 |
| 174 | N | LEU | 22 | 53.347 | 106.041 | 44.757 |
| 175 | CA | LEU | 22 | 54.770 | 106.109 | 45.092 |
| 176 | C | LEU | 22 | 55.038 | 107.344 | 45.942 |
| 177 | O | LEU | 22 | 55.712 | 107.237 | 46.977 |
| 178 | CB | LEU | 22 | 55.589 | 106.187 | 43.810 |
| 179 | CG | LEU | 22 | 55.512 | 104.887 | 43.022 |
| 180 | CD1 | LEU | 22 | 56.184 | 105.037 | 41.664 |
| 181 | CD2 | LEU | 22 | 56.132 | 103.737 | 43.807 |
| 182 | N | VAL | 23 | 54.263 | 108.389 | 45.684 |
| 183 | CA | VAL | 23 | 54.337 | 109.613 | 46.486 |
| 184 | C | VAL | 23 | 53.855 | 109.342 | 47.900 |
| 185 | O | VAL | 23 | 54.632 | 109.491 | 48.848 |
| 186 | CB | VAL | 23 | 53.402 | 110.657 | 45.885 |
| 187 | CG1 | VAL | 23 | 53.398 | 111.944 | 46.703 |
| 188 | CG2 | VAL | 23 | 53.722 | 110.938 | 44.427 |
| 189 | N | LEU | 24 | 52.722 | 108.667 | 47.992 |
| 190 | CA | LEU | 24 | 52.076 | 108.428 | 49.284 |
| 191 | C | LEU | 24 | 52.798 | 107.400 | 50.146 |
| 192 | O | LEU | 24 | 52.925 | 107.611 | 51.360 |
| 193 | CB | LEU | 24 | 50.690 | 107.905 | 48.971 |
| 194 | CG | LEU | 24 | 49.931 | 108.878 | 48.086 |
| 195 | CD1 | LEU | 24 | 48.816 | 108.160 | 47.353 |
| 196 | CD2 | LEU | 24 | 49.413 | 110.077 | 48.868 |
| 197 | N | ALA | 25 | 53.449 | 106.438 | 49.514 |
| 198 | CA | ALA | 25 | 54.186 | 105.434 | 50.275 |
| 199 | C | ALA | 25 | 55.414 | 106.046 | 50.918 |
| 200 | O | ALA | 25 | 55.544 | 105.993 | 52.148 |
| 201 | CB | ALA | 25 | 54.627 | 104.334 | 49.325 |
| 202 | N | THR | 26 | 56.103 | 106.878 | 50.157 |
| 203 | CA | THR | 26 | 57.319 | 107.519 | 50.666 |
| 204 | C | THR | 26 | 57.023 | 108.737 | 51.542 |
| 205 | O | THR | 26 | 57.861 | 109.120 | 52.363 |
| 206 | CB | THR | 26 | 58.153 | 107.949 | 49.467 |
| 207 | OG1 | THR | 26 | 57.432 | 108.932 | 48.735 |
| 208 | CG2 | THR | 26 | 58.417 | 106.770 | 48.542 |
| 209 | N | LEU | 27 | 55.800 | 109.234 | 51.476 |
| 210 | CA | LEU | 27 | 55.403 | 110.400 | 52.265 |
| 211 | C | LEU | 27 | 54.856 | 110.001 | 53.633 |
| 212 | O | LEU | 27 | 54.945 | 110.779 | 54.590 |
| 213 | CB | LEU | 27 | 54.300 | 111.105 | 51.481 |
| 214 | CG | LEU | 27 | 54.569 | 112.590 | 51.274 |
| 215 | CD1 | LEU | 27 | 54.466 | 113.364 | 52.581 |
| 216 | CD2 | LEU | 27 | 55.915 | 112.821 | 50.595 |
| 217 | N | SER | 28 | 54.327 | 108.793 | 53.732 |
| 218 | CA | SER | 28 | 53.763 | 108.346 | 55.007 |
| 219 | C | SER | 28 | 54.644 | 107.311 | 55.698 |
| 220 | O | SER | 28 | 54.477 | 107.045 | 56.894 |
| 221 | CB | SER | 28 | 52.404 | 107.724 | 54.720 |
| 222 | OG | SER | 28 | 51.655 | 108.658 | 53.957 |
| 223 | N | GLY | 29 | 55.554 | 106.725 | 54.940 |
| 224 | CA | GLY | 29 | 56.417 | 105.664 | 55.464 |
| 225 | C | GLY | 29 | 55.657 | 104.342 | 55.424 |
| 226 | O | GLY | 29 | 55.778 | 103.505 | 56.326 |
| 227 | N | LYS | 30 | 54.840 | 104.190 | 54.395 |
| 228 | CA | LYS | 30 | 53.970 | 103.015 | 54.293 |
| 229 | C | LYS | 30 | 54.354 | 102.089 | 53.152 |
| 230 | O | LYS | 30 | 54.538 | 102.512 | 52.003 |
| 231 | CB | LYS | 30 | 52.524 | 103.459 | 54.098 |
| 232 | CG | LYS | 30 | 51.949 | 104.070 | 55.369 |
| 233 | CD | LYS | 30 | 50.477 | 104.423 | 55.193 |
| 234 | CE | LYS | 30 | 49.892 | 104.990 | 56.481 |

TABLE 10-continued

| Atom No. | Atom Type | Residue | Residue Position | X Coord. | Y Coord. | Z Coord. |
|---|---|---|---|---|---|---|
| 235 | NZ | LYS | 30 | 50.016 | 104.019 | 57.580 |
| 236 | N | PRO | 31 | 54.481 | 100.820 | 53.498 |
| 237 | CA | PRO | 31 | 54.447 | 99.750 | 52.502 |
| 238 | C | PRO | 31 | 53.135 | 99.760 | 51.721 |
| 239 | O | PRO | 31 | 52.049 | 99.965 | 52.277 |
| 240 | CB | PRO | 31 | 54.595 | 98.481 | 53.281 |
| 241 | CG | PRO | 31 | 54.584 | 98.803 | 54.768 |
| 242 | CD | PRO | 31 | 54.468 | 100.312 | 54.871 |
| 243 | N | ILE | 32 | 53.258 | 99.574 | 50.420 |
| 244 | CA | ILE | 32 | 52.086 | 99.540 | 49.536 |
| 245 | C | ILE | 32 | 52.155 | 98.356 | 48.571 |
| 246 | O | ILE | 32 | 53.176 | 98.110 | 47.911 |
| 247 | CB | ILE | 32 | 51.973 | 100.874 | 48.788 |
| 248 | CG1 | ILE | 32 | 51.490 | 101.982 | 49.718 |
| 249 | CG2 | ILE | 32 | 51.064 | 100.785 | 47.567 |
| 250 | CD1 | ILE | 32 | 51.222 | 103.274 | 48.956 |
| 251 | N | LYS | 33 | 51.072 | 97.595 | 48.561 |
| 252 | CA | LYS | 33 | 50.936 | 96.454 | 47.654 |
| 253 | C | LYS | 33 | 49.820 | 96.707 | 46.641 |
| 254 | O | LYS | 33 | 48.629 | 96.624 | 46.965 |
| 255 | CB | LYS | 33 | 50.616 | 95.205 | 48.463 |
| 256 | CG | LYS | 33 | 50.523 | 93.983 | 47.555 |
| 257 | CD | LYS | 33 | 50.079 | 92.746 | 48.323 |
| 258 | CE | LYS | 33 | 48.659 | 92.910 | 48.851 |
| 259 | NZ | LYS | 33 | 47.708 | 93.096 | 47.743 |
| 260 | N | ILE | 34 | 50.211 | 97.028 | 45.423 |
| 261 | CA | ILE | 34 | 49.218 | 97.302 | 44.379 |
| 262 | C | ILE | 34 | 49.053 | 96.101 | 43.443 |
| 263 | O | ILE | 34 | 50.018 | 95.582 | 42.865 |
| 264 | CB | ILE | 34 | 49.610 | 98.583 | 43.643 |
| 265 | CG1 | ILE | 34 | 48.635 | 98.902 | 42.512 |
| 266 | CG2 | ILE | 34 | 51.046 | 98.511 | 43.136 |
| 267 | CD1 | ILE | 34 | 48.956 | 100.236 | 41.850 |
| 268 | N | THR | 35 | 47.821 | 95.625 | 43.385 |
| 269 | CA | THR | 35 | 47.468 | 94.450 | 42.585 |
| 270 | C | THR | 35 | 47.384 | 94.781 | 41.106 |
| 271 | O | THR | 35 | 46.986 | 95.886 | 40.735 |
| 272 | CB | THR | 35 | 46.100 | 93.938 | 43.025 |
| 273 | OG1 | THR | 35 | 45.105 | 94.871 | 42.615 |
| 274 | CG2 | THR | 35 | 46.012 | 93.762 | 44.536 |
| 275 | N | LYS | 36 | 47.820 | 93.819 | 40.310 |
| 276 | CA | LYS | 36 | 47.676 | 93.787 | 38.835 |
| 277 | C | LYS | 36 | 47.609 | 95.136 | 38.116 |
| 278 | O | LYS | 36 | 46.579 | 95.474 | 37.516 |
| 279 | CB | LYS | 36 | 46.419 | 92.997 | 38.503 |
| 280 | CG | LYS | 36 | 46.564 | 91.541 | 38.916 |
| 281 | CD | LYS | 36 | 45.385 | 90.701 | 38.443 |
| 282 | CE | LYS | 36 | 45.579 | 89.238 | 38.821 |
| 283 | NZ | LYS | 36 | 46.835 | 88.717 | 38.258 |
| 284 | N | ILE | 37 | 48.717 | 95.857 | 38.122 |
| 285 | CA | ILE | 37 | 48.798 | 97.151 | 37.445 |
| 286 | C | ILE | 37 | 48.638 | 96.943 | 35.947 |
| 287 | O | ILE | 37 | 49.227 | 96.005 | 35.399 |
| 288 | CB | ILE | 37 | 50.180 | 97.731 | 37.738 |
| 289 | CG1 | ILE | 37 | 50.445 | 97.746 | 39.235 |
| 290 | CG2 | ILE | 37 | 50.339 | 99.140 | 37.176 |
| 291 | CD1 | ILE | 37 | 51.796 | 98.382 | 39.526 |
| 292 | N | ARG | 38 | 47.751 | 97.720 | 35.340 |
| 293 | CA | ARG | 38 | 47.551 | 97.703 | 33.880 |
| 294 | C | ARG | 38 | 47.341 | 96.296 | 33.331 |
| 295 | O | ARG | 38 | 48.272 | 95.684 | 32.793 |
| 296 | CB | ARG | 38 | 48.797 | 98.295 | 33.234 |
| 297 | CG | ARG | 38 | 49.014 | 99.740 | 33.653 |
| 298 | CD | ARG | 38 | 50.324 | 100.265 | 33.090 |
| 299 | NE | ARG | 38 | 50.333 | 100.142 | 31.626 |
| 300 | CZ | ARG | 38 | 51.441 | 99.899 | 30.925 |
| 301 | NH1 | ARG | 38 | 52.609 | 99.761 | 31.554 |
| 302 | NH2 | ARG | 38 | 51.384 | 99.817 | 29.594 |
| 303 | N | SER | 39 | 46.147 | 95.765 | 33.518 |
| 304 | CA | SER | 39 | 45.879 | 94.396 | 33.067 |
| 305 | C | SER | 39 | 44.937 | 94.319 | 31.864 |
| 306 | O | SER | 39 | 44.589 | 93.221 | 31.419 |
| 307 | CB | SER | 39 | 45.318 | 93.622 | 34.250 |
| 308 | OG | SER | 39 | 46.300 | 93.689 | 35.275 |
| 309 | N | GLN | 40 | 44.551 | 95.466 | 31.331 |
| 310 | CA | GLN | 40 | 43.627 | 95.486 | 30.185 |
| 311 | C | GLN | 40 | 44.284 | 96.018 | 28.910 |
| 312 | O | GLN | 40 | 43.599 | 96.464 | 27.982 |
| 313 | CB | GLN | 40 | 42.406 | 96.324 | 30.546 |
| 314 | CG | GLN | 40 | 42.757 | 97.773 | 30.863 |
| 315 | CD | GLN | 40 | 41.488 | 98.499 | 31.295 |
| 316 | OE1 | GLN | 40 | 40.527 | 97.860 | 31.739 |
| 317 | NE2 | GLN | 40 | 41.532 | 99.819 | 31.254 |
| 318 | N | ASP | 41 | 45.605 | 96.016 | 28.889 |
| 319 | CA | ASP | 41 | 46.348 | 96.604 | 27.766 |
| 320 | C | ASP | 41 | 47.394 | 95.637 | 27.220 |
| 321 | O | ASP | 41 | 47.614 | 94.561 | 27.786 |
| 322 | CB | ASP | 41 | 46.995 | 97.907 | 28.226 |
| 323 | CG | ASP | 41 | 47.769 | 97.687 | 29.520 |
| 324 | OD1 | ASP | 41 | 47.178 | 97.895 | 30.574 |
| 325 | OD2 | ASP | 41 | 48.886 | 97.199 | 29.426 |
| 326 | N | LEU | 42 | 48.115 | 96.084 | 26.202 |
| 327 | CA | LEU | 42 | 49.076 | 95.217 | 25.501 |
| 328 | C | LEU | 42 | 50.433 | 95.084 | 26.196 |
| 329 | O | LEU | 42 | 51.247 | 94.245 | 25.791 |
| 330 | CB | LEU | 42 | 49.288 | 95.780 | 24.101 |
| 331 | CG | LEU | 42 | 47.993 | 95.780 | 23.296 |
| 332 | CD1 | LEU | 42 | 48.171 | 96.515 | 21.973 |
| 333 | CD2 | LEU | 42 | 47.486 | 94.360 | 23.062 |
| 334 | N | ASN | 43 | 50.669 | 95.859 | 27.242 |
| 335 | CA | ASN | 43 | 51.919 | 95.719 | 28.003 |
| 336 | C | ASN | 43 | 51.616 | 95.607 | 29.496 |
| 337 | O | ASN | 43 | 51.866 | 96.560 | 30.242 |
| 338 | CB | ASN | 43 | 52.791 | 96.949 | 27.764 |
| 339 | CG | ASN | 43 | 53.020 | 97.175 | 26.272 |
| 340 | OD1 | ASN | 43 | 52.335 | 97.991 | 25.643 |
| 341 | ND2 | ASN | 43 | 53.956 | 96.424 | 25.716 |
| 342 | N | PRO | 44 | 51.184 | 94.432 | 29.933 |
| 343 | CA | PRO | 44 | 50.621 | 94.288 | 31.277 |
| 344 | C | PRO | 44 | 51.677 | 94.435 | 32.365 |
| 345 | O | PRO | 44 | 52.858 | 94.122 | 32.165 |
| 346 | CB | PRO | 44 | 49.995 | 92.929 | 31.310 |
| 347 | CG | PRO | 44 | 50.307 | 92.202 | 30.013 |
| 348 | CD | PRO | 44 | 51.093 | 93.185 | 29.163 |
| 349 | N | GLY | 45 | 51.239 | 94.966 | 33.491 |
| 350 | CA | GLY | 45 | 52.107 | 95.135 | 34.654 |
| 351 | C | GLY | 45 | 53.220 | 96.144 | 34.410 |
| 352 | O | GLY | 45 | 53.051 | 97.171 | 33.739 |
| 353 | N | LEU | 46 | 54.356 | 95.840 | 35.006 |
| 354 | CA | LEU | 46 | 55.548 | 96.678 | 34.880 |
| 355 | C | LEU | 46 | 56.221 | 96.627 | 33.514 |
| 356 | O | LEU | 46 | 57.051 | 95.754 | 33.229 |
| 357 | CB | LEU | 46 | 56.543 | 96.215 | 35.929 |
| 358 | CG | LEU | 46 | 55.979 | 96.447 | 37.317 |
| 359 | CD1 | LEU | 46 | 56.819 | 95.749 | 38.376 |
| 360 | CD2 | LEU | 46 | 55.842 | 97.938 | 37.593 |
| 361 | N | LYS | 47 | 55.903 | 97.621 | 32.704 |
| 362 | CA | LYS | 47 | 56.688 | 97.903 | 31.499 |
| 363 | C | LYS | 47 | 58.053 | 98.417 | 31.970 |
| 364 | O | LYS | 47 | 58.167 | 98.825 | 33.131 |
| 365 | CB | LYS | 47 | 55.942 | 98.976 | 30.710 |
| 366 | CG | LYS | 47 | 56.273 | 98.959 | 29.223 |
| 367 | CD | LYS | 47 | 55.547 | 100.074 | 28.484 |
| 368 | CE | LYS | 47 | 55.868 | 100.030 | 26.996 |
| 369 | NZ | LYS | 47 | 57.320 | 100.112 | 26.778 |
| 370 | N | ASP | 48 | 59.038 | 98.519 | 31.086 |
| 371 | CA | ASP | 48 | 60.393 | 98.933 | 31.507 |
| 372 | C | ASP | 48 | 60.463 | 100.380 | 32.010 |
| 373 | O | ASP | 48 | 61.235 | 100.656 | 32.935 |
| 374 | CB | ASP | 48 | 61.353 | 98.757 | 30.335 |
| 375 | CG | ASP | 48 | 62.773 | 99.128 | 30.765 |
| 376 | OD1 | ASP | 48 | 63.208 | 100.214 | 30.411 |
| 377 | OD2 | ASP | 48 | 63.355 | 98.355 | 31.512 |
| 378 | N | HIS | 49 | 59.479 | 101.185 | 31.639 |
| 379 | CA | HIS | 49 | 59.336 | 102.540 | 32.181 |
| 380 | C | HIS | 49 | 59.067 | 102.503 | 33.684 |
| 381 | O | HIS | 49 | 59.817 | 103.112 | 34.456 |
| 382 | CB | HIS | 49 | 58.134 | 103.164 | 31.479 |
| 383 | CG | HIS | 49 | 57.780 | 104.575 | 31.895 |
| 384 | ND1 | HIS | 49 | 58.632 | 105.550 | 32.261 |
| 385 | CD2 | HIS | 49 | 56.511 | 105.101 | 31.968 |
| 386 | CE1 | HIS | 49 | 57.930 | 106.666 | 32.550 |

TABLE 10-continued

| Atom No. | Atom Type | Residue | Residue Position | X Coord. | Y Coord. | Z Coord. |
|---|---|---|---|---|---|---|
| 387 | NE2 | HIS | 49 | 56.620 | 106.386 | 32.372 |
| 388 | N | GLU | 50 | 58.230 | 101.561 | 34.090 |
| 389 | CA | GLU | 50 | 57.846 | 101.451 | 35.493 |
| 390 | C | GLU | 50 | 58.853 | 100.614 | 36.281 |
| 391 | O | GLU | 50 | 59.076 | 100.904 | 37.459 |
| 392 | CB | GLU | 50 | 56.471 | 100.796 | 35.556 |
| 393 | CG | GLU | 50 | 55.422 | 101.538 | 34.730 |
| 394 | CD | GLU | 50 | 55.120 | 102.918 | 35.313 |
| 395 | OE1 | GLU | 50 | 55.183 | 103.057 | 36.524 |
| 396 | OE2 | GLU | 50 | 54.689 | 103.766 | 34.540 |
| 397 | N | VAL | 51 | 59.615 | 99.776 | 35.595 |
| 398 | CA | VAL | 51 | 60.662 | 98.997 | 36.270 |
| 399 | C | VAL | 51 | 61.859 | 99.875 | 36.620 |
| 400 | O | VAL | 51 | 62.318 | 99.858 | 37.770 |
| 401 | CB | VAL | 51 | 61.113 | 97.871 | 35.345 |
| 402 | CG1 | VAL | 51 | 62.316 | 97.126 | 35.911 |
| 403 | CG2 | VAL | 51 | 59.975 | 96.902 | 35.059 |
| 404 | N | SER | 52 | 62.138 | 100.836 | 35.754 |
| 405 | CA | SER | 52 | 63.240 | 101.769 | 36.000 |
| 406 | C | SER | 52 | 62.831 | 102.806 | 37.041 |
| 407 | O | SER | 52 | 63.595 | 103.087 | 37.974 |
| 408 | CB | SER | 52 | 63.576 | 102.476 | 34.690 |
| 409 | OG | SER | 52 | 63.889 | 101.490 | 33.714 |
| 410 | N | PHE | 53 | 61.539 | 103.087 | 37.058 |
| 411 | CA | PHE | 53 | 60.969 | 104.043 | 38.002 |
| 412 | C | PHE | 53 | 60.856 | 103.460 | 39.411 |
| 413 | O | PHE | 53 | 61.105 | 104.177 | 40.390 |
| 414 | CB | PHE | 53 | 59.588 | 104.384 | 37.463 |
| 415 | CG | PHE | 53 | 58.935 | 105.589 | 38.106 |
| 416 | CD1 | PHE | 53 | 59.719 | 106.564 | 38.708 |
| 417 | CD2 | PHE | 53 | 57.554 | 105.727 | 38.081 |
| 418 | CE1 | PHE | 53 | 59.121 | 107.671 | 39.291 |
| 419 | CE2 | PHE | 53 | 56.959 | 106.837 | 38.661 |
| 420 | CZ | PHE | 53 | 57.744 | 107.805 | 39.264 |
| 421 | N | LEU | 54 | 60.760 | 102.144 | 39.496 |
| 422 | CA | LEU | 54 | 60.762 | 101.470 | 40.794 |
| 423 | C | LEU | 54 | 62.123 | 101.548 | 41.452 |
| 424 | O | LEU | 54 | 62.201 | 102.051 | 42.581 |
| 425 | CB | LEU | 54 | 60.410 | 100.006 | 40.591 |
| 426 | CG | LEU | 54 | 58.908 | 99.822 | 40.496 |
| 427 | CD1 | LEU | 54 | 58.576 | 98.456 | 39.925 |
| 428 | CD2 | LEU | 54 | 58.264 | 100.025 | 41.861 |
| 429 | N | ARG | 55 | 63.172 | 101.387 | 40.662 |
| 430 | CA | ARG | 55 | 64.524 | 101.430 | 41.223 |
| 431 | C | ARG | 55 | 64.938 | 102.859 | 41.565 |
| 432 | O | ARG | 55 | 65.585 | 103.076 | 42.595 |
| 433 | CB | ARG | 55 | 65.486 | 100.859 | 40.194 |
| 434 | CG | ARG | 55 | 64.977 | 99.529 | 39.655 |
| 435 | CD | ARG | 55 | 65.985 | 98.920 | 38.692 |
| 436 | NE | ARG | 55 | 66.423 | 99.914 | 37.700 |
| 437 | CZ | ARG | 55 | 66.339 | 99.728 | 36.381 |
| 438 | NH1 | ARG | 55 | 65.745 | 98.635 | 35.897 |
| 439 | NH2 | ARG | 55 | 66.791 | 100.667 | 35.548 |
| 440 | N | LEU | 56 | 64.342 | 103.821 | 40.879 |
| 441 | CA | LEU | 56 | 64.579 | 105.238 | 41.182 |
| 442 | C | LEU | 56 | 63.959 | 105.608 | 42.528 |
| 443 | O | LEU | 56 | 64.670 | 106.027 | 43.454 |
| 444 | CB | LEU | 56 | 63.916 | 106.077 | 40.089 |
| 445 | CG | LEU | 56 | 64.856 | 106.549 | 38.977 |
| 446 | CD1 | LEU | 56 | 65.664 | 105.433 | 38.321 |
| 447 | CD2 | LEU | 56 | 64.081 | 107.324 | 37.920 |
| 448 | N | LEU | 57 | 62.721 | 105.176 | 42.702 |
| 449 | CA | LEU | 57 | 61.943 | 105.468 | 43.911 |
| 450 | C | LEU | 57 | 62.555 | 104.787 | 45.133 |
| 451 | O | LEU | 57 | 62.902 | 105.454 | 46.118 |
| 452 | CB | LEU | 57 | 60.539 | 104.916 | 43.630 |
| 453 | CG | LEU | 57 | 59.453 | 105.298 | 44.637 |
| 454 | CD1 | LEU | 57 | 59.422 | 104.428 | 45.891 |
| 455 | CD2 | LEU | 57 | 59.472 | 106.782 | 44.966 |
| 456 | N | GLU | 58 | 62.932 | 103.535 | 44.944 |
| 457 | CA | GLU | 58 | 63.434 | 102.714 | 46.043 |
| 458 | C | GLU | 58 | 64.907 | 102.950 | 46.364 |
| 459 | O | GLU | 58 | 65.333 | 102.601 | 47.471 |
| 460 | CB | GLU | 58 | 63.184 | 101.267 | 45.654 |
| 461 | CG | GLU | 58 | 61.681 | 101.036 | 45.532 |
| 462 | CD | GLU | 58 | 61.389 | 99.899 | 44.562 |
| 463 | OE1 | GLU | 58 | 62.307 | 99.496 | 43.859 |
| 464 | OE2 | GLU | 58 | 60.220 | 99.566 | 44.421 |
| 465 | N | ALA | 59 | 65.624 | 103.671 | 45.519 |
| 466 | CA | ALA | 59 | 66.997 | 104.028 | 45.871 |
| 467 | C | ALA | 59 | 67.038 | 105.320 | 46.677 |
| 468 | O | ALA | 59 | 67.771 | 105.394 | 47.669 |
| 469 | CB | ALA | 59 | 67.815 | 104.202 | 44.597 |
| 470 | N | VAL | 60 | 66.116 | 106.230 | 46.400 |
| 471 | CA | VAL | 60 | 66.140 | 107.510 | 47.115 |
| 472 | C | VAL | 60 | 65.359 | 107.437 | 48.427 |
| 473 | O | VAL | 60 | 65.683 | 108.140 | 49.393 |
| 474 | CB | VAL | 60 | 65.534 | 108.585 | 46.218 |
| 475 | CG1 | VAL | 60 | 65.762 | 109.972 | 46.811 |
| 476 | CG2 | VAL | 60 | 66.120 | 108.523 | 44.813 |
| 477 | N | THR | 61 | 64.413 | 106.517 | 48.498 |
| 478 | CA | THR | 61 | 63.652 | 106.354 | 49.736 |
| 479 | C | THR | 61 | 64.109 | 105.138 | 50.541 |
| 480 | O | THR | 61 | 63.549 | 104.872 | 51.614 |
| 481 | CB | THR | 61 | 62.173 | 106.223 | 49.395 |
| 482 | OG1 | THR | 61 | 61.868 | 107.162 | 48.374 |
| 483 | CG2 | THR | 61 | 61.300 | 106.529 | 50.608 |
| 484 | N | ASN | 62 | 65.125 | 104.438 | 50.054 |
| 485 | CA | ASN | 62 | 65.611 | 103.212 | 50.710 |
| 486 | C | ASN | 62 | 64.451 | 102.256 | 50.952 |
| 487 | O | ASN | 62 | 63.923 | 102.167 | 52.068 |
| 488 | CB | ASN | 62 | 66.291 | 103.559 | 52.036 |
| 489 | CG | ASN | 62 | 67.625 | 104.271 | 51.817 |
| 490 | OD1 | ASN | 62 | 68.652 | 103.620 | 51.595 |
| 491 | ND2 | ASN | 62 | 67.615 | 105.584 | 51.969 |
| 492 | N | GLY | 63 | 63.994 | 101.629 | 49.885 |
| 493 | CA | GLY | 63 | 62.785 | 100.812 | 49.978 |
| 494 | C | GLY | 63 | 62.940 | 99.397 | 49.441 |
| 495 | O | GLY | 63 | 63.312 | 99.186 | 48.277 |
| 496 | N | SER | 64 | 62.498 | 98.455 | 50.258 |
| 497 | CA | SER | 64 | 62.457 | 97.039 | 49.873 |
| 498 | C | SER | 64 | 61.423 | 96.871 | 48.770 |
| 499 | O | SER | 64 | 60.518 | 97.704 | 48.643 |
| 500 | CB | SER | 64 | 62.066 | 96.199 | 51.083 |
| 501 | OG | SER | 64 | 63.048 | 96.407 | 52.089 |
| 502 | N | HIS | 65 | 61.588 | 95.860 | 47.938 |
| 503 | CA | HIS | 65 | 60.710 | 95.759 | 46.772 |
| 504 | C | HIS | 65 | 60.515 | 94.341 | 46.246 |
| 505 | O | HIS | 65 | 61.401 | 93.722 | 45.644 |
| 506 | CB | HIS | 65 | 61.236 | 96.690 | 45.679 |
| 507 | CG | HIS | 65 | 62.726 | 96.640 | 45.365 |
| 508 | ND1 | HIS | 65 | 63.688 | 97.422 | 45.894 |
| 509 | CD2 | HIS | 65 | 63.346 | 95.801 | 44.466 |
| 510 | CE1 | HIS | 65 | 64.880 | 97.092 | 45.354 |
| 511 | NE2 | HIS | 65 | 64.665 | 96.088 | 44.471 |
| 512 | N | ILE | 66 | 59.323 | 93.836 | 46.497 |
| 513 | CA | ILE | 66 | 58.900 | 92.564 | 45.920 |
| 514 | C | ILE | 66 | 58.178 | 92.848 | 44.608 |
| 515 | O | ILE | 66 | 57.331 | 93.748 | 44.549 |
| 516 | CB | ILE | 66 | 57.976 | 91.867 | 46.918 |
| 517 | CG1 | ILE | 66 | 58.733 | 91.487 | 48.184 |
| 518 | CG2 | ILE | 66 | 57.316 | 90.627 | 46.319 |
| 519 | CD1 | ILE | 66 | 59.785 | 90.423 | 47.893 |
| 520 | N | GLU | 67 | 58.593 | 92.148 | 43.563 |
| 521 | CA | GLU | 67 | 57.988 | 92.270 | 42.229 |
| 522 | C | GLU | 67 | 58.301 | 93.600 | 41.559 |
| 523 | O | GLU | 67 | 57.473 | 94.515 | 41.554 |
| 524 | CB | GLU | 67 | 56.473 | 92.095 | 42.324 |
| 525 | CG | GLU | 67 | 56.002 | 90.682 | 41.999 |
| 526 | CD | GLU | 67 | 55.886 | 90.520 | 40.488 |
| 527 | OE1 | GLU | 67 | 56.926 | 90.525 | 39.838 |
| 528 | OE2 | GLU | 67 | 54.762 | 90.495 | 39.998 |
| 529 | N | ILE | 68 | 59.522 | 93.706 | 41.062 |
| 530 | CA | ILE | 68 | 59.913 | 94.833 | 40.210 |
| 531 | C | ILE | 68 | 60.177 | 94.345 | 38.783 |
| 532 | O | ILE | 68 | 60.592 | 95.113 | 37.908 |
| 533 | CB | ILE | 68 | 61.126 | 95.542 | 40.821 |
| 534 | CG1 | ILE | 68 | 62.267 | 94.591 | 41.188 |
| 535 | CG2 | ILE | 68 | 60.701 | 96.351 | 42.041 |
| 536 | CD1 | ILE | 68 | 63.200 | 94.284 | 40.019 |
| 537 | N | SER | 69 | 59.906 | 93.065 | 38.577 |
| 538 | CA | SER | 69 | 60.211 | 92.373 | 37.321 |

TABLE 10-continued

| Atom No. | Atom Type | Residue | Residue Position | X Coord. | Y Coord. | Z Coord. |
|---|---|---|---|---|---|---|
| 539 | C | SER | 69 | 59.398 | 92.907 | 36.155 |
| 540 | O | SER | 69 | 58.344 | 93.529 | 36.337 |
| 541 | CB | SER | 69 | 59.846 | 90.902 | 37.477 |
| 542 | OG | SER | 69 | 58.428 | 90.804 | 37.396 |
| 543 | N | TYR | 70 | 59.895 | 92.624 | 34.964 |
| 544 | CA | TYR | 70 | 59.156 | 92.930 | 33.739 |
| 545 | C | TYR | 70 | 57.836 | 92.173 | 33.752 |
| 546 | O | TYR | 70 | 57.773 | 91.019 | 34.195 |
| 547 | CB | TYR | 70 | 59.995 | 92.519 | 32.536 |
| 548 | CG | TYR | 70 | 61.294 | 93.308 | 32.410 |
| 549 | CD1 | TYR | 70 | 62.518 | 92.648 | 32.392 |
| 550 | CD2 | TYR | 70 | 61.249 | 94.692 | 32.317 |
| 551 | CE1 | TYR | 70 | 63.697 | 93.375 | 32.279 |
| 552 | CE2 | TYR | 70 | 62.426 | 95.420 | 32.205 |
| 553 | CZ | TYR | 70 | 63.647 | 94.759 | 32.186 |
| 554 | OH | TYR | 70 | 64.810 | 95.486 | 32.059 |
| 555 | N | THR | 71 | 56.787 | 92.923 | 33.450 |
| 556 | CA | THR | 71 | 55.373 | 92.503 | 33.512 |
| 557 | C | THR | 71 | 54.983 | 91.933 | 34.877 |
| 558 | O | THR | 71 | 54.149 | 91.022 | 34.972 |
| 559 | CB | THR | 71 | 55.021 | 91.526 | 32.389 |
| 560 | OG1 | THR | 71 | 55.651 | 90.272 | 32.605 |
| 561 | CG2 | THR | 71 | 55.430 | 92.060 | 31.020 |
| 562 | N | GLY | 72 | 55.555 | 92.503 | 35.926 |
| 563 | CA | GLY | 72 | 55.148 | 92.165 | 37.284 |
| 564 | C | GLY | 72 | 53.879 | 92.940 | 37.571 |
| 565 | O | GLY | 72 | 53.843 | 94.168 | 37.432 |
| 566 | N | THR | 73 | 52.811 | 92.223 | 37.849 |
| 567 | CA | THR | 73 | 51.540 | 92.919 | 38.001 |
| 568 | C | THR | 73 | 51.302 | 93.376 | 39.432 |
| 569 | O | THR | 73 | 50.711 | 94.439 | 39.635 |
| 570 | CB | THR | 73 | 50.404 | 92.010 | 37.538 |
| 571 | OG1 | THR | 73 | 50.319 | 90.883 | 38.402 |
| 572 | CG2 | THR | 73 | 50.618 | 91.520 | 36.110 |
| 573 | N | THR | 74 | 51.859 | 92.685 | 40.407 |
| 574 | CA | THR | 74 | 51.533 | 93.051 | 41.785 |
| 575 | C | THR | 74 | 52.774 | 93.331 | 42.619 |
| 576 | O | THR | 74 | 53.487 | 92.415 | 43.047 |
| 577 | CB | THR | 74 | 50.675 | 91.940 | 42.369 |
| 578 | OG1 | THR | 74 | 49.502 | 91.880 | 41.561 |
| 579 | CG2 | THR | 74 | 50.262 | 92.239 | 43.807 |
| 580 | N | ILE | 75 | 52.988 | 94.613 | 42.861 |
| 581 | CA | ILE | 75 | 54.200 | 95.080 | 43.550 |
| 582 | C | ILE | 75 | 53.985 | 95.222 | 45.051 |
| 583 | O | ILE | 75 | 53.016 | 95.849 | 45.496 |
| 584 | CB | ILE | 75 | 54.579 | 96.444 | 42.990 |
| 585 | CG1 | ILE | 75 | 54.559 | 96.433 | 41.475 |
| 586 | CG2 | ILE | 75 | 55.962 | 96.881 | 43.465 |
| 587 | CD1 | ILE | 75 | 54.996 | 97.795 | 40.962 |
| 588 | N | ILE | 76 | 54.930 | 94.695 | 45.810 |
| 589 | CA | ILE | 76 | 54.905 | 94.797 | 47.273 |
| 590 | C | ILE | 76 | 56.151 | 95.537 | 47.759 |
| 591 | O | ILE | 76 | 57.166 | 94.922 | 48.118 |
| 592 | CB | ILE | 76 | 54.890 | 93.392 | 47.860 |
| 593 | CG1 | ILE | 76 | 53.837 | 92.525 | 47.181 |
| 594 | CG2 | ILE | 76 | 54.641 | 93.441 | 49.364 |
| 595 | CD1 | ILE | 76 | 53.815 | 91.118 | 47.764 |
| 596 | N | TYR | 77 | 56.076 | 96.855 | 47.755 |
| 597 | CA | TYR | 77 | 57.246 | 97.657 | 48.132 |
| 598 | C | TYR | 77 | 57.092 | 98.308 | 49.506 |
| 599 | O | TYR | 77 | 55.985 | 98.629 | 49.953 |
| 600 | CB | TYR | 77 | 57.540 | 98.696 | 47.050 |
| 601 | CG | TYR | 77 | 56.466 | 99.752 | 46.792 |
| 602 | CD1 | TYR | 77 | 56.528 | 100.969 | 47.459 |
| 603 | CD2 | TYR | 77 | 55.453 | 99.518 | 45.869 |
| 604 | CE1 | TYR | 77 | 55.564 | 101.938 | 47.223 |
| 605 | CE2 | TYR | 77 | 54.486 | 100.486 | 45.634 |
| 606 | CZ | TYR | 77 | 54.544 | 101.694 | 46.314 |
| 607 | OH | TYR | 77 | 53.585 | 102.659 | 46.087 |
| 608 | N | ARG | 78 | 58.224 | 98.493 | 50.163 |
| 609 | CA | ARG | 78 | 58.248 | 99.056 | 51.521 |
| 610 | C | ARG | 78 | 59.364 | 100.091 | 51.695 |
| 611 | O | ARG | 78 | 60.507 | 99.738 | 52.016 |
| 612 | CB | ARG | 78 | 58.454 | 97.898 | 52.490 |
| 613 | CG | ARG | 78 | 58.340 | 98.331 | 53.946 |
| 614 | CD | ARG | 78 | 58.445 | 97.119 | 54.862 |
| 615 | NE | ARG | 78 | 57.442 | 96.111 | 54.478 |
| 616 | CZ | ARG | 78 | 56.493 | 95.657 | 55.300 |
| 617 | NH1 | ARG | 78 | 56.437 | 96.090 | 56.561 |
| 618 | NH2 | ARG | 78 | 55.610 | 94.756 | 54.864 |
| 619 | N | PRO | 79 | 59.017 | 101.352 | 51.485 |
| 620 | CA | PRO | 79 | 59.975 | 102.462 | 51.598 |
| 621 | C | PRO | 79 | 60.339 | 102.782 | 53.049 |
| 622 | O | PRO | 79 | 59.596 | 102.436 | 53.975 |
| 623 | CB | PRO | 79 | 59.281 | 103.627 | 50.966 |
| 624 | CG | PRO | 79 | 57.825 | 103.271 | 50.720 |
| 625 | CD | PRO | 79 | 57.676 | 101.814 | 51.120 |
| 626 | N | GLY | 80 | 61.484 | 103.417 | 53.231 |
| 627 | CA | GLY | 80 | 61.917 | 103.840 | 54.564 |
| 628 | C | GLY | 80 | 62.381 | 105.298 | 54.604 |
| 629 | O | GLY | 80 | 61.566 | 106.228 | 54.670 |
| 630 | N | ILE | 81 | 63.691 | 105.485 | 54.607 |
| 631 | CA | ILE | 81 | 64.273 | 106.821 | 54.820 |
| 632 | C | ILE | 81 | 64.578 | 107.566 | 53.516 |
| 633 | O | ILE | 81 | 65.360 | 107.097 | 52.681 |
| 634 | CB | ILE | 81 | 65.549 | 106.636 | 55.642 |
| 635 | CG1 | ILE | 81 | 65.217 | 106.003 | 56.989 |
| 636 | CG2 | ILE | 81 | 66.286 | 107.957 | 55.845 |
| 637 | CD1 | ILE | 81 | 66.462 | 105.812 | 57.846 |
| 638 | N | ILE | 82 | 63.971 | 108.734 | 53.365 |
| 639 | CA | ILE | 82 | 64.244 | 109.595 | 52.203 |
| 640 | C | ILE | 82 | 65.538 | 110.400 | 52.375 |
| 641 | O | ILE | 82 | 65.596 | 111.370 | 53.148 |
| 642 | CB | ILE | 82 | 63.091 | 110.576 | 52.051 |
| 643 | CG1 | ILE | 82 | 61.750 | 109.860 | 52.094 |
| 644 | CG2 | ILE | 82 | 63.227 | 111.348 | 50.743 |
| 645 | CD1 | ILE | 82 | 60.602 | 110.861 | 52.062 |
| 646 | N | ILE | 83 | 66.535 | 110.045 | 51.581 |
| 647 | CA | ILE | 83 | 67.826 | 110.744 | 51.626 |
| 648 | C | ILE | 83 | 67.888 | 111.892 | 50.622 |
| 649 | O | ILE | 83 | 66.967 | 112.094 | 49.822 |
| 650 | CB | ILE | 83 | 68.950 | 109.750 | 51.357 |
| 651 | CG1 | ILE | 83 | 68.701 | 108.973 | 50.069 |
| 652 | CG2 | ILE | 83 | 69.126 | 108.808 | 52.542 |
| 653 | CD1 | ILE | 83 | 69.789 | 107.936 | 49.817 |
| 654 | N | GLY | 84 | 68.904 | 112.720 | 50.787 |
| 655 | CA | GLY | 84 | 69.129 | 113.837 | 49.869 |
| 656 | C | GLY | 84 | 70.437 | 113.658 | 49.101 |
| 657 | O | GLY | 84 | 70.861 | 112.531 | 48.818 |
| 658 | N | GLY | 85 | 71.037 | 114.775 | 48.728 |
| 659 | CA | GLY | 85 | 72.307 | 114.756 | 47.994 |
| 660 | C | GLY | 85 | 72.124 | 115.135 | 46.525 |
| 661 | O | GLY | 85 | 71.619 | 116.217 | 46.200 |
| 662 | N | ASP | 86 | 72.586 | 114.255 | 45.652 |
| 663 | CA | ASP | 86 | 72.462 | 114.470 | 44.203 |
| 664 | C | ASP | 86 | 72.536 | 113.157 | 43.433 |
| 665 | O | ASP | 86 | 73.587 | 112.509 | 43.373 |
| 666 | CB | ASP | 86 | 73.566 | 115.399 | 43.704 |
| 667 | CG | ASP | 86 | 73.489 | 115.525 | 42.180 |
| 668 | OD1 | ASP | 86 | 74.296 | 114.886 | 41.519 |
| 669 | OD2 | ASP | 86 | 72.658 | 116.290 | 41.708 |
| 670 | N | LEU | 87 | 71.419 | 112.781 | 42.839 |
| 671 | CA | LEU | 87 | 71.399 | 111.586 | 41.991 |
| 672 | C | LEU | 87 | 71.212 | 111.954 | 40.524 |
| 673 | O | LEU | 87 | 70.855 | 113.089 | 40.187 |
| 674 | CB | LEU | 87 | 70.313 | 110.626 | 42.462 |
| 675 | CG | LEU | 87 | 70.707 | 109.976 | 43.786 |
| 676 | CD1 | LEU | 87 | 69.610 | 109.056 | 44.306 |
| 677 | CD2 | LEU | 87 | 72.017 | 109.209 | 43.644 |
| 678 | N | THR | 88 | 71.591 | 111.029 | 39.663 |
| 679 | CA | THR | 88 | 71.443 | 111.226 | 38.218 |
| 680 | C | THR | 88 | 70.949 | 109.936 | 37.571 |
| 681 | O | THR | 88 | 71.633 | 108.907 | 37.593 |
| 682 | CB | THR | 88 | 72.787 | 111.652 | 37.636 |
| 683 | OG1 | THR | 88 | 73.117 | 112.909 | 38.214 |
| 684 | CG2 | THR | 88 | 72.727 | 111.832 | 36.122 |
| 685 | N | HIS | 89 | 69.754 | 110.006 | 37.015 |
| 686 | CA | HIS | 89 | 69.110 | 108.810 | 36.464 |
| 687 | C | HIS | 89 | 68.883 | 108.922 | 34.960 |
| 688 | O | HIS | 89 | 68.242 | 109.859 | 34.467 |
| 689 | CB | HIS | 89 | 67.788 | 108.605 | 37.189 |
| 690 | CG | HIS | 89 | 67.946 | 108.417 | 38.686 |

TABLE 10-continued

| Atom No. | Atom Type | Residue | Residue Position | X Coord. | Y Coord. | Z Coord. |
|---|---|---|---|---|---|---|
| 691 | ND1 | HIS | 89 | 67.381 | 109.167 | 39.651 |
| 692 | CD2 | HIS | 89 | 68.693 | 107.450 | 39.318 |
| 693 | CE1 | HIS | 89 | 67.751 | 108.695 | 40.858 |
| 694 | NE2 | HIS | 89 | 68.562 | 107.634 | 40.652 |
| 695 | N | ASN | 90 | 69.403 | 107.939 | 34.245 |
| 696 | CA | ASN | 90 | 69.283 | 107.913 | 32.786 |
| 697 | C | ASN | 90 | 68.237 | 106.900 | 32.325 |
| 698 | O | ASN | 90 | 68.384 | 105.688 | 32.524 |
| 699 | CB | ASN | 90 | 70.645 | 107.560 | 32.194 |
| 700 | CG | ASN | 90 | 70.575 | 107.462 | 30.670 |
| 701 | OD1 | ASN | 90 | 69.932 | 108.280 | 30.002 |
| 702 | ND2 | ASN | 90 | 71.210 | 106.431 | 30.141 |
| 703 | N | CYS | 91 | 67.181 | 107.426 | 31.732 |
| 704 | CA | CYS | 91 | 66.137 | 106.609 | 31.104 |
| 705 | C | CYS | 91 | 65.888 | 107.152 | 29.696 |
| 706 | O | CYS | 91 | 64.867 | 107.799 | 29.435 |
| 707 | CB | CYS | 91 | 64.864 | 106.679 | 31.942 |
| 708 | SG | CYS | 91 | 64.992 | 106.020 | 33.621 |
| 709 | N | PRO | 92 | 66.689 | 106.653 | 28.767 |
| 710 | CA | PRO | 92 | 67.101 | 107.453 | 27.605 |
| 711 | C | PRO | 92 | 66.016 | 107.677 | 26.551 |
| 712 | O | PRO | 92 | 65.079 | 108.463 | 26.743 |
| 713 | CB | PRO | 92 | 68.264 | 106.716 | 27.008 |
| 714 | CG | PRO | 92 | 68.522 | 105.442 | 27.795 |
| 715 | CD | PRO | 92 | 67.526 | 105.457 | 28.939 |
| 716 | N | ASP | 93 | 66.118 | 106.889 | 25.490 |
| 717 | CA | ASP | 93 | 65.404 | 107.132 | 24.226 |
| 718 | C | ASP | 93 | 63.911 | 107.413 | 24.372 |
| 719 | O | ASP | 93 | 63.509 | 108.574 | 24.303 |
| 720 | CB | ASP | 93 | 65.609 | 105.939 | 23.300 |
| 721 | CG | ASP | 93 | 65.566 | 106.402 | 21.845 |
| 722 | OD1 | ASP | 93 | 65.195 | 105.599 | 21.002 |
| 723 | OD2 | ASP | 93 | 66.105 | 107.474 | 21.600 |
| 724 | N | THR | 94 | 63.119 | 106.406 | 24.691 |
| 725 | CA | THR | 94 | 61.662 | 106.604 | 24.668 |
| 726 | C | THR | 94 | 61.009 | 106.853 | 26.030 |
| 727 | O | THR | 94 | 59.778 | 106.779 | 26.115 |
| 728 | CB | THR | 94 | 61.001 | 105.392 | 24.023 |
| 729 | OG1 | THR | 94 | 61.236 | 104.263 | 24.851 |
| 730 | CG2 | THR | 94 | 61.567 | 105.110 | 22.636 |
| 731 | N | LYS | 95 | 61.774 | 107.115 | 27.078 |
| 732 | CA | LYS | 95 | 61.130 | 107.234 | 28.395 |
| 733 | C | LYS | 95 | 60.870 | 108.697 | 28.752 |
| 734 | O | LYS | 95 | 61.800 | 109.509 | 28.829 |
| 735 | CB | LYS | 95 | 62.008 | 106.579 | 29.455 |
| 736 | CG | LYS | 95 | 62.423 | 105.134 | 29.148 |
| 737 | CD | LYS | 95 | 61.321 | 104.081 | 29.315 |
| 738 | CE | LYS | 95 | 60.422 | 103.930 | 28.090 |
| 739 | NZ | LYS | 95 | 59.477 | 102.815 | 28.246 |
| 740 | N | SER | 96 | 59.603 | 109.021 | 28.961 |
| 741 | CA | SER | 96 | 59.211 | 110.401 | 29.289 |
| 742 | C | SER | 96 | 59.604 | 110.798 | 30.708 |
| 743 | O | SER | 96 | 59.013 | 110.321 | 31.686 |
| 744 | CB | SER | 96 | 57.702 | 110.537 | 29.133 |
| 745 | OG | SER | 96 | 57.345 | 111.850 | 29.546 |
| 746 | N | ILE | 97 | 60.383 | 111.866 | 30.785 |
| 747 | CA | ILE | 97 | 60.937 | 112.343 | 32.058 |
| 748 | C | ILE | 97 | 59.916 | 113.114 | 32.889 |
| 749 | O | ILE | 97 | 59.978 | 113.053 | 34.124 |
| 750 | CB | ILE | 97 | 62.150 | 113.215 | 31.734 |
| 751 | CG1 | ILE | 97 | 63.289 | 112.352 | 31.217 |
| 752 | CG2 | ILE | 97 | 62.616 | 114.033 | 32.928 |
| 753 | CD1 | ILE | 97 | 63.703 | 111.305 | 32.245 |
| 754 | N | GLY | 98 | 58.829 | 113.523 | 32.252 |
| 755 | CA | GLY | 98 | 57.725 | 114.195 | 32.948 |
| 756 | C | GLY | 98 | 57.073 | 113.298 | 34.002 |
| 757 | O | GLY | 98 | 56.921 | 113.719 | 35.158 |
| 758 | N | TYR | 99 | 56.918 | 112.022 | 33.672 |
| 759 | CA | TYR | 99 | 56.264 | 111.072 | 34.583 |
| 760 | C | TYR | 99 | 57.202 | 110.551 | 35.676 |
| 761 | O | TYR | 99 | 56.733 | 109.996 | 36.675 |
| 762 | CB | TYR | 99 | 55.738 | 109.905 | 33.760 |
| 763 | CG | TYR | 99 | 54.749 | 110.301 | 32.667 |
| 764 | CD1 | TYR | 99 | 54.883 | 109.761 | 31.395 |
| 765 | CD2 | TYR | 99 | 53.715 | 111.190 | 32.941 |
| 766 | CE1 | TYR | 99 | 53.995 | 110.121 | 30.390 |
| 767 | CE2 | TYR | 99 | 52.826 | 111.552 | 31.937 |
| 768 | CZ | TYR | 99 | 52.973 | 111.020 | 30.662 |
| 769 | OH | TYR | 99 | 52.154 | 111.447 | 29.639 |
| 770 | N | PHE | 100 | 58.491 | 110.821 | 35.545 |
| 771 | CA | PHE | 100 | 59.424 | 110.521 | 36.629 |
| 772 | C | PHE | 100 | 59.469 | 111.709 | 37.578 |
| 773 | O | PHE | 100 | 59.210 | 111.558 | 38.779 |
| 774 | CB | PHE | 100 | 60.829 | 110.310 | 36.072 |
| 775 | CG | PHE | 100 | 61.034 | 109.078 | 35.196 |
| 776 | CD1 | PHE | 100 | 61.183 | 109.214 | 33.823 |
| 777 | CD2 | PHE | 100 | 61.105 | 107.820 | 35.779 |
| 778 | CE1 | PHE | 100 | 61.388 | 108.092 | 33.031 |
| 779 | CE2 | PHE | 100 | 61.310 | 106.697 | 34.988 |
| 780 | CZ | PHE | 100 | 61.452 | 106.834 | 33.614 |
| 781 | N | ILE | 101 | 59.505 | 112.891 | 36.980 |
| 782 | CA | ILE | 101 | 59.642 | 114.150 | 37.725 |
| 783 | C | ILE | 101 | 58.486 | 114.410 | 38.682 |
| 784 | O | ILE | 101 | 58.742 | 114.686 | 39.860 |
| 785 | CB | ILE | 101 | 59.728 | 115.296 | 36.716 |
| 786 | CG1 | ILE | 101 | 61.079 | 115.332 | 36.022 |
| 787 | CG2 | ILE | 101 | 59.437 | 116.650 | 37.350 |
| 788 | CD1 | ILE | 101 | 61.181 | 116.537 | 35.098 |
| 789 | N | GLU | 102 | 57.277 | 114.065 | 38.268 |
| 790 | CA | GLU | 102 | 56.103 | 114.303 | 39.118 |
| 791 | C | GLU | 102 | 56.218 | 113.594 | 40.484 |
| 792 | O | GLU | 102 | 56.476 | 114.311 | 41.460 |
| 793 | CB | GLU | 102 | 54.851 | 113.956 | 38.316 |
| 794 | CG | GLU | 102 | 54.772 | 114.843 | 37.076 |
| 795 | CD | GLU | 102 | 53.877 | 114.219 | 36.010 |
| 796 | OE1 | GLU | 102 | 53.431 | 114.960 | 35.146 |
| 797 | OE2 | GLU | 102 | 53.782 | 113.000 | 35.993 |
| 798 | N | PRO | 103 | 56.176 | 112.268 | 40.591 |
| 799 | CA | PRO | 103 | 56.306 | 111.669 | 41.927 |
| 800 | C | PRO | 103 | 57.716 | 111.703 | 42.538 |
| 801 | O | PRO | 103 | 57.815 | 111.771 | 43.771 |
| 802 | CB | PRO | 103 | 55.841 | 110.253 | 41.761 |
| 803 | CG | PRO | 103 | 55.586 | 109.974 | 40.288 |
| 804 | CD | PRO | 103 | 55.963 | 111.247 | 39.553 |
| 805 | N | MET | 104 | 58.755 | 111.875 | 41.731 |
| 806 | CA | MET | 104 | 60.120 | 111.872 | 42.271 |
| 807 | C | MET | 104 | 60.548 | 113.203 | 42.877 |
| 808 | O | MET | 104 | 61.597 | 113.250 | 43.527 |
| 809 | CB | MET | 104 | 61.120 | 111.507 | 41.183 |
| 810 | CG | MET | 104 | 61.029 | 110.044 | 40.779 |
| 811 | SD | MET | 104 | 61.526 | 108.842 | 42.031 |
| 812 | CE | MET | 104 | 63.248 | 109.357 | 42.225 |
| 813 | N | LEU | 105 | 59.768 | 114.256 | 42.696 |
| 814 | CA | LEU | 105 | 60.104 | 115.512 | 43.365 |
| 815 | C | LEU | 105 | 59.279 | 115.720 | 44.628 |
| 816 | O | LEU | 105 | 59.655 | 116.552 | 45.461 |
| 817 | CB | LEU | 105 | 59.892 | 116.695 | 42.430 |
| 818 | CG | LEU | 105 | 60.738 | 116.595 | 41.165 |
| 819 | CD1 | LEU | 105 | 60.605 | 117.877 | 40.359 |
| 820 | CD2 | LEU | 105 | 62.206 | 116.315 | 41.475 |
| 821 | N | MET | 106 | 58.285 | 114.870 | 44.848 |
| 822 | CA | MET | 106 | 57.400 | 115.031 | 46.012 |
| 823 | C | MET | 106 | 58.141 | 114.759 | 47.317 |
| 824 | O | MET | 106 | 58.439 | 115.674 | 48.096 |
| 825 | CB | MET | 106 | 56.274 | 114.016 | 45.883 |
| 826 | CG | MET | 106 | 55.473 | 114.191 | 44.598 |
| 827 | SD | MET | 106 | 54.496 | 115.706 | 44.480 |
| 828 | CE | MET | 106 | 53.651 | 115.397 | 42.910 |
| 829 | N | PHE | 107 | 58.581 | 113.523 | 47.457 |
| 830 | CA | PHE | 107 | 59.270 | 113.098 | 48.680 |
| 831 | C | PHE | 107 | 60.652 | 113.726 | 49.000 |
| 832 | O | PHE | 107 | 60.874 | 113.885 | 50.205 |
| 833 | CB | PHE | 107 | 59.348 | 111.568 | 48.695 |
| 834 | CG | PHE | 107 | 60.175 | 110.905 | 47.596 |
| 835 | CD1 | PHE | 107 | 61.483 | 110.527 | 47.861 |
| 836 | CD2 | PHE | 107 | 59.620 | 110.649 | 46.348 |
| 837 | CE1 | PHE | 107 | 62.248 | 109.928 | 46.872 |
| 838 | CE2 | PHE | 107 | 60.388 | 110.052 | 45.359 |
| 839 | CZ | PHE | 107 | 61.703 | 109.693 | 45.619 |
| 840 | N | PRO | 108 | 61.515 | 114.177 | 48.081 |
| 841 | CA | PRO | 108 | 62.710 | 114.931 | 48.520 |
| 842 | C | PRO | 108 | 62.446 | 116.326 | 49.116 |

TABLE 10-continued

| Atom No. | Atom Type | Residue | Residue Position | X Coord. | Y Coord. | Z Coord. |
|---|---|---|---|---|---|---|
| 843 | O | PRO | 108 | 63.385 | 116.920 | 49.659 |
| 844 | CB | PRO | 108 | 63.571 | 115.073 | 47.317 |
| 845 | CG | PRO | 108 | 62.830 | 114.571 | 46.096 |
| 846 | CD | PRO | 108 | 61.512 | 114.037 | 46.617 |
| 847 | N | LEU | 109 | 61.211 | 116.804 | 49.123 |
| 848 | CA | LEU | 109 | 60.910 | 118.047 | 49.829 |
| 849 | C | LEU | 109 | 60.592 | 117.766 | 51.303 |
| 850 | O | LEU | 109 | 60.599 | 118.677 | 52.141 |
| 851 | CB | LEU | 109 | 59.735 | 118.700 | 49.107 |
| 852 | CG | LEU | 109 | 60.103 | 118.962 | 47.650 |
| 853 | CD1 | LEU | 109 | 58.883 | 119.266 | 46.790 |
| 854 | CD2 | LEU | 109 | 61.144 | 120.064 | 47.514 |
| 855 | N | PHE | 110 | 60.422 | 116.485 | 51.605 |
| 856 | CA | PHE | 110 | 60.271 | 115.968 | 52.974 |
| 857 | C | PHE | 110 | 61.502 | 115.170 | 53.415 |
| 858 | O | PHE | 110 | 61.485 | 114.527 | 54.470 |
| 859 | CB | PHE | 110 | 59.060 | 115.044 | 53.029 |
| 860 | CG | PHE | 110 | 57.707 | 115.744 | 53.050 |
| 861 | CD1 | PHE | 110 | 57.060 | 116.073 | 51.866 |
| 862 | CD2 | PHE | 110 | 57.118 | 116.045 | 54.271 |
| 863 | CE1 | PHE | 110 | 55.824 | 116.703 | 51.905 |
| 864 | CE2 | PHE | 110 | 55.882 | 116.675 | 54.310 |
| 865 | CZ | PHE | 110 | 55.235 | 117.003 | 53.127 |
| 866 | N | SER | 111 | 62.527 | 115.178 | 52.578 |
| 867 | CA | SER | 111 | 63.773 | 114.440 | 52.827 |
| 868 | C | SER | 111 | 64.506 | 114.966 | 54.059 |
| 869 | O | SER | 111 | 64.210 | 116.056 | 54.560 |
| 870 | CB | SER | 111 | 64.645 | 114.618 | 51.584 |
| 871 | OG | SER | 111 | 65.905 | 113.982 | 51.761 |
| 872 | N | LYS | 112 | 65.437 | 114.174 | 54.566 |
| 873 | CA | LYS | 112 | 66.316 | 114.652 | 55.636 |
| 874 | C | LYS | 112 | 67.439 | 115.553 | 55.107 |
| 875 | O | LYS | 112 | 68.149 | 116.177 | 55.904 |
| 876 | CB | LYS | 112 | 66.930 | 113.453 | 56.345 |
| 877 | CG | LYS | 112 | 65.868 | 112.611 | 57.040 |
| 878 | CD | LYS | 112 | 66.503 | 111.462 | 57.815 |
| 879 | CE | LYS | 112 | 65.455 | 110.644 | 58.561 |
| 880 | NZ | LYS | 112 | 66.083 | 109.548 | 59.315 |
| 881 | N | LYS | 113 | 67.589 | 115.643 | 53.794 |
| 882 | CA | LYS | 113 | 68.602 | 116.529 | 53.214 |
| 883 | C | LYS | 113 | 68.068 | 117.092 | 51.897 |
| 884 | O | LYS | 113 | 67.241 | 116.437 | 51.256 |
| 885 | CB | LYS | 113 | 69.852 | 115.677 | 52.982 |
| 886 | CG | LYS | 113 | 71.059 | 116.471 | 52.492 |
| 887 | CD | LYS | 113 | 72.232 | 115.553 | 52.171 |
| 888 | CE | LYS | 113 | 73.400 | 116.338 | 51.587 |
| 889 | NZ | LYS | 113 | 74.505 | 115.438 | 51.223 |
| 890 | N | LYS | 114 | 68.465 | 118.305 | 51.536 |
| 891 | CA | LYS | 114 | 68.129 | 118.853 | 50.211 |
| 892 | C | LYS | 114 | 68.589 | 117.881 | 49.127 |
| 893 | O | LYS | 114 | 69.586 | 117.171 | 49.314 |
| 894 | CB | LYS | 114 | 68.845 | 120.185 | 50.029 |
| 895 | CG | LYS | 114 | 68.468 | 121.175 | 51.124 |
| 896 | CD | LYS | 114 | 69.147 | 122.520 | 50.899 |
| 897 | CE | LYS | 114 | 68.739 | 123.530 | 51.965 |
| 898 | NZ | LYS | 114 | 69.387 | 124.831 | 51.731 |
| 899 | N | PHE | 115 | 67.879 | 117.843 | 48.014 |
| 900 | CA | PHE | 115 | 68.153 | 116.801 | 47.024 |
| 901 | C | PHE | 115 | 68.066 | 117.292 | 45.582 |
| 902 | O | PHE | 115 | 66.997 | 117.641 | 45.065 |
| 903 | CB | PHE | 115 | 67.162 | 115.662 | 47.234 |
| 904 | CG | PHE | 115 | 67.344 | 114.486 | 46.278 |
| 905 | CD1 | PHE | 115 | 66.340 | 114.162 | 45.376 |
| 906 | CD2 | PHE | 115 | 68.514 | 113.741 | 46.307 |
| 907 | CE1 | PHE | 115 | 66.504 | 113.091 | 44.508 |
| 908 | CE2 | PHE | 115 | 68.681 | 112.672 | 45.439 |
| 909 | CZ | PHE | 115 | 67.676 | 112.346 | 44.539 |
| 910 | N | SER | 116 | 69.211 | 117.250 | 44.927 |
| 911 | CA | SER | 116 | 69.282 | 117.520 | 43.493 |
| 912 | C | SER | 116 | 69.198 | 116.208 | 42.710 |
| 913 | O | SER | 116 | 69.612 | 115.149 | 43.205 |
| 914 | CB | SER | 116 | 70.595 | 118.234 | 43.207 |
| 915 | OG | SER | 116 | 70.662 | 118.478 | 41.811 |
| 916 | N | ILE | 117 | 68.597 | 116.267 | 41.535 |
| 917 | CA | ILE | 117 | 68.461 | 115.062 | 40.711 |
| 918 | C | ILE | 117 | 68.370 | 115.377 | 39.213 |

TABLE 10-continued

| Atom No. | Atom Type | Residue | Residue Position | X Coord. | Y Coord. | Z Coord. |
|---|---|---|---|---|---|---|
| 919 | O | ILE | 117 | 67.452 | 116.054 | 38.736 |
| 920 | CB | ILE | 117 | 67.258 | 114.263 | 41.212 |
| 921 | CG1 | ILE | 117 | 67.042 | 112.992 | 40.401 |
| 922 | CG2 | ILE | 117 | 65.986 | 115.105 | 41.252 |
| 923 | CD1 | ILE | 117 | 65.897 | 112.177 | 40.986 |
| 924 | N | ILE | 118 | 69.363 | 114.895 | 38.487 |
| 925 | CA | ILE | 118 | 69.406 | 115.089 | 37.035 |
| 926 | C | ILE | 118 | 68.716 | 113.929 | 36.319 |
| 927 | O | ILE | 118 | 69.091 | 112.764 | 36.495 |
| 928 | CB | ILE | 118 | 70.869 | 115.157 | 36.612 |
| 929 | CG1 | ILE | 118 | 71.622 | 116.160 | 37.476 |
| 930 | CG2 | ILE | 118 | 70.995 | 115.527 | 35.137 |
| 931 | CD1 | ILE | 118 | 73.098 | 116.228 | 37.101 |
| 932 | N | PHE | 119 | 67.682 | 114.249 | 35.562 |
| 933 | CA | PHE | 119 | 66.981 | 113.235 | 34.764 |
| 934 | C | PHE | 119 | 67.338 | 113.304 | 33.281 |
| 935 | O | PHE | 119 | 67.298 | 114.374 | 32.663 |
| 936 | CB | PHE | 119 | 65.482 | 113.432 | 34.927 |
| 937 | CG | PHE | 119 | 64.876 | 112.760 | 36.153 |
| 938 | CD1 | PHE | 119 | 63.950 | 113.438 | 36.934 |
| 939 | CD2 | PHE | 119 | 65.244 | 111.462 | 36.480 |
| 940 | CE1 | PHE | 119 | 63.388 | 112.817 | 38.041 |
| 941 | CE2 | PHE | 119 | 64.681 | 110.841 | 37.587 |
| 942 | CZ | PHE | 119 | 63.752 | 111.517 | 38.365 |
| 943 | N | LYS | 120 | 67.702 | 112.155 | 32.736 |
| 944 | CA | LYS | 120 | 67.998 | 112.030 | 31.301 |
| 945 | C | LYS | 120 | 66.945 | 111.199 | 30.570 |
| 946 | O | LYS | 120 | 66.607 | 110.095 | 31.009 |
| 947 | CB | LYS | 120 | 69.349 | 111.349 | 31.147 |
| 948 | CG | LYS | 120 | 70.487 | 112.230 | 31.645 |
| 949 | CD | LYS | 120 | 71.822 | 111.492 | 31.596 |
| 950 | CE | LYS | 120 | 72.133 | 110.953 | 30.201 |
| 951 | NZ | LYS | 120 | 72.253 | 112.033 | 29.207 |
| 952 | N | GLY | 121 | 66.461 | 111.713 | 29.452 |
| 953 | CA | GLY | 121 | 65.476 | 110.978 | 28.640 |
| 954 | C | GLY | 121 | 64.675 | 111.883 | 27.700 |
| 955 | O | GLY | 121 | 65.256 | 112.643 | 26.910 |
| 956 | N | LEU | 122 | 63.369 | 111.677 | 27.673 |
| 957 | CA | LEU | 122 | 62.488 | 112.540 | 26.873 |
| 958 | C | LEU | 122 | 61.962 | 113.723 | 27.667 |
| 959 | O | LEU | 122 | 61.158 | 113.562 | 28.594 |
| 960 | CB | LEU | 122 | 61.283 | 111.761 | 26.369 |
| 961 | CG | LEU | 122 | 61.656 | 110.785 | 25.271 |
| 962 | CD1 | LEU | 122 | 60.411 | 110.093 | 24.733 |
| 963 | CD2 | LEU | 122 | 62.388 | 111.506 | 24.149 |
| 964 | N | THR | 123 | 62.259 | 114.908 | 27.165 |
| 965 | CA | THR | 123 | 61.762 | 116.122 | 27.813 |
| 966 | C | THR | 123 | 60.539 | 116.637 | 27.067 |
| 967 | O | THR | 123 | 59.849 | 117.549 | 27.544 |
| 968 | CB | THR | 123 | 62.841 | 117.196 | 27.827 |
| 969 | OG1 | THR | 123 | 63.022 | 117.671 | 26.504 |
| 970 | CG2 | THR | 123 | 64.171 | 116.667 | 28.349 |
| 971 | N | ASN | 124 | 60.267 | 116.020 | 25.927 |
| 972 | CA | ASN | 124 | 59.111 | 116.387 | 25.104 |
| 973 | C | ASN | 124 | 58.689 | 115.227 | 24.188 |
| 974 | O | ASN | 124 | 59.288 | 114.977 | 23.132 |
| 975 | CB | ASN | 124 | 59.413 | 117.680 | 24.324 |
| 976 | CG | ASN | 124 | 60.698 | 117.646 | 23.485 |
| 977 | OD1 | ASN | 124 | 61.810 | 117.486 | 24.003 |
| 978 | ND2 | ASN | 124 | 60.556 | 117.950 | 22.208 |
| 979 | N | ILE | 125 | 57.694 | 114.477 | 24.637 |
| 980 | CA | ILE | 125 | 57.207 | 113.349 | 23.830 |
| 981 | C | ILE | 125 | 55.946 | 113.740 | 23.049 |
| 982 | O | ILE | 125 | 54.891 | 114.066 | 23.617 |
| 983 | CB | ILE | 125 | 57.033 | 112.115 | 24.722 |
| 984 | CG1 | ILE | 125 | 56.646 | 110.874 | 23.929 |
| 985 | CG2 | ILE | 125 | 56.035 | 112.347 | 25.842 |
| 986 | CD1 | ILE | 125 | 56.524 | 109.659 | 24.845 |
| 987 | N | ALA | 126 | 56.089 | 113.661 | 21.733 |
| 988 | CA | ALA | 126 | 55.110 | 114.190 | 20.768 |
| 989 | C | ALA | 126 | 53.693 | 113.665 | 20.947 |
| 990 | O | ALA | 126 | 53.412 | 112.480 | 20.751 |
| 991 | CB | ALA | 126 | 55.599 | 113.850 | 19.366 |
| 992 | N | GLY | 127 | 52.817 | 114.571 | 21.354 |
| 993 | CA | GLY | 127 | 51.399 | 114.265 | 21.585 |
| 994 | C | GLY | 127 | 51.092 | 113.275 | 22.717 |

TABLE 10-continued

| Atom No. | Atom Type | Residue | Residue Position | X Coord. | Y Coord. | Z Coord. |
|---|---|---|---|---|---|---|
| 995 | O | GLY | 127 | 49.968 | 112.759 | 22.774 |
| 996 | N | ASN | 128 | 52.054 | 112.961 | 23.572 |
| 997 | CA | ASN | 128 | 51.763 | 112.009 | 24.647 |
| 998 | C | ASN | 128 | 51.704 | 112.745 | 25.976 |
| 999 | O | ASN | 128 | 51.071 | 112.290 | 26.936 |
| 1000 | CB | ASN | 128 | 52.820 | 110.909 | 24.674 |
| 1001 | CG | ASN | 128 | 52.833 | 110.111 | 23.368 |
| 1002 | OD1 | ASN | 128 | 53.896 | 109.894 | 22.775 |
| 1003 | ND2 | ASN | 128 | 51.663 | 109.664 | 22.945 |
| 1004 | N | ASP | 129 | 52.379 | 113.882 | 26.019 |
| 1005 | CA | ASP | 129 | 52.209 | 114.822 | 27.136 |
| 1006 | C | ASP | 129 | 52.738 | 116.200 | 26.782 |
| 1007 | O | ASP | 129 | 53.377 | 116.403 | 25.741 |
| 1008 | CB | ASP | 129 | 52.883 | 114.339 | 28.432 |
| 1009 | CG | ASP | 129 | 54.405 | 114.131 | 28.370 |
| 1010 | OD1 | ASP | 129 | 54.864 | 113.264 | 29.101 |
| 1011 | OD2 | ASP | 129 | 55.065 | 114.720 | 27.521 |
| 1012 | N | THR | 130 | 52.377 | 117.154 | 27.620 |
| 1013 | CA | THR | 130 | 53.101 | 118.420 | 27.630 |
| 1014 | C | THR | 130 | 54.480 | 118.100 | 28.189 |
| 1015 | O | THR | 130 | 54.612 | 117.216 | 29.046 |
| 1016 | CB | THR | 130 | 52.398 | 119.421 | 28.535 |
| 1017 | OG1 | THR | 130 | 52.494 | 118.953 | 29.873 |
| 1018 | CG2 | THR | 130 | 50.926 | 119.578 | 28.172 |
| 1019 | N | GLY | 131 | 55.485 | 118.799 | 27.704 |
| 1020 | CA | GLY | 131 | 56.857 | 118.485 | 28.091 |
| 1021 | C | GLY | 131 | 57.176 | 118.945 | 29.507 |
| 1022 | O | GLY | 131 | 56.325 | 119.489 | 30.227 |
| 1023 | N | VAL | 132 | 58.463 | 118.910 | 29.809 |
| 1024 | CA | VAL | 132 | 58.965 | 119.309 | 31.131 |
| 1025 | C | VAL | 132 | 58.959 | 120.832 | 31.321 |
| 1026 | O | VAL | 132 | 58.815 | 121.322 | 32.451 |
| 1027 | CB | VAL | 132 | 60.376 | 118.743 | 31.250 |
| 1028 | CG1 | VAL | 132 | 61.049 | 119.155 | 32.548 |
| 1029 | CG2 | VAL | 132 | 60.356 | 117.224 | 31.126 |
| 1030 | N | ASP | 133 | 58.744 | 121.531 | 30.216 |
| 1031 | CA | ASP | 133 | 58.621 | 122.988 | 30.224 |
| 1032 | C | ASP | 133 | 57.268 | 123.440 | 30.791 |
| 1033 | O | ASP | 133 | 57.206 | 124.508 | 31.414 |
| 1034 | CB | ASP | 133 | 58.749 | 123.443 | 28.772 |
| 1035 | CG | ASP | 133 | 58.998 | 124.944 | 28.682 |
| 1036 | OD1 | ASP | 133 | 59.982 | 125.369 | 29.272 |
| 1037 | OD2 | ASP | 133 | 58.364 | 125.579 | 27.853 |
| 1038 | N | ALA | 134 | 56.299 | 122.532 | 30.839 |
| 1039 | CA | ALA | 134 | 54.989 | 122.861 | 31.412 |
| 1040 | C | ALA | 134 | 54.969 | 122.678 | 32.925 |
| 1041 | O | ALA | 134 | 54.200 | 123.350 | 33.622 |
| 1042 | CB | ALA | 134 | 53.935 | 121.954 | 30.794 |
| 1043 | N | ILE | 135 | 55.933 | 121.936 | 33.441 |
| 1044 | CA | ILE | 135 | 56.042 | 121.804 | 34.889 |
| 1045 | C | ILE | 135 | 56.772 | 123.029 | 35.420 |
| 1046 | O | ILE | 135 | 56.287 | 123.677 | 36.359 |
| 1047 | CB | ILE | 135 | 56.820 | 120.532 | 35.204 |
| 1048 | CG1 | ILE | 135 | 56.178 | 119.336 | 34.508 |
| 1049 | CG2 | ILE | 135 | 56.881 | 120.304 | 36.711 |
| 1050 | CD1 | ILE | 135 | 56.970 | 118.054 | 34.739 |
| 1051 | N | LYS | 136 | 57.687 | 123.514 | 34.596 |
| 1052 | CA | LYS | 136 | 58.445 | 124.721 | 34.919 |
| 1053 | C | LYS | 136 | 57.546 | 125.955 | 34.934 |
| 1054 | O | LYS | 136 | 57.222 | 126.451 | 36.019 |
| 1055 | CB | LYS | 136 | 59.549 | 124.875 | 33.880 |
| 1056 | CG | LYS | 136 | 60.518 | 125.998 | 34.228 |
| 1057 | CD | LYS | 136 | 61.655 | 126.057 | 33.216 |
| 1058 | CE | LYS | 136 | 62.642 | 127.172 | 33.542 |
| 1059 | NZ | LYS | 136 | 63.743 | 127.192 | 32.565 |
| 1060 | N | TRP | 137 | 56.930 | 126.256 | 33.803 |
| 1061 | CA | TRP | 137 | 56.137 | 127.488 | 33.682 |
| 1062 | C | TRP | 137 | 54.656 | 127.338 | 34.043 |
| 1063 | O | TRP | 137 | 53.877 | 128.262 | 33.789 |
| 1064 | CB | TRP | 137 | 56.246 | 127.994 | 32.248 |
| 1065 | CG | TRP | 137 | 57.655 | 128.291 | 31.780 |
| 1066 | CD1 | TRP | 137 | 58.423 | 127.511 | 30.944 |
| 1067 | CD2 | TRP | 137 | 58.453 | 129.450 | 32.103 |
| 1068 | NE1 | TRP | 137 | 59.622 | 128.120 | 30.764 |
| 1069 | CE2 | TRP | 137 | 59.681 | 129.283 | 31.440 |
| 1070 | CE3 | TRP | 137 | 58.225 | 130.575 | 32.881 |
| 1071 | CZ2 | TRP | 137 | 60.671 | 130.246 | 31.568 |
| 1072 | CZ3 | TRP | 137 | 59.222 | 131.535 | 33.004 |
| 1073 | CH2 | TRP | 137 | 60.438 | 131.371 | 32.351 |
| 1074 | N | GLY | 138 | 54.254 | 126.209 | 34.600 |
| 1075 | CA | GLY | 138 | 52.834 | 126.015 | 34.903 |
| 1076 | C | GLY | 138 | 52.584 | 125.462 | 36.302 |
| 1077 | O | GLY | 138 | 51.491 | 125.658 | 36.849 |
| 1078 | N | LEU | 139 | 53.533 | 124.713 | 36.839 |
| 1079 | CA | LEU | 139 | 53.339 | 124.143 | 38.179 |
| 1080 | C | LEU | 139 | 54.231 | 124.818 | 39.217 |
| 1081 | O | LEU | 139 | 53.730 | 125.228 | 40.277 |
| 1082 | CB | LEU | 139 | 53.653 | 122.654 | 38.133 |
| 1083 | CG | LEU | 139 | 53.387 | 121.979 | 39.472 |
| 1084 | CD1 | LEU | 139 | 51.916 | 122.079 | 39.860 |
| 1085 | CD2 | LEU | 139 | 53.833 | 120.522 | 39.442 |
| 1086 | N | LEU | 140 | 55.473 | 125.087 | 38.841 |
| 1087 | CA | LEU | 140 | 56.425 | 125.731 | 39.766 |
| 1088 | C | LEU | 140 | 55.923 | 127.038 | 40.399 |
| 1089 | O | LEU | 140 | 55.908 | 127.076 | 41.636 |
| 1090 | CB | LEU | 140 | 57.770 | 125.999 | 39.097 |
| 1091 | CG | LEU | 140 | 58.505 | 124.742 | 38.647 |
| 1092 | CD1 | LEU | 140 | 59.890 | 125.125 | 38.144 |
| 1093 | CD2 | LEU | 140 | 58.634 | 123.727 | 39.774 |
| 1094 | N | PRO | 141 | 55.425 | 128.034 | 39.664 |
| 1095 | CA | PRO | 141 | 55.025 | 129.269 | 40.352 |
| 1096 | C | PRO | 141 | 53.886 | 129.091 | 41.359 |
| 1097 | O | PRO | 141 | 54.065 | 129.537 | 42.495 |
| 1098 | CB | PRO | 141 | 54.629 | 130.229 | 39.270 |
| 1099 | CG | PRO | 141 | 54.739 | 129.544 | 37.915 |
| 1100 | CD | PRO | 141 | 55.277 | 128.158 | 38.200 |
| 1101 | N | VAL | 142 | 52.945 | 128.193 | 41.104 |
| 1102 | CA | VAL | 142 | 51.797 | 128.048 | 42.009 |
| 1103 | C | VAL | 142 | 52.190 | 127.308 | 43.290 |
| 1104 | O | VAL | 142 | 51.875 | 127.775 | 44.400 |
| 1105 | CB | VAL | 142 | 50.729 | 127.254 | 41.271 |
| 1106 | CG1 | VAL | 142 | 49.467 | 127.141 | 42.112 |
| 1107 | CG2 | VAL | 142 | 50.417 | 127.891 | 39.915 |
| 1108 | N | MET | 143 | 53.141 | 126.399 | 43.124 |
| 1109 | CA | MET | 143 | 53.684 | 125.618 | 44.235 |
| 1110 | C | MET | 143 | 54.684 | 126.409 | 45.081 |
| 1111 | O | MET | 143 | 54.846 | 126.098 | 46.266 |
| 1112 | CB | MET | 143 | 54.345 | 124.381 | 43.620 |
| 1113 | CG | MET | 143 | 55.234 | 123.630 | 44.597 |
| 1114 | SD | MET | 143 | 56.012 | 122.131 | 43.945 |
| 1115 | CE | MET | 143 | 56.272 | 122.688 | 42.242 |
| 1116 | N | GLU | 144 | 55.183 | 127.515 | 44.558 |
| 1117 | CA | GLU | 144 | 56.073 | 128.379 | 45.340 |
| 1118 | C | GLU | 144 | 55.319 | 129.572 | 45.937 |
| 1119 | O | GLU | 144 | 55.773 | 130.151 | 46.931 |
| 1120 | CB | GLU | 144 | 57.173 | 128.854 | 44.399 |
| 1121 | CG | GLU | 144 | 58.252 | 129.658 | 45.116 |
| 1122 | CD | GLU | 144 | 59.300 | 130.100 | 44.103 |
| 1123 | OE1 | GLU | 144 | 60.340 | 129.461 | 44.031 |
| 1124 | OE2 | GLU | 144 | 59.013 | 131.036 | 43.369 |
| 1125 | N | LYS | 145 | 54.151 | 129.877 | 45.392 |
| 1126 | CA | LYS | 145 | 53.326 | 130.969 | 45.921 |
| 1127 | C | LYS | 145 | 52.568 | 130.539 | 47.167 |
| 1128 | O | LYS | 145 | 52.956 | 130.861 | 48.296 |
| 1129 | CB | LYS | 145 | 52.307 | 131.393 | 44.869 |
| 1130 | CG | LYS | 145 | 52.953 | 132.071 | 43.672 |
| 1131 | CD | LYS | 145 | 51.955 | 132.252 | 42.532 |
| 1132 | CE | LYS | 145 | 52.630 | 132.845 | 41.298 |
| 1133 | NZ | LYS | 145 | 51.695 | 132.922 | 40.164 |
| 1134 | N | PHE | 146 | 51.467 | 129.841 | 46.943 |
| 1135 | CA | PHE | 146 | 50.608 | 129.430 | 48.059 |
| 1136 | C | PHE | 146 | 50.836 | 127.978 | 48.467 |
| 1137 | O | PHE | 146 | 50.202 | 127.485 | 49.407 |
| 1138 | CB | PHE | 146 | 49.147 | 129.677 | 47.711 |
| 1139 | CG | PHE | 146 | 48.752 | 131.149 | 47.795 |
| 1140 | CD1 | PHE | 146 | 49.278 | 131.941 | 48.807 |
| 1141 | CD2 | PHE | 146 | 47.872 | 131.701 | 46.871 |
| 1142 | CE1 | PHE | 146 | 48.935 | 133.282 | 48.895 |
| 1143 | CE2 | PHE | 146 | 47.528 | 133.044 | 46.958 |
| 1144 | CZ | PHE | 146 | 48.060 | 133.836 | 47.969 |
| 1145 | N | GLY | 147 | 51.710 | 127.299 | 47.745 |
| 1146 | CA | GLY | 147 | 52.134 | 125.967 | 48.170 |

TABLE 10-continued

| Atom No. | Atom Type | Residue | Residue Position | X Coord. | Y Coord. | Z Coord. |
|---|---|---|---|---|---|---|
| 1147 | C | GLY | 147 | 53.120 | 126.089 | 49.329 |
| 1148 | O | GLY | 147 | 52.717 | 126.321 | 50.479 |
| 1149 | N | VAL | 148 | 54.369 | 125.750 | 49.037 |
| 1150 | CA | VAL | 148 | 55.500 | 125.911 | 49.968 |
| 1151 | C | VAL | 148 | 56.848 | 125.617 | 49.316 |
| 1152 | O | VAL | 148 | 57.890 | 126.104 | 49.772 |
| 1153 | CB | VAL | 148 | 55.428 | 124.955 | 51.165 |
| 1154 | CG1 | VAL | 148 | 55.201 | 125.681 | 52.482 |
| 1155 | CG2 | VAL | 148 | 54.514 | 123.746 | 50.984 |
| 1156 | N | ARG | 149 | 56.823 | 124.840 | 48.248 |
| 1157 | CA | ARG | 149 | 58.018 | 124.063 | 47.903 |
| 1158 | C | ARG | 149 | 59.010 | 124.680 | 46.925 |
| 1159 | O | ARG | 149 | 58.675 | 125.251 | 45.878 |
| 1160 | CB | ARG | 149 | 57.534 | 122.690 | 47.466 |
| 1161 | CG | ARG | 149 | 56.866 | 122.072 | 48.688 |
| 1162 | CD | ARG | 149 | 56.251 | 120.699 | 48.479 |
| 1163 | NE | ARG | 149 | 55.797 | 120.216 | 49.791 |
| 1164 | CZ | ARG | 149 | 54.518 | 120.200 | 50.168 |
| 1165 | NH1 | ARG | 149 | 53.549 | 120.390 | 49.271 |
| 1166 | NH2 | ARG | 149 | 54.207 | 119.858 | 51.418 |
| 1167 | N | GLU | 150 | 60.264 | 124.513 | 47.319 |
| 1168 | CA | GLU | 150 | 61.422 | 124.944 | 46.528 |
| 1169 | C | GLU | 150 | 61.924 | 123.824 | 45.622 |
| 1170 | O | GLU | 150 | 62.583 | 122.881 | 46.081 |
| 1171 | CB | GLU | 150 | 62.544 | 125.330 | 47.488 |
| 1172 | CG | GLU | 150 | 63.803 | 125.761 | 46.740 |
| 1173 | CD | GLU | 150 | 64.955 | 125.945 | 47.725 |
| 1174 | OE1 | GLU | 150 | 66.096 | 125.879 | 47.292 |
| 1175 | OE2 | GLU | 150 | 64.669 | 126.147 | 48.897 |
| 1176 | N | VAL | 151 | 61.631 | 123.964 | 44.341 |
| 1177 | CA | VAL | 151 | 62.118 | 123.020 | 43.329 |
| 1178 | C | VAL | 151 | 62.362 | 123.731 | 41.996 |
| 1179 | O | VAL | 151 | 61.430 | 124.117 | 41.282 |
| 1180 | CB | VAL | 151 | 61.118 | 121.875 | 43.187 |
| 1181 | CG1 | VAL | 151 | 59.679 | 122.371 | 43.224 |
| 1182 | CG2 | VAL | 151 | 61.390 | 121.031 | 41.948 |
| 1183 | N | SER | 152 | 63.629 | 123.964 | 41.706 |
| 1184 | CA | SER | 152 | 63.991 | 124.634 | 40.452 |
| 1185 | C | SER | 152 | 64.182 | 123.627 | 39.323 |
| 1186 | O | SER | 152 | 64.934 | 122.654 | 39.453 |
| 1187 | CB | SER | 152 | 65.269 | 125.431 | 40.659 |
| 1188 | OG | SER | 152 | 65.527 | 126.121 | 39.445 |
| 1189 | N | LEU | 153 | 63.494 | 123.874 | 38.222 |
| 1190 | CA | LEU | 153 | 63.551 | 122.975 | 37.063 |
| 1191 | C | LEU | 153 | 64.433 | 123.569 | 35.963 |
| 1192 | O | LEU | 153 | 64.096 | 124.589 | 35.352 |
| 1193 | CB | LEU | 153 | 62.107 | 122.766 | 36.604 |
| 1194 | CG | LEU | 153 | 61.916 | 121.676 | 35.554 |
| 1195 | CD1 | LEU | 153 | 60.544 | 121.029 | 35.698 |
| 1196 | CD2 | LEU | 153 | 62.116 | 122.194 | 34.136 |
| 1197 | N | HIS | 154 | 65.551 | 122.910 | 35.710 |
| 1198 | CA | HIS | 154 | 66.501 | 123.392 | 34.700 |
| 1199 | C | HIS | 154 | 66.540 | 122.491 | 33.472 |
| 1200 | O | HIS | 154 | 67.121 | 121.400 | 33.515 |
| 1201 | CB | HIS | 154 | 67.900 | 123.405 | 35.307 |
| 1202 | CG | HIS | 154 | 68.074 | 124.257 | 36.548 |
| 1203 | ND1 | HIS | 154 | 68.014 | 123.836 | 37.827 |
| 1204 | CD2 | HIS | 154 | 68.339 | 125.605 | 36.583 |
| 1205 | CE1 | HIS | 154 | 68.235 | 124.879 | 38.651 |
| 1206 | NE2 | HIS | 154 | 68.433 | 125.973 | 37.880 |
| 1207 | N | ILE | 155 | 65.992 | 122.965 | 32.369 |
| 1208 | CA | ILE | 155 | 66.090 | 122.192 | 31.125 |
| 1209 | C | ILE | 155 | 67.403 | 122.526 | 30.427 |
| 1210 | O | ILE | 155 | 67.520 | 123.548 | 29.741 |
| 1211 | CB | ILE | 155 | 64.917 | 122.528 | 30.214 |
| 1212 | CG1 | ILE | 155 | 63.603 | 122.334 | 30.955 |
| 1213 | CG2 | ILE | 155 | 64.955 | 121.644 | 28.972 |
| 1214 | CD1 | ILE | 155 | 62.416 | 122.796 | 30.121 |
| 1215 | N | LEU | 156 | 68.368 | 121.636 | 30.584 |
| 1216 | CA | LEU | 156 | 69.712 | 121.858 | 30.050 |
| 1217 | C | LEU | 156 | 69.778 | 121.391 | 28.605 |
| 1218 | O | LEU | 156 | 70.508 | 121.954 | 27.781 |
| 1219 | CB | LEU | 156 | 70.684 | 120.995 | 30.850 |
| 1220 | CG | LEU | 156 | 70.543 | 121.167 | 32.359 |
| 1221 | CD1 | LEU | 156 | 71.266 | 120.046 | 33.098 |
| 1222 | CD2 | LEU | 156 | 71.042 | 122.530 | 32.824 |

TABLE 10-continued

| Atom No. | Atom Type | Residue | Residue Position | X Coord. | Y Coord. | Z Coord. |
|---|---|---|---|---|---|---|
| 1223 | N | LYS | 157 | 68.949 | 120.407 | 28.301 |
| 1224 | CA | LYS | 157 | 68.947 | 119.817 | 26.963 |
| 1225 | C | LYS | 157 | 67.572 | 119.283 | 26.574 |
| 1226 | O | LYS | 157 | 66.973 | 118.479 | 27.298 |
| 1227 | CB | LYS | 157 | 69.980 | 118.691 | 26.965 |
| 1228 | CG | LYS | 157 | 70.025 | 117.926 | 25.649 |
| 1229 | CD | LYS | 157 | 71.132 | 116.881 | 25.647 |
| 1230 | CE | LYS | 157 | 71.199 | 116.154 | 24.309 |
| 1231 | NZ | LYS | 157 | 72.308 | 115.188 | 24.291 |
| 1232 | N | ARG | 158 | 67.070 | 119.777 | 25.455 |
| 1233 | CA | ARG | 158 | 65.844 | 119.246 | 24.844 |
| 1234 | C | ARG | 158 | 66.032 | 117.782 | 24.413 |
| 1235 | O | ARG | 158 | 67.122 | 117.397 | 23.978 |
| 1236 | CB | ARG | 158 | 65.572 | 120.114 | 23.613 |
| 1237 | CG | ARG | 158 | 64.231 | 119.866 | 22.920 |
| 1238 | CD | ARG | 158 | 63.097 | 120.730 | 23.475 |
| 1239 | NE | ARG | 158 | 62.673 | 120.336 | 24.827 |
| 1240 | CZ | ARG | 158 | 62.526 | 121.191 | 25.840 |
| 1241 | NH1 | ARG | 158 | 62.820 | 122.481 | 25.671 |
| 1242 | NH2 | ARG | 158 | 62.109 | 120.750 | 27.028 |
| 1243 | N | GLY | 159 | 65.036 | 116.950 | 24.673 |
| 1244 | CA | GLY | 159 | 65.060 | 115.558 | 24.195 |
| 1245 | C | GLY | 159 | 63.760 | 115.212 | 23.471 |
| 1246 | O | GLY | 159 | 62.785 | 114.770 | 24.103 |
| 1247 | N | SER | 160 | 63.795 | 115.364 | 22.155 |
| 1248 | CA | SER | 160 | 62.596 | 115.223 | 21.318 |
| 1249 | C | SER | 160 | 62.317 | 113.788 | 20.891 |
| 1250 | O | SER | 160 | 63.030 | 113.220 | 20.055 |
| 1251 | CB | SER | 160 | 62.766 | 116.083 | 20.071 |
| 1252 | OG | SER | 160 | 62.770 | 117.450 | 20.467 |
| 1253 | N | ALA | 161 | 61.161 | 113.305 | 21.318 |
| 1254 | CA | ALA | 161 | 60.722 | 111.929 | 21.027 |
| 1255 | C | ALA | 161 | 60.721 | 111.593 | 19.537 |
| 1256 | O | ALA | 161 | 60.370 | 112.440 | 18.709 |
| 1257 | CB | ALA | 161 | 59.309 | 111.757 | 21.559 |
| 1258 | N | PRO | 162 | 61.101 | 110.368 | 19.196 |
| 1259 | CA | PRO | 162 | 61.537 | 109.334 | 20.155 |
| 1260 | C | PRO | 162 | 63.014 | 109.398 | 20.576 |
| 1261 | O | PRO | 162 | 63.474 | 108.489 | 21.280 |
| 1262 | CB | PRO | 162 | 61.294 | 108.047 | 19.428 |
| 1263 | CG | PRO | 162 | 61.138 | 108.345 | 17.943 |
| 1264 | CD | PRO | 162 | 61.101 | 109.861 | 17.822 |
| 1265 | N | LEU | 163 | 63.752 | 110.390 | 20.098 |
| 1266 | CA | LEU | 163 | 65.180 | 110.515 | 20.397 |
| 1267 | C | LEU | 163 | 65.366 | 111.149 | 21.774 |
| 1268 | O | LEU | 163 | 65.230 | 112.366 | 21.962 |
| 1269 | CB | LEU | 163 | 65.808 | 111.377 | 19.299 |
| 1270 | CG | LEU | 163 | 67.327 | 111.235 | 19.189 |
| 1271 | CD1 | LEU | 163 | 68.101 | 112.085 | 20.194 |
| 1272 | CD2 | LEU | 163 | 67.756 | 109.772 | 19.233 |
| 1273 | N | GLY | 164 | 65.750 | 110.307 | 22.712 |
| 1274 | CA | GLY | 164 | 65.948 | 110.743 | 24.093 |
| 1275 | C | GLY | 164 | 67.413 | 111.001 | 24.399 |
| 1276 | O | GLY | 164 | 68.322 | 110.474 | 23.746 |
| 1277 | N | GLY | 165 | 67.619 | 111.817 | 25.414 |
| 1278 | CA | GLY | 165 | 68.966 | 112.204 | 25.830 |
| 1279 | C | GLY | 165 | 68.923 | 113.572 | 26.497 |
| 1280 | O | GLY | 165 | 69.929 | 114.053 | 27.033 |
| 1281 | N | GLY | 166 | 67.729 | 114.139 | 26.529 |
| 1282 | CA | GLY | 166 | 67.518 | 115.455 | 27.126 |
| 1283 | C | GLY | 166 | 67.734 | 115.401 | 28.629 |
| 1284 | O | GLY | 166 | 67.408 | 114.403 | 29.280 |
| 1285 | N | GLU | 167 | 68.344 | 116.448 | 29.152 |
| 1286 | CA | GLU | 167 | 68.707 | 116.478 | 30.569 |
| 1287 | C | GLU | 167 | 68.023 | 117.616 | 31.313 |
| 1288 | O | GLU | 167 | 68.103 | 118.788 | 30.919 |
| 1289 | CB | GLU | 167 | 70.217 | 116.629 | 30.699 |
| 1290 | CG | GLU | 167 | 70.954 | 115.518 | 29.963 |
| 1291 | CD | GLU | 167 | 72.434 | 115.557 | 30.319 |
| 1292 | OE1 | GLU | 167 | 72.723 | 115.730 | 31.496 |
| 1293 | OE2 | GLU | 167 | 73.248 | 115.403 | 29.421 |
| 1294 | N | VAL | 168 | 67.339 | 117.243 | 32.379 |
| 1295 | CA | VAL | 168 | 66.693 | 118.219 | 33.263 |
| 1296 | C | VAL | 168 | 67.249 | 118.112 | 34.683 |
| 1297 | O | VAL | 168 | 67.110 | 117.081 | 35.354 |
| 1298 | CB | VAL | 168 | 65.188 | 117.968 | 33.266 |

TABLE 10-continued

| Atom No. | Atom Type | Residue | Residue Position | X Coord. | Y Coord. | Z Coord. |
|---|---|---|---|---|---|---|
| 1299 | CG1 | VAL | 168 | 64.467 | 118.947 | 34.186 |
| 1300 | CG2 | VAL | 168 | 64.615 | 118.059 | 31.856 |
| 1301 | N | HIS | 169 | 67.886 | 119.182 | 35.123 |
| 1302 | CA | HIS | 169 | 68.437 | 119.243 | 36.477 |
| 1303 | C | HIS | 169 | 67.385 | 119.766 | 37.448 |
| 1304 | O | HIS | 169 | 66.964 | 120.928 | 37.371 |
| 1305 | CB | HIS | 169 | 69.633 | 120.189 | 36.471 |
| 1306 | CG | HIS | 169 | 70.330 | 120.345 | 37.811 |
| 1307 | ND1 | HIS | 169 | 71.443 | 119.706 | 38.210 |
| 1308 | CD2 | HIS | 169 | 69.959 | 121.176 | 38.844 |
| 1309 | CE1 | HIS | 169 | 71.770 | 120.104 | 39.455 |
| 1310 | NE2 | HIS | 169 | 70.848 | 121.013 | 39.848 |
| 1311 | N | LEU | 170 | 66.944 | 118.900 | 38.339 |
| 1312 | CA | LEU | 170 | 66.007 | 119.333 | 39.376 |
| 1313 | C | LEU | 170 | 66.769 | 119.712 | 40.638 |
| 1314 | O | LEU | 170 | 67.683 | 119.003 | 41.078 |
| 1315 | CB | LEU | 170 | 64.985 | 118.244 | 39.706 |
| 1316 | CG | LEU | 170 | 63.917 | 118.013 | 38.631 |
| 1317 | CD1 | LEU | 170 | 63.421 | 119.334 | 38.055 |
| 1318 | CD2 | LEU | 170 | 64.364 | 117.069 | 37.516 |
| 1319 | N | LEU | 171 | 66.429 | 120.870 | 41.169 |
| 1320 | CA | LEU | 171 | 67.034 | 121.330 | 42.419 |
| 1321 | C | LEU | 171 | 65.978 | 121.460 | 43.516 |
| 1322 | O | LEU | 171 | 65.324 | 122.505 | 43.648 |
| 1323 | CB | LEU | 171 | 67.696 | 122.676 | 42.155 |
| 1324 | CG | LEU | 171 | 68.483 | 123.162 | 43.366 |
| 1325 | CD1 | LEU | 171 | 69.567 | 122.159 | 43.748 |
| 1326 | CD2 | LEU | 171 | 69.090 | 124.534 | 43.097 |
| 1327 | N | CYS | 172 | 65.795 | 120.379 | 44.257 |
| 1328 | CA | CYS | 172 | 64.816 | 120.355 | 45.347 |
| 1329 | C | CYS | 172 | 65.475 | 120.561 | 46.700 |
| 1330 | O | CYS | 172 | 66.650 | 120.237 | 46.915 |
| 1331 | CB | CYS | 172 | 64.118 | 119.004 | 45.359 |
| 1332 | SG | CYS | 172 | 63.261 | 118.568 | 43.837 |
| 1333 | N | SER | 173 | 64.714 | 121.136 | 47.608 |
| 1334 | CA | SER | 173 | 65.204 | 121.285 | 48.975 |
| 1335 | C | SER | 173 | 64.140 | 120.894 | 49.984 |
| 1336 | O | SER | 173 | 63.000 | 121.358 | 49.880 |
| 1337 | CB | SER | 173 | 65.586 | 122.741 | 49.195 |
| 1338 | OG | SER | 173 | 66.562 | 123.087 | 48.221 |
| 1339 | N | SER | 174 | 64.490 | 119.986 | 50.881 |
| 1340 | CA | SER | 174 | 63.633 | 119.736 | 52.045 |
| 1341 | C | SER | 174 | 63.503 | 121.043 | 52.822 |
| 1342 | O | SER | 174 | 64.504 | 121.663 | 53.206 |
| 1343 | CB | SER | 174 | 64.235 | 118.628 | 52.900 |
| 1344 | OG | SER | 174 | 65.558 | 118.990 | 53.269 |
| 1345 | N | LEU | 175 | 62.269 | 121.486 | 52.984 |
| 1346 | CA | LEU | 175 | 62.039 | 122.886 | 53.359 |
| 1347 | C | LEU | 175 | 61.242 | 123.104 | 54.642 |
| 1348 | O | LEU | 175 | 61.056 | 122.208 | 55.473 |
| 1349 | CB | LEU | 175 | 61.317 | 123.577 | 52.197 |
| 1350 | CG | LEU | 175 | 60.000 | 122.888 | 51.827 |
| 1351 | CD1 | LEU | 175 | 58.833 | 123.866 | 51.894 |
| 1352 | CD2 | LEU | 175 | 60.066 | 122.243 | 50.451 |
| 1353 | N | ILE | 176 | 60.891 | 124.372 | 54.808 |
| 1354 | CA | ILE | 176 | 60.044 | 124.876 | 55.902 |
| 1355 | C | ILE | 176 | 58.804 | 124.003 | 56.114 |
| 1356 | O | ILE | 176 | 58.058 | 123.720 | 55.170 |
| 1357 | CB | ILE | 176 | 59.625 | 126.288 | 55.477 |
| 1358 | CG1 | ILE | 176 | 60.859 | 127.131 | 55.168 |
| 1359 | CG2 | ILE | 176 | 58.768 | 126.987 | 56.531 |
| 1360 | CD1 | ILE | 176 | 60.479 | 128.533 | 54.702 |
| 1361 | N | PRO | 177 | 58.565 | 123.646 | 57.368 |
| 1362 | CA | PRO | 177 | 57.519 | 122.677 | 57.749 |
| 1363 | C | PRO | 177 | 56.066 | 123.191 | 57.751 |
| 1364 | O | PRO | 177 | 55.213 | 122.531 | 58.352 |
| 1365 | CB | PRO | 177 | 57.889 | 122.247 | 59.136 |
| 1366 | CG | PRO | 177 | 58.989 | 123.151 | 59.670 |
| 1367 | CD | PRO | 177 | 59.379 | 124.059 | 58.518 |
| 1368 | N | GLN | 178 | 55.780 | 124.336 | 57.150 |
| 1369 | CA | GLN | 178 | 54.404 | 124.866 | 57.185 |
| 1370 | C | GLN | 178 | 53.783 | 124.982 | 55.794 |
| 1371 | O | GLN | 178 | 53.845 | 126.065 | 55.202 |
| 1372 | CB | GLN | 178 | 54.410 | 126.267 | 57.786 |
| 1373 | CG | GLN | 178 | 54.863 | 126.308 | 59.239 |
| 1374 | CD | GLN | 178 | 54.747 | 127.745 | 59.744 |
| 1375 | OE1 | GLN | 178 | 53.685 | 128.369 | 59.639 |
| 1376 | NE2 | GLN | 178 | 55.845 | 128.259 | 60.270 |
| 1377 | N | PRO | 179 | 53.128 | 123.931 | 55.321 |
| 1378 | CA | PRO | 179 | 52.407 | 124.003 | 54.044 |
| 1379 | C | PRO | 179 | 51.164 | 124.874 | 54.181 |
| 1380 | O | PRO | 179 | 50.500 | 124.838 | 55.222 |
| 1381 | CB | PRO | 179 | 52.048 | 122.585 | 53.730 |
| 1382 | CG | PRO | 179 | 52.316 | 121.720 | 54.954 |
| 1383 | CD | PRO | 179 | 52.942 | 122.639 | 55.989 |
| 1384 | N | LEU | 180 | 50.890 | 125.699 | 53.186 |
| 1385 | CA | LEU | 180 | 49.709 | 126.555 | 53.309 |
| 1386 | C | LEU | 180 | 48.634 | 126.285 | 52.257 |
| 1387 | O | LEU | 180 | 48.765 | 125.453 | 51.348 |
| 1388 | CB | LEU | 180 | 50.079 | 128.041 | 53.376 |
| 1389 | CG | LEU | 180 | 50.983 | 128.550 | 52.257 |
| 1390 | CD1 | LEU | 180 | 50.476 | 129.890 | 51.737 |
| 1391 | CD2 | LEU | 180 | 52.438 | 128.673 | 52.713 |
| 1392 | N | THR | 181 | 47.507 | 126.921 | 52.521 |
| 1393 | CA | THR | 181 | 46.278 | 126.763 | 51.743 |
| 1394 | C | THR | 181 | 46.322 | 127.464 | 50.387 |
| 1395 | O | THR | 181 | 46.488 | 128.687 | 50.287 |
| 1396 | CB | THR | 181 | 45.165 | 127.332 | 52.619 |
| 1397 | OG1 | THR | 181 | 44.983 | 126.425 | 53.697 |
| 1398 | CG2 | THR | 181 | 43.831 | 127.466 | 51.899 |
| 1399 | N | ILE | 182 | 46.138 | 126.668 | 49.347 |
| 1400 | CA | ILE | 182 | 46.101 | 127.205 | 47.983 |
| 1401 | C | ILE | 182 | 44.665 | 127.531 | 47.578 |
| 1402 | O | ILE | 182 | 43.777 | 126.669 | 47.588 |
| 1403 | CB | ILE | 182 | 46.709 | 126.171 | 47.038 |
| 1404 | CG1 | ILE | 182 | 48.063 | 125.706 | 47.563 |
| 1405 | CG2 | ILE | 182 | 46.871 | 126.741 | 45.632 |
| 1406 | CD1 | ILE | 182 | 48.726 | 124.721 | 46.608 |
| 1407 | N | HIS | 183 | 44.431 | 128.795 | 47.275 |
| 1408 | CA | HIS | 183 | 43.100 | 129.211 | 46.816 |
| 1409 | C | HIS | 183 | 43.090 | 129.591 | 45.340 |
| 1410 | O | HIS | 183 | 43.258 | 130.761 | 44.968 |
| 1411 | CB | HIS | 183 | 42.602 | 130.370 | 47.665 |
| 1412 | CG | HIS | 183 | 41.759 | 129.938 | 48.844 |
| 1413 | ND1 | HIS | 183 | 40.871 | 130.700 | 49.503 |
| 1414 | CD2 | HIS | 183 | 41.736 | 128.696 | 49.437 |
| 1415 | CE1 | HIS | 183 | 40.302 | 129.978 | 50.490 |
| 1416 | NE2 | HIS | 183 | 40.838 | 128.737 | 50.446 |
| 1417 | N | ALA | 184 | 42.777 | 128.602 | 44.523 |
| 1418 | CA | ALA | 184 | 42.663 | 128.781 | 43.070 |
| 1419 | C | ALA | 184 | 41.279 | 129.294 | 42.672 |
| 1420 | O | ALA | 184 | 40.394 | 128.517 | 42.285 |
| 1421 | CB | ALA | 184 | 42.918 | 127.436 | 42.391 |
| 1422 | N | LEU | 185 | 41.109 | 130.601 | 42.794 |
| 1423 | CA | LEU | 185 | 39.857 | 131.263 | 42.404 |
| 1424 | C | LEU | 185 | 39.880 | 131.571 | 40.913 |
| 1425 | O | LEU | 185 | 40.163 | 130.696 | 40.094 |
| 1426 | CB | LEU | 185 | 39.648 | 132.565 | 43.186 |
| 1427 | CG | LEU | 185 | 38.879 | 132.399 | 44.501 |
| 1428 | CD1 | LEU | 185 | 37.586 | 131.617 | 44.278 |
| 1429 | CD2 | LEU | 185 | 39.702 | 131.754 | 45.610 |
| 1430 | N | ASP | 186 | 39.515 | 132.793 | 40.573 |
| 1431 | CA | ASP | 186 | 39.534 | 133.249 | 39.177 |
| 1432 | C | ASP | 186 | 40.919 | 133.762 | 38.777 |
| 1433 | O | ASP | 186 | 41.787 | 133.963 | 39.633 |
| 1434 | CB | ASP | 186 | 38.490 | 134.353 | 39.008 |
| 1435 | CG | ASP | 186 | 38.658 | 135.428 | 40.083 |
| 1436 | OD1 | ASP | 186 | 39.597 | 136.201 | 39.976 |
| 1437 | OD2 | ASP | 186 | 37.872 | 135.420 | 41.019 |
| 1438 | N | ILE | 187 | 41.118 | 133.946 | 37.480 |
| 1439 | CA | ILE | 187 | 42.383 | 134.517 | 36.975 |
| 1440 | C | ILE | 187 | 42.579 | 136.004 | 37.355 |
| 1441 | O | ILE | 187 | 43.716 | 136.356 | 37.689 |
| 1442 | CB | ILE | 187 | 42.462 | 134.307 | 35.461 |
| 1443 | CG1 | ILE | 187 | 42.244 | 132.843 | 35.104 |
| 1444 | CG2 | ILE | 187 | 43.804 | 134.785 | 34.910 |
| 1445 | CD1 | ILE | 187 | 42.333 | 132.618 | 33.598 |
| 1446 | N | PRO | 188 | 41.569 | 136.875 | 37.322 |
| 1447 | CA | PRO | 188 | 40.422 | 136.840 | 36.387 |
| 1448 | C | PRO | 188 | 40.714 | 137.303 | 34.948 |
| 1449 | O | PRO | 188 | 39.951 | 136.952 | 34.041 |
| 1450 | CB | PRO | 188 | 39.432 | 137.780 | 37.007 |

TABLE 10-continued

| Atom No. | Atom Type | Residue | Residue Position | X Coord. | Y Coord. | Z Coord. |
|---|---|---|---|---|---|---|
| 1451 | CG | PRO | 188 | 40.171 | 138.692 | 37.977 |
| 1452 | CD | PRO | 188 | 41.590 | 138.153 | 38.043 |
| 1453 | N | LYS | 189 | 41.810 | 138.015 | 34.728 |
| 1454 | CA | LYS | 189 | 42.073 | 138.614 | 33.414 |
| 1455 | C | LYS | 189 | 43.418 | 138.193 | 32.831 |
| 1456 | O | LYS | 189 | 44.367 | 137.863 | 33.548 |
| 1457 | CB | LYS | 189 | 42.059 | 140.132 | 33.567 |
| 1458 | CG | LYS | 189 | 40.726 | 140.644 | 34.105 |
| 1459 | CD | LYS | 189 | 40.760 | 142.149 | 34.348 |
| 1460 | CE | LYS | 189 | 41.017 | 142.925 | 33.060 |
| 1461 | NZ | LYS | 189 | 39.932 | 142.709 | 32.089 |
| 1462 | N | PHE | 190 | 43.469 | 138.177 | 31.514 |
| 1463 | CA | PHE | 190 | 44.729 | 137.911 | 30.819 |
| 1464 | C | PHE | 190 | 45.540 | 139.197 | 30.753 |
| 1465 | O | PHE | 190 | 45.016 | 140.251 | 30.378 |
| 1466 | CB | PHE | 190 | 44.435 | 137.433 | 29.400 |
| 1467 | CG | PHE | 190 | 43.502 | 136.229 | 29.317 |
| 1468 | CD1 | PHE | 190 | 42.213 | 136.384 | 28.825 |
| 1469 | CD2 | PHE | 190 | 43.945 | 134.976 | 29.723 |
| 1470 | CE1 | PHE | 190 | 41.360 | 135.291 | 28.754 |
| 1471 | CE2 | PHE | 190 | 43.091 | 133.883 | 29.651 |
| 1472 | CZ | PHE | 190 | 41.798 | 134.040 | 29.169 |
| 1473 | N | SER | 191 | 46.786 | 139.129 | 31.181 |
| 1474 | CA | SER | 191 | 47.639 | 140.313 | 31.087 |
| 1475 | C | SER | 191 | 48.741 | 140.081 | 30.063 |
| 1476 | O | SER | 191 | 49.246 | 141.023 | 29.441 |
| 1477 | CB | SER | 191 | 48.234 | 140.597 | 32.458 |
| 1478 | OG | SER | 191 | 47.148 | 140.737 | 33.364 |
| 1479 | N | ALA | 192 | 49.078 | 138.818 | 29.874 |
| 1480 | CA | ALA | 192 | 50.089 | 138.461 | 28.876 |
| 1481 | C | ALA | 192 | 49.671 | 137.266 | 28.028 |
| 1482 | O | ALA | 192 | 49.009 | 136.335 | 28.506 |
| 1483 | CB | ALA | 192 | 51.403 | 138.160 | 29.586 |
| 1484 | N | ILE | 193 | 50.057 | 137.331 | 26.764 |
| 1485 | CA | ILE | 193 | 49.837 | 136.232 | 25.815 |
| 1486 | C | ILE | 193 | 51.168 | 135.922 | 25.138 |
| 1487 | O | ILE | 193 | 51.621 | 136.677 | 24.269 |
| 1488 | CB | ILE | 193 | 48.814 | 136.644 | 24.755 |
| 1489 | CG1 | ILE | 193 | 47.476 | 137.033 | 25.374 |
| 1490 | CG2 | ILE | 193 | 48.606 | 135.522 | 23.743 |
| 1491 | CD1 | ILE | 193 | 46.459 | 137.404 | 24.300 |
| 1492 | N | ARG | 194 | 51.846 | 134.893 | 25.608 |
| 1493 | CA | ARG | 194 | 53.152 | 134.556 | 25.027 |
| 1494 | C | ARG | 194 | 53.076 | 133.343 | 24.108 |
| 1495 | O | ARG | 194 | 52.325 | 132.401 | 24.367 |
| 1496 | CB | ARG | 194 | 54.137 | 134.319 | 26.158 |
| 1497 | CG | ARG | 194 | 54.424 | 135.623 | 26.894 |
| 1498 | CD | ARG | 194 | 55.306 | 135.389 | 28.112 |
| 1499 | NE | ARG | 194 | 56.515 | 134.634 | 27.754 |
| 1500 | CZ | ARG | 194 | 56.953 | 133.592 | 28.464 |
| 1501 | NH1 | ARG | 194 | 58.026 | 132.911 | 28.055 |
| 1502 | NH2 | ARG | 194 | 56.290 | 133.200 | 29.555 |
| 1503 | N | GLY | 195 | 53.859 | 133.373 | 23.046 |
| 1504 | CA | GLY | 195 | 53.848 | 132.275 | 22.073 |
| 1505 | C | GLY | 195 | 55.264 | 131.899 | 21.662 |
| 1506 | O | GLY | 195 | 55.803 | 132.435 | 20.687 |
| 1507 | N | VAL | 196 | 55.838 | 130.952 | 22.384 |
| 1508 | CA | VAL | 196 | 57.223 | 130.539 | 22.127 |
| 1509 | C | VAL | 196 | 57.311 | 129.094 | 21.628 |
| 1510 | O | VAL | 196 | 56.910 | 128.138 | 22.304 |
| 1511 | CB | VAL | 196 | 58.042 | 130.772 | 23.398 |
| 1512 | CG1 | VAL | 196 | 57.240 | 130.518 | 24.667 |
| 1513 | CG2 | VAL | 196 | 59.366 | 130.014 | 23.402 |
| 1514 | N | ALA | 197 | 57.783 | 128.966 | 20.400 |
| 1515 | CA | ALA | 197 | 57.925 | 127.654 | 19.765 |
| 1516 | C | ALA | 197 | 59.366 | 127.149 | 19.790 |
| 1517 | O | ALA | 197 | 60.279 | 127.814 | 19.284 |
| 1518 | CB | ALA | 197 | 57.457 | 127.773 | 18.320 |
| 1519 | N | TYR | 198 | 59.546 | 125.969 | 20.358 |
| 1520 | CA | TYR | 198 | 60.849 | 125.293 | 20.357 |
| 1521 | C | TYR | 198 | 61.149 | 124.716 | 18.981 |
| 1522 | O | TYR | 198 | 60.228 | 124.393 | 18.215 |
| 1523 | CB | TYR | 198 | 60.860 | 124.198 | 21.415 |
| 1524 | CG | TYR | 198 | 60.890 | 124.749 | 22.835 |
| 1525 | CD1 | TYR | 198 | 59.890 | 124.416 | 23.741 |
| 1526 | CD2 | TYR | 198 | 61.922 | 125.597 | 23.216 |

TABLE 10-continued

| Atom No. | Atom Type | Residue | Residue Position | X Coord. | Y Coord. | Z Coord. |
|---|---|---|---|---|---|---|
| 1527 | CE1 | TYR | 198 | 59.927 | 124.930 | 25.031 |
| 1528 | CE2 | TYR | 198 | 61.960 | 126.110 | 24.505 |
| 1529 | CZ | TYR | 198 | 60.962 | 125.775 | 25.409 |
| 1530 | OH | TYR | 198 | 61.006 | 126.278 | 26.691 |
| 1531 | N | CYS | 199 | 62.428 | 124.517 | 18.718 |
| 1532 | CA | CYS | 199 | 62.885 | 124.202 | 17.364 |
| 1533 | C | CYS | 199 | 64.254 | 123.521 | 17.342 |
| 1534 | O | CYS | 199 | 65.302 | 124.180 | 17.396 |
| 1535 | CB | CYS | 199 | 62.961 | 125.528 | 16.612 |
| 1536 | SG | CYS | 199 | 63.649 | 125.477 | 14.943 |
| 1537 | N | THR | 200 | 64.242 | 122.202 | 17.302 |
| 1538 | CA | THR | 200 | 65.487 | 121.462 | 17.068 |
| 1539 | C | THR | 200 | 65.469 | 120.868 | 15.658 |
| 1540 | O | THR | 200 | 64.741 | 119.908 | 15.369 |
| 1541 | CB | THR | 200 | 65.689 | 120.402 | 18.148 |
| 1542 | OG1 | THR | 200 | 64.577 | 119.518 | 18.184 |
| 1543 | CG2 | THR | 200 | 65.833 | 121.025 | 19.529 |
| 1544 | N | ARG | 201 | 66.317 | 121.442 | 14.814 |
| 1545 | CA | ARG | 201 | 66.341 | 121.175 | 13.362 |
| 1546 | C | ARG | 201 | 64.952 | 121.196 | 12.745 |
| 1547 | O | ARG | 201 | 64.401 | 120.157 | 12.360 |
| 1548 | CB | ARG | 201 | 67.006 | 119.847 | 13.034 |
| 1549 | CG | ARG | 201 | 68.526 | 119.946 | 13.037 |
| 1550 | CD | ARG | 201 | 69.154 | 118.617 | 12.625 |
| 1551 | NE | ARG | 201 | 68.676 | 118.185 | 11.302 |
| 1552 | CZ | ARG | 201 | 68.038 | 117.030 | 11.091 |
| 1553 | NH1 | ARG | 201 | 67.752 | 116.227 | 12.118 |
| 1554 | NH2 | ARG | 201 | 67.640 | 116.705 | 9.859 |
| 1555 | N | VAL | 202 | 64.363 | 122.377 | 12.754 |
| 1556 | CA | VAL | 202 | 63.076 | 122.608 | 12.100 |
| 1557 | C | VAL | 202 | 63.213 | 123.885 | 11.279 |
| 1558 | O | VAL | 202 | 63.796 | 124.859 | 11.767 |
| 1559 | CB | VAL | 202 | 61.988 | 122.761 | 13.169 |
| 1560 | CG1 | VAL | 202 | 60.626 | 123.078 | 12.561 |
| 1561 | CG2 | VAL | 202 | 61.888 | 121.521 | 14.050 |
| 1562 | N | SER | 203 | 62.779 | 123.847 | 10.029 |
| 1563 | CA | SER | 203 | 62.826 | 125.046 | 9.181 |
| 1564 | C | SER | 203 | 62.186 | 126.236 | 9.881 |
| 1565 | O | SER | 203 | 61.087 | 126.119 | 10.440 |
| 1566 | CB | SER | 203 | 62.062 | 124.771 | 7.888 |
| 1567 | OG | SER | 203 | 61.853 | 126.016 | 7.227 |
| 1568 | N | PRO | 204 | 62.807 | 127.399 | 9.737 |
| 1569 | CA | PRO | 204 | 62.288 | 128.620 | 10.358 |
| 1570 | C | PRO | 204 | 60.926 | 129.065 | 9.810 |
| 1571 | O | PRO | 204 | 60.137 | 129.613 | 10.585 |
| 1572 | CB | PRO | 204 | 63.331 | 129.663 | 10.098 |
| 1573 | CG | PRO | 204 | 64.434 | 129.074 | 9.232 |
| 1574 | CD | PRO | 204 | 64.060 | 127.620 | 9.007 |
| 1575 | N | SER | 205 | 60.526 | 128.564 | 8.649 |
| 1576 | CA | SER | 205 | 59.221 | 128.938 | 8.101 |
| 1577 | C | SER | 205 | 58.116 | 128.036 | 8.649 |
| 1578 | O | SER | 205 | 56.959 | 128.461 | 8.718 |
| 1579 | CB | SER | 205 | 59.265 | 128.819 | 6.582 |
| 1580 | OG | SER | 205 | 59.469 | 127.451 | 6.251 |
| 1581 | N | ILE | 206 | 58.509 | 126.923 | 9.249 |
| 1582 | CA | ILE | 206 | 57.546 | 125.983 | 9.816 |
| 1583 | C | ILE | 206 | 57.205 | 126.380 | 11.246 |
| 1584 | O | ILE | 206 | 56.023 | 126.443 | 11.606 |
| 1585 | CB | ILE | 206 | 58.175 | 124.594 | 9.777 |
| 1586 | CG1 | ILE | 206 | 58.342 | 124.128 | 8.336 |
| 1587 | CG2 | ILE | 206 | 57.363 | 123.586 | 10.579 |
| 1588 | CD1 | ILE | 206 | 58.942 | 122.729 | 8.273 |
| 1589 | N | VAL | 207 | 58.193 | 126.911 | 11.947 |
| 1590 | CA | VAL | 207 | 57.920 | 127.414 | 13.293 |
| 1591 | C | VAL | 207 | 57.348 | 128.830 | 13.243 |
| 1592 | O | VAL | 207 | 56.467 | 129.150 | 14.052 |
| 1593 | CB | VAL | 207 | 59.184 | 127.331 | 14.142 |
| 1594 | CG1 | VAL | 207 | 59.381 | 125.923 | 14.688 |
| 1595 | CG2 | VAL | 207 | 60.416 | 127.786 | 13.373 |
| 1596 | N | ASN | 208 | 57.580 | 129.515 | 12.132 |
| 1597 | CA | ASN | 208 | 56.945 | 130.811 | 11.908 |
| 1598 | C | ASN | 208 | 55.495 | 130.629 | 11.473 |
| 1599 | O | ASN | 208 | 54.641 | 131.413 | 11.900 |
| 1600 | CB | ASN | 208 | 57.708 | 131.561 | 10.822 |
| 1601 | CG | ASN | 208 | 57.091 | 132.940 | 10.631 |
| 1602 | OD1 | ASN | 208 | 57.034 | 133.736 | 11.576 |

TABLE 10-continued

| Atom No. | Atom Type | Residue | Residue Position | X Coord. | Y Coord. | Z Coord. |
|---|---|---|---|---|---|---|
| 1603 | ND2 | ASN | 208 | 56.595 | 133.190 | 9.432 |
| 1604 | N | ARG | 209 | 55.179 | 129.469 | 10.917 |
| 1605 | CA | ARG | 209 | 53.794 | 129.163 | 10.559 |
| 1606 | C | ARG | 209 | 52.950 | 128.889 | 11.802 |
| 1607 | O | ARG | 209 | 51.829 | 129.406 | 11.883 |
| 1608 | CB | ARG | 209 | 53.796 | 127.932 | 9.664 |
| 1609 | CG | ARG | 209 | 52.390 | 127.527 | 9.242 |
| 1610 | CD | ARG | 209 | 51.735 | 128.590 | 8.370 |
| 1611 | NE | ARG | 209 | 50.422 | 128.127 | 7.896 |
| 1612 | CZ | ARG | 209 | 50.220 | 127.643 | 6.668 |
| 1613 | NH1 | ARG | 209 | 51.229 | 127.592 | 5.795 |
| 1614 | NH2 | ARG | 209 | 49.004 | 127.233 | 6.305 |
| 1615 | N | MET | 210 | 53.572 | 128.372 | 12.852 |
| 1616 | CA | MET | 210 | 52.844 | 128.200 | 14.114 |
| 1617 | C | MET | 210 | 52.700 | 129.527 | 14.855 |
| 1618 | O | MET | 210 | 51.623 | 129.801 | 15.400 |
| 1619 | CB | MET | 210 | 53.585 | 127.224 | 15.015 |
| 1620 | CG | MET | 210 | 53.706 | 125.843 | 14.392 |
| 1621 | SD | MET | 210 | 54.360 | 124.584 | 15.506 |
| 1622 | CE | MET | 210 | 55.898 | 125.403 | 15.982 |
| 1623 | N | ILE | 211 | 53.640 | 130.433 | 14.636 |
| 1624 | CA | ILE | 211 | 53.536 | 131.773 | 15.227 |
| 1625 | C | ILE | 211 | 52.505 | 132.625 | 14.481 |
| 1626 | O | ILE | 211 | 51.701 | 133.312 | 15.122 |
| 1627 | CB | ILE | 211 | 54.913 | 132.429 | 15.167 |
| 1628 | CG1 | ILE | 211 | 55.920 | 131.649 | 16.005 |
| 1629 | CG2 | ILE | 211 | 54.849 | 133.878 | 15.636 |
| 1630 | CD1 | ILE | 211 | 55.540 | 131.641 | 17.483 |
| 1631 | N | ASP | 212 | 52.326 | 132.330 | 13.202 |
| 1632 | CA | ASP | 212 | 51.282 | 132.973 | 12.399 |
| 1633 | C | ASP | 212 | 49.900 | 132.427 | 12.747 |
| 1634 | O | ASP | 212 | 48.939 | 133.202 | 12.808 |
| 1635 | CB | ASP | 212 | 51.545 | 132.694 | 10.920 |
| 1636 | CG | ASP | 212 | 52.871 | 133.283 | 10.447 |
| 1637 | OD1 | ASP | 212 | 53.170 | 134.403 | 10.838 |
| 1638 | OD2 | ASP | 212 | 53.448 | 132.697 | 9.537 |
| 1639 | N | SER | 213 | 49.849 | 131.187 | 13.210 |
| 1640 | CA | SER | 213 | 48.579 | 130.599 | 13.644 |
| 1641 | C | SER | 213 | 48.172 | 131.144 | 15.010 |
| 1642 | O | SER | 213 | 47.012 | 131.539 | 15.185 |
| 1643 | CB | SER | 213 | 48.738 | 129.085 | 13.734 |
| 1644 | OG | SER | 213 | 49.112 | 128.596 | 12.452 |
| 1645 | N | ALA | 214 | 49.163 | 131.453 | 15.833 |
| 1646 | CA | ALA | 214 | 48.890 | 132.051 | 17.143 |
| 1647 | C | ALA | 214 | 48.468 | 133.512 | 17.011 |
| 1648 | O | ALA | 214 | 47.482 | 133.901 | 17.649 |
| 1649 | CB | ALA | 214 | 50.149 | 131.955 | 17.997 |
| 1650 | N | ARG | 215 | 48.973 | 134.167 | 15.975 |
| 1651 | CA | ARG | 215 | 48.630 | 135.561 | 15.653 |
| 1652 | C | ARG | 215 | 47.288 | 135.679 | 14.913 |
| 1653 | O | ARG | 215 | 46.698 | 136.763 | 14.837 |
| 1654 | CB | ARG | 215 | 49.757 | 136.077 | 14.757 |
| 1655 | CG | ARG | 215 | 49.590 | 137.533 | 14.331 |
| 1656 | CD | ARG | 215 | 49.714 | 138.489 | 15.511 |
| 1657 | NE | ARG | 215 | 51.064 | 138.424 | 16.092 |
| 1658 | CZ | ARG | 215 | 51.502 | 139.288 | 17.009 |
| 1659 | NH1 | ARG | 215 | 50.700 | 140.262 | 17.443 |
| 1660 | NH2 | ARG | 215 | 52.738 | 139.168 | 17.500 |
| 1661 | N | ALA | 216 | 46.780 | 134.558 | 14.429 |
| 1662 | CA | ALA | 216 | 45.480 | 134.549 | 13.761 |
| 1663 | C | ALA | 216 | 44.360 | 134.126 | 14.707 |
| 1664 | O | ALA | 216 | 43.176 | 134.269 | 14.373 |
| 1665 | CB | ALA | 216 | 45.545 | 133.587 | 12.579 |
| 1666 | N | VAL | 217 | 44.727 | 133.608 | 15.867 |
| 1667 | CA | VAL | 217 | 43.718 | 133.228 | 16.857 |
| 1668 | C | VAL | 217 | 43.643 | 134.282 | 17.954 |
| 1669 | O | VAL | 217 | 42.552 | 134.710 | 18.350 |
| 1670 | CB | VAL | 217 | 44.093 | 131.870 | 17.445 |
| 1671 | CG1 | VAL | 217 | 43.155 | 131.472 | 18.581 |
| 1672 | CG2 | VAL | 217 | 44.103 | 130.798 | 16.362 |
| 1673 | N | LEU | 218 | 44.806 | 134.723 | 18.400 |
| 1674 | CA | LEU | 218 | 44.900 | 135.788 | 19.401 |
| 1675 | C | LEU | 218 | 45.994 | 136.764 | 19.007 |
| 1676 | O | LEU | 218 | 46.592 | 136.656 | 17.933 |
| 1677 | CB | LEU | 218 | 45.223 | 135.202 | 20.773 |
| 1678 | CG | LEU | 218 | 44.018 | 134.517 | 21.410 |
| 1679 | CD1 | LEU | 218 | 44.399 | 133.867 | 22.734 |
| 1680 | CD2 | LEU | 218 | 42.876 | 135.508 | 21.614 |
| 1681 | N | LYS | 219 | 46.215 | 137.741 | 19.867 |
| 1682 | CA | LYS | 219 | 47.306 | 138.695 | 19.650 |
| 1683 | C | LYS | 219 | 48.416 | 138.476 | 20.675 |
| 1684 | O | LYS | 219 | 48.311 | 138.954 | 21.811 |
| 1685 | CB | LYS | 219 | 46.740 | 140.101 | 19.807 |
| 1686 | CG | LYS | 219 | 45.524 | 140.298 | 18.910 |
| 1687 | CD | LYS | 219 | 44.872 | 141.658 | 19.129 |
| 1688 | CE | LYS | 219 | 43.593 | 141.783 | 18.308 |
| 1689 | NZ | LYS | 219 | 42.641 | 140.719 | 18.667 |
| 1690 | N | PRO | 220 | 49.418 | 137.691 | 20.308 |
| 1691 | CA | PRO | 220 | 50.568 | 137.493 | 21.186 |
| 1692 | C | PRO | 220 | 51.311 | 138.797 | 21.445 |
| 1693 | O | PRO | 220 | 51.572 | 139.599 | 20.543 |
| 1694 | CB | PRO | 220 | 51.440 | 136.491 | 20.494 |
| 1695 | CG | PRO | 220 | 50.827 | 136.142 | 19.148 |
| 1696 | CD | PRO | 220 | 49.551 | 136.961 | 19.047 |
| 1697 | N | THR | 221 | 51.670 | 138.970 | 22.701 |
| 1698 | CA | THR | 221 | 52.432 | 140.136 | 23.142 |
| 1699 | C | THR | 221 | 53.918 | 139.795 | 23.179 |
| 1700 | O | THR | 221 | 54.771 | 140.680 | 23.306 |
| 1701 | CB | THR | 221 | 51.954 | 140.543 | 24.535 |
| 1702 | OG1 | THR | 221 | 52.232 | 139.485 | 25.445 |
| 1703 | CG2 | THR | 221 | 50.452 | 140.802 | 24.558 |
| 1704 | N | GLY | 222 | 54.213 | 138.511 | 23.050 |
| 1705 | CA | GLY | 222 | 55.606 | 138.057 | 22.988 |
| 1706 | C | GLY | 222 | 55.751 | 136.777 | 22.168 |
| 1707 | O | GLY | 222 | 55.650 | 135.665 | 22.706 |
| 1708 | N | CYS | 223 | 55.933 | 136.944 | 20.869 |
| 1709 | CA | CYS | 223 | 56.148 | 135.798 | 19.974 |
| 1710 | C | CYS | 223 | 57.635 | 135.446 | 19.880 |
| 1711 | O | CYS | 223 | 58.499 | 136.328 | 19.815 |
| 1712 | CB | CYS | 223 | 55.588 | 136.134 | 18.596 |
| 1713 | SG | CYS | 223 | 56.303 | 137.581 | 17.780 |
| 1714 | N | GLU | 224 | 57.922 | 134.158 | 19.977 |
| 1715 | CA | GLU | 224 | 59.306 | 133.672 | 19.950 |
| 1716 | C | GLU | 224 | 59.495 | 132.406 | 19.113 |
| 1717 | O | GLU | 224 | 58.704 | 131.456 | 19.177 |
| 1718 | CB | GLU | 224 | 59.751 | 133.353 | 21.370 |
| 1719 | CG | GLU | 224 | 60.016 | 134.578 | 22.233 |
| 1720 | CD | GLU | 224 | 60.633 | 134.127 | 23.552 |
| 1721 | OE1 | GLU | 224 | 61.854 | 134.024 | 23.608 |
| 1722 | OE2 | GLU | 224 | 59.878 | 133.905 | 24.490 |
| 1723 | N | VAL | 225 | 60.574 | 132.411 | 18.350 |
| 1724 | CA | VAL | 225 | 61.018 | 131.221 | 17.612 |
| 1725 | C | VAL | 225 | 62.380 | 130.803 | 18.162 |
| 1726 | O | VAL | 225 | 63.415 | 131.395 | 17.827 |
| 1727 | CB | VAL | 225 | 61.121 | 131.557 | 16.126 |
| 1728 | CG1 | VAL | 225 | 61.759 | 130.417 | 15.341 |
| 1729 | CG2 | VAL | 225 | 59.759 | 131.916 | 15.541 |
| 1730 | N | ASN | 226 | 62.375 | 129.782 | 18.998 |
| 1731 | CA | ASN | 226 | 63.584 | 129.447 | 19.748 |
| 1732 | C | ASN | 226 | 64.244 | 128.156 | 19.296 |
| 1733 | O | ASN | 226 | 63.802 | 127.054 | 19.647 |
| 1734 | CB | ASN | 226 | 63.236 | 129.335 | 21.229 |
| 1735 | CG | ASN | 226 | 62.920 | 130.711 | 21.808 |
| 1736 | OD1 | ASN | 226 | 61.859 | 131.291 | 21.545 |
| 1737 | ND2 | ASN | 226 | 63.855 | 131.226 | 22.588 |
| 1738 | N | ILE | 227 | 65.324 | 128.323 | 18.548 |
| 1739 | CA | ILE | 227 | 66.233 | 127.208 | 18.258 |
| 1740 | C | ILE | 227 | 66.727 | 126.709 | 19.611 |
| 1741 | O | ILE | 227 | 67.151 | 127.504 | 20.462 |
| 1742 | CB | ILE | 227 | 67.377 | 127.733 | 17.398 |
| 1743 | CG1 | ILE | 227 | 66.819 | 128.524 | 16.219 |
| 1744 | CG2 | ILE | 227 | 68.247 | 126.588 | 16.889 |
| 1745 | CD1 | ILE | 227 | 67.934 | 129.110 | 15.359 |
| 1746 | N | THR | 228 | 66.562 | 125.424 | 19.858 |
| 1747 | CA | THR | 228 | 66.580 | 124.988 | 21.252 |
| 1748 | C | THR | 228 | 67.921 | 124.479 | 21.772 |
| 1749 | O | THR | 228 | 68.161 | 123.277 | 21.925 |
| 1750 | CB | THR | 228 | 65.480 | 123.960 | 21.454 |
| 1751 | OG1 | THR | 228 | 64.304 | 124.484 | 20.851 |
| 1752 | CG2 | THR | 228 | 65.206 | 123.741 | 22.938 |
| 1753 | N | ALA | 229 | 68.695 | 125.449 | 22.232 |
| 1754 | CA | ALA | 229 | 69.884 | 125.190 | 23.045 |

TABLE 10-continued

| Atom No. | Atom Type | Residue | Residue Position | X Coord. | Y Coord. | Z Coord. |
|---|---|---|---|---|---|---|
| 1755 | C | ALA | 229 | 69.561 | 125.487 | 24.511 |
| 1756 | O | ALA | 229 | 70.435 | 125.423 | 25.386 |
| 1757 | CB | ALA | 229 | 71.028 | 126.078 | 22.569 |
| 1758 | N | ASP | 230 | 68.278 | 125.710 | 24.772 |
| 1759 | CA | ASP | 230 | 67.807 | 126.182 | 26.081 |
| 1760 | C | ASP | 230 | 68.536 | 127.471 | 26.441 |
| 1761 | O | ASP | 230 | 68.783 | 128.301 | 25.559 |
| 1762 | CB | ASP | 230 | 68.005 | 125.093 | 27.136 |
| 1763 | CG | ASP | 230 | 67.055 | 123.926 | 26.864 |
| 1764 | OD1 | ASP | 230 | 65.861 | 124.186 | 26.809 |
| 1765 | OD2 | ASP | 230 | 67.536 | 122.841 | 26.564 |
| 1766 | N | VAL | 231 | 68.826 | 127.669 | 27.716 |
| 1767 | CA | VAL | 231 | 69.587 | 128.857 | 28.140 |
| 1768 | C | VAL | 231 | 71.103 | 128.589 | 28.100 |
| 1769 | O | VAL | 231 | 71.920 | 129.489 | 28.327 |
| 1770 | CB | VAL | 231 | 69.136 | 129.211 | 29.559 |
| 1771 | CG1 | VAL | 231 | 69.703 | 130.548 | 30.031 |
| 1772 | CG2 | VAL | 231 | 67.614 | 129.248 | 29.642 |
| 1773 | N | TRP | 232 | 71.459 | 127.374 | 27.720 |
| 1774 | CA | TRP | 232 | 72.844 | 126.927 | 27.771 |
| 1775 | C | TRP | 232 | 73.398 | 126.652 | 26.380 |
| 1776 | O | TRP | 232 | 72.897 | 127.150 | 25.365 |
| 1777 | CB | TRP | 232 | 72.903 | 125.662 | 28.625 |
| 1778 | CG | TRP | 232 | 72.629 | 125.910 | 30.100 |
| 1779 | CD1 | TRP | 232 | 73.569 | 126.240 | 31.050 |
| 1780 | CD2 | TRP | 232 | 71.359 | 125.847 | 30.791 |
| 1781 | NE1 | TRP | 232 | 72.942 | 126.406 | 32.241 |
| 1782 | CE2 | TRP | 232 | 71.618 | 126.195 | 32.129 |
| 1783 | CE3 | TRP | 232 | 70.064 | 125.567 | 30.385 |
| 1784 | CZ2 | TRP | 232 | 70.573 | 126.275 | 33.039 |
| 1785 | CZ3 | TRP | 232 | 69.024 | 125.647 | 31.303 |
| 1786 | CH2 | TRP | 232 | 69.275 | 126.000 | 32.624 |
| 1787 | N | ARG | 233 | 74.566 | 126.037 | 26.383 |
| 1788 | CA | ARG | 233 | 75.216 | 125.610 | 25.145 |
| 1789 | C | ARG | 233 | 74.946 | 124.126 | 24.911 |
| 1790 | O | ARG | 233 | 75.135 | 123.304 | 25.816 |
| 1791 | CB | ARG | 233 | 76.709 | 125.882 | 25.292 |
| 1792 | CG | ARG | 233 | 76.960 | 127.381 | 25.406 |
| 1793 | CD | ARG | 233 | 78.090 | 127.704 | 26.381 |
| 1794 | NE | ARG | 233 | 77.779 | 127.190 | 27.729 |
| 1795 | CZ | ARG | 233 | 77.025 | 127.825 | 28.634 |
| 1796 | NH1 | ARG | 233 | 76.555 | 129.050 | 28.386 |
| 1797 | NH2 | ARG | 233 | 76.787 | 127.252 | 29.815 |
| 1798 | N | GLY | 234 | 74.510 | 123.794 | 23.706 |
| 1799 | CA | GLY | 234 | 74.180 | 122.397 | 23.401 |
| 1800 | C | GLY | 234 | 74.000 | 122.131 | 21.909 |
| 1801 | O | GLY | 234 | 74.051 | 123.039 | 21.068 |
| 1802 | N | GLU | 235 | 73.819 | 120.860 | 21.592 |
| 1803 | CA | GLU | 235 | 73.640 | 120.467 | 20.192 |
| 1804 | C | GLU | 235 | 72.186 | 120.576 | 19.755 |
| 1805 | O | GLU | 235 | 71.429 | 119.607 | 19.875 |
| 1806 | CB | GLU | 235 | 74.096 | 119.023 | 20.009 |
| 1807 | CG | GLU | 235 | 75.588 | 118.856 | 20.266 |
| 1808 | CD | GLU | 235 | 76.006 | 117.419 | 19.974 |
| 1809 | OE1 | GLU | 235 | 75.372 | 116.813 | 19.123 |
| 1810 | OE2 | GLU | 235 | 76.940 | 116.960 | 20.615 |
| 1811 | N | ASN | 236 | 71.891 | 121.629 | 19.012 |
| 1812 | CA | ASN | 236 | 70.547 | 121.832 | 18.446 |
| 1813 | C | ASN | 236 | 70.199 | 120.734 | 17.434 |
| 1814 | O | ASN | 236 | 69.129 | 120.117 | 17.514 |
| 1815 | CB | ASN | 236 | 70.537 | 123.184 | 17.732 |
| 1816 | CG | ASN | 236 | 70.729 | 124.349 | 18.708 |
| 1817 | OD1 | ASN | 236 | 69.762 | 124.785 | 19.342 |
| 1818 | ND2 | ASN | 236 | 71.908 | 124.951 | 18.688 |
| 1819 | N | SER | 237 | 71.228 | 120.299 | 16.722 |
| 1820 | CA | SER | 237 | 71.119 | 119.202 | 15.753 |
| 1821 | C | SER | 237 | 71.275 | 117.803 | 16.369 |
| 1822 | O | SER | 237 | 71.343 | 116.819 | 15.628 |
| 1823 | CB | SER | 237 | 72.188 | 119.404 | 14.687 |
| 1824 | OG | SER | 237 | 71.933 | 120.654 | 14.059 |
| 1825 | N | GLY | 238 | 71.317 | 117.716 | 17.690 |
| 1826 | CA | GLY | 238 | 71.426 | 116.430 | 18.381 |
| 1827 | C | GLY | 238 | 70.212 | 116.211 | 19.282 |
| 1828 | O | GLY | 238 | 69.977 | 115.102 | 19.774 |
| 1829 | N | LYS | 239 | 69.511 | 117.302 | 19.561 |
| 1830 | CA | LYS | 239 | 68.228 | 117.248 | 20.283 |

TABLE 10-continued

| Atom No. | Atom Type | Residue | Residue Position | X Coord. | Y Coord. | Z Coord. |
|---|---|---|---|---|---|---|
| 1831 | C | LYS | 239 | 67.075 | 117.149 | 19.285 |
| 1832 | O | LYS | 239 | 65.899 | 117.022 | 19.653 |
| 1833 | CB | LYS | 239 | 68.088 | 118.545 | 21.066 |
| 1834 | CG | LYS | 239 | 69.318 | 118.808 | 21.922 |
| 1835 | CD | LYS | 239 | 69.293 | 120.205 | 22.529 |
| 1836 | CE | LYS | 239 | 70.593 | 120.492 | 23.268 |
| 1837 | NZ | LYS | 239 | 70.565 | 121.812 | 23.912 |
| 1838 | N | SER | 240 | 67.449 | 117.354 | 18.035 |
| 1839 | CA | SER | 240 | 66.577 | 117.240 | 16.864 |
| 1840 | C | SER | 240 | 66.207 | 115.797 | 16.536 |
| 1841 | O | SER | 240 | 66.826 | 114.867 | 17.062 |
| 1842 | CB | SER | 240 | 67.401 | 117.776 | 15.709 |
| 1843 | OG | SER | 240 | 68.461 | 116.857 | 15.484 |
| 1844 | N | PRO | 241 | 65.248 | 115.612 | 15.638 |
| 1845 | CA | PRO | 241 | 64.312 | 116.660 | 15.198 |
| 1846 | C | PRO | 241 | 63.159 | 116.848 | 16.186 |
| 1847 | O | PRO | 241 | 62.725 | 115.887 | 16.832 |
| 1848 | CB | PRO | 241 | 63.795 | 116.147 | 13.891 |
| 1849 | CG | PRO | 241 | 64.069 | 114.649 | 13.820 |
| 1850 | CD | PRO | 241 | 64.894 | 114.318 | 15.055 |
| 1851 | N | GLY | 242 | 62.629 | 118.057 | 16.262 |
| 1852 | CA | GLY | 242 | 61.484 | 118.287 | 17.154 |
| 1853 | C | GLY | 242 | 61.102 | 119.752 | 17.356 |
| 1854 | O | GLY | 242 | 61.896 | 120.574 | 17.837 |
| 1855 | N | PHE | 243 | 59.859 | 120.048 | 17.018 |
| 1856 | CA | PHE | 243 | 59.283 | 121.380 | 17.260 |
| 1857 | C | PHE | 243 | 58.117 | 121.301 | 18.245 |
| 1858 | O | PHE | 243 | 57.487 | 120.248 | 18.405 |
| 1859 | CB | PHE | 243 | 58.864 | 122.059 | 15.948 |
| 1860 | CG | PHE | 243 | 57.708 | 121.500 | 15.099 |
| 1861 | CD1 | PHE | 243 | 56.975 | 122.394 | 14.328 |
| 1862 | CD2 | PHE | 243 | 57.398 | 120.147 | 15.055 |
| 1863 | CE1 | PHE | 243 | 55.927 | 121.939 | 13.538 |
| 1864 | CE2 | PHE | 243 | 56.351 | 119.690 | 14.263 |
| 1865 | CZ | PHE | 243 | 55.613 | 120.587 | 13.506 |
| 1866 | N | GLY | 244 | 57.872 | 122.393 | 18.946 |
| 1867 | CA | GLY | 244 | 56.792 | 122.394 | 19.946 |
| 1868 | C | GLY | 244 | 56.437 | 123.790 | 20.444 |
| 1869 | O | GLY | 244 | 57.248 | 124.447 | 21.110 |
| 1870 | N | ILE | 245 | 55.202 | 124.196 | 20.203 |
| 1871 | CA | ILE | 245 | 54.790 | 125.561 | 20.556 |
| 1872 | C | ILE | 245 | 54.087 | 125.615 | 21.917 |
| 1873 | O | ILE | 245 | 53.304 | 124.724 | 22.277 |
| 1874 | CB | ILE | 245 | 53.912 | 126.107 | 19.425 |
| 1875 | CG1 | ILE | 245 | 53.384 | 127.510 | 19.715 |
| 1876 | CG2 | ILE | 245 | 52.767 | 125.157 | 19.105 |
| 1877 | CD1 | ILE | 245 | 52.483 | 128.012 | 18.594 |
| 1878 | N | THR | 246 | 54.528 | 126.561 | 22.731 |
| 1879 | CA | THR | 246 | 53.890 | 126.820 | 24.026 |
| 1880 | C | THR | 246 | 53.205 | 128.196 | 24.040 |
| 1881 | O | THR | 246 | 53.831 | 129.239 | 23.800 |
| 1882 | CB | THR | 246 | 54.956 | 126.726 | 25.119 |
| 1883 | OG1 | THR | 246 | 55.854 | 127.815 | 24.998 |
| 1884 | CG2 | THR | 246 | 55.778 | 125.448 | 25.000 |
| 1885 | N | LEU | 247 | 51.905 | 128.176 | 24.286 |
| 1886 | CA | LEU | 247 | 51.121 | 129.416 | 24.376 |
| 1887 | C | LEU | 247 | 50.700 | 129.690 | 25.823 |
| 1888 | O | LEU | 247 | 49.806 | 129.046 | 26.384 |
| 1889 | CB | LEU | 247 | 49.901 | 129.293 | 23.470 |
| 1890 | CG | LEU | 247 | 49.715 | 130.535 | 22.599 |
| 1891 | CD1 | LEU | 247 | 48.697 | 130.286 | 21.492 |
| 1892 | CD2 | LEU | 247 | 49.337 | 131.766 | 23.416 |
| 1893 | N | VAL | 248 | 51.313 | 130.716 | 26.381 |
| 1894 | CA | VAL | 248 | 51.135 | 131.060 | 27.792 |
| 1895 | C | VAL | 248 | 50.056 | 132.121 | 28.008 |
| 1896 | O | VAL | 248 | 50.246 | 133.294 | 27.658 |
| 1897 | CB | VAL | 248 | 52.468 | 131.605 | 28.296 |
| 1898 | CG1 | VAL | 248 | 52.440 | 131.829 | 29.802 |
| 1899 | CG2 | VAL | 248 | 53.618 | 130.678 | 27.918 |
| 1900 | N | ALA | 249 | 48.943 | 131.694 | 28.584 |
| 1901 | CA | ALA | 249 | 47.918 | 132.632 | 29.071 |
| 1902 | C | ALA | 249 | 48.334 | 133.051 | 30.476 |
| 1903 | O | ALA | 249 | 48.318 | 132.235 | 31.406 |
| 1904 | CB | ALA | 249 | 46.570 | 131.921 | 29.115 |
| 1905 | N | GLU | 250 | 48.724 | 134.303 | 30.629 |
| 1906 | CA | GLU | 250 | 49.469 | 134.666 | 31.837 |

TABLE 10-continued

| Atom No. | Atom Type | Residue | Residue Position | X Coord. | Y Coord. | Z Coord. |
|---|---|---|---|---|---|---|
| 1907 | C | GLU | 250 | 48.967 | 135.875 | 32.636 |
| 1908 | O | GLU | 250 | 48.535 | 136.888 | 32.064 |
| 1909 | CB | GLU | 250 | 50.877 | 134.941 | 31.315 |
| 1910 | CG | GLU | 250 | 51.908 | 135.234 | 32.392 |
| 1911 | CD | GLU | 250 | 53.232 | 135.569 | 31.721 |
| 1912 | OE1 | GLU | 250 | 53.463 | 135.035 | 30.647 |
| 1913 | OE2 | GLU | 250 | 53.964 | 136.381 | 32.269 |
| 1914 | N | LEU | 251 | 48.860 | 135.641 | 33.942 |
| 1915 | CA | LEU | 251 | 48.929 | 136.677 | 35.001 |
| 1916 | C | LEU | 251 | 47.644 | 137.042 | 35.736 |
| 1917 | O | LEU | 251 | 46.972 | 136.205 | 36.359 |
| 1918 | CB | LEU | 251 | 49.621 | 137.956 | 34.544 |
| 1919 | CG | LEU | 251 | 51.138 | 137.825 | 34.619 |
| 1920 | CD1 | LEU | 251 | 51.819 | 139.091 | 34.115 |
| 1921 | CD2 | LEU | 251 | 51.587 | 137.494 | 36.040 |
| 1922 | N | LYS | 252 | 47.486 | 138.356 | 35.808 |
| 1923 | CA | LYS | 252 | 46.547 | 139.066 | 36.688 |
| 1924 | C | LYS | 252 | 46.782 | 138.704 | 38.152 |
| 1925 | O | LYS | 252 | 47.785 | 139.132 | 38.732 |
| 1926 | CB | LYS | 252 | 45.107 | 138.799 | 36.284 |
| 1927 | CG | LYS | 252 | 44.248 | 140.007 | 36.637 |
| 1928 | CD | LYS | 252 | 44.786 | 141.248 | 35.942 |
| 1929 | CE | LYS | 252 | 43.990 | 142.486 | 36.331 |
| 1930 | NZ | LYS | 252 | 44.521 | 143.675 | 35.647 |
| 1931 | N | ARG | 253 | 45.899 | 137.904 | 38.731 |
| 1932 | CA | ARG | 253 | 46.022 | 137.530 | 40.144 |
| 1933 | C | ARG | 253 | 46.887 | 136.292 | 40.360 |
| 1934 | O | ARG | 253 | 47.139 | 135.919 | 41.512 |
| 1935 | CB | ARG | 253 | 44.633 | 137.323 | 40.737 |
| 1936 | CG | ARG | 253 | 43.932 | 138.667 | 40.906 |
| 1937 | CD | ARG | 253 | 44.741 | 139.573 | 41.830 |
| 1938 | NE | ARG | 253 | 44.143 | 140.913 | 41.925 |
| 1939 | CZ | ARG | 253 | 44.349 | 141.729 | 42.960 |
| 1940 | NH1 | ARG | 253 | 45.089 | 141.322 | 43.994 |
| 1941 | NH2 | ARG | 253 | 43.786 | 142.939 | 42.978 |
| 1942 | N | GLY | 254 | 47.348 | 135.676 | 39.286 |
| 1943 | CA | GLY | 254 | 48.354 | 134.628 | 39.440 |
| 1944 | C | GLY | 254 | 48.062 | 133.351 | 38.666 |
| 1945 | O | GLY | 254 | 48.444 | 132.259 | 39.108 |
| 1946 | N | TRP | 255 | 47.429 | 133.467 | 37.514 |
| 1947 | CA | TRP | 255 | 47.210 | 132.252 | 36.730 |
| 1948 | C | TRP | 255 | 47.996 | 132.220 | 35.435 |
| 1949 | O | TRP | 255 | 47.821 | 133.042 | 34.529 |
| 1950 | CB | TRP | 255 | 45.727 | 132.001 | 36.523 |
| 1951 | CG | TRP | 255 | 45.133 | 131.400 | 37.776 |
| 1952 | CD1 | TRP | 255 | 44.065 | 131.871 | 38.508 |
| 1953 | CD2 | TRP | 255 | 45.599 | 130.210 | 38.448 |
| 1954 | NE1 | TRP | 255 | 43.891 | 131.060 | 39.585 |
| 1955 | CE2 | TRP | 255 | 44.803 | 130.069 | 39.598 |
| 1956 | CE3 | TRP | 255 | 46.624 | 129.316 | 38.193 |
| 1957 | CZ2 | TRP | 255 | 45.076 | 129.052 | 40.498 |
| 1958 | CZ3 | TRP | 255 | 46.877 | 128.286 | 39.091 |
| 1959 | CH2 | TRP | 255 | 46.105 | 128.159 | 40.243 |
| 1960 | N | ARG | 256 | 48.944 | 131.300 | 35.427 |
| 1961 | CA | ARG | 256 | 49.773 | 131.063 | 34.249 |
| 1962 | C | ARG | 256 | 49.480 | 129.677 | 33.673 |
| 1963 | O | ARG | 256 | 49.763 | 128.640 | 34.289 |
| 1964 | CB | ARG | 256 | 51.234 | 131.186 | 34.656 |
| 1965 | CG | ARG | 256 | 52.152 | 131.167 | 33.442 |
| 1966 | CD | ARG | 256 | 53.601 | 131.387 | 33.856 |
| 1967 | NE | ARG | 256 | 53.719 | 132.611 | 34.661 |
| 1968 | CZ | ARG | 256 | 54.648 | 133.546 | 34.449 |
| 1969 | NH1 | ARG | 256 | 55.530 | 133.399 | 33.457 |
| 1970 | NH2 | ARG | 256 | 54.685 | 134.634 | 35.223 |
| 1971 | N | ILE | 257 | 48.826 | 129.684 | 32.526 |
| 1972 | CA | ILE | 257 | 48.447 | 128.440 | 31.854 |
| 1973 | C | ILE | 257 | 49.251 | 128.251 | 30.571 |
| 1974 | O | ILE | 257 | 49.005 | 128.910 | 29.551 |
| 1975 | CB | ILE | 257 | 46.956 | 128.511 | 31.542 |
| 1976 | CG1 | ILE | 257 | 46.165 | 128.826 | 32.809 |
| 1977 | CG2 | ILE | 257 | 46.471 | 127.201 | 30.931 |
| 1978 | CD1 | ILE | 257 | 44.683 | 129.020 | 32.512 |
| 1979 | N | VAL | 258 | 50.226 | 127.361 | 30.640 |
| 1980 | CA | VAL | 258 | 51.072 | 127.081 | 29.476 |
| 1981 | C | VAL | 258 | 50.495 | 125.981 | 28.584 |
| 1982 | O | VAL | 258 | 50.701 | 124.779 | 28.799 |
| 1983 | CB | VAL | 258 | 52.470 | 126.723 | 29.970 |
| 1984 | CG1 | VAL | 258 | 53.221 | 127.980 | 30.385 |
| 1985 | CG2 | VAL | 258 | 52.425 | 125.720 | 31.118 |
| 1986 | N | THR | 259 | 49.848 | 126.426 | 27.523 |
| 1987 | CA | THR | 259 | 49.233 | 125.521 | 26.548 |
| 1988 | C | THR | 259 | 50.271 | 125.017 | 25.549 |
| 1989 | O | THR | 259 | 50.579 | 125.686 | 24.557 |
| 1990 | CB | THR | 259 | 48.159 | 126.310 | 25.811 |
| 1991 | OG1 | THR | 259 | 47.248 | 126.826 | 26.770 |
| 1992 | CG2 | THR | 259 | 47.389 | 125.435 | 24.837 |
| 1993 | N | GLU | 260 | 50.837 | 123.859 | 25.834 |
| 1994 | CA | GLU | 260 | 51.879 | 123.307 | 24.963 |
| 1995 | C | GLU | 260 | 51.353 | 122.229 | 24.026 |
| 1996 | O | GLU | 260 | 50.212 | 121.766 | 24.164 |
| 1997 | CB | GLU | 260 | 52.958 | 122.660 | 25.820 |
| 1998 | CG | GLU | 260 | 53.497 | 123.579 | 26.906 |
| 1999 | CD | GLU | 260 | 54.736 | 122.926 | 27.509 |
| 2000 | OE1 | GLU | 260 | 55.630 | 123.649 | 27.921 |
| 2001 | OE2 | GLU | 260 | 54.839 | 121.709 | 27.403 |
| 2002 | N | ASN | 261 | 52.129 | 121.986 | 22.981 |
| 2003 | CA | ASN | 261 | 52.034 | 120.717 | 22.244 |
| 2004 | C | ASN | 261 | 53.325 | 120.421 | 21.477 |
| 2005 | O | ASN | 261 | 53.928 | 121.292 | 20.834 |
| 2006 | CB | ASN | 261 | 50.799 | 120.628 | 21.340 |
| 2007 | CG | ASN | 261 | 50.806 | 121.498 | 20.083 |
| 2008 | OD1 | ASN | 261 | 51.733 | 122.264 | 19.789 |
| 2009 | ND2 | ASN | 261 | 49.735 | 121.336 | 19.330 |
| 2010 | N | VAL | 262 | 53.818 | 119.214 | 21.692 |
| 2011 | CA | VAL | 262 | 54.988 | 118.742 | 20.951 |
| 2012 | C | VAL | 262 | 54.524 | 118.135 | 19.630 |
| 2013 | O | VAL | 262 | 53.765 | 117.157 | 19.622 |
| 2014 | CB | VAL | 262 | 55.703 | 117.693 | 21.793 |
| 2015 | CG1 | VAL | 262 | 57.037 | 117.306 | 21.162 |
| 2016 | CG2 | VAL | 262 | 55.916 | 118.202 | 23.214 |
| 2017 | N | GLY | 263 | 55.011 | 118.696 | 18.538 |
| 2018 | CA | GLY | 263 | 54.576 | 118.276 | 17.206 |
| 2019 | C | GLY | 263 | 55.420 | 117.136 | 16.648 |
| 2020 | O | GLY | 263 | 56.652 | 117.214 | 16.563 |
| 2021 | N | SER | 264 | 54.728 | 116.071 | 16.280 |
| 2022 | CA | SER | 264 | 55.378 | 114.919 | 15.646 |
| 2023 | C | SER | 264 | 55.832 | 115.287 | 14.241 |
| 2024 | O | SER | 264 | 55.270 | 116.200 | 13.624 |
| 2025 | CB | SER | 264 | 54.385 | 113.770 | 15.532 |
| 2026 | OG | SER | 264 | 53.481 | 114.098 | 14.486 |
| 2027 | N | ALA | 265 | 56.639 | 114.410 | 13.664 |
| 2028 | CA | ALA | 265 | 57.214 | 114.618 | 12.323 |
| 2029 | C | ALA | 265 | 56.256 | 114.392 | 11.142 |
| 2030 | O | ALA | 265 | 56.695 | 114.404 | 9.988 |
| 2031 | CB | ALA | 265 | 58.419 | 113.696 | 12.172 |
| 2032 | N | GLY | 266 | 54.979 | 114.181 | 11.418 |
| 2033 | CA | GLY | 266 | 53.991 | 114.030 | 10.354 |
| 2034 | C | GLY | 266 | 52.956 | 115.148 | 10.448 |
| 2035 | O | GLY | 266 | 52.029 | 115.222 | 9.632 |
| 2036 | N | SER | 267 | 53.116 | 116.003 | 11.444 |
| 2037 | CA | SER | 267 | 52.166 | 117.098 | 11.644 |
| 2038 | C | SER | 267 | 52.596 | 118.342 | 10.879 |
| 2039 | O | SER | 267 | 53.711 | 118.843 | 11.055 |
| 2040 | CB | SER | 267 | 52.110 | 117.431 | 13.131 |
| 2041 | OG | SER | 267 | 51.766 | 116.246 | 13.833 |
| 2042 | N | LEU | 268 | 51.687 | 118.857 | 10.069 |
| 2043 | CA | LEU | 268 | 51.922 | 120.137 | 9.394 |
| 2044 | C | LEU | 268 | 51.970 | 121.245 | 10.442 |
| 2045 | O | LEU | 268 | 51.316 | 121.129 | 11.488 |
| 2046 | CB | LEU | 268 | 50.777 | 120.393 | 8.416 |
| 2047 | CG | LEU | 268 | 50.705 | 119.322 | 7.335 |
| 2048 | CD1 | LEU | 268 | 49.448 | 119.485 | 6.489 |
| 2049 | CD2 | LEU | 268 | 51.954 | 119.338 | 6.459 |
| 2050 | N | PRO | 269 | 52.662 | 122.335 | 10.144 |
| 2051 | CA | PRO | 269 | 52.839 | 123.402 | 11.140 |
| 2052 | C | PRO | 269 | 51.524 | 124.077 | 11.544 |
| 2053 | O | PRO | 269 | 51.290 | 124.262 | 12.746 |
| 2054 | CB | PRO | 269 | 53.756 | 124.387 | 10.490 |
| 2055 | CG | PRO | 269 | 54.071 | 123.939 | 9.071 |
| 2056 | CD | PRO | 269 | 53.389 | 122.594 | 8.896 |
| 2057 | N | GLU | 270 | 50.571 | 124.119 | 10.623 |
| 2058 | CA | GLU | 270 | 49.252 | 124.679 | 10.931 |

TABLE 10-continued

| Atom No. | Atom Type | Residue | Residue Position | X Coord. | Y Coord. | Z Coord. |
|---|---|---|---|---|---|---|
| 2059 | C | GLU | 270 | 48.416 | 123.742 | 11.807 |
| 2060 | O | GLU | 270 | 47.663 | 124.240 | 12.648 |
| 2061 | CB | GLU | 270 | 48.508 | 124.931 | 9.622 |
| 2062 | CG | GLU | 270 | 47.112 | 125.502 | 9.864 |
| 2063 | CD | GLU | 270 | 46.375 | 125.667 | 8.540 |
| 2064 | OE1 | GLU | 270 | 46.754 | 124.979 | 7.602 |
| 2065 | OE2 | GLU | 270 | 45.506 | 126.524 | 8.470 |
| 2066 | N | ASP | 271 | 48.762 | 122.463 | 11.841 |
| 2067 | CA | ASP | 271 | 48.011 | 121.523 | 12.674 |
| 2068 | C | ASP | 271 | 48.472 | 121.654 | 14.117 |
| 2069 | O | ASP | 271 | 47.629 | 121.799 | 15.011 |
| 2070 | CB | ASP | 271 | 48.257 | 120.084 | 12.225 |
| 2071 | CG | ASP | 271 | 47.899 | 119.854 | 10.761 |
| 2072 | OD1 | ASP | 271 | 48.538 | 118.994 | 10.166 |
| 2073 | OD2 | ASP | 271 | 47.067 | 120.581 | 10.236 |
| 2074 | N | SER | 272 | 49.759 | 121.905 | 14.299 |
| 2075 | CA | SER | 272 | 50.282 | 122.062 | 15.655 |
| 2076 | C | SER | 272 | 49.857 | 123.403 | 16.238 |
| 2077 | O | SER | 272 | 49.289 | 123.422 | 17.339 |
| 2078 | CB | SER | 272 | 51.799 | 121.969 | 15.631 |
| 2079 | OG | SER | 272 | 52.249 | 122.188 | 16.961 |
| 2080 | N | GLY | 273 | 49.831 | 124.419 | 15.388 |
| 2081 | CA | GLY | 273 | 49.357 | 125.748 | 15.788 |
| 2082 | C | GLY | 273 | 47.878 | 125.724 | 16.175 |
| 2083 | O | GLY | 273 | 47.527 | 126.090 | 17.305 |
| 2084 | N | GLU | 274 | 47.067 | 125.094 | 15.341 |
| 2085 | CA | GLU | 274 | 45.619 | 125.045 | 15.561 |
| 2086 | C | GLU | 274 | 45.207 | 124.129 | 16.715 |
| 2087 | O | GLU | 274 | 44.235 | 124.446 | 17.410 |
| 2088 | CB | GLU | 274 | 44.991 | 124.538 | 14.269 |
| 2089 | CG | GLU | 274 | 43.473 | 124.476 | 14.341 |
| 2090 | CD | GLU | 274 | 42.938 | 123.899 | 13.037 |
| 2091 | OE1 | GLU | 274 | 41.839 | 124.272 | 12.652 |
| 2092 | OE2 | GLU | 274 | 43.673 | 123.144 | 12.413 |
| 2093 | N | LEU | 275 | 46.021 | 123.142 | 17.053 |
| 2094 | CA | LEU | 275 | 45.706 | 122.311 | 18.220 |
| 2095 | C | LEU | 275 | 46.132 | 122.991 | 19.517 |
| 2096 | O | LEU | 275 | 45.407 | 122.898 | 20.516 |
| 2097 | CB | LEU | 275 | 46.399 | 120.962 | 18.085 |
| 2098 | CG | LEU | 275 | 45.834 | 120.161 | 16.919 |
| 2099 | CD1 | LEU | 275 | 46.656 | 118.904 | 16.666 |
| 2100 | CD2 | LEU | 275 | 44.365 | 119.820 | 17.142 |
| 2101 | N | THR | 276 | 47.099 | 123.891 | 19.421 |
| 2102 | CA | THR | 276 | 47.499 | 124.677 | 20.590 |
| 2103 | C | THR | 276 | 46.428 | 125.721 | 20.869 |
| 2104 | O | THR | 276 | 45.928 | 125.803 | 22.000 |
| 2105 | CB | THR | 276 | 48.818 | 125.383 | 20.297 |
| 2106 | OG1 | THR | 276 | 49.797 | 124.397 | 20.029 |
| 2107 | CG2 | THR | 276 | 49.297 | 126.203 | 21.488 |
| 2108 | N | ALA | 277 | 45.861 | 126.233 | 19.788 |
| 2109 | CA | ALA | 277 | 44.775 | 127.207 | 19.883 |
| 2110 | C | ALA | 277 | 43.467 | 126.577 | 20.353 |
| 2111 | O | ALA | 277 | 42.796 | 127.172 | 21.204 |
| 2112 | CB | ALA | 277 | 44.568 | 127.826 | 18.507 |
| 2113 | N | TYR | 278 | 43.239 | 125.314 | 20.021 |
| 2114 | CA | TYR | 278 | 42.037 | 124.625 | 20.505 |
| 2115 | C | TYR | 278 | 42.098 | 124.369 | 22.004 |
| 2116 | O | TYR | 278 | 41.175 | 124.786 | 22.714 |
| 2117 | CB | TYR | 278 | 41.875 | 123.291 | 19.785 |
| 2118 | CG | TYR | 278 | 41.321 | 123.377 | 18.367 |
| 2119 | CD1 | TYR | 278 | 41.561 | 122.341 | 17.473 |
| 2120 | CD2 | TYR | 278 | 40.555 | 124.469 | 17.979 |
| 2121 | CE1 | TYR | 278 | 41.044 | 122.401 | 16.186 |
| 2122 | CE2 | TYR | 278 | 40.040 | 124.532 | 16.691 |
| 2123 | CZ | TYR | 278 | 40.285 | 123.497 | 15.799 |
| 2124 | OH | TYR | 278 | 39.757 | 123.548 | 14.527 |
| 2125 | N | GLN | 279 | 43.272 | 124.003 | 22.494 |
| 2126 | CA | GLN | 279 | 43.434 | 123.736 | 23.927 |
| 2127 | C | GLN | 279 | 43.370 | 125.025 | 24.745 |
| 2128 | O | GLN | 279 | 42.666 | 125.070 | 25.764 |
| 2129 | CB | GLN | 279 | 44.790 | 123.069 | 24.127 |
| 2130 | CG | GLN | 279 | 44.890 | 121.773 | 23.332 |
| 2131 | CD | GLN | 279 | 46.321 | 121.238 | 23.342 |
| 2132 | OE1 | GLN | 279 | 46.540 | 120.025 | 23.238 |
| 2133 | NE2 | GLN | 279 | 47.276 | 122.152 | 23.372 |
| 2134 | N | LEU | 280 | 43.839 | 126.111 | 24.151 |

TABLE 10-continued

| Atom No. | Atom Type | Residue | Residue Position | X Coord. | Y Coord. | Z Coord. |
|---|---|---|---|---|---|---|
| 2135 | CA | LEU | 280 | 43.805 | 127.410 | 24.821 |
| 2136 | C | LEU | 280 | 42.382 | 127.968 | 24.871 |
| 2137 | O | LEU | 280 | 41.902 | 128.312 | 25.961 |
| 2138 | CB | LEU | 280 | 44.711 | 128.352 | 24.035 |
| 2139 | CG | LEU | 280 | 44.842 | 129.714 | 24.703 |
| 2140 | CD1 | LEU | 280 | 45.413 | 129.584 | 26.110 |
| 2141 | CD2 | LEU | 280 | 45.711 | 130.638 | 23.860 |
| 2142 | N | LEU | 281 | 41.631 | 127.758 | 23.801 |
| 2143 | CA | LEU | 281 | 40.245 | 128.237 | 23.742 |
| 2144 | C | LEU | 281 | 39.271 | 127.339 | 24.503 |
| 2145 | O | LEU | 281 | 38.180 | 127.796 | 24.853 |
| 2146 | CB | LEU | 281 | 39.810 | 128.328 | 22.285 |
| 2147 | CG | LEU | 281 | 40.605 | 129.381 | 21.521 |
| 2148 | CD1 | LEU | 281 | 40.284 | 129.328 | 20.032 |
| 2149 | CD2 | LEU | 281 | 40.364 | 130.779 | 22.082 |
| 2150 | N | GLU | 282 | 39.714 | 126.165 | 24.919 |
| 2151 | CA | GLU | 282 | 38.875 | 125.319 | 25.770 |
| 2152 | C | GLU | 282 | 38.956 | 125.741 | 27.234 |
| 2153 | O | GLU | 282 | 37.990 | 125.530 | 27.980 |
| 2154 | CB | GLU | 282 | 39.312 | 123.869 | 25.613 |
| 2155 | CG | GLU | 282 | 38.959 | 123.346 | 24.226 |
| 2156 | CD | GLU | 282 | 39.552 | 121.959 | 24.009 |
| 2157 | OE1 | GLU | 282 | 38.873 | 120.994 | 24.330 |
| 2158 | OE2 | GLU | 282 | 40.651 | 121.885 | 23.473 |
| 2159 | N | GLU | 283 | 39.995 | 126.481 | 27.592 |
| 2160 | CA | GLU | 283 | 40.061 | 127.057 | 28.938 |
| 2161 | C | GLU | 283 | 39.304 | 128.380 | 28.940 |
| 2162 | O | GLU | 283 | 38.369 | 128.552 | 29.729 |
| 2163 | CB | GLU | 283 | 41.518 | 127.327 | 29.300 |
| 2164 | CG | GLU | 283 | 41.699 | 127.654 | 30.782 |
| 2165 | CD | GLU | 283 | 41.888 | 126.369 | 31.587 |
| 2166 | OE1 | GLU | 283 | 42.344 | 126.489 | 32.715 |
| 2167 | OE2 | GLU | 283 | 42.004 | 125.348 | 30.919 |
| 2168 | N | ILE | 284 | 39.470 | 129.103 | 27.839 |
| 2169 | CA | ILE | 284 | 38.855 | 130.433 | 27.654 |
| 2170 | C | ILE | 284 | 37.353 | 130.370 | 27.312 |
| 2171 | O | ILE | 284 | 36.654 | 131.390 | 27.339 |
| 2172 | CB | ILE | 284 | 39.641 | 131.128 | 26.536 |
| 2173 | CG1 | ILE | 284 | 41.124 | 131.188 | 26.878 |
| 2174 | CG2 | ILE | 284 | 39.139 | 132.541 | 26.257 |
| 2175 | CD1 | ILE | 284 | 41.913 | 131.892 | 25.780 |
| 2176 | N | SER | 285 | 36.839 | 129.167 | 27.115 |
| 2177 | CA | SER | 285 | 35.409 | 128.979 | 26.857 |
| 2178 | C | SER | 285 | 34.616 | 128.797 | 28.150 |
| 2179 | O | SER | 285 | 33.388 | 128.664 | 28.103 |
| 2180 | CB | SER | 285 | 35.214 | 127.744 | 25.986 |
| 2181 | OG | SER | 285 | 35.642 | 126.611 | 26.729 |
| 2182 | N | ASN | 286 | 35.306 | 128.720 | 29.276 |
| 2183 | CA | ASN | 286 | 34.623 | 128.613 | 30.567 |
| 2184 | C | ASN | 286 | 35.338 | 129.426 | 31.640 |
| 2185 | O | ASN | 286 | 36.011 | 130.420 | 31.348 |
| 2186 | CB | ASN | 286 | 34.489 | 127.146 | 30.971 |
| 2187 | CG | ASN | 286 | 35.798 | 126.385 | 30.811 |
| 2188 | OD1 | ASN | 286 | 36.767 | 126.632 | 31.539 |
| 2189 | ND2 | ASN | 286 | 35.741 | 125.354 | 29.987 |
| 2190 | N | SER | 287 | 35.095 | 129.055 | 32.884 |
| 2191 | CA | SER | 287 | 35.691 | 129.780 | 34.007 |
| 2192 | C | SER | 287 | 36.600 | 128.891 | 34.855 |
| 2193 | O | SER | 287 | 36.827 | 129.189 | 36.035 |
| 2194 | CB | SER | 287 | 34.581 | 130.415 | 34.835 |
| 2195 | OG | SER | 287 | 33.577 | 129.436 | 35.050 |
| 2196 | N | GLY | 288 | 37.035 | 127.778 | 34.287 |
| 2197 | CA | GLY | 288 | 38.014 | 126.919 | 34.954 |
| 2198 | C | GLY | 288 | 39.405 | 127.499 | 34.735 |
| 2199 | O | GLY | 288 | 39.862 | 127.653 | 33.595 |
| 2200 | N | VAL | 289 | 40.075 | 127.792 | 35.835 |
| 2201 | CA | VAL | 289 | 41.344 | 128.525 | 35.779 |
| 2202 | C | VAL | 289 | 42.576 | 127.621 | 35.752 |
| 2203 | O | VAL | 289 | 43.701 | 128.111 | 35.596 |
| 2204 | CB | VAL | 289 | 41.386 | 129.439 | 36.994 |
| 2205 | CG1 | VAL | 289 | 40.172 | 130.362 | 36.973 |
| 2206 | CG2 | VAL | 289 | 41.427 | 128.628 | 38.287 |
| 2207 | N | VAL | 290 | 42.371 | 126.329 | 35.953 |
| 2208 | CA | VAL | 290 | 43.477 | 125.375 | 35.846 |
| 2209 | C | VAL | 290 | 43.186 | 124.295 | 34.812 |
| 2210 | O | VAL | 290 | 42.105 | 123.690 | 34.790 |

TABLE 10-continued

| Atom No. | Atom Type | Residue | Residue Position | X Coord. | Y Coord. | Z Coord. |
|---|---|---|---|---|---|---|
| 2211 | CB | VAL | 290 | 43.762 | 124.756 | 37.210 |
| 2212 | CG1 | VAL | 290 | 44.732 | 125.607 | 38.017 |
| 2213 | CG2 | VAL | 290 | 42.481 | 124.496 | 37.992 |
| 2214 | N | GLY | 291 | 44.188 | 124.043 | 33.988 |
| 2215 | CA | GLY | 291 | 44.094 | 123.004 | 32.963 |
| 2216 | C | GLY | 291 | 44.186 | 121.615 | 33.583 |
| 2217 | O | GLY | 291 | 44.699 | 121.440 | 34.697 |
| 2218 | N | ARG | 292 | 43.897 | 120.620 | 32.762 |
| 2219 | CA | ARG | 292 | 43.802 | 119.231 | 33.237 |
| 2220 | C | ARG | 292 | 45.149 | 118.554 | 33.510 |
| 2221 | O | ARG | 292 | 45.181 | 117.538 | 34.208 |
| 2222 | CB | ARG | 292 | 43.031 | 118.397 | 32.214 |
| 2223 | CG | ARG | 292 | 41.509 | 118.474 | 32.359 |
| 2224 | CD | ARG | 292 | 40.857 | 119.729 | 31.792 |
| 2225 | NE | ARG | 292 | 39.389 | 119.643 | 31.881 |
| 2226 | CZ | ARG | 292 | 38.611 | 119.442 | 30.812 |
| 2227 | NH1 | ARG | 292 | 39.162 | 119.263 | 29.609 |
| 2228 | NH2 | ARG | 292 | 37.285 | 119.406 | 30.946 |
| 2229 | N | TYR | 293 | 46.249 | 119.159 | 33.087 |
| 2230 | CA | TYR | 293 | 47.567 | 118.611 | 33.427 |
| 2231 | C | TYR | 293 | 48.109 | 119.265 | 34.701 |
| 2232 | O | TYR | 293 | 48.928 | 118.669 | 35.411 |
| 2233 | CB | TYR | 293 | 48.519 | 118.857 | 32.259 |
| 2234 | CG | TYR | 293 | 49.870 | 118.147 | 32.364 |
| 2235 | CD1 | TYR | 293 | 49.985 | 116.826 | 31.945 |
| 2236 | CD2 | TYR | 293 | 50.978 | 118.812 | 32.874 |
| 2237 | CE1 | TYR | 293 | 51.209 | 116.175 | 32.027 |
| 2238 | CE2 | TYR | 293 | 52.203 | 118.161 | 32.959 |
| 2239 | CZ | TYR | 293 | 52.315 | 116.845 | 32.530 |
| 2240 | OH | TYR | 293 | 53.548 | 116.229 | 32.523 |
| 2241 | N | GLN | 294 | 47.534 | 120.402 | 35.063 |
| 2242 | CA | GLN | 294 | 47.941 | 121.084 | 36.291 |
| 2243 | C | GLN | 294 | 47.114 | 120.533 | 37.440 |
| 2244 | O | GLN | 294 | 47.651 | 120.266 | 38.523 |
| 2245 | CB | GLN | 294 | 47.680 | 122.582 | 36.139 |
| 2246 | CG | GLN | 294 | 48.530 | 123.199 | 35.032 |
| 2247 | CD | GLN | 294 | 48.090 | 124.635 | 34.753 |
| 2248 | OE1 | GLN | 294 | 47.073 | 124.854 | 34.078 |
| 2249 | NE2 | GLN | 294 | 48.825 | 125.588 | 35.301 |
| 2250 | N | LEU | 295 | 45.906 | 120.122 | 37.087 |
| 2251 | CA | LEU | 295 | 44.943 | 119.510 | 38.013 |
| 2252 | C | LEU | 295 | 45.523 | 118.421 | 38.942 |
| 2253 | O | LEU | 295 | 45.606 | 118.719 | 40.142 |
| 2254 | CB | LEU | 295 | 43.771 | 119.011 | 37.164 |
| 2255 | CG | LEU | 295 | 42.723 | 118.239 | 37.954 |
| 2256 | CD1 | LEU | 295 | 42.285 | 118.994 | 39.204 |
| 2257 | CD2 | LEU | 295 | 41.533 | 117.893 | 37.064 |
| 2258 | N | PRO | 296 | 46.056 | 117.294 | 38.470 |
| 2259 | CA | PRO | 296 | 46.402 | 116.235 | 39.427 |
| 2260 | C | PRO | 296 | 47.643 | 116.548 | 40.269 |
| 2261 | O | PRO | 296 | 47.660 | 116.218 | 41.461 |
| 2262 | CB | PRO | 296 | 46.632 | 115.012 | 38.592 |
| 2263 | CG | PRO | 296 | 46.602 | 115.389 | 37.120 |
| 2264 | CD | PRO | 296 | 46.266 | 116.866 | 37.077 |
| 2265 | N | LEU | 297 | 48.515 | 117.404 | 39.759 |
| 2266 | CA | LEU | 297 | 49.759 | 117.706 | 40.462 |
| 2267 | C | LEU | 297 | 49.519 | 118.792 | 41.498 |
| 2268 | O | LEU | 297 | 49.912 | 118.640 | 42.663 |
| 2269 | CB | LEU | 297 | 50.769 | 118.188 | 39.427 |
| 2270 | CG | LEU | 297 | 50.972 | 117.150 | 38.328 |
| 2271 | CD1 | LEU | 297 | 51.825 | 117.707 | 37.194 |
| 2272 | CD2 | LEU | 297 | 51.581 | 115.867 | 38.886 |
| 2273 | N | ALA | 298 | 48.618 | 119.699 | 41.157 |
| 2274 | CA | ALA | 298 | 48.266 | 120.781 | 42.067 |
| 2275 | C | ALA | 298 | 47.349 | 120.286 | 43.171 |
| 2276 | O | ALA | 298 | 47.530 | 120.717 | 44.313 |
| 2277 | CB | ALA | 298 | 47.574 | 121.892 | 41.288 |
| 2278 | N | LEU | 299 | 46.629 | 119.201 | 42.927 |
| 2279 | CA | LEU | 299 | 45.784 | 118.642 | 43.984 |
| 2280 | C | LEU | 299 | 46.622 | 117.888 | 45.019 |
| 2281 | O | LEU | 299 | 46.287 | 117.969 | 46.204 |
| 2282 | CB | LEU | 299 | 44.735 | 117.720 | 43.364 |
| 2283 | CG | LEU | 299 | 43.355 | 117.882 | 44.012 |
| 2284 | CD1 | LEU | 299 | 42.285 | 117.129 | 43.232 |
| 2285 | CD2 | LEU | 299 | 43.319 | 117.467 | 45.480 |
| 2286 | N | VAL | 300 | 47.821 | 117.457 | 44.659 |

TABLE 10-continued

| Atom No. | Atom Type | Residue | Residue Position | X Coord. | Y Coord. | Z Coord. |
|---|---|---|---|---|---|---|
| 2287 | CA | VAL | 300 | 48.696 | 116.845 | 45.662 |
| 2288 | C | VAL | 300 | 49.277 | 117.908 | 46.596 |
| 2289 | O | VAL | 300 | 49.229 | 117.736 | 47.821 |
| 2290 | CB | VAL | 300 | 49.829 | 116.118 | 44.945 |
| 2291 | CG1 | VAL | 300 | 50.812 | 115.520 | 45.944 |
| 2292 | CG2 | VAL | 300 | 49.293 | 115.038 | 44.012 |
| 2293 | N | TYR | 301 | 49.494 | 119.096 | 46.056 |
| 2294 | CA | TYR | 301 | 50.025 | 120.191 | 46.869 |
| 2295 | C | TYR | 301 | 48.927 | 120.903 | 47.653 |
| 2296 | O | TYR | 301 | 49.171 | 121.334 | 48.785 |
| 2297 | CB | TYR | 301 | 50.738 | 121.160 | 45.939 |
| 2298 | CG | TYR | 301 | 51.921 | 120.513 | 45.205 |
| 2299 | CD1 | TYR | 301 | 52.882 | 119.831 | 45.927 |
| 2300 | CD2 | TYR | 301 | 52.013 | 120.608 | 43.823 |
| 2301 | CE1 | TYR | 301 | 53.956 | 119.241 | 45.269 |
| 2302 | CE2 | TYR | 301 | 53.071 | 120.004 | 43.162 |
| 2303 | CZ | TYR | 301 | 54.050 | 119.322 | 43.886 |
| 2304 | OH | TYR | 301 | 55.121 | 118.761 | 43.242 |
| 2305 | N | MET | 302 | 47.695 | 120.781 | 47.186 |
| 2306 | CA | MET | 302 | 46.532 | 121.295 | 47.918 |
| 2307 | C | MET | 302 | 46.122 | 120.355 | 49.047 |
| 2308 | O | MET | 302 | 45.704 | 120.808 | 50.123 |
| 2309 | CB | MET | 302 | 45.389 | 121.394 | 46.923 |
| 2310 | CG | MET | 302 | 45.632 | 122.480 | 45.886 |
| 2311 | SD | MET | 302 | 44.368 | 122.617 | 44.601 |
| 2312 | CE | MET | 302 | 45.061 | 123.995 | 43.660 |
| 2313 | N | THR | 303 | 46.447 | 119.087 | 48.864 |
| 2314 | CA | THR | 303 | 46.198 | 118.070 | 49.878 |
| 2315 | C | THR | 303 | 47.129 | 118.247 | 51.062 |
| 2316 | O | THR | 303 | 46.637 | 118.404 | 52.183 |
| 2317 | CB | THR | 303 | 46.422 | 116.704 | 49.245 |
| 2318 | OG1 | THR | 303 | 45.315 | 116.442 | 48.393 |
| 2319 | CG2 | THR | 303 | 46.472 | 115.602 | 50.292 |
| 2320 | N | ILE | 304 | 48.398 | 118.519 | 50.794 |
| 2321 | CA | ILE | 304 | 49.331 | 118.722 | 51.906 |
| 2322 | C | ILE | 304 | 49.297 | 120.170 | 52.404 |
| 2323 | O | ILE | 304 | 49.766 | 120.457 | 53.510 |
| 2324 | CB | ILE | 304 | 50.739 | 118.332 | 51.476 |
| 2325 | CG1 | ILE | 304 | 50.712 | 117.094 | 50.590 |
| 2326 | CG2 | ILE | 304 | 51.578 | 118.036 | 52.715 |
| 2327 | CD1 | ILE | 304 | 52.113 | 116.714 | 50.126 |
| 2328 | N | GLY | 305 | 48.658 | 121.044 | 51.639 |
| 2329 | CA | GLY | 305 | 48.333 | 122.403 | 52.096 |
| 2330 | C | GLY | 305 | 47.222 | 122.371 | 53.149 |
| 2331 | O | GLY | 305 | 47.021 | 123.356 | 53.873 |
| 2332 | N | LYS | 306 | 46.388 | 121.340 | 53.038 |
| 2333 | CA | LYS | 306 | 45.443 | 120.881 | 54.077 |
| 2334 | C | LYS | 306 | 44.129 | 121.644 | 54.035 |
| 2335 | O | LYS | 306 | 43.298 | 121.496 | 54.943 |
| 2336 | CB | LYS | 306 | 46.046 | 121.027 | 55.474 |
| 2337 | CG | LYS | 306 | 47.338 | 120.241 | 55.668 |
| 2338 | CD | LYS | 306 | 47.948 | 120.563 | 57.025 |
| 2339 | CE | LYS | 306 | 49.345 | 119.978 | 57.174 |
| 2340 | NZ | LYS | 306 | 49.857 | 120.204 | 58.534 |
| 2341 | N | GLU | 307 | 43.860 | 122.215 | 52.873 |
| 2342 | CA | GLU | 307 | 42.732 | 123.133 | 52.678 |
| 2343 | C | GLU | 307 | 42.937 | 123.857 | 51.353 |
| 2344 | O | GLU | 307 | 43.987 | 124.474 | 51.135 |
| 2345 | CB | GLU | 307 | 42.672 | 124.145 | 53.823 |
| 2346 | CG | GLU | 307 | 41.457 | 125.067 | 53.734 |
| 2347 | CD | GLU | 307 | 40.161 | 124.259 | 53.752 |
| 2348 | OE1 | GLU | 307 | 39.687 | 123.933 | 52.669 |
| 2349 | OE2 | GLU | 307 | 39.632 | 124.047 | 54.833 |
| 2350 | N | ASP | 308 | 41.970 | 123.750 | 50.458 |
| 2351 | CA | ASP | 308 | 42.130 | 124.421 | 49.165 |
| 2352 | C | ASP | 308 | 40.830 | 124.683 | 48.424 |
| 2353 | O | ASP | 308 | 39.834 | 123.962 | 48.555 |
| 2354 | CB | ASP | 308 | 43.008 | 123.569 | 48.255 |
| 2355 | CG | ASP | 308 | 42.270 | 122.315 | 47.787 |
| 2356 | OD1 | ASP | 308 | 41.672 | 122.344 | 46.721 |
| 2357 | OD2 | ASP | 308 | 42.279 | 121.339 | 48.524 |
| 2358 | N | ILE | 309 | 40.904 | 125.725 | 47.618 |
| 2359 | CA | ILE | 309 | 39.920 | 125.988 | 46.566 |
| 2360 | C | ILE | 309 | 40.612 | 125.712 | 45.232 |
| 2361 | O | ILE | 309 | 41.801 | 126.021 | 45.091 |
| 2362 | CB | ILE | 309 | 39.438 | 127.435 | 46.698 |

TABLE 10-continued

| Atom No. | Atom Type | Residue | Residue Position | X Coord. | Y Coord. | Z Coord. |
|---|---|---|---|---|---|---|
| 2363 | CG1 | ILE | 309 | 38.407 | 127.546 | 47.812 |
| 2364 | CG2 | ILE | 309 | 38.875 | 128.011 | 45.403 |
| 2365 | CD1 | ILE | 309 | 37.824 | 128.951 | 47.874 |
| 2366 | N | GLY | 310 | 39.939 | 125.019 | 44.332 |
| 2367 | CA | GLY | 310 | 40.523 | 124.728 | 43.017 |
| 2368 | C | GLY | 310 | 39.461 | 124.714 | 41.922 |
| 2369 | O | GLY | 310 | 38.816 | 123.683 | 41.694 |
| 2370 | N | ARG | 311 | 39.290 | 125.846 | 41.260 |
| 2371 | CA | ARG | 311 | 38.293 | 125.971 | 40.188 |
| 2372 | C | ARG | 311 | 38.727 | 125.351 | 38.852 |
| 2373 | O | ARG | 311 | 39.494 | 125.928 | 38.067 |
| 2374 | CB | ARG | 311 | 37.997 | 127.455 | 40.039 |
| 2375 | CG | ARG | 311 | 37.229 | 127.946 | 41.260 |
| 2376 | CD | ARG | 311 | 36.976 | 129.445 | 41.212 |
| 2377 | NE | ARG | 311 | 36.332 | 129.836 | 39.952 |
| 2378 | CZ | ARG | 311 | 35.842 | 131.058 | 39.734 |
| 2379 | NH1 | ARG | 311 | 35.269 | 131.346 | 38.565 |
| 2380 | NH2 | ARG | 311 | 35.926 | 131.990 | 40.686 |
| 2381 | N | LEU | 312 | 38.177 | 124.175 | 38.607 |
| 2382 | CA | LEU | 312 | 38.447 | 123.378 | 37.401 |
| 2383 | C | LEU | 312 | 37.406 | 123.605 | 36.316 |
| 2384 | O | LEU | 312 | 36.288 | 124.057 | 36.582 |
| 2385 | CB | LEU | 312 | 38.390 | 121.890 | 37.754 |
| 2386 | CG | LEU | 312 | 39.736 | 121.282 | 38.130 |
| 2387 | CD1 | LEU | 312 | 40.766 | 121.566 | 37.044 |
| 2388 | CD2 | LEU | 312 | 40.234 | 121.750 | 39.496 |
| 2389 | N | LYS | 313 | 37.751 | 123.220 | 35.102 |
| 2390 | CA | LYS | 313 | 36.746 | 123.213 | 34.041 |
| 2391 | C | LYS | 313 | 35.769 | 122.067 | 34.303 |
| 2392 | O | LYS | 313 | 34.631 | 122.310 | 34.732 |
| 2393 | CB | LYS | 313 | 37.435 | 123.048 | 32.692 |
| 2394 | CG | LYS | 313 | 38.471 | 124.148 | 32.489 |
| 2395 | CD | LYS | 313 | 38.990 | 124.192 | 31.057 |
| 2396 | CE | LYS | 313 | 39.727 | 122.918 | 30.681 |
| 2397 | NZ | LYS | 313 | 40.173 | 122.943 | 29.281 |
| 2398 | N | LEU | 314 | 36.259 | 120.839 | 34.191 |
| 2399 | CA | LEU | 314 | 35.425 | 119.662 | 34.493 |
| 2400 | C | LEU | 314 | 36.274 | 118.404 | 34.714 |
| 2401 | O | LEU | 314 | 36.939 | 117.910 | 33.797 |
| 2402 | CB | LEU | 314 | 34.459 | 119.434 | 33.330 |
| 2403 | CG | LEU | 314 | 33.376 | 118.419 | 33.679 |
| 2404 | CD1 | LEU | 314 | 32.574 | 118.887 | 34.889 |
| 2405 | CD2 | LEU | 314 | 32.448 | 118.174 | 32.493 |
| 2406 | N | GLN | 315 | 36.209 | 117.863 | 35.920 |
| 2407 | CA | GLN | 315 | 36.957 | 116.638 | 36.235 |
| 2408 | C | GLN | 315 | 36.107 | 115.374 | 36.022 |
| 2409 | O | GLN | 315 | 35.774 | 115.072 | 34.864 |
| 2410 | CB | GLN | 315 | 37.549 | 116.769 | 37.640 |
| 2411 | CG | GLN | 315 | 36.584 | 117.321 | 38.693 |
| 2412 | CD | GLN | 315 | 36.287 | 116.216 | 39.707 |
| 2413 | OE1 | GLN | 315 | 37.065 | 115.264 | 39.816 |
| 2414 | NE2 | GLN | 315 | 35.073 | 116.212 | 40.221 |
| 2415 | N | LYS | 316 | 35.996 | 114.544 | 37.049 |
| 2416 | CA | LYS | 316 | 35.071 | 113.401 | 37.090 |
| 2417 | C | LYS | 316 | 35.551 | 112.212 | 36.286 |
| 2418 | O | LYS | 316 | 36.173 | 112.383 | 35.236 |
| 2419 | CB | LYS | 316 | 33.692 | 113.789 | 36.559 |
| 2420 | CG | LYS | 316 | 32.932 | 114.742 | 37.468 |
| 2421 | CD | LYS | 316 | 31.545 | 114.998 | 36.893 |
| 2422 | CE | LYS | 316 | 30.710 | 115.897 | 37.794 |
| 2423 | NZ | LYS | 316 | 31.341 | 117.212 | 37.953 |
| 2424 | N | SER | 317 | 34.917 | 111.086 | 36.568 |
| 2425 | CA | SER | 317 | 35.173 | 109.838 | 35.833 |
| 2426 | C | SER | 317 | 34.554 | 109.823 | 34.428 |
| 2427 | O | SER | 317 | 34.672 | 108.817 | 33.725 |
| 2428 | CB | SER | 317 | 34.591 | 108.676 | 36.625 |
| 2429 | OG | SER | 317 | 33.176 | 108.796 | 36.591 |
| 2430 | N | GLU | 318 | 33.909 | 110.910 | 34.029 |
| 2431 | CA | GLU | 318 | 33.371 | 111.039 | 32.680 |
| 2432 | C | GLU | 318 | 34.353 | 111.778 | 31.771 |
| 2433 | O | GLU | 318 | 34.303 | 111.607 | 30.548 |
| 2434 | CB | GLU | 318 | 32.082 | 111.846 | 32.763 |
| 2435 | CG | GLU | 318 | 31.053 | 111.168 | 33.657 |
| 2436 | CD | GLU | 318 | 29.913 | 112.141 | 33.928 |
| 2437 | OE1 | GLU | 318 | 30.228 | 113.292 | 34.200 |
| 2438 | OE2 | GLU | 318 | 28.792 | 111.677 | 34.069 |

TABLE 10-continued

| Atom No. | Atom Type | Residue | Residue Position | X Coord. | Y Coord. | Z Coord. |
|---|---|---|---|---|---|---|
| 2439 | N | ILE | 319 | 35.228 | 112.586 | 32.355 |
| 2440 | CA | ILE | 319 | 36.217 | 113.333 | 31.562 |
| 2441 | C | ILE | 319 | 37.608 | 113.048 | 32.123 |
| 2442 | O | ILE | 319 | 38.374 | 112.233 | 31.589 |
| 2443 | CB | ILE | 319 | 35.928 | 114.838 | 31.654 |
| 2444 | CG1 | ILE | 319 | 34.485 | 115.173 | 31.292 |
| 2445 | CG2 | ILE | 319 | 36.862 | 115.627 | 30.737 |
| 2446 | CD1 | ILE | 319 | 34.201 | 114.933 | 29.812 |
| 2447 | N | ASP | 320 | 37.864 | 113.618 | 33.287 |
| 2448 | CA | ASP | 320 | 39.141 | 113.415 | 33.975 |
| 2449 | C | ASP | 320 | 39.077 | 112.249 | 34.950 |
| 2450 | O | ASP | 320 | 39.151 | 112.424 | 36.176 |
| 2451 | CB | ASP | 320 | 39.549 | 114.681 | 34.710 |
| 2452 | CG | ASP | 320 | 40.332 | 115.586 | 33.773 |
| 2453 | OD1 | ASP | 320 | 39.917 | 115.743 | 32.635 |
| 2454 | OD2 | ASP | 320 | 41.445 | 115.919 | 34.157 |
| 2455 | N | GLU | 321 | 39.223 | 111.068 | 34.372 |
| 2456 | CA | GLU | 321 | 39.204 | 109.811 | 35.127 |
| 2457 | C | GLU | 321 | 40.531 | 109.588 | 35.854 |
| 2458 | O | GLU | 321 | 40.565 | 108.989 | 36.938 |
| 2459 | CB | GLU | 321 | 38.985 | 108.706 | 34.105 |
| 2460 | CG | GLU | 321 | 37.794 | 109.045 | 33.215 |
| 2461 | CD | GLU | 321 | 37.759 | 108.108 | 32.015 |
| 2462 | OE1 | GLU | 321 | 38.832 | 107.646 | 31.651 |
| 2463 | OE2 | GLU | 321 | 36.695 | 107.928 | 31.441 |
| 2464 | N | ASN | 322 | 41.536 | 110.323 | 35.404 |
| 2465 | CA | ASN | 322 | 42.838 | 110.334 | 36.062 |
| 2466 | C | ASN | 322 | 42.821 | 111.161 | 37.348 |
| 2467 | O | ASN | 322 | 43.491 | 110.774 | 38.313 |
| 2468 | CB | ASN | 322 | 43.855 | 110.933 | 35.098 |
| 2469 | CG | ASN | 322 | 45.205 | 111.003 | 35.796 |
| 2470 | OD1 | ASN | 322 | 45.548 | 110.103 | 36.570 |
| 2471 | ND2 | ASN | 322 | 45.921 | 112.091 | 35.570 |
| 2472 | N | LEU | 323 | 41.870 | 112.074 | 37.480 |
| 2473 | CA | LEU | 323 | 41.810 | 112.835 | 38.726 |
| 2474 | C | LEU | 323 | 41.126 | 112.010 | 39.805 |
| 2475 | O | LEU | 323 | 41.545 | 112.063 | 40.965 |
| 2476 | CB | LEU | 323 | 41.027 | 114.127 | 38.555 |
| 2477 | CG | LEU | 323 | 41.105 | 114.899 | 39.868 |
| 2478 | CD1 | LEU | 323 | 42.550 | 115.282 | 40.170 |
| 2479 | CD2 | LEU | 323 | 40.201 | 116.122 | 39.883 |
| 2480 | N | VAL | 324 | 40.308 | 111.060 | 39.386 |
| 2481 | CA | VAL | 324 | 39.658 | 110.189 | 40.358 |
| 2482 | C | VAL | 324 | 40.624 | 109.079 | 40.767 |
| 2483 | O | VAL | 324 | 40.686 | 108.734 | 41.955 |
| 2484 | CB | VAL | 324 | 38.401 | 109.621 | 39.719 |
| 2485 | CG1 | VAL | 324 | 37.453 | 109.114 | 40.797 |
| 2486 | CG2 | VAL | 324 | 37.705 | 110.702 | 38.906 |
| 2487 | N | SER | 325 | 41.539 | 108.757 | 39.863 |
| 2488 | CA | SER | 325 | 42.654 | 107.853 | 40.175 |
| 2489 | C | SER | 325 | 43.513 | 108.460 | 41.276 |
| 2490 | O | SER | 325 | 43.507 | 107.961 | 42.412 |
| 2491 | CB | SER | 325 | 43.540 | 107.699 | 38.942 |
| 2492 | OG | SER | 325 | 42.784 | 107.155 | 37.872 |
| 2493 | N | VAL | 326 | 43.977 | 109.674 | 41.015 |
| 2494 | CA | VAL | 326 | 44.840 | 110.403 | 41.953 |
| 2495 | C | VAL | 326 | 44.153 | 110.712 | 43.285 |
| 2496 | O | VAL | 326 | 44.743 | 110.426 | 44.337 |
| 2497 | CB | VAL | 326 | 45.259 | 111.703 | 41.266 |
| 2498 | CG1 | VAL | 326 | 45.946 | 112.675 | 42.221 |
| 2499 | CG2 | VAL | 326 | 46.142 | 111.415 | 40.057 |
| 2500 | N | LEU | 327 | 42.859 | 110.985 | 43.246 |
| 2501 | CA | LEU | 327 | 42.109 | 111.275 | 44.468 |
| 2502 | C | LEU | 327 | 41.956 | 110.050 | 45.358 |
| 2503 | O | LEU | 327 | 42.303 | 110.136 | 46.541 |
| 2504 | CB | LEU | 327 | 40.714 | 111.765 | 44.107 |
| 2505 | CG | LEU | 327 | 39.924 | 112.065 | 45.375 |
| 2506 | CD1 | LEU | 327 | 40.512 | 113.270 | 46.104 |
| 2507 | CD2 | LEU | 327 | 38.450 | 112.285 | 45.069 |
| 2508 | N | ARG | 328 | 41.686 | 108.889 | 44.782 |
| 2509 | CA | ARG | 328 | 41.531 | 107.695 | 45.617 |
| 2510 | C | ARG | 328 | 42.873 | 107.103 | 46.022 |
| 2511 | O | ARG | 328 | 42.982 | 106.577 | 47.137 |
| 2512 | CB | ARG | 328 | 40.699 | 106.661 | 44.882 |
| 2513 | CG | ARG | 328 | 39.252 | 107.120 | 44.781 |
| 2514 | CD | ARG | 328 | 38.453 | 106.128 | 43.957 |

TABLE 10-continued

| Atom No. | Atom Type | Residue | Residue Position | X Coord. | Y Coord. | Z Coord. |
|---|---|---|---|---|---|---|
| 2515 | NE | ARG | 328 | 39.091 | 105.998 | 42.644 |
| 2516 | CZ | ARG | 328 | 38.427 | 105.742 | 41.520 |
| 2517 | NH1 | ARG | 328 | 39.059 | 105.834 | 40.352 |
| 2518 | NH2 | ARG | 328 | 37.107 | 105.543 | 41.553 |
| 2519 | N | ASP | 329 | 43.918 | 107.431 | 45.278 |
| 2520 | CA | ASP | 329 | 45.272 | 107.089 | 45.714 |
| 2521 | C | ASP | 329 | 45.579 | 107.857 | 46.999 |
| 2522 | O | ASP | 329 | 45.780 | 107.236 | 48.054 |
| 2523 | CB | ASP | 329 | 46.282 | 107.490 | 44.636 |
| 2524 | CG | ASP | 329 | 46.078 | 106.738 | 43.319 |
| 2525 | OD1 | ASP | 329 | 46.327 | 107.336 | 42.280 |
| 2526 | OD2 | ASP | 329 | 45.683 | 105.580 | 43.367 |
| 2527 | N | ILE | 330 | 45.299 | 109.153 | 46.966 |
| 2528 | CA | ILE | 330 | 45.572 | 110.023 | 48.116 |
| 2529 | C | ILE | 330 | 44.669 | 109.722 | 49.306 |
| 2530 | O | ILE | 330 | 45.195 | 109.509 | 50.404 |
| 2531 | CB | ILE | 330 | 45.356 | 111.473 | 47.692 |
| 2532 | CG1 | ILE | 330 | 46.371 | 111.896 | 46.640 |
| 2533 | CG2 | ILE | 330 | 45.423 | 112.407 | 48.894 |
| 2534 | CD1 | ILE | 330 | 46.177 | 113.351 | 46.227 |
| 2535 | N | GLN | 331 | 43.420 | 109.383 | 49.034 |
| 2536 | CA | GLN | 331 | 42.432 | 109.130 | 50.086 |
| 2537 | C | GLN | 331 | 42.588 | 107.758 | 50.757 |
| 2538 | O | GLN | 331 | 42.023 | 107.535 | 51.836 |
| 2539 | CB | GLN | 331 | 41.062 | 109.231 | 49.416 |
| 2540 | CG | GLN | 331 | 39.891 | 109.207 | 50.393 |
| 2541 | CD | GLN | 331 | 39.864 | 110.470 | 51.251 |
| 2542 | OE1 | GLN | 331 | 39.593 | 111.572 | 50.753 |
| 2543 | NE2 | GLN | 331 | 40.215 | 110.304 | 52.514 |
| 2544 | N | GLU | 332 | 43.396 | 106.882 | 50.177 |
| 2545 | CA | GLU | 332 | 43.664 | 105.581 | 50.797 |
| 2546 | C | GLU | 332 | 44.935 | 105.582 | 51.647 |
| 2547 | O | GLU | 332 | 45.181 | 104.605 | 52.364 |
| 2548 | CB | GLU | 332 | 43.793 | 104.528 | 49.700 |
| 2549 | CG | GLU | 332 | 42.458 | 104.265 | 49.012 |
| 2550 | CD | GLU | 332 | 42.661 | 103.419 | 47.757 |
| 2551 | OE1 | GLU | 332 | 41.973 | 103.681 | 46.777 |
| 2552 | OE2 | GLU | 332 | 43.519 | 102.548 | 47.781 |
| 2553 | N | VAL | 333 | 45.733 | 106.636 | 51.572 |
| 2554 | CA | VAL | 333 | 46.958 | 106.671 | 52.379 |
| 2555 | C | VAL | 333 | 46.950 | 107.863 | 53.336 |
| 2556 | O | VAL | 333 | 47.444 | 107.776 | 54.467 |
| 2557 | CB | VAL | 333 | 48.163 | 106.750 | 51.443 |
| 2558 | CG1 | VAL | 333 | 49.469 | 106.791 | 52.228 |
| 2559 | CG2 | VAL | 333 | 48.182 | 105.580 | 50.464 |
| 2560 | N | PHE | 334 | 46.376 | 108.960 | 52.877 |
| 2561 | CA | PHE | 334 | 46.261 | 110.173 | 53.689 |
| 2562 | C | PHE | 334 | 44.855 | 110.343 | 54.244 |
| 2563 | O | PHE | 334 | 43.859 | 110.024 | 53.580 |
| 2564 | CB | PHE | 334 | 46.576 | 111.398 | 52.837 |
| 2565 | CG | PHE | 334 | 48.046 | 111.667 | 52.534 |
| 2566 | CD1 | PHE | 334 | 48.384 | 112.531 | 51.500 |
| 2567 | CD2 | PHE | 334 | 49.044 | 111.088 | 53.307 |
| 2568 | CE1 | PHE | 334 | 49.718 | 112.795 | 51.222 |
| 2569 | CE2 | PHE | 334 | 50.379 | 111.351 | 53.027 |
| 2570 | CZ | PHE | 334 | 50.716 | 112.202 | 51.983 |
| 2571 | N | GLY | 335 | 44.789 | 111.004 | 55.389 |
| 2572 | CA | GLY | 335 | 43.508 | 111.340 | 56.024 |
| 2573 | C | GLY | 335 | 42.982 | 112.676 | 55.497 |
| 2574 | O | GLY | 335 | 43.079 | 113.716 | 56.165 |
| 2575 | N | THR | 336 | 42.549 | 112.630 | 54.249 |
| 2576 | CA | THR | 336 | 42.004 | 113.793 | 53.546 |
| 2577 | C | THR | 336 | 40.494 | 113.697 | 53.403 |
| 2578 | O | THR | 336 | 39.847 | 112.810 | 53.977 |
| 2579 | CB | THR | 336 | 42.605 | 113.860 | 52.147 |
| 2580 | OG1 | THR | 336 | 42.238 | 112.687 | 51.433 |
| 2581 | CG2 | THR | 336 | 44.119 | 113.931 | 52.192 |
| 2582 | N | GLU | 337 | 39.962 | 114.650 | 52.656 |
| 2583 | CA | GLU | 337 | 38.539 | 114.690 | 52.302 |
| 2584 | C | GLU | 337 | 38.297 | 115.823 | 51.311 |
| 2585 | O | GLU | 337 | 38.263 | 117.001 | 51.696 |
| 2586 | CB | GLU | 337 | 37.681 | 114.883 | 53.548 |
| 2587 | CG | GLU | 337 | 36.201 | 114.771 | 53.199 |
| 2588 | CD | GLU | 337 | 35.363 | 114.614 | 54.464 |
| 2589 | OE1 | GLU | 337 | 34.982 | 113.487 | 54.750 |
| 2590 | OE2 | GLU | 337 | 35.034 | 115.629 | 55.060 |

TABLE 10-continued

| Atom No. | Atom Type | Residue | Residue Position | X Coord. | Y Coord. | Z Coord. |
|---|---|---|---|---|---|---|
| 2591 | N | ALA | 338 | 38.163 | 115.459 | 50.045 |
| 2592 | CA | ALA | 338 | 37.987 | 116.453 | 48.977 |
| 2593 | C | ALA | 338 | 36.565 | 116.522 | 48.426 |
| 2594 | O | ALA | 338 | 36.043 | 115.545 | 47.879 |
| 2595 | CB | ALA | 338 | 38.939 | 116.112 | 47.837 |
| 2596 | N | PHE | 339 | 35.970 | 117.694 | 48.549 |
| 2597 | CA | PHE | 339 | 34.655 | 117.951 | 47.950 |
| 2598 | C | PHE | 339 | 34.813 | 118.540 | 46.550 |
| 2599 | O | PHE | 339 | 35.838 | 119.160 | 46.240 |
| 2600 | CB | PHE | 339 | 33.879 | 118.908 | 48.845 |
| 2601 | CG | PHE | 339 | 33.652 | 118.373 | 50.255 |
| 2602 | CD1 | PHE | 339 | 32.786 | 117.307 | 50.461 |
| 2603 | CD2 | PHE | 339 | 34.320 | 118.945 | 51.332 |
| 2604 | CE1 | PHE | 339 | 32.584 | 116.815 | 51.744 |
| 2605 | CE2 | PHE | 339 | 34.118 | 118.452 | 52.614 |
| 2606 | CZ | PHE | 339 | 33.249 | 117.388 | 52.820 |
| 2607 | N | PHE | 340 | 33.839 | 118.269 | 45.698 |
| 2608 | CA | PHE | 340 | 33.878 | 118.747 | 44.307 |
| 2609 | C | PHE | 340 | 32.528 | 119.294 | 43.846 |
| 2610 | O | PHE | 340 | 31.656 | 118.531 | 43.414 |
| 2611 | CB | PHE | 340 | 34.252 | 117.578 | 43.407 |
| 2612 | CG | PHE | 340 | 35.675 | 117.055 | 43.569 |
| 2613 | CD1 | PHE | 340 | 36.754 | 117.925 | 43.479 |
| 2614 | CD2 | PHE | 340 | 35.892 | 115.701 | 43.784 |
| 2615 | CE1 | PHE | 340 | 38.049 | 117.445 | 43.619 |
| 2616 | CE2 | PHE | 340 | 37.187 | 115.221 | 43.922 |
| 2617 | CZ | PHE | 340 | 38.266 | 116.092 | 43.842 |
| 2618 | N | LYS | 341 | 32.418 | 120.609 | 43.808 |
| 2619 | CA | LYS | 341 | 31.137 | 121.238 | 43.451 |
| 2620 | C | LYS | 341 | 31.156 | 121.984 | 42.110 |
| 2621 | O | LYS | 341 | 31.710 | 123.083 | 41.980 |
| 2622 | CB | LYS | 341 | 30.744 | 122.167 | 44.596 |
| 2623 | CG | LYS | 341 | 31.888 | 123.093 | 44.996 |
| 2624 | CD | LYS | 341 | 31.537 | 123.916 | 46.227 |
| 2625 | CE | LYS | 341 | 31.280 | 123.014 | 47.428 |
| 2626 | NZ | LYS | 341 | 30.948 | 123.810 | 48.620 |
| 2627 | N | ASP | 342 | 30.552 | 121.365 | 41.108 |
| 2628 | CA | ASP | 342 | 30.406 | 122.026 | 39.802 |
| 2629 | C | ASP | 342 | 29.117 | 122.832 | 39.763 |
| 2630 | O | ASP | 342 | 28.033 | 122.293 | 40.014 |
| 2631 | CB | ASP | 342 | 30.385 | 120.991 | 38.677 |
| 2632 | CG | ASP | 342 | 30.263 | 121.672 | 37.310 |
| 2633 | OD1 | ASP | 342 | 29.143 | 121.900 | 36.877 |
| 2634 | OD2 | ASP | 342 | 31.294 | 121.991 | 36.729 |
| 2635 | N | ASP | 343 | 29.229 | 124.107 | 39.438 |
| 2636 | CA | ASP | 343 | 28.019 | 124.923 | 39.322 |
| 2637 | C | ASP | 343 | 27.608 | 125.130 | 37.861 |
| 2638 | O | ASP | 343 | 26.407 | 125.054 | 37.569 |
| 2639 | CB | ASP | 343 | 28.173 | 126.256 | 40.070 |
| 2640 | CG | ASP | 343 | 29.155 | 127.259 | 39.447 |
| 2641 | OD1 | ASP | 343 | 28.810 | 128.432 | 39.438 |
| 2642 | OD2 | ASP | 343 | 30.223 | 126.852 | 39.010 |
| 2643 | N | ALA | 344 | 28.584 | 125.196 | 36.961 |
| 2644 | CA | ALA | 344 | 28.332 | 125.407 | 35.518 |
| 2645 | C | ALA | 344 | 29.630 | 125.741 | 34.789 |
| 2646 | O | ALA | 344 | 30.019 | 126.915 | 34.759 |
| 2647 | CB | ALA | 344 | 27.384 | 126.587 | 35.309 |
| 2648 | N | GLU | 345 | 30.222 | 124.745 | 34.137 |
| 2649 | CA | GLU | 345 | 31.533 | 124.906 | 33.472 |
| 2650 | C | GLU | 345 | 32.539 | 125.479 | 34.457 |
| 2651 | O | GLU | 345 | 33.230 | 126.469 | 34.161 |
| 2652 | CB | GLU | 345 | 31.412 | 125.836 | 32.266 |
| 2653 | CG | GLU | 345 | 30.776 | 125.160 | 31.058 |
| 2654 | CD | GLU | 345 | 31.669 | 124.021 | 30.579 |
| 2655 | OE1 | GLU | 345 | 31.335 | 122.881 | 30.876 |
| 2656 | OE2 | GLU | 345 | 32.687 | 124.304 | 29.955 |
| 2657 | N | GLU | 346 | 32.665 | 124.768 | 35.565 |
| 2658 | CA | GLU | 346 | 33.356 | 125.273 | 36.745 |
| 2659 | C | GLU | 346 | 33.070 | 124.351 | 37.920 |
| 2660 | O | GLU | 346 | 31.949 | 124.327 | 38.450 |
| 2661 | CB | GLU | 346 | 32.840 | 126.659 | 37.118 |
| 2662 | CG | GLU | 346 | 33.983 | 127.626 | 37.405 |
| 2663 | CD | GLU | 346 | 35.064 | 126.968 | 38.244 |
| 2664 | OE1 | GLU | 346 | 36.115 | 126.687 | 37.689 |
| 2665 | OE2 | GLU | 346 | 34.768 | 126.609 | 39.379 |
| 2666 | N | LEU | 347 | 34.073 | 123.579 | 38.281 |

TABLE 10-continued

| Atom No. | Atom Type | Residue | Residue Position | X Coord. | Y Coord. | Z Coord. |
|---|---|---|---|---|---|---|
| 2667 | CA | LEU | 347 | 33.997 | 122.747 | 39.475 |
| 2668 | C | LEU | 347 | 35.009 | 123.203 | 40.517 |
| 2669 | O | LEU | 347 | 36.221 | 123.064 | 40.323 |
| 2670 | CB | LEU | 347 | 34.258 | 121.299 | 39.085 |
| 2671 | CG | LEU | 347 | 34.200 | 120.383 | 40.304 |
| 2672 | CD1 | LEU | 347 | 33.337 | 119.165 | 40.030 |
| 2673 | CD2 | LEU | 347 | 35.589 | 119.984 | 40.798 |
| 2674 | N | ASP | 348 | 34.515 | 123.651 | 41.657 |
| 2675 | CA | ASP | 348 | 35.416 | 124.039 | 42.740 |
| 2676 | C | ASP | 348 | 35.764 | 122.841 | 43.626 |
| 2677 | O | ASP | 348 | 34.889 | 122.172 | 44.192 |
| 2678 | CB | ASP | 348 | 34.765 | 125.140 | 43.567 |
| 2679 | CG | ASP | 348 | 35.809 | 125.762 | 44.490 |
| 2680 | OD1 | ASP | 348 | 36.967 | 125.764 | 44.093 |
| 2681 | OD2 | ASP | 348 | 35.405 | 126.416 | 45.439 |
| 2682 | N | SER | 349 | 37.045 | 122.516 | 43.615 |
| 2683 | CA | SER | 349 | 37.616 | 121.477 | 44.484 |
| 2684 | C | SER | 349 | 37.920 | 122.035 | 45.874 |
| 2685 | O | SER | 349 | 38.319 | 123.198 | 45.992 |
| 2686 | CB | SER | 349 | 38.918 | 121.010 | 43.843 |
| 2687 | OG | SER | 349 | 38.626 | 120.600 | 42.512 |
| 2688 | N | ASP | 350 | 37.640 | 121.254 | 46.906 |
| 2689 | CA | ASP | 350 | 37.927 | 121.664 | 48.298 |
| 2690 | C | ASP | 350 | 38.315 | 120.488 | 49.202 |
| 2691 | O | ASP | 350 | 37.450 | 119.831 | 49.797 |
| 2692 | CB | ASP | 350 | 36.712 | 122.380 | 48.892 |
| 2693 | CG | ASP | 350 | 36.543 | 123.803 | 48.352 |
| 2694 | OD1 | ASP | 350 | 36.817 | 124.719 | 49.113 |
| 2695 | OD2 | ASP | 350 | 35.888 | 123.932 | 47.322 |
| 2696 | N | ASP | 351 | 39.613 | 120.250 | 49.324 |
| 2697 | CA | ASP | 351 | 40.139 | 119.150 | 50.153 |
| 2698 | C | ASP | 351 | 40.745 | 119.641 | 51.465 |
| 2699 | O | ASP | 351 | 41.492 | 120.625 | 51.478 |
| 2700 | CB | ASP | 351 | 41.226 | 118.439 | 49.344 |
| 2701 | CG | ASP | 351 | 41.927 | 117.327 | 50.128 |
| 2702 | OD1 | ASP | 351 | 43.145 | 117.399 | 50.218 |
| 2703 | OD2 | ASP | 351 | 41.281 | 116.314 | 50.366 |
| 2704 | N | LYS | 352 | 40.389 | 118.971 | 52.551 |
| 2705 | CA | LYS | 352 | 41.075 | 119.167 | 53.837 |
| 2706 | C | LYS | 352 | 41.965 | 117.961 | 54.127 |
| 2707 | O | LYS | 352 | 41.877 | 116.954 | 53.414 |
| 2708 | CB | LYS | 352 | 40.057 | 119.337 | 54.953 |
| 2709 | CG | LYS | 352 | 39.130 | 120.510 | 54.670 |
| 2710 | CD | LYS | 352 | 38.175 | 120.738 | 55.833 |
| 2711 | CE | LYS | 352 | 37.131 | 121.790 | 55.491 |
| 2712 | NZ | LYS | 352 | 36.271 | 121.334 | 54.385 |
| 2713 | N | PHE | 353 | 42.835 | 118.096 | 55.117 |
| 2714 | CA | PHE | 353 | 43.780 | 117.022 | 55.482 |
| 2715 | C | PHE | 353 | 44.367 | 117.219 | 56.883 |
| 2716 | O | PHE | 353 | 44.536 | 118.371 | 57.298 |
| 2717 | CB | PHE | 353 | 44.910 | 117.047 | 54.447 |
| 2718 | CG | PHE | 353 | 46.138 | 116.169 | 54.714 |
| 2719 | CD1 | PHE | 353 | 47.401 | 116.745 | 54.724 |
| 2720 | CD2 | PHE | 353 | 46.002 | 114.805 | 54.931 |
| 2721 | CE1 | PHE | 353 | 48.524 | 115.964 | 54.958 |
| 2722 | CE2 | PHE | 353 | 47.124 | 114.023 | 55.170 |
| 2723 | CZ | PHE | 353 | 48.386 | 114.602 | 55.183 |
| 2724 | N | MET | 354 | 44.466 | 116.116 | 57.623 |
| 2725 | CA | MET | 354 | 45.300 | 115.953 | 58.843 |
| 2726 | C | MET | 354 | 44.570 | 115.348 | 60.030 |
| 2727 | O | MET | 354 | 43.540 | 115.834 | 60.501 |
| 2728 | CB | MET | 354 | 46.033 | 117.191 | 59.329 |
| 2729 | CG | MET | 354 | 47.425 | 117.262 | 58.727 |
| 2730 | SD | MET | 354 | 48.464 | 115.826 | 59.062 |
| 2731 | CE | MET | 354 | 50.030 | 116.428 | 58.389 |
| 2732 | N | THR | 355 | 45.312 | 114.461 | 60.664 |
| 2733 | CA | THR | 355 | 44.830 | 113.730 | 61.834 |
| 2734 | C | THR | 355 | 45.611 | 114.209 | 63.063 |
| 2735 | O | THR | 355 | 46.122 | 113.404 | 63.857 |
| 2736 | CB | THR | 355 | 45.078 | 112.243 | 61.577 |
| 2737 | OG1 | THR | 355 | 44.905 | 112.007 | 60.186 |
| 2738 | CG2 | THR | 355 | 44.111 | 111.354 | 62.345 |
| 2739 | N | VAL | 356 | 45.674 | 115.525 | 63.226 |
| 2740 | CA | VAL | 356 | 46.530 | 116.117 | 64.262 |
| 2741 | C | VAL | 356 | 46.063 | 115.734 | 65.661 |
| 2742 | O | VAL | 356 | 44.855 | 115.676 | 65.918 |
| 2743 | CB | VAL | 356 | 46.535 | 117.636 | 64.095 |
| 2744 | CG1 | VAL | 356 | 47.129 | 118.348 | 65.303 |
| 2745 | CG2 | VAL | 356 | 47.268 | 118.031 | 62.819 |
| 2746 | N | SER | 357 | 47.020 | 115.141 | 66.370 |
| 2747 | CA | SER | 357 | 46.944 | 114.730 | 67.793 |
| 2748 | C | SER | 357 | 46.129 | 113.459 | 68.034 |
| 2749 | O | SER | 357 | 46.257 | 112.855 | 69.105 |
| 2750 | CB | SER | 357 | 46.371 | 115.851 | 68.654 |
| 2751 | OG | SER | 357 | 44.950 | 115.767 | 68.637 |
| 2752 | N | ILE | 358 | 45.497 | 112.925 | 66.999 |
| 2753 | CA | ILE | 358 | 44.728 | 111.692 | 67.157 |
| 2754 | C | ILE | 358 | 45.637 | 110.503 | 66.902 |
| 2755 | O | ILE | 358 | 45.426 | 109.411 | 67.442 |
| 2756 | CB | ILE | 358 | 43.548 | 111.702 | 66.191 |
| 2757 | CG1 | ILE | 358 | 42.659 | 112.908 | 66.460 |
| 2758 | CG2 | ILE | 358 | 42.737 | 110.419 | 66.315 |
| 2759 | CD1 | ILE | 358 | 41.455 | 112.932 | 65.524 |
| 2760 | N | LYS | 359 | 46.801 | 110.837 | 66.369 |
| 2761 | CA | LYS | 359 | 47.897 | 109.877 | 66.220 |
| 2762 | C | LYS | 359 | 48.479 | 109.484 | 67.581 |
| 2763 | O | LYS | 359 | 48.817 | 108.311 | 67.777 |
| 2764 | CB | LYS | 359 | 48.985 | 110.582 | 65.425 |
| 2765 | CG | LYS | 359 | 48.391 | 111.352 | 64.253 |
| 2766 | CD | LYS | 359 | 49.425 | 112.268 | 63.607 |
| 2767 | CE | LYS | 359 | 48.804 | 113.111 | 62.500 |
| 2768 | NZ | LYS | 359 | 49.755 | 114.100 | 61.975 |
| 2769 | N | GLY | 360 | 48.361 | 110.373 | 68.559 |
| 2770 | CA | GLY | 360 | 48.835 | 110.098 | 69.921 |
| 2771 | C | GLY | 360 | 47.899 | 109.112 | 70.609 |
| 2772 | O | GLY | 360 | 48.352 | 108.128 | 71.209 |
| 2773 | N | VAL | 361 | 46.610 | 109.277 | 70.350 |
| 2774 | CA | VAL | 361 | 45.604 | 108.354 | 70.879 |
| 2775 | C | VAL | 361 | 45.742 | 106.983 | 70.219 |
| 2776 | O | VAL | 361 | 45.765 | 105.967 | 70.921 |
| 2777 | CB | VAL | 361 | 44.231 | 108.935 | 70.568 |
| 2778 | CG1 | VAL | 361 | 43.122 | 108.051 | 71.126 |
| 2779 | CG2 | VAL | 361 | 44.107 | 110.357 | 71.105 |
| 2780 | N | GLY | 362 | 46.085 | 106.984 | 68.941 |
| 2781 | CA | GLY | 362 | 46.393 | 105.750 | 68.216 |
| 2782 | C | GLY | 362 | 47.545 | 104.987 | 68.868 |
| 2783 | O | GLY | 362 | 47.361 | 103.830 | 69.271 |
| 2784 | N | PHE | 363 | 48.633 | 105.688 | 69.150 |
| 2785 | CA | PHE | 363 | 49.813 | 105.055 | 69.751 |
| 2786 | C | PHE | 363 | 49.576 | 104.579 | 71.183 |
| 2787 | O | PHE | 363 | 49.944 | 103.443 | 71.499 |
| 2788 | CB | PHE | 363 | 50.971 | 106.049 | 69.746 |
| 2789 | CG | PHE | 363 | 51.474 | 106.455 | 68.363 |
| 2790 | CD1 | PHE | 363 | 51.934 | 107.748 | 68.151 |
| 2791 | CD2 | PHE | 363 | 51.484 | 105.535 | 67.321 |
| 2792 | CE1 | PHE | 363 | 52.390 | 108.126 | 66.895 |
| 2793 | CE2 | PHE | 363 | 51.940 | 105.913 | 66.065 |
| 2794 | CZ | PHE | 363 | 52.392 | 107.208 | 65.852 |
| 2795 | N | THR | 364 | 48.779 | 105.305 | 71.951 |
| 2796 | CA | THR | 364 | 48.508 | 104.870 | 73.327 |
| 2797 | C | THR | 364 | 47.523 | 103.702 | 73.379 |
| 2798 | O | THR | 364 | 47.739 | 102.772 | 74.167 |
| 2799 | CB | THR | 364 | 47.972 | 106.041 | 74.146 |
| 2800 | OG1 | THR | 364 | 46.796 | 106.545 | 73.524 |
| 2801 | CG2 | THR | 364 | 48.987 | 107.174 | 74.237 |
| 2802 | N | ASN | 365 | 46.659 | 103.606 | 72.380 |
| 2803 | CA | ASN | 365 | 45.732 | 102.478 | 72.304 |
| 2804 | C | ASN | 365 | 46.466 | 101.214 | 71.888 |
| 2805 | O | ASN | 365 | 46.381 | 100.203 | 72.599 |
| 2806 | CB | ASN | 365 | 44.652 | 102.769 | 71.269 |
| 2807 | CG | ASN | 365 | 43.709 | 103.882 | 71.715 |
| 2808 | OD1 | ASN | 365 | 43.714 | 104.325 | 72.871 |
| 2809 | ND2 | ASN | 365 | 42.856 | 104.281 | 70.788 |
| 2810 | N | VAL | 366 | 47.395 | 101.349 | 70.952 |
| 2811 | CA | VAL | 366 | 48.136 | 100.172 | 70.490 |
| 2812 | C | VAL | 366 | 49.264 | 99.774 | 71.443 |
| 2813 | O | VAL | 366 | 49.670 | 98.609 | 71.411 |
| 2814 | CB | VAL | 366 | 48.676 | 100.382 | 69.077 |
| 2815 | CG1 | VAL | 366 | 47.542 | 100.668 | 68.100 |
| 2816 | CG2 | VAL | 366 | 49.736 | 101.473 | 69.004 |
| 2817 | N | SER | 367 | 49.542 | 100.590 | 72.450 |
| 2818 | CA | SER | 367 | 50.495 | 100.178 | 73.483 |

TABLE 10-continued

| Atom No. | Atom Type | Residue | Residue Position | X Coord. | Y Coord. | Z Coord. |
|---|---|---|---|---|---|---|
| 2819 | C | SER | 367 | 49.882 | 99.106 | 74.382 |
| 2820 | O | SER | 367 | 50.598 | 98.212 | 74.846 |
| 2821 | CB | SER | 367 | 50.877 | 101.388 | 74.329 |
| 2822 | OG | SER | 367 | 51.546 | 102.320 | 73.492 |
| 2823 | N | LYS | 368 | 48.561 | 99.090 | 74.476 |
| 2824 | CA | LYS | 368 | 47.892 | 98.016 | 75.207 |
| 2825 | C | LYS | 368 | 47.389 | 96.934 | 74.252 |
| 2826 | O | LYS | 368 | 47.540 | 95.739 | 74.534 |
| 2827 | CB | LYS | 368 | 46.715 | 98.621 | 75.961 |
| 2828 | CG | LYS | 368 | 47.171 | 99.771 | 76.856 |
| 2829 | CD | LYS | 368 | 46.048 | 100.389 | 77.692 |
| 2830 | CE | LYS | 368 | 45.832 | 99.703 | 79.045 |
| 2831 | NZ | LYS | 368 | 45.232 | 98.361 | 78.941 |
| 2832 | N | LYS | 369 | 47.030 | 97.347 | 73.046 |
| 2833 | CA | LYS | 369 | 46.435 | 96.424 | 72.065 |
| 2834 | C | LYS | 369 | 47.430 | 95.568 | 71.273 |
| 2835 | O | LYS | 369 | 46.998 | 94.674 | 70.537 |
| 2836 | CB | LYS | 369 | 45.582 | 97.234 | 71.099 |
| 2837 | CG | LYS | 369 | 44.395 | 97.854 | 71.823 |

TABLE 10-continued

| Atom No. | Atom Type | Residue | Residue Position | X Coord. | Y Coord. | Z Coord. |
|---|---|---|---|---|---|---|
| 2838 | CD | LYS | 369 | 43.577 | 98.744 | 70.897 |
| 2839 | CE | LYS | 369 | 42.417 | 99.392 | 71.644 |
| 2840 | NZ | LYS | 369 | 41.646 | 100.273 | 70.753 |
| 2841 | N | ILE | 370 | 48.725 | 95.792 | 71.434 |
| 2842 | CA | ILE | 370 | 49.711 | 94.880 | 70.839 |
| 2843 | C | ILE | 370 | 50.001 | 93.695 | 71.773 |
| 2844 | O | ILE | 370 | 50.481 | 92.645 | 71.325 |
| 2845 | CB | ILE | 370 | 50.974 | 95.682 | 70.504 |
| 2846 | CG1 | ILE | 370 | 50.701 | 96.630 | 69.341 |
| 2847 | CG2 | ILE | 370 | 52.167 | 94.792 | 70.170 |
| 2848 | CD1 | ILE | 370 | 51.931 | 97.466 | 69.005 |
| 2849 | N | ALA | 371 | 49.548 | 93.802 | 73.013 |
| 2850 | CA | ALA | 371 | 49.715 | 92.703 | 73.967 |
| 2851 | C | ALA | 371 | 48.548 | 91.720 | 73.892 |
| 2852 | O | ALA | 371 | 47.662 | 91.823 | 74.727 |
| 2853 | CB | ALA | 371 | 49.813 | 93.282 | 75.375 |
| 2854 | OXT | ALA | 371 | 48.638 | 90.804 | 73.082 |

What is claimed is:

1. An isolated nucleic acid molecule consisting of a polynucleotide selected from the group consisting of (a) an isolated polynucleotide encoding a polypeptide consisting of amino acids 1 to 622 of SEQ ID NO:13; and (b) an isolated polynucleotide encoding a polypeptide consisting of amino acids 2 to 622 of SEQ ID NO:13, wherein said encoded polypeptide has arginyl-tRNA synthetase activity.

2. The isolated nucleic acid molecule of claim 1, wherein said polynucleotide is (a).

3. The isolated nucleic acid molecule of claim 1, wherein said polynucleotide consists of nucleotides 1 to 1866 of SEQ ID NO:2.

4. The isolated nucleic acid molecule of claim 1, wherein said polynucleotide is (b).

5. The isolated nucleic acid molecule of claim 1, wherein said polynucleotide consists of nucleotides 4 to 1866 of SEQ ID NO:2.

6. A recombinant vector comprising the isolated nucleic acid molecule of claim 1, wherein said recombinant vector expresses an isolated polypeptide consisting of amino acids 1 to 622 of SEQ ID NO:13 or an isolated polypeptide consisting of amino acids 2 to 622 of SEQ ID NO:13 when transfected into a host cell under conditions suitable for expression of said polypeptide.

7. An isolated recombinant host cell comprising the recombinant vector of claim 6.

8. A method of making an isolated polypeptide consisting of amino acids 1 to 622 of SEQ ID NO:13 or an isolated polypeptide consisting of amino acids 2 to 622 of SEQ ID NO:13, comprising:

(a) culturing the isolated recombinant host cell of claim 7 under conditions such that said polypeptide is expressed; and (b) recovering said polypeptide.

9. An isolated polynucleotide consisting of the complete complementary sequence of (a) or (b) of claim 1.

* * * * *

UNITED STATES PATENT AND TRADEMARK OFFICE

CERTIFICATE OF CORRECTION

PATENT NO. : 7,790,428 B2
APPLICATION NO. : 11/726434
DATED : September 7, 2010
INVENTOR(S) : Matthew Healy et al.

It is certified that error appears in the above-identified patent and that said Letters Patent is hereby corrected as shown below:

Col. 549, claim 1 – line 29 – add ":" after "of"

Col. 549, claim 3 – line 39 – change "claim 1" to "claim 2,"

Col. 549, claim 5 – line 44 – change "claim 1," to "claim 4"

Signed and Sealed this
Twelfth Day of April, 2011

David J. Kappos
*Director of the United States Patent and Trademark Office*

SEQUENCE LISTING

```
<160> NUMBER OF SEQ ID NOS: 256

<210> SEQ ID NO 1
<211> LENGTH: 1041
<212> TYPE: DNA
<213> ORGANISM: Candida albicans
<220> FEATURE:
<221> NAME/KEY: misc_feature
<223> OTHER INFORMATION: FCG5 or CaYLR100wORF

<400> SEQUENCE: 1

atgtcacttt taaaggattc tacagttgca gtcattaccg ggacatcttc aaatttagga      60

ttcaatatag ctgttcgttt gttggagggg cttcctgaca acaaagaaat tactcttgtt     120

gttacttcca gaacattacc aaaagtaaag gaagtgattt ctgatattaa aaaatatatt     180

gtggcaaaaa tcccaactaa agtaaacaag gtggaatttg actatttatt ggtggatttc     240

actgatatgg tatcaatttt atcagcatat tatgaattga ataaacgata caaacatatt     300

gattacttgt ttattaatgc ggcccaagga gtatacggag gcatagattg gactggcgca     360

gttctcgaag ttttgcaaag cccaattgag gcagtcacta atccaactta taaattacaa     420

aaagttggag tagaaagtgg cgataaattg ggattagtct ttcaagcaaa tgtgtttgga     480

ccatattatt ttatccacag aatcaaacac ttgttggaaa atggtgggaa aatagtgtgg     540

gtcagctcat taatgtcaag tccaaaatat ttgtctttca atgatttaca attattgaga     600

tcaccagcaa gctatgaagg ctcaaaaaga ttggttgact tgatgcattt tggaacttac     660

aacaagctag aaagagaaca tggaatcaaa cagtatttag ttcatcctgg gatattcaca     720

agtttctcgt ttttccaata tttgaacgtt ttcacatact atggtatgtt atttttattc     780

taccttgcaa gatttttagg gtcaccatat cacaatattt ctgggtatat tgctgcgaac     840

gctcctgttg ctgctgcttt aggtcaaact aaacaaaact gcaaaactgc ctcggcttgt     900

actagatctg gtaaagagta tttattagaa gaagagattg acagcactgg tctggacgac     960

gttgtcctgt atttggacac acttactaaa gagtgggacg aaaagttgaa ggatcaaata    1020

gtaaatacac gtcaaccttg a                                              1041
```

-continued

<210> SEQ ID NO 2
<211> LENGTH: 1869
<212> TYPE: DNA
<213> ORGANISM: Candida albicans
<220> FEATURE:
<221> NAME/KEY: misc_feature
<223> OTHER INFORMATION: FCG6 or CaYDR341cORF

<400> SEQUENCE: 2

```
atgtcagtcg aaacaattag tgatagtttg aaacaattgg gattaagtca accagcagcc      60
attgaaggta cccaccctca atataatgtg gttgatgtct ttagaaacta tatcgctgaa     120
gaattacatc gtatttcatc agttgacaaa tctattatca ttcaagcttt ggatacacca     180
aaagtattag atcaaggtga tattattgtt cctattccaa aattaagatt aaaaggaatc     240
aatcctaatg aaaaatccaa ggaatgggct gaaaatttca ataaagggaa attcatttct     300
gaaatcaaac ctcaaggagt gtttttacaa ttctattttg ctaaaacatt attgtataat     360
ttggtcattg aagatgtttt aaagagaaaa tcagattatg gttacttacc tttgggtgtt     420
ggtaaaaaag ccattgttga attctcgtct ccaaatattg ccaaaccttt ccatgctgga     480
catttaagat ctactattat aggtgggttc atttctaact tgtacgaaaa agttggctgg     540
gatgtcacca gaatcaatta tttgggagat tgggggaaac aatttggttt gttagctgtt     600
ggttttgaaa gatacggtga cgaatctaag ttagcttcag atccaatcaa ccacttgttt     660
gaagtttatg tcaagattaa tcaagatgtc accaaggaga caagtgaagc cactggtgaa     720
actccagcag aaaccattga tgcttctgaa caggatgaaa agaaaatcca atcctctacc     780
aatgaagaag ctagaagatt tttcagaaga atggaagatg gtgatgaatc agcattgaaa     840
atttgggcaa gattcagaga tttgtctatt gaaaaatatg ttgacactta tggtcgactt     900
aatattaaat atgatgttta ttctggtgaa tctcaagttc cacaagagaa aatgaaagaa     960
gctaccaaat tgttcgaaga taaaggtttg attgatattg accgtggtgc caaattaatt    1020
gacttgacta aatttaacaa aaaattgggt aaagcattag ttgaaaaatc agatggtact    1080
tccctttatt tgactcgtga tgttggtgaa gctattaagc gttatgaaac ctacaagttt    1140
gataagatga tttacgttat tgctgcccaa caagatttgc attgtgctca attctttgaa    1200
attttgaaac aaatgggatt cgaatgggcc cacaatttgg aacatgttaa ctttggtatg    1260
gtccaaggta tgagtaccag aaaaggtact gttgtgtttt tagataacat tttacaagaa    1320
accaaagaaa agatgcacga agttatgcag aaaaacgaag agaaatatgc tcaaatcgaa    1380
gacccagata agattgctga tttgattggt atttctgctg ttatgattca agatatgcaa    1440
tctaaacgta ttcacaatta cgaattcaaa tgggacagaa tgacttcatt tgaaggtgac    1500
actggtccat acttgcaata tgctcactct cgtttgtgtt ccatgcaaag aaaatcaggt    1560
atttctatag aggaattaga acatgccaac tttgatttgt tggttgaacc atgtgccagt    1620
gcattagcaa gaactttagc gcaataccg gacgttatta aaaaggctgt caaagggttg    1680
gaaccatcca caatcgttac ttatttgttc agtgtgacac atattgtctc ccaatgttac    1740
gatattttat gggtttctgg tcaagaaaag gatgttgcca ttgcaagatt ggctttatat    1800
gaagctgcta gacaagttat aaataacggt atgaccttgt taggtttgac tccagttaat    1860
cgtatgtaa                                                            1869
```

<210> SEQ ID NO 3
<211> LENGTH: 768
<212> TYPE: DNA

-continued

<213> ORGANISM: Candida albicans
<220> FEATURE:
<221> NAME/KEY: misc_feature
<223> OTHER INFORMATION: FCG7 or CaYLR022cORF

<400> SEQUENCE: 3
atggcggtga ttaatcaacc aaatagtcag atcagactta caaatgtttc cttagtccga 60
atgaaaaagg gaaagaaaag atttgagatt gcatgttatc aaaataaagt tcaagattgg 120
agactgaaag tggaaaagga tattgacgaa gtgttacaaa tcccacaagt tttcataaat 180
gtttccaaag gtcaagttgc taataatgac gatttacaaa aatgttttgg caccactaat 240
caagatgaaa ttatagctga aatcttaaac aaaggagaaa ttcagttgaa tgaaaaggaa 300
agaaatgcaa atttacaaca aaagcaaaat gaattcttaa atataatttc cactaaatgt 360
ataaatccaa gatctaaaaa gagatatcct ccaagcatga ttgaaaaggt attgaatgaa 420
gtcaaatttc atttgaatcc tactaaacca accaaaattc aagcattgga tgccatcaaa 480
ttattagttg aaaaacaaat catacctatt gccagagctc aaatgaaagt gagaattacg 540
ttatctaaaa aagcatactt aaagactttt caagatgaaa taaaacctgt tattgatcaa 600
attgtggagg aagataacaa tgggaaacaa tatgagattg ttggtattat agatcctata 660
aattatagag tcttggtcac attaattgaa aatacagatg gaagcaacaa agtcgctaaa 720
ggagaagggt ctatagaagt attagatatg tctgccataa aggaataa 768

<210> SEQ ID NO 4
<211> LENGTH: 879
<212> TYPE: DNA
<213> ORGANISM: Candida albicans
<220> FEATURE:
<221> NAME/KEY: misc_feature
<223> OTHER INFORMATION: FCG8 or CaYOL077cORF

<400> SEQUENCE: 4
atgtcagcta tctataaggc attacaatcc aaatcatcta aggaaacatc ggaaaaaacc 60
aaacatatta atagacaaag attattggtg atatcatctc gtggtattac ttataggcat 120
cgtcatttaa ttcaagattt attagcatta ttaccacacg ctagaaaaga accaaaattt 180
gattctaaaa aaaatttaca tcaattaaat gaagttgctg aattatacaa ttgtaataat 240
attttctttt ttgaatgtag aaaacatcaa gatttatatt tatggatttc aaaaccacca 300
aatggaccaa ctttaaaatt tcatattcaa aatttacata ctttagatga attgaatttc 360
actgggaatt gtttaaaagg ttcaagacca attttaagtt ttgataaaag ttttttagaa 420
aatgatcatt ataaattatt aaaagaaatg tttcttcaaa cttttggagt tccaccaaat 480
gctagaaaat caaaaccatt tattgatcat gtcatgactt tttctatagt tgatgggaaa 540
atttggattc gaaactatca aatcaatgaa actttggatg ttaaagaaaa tgataaaatt 600
gaagatgatg aagattatga tgttgatcaa ttgaatttag tggaaattgg tccaagatta 660
gtattgactt taatcaccgt tttagaagga tcattttctg gtccaaaaat atatgaaaat 720
aaacaatacg tttcaccaaa ctttgttaga gctcaattga aacaacaagc tgctgatcaa 780
gcaaaatcta gatctcaagc tgctttagaa agaaagatta aaaagagaaa ccaagttttg 840
aaagctgatc cattatccaa tgatgcttta tttaaatag 879

<210> SEQ ID NO 5
<211> LENGTH: 3129
<212> TYPE: DNA
<213> ORGANISM: Candida albicans -continued
<220> FEATURE:
<221> NAME/KEY: misc_feature
<223> OTHER INFORMATION: FCG10 or CaYNL132wORF

<400> SEQUENCE: 5
atgggtaaaa aagcaattga tgcacgtatt cctgccttga tacgtaatgg cgttcaagaa 60
aagcaaagat ctttttcat cattgtgggt gataaagctc gtaatcaatt accaaacttg 120
cattatttga tgatgagtgc tgatttgaag atgaataagt cagtattatg ggcatacaag 180
aaaaaattat taggcttcac ctcccacaga cagaagcgtg aagcaaaaat taagaaagac 240
ataaagcgtg gaattagaga agtcaacgaa caagatcctt ttgaagcatt tatatctaat 300
caacatatca gatatgttta ctacaaagaa actgaaaaaa tcttgggtaa cacttacgga 360
atgtgtattc tacaagattt tgaagccatc accccctaatt tgttggctag aacaattgaa 420
acagtcgaag gtggtggatt agttgttatc ttgctcaaga atatgacatc attgaagcag 480
ttatatacta tgtccatgga tatacattca agatacagaa ctgaagcaca tgatgatgtt 540
gttgccagat tcaatgaaag attcttactt tctttagggt cttgcgaaaa ttgtttagtt 600
gttgatgatg aattgaatgt cttacctatt tcagggggca aacatgttaa accattgcca 660
cctaaagacg acgacgaatt gactcctaat gccaaggaat taaaggagtt gaaagagagt 720
cttgctgacg tacaacctgc tgggtcatta gtggccttgt ccaaaactat aaatcaagca 780
caagcaattt tgacttttat tgatgtcatc tcagaaaaga cattgagaaa tacagtcaca 840
ttaactgcag gaagaggtcg tggtaaatct gctgctttag gtattgctat tgctgcagct 900
atttcccatg gatattccaa tatttttgtt acttcaccat cacctgaaaa cttgaagaca 960
ttgtttgaat ttattttcaa aggttttgat gcattaggat ataccgaaca tatggattat 1020
gacattattc agtctactaa tccatctttc aacaaagcta ttgtcagagt tgatgttaaa 1080
agagaacaca gacaaacgat tcagtacatt tctccaaatg atagtcatgt tttaggacaa 1140
gcagaattat tgattatcga tgaagcagca gccataccac ttccaatcgt gaaaaaattg 1200
atggggccct atttgatttt tatggcttct accattaatg ggtatgaagg tactggaaga 1260
tcattatcat tgaaattgat tcaacaattg agaactcagt ccaataatgc aacaccttca 1320
gaaactaccg tggtatccag agataagaaa tccaatgaaa ttactggagc tttgactaga 1380
acattgaaag aagttgtatt ggatgagcct attagatatg caccaggcga ccctattgaa 1440
aaatggttaa ataaattgct ttgtcttgat gtttcattat ctaaaaatgc caagtttgca 1500
acaaagggca ctccacatcc atctcagtgt caacttttct atgtaaatag agatactttg 1560
ttctcctatc accctgtctc tgaagcattc ttacaaaaga tgatggcatt gtatgttgct 1620
tctcattaca aaaattcacc taatgattta caattgatga gtgatgctcc agcacatcag 1680
ttattcgtgt tgttacctcc aatagaggca ggtgataata gagtacctga cccattgtgt 1740
gttattcaat tagcattgga gggtgaaata tccaaagaaa gtgtaagaaa atctttatct 1800
cgtggacaaa gagccggagg ggatttgata ccttggttaa tctcacaaca attccaagac 1860
gaagaatttg cctcattgtc aggtgcaaga gttgttagaa tcgctacaaa ccccgaatac 1920
tctggtatgg gttatgggtc tagagcaatg gaattattga gggactatta ctccggtaag 1980
tttaccgata tcagtgaatc caccgaattg aatgatcaca caattacaag agtcactgat 2040
agcgaattgg ccaacgcatc actaaaagat gaaattaagt tgagagacgt taagacatta 2100
cctccgttgt tattgaaatt atcagaaaaa gccccttact acttgcacta cttgggtgtc 2160
tcttatggtt tcacgtctca attacacaaa ttctggaaga aagcagggtt cactccagtt 2220

-continued

```
tatttgagac aaacacctaa tgaattaact ggggaacata cttcggttgt tataagtgtt   2280

ttaccaggaa gagaagataa atggttacat gaattctcga aagatttcca caaaagattt   2340

ttgagtttgt tatcatatga attcaaaaaa ttccaggctt cccaagcttt aagcattatt   2400

gaagctgcag agcaaggcga aggtgatgaa actactagtc aaaaattaac caaagaacaa   2460

ttagatctgt tgttgtctcc atttgattta aagagattgg actcgtatgc caataattta   2520

ttggattatc atgtaattgt tgatatgtta ccactaatct cccaattgtt tttttcaaaa   2580

aaaactgggc aagatatcag tttatcatca gttcaatctg ccattttatt ggctattggg   2640

ttgcagcata aagacatgga ccagatagca aaagagttga acttaccaac gaaccaagcc   2700

atggcaatgt ttgctaaaat tattcgtaaa ttctcaacct atttcagaaa agttctcagt   2760

aaagcaattg aagaaagtat gccagattta gaagatgaga atgtcgacgc catgaatggt   2820

aaggaaacgg aacaaatcga ttataaagcc attgagcaga aattgcaaga tgacttggaa   2880

gaggctggtg atgaggcaat aaaagaaatg agagaaaaac aacgtgaatt gattaatgct   2940

cttaatttag ataaatatgc tattgcagaa gatgctgaat gggatgaaaa atcaatggat   3000

aaagctacta agggaaaagg taatgttgtt agtattaaga gtgggaaaag gaaatctaaa   3060

gaaaatgcta atgatattta tgagaaagaa atgaaagcag ttaagaaatc aaagaaatca   3120

aaaaaataa                                                           3129
```

```
<210> SEQ ID NO 6
<211> LENGTH: 2253
<212> TYPE: DNA
<213> ORGANISM: Candida albicans
<220> FEATURE:
<221> NAME/KEY: misc_feature
<223> OTHER INFORMATION: FCG12 or CaYGR145wORF

<400> SEQUENCE: 6
```

```
atggttttaa aatcaacaac tgcagggaat gtatcagtat atcaagtttc tggtaccaat     60

gtttctcgat cattacctga ttggatagac aagaaacgta aacgagctct taaacatgat    120

ttagaatatc aaaatagaat agaattaatt caagattttg aattcagtga agcatcaaat    180

aaaattaaag tgactaatga tggacaatat tgtatggcca ccgggactta taaaccacaa    240

attcatgttt atgaatttgc caatttatca ttaaaatttg atcgtcatac taatgtggaa    300

aacattgatt ttttaatttt aagtaatgat tggactaaaa gtgttcattt acaatgtgat    360

agaagtattg aatttcaaac tgctggtgga gtacattatc gtactagaat acctaaattt    420

ggtcgatgtt tgacatataa tccaattaat tgtgatttga tcgttggtag ttcaagtgat    480

gaattatatc gattgaattt agatcaagga aggtttttat ccccattgaa attggatatg    540

actgatggtg gcaatattga cagtggatgt aacgccgttg atattaattc tatgcatggt    600

ttaataagtg ctgggttaga tgatggtacc gttgaatttt gggatccaag atcaaaacaa    660

agagccggga aactatttgt tagtgatcaa ttaattaata gtactaataa cactgaacaa    720

agttcttgtg gtattacatc acttgcattc cgacctcaag atgcattaaa ttttgcttgt    780

gggacaagta atggacaaac attattatat gatttacgtg catctgaacc ctatcaaatt    840

aaagatcaag gatatgggta tgatattaaa aaaatcattt ggtgtcaaga ttcattaaaa    900

ccagaaatga ttttaactag tgataaaaga attgtgaaaa tttgggatca tactaatggt    960

aaatcatttg cctccatgga accgaccgtt gatatcaatg atatttgtca tattcctcaa   1020

tcaggaatgt ttttcatggc taacgaaggg atgcccatgc atacttatta tatccctaat   1080
```

-continued

```
ttgggttcag cacctaattg gtgttcattc ttggataatg ttactgaaga attggaggaa   1140
aaaccttcaa attcaattta tcctaccttt aaatttatta ctcgtgatga aatggtgaaa   1200
ttgaatttga ctcatttgat tgggatcaaa gttttacgtt cttatatgca tgggtttttc   1260
attaatactg aattatatga taaagtcaat ttaatcagta atcccaattc aatttatgat   1320
caacgtaaac gtgaaattgc taacaaaatc aatgaagaaa gaaaatcaag aattcttact   1380
agttccaatg gtaatgactt accaacgaaa attaaagtca ataaagattt ggtcaataaa   1440
ttacaaacta aatttgctga aaatggtact cctgatggta atgccaatgg tgccaccgat   1500
tatgttgaat caattgttaa tgatgatcgt tttagagaaa tgtttgaaaa ccctgatttt   1560
gaaattgatg aagaatctca tgaatataaa caattgaatc cggttaaatc aaccaaagat   1620
ataaccacca ccaatactgg tactactaat tcaagaggaa gaggattgac tgcagctgaa   1680
gagtcagatg aagaaagatt gaacatgaaa gattcacacc acactggatt agattcagat   1740
gaatcagatg aagaatcaga ttctgaatct gaagaacaat ctgaagatga agctaaatca   1800
gccgaaacta gagaaagagt cggtaaggaa ttgaataaaa tacgtcaatc aaaacaaaaa   1860
caacaacagc aagattcaaa gaaattccaa aatgaaatga aaatcttatc tcaacaatca   1920
tcttcatctt catcatcctt ggcaaatacc gagaaggcat cagtatcatt tggctctcaa   1980
gtaaacaaat taaacaaaat ttctaaacag aacaaaaata ataatagtat tagtaatgct   2040
aaagatgcta gattacgtcg acatgctcgt ggtgaagctg aattgacatt tgtgccccaa   2100
aaatcaaaat caaaatcaac taaactgaaa tttaataaca accacagtga tgatgaaaag   2160
ctggatagtg gtaagactaa agatagtggt agaactaaac agagatttga aggtcgtaga   2220
atagcatcca agaataagtt tagaggtatg taa                                2253
```

<210> SEQ ID NO 7
<211> LENGTH: 807
<212> TYPE: DNA
<213> ORGANISM: Candida albicans
<220> FEATURE:
<221> NAME/KEY: misc_feature
<223> OTHER INFORMATION: FCG13 or CaYDR412wORF

<400> SEQUENCE: 7

```
atggcaggat ttaaaaagaa tagagaaatt ttaactggag gtaagaaata tatccaacaa     60
aaacaaaaga aacatttagt tgatgaagtt gtatttgata aagaatcccg tcatgaatat    120
ttaactggtt tccataaacg taaattacaa cgacagaaaa aagctcaaga atttcataaa    180
gaacaagaac ggttagctaa aattgaagaa cgtaaacaat taaaacaaga acgtgaacga    240
gatttacaaa atcaattaca acaatttaag aaaactgctc aagaaattgc tgccataaat    300
aatgatattg gatttgatca atcagatgac aataatgaca atgataatga aaatgaagaa    360
tggagtggat tccaagaaga tgaagaagga gaaggagaag aagtaactga tgaagatgac    420
gaagataagg aaaaaccttt gaaggggatt ttacatcata ctgaaatata taaacaagat    480
ccctcattat caaatattac taataatggt gccataatag atgatgaaac aacagtagtg    540
gtagaatcat tagataatcc aaatgctgtt gatactgaag aaaaacttca acaattggct    600
aaattaaata atgttaatct tgataaatct gatcaaattt tagaaaaatc tattgaacga    660
gctaaaaatt atgctgtgat atgtggagtt gctaaaccta atccaatcaa acaaaagaag    720
aagaaattca gatatttaac aaaagcagaa cgtagagaaa atgttcgtaa agagaaatca    780
aaatcaaaat caaagggcaa gaagtaa                                        807
```

<210> SEQ ID NO 8
<211> LENGTH: 1116
<212> TYPE: DNA
<213> ORGANISM: Candida albicans
<220> FEATURE:
<221> NAME/KEY: misc_feature
<223> OTHER INFORMATION: FCG14 or CaYOL010wORF

<400> SEQUENCE: 8

```
atgtccagtg ttgcttccaa aaagataata acatttgaag ggcacaggaa tttcagatta     60

agattggtgc tagccacatt atctggaaaa cctatcaaaa ttactaaaat tcgttctcaa    120

gacttgaacc caggtttgaa agatcatgaa gtttcttttc ttagattact agaagccgta    180

accaatggat cccatattga aatttcatat accggtacaa caatcattta tagacctggg    240

attataatag gtggagatct tacccacaat tgtcctgata caaaatctat tggatatttc    300

attgaaccaa tgttaatgtt cccgcttttt tcgaaaaaaa aattcagcat tattttcaaa    360

ggattgacta atatagcagg taatgacact ggagttgatg ccattaaatg gggggttatta   420

ccagtaatgg aaaagtttgg tgtgagagaa gtctcgttac atattttgaa gagaggatca    480

gccccccttgg gtggaggaga agtgcatttg ttatgtagct ctttgattcc acaaccattg   540

actattcacg cgttggacat tcccaagttc tctgccatta gaggagttgc ttattgtaca    600

agagtttccc catcgattgt taatagaatg attgattcag caagagcagt attgaagcca    660

acaggatgcg aggttaatat caccgctgat gtctggagag gagaaaattc aggaaaatca    720

ccagggtttg gcatcacctt agtcgctgag ctgaagcgtg gatggagaat tgttaccgag    780

aatgttggtt cggctgggag tttacctgaa gattctggtg agttaacagc ttaccaatta    840

ctcgaagaaa tatcaaatag tggagttgtt ggaagatacc agttgccatt agcacttgtg    900

tatatgacta ttggaaaaga agacattggt cgtttgaaac tccaaaaaag tgagatcgac    960

gagaatttgg tgtccgtgct cagagatatt caagaagttt ttggcacaga agctttcttc   1020

aaagatgatg cagaagagct tgatagtgat gataaattca tgacagtttc tatcaaggga   1080

gtagggttca ccaatgtttc taaaaaaata gcttga                             1116
```

<210> SEQ ID NO 9
<211> LENGTH: 774
<212> TYPE: DNA
<213> ORGANISM: Candida albicans
<220> FEATURE:
<221> NAME/KEY: misc_feature
<223> OTHER INFORMATION: FCG15 or CaYOR004wORF

<400> SEQUENCE: 9

```
atgagacaaa agcgtgccaa ggcctataag aaacaaatga gtgtgtatgt ccacgcattc     60

aaattcagag aaccatacca aataatagta gacaatgaac tcatcaccac ttgtcaatca    120

gcatcatttg acattaataa agggtttact cgaactatcc aagcagaaaa caaacccatg    180

attactcaat gttgtatcca agcattatat gatactaaga atcaaccagc aatagatatt    240

gctaaatcat ttgaacgaag aaaatgtaat catcgtgaag ccatcgatcc tagtcaatgt    300

attgaatcaa tcgttaatat taaaggacaa aataaacatc gatatatcgt tgccagtcaa    360

gatttacaat tacgtaaaaa attgcggaaa atccctggag taccattgat ttatatgaat    420

cgatcagtga tggttatgga accgatcagt gatgttagta atcaatataa tatgaattat    480

gaatcgaaaa aattgaccgg aggattgaat gatattgaag ctgggaaatt ggaaaagcaa    540
```

-continued

```
aatgaaggtg aagatgggga tggggatgaa ctggaagtta aaaagaagaa aagaaaagga    600

cctaaagaac caaacccatt aagtgtcaaa aagaagaaaa cagataatgc aactgctgcc    660

agtactaatc aagagcagaa aaagaaacca aatagaagaa aaagacatgc gcaagtcaaa    720

agcagaagag aaggaagacc aagaacagga gcaagtgaac gaagcaacaa ctaa          774
```

<210> SEQ ID NO 10
<211> LENGTH: 1401
<212> TYPE: DNA
<213> ORGANISM: Candida albicans
<220> FEATURE:
<221> NAME/KEY: misc_feature
<223> OTHER INFORMATION: FCG16 or CaYOR056cORF

<400> SEQUENCE: 10

```
atgtctgaaa caaaaaatat tgagtctttg atttcggatg ctggtccatt gattacacag     60

ccagctacta ctttgcagca atacgccact gcatattata ccacaccagg ggtgcatagt    120

gagttaaaag atgaatatgc tagacaacaa ttagcaattt ggggtgatag tttaaaaatt    180

aaacagccaa aacaggaata tattgataga gttgtcaagt ttgcgaaatt aacaggtgat    240

tattctgtgt tgtcagtgaa cgatttgcac attgttgcgt tagcatatga gttggagtgt    300

ttgaacaatg gagaagacaa cttaagaagt tttccaggtg aagtcttgaa gaatcaacaa    360

gctgaaaatg aaaatggctc aaacaaaatg tcaaacataa taggggatga cgatgggttc    420

gtagttgcca caaaaagaag aggaggtaga agacaaagag agaaggcaga gttaaggaag    480

aaagggttgt tgccaacgtt ttccccaaaa ccaaagggtg gcctggaaac agaagaacct    540

aatgaactgt caaatgataa aactatagat gaaacacctc aaacagactt gatcaaaggt    600

gttgatgtgc aagaacagga atcccaagaa gaaccagtat ctgaatctaa tactgttggt    660

ctagatgaaa taactgaaga atacaatgaa gacgatgatg acggggaatg gattactcca    720

gaaaatttac aagaggagat aataaaagac aaaaatgaac aagtccaaga gtctaatacc    780

aatggtccgc ttattaaagt ggctcttgca actggtgatt ttgcctgtca aaatgtggcc    840

atgcaaattg gtataaagtt attgaacgcg atgtcaggga aacagattac tcgggttcgt    900

aattacatgt atagatgcca tgcttgtttc agattgacgc caatgagtaa agatggtaga    960

ccgaaacatt tttgtccaaa atgtggtggc aatacattat tgagatgtgc tgtatctgtc   1020

gacaacaaga cgggaaaaat aactcctcat ttaaaacaga actttcagtg gatcagacgt   1080

ggtgaacgat actcgttacc atcaccattg agtaagaacc aaaagaaatt acaaggtaac   1140

ggaggctatc agcataataa agaaaaccgt cacaagtcat tgcagacacc attgatattg   1200

aatgaagacc agaaggagta tcaacgggcg ttaaaaaatg acgagtggga aagaaaacaa   1260

caagataaaa tgttacaaga atggattgga ggaggcagtg ctgacaattt tgtttctcct   1320

tttgggaaca cgattagaaa ctctggtgtc aaagtgggac gcggaagata tgcaaactct   1380

tccaaaaaga aaagaaagta g                                             1401
```

<210> SEQ ID NO 11
<211> LENGTH: 588
<212> TYPE: DNA
<213> ORGANISM: Candida albicans
<220> FEATURE:
<221> NAME/KEY: misc_feature
<223> OTHER INFORMATION: FCG17 or CaYLR009wORF

<400> SEQUENCE: 11

```
atgaggattt atcaatgtca tttttgttca tcaccggtat atccattaca tgggatcaca     60
```

-continued

```
tttgtaagaa atgatgccaa agaattccgt ttctgtcgtt ctaaatgtca taaagcattc    120

aaacaacgta gaaacccaag aaaattacgt tggactaaag catttagaaa agctgctggt    180

aaagaattgg tggttgattc tacattaaca tttgctgcta gaagaaatgt tccagttaga    240

tataatagag atttggttgc cactactttg aaaggtatga gtagaattga agaaattaga    300

caaagaagag aaagagcatt ctataagaat agaatgaagg gtaataaaga aagacagttg    360

gctgctgata gaaaattggt tgctgataat ccagaattat taagattaag agaagttgaa    420

ttaagaagaa aagccgagaa attagctgct aaagaaaatg ccatggaaga agatgaagaa    480

acagaggttg aagaggaagg agaaggtgat gaagaaatga taagtggaga ggaagaatgg    540

gaaagtgaag atgaaagtga aagggaaagt gacacaaaaa cgtgttaa                588


<210> SEQ ID NO 12
<211> LENGTH: 346
<212> TYPE: PRT
<213> ORGANISM: Candida albicans
<220> FEATURE:
<221> NAME/KEY: MISC_FEATURE
<223> OTHER INFORMATION: FCG5 or CaYLR100w

<400> SEQUENCE: 12

Met Ser Leu Leu Lys Asp Ser Thr Val Ala Val Ile Thr Gly Thr Ser
1               5                   10                  15

Ser Asn Leu Gly Phe Asn Ile Ala Val Arg Leu Leu Glu Gly Leu Pro
            20                  25                  30

Asp Asn Lys Glu Ile Thr Leu Val Val Thr Ser Arg Thr Leu Pro Lys
        35                  40                  45

Val Lys Glu Val Ile Ser Asp Ile Lys Lys Tyr Ile Val Ala Lys Ile
    50                  55                  60

Pro Thr Lys Val Asn Lys Val Glu Phe Asp Tyr Leu Leu Val Asp Phe
65                  70                  75                  80

Thr Asp Met Val Ser Ile Leu Ser Ala Tyr Tyr Glu Leu Asn Lys Arg
                85                  90                  95

Tyr Lys His Ile Asp Tyr Leu Phe Ile Asn Ala Ala Gln Gly Val Tyr
            100                 105                 110

Gly Gly Ile Asp Trp Thr Gly Ala Val Leu Glu Val Leu Gln Ser Pro
        115                 120                 125

Ile Glu Ala Val Thr Asn Pro Thr Tyr Lys Leu Gln Lys Val Gly Val
    130                 135                 140

Glu Ser Gly Asp Lys Leu Gly Leu Val Phe Gln Ala Asn Val Phe Gly
145                 150                 155                 160

Pro Tyr Tyr Phe Ile His Arg Ile Lys His Leu Leu Glu Asn Gly Gly
                165                 170                 175

Lys Ile Val Trp Val Ser Ser Leu Met Ser Ser Pro Lys Tyr Leu Ser
            180                 185                 190

Phe Asn Asp Leu Gln Leu Leu Arg Ser Pro Ala Ser Tyr Glu Gly Ser
        195                 200                 205

Lys Arg Leu Val Asp Leu Met His Phe Gly Thr Tyr Asn Lys Leu Glu
    210                 215                 220

Arg Glu His Gly Ile Lys Gln Tyr Leu Val His Pro Gly Ile Phe Thr
225                 230                 235                 240

Ser Phe Ser Phe Phe Gln Tyr Leu Asn Val Phe Thr Tyr Tyr Gly Met
                245                 250                 255

Leu Phe Leu Phe Tyr Leu Ala Arg Phe Leu Gly Ser Pro Tyr His Asn
```

-continued

```
            260                 265                 270

Ile Ser Gly Tyr Ile Ala Ala Asn Ala Pro Val Ala Ala Ala Leu Gly
        275                 280                 285

Gln Thr Lys Gln Asn Cys Lys Thr Ala Ser Ala Cys Thr Arg Ser Gly
    290                 295                 300

Lys Glu Tyr Leu Leu Glu Glu Glu Ile Asp Ser Thr Gly Leu Asp Asp
305                 310                 315                 320

Val Val Leu Tyr Leu Asp Thr Leu Thr Lys Glu Trp Asp Glu Lys Leu
                325                 330                 335

Lys Asp Gln Ile Val Asn Thr Arg Gln Pro
            340                 345


<210> SEQ ID NO 13
<211> LENGTH: 622
<212> TYPE: PRT
<213> ORGANISM: Candida albicans
<220> FEATURE:
<221> NAME/KEY: MISC_FEATURE
<223> OTHER INFORMATION: FCG6 or CaYDR341c

<400> SEQUENCE: 13

Met Ser Val Glu Thr Ile Ser Asp Ser Leu Lys Gln Leu Gly Leu Ser
1               5                   10                  15

Gln Pro Ala Ala Ile Glu Gly Thr His Pro Gln Tyr Asn Val Val Asp
            20                  25                  30

Val Phe Arg Asn Tyr Ile Ala Glu Glu Leu His Arg Ile Ser Ser Val
        35                  40                  45

Asp Lys Ser Ile Ile Ile Gln Ala Leu Asp Thr Pro Lys Val Leu Asp
    50                  55                  60

Gln Gly Asp Ile Ile Val Pro Ile Pro Lys Leu Arg Leu Lys Gly Ile
65                  70                  75                  80

Asn Pro Asn Glu Lys Ser Lys Glu Trp Ala Glu Asn Phe Asn Lys Gly
                85                  90                  95

Lys Phe Ile Ser Glu Ile Lys Pro Gln Gly Val Phe Leu Gln Phe Tyr
            100                 105                 110

Phe Ala Lys Thr Leu Leu Tyr Asn Leu Val Ile Glu Asp Val Leu Lys
        115                 120                 125

Arg Lys Ser Asp Tyr Gly Tyr Leu Pro Leu Gly Val Gly Lys Lys Ala
    130                 135                 140

Ile Val Glu Phe Ser Ser Pro Asn Ile Ala Lys Pro Phe His Ala Gly
145                 150                 155                 160

His Leu Arg Ser Thr Ile Ile Gly Gly Phe Ile Ser Asn Leu Tyr Glu
                165                 170                 175

Lys Val Gly Trp Asp Val Thr Arg Ile Asn Tyr Leu Gly Asp Trp Gly
            180                 185                 190

Lys Gln Phe Gly Leu Leu Ala Val Gly Phe Glu Arg Tyr Gly Asp Glu
        195                 200                 205

Ser Lys Leu Ala Ser Asp Pro Ile Asn His Leu Phe Glu Val Tyr Val
    210                 215                 220

Lys Ile Asn Gln Asp Val Thr Lys Glu Thr Ser Glu Ala Thr Gly Glu
225                 230                 235                 240

Thr Pro Ala Glu Thr Ile Asp Ala Ser Glu Gln Asp Glu Lys Lys Ile
                245                 250                 255

Gln Ser Ser Thr Asn Glu Glu Ala Arg Arg Phe Phe Arg Arg Met Glu
            260                 265                 270
```

-continued

```
Asp Gly Asp Glu Ser Ala Leu Lys Ile Trp Ala Arg Phe Arg Asp Leu
        275                 280                 285

Ser Ile Glu Lys Tyr Val Asp Thr Tyr Gly Arg Leu Asn Ile Lys Tyr
    290                 295                 300

Asp Val Tyr Ser Gly Glu Ser Gln Val Pro Gln Glu Lys Met Lys Glu
305                 310                 315                 320

Ala Thr Lys Leu Phe Glu Asp Lys Gly Leu Ile Asp Ile Asp Arg Gly
                325                 330                 335

Ala Lys Leu Ile Asp Leu Thr Lys Phe Asn Lys Lys Leu Gly Lys Ala
            340                 345                 350

Leu Val Glu Lys Ser Asp Gly Thr Ser Leu Tyr Leu Thr Arg Asp Val
        355                 360                 365

Gly Glu Ala Ile Lys Arg Tyr Glu Thr Tyr Lys Phe Asp Lys Met Ile
    370                 375                 380

Tyr Val Ile Ala Ala Gln Gln Asp Leu His Cys Ala Gln Phe Phe Glu
385                 390                 395                 400

Ile Leu Lys Gln Met Gly Phe Glu Trp Ala His Asn Leu Glu His Val
                405                 410                 415

Asn Phe Gly Met Val Gln Gly Met Ser Thr Arg Lys Gly Thr Val Val
            420                 425                 430

Phe Leu Asp Asn Ile Leu Gln Glu Thr Lys Glu Lys Met His Glu Val
        435                 440                 445

Met Gln Lys Asn Glu Glu Lys Tyr Ala Gln Ile Glu Asp Pro Asp Lys
    450                 455                 460

Ile Ala Asp Leu Ile Gly Ile Ser Ala Val Met Ile Gln Asp Met Gln
465                 470                 475                 480

Ser Lys Arg Ile His Asn Tyr Glu Phe Lys Trp Asp Arg Met Thr Ser
                485                 490                 495

Phe Glu Gly Asp Thr Gly Pro Tyr Leu Gln Tyr Ala His Ser Arg Leu
            500                 505                 510

Cys Ser Met Gln Arg Lys Ser Gly Ile Ser Ile Glu Glu Leu Glu His
        515                 520                 525

Ala Asn Phe Asp Leu Leu Val Glu Pro Cys Ala Ser Ala Leu Ala Arg
    530                 535                 540

Thr Leu Ala Gln Tyr Pro Asp Val Ile Lys Lys Ala Val Lys Gly Leu
545                 550                 555                 560

Glu Pro Ser Thr Ile Val Thr Tyr Leu Phe Ser Val Thr His Ile Val
                565                 570                 575

Ser Gln Cys Tyr Asp Ile Leu Trp Val Ser Gly Gln Glu Lys Asp Val
            580                 585                 590

Ala Ile Ala Arg Leu Ala Leu Tyr Glu Ala Ala Arg Gln Val Ile Asn
        595                 600                 605

Asn Gly Met Thr Leu Leu Gly Leu Thr Pro Val Asn Arg Met
    610                 615                 620


<210> SEQ ID NO 14
<211> LENGTH: 255
<212> TYPE: PRT
<213> ORGANISM: Candida albicans
<220> FEATURE:
<221> NAME/KEY: MISC_FEATURE
<223> OTHER INFORMATION: FCG7 or CaYLR022c

<400> SEQUENCE: 14

Met Ala Val Ile Asn Gln Pro Asn Ser Gln Ile Arg Leu Thr Asn Val
1               5                   10                  15
```

Ser Leu Val Arg Met Lys Lys Gly Lys Lys Arg Phe Glu Ile Ala Cys
20 25 30

Tyr Gln Asn Lys Val Gln Asp Trp Arg Leu Lys Val Glu Lys Asp Ile
35 40 45

Asp Glu Val Leu Gln Ile Pro Gln Val Phe Ile Asn Val Ser Lys Gly
50 55 60

Gln Val Ala Asn Asn Asp Asp Leu Gln Lys Cys Phe Gly Thr Thr Asn
65 70 75 80

Gln Asp Glu Ile Ile Ala Glu Ile Leu Asn Lys Gly Glu Ile Gln Leu
85 90 95

Asn Glu Lys Glu Arg Asn Ala Asn Leu Gln Gln Lys Gln Asn Glu Phe
100 105 110

Leu Asn Ile Ile Ser Thr Lys Cys Ile Asn Pro Arg Ser Lys Lys Arg
115 120 125

Tyr Pro Pro Ser Met Ile Glu Lys Val Leu Asn Glu Val Lys Phe His
130 135 140

Leu Asn Pro Thr Lys Pro Thr Lys Ile Gln Ala Leu Asp Ala Ile Lys
145 150 155 160

Leu Leu Val Glu Lys Gln Ile Ile Pro Ile Ala Arg Ala Gln Met Lys
165 170 175

Val Arg Ile Thr Leu Ser Lys Lys Ala Tyr Leu Lys Thr Phe Gln Asp
180 185 190

Glu Ile Lys Pro Val Ile Asp Gln Ile Val Glu Glu Asp Asn Asn Gly
195 200 205

Lys Gln Tyr Glu Ile Val Gly Ile Ile Asp Pro Ile Asn Tyr Arg Val
210 215 220

Leu Val Thr Leu Ile Glu Asn Thr Asp Gly Ser Asn Lys Val Ala Lys
225 230 235 240

Gly Glu Gly Ser Ile Glu Val Leu Asp Met Ser Ala Ile Lys Glu
245 250 255

<210> SEQ ID NO 15
<211> LENGTH: 292
<212> TYPE: PRT
<213> ORGANISM: Candida albicans
<220> FEATURE:
<221> NAME/KEY: MISC_FEATURE
<223> OTHER INFORMATION: <FCG8 or CaYOL077c

<400> SEQUENCE: 15

Met Ser Ala Ile Tyr Lys Ala Leu Gln Ser Lys Ser Ser Lys Glu Thr
1 5 10 15

Ser Glu Lys Thr Lys His Ile Asn Arg Gln Arg Leu Leu Val Ile Ser
20 25 30

Ser Arg Gly Ile Thr Tyr Arg His Arg His Leu Ile Gln Asp Leu Leu
35 40 45

Ala Leu Leu Pro His Ala Arg Lys Glu Pro Lys Phe Asp Ser Lys Lys
50 55 60

Asn Leu His Gln Leu Asn Glu Val Ala Glu Leu Tyr Asn Cys Asn Asn
65 70 75 80

Ile Phe Phe Phe Glu Cys Arg Lys His Gln Asp Leu Tyr Leu Trp Ile
85 90 95

Ser Lys Pro Pro Asn Gly Pro Thr Leu Lys Phe His Ile Gln Asn Leu
100 105 110

His Thr Leu Asp Glu Leu Asn Phe Thr Gly Asn Cys Leu Lys Gly Ser

-continued

```
        115                 120                 125

Arg Pro Ile Leu Ser Phe Asp Lys Ser Phe Leu Glu Asn Asp His Tyr
    130                 135                 140

Lys Leu Leu Lys Glu Met Phe Leu Gln Thr Phe Gly Val Pro Pro Asn
145                 150                 155                 160

Ala Arg Lys Ser Lys Pro Phe Ile Asp His Val Met Thr Phe Ser Ile
                165                 170                 175

Val Asp Gly Lys Ile Trp Ile Arg Asn Tyr Gln Ile Asn Glu Thr Leu
            180                 185                 190

Asp Val Lys Glu Asn Asp Lys Ile Glu Asp Asp Glu Asp Tyr Asp Val
        195                 200                 205

Asp Gln Leu Asn Leu Val Glu Ile Gly Pro Arg Leu Val Leu Thr Leu
    210                 215                 220

Ile Thr Val Leu Glu Gly Ser Phe Ser Gly Pro Lys Ile Tyr Glu Asn
225                 230                 235                 240

Lys Gln Tyr Val Ser Pro Asn Phe Val Arg Ala Gln Leu Lys Gln Gln
                245                 250                 255

Ala Ala Asp Gln Ala Lys Ser Arg Ser Gln Ala Ala Leu Glu Arg Lys
            260                 265                 270

Ile Lys Lys Arg Asn Gln Val Leu Lys Ala Asp Pro Leu Ser Asn Asp
        275                 280                 285

Ala Leu Phe Lys
    290


<210> SEQ ID NO 16
<211> LENGTH: 1042
<212> TYPE: PRT
<213> ORGANISM: Candida albicans
<220> FEATURE:
<221> NAME/KEY: MISC_FEATURE
<223> OTHER INFORMATION: FCG10 or CaYNL132w

<400> SEQUENCE: 16

Met Gly Lys Lys Ala Ile Asp Ala Arg Ile Pro Ala Leu Ile Arg Asn
1               5                   10                  15

Gly Val Gln Glu Lys Gln Arg Ser Phe Phe Ile Ile Val Gly Asp Lys
            20                  25                  30

Ala Arg Asn Gln Leu Pro Asn Leu His Tyr Leu Met Met Ser Ala Asp
        35                  40                  45

Leu Lys Met Asn Lys Ser Val Leu Trp Ala Tyr Lys Lys Lys Leu Leu
    50                  55                  60

Gly Phe Thr Ser His Arg Gln Lys Arg Glu Ala Lys Ile Lys Lys Asp
65                  70                  75                  80

Ile Lys Arg Gly Ile Arg Glu Val Asn Glu Gln Asp Pro Phe Glu Ala
                85                  90                  95

Phe Ile Ser Asn Gln His Ile Arg Tyr Val Tyr Tyr Lys Glu Thr Glu
            100                 105                 110

Lys Ile Leu Gly Asn Thr Tyr Gly Met Cys Ile Leu Gln Asp Phe Glu
        115                 120                 125

Ala Ile Thr Pro Asn Leu Leu Ala Arg Thr Ile Glu Thr Val Glu Gly
    130                 135                 140

Gly Gly Leu Val Val Ile Leu Leu Lys Asn Met Thr Ser Leu Lys Gln
145                 150                 155                 160

Leu Tyr Thr Met Ser Met Asp Ile His Ser Arg Tyr Arg Thr Glu Ala
                165                 170                 175
```

-continued

```
His Asp Asp Val Val Ala Arg Phe Asn Glu Arg Phe Leu Leu Ser Leu
            180                 185                 190

Gly Ser Cys Glu Asn Cys Leu Val Val Asp Asp Glu Leu Asn Val Leu
        195                 200                 205

Pro Ile Ser Gly Gly Lys His Val Lys Pro Leu Pro Pro Lys Asp Asp
    210                 215                 220

Asp Glu Leu Thr Pro Asn Ala Lys Glu Leu Lys Glu Leu Lys Glu Ser
225                 230                 235                 240

Leu Ala Asp Val Gln Pro Ala Gly Ser Leu Val Ala Leu Ser Lys Thr
                245                 250                 255

Ile Asn Gln Ala Gln Ala Ile Leu Thr Phe Ile Asp Val Ile Ser Glu
            260                 265                 270

Lys Thr Leu Arg Asn Thr Val Thr Leu Thr Ala Gly Arg Gly Arg Gly
        275                 280                 285

Lys Ser Ala Ala Leu Gly Ile Ala Ile Ala Ala Ala Ile Ser His Gly
    290                 295                 300

Tyr Ser Asn Ile Phe Val Thr Ser Pro Ser Pro Glu Asn Leu Lys Thr
305                 310                 315                 320

Leu Phe Glu Phe Ile Phe Lys Gly Phe Asp Ala Leu Gly Tyr Thr Glu
                325                 330                 335

His Met Asp Tyr Asp Ile Ile Gln Ser Thr Asn Pro Ser Phe Asn Lys
            340                 345                 350

Ala Ile Val Arg Val Asp Val Lys Arg Glu His Arg Gln Thr Ile Gln
        355                 360                 365

Tyr Ile Ser Pro Asn Asp Ser His Val Leu Gly Gln Ala Glu Leu Leu
    370                 375                 380

Ile Ile Asp Glu Ala Ala Ala Ile Pro Leu Pro Ile Val Lys Lys Leu
385                 390                 395                 400

Met Gly Pro Tyr Leu Ile Phe Met Ala Ser Thr Ile Asn Gly Tyr Glu
                405                 410                 415

Gly Thr Gly Arg Ser Leu Ser Leu Lys Leu Ile Gln Gln Leu Arg Thr
            420                 425                 430

Gln Ser Asn Asn Ala Thr Pro Ser Glu Thr Thr Val Val Ser Arg Asp
        435                 440                 445

Lys Lys Ser Asn Glu Ile Thr Gly Ala Leu Thr Arg Thr Leu Lys Glu
    450                 455                 460

Val Val Leu Asp Glu Pro Ile Arg Tyr Ala Pro Gly Asp Pro Ile Glu
465                 470                 475                 480

Lys Trp Leu Asn Lys Leu Leu Cys Leu Asp Val Ser Leu Ser Lys Asn
                485                 490                 495

Ala Lys Phe Ala Thr Lys Gly Thr Pro His Pro Ser Gln Cys Gln Leu
            500                 505                 510

Phe Tyr Val Asn Arg Asp Thr Leu Phe Ser Tyr His Pro Val Ser Glu
        515                 520                 525

Ala Phe Leu Gln Lys Met Met Ala Leu Tyr Val Ala Ser His Tyr Lys
    530                 535                 540

Asn Ser Pro Asn Asp Leu Gln Leu Met Ser Asp Ala Pro Ala His Gln
545                 550                 555                 560

Leu Phe Val Leu Leu Pro Pro Ile Glu Ala Gly Asp Asn Arg Val Pro
                565                 570                 575

Asp Pro Leu Cys Val Ile Gln Leu Ala Leu Glu Gly Glu Ile Ser Lys
            580                 585                 590

Glu Ser Val Arg Lys Ser Leu Ser Arg Gly Gln Arg Ala Gly Gly Asp
```

-continued

```
        595                 600                 605

Leu Ile Pro Trp Leu Ile Ser Gln Gln Phe Gln Asp Glu Glu Phe Ala
    610                 615                 620

Ser Leu Ser Gly Ala Arg Val Val Arg Ile Ala Thr Asn Pro Glu Tyr
625                 630                 635                 640

Ser Gly Met Gly Tyr Gly Ser Arg Ala Met Glu Leu Leu Arg Asp Tyr
                645                 650                 655

Tyr Ser Gly Lys Phe Thr Asp Ile Ser Glu Ser Thr Glu Leu Asn Asp
            660                 665                 670

His Thr Ile Thr Arg Val Thr Asp Ser Glu Leu Ala Asn Ala Ser Leu
        675                 680                 685

Lys Asp Glu Ile Lys Leu Arg Asp Val Lys Thr Leu Pro Pro Leu Leu
    690                 695                 700

Leu Lys Leu Ser Glu Lys Ala Pro Tyr Tyr Leu His Tyr Leu Gly Val
705                 710                 715                 720

Ser Tyr Gly Phe Thr Ser Gln Leu His Lys Phe Trp Lys Lys Ala Gly
                725                 730                 735

Phe Thr Pro Val Tyr Leu Arg Gln Thr Pro Asn Glu Leu Thr Gly Glu
            740                 745                 750

His Thr Ser Val Val Ile Ser Val Leu Pro Gly Arg Glu Asp Lys Trp
        755                 760                 765

Leu His Glu Phe Ser Lys Asp Phe His Lys Arg Phe Leu Ser Leu Leu
    770                 775                 780

Ser Tyr Glu Phe Lys Lys Phe Gln Ala Ser Gln Ala Leu Ser Ile Ile
785                 790                 795                 800

Glu Ala Ala Glu Gln Gly Glu Gly Asp Glu Thr Thr Ser Gln Lys Leu
                805                 810                 815

Thr Lys Glu Gln Leu Asp Leu Leu Leu Ser Pro Phe Asp Leu Lys Arg
            820                 825                 830

Leu Asp Ser Tyr Ala Asn Asn Leu Leu Asp Tyr His Val Ile Val Asp
        835                 840                 845

Met Leu Pro Leu Ile Ser Gln Leu Phe Phe Ser Lys Lys Thr Gly Gln
    850                 855                 860

Asp Ile Ser Leu Ser Ser Val Gln Ser Ala Ile Leu Leu Ala Ile Gly
865                 870                 875                 880

Leu Gln His Lys Asp Met Asp Gln Ile Ala Lys Glu Leu Asn Leu Pro
                885                 890                 895

Thr Asn Gln Ala Met Ala Met Phe Ala Lys Ile Ile Arg Lys Phe Ser
            900                 905                 910

Thr Tyr Phe Arg Lys Val Leu Ser Lys Ala Ile Glu Glu Ser Met Pro
        915                 920                 925

Asp Leu Glu Asp Glu Asn Val Asp Ala Met Asn Gly Lys Glu Thr Glu
    930                 935                 940

Gln Ile Asp Tyr Lys Ala Ile Glu Gln Lys Leu Gln Asp Asp Leu Glu
945                 950                 955                 960

Glu Ala Gly Asp Glu Ala Ile Lys Glu Met Arg Glu Lys Gln Arg Glu
                965                 970                 975

Leu Ile Asn Ala Leu Asn Leu Asp Lys Tyr Ala Ile Ala Glu Asp Ala
            980                 985                 990

Glu Trp Asp Glu Lys Ser Met Asp  Lys Ala Thr Lys Gly  Lys Gly Asn
        995                 1000                1005

Val Val  Ser Ile Lys Ser Gly  Lys Arg Lys Ser Lys  Glu Asn Ala
    1010                1015                1020
```

```
Asn Asp  Ile Tyr Glu Lys Glu  Met Lys Ala Val Lys  Lys Ser Lys
    1025                 1030                 1035

Lys Ser  Lys Lys
    1040


<210> SEQ ID NO 17
<211> LENGTH: 750
<212> TYPE: PRT
<213> ORGANISM: Candida albicans
<220> FEATURE:
<221> NAME/KEY: MISC_FEATURE
<223> OTHER INFORMATION: FCG12 or CaYGR145w

<400> SEQUENCE: 17

Met Val Leu Lys Ser Thr Thr Ala Gly Asn Val Ser Val Tyr Gln Val
1               5                   10                  15

Ser Gly Thr Asn Val Ser Arg Ser Leu Pro Asp Trp Ile Asp Lys Lys
            20                  25                  30

Arg Lys Arg Ala Leu Lys His Asp Leu Glu Tyr Gln Asn Arg Ile Glu
        35                  40                  45

Leu Ile Gln Asp Phe Glu Phe Ser Glu Ala Ser Asn Lys Ile Lys Val
    50                  55                  60

Thr Asn Asp Gly Gln Tyr Cys Met Ala Thr Gly Thr Tyr Lys Pro Gln
65                  70                  75                  80

Ile His Val Tyr Glu Phe Ala Asn Leu Ser Leu Lys Phe Asp Arg His
                85                  90                  95

Thr Asn Val Glu Asn Ile Asp Phe Leu Ile Leu Ser Asn Asp Trp Thr
            100                 105                 110

Lys Ser Val His Leu Gln Cys Asp Arg Ser Ile Glu Phe Gln Thr Ala
        115                 120                 125

Gly Gly Val His Tyr Arg Thr Arg Ile Pro Lys Phe Gly Arg Cys Leu
    130                 135                 140

Thr Tyr Asn Pro Ile Asn Cys Asp Leu Ile Val Gly Ser Ser Ser Asp
145                 150                 155                 160

Glu Leu Tyr Arg Leu Asn Leu Asp Gln Gly Arg Phe Leu Ser Pro Leu
                165                 170                 175

Lys Leu Asp Met Thr Asp Gly Gly Asn Ile Asp Ser Gly Cys Asn Ala
            180                 185                 190

Val Asp Ile Asn Ser Met His Gly Leu Ile Ser Ala Gly Leu Asp Asp
        195                 200                 205

Gly Thr Val Glu Phe Trp Asp Pro Arg Ser Lys Gln Arg Ala Gly Lys
    210                 215                 220

Leu Phe Val Ser Asp Gln Leu Ile Asn Ser Thr Asn Asn Thr Glu Gln
225                 230                 235                 240

Ser Ser Cys Gly Ile Thr Ser Leu Ala Phe Arg Pro Gln Asp Ala Leu
                245                 250                 255

Asn Phe Ala Cys Gly Thr Ser Asn Gly Gln Thr Leu Leu Tyr Asp Leu
            260                 265                 270

Arg Ala Ser Glu Pro Tyr Gln Ile Lys Asp Gln Gly Tyr Gly Tyr Asp
        275                 280                 285

Ile Lys Lys Ile Ile Trp Cys Gln Asp Ser Leu Lys Pro Glu Met Ile
    290                 295                 300

Leu Thr Ser Asp Lys Arg Ile Val Lys Ile Trp Asp His Thr Asn Gly
305                 310                 315                 320

Lys Ser Phe Ala Ser Met Glu Pro Thr Val Asp Ile Asn Asp Ile Cys
```

-continued

```
                325                 330                 335

His Ile Pro Gln Ser Gly Met Phe Phe Met Ala Asn Glu Gly Met Pro
            340                 345                 350

Met His Thr Tyr Tyr Ile Pro Asn Leu Gly Ser Ala Pro Asn Trp Cys
        355                 360                 365

Ser Phe Leu Asp Asn Val Thr Glu Glu Leu Glu Glu Lys Pro Ser Asn
    370                 375                 380

Ser Ile Tyr Pro Thr Phe Lys Phe Ile Thr Arg Asp Glu Met Val Lys
385                 390                 395                 400

Leu Asn Leu Thr His Leu Ile Gly Ile Lys Val Leu Arg Ser Tyr Met
                405                 410                 415

His Gly Phe Phe Ile Asn Thr Glu Leu Tyr Asp Lys Val Asn Leu Ile
            420                 425                 430

Ser Asn Pro Asn Ser Ile Tyr Asp Gln Arg Lys Arg Glu Ile Ala Asn
        435                 440                 445

Lys Ile Asn Glu Glu Arg Lys Ser Arg Ile Leu Thr Ser Ser Asn Gly
    450                 455                 460

Asn Asp Leu Pro Thr Lys Ile Lys Val Asn Lys Asp Leu Val Asn Lys
465                 470                 475                 480

Leu Gln Thr Lys Phe Ala Glu Asn Gly Thr Pro Asp Gly Asn Ala Asn
                485                 490                 495

Gly Ala Thr Asp Tyr Val Glu Ser Ile Val Asn Asp Asp Arg Phe Arg
            500                 505                 510

Glu Met Phe Glu Asn Pro Asp Phe Glu Ile Asp Glu Glu Ser His Glu
        515                 520                 525

Tyr Lys Gln Leu Asn Pro Val Lys Ser Thr Lys Asp Ile Thr Thr Thr
    530                 535                 540

Asn Thr Gly Thr Thr Asn Ser Arg Gly Arg Gly Leu Thr Ala Ala Glu
545                 550                 555                 560

Glu Ser Asp Glu Glu Arg Leu Asn Met Lys Asp Ser His His Thr Gly
                565                 570                 575

Leu Asp Ser Asp Glu Ser Asp Glu Glu Ser Asp Ser Glu Ser Glu Glu
            580                 585                 590

Gln Ser Glu Asp Glu Ala Lys Ser Ala Glu Thr Arg Glu Arg Val Gly
        595                 600                 605

Lys Glu Leu Asn Lys Ile Arg Gln Ser Lys Gln Lys Gln Gln Gln Gln
    610                 615                 620

Asp Ser Lys Lys Phe Gln Asn Glu Met Lys Ile Leu Ser Gln Gln Ser
625                 630                 635                 640

Ser Ser Ser Ser Ser Ser Leu Ala Asn Thr Glu Lys Ala Ser Val Ser
                645                 650                 655

Phe Gly Ser Gln Val Asn Lys Leu Asn Lys Ile Ser Lys Gln Asn Lys
            660                 665                 670

Asn Asn Asn Ser Ile Ser Asn Ala Lys Asp Ala Arg Leu Arg Arg His
        675                 680                 685

Ala Arg Gly Glu Ala Glu Leu Thr Phe Val Pro Gln Lys Ser Lys Ser
    690                 695                 700

Lys Ser Thr Lys Leu Lys Phe Asn Asn Asn His Ser Asp Asp Glu Lys
705                 710                 715                 720

Leu Asp Ser Gly Lys Thr Lys Asp Ser Gly Arg Thr Lys Gln Arg Phe
                725                 730                 735

Glu Gly Arg Arg Ile Ala Ser Lys Asn Lys Phe Arg Gly Met
            740                 745                 750
```

-continued

<210> SEQ ID NO 18
<211> LENGTH: 268
<212> TYPE: PRT
<213> ORGANISM: Candida albicans
<220> FEATURE:
<221> NAME/KEY: MISC_FEATURE
<223> OTHER INFORMATION: FCG13 or CaYDR412w

<400> SEQUENCE: 18

```
Met Ala Gly Phe Lys Lys Asn Arg Glu Ile Leu Thr Gly Gly Lys Lys
1               5                   10                  15

Tyr Ile Gln Gln Lys Gln Lys Lys His Leu Val Asp Glu Val Val Phe
            20                  25                  30

Asp Lys Glu Ser Arg His Glu Tyr Leu Thr Gly Phe His Lys Arg Lys
        35                  40                  45

Leu Gln Arg Gln Lys Lys Ala Gln Glu Phe His Lys Glu Gln Glu Arg
    50                  55                  60

Leu Ala Lys Ile Glu Glu Arg Lys Gln Leu Lys Gln Glu Arg Glu Arg
65                  70                  75                  80

Asp Leu Gln Asn Gln Leu Gln Gln Phe Lys Lys Thr Ala Gln Glu Ile
                85                  90                  95

Ala Ala Ile Asn Asn Asp Ile Gly Phe Asp Gln Ser Asp Asp Asn Asn
            100                 105                 110

Asp Asn Asp Asn Glu Asn Glu Glu Trp Ser Gly Phe Gln Glu Asp Glu
        115                 120                 125

Glu Gly Glu Gly Glu Glu Val Thr Asp Glu Asp Asp Glu Asp Lys Glu
    130                 135                 140

Lys Pro Leu Lys Gly Ile Leu His His Thr Glu Ile Tyr Lys Gln Asp
145                 150                 155                 160

Pro Ser Leu Ser Asn Ile Thr Asn Asn Gly Ala Ile Ile Asp Asp Glu
                165                 170                 175

Thr Thr Val Val Val Glu Ser Leu Asp Asn Pro Asn Ala Val Asp Thr
            180                 185                 190

Glu Glu Lys Leu Gln Gln Leu Ala Lys Leu Asn Asn Val Asn Leu Asp
        195                 200                 205

Lys Ser Asp Gln Ile Leu Glu Lys Ser Ile Glu Arg Ala Lys Asn Tyr
    210                 215                 220

Ala Val Ile Cys Gly Val Ala Lys Pro Asn Pro Ile Lys Gln Lys Lys
225                 230                 235                 240

Lys Lys Phe Arg Tyr Leu Thr Lys Ala Glu Arg Arg Glu Asn Val Arg
                245                 250                 255

Lys Glu Lys Ser Lys Ser Lys Ser Lys Gly Lys Lys
            260                 265
```

<210> SEQ ID NO 19
<211> LENGTH: 371
<212> TYPE: PRT
<213> ORGANISM: Candida albicans
<220> FEATURE:
<221> NAME/KEY: MISC_FEATURE
<223> OTHER INFORMATION: FCG14 or CaYOL010w

<400> SEQUENCE: 19

```
Met Ser Ser Val Ala Ser Lys Lys Ile Ile Thr Phe Glu Gly His Arg
1               5                   10                  15

Asn Phe Arg Leu Arg Leu Val Leu Ala Thr Leu Ser Gly Lys Pro Ile
            20                  25                  30
```

-continued

```
Lys Ile Thr Lys Ile Arg Ser Gln Asp Leu Asn Pro Gly Leu Lys Asp
        35                  40                  45

His Glu Val Ser Phe Leu Arg Leu Leu Glu Ala Val Thr Asn Gly Ser
    50                  55                  60

His Ile Glu Ile Ser Tyr Thr Gly Thr Thr Ile Ile Tyr Arg Pro Gly
65                  70                  75                  80

Ile Ile Ile Gly Gly Asp Leu Thr His Asn Cys Pro Asp Thr Lys Ser
                85                  90                  95

Ile Gly Tyr Phe Ile Glu Pro Met Leu Met Phe Pro Leu Phe Ser Lys
            100                 105                 110

Lys Lys Phe Ser Ile Ile Phe Lys Gly Leu Thr Asn Ile Ala Gly Asn
        115                 120                 125

Asp Thr Gly Val Asp Ala Ile Lys Trp Gly Leu Leu Pro Val Met Glu
    130                 135                 140

Lys Phe Gly Val Arg Glu Val Ser Leu His Ile Leu Lys Arg Gly Ser
145                 150                 155                 160

Ala Pro Leu Gly Gly Gly Glu Val His Leu Leu Cys Ser Ser Leu Ile
                165                 170                 175

Pro Gln Pro Leu Thr Ile His Ala Leu Asp Ile Pro Lys Phe Ser Ala
            180                 185                 190

Ile Arg Gly Val Ala Tyr Cys Thr Arg Val Ser Pro Ser Ile Val Asn
        195                 200                 205

Arg Met Ile Asp Ser Ala Arg Ala Val Leu Lys Pro Thr Gly Cys Glu
    210                 215                 220

Val Asn Ile Thr Ala Asp Val Trp Arg Gly Glu Asn Ser Gly Lys Ser
225                 230                 235                 240

Pro Gly Phe Gly Ile Thr Leu Val Ala Glu Leu Lys Arg Gly Trp Arg
                245                 250                 255

Ile Val Thr Glu Asn Val Gly Ser Ala Gly Ser Leu Pro Glu Asp Ser
            260                 265                 270

Gly Glu Leu Thr Ala Tyr Gln Leu Leu Glu Glu Ile Ser Asn Ser Gly
        275                 280                 285

Val Val Gly Arg Tyr Gln Leu Pro Leu Ala Leu Val Tyr Met Thr Ile
    290                 295                 300

Gly Lys Glu Asp Ile Gly Arg Leu Lys Leu Gln Lys Ser Glu Ile Asp
305                 310                 315                 320

Glu Asn Leu Val Ser Val Leu Arg Asp Ile Gln Glu Val Phe Gly Thr
                325                 330                 335

Glu Ala Phe Phe Lys Asp Asp Ala Glu Glu Leu Asp Ser Asp Asp Lys
            340                 345                 350

Phe Met Thr Val Ser Ile Lys Gly Val Gly Phe Thr Asn Val Ser Lys
        355                 360                 365

Lys Ile Ala
    370


<210> SEQ ID NO 20
<211> LENGTH: 257
<212> TYPE: PRT
<213> ORGANISM: Candida albicans
<220> FEATURE:
<221> NAME/KEY: MISC_FEATURE
<223> OTHER INFORMATION: FCG15 or CaYOR004w;PRT

<400> SEQUENCE: 20

Met Arg Gln Lys Arg Ala Lys Ala Tyr Lys Lys Gln Met Ser Val Tyr
```

-continued

```
1               5                   10                  15

Val His Ala Phe Lys Phe Arg Glu Pro Tyr Gln Ile Ile Val Asp Asn
            20                  25                  30

Glu Leu Ile Thr Thr Cys Gln Ser Ala Ser Phe Asp Ile Asn Lys Gly
        35                  40                  45

Phe Thr Arg Thr Ile Gln Ala Glu Asn Lys Pro Met Ile Thr Gln Cys
    50                  55                  60

Cys Ile Gln Ala Leu Tyr Asp Thr Lys Asn Gln Pro Ala Ile Asp Ile
65                  70                  75                  80

Ala Lys Ser Phe Glu Arg Arg Lys Cys Asn His Arg Glu Ala Ile Asp
                85                  90                  95

Pro Ser Gln Cys Ile Glu Ser Ile Val Asn Ile Lys Gly Gln Asn Lys
            100                 105                 110

His Arg Tyr Ile Val Ala Ser Gln Asp Leu Gln Leu Arg Lys Lys Leu
        115                 120                 125

Arg Lys Ile Pro Gly Val Pro Leu Ile Tyr Met Asn Arg Ser Val Met
    130                 135                 140

Val Met Glu Pro Ile Ser Asp Val Ser Asn Gln Tyr Asn Met Asn Tyr
145                 150                 155                 160

Glu Ser Lys Lys Leu Thr Gly Gly Leu Asn Asp Ile Glu Ala Gly Lys
                165                 170                 175

Leu Glu Lys Gln Asn Glu Gly Glu Asp Gly Asp Gly Asp Glu Leu Glu
            180                 185                 190

Val Lys Lys Lys Lys Arg Lys Gly Pro Lys Glu Pro Asn Pro Leu Ser
        195                 200                 205

Val Lys Lys Lys Lys Thr Asp Asn Ala Thr Ala Ala Ser Thr Asn Gln
    210                 215                 220

Glu Gln Lys Lys Lys Pro Asn Arg Arg Lys Arg His Ala Gln Val Lys
225                 230                 235                 240

Ser Arg Arg Glu Gly Arg Pro Arg Thr Gly Ala Ser Glu Arg Ser Asn
                245                 250                 255

Asn


<210> SEQ ID NO 21
<211> LENGTH: 466
<212> TYPE: PRT
<213> ORGANISM: Candida albicans
<220> FEATURE:
<221> NAME/KEY: MISC_FEATURE
<223> OTHER INFORMATION: FCG16 or CaYOR056c

<400> SEQUENCE: 21

Met Ser Glu Thr Lys Asn Ile Glu Ser Leu Ile Ser Asp Ala Gly Pro
1               5                   10                  15

Leu Ile Thr Gln Pro Ala Thr Thr Leu Gln Gln Tyr Ala Thr Ala Tyr
            20                  25                  30

Tyr Thr Thr Pro Gly Val His Ser Glu Leu Lys Asp Glu Tyr Ala Arg
        35                  40                  45

Gln Gln Leu Ala Ile Trp Gly Asp Ser Leu Lys Ile Lys Gln Pro Lys
    50                  55                  60

Gln Glu Tyr Ile Asp Arg Val Val Lys Phe Ala Lys Leu Thr Gly Asp
65                  70                  75                  80

Tyr Ser Val Leu Ser Val Asn Asp Leu His Ile Val Ala Leu Ala Tyr
                85                  90                  95

Glu Leu Glu Cys Leu Asn Asn Gly Glu Asp Asn Leu Arg Ser Phe Pro
```

-continued

```
            100                 105                 110

Gly Glu Val Leu Lys Asn Gln Gln Ala Glu Asn Glu Asn Gly Ser Asn
        115                 120                 125

Lys Met Ser Asn Ile Ile Gly Asp Asp Asp Gly Phe Val Val Ala Thr
    130                 135                 140

Lys Arg Arg Gly Gly Arg Arg Gln Arg Glu Lys Ala Glu Leu Arg Lys
145                 150                 155                 160

Lys Gly Leu Leu Pro Thr Phe Ser Pro Lys Pro Lys Gly Gly Leu Glu
                165                 170                 175

Thr Glu Glu Pro Asn Glu Leu Ser Asn Asp Lys Thr Ile Asp Glu Thr
            180                 185                 190

Pro Gln Thr Asp Leu Ile Lys Gly Val Asp Val Gln Glu Gln Glu Ser
        195                 200                 205

Gln Glu Glu Pro Val Ser Glu Ser Asn Thr Val Gly Leu Asp Glu Ile
    210                 215                 220

Thr Glu Glu Tyr Asn Glu Asp Asp Asp Asp Gly Glu Trp Ile Thr Pro
225                 230                 235                 240

Glu Asn Leu Gln Glu Glu Ile Ile Lys Asp Lys Asn Glu Gln Val Gln
                245                 250                 255

Glu Ser Asn Thr Asn Gly Pro Leu Ile Lys Val Ala Leu Ala Thr Gly
            260                 265                 270

Asp Phe Ala Cys Gln Asn Val Ala Met Gln Ile Gly Ile Lys Leu Leu
        275                 280                 285

Asn Ala Met Ser Gly Lys Gln Ile Thr Arg Val Arg Asn Tyr Met Tyr
    290                 295                 300

Arg Cys His Ala Cys Phe Arg Leu Thr Pro Met Ser Lys Asp Gly Arg
305                 310                 315                 320

Pro Lys His Phe Cys Pro Lys Cys Gly Gly Asn Thr Leu Leu Arg Cys
                325                 330                 335

Ala Val Ser Val Asp Asn Lys Thr Gly Lys Ile Thr Pro His Leu Lys
            340                 345                 350

Gln Asn Phe Gln Trp Ile Arg Arg Gly Glu Arg Tyr Ser Leu Pro Ser
        355                 360                 365

Pro Leu Ser Lys Asn Gln Lys Lys Leu Gln Gly Asn Gly Gly Tyr Gln
    370                 375                 380

His Asn Lys Glu Asn Arg His Lys Ser Leu Gln Thr Pro Leu Ile Leu
385                 390                 395                 400

Asn Glu Asp Gln Lys Glu Tyr Gln Arg Ala Leu Lys Asn Asp Glu Trp
                405                 410                 415

Glu Arg Lys Gln Gln Asp Lys Met Leu Gln Glu Trp Ile Gly Gly Gly
            420                 425                 430

Ser Ala Asp Asn Phe Val Ser Pro Phe Gly Asn Thr Ile Arg Asn Ser
        435                 440                 445

Gly Val Lys Val Gly Arg Gly Arg Tyr Ala Asn Ser Ser Lys Lys Lys
    450                 455                 460

Arg Lys
465
```

<210> SEQ ID NO 22
<211> LENGTH: 195
<212> TYPE: PRT
<213> ORGANISM: Candida albicans
<220> FEATURE:
<221> NAME/KEY: MISC_FEATURE
<223> OTHER INFORMATION: FCG17 or CaYLR009w

<400> SEQUENCE: 22

Met Arg Ile Tyr Gln Cys His Phe Cys Ser Ser Pro Val Tyr Pro Leu
1 5 10 15

His Gly Ile Thr Phe Val Arg Asn Asp Ala Lys Glu Phe Arg Phe Cys
20 25 30

Arg Ser Lys Cys His Lys Ala Phe Lys Gln Arg Arg Asn Pro Arg Lys
35 40 45

Leu Arg Trp Thr Lys Ala Phe Arg Lys Ala Ala Gly Lys Glu Leu Val
50 55 60

Val Asp Ser Thr Leu Thr Phe Ala Ala Arg Arg Asn Val Pro Val Arg
65 70 75 80

Tyr Asn Arg Asp Leu Val Ala Thr Thr Leu Lys Gly Met Ser Arg Ile
85 90 95

Glu Glu Ile Arg Gln Arg Arg Glu Arg Ala Phe Tyr Lys Asn Arg Met
100 105 110

Lys Gly Asn Lys Glu Arg Gln Leu Ala Ala Asp Arg Lys Leu Val Ala
115 120 125

Asp Asn Pro Glu Leu Leu Arg Leu Arg Glu Val Glu Leu Arg Arg Lys
130 135 140

Ala Glu Lys Leu Ala Ala Lys Glu Asn Ala Met Glu Glu Asp Glu Glu
145 150 155 160

Thr Glu Val Glu Glu Glu Gly Glu Gly Asp Glu Glu Met Ile Ser Gly
165 170 175

Glu Glu Glu Trp Glu Ser Glu Asp Glu Ser Glu Arg Glu Ser Asp Thr
180 185 190

Lys Thr Cys
195

<210> SEQ ID NO 23
<211> LENGTH: 347
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_170752

<400> SEQUENCE: 23

Met Asn Arg Lys Val Ala Ile Val Thr Gly Thr Asn Ser Asn Leu Gly
1 5 10 15

Leu Asn Ile Val Phe Arg Leu Ile Glu Thr Glu Asp Thr Asn Val Arg
20 25 30

Leu Thr Ile Val Val Thr Ser Arg Thr Leu Pro Arg Val Gln Glu Val
35 40 45

Ile Asn Gln Ile Lys Asp Phe Tyr Asn Lys Ser Gly Arg Val Glu Asp
50 55 60

Leu Glu Ile Asp Phe Asp Tyr Leu Leu Val Asp Phe Thr Asn Met Val
65 70 75 80

Ser Val Leu Asn Ala Tyr Tyr Asp Ile Asn Lys Lys Tyr Arg Ala Ile
85 90 95

Asn Tyr Leu Phe Val Asn Ala Ala Gln Gly Ile Phe Asp Gly Ile Asp
100 105 110

Trp Ile Gly Ala Val Lys Glu Val Phe Thr Asn Pro Leu Glu Ala Val
115 120 125

Thr Asn Pro Thr Tyr Lys Ile Gln Leu Val Gly Val Lys Ser Lys Asp
130 135 140

-continued

Asp Met Gly Leu Ile Phe Gln Ala Asn Val Phe Gly Pro Tyr Tyr Phe
145 150 155 160

Ile Ser Lys Ile Leu Pro Gln Leu Thr Arg Gly Lys Ala Tyr Ile Val
165 170 175

Trp Ile Ser Ser Ile Met Ser Asp Pro Lys Tyr Leu Ser Leu Asn Asp
180 185 190

Ile Glu Leu Leu Lys Thr Asn Ala Ser Tyr Glu Gly Ser Lys Arg Leu
195 200 205

Val Asp Leu Leu His Leu Ala Thr Tyr Lys Asp Leu Lys Lys Leu Gly
210 215 220

Ile Asn Gln Tyr Val Val Gln Pro Gly Ile Phe Thr Ser His Ser Phe
225 230 235 240

Ser Glu Tyr Leu Asn Phe Phe Thr Tyr Phe Gly Met Leu Cys Leu Phe
245 250 255

Tyr Leu Ala Arg Leu Leu Gly Ser Pro Trp His Asn Ile Asp Gly Tyr
260 265 270

Lys Ala Ala Asn Ala Pro Val Tyr Val Thr Arg Leu Ala Asn Pro Asn
275 280 285

Phe Glu Lys Gln Asp Val Lys Tyr Gly Ser Ala Thr Ser Arg Asp Gly
290 295 300

Met Pro Tyr Ile Lys Thr Gln Glu Ile Asp Pro Thr Gly Met Ser Asp
305 310 315 320

Val Phe Ala Tyr Ile Gln Lys Lys Lys Leu Glu Trp Asp Glu Lys Leu
325 330 335

Lys Asp Gln Ile Val Glu Thr Arg Thr Pro Ile
340 345

<210> SEQ ID NO 24
<211> LENGTH: 347
<212> TYPE: PRT
<213> ORGANISM: Saccharomyces cerevisiae
<220> FEATURE:
<221> NAME/KEY: MISC_FEATURE
<223> OTHER INFORMATION: PAT_PROT|BMSPATENT_AAB19089

<400> SEQUENCE: 24

Met Asn Arg Lys Val Ala Ile Val Thr Gly Thr Asn Ser Asn Leu Gly
1 5 10 15

Leu Asn Ile Val Phe Arg Leu Ile Glu Thr Glu Asp Thr Asn Val Arg
20 25 30

Leu Thr Ile Val Val Thr Ser Arg Thr Leu Pro Arg Val Gln Glu Val
35 40 45

Ile Asn Gln Ile Lys Asp Phe Tyr Asn Lys Ser Gly Arg Val Glu Asp
50 55 60

Leu Glu Ile Asp Phe Asp Tyr Leu Leu Val Asp Phe Thr Asn Met Val
65 70 75 80

Ser Val Leu Asn Ala Tyr Tyr Asp Ile Asn Lys Lys Tyr Arg Ala Ile
85 90 95

Asn Tyr Leu Phe Val Asn Ala Ala Gln Gly Ile Phe Asp Gly Ile Asp
100 105 110

Trp Ile Gly Ala Val Lys Glu Val Phe Thr Asn Pro Leu Glu Ala Val
115 120 125

Thr Asn Pro Thr Tyr Lys Ile Gln Leu Val Gly Val Lys Ser Lys Asp
130 135 140

Asp Met Gly Leu Ile Phe Gln Ala Asn Val Phe Gly Pro Tyr Tyr Phe

-continued

```
145                 150                 155                 160

Ile Ser Lys Ile Leu Pro Gln Leu Thr Arg Gly Lys Ala Tyr Ile Val
                165                 170                 175

Trp Ile Ser Ser Ile Met Ser Asp Pro Lys Tyr Leu Ser Leu Asn Asp
            180                 185                 190

Ile Glu Leu Leu Lys Thr Asn Ala Ser Tyr Glu Gly Ser Lys Arg Leu
        195                 200                 205

Val Asp Leu Leu His Leu Ala Thr Tyr Lys Asp Leu Lys Lys Leu Gly
    210                 215                 220

Ile Asn Gln Tyr Val Val Gln Pro Gly Ile Phe Thr Ser His Ser Phe
225                 230                 235                 240

Ser Glu Tyr Leu Asn Phe Phe Thr Tyr Phe Gly Met Leu Cys Leu Phe
                245                 250                 255

Tyr Leu Ala Arg Leu Leu Gly Ser Pro Trp His Asn Ile Asp Gly Tyr
            260                 265                 270

Lys Ala Ala Asn Ala Pro Val Tyr Val Thr Arg Leu Ala Asn Pro Asn
        275                 280                 285

Phe Glu Lys Gln Asp Val Lys Tyr Gly Ser Ala Thr Ser Arg Asp Gly
    290                 295                 300

Met Pro Tyr Ile Lys Thr Gln Glu Ile Asp Pro Thr Gly Met Ser Asp
305                 310                 315                 320

Val Phe Ala Tyr Ile Gln Lys Lys Lys Leu Glu Trp Asp Glu Lys Leu
                325                 330                 335

Lys Asp Gln Ile Val Glu Thr Arg Thr Pro Ile
            340                 345


<210> SEQ ID NO 25
<211> LENGTH: 607
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_168653

<400> SEQUENCE: 25

Met Ala Ser Thr Ala Asn Met Ile Ser Gln Leu Lys Lys Leu Ser Ile
1               5                   10                  15

Ala Glu Pro Ala Val Ala Lys Asp Ser His Pro Asp Val Asn Ile Val
            20                  25                  30

Asp Leu Met Arg Asn Tyr Ile Ser Gln Glu Leu Ser Lys Ile Ser Gly
        35                  40                  45

Val Asp Ser Ser Leu Ile Phe Pro Ala Leu Glu Trp Thr Asn Thr Met
    50                  55                  60

Glu Arg Gly Asp Leu Leu Ile Pro Ile Pro Arg Leu Arg Ile Lys Gly
65                  70                  75                  80

Ala Asn Pro Lys Asp Leu Ala Val Gln Trp Ala Glu Lys Phe Pro Cys
                85                  90                  95

Gly Asp Phe Leu Glu Lys Val Glu Ala Asn Gly Pro Phe Ile Gln Phe
            100                 105                 110

Phe Phe Asn Pro Gln Phe Leu Ala Lys Leu Val Ile Pro Asp Ile Leu
        115                 120                 125

Thr Arg Lys Glu Asp Tyr Gly Ser Cys Lys Leu Val Glu Asn Lys Lys
    130                 135                 140

Val Ile Ile Glu Phe Ser Ser Pro Asn Ile Ala Lys Pro Phe His Ala
145                 150                 155                 160
```

-continued

```
Gly His Leu Arg Ser Thr Ile Ile Gly Gly Phe Leu Ala Asn Leu Tyr
                165                 170                 175

Glu Lys Leu Gly Trp Glu Val Ile Arg Met Asn Tyr Leu Gly Asp Trp
            180                 185                 190

Gly Lys Gln Phe Gly Leu Leu Ala Val Gly Phe Glu Arg Tyr Gly Asn
        195                 200                 205

Glu Glu Ala Leu Val Lys Asp Pro Ile His His Leu Phe Asp Val Tyr
    210                 215                 220

Val Arg Ile Asn Lys Asp Ile Glu Glu Glu Gly Asp Ser Ile Pro Leu
225                 230                 235                 240

Glu Gln Ser Thr Asn Gly Lys Ala Arg Glu Tyr Phe Lys Arg Met Glu
                245                 250                 255

Asp Gly Asp Glu Glu Ala Leu Lys Ile Trp Lys Arg Phe Arg Glu Phe
            260                 265                 270

Ser Ile Glu Lys Tyr Ile Asp Thr Tyr Ala Arg Leu Asn Ile Lys Tyr
        275                 280                 285

Asp Val Tyr Ser Gly Glu Ser Gln Val Ser Lys Glu Ser Met Leu Lys
    290                 295                 300

Ala Ile Asp Leu Phe Lys Glu Lys Gly Leu Thr His Glu Asp Lys Gly
305                 310                 315                 320

Ala Val Leu Ile Asp Leu Thr Lys Phe Asn Lys Lys Leu Gly Lys Ala
                325                 330                 335

Ile Val Gln Lys Ser Asp Gly Thr Thr Leu Tyr Leu Thr Arg Asp Val
            340                 345                 350

Gly Ala Ala Met Asp Arg Tyr Glu Lys Tyr His Phe Asp Lys Met Ile
        355                 360                 365

Tyr Val Ile Ala Ser Gln Gln Asp Leu His Ala Ala Gln Phe Phe Glu
    370                 375                 380

Ile Leu Lys Gln Met Gly Phe Glu Trp Ala Lys Asp Leu Gln His Val
385                 390                 395                 400

Asn Phe Gly Met Val Gln Gly Met Ser Thr Arg Lys Gly Thr Val Val
                405                 410                 415

Phe Leu Asp Asn Ile Leu Glu Glu Thr Lys Glu Lys Met His Glu Val
            420                 425                 430

Met Lys Lys Asn Glu Asn Lys Tyr Ala Gln Ile Glu His Pro Glu Glu
        435                 440                 445

Val Ala Asp Leu Val Gly Ile Ser Ala Val Met Ile Gln Asp Met Gln
    450                 455                 460

Gly Lys Arg Ile Asn Asn Tyr Glu Phe Lys Trp Glu Arg Met Leu Ser
465                 470                 475                 480

Phe Glu Gly Asp Thr Gly Pro Tyr Leu Gln Tyr Ala His Ser Arg Leu
                485                 490                 495

Arg Ser Val Glu Arg Asn Ala Ser Gly Ile Thr Gln Glu Lys Trp Ile
            500                 505                 510

Asn Ala Asp Phe Ser Leu Leu Lys Glu Pro Ala Ala Lys Leu Leu Ile
        515                 520                 525

Arg Leu Leu Gly Gln Tyr Pro Asp Val Leu Arg Asn Ala Ile Lys Thr
    530                 535                 540

His Glu Pro Thr Thr Val Val Thr Tyr Leu Phe Lys Leu Thr His Gln
545                 550                 555                 560

Val Ser Ser Cys Tyr Asp Val Leu Trp Val Ala Gly Gln Thr Glu Glu
                565                 570                 575

Leu Ala Thr Ala Arg Leu Ala Leu Tyr Gly Ala Ala Arg Gln Val Leu
```

-continued

```
        580                 585                 590

Tyr Asn Gly Met Arg Leu Leu Gly Leu Thr Pro Val Glu Arg Met
    595                 600                 605


<210> SEQ ID NO 26
<211> LENGTH: 638
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAB94675

<400> SEQUENCE: 26

Met Gln Val Ser Ser Leu Asn Glu Val Lys Ile Tyr Ser Leu Ser Cys
1               5                   10                  15

Gly Lys Ser Leu Pro Glu Trp Leu Ser Asp Arg Lys Lys Arg Ala Leu
            20                  25                  30

Gln Lys Lys Asp Val Asp Val Arg Arg Arg Ile Glu Leu Ile Gln Asp
        35                  40                  45

Phe Glu Met Pro Thr Val Cys Thr Thr Ile Lys Val Ser Lys Asp Gly
    50                  55                  60

Gln Tyr Ile Leu Ala Thr Gly Thr Tyr Lys Pro Arg Val Arg Cys Tyr
65                  70                  75                  80

Asp Thr Tyr Gln Leu Ser Leu Lys Phe Glu Arg Cys Leu Asp Ser Glu
                85                  90                  95

Val Val Thr Phe Glu Ile Leu Ser Asp Asp Tyr Ser Lys Ile Val Phe
            100                 105                 110

Leu His Asn Asp Arg Tyr Ile Glu Phe His Ser Gln Ser Gly Phe Tyr
        115                 120                 125

Tyr Lys Thr Arg Ile Pro Lys Phe Gly Arg Asp Phe Ser Tyr His Tyr
    130                 135                 140

Pro Ser Cys Asp Leu Tyr Phe Val Gly Ala Ser Ser Glu Val Tyr Arg
145                 150                 155                 160

Leu Asn Leu Glu Gln Gly Arg Tyr Leu Asn Pro Leu Gln Thr Asp Ala
                165                 170                 175

Ala Glu Asn Asn Val Cys Asp Ile Asn Ser Val His Gly Leu Phe Ala
            180                 185                 190

Thr Gly Thr Ile Glu Gly Arg Val Glu Cys Trp Asp Pro Arg Thr Arg
        195                 200                 205

Asn Arg Val Gly Leu Leu Asp Cys Ala Leu Asn Ser Val Thr Ala Asp
    210                 215                 220

Ser Glu Ile Asn Ser Leu Pro Thr Ile Ser Ala Leu Lys Phe Asn Gly
225                 230                 235                 240

Ala Leu Thr Met Ala Val Gly Thr Thr Thr Gly Gln Gly Lys Ile Phe
                245                 250                 255

Thr Ser Leu Glu Pro Glu His Asp Leu Asn Asp Val Cys Leu Tyr Pro
            260                 265                 270

Asn Ser Gly Met Leu Leu Thr Ala Asn Glu Thr Pro Lys Met Gly Ile
        275                 280                 285

Tyr Tyr Ile Pro Val Leu Gly Pro Ala Pro Arg Trp Cys Ser Phe Leu
    290                 295                 300

Asp Asn Leu Thr Glu Glu Leu Glu Glu Asn Pro Glu Ser Thr Val Tyr
305                 310                 315                 320

Asp Asp Tyr Lys Phe Val Thr Lys Lys Asp Leu Glu Asn Leu Gly Leu
                325                 330                 335
```

-continued

```
Thr His Leu Ile Gly Ser Pro Phe Leu Arg Ala Tyr Met His Gly Phe
            340                 345                 350

Phe Met Asp Ile Arg Leu Tyr His Lys Val Lys Leu Met Val Asn Pro
        355                 360                 365

Phe Ala Tyr Glu Glu Tyr Arg Lys Asp Lys Ile Arg Gln Lys Ile Glu
    370                 375                 380

Glu Thr Arg Ala Gln Arg Val Gln Leu Lys Lys Leu Pro Lys Val Asn
385                 390                 395                 400

Lys Glu Leu Ala Leu Lys Leu Ile Glu Glu Glu Glu Glu Lys Gln Lys
                405                 410                 415

Ser Thr Trp Lys Lys Lys Val Lys Ser Leu Pro Asn Ile Leu Thr Asp
            420                 425                 430

Asp Arg Phe Lys Val Met Phe Glu Asn Pro Asp Leu Gln Val Asp Glu
        435                 440                 445

Glu Ser Glu Glu Phe Arg Leu Leu Asn Pro Leu Val Ser Lys Ile Ser
    450                 455                 460

Glu Lys Arg Lys Lys Lys Leu Arg Leu Leu Glu Gln Gln Glu Leu Arg
465                 470                 475                 480

Glu Lys Glu Glu Glu Glu Glu Pro Glu Gly Lys Pro Ser Asp Ala Glu
                485                 490                 495

Ser Ser Glu Ser Ser Asp Asp Glu Lys Ala Trp Val Glu Glu Val Arg
            500                 505                 510

Lys Gln Arg Arg Leu Leu Gln Arg Glu Glu Lys Val Lys Arg Gln Glu
        515                 520                 525

Arg Leu Lys Glu Asp Gln Gln Thr Val Leu Lys Pro Gln Phe Tyr Glu
    530                 535                 540

Ile Lys Ala Gly Glu Glu Phe Arg Ser Phe Lys Asp Ser Ala Thr Lys
545                 550                 555                 560

Gln Lys Leu Met Asn Lys Thr Leu Glu Asp Arg Leu Lys Ile Glu Ala
                565                 570                 575

Lys Asn Gly Thr Leu Ser Val Ser Asp Thr Thr Val Gly Ser Lys Gln
            580                 585                 590

Leu Thr Phe Thr Leu Lys Arg Ser Glu Gln Gln Lys Lys Gln Gln Glu
        595                 600                 605

Ala Glu Lys Leu His Arg Gln Glu Arg Lys Arg Leu Arg Arg Ser Ala
    610                 615                 620

Gly His Leu Lys Ser Arg His Lys Arg Gly Arg Ser Phe His
625                 630                 635


<210> SEQ ID NO 27
<211> LENGTH: 250
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_178714

<400> SEQUENCE: 27

Met Pro Ile Asn Gln Pro Ser Gly Gln Ile Lys Leu Thr Asn Val Ser
1               5                   10                  15

Leu Val Arg Leu Lys Lys Ala Arg Lys Arg Phe Glu Val Ala Cys Tyr
            20                  25                  30

Gln Asn Lys Val Gln Asp Tyr Arg Lys Gly Ile Glu Lys Asp Leu Asp
        35                  40                  45

Glu Val Leu Gln Ile His Gln Val Phe Met Asn Val Ser Lys Gly Leu
    50                  55                  60
```

-continued

```
Val Ala Asn Lys Glu Asp Leu Gln Lys Cys Phe Gly Thr Thr Asn Val
65                  70                  75                  80

Asp Asp Val Ile Glu Glu Ile Met His Lys Gly Glu Ile Gln Leu Ser
                85                  90                  95

Glu Lys Glu Arg Gln Leu Met Leu Asn Lys Val Asn Asn Glu Met Leu
            100                 105                 110

Thr Ile Val Ser Ala Lys Cys Ile Asn Pro Val Ser Lys Lys Arg Tyr
        115                 120                 125

Pro Pro Thr Met Ile His Lys Ala Leu Gln Glu Leu Lys Phe Ser Pro
    130                 135                 140

Val Ile Asn Lys Pro Ala Lys Leu Gln Ala Leu Glu Ala Ile Lys Leu
145                 150                 155                 160

Leu Val Ser Lys Gln Ile Ile Pro Ile Val Arg Ala Lys Met Lys Val
                165                 170                 175

Lys Val Ala Ile Ser Glu Pro Ser Arg Gln Pro Glu Leu Ile Glu Lys
            180                 185                 190

Ile Ser Lys Leu Ile Ala Ser Ser Pro Gly Glu Ser Thr Lys Pro Glu
        195                 200                 205

Leu Asp Pro Trp Thr Cys Thr Gly Leu Ile Asp Pro Val Asn Tyr Arg
    210                 215                 220

Asp Leu Met Thr Leu Cys Asp Lys Lys Gly Thr Val Gln Val Leu Asp
225                 230                 235                 240

Met Ala Val Ile Asp Asn Thr Thr His Asn
                245                 250


<210> SEQ ID NO 28
<211> LENGTH: 250
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAB42957

<400> SEQUENCE: 28

Met Ser Ile Phe Thr Pro Thr Asn Gln Ile Arg Leu Thr Asn Val Ala
1               5                   10                  15

Val Val Arg Met Lys Arg Ala Gly Lys Arg Phe Glu Ile Ala Cys Tyr
            20                  25                  30

Lys Asn Lys Val Val Gly Trp Arg Ser Gly Val Glu Lys Asp Leu Asp
        35                  40                  45

Glu Val Leu Gln Thr His Ser Val Phe Val Asn Val Ser Lys Gly Gln
    50                  55                  60

Val Ala Lys Lys Glu Asp Leu Ile Ser Ala Phe Gly Thr Asp Asp Gln
65                  70                  75                  80

Thr Glu Ile Cys Lys Gln Ile Leu Thr Lys Gly Glu Val Gln Val Ser
                85                  90                  95

Asp Lys Glu Arg His Thr Gln Leu Glu Gln Met Phe Arg Asp Ile Ala
            100                 105                 110

Thr Ile Val Ala Asp Lys Cys Val Asn Pro Glu Thr Lys Arg Pro Tyr
        115                 120                 125

Thr Val Ile Leu Ile Glu Arg Ala Met Lys Asp Ile His Tyr Ser Val
    130                 135                 140

Lys Thr Asn Lys Ser Thr Lys Gln Gln Ala Leu Glu Val Ile Lys Gln
145                 150                 155                 160

Leu Lys Glu Lys Met Lys Ile Glu Arg Ala His Met Arg Leu Arg Phe
```

-continued

```
                165                 170                 175

Ile Leu Pro Val Asn Glu Gly Lys Lys Leu Lys Glu Lys Leu Lys Pro
            180                 185                 190

Leu Ile Lys Val Ile Glu Ser Glu Asp Tyr Gly Gln Gln Leu Glu Ile
        195                 200                 205

Val Cys Leu Ile Asp Pro Gly Cys Phe Arg Glu Ile Asp Glu Leu Ile
    210                 215                 220

Lys Lys Glu Thr Lys Gly Lys Gly Ser Leu Glu Val Leu Asn Leu Lys
225                 230                 235                 240

Asp Val Glu Glu Gly Asp Glu Lys Phe Glu
                245                 250


<210> SEQ ID NO 29
<211> LENGTH: 291
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_182338

<400> SEQUENCE: 29

Met Ser Ser Ile Tyr Lys Ala Leu Ala Gly Lys Ser Lys Asp Asn Lys
1               5                   10                  15

Ser Glu Lys Lys Gln Gly Asn Val Lys Gln Phe Met Asn Lys Gln Arg
            20                  25                  30

Thr Leu Leu Ile Ser Ser Arg Gly Val Asn Tyr Arg His Arg His Leu
        35                  40                  45

Ile Gln Asp Leu Ser Gly Leu Leu Pro His Ser Arg Lys Glu Pro Lys
    50                  55                  60

Leu Asp Thr Lys Lys Asp Leu Gln Gln Leu Asn Glu Ile Ala Glu Leu
65                  70                  75                  80

Tyr Asn Cys Asn Asn Val Leu Phe Phe Glu Ala Arg Lys His Gln Asp
                85                  90                  95

Leu Tyr Leu Trp Leu Ser Lys Pro Pro Asn Gly Pro Thr Ile Lys Phe
            100                 105                 110

Tyr Ile Gln Asn Leu His Thr Met Asp Glu Leu Asn Phe Thr Gly Asn
        115                 120                 125

Cys Leu Lys Gly Ser Arg Pro Val Leu Ser Phe Asp Gln Arg Phe Glu
    130                 135                 140

Ser Ser Pro His Tyr Gln Leu Ile Lys Glu Leu Leu Val His Asn Phe
145                 150                 155                 160

Cys Val Pro Pro Asn Ala Arg Lys Ser Lys Pro Phe Ile Asp His Val
                165                 170                 175

Met Ser Phe Ser Ile Val Asp Asp Lys Ile Trp Val Arg Thr Tyr Glu
            180                 185                 190

Ile Ser His Ser Thr Lys Asn Lys Glu Glu Tyr Glu Asp Gly Glu Glu
        195                 200                 205

Asp Ile Ser Leu Val Glu Ile Gly Pro Arg Phe Val Met Thr Val Ile
    210                 215                 220

Leu Ile Leu Glu Gly Ser Phe Gly Gly Pro Lys Ile Tyr Glu Asn Lys
225                 230                 235                 240

Gln Tyr Val Ser Pro Asn Val Val Arg Ala Gln Ile Lys Gln Gln Ala
                245                 250                 255

Ala Glu Glu Ala Lys Ser Arg Ala Glu Ala Ala Val Glu Arg Lys Ile
            260                 265                 270
```

```
Lys Arg Arg Glu Asn Val Leu Ala Ala Asp Pro Leu Ser Asn Asp Ala
        275                 280                 285

Leu Phe Lys
    290


<210> SEQ ID NO 30
<211> LENGTH: 291
<212> TYPE: PRT
<213> ORGANISM: Saccharomyces cerevisiae
<220> FEATURE:
<221> NAME/KEY: MISC_FEATURE
<223> OTHER INFORMATION: PAT_PROT|BMSPATENT_AAB62453

<400> SEQUENCE: 30

Met Ser Ser Ile Tyr Lys Ala Leu Ala Gly Lys Ser Lys Asp Asn Lys
1               5                   10                  15

Ser Glu Lys Lys Gln Gly Asn Val Lys Gln Phe Met Asn Lys Gln Arg
            20                  25                  30

Thr Leu Leu Ile Ser Ser Arg Gly Val Asn Tyr Arg His Arg His Leu
        35                  40                  45

Ile Gln Asp Leu Ser Gly Leu Leu Pro His Ser Arg Lys Glu Pro Lys
    50                  55                  60

Leu Asp Thr Lys Lys Asp Leu Gln Gln Leu Asn Glu Ile Ala Glu Leu
65                  70                  75                  80

Tyr Asn Cys Asn Asn Val Leu Phe Phe Glu Ala Arg Lys His Gln Asp
                85                  90                  95

Leu Tyr Leu Trp Leu Ser Lys Pro Pro Asn Gly Pro Thr Ile Lys Phe
            100                 105                 110

Tyr Ile Gln Asn Leu His Thr Met Asp Glu Leu Asn Phe Thr Gly Asn
        115                 120                 125

Cys Leu Lys Gly Ser Arg Pro Val Leu Ser Phe Asp Gln Arg Phe Glu
    130                 135                 140

Ser Ser Pro His Tyr Gln Leu Ile Lys Glu Leu Leu Val His Asn Phe
145                 150                 155                 160

Cys Val Pro Pro Asn Ala Arg Lys Ser Lys Pro Phe Ile Asp His Val
                165                 170                 175

Met Ser Phe Ser Ile Val Asp Asp Lys Ile Trp Val Arg Thr Tyr Glu
            180                 185                 190

Ile Ser His Ser Thr Lys Asn Lys Glu Glu Tyr Glu Asp Gly Glu Glu
        195                 200                 205

Asp Ile Ser Leu Val Glu Ile Gly Pro Arg Phe Val Met Thr Val Ile
    210                 215                 220

Leu Ile Leu Glu Gly Ser Phe Gly Gly Pro Lys Ile Tyr Glu Asn Lys
225                 230                 235                 240

Gln Tyr Val Ser Pro Asn Val Val Arg Ala Gln Ile Lys Gln Gln Ala
                245                 250                 255

Ala Glu Glu Ala Lys Ser Arg Ala Glu Ala Ala Val Glu Arg Lys Ile
            260                 265                 270

Lys Arg Arg Glu Asn Val Leu Ala Ala Asp Pro Leu Ser Asn Asp Ala
        275                 280                 285

Leu Phe Lys
    290


<210> SEQ ID NO 31
<211> LENGTH: 1056
<212> TYPE: PRT
<213> ORGANISM: Saccharomyces cerevisiae
```

-continued

<220> FEATURE:
<221> NAME/KEY: MISC_FEATURE
<223> OTHER INFORMATION: NR|BMSPROT_P1_137216

<400> SEQUENCE: 31

```
Met Ala Lys Lys Ala Ile Asp Ser Arg Ile Pro Ser Leu Ile Arg Asn
1               5                   10                  15

Gly Val Gln Thr Lys Gln Arg Ser Ile Phe Val Ile Val Gly Asp Arg
            20                  25                  30

Ala Arg Asn Gln Leu Pro Asn Leu His Tyr Leu Met Met Ser Ala Asp
        35                  40                  45

Leu Lys Met Asn Lys Ser Val Leu Trp Ala Tyr Lys Lys Lys Leu Leu
    50                  55                  60

Gly Phe Thr Ser His Arg Lys Lys Arg Glu Asn Lys Ile Lys Lys Glu
65                  70                  75                  80

Ile Lys Arg Gly Thr Arg Glu Val Asn Glu Met Asp Pro Phe Glu Ser
                85                  90                  95

Phe Ile Ser Asn Gln Asn Ile Arg Tyr Val Tyr Tyr Lys Glu Ser Glu
            100                 105                 110

Lys Ile Leu Gly Asn Thr Tyr Gly Met Cys Ile Leu Gln Asp Phe Glu
        115                 120                 125

Ala Leu Thr Pro Asn Leu Leu Ala Arg Thr Ile Glu Thr Val Glu Gly
    130                 135                 140

Gly Gly Ile Val Val Ile Leu Leu Lys Ser Met Ser Ser Leu Lys Gln
145                 150                 155                 160

Leu Tyr Thr Met Thr Met Asp Val His Ala Arg Tyr Arg Thr Glu Ala
                165                 170                 175

His Gly Asp Val Val Ala Arg Phe Asn Glu Arg Phe Ile Leu Ser Leu
            180                 185                 190

Gly Ser Asn Pro Asn Cys Leu Val Val Asp Asp Glu Leu Asn Val Leu
        195                 200                 205

Pro Leu Ser Gly Ala Lys Asn Val Lys Pro Leu Pro Pro Lys Glu Asp
    210                 215                 220

Asp Glu Leu Pro Pro Lys Gln Leu Glu Leu Gln Glu Leu Lys Glu Ser
225                 230                 235                 240

Leu Glu Asp Val Gln Pro Ala Gly Ser Leu Val Ser Leu Ser Lys Thr
                245                 250                 255

Val Asn Gln Ala His Ala Ile Leu Ser Phe Ile Asp Ala Ile Ser Glu
            260                 265                 270

Lys Thr Leu Asn Phe Thr Val Ala Leu Thr Ala Gly Arg Gly Arg Gly
        275                 280                 285

Lys Ser Ala Ala Leu Gly Ile Ser Ile Ala Ala Ala Val Ser His Gly
    290                 295                 300

Tyr Ser Asn Ile Phe Val Thr Ser Pro Ser Pro Glu Asn Leu Lys Thr
305                 310                 315                 320

Leu Phe Glu Phe Ile Phe Lys Gly Phe Asp Ala Leu Gly Tyr Gln Glu
                325                 330                 335

His Ile Asp Tyr Asp Ile Ile Gln Ser Thr Asn Pro Asp Phe Asn Lys
            340                 345                 350

Ala Ile Val Arg Val Asp Ile Lys Arg Asp His Arg Gln Thr Ile Gln
        355                 360                 365

Tyr Ile Val Pro Gln Asp His Gln Val Leu Gly Gln Ala Glu Leu Val
    370                 375                 380

Val Ile Asp Glu Ala Ala Ala Ile Pro Leu Pro Ile Val Lys Asn Leu
```

-continued

```
385                 390                 395                 400

Leu Gly Pro Tyr Leu Val Phe Met Ala Ser Thr Ile Asn Gly Tyr Glu
                405                 410                 415

Gly Thr Gly Arg Ser Leu Ser Leu Lys Leu Ile Gln Gln Leu Arg Asn
            420                 425                 430

Gln Asn Asn Thr Ser Gly Arg Glu Ser Thr Gln Thr Ala Val Val Ser
        435                 440                 445

Arg Asp Asn Lys Glu Lys Asp Ser His Leu His Ser Gln Ser Arg Gln
    450                 455                 460

Leu Arg Glu Ile Ser Leu Asp Glu Pro Ile Arg Tyr Ala Pro Gly Asp
465                 470                 475                 480

Pro Ile Glu Lys Trp Leu Asn Lys Leu Leu Cys Leu Asp Val Thr Leu
                485                 490                 495

Ile Lys Asn Pro Arg Phe Ala Thr Arg Gly Thr Pro His Pro Ser Gln
            500                 505                 510

Cys Asn Leu Phe Val Val Asn Arg Asp Thr Leu Phe Ser Tyr His Pro
        515                 520                 525

Val Ser Glu Asn Phe Leu Glu Lys Met Met Ala Leu Tyr Val Ser Ser
    530                 535                 540

His Tyr Lys Asn Ser Pro Asn Asp Leu Gln Leu Met Ser Asp Ala Pro
545                 550                 555                 560

Ala His Lys Leu Phe Val Leu Leu Pro Pro Ile Asp Pro Lys Asp Gly
                565                 570                 575

Gly Arg Ile Pro Asp Pro Leu Cys Val Ile Gln Ile Ala Leu Glu Gly
            580                 585                 590

Glu Ile Ser Lys Glu Ser Val Arg Asn Ser Leu Ser Arg Gly Gln Arg
        595                 600                 605

Ala Gly Gly Asp Leu Ile Pro Trp Leu Ile Ser Gln Gln Phe Gln Asp
    610                 615                 620

Glu Glu Phe Ala Ser Leu Ser Gly Ala Arg Ile Val Arg Ile Ala Thr
625                 630                 635                 640

Asn Pro Glu Tyr Ala Ser Met Gly Tyr Gly Ser Arg Ala Ile Glu Leu
                645                 650                 655

Leu Arg Asp Tyr Phe Glu Gly Lys Phe Thr Asp Met Ser Glu Asp Val
            660                 665                 670

Arg Pro Lys Asp Tyr Ser Ile Lys Arg Val Ser Asp Lys Glu Leu Ala
        675                 680                 685

Lys Thr Asn Leu Leu Lys Asp Asp Val Lys Leu Arg Asp Ala Lys Thr
    690                 695                 700

Leu Pro Pro Leu Leu Leu Lys Leu Ser Glu Gln Pro Pro His Tyr Leu
705                 710                 715                 720

His Tyr Leu Gly Val Ser Tyr Gly Leu Thr Gln Ser Leu His Lys Phe
                725                 730                 735

Trp Lys Asn Asn Ser Phe Val Pro Val Tyr Leu Arg Gln Thr Ala Asn
            740                 745                 750

Asp Leu Thr Gly Glu His Thr Cys Val Met Leu Asn Val Leu Glu Gly
        755                 760                 765

Arg Glu Ser Asn Trp Leu Val Glu Phe Ala Lys Asp Phe Arg Lys Arg
    770                 775                 780

Phe Leu Ser Leu Leu Ser Tyr Asp Phe His Lys Phe Thr Ala Val Gln
785                 790                 795                 800

Ala Leu Ser Val Ile Glu Ser Ser Lys Lys Ala Gln Asp Leu Ser Asp
                805                 810                 815
```

-continued

```
Asp Glu Lys His Asp Asn Lys Glu Leu Thr Arg Thr His Leu Asp Asp
            820                 825                 830

Ile Phe Ser Pro Phe Asp Leu Lys Arg Leu Asp Ser Tyr Ser Asn Asn
        835                 840                 845

Leu Leu Asp Tyr His Val Ile Gly Asp Met Ile Pro Met Leu Ala Leu
    850                 855                 860

Leu Tyr Phe Gly Asp Lys Met Gly Asp Ser Val Lys Leu Ser Ser Val
865                 870                 875                 880

Gln Ser Ala Ile Leu Leu Ala Ile Gly Leu Gln Arg Lys Asn Ile Asp
                885                 890                 895

Thr Ile Ala Lys Glu Leu Asn Leu Pro Ser Asn Gln Thr Ile Ala Met
            900                 905                 910

Phe Ala Lys Ile Met Arg Lys Met Ser Gln Tyr Phe Arg Gln Leu Leu
        915                 920                 925

Ser Gln Ser Ile Glu Glu Thr Leu Pro Asn Ile Lys Asp Asp Ala Ile
    930                 935                 940

Ala Glu Met Asp Gly Glu Glu Ile Lys Asn Tyr Asn Ala Ala Glu Ala
945                 950                 955                 960

Leu Asp Gln Met Glu Glu Asp Leu Glu Glu Ala Gly Ser Glu Ala Val
                965                 970                 975

Gln Ala Met Arg Glu Lys Gln Lys Glu Leu Ile Asn Ser Leu Asn Leu
            980                 985                 990

Asp Lys Tyr Ala Ile Asn Asp Asn  Ser Glu Glu Trp Ala  Glu Ser Gln
        995                 1000                1005

Lys Ser  Leu Glu Ile Ala Ala  Lys Ala Lys Gly Val  Val Ser Leu
    1010                1015                1020

Lys Thr  Gly Lys Lys Arg Thr  Thr Glu Lys Ala Glu  Asp Ile Tyr
    1025                1030                1035

Arg Gln  Glu Met Lys Ala Met  Lys Lys Pro Arg Lys  Ser Lys Lys
    1040                1045                1050

Ala Ala  Asn
    1055


<210> SEQ ID NO 32
<211> LENGTH: 1025
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAB93917

<400> SEQUENCE: 32

Met His Arg Lys Lys Val Asp Asn Arg Ile Arg Ile Leu Ile Glu Asn
1               5                   10                  15

Gly Val Ala Glu Arg Gln Arg Ser Leu Phe Val Val Val Gly Asp Arg
            20                  25                  30

Gly Lys Asp Gln Val Val Ile Leu His His Met Leu Ser Lys Ala Thr
        35                  40                  45

Val Lys Ala Arg Pro Ser Val Leu Trp Cys Tyr Lys Lys Glu Leu Gly
    50                  55                  60

Phe Ser Ser His Arg Lys Lys Arg Met Arg Gln Leu Gln Lys Lys Ile
65                  70                  75                  80

Lys Asn Gly Thr Leu Asn Ile Lys Gln Asp Asp Pro Phe Glu Leu Phe
                85                  90                  95

Ile Ala Ala Thr Asn Ile Arg Tyr Cys Tyr Tyr Asn Glu Thr His Lys
```

-continued

```
            100                 105                 110

Ile Leu Gly Asn Thr Phe Gly Met Cys Val Leu Gln Asp Phe Glu Ala
        115                 120                 125

Leu Thr Pro Asn Leu Leu Ala Arg Thr Val Glu Thr Val Glu Gly Gly
    130                 135                 140

Gly Leu Val Val Ile Leu Leu Arg Thr Met Asn Ser Leu Lys Gln Leu
145                 150                 155                 160

Tyr Thr Val Thr Met Asp Val His Ser Arg Tyr Arg Thr Glu Ala His
                165                 170                 175

Gln Asp Val Val Gly Arg Phe Asn Glu Arg Phe Ile Leu Ser Leu Ala
            180                 185                 190

Ser Cys Lys Lys Cys Leu Val Ile Asp Asp Gln Leu Asn Ile Leu Pro
        195                 200                 205

Ile Ser Ser His Val Ala Thr Met Glu Ala Leu Pro Pro Gln Thr Pro
    210                 215                 220

Asp Glu Ser Leu Gly Pro Ser Asp Leu Glu Leu Arg Glu Leu Lys Glu
225                 230                 235                 240

Ser Leu Gln Asp Thr Gln Pro Val Gly Val Leu Val Asp Cys Cys Lys
                245                 250                 255

Thr Leu Asp Gln Ala Lys Ala Val Leu Lys Phe Ile Glu Gly Ile Ser
            260                 265                 270

Glu Lys Thr Leu Arg Ser Thr Val Ala Leu Thr Ala Ala Arg Gly Arg
        275                 280                 285

Gly Lys Ser Ala Ala Leu Gly Leu Ala Ile Ala Gly Ala Val Ala Phe
    290                 295                 300

Gly Tyr Ser Asn Ile Phe Val Thr Ser Pro Cys Pro Asp Asn Leu His
305                 310                 315                 320

Thr Leu Phe Glu Phe Val Phe Lys Gly Phe Asp Ala Leu Gln Tyr Gln
                325                 330                 335

Glu His Leu Asp Tyr Glu Ile Ile Gln Ser Leu Asn Pro Glu Phe Asn
            340                 345                 350

Lys Ala Val Ile Arg Val Asn Val Phe Arg Glu His Arg Gln Thr Ile
        355                 360                 365

Gln Tyr Ile His Pro Ala Asp Ala Val Lys Leu Gly Gln Ala Glu Leu
    370                 375                 380

Val Val Ile Asp Glu Ala Ala Ala Ile Pro Leu Pro Leu Val Lys Ser
385                 390                 395                 400

Leu Leu Gly Pro Tyr Leu Val Phe Met Ala Ser Thr Ile Asn Gly Tyr
                405                 410                 415

Glu Gly Thr Gly Arg Ser Leu Ser Leu Lys Leu Ile Gln Gln Leu Arg
            420                 425                 430

Gln Gln Ser Ala Gln Ser Gln Val Ser Thr Thr Ala Glu Asn Lys Thr
        435                 440                 445

Thr Thr Thr Ala Arg Leu Ala Ser Ala Arg Thr Leu His Glu Val Ser
    450                 455                 460

Leu Gln Glu Ser Ile Arg Tyr Ala Pro Gly Asp Ala Val Glu Lys Trp
465                 470                 475                 480

Leu Asn Asp Leu Leu Cys Leu Asp Cys Leu Asn Ile Thr Arg Ile Val
                485                 490                 495

Ser Gly Cys Pro Leu Pro Glu Ala Cys Glu Leu Tyr Tyr Val Asn Arg
            500                 505                 510

Asp Thr Leu Phe Cys Tyr His Lys Ala Ser Glu Val Phe Leu Gln Arg
        515                 520                 525
```

```
Leu Met Ala Leu Tyr Val Ala Ser His Tyr Lys Asn Ser Pro Asn Asp
    530                 535                 540

Leu Gln Met Leu Ser Asp Ala Pro Ala His His Leu Phe Cys Leu Leu
545                 550                 555                 560

Pro Pro Val Pro Pro Thr Gln Asn Ala Leu Pro Glu Val Leu Ala Val
                565                 570                 575

Ile Gln Val Cys Leu Glu Gly Glu Ile Ser Arg Gln Ser Ile Leu Asn
            580                 585                 590

Ser Leu Ser Arg Gly Lys Lys Ala Ser Gly Asp Leu Ile Pro Trp Thr
        595                 600                 605

Val Ser Glu Gln Phe Gln Asp Pro Asp Phe Gly Gly Leu Ser Gly Gly
    610                 615                 620

Arg Val Val Arg Ile Ala Val His Pro Asp Tyr Gln Gly Met Gly Tyr
625                 630                 635                 640

Gly Ser Arg Ala Leu Gln Leu Leu Gln Met Tyr Tyr Glu Gly Arg Phe
                645                 650                 655

Pro Cys Leu Glu Glu Lys Val Leu Glu Thr Pro Gln Glu Ile His Thr
            660                 665                 670

Val Ser Ser Glu Ala Val Ser Leu Leu Glu Glu Val Ile Thr Pro Arg
        675                 680                 685

Lys Asp Leu Pro Pro Leu Leu Leu Lys Leu Asn Glu Arg Pro Ala Glu
    690                 695                 700

Arg Leu Asp Tyr Leu Gly Val Ser Tyr Gly Leu Thr Pro Arg Leu Leu
705                 710                 715                 720

Lys Phe Trp Lys Arg Ala Gly Phe Val Pro Val Tyr Leu Arg Gln Thr
                725                 730                 735

Pro Asn Asp Leu Thr Gly Glu His Ser Cys Ile Met Leu Lys Thr Leu
            740                 745                 750

Thr Asp Glu Asp Glu Ala Asp Gln Gly Gly Trp Leu Ala Ala Phe Trp
        755                 760                 765

Lys Asp Phe Arg Arg Arg Phe Leu Ala Leu Leu Ser Tyr Gln Phe Ser
    770                 775                 780

Thr Phe Ser Pro Ser Leu Ala Leu Asn Ile Ile Gln Asn Arg Asn Met
785                 790                 795                 800

Gly Lys Pro Ala Gln Pro Ala Leu Ser Arg Glu Glu Leu Glu Ala Leu
                805                 810                 815

Phe Leu Pro Tyr Asp Leu Lys Arg Leu Glu Met Tyr Ser Arg Asn Met
            820                 825                 830

Val Asp Tyr His Leu Ile Met Asp Met Ile Pro Ala Ile Ser Arg Ile
        835                 840                 845

Tyr Phe Leu Asn Gln Leu Gly Asp Leu Ala Leu Ser Ala Ala Gln Ser
    850                 855                 860

Ala Leu Leu Leu Gly Ile Gly Leu Gln His Lys Ser Val Asp Arg Leu
865                 870                 875                 880

Glu Lys Glu Ile Glu Leu Pro Ser Gly Gln Leu Met Gly Leu Phe Asn
                885                 890                 895

Arg Ile Ile Arg Lys Val Val Lys Leu Phe Asn Glu Val Gln Glu Lys
            900                 905                 910

Ala Ile Glu Glu Gln Met Val Ala Ala Lys Asp Val Val Met Glu Pro
        915                 920                 925

Thr Met Lys Thr Leu Ser Asp Asp Leu Asp Glu Ala Ala Lys Glu Phe
    930                 935                 940
```

-continued

```
Gln Glu Lys His Lys Lys Glu Val Gly Lys Leu Lys Ser Met Asp Leu
945                 950                 955                 960

Ser Glu Tyr Ile Ile Arg Gly Asp Asp Glu Glu Trp Asn Glu Val Leu
                965                 970                 975

Asn Lys Ala Gly Pro Asn Ala Ser Ile Ile Ser Leu Lys Ser Asp Lys
            980                 985                 990

Lys Arg Lys Leu Glu Ala Lys Gln  Glu Pro Lys Gln Ser  Lys Lys Leu
        995                 1000                1005

Lys Asn  Arg Glu Thr Lys Asn  Lys Lys Asp Met Lys  Leu Lys Arg
    1010                1015                1020

Lys Lys
    1025


<210> SEQ ID NO 33
<211> LENGTH: 707
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_150732

<400> SEQUENCE: 33

Met Val Leu Lys Ser Thr Ser Ala Asn Asp Val Ser Val Tyr Gln Val
1               5                   10                  15

Ser Gly Thr Asn Val Ser Arg Ser Leu Pro Asp Trp Ile Ala Lys Lys
            20                  25                  30

Arg Lys Arg Gln Leu Lys Asn Asp Leu Glu Tyr Gln Asn Arg Val Glu
        35                  40                  45

Leu Ile Gln Asp Phe Glu Phe Ser Glu Ala Ser Asn Lys Ile Lys Val
    50                  55                  60

Ser Arg Asp Gly Gln Tyr Cys Met Ala Thr Gly Thr Tyr Lys Pro Gln
65                  70                  75                  80

Ile His Val Tyr Asp Phe Ala Asn Leu Ser Leu Lys Phe Asp Arg His
                85                  90                  95

Thr Asp Ala Glu Asn Val Asp Phe Thr Ile Leu Ser Asp Asp Trp Thr
            100                 105                 110

Lys Ser Val His Leu Gln Asn Asp Arg Ser Ile Gln Phe Gln Asn Lys
        115                 120                 125

Gly Gly Leu His Tyr Thr Thr Arg Ile Pro Lys Phe Gly Arg Ser Leu
    130                 135                 140

Val Tyr Asn Lys Val Asn Cys Asp Leu Tyr Val Gly Ala Ser Gly Asn
145                 150                 155                 160

Glu Leu Tyr Arg Leu Asn Leu Glu Lys Gly Arg Phe Leu Asn Pro Phe
                165                 170                 175

Lys Leu Asp Thr Glu Gly Val Asn His Val Ser Ile Asn Glu Val Asn
            180                 185                 190

Gly Leu Leu Ala Ala Gly Thr Glu Thr Asn Val Val Glu Phe Trp Asp
        195                 200                 205

Pro Arg Ser Arg Ser Arg Val Ser Lys Leu Tyr Leu Glu Asn Asn Ile
    210                 215                 220

Asp Asn Arg Pro Phe Gln Val Thr Thr Thr Ser Phe Arg Asn Asp Gly
225                 230                 235                 240

Leu Thr Phe Ala Cys Gly Thr Ser Asn Gly Tyr Ser Tyr Ile Tyr Asp
                245                 250                 255

Leu Arg Thr Ser Glu Pro Ser Ile Ile Lys Asp Gln Gly Tyr Gly Phe
            260                 265                 270
```

-continued

```
Asp Ile Lys Lys Ile Ile Trp Leu Asp Asn Val Gly Thr Glu Asn Lys
        275                 280                 285

Ile Val Thr Cys Asp Lys Arg Ile Ala Lys Ile Trp Asp Arg Leu Asp
    290                 295                 300

Gly Lys Ala Tyr Ala Ser Met Glu Pro Ser Val Asp Ile Asn Asp Ile
305                 310                 315                 320

Glu His Val Pro Gly Thr Gly Met Phe Phe Thr Ala Asn Glu Ser Ile
                325                 330                 335

Pro Met His Thr Tyr Tyr Ile Pro Ser Leu Gly Pro Ser Pro Arg Trp
            340                 345                 350

Cys Ser Phe Leu Asp Ser Ile Thr Glu Glu Leu Glu Glu Lys Pro Ser
        355                 360                 365

Asp Thr Val Tyr Ser Asn Tyr Arg Phe Ile Thr Arg Asp Asp Val Lys
    370                 375                 380

Lys Leu Asn Leu Thr His Leu Val Gly Ser Arg Val Leu Arg Ala Tyr
385                 390                 395                 400

Met His Gly Phe Phe Ile Asn Thr Glu Leu Tyr Asp Lys Val Ser Leu
                405                 410                 415

Ile Ala Asn Pro Asp Ala Tyr Lys Asp Glu Arg Glu Arg Glu Ile Arg
            420                 425                 430

Arg Arg Ile Glu Lys Glu Arg Glu Ser Arg Ile Arg Ser Ser Gly Ala
        435                 440                 445

Val Gln Lys Pro Lys Ile Lys Val Asn Lys Thr Leu Val Asp Lys Leu
    450                 455                 460

Ser Gln Lys Arg Gly Asp Lys Val Ala Gly Lys Val Leu Thr Asp Asp
465                 470                 475                 480

Arg Phe Lys Glu Met Phe Glu Asp Glu Glu Phe Gln Val Asp Glu Asp
                485                 490                 495

Asp Tyr Asp Phe Lys Gln Leu Asn Pro Val Lys Ser Ile Lys Glu Thr
            500                 505                 510

Glu Glu Gly Ala Ala Lys Arg Ile Arg Ala Leu Thr Ala Ala Glu Glu
        515                 520                 525

Ser Asp Glu Glu Arg Ile Ala Met Lys Asp Gly Arg Gly His Tyr Asp
    530                 535                 540

Tyr Glu Asp Glu Glu Ser Asp Glu Glu Glu Ser Asp Asp Glu Thr Asn
545                 550                 555                 560

Gln Lys Ser Asn Lys Glu Glu Leu Ser Glu Lys Asp Leu Arg Lys Met
                565                 570                 575

Glu Lys Gln Lys Ala Leu Ile Glu Arg Arg Lys Lys Glu Lys Glu Gln
            580                 585                 590

Ser Glu Arg Phe Met Asn Glu Met Lys Ala Gly Thr Ser Thr Ser Thr
        595                 600                 605

Gln Arg Asp Glu Ser Ala His Val Thr Phe Gly Glu Gln Val Gly Glu
    610                 615                 620

Leu Leu Glu Val Glu Asn Gly Lys Lys Ser Asn Glu Ser Ile Leu Arg
625                 630                 635                 640

Arg Asn Gln Arg Gly Glu Ala Glu Leu Thr Phe Ile Pro Gln Arg Lys
                645                 650                 655

Ser Lys Lys Asp Gly Asn Tyr Lys Ser Arg Arg His Asp Asn Ser Ser
            660                 665                 670

Asp Glu Glu Gly Ile Glu Glu Asn Gly Asn Lys Lys Asp Asn Gly Arg
        675                 680                 685
```

-continued

```
Ser Lys Pro Arg Phe Glu Asn Arg Arg Arg Ala Ser Lys Asn Ala Phe
    690                 695                 700

Arg Gly Met
705


<210> SEQ ID NO 34
<211> LENGTH: 578
<212> TYPE: PRT
<213> ORGANISM: Saccharomyces cerevisiae

<400> SEQUENCE: 34

Met Ala Cys Gly Phe Arg Arg Ala Ile Ala Cys Gln Leu Ser Arg Val
1               5                   10                  15

Leu Asn Leu Pro Pro Glu Asn Leu Ile Thr Ser Ile Ser Ala Val Pro
            20                  25                  30

Ile Ser Gln Lys Glu Glu Val Ala Asp Phe Gln Leu Ser Val Asp Pro
        35                  40                  45

Leu Leu Glu Lys Asp Asn Asp His Ser Arg Pro Asp Ile Gln Val Gln
    50                  55                  60

Ala Lys Arg Leu Ala Glu Lys Leu Arg Cys Asp Thr Val Val Ser Glu
65                  70                  75                  80

Ile Ser Thr Gly Gln Arg Thr Val Asn Phe Lys Ile Asn Arg Glu Leu
                85                  90                  95

Leu Thr Lys Thr Val Leu Gln Gln Val Ile Glu Asp Gly Ser Lys Tyr
            100                 105                 110

Gly Leu Lys Ser Glu Leu Phe Ser Gly Leu Pro Gln Lys Lys Ile Val
        115                 120                 125

Val Glu Phe Ser Ser Pro Asn Val Ala Lys Lys Phe His Val Gly His
    130                 135                 140

Leu Arg Ser Thr Val Ile Gly Asn Phe Ile Ala Asn Leu Lys Glu Ala
145                 150                 155                 160

Leu Gly His Gln Val Ile Arg Ile Asn Tyr Leu Gly Asp Trp Gly Met
                165                 170                 175

Gln Phe Gly Leu Leu Gly Thr Gly Phe Gln Leu Phe Gly Tyr Glu Glu
            180                 185                 190

Lys Leu Gln Ser Asn Pro Leu Gln His Leu Phe Glu Val Tyr Val Gln
        195                 200                 205

Val Asn Lys Glu Ala Ala Asp Asp Lys Ser Val Ala Lys Ala Ala Gln
    210                 215                 220

Glu Phe Phe Gln Arg Leu Glu Leu Gly Asp Val Gln Ala Leu Ser Leu
225                 230                 235                 240

Trp Gln Lys Phe Arg Asp Leu Ser Ile Glu Glu Tyr Ile Arg Val Tyr
                245                 250                 255

Lys Arg Leu Gly Val Tyr Phe Asp Glu Tyr Ser Gly Glu Ser Phe Tyr
            260                 265                 270

Arg Glu Lys Ser Gln Glu Val Leu Lys Leu Leu Glu Ser Lys Gly Leu
        275                 280                 285

Leu Leu Lys Thr Ile Lys Gly Thr Ala Val Val Asp Leu Ser Gly Asn
    290                 295                 300

Gly Asp Pro Ser Ser Ile Cys Thr Val Met Arg Ser Asp Gly Thr Ser
305                 310                 315                 320

Leu Tyr Ala Thr Arg Asp Leu Ala Ala Ala Val Asp Arg Met Asp Lys
                325                 330                 335

Tyr Asn Phe Asp Thr Met Ile Tyr Val Thr Asp Lys Gly Gln Lys Lys
            340                 345                 350
```

His Phe Gln Gln Val Phe Gln Met Leu Lys Ile Met Gly Tyr Asp Trp
355 360 365

Ala Glu Arg Cys Gln His Val Pro Phe Gly Val Val Gln Gly Met Lys
370 375 380

Thr Arg Arg Gly Asp Val Thr Phe Leu Glu Asp Val Leu Asn Glu Ile
385 390 395 400

Gln Leu Arg Met Leu Gln Asn Met Ala Ser Ile Lys Thr Thr Lys Glu
405 410 415

Leu Lys Asn Pro Gln Glu Thr Ala Glu Arg Val Gly Leu Ala Ala Leu
420 425 430

Ile Ile Gln Asp Phe Lys Gly Leu Leu Leu Ser Asp Tyr Lys Phe Ser
435 440 445

Trp Asp Arg Val Phe Gln Ser Arg Gly Asp Thr Gly Val Phe Leu Gln
450 455 460

Tyr Thr His Ala Arg Leu His Ser Leu Glu Glu Thr Phe Gly Cys Gly
465 470 475 480

Tyr Leu Asn Asp Phe Asn Thr Ala Cys Leu Gln Glu Pro Gln Ser Val
485 490 495

Ser Ile Leu Gln His Leu Leu Arg Phe Asp Glu Val Leu Tyr Lys Ser
500 505 510

Ser Gln Asp Phe Gln Pro Arg His Ile Val Ser Tyr Leu Leu Thr Leu
515 520 525

Ser His Leu Ala Ala Val Ala His Lys Thr Leu Gln Ile Lys Asp Ser
530 535 540

Pro Pro Glu Val Ala Gly Ala Arg Leu His Leu Phe Lys Ala Val Arg
545 550 555 560

Ser Val Leu Ala Asn Gly Met Lys Leu Leu Gly Ile Thr Pro Val Cys
565 570 575

Arg Met

<210> SEQ ID NO 35
<211> LENGTH: 235
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_142340

<400> SEQUENCE: 35

Met Ala Val His Thr Asn Arg Gln Ile Leu Thr Arg Gly Lys Asn Tyr
1 5 10 15

Ala Thr Lys Gln Ser Lys Lys Phe Gly Thr Asp Glu Val Thr Phe Asp
20 25 30

Lys Asp Ser Arg Leu Asp Tyr Leu Thr Gly Phe His Lys Arg Lys Leu
35 40 45

Gln Arg Gln Lys Lys Ala Gln Glu Phe Ile Lys Glu Gln Glu Arg Leu
50 55 60

Arg Lys Ile Glu Glu Arg Gln Lys Ile Arg Gln Glu Arg Lys Glu Val
65 70 75 80

Met Glu Glu Gln Leu Lys Thr Phe Lys Glu Ser Leu Asn Leu Glu Ala
85 90 95

Glu Ile Glu Asp Ala Lys Asn Asp Lys Thr Glu Asp Leu Gln Val Glu
100 105 110

Ser Asp Glu Ser Trp His Gly Phe Asp Ser Asp Lys Asp Asp Gly Asp
115 120 125

Asn Asp Asn Asn Glu Ser Ser Val Lys Pro Ile Leu Lys Lys Gly Ala
    130                 135                 140

Ile Thr Glu Ile Tyr Asp Asp Ser Thr Thr Val Glu Leu Glu Thr Leu
145                 150                 155                 160

Glu Pro Asn Asp Asn Phe Glu Tyr Leu Ala Gln Leu Asn Asn Val Lys
                165                 170                 175

Leu Glu Lys Ala Glu Lys Val Leu Lys Gln Ser Ile Asn Arg Ala Thr
            180                 185                 190

Lys Tyr Ala Lys Phe Leu Gly Val Asp Glu Lys Gln Lys Lys Lys Pro
        195                 200                 205

Arg Val Lys Lys Phe Arg Tyr Leu Thr Lys Asn Glu Arg Arg Ile Asn
    210                 215                 220

Gln Arg Lys Ala Asn Asp Asn Lys Arg Arg Arg
225                 230                 235

<210> SEQ ID NO 36
<211> LENGTH: 203
<212> TYPE: PRT
<213> ORGANISM: yeast
<220> FEATURE:
<221> NAME/KEY: MISC_FEATURE
<223> OTHER INFORMATION: PAT_PROT|BMSPATENT_AAW33110

<400> SEQUENCE: 36

Met Asp Asn Thr Ser Leu Leu Thr Arg Gly Gly Glu Ile Tyr Ser Arg
1               5                   10                  15

Lys Lys Gly Lys Lys Gln Arg Leu Glu Glu Ile Val Phe Asp Lys Glu
            20                  25                  30

Lys Arg Lys Glu Tyr Leu Thr Gly Phe His Lys Arg Lys Val Glu Arg
        35                  40                  45

Arg Lys His Ala Gln Val Gln Leu Glu Gln Gln Lys Arg Glu Glu Arg
    50                  55                  60

Leu Ala Leu Arg Lys Ser Leu Arg Glu Gln Arg Lys Arg Glu Leu Ala
65                  70                  75                  80

Glu Arg Leu Ala Phe Ser Lys Glu Leu Asn Ser Ser Leu Glu Asn Asp
                85                  90                  95

Glu Glu Ser Ser Gln Gln Glu Asp Ser Ser Ser Lys Ser Asp Ser Glu
            100                 105                 110

Glu Glu Ser Ser Met Glu Pro Lys Thr Thr Glu Tyr Asp Glu Asp Asp
        115                 120                 125

Lys His Val Thr Val Glu Ile Val Glu Asp Asp Asp Asp Glu Glu Ile
    130                 135                 140

Ala Tyr Pro Lys Glu Gly Phe Val Thr Pro Arg Ile Ser Pro Pro Pro
145                 150                 155                 160

Asp Val Pro Leu Arg Pro His Lys Pro Lys Asn Ala Ala Lys Lys Lys
                165                 170                 175

Phe Arg Tyr Glu Ser Lys Phe Glu Arg Thr Gln Asp Arg Arg Lys Glu
            180                 185                 190

Lys Ile Arg Arg Leu Lys Lys Lys Ile Arg Arg
        195                 200

<210> SEQ ID NO 37
<211> LENGTH: 367
<212> TYPE: PRT
<213> ORGANISM: Saccharomyces cerevisiae
<220> FEATURE:
<221> NAME/KEY: MISC_FEATURE

<223> OTHER INFORMATION: NR|BMSPROT_P1_182291;PRT

<400> SEQUENCE: 37

```
Met Ser Ser Ser Ala Pro Lys Tyr Thr Thr Phe Gln Gly Ser Gln Asn
1               5                   10                  15

Phe Arg Leu Arg Ile Val Leu Ala Thr Leu Ser Gly Lys Pro Ile Lys
            20                  25                  30

Ile Glu Lys Ile Arg Ser Gly Asp Leu Asn Pro Gly Leu Lys Asp Tyr
        35                  40                  45

Glu Val Ser Phe Leu Arg Leu Ile Glu Ser Val Thr Asn Gly Ser Val
    50                  55                  60

Ile Glu Ile Ser Tyr Thr Gly Thr Thr Val Ile Tyr Arg Pro Gly Ile
65                  70                  75                  80

Ile Val Gly Gly Ala Ser Thr His Ile Cys Pro Ser Ser Lys Pro Val
                85                  90                  95

Gly Tyr Phe Val Glu Pro Met Leu Tyr Leu Ala Pro Phe Ser Lys Lys
            100                 105                 110

Lys Phe Ser Ile Leu Phe Lys Gly Ile Thr Ala Ser His Asn Asp Ala
        115                 120                 125

Gly Ile Glu Ala Ile Lys Trp Gly Leu Met Pro Val Met Glu Lys Phe
    130                 135                 140

Gly Val Arg Glu Cys Ala Leu His Thr Leu Lys Arg Gly Ser Pro Pro
145                 150                 155                 160

Leu Gly Gly Gly Glu Val His Leu Val Val Asp Ser Leu Ile Ala Gln
                165                 170                 175

Pro Ile Thr Met His Glu Ile Asp Arg Pro Ile Ile Ser Ser Ile Thr
            180                 185                 190

Gly Val Ala Tyr Ser Thr Arg Val Ser Pro Ser Leu Val Asn Arg Met
        195                 200                 205

Ile Asp Gly Ala Lys Lys Val Leu Lys Asn Leu Gln Cys Glu Val Asn
    210                 215                 220

Ile Thr Ala Asp Val Trp Arg Gly Glu Asn Ser Gly Lys Ser Pro Gly
225                 230                 235                 240

Trp Gly Ile Thr Leu Val Ala Gln Ser Lys Gln Lys Gly Trp Ser Tyr
                245                 250                 255

Phe Ala Glu Asp Ile Gly Asp Ala Gly Ser Ile Pro Glu Glu Leu Gly
            260                 265                 270

Glu Lys Val Ala Cys Gln Leu Leu Glu Glu Ile Ser Lys Ser Ala Ala
        275                 280                 285

Val Gly Arg Asn Gln Leu Pro Leu Ala Ile Val Tyr Met Val Ile Gly
    290                 295                 300

Lys Glu Asp Ile Gly Arg Leu Arg Ile Asn Lys Glu Gln Ile Asp Glu
305                 310                 315                 320

Arg Phe Ile Ile Leu Leu Arg Asp Ile Lys Lys Ile Phe Asn Thr Glu
                325                 330                 335

Val Phe Leu Lys Pro Val Asp Glu Ala Asp Asn Glu Asp Met Ile Ala
            340                 345                 350

Thr Ile Lys Gly Ile Gly Phe Thr Asn Thr Ser Lys Lys Ile Ala
        355                 360                 365
```

<210> SEQ ID NO 38
<211> LENGTH: 367
<212> TYPE: PRT
<213> ORGANISM: Saccharomyces cerevisiae
<220> FEATURE:

-continued

<221> NAME/KEY: MISC_FEATURE
<223> OTHER INFORMATION: PAT_PROT|BMSPATENT_AAW60075

<400> SEQUENCE: 38

Met Ser Ser Ser Ala Pro Lys Tyr Thr Thr Phe Gln Gly Ser Gln Asn
1 5 10 15

Phe Arg Leu Arg Ile Val Leu Ala Thr Leu Ser Gly Lys Pro Ile Lys
20 25 30

Ile Glu Lys Ile Arg Ser Gly Asp Leu Asn Pro Gly Leu Lys Asp Tyr
35 40 45

Glu Val Ser Phe Leu Arg Leu Ile Glu Ser Val Thr Asn Gly Ser Val
50 55 60

Ile Glu Ile Ser Tyr Thr Gly Thr Thr Val Ile Tyr Arg Pro Gly Ile
65 70 75 80

Ile Val Gly Gly Ala Ser Thr His Ile Cys Pro Ser Ser Lys Pro Val
85 90 95

Gly Tyr Phe Val Glu Pro Met Leu Tyr Leu Ala Pro Phe Ser Lys Lys
100 105 110

Lys Phe Ser Ile Leu Phe Lys Gly Ile Thr Ala Ser His Asn Asp Ala
115 120 125

Gly Ile Glu Ala Ile Lys Trp Gly Leu Met Pro Val Met Glu Lys Phe
130 135 140

Gly Val Arg Glu Cys Ala Leu His Thr Leu Lys Arg Gly Ser Pro Pro
145 150 155 160

Leu Gly Gly Gly Glu Val His Leu Val Val Asp Ser Leu Ile Ala Gln
165 170 175

Pro Ile Thr Met His Glu Ile Asp Arg Pro Ile Ile Ser Ser Ile Thr
180 185 190

Gly Val Ala Tyr Ser Thr Arg Val Ser Pro Ser Leu Val Asn Arg Met
195 200 205

Ile Asp Gly Ala Lys Lys Val Leu Lys Asn Leu Gln Cys Glu Val Asn
210 215 220

Ile Thr Ala Asp Val Trp Arg Gly Glu Asn Ser Gly Lys Ser Pro Gly
225 230 235 240

Trp Gly Ile Thr Leu Val Ala Gln Ser Lys Gln Lys Gly Trp Ser Tyr
245 250 255

Phe Ala Glu Asp Ile Gly Asp Ala Gly Ser Ile Pro Glu Glu Leu Gly
260 265 270

Glu Lys Val Ala Cys Gln Leu Leu Glu Glu Ile Ser Lys Ser Ala Ala
275 280 285

Val Gly Arg Asn Gln Leu Pro Leu Ala Ile Val Tyr Met Val Ile Gly
290 295 300

Lys Glu Asp Ile Gly Arg Leu Arg Ile Asn Lys Glu Gln Ile Asp Glu
305 310 315 320

Arg Phe Ile Ile Leu Leu Arg Asp Ile Lys Lys Ile Phe Asn Thr Glu
325 330 335

Val Phe Leu Lys Pro Val Asp Glu Ala Asp Asn Glu Asp Met Ile Ala
340 345 350

Thr Ile Lys Gly Ile Gly Phe Thr Asn Thr Ser Lys Lys Ile Ala
355 360 365

<210> SEQ ID NO 39
<211> LENGTH: 254
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_161797

<400> SEQUENCE: 39

```
Met Arg Gln Lys Arg Ala Lys Ser Tyr Arg Lys Gln Leu Leu Val Tyr
1               5                   10                  15

Ser His Thr Phe Lys Phe Arg Glu Pro Tyr Gln Val Leu Val Asp Asn
            20                  25                  30

Gln Leu Val Leu Glu Cys Asn Asn Ser Asn Phe Asn Leu Pro Ser Gly
        35                  40                  45

Leu Lys Arg Thr Leu Gln Ala Asp Val Lys Val Met Ile Thr Gln Cys
    50                  55                  60

Cys Ile Gln Ala Leu Tyr Glu Thr Arg Asn Asp Gly Ala Ile Asn Leu
65                  70                  75                  80

Ala Lys Gln Phe Glu Arg Arg Arg Cys Asn His Ser Phe Lys Asp Pro
                85                  90                  95

Lys Ser Pro Ala Glu Cys Ile Glu Ser Val Val Asn Ile Ser Gly Ala
            100                 105                 110

Asn Lys His Arg Tyr Val Val Ala Ser Gln Asp Ile Asp Leu Arg Arg
        115                 120                 125

Lys Leu Arg Thr Val Pro Gly Val Pro Leu Ile His Leu Thr Arg Ser
    130                 135                 140

Val Met Val Met Glu Pro Leu Ser Thr Ala Ser Ala Lys Ala Ser Lys
145                 150                 155                 160

Ile Thr Glu Glu Gln Lys Leu Tyr Lys Gly Leu Asn Asp Pro Asn Ile
                165                 170                 175

Glu Lys Leu Gln Glu Ser Gly Asp Gly Ser Gly Lys Glu Ser Ile Thr
            180                 185                 190

Lys Lys Arg Lys Leu Gly Pro Lys Ala Pro Asn Pro Leu Ser Val Lys
        195                 200                 205

Lys Lys Lys Lys Val Asn Ser Pro Ser Asp Glu Val Lys Asp Lys Glu
    210                 215                 220

Asp Thr Ser Lys Glu Lys Lys Lys Arg Arg Arg Arg Lys His Lys Ser
225                 230                 235                 240

Asn Thr Asn Val Pro Val Ser Asn Gly Thr Thr Ala Ala Gln
                245                 250
```

<210> SEQ ID NO 40
<211> LENGTH: 281
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAG48012

<400> SEQUENCE: 40

```
Met Arg Val Lys Arg Gln Lys Lys Asn Arg Arg Thr Val Arg Phe Phe
1               5                   10                  15

Thr Val Cys Tyr Gly Phe Arg Gln Pro Tyr Lys Val Leu Cys Asp Gly
            20                  25                  30

Thr Phe Val His His Leu Val Thr Asn Glu Ile Thr Pro Ala Asp Thr
        35                  40                  45

Ala Val Ser Glu Leu Leu Gly Gly Pro Val Lys Leu Phe Thr Thr Arg
    50                  55                  60

Cys Val Ile Ala Glu Leu Glu Lys Leu Gly Lys Asp Phe Ala Glu Ser
65                  70                  75                  80
```

-continued

```
Leu Glu Ala Ala Gln Thr Leu Asn Thr Ala Thr Cys Glu His Glu Glu
                85                  90                  95

Ala Lys Thr Ala Asp Glu Cys Leu Ser Glu Val Ile Gly Val Gln Asn
            100                 105                 110

Thr Glu His Phe Phe Leu Gly Thr Gln Asp Ala Glu Phe Arg Arg Lys
        115                 120                 125

Leu Gln Gln Glu Ser Ile Val Pro Leu Val Phe Gly Leu Arg Asn Ile
    130                 135                 140

Leu Leu Ile Asp Gln Pro Ser Asp Phe Gln Arg Gln Ser Ala Lys Asp
145                 150                 155                 160

Ser Glu Asn Lys Arg Leu Thr Met Thr Asp Thr Glu Lys Lys Leu Leu
                165                 170                 175

Val Lys Arg Thr Ala Lys Ile Ile Ala Ser Asn Arg Lys Glu Ala Thr
            180                 185                 190

Ile Ala Asn Glu Glu Trp Gly Met Pro Arg Val Val Ser Thr Lys Asn
        195                 200                 205

Gly Leu Gly Val Lys Asp Arg Pro Gln Phe Lys Arg Asn Arg Ala Lys
    210                 215                 220

Gly Pro Asn Pro Leu Ser Cys Met Lys Lys Lys Lys Glu Asn Pro Gln
225                 230                 235                 240

Ser Lys Ser Lys Ala Asp Ser Asn Ser Asn Ala Gln Lys Glu Lys Lys
                245                 250                 255

Glu Gly Gly Ser Asp Thr Gln Lys Arg Ser Arg Lys Arg Ser Lys Lys
            260                 265                 270

Gly Lys Ser Gly Pro Glu Arg Thr Glu
        275                 280
```

<210> SEQ ID NO 41
<211> LENGTH: 459
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_182387

<400> SEQUENCE: 41

```
Met Thr Glu Asn Gln Thr Ala His Val Arg Ala Leu Ile Leu Asp Ala
1               5                   10                  15

Thr Pro Leu Ile Thr Gln Ser Tyr Thr His Tyr Gln Asn Tyr Ala Gln
            20                  25                  30

Ser Phe Tyr Thr Thr Pro Thr Val Phe Gln Glu Ile Lys Asp Ala Gln
        35                  40                  45

Ala Arg Lys Asn Leu Glu Ile Trp Gln Ser Leu Gly Thr Leu Lys Leu
    50                  55                  60

Val His Pro Ser Glu Asn Ser Ile Ala Lys Val Ser Thr Phe Ala Lys
65                  70                  75                  80

Leu Thr Gly Asp Tyr Ser Val Leu Ser Ala Asn Asp Leu His Ile Leu
                85                  90                  95

Ala Leu Thr Tyr Glu Leu Glu Ile Lys Leu Asn Asn Gly Asp Trp Arg
            100                 105                 110

Leu Arg Lys Lys Pro Gly Asp Ala Leu Asp Ala Ser Lys Ala Asp Val
        115                 120                 125

Gly Thr Asp Gly Lys Gln Lys Leu Thr Glu Asp Asn Lys Lys Glu Glu
    130                 135                 140

Asp Ser Glu Ser Val Pro Lys Lys Lys Asn Lys Arg Arg Gly Gly Lys
```

-continued 145 150 155 160

Lys Gln Lys Ala Lys Arg Glu Ala Arg Glu Ala Arg Glu Ala Glu Asn
165 170 175

Ala Asn Leu Glu Leu Glu Ser Lys Ala Glu Glu His Val Glu Glu Ala
180 185 190

Gly Ser Lys Glu Gln Ile Cys Asn Asp Glu Asn Ile Lys Glu Ser Ser
195 200 205

Asp Leu Asn Glu Val Phe Glu Asp Ala Asp Asp Asp Gly Asp Trp Ile
210 215 220

Thr Pro Glu Asn Leu Thr Glu Ala Ile Ile Lys Asp Ser Gly Glu Asp
225 230 235 240

Thr Thr Gly Ser Leu Gly Val Glu Ala Ser Glu Glu Asp Arg His Val
245 250 255

Ala Leu Asn Arg Pro Glu Asn Gln Val Ala Leu Ala Thr Gly Asp Phe
260 265 270

Ala Val Gln Asn Val Ala Leu Gln Met Asn Leu Asn Leu Met Asn Phe
275 280 285

Met Ser Gly Leu Lys Ile Lys Arg Ile Arg Asn Tyr Met Leu Arg Cys
290 295 300

His Ala Cys Phe Lys Ile Phe Pro Leu Pro Lys Asp Gly Lys Pro Lys
305 310 315 320

His Phe Cys Ala Ser Cys Gly Gly Gln Gly Thr Leu Leu Arg Cys Ala
325 330 335

Val Ser Val Asp Ser Arg Thr Gly Asn Val Thr Pro His Leu Lys Ser
340 345 350

Asn Phe Gln Trp Asn Asn Arg Gly Asn Arg Tyr Ser Val Ala Ser Pro
355 360 365

Leu Ser Lys Asn Ser Gln Lys Arg Tyr Gly Lys Lys Gly His Val His
370 375 380

Ser Lys Pro Gln Glu Asn Val Ile Leu Arg Glu Asp Gln Lys Glu Tyr
385 390 395 400

Glu Lys Val Ile Lys Gln Glu Glu Trp Thr Arg Arg His Asn Glu Lys
405 410 415

Ile Leu Asn Asn Trp Ile Gly Gly Gly Ser Ala Asp Asn Tyr Ile Ser
420 425 430

Pro Phe Ala Ile Thr Gly Leu Lys Gln His Asn Val Arg Ile Gly Lys
435 440 445

Gly Arg Tyr Val Asn Ser Ser Lys Arg Arg Ser
450 455

<210> SEQ ID NO 42
<211> LENGTH: 412
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAB09929

<400> SEQUENCE: 42

Met Ala Pro Val Glu His Val Val Ala Asp Ala Gly Ala Phe Leu Arg
1 5 10 15

His Ala Ala Leu Gln Asp Ile Gly Lys Asn Ile Tyr Thr Ile Arg Glu
20 25 30

Val Val Thr Glu Ile Arg Asp Lys Ala Thr Arg Arg Arg Leu Ala Val
35 40 45

-continued

```
Leu Pro Tyr Glu Leu Arg Phe Lys Glu Pro Leu Pro Glu Tyr Val Arg
    50                  55                  60

Leu Val Thr Glu Phe Ser Lys Lys Thr Gly Asp Tyr Pro Ser Leu Ser
65                  70                  75                  80

Ala Thr Asp Ile Gln Val Leu Ala Leu Thr Tyr Gln Leu Glu Ala Glu
                85                  90                  95

Phe Val Gly Val Ser His Leu Lys Gln Glu Pro Gln Lys Val Lys Val
            100                 105                 110

Ser Ser Ser Ile Gln His Pro Glu Thr Pro Leu His Ile Ser Gly Phe
        115                 120                 125

His Leu Pro Tyr Lys Pro Lys Pro Pro Gln Glu Thr Glu Lys Gly His
    130                 135                 140

Ser Ala Cys Glu Pro Glu Asn Leu Glu Phe Ser Ser Phe Met Phe Trp
145                 150                 155                 160

Arg Asn Pro Leu Pro Asn Ile Asp His Glu Leu Gln Glu Leu Leu Ile
                165                 170                 175

Asp Arg Gly Glu Asp Val Pro Ser Glu Glu Glu Glu Glu Glu Glu Asn
            180                 185                 190

Gly Phe Glu Asp Arg Lys Asp Asp Ser Asp Asp Asp Gly Gly Gly Trp
        195                 200                 205

Ile Thr Pro Ser Asn Ile Lys Gln Ile Gln Gln Glu Leu Glu Gln Cys
    210                 215                 220

Asp Val Pro Glu Asp Val Arg Val Gly Cys Leu Thr Thr Asp Phe Ala
225                 230                 235                 240

Met Gln Asn Val Leu Leu Gln Met Gly Leu His Val Leu Ala Val Asn
                245                 250                 255

Gly Met Leu Ile Arg Glu Ala Arg Ser Tyr Ile Leu Arg Cys His Gly
            260                 265                 270

Cys Phe Lys Thr Thr Ser Asp Met Ser Arg Val Phe Cys Ser His Cys
        275                 280                 285

Gly Asn Lys Thr Leu Lys Lys Val Ser Val Thr Val Ser Asp Asp Gly
    290                 295                 300

Thr Leu His Met His Phe Ser Arg Asn Pro Lys Val Leu Asn Pro Arg
305                 310                 315                 320

Gly Leu Arg Tyr Ser Leu Pro Thr Pro Lys Gly Gly Lys Tyr Ala Ile
                325                 330                 335

Asn Pro His Leu Thr Glu Asp Gln Arg Phe Pro Gln Leu Arg Leu Ser
            340                 345                 350

Gln Lys Ala Arg Gln Lys Thr Asn Val Phe Ala Pro Asp Tyr Ile Ala
        355                 360                 365

Gly Val Ser Pro Phe Val Glu Asn Asp Ile Ser Ser Arg Ser Ala Thr
    370                 375                 380

Leu Gln Val Arg Asp Ser Thr Leu Gly Ala Gly Arg Arg Arg Leu Asn
385                 390                 395                 400

Pro Asn Ala Ser Arg Lys Lys Phe Val Lys Lys Arg
                405                 410
```

```
<210> SEQ ID NO 43
<211> LENGTH: 199
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_178703

<400> SEQUENCE: 43
```

-continued

```
Met Arg Ile Tyr Gln Cys His Phe Cys Ser Ser Pro Cys Tyr Pro Gly
1               5                   10                  15

His Gly Ile Met Phe Val Arg Asn Asp Ala Lys Glu Phe Arg Phe Cys
            20                  25                  30

Arg Ser Lys Cys His Lys Ala Phe Lys Gln Arg Arg Asn Pro Arg Lys
        35                  40                  45

Leu Lys Trp Thr Lys Ala Phe Arg Lys Ala Ala Gly Lys Glu Leu Ala
    50                  55                  60

Val Asp Ser Thr Leu Thr Phe Ala Gln Arg Arg Asn Val Pro Val Arg
65                  70                  75                  80

Tyr Asn Arg Glu Leu Val Ala Thr Thr Leu Lys Ala Met Ala Arg Ile
                85                  90                  95

Glu Glu Ile Arg Gln Lys Arg Glu Arg Ala Phe Tyr Lys Asn Arg Met
            100                 105                 110

Arg Gly Asn Lys Glu Lys Asp Phe Leu Arg Asp Lys Lys Leu Val Glu
        115                 120                 125

Ser Asn Pro Glu Leu Leu Arg Ile Arg Glu Val Glu Ile Ala Arg Lys
    130                 135                 140

Leu Ala Lys Glu Gln Glu Arg Ala Glu Ser Val Ser Glu Gln Glu Glu
145                 150                 155                 160

Ser Glu Glu Glu Glu Glu Asp Met Glu Ile Asp Ser Asp Glu Glu Glu
                165                 170                 175

Glu Glu Gln Leu Glu Lys Gln Lys Ile Leu Leu Lys Asn Arg Arg Arg
            180                 185                 190

Asn Thr Lys Lys Ile Ala Phe
        195


<210> SEQ ID NO 44
<211> LENGTH: 184
<212> TYPE: PRT
<213> ORGANISM: Homo sapiens
<220> FEATURE:
<221> NAME/KEY: MISC_FEATURE
<223> OTHER INFORMATION: PAT_PROT|BMSPATENT_AAB43803

<400> SEQUENCE: 44

Trp Ile Pro Arg Ala Cys Arg Glu Phe Gly Thr Arg Phe Gly Gly Val
1               5                   10                  15

Thr Arg Gly Phe Asn Met Arg Ile Glu Lys Cys Tyr Phe Cys Ser Gly
            20                  25                  30

Pro Ile Tyr Pro Gly His Gly Met Met Phe Val Arg Asn Asp Cys Lys
        35                  40                  45

Val Phe Arg Phe Cys Lys Ser Lys Cys His Lys Asn Phe Lys Lys Lys
    50                  55                  60

Arg Asn Pro Arg Lys Val Arg Trp Thr Lys Ala Phe Arg Lys Ala Ala
65                  70                  75                  80

Gly Lys Glu Leu Thr Val Asp Asn Ser Phe Glu Phe Glu Lys Arg Arg
                85                  90                  95

Asn Glu Pro Ile Lys Tyr Gln Arg Glu Leu Trp Asn Lys Thr Ile Asp
            100                 105                 110

Ala Met Lys Arg Val Glu Glu Ile Lys Gln Lys Arg Gln Ala Lys Phe
        115                 120                 125

Ile Met Asn Arg Leu Lys Lys Asn Lys Glu Leu Gln Lys Val Gln Asp
    130                 135                 140

Ile Lys Glu Val Lys Gln Asn Ile His Leu Ile Arg Ala Pro Leu Ala
```

-continued

```
145                 150                 155                 160

Gly Lys Gly Lys Gln Leu Glu Glu Lys Met Val Gln Gln Leu Gln Glu
                165                 170                 175

Asp Val Asp Met Glu Asp Ala Pro
            180


<210> SEQ ID NO 45
<211> LENGTH: 388
<212> TYPE: PRT
<213> ORGANISM: Candida albicans
<220> FEATURE:
<221> NAME/KEY: MISC_FEATURE
<223> OTHER INFORMATION: CaYJR072c

<400> SEQUENCE: 45

Met Pro Thr Pro Pro Pro Thr Ile Ile Cys Ile Gly Met Ala Gly Ser
1               5                   10                  15

Gly Lys Thr Thr Phe Val Gln Arg Leu Asn Ser His Leu His Ser Lys
            20                  25                  30

Lys Thr Pro Pro Tyr Leu Ile Asn Leu Asp Pro Ala Val Leu Lys Ile
        35                  40                  45

Pro Phe Gly Ala Asn Ile Asp Ile Arg Asp Ser Val Lys Tyr Lys Lys
    50                  55                  60

Val Met Glu Glu Tyr Asn Leu Gly Pro Asn Gly Ala Ile Val Thr Ser
65                  70                  75                  80

Leu Asn Leu Phe Ser Thr Lys Ile Asp Gln Val Ile Lys Leu Ile Asp
                85                  90                  95

Lys Lys Gln Asp Lys Ile Asn Asn Val Val Ile Asp Thr Pro Gly Gln
            100                 105                 110

Ile Glu Cys Phe Ile Trp Ser Ala Ser Gly Ser Ile Ile Thr Glu Ser
        115                 120                 125

Phe Ala Ser Glu Phe Pro Thr Val Ile Ala Tyr Ile Val Asp Thr Pro
    130                 135                 140

Arg Asn Thr Ser Pro Thr Thr Phe Met Ser Asn Met Leu Tyr Ala Cys
145                 150                 155                 160

Ser Ile Leu Tyr Lys Thr Lys Leu Pro Met Ile Val Val Phe Asn Lys
                165                 170                 175

Thr Asp Val Thr Lys Asp Asp Phe Ala Lys Glu Trp Met Thr Asp Phe
            180                 185                 190

Glu Ser Phe Gln Met Ala Ile Gln Lys Asp Lys Asp Leu Asn Asn Glu
        195                 200                 205

Gln Gly Ser Gly Tyr Met Ser Ser Leu Ile Asn Ser Met Ser Leu Met
    210                 215                 220

Leu Glu Glu Phe Tyr Ser Asn Leu Asp Val Val Gly Val Ser Ser Tyr
225                 230                 235                 240

Thr Gly Gln Gly Phe Asp Lys Phe Met Glu Ala Val Asp Asn Lys Val
                245                 250                 255

Asp Glu Tyr Asn Glu Phe Tyr Lys Ala Glu Lys Glu Arg Ile Leu Lys
            260                 265                 270

Gln Lys Glu Glu Asp Glu Lys Lys Arg Gln Thr Lys Ser Leu Asn Lys
        275                 280                 285

Leu Met Lys Asp Met Lys Met Lys Asp Thr Lys Gly Asp His Thr Lys
    290                 295                 300

Lys Asp Ser Glu Val Leu Ser Asp Tyr Glu Glu Asp Asp Asn Glu Ile
305                 310                 315                 320
```

-continued

```
Asp Asp Glu Ile Gln Gly Glu Val Leu Arg Asp Glu Asp Glu Pro Glu
                325                 330                 335

Arg Glu Tyr Thr Phe Pro Glu Asp Arg Gln Ser Glu Val Asn Ser Arg
            340                 345                 350

Thr Asp Ala Asp Leu Gln Ser Arg Tyr Gln Gln Ala Phe Glu Ser Thr
        355                 360                 365

Ala Lys Pro Ala Ser Ser Lys Thr Ala Glu Asn Ile Ala Asn Tyr Ile
    370                 375                 380

Asn Arg Thr Gln
385


<210> SEQ ID NO 46
<211> LENGTH: 385
<212> TYPE: PRT
<213> ORGANISM: Saccharomyces cerevisiae
<220> FEATURE:
<221> NAME/KEY: MISC_FEATURE
<223> OTHER INFORMATION: NR|BMSPROT_P1_149006

<400> SEQUENCE: 46

Met Ser Leu Ser Thr Ile Ile Cys Ile Gly Met Ala Gly Ser Gly Lys
1               5                   10                  15

Thr Thr Phe Met Gln Arg Leu Asn Ser His Leu Arg Ala Glu Lys Thr
            20                  25                  30

Pro Pro Tyr Val Ile Asn Leu Asp Pro Ala Val Leu Arg Val Pro Tyr
        35                  40                  45

Gly Ala Asn Ile Asp Ile Arg Asp Ser Ile Lys Tyr Lys Lys Val Met
    50                  55                  60

Glu Asn Tyr Gln Leu Gly Pro Asn Gly Ala Ile Val Thr Ser Leu Asn
65                  70                  75                  80

Leu Phe Ser Thr Lys Ile Asp Gln Val Ile Arg Leu Val Glu Gln Lys
                85                  90                  95

Lys Asp Lys Phe Gln Asn Cys Ile Ile Asp Thr Pro Gly Gln Ile Glu
            100                 105                 110

Cys Phe Val Trp Ser Ala Ser Gly Ala Ile Ile Thr Glu Ser Phe Ala
        115                 120                 125

Ser Ser Phe Pro Thr Val Ile Ala Tyr Ile Val Asp Thr Pro Arg Asn
    130                 135                 140

Ser Ser Pro Thr Thr Phe Met Ser Asn Met Leu Tyr Ala Cys Ser Ile
145                 150                 155                 160

Leu Tyr Lys Thr Lys Leu Pro Met Ile Val Val Phe Asn Lys Thr Asp
                165                 170                 175

Val Cys Lys Ala Asp Phe Ala Lys Glu Trp Met Thr Asp Phe Glu Ser
            180                 185                 190

Phe Gln Ala Ala Ile Lys Glu Asp Gln Asp Leu Asn Gly Asp Asn Gly
        195                 200                 205

Leu Gly Ser Gly Tyr Met Ser Ser Leu Val Asn Ser Met Ser Leu Met
    210                 215                 220

Leu Glu Glu Phe Tyr Ser Gln Leu Asp Val Val Gly Val Ser Ser Phe
225                 230                 235                 240

Thr Gly Asp Gly Phe Asp Glu Phe Met Gln Cys Val Asp Lys Lys Val
                245                 250                 255

Asp Glu Tyr Asp Gln Tyr Tyr Lys Gln Glu Arg Glu Lys Ala Leu Asn
            260                 265                 270

Leu Lys Lys Lys Lys Glu Glu Met Arg Lys Gln Lys Ser Leu Asn Gly
        275                 280                 285
```

Leu Met Lys Asp Leu Gly Leu Asn Glu Lys Ser Ser Ala Ala Ala Ser
    290                 295                 300

Asp Asn Asp Ser Ile Asp Ala Ile Ser Asp Leu Glu Glu Asp Ala Asn
305                 310                 315                 320

Asp Gly Leu Val Asp Arg Asp Glu Asp Glu Gly Val Glu Arg Glu Tyr
                325                 330                 335

Thr Phe Pro Gly Glu Glu Arg Thr Lys Gly Glu Val Asn Glu Asn Ser
            340                 345                 350

Ala Pro Asp Leu Gln Arg Arg Tyr Gln Glu Ala Met Gln Gln Val Gly
        355                 360                 365

Lys Thr Ala Ser Ser Glu Thr Ala Glu Asn Ile Ala Lys Tyr Ile Arg
    370                 375                 380

Asn
385

<210> SEQ ID NO 47
<211> LENGTH: 379
<212> TYPE: PRT
<213> ORGANISM: Arabidopsis thaliana
<220> FEATURE:
<221> NAME/KEY: MISC_FEATURE
<223> OTHER INFORMATION: PAT_PROTBMS|PATENT_AAG46965

<400> SEQUENCE: 47

Met Asp Pro Met Glu Ser Ser Ser Glu Gln Asp Ile Val Glu Glu Ser
1               5                   10                  15

Gln Lys Leu Val Asp Ser Leu Asp Lys Leu Arg Val Ser Ala Ala Ser
            20                  25                  30

Ser Ser Ser Asn Phe Lys Lys Lys Pro Ile Ile Ile Ile Val Val Gly
        35                  40                  45

Met Ala Gly Ser Gly Lys Thr Ser Phe Leu His Arg Leu Val Cys His
    50                  55                  60

Thr Phe Asp Ser Lys Ser His Gly Tyr Val Val Asn Leu Asp Pro Ala
65                  70                  75                  80

Val Met Ser Leu Pro Phe Gly Ala Asn Ile Asp Ile Arg Asp Thr Val
                85                  90                  95

Lys Tyr Lys Glu Val Met Lys Gln Tyr Asn Leu Gly Pro Asn Gly Gly
            100                 105                 110

Ile Leu Thr Ser Leu Asn Leu Phe Ala Thr Lys Phe Asp Glu Val Val
        115                 120                 125

Ser Val Ile Glu Lys Arg Ala Asp Gln Leu Asp Tyr Val Leu Val Asp
    130                 135                 140

Thr Pro Gly Gln Ile Glu Ile Phe Thr Trp Ser Ala Ser Gly Ala Ile
145                 150                 155                 160

Ile Thr Glu Ala Phe Ala Ser Thr Phe Pro Thr Val Val Thr Tyr Val
                165                 170                 175

Val Asp Thr Pro Arg Ser Ser Ser Pro Ile Thr Phe Met Ser Asn Met
            180                 185                 190

Leu Tyr Ala Cys Ser Ile Leu Tyr Lys Thr Arg Leu Pro Leu Val Leu
        195                 200                 205

Ala Phe Asn Lys Thr Asp Val Ala Asp His Lys Phe Ala Leu Glu Trp
    210                 215                 220

Met Glu Asp Phe Glu Val Phe Gln Ala Ala Ile Gln Ser Asp Asn Ser
225                 230                 235                 240

Tyr Thr Ala Thr Leu Ala Asn Ser Leu Ser Leu Ser Leu Tyr Glu Phe

-continued

```
                245                 250                 255

Tyr Arg Asn Ile Arg Ser Val Gly Val Ser Ala Ile Ser Gly Ala Gly
            260                 265                 270

Met Asp Gly Phe Phe Lys Ala Ile Glu Ala Ser Ala Glu Glu Tyr Met
        275                 280                 285

Glu Thr Tyr Lys Ala Asp Leu Asp Met Arg Lys Ala Asp Lys Glu Arg
    290                 295                 300

Leu Glu Glu Glu Arg Lys Lys His Glu Met Glu Lys Leu Arg Lys Asp
305                 310                 315                 320

Met Glu Ser Ser Gln Gly Gly Thr Val Val Leu Asn Thr Gly Leu Lys
                325                 330                 335

Asp Arg Asp Ala Thr Glu Lys Met Met Leu Glu Glu Asp Asp Glu Asp
            340                 345                 350

Phe Gln Val Glu Asp Glu Glu Asp Ser Asp Asp Ala Ile Asp Glu Asp
        355                 360                 365

Asp Glu Asp Asp Glu Thr Lys His Tyr Tyr Leu
    370                 375


<210> SEQ ID NO 48
<211> LENGTH: 154
<212> TYPE: PRT
<213> ORGANISM: Aspergillus fumigatus
<220> FEATURE:
<221> NAME/KEY: MISC_FEATURE
<223> OTHER INFORMATION: CaYLR100w_GTC_AF

<400> SEQUENCE: 48

Val Asp Leu Ser Asn Leu Val Ser Val Arg Ala Leu Ser Arg Arg Leu
1               5                   10                  15

Asn Lys Thr Phe Pro Lys Leu Asp Ala Ile Val Leu Asn Ala Gly Leu
            20                  25                  30

Gly Gly Trp Thr Gly Ile Asn Trp Pro Lys Ala Ile Trp Gly Val Met
        35                  40                  45

Thr Asp Leu Val His Glu Val Ser Trp Pro Ser Phe Lys Ile Ala Pro
    50                  55                  60

Ala Gly Met Gly Asp Gly Cys Pro Asp Arg Thr Gly Arg Asp Lys Glu
65                  70                  75                  80

Pro Arg Leu Gly Ala Val Phe Cys Ala Asn Val Phe Gly His Tyr Met
                85                  90                  95

Leu Ala His Gln Cys His Ala Ala Ala Arg His Ser Asp Met Leu His
            100                 105                 110

Gly Pro Gly Arg Ile Ile Trp Val Ser Ser Leu Glu Ala Thr Val Lys
        115                 120                 125

His Leu Asp Ile Asp Asp Ile Gln Gly Leu Arg Thr Leu Ala Pro Tyr
    130                 135                 140

Glu Ser Ser Lys Ala Leu Thr Asp Ile Leu
145                 150


<210> SEQ ID NO 49
<211> LENGTH: 154
<212> TYPE: PRT
<213> ORGANISM: Aspergillus fumigatus
<220> FEATURE:
<221> NAME/KEY: MISC_FEATURE
<223> OTHER INFORMATION: CaYLR100w_TIGR_AF

<400> SEQUENCE: 49

Val Asp Leu Ser Asn Leu Val Ser Val Arg Ala Leu Ser Arg Arg Leu
```

-continued 1 5 10 15

Asn Lys Thr Phe Pro Lys Leu Asp Ala Ile Val Leu Asn Ala Gly Leu
20 25 30

Gly Gly Trp Thr Gly Ile Asn Trp Pro Lys Ala Ile Trp Gly Val Met
35 40 45

Thr Asp Leu Val His Glu Val Ser Trp Pro Ser Phe Lys Ile Ala Pro
50 55 60

Ala Gly Met Gly Asp Gly Cys Pro Asp Arg Thr Gly Arg Asp Lys Glu
65 70 75 80

Pro Arg Leu Gly Ala Val Phe Cys Ala Asn Val Phe Gly His Tyr Met
85 90 95

Leu Ala His Gln Cys His Ala Ala Ala Arg His Ser Asp Met Leu His
100 105 110

Gly Pro Gly Arg Ile Ile Trp Val Ser Ser Leu Glu Ala Thr Val Lys
115 120 125

His Leu Asp Ile Asp Asp Ile Gln Gly Leu Arg Thr Leu Ala Pro Tyr
130 135 140

Glu Ser Ser Lys Ala Leu Thr Asp Ile Leu
145 150

<210> SEQ ID NO 50
<211> LENGTH: 49
<212> TYPE: PRT
<213> ORGANISM: Aspergillus fumigatus
<220> FEATURE:
<221> NAME/KEY: MISC_FEATURE
<223> OTHER INFORMATION: CaYDR341c_GTC_2

<400> SEQUENCE: 50

Met Thr Asn Ile Phe Ser Ser Ser Asp Val Phe Lys Leu Leu Gly Ser
1 5 10 15

Glu Pro Glu Phe Lys Lys Pro Val Met Ala Leu Tyr Glu Gly Ala Arg
20 25 30

Gln Val Leu His Asn Gly Met Arg Phe Met Val Leu Ser Pro Val Glu
35 40 45

Arg

<210> SEQ ID NO 51
<211> LENGTH: 89
<212> TYPE: PRT
<213> ORGANISM: Aspergillus fumigatus
<220> FEATURE:
<221> NAME/KEY: MISC_FEATURE
<223> OTHER INFORMATION: CaYDR341c_TIGR_1

<400> SEQUENCE: 51

Leu Leu Thr Glu Pro His Ala Val Asp Leu Val Arg Leu Leu Ala Thr
1 5 10 15

Trp Pro Asp Val Leu Leu Asn Thr Thr Lys Thr Leu Glu Pro Thr Thr
20 25 30

Ile Leu Thr Tyr Leu Phe Arg Met Thr His Ile Leu Ser Ser Ser Tyr
35 40 45

Asp Val Leu Lys Val Val Gly Ser Glu Pro Glu Leu Lys Lys Ala Arg
50 55 60

Met Ala Leu Tyr Glu Ala Ala Arg Gln Val Leu His Asn Gly Met Arg
65 70 75 80

Val Leu Gly Leu Ser Pro Val Glu Arg
85

-continued

<210> SEQ ID NO 52
<211> LENGTH: 351
<212> TYPE: PRT
<213> ORGANISM: Aspergillus fumigatus
<220> FEATURE:
<221> NAME/KEY: MISC_FEATURE
<223> OTHER INFORMATION: CaYDR341c_GTC_1

<400> SEQUENCE: 52

```
Lys Arg Phe Ile Val Lys Phe Trp Ser Pro Asn Met Ala Arg Pro Phe
1               5                   10                  15

Asn Gly Ser Leu Arg Ser Pro Ile Ile Gly Phe Leu Ala Asn Leu Tyr
            20                  25                  30

Thr Val Met Gly Trp Asp Val Ile Lys Met Asn Tyr Leu Gly Asp Trp
        35                  40                  45

Gly Lys Gln Tyr Gly Leu Leu Ala Asn Gly Phe Lys Arg Phe Gly Asn
    50                  55                  60

Glu Glu Glu Leu Leu Lys Asn Pro Ile Asn His Leu Phe Asp Val Tyr
65                  70                  75                  80

Val Lys Ile Asn Gln Ile Val Ala Pro Ala Gly Gly Pro Tyr Gln Gly
                85                  90                  95

Val Lys Glu Gln Ile Lys Ala Lys Lys Glu Lys Asn Glu Asp Val Ser
            100                 105                 110

Val Leu Glu Ala Glu Leu Ala Lys Leu Val Asp Val Ser Glu Asp Glu
        115                 120                 125

Lys Ala Arg Arg Tyr Phe Lys Ser Met Glu Asp Gly Asp Glu Glu Ala
    130                 135                 140

Leu Ala Leu Trp Arg Arg Phe Arg Asp Leu Ser Ile Glu Lys Tyr Lys
145                 150                 155                 160

Gln Thr Tyr Ala Arg Leu Asn Ile Asp Phe Asp Val Tyr Ser Gly Glu
                165                 170                 175

Ser Gln Ile Lys Asn Glu Ser Met Thr Ala Ala Tyr Glu Thr Met Glu
            180                 185                 190

Lys Thr Gly Val Ser Glu Lys Ser Glu Gly Ala Val Ile Val Asp Phe
        195                 200                 205

Thr Lys His Gly Arg Lys Lys Leu Gly Lys Ala Ile Ile Val Arg Lys
    210                 215                 220

Asp Gly Thr Pro Leu Tyr Leu Thr Arg Asp Ile Gly Ala Ile Met Glu
225                 230                 235                 240

Arg Asp Glu Ala Tyr His Phe Asp Lys Met Ile Tyr Val Val Ala Ala
                245                 250                 255

Gln Gln Asp Leu His Leu Ala Gln Leu Phe Lys Ile Thr Glu Leu Met
            260                 265                 270

Gly Pro Lys Asp Leu Ala Ser Arg Cys Gln His Ile Lys Phe Gly Met
        275                 280                 285

Val Arg Gly Met Ser Thr Arg Lys Gly Thr Val Lys Phe Leu Asp Asp
    290                 295                 300

Ile Leu Arg Asp Val Ala Asp Lys Met His Glu Val Met Lys Gly Asn
305                 310                 315                 320

Ala Glu Lys Tyr Ala Gln Val Glu Asn Pro Glu Glu Thr Ala Asp Ile
                325                 330                 335

Leu Gly Leu Thr Ser Val Met Val Gln Asp Met Thr Gly Lys Arg
            340                 345                 350
```

-continued

<210> SEQ ID NO 53
<211> LENGTH: 81
<212> TYPE: PRT
<213> ORGANISM: Aspergillus fumigatus
<220> FEATURE:
<221> NAME/KEY: MISC_FEATURE
<223> OTHER INFORMATION: CaYLR022c_TIGR_AF

<400> SEQUENCE: 53

```
Ser Lys Ala Gln Thr Ala Pro Ser Ala Glu Leu Thr Lys Ala Phe Gly
1               5                   10                  15

Pro Asn Val Ser Ala Asp Glu Ile Arg Gln Glu Ile Leu Arg Lys Gly
            20                  25                  30

Glu Val Gln Val Gly Glu Arg Glu Arg Lys Glu Met Leu Glu Arg Val
        35                  40                  45

Glu Lys Glu Val Leu Asp Ile Val Ser Gly Arg Leu Val Asp Pro Asn
    50                  55                  60

Thr Lys Arg Val Tyr Thr Pro Gly Met Ile Ser Lys Ala Leu Asp Gln
65                  70                  75                  80

Leu
```

<210> SEQ ID NO 54
<211> LENGTH: 36
<212> TYPE: PRT
<213> ORGANISM: Aspergillus fumigatus
<220> FEATURE:
<221> NAME/KEY: MISC_FEATURE
<223> OTHER INFORMATION: CaYLR022c_GTC_AF

<400> SEQUENCE: 54

```
Val Thr Pro Asn Lys Ser Ala Lys Ser Gln Ala Leu Glu Ala Met Lys
1               5                   10                  15

Ala Leu Ile Ala Trp Gln Pro Ile Pro Val Met Arg Ala Arg Met Arg
            20                  25                  30

Leu Arg Val Thr
        35
```

<210> SEQ ID NO 55
<211> LENGTH: 246
<212> TYPE: PRT
<213> ORGANISM: Aspergillus fumigatus
<220> FEATURE:
<221> NAME/KEY: MISC_FEATURE
<223> OTHER INFORMATION: CaYOL077c_TIGR

<400> SEQUENCE: 55

```
His Arg His Leu Leu Ser Asp Leu Cys Ala Leu Leu Pro His Thr His
1               5                   10                  15

Lys Glu Ser Lys Leu Asp Thr Lys Lys Lys Thr Ala Arg Leu Gln Ser
            20                  25                  30

Leu Leu Asn Ser Leu Ala Asp Leu His Ser Cys Asn Val Ile Phe Phe
        35                  40                  45

Leu Glu Ala Arg Lys Arg Arg Gln Asp Leu Tyr Leu Trp Leu Ala Arg
    50                  55                  60

Pro Pro Asn Gly Pro Thr Ile Lys Phe His Val Thr Asn Leu His Thr
65                  70                  75                  80

Met Gly Glu Leu Asn His Trp Phe Ser Gly Asn Cys Leu Lys Gly Gly
                85                  90                  95

Arg Gly Ile Val Val Phe Asp Arg Ser Phe Asp Glu Ala Gly Ser Gly
            100                 105                 110
```

-continued

```
Asp Glu Gln Pro Arg Asn Glu Tyr Arg Gly Leu Ile Arg Glu Met Leu
        115                 120                 125

Arg Gly Val Phe Cys Val Pro Lys Arg Gly Val Lys Gly His Lys Pro
    130                 135                 140

Phe Ile Asp Arg Val Ile Gly Val Phe Gly Val Asp Gly Lys Ile Trp
145                 150                 155                 160

Ile Arg Val Tyr Glu Ile Arg Glu Ser Arg Arg Trp Ser Lys Lys Asp
                165                 170                 175

Glu Glu Asn Ser Lys Pro Ala Pro Lys Gly Lys Asn Ala Glu Pro Glu
            180                 185                 190

Ile Ser Leu Val Glu Ile Gly Pro Arg Phe Val Leu Thr Pro Ile Val
        195                 200                 205

Ile Leu Glu Gly Ser Phe Gly Gly Pro Val Ile Tyr Glu Asn Lys Glu
    210                 215                 220

Tyr Val Ser Pro Asn Gln Val Arg Ser Glu Ile Arg Leu Ser Lys Ala
225                 230                 235                 240

Ala Arg Tyr Ala Lys Arg
                245


<210> SEQ ID NO 56
<211> LENGTH: 213
<212> TYPE: PRT
<213> ORGANISM: Aspergillus fumigatus
<220> FEATURE:
<221> NAME/KEY: MISC_FEATURE
<223> OTHER INFORMATION: CaYOL077c_GTC

<400> SEQUENCE: 56

Leu Asn Ser Leu Ala Asp Leu His Ser Cys Asn Val Ile Phe Phe Leu
1               5                   10                  15

Glu Ala Arg Lys Arg Arg Gln Asp Leu Tyr Leu Trp Leu Ala Arg Pro
            20                  25                  30

Pro Asn Gly Pro Thr Ile Lys Phe His Val Thr Asn Leu His Thr Met
        35                  40                  45

Gly Glu Leu Asn His Trp Phe Ser Gly Asn Cys Leu Lys Gly Gly Arg
    50                  55                  60

Gly Ile Val Val Phe Asp Arg Ser Phe Asp Glu Ala Gly Ser Gly Asp
65                  70                  75                  80

Glu Gln Pro Arg Asn Glu Tyr Arg Gly Leu Ile Arg Glu Met Leu Arg
                85                  90                  95

Gly Val Phe Cys Val Pro Lys Arg Gly Val Lys Gly His Lys Pro Phe
            100                 105                 110

Ile Asp Arg Val Ile Gly Val Phe Gly Val Asp Gly Lys Ile Trp Ile
        115                 120                 125

Arg Val Tyr Glu Ile Arg Glu Ser Arg Arg Trp Ser Lys Lys Asp Glu
    130                 135                 140

Glu Asn Ser Lys Pro Ala Pro Lys Gly Lys Asn Ala Glu Pro Glu Ile
145                 150                 155                 160

Ser Leu Val Glu Ile Gly Pro Arg Phe Val Leu Thr Pro Ile Val Ile
                165                 170                 175

Leu Glu Gly Ser Phe Gly Gly Pro Val Ile Tyr Glu Asn Lys Glu Tyr
            180                 185                 190

Val Ser Pro Asn Gln Val Arg Ser Glu Ile Arg Leu Ser Lys Ala Ala
        195                 200                 205

Arg Tyr Ala Lys Arg
    210
```

-continued

<210> SEQ ID NO 57
<211> LENGTH: 712
<212> TYPE: PRT
<213> ORGANISM: Aspergillus fumigatus
<220> FEATURE:
<221> NAME/KEY: MISC_FEATURE
<223> OTHER INFORMATION: CaYNL132w_GTC_AF_1

<400> SEQUENCE: 57

```
Arg Phe Ile Leu Ser Leu Gly Ser Cys Asp Ser Cys Leu Val Val Asp
1               5                   10                  15

Asp Glu Leu Asn Val Leu Pro Ile Ser Gly Gly Lys Asn Val Lys Pro
            20                  25                  30

Leu Pro Pro Pro Glu Thr Pro Asp Asp Asn Thr Gly Thr Lys Lys Glu
        35                  40                  45

Leu Lys Glu Ile Lys Asp Ser Leu Ala Asp Thr Gln Pro Val Gly Ser
    50                  55                  60

Leu Val Ser Leu Ala Arg Thr Val Asp Gln Ala Lys Ala Leu Leu Thr
65                  70                  75                  80

Phe Val Asp Val Ile Ala Glu Lys Thr Leu Arg Ser Thr Val Thr Leu
                85                  90                  95

Thr Ala Ala Arg Gly Arg Gly Lys Ser Ala Ala Leu Gly Val Ala Ile
            100                 105                 110

Ala Ala Ala Val Ala His Gly Tyr Ser Asn Ile Phe Ile Thr Ser Pro
        115                 120                 125

Ser Pro Glu Asn Leu Lys Thr Leu Phe Glu Phe Ile Phe Lys Gly Phe
    130                 135                 140

Asp Ala Leu Gly Tyr Leu Asp His Val Asp Tyr Thr Ile Leu Gln Ser
145                 150                 155                 160

Thr Asn Pro Asp Phe Asn Lys Ala Ile Val Arg Val Asn Ile His Arg
                165                 170                 175

Gln His Arg Gln Thr Ile Gln Tyr Ile Gln Pro Gln Asp Ala His Val
            180                 185                 190

Leu Gly Gln Ala Glu Leu Leu Val Ile Asp Glu Ala Ala Ala Ile Pro
        195                 200                 205

Leu Pro Leu Val Arg Lys Leu Met Gly Pro Tyr Leu Val Phe Met Ala
    210                 215                 220

Ser Thr Ile Asn Gly Tyr Glu Gly Thr Gly Arg Ser Leu Ser Leu Lys
225                 230                 235                 240

Leu Ile Gln Gln Leu Arg Glu Gln Ser Arg Gly Gly Leu Lys Ala Gln
                245                 250                 255

Arg Arg Thr Ile Gln Ile Ser Leu Ile Glu Pro Gln Ala Arg Leu Pro
            260                 265                 270

Arg Ala Gln Arg Arg Thr Leu Gly Gly Arg Leu Arg Glu Ile Thr Leu
        275                 280                 285

Ser Glu Pro Ile Arg Tyr Ala Pro Gly Asp Ser Val Glu Lys Trp Leu
    290                 295                 300

Asn Lys Val Leu Cys Leu Asp Ala Thr Leu Pro Lys Ser Lys Ile Asn
305                 310                 315                 320

Thr Gln Gly Cys Pro His Pro Ser Gln Cys Gln Leu Leu Gln Val Asn
                325                 330                 335

Arg Asp Thr Leu Phe Ser Phe His Pro Val Ser Glu Lys Phe Leu Gln
            340                 345                 350

Gln Met Met Ala Leu Tyr Val Ala Ser His Tyr Lys Asn Thr Pro Asn
```

-continued

```
        355                 360                 365

Asp Leu Gln Leu Met Ser Asp Ala Pro Ala His Gln Leu Phe Val Leu
    370                 375                 380

Val Pro Pro Ile Asp Glu Glu Ala Thr Lys Leu Pro Glu Pro Leu Cys
385                 390                 395                 400

Val Ile Gln Val Ala Leu Glu Gly Arg Ile Ser Arg Gln Ser Val Leu
                405                 410                 415

Asn Ser Leu Ser Arg Gly Gln Arg Ala Gly Gly Asp Leu Ile Pro Trp
            420                 425                 430

Leu Val Ser Gln Gln Tyr Gln Asp Glu Asp Phe Ala Ser Leu Ser Gly
        435                 440                 445

Ala Arg Ile Val Arg Ile Ala Thr Asn Pro Glu Tyr Met Asn Met Gly
    450                 455                 460

Tyr Gly Ser Arg Ala Leu Glu Leu Leu Ile Asp Phe Tyr Glu Gly Lys
465                 470                 475                 480

Phe Thr Asp Leu Ser Glu Lys Ile Pro Asp Val Gln Glu Glu Met Val
                485                 490                 495

Arg Val Thr Asp Glu Glu Leu Ala Asn Ser Ser Leu Leu Asp Asp Gln
            500                 505                 510

Ile His Val Arg Asp Ile Arg Ser Met Pro Pro Leu Phe Gly Lys Leu
        515                 520                 525

Ser Glu Arg Arg Pro Asp Ala Leu Asp Tyr Val Gly Val Ser Tyr Gly
    530                 535                 540

Leu Thr Pro Pro Leu His Lys Phe Trp Lys Arg Ala Ser Phe Val Pro
545                 550                 555                 560

Val Tyr Leu Arg Gln Thr Pro Asn Glu Leu Thr Gly Glu His Ser Cys
                565                 570                 575

Val Met Leu Arg Thr Leu Arg Leu Ala Ala Ser Asp Ala Ser Trp Leu
            580                 585                 590

Gly Glu Phe Ala Arg Asp Phe His Lys Arg Phe Ile Ala Leu Leu Ser
        595                 600                 605

Tyr Gln Phe Arg Glu Phe Pro Ser Val Leu Ser Leu Ser Ile Cys Glu
    610                 615                 620

Ser Val Thr Ala Gly Ala Lys Leu Asp Thr Leu Val Thr Pro Ser Leu
625                 630                 635                 640

Leu Thr Lys Ser Asp Leu Asp Ala Ala Phe Ser Pro Phe Asp Leu Lys
                645                 650                 655

Arg Leu Asp Ser Tyr Ala Asn Asn Leu Leu Asp Tyr His Val Ile Leu
            660                 665                 670

Asp Met Val Pro Thr Ile Ala Glu Tyr Tyr Phe Ser Gly Arg Leu Ser
        675                 680                 685

Gly Lys Val Asn Leu Ser Gly Val Gln Gln Ser Ile Leu Leu Ala Ile
    690                 695                 700

Gly Leu Gln Arg Lys His Leu Asp
705                 710
```

<210> SEQ ID NO 58
<211> LENGTH: 586
<212> TYPE: PRT
<213> ORGANISM: Aspergillus fumigatus
<220> FEATURE:
<221> NAME/KEY: MISC_FEATURE
<222> LOCATION: (70)..(70)
<223> OTHER INFORMATION: unknown amino acid at all X locations
<220> FEATURE:
<221> NAME/KEY: MISC_FEATURE -continued
<222> LOCATION: (70)..(70)
<223> OTHER INFORMATION: CaYNL132w_TIGR_AF_1

<400> SEQUENCE: 58

Ile Asn Gly Tyr Glu Gly Thr Gly Arg Ser Leu Ser Leu Lys Leu Ile
1               5                   10                  15

Gln Gln Leu Arg Glu Gln Ser Arg Gly Gly Leu Lys Ala Gln Arg Arg
            20                  25                  30

Thr Ile Gln Ile Ser Leu Ile Glu Pro Gln Ala Arg Leu Pro Arg Ala
        35                  40                  45

Gln Arg Arg Thr Leu Gly Gly Arg Leu Arg Glu Ile Thr Leu Ser Glu
    50                  55                  60

Pro Ile Arg Tyr Ala Xaa Gly Asp Ser Val Glu Lys Trp Leu Asn Lys
65                  70                  75                  80

Val Leu Cys Leu Asp Ala Thr Leu Pro Lys Ser Lys Ile Asn Thr Gln
                85                  90                  95

Gly Cys Pro His Pro Ser Gln Cys Gln Leu Leu Gln Val Asn Arg Asp
            100                 105                 110

Thr Leu Phe Ser Phe His Pro Val Ser Glu Lys Phe Leu Gln Gln Met
        115                 120                 125

Met Ala Leu Tyr Val Ala Ser His Tyr Lys Asn Thr Pro Asn Asp Leu
    130                 135                 140

Gln Leu Met Ser Asp Ala Pro Ala His Gln Leu Phe Val Leu Val Pro
145                 150                 155                 160

Pro Ile Asp Glu Glu Ala Thr Lys Leu Pro Glu Pro Leu Cys Val Ile
                165                 170                 175

Gln Val Ala Leu Glu Gly Arg Ile Ser Arg Gln Ser Val Leu Asn Ser
            180                 185                 190

Leu Ser Arg Gly Gln Arg Ala Gly Gly Asp Leu Ile Pro Trp Leu Val
        195                 200                 205

Ser Gln Gln Tyr Gln Asp Glu Asp Phe Ala Ser Leu Ser Gly Ala Arg
    210                 215                 220

Ile Val Arg Ile Ala Thr Asn Pro Glu Tyr Met Asn Met Gly Tyr Gly
225                 230                 235                 240

Ser Arg Ala Leu Glu Leu Leu Ile Asp Phe Tyr Glu Gly Lys Phe Thr
                245                 250                 255

Asp Leu Ser Glu Lys Ile Pro Asp Val Gln Glu Glu Met Val Arg Val
            260                 265                 270

Thr Asp Glu Glu Leu Ala Asn Ser Ser Leu Leu Asp Asp Gln Ile His
        275                 280                 285

Val Arg Asp Ile Arg Ser Met Pro Pro Leu Phe Gly Lys Leu Ser Glu
    290                 295                 300

Arg Arg Pro Asp Ala Leu Asp Tyr Val Gly Val Ser Tyr Gly Leu Thr
305                 310                 315                 320

Pro Pro Leu His Lys Phe Trp Lys Arg Ala Ser Phe Val Pro Val Tyr
                325                 330                 335

Leu Arg Gln Thr Pro Asn Glu Leu Thr Gly Glu His Ser Cys Val Met
            340                 345                 350

Leu Arg Thr Leu Arg Leu Ala Ala Ser Asp Ala Ser Trp Leu Gly Glu
        355                 360                 365

Phe Ala Arg Asp Phe His Lys Arg Phe Ile Ala Leu Leu Ser Tyr Gln
    370                 375                 380

Phe Arg Glu Phe Pro Ser Val Leu Ser Leu Ser Ile Cys Glu Ser Ala
385                 390                 395                 400

```
Thr Ala Gly Ala Lys Leu Asp Thr Leu Val Thr Pro Ser Leu Leu Thr
                405                 410                 415

Lys Ser Asp Leu Asp Ala Ala Phe Ser Pro Phe Asp Leu Lys Arg Leu
            420                 425                 430

Asp Ser Tyr Ala Asn Asn Leu Leu Asp Tyr His Val Ile Leu Asp Met
        435                 440                 445

Val Pro Thr Ile Ala Glu Tyr Tyr Phe Ser Gly Arg Leu Ser Gly Lys
    450                 455                 460

Val Asn Leu Ser Gly Val Gln Gln Ser Ile Leu Leu Ala Ile Gly Leu
465                 470                 475                 480

Gln Arg Lys Asn Leu Asp Asp Ile Glu Lys Glu Leu Asn Leu Pro Ser
                485                 490                 495

Ser Gln Leu Leu Ala Met Phe Leu Lys Ile Val Arg Lys Met Ser Thr
            500                 505                 510

Tyr Phe Arg Gly Leu Val Glu Gly Ala Val Ala Glu Thr Leu Pro Ala
        515                 520                 525

Glu Lys Val Pro Ile Ala Gln Ser Ser Ala Asp Ala His Asp Glu Val
    530                 535                 540

Val Asp Arg Ala Phe Lys Pro Leu Asp Thr Gly Leu Glu Asp Glu Leu
545                 550                 555                 560

Arg Glu Gly Gly Gln Gln Val Asp Glu Glu Leu Arg Glu Lys Gln Arg
                565                 570                 575

Ala Leu Ile Asp Ser Leu Pro Leu Asp Lys
            580                 585


<210> SEQ ID NO 59
<211> LENGTH: 604
<212> TYPE: PRT
<213> ORGANISM: Aspergillus fumigatus
<220> FEATURE:
<221> NAME/KEY: MISC_FEATURE
<223> OTHER INFORMATION: GTC_CaYGR145w_AF

<400> SEQUENCE: 59

Met Lys Leu Ser Asn Gln Ser Glu Val Pro Val Tyr Thr Ile Ser Gly
1               5                   10                  15

Ser Asn Thr Ala Arg Pro Leu Pro Glu Trp Leu Ala Arg Arg Arg Lys
            20                  25                  30

Arg Ser Leu Lys Asn Asp Pro Glu Tyr Ala Asn Arg Ile Glu Leu Leu
        35                  40                  45

Gln Asp Phe Glu Phe Glu Glu Ala Ser Gln Cys Ile Arg Val Ser Glu
    50                  55                  60

Asp Gly Glu Trp Val Met Ser Thr Arg Ser Val Leu Pro Gly Glu Val
65                  70                  75                  80

His Ala Val Phe Ile Glu Ser Arg Asn Leu Trp Cys Cys Gly Thr Tyr
                85                  90                  95

Lys Pro Gln Ile His Thr His Tyr Leu Pro Gln Leu Ser Leu Ser Trp
            100                 105                 110

Ala Arg His Thr Asp Ala Leu Asn Thr Thr Phe Leu Leu Leu Ser Ser
        115                 120                 125

Asp Tyr Ser Lys Ser Ile His Leu Gln Ser Asp Arg Ser Leu Glu Phe
    130                 135                 140

His Thr Pro Ser Gly Cys His Tyr Gly Thr Arg Leu Pro Arg Tyr Gly
145                 150                 155                 160

His Asp Val Val Tyr Asp Arg Gln Ser Thr Glu Ala Leu Ser Ala Gly
```

-continued

```
                165                 170                 175

Val Gly Val Asn Gln Asp Trp Tyr Gly Glu Val Phe Arg Leu Asn Leu
            180                 185                 190

Glu Met Gly Arg Tyr Met Arg Ser Phe Glu Val Asp Val Trp Trp Gly
        195                 200                 205

Arg Phe His Ile Thr Gly Gly Gly Thr Leu Gln Gly Gly Ile His Thr
    210                 215                 220

Gly Ala Val Asn Thr Gly Gly Tyr Cys Gly Gly Ser His Asn Leu Leu
225                 230                 235                 240

Ala Phe Gly Thr Ser Met Gly Thr Val Glu Leu Trp Asp Pro Arg Ala
                245                 250                 255

Lys Gly Arg Ala Gly Val Leu Leu Pro Pro Asn Gln Thr Gly Pro Asp
            260                 265                 270

Asp Gly Arg Ser Glu Ile Thr Ala Leu Glu Phe His Arg Ser Gly Leu
        275                 280                 285

Thr Phe Ala Thr Gly Ser Ser Asn Gly Leu Ile His Leu Tyr Asp Leu
    290                 295                 300

Arg Ser Pro Val Pro Leu Leu Lys Lys Asp Gln Gly Tyr Gly Phe Pro
305                 310                 315                 320

Val His Thr Leu Lys Phe Leu Gln Pro Ser Asp Ile Arg Thr Arg Thr
                325                 330                 335

Thr Met Glu Pro Lys Ile Leu Ser Ser Asp Lys Lys Ile Ile Lys Ile
            340                 345                 350

Trp Asp Pro Arg Asp Gly Lys Pro Trp Thr Ser Val Glu Pro Ala Val
        355                 360                 365

Asp Ile Asn Ser Val Ala Trp Cys Lys Asp Ser Gly Met Leu Leu Thr
    370                 375                 380

Ala Asn Glu Gly Arg Gln Gln His Ala Phe Phe Ile Pro Gln Leu Gly
385                 390                 395                 400

Pro Ala Pro Arg Trp Cys Ser Phe Leu Asp Asn Leu Val Glu Glu Met
                405                 410                 415

Ala Glu Asp Pro Asn Asp Ser Cys Phe Gln Tyr Arg Pro Asp Arg Ala
            420                 425                 430

Val Tyr Asp Asn Tyr Lys Phe Leu Thr Val Pro Gln Leu Lys Thr Leu
        435                 440                 445

Asn Leu Asp His Leu Ile Gly Gln Thr Asn Leu Leu Arg Pro Tyr Met
    450                 455                 460

His Gly Tyr Phe Val Ala Gln Arg Leu Tyr Glu Glu Ala Arg Leu Ile
465                 470                 475                 480

Thr Asn Pro Tyr Ile Trp Glu Glu Glu Arg Ala Lys Arg Val Lys Glu
                485                 490                 495

Lys Ile Asp Lys Glu Arg Glu Ser Arg Ile Arg Gly Lys Lys Lys Gly
            500                 505                 510

Cys Arg Gln Gly Asn Lys Lys Leu Ala Glu Lys Leu Met Ala Ile Glu
        515                 520                 525

Glu Lys Asn Glu Arg Arg Gln Ala Gln Arg Val Leu Lys Gln Gly Gly
    530                 535                 540

Asp Glu Asn His Gly Ala Pro Arg Thr Glu Lys Pro Ala Thr Gly Leu
545                 550                 555                 560

Phe Gly Asp Ser Arg Phe Ala Lys Met Phe Glu Asp Glu Glu Phe Ala
                565                 570                 575

Val Asp Glu Thr Ser Arg Glu Phe Gln Leu Leu Asn Pro Ser Thr Ile
            580                 585                 590
```

-continued

```
Pro Glu Pro Val Glu Arg Lys Glu Arg Gly Leu Thr
        595                 600


<210> SEQ ID NO 60
<211> LENGTH: 413
<212> TYPE: PRT
<213> ORGANISM: Aspergillus fumigatus
<220> FEATURE:
<221> NAME/KEY: MISC_FEATURE
<223> OTHER INFORMATION: TIGR_CaYGR145w_AF_1
<220> FEATURE:
<221> NAME/KEY: MISC_FEATURE
<222> LOCATION: (300)..(300)
<223> OTHER INFORMATION: unknown at all "N" locations
<220> FEATURE:
<221> NAME/KEY: MISC_FEATURE
<222> LOCATION: (300)..(300)
<223> OTHER INFORMATION: unknown at all "N" locations

<400> SEQUENCE: 60

Gly Thr Tyr Lys Pro Gln Ile His Thr His Tyr Leu Pro Gln Leu Ser
1               5                   10                  15

Leu Ser Trp Ala Arg His Thr Asp Ala Leu Asn Thr Thr Phe Leu Leu
            20                  25                  30

Leu Ser Ser Asp Tyr Ser Lys Ser Ile His Leu Gln Ser Asp Arg Ser
        35                  40                  45

Leu Glu Phe His Thr Pro Ser Gly Cys His Tyr Arg Thr Arg Leu Pro
    50                  55                  60

Arg Tyr Gly Arg Asp Leu Val Tyr Asp Arg Gln Ser Thr Glu Ala Leu
65                  70                  75                  80

Ser Ala Gly Val Gly Val Asn Gln Asp Trp Tyr Gly Glu Val Phe Arg
                85                  90                  95

Leu Asn Leu Glu Met Gly Arg Tyr Met Arg Ser Phe Glu Val Asp Val
            100                 105                 110

Trp Trp Gly Arg Phe His Ile Thr Gly Gly Gly Thr Leu Gln Gly Gly
        115                 120                 125

Ile His Thr Gly Ala Val Asn Thr Gly Gly Tyr Cys Gly Gly Ser His
    130                 135                 140

Asn Leu Leu Ala Phe Gly Thr Ser Met Gly Thr Val Glu Leu Trp Asp
145                 150                 155                 160

Pro Arg Ala Lys Gly Arg Ala Gly Val Leu Leu Pro Pro Asn Gln Thr
                165                 170                 175

Gly Pro Asp Asp Gly Arg Ser Glu Ile Thr Ala Leu Glu Phe His Arg
            180                 185                 190

Ser Gly Leu Thr Phe Ala Thr Gly Ser Ser Asn Gly Leu Ile His Leu
        195                 200                 205

Tyr Asp Leu Arg Ser Pro Val Pro Leu Leu Lys Lys Asp Gln Gly Tyr
    210                 215                 220

Gly Phe Pro Val His Thr Leu Lys Phe Leu Gln Pro Ser Asp Ile Arg
225                 230                 235                 240

Thr Arg Thr Thr Met Glu Pro Lys Ile Leu Ser Ser Asp Lys Lys Ile
                245                 250                 255

Ile Lys Ile Trp Asp Pro Arg Asp Gly Lys Pro Trp Thr Ser Val Glu
            260                 265                 270

Leu Ala Val Asp Ile Asn Ser Val Ala Trp Cys Lys Asp Ser Gly Met
        275                 280                 285

Leu Leu Thr Ala Asn Glu Gly Arg Gln Gln His Xaa Phe Phe Ile Pro
    290                 295                 300
```

-continued

Gln Leu Gly Pro Ala Pro Arg Trp Cys Ser Phe Leu Asp Asn Leu Val
305 310 315 320

Glu Glu Met Ala Glu Asp Pro Asn Asp Ser Cys Phe Gln Tyr Arg Pro
325 330 335

Asp Arg Ala Val Tyr Asp Asn Tyr Lys Phe Leu Thr Val Pro Gln Leu
340 345 350

Lys Thr Leu Asn Leu Asp His Leu Ile Gly Gln Thr Asn Leu Leu Arg
355 360 365

Pro Tyr Met His Gly Tyr Phe Val Ala Gln Arg Leu Tyr Glu Glu Ala
370 375 380

Arg Leu Ile Thr Asn Pro Tyr Ile Trp Glu Glu Glu Arg Ala Lys Arg
385 390 395 400

Val Lys Gly Glu Ile Asp Lys Glu Arg Glu Ser Arg Ile
405 410

<210> SEQ ID NO 61
<211> LENGTH: 75
<212> TYPE: PRT
<213> ORGANISM: Aspergillus fumigatus
<220> FEATURE:
<221> NAME/KEY: MISC_FEATURE
<223> OTHER INFORMATION: TIGR_CaYGR145w_AF_2

<400> SEQUENCE: 61

Met Lys Leu Ser Asn Gln Ser Glu Val Pro Val Tyr Thr Ile Ser Gly
1 5 10 15

Ser Asn Thr Ala Arg Pro Leu Pro Glu Trp Leu Ala Arg Arg Arg Lys
20 25 30

Arg Ser Leu Lys Asn Asp Pro Glu Tyr Ala Asn Arg Ile Glu Leu Leu
35 40 45

Gln Asp Phe Glu Phe Glu Glu Ala Ser Gln Cys Ile Arg Val Ser Glu
50 55 60

Asp Gly Glu Trp Val Met Ser Thr Gly Arg Phe
65 70 75

<210> SEQ ID NO 62
<211> LENGTH: 48
<212> TYPE: PRT
<213> ORGANISM: Aspergillus fumigatus
<220> FEATURE:
<221> NAME/KEY: MISC_FEATURE
<223> OTHER INFORMATION: CaYDR412w_GTC_AF

<400> SEQUENCE: 62

Ile Glu Glu Ile Asn Phe Asp Pro Ala Asp Arg Gln Glu Phe Leu Thr
1 5 10 15

Gly Phe Arg Lys Arg Lys Gln Gln Arg Ile Arg His Ala Gln Glu Leu
20 25 30

Ala Ala Lys Arg Ala Arg Glu Glu Lys Arg Leu Glu Arg Lys Lys Leu
35 40 45

<210> SEQ ID NO 63
<211> LENGTH: 48
<212> TYPE: PRT
<213> ORGANISM: Aspergillus fumigatus
<220> FEATURE:
<221> NAME/KEY: MISC_FEATURE
<223> OTHER INFORMATION: CaYDR412w_TIGR_AF

<400> SEQUENCE: 63

-continued

Ile Ala Glu Ile Asn Phe Asp Pro Ala Asp Arg Gln Glu Phe Leu Thr
1 5 10 15

Gly Phe Arg Lys Arg Lys Gln Gln Arg Ile Arg His Ala Gln Glu Leu
20 25 30

Ala Ala Lys Arg Ala Arg Glu Glu Lys Arg Leu Glu Arg Lys Lys Val
35 40 45

<210> SEQ ID NO 64
<211> LENGTH: 126
<212> TYPE: PRT
<213> ORGANISM: Aspergillus fumigatus
<220> FEATURE:
<221> NAME/KEY: MISC_FEATURE
<223> OTHER INFORMATION: CaYOR004w_GTC

<400> SEQUENCE: 64

Lys Leu Arg Ile Gly Ala Arg Ser Ile Pro Gly Val Pro Ile Val Tyr
1 5 10 15

Val Lys Arg Ser Val Met Ile Leu Glu Pro Met Ser Thr Pro Ser Glu
20 25 30

Glu Val Arg Asp Gly Val Glu Asn Arg Lys Phe Arg Val Gly Leu Asn
35 40 45

Asp Glu Ala Val Leu Gly Lys Arg Lys Arg Thr Glu Asp Gly Glu Glu
50 55 60

Lys Lys Lys Lys Arg Gly Pro Lys Lys Pro Lys Gly Pro Asn Pro Leu
65 70 75 80

Ser Val Lys Lys Pro Lys Lys Lys Pro Ala Glu Thr Ala Ser Gly Pro
85 90 95

Lys Gln Glu Lys Arg Lys Glu Gln Lys Arg Arg Gly Ala Gly Gln Asp
100 105 110

Lys Arg Arg Arg Ile Arg Arg Thr Gln Ala Glu Glu Lys Thr
115 120 125

<210> SEQ ID NO 65
<211> LENGTH: 101
<212> TYPE: PRT
<213> ORGANISM: Aspergillus fumigatus
<220> FEATURE:
<221> NAME/KEY: MISC_FEATURE
<223> OTHER INFORMATION: CaYOR004w_TIGR

<400> SEQUENCE: 65

Lys Leu Arg Ile Gly Ala Arg Ser Ile Pro Gly Val Pro Ile Val Tyr
1 5 10 15

Val Lys Arg Ser Val Met Ile Leu Glu Pro Met Ser Thr Pro Ser Glu
20 25 30

Glu Val Arg Asp Gly Val Glu Asn Arg Lys Phe Arg Val Gly Leu Asn
35 40 45

Asp Glu Ala Val Leu Gly Lys Arg Lys Arg Thr Glu Asp Gly Glu Glu
50 55 60

Lys Lys Lys Lys Arg Gly Pro Lys Lys Pro Lys Gly Pro Asn Pro Leu
65 70 75 80

Ser Val Lys Lys Pro Lys Lys Lys Pro Ala Glu Thr Ala Ser Gly Pro
85 90 95

Lys Gln Glu Lys Arg
100

<210> SEQ ID NO 66
<211> LENGTH: 89

-continued

<212> TYPE: PRT
<213> ORGANISM: Aspergillus fumigatus
<220> FEATURE:
<221> NAME/KEY: MISC_FEATURE
<223> OTHER INFORMATION: CaYOR056c_TIGR_1

<400> SEQUENCE: 66

```
Cys Gln Asn Val Leu Leu Gln Met Asn Leu Asn Leu Leu Ser Thr Thr
1               5                   10                  15

Thr Leu Gln Arg Ile Arg His Leu Lys Ser Phe Ile Lys Arg Cys His
            20                  25                  30

Gly Cys Phe Phe Thr Thr Lys Asp Met Thr Lys Gln Phe Cys Pro Arg
        35                  40                  45

Cys Gly Lys Asp Thr Leu Thr Arg Val Ser Cys Thr Thr Asp Ala Asn
    50                  55                  60

Gly Gln Phe Lys Met His Leu Lys Lys Asn Met Gln Trp Asn Asn Arg
65                  70                  75                  80

Gly Asn Arg Tyr Ser Ile Pro Lys Pro
                85
```

<210> SEQ ID NO 67
<211> LENGTH: 89
<212> TYPE: PRT
<213> ORGANISM: Aspergillus fumigatus
<220> FEATURE:
<221> NAME/KEY: MISC_FEATURE
<223> OTHER INFORMATION: CaYOR056c_GTC

<400> SEQUENCE: 67

```
Cys Pro Asn Val Leu Leu Gln Met Asn Leu Asn Leu Leu Ser Thr Thr
1               5                   10                  15

Thr Leu Gln Arg Ile Arg His Leu Lys Ser Phe Ile Lys Arg Cys His
            20                  25                  30

Gly Cys Phe Phe Thr Thr Lys Asp Met Thr Lys Gln Phe Cys Pro Arg
        35                  40                  45

Cys Gly Lys Asp Thr Leu Thr Arg Val Ser Cys Thr Thr Asp Ala Asn
    50                  55                  60

Gly Gln Phe Lys Met His Leu Lys Lys Asn Met Gln Trp Asn Asn Arg
65                  70                  75                  80

Gly Asn Arg Tyr Ser Ile Pro Lys Pro
                85
```

<210> SEQ ID NO 68
<211> LENGTH: 89
<212> TYPE: PRT
<213> ORGANISM: Aspergillus fumigatus
<220> FEATURE:
<221> NAME/KEY: MISC_FEATURE
<223> OTHER INFORMATION: CaYOR056c_TIGR_2

<400> SEQUENCE: 68

```
Thr Lys Pro Val His Thr Ile Ile Leu Asp Ala Gly Pro Ile Leu Glu
1               5                   10                  15

Glu Thr Pro Pro Leu Ser Thr Leu Leu Thr Gln Cys Glu Glu Leu Leu
            20                  25                  30

Ile Thr Pro Ser Val Val Arg Glu Ile Arg Asp Pro Asp Ala Arg Leu
        35                  40                  45

Arg Val Arg Thr Leu Tyr Leu Pro Phe Leu Lys Gln Arg Thr Pro Ser
    50                  55                  60

Pro Lys Ser Val Ser Val Ile Ser Glu Phe Ala Arg Lys Thr Gly Asp
```

-continued

```
65                  70                  75                  80

Arg Ala Val Leu Ser Lys Thr Asp Leu
                85


<210> SEQ ID NO 69
<211> LENGTH: 141
<212> TYPE: PRT
<213> ORGANISM: Aspergillus fumigatus
<220> FEATURE:
<221> NAME/KEY: MISC_FEATURE
<223> OTHER INFORMATION: CaYLR009w_GTC

<400> SEQUENCE: 69

Arg Ser Lys Cys His Ala Asn Phe Lys Met Lys Arg Gln Pro Arg Lys
1               5                   10                  15

Leu Lys Trp Thr Lys Thr His Arg Ala Ala Arg Gly Lys Glu Met Ile
            20                  25                  30

Val Asp Ser Ser Leu Val Ala Val Ser Phe Ala Lys Lys Arg Asn Ile
        35                  40                  45

Pro Val Lys Tyr Asp Arg Asn Leu Val Ala Ala Thr Ile Lys Ala Met
    50                  55                  60

Glu Arg Val Glu Glu Ile Arg Ala Arg Arg Glu Arg Ala Phe Thr Lys
65                  70                  75                  80

Arg Arg Leu Gly Gly Lys Ala Gly Arg Glu Arg Lys Arg Glu Glu Asp
                85                  90                  95

Arg Met Val Val Ala Glu Gly Pro Ser Thr Ser Ser Ala Arg Glu Leu
            100                 105                 110

Arg Glu Arg Glu Glu Gly Pro Ala Phe Gly Cys Gln Gln Asp Ile Lys
        115                 120                 125

Gln Ser Gly Arg Arg Gly Glu Ala Gln Thr Glu Glu Glu
    130                 135                 140


<210> SEQ ID NO 70
<211> LENGTH: 108
<212> TYPE: PRT
<213> ORGANISM: Aspergillus fumigatus
<220> FEATURE:
<221> NAME/KEY: MISC_FEATURE
<223> OTHER INFORMATION: CaYLR009w_TIGR

<400> SEQUENCE: 70

Arg Ser Lys Cys His Ala Asn Phe Lys Met Lys Arg Gln Pro Arg Lys
1               5                   10                  15

Leu Lys Trp Thr Lys Thr His Arg Ala Ala Arg Gly Lys Glu Met Ile
            20                  25                  30

Val Asp Ser Ser Leu Val Ala Val Ser Phe Ala Lys Lys Arg Asn Ile
        35                  40                  45

Pro Val Lys Tyr Asp Arg Asn Leu Val Ala Ala Thr Ile Lys Ala Met
    50                  55                  60

Glu Arg Val Glu Glu Ile Arg Ala Arg Arg Glu Arg Ala Phe Thr Lys
65                  70                  75                  80

Arg Arg Leu Gly Gly Lys Ala Gly Arg Glu Arg Lys Arg Glu Glu Asp
                85                  90                  95

Arg Arg Val Val Ala Glu Gly Glu His Leu Ile Arg
            100                 105


<210> SEQ ID NO 71
<211> LENGTH: 257
<212> TYPE: PRT
```

<213> ORGANISM: Aspergillus fumigatus
<220> FEATURE:
<221> NAME/KEY: MISC_FEATURE
<223> OTHER INFORMATION: CaYOL010w_GTC_2

<400> SEQUENCE: 71

Asp Met Ser Val Asp Ser Val Arg Thr Ala Ile Leu Pro Leu Tyr Asn
1 5 10 15

Gln Phe Gly Ile Leu Asn Asn Ile Glu Leu Arg Val Leu Arg Arg Ser
20 25 30

Pro Arg Thr Asn Gly Arg Gly Gly Gly Gly Glu Val Gln Leu Val Phe
35 40 45

Gly His Gln Val Arg Leu Pro Lys Thr Leu His Leu Met Asn Pro Gly
50 55 60

Arg Val Lys Lys Val Arg Gly Val Ala Tyr Ser Val Gly Val Ser Ala
65 70 75 80

Ser Asn Asn Ala Arg Met Ile Asp Val Ala Arg Gly Ile Leu Asn Pro
85 90 95

Leu Val Pro Asp Thr Tyr Ile Phe Ser Asp Val Val Val Cys Ala Trp
100 105 110

Val Pro Arg Asn Asn Pro Ser Ala Lys Lys Lys Asp Arg Ser Gly Phe
115 120 125

Gly Leu Ser Leu Val Ala Glu Ser Ser Thr Gly Leu Leu Tyr Ser Ala
130 135 140

Asp Val Ala Ser Pro Pro Ala Gly Gly Gln Ala Pro Glu Asp Ile Gly
145 150 155 160

Lys Gln Cys Ala Tyr Gln Leu Leu Glu Thr Ile Ser Lys Gly Gly Cys
165 170 175

Val Ala Pro Ala Ala Ala Ser Thr Met Leu Gly Leu Met Thr Met Gly
180 185 190

Ser Glu Asp Val Gly Arg Leu Gln Phe Gly Arg Glu Val Ile Cys Asp
195 200 205

Glu Ser Ile Ile Gln Leu Ala Arg Asp Leu Ala Lys Phe Gly Ala Pro
210 215 220

Gly Trp Gly Leu Arg Asp Ala Thr Gly Glu Asn Glu Gln Gly Asp Val
225 230 235 240

Ile Val Ser Val Val Gly Arg Gly Ile Gly Asn Val Gly Arg Lys Val
245 250 255

Ala

<210> SEQ ID NO 72
<211> LENGTH: 400
<212> TYPE: PRT
<213> ORGANISM: Aspergillus fumigatus
<220> FEATURE:
<221> NAME/KEY: MISC_FEATURE
<223> OTHER INFORMATION: CaYOL010w_TIGR

<400> SEQUENCE: 72

Ala Thr Thr Ser Gln Pro Pro Leu Arg Phe Thr Gly His Lys Asn Phe
1 5 10 15

Val Asn Arg Leu Val Phe Ser Thr Leu Thr Gly Arg Ala Val His Ile
20 25 30

Ser Gln Ile Arg Ser Ser Ser Pro Thr Asn Pro Gly Leu Ala Pro His
35 40 45

Glu Ile Ser Phe Leu Arg Leu Leu Glu Ala Val Thr Asn Gly Ser Gln
50 55 60

-continued

```
Ile Glu Ile Ser Tyr Thr Gly Thr Ile Val Val Tyr Lys Pro Gly Leu
65                  70                  75                  80

Ile His Trp Arg His Cys Arg Gln Arg Gly His Thr Gly Gly Val Ile
                85                  90                  95

Arg His Glu Leu Pro Ala Arg Met Thr Arg Gly Val Ser Tyr Phe Leu
            100                 105                 110

Ile Pro Leu Cys Leu Leu Ala Pro Phe Ser Lys Ala Pro Ile Lys Val
        115                 120                 125

Leu Phe Thr Gly Pro Gly Val Ile Thr Ser Arg His Thr His Gly Asp
    130                 135                 140

Met Ser Val Asp Ser Val Arg Thr Ala Ile Leu Pro Leu Tyr Asn Gln
145                 150                 155                 160

Phe Gly Ile Leu Asn Asn Ile Glu Leu Arg Val Leu Arg Arg Ser Pro
                165                 170                 175

Arg Thr Asn Gly Arg Gly Gly Gly Gly Glu Val Gln Leu Val Phe Gly
            180                 185                 190

His Gln Val Arg Leu Pro Lys Thr Leu His Leu Met Asn Pro Gly Arg
        195                 200                 205

Val Lys Lys Val Arg Gly Val Ala Tyr Ser Val Gly Val Ser Ala Ser
    210                 215                 220

Asn Asn Ala Arg Met Ile Asp Val Ala Arg Gly Ile Leu Asn Pro Leu
225                 230                 235                 240

Val Pro Asp Thr Tyr Ile Phe Ser Asp Val Val Val Cys Ala Trp Val
                245                 250                 255

Pro Arg Asn Asn Pro Ser Ala Lys Lys Lys Asp Arg Ser Gly Phe Gly
            260                 265                 270

Leu Ser Leu Val Ala Glu Ser Ser Thr Gly Leu Leu Tyr Ser Ala Asp
        275                 280                 285

Val Ala Ser Pro Pro Ala Gly Gly Gln Ala Pro Glu Asp Ile Gly Lys
    290                 295                 300

Gln Cys Ala Tyr Gln Leu Leu Glu Thr Ile Ser Lys Gly Gly Cys Val
305                 310                 315                 320

Ala Pro Ala Ala Ala Ser Thr Met Leu Gly Leu Met Thr Met Gly Ser
                325                 330                 335

Glu Asp Val Gly Arg Leu Gln Phe Gly Arg Glu Val Ile Cys Asp Glu
            340                 345                 350

Ser Ile Ile Gln Leu Ala Arg Asp Leu Ala Lys Phe Gly Ala Pro Gly
        355                 360                 365

Trp Gly Leu Arg Asp Ala Thr Gly Glu Asn Glu Gln Gly Asp Val Ile
    370                 375                 380

Val Ser Val Val Gly Arg Gly Ile Gly Asn Val Gly Arg Lys Val Ala
385                 390                 395                 400


<210> SEQ ID NO 73
<211> LENGTH: 84
<212> TYPE: PRT
<213> ORGANISM: Aspergillus fumigatus
<220> FEATURE:
<221> NAME/KEY: MISC_FEATURE
<223> OTHER INFORMATION: CaYOL010w_GTC_1

<400> SEQUENCE: 73

Ala Thr Thr Ser Gln Pro Pro Leu Arg Phe Thr Gly His Lys Asn Phe
1               5                   10                  15

Val Asn Arg Leu Val Phe Ser Thr Leu Thr Gly Arg Ala Val His Ile
```

-continued

```
            20                  25                  30

Ser Gln Ile Arg Ser Ser Ser Pro Thr Asn Pro Gly Leu Ala Pro His
        35                  40                  45

Glu Ile Ser Phe Leu Arg Leu Leu Glu Ala Val Thr Asn Gly Ser Gln
    50                  55                  60

Ile Glu Ile Ser Tyr Thr Gly Thr Ile Val Val Tyr Lys Pro Gly Leu
65                  70                  75                  80

Val Thr Gly Gly


<210> SEQ ID NO 74
<211> LENGTH: 329
<212> TYPE: PRT
<213> ORGANISM: Aspergillus fumigatus
<220> FEATURE:
<221> NAME/KEY: MISC_FEATURE
<223> OTHER INFORMATION: CaYJR072c_GTC_1

<400> SEQUENCE: 74

Cys His Phe Thr Leu Gly Ser Gly Lys Thr Thr Phe Met Gln Arg Ile
1               5                   10                  15

Asn Ala Tyr Leu His Ser Lys Lys Lys Ile Pro Tyr Val Leu Asn Leu
            20                  25                  30

Asp Pro Ala Val Tyr Ser Val Pro Phe Glu Ser Asn Ile Asp Ile Arg
        35                  40                  45

Asp Ser Ile Asn Tyr Lys Glu Val Met Lys Gln Tyr Asn Leu Gly Pro
    50                  55                  60

Asn Gly Gly Ile Leu Thr Ser Leu Asn Leu Phe Ala Thr Lys Val Asp
65                  70                  75                  80

Gln Ile Ile Ser Leu Leu Glu Lys Arg His Arg Thr Gln Ser Arg Lys
                85                  90                  95

Pro Ile Ala Lys Pro Ile Glu His Ile Leu Val Asp Thr Pro Gly Gln
            100                 105                 110

Ile Glu Val Phe Val Trp Ser Ala Ser Gly Ser Ile Leu Leu Glu Thr
        115                 120                 125

Leu Ala Ser Ser Phe Pro Thr Val Ile Ala Tyr Val Ile Asp Thr Pro
    130                 135                 140

Arg Thr Thr Ser Thr Ser Thr Phe Met Ser Asn Met Leu Tyr Ala Cys
145                 150                 155                 160

Ser Ile Leu Tyr Lys Thr Lys Leu Pro Met Ile Leu Val Phe Asn Lys
                165                 170                 175

Thr Asp Val Gln Asp Ala Glu Phe Ala Lys Glu Trp Met Thr Asp Phe
            180                 185                 190

Asp Ala Phe Gln Gln Ala Leu Arg Asp Glu Glu Glu Val Trp Cys Phe
        195                 200                 205

Trp Arg Gly Gly Gln His Ala Gly Phe Gly Ala Gly Ser Gly Tyr Met
    210                 215                 220

Gly Ser Leu Leu Asn Ser Met Ser Leu Met Leu Glu Glu Phe Tyr Arg
225                 230                 235                 240

His Leu Ser Val Val Gly Val Ser Ser Met Thr Gly Asp Gly Ile Asp
                245                 250                 255

Glu Phe Phe Gln Ala Val Glu Glu Lys Arg Gln Glu Phe Glu Arg Asp
            260                 265                 270

Tyr Lys Pro Glu Leu Glu Arg Lys Lys Lys Glu Arg Glu Glu Thr Lys
        275                 280                 285

Ala Ala Gln Arg Glu Leu Glu Leu Gly Lys Leu Met Lys Asp Met Ser
```

-continued

```
    290                 295                 300

Val Ser Asp Leu Arg Gly Ser Arg Val Pro Arg Glu Ala Glu Thr Val
305                 310                 315                 320

Ser Glu Ala Glu Glu Glu Glu Glu Glu
                325


<210> SEQ ID NO 75
<211> LENGTH: 89
<212> TYPE: PRT
<213> ORGANISM: Aspergillus fumigatus
<220> FEATURE:
<221> NAME/KEY: MISC_FEATURE
<223> OTHER INFORMATION: CaYJR072c_TIGR_1

<400> SEQUENCE: 75

Cys His Phe Thr Leu Gly Ser Gly Lys Thr Thr Phe Met Gln Arg Ile
1               5                   10                  15

Asn Ala Tyr Leu His Ser Lys Lys Lys Met Pro Tyr Val Leu Asn Leu
            20                  25                  30

Asp Pro Ala Val Tyr Ser Val Pro Phe Glu Ser Asn Ile Asp Ile Arg
        35                  40                  45

Asp Ser Ile Asn Tyr Lys Glu Val Met Lys Gln Tyr Asn Leu Gly Pro
    50                  55                  60

Asn Gly Gly Ile Leu Thr Ser Leu Asn Leu Phe Ala Thr Lys Val Asp
65                  70                  75                  80

Gln Ile Ile Ser Leu Leu Glu Lys Arg
                85


<210> SEQ ID NO 76
<211> LENGTH: 198
<212> TYPE: PRT
<213> ORGANISM: Aspergillus fumigatus
<220> FEATURE:
<221> NAME/KEY: MISC_FEATURE
<223> OTHER INFORMATION: CaYJR072c_GTC_2

<400> SEQUENCE: 76

Val Leu Val Met Gly Pro Ala Gly Ala Gly Lys Ser Thr Phe Cys Ser
1               5                   10                  15

Ala Leu Ile Gln His Leu Gln Thr Thr Arg Arg Ser Cys Phe Tyr Val
            20                  25                  30

Asn Leu Asp Pro Ala Ala Glu Ser Phe Asn Tyr Glu Pro Asp Leu Asp
        35                  40                  45

Ile Arg Glu Leu Ile Thr Leu Glu Asp Val Met Glu Glu Met Glu Leu
    50                  55                  60

Gly Pro Asn Gly Gly Leu Ile Tyr Cys Phe Glu Phe Leu Leu Gln Asn
65                  70                  75                  80

Leu Asp Phe Leu Ser Gln Ala Leu Asp Pro Leu Ser Glu Glu Tyr Leu
                85                  90                  95

Ile Ile Phe Asp Met Pro Gly Gln Ile Glu Leu Tyr Thr His Tyr Pro
            100                 105                 110

Ala Ala Val Ala Gly Ala Val Ser Phe Thr Thr Gly Ala Ala Glu His
        115                 120                 125

Gln Pro Val Ala Ala Tyr Leu Leu Glu Ser Thr Phe Val Ile Asp Lys
    130                 135                 140

Ala Lys Phe Phe Ala Gly Thr Leu Ser Ala Met Ser Ala Met Leu Met
145                 150                 155                 160

Leu Glu Met Pro His Val Asn Ile Leu Ser Lys Met Asp Gln Val Arg
```

-continued

```
                165                 170                 175

Asp Met Val Ser Arg Lys Glu Leu Lys Arg Phe Val Asn Val Asp Val
            180                 185                 190

Asn Leu Leu Gln Asp Glu
        195
```

<210> SEQ ID NO 77
<211> LENGTH: 108
<212> TYPE: PRT
<213> ORGANISM: Aspergillus fumigatus
<220> FEATURE:
<221> NAME/KEY: MISC_FEATURE
<223> OTHER INFORMATION: CaYJR072c_TIGR_2

<400> SEQUENCE: 77

```
Val Leu Val Met Gly Pro Ala Gly Ala Gly Lys Ser Thr Phe Cys Ser
1               5                   10                  15

Ala Leu Ile Gln His Leu Gln Thr Thr Arg Arg Ser Cys Phe Tyr Val
            20                  25                  30

Asn Leu Asp Pro Ala Ala Glu Ser Phe Asn Tyr Glu Pro Asp Leu Asp
        35                  40                  45

Ile Arg Glu Leu Ile Thr Leu Glu Asp Val Met Glu Glu Met Glu Leu
    50                  55                  60

Gly Pro Asn Gly Gly Leu Ile Tyr Cys Phe Glu Phe Leu Leu Gln Asn
65                  70                  75                  80

Leu Asp Phe Leu Ser Gln Ala Leu Asp Pro Leu Ser Glu Glu Tyr Leu
                85                  90                  95

Ile Ile Phe Asp Met Pro Gly Gln Ile Glu Leu Tyr
            100                 105
```

<210> SEQ ID NO 78
<211> LENGTH: 73
<212> TYPE: PRT
<213> ORGANISM: Aspergillus fumigatus
<220> FEATURE:
<221> NAME/KEY: MISC_FEATURE
<223> OTHER INFORMATION: CaYJR072c_TIGR_3

<400> SEQUENCE: 78

```
Leu Val Ile Gly Pro Pro Gly Ala Gly Lys Ser Thr Tyr Cys Asn Gly
1               5                   10                  15

Met His Gln Phe Leu Gly Ala Ile Gly Arg Lys Cys Ser Ile Val Asn
            20                  25                  30

Leu Asp Pro Ala Asn Asp Lys Thr Ser Tyr Pro Cys Ala Leu Asp Val
        35                  40                  45

Arg Asp Leu Val Thr Leu Glu Glu Ile Met Ser Glu Asp Gln Leu Gly
    50                  55                  60

Pro Asn Gly Gly Val Leu Tyr Ala Leu
65                  70
```

<210> SEQ ID NO 79
<211> LENGTH: 73
<212> TYPE: PRT
<213> ORGANISM: Aspergillus fumigatus
<220> FEATURE:
<221> NAME/KEY: MISC_FEATURE
<223> OTHER INFORMATION: CaYJR072c_GTC_3

<400> SEQUENCE: 79

```
Leu Val Ile Gly Pro Pro Gly Ala Gly Lys Ser Thr Tyr Cys Asn Gly
1               5                   10                  15
```

-continued

```
Met His Gln Phe Leu Gly Ala Ile Gly Arg Lys Cys Ser Ile Val Asn
            20                  25                  30

Leu Asp Pro Ala Asn Asp Lys Thr Ser Tyr Pro Cys Ala Leu Asp Val
        35                  40                  45

Arg Asp Leu Val Thr Leu Glu Glu Ile Met Ser Glu Asp Gln Leu Gly
    50                  55                  60

Pro Asn Gly Gly Val Leu Tyr Ala Leu
65                  70
```

<210> SEQ ID NO 80
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: CaERG1PSF
<220> FEATURE:
<221> NAME/KEY: misc_feature
<223> OTHER INFORMATION: CaERG1PSF Met3 Swapping Primer

<400> SEQUENCE: 80

```
acctggttac aagaagctga cgaagaagat agtgatgagg atgatgagga tagtgaatag     60

tgtggaattg tgagcggata                                                 80
```

<210> SEQ ID NO 81
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: CaERG1PSR
<220> FEATURE:
<221> NAME/KEY: misc_feature
<223> OTHER INFORMATION: CaERG1PSR Met3 Swapping Primer

<400> SEQUENCE: 81

```
caatggtggg accaataacc cctgcaccaa taataatagc atcatactta actgaactca     60

tgttttctgg ggagggtatt                                                 80
```

<210> SEQ ID NO 82
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: RAM2PSF
<220> FEATURE:
<221> NAME/KEY: misc_feature
<223> OTHER INFORMATION: RAM2PSF Met3 Swapping Primer

<400> SEQUENCE: 82

```
aatcaattta aatgatatat ttattggaaa actccaccat tgaaaccatt aaaccacttt     60

tgtggaattg tgagcggata                                                 80
```

<210> SEQ ID NO 83
<211> LENGTH: 80
<212> TYPE: DNA
<213> ORGANISM: Artificial Sequence
<220> FEATURE:

```
<223> OTHER INFORMATION: reverse primer
<220> FEATURE:
<221> NAME/KEY: misc_feature
<223> OTHER INFORMATION: RAM2PSR
<220> FEATURE:
<221> NAME/KEY: misc_feature
<223> OTHER INFORMATION: RAM2PSR Met3 Swapping Primer

<400> SEQUENCE: 83

ctcttcagtg tttatatcga caggagtaat gtcagaatag tcatatttgg agtctgtcat    60

gttttctggg gagggtattt                                                80

<210> SEQ ID NO 84
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: PFY1PSF
<220> FEATURE:
<221> NAME/KEY: misc_feature
<223> OTHER INFORMATION: PFY1PSF Met3 Swapping Primer

<400> SEQUENCE: 84

agatatgaag attgtagaac cacctgtaaa gaagagaaaa cttgactaga tcaactttga    60

tgtggaattg tgagcggata                                                80

<210> SEQ ID NO 85
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: PFY1PSR
<220> FEATURE:
<221> NAME/KEY: misc_feature
<223> OTHER INFORMATION: PFY1PSR Met3 Swapping Primer

<400> SEQUENCE: 85

ggctgcttta tcgactttac cgttagcaat taagttatca gtgtaggctt gccaagacat    60

gttttctggg gagggtattt                                                80

<210> SEQ ID NO 86
<211> LENGTH: 72
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: CaNMT1PSF
<220> FEATURE:
<221> NAME/KEY: misc_feature
<223> OTHER INFORMATION: CaNMT1PSF Met3 Swapping Primer

<400> SEQUENCE: 86

aatttttttt atagccaact actccataaa ttcattattt acttttaaag tctgtggaat    60

tgtgagcgga ta                                                        72

<210> SEQ ID NO 87
<211> LENGTH: 78
<212> TYPE: DNA
<213> ORGANISM: Artificial Sequence
```

-continued

<220> FEATURE:
<223> OTHER INFORMATION: reverse primer
<220> FEATURE:
<221> NAME/KEY: misc_feature
<223> OTHER INFORMATION: CaNMT1PSR
<220> FEATURE:
<221> NAME/KEY: misc_feature
<223> OTHER INFORMATION: CaNMT1PSR Met3 Swapping Primer

<400> SEQUENCE: 87
cttcaattga ttttgaaggt gctgaattgg atttattccc tgtgttatct cccgacatgt 60
tttctgggga gggtattt 78

<210> SEQ ID NO 88
<211> LENGTH: 78
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YLR100wPSF
<220> FEATURE:
<221> NAME/KEY: misc_feature
<223> OTHER INFORMATION: YLR100wPSF Met3 Swapping Primer

<400> SEQUENCE: 88
gaatcaaata acggagataa ggctgctaaa agatcgaaaa cccttgccac tacaagcctg 60
tggaattgtg agcggata 78

<210> SEQ ID NO 89
<211> LENGTH: 79
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YLR100wPSR
<220> FEATURE:
<221> NAME/KEY: misc_feature
<223> OTHER INFORMATION: YLR100wPSR Met3 Swapping Primer

<400> SEQUENCE: 89
cctaaatttg aagatgtccc ggtaatgact gcaactgtag aatcctttaa aagtgacatg 60
ttttctgggg agggtattt 79

<210> SEQ ID NO 90
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YDR341CPSF
<220> FEATURE:
<221> NAME/KEY: misc_feature
<223> OTHER INFORMATION: YDR341CPSF Met3 Swapping Primer

<400> SEQUENCE: 90
gatttgtctc gcgtacagag tttcctgttc cataccacat aggggtttcc tataacatct 60
gtggaattgt gagcggata 79

<210> SEQ ID NO 91
<211> LENGTH: 83
<212> TYPE: DNA

-continued

<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YDR341CPSR
<220> FEATURE:
<221> NAME/KEY: misc_feature
<223> OTHER INFORMATION: YDR341CPSR Met3 Swapping Primer

<400> SEQUENCE: 91
tgaatggtat cttctttgac tataaaatat tgtagaggaa aataacttct tcaatatttt 60
catgttttct ggggagggta ttt 83

<210> SEQ ID NO 92
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YLR022CPSF
<220> FEATURE:
<221> NAME/KEY: misc_feature
<223> OTHER INFORMATION: YLR022CPSF Met3 Swapping Primer

<400> SEQUENCE: 92
gattattgaa agatggaatg actttcaaaa ctagtgattg gggaaataca aggaataggt 60
gtggaattgt gagcggata 79

<210> SEQ ID NO 93
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YLR022CPSR
<220> FEATURE:
<221> NAME/KEY: misc_feature
<223> OTHER INFORMATION: YLR022CPSR Met3 Swapping Primer

<400> SEQUENCE: 93
tcggactaag gaaacatttg taagtctgat ctgactattt ggttgattaa tcaccgccat 60
gttttctggg gagggtattt 80

<210> SEQ ID NO 94
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YOL077CPSF
<220> FEATURE:
<221> NAME/KEY: misc_feature
<223> OTHER INFORMATION: YOL077CPSF Met3 Swapping Primer

<400> SEQUENCE: 94
tttaactgaa atgttacttc ttggaagaaa accaaacgag atttttgcta gatgacaagt 60
gtggaattgt gagcggata 79

<210> SEQ ID NO 95
<211> LENGTH: 80

-continued

<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YOL077CPSR
<220> FEATURE:
<221> NAME/KEY: misc_feature
<223> OTHER INFORMATION: YOL077CPSR Met3 Swapping Primer

<400> SEQUENCE: 95
ggttttttcc gatgtttcct tagatgattt ggattgtaat gccttataga tagctgacat 60
gttttctggg gagggtattt 80

<210> SEQ ID NO 96
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YNL132WPSF
<220> FEATURE:
<221> NAME/KEY: misc_feature
<223> OTHER INFORMATION: YNL132WPSF Met3 Swapping Primer

<400> SEQUENCE: 96
tcctatggaa ggagaggtta gtcatgaaca atagccgccc ttataattca gtggataagc 60
tgtggaattg tgagcggata 80

<210> SEQ ID NO 97
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YNL132WPSR
<220> FEATURE:
<221> NAME/KEY: misc_feature
<223> OTHER INFORMATION: YNL132WPSR Met3 Swapping Primer

<400> SEQUENCE: 97
ttcttgaacg ccattacgta tcaaggcagg aatacgtgca tcaattgctt ttttacccat 60
gttttctggg gagggtattt 80

<210> SEQ ID NO 98
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YJR072CPSF
<220> FEATURE:
<221> NAME/KEY: misc_feature
<223> OTHER INFORMATION: YJR072CPSF Met3 Swapping Primer

<400> SEQUENCE: 98
gtttacttaa atattgtgta tcattagtaa tcatcatcat caccatcacc atcgtactct 60
gtggaattgt gagcggata 79

<210> SEQ ID NO 99

-continued

<211> LENGTH: 78
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YJR072CPSR
<220> FEATURE:
<221> NAME/KEY: misc_feature
<223> OTHER INFORMATION: YJR072CPSR Met3 Swapping Primer

<400> SEQUENCE: 99
tggttttacc acttccggcc attccaatac atataatcgt aggtggtggt gttggcatgt 60
tttctgggga gggtattt 78

<210> SEQ ID NO 100
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YGR145WPSF
<220> FEATURE:
<221> NAME/KEY: misc_feature
<223> OTHER INFORMATION: YGR145WPSF Met3 Swapping Primer

<400> SEQUENCE: 100
cggaaacaaa gaacccaaac atgattagca atgtagacca ataacgtgct actaacatat 60
gtggaattgt gagcggata 79

<210> SEQ ID NO 101
<211> LENGTH: 77
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YGR145WPSR
<220> FEATURE:
<221> NAME/KEY: misc_feature
<223> OTHER INFORMATION: YGR145WPSR Met3 Swapping Primer

<400> SEQUENCE: 101
ggtaccagaa acttgatata ctgatacatt ccctgcagtt gttgatttta aaaccatgtt 60
ttctggggag ggtattt 77

<210> SEQ ID NO 102
<211> LENGTH: 75
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YDR412WPSF
<220> FEATURE:
<221> NAME/KEY: misc_feature
<223> OTHER INFORMATION: YDR412WPSF Met3 Swapping Primer

<400> SEQUENCE: 102
gttcctcgga tgtagaagtg gtagaggtgg ttgatgatgt tgtgttgata tttagtgtgg 60
aattgtgagc ggata 75

-continued

<210> SEQ ID NO 103
<211> LENGTH: 78
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YDR412WPSR
<220> FEATURE:
<221> NAME/KEY: misc_feature
<223> OTHER INFORMATION: YDR412WPSR Met3 Swapping Primer

<400> SEQUENCE: 103
gttggatata tttcttacct ccagttaaaa tttctctatt ctttttaaat cctgccatgt 60
tttctgggga gggtattt 78

<210> SEQ ID NO 104
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YOL010WPSF
<220> FEATURE:
<221> NAME/KEY: misc_feature
<223> OTHER INFORMATION: YOL010WPSF Met3 Swapping Primer

<400> SEQUENCE: 104
atgctactga aacctgtaga ttataccctg gaacaagaac cttactatta tcaacacaat 60
tgtggaattg tgagcggata 80

<210> SEQ ID NO 105
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YOL010WPSR
<220> FEATURE:
<221> NAME/KEY: misc_feature
<223> OTHER INFORMATION: YOL010WPSR Met3 Swapping Primer

<400> SEQUENCE: 105
taatctgaaa ttcctgtgcc cttcaaatgt tattatcttt ttggaagcaa cactggacat 60
gttttctggg gagggtattt 80

<210> SEQ ID NO 106
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YOR004WPSF
<220> FEATURE:
<221> NAME/KEY: misc_feature
<223> OTHER INFORMATION: YOR004WPSF Met3 Swapping Primer

<400> SEQUENCE: 106
agattcaaat agaaaacaat ccagatattg agtatcaaaa gttatatctg atattaggtg 60
tgtggaattg tgagcggata 80

-continued

<210> SEQ ID NO 107
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YOR004WPSR
<220> FEATURE:
<221> NAME/KEY: misc_feature
<223> OTHER INFORMATION: YOR004WPSRMet3 Swapping Primer

<400> SEQUENCE: 107
gaatgcgtgg acatacacac tcatttgttt cttataggcc ttggcacgct tttgtctcat 60
gttttctggg gagggtattt 80

<210> SEQ ID NO 108
<211> LENGTH: 79
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YOR056CPSF
<220> FEATURE:
<221> NAME/KEY: misc_feature
<223> OTHER INFORMATION: YOR056CPSF Met3 Swapping Primer

<400> SEQUENCE: 108
ataaagaaaa tccaaatttt agatatagca tttagagtct ttttttcta tagagtatct 60 gtggaattgt gagcggata 79

<210> SEQ ID NO 109
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YOR056CPSR
<220> FEATURE:
<221> NAME/KEY: misc_feature
<223> OTHER INFORMATION: YOR056CPSR Met3 Swapping Primer

<400> SEQUENCE: 109
ctgtgtaatc aatggaccag catccgaaat caaagactca atattttttg tttcagacat 60
gttttctggg gagggtattt 80

<210> SEQ ID NO 110
<211> LENGTH: 80
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: YLR009WPSF
<220> FEATURE:
<221> NAME/KEY: misc_feature
<223> OTHER INFORMATION: YLR009WPSF Met3 Swapping Primer

<400> SEQUENCE: 110
gaaattgttg ttgttgctgt tggtgagtgt tattttctcc aggtatagct aatattggtg 60
tgtggaattg tgagcggata 80

<210> SEQ ID NO 111
<211> LENGTH: 80
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: YLR009WPSR Met3 Swapping Primer

<400> SEQUENCE: 111
tgtgatccca tgtaatggat ataccggtga tgaacaaaaa tgacattgat aaatcctcat 60
gttttctggg gagggtattt 80

<210> SEQ ID NO 112
<211> LENGTH: 77
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: CaAAH1PSF
<220> FEATURE:
<221> NAME/KEY: misc_feature
<223> OTHER INFORMATION: CaAAH1PSF Met3 Swapping Primer

<400> SEQUENCE: 112
gttttaccaa cctgggccga tcaagttttg aacaaaaagg actaattatt actcatttgt 60
ggaattgtga gcggata 77

<210> SEQ ID NO 113
<211> LENGTH: 79
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<223> OTHER INFORMATION: CaAAH1PSR Met3 Swapping Primer

<400> SEQUENCE: 113
gtaccttcca aatgaacgtg atgttcacat ttaggtaatt ctctaaggaa attttccatg 60
ttttctgggg agggtattt 79

<210> SEQ ID NO 114
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: 5' promoter-specific confirmation primer,
upstream of the promoter
<220> FEATURE:
<221> NAME/KEY: misc_feature
<223> OTHER INFORMATION: ERG1GSF

<400> SEQUENCE: 114
ccacaagaag ctgctacc 18

<210> SEQ ID NO 115
<211> LENGTH: 20
<212> TYPE: DNA
<213> ORGANISM: Artificial Sequence -continued
<220> FEATURE:
<223> OTHER INFORMATION: Reverse Primer
<220> FEATURE:
<221> NAME/KEY: misc_feature
<223> OTHER INFORMATION: CaERG1 3' promoter-specific confirmation
primer, downstream of ATG start codon
<220> FEATURE:
<221> NAME/KEY: misc_feature
<223> OTHER INFORMATION: ERG1GSR

<400> SEQUENCE: 115
cttaatgcct tgataccagc 20

<210> SEQ ID NO 116
<211> LENGTH: 20
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaRAM2 5' promoter-specific confirmation
forward primer, upstream of the promoter
<220> FEATURE:
<221> NAME/KEY: misc_feature
<223> OTHER INFORMATION: RAM2GSF

<400> SEQUENCE: 116
gaataacagt ggggtgttag 20

<210> SEQ ID NO 117
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaRAM2 3' promoter-specific confirmaton reverse
primer, downstream of ATG start codon):
<220> FEATURE:
<221> NAME/KEY: misc_feature
<223> OTHER INFORMATION: RAM2GSR

<400> SEQUENCE: 117
gctagttcgt taatgccc 18

<210> SEQ ID NO 118
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: 5' promoter-specific confirmation forward
primer, upstream of the promoter):
<220> FEATURE:
<221> NAME/KEY: misc_feature
<223> OTHER INFORMATION: PFY1GSF

<400> SEQUENCE: 118
gaagagaaca atggtgag 18

<210> SEQ ID NO 119
<211> LENGTH: 18
<212> TYPE: DNA
<213> ORGANISM: Artificial Sequence
<220> FEATURE:
<223> OTHER INFORMATION: Reverse Primer
<220> FEATURE:

-continued

<221> NAME/KEY: misc_feature
<223> OTHER INFORMATION: CaPFY1 3' promoter-specific confirmation
      reverse primer, downstream of ATG start codon):
<220> FEATURE:
<221> NAME/KEY: misc_feature
<223> OTHER INFORMATION: PFY1GSR

<400> SEQUENCE: 119
tttgcaaacc ttcagcac 18

<210> SEQ ID NO 120
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaNMT1 3' promoter-specific confirmation
      primer, downstream of ATG start codon
<220> FEATURE:
<221> NAME/KEY: misc_feature
<223> OTHER INFORMATION: CaNMT1GSR

<400> SEQUENCE: 120
tggtacaggt tgagtcttc 19

<210> SEQ ID NO 121
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYLR100w 5' promoter-specific confirmation
      forward primer
<220> FEATURE:
<221> NAME/KEY: misc_feature
<223> OTHER INFORMATION: YLR100wGSF

<400> SEQUENCE: 121
cttcgtcgtc aatcgttg 18

<210> SEQ ID NO 122
<211> LENGTH: 20
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYLR100w 3' promoter-specific confirmation
      reverse primer
<220> FEATURE:
<221> NAME/KEY: misc_feature
<223> OTHER INFORMATION: YLR100wGSR

<400> SEQUENCE: 122
ccatatcagt gaaatccacc 20

<210> SEQ ID NO 123
<211> LENGTH: 19
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: YDR341CGSF
<220> FEATURE:

<221> NAME/KEY: misc_feature
<223> OTHER INFORMATION: 5' promoter-specific confirmation forward
      primer

<400> SEQUENCE: 123
ggggttgtta ctcaagttg 19

<210> SEQ ID NO 124
<211> LENGTH: 21
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYDR341C 3' promoter-specific confirmation
      reverse primer
<220> FEATURE:
<221> NAME/KEY: misc_feature
<223> OTHER INFORMATION: YDR341CGSR

<400> SEQUENCE: 124
gtgggtacct tcaatggctg c 21

<210> SEQ ID NO 125
<211> LENGTH: 20
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYLR022C 5' promoter-specific confirmation
      forward primer
<220> FEATURE:
<221> NAME/KEY: misc_feature
<223> OTHER INFORMATION: YLR022CGSF

<400> SEQUENCE: 125
gtgggaggaa cacaacaaag 20

<210> SEQ ID NO 126
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYLR022C 3' promoter-specific confirmation
      reverse primer
<220> FEATURE:
<221> NAME/KEY: misc_feature
<223> OTHER INFORMATION: YLR022CGSR

<400> SEQUENCE: 126
cttgtgggat ttgtaacac 19

<210> SEQ ID NO 127
<211> LENGTH: 19
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYOL077C 5' promoter specific confirmation
      primer, upstream of the promoter
<220> FEATURE:
<221> NAME/KEY: misc_feature
<223> OTHER INFORMATION: YOL077C 5' promoter specific confirmation -continued primer, upstream of the promoter

<400> SEQUENCE: 127
gcctcctctc cagaagaag 19

<210> SEQ ID NO 128
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: Ca YOL077C 3' promoter specific confirmation primer, downstream of ATG start condon):
<220> FEATURE:
<221> NAME/KEY: misc_feature
<223> OTHER INFORMATION: YOL077CGSR

<400> SEQUENCE: 128
agcgtgtggt aataatgc 18

<210> SEQ ID NO 129
<211> LENGTH: 19
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: YNL132W 5' promoter specific confirmation primer, upstream of the promoter
<220> FEATURE:
<221> NAME/KEY: misc_feature
<223> OTHER INFORMATION: YNL132WGSF

<400> SEQUENCE: 129
cttgaaaagg gggacctac 19

<210> SEQ ID NO 130
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: Ca YNL132W 3' promoter specific confirmation primer, downstream of ATG start condon):
<220> FEATURE:
<221> NAME/KEY: misc_feature
<223> OTHER INFORMATION: Ca YNL132W 3' promoter specific confirmation primer, downstream of ATG start condon):
<220> FEATURE:
<221> NAME/KEY: misc_feature
<223> OTHER INFORMATION: YNL132WGSR

<400> SEQUENCE: 130
cttgtatgcc cataatac 18

<210> SEQ ID NO 131
<211> LENGTH: 20
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYJR072C 5' promoter-specific confirmation forward primer
<220> FEATURE:

-continued

```
<221> NAME/KEY: misc_feature
<223> OTHER INFORMATION: YJR072CGSF

<400> SEQUENCE: 131

ttgagtggac caggggcacc                                               20


<210> SEQ ID NO 132
<211> LENGTH: 23
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYJR072C 3' promoter-specific confirmation
      reverse primer
<220> FEATURE:
<221> NAME/KEY: misc_feature
<223> OTHER INFORMATION: YJR072CGSR

<400> SEQUENCE: 132

gttacaatag ctccatttgg tcc                                           23


<210> SEQ ID NO 133
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYGR145W 5' promoter-specific confirmation
      forward primer
<220> FEATURE:
<221> NAME/KEY: misc_feature
<223> OTHER INFORMATION: YGR145WGSF

<400> SEQUENCE: 133

atcaacaaca ggggcacg                                                 18


<210> SEQ ID NO 134
<211> LENGTH: 20
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYGR145W 3' promoter-specific confirmation
      reverse primer
<220> FEATURE:
<221> NAME/KEY: misc_feature
<223> OTHER INFORMATION: YGR145WGSR

<400> SEQUENCE: 134

taagtcccgg tggccataca                                               20


<210> SEQ ID NO 135
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaYDR412W 5' gene-specific confirmation forward
      primer
<220> FEATURE:
<221> NAME/KEY: misc_feature
<223> OTHER INFORMATION: YDR412WGSF
```

-continued

<400> SEQUENCE: 135
gggatgagaa tcagtatc 18

<210> SEQ ID NO 136
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaYDR412W 3' gene-specific confirmation reverse primer
<220> FEATURE:
<221> NAME/KEY: misc_feature
<223> OTHER INFORMATION: YDR412WGSR

<400> SEQUENCE: 136
agctaaccgt tcttgttc 18

<210> SEQ ID NO 137
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: Ca YOL010W 5' promoter specific confirmation primer, upstream of the promoter
<220> FEATURE:
<221> NAME/KEY: misc_feature
<223> OTHER INFORMATION: YOL010WGSF

<400> SEQUENCE: 137
gggaattgag agctaagg 18

<210> SEQ ID NO 138
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: Ca YOL010W 3' promoter specific confirmation primer, downstream of ATG start codon):
<220> FEATURE:
<221> NAME/KEY: misc_feature
<223> OTHER INFORMATION: YOL010WGSR

<400> SEQUENCE: 138
tccattggtt acggcttc 18

<210> SEQ ID NO 139
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: Ca YOR004W 5' promoter specific confirmation primer, upstream of the promoter
<220> FEATURE:
<221> NAME/KEY: misc_feature
<223> OTHER INFORMATION: YOR004WGSF

<400> SEQUENCE: 139
cggcagtgaa taggattc 18

<210> SEQ ID NO 140
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: Ca YOR004W 3' promoter specific confirmation
primer, downstream of ATG start condon):
<220> FEATURE:
<221> NAME/KEY: misc_feature
<223> OTHER INFORMATION: YOR004WGSR

<400> SEQUENCE: 140
gcttggatac aacattgag 19

<210> SEQ ID NO 141
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: YOR056CGSF

<400> SEQUENCE: 141
accaggctac accggagc 18

<210> SEQ ID NO 142
<211> LENGTH: 18
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: . YOR056CGSR

<400> SEQUENCE: 142
actatcaccc caaattgc 18

<210> SEQ ID NO 143
<211> LENGTH: 19
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: YLR009WGSF

<400> SEQUENCE: 143
tgatcacagg atgatctcc 19

<210> SEQ ID NO 144
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: LR009WGSR

<400> SEQUENCE: 144
taaatgcttt agtccaacg 19

-continued

<210> SEQ ID NO 145
<211> LENGTH: 18
<212> TYPE: DNA
<213> ORGANISM: Artificial Sequence
<220> FEATURE:
<223> OTHER INFORMATION: forward Primer
<220> FEATURE:
<221> NAME/KEY: misc_feature
<223> OTHER INFORMATION: CaAAH1 promoter-specific confirmation primer,
upstream of the promoter
<220> FEATURE:
<221> NAME/KEY: misc_feature
<223> OTHER INFORMATION: AAH1GSF

<400> SEQUENCE: 145
cccagttgct gaatacgc 18

<210> SEQ ID NO 146
<211> LENGTH: 20
<212> TYPE: DNA
<213> ORGANISM: Artificial Sequence
<220> FEATURE:
<223> OTHER INFORMATION: Reverse Primer
<220> FEATURE:
<221> NAME/KEY: misc_feature
<223> OTHER INFORMATION: CaAAH1 3' promoter-specific confirmation primer
<220> FEATURE:
<221> NAME/KEY: misc_feature
<223> OTHER INFORMATION: CaAAH1GSR

<400> SEQUENCE: 146
cgttttaggg aaagtctcag 20

<210> SEQ ID NO 147
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: CaURA3, confirmation primer, pairs with 3'
promoter-specific primers
<220> FEATURE:
<221> NAME/KEY: misc_feature
<223> OTHER INFORMATION: CaURA3, confirmation primer, pairs with 3'
promoter-specific primers
<220> FEATURE:
<221> NAME/KEY: misc_feature
<223> OTHER INFORMATION: URA3CF1c or 5'-PTURA

<400> SEQUENCE: 147
caatggcact acagcaac 18

<210> SEQ ID NO 148
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: CaURA3, confirmation primer, pairs with 5'
promoter-specific confirmation primer)
<220> FEATURE:
<221> NAME/KEY: misc_feature
<223> OTHER INFORMATION: CaURA3, confirmation primer, pairs with 5'
promoter-specific confirmation primer)
<220> FEATURE:
<221> NAME/KEY: misc_feature
<223> OTHER INFORMATION: URA3CF1w or 3'-PTURA -continued

<400> SEQUENCE: 148
gacgttgata ccactaagg 19

<210> SEQ ID NO 149
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: confirmation PCR primer for checking MET3
promoter construct, pairs with 3' promoter-specific primers,)
<220> FEATURE:
<221> NAME/KEY: misc_feature
<223> OTHER INFORMATION: confirmation PCR primer for checking MET3
promoter construct, pairs with 3' promoter-specific primers,)
<220> FEATURE:
<221> NAME/KEY: misc_feature
<223> OTHER INFORMATION: ARGfw or 5'-PTARG

<400> SEQUENCE: 149
ctgtgcaata actttctgtc 20

<210> SEQ ID NO 150
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: (confirmation PCR primer for checking MET3
promoter construct, pairs with 5' promoter-specific confirmation
primer)
<220> FEATURE:
<221> NAME/KEY: misc_feature
<223> OTHER INFORMATION: (confirmation PCR primer for checking MET3
promoter construct, pairs with 5' promoter-specific confirmation
primer)
<220> FEATURE:
<221> NAME/KEY: misc_feature
<223> OTHER INFORMATION: ARGrv or 3'-ARG

<400> SEQUENCE: 150
ctggttcttc attgatgcc 19

<210> SEQ ID NO 151
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAERG1FC

<400> SEQUENCE: 151
ccagtccatc atgagttcag 20

<210> SEQ ID NO 152
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAERG1RC -continued

<400> SEQUENCE: 152
gccaatggga atcccaaaag 20

<210> SEQ ID NO 153
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CARAM2CF2

<400> SEQUENCE: 153
gaaccgcact tttcaattg 19

<210> SEQ ID NO 154
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CARAM2RC

<400> SEQUENCE: 154
ccgatgtgag tttggaaatc 20

<210> SEQ ID NO 155
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAPFY1FC

<400> SEQUENCE: 155
gtcttggcaa gcatacattg 20

<210> SEQ ID NO 156
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAPFY1RC

<400> SEQUENCE: 156
ccgacattga tcaagtagtc 20

<210> SEQ ID NO 157
<211> LENGTH: 21
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMT1CF

<400> SEQUENCE: 157
caattaacga tcaagtatag g 21

<210> SEQ ID NO 158
<211> LENGTH: 29
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMT1CR

<400> SEQUENCE: 158
ctagcaatca taaccaaaac atggaatgc 29

<210> SEQ ID NO 159
<211> LENGTH: 22
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR100FC

<400> SEQUENCE: 159
acaccatcgc ttgcaacaca tc 22

<210> SEQ ID NO 160
<211> LENGTH: 22
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR100RC

<400> SEQUENCE: 160
ccttcaactt ttcgtcccac tc 22

<210> SEQ ID NO 161
<211> LENGTH: 21
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR341CCF

<400> SEQUENCE: 161
ttcttgcttc ttcatcaccc c 21

<210> SEQ ID NO 162
<211> LENGTH: 21
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR341CCR

<400> SEQUENCE: 162
ctggagtcaa acctaacaag g 21

<210> SEQ ID NO 163
<211> LENGTH: 20
<212> TYPE: DNA

-continued

<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR022CF2

<400> SEQUENCE: 163
gctcatcttc atcgtcttgc 20

<210> SEQ ID NO 164
<211> LENGTH: 23
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR022CR1

<400> SEQUENCE: 164
ctatagaccc ttctccttta gcg 23

<210> SEQ ID NO 165
<211> LENGTH: 25
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL077FC

<400> SEQUENCE: 165
ccagttccat ccatccaacc tatac 25

<210> SEQ ID NO 166
<211> LENGTH: 23
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL077RC

<400> SEQUENCE: 166
gcatcattgg ataatggatc agc 23

<210> SEQ ID NO 167
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYNL132CF2

<400> SEQUENCE: 167
cagtcctcat ctcaaagag 19

<210> SEQ ID NO 168
<211> LENGTH: 22
<212> TYPE: DNA
<213> ORGANISM: Artificial Sequence
<220> FEATURE:
<223> OTHER INFORMATION: Synthesized Primer
<220> FEATURE:

-continued

<221> NAME/KEY: misc_feature
<223> OTHER INFORMATION: CAYNL132RC

<400> SEQUENCE: 168
catcccattc agcatcttct gc 22

<210> SEQ ID NO 169
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYJR072FC

<400> SEQUENCE: 169
ccatcgtact ctctgtaacc 20

<210> SEQ ID NO 170
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYJR072RC

<400> SEQUENCE: 170
gcagttttgg aagaagcagg 20

<210> SEQ ID NO 171
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYGR145CF2

<400> SEQUENCE: 171
catatctgtc aatctacag 19

<210> SEQ ID NO 172
<211> LENGTH: 21
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYGR145RC

<400> SEQUENCE: 172
ggatgctatt ctacgacctt c 21

<210> SEQ ID NO 173
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR412WCF

<400> SEQUENCE: 173

-continued cttattccat aatggcagg 19

<210> SEQ ID NO 174
<211> LENGTH: 18
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR412CR

<400> SEQUENCE: 174
ttacttcttg ccctttga 18

<210> SEQ ID NO 175
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL010CF2

<400> SEQUENCE: 175
cgcatttggt atgagcaga 19

<210> SEQ ID NO 176
<211> LENGTH: 23
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL010WCR

<400> SEQUENCE: 176
acgagaaacc tccccattca agc 23

<210> SEQ ID NO 177
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR004CF2

<400> SEQUENCE: 177
gatttgcgag aaggagaag 19

<210> SEQ ID NO 178
<211> LENGTH: 22
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR004WCR

<400> SEQUENCE: 178
tagctgttat tgcctcctgt gc 22

-continued

<210> SEQ ID NO 179
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR056CCF

<400> SEQUENCE: 179
gtacacagaa tcaaatctc 19

<210> SEQ ID NO 180
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR056CCR

<400> SEQUENCE: 180
ggaagagttt gcatatcttc 20

<210> SEQ ID NO 181
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR009WFC

<400> SEQUENCE: 181
gttcatcacc ggtatatcc 19

<210> SEQ ID NO 182
<211> LENGTH: 19
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR009RC

<400> SEQUENCE: 182
gtgtcacttt ccctttcac 19

<210> SEQ ID NO 183
<211> LENGTH: 21
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAAAH1FC

<400> SEQUENCE: 183
ggaaggtact ttggaaccat c 21

<210> SEQ ID NO 184
<211> LENGTH: 18
<212> TYPE: DNA
<213> ORGANISM: Artificial Sequence -continued
<220> FEATURE:
<223> OTHER INFORMATION: Synthesized Primer
<220> FEATURE:
<221> NAME/KEY: misc_feature
<223> OTHER INFORMATION: CAAAH1CR

<400> SEQUENCE: 184
cttcttcaac caagctaa 18

<210> SEQ ID NO 185
<211> LENGTH: 79
<212> TYPE: DNA
<213> ORGANISM: Artificial Sequence
<220> FEATURE:
<223> OTHER INFORMATION: synthesized primer
<220> FEATURE:
<221> NAME/KEY: misc_feature
<223> OTHER INFORMATION: CaERG1FD

<400> SEQUENCE: 185
gtggaaagag actggtccaa gccagataga aatgttggag agttgatgca accggctggg 60
ttttcccagt cacgacgtt 79

<210> SEQ ID NO 186
<211> LENGTH: 83
<212> TYPE: DNA
<213> ORGANISM: Artificial Sequence
<220> FEATURE:
<223> OTHER INFORMATION: Synthesized primer
<220> FEATURE:
<221> NAME/KEY: misc_feature
<223> OTHER INFORMATION: CaERG1RD

<400> SEQUENCE: 186
gggaatggta acataccact caataatcca attggcccgt taacacattc tccacctctt 60
gtttgtggaa ttgtgagcgg ata 83

<210> SEQ ID NO 187
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CARAM2FD

<400> SEQUENCE: 187
cagactccaa atatgactat tctgacatta ctcctgtcga tataaacact gaagagcctc 60
gttttcccag tcacgacgtt 80

<210> SEQ ID NO 188
<211> LENGTH: 78
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CARAM2RD

<400> SEQUENCE: 188
cgatcaaacc gttcatgaat ccccaataaa taattccaag tacttggatt ctgtggactg 60
tggaattgtg agcggata 78

-continued

<210> SEQ ID NO 189
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAPFY1FD

<400> SEQUENCE: 189
ggtaaagtcg ataaagcagc cttatattca agagccggtg acgcattatg ggcccaatcg 60
gttttcccag tcacgacgtt 80

<210> SEQ ID NO 190
<211> LENGTH: 73
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAPFY1RD

<400> SEQUENCE: 190
caacaagagt ggtagcttca cctggttgaa caccacttgg ataatgggcg atctgtggaa 60
ttgtgagcgg ata 73

<210> SEQ ID NO 191
<211> LENGTH: 84
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMT1KF1

<400> SEQUENCE: 191
cgatcaagta taggttatta gaatatgtcg ggagataacg cagggaataa atccaattca 60
gcacgttttc ccagtcacga cgtt 84

<210> SEQ ID NO 192
<211> LENGTH: 76
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMTKR1

<400> SEQUENCE: 192
cactctaatt ataataaaac tacacctata ccacttgttt gatcttcgac aacttctgtg 60
gaattgtgag cggata 76

<210> SEQ ID NO 193
<211> LENGTH: 78
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMT1KF2

<400> SEQUENCE: 193

-continued ggaagactca acctgtacca tcattaagtg aaaccgtcac tgaagaaggt cctattgagt 60
tttcccagtc acgacgtt 78

<210> SEQ ID NO 194
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CANMT1KR2

<400> SEQUENCE: 194
ggaatcactg gcataataaa acaaataagc aattcctaat tcatcatgtt gagcattgtc 60
tgtggaattg tgagcggata 80

<210> SEQ ID NO 195
<211> LENGTH: 81
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR100FD

<400> SEQUENCE: 195
ggattcaata tagctgttcg tttgttggag gggcttcctg acaacaaaga aattactctt 60
ggttttccca gtcacgacgt t 81

<210> SEQ ID NO 196
<211> LENGTH: 77
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR100RD

<400> SEQUENCE: 196
caacgtcgtc cagaccagtg ctgtcaatct cttcttctaa taaatactct ttaccagtgt 60
ggaattgtga gcggata 77

<210> SEQ ID NO 197
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR341FD

<400> SEQUENCE: 197
attttcctct acaatatttt atagtcaaag aagataccat tcaatgtcag tcgaaacaat 60
gttttcccag tcacgacgtt 80

<210> SEQ ID NO 198
<211> LENGTH: 80
<212> TYPE: DNA
<213> ORGANISM: Artificial Sequence
<220> FEATURE:

-continued

<223> OTHER INFORMATION: Synthesized Primer
<220> FEATURE:
<221> NAME/KEY: misc_feature
<223> OTHER INFORMATION: CAYDR341RD

<400> SEQUENCE: 198
gaaacccata aaatatcgta acattgggag acaatatgtg tcacactgaa caaataagta 60
tgtggaattg tgagcggata 80

<210> SEQ ID NO 199
<211> LENGTH: 78
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR022FD

<400> SEQUENCE: 199
gttcaagatt ggagactgaa agtggaaaag gatattgacg aagtgttaca aatcccacgt 60
tttcccagtc acgacgtt 78

<210> SEQ ID NO 200
<211> LENGTH: 79
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR022RD

<400> SEQUENCE: 200
ccaacaatct catattgttt cccattgtta tcttcctcca caatttgatc aataacaggt 60
gtggaattgt gagcggata 79

<210> SEQ ID NO 201
<211> LENGTH: 76
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL077FD

<400> SEQUENCE: 201
caatcatgtc agctatctat aaggcattac aatccaaaca tctaaggaaa catcgggttt 60
tcccagtcac gacgtt 76

<210> SEQ ID NO 202
<211> LENGTH: 71
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL077RD

<400> SEQUENCE: 202
ctttctttct aaagcagctt gagatctaga ttttgcttga tcagcagcct gtgtggaatt 60
gtgagcggat a 71

<210> SEQ ID NO 203
<211> LENGTH: 75
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYNL132FD

<400> SEQUENCE: 203
gggcatacaa gaaaaaatta ttaggcttca cctcccacag acagaagcgt gaagcgtttt 60
cccagtcacg acgtt 75

<210> SEQ ID NO 204
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYNL132RD

<400> SEQUENCE: 204
caattcacgt tgtttttctc tcatttcttt tattgcctca tcaccagcct cttccaagtc 60
tgtggaattg tgagcggata 80

<210> SEQ ID NO 205
<211> LENGTH: 77
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYJR072FD

<400> SEQUENCE: 205
gccaacacca ccacctacga ttatatgtat tggaatggcc ggaagtggta aaaccacgtt 60
ttcccagtca cgacgtt 77

<210> SEQ ID NO 206
<211> LENGTH: 79
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYJR072RD

<400> SEQUENCE: 206
gcatcggttc tagagttgac ctctgattga cgttcaggga atgtatattc tctttctggt 60
gtggaattgt gagcggata 79

<210> SEQ ID NO 207
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYGR145FD -continued

<400> SEQUENCE: 207
ctggtaccaa tgtttctcga tcattacctg attggataga caagaaacgt aaacgagctc 60
gttttcccag tcacgacgtt 80

<210> SEQ ID NO 208
<211> LENGTH: 77
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYGR145RD

<400> SEQUENCE: 208
cgaccttcaa atctctgttt agttctacca ctatctttag tcttaccact atccagctgt 60
ggaattgtga gcggata 77

<210> SEQ ID NO 209
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR412FD

<400> SEQUENCE: 209
gaaacattta gttgatgaag ttgtatttga taaagaatcc cgtcatgaat atttaactgg 60
gttttcccag tcacgacgtt 80

<210> SEQ ID NO 210
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYDR412RD

<400> SEQUENCE: 210
ctgcttttgt taaatatctg aatttcttct tcttttgttt gattggatta ggtttagcaa 60
tgtggaattg tgagcggata 80

<210> SEQ ID NO 211
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOL010FD

<400> SEQUENCE: 211
cacaggaatt tcagattaag attggtgcta gccacattat ctggaaaacc tatcaaaatt 60
gttttcccag tcacgacgtt 80

<210> SEQ ID NO 212
<211> LENGTH: 80
<212> TYPE: DNA
<213> ORGANISM: Artificial Sequence -continued
<220> FEATURE:
<223> OTHER INFORMATION: Synthesized Primer
<220> FEATURE:
<221> NAME/KEY: misc_feature
<223> OTHER INFORMATION: CAYOL010RD

<400> SEQUENCE: 212
tagaaactgt catgaattta tcatcactat caagctcttc tgcatcatct ttgaagaaag 60
tgtggaattg tgagcggata 80

<210> SEQ ID NO 213
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR004FD

<400> SEQUENCE: 213
acgcattcaa attcagagaa ccataccaaa taatagtaga caatgaactc atcaccactt 60
gttttcccag tcacgacgtt 80

<210> SEQ ID NO 214
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR004RD

<400> SEQUENCE: 214
cttcgttcac ttgctcctgt tcttggtctt ccttctcttc tgcttttgac ttgccatgtc 60
tgtggaattg tgagcggata 80

<210> SEQ ID NO 215
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR056FD

<400> SEQUENCE: 215
ttgagtcttt gatttcggat gctggtccat tgattacaca gccagctact actttgcagc 60
gttttcccag tcacgacgtt 80

<210> SEQ ID NO 216
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYOR056RD

<400> SEQUENCE: 216
tgacaccaga gtttctaatc gtgttcccaa aaggagaaac aaaattgtca gcactgcctc 60
tgtggaattg tgagcggata 80

-continued

<210> SEQ ID NO 217
<211> LENGTH: 82
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR009FD

<400> SEQUENCE: 217
gctgctggta aagaattggt aattgattct acattaacat ttgctgctag aagaaatgtt 60
ccgttttccc agtcacgacg tt 82

<210> SEQ ID NO 218
<211> LENGTH: 80
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAYLR009RD

<400> SEQUENCE: 218
cccattcttc ctctccactt atcatttctt catcaccttc tccttcctct tcaacctctg 60
tgtggaattg tgagcggata 80

<210> SEQ ID NO 219
<211> LENGTH: 71
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAAAH1FD

<400> SEQUENCE: 219
gcctgagact ttccctaaaa aggttgaaga atgtaatgat agatacaaca ggttttccca 60
gtcacgacgt t 71

<210> SEQ ID NO 220
<211> LENGTH: 70
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: CAAAH1RD

<400> SEQUENCE: 220
gcaattattt tccattggtc tttggtgaat ccaaatcttg tgtgaacagc tgtggaattg 60
tgagcggata 70

<210> SEQ ID NO 221
<211> LENGTH: 20
<212> TYPE: DNA
<213> ORGANISM: Artificial Sequence
<220> FEATURE:
<223> OTHER INFORMATION: synthesized primer
<220> FEATURE:
<221> NAME/KEY: misc_feature
<223> OTHER INFORMATION: 5DR -continued

<400> SEQUENCE: 221
gttttcccag tcacgacgtt 20

<210> SEQ ID NO 222
<211> LENGTH: 20
<212> TYPE: DNA
<213> ORGANISM: Artificial Sequence
<220> FEATURE:
<223> OTHER INFORMATION: Synthesized primer
<220> FEATURE:
<221> NAME/KEY: misc_feature
<223> OTHER INFORMATION: 3DR

<400> SEQUENCE: 222
tgtggaattg tgagcggata 20

<210> SEQ ID NO 223
<211> LENGTH: 30
<212> TYPE: DNA
<213> ORGANISM: Artificial Sequence
<220> FEATURE:
<223> OTHER INFORMATION: synthesized primer
<220> FEATURE:
<221> NAME/KEY: misc_feature
<223> OTHER INFORMATION: MET3SPHI

<400> SEQUENCE: 223
gtcagcatgc gtggagcatc acggatgacc 30

<210> SEQ ID NO 224
<211> LENGTH: 30
<212> TYPE: DNA
<213> ORGANISM: Artificial sequence
<220> FEATURE:
<223> OTHER INFORMATION: Synthesized Primer
<220> FEATURE:
<221> NAME/KEY: misc_feature
<223> OTHER INFORMATION: MET3ncoi

<400> SEQUENCE: 224
gtgaccatgg aattgtctat tccaagcctg 30

<210> SEQ ID NO 225
<211> LENGTH: 20
<212> TYPE: DNA
<213> ORGANISM: Artificial Sequence
<220> FEATURE:
<223> OTHER INFORMATION: Synthesized Primer
<220> FEATURE:
<221> NAME/KEY: misc_feature
<223> OTHER INFORMATION: Met3pf

<400> SEQUENCE: 225
tgtggaattg tgagcggata 20

<210> SEQ ID NO 226
<211> LENGTH: 20
<212> TYPE: DNA
<213> ORGANISM: Artificial Sequence
<220> FEATURE:
<223> OTHER INFORMATION: synthesized primer
<220> FEATURE:
<221> NAME/KEY: misc_feature
<223> OTHER INFORMATION: Met3PR

<400> SEQUENCE: 226
gttttctggg gagggtattt 20

<210> SEQ ID NO 227
<211> LENGTH: 25
<212> TYPE: DNA
<213> ORGANISM: artificial
<220> FEATURE:
<223> OTHER INFORMATION: Sequencing primer specific to the pDONR201 vector.

<400> SEQUENCE: 227
tcgcgttaac gctagcatgg atctc 25

<210> SEQ ID NO 228
<211> LENGTH: 24
<212> TYPE: DNA
<213> ORGANISM: artificial
<220> FEATURE:
<223> OTHER INFORMATION: Sequencing primer specific to the pDONR201 vector.

<400> SEQUENCE: 228
gtaacatcag agattttgag acac 24

<210> SEQ ID NO 229
<211> LENGTH: 66
<212> TYPE: DNA
<213> ORGANISM: Candida albicans

<400> SEQUENCE: 229
ggggacaagt ttgtacaaaa aagcaggctt ggttccgcgt ggtagcatgt cacttttaaa 60
ggattc 66

<210> SEQ ID NO 230
<211> LENGTH: 57
<212> TYPE: DNA
<213> ORGANISM: Candida albicans

<400> SEQUENCE: 230
ggggaccact ttgtacaaga aagctgggtc ctaaggttga cgtgtattta ctatttg 57

<210> SEQ ID NO 231
<211> LENGTH: 66
<212> TYPE: DNA
<213> ORGANISM: Candida albicans

<400> SEQUENCE: 231
ggggacaagt ttgtacaaaa aagcaggctt ggttccgcgt ggtagcatgt cagtcgaaac 60
aattag 66

<210> SEQ ID NO 232
<211> LENGTH: 56
<212> TYPE: DNA
<213> ORGANISM: Candida albicans

<400> SEQUENCE: 232
ggggaccact ttgtacaaga aagctgggtc ctacatacga ttaactggag tcaaac 56

<210> SEQ ID NO 233
<211> LENGTH: 66
<212> TYPE: DNA
<213> ORGANISM: Candida albicans

<400> SEQUENCE: 233

-continued

```
ggggacaagt ttgtacaaaa aagcaggctt ggttccgcgt ggtagcatgg cggtgattaa     60

tcaacc                                                                66


<210> SEQ ID NO 234
<211> LENGTH: 54
<212> TYPE: DNA
<213> ORGANISM: Candida albicans

<400> SEQUENCE: 234

ggggaccact ttgtacaaga aagctgggtc ctattccttt atggcagaca tatc           54


<210> SEQ ID NO 235
<211> LENGTH: 66
<212> TYPE: DNA
<213> ORGANISM: Candida albicans

<400> SEQUENCE: 235

ggggacaagt ttgtacaaaa aagcaggctt ggttccgcgt ggtagcatgt cagctatcta     60

taaggc                                                                66


<210> SEQ ID NO 236
<211> LENGTH: 53
<212> TYPE: DNA
<213> ORGANISM: Candida albicans

<400> SEQUENCE: 236

ggggaccact ttgtacaaga aagctgggtc ctatttaaat aaagcatcat tgg            53


<210> SEQ ID NO 237
<211> LENGTH: 68
<212> TYPE: DNA
<213> ORGANISM: Candida albicans

<400> SEQUENCE: 237

ggggacaagt ttgtacaaaa aagcaggctt ggttccgcgt ggtagcatgg gtaaaaaagc     60

aattgatg                                                              68


<210> SEQ ID NO 238
<211> LENGTH: 55
<212> TYPE: DNA
<213> ORGANISM: Candida albicans

<400> SEQUENCE: 238

ggggaccact ttgtacaaga aagctgggtc ctattttttt gatttctttg atttc          55


<210> SEQ ID NO 239
<211> LENGTH: 66
<212> TYPE: DNA
<213> ORGANISM: Candida albicans

<400> SEQUENCE: 239

ggggacaagt ttgtacaaaa aagcaggctt ggttccgcgt ggtagcatgg ttttaaaatc     60

aacaac                                                                66


<210> SEQ ID NO 240
<211> LENGTH: 55
<212> TYPE: DNA
<213> ORGANISM: Candida albicans

<400> SEQUENCE: 240

ggggaccact ttgtacaaga aagctgggtc ctacatacct ctaaacttat tcttg          55
```

-continued

<210> SEQ ID NO 241
<211> LENGTH: 69
<212> TYPE: DNA
<213> ORGANISM: Candida albicans

<400> SEQUENCE: 241
ggggacaagt ttgtacaaaa aagcaggctt ggttccgcgt ggtagcatgg caggatttaa 60
aaagaatag 69

<210> SEQ ID NO 242
<211> LENGTH: 53
<212> TYPE: DNA
<213> ORGANISM: Candida albicans

<400> SEQUENCE: 242
ggggaccact ttgtacaaga aagctgggtc ctacttcttg ccctttgatt ttg 53

<210> SEQ ID NO 243
<211> LENGTH: 70
<212> TYPE: DNA
<213> ORGANISM: Candida albicans

<400> SEQUENCE: 243
ggggacaagt ttgtacaaaa aagcaggctt ggttccgcgt ggtagcatgt ccagtgttgc 60
ttccaaaaag 70

<210> SEQ ID NO 244
<211> LENGTH: 55
<212> TYPE: DNA
<213> ORGANISM: Candida albicans

<400> SEQUENCE: 244
ggggaccact ttgtacaaga aagctgggtc ctaagctatt tttttagaaa cattg 55

<210> SEQ ID NO 245
<211> LENGTH: 67
<212> TYPE: DNA
<213> ORGANISM: Candida albicans

<400> SEQUENCE: 245
ggggacaagt ttgtacaaaa aagcaggctt ggttccgcgt ggtagcatga gacaaaagcg 60
tgccaag 67

<210> SEQ ID NO 246
<211> LENGTH: 54
<212> TYPE: DNA
<213> ORGANISM: Candida albicans

<400> SEQUENCE: 246
ggggaccact ttgtacaaga aagctgggtc ctagttgttg cttcgttcac ttgc 54

<210> SEQ ID NO 247
<211> LENGTH: 68
<212> TYPE: DNA
<213> ORGANISM: Candida albicans

<400> SEQUENCE: 247
ggggacaagt ttgtacaaaa aagcaggctt ggttccgcgt ggtagcatgt ctgaaacaaa 60
aaatattg 68

-continued

<210> SEQ ID NO 248
<211> LENGTH: 53
<212> TYPE: DNA
<213> ORGANISM: Candida albicans

<400> SEQUENCE: 248
ggggaccact ttgtacaaga aagctgggtc ctactttctt ttctttttgg aag 53

<210> SEQ ID NO 249
<211> LENGTH: 66
<212> TYPE: DNA
<213> ORGANISM: Candida albicans

<400> SEQUENCE: 249
ggggacaagt ttgtacaaaa aagcaggctt ggttccgcgt ggtagcatga ggatttatca 60
atgtca 66

<210> SEQ ID NO 250
<211> LENGTH: 54
<212> TYPE: DNA
<213> ORGANISM: Candida albicans

<400> SEQUENCE: 250
ggggaccact ttgtacaaga aagctgggtc ctaacacgtt tttgtgtcac tttc 54

<210> SEQ ID NO 251
<211> LENGTH: 288
<212> TYPE: PRT
<213> ORGANISM: Sus scrofa

<400> SEQUENCE: 251

Ser Ser Asn Thr Arg Val Ala Leu Val Thr Gly Ala Asn Lys Gly Ile
1 5 10 15

Gly Phe Ala Ile Val Arg Asp Leu Cys Arg Gln Phe Ala Gly Asp Val
20 25 30

Val Leu Thr Ala Arg Asp Val Ala Arg Gly Gln Ala Ala Val Lys Gln
35 40 45

Leu Gln Ala Glu Gly Leu Ser Pro Arg Phe His Gln Leu Asp Ile Ile
50 55 60

Asp Leu Gln Ser Ile Arg Ala Leu Cys Asp Phe Leu Arg Lys Glu Tyr
65 70 75 80

Gly Gly Leu Asp Val Leu Val Asn Asn Ala Ala Ile Ala Phe Gln Leu
85 90 95

Asp Asn Pro Thr Pro Phe His Ile Gln Ala Glu Leu Thr Met Lys Thr
100 105 110

Asn Phe Met Gly Thr Arg Asn Val Cys Thr Glu Leu Leu Pro Leu Ile
115 120 125

Lys Pro Gln Gly Arg Val Val Asn Val Ser Ser Thr Glu Gly Val Arg
130 135 140

Ala Leu Asn Glu Cys Ser Pro Glu Leu Gln Gln Lys Phe Lys Ser Glu
145 150 155 160

Thr Ile Thr Glu Glu Glu Leu Val Gly Leu Met Asn Lys Phe Val Glu
165 170 175

Asp Thr Lys Asn Gly Val His Arg Lys Glu Gly Trp Ser Asp Ser Thr
180 185 190

Tyr Gly Val Thr Lys Ile Gly Val Ser Val Leu Ser Arg Ile Tyr Ala
195 200 205

-continued

Arg Lys Leu Arg Glu Gln Arg Ala Gly Asp Lys Ile Leu Leu Asn Ala
    210                 215                 220

Cys Cys Pro Gly Trp Val Arg Thr Asp Met Gly Gly Pro Lys Ala Pro
225                 230                 235                 240

Lys Ser Pro Glu Val Gly Ala Glu Thr Pro Val Tyr Leu Ala Leu Leu
                245                 250                 255

Pro Ser Asp Ala Glu Gly Pro His Gly Gln Phe Val Thr Asp Lys Lys
            260                 265                 270

Val Val Glu Trp Gly Val Pro Pro Glu Ser Tyr Pro Trp Val Asn Ala
        275                 280                 285

<210> SEQ ID NO 252
<211> LENGTH: 606
<212> TYPE: PRT
<213> ORGANISM: Saccharomyces cerevisiae

<400> SEQUENCE: 252

Ala Ser Thr Ala Asn Met Ile Ser Gln Leu Lys Lys Leu Ser Ile Ala
1               5                   10                  15

Glu Pro Ala Val Ala Lys Asp Ser His Pro Asp Val Asn Ile Val Asp
            20                  25                  30

Leu Met Arg Asn Tyr Ile Ser Gln Glu Leu Ser Lys Ile Ser Gly Val
        35                  40                  45

Asp Ser Ser Leu Ile Phe Pro Ala Leu Glu Trp Thr Asn Thr Met Glu
    50                  55                  60

Arg Gly Asp Leu Leu Ile Pro Ile Pro Arg Leu Arg Ile Lys Gly Ala
65                  70                  75                  80

Asn Pro Lys Asp Leu Ala Val Gln Trp Ala Glu Lys Phe Pro Cys Gly
                85                  90                  95

Asp Phe Leu Glu Lys Val Glu Ala Asn Gly Pro Phe Ile Gln Phe Phe
            100                 105                 110

Phe Asn Pro Gln Phe Leu Ala Lys Leu Val Ile Pro Asp Ile Leu Thr
        115                 120                 125

Arg Lys Glu Asp Tyr Gly Ser Cys Lys Leu Val Glu Asn Lys Lys Val
    130                 135                 140

Ile Ile Glu Phe Ser Ser Pro Asn Ile Ala Lys Pro Phe His Ala Gly
145                 150                 155                 160

His Leu Arg Ser Thr Ile Ile Gly Gly Phe Leu Ala Asn Leu Tyr Glu
                165                 170                 175

Lys Leu Gly Trp Glu Val Ile Arg Met Asn Tyr Leu Gly Asp Trp Gly
            180                 185                 190

Lys Gln Phe Gly Leu Leu Ala Val Gly Phe Glu Arg Tyr Gly Asn Glu
        195                 200                 205

Glu Ala Leu Val Lys Asp Pro Ile His His Leu Phe Asp Val Tyr Val
    210                 215                 220

Arg Ile Asn Lys Asp Ile Glu Glu Glu Gly Asp Ser Ile Pro Leu Glu
225                 230                 235                 240

Gln Ser Thr Asn Gly Lys Ala Arg Glu Tyr Phe Lys Arg Met Glu Asp
                245                 250                 255

Gly Asp Glu Glu Ala Leu Lys Ile Trp Lys Arg Phe Arg Glu Phe Ser
            260                 265                 270

Ile Glu Lys Tyr Ile Asp Thr Tyr Ala Arg Leu Asn Ile Lys Tyr Asp
        275                 280                 285

Val Tyr Ser Gly Glu Ser Gln Val Ser Lys Glu Ser Met Leu Lys Ala
    290                 295                 300

-continued

```
Ile Asp Leu Phe Lys Glu Lys Gly Leu Thr His Glu Asp Lys Gly Ala
305                 310                 315                 320

Val Leu Ile Asp Leu Thr Lys Phe Asn Lys Lys Leu Gly Lys Ala Ile
                325                 330                 335

Val Gln Lys Ser Asp Gly Thr Thr Leu Tyr Leu Thr Arg Asp Val Gly
            340                 345                 350

Ala Ala Met Asp Arg Tyr Glu Lys Tyr His Phe Asp Lys Met Ile Tyr
        355                 360                 365

Val Ile Ala Ser Gln Gln Asp Leu His Ala Ala Gln Phe Phe Glu Ile
    370                 375                 380

Leu Lys Gln Met Gly Phe Glu Trp Ala Lys Asp Leu Gln His Val Asn
385                 390                 395                 400

Phe Gly Met Val Gln Gly Met Ser Thr Arg Lys Gly Thr Val Val Phe
                405                 410                 415

Leu Asp Asn Ile Leu Glu Glu Thr Lys Glu Lys Met His Glu Val Met
            420                 425                 430

Lys Lys Asn Glu Asn Lys Tyr Ala Gln Ile Glu His Pro Glu Glu Val
        435                 440                 445

Ala Asp Leu Val Gly Ile Ser Ala Val Met Ile Gln Asp Met Gln Gly
    450                 455                 460

Lys Arg Ile Asn Asn Tyr Glu Phe Lys Trp Glu Arg Met Leu Ser Phe
465                 470                 475                 480

Glu Gly Asp Thr Gly Pro Tyr Leu Gln Tyr Ala His Ser Arg Leu Arg
                485                 490                 495

Ser Val Glu Arg Asn Ala Ser Gly Ile Thr Gln Glu Lys Trp Ile Asn
            500                 505                 510

Ala Asp Phe Ser Leu Leu Lys Glu Pro Ala Ala Lys Leu Leu Ile Arg
        515                 520                 525

Leu Leu Gly Gln Tyr Pro Asp Val Leu Arg Asn Ala Ile Lys Thr His
    530                 535                 540

Glu Pro Thr Thr Val Val Thr Tyr Leu Phe Lys Leu Thr His Gln Val
545                 550                 555                 560

Ser Ser Cys Tyr Asp Val Leu Trp Val Ala Gly Gln Thr Glu Glu Leu
                565                 570                 575

Ala Thr Ala Arg Leu Ala Leu Tyr Gly Ala Ala Arg Gln Val Leu Tyr
            580                 585                 590

Asn Gly Met Arg Leu Leu Gly Leu Thr Pro Val Glu Arg Met
        595                 600                 605


<210> SEQ ID NO 253
<211> LENGTH: 334
<212> TYPE: PRT
<213> ORGANISM: Escherichia coli

<400> SEQUENCE: 253

Met Ile Ala Leu Asp Gly Ala Gln Gly Glu Gly Gly Gly Gln Ile Leu
1               5                   10                  15

Arg Ser Ala Leu Ser Leu Ser Met Ile Thr Gly Gln Pro Phe Thr Ile
            20                  25                  30

Thr Ser Ile Arg Ala Gly Arg Ala Lys Pro Gly Leu Leu Arg Gln His
        35                  40                  45

Leu Thr Ala Val Lys Ala Ala Thr Glu Ile Cys Gly Ala Thr Val Glu
    50                  55                  60

Gly Ala Glu Leu Gly Ser Gln Arg Leu Leu Phe Arg Pro Gly Thr Val
```

-continued 65 70 75 80

Arg Gly Gly Asp Tyr Arg Phe Ala Ile Gly Ser Ala Gly Ser Cys Thr
85 90 95

Leu Val Leu Gln Thr Val Leu Pro Ala Leu Trp Phe Ala Asp Gly Pro
100 105 110

Ser Arg Val Glu Val Ser Gly Gly Thr Asp Asn Pro Ser Ala Pro Pro
115 120 125

Ala Asp Phe Ile Arg Arg Val Leu Glu Pro Leu Leu Ala Lys Ile Gly
130 135 140

Ile His Gln Gln Thr Thr Leu Leu Arg His Gly Phe Tyr Pro Ala Gly
145 150 155 160

Gly Gly Val Val Ala Thr Glu Val Ser Pro Val Ala Ser Phe Asn Thr
165 170 175

Leu Gln Leu Gly Glu Arg Gly Asn Ile Val Gln Met Arg Gly Glu Val
180 185 190

Leu Leu Ala Gly Val Pro Arg His Val Ala Glu Arg Glu Ile Ala Thr
195 200 205

Leu Ala Gly Ser Phe Ser Leu His Glu Gln Asn Ile His Asn Leu Pro
210 215 220

Arg Asp Gln Gly Pro Gly Asn Thr Val Ser Leu Glu Val Glu Ser Glu
225 230 235 240

Asn Ile Thr Glu Arg Phe Phe Val Val Gly Glu Lys Arg Val Ser Ala
245 250 255

Glu Val Val Ala Ala Gln Leu Val Lys Glu Val Lys Arg Tyr Leu Ala
260 265 270

Ser Thr Ala Ala Val Gly Glu Tyr Leu Ala Asp Gln Leu Val Leu Pro
275 280 285

Met Ala Leu Ala Gly Ala Gly Glu Phe Thr Val Ala His Pro Ser Cys
290 295 300

His Leu Leu Thr Asn Ile Ala Val Val Glu Arg Phe Leu Pro Val Arg
305 310 315 320

Phe Ser Leu Ile Glu Thr Asp Gly Val Thr Arg Val Ser Ile
325 330

<210> SEQ ID NO 254
<211> LENGTH: 5
<212> TYPE: PRT
<213> ORGANISM: Artificial Sequence
<220> FEATURE:
<223> OTHER INFORMATION: Short Chain Dehydrogenase/Reductase Catalytic Triad Consensus Sequence.
<220> FEATURE:
<221> NAME/KEY: MISC_FEATURE
<222> LOCATION: (2)..(4)
<223> OTHER INFORMATION: wherein "X" equals any naturally occurring amino acid.

<400> SEQUENCE: 254

Tyr Xaa Xaa Xaa Lys
1 5

<210> SEQ ID NO 255
<211> LENGTH: 4
<212> TYPE: PRT
<213> ORGANISM: Artificial Sequence
<220> FEATURE:
<223> OTHER INFORMATION: Aminoacyl-tRNA Synthetase Tetrapeptide Sequence.

<400> SEQUENCE: 255

-continued

```
His Ile Gly His
1


<210> SEQ ID NO 256
<211> LENGTH: 9
<212> TYPE: PRT
<213> ORGANISM: Artificial Sequence
<220> FEATURE:
<223> OTHER INFORMATION: RNA 3'-terminal Phosphate Cyclase Signature
      Sequence.
<220> FEATURE:
<221> NAME/KEY: MISC_FEATURE
<222> LOCATION: (1)..(1)
<223> OTHER INFORMATION: wherein "X" equals 'H' or 'R'.
<220> FEATURE:
<221> NAME/KEY: MISC_FEATURE
<222> LOCATION: (3)..(8)
<223> OTHER INFORMATION: wherein "X" equals any naturally occuring amino
      acid.

<400> SEQUENCE: 256

Xaa Gly Xaa Pro Gly Gly Gly Xaa Val
1               5
```